US012454520B2

(12) United States Patent
Zhang et al.

(10) Patent No.: US 12,454,520 B2
(45) Date of Patent: Oct. 28, 2025

(54) PROTEIN DEGRADERS AND USES THEREOF

(71) Applicant: Kymera Therapeutics, Inc., Watertown, MA (US)

(72) Inventors: Yi Zhang, Belmont, MA (US); Nan Ji, Arlington, MA (US); Arthur F. Kluge, Concord, MA (US); Matthew M. Weiss, Boston, MA (US)

(73) Assignee: Kymera Therapeutics, Inc., Watertown, MA (US)

( * ) Notice: Subject to any disclaimer, the term of this patent is extended or adjusted under 35 U.S.C. 154(b) by 906 days.

(21) Appl. No.: 17/258,339

(22) PCT Filed: Jul. 3, 2019

(86) PCT No.: PCT/US2019/040545

§ 371 (c)(1),
(2) Date: Jan. 6, 2021

(87) PCT Pub. No.: WO2020/010227

PCT Pub. Date: Jan. 9, 2020

(65) Prior Publication Data

US 2022/0348556 A1 Nov. 3, 2022

Related U.S. Application Data

(60) Provisional application No. 62/863,954, filed on Jun. 20, 2019, provisional application No. 62/820,641, filed on Mar. 19, 2019, provisional application No. 62/694,931, filed on Jul. 6, 2018.

(51) Int. Cl.
*C07D 401/14* (2006.01)
*A61P 35/00* (2006.01)

(52) U.S. Cl.
CPC ............ *C07D 401/14* (2013.01); *A61P 35/00* (2018.01)

(58) Field of Classification Search
CPC ........ C07D 401/04; A61K 31/45; A61P 35/00
See application file for complete search history.

(56) References Cited

U.S. PATENT DOCUMENTS

| | | | |
|---|---|---|---|
| 4,650,750 | A | 3/1987 | Giese |
| 4,709,016 | A | 11/1987 | Giese |
| 5,217,866 | A | 6/1993 | Summerton et al. |
| 5,360,811 | A | 11/1994 | Tegeler et al. |
| 5,360,819 | A | 11/1994 | Giese |
| 5,516,931 | A | 5/1996 | Giese et al. |
| 5,602,273 | A | 2/1997 | Giese et al. |
| 5,604,104 | A | 2/1997 | Giese et al. |
| 5,610,020 | A | 3/1997 | Giese et al. |
| 5,650,270 | A | 7/1997 | Giese et al. |
| 5,721,246 | A | 2/1998 | Yoshino et al. |
| 6,306,663 | B1 | 10/2001 | Kenten et al. |
| 6,552,065 | B2 | 4/2003 | Remiszewski et al. |
| 6,559,280 | B2 | 5/2003 | Kenten et al. |
| 6,627,754 | B2 | 9/2003 | Blumenkopf et al. |
| 6,949,537 | B2 | 9/2005 | Garlich et al. |
| 7,041,298 | B2 | 5/2006 | Deshaies et al. |
| 7,071,189 | B2 | 7/2006 | Kawashima et al. |
| 7,074,620 | B2 | 7/2006 | Kenten et al. |
| 7,173,015 | B2 | 2/2007 | Schreiber et al. |
| 7,208,157 | B2 | 4/2007 | Dashaies et al. |
| 7,273,920 | B2 | 9/2007 | Kenten et al. |
| 7,307,077 | B2 | 12/2007 | Kawashima et al. |
| 7,390,799 | B2 | 6/2008 | Bruncko et al. |
| 7,402,325 | B2 | 7/2008 | Addington |
| 7,449,458 | B2 | 11/2008 | Bhamidipati et al. |
| 7,501,496 | B1 | 3/2009 | Endl et al. |
| 7,514,444 | B2 | 4/2009 | Honigberg et al. |
| 7,528,143 | B2 | 5/2009 | Noronha et al. |
| 7,557,210 | B2 | 7/2009 | Singh et al. |
| 7,598,257 | B2 | 10/2009 | Rodgers et al. |
| 7,622,496 | B2 | 11/2009 | Larsen et al. |
| 7,667,039 | B2 | 2/2010 | Garcia-Echeverria et al. |
| 7,713,943 | B2 | 5/2010 | Klippel-Giese et al. |
| 7,781,433 | B2 | 8/2010 | Chuckowree et al. |
| 7,932,260 | B2 | 4/2011 | Fowler et al. |
| 7,989,622 | B2 | 8/2011 | Bajjalieh et al. |
| 8,138,347 | B2 | 3/2012 | Knight et al. |
| 8,185,616 | B2 | 5/2012 | Nagata et al. |
| 8,217,035 | B2 | 7/2012 | Burger et al. |
| 8,338,439 | B2 | 12/2012 | Singh et al. |
| 8,486,941 | B2 | 7/2013 | Burns et al. |
| 8,906,682 | B2 | 12/2014 | June et al. |
| 8,999,975 | B2 | 4/2015 | Grundl et al. |
| 9,500,653 | B2 | 11/2016 | Crews et al. |

(Continued)

FOREIGN PATENT DOCUMENTS

| | | | |
|---|---|---|---|
| CN | 105085620 | B | 5/2018 |
| WO | WO-1996007655 | A1 | 3/1996 |

(Continued)

OTHER PUBLICATIONS

Adams et al., "Big opportunities for small molecules in immuno-oncology," Nat Rev Drug Discov. 2015;14(9):603-22.
Aruri et al., "Metal-free Cross-Dehydrogenative Coupling of HN-azoles with a-C(sp3)-H Amides via C-H Activation and Its Mechanistic and Application Studies," J Org Chem. 2017;82(2):1000-1012.
Bailey et al., "Steric effects on [4+4]-photocycloaddition reactions between complementary anthracene derivatives," Dyes and Pigments. 2011;89(3):313-318.
Berge et al., "Pharmaceutical salts," J Pharm Sci. 1977;66(1): 1-19.
Berndsen et al., "New insights into ubiquitin E3 ligase mechanism," Nat Struct Mol Biol. 2014;21(4):301-7.
Bevilacqua et al., "SWI/SNF Chromatin-Remodeling Complexes in Cardiovascular Development and Disease," Cardiovasc Pathol. Mar.-Apr. 2014; 23(2): 85-91.
Blake et al., "Studies with deuterated drugs," J Pharm Sci. 1975;64(3):367-91.

(Continued)

*Primary Examiner* — Kamal A Saeed

(74) *Attorney, Agent, or Firm* — Dechert LLP; Andrea L. C. Reid; Matthew C. Stevens

(57) ABSTRACT

The present invention provides compounds, compositions thereof, and methods of using the same for the targeted degradation of proteins, and the treatment of target protein-mediated disorders.

16 Claims, No Drawings

(56) References Cited

U.S. PATENT DOCUMENTS 9,632,089 B2 4/2017 Crews et al.
9,694,084 B2 7/2017 Bradner et al.
9,750,816 B2 9/2017 Bradner et al.
9,770,512 B2 9/2017 Bradner et al.
9,821,068 B2 11/2017 Bradner et al.
9,969,710 B2 5/2018 Jorand-Lebrun et al.
10,125,114 B2 11/2018 Bradner et al.
10,336,744 B2 7/2019 Harling et al.
10,874,743 B2 12/2020 Mainolfi et al.
11,117,889 B1 9/2021 Mainolfi et al.
11,292,792 B2 * 4/2022 Ji .......................... C07D 495/04
11,352,350 B2 6/2022 Mainolfi et al.
11,485,743 B2 11/2022 Mainolfi et al.
11,623,932 B2 4/2023 Mainolfi et al.
12,006,329 B2 6/2024 Mainolfi et al.
2001/0053782 A1 12/2001 Blumenkopf et al.
2002/0042427 A1 4/2002 Tang et al.
2002/0068063 A1 6/2002 Deshaies et al.
2002/0183360 A1 12/2002 Muller et al.
2004/0029902 A1 2/2004 Singh et al.
2004/0048859 A1 3/2004 Germann et al.
2004/0106569 A1 6/2004 Klippel-Giese et al.
2004/0116421 A1 6/2004 Kawashima et al.
2004/0242631 A1 12/2004 Garlich et al.
2005/0014802 A1 1/2005 Attardo et al.
2005/0075306 A1 4/2005 Schreiber et al.
2006/0211657 A1 9/2006 Singh et al.
2007/0098719 A1 5/2007 Smith et al.
2007/0135461 A1 6/2007 Rodgers et al.
2007/0191405 A1 8/2007 Noronha et al.
2008/0076768 A1 3/2008 Chuckowree et al.
2008/0108636 A1 5/2008 Honigberg et al.
2008/0194579 A1 8/2008 Garcia-Echeverria et al.
2008/0275067 A1 11/2008 Fowler et al.
2009/0055944 A1 2/2009 Korman et al.
2009/0136494 A1 5/2009 Ponath et al.
2009/0233903 A1 9/2009 Rodgers et al.
2010/0087440 A1 4/2010 Bajalieh et al.
2010/0150892 A1 6/2010 Han
2010/0197671 A1 8/2010 Burns et al.
2010/0197686 A1 8/2010 Xing et al.
2010/0203056 A1 8/2010 Irving et al.
2010/0233183 A1 9/2010 Triebel et al.
2010/0247554 A1 9/2010 Lemke et al.
2010/0249092 A1 9/2010 Singh et al.
2010/0249126 A1 9/2010 Burger et al.
2010/0279316 A1 11/2010 Gorelik et al.
2011/0008331 A1 1/2011 Triebel
2011/0053941 A1 3/2011 Mautino et al.
2011/0136796 A1 6/2011 Mautino et al.
2011/0165156 A1 7/2011 Dimoudis et al.
2011/0196150 A1 8/2011 Man et al.
2011/0223611 A1 9/2011 Salamone et al.
2011/0274683 A1 11/2011 Wong et al.
2012/0015962 A1 1/2012 Arora et al.
2012/0189639 A1 7/2012 Schebye et al.
2012/0277217 A1 11/2012 Mautino et al.
2012/0283238 A1 11/2012 Romero et al.
2012/0329997 A1 12/2012 Fertig et al.
2013/0005949 A1 1/2013 Fertig et al.
2013/0149236 A1 6/2013 Johnson et al.
2013/0190340 A1 7/2013 Hedstrom et al.
2013/0231328 A1 9/2013 Harriman et al.
2013/0274241 A1 10/2013 Jorand-Lebrun et al.
2014/0018343 A1 1/2014 Romero et al.
2014/0018357 A1 1/2014 Harriman et al.
2014/0018361 A1 1/2014 Harriman et al.
2014/0066625 A1 3/2014 Mautino et al.
2014/0079699 A1 3/2014 Wong et al.
2014/0079706 A1 3/2014 Cannarile et al.
2014/0093511 A1 4/2014 Lonberg et al.
2014/0155379 A1 6/2014 Ho et al.
2014/0194404 A1 7/2014 McElroy et al.
2014/0302523 A1 10/2014 Crews et al.
2014/0329799 A1 11/2014 Seganish et al.
2014/0336363 A1 11/2014 Fertig et al.
2014/0341917 A1 11/2014 Nastri et al.
2014/0356322 A1 12/2014 Crews et al.
2015/0011532 A1 1/2015 Paidi et al.
2015/0018344 A1 1/2015 Paidi et al.
2015/0045347 A1 2/2015 Dodd et al.
2015/0094305 A1 4/2015 Romero et al.
2015/0133451 A1 5/2015 Yoshida et al.
2015/0141396 A1 5/2015 Crosignani et al.
2015/0191464 A1 7/2015 Santella et al.
2015/0225410 A1 8/2015 Castro et al.
2015/0225449 A1 8/2015 Donnell et al.
2015/0274708 A1 10/2015 Seganish et al.
2015/0274738 A1 10/2015 Gray et al.
2015/0284382 A1 10/2015 Bhide et al.
2015/0284405 A1 10/2015 Trzupek et al.
2015/0291562 A1 10/2015 Crew et al.
2015/0299224 A1 10/2015 Seganish et al.
2015/0329498 A1 11/2015 Romero et al.
2015/0374678 A1 12/2015 Chamberlain et al.
2015/0376167 A1 12/2015 Jorand-Lebrun et al.
2015/0376206 A1 12/2015 Jorand-Lebrun et al.
2016/0002265 A1 1/2016 Jenkins et al.
2016/0022642 A1 1/2016 Crews et al.
2016/0045607 A1 2/2016 Crew et al.
2016/0058872 A1 3/2016 Crew et al.
2016/0145252 A1 5/2016 Jorand-Lebrun et al.
2016/0176916 A1 6/2016 Bradner et al.
2016/0200705 A1 7/2016 Furet et al.
2016/0214972 A1 7/2016 Jin et al.
2016/0235730 A1 8/2016 Bradner et al.
2016/0235731 A1 8/2016 Bradner et al.
2016/0243247 A1 8/2016 Bradner et al.
2016/0256468 A1 9/2016 Schafer et al.
2016/0272596 A1 9/2016 Chen et al.
2016/0272639 A1 9/2016 Crew et al.
2016/0311833 A1 10/2016 Bothe et al.
2016/0311839 A1 10/2016 Kelley et al.
2016/0326151 A1 11/2016 Gummadi et al.
2016/0340366 A1 11/2016 Gummadi et al.
2017/0001990 A1 1/2017 Chen et al.
2017/0008896 A1 1/2017 Dahmann et al.
2017/0008904 A1 1/2017 Crew et al.
2017/0022189 A1 1/2017 Zhang
2017/0037004 A1 2/2017 Crew et al.
2017/0065719 A1 3/2017 Qian et al.
2017/0121321 A1 5/2017 Crews et al.
2017/0152263 A1 6/2017 Gummadi et al.
2017/0204093 A1 7/2017 Chan et al.
2017/0247388 A1 8/2017 Altman et al.
2017/0250346 A1 8/2017 Seo et al.
2017/0281784 A1 10/2017 Wang et al.
2017/0327469 A1 11/2017 Crew et al.
2017/0369476 A1 12/2017 Chen et al.
2018/0009779 A1 1/2018 Bradner et al.
2018/0015087 A1 1/2018 Liu et al.
2018/0051027 A1 2/2018 Lim et al.
2018/0051028 A1 2/2018 Lim et al.
2018/0051029 A1 2/2018 Lim et al.
2018/0051030 A1 2/2018 Lim et al.
2018/0051035 A1 2/2018 Lim et al.
2018/0085465 A1 3/2018 Bradner et al.
2018/0086720 A1 3/2018 Albrecht et al.
2018/0118733 A1 5/2018 Harling et al.
2018/0134684 A1 5/2018 Bradner et al.
2018/0147202 A1 5/2018 Crew et al.
2018/0169097 A1 6/2018 Hammerman et al.
2018/0186799 A1 7/2018 Gardner et al.
2018/0194724 A1 7/2018 Kemp et al.
2018/0201609 A1 7/2018 Gummadi et al.
2018/0208605 A1 7/2018 Gummadi et al.
2018/0228907 A1 8/2018 Crew et al.
2018/0230157 A1 8/2018 Bacon et al.
2019/0071415 A1 3/2019 Bradner et al.
2019/0076539 A1 3/2019 Phillips et al.
2019/0076540 A1 3/2019 Phillips et al.
2019/0076541 A1 3/2019 Phillips et al.
2019/0076542 A1 3/2019 Phillips et al.
2019/0151295 A1 5/2019 Crew et al.

(56) References Cited

U.S. PATENT DOCUMENTS

| | | | |
|---|---|---|---|
| 2019/0151457 | A1 | 5/2019 | Bradner et al. |
| 2019/0192532 | A1 | 6/2019 | Bradner et al. |
| 2019/0192668 | A1 | 6/2019 | Mainolfi et al. |
| 2019/0276474 | A1 | 9/2019 | Chan et al. |
| 2019/0300521 | A1 | 10/2019 | Crew et al. |
| 2019/0374528 | A1 | 12/2019 | Gray et al. |
| 2020/0010468 | A1 | 1/2020 | Ji et al. |
| 2020/0078933 | A1 | 3/2020 | Arai |
| 2020/0190105 | A1 | 6/2020 | Cravatt et al. |
| 2020/0347045 | A1 | 11/2020 | Mainolfi et al. |
| 2020/0377469 | A1 | 12/2020 | Mainolfi et al. |
| 2021/0002295 | A1 | 1/2021 | Gray et al. |
| 2021/0002296 | A1 | 1/2021 | Mainolfi et al. |
| 2021/0147382 | A1 | 5/2021 | Bellenie et al. |
| 2021/0228562 | A1 | 7/2021 | Weiss |
| 2021/0238193 | A1 | 8/2021 | Mainolfi et al. |
| 2021/0323952 | A1 | 10/2021 | Mainolfi et al. |
| 2023/0093080 | A1 | 3/2023 | Ji et al. |
| 2023/0115184 | A1 | 4/2023 | Mainolfi et al. |
| 2023/0295180 | A1 | 9/2023 | Mainolfi et al. |

FOREIGN PATENT DOCUMENTS

| | | | |
|---|---|---|---|
| WO | WO-2001042246 | A2 | 6/2001 |
| WO | WO-2002020740 | A2 | 3/2002 |
| WO | WO-2002088112 | A1 | 11/2002 |
| WO | WO-2003063794 | A2 | 8/2003 |
| WO | WO-2004019973 | A1 | 3/2004 |
| WO | WO-2004089925 | A1 | 10/2004 |
| WO | WO-2004106328 | A1 | 12/2004 |
| WO | WO-2005007623 | A2 | 1/2005 |
| WO | WO-2005113554 | A2 | 12/2005 |
| WO | WO-2006029879 | A2 | 3/2006 |
| WO | WO-2006078846 | A1 | 7/2006 |
| WO | WO-2006105021 | A2 | 10/2006 |
| WO | WO-2006122806 | A2 | 11/2006 |
| WO | WO-2007005874 | A2 | 1/2007 |
| WO | WO-2007016176 | A2 | 2/2007 |
| WO | WO-2007044729 | A2 | 4/2007 |
| WO | WO-2007053452 | A1 | 5/2007 |
| WO | WO-2007070514 | A1 | 6/2007 |
| WO | WO-2007084786 | A1 | 7/2007 |
| WO | WO-2007129161 | A2 | 11/2007 |
| WO | WO-2008039218 | A2 | 4/2008 |
| WO | WO-2008109943 | A1 | 9/2008 |
| WO | WO-2008118802 | A1 | 10/2008 |
| WO | WO-2008132601 | A1 | 11/2008 |
| WO | WO-2009009116 | A2 | 1/2009 |
| WO | WO-2009044273 | A2 | 4/2009 |
| WO | WO-2009073620 | A2 | 6/2009 |
| WO | WO-2009114512 | A1 | 9/2009 |
| WO | WO-2009132238 | A3 | 10/2009 |
| WO | WO-2010019570 | A2 | 2/2010 |
| WO | WO-2010077634 | A1 | 7/2010 |
| WO | WO-2011028683 | A1 | 3/2011 |
| WO | WO-2011043371 | A1 | 4/2011 |
| WO | WO-2011056652 | A1 | 5/2011 |
| WO | WO-2011070024 | A1 | 6/2011 |
| WO | WO-2011090760 | A1 | 7/2011 |
| WO | WO-2011107553 | A1 | 9/2011 |
| WO | WO-2011109400 | A2 | 9/2011 |
| WO | WO-2011131407 | A1 | 10/2011 |
| WO | WO-2011140249 | A2 | 11/2011 |
| WO | WO-2012003281 | A3 | 1/2012 |
| WO | WO-2012007375 | A1 | 1/2012 |
| WO | WO-2012032433 | A1 | 3/2012 |
| WO | WO-2012068546 | A1 | 5/2012 |
| WO | WO-2012078559 | A2 | 6/2012 |
| WO | WO-2012084704 | A1 | 6/2012 |
| WO | WO-2012097013 | A1 | 7/2012 |
| WO | WO-2012129258 | | 9/2012 |
| WO | WO-2012142237 | A1 | 10/2012 |
| WO | WO-2012145493 | A1 | 10/2012 |
| WO | WO-2013042137 | A1 | 3/2013 |
| WO | WO-2013066729 | A1 | 5/2013 |
| WO | WO-2013079174 | A1 | 6/2013 |
| WO | WO-2013087699 | A1 | 6/2013 |
| WO | WO-2013106535 | A1 | 7/2013 |
| WO | WO-2013106612 | A1 | 7/2013 |
| WO | WO-2013106614 | A1 | 7/2013 |
| WO | WO-2013106641 | A1 | 7/2013 |
| WO | WO-2013106643 | A2 | 7/2013 |
| WO | WO-2013106646 | A2 | 7/2013 |
| WO | WO-2013119716 | A1 | 8/2013 |
| WO | WO-2013132044 | A1 | 9/2013 |
| WO | WO-2013169264 | A1 | 11/2013 |
| WO | WO-2014008218 | A1 | 1/2014 |
| WO | WO-2014008992 | A1 | 1/2014 |
| WO | WO-2014011902 | A1 | 1/2014 |
| WO | WO-2014011906 | A2 | 1/2014 |
| WO | WO-2014011911 | A2 | 1/2014 |
| WO | WO-2014036357 | A1 | 3/2014 |
| WO | WO-2014044622 | A1 | 3/2014 |
| WO | WO-2014058685 | A1 | 4/2014 |
| WO | WO-2014058691 | A1 | 4/2014 |
| WO | WO-2014063061 | A1 | 4/2014 |
| WO | WO-2014074660 | A1 | 5/2014 |
| WO | WO-2014074675 | A1 | 5/2014 |
| WO | WO-2014108452 | A1 | 7/2014 |
| WO | WO-2014121931 | A1 | 8/2014 |
| WO | WO-2014121942 | A1 | 8/2014 |
| WO | WO-2014142237 | A1 | 9/2014 |
| WO | WO-2014143672 | A1 | 9/2014 |
| WO | WO-2015048281 | A1 | 4/2015 |
| WO | WO-2015068856 | A1 | 5/2015 |
| WO | WO-2015071393 | A1 | 5/2015 |
| WO | WO-2015091426 | A1 | 6/2015 |
| WO | WO-2015100331 | A2 | 7/2015 |
| WO | WO-2015103453 | A1 | 7/2015 |
| WO | WO-2015104662 | A1 | 7/2015 |
| WO | WO-2015104688 | A1 | 7/2015 |
| WO | WO-2015150995 | A1 | 10/2015 |
| WO | WO-2015160845 | A3 | 10/2015 |
| WO | WO-2015164374 | A1 | 10/2015 |
| WO | WO-2015193846 | A1 | 12/2015 |
| WO | WO-2016011390 | A1 | 1/2016 |
| WO | WO-2016053769 | A1 | 4/2016 |
| WO | WO-2016053770 | A1 | 4/2016 |
| WO | WO-2016053771 | A1 | 4/2016 |
| WO | WO-2016053772 | A1 | 4/2016 |
| WO | WO-2016081679 | A1 | 5/2016 |
| WO | WO-2016105518 | A1 | 6/2016 |
| WO | WO-2016118666 | A1 | 7/2016 |
| WO | WO-2016138114 | A1 | 9/2016 |
| WO | WO-2016144844 | A1 | 9/2016 |
| WO | WO-2016144846 | A1 | 9/2016 |
| WO | WO-2016144847 | A1 | 9/2016 |
| WO | WO-2016144848 | A1 | 9/2016 |
| WO | WO-2016144849 | A1 | 9/2016 |
| WO | WO-2016149668 | A1 | 9/2016 |
| WO | WO-2016169989 | A1 | 10/2016 |
| WO | WO-2016172560 | A1 | 10/2016 |
| WO | WO-2016174183 | A1 | 11/2016 |
| WO | WO-2016197032 | A1 | 12/2016 |
| WO | WO-2016197114 | A1 | 12/2016 |
| WO | WO-2016210034 | A1 | 12/2016 |
| WO | WO-2017004133 | A1 | 1/2017 |
| WO | WO-2017004134 | | 1/2017 |
| WO | WO-2017007612 | A1 | 1/2017 |
| WO | WO-2017009798 | A1 | 1/2017 |
| WO | WO-2017009806 | A1 | 1/2017 |
| WO | WO-2017011371 | A1 | 1/2017 |
| WO | WO-2017011590 | A1 | 1/2017 |
| WO | WO-2017024317 | A2 | 2/2017 |
| WO | WO-2017030814 | A1 | 2/2017 |
| WO | WO-2017033093 | A1 | 3/2017 |
| WO | WO-2017049068 | A1 | 3/2017 |
| WO | WO-2017059280 | A1 | 4/2017 |
| WO | WO-2017079267 | A1 | 5/2017 |
| WO | WO-2017108723 | A2 | 6/2017 |
| WO | WO-2017117473 | A1 | 7/2017 |
| WO | WO-2017117474 | A1 | 7/2017 |
| WO | WO-2017127430 | A1 | 7/2017 |
| WO | WO-2017161119 | A1 | 9/2017 |

(56) References Cited

FOREIGN PATENT DOCUMENTS

| | | | |
|---|---|---|---|
| WO | WO-2017176708 | A1 | 10/2017 |
| WO | WO-2017176957 | A1 | 10/2017 |
| WO | WO-2017176958 | A1 | 10/2017 |
| WO | WO-2017197036 | A1 | 11/2017 |
| WO | WO-2017197046 | A1 | 11/2017 |
| WO | WO-2017197051 | A1 | 11/2017 |
| WO | WO-2017197055 | A1 | 11/2017 |
| WO | WO-2017197056 | A1 | 11/2017 |
| WO | WO-2017201449 | A1 | 11/2017 |
| WO | WO-2017205762 | A1 | 11/2017 |
| WO | WO-2017205766 | A1 | 11/2017 |
| WO | WO-2017207385 | A1 | 12/2017 |
| WO | WO-2017211924 | A1 | 12/2017 |
| WO | WO-2018052058 | A1 | 3/2018 |
| WO | WO-2018089736 | A1 | 5/2018 |
| WO | WO-2018098367 | A1 | 5/2018 |
| WO | WO-2018119441 | A1 | 6/2018 |
| WO | WO-2018144649 | A1 | 8/2018 |
| WO | WO-2018209012 | A1 | 11/2018 |
| WO | WO-2018237026 | A1 | 12/2018 |
| WO | WO-2019043214 | A1 | 3/2019 |
| WO | WO-2019060693 | A1 | 3/2019 |
| WO | WO-2019060742 | A1 | 3/2019 |
| WO | WO-2019084026 | A1 | 5/2019 |
| WO | WO-2019084030 | A1 | 5/2019 |
| WO | WO-2019099868 | A1 | 5/2019 |
| WO | WO-2019099926 | A1 | 5/2019 |
| WO | WO-2019133531 | A1 | 7/2019 |
| WO | WO-2019140380 | A1 | 7/2019 |
| WO | WO-2019140387 | A1 | 7/2019 |
| WO | WO-2019152437 | A1 | 8/2019 |
| WO | WO-2019160915 | A1 | 8/2019 |
| WO | WO-2019165229 | A1 | 8/2019 |
| WO | WO-2019195201 | A1 | 10/2019 |
| WO | WO-2019213005 | A1 | 11/2019 |
| WO | WO-2019236483 | | 12/2019 |
| WO | WO-2020010177 | A1 | 1/2020 |
| WO | WO-2020010210 | A1 | 1/2020 |
| WO | WO-2020010227 | A1 | 1/2020 |
| WO | WO-2020018788 | A1 | 1/2020 |
| WO | WO-2020038378 | A1 | 2/2020 |
| WO | WO-2020078933 | A1 | 4/2020 |
| WO | WO-2020113233 | A1 | 6/2020 |
| WO | WO-2020160100 | A1 | 8/2020 |
| WO | WO-2020251969 | A1 | 12/2020 |
| WO | WO-2020251971 | A1 | 12/2020 |
| WO | WO-2020251972 | A1 | 12/2020 |
| WO | WO-2020251974 | A1 | 12/2020 |
| WO | WO-2020264490 | A1 | 12/2020 |
| WO | WO-2020264499 | A1 | 12/2020 |
| WO | WO-2021011631 | A1 | 1/2021 |
| WO | WO-2021011634 | A1 | 1/2021 |
| WO | WO-2021011868 | A1 | 1/2021 |
| WO | WO-2021011871 | A1 | 1/2021 |
| WO | WO-2021053555 | A1 | 3/2021 |
| WO | WO-2021067606 | A1 | 4/2021 |
| WO | WO-2021083949 | A1 | 5/2021 |
| WO | WO-2021086785 | A1 | 5/2021 |
| WO | WO-2021119159 | A1 | 6/2021 |
| WO | WO-2021127190 | A1 | 6/2021 |
| WO | WO-2021127278 | A1 | 6/2021 |
| WO | WO-2021127283 | A2 | 6/2021 |
| WO | WO-2021142247 | A1 | 7/2021 |
| WO | WO-2021207291 | A1 | 10/2021 |
| WO | WO-2021252666 | A1 | 12/2021 |
| WO | WO-2022029617 | A1 | 2/2022 |
| WO | WO2023192578 | A1 | 10/2023 |
| WO | WO2024092009 | A1 | 5/2024 |

OTHER PUBLICATIONS

Boehm et al., "Bromodomain Proteins in HIV Infection," Viruses. 2013;5:1571.

Boichenko et al., "A FRET-Based Assay for the Identification and Characterization of Cereblon Ligands," J Med Chem. 2016;59(2):770-4.

CAS STN Abstract, RN 1787975-60-3 (Pub. Jun. 24, 2015).

CAS STN Abstract, RN 1795294-81-3 (Pub. Jul. 6, 2015).

CAS STN Abstract, RN 1795451-20-5 (Pub. Jul. 6, 2015).

CAS STN Abstract, RN 1795527-49-9 (Pub. Jul. 6, 2015).

CAS STN Abstract, RN 1871221-08-7 (Pub. Feb. 21, 2016).

CAS STN Abstract, RN 1878956-45-6 (Pub. Mar. 3, 2016).

CAS STN Abstract, RN 1878983-55-1 (Pub. Mar. 3, 2016).

CAS STN Abstract, RN 742039-47-0 (Pub. Sep. 10, 2004).

CAS STN Abstract, RN 779303-42-3 (Pub. Nov. 12, 2004).

Chang et al., "What is the functional role of the thalidomide binding protein cereblon?" Int J Biochem Mol Biol. 2011;2(3):287-94.

Charrier et al., "Desulfonylative radical ring closure onto aromatics. A modular route to benzazepin-2-ones and 5-arylpiperidin-2-ones," Org Lett. 2012;14(8):2018-21.

Charrier et al., "Desulfonylative Radical Ring Closure onto Aromatics. A Modular Route to Benzazepin-2-ones and 5-Arylpiperidin-2-ones," Org. Lett. 2012, 14(8): 2018-2021.

Chou and Talalay, "Quantitative analysis of dose-effect relationships: the combined effects of multiple drugs or enzyme inhibitors," Adv Enzyme Regul. 1984;22:27-55.

Connolly et al., "Complexities of TGF-beta Targeted Cancer Therapy," Int J Biol Sci. 2012;8(7):964-978.

Contino-Pepin et al., "Preliminary biological evaluations of new thalidomide analogues for multiple sclerosis application," Bioorg Med Chem Lett. 2009;19(3):878-81.

Crews, "Targeting the Undruggable Proteome: The Small Molecules of My Dreams," Chem Biol. 2010;17(6):551-5.

Cruickshank et al., "SWI/SNF Subunits SMARCA4, SMARCD2 and DPF2 Collaborate in MLL- Rearranged Leukaemia Maintenance," PLoS One. 2015;10(11): e0142806

Deshaies and Joazeiro, "RING domain E3 ubiquitin ligases," Annu Rev Biochem. 2009;78:399-434.

Devi et al., "Medicinal Attributes of Imidazo[1,2-a]pyridine Derivatives: An Update," Curr Top Med Chem, 2016, 16(26):2963-2994.

Dinarello, "IL-1: Discoveries, controversies and future directions," Eur J Immunol. 2010:40(3):599-606.

El-Gamal et al., "Recent Advances of Colony-Stimulating Factor-1 Receptor (CSF-1R) Kinase and Its Inhibitors," J Med Chem. 2018;61(13):5450-5466.

Filippakopoulos et al., "Histone recognition and large-scale structural analysis of the human bromodomain family," Cell. 2012;149(1):214-31.

Fischer et al., "Structure of the DDB1-CRBN E3 ubiquitin ligase in complex with thalidomide," Nature. 2014;512(7512):49-53.

Fisher et al., "The complexities inherent in attempts to decrease drug clearance by blocking sites of CYP-mediated metabolism," Curr Opin Drug Discov Devel. 2006;9(1):101-9.

Foster, "Deuterium isotope effects in the metabolism of drugs and xenobiotics: implications for drug design," Advances in Drug Research. 1985;14:1-40.

Fukuto et al., "Determination of the mechanism of demethylenation of (methylenedioxy)phenyl compounds by cytochrome P450 using deuterium isotope effects," J Med Chem. 1991;34(9):2871-6.

Gerstenberger et al., "Identification of a Chemical Probe for Family VIII Bromodomains through Optimization of a Fragment Hit," J Med Chem. 2016;59(10):4800-11.

Hagner et al., "CC-122, a pleiotropic pathway modifier, mimics an interferon response and has antitumor activity in DLBCL," Blood. 2015; 126(6):779-89.

Heightman et al., "Structure-Activity and Structure-Conformation Relationships of Aryl Propionic Acid Inhibitors of the Kelch-like ECH-Associated Protein 1/Nuclear Factor Erythroid 2-Related Factor 2 (KEAP1/NRF2) Protein-Protein Interaction," J. Med. Chem., 2019, 62(9): 4683-4702.

Hines et al., "MDM2-Recruiting PROTAC Offers Superior, Synergistic Antiproliferative Activity via Simultaneous Degradation of BRD4 and Stabilization of p53," Cancer Res. 2019;79(1):251-262.

Hoffman et al., "Functional epigenetics approach identifies BRM/SMARCA2 as a critical synthetic lethal target in BRG1-deficient cancers," Proc Natl Acad Sci U S A. 2014;111(8):3128-33.

(56) References Cited

OTHER PUBLICATIONS

Hohmann and Vakoc, "A rationale to target the SWI/SNF complex for cancer therapy," Trends Genet. 2014;30(8): 356-363.
Iconomou and Saunders, "Systematic approaches to identify E3 ligase substrates," Biochem J. 2016;473(22):4083-4101.
Ito et al., "Identification of a primary target of thalidomide teratogenicity," Science. 2010;327(5971):1345-50.
Jeanmougin et al., "The bromodomain revisited," Trends Biochem Sci. 1997;22(5):151-3.
Kadoch and Crabtree "Mammalian SWI/SNF chromatin remodeling complexes and cancer: Mechanistic insights gained from human genomics," Sci Adv. 2015;1(5):e1500447.
Kester et al., "Optimization of Benzodiazepinones as Selective Inhibitors of the X-Linked Inhibitor of Apoptosis Protein (XIAP) Second Baculovirus IAP Repeat (BIR2) Domain," J Med Chem. 2013;56(20):7788-803.
Koga et al., "Involvement of SMARCA2/BRM in the SWI/SNF chromatin-remodeling complex in schizophrenia," Hum Mol Genet. 2009;18(13):2483-94.
Kosho et al., "Genotype-phenotype correlation of Coffin-Siris syndrome caused by mutations in SMARCB1, SMARCA4, SMARCE1, and ARID1A," Am. J. Med. Genet. 2014;166(3):262.
Krönke et al., "Lenalidomide causes selective degradation of IKZF1 and IKZF3 in multiple myeloma cells" Science. 2014;343(6168):301-305.
Kushner et al., "Pharmacological uses and perspectives of heavy water and deuterated compounds," Can J Physiol Pharmacol. 1999;77(2):79-88.
Li et al., "Genome-wide and functional annotation of human E3 ubiquitin ligases identifies MULAN, a mitochondrial E3 that regulates the organelle's dynamics and signaling," PLoS One. 2008;3(1):e1487.
Lu et al., "Discovery of a Keap1-dependent peptide PROTAC to knockdown Tau by ubiquitination-proteasome degradation pathway," Euro J Med Chem. 2018;46:251-9.
Lu et al., "Hijacking the E3 Ubiquitin Ligase Cereblon to Efficiently Target BRD4," Chem Biol. 2015;2(6):755-63.
Lu et al., "Identification of small molecule inhibitors targeting the SMARCA2 bromodomain from a high-throughput screening assay," Acta Pharmacol Sin. 2018;39(9): 1544-1552.
Lu et al., "The myeloma drug lenalidomide promotes the cereblon-dependent destruction of Ikaros proteins," Science. 2014;343(6168):305-309.
Mao et al., "Bioinformatic Analysis of Coronary Disease Associated SNPs and Genes to Identify Proteins Potentially Involved in the Pathogenesis of Atherosclerosis," J Proteom Genom Res. 2017;(1):1-12.
Matyskiela et al., "A Cereblon Modulator (CC-220) with Improved Degradation of Ikaros and Aiolos," J Med Chem. 2018;61(2):535-542.
Medina et al. "Genetic and epigenetic screening for gene alterations of the chromatin-remodeling factor, SMARCA4/BRG1, in lung tumors," Genes Chromosomes Cancer. 2004;41(2):170-7.
Muller et al., "Amino-Substituted Thalidomide Analogs: Potent Inhibitors of TNF-? Production," Bioorg Med Chem Lett. 1999;9(11):1625-30.
Muller et al., "Bromodomains as therapeutic targets," Expert Rev Mol Med. 2011;13:e29.
Ohoka et al., "In Vivo Knockdown of Pathogenic Proteins via Specific and Nongenetic Inhibitor of Apoptosis Protein (IAP)-dependent Protein Erasers (SNIPERs)," J Bio Chem. 2017;292(11):4556-4570.
Ohoka et al., "Development of Small Molecule Chimeras That Recruit AhR E3 Ligase to Target Proteins,"ACS Chem. Biol. 2019, 14(12):2822-2832.
Oike et al., "A synthetic lethality-based strategy to treat cancers harboring a genetic deficiency in the chromatin remodeling factor BRG1," Cancer Res. 2013; 73(17):5508-18.
Okazaki et al., "A rheostat for immune responses: the unique properties of PD-1 and their advantages for clinical application," Nat. Immunol. 2013; 14(12): 1212-1218.
Pandey et al., "SMARCA2 and THAP11: potential candidates for polyglutamine disorders as evidenced from polymorphism and protein-folding simulation studies," J. Hum. Genet. 2004;49:596-602.
Papillon et al., "Discovery of Orally Active Inhibitors of Brahma Homolog (BRM/SMARCA2 ATPase Activity for the Treatment of Brahman Related Gene 1 (BRG1/SMARCA4-Mutant Cancers," J. Med. Chem. 2018,61:10155-10172.
PCT International Preliminary Report on Patentability from PCT/US2018/067304, dated Jun. 30, 2020.
PCT International Preliminary Report on Patentability from PCT/US2019/040462, dated Jan. 21, 2021.
PCT International Search Report and Written Opinion from PCT/US2018/052181, dated Feb. 26, 2019.
PCT International Search Report and Written Opinion from PCT/US2018/052242, dated Jan. 30, 2019.
PCT International Search Report and Written Opinion from PCT/US2018/067304, dated Apr. 30, 2019.
PCT International Search Report and Written Opinion from PCT/US2019/013481, dated Mar. 15, 2019.
PCT International Search Report and Written Opinion from PCT/US2019/013491, dated Mar. 18, 2019.
PCT International Search Report and Written Opinion from PCT/US2019/040462, dated Sep. 20, 2019.
PCT International Search Report and Written Opinion from PCT/US2019/040520, dated Nov. 13, 2019.
PCT International Search Report and Written Opinion from PCT/US2019/040545, dated Oct. 21, 2019.
PCT International Search Report and Written Opinion from PCT/US2019/064070, dated Apr. 6, 2020.
PCT International Search Report and Written Opinion from PCT/US2020/026869, dated Jul. 27, 2020.
PCT International Search Report and Written Opinion from PCT/US2020/036913, dated Oct. 26, 2020.
PCT International Search Report and Written Opinion from PCT/US2020/036916, dated Oct. 26, 2020.
PCT International Search Report and Written Opinion from PCT/US2020/036918, dated Oct. 26, 2020.
PCT International Search Report and Written Opinion from PCT/US2020/036921, dated Oct. 26, 2020.
PCT International Search Report and Written Opinion from PCT/US2020/040101, dated Nov. 10, 2020.
PCT International Search Report and Written Opinion from PCT/US2020/040125, dated Nov. 13, 2020.
PCT International Search Report and Written Opinion from PCT/US2020/042105, dated Nov. 20, 2020.
PCT International Search Report and Written Opinion from PCT/US2020/042109, dated Dec. 10, 2020.
PCT International Search Report and Written Opinion from PCT/US2020/042530, dated Oct. 16, 2020.
PCT International Search Report and Written Opinion from PCT/US2020/042534, dated Oct. 26, 2020.
PCT International Search Report and Written Opinion from PCT/US2020/064061, dated Apr. 9, 2021.
PCT International Search Report and Written Opinion from PCT/US2020/065628, dated May 28, 2021.
PCT International Search Report and Written Opinion from PCT/US2020/065752, dated Mar. 25, 2021.
PCT International Search Report and Written Opinion from PCT/US2020/065757, dated May 28, 2021.
PCT International Search Report and Written Opinion from PCT/US2020/066859, dated May 4, 2021.
PCT International Search Report and Written Opinion from PCT/US2020/066864 dated Apr. 12, 2021.
PCT International Search Report and Written Opinion from PCT/US2021/062640, dated Feb. 8, 2022.
PCT International Search Report and Written Opinion from PCT/US2021/062656 dated Mar. 22, 2022.
PCT International Search Report and Written Opinion from PCT/US2021/062662 dated Jan. 27, 2022.

(56) References Cited

OTHER PUBLICATIONS

PCT International Search Report and Written Opinion from PCT/US2023/060645, dated Mar. 31, 2023.
PCT International Search Report from PCT/US2021/035745 dated Sep. 27, 2021.
PCT International Search Report from PCT/US2021/035747 dated Sep. 27, 2021.
PCT International Search Report from PCT/US2022/070662 dated Apr. 18, 2022.
PCT International Search Report from PCT/US2022/070664 dated May 3, 2022.
Piya et al., "BRD4 Proteolysis Targeting Chimera (PROTAC) Leads to Sustained Degradation of BRD4 with Broad Activity Against Acute Leukemias and Overcomes Stroma Mediated Resistance By Modulating Surface Expression of CXCR4," Blood. 2016;126(23): 675-676.
Prinjha et al., "Place your BETs: the therapeutic potential of bromodomains," Trends Pharmacol Sci. 2012;33(3):146-53.
Priyadarshini et al., "Copper catalyzed oxidative cross-coupling of aromatic amines with 2-pyrrolidinone: a facile synthesis of N-aryl-r-amino-r-lactams," Tetrahedron. 2014;70(36):6068-6074.
Pubmed Compound Summary for CID 101524675, "(2R)-3-Fluoro-2-(2-methylpropyl)-3-phenyl-1,3-azasilinan-6-one," *U.S. National Library of Medicine*, created Dec. 18, 2015, https://pubchem.ncbi.nlm.nih.gov/compound/101524675. Date Accessed: Sep. 5, 2019 (5 pages).
Pubmed Compound Summary for CID 102164987, "3-[(4S)-2,5-Dioxo-4-phenylimidazolidine-1-yl]-2,6-piperidinedione," U.S. National Library of Medicine, created Dec. 24, 2015, https://pubchem.ncbi.nlm.nih.gov/compound/102164987. Date Accessed: Feb. 25, 2020 (7 pages).
Pubmed Compound Summary for CID 110491408, 3-(5-Amino-2-oxo-3H-benzimidazol-1-yl)piperidine-2,6-dione, *U.S. Library of Medicine*, created Jan. 18, 2016, https://pubchem.ncbi.nlm.nih.gov/compound/110491408. Date Accessed: Feb. 25, 2020 (7 pages).
Pubmed Compound Summary for CID 110491555, 3-(6-Amino-2-oxo-3H-benzimidazol-1-yl)piperidine-2,6-dione, U.S. Library of Medicine, created Jan. 18, 2016, https://pubchem.ncbi.nlm.nih.gov/compound/110491555. Date Accessed: Feb. 25, 2020 (7 pages).
Pubmed Compound Summary for CID 115370667, "5-(2-Oxoimidazolidin-1-yl)piperidin-2-one." U.S. National Library of Medicine, created Oct. 22, 2012, https://pubchem.ncbi.nlm.nih.gov/compound/115370667. Date Accessed: Feb. 25, 2020 (10 pages).
Pubmed Compound Summary for CID 138728787, "3-(6-Ethylpyrido[2,3-b]indol-9-yl)piperidine-2,6-dione," U.S. National Library of Medicine, created Jul. 20, 2019, https://pubchem.ncbi.nlm.nih.gov/compound/138728787. Date Accessed: Sep. 5, 2019 (6 pages).
Pubmed Compound Summary for CID 17607528, "4-(Carbazol-9-ylmethyl)-1,3-oxazolidin-2-one," U.S. National Library of Medicine, Nov. 13, 2007, https://pubchem.ncbi.nlm.nih.gov/compound/17607528. Date Accessed: Feb. 25, 2020 (6 pages).
Pubmed Compound Summary for CID 5426, "Thalidomide," created Mar. 25, 2005.
Pubmed Compound Summary for CID 63661260, "5-[2-(1-Chloroethyl)benzimidazol-1-yl]piperidin-2-one," U.S. National Library of Medicine, created Oct. 22, 2012, https://pubchem.ncbi.nlm.nih.gov/compound/63661260. Date Accessed: Sep. 4, 2019 (6 pages).
Pubmed Compound Summary for CID 63661460, "6-Oxo-1-(6-oxopiperidin-3-yl)piperidine-3-carboxylic acid," U.S. National Library of Medicine, created Oct. 22, 2012, https://pubchem.ncbi.nlm.nih.gov/compound/63661460. Date Accessed: Feb. 25, 2020 (7 pages).
Pubmed Compound Summary for CID 65967733, "3-(2,5-Dioxo-3-phenylpyrrolidin-1-yl)piperidine-2,6-dione," *U.S. National Library of Medicine*, created Dec. 24, 2015, https://pubchem.ncbi.nlm.nih.gov/compound/65967733. Date Accessed: Feb. 25, 2020 (7 pages).
Pubmed Compound Summary for CID 65968760, "1-(2,6-Dioxopiperidin-3-yl)benzimidazole-5-carboxylic acid," U.S. National Library of Medicine, created Oct. 24, 2012, https://pubchem.ncbi.nlm.nih.gov/compound/65968760. Date Accessed: Sep. 4, 2019 (6 pages).
Pubmed Compound Summary for CID 67258040, "[1-(9H-Fluoren-9-yl)-1-(6-oxopiperidin-3-yl) ethyl] hydrogen carbonate," *U.S. National Library of Medicine*, Nov. 30, 2012, https://pubchem.ncbi.nlm.nih.gov/compound/67258040. Date Accessed: Feb. 25, 2020 (9 pages).
Pubmed Compound Summary for CID 83543479, "5(Aminomethyl)-5-(1H-indol-3-yl)piperidin-2-one," *U.S. National Library of Medicine*, created Oct. 20, 2014, https://pubchem.ncbi.nlm.nih.gov/compound/83543479. Date Accessed: Feb. 25, 2020 (6 pages).
Pubmed Compound Summary for CID 84036945, 1-Piperidin-3-yl-3H-indol-2-one, *U.S. Library of Medicine*, created Oct. 20, 2014, https://pubchem.ncbi.nlm.nih.gov/compound/84036945. Date Accessed: Feb. 25, 2020 (7 pages).
Pubmed Compound Summary for CID 86793742, 3-[(6-chloro-1H-1,3-benzodiazol-2-yl)sulfanyl]piperidine-2,6-dione, created Feb. 7, 2015, https://pubchem.ncbi.nlm.nih.gov/compound/86793742. Date Accessed: Jan. 10, 2022.
Pubmed Compound Summary for CID 91648396, 3-[(4-Fluorophenyl)sulfanyl]piperidine-2,6-dione, created Mar. 20, 2015, https://pubchem.ncbi.nlm.nih.gov/compound/91648396#section=Structures. Date Accessed: Jan. 10, 2022.
Pubmed Compound Summary for CID 99784232, (3S)-3-(4-fluorophenyl)sulfanylpiperidine-2,6-dione, created Dec. 11, 2015, https://pubchem.ncbi.nlm.nih.gov/compound/99784232. Date Accessed: Jan. 10, 2022.
Raina et al., "Chemical Inducers of Targeted Protein Degradation," J Biol Chem. 2010;285(15):11057-60.
Ramirez et al., "Defining causative factors contributing in the activation of hedgehog signaling in diffuse large B-cell lymphoma," Leuk. Res. 2012;36(10):1267-73.
Rokosz et al., "Kinase inhibitors as drugs for chronic inflammatory and immunological diseases: progress and challenges," Expert Opin Ther Targets. 2008; 12(7):883-903.
Ronnebaum et al., "Synthesis of 1, 2, 3-triazole 'click' analogues of thalidomide," Tetrahedron. 2016;72(40): 6136-6141.
Ross et al., "Bispecific T cell engager (BITE®) antibody constructs can mediate bystander tumor cell killing," PLoS One. 2017; 12(8): e0183390.
Rostovtsev et al., "A Stepwise Huisgen Cycloaddition Process: Copper(I)-Catalyzed Regioselective "Ligation" of Azides and Terminal Alkynes," Angew Chem Int Ed Engl. 2002;41(14):2596-9.
Rusnac et al., "Recognition of the Diglycine C-End Degron by CRL2 KLHDC2 Ubiquitin Ligase," Mol. Cell. 2018, 72(5):813-822.e4.
Schiaffino-Ortega et al. "SWI/SNF as targets in cancer therapy," J. Hematol. Oncol. 2014;7:81.
Schneekloth and Crews, "Chemical Approaches to Controlling Intracellular Protein Degradation," Chembiochem. 2005;6(1): 40-46.
Schnnekloth et al., "Chemical approaches to controlling intracellular protein degradation," Chembiochem. 2005;6(1):40-46.
Seela et al., "Pyrazolo[3,4-d][1,2,3]triazine DNA:? Synthesis and Base Pairing of 7-Deaza-2,8-diaza-2'-deoxyadenosine," J. Org. Chem. 2004;69(14) 4695-4700.
Seitz et al., "Sulfenylation and Halogenation of Di-and Trianions Derived from Substituted Glutarimides," Synthetic Communications. 1977;7(6):367-374.
Sen et al., "Transcriptional signaling by double-stranded RNA: role of TLR3," Cytokine Growth Factor Rev. 2005;16(1):1-14.
Shain and Pollack "The Spectrum of SWI/SNF Mutations, Ubiquitous in Human Cancers," PLoS One 2013;8:e55119.
Shanmugasundaram et al., "A modular PROTAC design for target destruction using a degradation signal based on a single amino acid," J Biol Chem. 2019;294(41):15172-15175.
Son and Crabtree "The Role of BAF (mSWI/SNF) Complexes in Mammalian Neural Development," Am. J. Med. Genet., Part C. 2014; 166C(3):333-39.
Spradin et al., "Harnessing the Anti-Cancer Natural Product Nimbolide for Targeted Protein Degradation," bioRxiv.org, https://www.biorxiv.org/content/biorxiv/early/2019/04/09/436998.full.pdf. Date Accessed, Oct. 3, 2019.

(56) References Cited

OTHER PUBLICATIONS

Spratt et al., "RBR E3 ubiquitin ligases: new structures, new insights, new question," Biochem J. 2014;458(3);421-37.
Stewart et al., "Efforts toward elucidating Thalidomide's molecular target: an expedient synthesis of the first Thalidomide biotin analogue," Organic & Biomolecular Chemistry. 2010;8(18): 4059-4062.
Struhl, "Histone acetylation and transcriptional regulatory mechanisms," Genes Dev. 1998;12(5):599-606.
Sun et al., "Carbohydrate and protein immobilization onto solid surfaces by sequential Diels-Alder and azide-alkyne cycloadditions," Bioconjug Chem. 2006;17(1):52-7.
Sutherell et al. "Identification and Development of 2,3-Dihydropyrrolo[1,2-a]quinazolin-5(1H)-one Inhibitors Targeting Bromodomains within the Switch/Sucrose Nonfermenting Complex," J. Med. Chem. 2016;59:5095-5101.
Tamkun et al., "brahma: a regulator of *Drosophila* homeotic genes structurally related to the yeast transcriptional activator SNF2/SWI2," Cell. 1992;68(3):561-72.
Tanaka et al. "Design and Characterization of Bivalent BET Inhibitors," Nat. Chem. Biol. 2016;12(12):1089-1096.
Tang et al., "New SMARCA2 mutation in a patient with Nicolaides-Baraitser syndrome and myoclonic astatic epilepsy," Am. J. Med. Genet. 2015;173(1):195-199.
Theodoulou et al. "Clinical progress and pharmacology of small molecule bromodomain inhibitors," Curr. Opin. Chem. Bio. 2016;33:58-66.
Tian, "Detection of differentially expressed genes involved in osteoarthritis pathology," J. Orthop. Surg. Res. 2018;13:49.
Tong et al., "Targeted Protein Degradation via a Covalent Reversible Degrader Based on Bardoxolone", ChemRxiv. First Posted Online: Apr. 2, 2020.
Toogood, "Small molecule immuno-oncology therapeutic agents," Bioorg. Med. Chem. Lett. 2018;28(3):319-329.
Toure and Crews, "Small-Molecule PROTACS: New Approaches to Protein Degradation," Angew Chem Int Ed Engl. 2016;55(6):1966-73.
Uehara et al., "Selective degradation of splicing factor CAPER? by anticancer sulfonamides," Nat Chem Biol. 2017;13(6):675-680.
Vangamudi et al., "The SMARCA2/4 ATPase domain surpasses the bromodomain as a drug target in SWI/SNF mutant cancers: Insights from cDNA rescue and PFI-3 inhibitor studies," Cancer Res. 2015;75(18):3865-3878.
Varfolomeev et al., "IAP antagonists induce autoubiquitination of c-IAPs, NF-kappaB activation, and TNFalpha-dependent apoptosis," Cell. 2007;131(4):669-81.
Wang et al., "Palladium-Catalyzed Allenylation/Intramolecular Diels-Alder Reaction of Furans with Propargyl Carboxylates for the Synthesis of Polycyclic Compounds," European Journal of Organic Chemistry. 2014;2014(17):3556-3560.
Wang et al., "Roles of F-box proteins in cancer," Nat Rev Cancer. 2014;14(4):233-47.
Wanior et al., "Pan-SMARCA/PB1 Bromodomain Inhibitors and Their Role in Regulating Adipogenesis," J Med Chem. 2020;63(23):14680-14699.
Ward et al., "Covalent Ligand Screening Uncovers a RNF4 E3 Ligase Recruiter for Targeted Protein Degradation Applications," *bioRxiv.org*, https://www.biorxiv.org/content/biorxiv/early/2018/11/16/439125.full.pdf. Date Accessed, Oct. 3, 2019 (24 pages).
Wilson and Roberts, "SWI/SNF Nucleosome Remodellers and Cancer," Nat. Rev. Cancer. 2011;11(7):481-92.
Winter et al., "Selective Target Protein Degradation via Phthalimide Conjugation," Science. 2015;348(6241):1376-1381.
Xia and Chen, "Iron-catalyzed N-alkylation of azoles via cleavage of an sp3 C-H bond adjacent to a nitrogen atom," J Org Chem. 2012;77(20):9366-73.
Yang et al., "Exploiting synthetic lethality for the therapy of ABC diffuse large B cell lymphoma," Cancer Cell. 2012;21(6):723-37.
Zhang et al., "Electrophilic PROTACs that degrade nuclear proteins by engaging DCAF16," *bioRxiv.org*, https://www.biorxiv.org/content/biorxiv/early/2018/10/15/443804.full.pdf. Date Accessed, Oct. 3, 2019.
Zhou et al., "Targets of curcumin," Curr Drug Targets. 2011;12(3): 332-347.
Zinc 170596280, Date Added Aug. 8, 2015, https://zinc.docking.org/substances/ZINC000170596280/. Date Accessed: Jan. 10, 2022.
Zou et al., "PD-L1 (B7-H1) and PD-1 pathway blockage for cancer therapy: Mechanisms, response biomarkers, and combinations," Sci Transl. Med. 2016;8(328):328rv4.
Balasubramanian et al., "Abstract 3646: Novel IRAK-4 inhibitors exhibit highly potent antiproliferative activity in DLBCL cell lines with activating MYD88 L265P mutation", AACR 106th Annual Meeting, 2015, 75(15), 2 pages.
Buckley et al., "IRAK-4 inhibitors. Part I: a series of amides", Bioorg Med Chem Lett., 2008, 18(11):3211-3214.
Buckley et al., "IRAK-4 inhibitors. Part II: a structure-based assessment of imidazo[1,2-a]pyridine binding", Bioorg Med Chem Lett., 2008, 18(11):3291-3295.
Buckley et al., "IRAK-4 inhibitors. Part Ill: A series of imidazo[1,2-a]pyridines", Bioorg Med Chem Lett., 2008, 18(12):3656-3660.
Cameron et al., "Loss of Interleukin Receptor-Associated Kinase 4 Signaling Suppresses Amyloid Pathology and Alters Microglial Phenotype in a Mouse Model of Alzheimer's Disease", J Neurosci., 2012, 32(43):15112-15123.
Cario, "Therapeutic Impact of Toll-like Receptors on Inflammatory Bowel Diseases: A Multiple-edged Sword", Inflamm Bowel Dis., 2008, 14(3):411-421.
Chaudhary et al., "Recent Advances in the Discovery of Small Molecule Inhibitors of Interleukin-1 Receptor-Associated Kinase 4 (IRAK4) as a Therapeutic Target for Inflammation and Oncology Disorders", J Med Chem., 2015, 58(1):96-110.
Chiang et al., "Immune Complex-Mediated Cell Activation from Systemic Lupus Erythematosus and Rheumatoid Arthritis Patients Elaborate Different Requirements for IRAK1/4 Kinase Activity across human Cell Types", J lmmunol., 2011, 186(2):1279-1288.
Cohen et al., "Targeting protein kinases for the development of anti-inflammatory drugs", Curr Opin Cell Biol., 2009, 21(2):17-24.
Cushing et al., "IRAK 4 kinase controls Toll-like receptor induced inflammation through the transcription factor IRF5 in primary human monocytes", J Biol Chem., 2017, 292(45):18689-18698.
Dalbeth et al., "Hyperuricaemia and gout: state of the art and future perspectives", Ann Rheum Dis., 2014, 73(9):1598-1600.
Degorce et al., "Optimization of permeability in a series of pyrrolotriazine inhibitors of IRAK4", Bioorg Med Chem., 2018, 26(4): 913-924.
Dinarello, "Interleukin 1 and interleukin 18 as mediators of inflammation and the aging process", Am J Clin Nutr., 2006, 83(suppl):447S-455S.
Dinarello, "lnterleukin-18 and the Pathogenesis of Inflammatory Diseases", Semin Nephrol., 2007, 27(1):98-114.
Dudhgaonkar et al., "Selective IRAK4 Inhibition Attenuates Disease in Murine Lupus Models and Demonstrates Steroid Sparing Activity", J Immunol., 2017, 198(3):1308-1319.
Dunne et al., "IRAK1 and IRAK4 Promote Phosphorylation, Ubiquitation, and Degradation of MyD88 Adaptor-like (Mal)", J Biol Chem., 2010, 285(24):18276-18282.
Flannery et al., "The interleukin-1 receptor-associated kinases: Critical regulators of innate immune signaling", Biochem Pharmacol., 2010, 80(12):1981-1991.
Gearing, "Targeting toll-like receptors for drug development: a summary of commercial approaches", Immunol Cell Biol., 2007, 85(6):490-494.
Geyer et al., "Actual status of antiinterleukin-1 therapies in rheumatic diseases", Curr Opin Rheumatol, 2010, 22(3):246-251.
Gottipati et al., "IRAK1: A critical signaling mediator of innate immunity", Cell Signal, 2008, 20(2):269-276.
Hennessy et al., "Targeting Toll-like receptors: emerging therapeutics?", Nat Rev Drug Discov., 2010, 9(4):293-307.
Hoffman et al., "Efficacy and Safety of Rilonacept (Interleukin-1 Trap) in Patients with Cryopyrin-Associated Periodic Syndromes", Arthritis Rheum., 2008, 58(8):2443-2445.

(56) References Cited

OTHER PUBLICATIONS

Iannello et al., "Role of Interleukin-18 in the Development and Pathogenesis of AIDS", AIDS Rev., 2009, 11(3):115-125.
Iriyama et al., "Clinical significance of genetic mutations of CD79B, CARD11, MYD88, and EZH2 genes in diffuse large B-cell lymphoma patients", Blood, 2011, 118(21), 6 pages.
Kargbo, "Protac Degradation of IRAK4 for the Treatment of Cancer", ACS Med. Chem. Lett., 2019, 10(10):1370-1371.
Kelly et al., "Selective interleukin-1 receptor-associated kinase 4 inhibitors for the treatment of autoimmune disorders and lymphoid malignancy", J Exp Med., 2015, 212(13):2189-2201.
Kim et al., "A critical role for IRAK4 kinase activity in Toll-like receptor-mediated innate immunity", J Exp Med., 2007, 204(5):1025-1036.
Kondo et al., "Renoprotective effects of novel interleukin-1 receptor-associated kinase 4 inhibitor AS2444697 through anti-inflammatory action in 5/6 nephrectomized rats", Naunyn Schmiedebergs Arch Pharmacol., 2014, 387(10):909-919.
Kou et al., "Effects of RuPeng15 Powder (RPP15) on Monosodium Urate Crystal-Induced Gouty Arthritis in Rats", Evid Based Complement Alternat Med., 2015, 2015(527019), 8 pages.
Koziczak-Holbro et al., "IRAK-4 Kinase Activity Is Required for Interleukin-1 (IL-1) Receptor- and Toll-like Receptor 7-mediated Signaling and Gene Expression", J Biol Chem., 2007, 282(18):13552-13560.
Ku et al., "Selective predisposition to bacterial infections in IRAK-4-deficient children: IRAK-4-dependent TLRs are otherwise redundant in protective immunity", J Exp Med., 2007, 204(10):2407-2422.
Kubo-Murai et al., "IRAK-4-dependent Degradation of IRAK-1 is a Negative Feedback Signal for TLR-mediated NF-kappaB Activation", J Biochem., 2008, 143(3):295-302.
Küppers, "IRAK inhibition to shut down TLR signaling in autoimmunity and MyD88-dependent lymphomas", J Exp Med., 2015, 212(13):2184.
Lebakken et al., "A Fluorescence Lifetime Based Binding Assay to Characterize Kinase Inhibitors", J Biomol Screen., 2007, 12(6):828-841.
Lee et al., "Discovery of Clinical Candidate 1-{[2S,3S,4S)-3-ethyl-4-fluoro-5-oxopyrrolidin-2-yl]methoxy}-7-methoxyisoquinoine-6-carboxamide (PF-06650833), a Potent, Selective Inhibitor of Interleukin-1 Receptor Associated Kinase 4 9IRAK4), by Fragment-Based Drug Design", J Med Chem., 2017, 60(13):5521-5542.
Li et al., "IRAK-4: A novel member of the IRAK family with the properties of an IRAK-kinase", Proc Natl Acad Sci USA., 2002, 99(8):5567-5572.
Li et al., "Targeting interleukin-1 receptor-associated kinase for human hepatocellular carcinoma", J Exp Clin Cancer Res., 2016, 35(1):140.
Li, "IRAK4 in TLR/IL-1R signaling: Possible clinical applications", Eur J Immunol., 2008, 38(3):614-618.
Lim et al., "Discovery of 5-Amino-N-(1H-pyrazol-4-yl)pyrazolo[1,5-a]pyrimidine-3-carboxamide Inhibitors of IRAK4", ACS Med Chem Lett., 2015, 6(6):683-688.
Lin et al., "Helical assembly in the MyD88-IRAK4-IRAK2 complex in Tlr /IL-1R signalling", Nature, 2010, 465(7300):885-890.
Lust et al., "Induction of a Chronic Disease State in patients With Smoldering of Indolent Multiple Myeloma by Targeting Interleukin 1beta-Induced Interleukin 6 Production and the Myeloma Proliferative Component", Mayo Clin Proc., 2009, 84(2):114-122.
Martinon et al., "Gout-associated uric acid crystals activate the NALP3 inflammasome", Nature, 2006, 440(7081):237-241.
Maschera et al., "Overexpression of an enzymatically inactive interleukin-1-receptor-associated kinase activates nuclear factor-kappaB", Biochem J. 1999, 339(Pt2):227-231.
McElroy et al., "Discovery and hit-to-lead optimization of 2,6-diaminopyrimidine Inhibitors of interleukin-1 receptor-associated kinase 4", Bioorg Med Chem Lett., 2015, 25(9):1836-1841.
McElroy et al., "Potent and Selective Amidopyrazole Inhibitors of IRAK4 That Are Efficacious in a Rodent Model of Inflammation", ACS Med Chem Lett., 2015, 6(6):677-682.
Moynagh, "The Pellino Family: Irak E3 ligases with emerging roles in innate immune signalling", Trends lmmunol., 2009, 30(1):33-42.
Ngo et al., "Oncogenically active MYD88 mutations in human lymphoma", Nature, 2011, 470(7332):115-119.
Nunes et al., "Targeting IRAK4 for Degradation with PROTACTSs", ACS Med Chem Lett., 2019, 10(7):1081-1085.
Picard et al., "Clinical features and outcome of patients with IRAK-4 and MyD88 deficiency", Medicine (Baltimore), 2010, 89(6):403-425.
Picard et al., "Inherited human IRAK-4 deficiency: an update", Immunol Res., 2007, 38(1-3):347-352.
Powers et al., "Discovery and initial SAR of inhibitors of interleukin-1 receptor-associated kinase-4", Bioorg Med Chem Lett., 2006, 16(11):2842-2845.
Pubchem Compound Summary for CID 11220940, "(3-{[5-(Phenyl)-furan-2°carbonyl]-amino}-phenyl)-acetic acid", National Center for Biotechnology Information, created Oct. 26, 2006, https://pubchem.ncbi.nlm.nih.gov/compound/11220940, Retrieved on May 28, 2023, 9 pages.
Pubchem Compound Summary for CID 115036573, "2-(2-Hydroxy-5-phenylphenyl)acetic acid", National Center for Biotechnology Information, created Jan. 29, 2016, https://pubchem.ncbi.nlm.nih.gov/compound/115036573, Retrieved on May 28, 2023, 8 pages.
Pubchem Compound Summary for CID 119351828, "2-[3-[[3-(Cyclohexanecarbonylamino)benzoyl]amino]phenyl]acetic acid", National Center for Biotechnology Information, created Jun. 15, 2016, https://pubchem.ncbi.nlm.nih.gov/compound/119351828, Retrieved on May 28, 2023, 8 pages.
Pubchem Compound Summary for CID 57503677, "2-(2-Oxo-3-phenylpyridin-1-yl)acetic acid", National Center for Biotechnology Information, created Aug. 8, 2012, https://pubchem.ncbi.nlm.nih.gov/compound/57503677, Retrieved on May 28, 2023, 8 pages.
Pubchem Compound Summary for CID 59654744, "2-[3-[(3-Phenylbenzoyl)amino]phenyl]acetic acid", National Center for Biotechnology Information, created Aug. 20, 2012, https://pubchem.ncbi.nlm.nih.gov/compound/59654744, Retrieved on May 28, 2023, 8 pages.
Pubchem Compound Summary for CID 82118589, "2-[5-{2-Fluorophenyl)-2-oxopyridin-1-yl]acetic acid", National Center for Biotechnology Information, created Oct. 20, 2014, https://pubchem.ncbi.nlm.nih.gov/compound/82118589, Retrieved on May 28, 2023, 9 pages.
Pubchem Compound Summary for CID 82120702, "2-[5-(2,3-Dimethylphenyl)-2-oxopyridin-1-yl]acetic acid", National Center for Biotechnology Information, created Oct. 20, 2014, https://pubchem.ncbi.nlm.nih.gov/compound/82120702, Retrieved on May 28, 2023, 8 pages.
Pubchem Compound Summary for CID 82122266, "2-[5-{2-Chlorophenyl)-2-oxopyridin-1-yl]acetic acid", National Center for Biotechnology Information, created Oct. 20, 2014, https://pubchem.ncbi.nlm.nih.gov/compound/82122266, Retrieved on May 28, 2023, 8 pages.
Pubchem Compound Summary for CID 82122267, "2-[5-{3-Chlorophenyl)-2-oxopyridin-1-yl]acetic acid", National Center for Biotechnology Information, created Oct. 20, 2014, https://pubchem.ncbi.nlm.nih.gov/compound/82122267, Retrieved on May 28, 2023, 8 pages.
Scott et al., "Discovery and Optimization of Pyrrolopyrimidine Inhibitors of Interleukin-1 Receptor Associated Kinase 4 (IRAK4) for the Treatment of Mutant MYD88L265P Diffuse Large B-Cell Lymphoma", J Med Chem., 2017, 60(24):10071-10091.
Seganish et al., "Discovery and Structure Enabled Synthesis of 2,6-diaminopyrimidine-4-one IRAK4 Inhibitors", ACS Med Chem Lett., 2015, 6(8):942-947.
Seganish et al., "Initial optimization and series evolution of diaminopyrimidine inhibitors of interleukin-1 receptor associated kinase 4", Bioorg Med Chem Lett., 2015, 25(16):3203-3207.
Smith et al., "Identification of quinazoline based inhibitors of IRAK4 for the treatment of inflammation", Bioorg Med Chem Lett., 2017, 27(12):2721-2726.

(56) References Cited

OTHER PUBLICATIONS

So et al., "A pilot study of IL-1 inhibition by anakinra in acute gout", Arthritis Res Ther., 2007, 9(2):R28.
Song et al., "The kinase activities of interleukin-1 receptor associated kinase (IRAK)-1 and 4 are redundant in the control of inflammatory cytokine expression in human cells", Mol Immunol., 2009, 46(7): 1458-466.
Suzuki et al., "IRAK-4 as the central TIR signaling mediator in innate immunity", Trends Immunol., 2002, 23(10):503-506.
Suzuki et al., "Severe impairment of interleukin-1 and Toll-like receptor signalling in mice lacking IRAK-4", Nature, 2002, 416(6882):750-756.
Swantek et al., "IL-1 Receptor-Associated Kinase Modulates Host Responsiveness to Endotoxin", Journal of Immunology 164: 4301-4306, J Immunol., 2000, 164(8):4301-4306.
Terkeltaub et al., "The interleukin 1 inhibitor rilonacept in treatment of chronic gouty arthritis: results of a placebo-controlled, monosequence crossover, non-randomised, single-blind pilot study", Ann Rheum Dis., 2009, 68(10):1613-1617.
Terkeltaub, "Update on gout: new therapeutic strategies and options", Nat Rev Rheumatol., 2010, 6(1):30-38.
Torres et al., "Hyperalgesia, synovitis and multiple biomarkers of inflammation are suppressed by interleukin 1 inhibition in a novel animal model of gouty arthritis", Ann Rheum Dis., 2009, 68(10):1602-1608.
Treon et al., "Whole genome sequencing reveals a widely expressed mutation (MYD88 L265P) with oncogenic activity in Waldenström's Macroglobulinemia", 53rd ASH Annual Meeting, Dec. 12, 2011, p. 1.
Troseid et al., "The role of interleukin-18 in the metabolic syndrome", Cardiovasc Diabetol., 2010, 9(11):1-8.
Tumey et al., "Identification and optimization of indolo[2,3-c]quinoline inhibitors of IRAK4", Bioorg Med Chem Lett., 2014, 24(9):2066-2072.
Vollmer et al., "The mechanism of activation of IRAK1 and IRAK4 by interleukin-1 and Toll-like receptor agonists", Biochem J., 2017, 474(12):2027-2038.
Wang et al., "Crystal Structure of IRAK-4 Kinase in Complex with Inhibitors: Serine/Threonine Kinase with Tyrosine as a Gatekeeper", Structure, 2006, 14(12):1835-1844.
Wang et al., "Discovery of potent, selective, and orally bioavailable inhibitors of interleukin-1 receptor-associated kinase 4", Bioorg Med Chem Lett., 2015, 25(23):5546-5550.
Wang et al., "IRAK-4 Inhibitors for Inflammation", Curr Top Med Chem., 2009, 9(8):724-737.
Weaver, "Epidemiology of gout", Cleve Clin J Med., 2008, 75 Suppl 5:S9-S12.
Xu et al., "A somatic variant in MYD88 (L256P) revealed by whole genome sequencing differentiates lymphoplasmacytic lymphoma from marginal zone lymphomas", 53rd ASH Annual Meeting, Dec. 12, 2011, 1 page.
Yang et al., "Disruption of MYD88 pathway signaling leads to loss of constitutive IRAK1, NK-kB and JAK/STAT signaling and induces apoptosis of cells expressing the MYD88 L265P mutation in Waldenström's Macroglobulinemia", 53rd ASH Annual Meeting, Dec. 12, 2011, 1 page.
Zhang et al., "Constitutive IRAK4 Activation Underlies Poor Prognosis and Chemoresistance in Pancreatic Ductal Adenocarcinoma", Clin Cancer Res., 2017, 23(7):1748-1759.
PCT International Preliminary Report on Patentability received for PCT Patent Application No. PCT/US2018/052242, dated Apr. 2, 2020, 6 pages.
PCT International Preliminary Report on Patentability received for PCT Patent Application No. PCT/US2019/013481, dated Jul. 23, 2020, 7 pages.
PCT International Preliminary Report on Patentability received for PCT Patent Application No. PCT/US2019/040545, dated Jan. 21, 2021, 6 pages.
PCT International Preliminary Report on Patentability received for PCT Patent Application No. PCT/US2020/042109, dated Jan. 27, 2022, 7 pages.
PCT International Search Report and Written Opinion received for PCT Patent Application No. PCT/US2023/017071, dated Jul. 24, 2023, 14 pages.
PCT International Search Report and Written Opinion received for PCT Patent Application No. PCT/US2023/077741, dated Mar. 6, 2024, 13 pages.
PCT Invitation to Pay Additional Fees received for PCT Patent Application No. PCT/US2023/077741, dated Jan. 17, 2024, 3 pages.
U.S. Appl. No. 18/602,701 of Mainolfi et al., filed on Mar. 12, 2024.

* cited by examiner

PROTEIN DEGRADERS AND USES THEREOF

CROSS-REFERENCE TO RELATED APPLICATIONS

This application is a National Stage Entry of PCT/US2019/040545, which claims the benefit of priority to U.S. Provisional Appl. No. 62/694,931, filed Jul. 6, 2018, U.S. Provisional Appl. No. 62/820,641, filed Mar. 19, 2019, and U.S. Provisional Appl. No. 62/863,954, filed Jun. 20, 2019, the entirety of each of which is herein incorporated by reference.

TECHNICAL FIELD OF THE INVENTION

The present invention relates to compounds and methods useful for the modulation of targeted ubiquitination, especially with respect to a variety of polypeptides and other proteins, which are degraded and/or otherwise inhibited by compounds according to the present invention. The invention also provides pharmaceutically acceptable compositions comprising compounds of the present invention and methods of using said compositions in the treatment of various disorders.

BACKGROUND OF THE INVENTION

Ubiquitin-Proteasome Pathway (UPP) is a critical pathway that regulates key regulator proteins and degrades misfolded or abnormal proteins. UPP is central to multiple cellular processes, and if defective or imbalanced, it leads to pathogenesis of a variety of diseases. The covalent attachment of ubiquitin to specific protein substrates is achieved through the action of E3 ubiquitin ligases. These ligases comprise over 500 different proteins and are categorized into multiple classes defined by the structural element of their E3 functional activity.

Cereblon (CRBN) interacts with damaged DNA binding protein 1 and forms an E3 ubiquitin ligase complex with Cullin 4 where it functions as a substrate receptor in which the proteins recognized by CRBN might be ubiquitinated and degraded by proteasomes.

Proteasome-mediated degradation of unneeded or damaged proteins plays a very important role in maintaining regular function of a cell, such as cell survival, proliferation and growth. A new role for CRBN has been identified; i.e., the binding of immunomodulatory drugs (IMiDs), e.g. thalidomide, to CRBN has now been associated with teratogenicity and also the cytotoxicity of IMiDs, including lenalidomide, which are widely used to treat multiple myeloma patients. CRBN is likely a key player in the binding, ubiquitination and degradation of factors involved in maintaining function of myeloma cells. These new findings regarding the role of CRBN in IMiD action stimulated intense investigation of CRBN's downstream factors involved in maintaining regular function of a cell (Chang and Stewart Int J Biochem Mol Biol. 2011; 2(3): 287-294).

UPP plays a key role in the degradation of short-lived and regulatory proteins important in a variety of basic cellular processes, including regulation of the cell cycle, modulation of cell surface receptors and ion channels, and antigen presentation. The pathway has been implicated in several forms of malignancy, in the pathogenesis of several genetic diseases (including cystic fibrosis, Angelman's syndrome, and Liddle syndrome), in immune surveillance/viral pathogenesis, and in the pathology of muscle wasting. Many diseases are associated with an abnormal UPP and negatively affect cell cycle and division, the cellular response to stress and to extracellular modulators, morphogenesis of neuronal networks, modulation of cell surface receptors, ion channels, the secretory pathway, DNA repair and biogenesis of organelles.

Aberrations in the process have recently been implicated in the pathogenesis of several diseases, both inherited and acquired. These diseases fall into two major groups: (a) those that result from loss of function with the resultant stabilization of certain proteins, and (b) those that result from gain of function, i.e. abnormal or accelerated degradation of the protein target.

The UPP is used to induce selective protein degradation, including use of fusion proteins to artificially ubiquitinate target proteins and synthetic small-molecule probes to induce proteasome-dependent degradation. Bifunctional compounds composed of a target protein-binding ligand and an E3 ubiquitin ligase ligand, induced proteasome-mediated degradation of selected proteins via their recruitment to E3 ubiquitin ligase and subsequent ubiquitination. These drug-like molecules offer the possibility of temporal control over protein expression. Such compounds are capable of inducing the inactivation of a protein of interest upon addition to cells or administration to an animal or human, and could be useful as biochemical reagents and lead to a new paradigm for the treatment of diseases by removing pathogenic or oncogenic proteins (Crews C, Chemistry & Biology, 2010, 17(6):551-555; Schnekloth J S Jr., Chembiochem, 2005, 6(1):40-46).

An ongoing need exists in the art for effective treatments for disease, especially hyperplasias and cancers, such as multiple myeloma. However, non-specific effects, and the inability to target and modulate certain classes of proteins altogether, such as transcription factors, remain as obstacles to the development of effective anti-cancer agents. As such, small molecule therapeutic agents that leverage or potentiate cereblon's substrate specificity and, at the same time, are "tunable" such that a wide range of protein classes can be targeted and modulated with specificity would be very useful as a therapeutic. Accordingly, there remains a need to find bifunctional compounds that are protein degraders useful as therapeutic agents.

SUMMARY OF THE INVENTION

The present application relates novel bifunctional compounds, which function to recruit targeted proteins to E3 Ubiquitin Ligase for degradation, and methods of preparation and uses thereof. In particular, the present disclosure provides bifunctional compounds, which find utility as modulators of targeted ubiquitination of a variety of polypeptides and other proteins, which are then degraded and/or otherwise inhibited by the bifunctional compounds as described herein. An advantage of the compounds provided herein is that a broad range of pharmacological activities is possible, consistent with the degradation/inhibition of targeted polypeptides from virtually any protein class or family. In addition, the description provides methods of using an effective amount of the compounds as described herein for the treatment or amelioration of a disease condition, such as cancer, e.g., multiple myeloma.

The present application further relates to targeted degradation of proteins through the use of bifunctional molecules, including bifunctional molecules that link a cereblon-binding moiety to a ligand that binds the targeted protein.

The present application also relates to a bifunctional compound having the following structure:

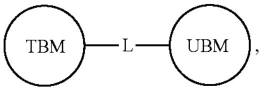

wherein,

TBM is a target binding moiety capable of binding to the targeted protein(s);

L is a bivalent moiety that connects TBM to UBM; and

UBM is a ubiquitin binding moiety capable of binding to a ubiquitin ligase such as an E3 Ubiquitin Ligase (e.g., cereblon).

It has now been found that compounds of this invention, and pharmaceutically acceptable compositions thereof, are effective for the modulation of targeted ubiquitination. Such compounds have the general formula I:

I

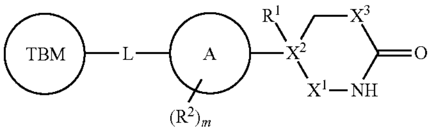

or a pharmaceutically acceptable salt thereof, wherein each variable is as defined and described herein.

Compounds of the present invention, and pharmaceutically acceptable compositions thereof, are useful for treating a variety of diseases, disorders or conditions. Such diseases, disorders, or conditions include those described herein.

Compounds provided by this invention are also useful for the study of CRBN and targeted proteins in biological and pathological phenomena; the study of CRBN and targeted proteins occurring in bodily tissues; and the comparative evaluation of new CRBN or targeted protein ligands or other regulators of CRBN or targeted proteins in vitro or in vivo.

DETAILED DESCRIPTION OF CERTAIN EMBODIMENTS

1. General Description of Certain Embodiments of the Invention

Compounds of the present invention, and compositions thereof, are useful for the modulation of targeted ubiquitination.

As defined herein, the terms "binder," "modulator," and "ligand" are used interchangeably and describe a compound that binds to, modulates or is a ligand for CRBN or a targeted protein.

In certain embodiments, the present invention provides a compound of formula I-a:

I-a

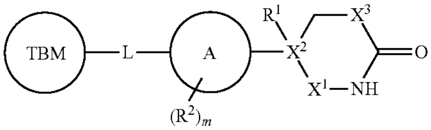

or a pharmaceutically acceptable salt thereof, wherein:

$X^1$ is a bivalent moiety selected from a covalent bond, —$CH_2$—, —C(O)—, —C(S)—, or

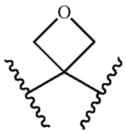

;

$X^2$ is a carbon atom or silicon atom;

$X^3$ is a bivalent moiety selected from —$CH_2$— or —Si($R^2$)—;

$R^1$ is hydrogen, deuterium, halogen, —CN, —OR, —SR, —S(O)R, —$S(O)_2R$, —$N(R)_2$, —$Si(R)_3$, or an optionally substituted $C_{1-4}$ aliphatic;

each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

each $R^2$ is independently hydrogen, deuterium, —$R^3$, halogen, —CN, —$NO_2$, —OR, —SR, —$N(R)_2$, —$Si(R)_3$, —$S(O)_2R$, —$S(O)_2N(R)_2$, —S(O)R, —C(O)R, —C(O)OR, —C(O)$N(R)_2$, —C(O)N(R)OR, —$C(R)_2$N(R)C(O)R, —$C(R)_2$N(R)C(O)$N(R)_2$, —OC(O)R, —OC(O)$N(R)_2$, —N(R)C(O)OR, —N(R)C(O)R, —N(R)C(O)$N(R)_2$, or —N(R)$S(O)_2R$;

each $R^3$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

Ring A is a tricyclic ring selected from

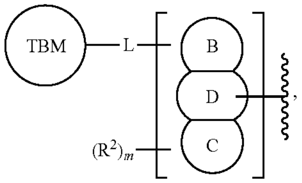

wherein each of Ring B, Ring C, and Ring D is independently a fused ring selected from 6-membered aryl containing 0-3 nitrogens, 5 to 7-membered saturated or partially unsaturated carbocyclyl, 5 to 7-membered saturated or partially unsaturated heterocyclyl ring with 1-3 heteroatoms independently selected from boron, nitrogen, oxygen, silicon, or sulfur, or 5-membered heteroaryl with 1-3 heteroatoms independently selected from nitrogen, oxygen or sulfur; and m is 0, 1, 2, 3, 4, 5, 6, 7, 8, 9, 10, 11, 12, 13, 14, 15, or 16;

L is a covalent bond or a bivalent, saturated or unsaturated, straight or branched $C_{1-50}$ hydrocarbon chain, wherein 0-6 methylene units of L are independently replaced by —C(D)(H)—, —C(D)$_2$- , -Cy-, —O—, —NR—, —S—, —OC(O)—, —C(O)O—, —C(O)—, —S(O)—, —S(O)$_2$—, —NRS(O)$_2$—, —Si(R$_2$)—, —S(O)$_2$NR—, —NRC(O)—, —C(O)NR—, —OC(O)NR—, —NRC(O)O—,

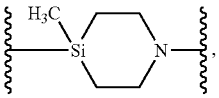, 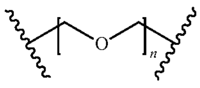, 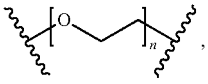, 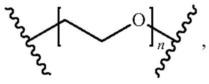, 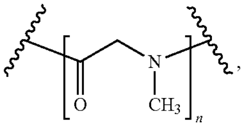, or 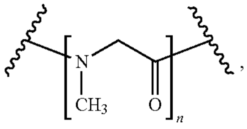, wherein:

each -Cy- is independently an optionally substituted bivalent ring selected from phenylenyl, an 8-10 membered bicyclic arylenyl, a 4-7 membered saturated or partially unsaturated carbocyclylenyl, a 4-7 membered saturated or partially unsaturated spiro carbocyclylenyl, an 8-10 membered bicyclic saturated or partially unsaturated carbocyclylenyl, a 4-7 membered saturated or partially unsaturated heterocyclylenyl having 1-2 heteroatoms independently selected from nitrogen, oxygen, and sulfur, a 4-7 membered saturated or partially unsaturated spiro heterocyclylenyl having 1-2 heteroatoms independently selected from nitrogen, oxygen, and sulfur, an 8-10 membered bicyclic saturated or partially unsaturated heterocyclylenyl having 1-2 heteroatoms independently selected from nitrogen, oxygen, and sulfur, a 5-6 membered heteroarylenyl having 1-4 heteroatoms independently selected from nitrogen, oxygen, and sulfur, or an 8-10 membered bicyclic heteroarylenyl having 1-5 heteroatoms independently selected from nitrogen, oxygen, or sulfur;

each of n is independently 1, 2, 3, 4, 5, 6, 7, 8, 9, or 10; and

TBM is a target binding moiety.

Where a point of attachment of

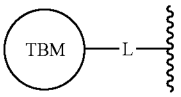

is depicted on Ring B, Ring C, or Ring D, it is intended, and one of ordinary skill in the art would appreciate, that the point of attachment of

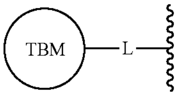

may be on Ring A and may also be at any available carbon or nitrogen atom on Ring A including the ring to which Ring B or Ring C is fused to Ring D.

Where a point of attachment of —(R$^2$)m is depicted on Ring B, Ring C, and Ring D, it is intended, and one of ordinary skill in the art would appreciate, that the point of attachment of —(R$^2$)$_m$ may be on Ring A and may also be at any available carbon or nitrogen atom on Ring A including the carbon atom to which Ring B or Ring C are fused to Ring D.

Where a point of attachment of

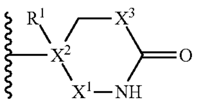

is depicted on Ring D, it is intended, and one of ordinary skill in the art would appreciate, that the point of attachment of

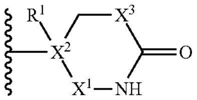

may be on any available carbon or nitrogen atom on Ring D including the carbon atom to which Ring B or Ring C are fused to Ring D.

In certain embodiments, the present invention provides a compound of formula I-a':

I-a'

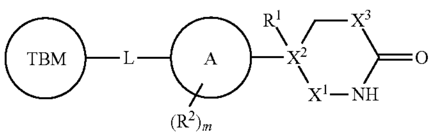

or a pharmaceutically acceptable salt thereof, wherein:

X$^1$ is a bivalent moiety selected from a covalent bond, —CH$_2$—, —CHCF$_3$—, —SO$_2$—, —S(O)—, —P(O)R—, —P(O)OR—, —P(O)NR$_2$—, —C(O)—, —C(S)—, or

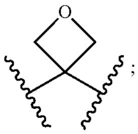 [SMILES: *C1(*)COC1];

X$^2$ is a carbon atom or silicon atom;

X$^3$ is a bivalent moiety selected from —CR$_2$—, —NR—, —O—, —S—, or —Si(R$_2$)—;

R$^1$ is hydrogen, deuterium, halogen, —CN, —OR, —SR, —S(O)R, —S(O)$_2$R, —N(R)$_2$, —P(O)(OR)$_2$, —P(O)(NR$_2$)OR, —P(O)(NR$_2$)$_2$, —Si(OH)$_2$R, —Si(OH)(R)$_2$, —Si(R)$_3$, or an optionally substituted C$_{1-4}$ aliphatic;

each R is independently hydrogen, or an optionally substituted group selected from C$_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

each $R^2$ is independently hydrogen, deuterium, —$R^3$, halogen, —CN, —$NO_2$, —OR, —SR, —$N(R)_2$, —$Si(R)_3$, —$S(O)_2R$, —$S(O)_2N(R)_2$, —S(O)R, —C(O)R, —C(O)OR, —$C(O)N(R)_2$, —C(O)N(R)OR, —$C(R)_2N(R)C(O)R$, —$C(R)_2N(R)C(O)N(R)_2$, —OC(O)R, —$OC(O)N(R)_2$, —$OP(O)R^2$, —$OP(O)(OR)_2$, —$OP(O)(OR)(NR_2)$, —$OP(O)(NR_2)_2$—, —N(R)C(O)OR, —N(R)C(O)R, —$N(R)C(O)N(R)_2$, —$N(R)S(O)_2R$, —$NP(O)R_2$, —$N(R)P(O)(OR)_2$, —$N(R)P(O)(OR)(NR_2)$, —$N(R)P(O)(NR_2)_2$, or —$N(R)S(O)_2R$;

each $R^3$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

Ring A is a tricyclic ring selected from

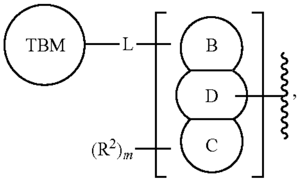

wherein each of Ring B, Ring C, and Ring D is independently a fused ring selected from 6-membered aryl, 6-membered heteroaryl containing 1-4 heteroatoms independently selected from nitrogen, oxygen, or sulfur, 5 to 7-membered saturated or partially unsaturated carbocyclyl, 5 to 7-membered saturated or partially unsaturated heterocyclyl ring with 1-3 heteroatoms independently selected from boron, nitrogen, oxygen, silicon, or sulfur, or 5-membered heteroaryl with 1-4 heteroatoms independently selected from nitrogen, oxygen or sulfur; and m is 0, 1, 2, 3, 4, 5, 6, 7, 8, 9, 10, 11, 12, 13, 14, 15, or 16;

L is a covalent bond or a bivalent, saturated or unsaturated, straight or branched $C_{1-50}$ hydrocarbon chain, wherein 0-6 methylene units of L are independently replaced by —C(D)(H)—, —$C(D)_2$-, -Cy-, —O—, —NR—, —$Si(R)_2$—, —Si(OH)(R)—, —$Si(OH)_2$—, —P(O)(OR)—, —P(O)(R)—, —$P(O)(NR_2)$—, —S—, —OC(O)—, —C(O)O—, —C(O)—, —S(O)—, —$S(O)_2$—, —$NRS(O)_2$—, —$S(O)_2NR$—, —NRC(O)—, —C(O)NR—, —OC(O)NR—, —NRC(O)O—,

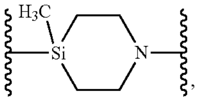,
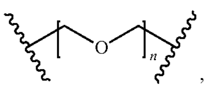,
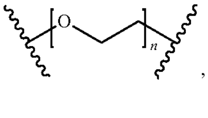,
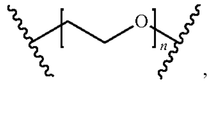,

-continued

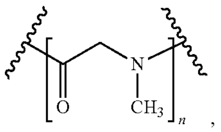, or 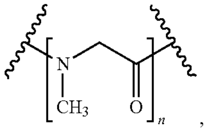, wherein:

each -Cy- is independently an optionally substituted bivalent ring selected from phenylenyl, an 8-10 membered bicyclic arylenyl, a 4-7 membered saturated or partially unsaturated carbocyclylenyl, a 4-7 membered saturated or partially unsaturated spiro carbocyclylenyl, an 8-10 membered bicyclic saturated or partially unsaturated carbocyclylenyl, a 4-7 membered saturated or partially unsaturated heterocyclylenyl having 1-2 heteroatoms independently selected from nitrogen, oxygen, and sulfur, a 4-7 membered saturated or partially unsaturated spiro heterocyclylenyl having 1-2 heteroatoms independently selected from nitrogen, oxygen, and sulfur, an 8-10 membered bicyclic saturated or partially unsaturated heterocyclylenyl having 1-2 heteroatoms independently selected from nitrogen, oxygen, and sulfur, a 5-6 membered heteroarylenyl having 1-4 heteroatoms independently selected from nitrogen, oxygen, and sulfur, or an 8-10 membered bicyclic heteroarylenyl having 1-5 heteroatoms independently selected from nitrogen, oxygen, or sulfur;

each of n is independently 1, 2, 3, 4, 5, 6, 7, 8, 9, or 10; and

TBM is a target binding moiety.

Where a point of attachment of

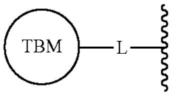

is depicted on Ring B, Ring C, or Ring D, it is intended, and one of ordinary skill in the art would appreciate, that the point of TBM L attachment of

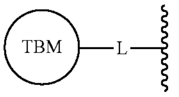

may be on Ring A and may also be at any available carbon or nitrogen atom on Ring A including the ring to which Ring B or Ring C is fused to Ring D.

Where a point of attachment of —$(R^2)_m$ is depicted on Ring B, Ring C, and Ring D, it is intended, and one of ordinary skill in the art would appreciate, that the point of attachment of —$(R^2)_m$ may be on Ring A and may also be at any available carbon or nitrogen atom on Ring A including the carbon atom to which Ring B or Ring C are fused to Ring D.

Where a point of attachment of

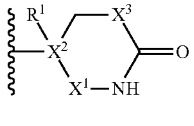

is depicted on Ring B, Ring C, and Ring D, it is intended, and one of ordinary skill in the art would appreciate, that the point of attachment of

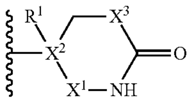

may be on any available carbon or nitrogen atom on Ring A, including the carbon atom to which Ring B or Ring C are fused to Ring D.

In certain embodiments, the present invention provides a compound of formula I-b:

I-b

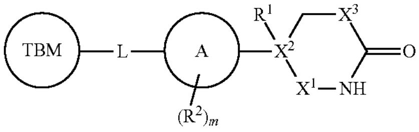

or a pharmaceutically acceptable salt thereof, wherein:

$X^1$ is a bivalent moiety selected from a covalent bond, —$CH_2$—, —$CHCF_3$—, —$SO_2$—, —S(O)—, —P(O)R—, —P(O)OR—, —P(O)$NR_2$—, —C(O)—, —C(S)—, or

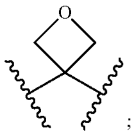 [SMILES: *C1(*)COC1]

;

$X^2$ is a carbon atom or silicon atom;

$X^3$ is a bivalent moiety selected from —$CR_2$—, —NR—, —O—, —S—, or —Si($R_2$)—;

$R^1$ is hydrogen, deuterium, halogen, —CN, —OR, —SR, —S(O)R, —$S(O)_2R$, —$N(R)_2$, —P(O)$(OR)_2$, —P(O)($NR_2$)OR, —P(O)$(NR_2)_2$, —Si$(OH)_2$R, —Si(OH)$(R)_2$, —Si$(R)_3$, or an optionally substituted $C_{1-4}$ aliphatic;

each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

each $R^2$ is independently hydrogen, deuterium, —$R^3$, halogen, —CN, —$NO_2$, —OR, —SR, —$N(R)_2$, —Si$(R)_3$, —$S(O)_2R$, —$S(O)_2N(R)_2$, —S(O)R, —C(O)R, —C(O)OR, —C(O)$N(R)_2$, —C(O)N(R)OR, —$C(R)_2$N(R)C(O)R, —$C(R)_2$N(R)C(O)$N(R)_2$, —OC(O)R, —OC(O)$N(R)_2$, —OP(O)$R_2$, —OP(O)$(OR)_2$, —OP(O)(OR)($NR_2$), —OP(O)$(NR_2)_2$—, —N(R)C(O)OR, —N(R)C(O)R, —N(R)C(O)$N(R)_2$, —N(R)$S(O)_2$R, —NP(O)$R_2$, —N(R)P(O)$(OR)_2$, —N(R)P(O)(OR)($NR_2$), —N(R)P(O)$(NR_2)_2$, or —N(R)$S(O)_2$R;

each $R^3$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

Ring A is a bicyclic ring system selected from,

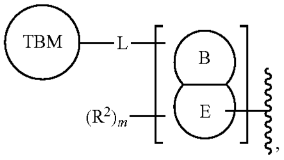

, wherein

Ring B is a fused ring selected from 6-membered aryl, 6-membered heteroaryl containing 1-4 heteroatoms independently selected from nitrogen, oxygen, or sulfur, 5 to 7-membered saturated or partially unsaturated carbocyclyl, 5 to 7-membered saturated or partially unsaturated heterocyclyl ring with 1-3 heteroatoms independently selected from boron, nitrogen, oxygen, silicon, or sulfur, or 5-membered heteroaryl with 1-4 heteroatoms independently selected from nitrogen, oxygen or sulfur;

Ring E is a fused ring selected from a 7-9 membered saturated or partially unsaturated carbocyclyl or hetercyclyl ring with 1-3 heteroatoms independently selected from boron, nitrogen, oxygen, silicon, or sulfur, wherein Ring E is optionally further substituted with 1-2 oxo groups; and m is 0, 1, 2, 3, 4, 5, 6, 7, 8, 9, 10, 11, 12, 13, 14, 15, or 16.

L is a covalent bond or a bivalent, saturated or unsaturated, straight or branched $C_{1-50}$ hydrocarbon chain, wherein 0-6 methylene units of L are independently replaced by —C(D)(H)—, —$C(D)_2$-, -Cy-, —O—, —NR—, —Si$(R)_2$—, —Si(OH)(R)—, —Si$(OH)_2$—, —P(O)(OR)—, —P(O)(R)—, —P(O)($NR_2$)—, —S—, —OC(O)—, —C(O)O—, —C(O)—, —S(O)—, —$S(O)_2$—, —NR$S(O)_2$—, —$S(O)_2$NR—, —NRC(O)—, —C(O)NR—, —OC(O)NR—, —NRC(O)O—,

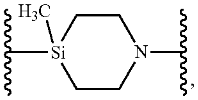

,

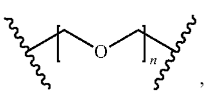

,

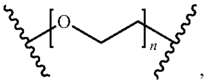

,

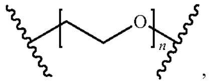

,

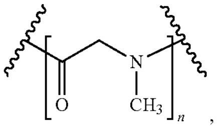

, or

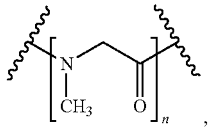

, wherein:

each -Cy- is independently an optionally substituted bivalent ring selected from phenylenyl, an 8-10 membered bicyclic arylenyl, a 4-7 membered saturated or partially unsaturated carbocyclylenyl, a 4-7 membered saturated or partially unsaturated spiro carbocyclylenyl, an 8-10 membered bicyclic saturated or partially unsaturated carbocyclylenyl, a 4-7 membered saturated or partially unsaturated heterocyclylenyl having 1-2 heteroatoms independently selected from nitrogen, oxygen, and sulfur, a 4-7 membered saturated or partially unsaturated spiro heterocyclylenyl having 1-2 heteroatoms independently selected from nitrogen, oxygen, and sulfur, an 8-10 membered bicyclic saturated or partially unsaturated heterocyclylenyl having 1-2 heteroatoms independently selected from nitrogen, oxygen, and sulfur, a 5-6 membered heteroarylenyl having 1-4 heteroatoms independently selected from nitrogen, oxygen, and sulfur, or an 8-10 membered bicyclic heteroarylenyl having 1-5 heteroatoms independently selected from nitrogen, oxygen, or sulfur;

each of n is independently 1, 2, 3, 4, 5, 6, 7, 8, 9, or 10; and

TBM is a target binding moiety.

Where a point of attachment of

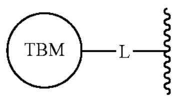

is depicted on Ring B or Ring E, it is intended, and one of ordinary skill in the art would appreciate, that the point of attachment of

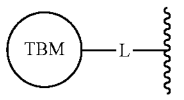

may be on Ring A and may also be at any available carbon or nitrogen atom on Ring A including the carbon atom to which Ring B and Ring E are fused.

Where a point of attachment of $-(R^2)_m$ is depicted on Ring B and Ring E, it is intended, and one of ordinary skill in the art would appreciate, that the point of attachment of $-(R^2)_m$ may be on Ring A and may also be at any available carbon or nitrogen atom on Ring A including the carbon atom to which Ring B and Ring E are fused.

Where a point of attachment of

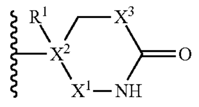

is depicted on Ring B and Ring E, it is intended, and one of ordinary skill in the art would appreciate, that the point of attachment of

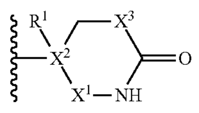

may be on Ring A and may also be at any available carbon or nitrogen atom on Ring A including the carbon atom to which Ring B and Ring E are fused.

In certain embodiments, the present invention provides a compound of formula I-α:

I-c

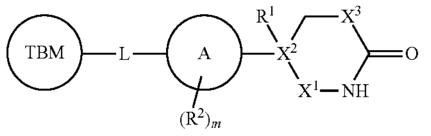

or a pharmaceutically acceptable salt thereof, wherein:

$X^1$ is a bivalent moiety selected from a covalent bond, $-CH_2-$, $-CHCF_3-$, $-SO_2-$, $-S(O)-$, $-P(O)R-$, $-P(O)OR-$, $-P(O)NR_2-$, $-C(O)-$, $-C(S)-$, or

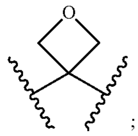

;

$X^2$ is a carbon atom or silicon atom;

$X^3$ is a bivalent moiety selected from $-CR_2-$, $-NR-$, $-O-$, $-S-$, or $-Si(R_2)-$;

$R^1$ is hydrogen, deuterium, halogen, $-CN$, $-OR$, $-SR$, $-S(O)R$, $-S(O)_2R$, $-NR_2$, $-P(O)(OR)_2$, $-P(O)(NR_2)OR$, $-P(O)(NR_2)_2$, $-Si(OH)_2R$, $-Si(OH)(R)_2$, $-Si(R)_3$, or an optionally substituted $C_{1-4}$ aliphatic;

each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

each $R^2$ is independently hydrogen, deuterium, $-R^3$, halogen, $-CN$, $-NO_2$, $-OR$, $-SR$, $-N(R)_2$, $-Si(R)_3$, $-S(O)_2R$, $-S(O)_2N(R)_2$, $-S(O)R$, $-C(O)R$, $-C(O)OR$, $-C(O)N(R)_2$, $-C(O)N(R)OR$, $-C(R)_2N(R)C(O)R$, $-C(R)_2N(R)C(O)N(R)_2$, $-OC(O)R$, $-OC(O)N(R)_2$, $-OP(O)R_2$, $-OP(O)(OR)_2$, $-OP(O)(OR)(NR_2)$, $-OP(O)(NR_2)_2-$, $-N(R)C(O)OR$, $-N(R)C(O)R$, $-N(R)C(O)N(R)_2$, $-N(R)S(O)_2R$, $-NP(O)R_2$, $-N(R)P(O)(OR)_2$, $-N(R)P(O)(OR)(NR_2)$, $-N(R)P(O)(NR_2)_2$, or $-N(R)S(O)_2R$;

each $R^3$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

Ring A is a tricyclic ring system selected from

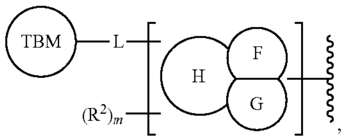

wherein each of Ring F and G is independently a fused ring selected from 6-membered aryl, 6-membered heteroaryl containing 1-4 heteroatoms independently selected from nitrogen, oxygen, and sulfur, 5 to 7-membered saturated or partially unsaturated carbocyclyl, 5 to 7-membered saturated or partially unsaturated heterocyclyl ring with 1-3 heteroatoms independently selected from boron, nitrogen, oxygen, silicon, or sulfur, or 5-membered heteroaryl with 1-4 heteroatoms independently selected from nitrogen, oxygen or sulfur;

Ring H is a fused ring selected from a 7-12 membered saturated or partially unsaturated carbocyclyl or heterocyclyl ring with 1-3 heteroatoms independently selected from boron, nitrogen, oxygen, silicon, or sulfur, wherein Ring H is optionally further substituted with 1-2 oxo groups;

m is 0, 1, 2, 3, 4, 5, 6, 7, 8, 9, 10, 11, 12, 13, 14, 15, or 16;

L is a covalent bond or a bivalent, saturated or unsaturated, straight or branched $C_{1-50}$ hydrocarbon chain, wherein 0-6 methylene units of L are independently replaced by —C(D)(H)—, —$C(D)_2$-, -Cy-, —O—, —NR—, —$Si(R)_2$—, —Si(OH)(R)—, —$Si(OH)_2$—, —P(O)(OR)—, —P(O)(R)—, —$P(O)(NR_2)$—, —S—, —OC(O)—, —C(O)O—, —C(O)—, —S(O)—, —$S(O)_2$—, —$NRS(O)_2$—, —$S(O)_2NR$—, —NRC(O)—, —C(O)NR—, —OC(O)NR—, —NRC(O)O—,

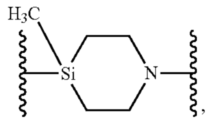,
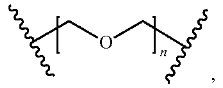,
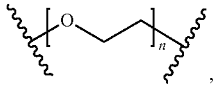,
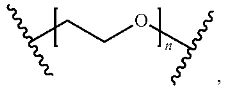,
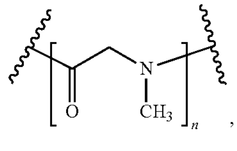, or
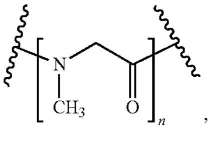, wherein:

each -Cy- is independently an optionally substituted bivalent ring selected from phenylenyl, an 8-10 membered bicyclic arylenyl, a 4-7 membered saturated or partially unsaturated carbocyclylenyl, a 4-7 membered saturated or partially unsaturated spiro carbocyclylenyl, an 8-10 membered bicyclic saturated or partially unsaturated carbocyclylenyl, a 4-7 membered saturated or partially unsaturated heterocyclylenyl having 1-2 heteroatoms independently selected from nitrogen, oxygen, and sulfur, a 4-7 membered saturated or partially unsaturated spiro heterocyclylenyl having 1-2 heteroatoms independently selected from nitrogen, oxygen, and sulfur, an 8-10 membered bicyclic saturated or partially unsaturated heterocyclylenyl having 1-2 heteroatoms independently selected from nitrogen, oxygen, and sulfur, a 5-6 membered heteroarylenyl having 1-4 heteroatoms independently selected from nitrogen, oxygen, and sulfur, or an 8-10 membered bicyclic heteroarylenyl having 1-5 heteroatoms independently selected from nitrogen, oxygen, or sulfur;

each of n is independently 1, 2, 3, 4, 5, 6, 7, 8, 9, or 10; and

TBM is a target binding moiety.

Where a point of attachment of

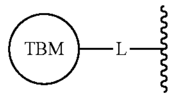

is depicted on Ring F, Ring G, or Ring H, it is intended, and one of ordinary skill in the art would appreciate, that the point of attachment of

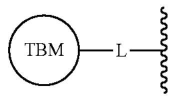

may be on Ring A and may also be at any available carbon or nitrogen atom on Ring A including the carbon atom to which Ring F, Ring G, and Ring H are fused.

Where a point of attachment of —$(R^2)_m$ is depicted on Ring F, Ring G, and Ring H, it is intended, and one of ordinary skill in the art would appreciate, that the point of attachment of —$(R^2)_m$ may be on Ring A and may also be at any available carbon or nitrogen atom on Ring A including the carbon atom to which Ring F, Ring G, and Ring H are fused.

Where a point of attachment of

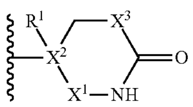

is depicted on Ring F, Ring G, and Ring H, it is intended, and one of ordinary skill in the art would appreciate, that the point of attachment of

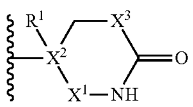

may be on Ring A and may also be at any available carbon or nitrogen atom on Ring A including the carbon atom to which Ring F, Ring G, and Ring H are fused.

In certain embodiments, the present invention provides a compound of formula I-d:

I-d

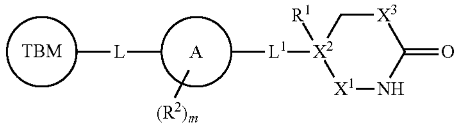

or a pharmaceutically acceptable salt thereof, wherein:

$X^1$ is a bivalent moiety selected from a covalent bond, —$CH_2$—, —$CHCF_3$—, —$SO_2$—, —S(O)—, —P(O)R—, —P(O)OR—, —P(O)$NR_2$—, —C(O)—, —C(S)—, or

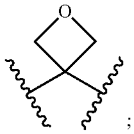 [SMILES: *C1(*)COC1]

;

$X^2$ is a carbon atom or silicon atom;

$X^3$ is a bivalent moiety selected from —$CR_2$—, —NR—, —O—, —S—, or —Si($R_2$)—;

$R^1$ is hydrogen, deuterium, halogen, —CN, —OR, —SR, —S(O)R, —S(O)$_2$R, —N(R)$_2$, —P(O)(OR)$_2$, —P(O)($NR_2$)OR, —P(O)($NR_2$)$_2$, —Si(OH)$_2$R, —Si(OH)(R)$_2$, —Si(R)$_3$, or an optionally substituted $C_{1-4}$ aliphatic;

each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

each $R^2$ is independently hydrogen, deuterium, —$R^3$, halogen, —CN, —$NO_2$, —OR, —SR, —N(R)$_2$, —Si(R)$_3$, —S(O)$_2$R, —S(O)$_2$N(R)$_2$, —S(O)R, —C(O)R, —C(O)OR, —C(O)N(R)$_2$, —C(O)N(R)OR, —C(R)$_2$N(R)C(O)R, —C(R)$_2$N(R)C(O)N(R)$_2$, —OC(O)R, —OC(O)N(R)$_2$, —OP(O)R$_2$, —OP(O)(OR)$_2$, —OP(O)(OR)($NR_2$), —OP(O)($NR_2$)$_2$—, —N(R)C(O)OR, —N(R)C(O)R, —N(R)C(O)N(R)$_2$, —N(R)S(O)$_2$R, —NP(O)R$_2$, —N(R)P(O)(OR)$_2$, —N(R)P(O)(OR)($NR_2$), —N(R)P(O)($NR_2$)$_2$, or —N(R)S(O)$_2$R;

each $R^3$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

Ring A is a tricyclic ring selected from

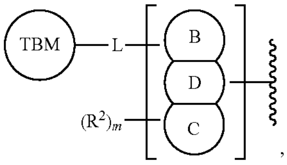

, wherein each of Ring B, Ring D, and Ring C is independently a fused ring selected from 6-membered aryl, 6-membered heteroaryl containing 1-4 heteroatoms independently selected from nitrogen, oxygen, or sulfur, 5 to 7-membered saturated or partially unsaturated carbocyclyl, 5 to 7-membered saturated or partially unsaturated heterocyclyl ring with 1-3 heteroatoms independently selected from boron, nitrogen, oxygen, silicon, or sulfur, or 5-membered heteroaryl with 1-4 heteroatoms independently selected from nitrogen, oxygen or sulfur;

$L^1$ is a covalent bond or a $C_{1-3}$ bivalent straight or branched saturated or unsaturated hydrocarbon chain wherein 1-2 methylene units of the chain are independently and optionally replaced with —O—, —C(O)—, —C(S)—, —$CR_2$—, —CFR—, —$CF_2$—, —NR—, —S—, —S(O)$_2$— or —CR═CR—;

m is 0, 1, 2, 3, 4, 5, 6, 7, 8, 9, 10, 11, 12, 13, 14, 15, or 16;

L is a covalent bond or a bivalent, saturated or unsaturated, straight or branched $C_{1-50}$ hydrocarbon chain, wherein 0-6 methylene units of L are independently replaced by —C(D)(H)—, —C(D)$_2$-, -Cy-, —O—, —NR—, —Si(R)$_2$—, —Si(OH)(R)—, —Si(OH)$_2$—, —P(O)(OR)—, —P(O)(R)—, —P(O)($NR_2$)—, —S—, —OC(O)—, —C(O)O—, —C(O)—, —S(O)—, —S(O)$_2$—, —NRS(O)$_2$—, —S(O)$_2$NR—, —NRC(O)—, —C(O)NR—, —OC(O)NR—, —NRC(O)O—,

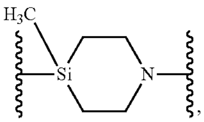

,

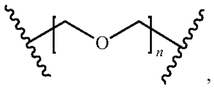

,

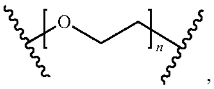

,

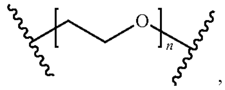

,

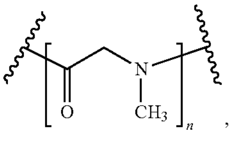

, or

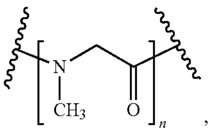

, wherein:

each -Cy- is independently an optionally substituted bivalent ring selected from phenylenyl, an 8-10 membered bicyclic arylenyl, a 4-7 membered saturated or partially unsaturated carbocyclylenyl, a 4-7 membered saturated or partially unsaturated spiro carbocyclylenyl, an 8-10 membered bicyclic saturated or partially unsaturated carbocyclylenyl, a 4-7 membered saturated or partially unsaturated heterocyclylenyl having 1-2 heteroatoms independently selected from nitrogen, oxygen, and sulfur, a 4-7 membered saturated or partially unsaturated spiro heterocyclylenyl having 1-2 heteroatoms independently selected from nitrogen, oxygen, and sulfur, an 8-10 membered bicyclic saturated or partially unsaturated heterocyclylenyl having 1-2 heteroatoms independently selected from nitrogen, oxygen, and sulfur, a 5-6 membered heteroarylenyl having 1-4 heteroatoms independently selected from nitrogen, oxygen, and sulfur, or an 8-10 membered bicyclic heteroarylenyl having 1-5 heteroatoms independently selected from nitrogen, oxygen, or sulfur;

each of n is independently 1, 2, 3, 4, 5, 6, 7, 8, 9, or 10; and

TBM is a target binding moiety.

Where a point of attachment of

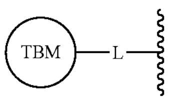

is depicted on Ring B, Ring D, or Ring C, it is intended, and one of ordinary skill in the art would appreciate, that the point of attachment of

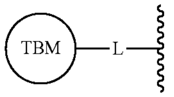

may be on any available carbon or nitrogen atom on Ring B, Ring D, or Ring C, including the ring to which Ring B or Ring C is fused to Ring D.

Where a point of attachment of —$(R^2)_m$ is depicted on Ring B, Ring D, or Ring C, it is intended, and one of ordinary skill in the art would appreciate, that the point of attachment of —$(R^2)_m$ may be at any available carbon or nitrogen atom on Ring B, Ring D, or Ring C including the carbon atom to which Ring B or Ring C are fused to Ring D.

Where a point of attachment of

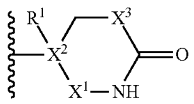

is depicted on Ring B, Ring D, or Ring C, it is intended, and one of ordinary skill in the art would appreciate, that the point of attachment of

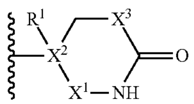

may be on any available carbon or nitrogen atom on Ring B, Ring D, or Ring C, including the carbon atom to which Ring B or Ring C are fused to Ring D.

In certain embodiments, the present invention provides a compound of formula II:

II

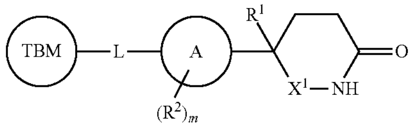

or a pharmaceutically acceptable salt thereof, wherein:

$X^1$ is a bivalent moiety selected from a covalent bond, —$CH_2$—, —C(O)—, —C(S)—, or

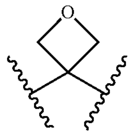

;

$R^1$ is hydrogen, deuterium, halogen, —CN, —OR, —SR, —S(O)R, —$S(O)_2R$, —$N(R)_2$, —$Si(R)_3$, or an optionally substituted $C_{1-4}$ aliphatic;

each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

each $R^2$ is independently hydrogen, deuterium, —$R^3$, halogen, —CN, —$NO_2$, —OR, —SR, —$N(R)_2$, —$Si(R)_3$, —$S(O)_2R$, —$S(O)_2N(R)_2$, —S(O)R, —C(O)R, —C(O)OR, —$C(O)N(R)_2$, —C(O)N(R)OR, —$C(R)_2N(R)C(O)R$, —$C(R)_2N(R)C(O)N(R)_2$, —OC(O)R, —$OC(O)N(R)_2$, —N(R)C(O)OR, —N(R)C(O)R, —$N(R)C(O)N(R)_2$, or —$N(R)S(O)_2R$;

each $R^3$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

Ring A is a tricyclic ring selected from

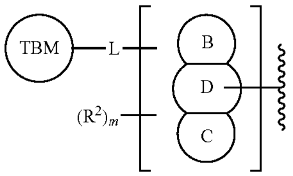

, wherein each of Ring B, Ring C, and Ring D is independently a fused ring selected from 6-membered aryl containing 0-3 nitrogens, 5 to 7-membered saturated or partially unsaturated carbocyclyl, 5 to 7-membered saturated or partially unsaturated heterocyclyl ring with 1-3 heteroatoms independently selected from boron, nitrogen, oxygen, silicon, or sulfur, or 5-membered heteroaryl with 1-3 heteroatoms independently selected from nitrogen, oxygen or sulfur; and m is 0, 1, 2, 3, 4, 5, 6, 7, 8, 9, 10, 11, 12, 13, 14, 15, or 16;

L is a covalent bond or a bivalent, saturated or unsaturated, straight or branched $C_{1-50}$ hydrocarbon chain, wherein 0-6 methylene units of L are independently replaced by —C(D)(H)—, —C(D)$_2$-, -Cy-, —O—, —NR—, —S—, —OC(O)—, —C(O)O—, —C(O)—, —S(O)—, —S(O)$_2$—, —NRS(O)$_2$—, —Si(R$_2$)—, —S(O)$_2$NR—, —NRC(O)—, —C(O)NR—, —OC(O)NR—, —NRC(O)O—,

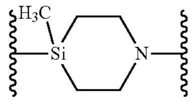, 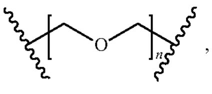,

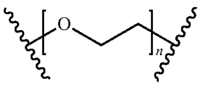, 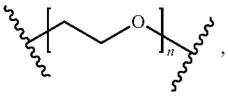,

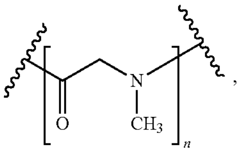, or 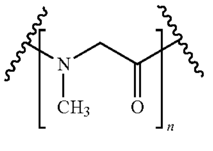, wherein:

each -Cy- is independently an optionally substituted bivalent ring selected from phenylenyl, an 8-10 membered bicyclic arylenyl, a 4-7 membered saturated or partially unsaturated carbocyclylenyl, a 4-7 membered saturated or partially unsaturated spiro carbocyclylenyl, an 8-10 membered bicyclic saturated or partially unsaturated carbocyclylenyl, a 4-7 membered saturated or partially unsaturated heterocyclylenyl having 1-2 heteroatoms independently selected from nitrogen, oxygen, and sulfur, a 4-7 membered saturated or partially unsaturated spiro heterocyclylenyl having 1-2 heteroatoms independently selected from nitrogen, oxygen, and sulfur, an 8-10 membered bicyclic saturated or partially unsaturated heterocyclylenyl having 1-2 heteroatoms independently selected from nitrogen, oxygen, and sulfur, a 5-6 membered heteroarylenyl having 1-4 heteroatoms independently selected from nitrogen, oxygen, and sulfur, or an 8-10 membered bicyclic heteroarylenyl having 1-5 heteroatoms independently selected from nitrogen, oxygen, or sulfur;

each of n is independently 1, 2, 3, 4, 5, 6, 7, 8, 9, or 10; and

TBM is a target binding moiety.

Where a point of attachment of

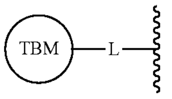

is depicted on Ring B, Ring C, or Ring D, it is intended, and one of ordinary skill in the art would appreciate, that the point of attachment of

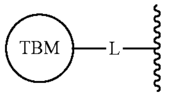

may be on Ring A and may also be at any available carbon or nitrogen atom on Ring A including the carbon atom to which Ring B or Ring C is fused to Ring D.

Where a point of attachment of —(R$^2$)$_m$ is depicted on Ring B, Ring C, and Ring D, it is intended, and one of ordinary skill in the art would appreciate, that the point of attachment of —(R$^2$)$_m$ may be on Ring A and may also be at any available carbon or nitrogen atom on Ring A including the carbon atom to which Ring B or Ring C are fused to Ring D.

Where a point of attachment of

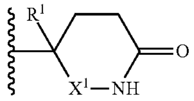

is depicted on Ring D, it is intended, and one of ordinary skill in the art would appreciate, that the point of attachment of

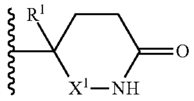

may be on any available carbon or nitrogen atom on Ring D including the carbon atom to which Ring B or Ring C are fused to Ring D.

In certain embodiments, the present invention provides a compound of formula II':

II'

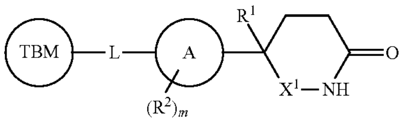

or a pharmaceutically acceptable salt thereof, wherein:

X$^1$ is a bivalent moiety selected from a covalent bond, —CH$_2$—, —CHCF$_3$—, —SO$_2$—, —S(O)—, —P(O)R—, —P(O)OR—, —P(O)NR$_2$—, —C(O)—, —C(S)—, or

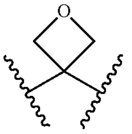;

R$^1$ is hydrogen, deuterium, halogen, —CN, —OR, —SR, —S(O)R, —S(O)$_2$R, —N(R)$_2$, —P(O)(OR)$_2$, —P(O)(NR$_2$)OR, —P(O)(NR$_2$)$_2$, —Si(OH)$_2$R, —Si(OH)(R)$_2$, —Si(R)$_3$, or an optionally substituted $C_{1-4}$ aliphatic;

each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

each $R^2$ is independently hydrogen, deuterium, —$R^3$, halogen, —CN, —$NO_2$, —OR, —SR, —$N(R)_2$, —$Si(R)_3$, —$S(O)_2R$, —$S(O)_2N(R)_2$, —S(O)R, —C(O)R, —C(O)OR, —$C(O)N(R)_2$, —C(O)N(R)OR, —$C(R)_2N(R)C(O)R$, —$C(R)_2N(R)C(O)N(R)_2$, —OC(O)R, —$OC(O)N(R)_2$, —$OP(O)R_2$, —$OP(O)(OR)_2$, —$OP(O)(OR)(NR_2)$, —$OP(O)(NR_2)_2$—, —N(R)C(O)OR, —N(R)C(O)R, —$N(R)C(O)N(R)_2$, —$N(R)S(O)_2R$, —$NP(O)R_2$, —$N(R)P(O)(OR)_2$, —$N(R)P(O)(OR)(NR_2)$, —$N(R)P(O)(NR_2)_2$, or —$N(R)S(O)_2R$;

each $R^3$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

Ring A is a tricyclic ring selected from

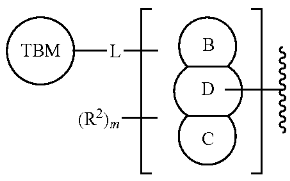

wherein each of Ring B, Ring C, and Ring D is independently a fused ring selected from 6-membered aryl, 6-membered heteroaryl containing 1-4 heteroatoms independently selected from nitrogen, oxygen, or sulfur, 5 to 7-membered saturated or partially unsaturated carbocyclyl, 5 to 7-membered saturated or partially unsaturated heterocyclyl ring with 1-3 heteroatoms independently selected from boron, nitrogen, oxygen, silicon, or sulfur, or 5-membered heteroaryl with 1-4 heteroatoms independently selected from nitrogen, oxygen or sulfur; and m is 0, 1, 2, 3, 4, 5, 6, 7, 8, 9, 10, 11, 12, 13, 14, 15, or 16;

L is a covalent bond or a bivalent, saturated or unsaturated, straight or branched $C_{1-50}$ hydrocarbon chain, wherein 0-6 methylene units of L are independently replaced by —C(D)(H)—, —$C(D)_2$-, -Cy-, —O—, —NR—, —$Si(R)_2$—, —Si(OH)(R)—, —$Si(OH)_2$—, —P(O)(OR)—, —P(O)(R)—, —$P(O)(NR_2)$—, —S—, —OC(O)—, —C(O)O—, —C(O)—, —S(O)—, —$S(O)_2$—, —$NRS(O)_2$—, —$S(O)_2NR$—, —NRC(O)—, —C(O)NR—, —OC(O)NR—, —NRC(O)O—,

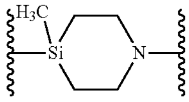,
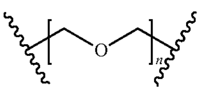,

-continued

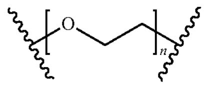,
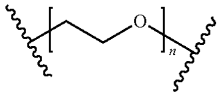,

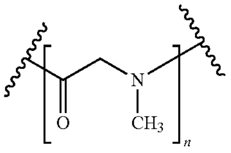, or
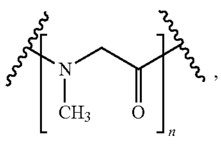, wherein:

each -Cy- is independently an optionally substituted bivalent ring selected from phenylenyl, an 8-10 membered bicyclic arylenyl, a 4-7 membered saturated or partially unsaturated carbocyclylenyl, a 4-7 membered saturated or partially unsaturated spiro carbocyclylenyl, an 8-10 membered bicyclic saturated or partially unsaturated carbocyclylenyl, a 4-7 membered saturated or partially unsaturated heterocyclylenyl having 1-2 heteroatoms independently selected from nitrogen, oxygen, and sulfur, a 4-7 membered saturated or partially unsaturated spiro heterocyclylenyl having 1-2 heteroatoms independently selected from nitrogen, oxygen, and sulfur, an 8-10 membered bicyclic saturated or partially unsaturated heterocyclylenyl having 1-2 heteroatoms independently selected from nitrogen, oxygen, and sulfur, a 5-6 membered heteroarylenyl having 1-4 heteroatoms independently selected from nitrogen, oxygen, and sulfur, or an 8-10 membered bicyclic heteroarylenyl having 1-5 heteroatoms independently selected from nitrogen, oxygen, or sulfur;

each of n is independently 1, 2, 3, 4, 5, 6, 7, 8, 9, or 10; and

TBM is a target binding moiety.

Where a point of attachment of

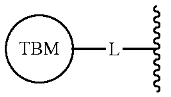

is depicted on Ring B, Ring C, or Ring D, it is intended, and one of ordinary skill in the art would appreciate, that the point of attachment of

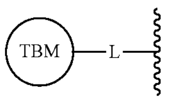

may be on Ring A and may also be at any available carbon or nitrogen atom on Ring A including the carbon atom to which Ring B or Ring C is fused to Ring D.

Where a point of attachment of —$(R^2)_m$ is depicted on Ring B, Ring C, and Ring D, it is intended, and one of ordinary skill in the art would appreciate, that the point of attachment of —$(R^2)_m$ may be on Ring A and may also be at any available carbon or nitrogen atom on Ring A including the carbon atom to which Ring B or Ring C are fused to Ring D.

Where a point of attachment of

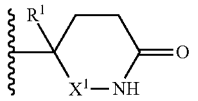

is depicted on Ring B, Ring C, and Ring D, it is intended, and one of ordinary skill in the art would appreciate, that the point of attachment of

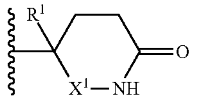

may be on any available carbon or nitrogen atom on Ring A including the carbon atom to which Ring B or Ring C are fused to Ring D.

In certain embodiments, the present invention provides a compound of formula II-a:

II-a

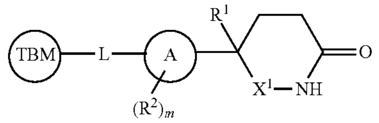

or a pharmaceutically acceptable salt thereof, wherein:

$X^1$ is a bivalent moiety selected from a covalent bond, —$CH_2$—, —C(O)—, —C(S)—, or

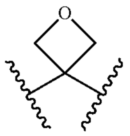

;

$R^1$ is hydrogen, deuterium, halogen, —CN, —OR, —SR, —S(O)R, —$S(O)_2R$, —$N(R)_2$, —$Si(R)_3$, or an optionally substituted $C_{1-4}$ aliphatic;

each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

each $R^2$ is independently hydrogen, —$R^3$, halogen, —CN, —$NO_2$, —OR, —SR, —$N(R)_2$, —$Si(R)_3$, —$S(O)_2R$, —$S(O)_2N(R)_2$, —S(O)R, —C(O)R, —C(O)OR, —$C(O)N(R)_2$, —C(O)N(R)OR, —$C(R)_2N(R)C(O)R$, —$C(R)_2N(R)C(O)N(R)_2$, —OC(O)R, —$OC(O)N(R)_2$, —N(R)C(O)OR, —N(R)C(O)R, —$N(R)C(O)N(R)_2$, or —$N(R)S(O)_2R$;

each $R^3$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

Ring A is a tricyclic ring selected from

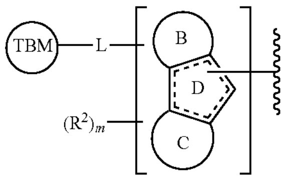

,

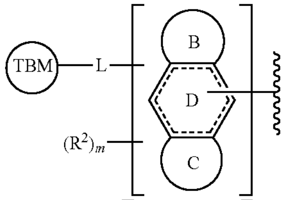

,

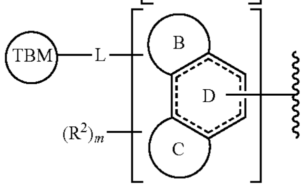

,

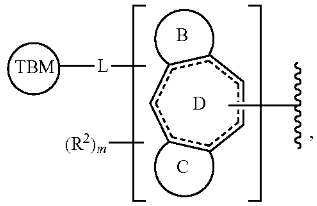

, or

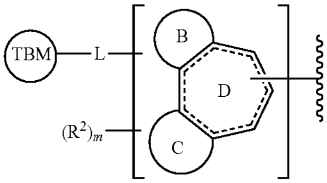

, wherein each of Ring B and Ring C is independently a fused ring selected from 6-membered aryl containing 0-3 nitrogens, 5 to 7-membered saturated or partially unsaturated carbocyclyl, 5 to 7-membered saturated or partially unsaturated heterocyclyl ring with 1-3 heteroatoms independently selected from boron, nitrogen, oxygen or sulfur, or 5-membered heteroaryl with 1-3 heteroatoms independently selected from nitrogen, oxygen or sulfur;

Ring D is a fused ring selected from aryl containing 0-3 nitrogens, saturated or partially unsaturated carbocyclyl, saturated or partially unsaturated heterocyclyl ring with 1-2 heteroatoms independently selected from nitrogen, oxygen, silicon, or sulfur, or heteroaryl with 1-3 heteroatoms independently selected from nitrogen, oxygen or sulfur;

is a single or double bond;

m is 0, 1, 2, 3, 4, 5, 6, 7, 8, 9, 10, 11, 12, 13, 14, 15, or 16;

L is a covalent bond or a bivalent, saturated or unsaturated, straight or branched $C_{1-50}$ hydrocarbon chain, wherein 0-6 methylene units of L are independently replaced by -Cy-, —O—, —NR—, —S—, —OC(O)—, —C(O)O—, —C(O)—, —S(O)—, —$S(O)_2$—, —$NRS(O)_2$—, —$Si(R_2)$—, —$S(O)_2NR$—, —NRC(O)—, —C(O)NR—, —OC(O)NR—, —NRC(O)O—,

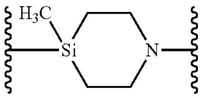,
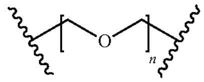,
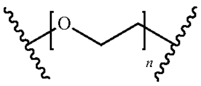,
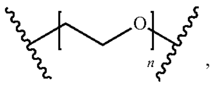,
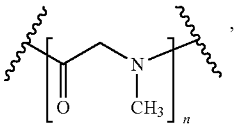, or
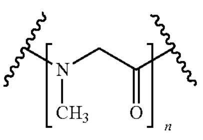, wherein:

each -Cy- is independently an optionally substituted bivalent ring selected from phenylenyl, an 8-10 membered bicyclic arylenyl, a 4-7 membered saturated or partially unsaturated carbocyclylenyl, a 4-7 membered saturated or partially unsaturated spiro carbocyclylenyl, an 8-10 membered bicyclic saturated or partially unsaturated carbocyclylenyl, a 4-7 membered saturated or partially unsaturated heterocyclylenyl having 1-2 heteroatoms independently selected from nitrogen, oxygen, and sulfur, a 4-7 membered saturated or partially unsaturated spiro heterocyclylenyl having 1-2 heteroatoms independently selected from nitrogen, oxygen, and sulfur, an 8-10 membered bicyclic saturated or partially unsaturated heterocyclylenyl having 1-2 heteroatoms independently selected from nitrogen, oxygen, and sulfur, a 5-6 membered heteroarylenyl having 1-4 heteroatoms independently selected from nitrogen, oxygen, and sulfur, or an 8-10 membered bicyclic heteroarylenyl having 1-5 heteroatoms independently selected from nitrogen, oxygen, or sulfur;

each of n is independently 1, 2, 3, 4, 5, 6, 7, 8, 9, or 10; and

TBM is a target binding moiety.

Where a point of attachment of

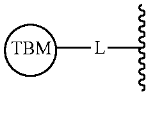

is depicted on Ring B, Ring C, or Ring D, it is intended, and one of ordinary skill in the art would appreciate, that the point of attachment of

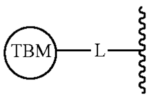

may be on Ring A and may also be at any available carbon or nitrogen atom on Ring A including the carbon atom to which Ring B or Ring C is fused to Ring D.

Where a point of attachment of —$(R^2)_m$ is depicted on Ring B, Ring C, and Ring D, it is intended, and one of ordinary skill in the art would appreciate, that the point of attachment of —$(R^2)_m$ may be on Ring A and may also be at any available carbon or nitrogen atom on Ring A including the carbon atom to which Ring B or Ring C are fused to Ring D.

Where a point of attachment of

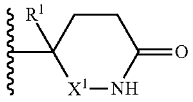

is depicted on Ring D, it is intended, and one of ordinary skill in the art would appreciate, that the point of attachment of

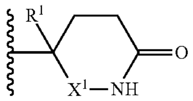

may be on any available carbon or nitrogen atom on Ring D including the carbon atom to which Ring B or Ring C are fused to Ring D.

In certain embodiments, the present invention provides a compound of formula II-b:

II-b

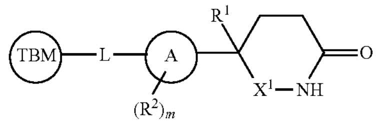

or a pharmaceutically acceptable salt thereof, wherein:

$X^1$ is a bivalent moiety selected from a covalent bond, —$CH_2$—, —C(O)—, —C(S)—, or

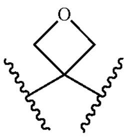;

$R^1$ is hydrogen, deuterium, halogen, —CN, —OR, —SR, —S(O)R, —$S(O)_2R$, —$N(R)_2$, —$Si(R)_3$, or an optionally substituted $C_{1-4}$ aliphatic;

each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

each $R^2$ is independently hydrogen, —$R^3$, halogen, —CN, —$NO_2$, —OR, —SR, —$N(R)_2$, —$Si(R)_3$, —$S(O)_2R$, —$S(O)_2N(R)_2$, —S(O)R, —C(O)R, —C(O)OR, —$C(O)N(R)_2$, —C(O)N(R)OR, —$C(R)_2N(R)C(O)R$, —$C(R)_2N(R)C(O)N(R)_2$, —OC(O)R, —$OC(O)N(R)_2$, —N(R)C(O)OR, —N(R)C(O)R, —$N(R)C(O)N(R)_2$, or —$N(R)S(O)_2R$;

each $R^3$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

Ring A is a tricyclic ring selected from

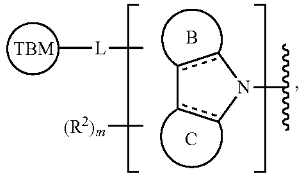
,
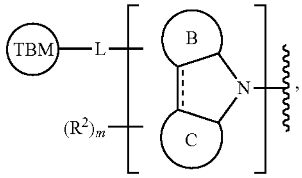
,
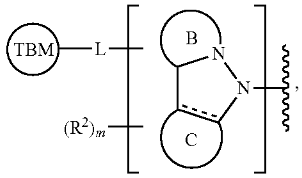
,
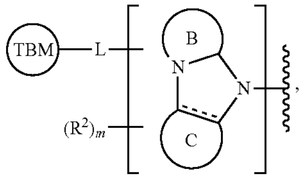
,
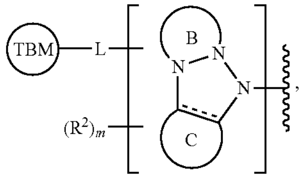
,
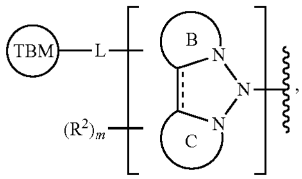
,
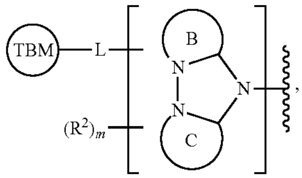
, -continued

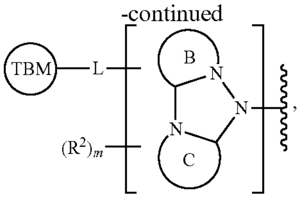
, or
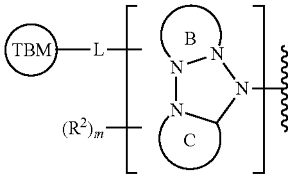
, wherein each of Ring B and Ring C is independently a fused ring selected from 6-membered aryl containing 0-2 nitrogens, 5 to 7-membered saturated or partially unsaturated carbocyclyl, 5 to 7-membered saturated or partially unsaturated heterocyclyl ring with 1-3 heteroatoms independently selected from boron, nitrogen, oxygen, silicon, or sulfur, or 5-membered heteroaryl with 1-3 heteroatoms independently selected from nitrogen, oxygen or sulfur;

$\overline{---}$ is a single or double bond;

m is 0, 1, 2, 3, 4, 5, 6, 7, or 8;

L is a covalent bond or a bivalent, saturated or unsaturated, straight or branched $C_{1-50}$ hydrocarbon chain, wherein 0-6 methylene units of L are independently replaced by -Cy-, —O—, —NR—, —S—, —OC(O)—, —C(O)O—, —C(O)—, —S(O)—, —$S(O)_2$—, —$NRS(O)_2$—, —$Si(R_2)$—, —$S(O)_2NR$—, —NRC(O)—, —C(O)NR—, —OC(O)NR—, —NRC(O)O—,

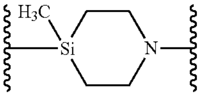
,
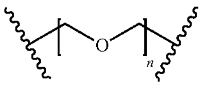
,
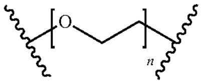
,
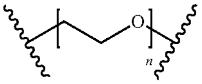
,
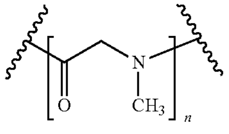
, or
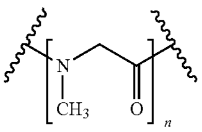
, wherein:

each -Cy- is independently an optionally substituted bivalent ring selected from phenylenyl, an 8-10 membered bicyclic arylenyl, a 4-7 membered saturated or partially unsaturated carbocyclylenyl, a 4-7 membered saturated or partially unsaturated spiro carbocyclylenyl, an 8-10 membered bicyclic saturated or partially unsaturated carbocyclylenyl, a 4-7 membered saturated or partially unsaturated heterocyclylenyl having 1-2 heteroatoms independently selected from nitrogen, oxygen, and sulfur, a 4-7 membered saturated or partially unsaturated spiro heterocyclylenyl having 1-2 heteroatoms independently selected from nitrogen, oxygen, and sulfur, an 8-10 membered bicyclic saturated or partially unsaturated heterocyclylenyl having 1-2 heteroatoms independently selected from nitrogen, oxygen, and sulfur, a 5-6 membered heteroarylenyl having 1-4 heteroatoms independently selected from nitrogen, oxygen, and sulfur, or an 8-10 membered bicyclic heteroarylenyl having 1-5 heteroatoms independently selected from nitrogen, oxygen, or sulfur;

each of n is independently 1, 2, 3, 4, 5, 6, 7, 8, 9, or 10; and

TBM is a target binding moiety.

Where a point of attachment of

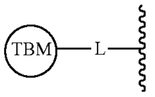

is depicted on Ring B or Ring C, it is intended, and one of ordinary skill in the art would appreciate, that the point of attachment of

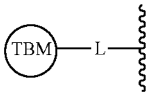

may be on Ring A and may also be at any available carbon or nitrogen atom on Ring A including the carbon atom to which Ring B or Ring C is fused.

Where a point of attachment of —$(R^2)_m$ is depicted on Ring B or Ring C, it is intended, and one of ordinary skill in the art would appreciate, that the point of attachment of —$(R^2)_m$ may be on Ring A and may also be at any available carbon or nitrogen atom on Ring A including the carbon atom ring to which Ring B or Ring C is fused.

In certain embodiments, the present invention provides a compound of formula II-c:

II-c

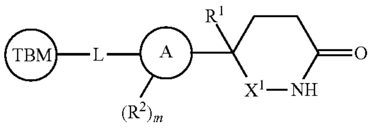

or a pharmaceutically acceptable salt thereof, wherein:

$X^1$ is a bivalent moiety selected from a covalent bond, —$CH_2$—, —$CHCF_3$—, —$SO_2$—, —S(O)—, —P(O)R—, —P(O)OR—, —P(O)$NR_2$—, —C(O)—, —C(S)—, or

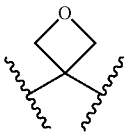

;

$R^1$ is hydrogen, deuterium, halogen, —CN, —OR, —SR, —S(O)R, —$S(O)_2R$, —$N(R)_2$, —$P(O)(OR)_2$, —P(O)($NR_2$)OR, —$P(O)(NR_2)_2$, —$Si(OH)_2R$, —Si(OH)$(R)_2$, —$Si(R)_3$, or an optionally substituted $C_{1-4}$ aliphatic;

each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

each $R^2$ is independently hydrogen, deuterium, —$R^3$, halogen, —CN, —$NO_2$, —OR, —SR, —$N(R)_2$, —$Si(R)_3$, —$S(O)_2R$, —$S(O)_2N(R)_2$, —S(O)R, —C(O)R, —C(O)OR, —C(O)$N(R)_2$, —C(O)N(R)OR, —$C(R)_2$N(R)C(O)R, —$C(R)_2$N(R)C(O)$N(R)_2$, —OC(O)R, —OC(O)$N(R)_2$, —OP(O)$R_2$, —OP(O)$(OR)_2$, —OP(O)(OR)($NR_2$), —OP(O)$(NR_2)_2$—, —N(R)C(O)OR, —N(R)C(O)R, —N(R)C(O)$N(R)_2$, —N(R)$S(O)_2R$, —NP(O)$R_2$, —N(R)P(O)$(OR)_2$, —N(R)P(O)(OR)($NR_2$), —N(R)P(O)$(NR_2)_2$, or —N(R)$S(O)_2R$;

each $R^3$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

Ring A is a bicyclic ring system selected from

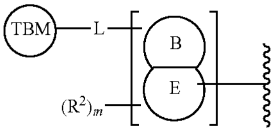

, wherein

Ring B is a fused ring selected from 6-membered aryl, 6-membered heteroaryl containing 1-4 heteroatoms independently selected from nitrogen, oxygen, or sulfur, 5 to 7-membered saturated or partially unsaturated carbocyclyl, 5 to 7-membered saturated or partially unsaturated heterocyclyl ring with 1-3 heteroatoms independently selected from boron, nitrogen, oxygen, silicon, or sulfur, or 5-membered heteroaryl with 1-4 heteroatoms independently selected from nitrogen, oxygen or sulfur;

Ring E is a ring selected from a 7-9 membered saturated or partially unsaturated carbocyclyl or hetercyclyl ring with 1-3 heteroatoms independently selected from boron, nitrogen, oxygen, silicon, or sulfur, wherein Ring E is optionally further substituted with 1-2 oxo groups; and m is 0, 1, 2, 3, 4, 5, 6, 7, 8, 9, 10, 11, 12, 13, 14, 15, or 16;

L is a covalent bond or a bivalent, saturated or unsaturated, straight or branched $C_{1-50}$ hydrocarbon chain, wherein 0-6 methylene units of L are independently replaced by —C(D)(H)—, —$C(D)_2$-, -Cy-, —O—, —NR—, —$Si(R)_2$—, —Si(OH)(R)—, —$Si(OH)_2$—, —P(O)(OR)—, —P(O)(R)—, —P(O)($NR_2$)—, —S—, —OC(O)—, —C(O)O—, —C(O)—, —S(O)—, —$S(O)_2$—, —NR$S(O)_2$—, —$S(O)_2$NR—, —NRC(O)—, —C(O)NR—, —OC(O)NR—, —NRC(O)O—,

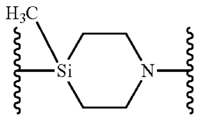, 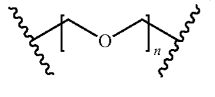,

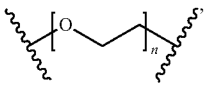, 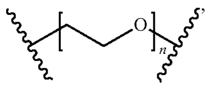,

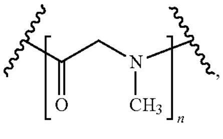, or 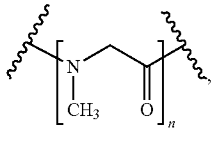, wherein:

each -Cy- is independently an optionally substituted bivalent ring selected from phenylenyl, an 8-10 membered bicyclic arylenyl, a 4-7 membered saturated or partially unsaturated carbocyclylenyl, a 4-7 membered saturated or partially unsaturated spiro carbocyclylenyl, an 8-10 membered bicyclic saturated or partially unsaturated carbocyclylenyl, a 4-7 membered saturated or partially unsaturated heterocyclylenyl having 1-2 heteroatoms independently selected from nitrogen, oxygen, and sulfur, a 4-7 membered saturated or partially unsaturated spiro heterocyclylenyl having 1-2 heteroatoms independently selected from nitrogen, oxygen, and sulfur, an 8-10 membered bicyclic saturated or partially unsaturated heterocyclylenyl having 1-2 heteroatoms independently selected from nitrogen, oxygen, and sulfur, a 5-6 membered heteroarylenyl having 1-4 heteroatoms independently selected from nitrogen, oxygen, and sulfur, or an 8-10 membered bicyclic heteroarylenyl having 1-5 heteroatoms independently selected from nitrogen, oxygen, or sulfur;

each of n is independently 1, 2, 3, 4, 5, 6, 7, 8, 9, or 10; and

TBM is a target binding moiety.

Where a point of attachment of

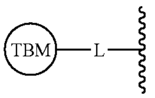

is depicted on Ring B or Ring E, it is intended, and one of ordinary skill in the art would appreciate, that the point of attachment of

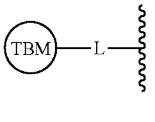

may be on Ring A and may also be at any available carbon or nitrogen atom on Ring A including the carbon atom to which Ring B and Ring E are fused.

Where a point of attachment of $-(R^2)_m$ is depicted on Ring B and Ring E, it is intended, and one of ordinary skill in the art would appreciate, that the point of attachment of $-(R^2)_m$ may be on Ring A and may also be at any available carbon or nitrogen atom on Ring A including the carbon atom to which Ring B and Ring E are fused.

Where a point of attachment of

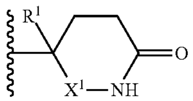

is depicted on Ring B and Ring E, it is intended, and one of ordinary skill in the art would appreciate, that the point of attachment of

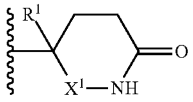

may be on Ring A and may also be at any available carbon or nitrogen atom on Ring A including the carbon atom to which Ring B and Ring E are fused.

In certain embodiments, the present invention provides a compound of formula II-d:

II-d

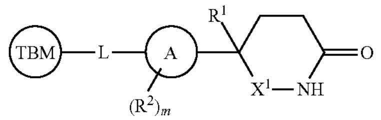

or a pharmaceutically acceptable salt thereof, wherein:

$X^1$ is a bivalent moiety selected from a covalent bond, $-CH_2-$, $-CHCF_3-$, $-SO_2-$, $-S(O)-$, $-P(O)R-$, $-P(O)OR-$, $-P(O)NR_2-$, $-C(O)-$, $-C(S)-$, or

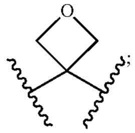;

$R^1$ is hydrogen, deuterium, halogen, $-CN$, $-OR$, $-SR$, $-S(O)R$, $-S(O)_2R$, $-NR_2$, $-P(O)(OR)_2$, $-P(O)(NR_2)OR$, $-P(O)(NR_2)_2$, $-Si(OH)_2R$, $-Si(OH)(R)_2$, $-Si(R)_3$, or an optionally substituted $C_{1-4}$ aliphatic;

each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

each $R^2$ is independently hydrogen, deuterium, $-R^3$, halogen, $-CN$, $-NO_2$, $-OR$, $-SR$, $-N(R)_2$, $-Si(R)_3$, $-S(O)_2R$, $-S(O)_2N(R)_2$, $-S(O)R$, $-C(O)R$, —C(O)OR, —C(O)N(R)$_2$, —C(O)N(R)OR, —C(R)$_2$N(R)C(O)R, —C(R)$_2$N(R)C(O)N(R)$_2$, —OC(O)R, —OC(O)N(R)$_2$, —OP(O)R$_2$, —OP(O)(OR)$_2$, —OP(O)(OR)(NR$_2$), —OP(O)(NR$_2$)$_2$—, —N(R)C(O)OR, —N(R)C(O)R, —N(R)C(O)N(R)$_2$, —N(R)S(O)$_2$R, —NP(O)R$_2$, —N(R)P(O)(OR)$_2$, —N(R)P(O)(OR)(NR$_2$), —N(R)P(O)(NR$_2$)$_2$, or —N(R)S(O)$_2$R;

each $R^3$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

Ring A is a tricyclic ring system selected from

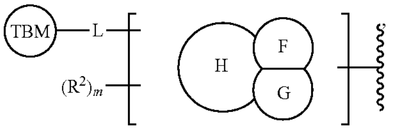

wherein each of Ring F and G is independently a fused ring selected from 6-membered aryl, 6-membered heteroaryl containing 1-4 heteroatoms independently selected from nitrogen, oxygen, or sulfur, 5 to 7-membered saturated or partially unsaturated carbocyclyl, 5 to 7-membered saturated or partially unsaturated heterocyclyl ring with 1-3 heteroatoms independently selected from boron, nitrogen, oxygen, silicon, or sulfur, or 5-membered heteroaryl with 1-4 heteroatoms independently selected from nitrogen, oxygen or sulfur;

Ring H is a fused ring selected from a 7-12 membered saturated or partially unsaturated carbocyclyl or hetercyclyl ring with 1-3 heteroatoms independently selected from boron, nitrogen, oxygen, silicon, or sulfur, wherein Ring H is optionally further substituted with 1-2 oxo groups;

m is 0, 1, 2, 3, 4, 5, 6, 7, 8, 9, 10, 11, 12, 13, 14, 15, or 16;

L is a covalent bond or a bivalent, saturated or unsaturated, straight or branched $C_{1-50}$ hydrocarbon chain, wherein 0-6 methylene units of L are independently replaced by —C(D)(H)—, —C(D)$_2$-, -Cy-, —O—, —NR—, —Si(R)$_2$—, —Si(OH)(R)—, —Si(OH)$_2$—, —P(O)(OR)—, —P(O)(R)—, —P(O)(NR$_2$)—, —S—, —OC(O)—, —C(O)O—, —C(O)—, —S(O)—, —S(O)$_2$—, —NRS(O)$_2$—, —S(O)$_2$NR—, —NRC(O)—, —C(O)NR—, —OC(O)NR—, —NRC(O)O—,

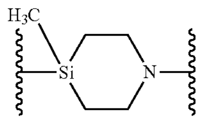,
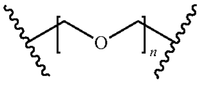,
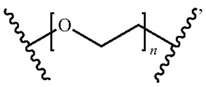,
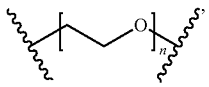,
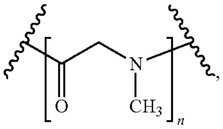, or
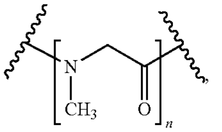

wherein:

each -Cy- is independently an optionally substituted bivalent ring selected from phenylenyl, an 8-10 membered bicyclic arylenyl, a 4-7 membered saturated or partially unsaturated carbocyclylenyl, a 4-7 membered saturated or partially unsaturated spiro carbocyclylenyl, an 8-10 membered bicyclic saturated or partially unsaturated carbocyclylenyl, a 4-7 membered saturated or partially unsaturated heterocyclylenyl having 1-2 heteroatoms independently selected from nitrogen, oxygen, and sulfur, a 4-7 membered saturated or partially unsaturated spiro heterocyclylenyl having 1-2 heteroatoms independently selected from nitrogen, oxygen, and sulfur, an 8-10 membered bicyclic saturated or partially unsaturated heterocyclylenyl having 1-2 heteroatoms independently selected from nitrogen, oxygen, and sulfur, a 5-6 membered heteroarylenyl having 1-4 heteroatoms independently selected from nitrogen, oxygen, and sulfur, or an 8-10 membered bicyclic heteroarylenyl having 1-5 heteroatoms independently selected from nitrogen, oxygen, or sulfur;

each of n is independently 1, 2, 3, 4, 5, 6, 7, 8, 9, or 10; and

TBM is a target binding moiety.

Where a point of attachment of

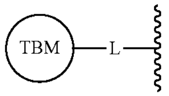

is depicted on Ring F, Ring G, or Ring H, it is intended, and one of ordinary skill in the art would appreciate, that the point of TBM L attachment of

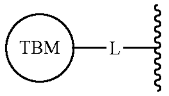

may be on Ring A and may also be at any available carbon or nitrogen atom on Ring A including the carbon atom to which Ring F, Ring G, and Ring H are fused.

Where a point of attachment of —$(R^2)_m$ is depicted on Ring F, Ring G, and Ring H, it is intended, and one of ordinary skill in the art would appreciate, that the point of attachment of —$(R^2)_m$ may be on Ring A and may also be at any available carbon or nitrogen atom on Ring A including the carbon atom to which Ring F, Ring G, and Ring H are fused.

Where a point of attachment of

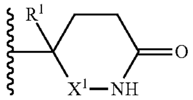

is depicted on Ring F, Ring G, and Ring H, it is intended, and one of ordinary skill in the art would appreciate, that the point of attachment of

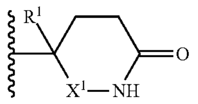

may be on Ring A and may also be at any available carbon or nitrogen atom on Ring A including the carbon atom to which Ring F, Ring G, and Ring H are fused.

In certain embodiments, the present invention provides a compound of formula III or IV:

III

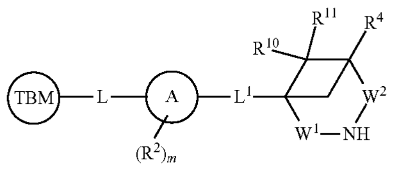

IV

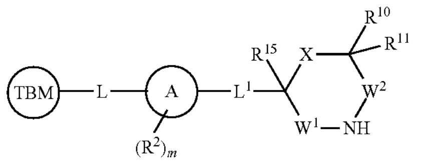

or a pharmaceutically acceptable salt thereof, wherein:

each $R^2$ is independently hydrogen, deuterium, —$R^3$, halogen, —CN, —$NO_2$, —OR, —SR, —$NR_2$, —$SiR_3$, —$S(O)_2R$, —$S(O)_2NR_2$, —S(O)R, —C(O)R, —C(O)OR, —C(O)$NR_2$, —C(O)N(R)OR, —C$(R)_2$N(R)C(O)R, —C$(R)_2$N(R)C(O)N$(R)_2$, —OC(O)R, —OC(O)N$(R)_2$, —OP(O)$R^2$, —OP(O)$(OR)_2$, —OP(O)(OR)$NR_2$, —OP(O)$(NR_2)_2$—, —N(R)C(O)OR, —N(R)C(O)R, —N(R)C(O)$NR_2$, —N(R)$S(O)_2R$, —NP(O)$R_2$, —N(R)P(O)$(OR)_2$, —N(R)P(O)(OR)$NR_2$, —N(R)P(O)$(NR_2)_2$, or —N(R)$S(O)_2R$;

each $R^3$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

Ring A is a tricyclic ring selected from

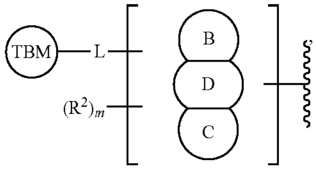

wherein each of Ring B, Ring D, and Ring C is independently a fused ring selected from 6-membered aryl, 6-membered heteroaryl containing 1-4 heteroatoms independently selected from nitrogen, oxygen, or sulfur, 5 to 7-membered saturated or partially unsaturated carbocyclyl, 5 to 7-membered saturated or partially unsaturated heterocyclyl with 1-3 heteroatoms independently selected from boron, nitrogen, oxygen, silicon, or sulfur, or 5-membered heteroaryl with 1-4 heteroatoms independently selected from nitrogen, oxygen or sulfur;

each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

$L^1$ is a covalent bond or a $C_{1-3}$ bivalent straight or branched saturated or unsaturated hydrocarbon chain wherein 1-2 methylene units of the chain are independently and optionally replaced with —O—, —C(O)—, —C(S)—, —$CR_2$—, —CFR—, —$CF_2$—, —NR—, —S—, —$S(O)_2$— or —CR═CR—;

m is 0, 1, 2, 3, 4, 5, 6, 7, 8, 9, 10, 11, 12, 13, 14, 15, or 16;

L is a covalent bond or a bivalent, saturated or unsaturated, straight or branched $C_{1-50}$ hydrocarbon chain, wherein 0-6 methylene units of L are independently replaced by —C(D)(H)—, —C$(D)_2$-, -Cy-, —O—, —NR—, —Si$(R)_2$—, —Si(OH)(R)—, —Si$(OH)_2$—, —P(O)(OR)—, —P(O)(R)—, —P(O)$(NR_2)$—, —S—, —OC(O)—, —C(O)O—, —C(O)—, —S(O)—, —$S(O)_2$—, —NRS$(O)_2$—, —$S(O)_2$NR—, —NRC(O)—, —C(O)NR—, —OC(O)NR—, —NRC(O)O—,

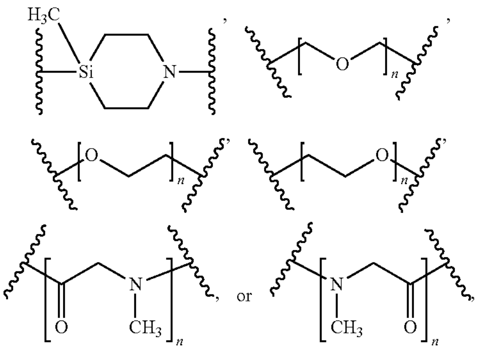

wherein:

each -Cy- is independently an optionally substituted bivalent ring selected from phenylenyl, an 8-10 membered bicyclic arylenyl, a 4-7 membered saturated or partially unsaturated carbocyclylenyl, a 4-7 membered saturated or partially unsaturated spiro carbocyclylenyl, an 8-10 membered bicyclic saturated or partially unsaturated carbocyclylenyl, a 4-7 membered saturated or partially unsaturated heterocyclylenyl having 1-2 heteroatoms independently selected from nitrogen, oxygen, and sulfur, a 4-7 membered saturated or partially unsaturated spiro heterocyclylenyl having 1-2 heteroatoms independently selected from nitrogen, oxygen, and sulfur, an 8-10 membered bicyclic saturated or partially unsaturated heterocyclylenyl having 1-2 heteroatoms independently selected from nitrogen, oxygen, and sulfur, a 5-6 membered heteroarylenyl having 1-4 heteroatoms independently selected from nitrogen, oxygen, and sulfur, or an 8-10 membered bicyclic heteroarylenyl having 1-5 heteroatoms independently selected from nitrogen, oxygen, or sulfur;

each of n is independently 1, 2, 3, 4, 5, 6, 7, 8, 9, or 10; and

TBM is a target binding moiety; and $R^4$, $R^{10}$, $R^{11}$, $R^{15}$, $W^1$, $W^2$, and X is as defined in WO 2019/099868, the entirety of each of which is herein incorporated by reference.

Where a point of attachment of

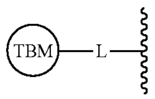

is depicted on Ring B, Ring D, or Ring C, it is intended, and one of ordinary skill in the art would appreciate, that the point of attachment of

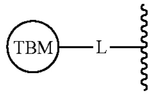

may be on any available carbon or nitrogen atom on Ring B, Ring D, or Ring C, including the ring to which Ring B or Ring C is fused to Ring D.

Where a point of attachment of $-(R^2)_m$ is depicted on Ring B, Ring D, or Ring C, it is intended, and one of ordinary skill in the art would appreciate, that the point of attachment of $-(R^2)_m$ may be at any available carbon or nitrogen atom on Ring B, Ring D, or Ring C including the carbon atom to which Ring B or Ring C are fused to Ring D.

Where a point of attachment of

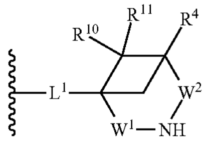
or
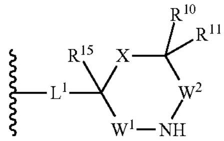

is depicted on Ring B, Ring D, or Ring C, it is intended, and one of ordinary skill in the art would appreciate, that the point of attachment of

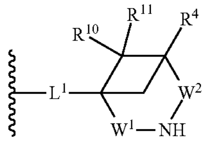
or
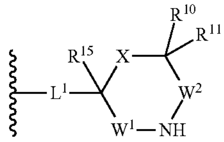

may be on any available carbon or nitrogen atom on Ring B, Ring D, or Ring C, including the carbon atom to which Ring B or Ring C are fused to Ring D.

2. Compounds and Definitions

Compounds of the present invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

As used herein, the term "bridged bicyclic" refers to any bicyclic ring system, i.e. carbocyclic or heterocyclic, saturated or partially unsaturated, having at least one bridge. As defined by IUPAC, a "bridge" is an unbranched chain of atoms or an atom or a valence bond connecting two bridgeheads, where a "bridgehead" is any skeletal atom of the ring system which is bonded to three or more skeletal atoms (excluding hydrogen). In some embodiments, a bridged bicyclic group has 7-12 ring members and 0-4 heteroatoms independently selected from nitrogen, oxygen, or sulfur. Such bridged bicyclic groups are well known in the art and include those groups set forth below where each group is attached to the rest of the molecule at any substitutable carbon or nitrogen atom. Unless otherwise specified, a bridged bicyclic group is optionally substituted with one or more substituents as set forth for aliphatic groups. Additionally or alternatively, any substitutable nitrogen of a bridged bicyclic group is optionally substituted. Exemplary bridged bicyclics include:

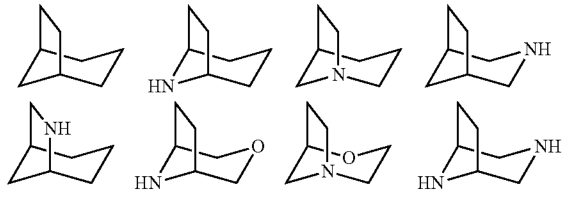

-continued

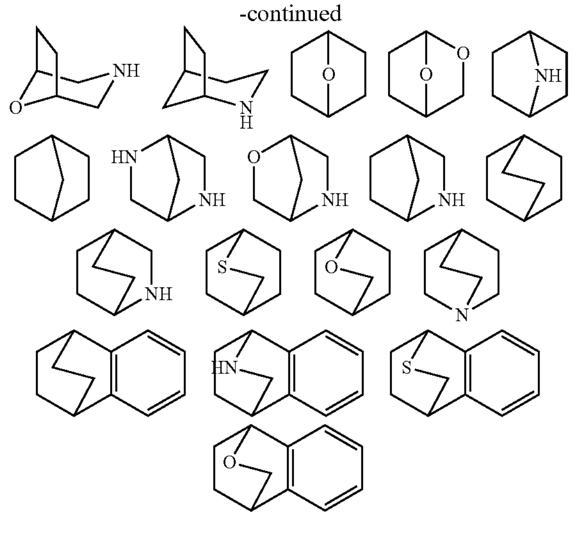

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated," as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., $-(CH_2)_n-$, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

As used herein, the term "cyclopropylenyl" refers to a bivalent cyclopropyl group of the following structure:

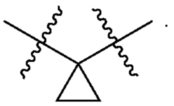 [SMILES: *C1(*)CC1]

The term "halogen" means F, Cl, Br, or I.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 9-membered monocyclic or 7- to 11-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+NR$ (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, 2-oxa-6-azaspiro[3.3]heptane, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; $—(CH_2)_{0-4}R^\circ$; $—(CH_2)_{0-4}R^\circ$; $—O(CH_2)_{0-4}R^\circ$, $—O—(CH_2)_{0-4}C(O)OR^\circ$; $—(CH_2)_{0-4}CH(OR^\circ)_2$; $—(CH_2)_{0-4}SR^\circ$; $—(CH_2)_{0-4}Ph$, which may be substituted with $R^\circ$; $—(CH_2)_{0-4}O(CH_2)_{0-1}$ Ph which may be substituted with $R^\circ$; $—CH{=}CHPh$, which may be substituted with $R^\circ$; $—(CH_2)_{0-4}O(CH_2)_{0-1}$-pyridyl which may be substituted with $R^\circ$; $—NO_2$; $—CN$; $—N_3$; $—(CH_2)_{0-4}N(R^\circ)_2$; $—(CH_2)_{0-4}N(R^\circ)C(O)R^\circ$; $—N(R^\circ)C(S)R^\circ$; $—(CH_2)_{0-4}N(R^\circ)C(O)NR^\circ_2$; $—N(R^\circ)C(S)NR^\circ_2$; $—(CH_2)_{0-4}$ $N(R^\circ)C(O)OR^\circ$; $—N(R^\circ)N(R^\circ)C(O)R^\circ$; $—N(R^\circ)N(R^\circ)C(O)NR^\circ_2$; $—N(R^\circ)N(R^\circ)C(O)OR^\circ$; $—(CH_2)_{0-4}C(O)R^\circ$; $—C(S)R^\circ$; $—(CH_2)_{0-4}C(O)OR^\circ$; $—(CH_2)_{0-4}C(O)SR^\circ$; $—(CH_2)_{0-4}C(O)OSiR^\circ_3$; $—(CH_2)_{0-4}C(O)R^\circ$; $—OC(O)(CH_2)_{0-4}SR^\circ$; $—SC(S)SR^\circ$; $—(CH_2)_{0-4}C(O)R^\circ$; $—(CH_2)_{0-4}C(O)NR^\circ_2$; $—C(S)NR^\circ_2$; $—C(S)SR^\circ$; $—(CH_2)_{0-4}C(O)NR^\circ_2$; $—C(O)N(OR^\circ)R^\circ$; $—C(O)C(O)R^\circ$; $—C(O)CH_2C(O)R^\circ$; $—C(NOR^\circ)R^\circ$; $—(CH_2)_{0-4}SSR^\circ$; $—(CH_2)_{0-4}$ $S(O)_2R^\circ$; $—(CH_2)_{0-4}S(O)_2OR^\circ$; $—(CH_2)_{0-4}OS(O)_2R^\circ$; $—S(O)_2NR^\circ_2$; $—(CH_2)_{0-4}S(O)R^\circ$; $—N(R^\circ)S(O)_2NR^\circ_2$; $—N(R^\circ)S(O)_2R^\circ$; $—N(OR^\circ)R^\circ$; $—C(NH)NR^\circ_2$; $—P(O)_2R^\circ$; $—P(O)R^\circ_2$; $—OP(O)R^\circ_2$; $—OP(O)(OR^\circ)_2$; $—SiR^\circ_3$; $—(C_{1-4}$ straight or branched alkylene)$O—N(R^\circ)_2$; or $—(C_{1-4}$ straight or branched alkylene)$C(O)O—N(R^\circ)_2$, wherein each $R^\circ$ may be substituted as defined below and is independently hydrogen, $C_{1-6}$ aliphatic, $—CH_2Ph$, $—O(CH_2)_{0-1}Ph$, $—CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^\circ$ (or the ring formed by taking two independent occurrences of $R^\circ$ together with their intervening atoms), are independently halogen, $—(CH_2)_{0-2}R^\bullet$, -(halo$R^\bullet$), $—(CH_2)_{0-2}OH$, $—(CH_2)_{0-2}OR^\bullet$, $—(CH_2)_{0-2}CH(OR^\bullet)_2$; —O(halo$R^\bullet$), $—CN$, $—N_3$, $—(CH_2)_{0-2}C(O)R^\bullet$, $—(CH_2)_{0-2}C(O)OH$, $—(CH_2)_{0-2}C(O)OR^\bullet$, $—(CH_2)_{0-2}SR^\bullet$, $—(CH_2)_{0-2}SH$, $—(CH_2)_{0-2}NH_2$, $—(CH_2)_{0-2}NHR^\bullet$, $—(CH_2)_{0-2}NR^\bullet_2$, $—NO_2$, $—SiR^\bullet_3$, $—OSiR^\bullet_3$, $—C(O)SR^\bullet$, $—(C_{1-4}$ straight or branched alkylene)$C(O)OR^\bullet$, or $—SSR^\bullet$ wherein each $R^\bullet$ is unsubstituted or where preceded by "halo" is substituted only with one or more halogens, and is independently selected from $C_{1-4}$ aliphatic, $—CH_2Ph$, $—O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R^\circ$ include $=O$ and $=S$.

Suitable divalent substituents on a saturated carbon atom of an "optionally substituted" group include the following: $=O$, $=S$, $=NNR^*_2$, $=NNHC(O)R^*$, $=NNHC(O)OR^*$, $=NNHS(O)_2R^*$, $=NR^*$, $=NOR^*$, $—O(C(R^*_2))_{2-3}O—$, or $—S(C(R^*_2))_{2-3}S—$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: $—O(CR^*_2)_{2-3}$ $O—$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of $R^*$ include halogen, $—R^\bullet$, -(halo$R^\bullet$), $—OH$, $—OR^\bullet$, —O(halo$R^\bullet$), $—CN$, $—C(O)OH$, $—C(O)OR^\bullet$, $—NH_2$, $—NHR^\bullet$, $—NR^\bullet_2$, or $—NO_2$, wherein each $R^\bullet$ is unsubstituted or where preceded by "halo" is substituted only with one or more halogens, and is independently $C_{1-4}$ aliphatic, $—CH_2Ph$, $—O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include $—R^\dagger$, $—NR^\dagger_2$, $—C(O)R^\dagger$, $—C(O)OR^\dagger$, $—C(O)C(O)R^\dagger$, $—C(O)CH_2C(O)R^\dagger$, $—S(O)_2R^\dagger$, $—S(O)_2NR^\dagger_2$, $—C(S)NR^\dagger_2$, $—C(NH)NR^\dagger_2$, or $—N(R^\dagger)S(O)_2R^\dagger$; wherein each $R^\dagger$ is independently hydrogen, $C_{1-6}$ aliphatic which may be substituted as defined below, unsubstituted $—OPh$, or an unsubstituted 5-6-membered saturated, partially unsaturated, or aryl ring having 0-4 heteroatoms independently selected from nitrogen, oxygen, or sulfur, or, notwithstanding the definition above, two independent occurrences of $R^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of $R^\dagger$ are independently halogen, $—R^\bullet$, -(halo$R^\bullet$), $—OH$, $—OR^\bullet$, —O(halo$R^\bullet$), $—CN$, $—C(O)OH$, $—C(O)OR^\bullet$, $—NH_2$, —NHR$^\bullet$, —NR$^\bullet_2$, or —$NO_2$, wherein each R$^\bullet$ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}C$- or $^{14}C$-enriched carbon are within the scope of this invention. Such compounds are useful, for example, as analytical tools, as probes in biological assays, or as therapeutic agents in accordance with the present invention. In certain embodiments, a provided compound may be substituted with one or more deuterium atoms.

As used herein, the term "provided compound" refers to any genus, subgenus, and/or species set forth herein.

As used herein, the term "binder" or "inhibitor" is defined as a compound that binds to CRBN and binds to or inhibits a targeted protein with measurable affinity. In certain embodiments, an inhibitor has an $IC_{50}$ and/or binding constant of less than about 50 μM, less than about 1 μM, less than about 500 nM, less than about 100 nM, less than about 10 nM, or less than about 1 nM.

A compound of the present invention may be tethered to a detectable moiety. It will be appreciated that such compounds are useful as imaging agents. One of ordinary skill in the art will recognize that a detectable moiety may be attached to a provided compound via a suitable substituent. As used herein, the term "suitable substituent" refers to a moiety that is capable of covalent attachment to a detectable moiety. Such moieties are well known to one of ordinary skill in the art and include groups containing, e.g., a carboxylate moiety, an amino moiety, a thiol moiety, or a hydroxyl moiety, to name but a few. It will be appreciated that such moieties may be directly attached to a provided compound or via a tethering group, such as a bivalent saturated or unsaturated hydrocarbon chain. In some embodiments, such moieties may be attached via click chemistry. In some embodiments, such moieties may be attached via a 1,3-cycloaddition of an azide with an alkyne, optionally in the presence of a copper catalyst. Methods of using click chemistry are known in the art and include those described by Rostovtsev et al., Angew. Chem. Int. Ed. 2002, 41, 2596-99 and Sun et al., Bioconjugate Chem., 2006, 17, 52-57.

As used herein, the term "detectable moiety" is used interchangeably with the term "label" and relates to any moiety capable of being detected, e.g., primary labels and secondary labels. Primary labels, such as radioisotopes (e.g., tritium, $^{32}P$, $^{33}P$, $^{35}S$, or $^{14}C$), mass-tags, and fluorescent labels are signal generating reporter groups which can be detected without further modifications. Detectable moieties also include luminescent and phosphorescent groups.

The term "secondary label" as used herein refers to moieties such as biotin and various protein antigens that require the presence of a second intermediate for production of a detectable signal. For biotin, the secondary intermediate may include streptavidin-enzyme conjugates. For antigen labels, secondary intermediates may include antibody-enzyme conjugates. Some fluorescent groups act as secondary labels because they transfer energy to another group in the process of nonradiative fluorescent resonance energy transfer (FRET), and the second group produces the detected signal.

The terms "fluorescent label", "fluorescent dye", and "fluorophore" as used herein refer to moieties that absorb light energy at a defined excitation wavelength and emit light energy at a different wavelength. Examples of fluorescent labels include, but are not limited to: Alexa Fluor dyes (Alexa Fluor 350, Alexa Fluor 488, Alexa Fluor 532, Alexa Fluor 546, Alexa Fluor 568, Alexa Fluor 594, Alexa Fluor 633, Alexa Fluor 660 and Alexa Fluor 680), AMCA, AMCA-S, BODIPY dyes (BODIPY FL, BODIPY R6G, BODIPY TMR, BODIPY TR, BODIPY 530/550, BODIPY 558/568, BODIPY 564/570, BODIPY 576/589, BODIPY 581/591, BODIPY 630/650, BODIPY 650/665), Carboxyrhodamine 6G, carboxy-X-rhodamine (ROX), Cascade Blue, Cascade Yellow, Coumarin 343, Cyanine dyes (Cy3, Cy5, Cy3.5, Cy5.5), Dansyl, Dapoxyl, Dialkylaminocoumarin, 4',5'-Dichloro-2',7'-dimethoxy-fluorescein, DM-NERF, Eosin, Erythrosin, Fluorescein, FAM, Hydroxycoumarin, IRDyes (IRD40, IRD 700, IRD 800), JOE, Lissamine rhodamine B, Marina Blue, Methoxycoumarin, Naphthofluorescein, Oregon Green 488, Oregon Green 500, Oregon Green 514, Pacific Blue, PyMPO, Pyrene, Rhodamine B, Rhodamine 6G, Rhodamine Green, Rhodamine Red, Rhodol Green, 2',4',5',7'-Tetra-bromosulfone-fluorescein, Tetramethyl-rhodamine (TMR), Carboxytetramethylrhodamine (TAMRA), Texas Red, Texas Red-X.

The term "mass-tag" as used herein refers to any moiety that is capable of being uniquely detected by virtue of its mass using mass spectrometry (MS) detection techniques. Examples of mass-tags include electrophore release tags such as N-[3-[4'-[(p-Methoxytetrafluorobenzyl)oxy]phenyl]-3-methylglyceronyl]isonipecotic Acid, 4'-[2,3,5,6-Tetrafluoro-4-(pentafluorophenoxyl)]methyl acetophenone, and their derivatives. The synthesis and utility of these mass-tags is described in U.S. Pat. Nos. 4,650,750, 4,709,016, 5,360,8191, 5,516,931, 5,602,273, 5,604,104, 5,610,020, and 5,650,270. Other examples of mass-tags include, but are not limited to, nucleotides, dideoxynucleotides, oligonucleotides of varying length and base composition, oligopeptides, oligosaccharides, and other synthetic polymers of varying length and monomer composition. A large variety of organic molecules, both neutral and charged (biomolecules or synthetic compounds) of an appropriate mass range (100-2000 Daltons) may also be used as mass-tags.

The terms "measurable affinity" and "measurably modulate," as used herein, means a measurable change in a CRBN activity between a sample comprising a compound of the present invention, or composition thereof, and CRBN, and an equivalent sample comprising CRBN, in the absence of said compound, or composition thereof.

3. Description of Exemplary Embodiments

As described above, in certain embodiments, the present invention provides a compound of formula I-a:

I-a

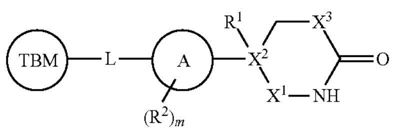

or a pharmaceutically acceptable salt thereof, wherein L and TBM are as defined above and described in embodiments herein, and wherein:

$X^1$ is a bivalent moiety selected from a covalent bond, $-CH_2-$, $-C(O)-$, $-C(S)-$, or

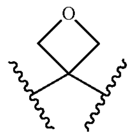

;

$X^2$ is a carbon atom or silicon atom;

$X^3$ is a bivalent moiety selected from $-CH_2-$ or $-Si(R_2)-$;

$R^1$ is hydrogen, deuterium, halogen, $-CN$, $-OR$, $-SR$, $-S(O)R$, $-S(O)_2R$, $-N(R)_2$, $-Si(R)_3$, or an optionally substituted $C_{1-4}$ aliphatic;

each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

each $R^2$ is independently hydrogen, $-R^3$, halogen, $-CN$, $-NO_2$, $-OR$, $-SR$, $-N(R)_2$, $-Si(R)_3$, $-S(O)_2R$, $-S(O)_2N(R)_2$, $-S(O)R$, $-C(O)R$, $-C(O)OR$, $-C(O)N(R)_2$, $-C(O)N(R)OR$, $-C(R)_2N(R)C(O)R$, $-C(R)_2N(R)C(O)N(R)_2$, $-OC(O)R$, $-OC(O)N(R)_2$, $-N(R)C(O)OR$, $-N(R)C(O)R$, $-N(R)C(O)N(R)_2$, or $-N(R)S(O)_2R$;

each $R^3$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

Ring A is a tricyclic ring selected from

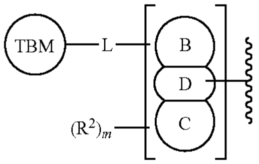

, wherein each of Ring B, Ring C, and Ring D is independently a fused ring selected from 6-membered aryl containing 0-3 nitrogens, 5 to 7-membered saturated or partially unsaturated carbocyclyl, 5 to 7-membered saturated or partially unsaturated heterocyclyl ring with 1-3 heteroatoms independently selected from boron, nitrogen, oxygen, silicon, or sulfur, or 5-membered heteroaryl with 1-3 heteroatoms independently selected from nitrogen, oxygen or sulfur; and m is 0, 1, 2, 3, 4, 5, 6, 7, 8, 9, 10, 11, 12, 13, 14, 15, or 16.

As described above, in certain embodiments, the present invention provides a compound of formula I-a':

I-a'

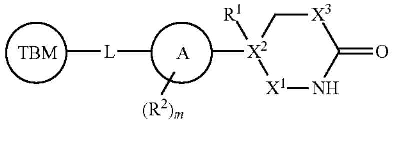

or a pharmaceutically acceptable salt thereof, wherein L and TBM are as defined above and described in embodiments herein, and wherein:

$X^1$ is a bivalent moiety selected from a covalent bond, —$CH_2$—, —$CHCF_3$—, —$SO_2$—, —S(O)—, —P(O)R—, —P(O)OR—, —P(O)$NR_2$—, —C(O)—, —C(S)—, or

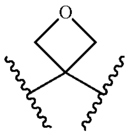

;

$X^2$ is a carbon atom or silicon atom;

$X^3$ is a bivalent moiety selected from —$CR_2$—, —NR—, —O—, —S—, or —Si($R_2$)—;

$R^1$ is hydrogen, deuterium, halogen, —CN, —OR, —SR, —S(O)R, —S$(O)_2$R, —N$(R)_2$, —P(O)$(OR)_2$, —P(O)($NR_2$)OR, —P(O)$(NR_2)_2$, —Si$(OH)_2$R, —Si(OH)$(R)_2$, —Si$(R)_3$, or an optionally substituted $C_{1-4}$ aliphatic;

each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

each $R^2$ is independently hydrogen, deuterium, —$R^3$, halogen, —CN, —$NO_2$, —OR, —SR, —N$(R)_2$, —Si$(R)_3$, —S$(O)_2$R, —S$(O)_2$N$(R)_2$, —S(O)R, —C(O)R, —C(O)OR, —C(O)N$(R)_2$, —C(O)N(R)OR, —C$(R)_2$N(R)C(O)R, —C$(R)_2$N(R)C(O)N$(R)_2$, —OC(O)R, —OC(O)N$(R)_2$, —OP(O)$R_2$, —OP(O)$(OR)_2$, —OP(O)(OR)($NR_2$), —OP(O)$(NR_2)_2$—, —N(R)C(O)OR, —N(R)C(O)R, —N(R)C(O)N$(R)_2$, —N(R)S$(O)_2$R, —NP(O)$R_2$, —N(R)P(O)$(OR)_2$, —N(R)P(O)(OR)($NR_2$), —N(R)P(O)$(NR_2)_2$, or —N(R)S$(O)_2$R;

each $R^3$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

Ring A is a tricyclic ring selected from

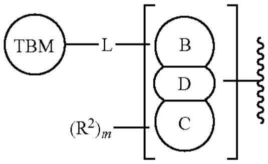

, wherein each of Ring B, Ring C, and Ring D is independently a fused ring selected from 6-membered aryl, 6-membered heteroaryl containing 1-4 heteroatoms independently selected from nitrogen, oxygen, or sulfur, 5 to 7-membered saturated or partially unsaturated carbocyclyl, 5 to 7-membered saturated or partially unsaturated heterocyclyl ring with 1-3 heteroatoms independently selected from boron, nitrogen, oxygen, silicon, or sulfur, or 5-membered heteroaryl with 1-4 heteroatoms independently selected from nitrogen, oxygen or sulfur; and m is 0, 1, 2, 3, 4, 5, 6, 7, 8, 9, 10, 11, 12, 13, 14, 15, or 16.

In some embodiments, a compound of formula I-a' above is provided as a compound of formula I-a" or formula I-a'":

I-a″

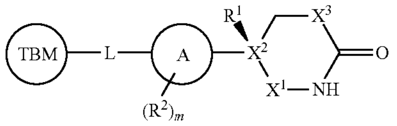

I-a‴

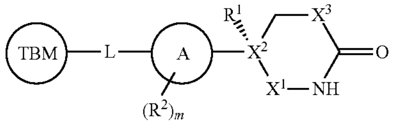

or a pharmaceutically acceptable salt thereof, wherein:

each of TBM, L, Ring A, $X^1$, $X^2$, $X^3$, $R^1$, $R^2$, and m is as defined above.

As described above, in certain embodiments, the present invention provides a compound of formula I-b:

I-b

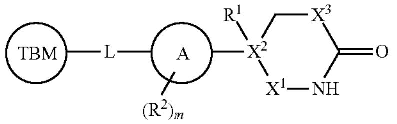

or a pharmaceutically acceptable salt thereof, wherein L and TBM are as defined above and described in embodiments herein, and wherein:

$X^1$ is a bivalent moiety selected from a covalent bond, —$CH_2$—, —$CHCF_3$—, —$SO_2$—, —S(O)—, —P(O)R—, —P(O)OR—, —P(O)$NR_2$—, —C(O)—, —C(S)—, or;

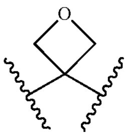

;

$X^2$ is a carbon atom or silicon atom;

$X^3$ is a bivalent moiety selected from —$CR_2$—, —NR—, —O—, —S—, or —Si($R_2$)—;

$R^1$ is hydrogen, deuterium, halogen, —CN, —OR, —SR, —S(O)R, —S$(O)_2$R, —N$(R)_2$, —P(O)$(OR)_2$, —P(O)($NR_2$)OR, —P(O)$(NR_2)_2$, —Si$(OH)_2$R, —Si(OH)$(R)_2$, —Si$(R)_3$, or an optionally substituted $C_{1-4}$ aliphatic;

each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

each $R^2$ is independently hydrogen, deuterium, —$R^3$, halogen, —CN, —$NO_2$, —OR, —SR, —$N(R)_2$, —Si$(R)_3$, —$S(O)_2R$, —$S(O)_2N(R)_2$, —S(O)R, —C(O)R, —C(O)OR, —$C(O)N(R)_2$, —C(O)N(R)OR, —$C(R)_2N(R)C(O)R$, —$C(R)_2N(R)C(O)N(R)_2$, —OC(O)R, —$OC(O)N(R)_2$, —$OP(O)R_2$, —$OP(O)(OR)_2$, —OP(O)(OR)($NR_2$), —$OP(O)(NR_2)_2$—, —N(R)C(O)OR, —N(R)C(O)R, —$N(R)C(O)N(R)_2$, —$N(R)S(O)_2R$, —$NP(O)R_2$, —$N(R)P(O)(OR)_2$, —N(R)P(O)(OR)($NR_2$), —$N(R)P(O)(NR_2)_2$, or —$N(R)S(O)_2R$;

each $R^3$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

Ring A is a bicyclic ring system selected from

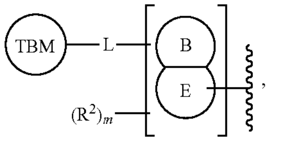

wherein

Ring B is a fused ring selected from 6-membered aryl, 6-membered heteroaryl containing 1-4 heteroatoms independently selected from nitrogen, oxygen, or sulfur, 5 to 7-membered saturated or partially unsaturated carbocyclyl, 5 to 7-membered saturated or partially unsaturated heterocyclyl ring with 1-3 heteroatoms independently selected from boron, nitrogen, oxygen, silicon, or sulfur, or 5-membered heteroaryl with 1-4 heteroatoms independently selected from nitrogen, oxygen or sulfur;

Ring E is a ring selected from a 7-9 membered saturated or partially unsaturated carbocyclyl or hetercyclyl ring with 1-3 heteroatoms independently selected from boron, nitrogen, oxygen, silicon, or sulfur, wherein Ring E is optionally further substituted with 1-2 oxo groups; and m is 0, 1, 2, 3, 4, 5, 6, 7, 8, 9, 10, 11, 12, 13, 14, 15, or 16.

In some embodiments, a compound of formula I-b above is provided as a compound of formula I-b' or formula I-b":

I-b'

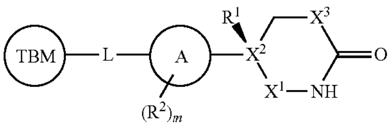

-continued

I-b"

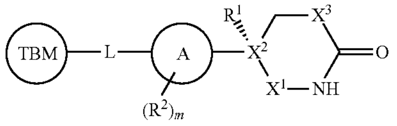

or a pharmaceutically acceptable salt thereof, wherein:

each of TBM, L, Ring A, $X^1$, $X^2$, $X^3$, $R^1$, $R^2$, and m is as defined above.

As described above, in certain embodiments, the present invention provides a compound of formula I-c:

I-c

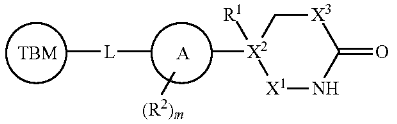

or a pharmaceutically acceptable salt thereof, wherein L and TBM are as defined above and described in embodiments herein, and wherein:

$X^1$ is a bivalent moiety selected from a covalent bond, —$CH_2$—, —$CHCF_3$—, —$SO_2$—, —S(O)—, —P(O)R—, —P(O)OR—, —$P(O)NR_2$—, —C(O)—, —C(S)—, or

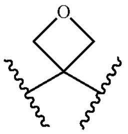

;

$X^2$ is a carbon atom or silicon atom;

$X^3$ is a bivalent moiety selected from —$CR_2$—, —NR—, —O—, —S—, or —$Si(R_2)$—;

$R^1$ is hydrogen, deuterium, halogen, —CN, —OR, —SR, —S(O)R, —$S(O)_2R$, —$NR_2$, —$P(O)(OR)_2$, —P(O)($NR_2$)OR, —$P(O)(NR_2)_2$, —$Si(OH)_2R$, —$Si(OH)(R)_2$, —$Si(R)_3$, or an optionally substituted $C_{1-4}$ aliphatic;

each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

each $R^2$ is independently hydrogen, deuterium, —$R^3$, halogen, —CN, —$NO_2$, —OR, —SR, —$N(R)_2$, —Si$(R)_3$, —$S(O)_2R$, —$S(O)_2N(R)_2$, —S(O)R, —C(O)R, —C(O)OR, —$C(O)N(R)_2$, —C(O)N(R)OR, —$C(R)_2N(R)C(O)R$, —$C(R)_2N(R)C(O)N(R)_2$, —OC(O)R, —$OC(O)N(R)_2$, —$OP(O)R_2$, —$OP(O)(OR)_2$, —OP(O)(OR)($NR_2$), —$OP(O)(NR_2)_2$—, —N(R)C(O)OR, —N(R)C(O)R, —$N(R)C(O)N(R)_2$, —$N(R)S(O)_2R$, —NP(O)$R_2$, —N(R)P(O)$(OR)_2$, —N(R)P(O)(OR)$(NR_2)$, —N(R)P(O)$(NR_2)_2$, or —N(R)S$(O)_2$R;

each $R^3$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

Ring A is a tricyclic ring system selected from

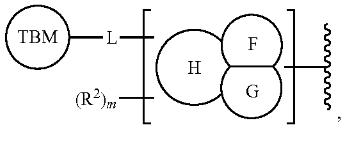

wherein each of Ring F and G is independently a fused ring selected from 6-membered aryl, 6-membered heteroaryl containing 1-4 heteroatoms independently selected from nitrogen, oxygen, or sulfur, 5 to 7-membered saturated or partially unsaturated carbocyclyl, 5 to 7-membered saturated or partially unsaturated heterocyclyl ring with 1-3 heteroatoms independently selected from boron, nitrogen, oxygen, silicon, or sulfur, or 5-membered heteroaryl with 1-4 heteroatoms independently selected from nitrogen, oxygen or sulfur;

Ring H is a fused ring selected from a 7-12 membered saturated or partially unsaturated carbocyclyl or hetercyclyl ring with 1-3 heteroatoms independently selected from boron, nitrogen, oxygen, silicon, or sulfur, wherein Ring H is optionally further substituted with 1-2 oxo groups;

m is 0, 1, 2, 3, 4, 5, 6, 7, 8, 9, 10, 11, 12, 13, 14, 15, or 16.

In some embodiments, a compound of formula I-c above is provided as a compound of formula I-c' or formula I-c":

I-c'

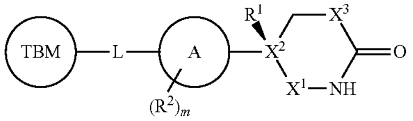

I-c"

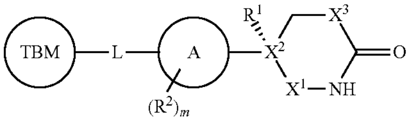

or a pharmaceutically acceptable salt thereof, wherein:

each of TBM, L, Ring A, $X^1$, $X^2$, $X^3$, $R^1$, $R^2$, and m is as defined above.

In certain embodiments, the present invention provides a compound of formula I-d:

I-d

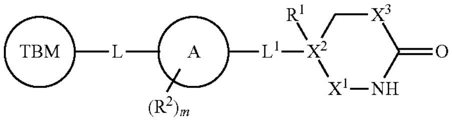

or a pharmaceutically acceptable salt thereof, wherein L and TBM are as defined above and described in embodiments herein, and wherein:

$X^1$ is a bivalent moiety selected from a covalent bond, —$CH_2$—, —$CHCF_3$—, —$SO_2$—, —S(O)—, —P(O)R—, —P(O)OR—, —P(O)$NR_2$—, —C(O)—, —C(S)—, or

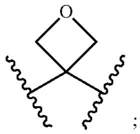 [SMILES: *C1(*)COC1]

;

$X^2$ is a carbon atom or silicon atom;

$X^3$ is a bivalent moiety selected from —$CR_2$—, —NR—, —O—, —S—, or —Si$(R_2)$—;

$R^1$ is hydrogen, deuterium, halogen, —CN, —OR, —SR, —S(O)R, —S$(O)_2$R, —N$(R)_2$, —P(O)$(OR)_2$, —P(O)$(NR_2)$OR, —P(O)$(NR_2)_2$, —Si$(OH)_2$R, —Si(OH)$(R)_2$, —Si$(R)_3$, or an optionally substituted $C_{1-4}$ aliphatic;

each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

each $R^2$ is independently hydrogen, deuterium, —$R^3$, halogen, —CN, —$NO_2$, —OR, —SR, —N$(R)_2$, —Si$(R)_3$, —S$(O)_2$R, —S$(O)_2$N$(R)_2$, —S(O)R, —C(O)R, —C(O)OR, —C(O)N$(R)_2$, —C(O)N(R)OR, —C$(R)_2$N(R)C(O)R, —C$(R)_2$N(R)C(O)N$(R)_2$, —OC(O)R, —OC(O)N$(R)_2$, —OP(O)$R_2$, —OP(O)$(OR)_2$, —OP(O)(OR)$(NR_2)$, —OP(O)$(NR_2)_2$—, —N(R)C(O)OR, —N(R)C(O)R, —N(R)C(O)N$(R)_2$, —N(R)S$(O)_2$R, —NP(O)$R_2$, —N(R)P(O)$(OR)_2$, —N(R)P(O)(OR)$(NR_2)$, —N(R)P(O)$(NR_2)_2$, or —N(R)S$(O)_2$R;

each $R^3$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

Ring A is a tricyclic ring selected from

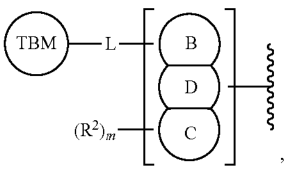

wherein each of Ring B, Ring D, and Ring C is independently a fused ring selected from 6-membered aryl, 6-membered heteroaryl containing 1-4 heteroatoms independently selected from nitrogen, oxygen, or sulfur, 5 to 7-membered saturated or partially unsaturated carbocyclyl, 5 to 7-membered saturated or partially unsaturated heterocyclyl ring with 1-3 heteroatoms independently selected from boron, nitrogen, oxygen, silicon, or sulfur, or 5-membered heteroaryl with 1-4 heteroatoms independently selected from nitrogen, oxygen or sulfur;

$L^1$ is a covalent bond or a $C_{1-3}$ bivalent straight or branched saturated or unsaturated hydrocarbon chain wherein 1-2 methylene units of the chain are independently and optionally replaced with —O—, —C(O)—, —C(S)—, —$CR_2$—, —CFR—, —$CF_2$—, —NR—, —S—, —$S(O)_2$— or —CR═CR—; and m is 0, 1, 2, 3, 4, 5, 6, 7, 8, 9, 10, 11, 12, 13, 14, 15, or 16.

In some embodiments, a compound of formula I-d above is provided as a compound of formula I-d' or formula I-d":

I-d'

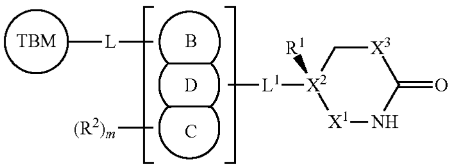

I-d"

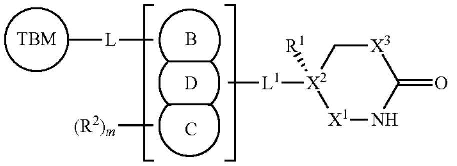

or a pharmaceutically acceptable salt thereof, wherein:

each of TAMBM, Ring E, Ring F, Ring G, L, $L^1$, $R^1$, $R^2$, $X^1$, $X^2$, $X^3$, and m is as defined above.

As described above, in certain embodiments, the present invention provides a compound of formula II:

II

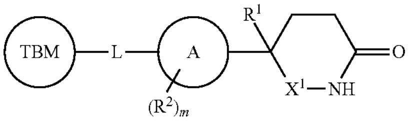

or a pharmaceutically acceptable salt thereof, wherein L and TBM are as defined above and described in embodiments herein, and wherein:

$X^1$ is a bivalent moiety selected from a covalent bond, —$CH_2$—, —C(O)—, —C(S)—, or

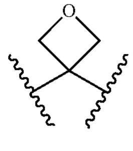

;

$R^1$ is hydrogen, deuterium, halogen, —CN, —OR, —SR, —S(O)R, —$S(O)_2R$, —$N(R)_2$, —$Si(R)_3$, or an optionally substituted $C_{1-4}$ aliphatic;

each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

each $R^2$ is independently hydrogen, —$R^3$, halogen, —CN, —$NO_2$, —OR, —SR, —$N(R)_2$, —$Si(R)_3$, —$S(O)_2R$, —$S(O)_2N(R)_2$, —S(O)R, —C(O)R, —C(O)OR, —$C(O)N(R)_2$, —C(O)N(R)OR, —$C(R)_2N(R)C(O)R$, —$C(R)_2N(R)C(O)N(R)_2$, —OC(O)R, —$OC(O)N(R)_2$, —N(R)C(O)OR, —N(R)C(O)R, —$N(R)C(O)N(R)_2$, or —$N(R)S(O)_2R$;

each $R^3$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

Ring A is a tricyclic ring selected from

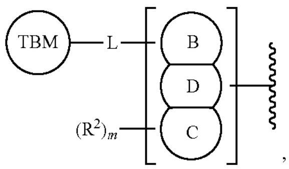

, wherein each of Ring B, Ring C, and Ring D is independently a fused ring selected from 6-membered aryl containing 0-3 nitrogens, 5 to 7-membered saturated or partially unsaturated carbocyclyl, 5 to 7-membered saturated or partially unsaturated heterocyclyl ring with 1-3 heteroatoms independently selected from boron, nitrogen, oxygen, silicon, or sulfur, or 5-membered heteroaryl with 1-3 heteroatoms independently selected from nitrogen, oxygen or sulfur; and m is 0, 1, 2, 3, 4, 5, 6, 7, 8, 9, 10, 11, 12, 13, 14, 15, or 16.

As described above, in certain embodiments, the present invention provides a compound of formula II':

II'

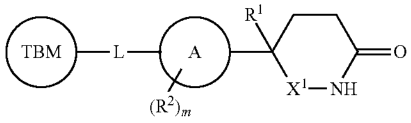

or a pharmaceutically acceptable salt thereof, wherein L and TBM are as defined above and described in embodiments herein, and wherein:

$X^1$ is a bivalent moiety selected from a covalent bond, —$CH_2$—, —$CHCF_3$—, —$SO_2$—, —S(O)—, —P(O)R—, —P(O)OR—, —$P(O)NR_2$—, —C(O)—, —C(S)—, or

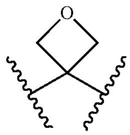

;

$R^1$ is hydrogen, deuterium, halogen, —CN, —OR, —SR, —S(O)R, —$S(O)_2R$, —$N(R)_2$, —$P(O)(OR)_2$, —P(O)($NR_2$)OR, —P(O)($NR_2)_2$, —$Si(OH)_2R$, —Si(OH)$(R)_2$, —$Si(R)_3$, or an optionally substituted $C_{1-4}$ aliphatic;

each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

each $R^2$ is independently hydrogen, deuterium, —$R^3$, halogen, —CN, —$NO_2$, —OR, —SR, —$N(R)_2$, —Si$(R)_3$, —$S(O)_2R$, —$S(O)_2N(R)_2$, —S(O)R, —C(O)R, —C(O)OR, —C(O)$N(R)_2$, —C(O)N(R)OR, —$C(R)_2$N(R)C(O)R, —$C(R)_2$N(R)C(O)$N(R)_2$, —OC(O)R, —OC(O)$N(R)_2$, —$OP(O)R_2$, —$OP(O)(OR)_2$, —OP(O)(OR)($NR_2$), —OP(O)$(NR_2)_2$—, —N(R)C(O)OR, —N(R)C(O)R, —N(R)C(O)$N(R)_2$, —N(R)$S(O)_2R$, —$NP(O)R_2$, —N(R)P(O)$(OR)_2$, —N(R)P(O)(OR)($NR_2$), —N(R)P(O)$(NR_2)_2$, or —N(R)$S(O)_2R$;

each $R^3$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

Ring A is a tricyclic ring selected from

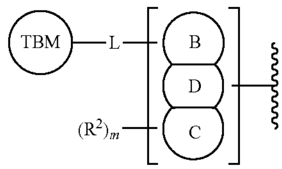

, wherein each of Ring B, Ring C, and Ring D is independently a fused ring selected from 6-membered aryl, 6-membered heteroaryl containing 1-4 heteroatoms independently selected from nitrogen, oxygen, or sulfur, 5 to 7-membered saturated or partially unsaturated carbocyclyl, 5 to 7-membered saturated or partially unsaturated heterocyclyl ring with 1-3 heteroatoms independently selected from boron, nitrogen, oxygen, silicon, or sulfur, or 5-membered heteroaryl with 1-4 heteroatoms independently selected from nitrogen, oxygen or sulfur; and m is 0, 1, 2, 3, 4, 5, 6, 7, 8, 9, 10, 11, 12, 13, 14, 15, or 16.

In some embodiments, a compound of formula II' above is provided as a compound of formula II" or formula II'":

II"

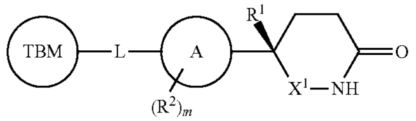

II'"

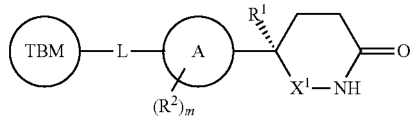

or a pharmaceutically acceptable salt thereof, wherein:

each of TBM, L, Ring A, $X^1$, $R^1$, $R^2$, and m is as defined above.

As described above, in certain embodiments, the present invention provides a compound of formula II-a:

II-a

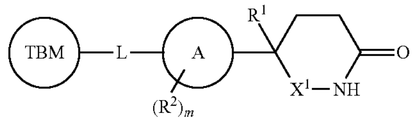

or a pharmaceutically acceptable salt thereof, wherein L and TBM are as defined above and described in embodiments herein, and wherein:

$X^1$ is a bivalent moiety selected from a covalent bond, —$CH_2$—, —C(O)—, —C(S)—, or

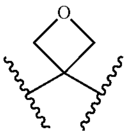

;

$R^1$ is hydrogen, deuterium, halogen, —CN, —OR, —SR, —S(O)R, —$S(O)_2R$, —$N(R)_2$, —$Si(R)_3$, or an optionally substituted $C_{1-4}$ aliphatic;

each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

each $R^2$ is independently hydrogen, —$R^3$, halogen, —CN, —$NO_2$, —OR, —SR, —$N(R)_2$, —$Si(R)_3$, —$S(O)_2R$, —$S(O)_2N(R)_2$, —S(O)R, —C(O)R, —C(O)OR, —C(O)$N(R)_2$, —C(O)N(R)OR, —$C(R)_2$N(R)C(O)R, —$C(R)_2$N(R)C(O)$N(R)_2$, —OC(O)R, —OC(O)$N(R)_2$, —N(R)C(O)OR, —N(R)C(O)R, —N(R)C(O)$N(R)_2$, or —N(R)$S(O)_2R$;

each $R^3$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

Ring A is a tricyclic ring selected from

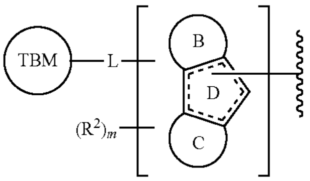

,

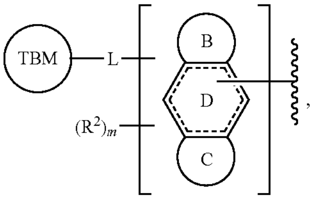

,

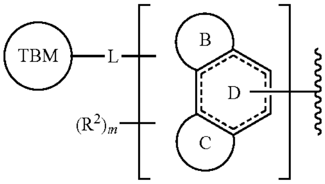

,

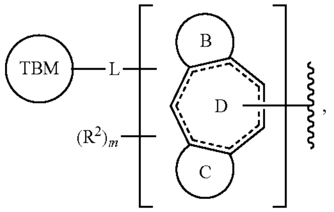

, or

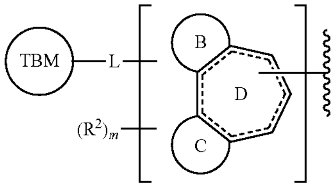

, wherein each of Ring B and Ring C is independently a fused ring selected from 6-membered aryl containing 0-3 nitrogens, 5 to 7-membered saturated or partially unsaturated carbocyclyl, 5 to 7-membered saturated or partially unsaturated heterocyclyl ring with 1-3 heteroatoms independently selected from boron, nitrogen, oxygen or sulfur, or 5-membered heteroaryl with 1-3 heteroatoms independently selected from nitrogen, oxygen or sulfur;

Ring D is a fused ring selected from aryl containing 0-3 nitrogens, saturated or partially unsaturated carbocyclyl, saturated or partially unsaturated heterocyclyl ring with 1-2 heteroatoms independently selected from nitrogen, oxygen, silicon, or sulfur, or heteroaryl with 1-3 heteroatoms independently selected from nitrogen, oxygen or sulfur;

$\overset{---}{\_\_}$ is a single or double bond;

m is 0, 1, 2, 3, 4, 5, 6, 7, 8, 9, 10, 11, 12, 13, 14, 15, or 16.

As described above, in certain embodiments, the present invention provides a compound of formula II-b:

II-b

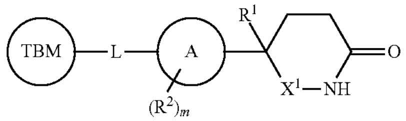

or a pharmaceutically acceptable salt thereof, wherein L and TBM are as defined above and described in embodiments herein, and wherein:

$X^1$ is a bivalent moiety selected from a covalent bond, $—CH_2—$, $—C(O)—$, $—C(S)—$, or

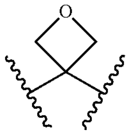

;

$R^1$ is hydrogen, deuterium, halogen, —CN, —OR, —SR, —S(O)R, $—S(O)_2R$, $—N(R)_2$, $—Si(R)_3$, or an optionally substituted $C_{1-4}$ aliphatic;

each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

each $R^2$ is independently hydrogen, $—R^3$, halogen, —CN, $—NO_2$, —OR, —SR, $—N(R)_2$, $—Si(R)_3$, $—S(O)_2R$, $—S(O)_2N(R)_2$, —S(O)R, —C(O)R, —C(O)OR, $—C(O)N(R)_2$, —C(O)N(R)OR, $—C(R)_2N(R)C(O)R$, $—C(R)_2N(R)C(O)N(R)_2$, —OC(O)R, $—OC(O)N(R)_2$, —N(R)C(O)OR, —N(R)C(O)R, $—N(R)C(O)N(R)_2$, or $—N(R)S(O)_2R$;

each $R^3$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

Ring A is a tricyclic ring selected from

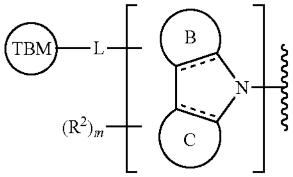

,

-continued

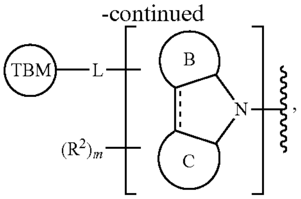

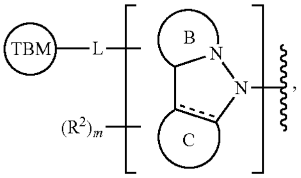

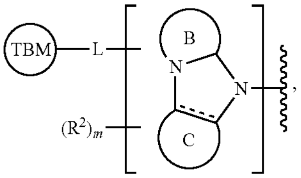

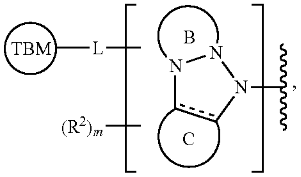

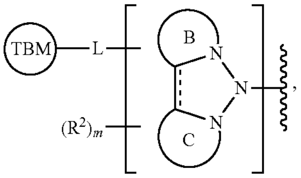

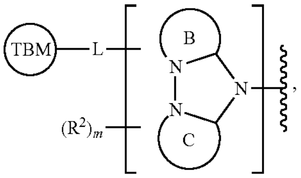

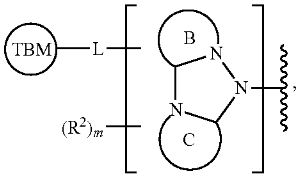

or

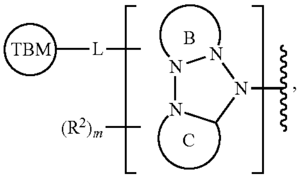

wherein each of Ring B and Ring C is independently a fused ring selected from 6-membered aryl containing 0-2 nitrogens, 5 to 7-membered saturated or partially unsaturated carbocyclyl, 5 to 7-membered saturated or partially unsaturated heterocyclyl ring with 1-3 heteroatoms independently selected from boron, nitrogen, oxygen, silicon, or sulfur, or 5-membered heteroaryl with 1-3 heteroatoms independently selected from nitrogen, oxygen or sulfur;

⎓ is a single or double bond;

m is 0, 1, 2, 3, 4, 5, 6, 7, or 8.

As described above, in certain embodiments, the present invention provides a compound of formula II-c:

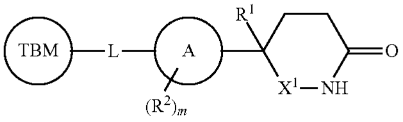

II-c or a pharmaceutically acceptable salt thereof, wherein L and TBM are as defined above and described in embodiments herein, and wherein:

$X^1$ is a bivalent moiety selected from a covalent bond, —$CH_2$—, —$CHCF_3$—, —$SO_2$—, —S(O)—, —P(O)R—, —P(O)OR—, —P(O)$NR_2$—, —C(O)—, —C(S)—, or

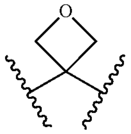

;

$R^1$ is hydrogen, deuterium, halogen, —CN, —OR, —SR, —S(O)R, —$S(O)_2R$, —$N(R)_2$, —$P(O)(OR)_2$, —P(O)($NR_2$)OR, —$P(O)(NR_2)_2$, —$Si(OH)_2R$, —Si(OH)$(R)_2$, —$Si(R)_3$, or an optionally substituted $C_{1-4}$ aliphatic;

each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

each $R^2$ is independently hydrogen, deuterium, —$R^3$, halogen, —CN, —$NO_2$, —OR, —SR, —$N(R)_2$, —$Si(R)_3$, —$S(O)_2R$, —$S(O)_2N(R)_2$, —S(O)R, —C(O)R, —C(O)OR, —C(O)$N(R)_2$, —C(O)N(R)OR, —$C(R)_2$N(R)C(O)R, —$C(R)_2$N(R)C(O)$N(R)_2$, —OC(O)R, —OC(O)$N(R)_2$, —OP(O)$R_2$, —OP(O)$(OR)_2$, —OP(O)(OR)($NR_2$), —OP(O)$(NR_2)_2$—, —N(R)C(O)OR, —N(R)C(O)R, —N(R)C(O)$N(R)_2$, —N(R)$S(O)_2R$, —NP(O)$R_2$, —N(R)P(O)$(OR)_2$, —N(R)P(O)(OR)($NR_2$), —N(R)P(O)$(NR_2)_2$, or —N(R)$S(O)_2R$;

each $R^3$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

Ring A is a bicyclic ring system selected from

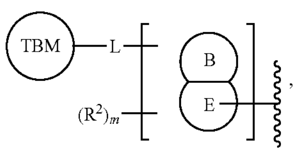

wherein

Ring B is a fused ring selected from 6-membered aryl, 6-membered heteroaryl containing 1-4 heteroatoms independently selected from nitrogen, oxygen, or sulfur, 5 to 7-membered saturated or partially unsaturated carbocyclyl, 5 to 7-membered saturated or partially unsaturated heterocyclyl ring with 1-3 heteroatoms independently selected from boron, nitrogen, oxygen, silicon, or sulfur, or 5-membered heteroaryl with 1-4 heteroatoms independently selected from nitrogen, oxygen or sulfur;

Ring E is a ring selected from a 7-9 membered saturated or partially unsaturated carbocyclyl or hetercyclyl ring with 1-3 heteroatoms independently selected from boron, nitrogen, oxygen, silicon, or sulfur, wherein Ring E is optionally further substituted with 1-2 oxo groups; and m is 0, 1, 2, 3, 4, 5, 6, 7, 8, 9, 10, 11, 12, 13, 14, 15, or 16.

In some embodiments, a compound of formula II-c above is provided as a compound of formula II-c' or formula II-c":

II-c'

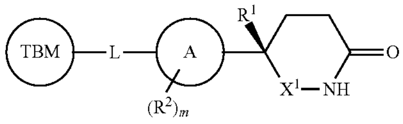

II-c"

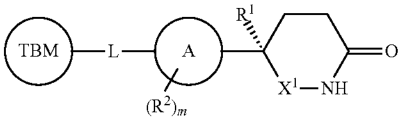

or a pharmaceutically acceptable salt thereof, wherein: each of TBM, L, Ring A, $X^1$, $R^1$, $R^2$, and m is as defined above.

In some embodiments, a compound of formula II-c above is provided as a compound of formula II-c-1:

II-c-1

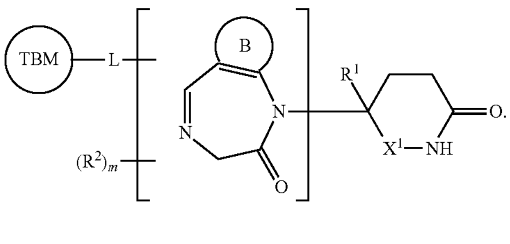

or a pharmaceutically acceptable salt thereof, wherein: each of TBM, L, Ring B, $X^1$, $R^1$, $R^2$, and m is as defined above.

As described above, in certain embodiments, the present invention provides a compound of formula II-d:

II-d

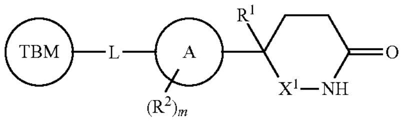

or a pharmaceutically acceptable salt thereof, wherein L and TBM are as defined above and described in embodiments herein, and wherein:

$X^1$ is a bivalent moiety selected from a covalent bond, —$CH_2$—, —$CHCF_3$—, —$SO_2$—, —S(O)—, —P(O)R—, —P(O)OR—, —P(O)$NR_2$—, —C(O)—, —C(S)—, or

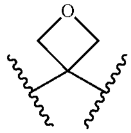 ;

$R^1$ is hydrogen, deuterium, halogen, —CN, —OR, —SR, —S(O)R, —$S(O)_2R$, —$NR_2$, —$P(O)(OR)_2$, —P(O)($NR_2$)OR, —$P(O)(NR_2)_2$, —$Si(OH)_2R$, —Si(OH)$(R)_2$, —$Si(R)_3$, or an optionally substituted $C_{1-4}$ aliphatic;

each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

each $R^2$ is independently hydrogen, deuterium, —$R^3$, halogen, —CN, —$NO_2$, —OR, —SR, —$N(R)_2$, —$Si(R)_3$, —$S(O)_2R$, —$S(O)_2N(R)_2$, —S(O)R, —C(O)R, —C(O)OR, —C(O)$N(R)_2$, —C(O)N(R)OR, —$C(R)_2$N(R)C(O)R, —$C(R)_2$N(R)C(O)$N(R)_2$, —OC(O)R, —OC(O)$N(R)_2$, —OP(O)$R_2$, —OP(O)$(OR)_2$, —OP(O)(OR)($NR_2$), —OP(O)$(NR_2)_2$—, —N(R)C(O)OR, —N(R)C(O)R, —N(R)C(O)$N(R)_2$, —N(R)$S(O)_2R$, —NP(O)$R_2$, —N(R)P(O)$(OR)_2$, —N(R)P(O)(OR)($NR_2$), —N(R)P(O)$(NR_2)_2$, or —N(R)$S(O)_2R$;

each $R^3$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

Ring A is a tricyclic ring system selected from

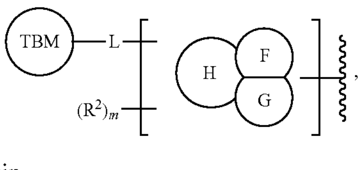

wherein each of Ring F and G is independently a fused ring selected from 6-membered aryl, 6-membered heteroaryl containing 1-4 heteroatoms independently selected from nitrogen, oxygen, or sulfur, 5 to 7-membered saturated or partially unsaturated carbocyclyl, 5 to 7-membered saturated or partially unsaturated heterocyclyl ring with 1-3 heteroatoms independently selected from boron, nitrogen, oxygen, silicon, or sulfur, or 5-membered heteroaryl with 1-4 heteroatoms independently selected from nitrogen, oxygen or sulfur;

Ring H is a fused ring selected from a 7-12 membered saturated or partially unsaturated carbocyclyl or hetercyclyl ring with 1-3 heteroatoms independently selected from boron, nitrogen, oxygen, silicon, or sulfur, wherein Ring H is optionally further substituted with 1-2 oxo groups;

m is 0, 1, 2, 3, 4, 5, 6, 7, 8, 9, 10, 11, 12, 13, 14, 15, or 16.

In some embodiments, a compound of formula II-d above is provided as a compound of formula II-d' or formula II-d":

II-d'

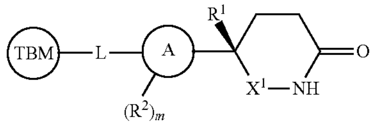

II-d"

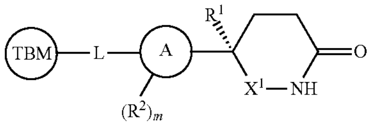

or a pharmaceutically acceptable salt thereof, wherein:

each of TBM, L, Ring A, $X^1$, $R^1$, $R^2$, and m is as defined above.

In some embodiments, a compound of formula II-d above is provided as a compound of formula II-d-1:

II-d-1

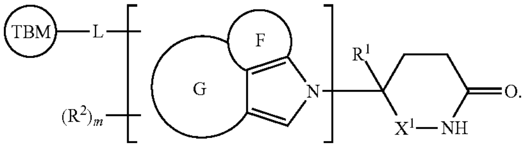

or a pharmaceutically acceptable salt thereof, wherein L and TBM are as defined above and described in embodiments herein, and wherein:

each of TBM, L, Ring F, Ring G, $X^1$, $R^1$, $R^2$, and m is as defined above.

In certain embodiments, the present invention provides a compound of formula III or IV:

III

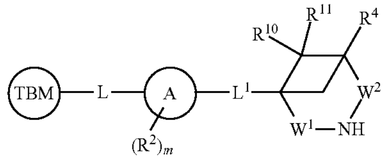

-continued

IV

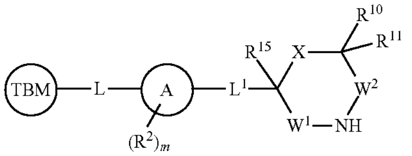

or a pharmaceutically acceptable salt thereof, wherein L and TBM are as defined above and described in embodiments herein, and wherein:

each $R^2$ is independently hydrogen, deuterium, —$R^3$, halogen, —CN, —$NO_2$, —OR, —SR, —$NR_2$, —$SiR_3$, —$S(O)_2R$, —$S(O)_2NR_2$, —S(O)R, —C(O)R, —C(O)OR, —$C(O)NR_2$, —C(O)N(R)OR, —$C(R)_2N(R)C(O)R$, —$C(R)_2N(R)C(O)N(R)_2$, —OC(O)R, —$OC(O)N(R)_2$, —$OP(O)R_2$, —$OP(O)(OR)_2$, —$OP(O)(OR)NR_2$, —$OP(O)(NR_2)_2$—, —N(R)C(O)OR, —N(R)C(O)R, —$N(R)C(O)NR_2$, —$N(R)S(O)_2R$, —$NP(O)R_2$, —$N(R)P(O)(OR)_2$, —$N(R)P(O)(OR)NR_2$, —$N(R)P(O)(NR_2)_2$, or —$N(R)S(O)_2R$;

each $R^3$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

Ring A is a tricyclic ring selected from

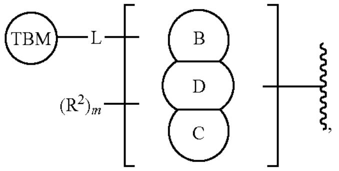

wherein each of Ring B, Ring D, and Ring C is independently a fused ring selected from 6-membered aryl, 6-membered heteroaryl containing 1-4 heteroatoms independently selected from nitrogen, oxygen, or sulfur, 5 to 7-membered saturated or partially unsaturated carbocyclyl, 5 to 7-membered saturated or partially unsaturated heterocyclyl with 1-3 heteroatoms independently selected from boron, nitrogen, oxygen, silicon, or sulfur, or 5-membered heteroaryl with 1-4 heteroatoms independently selected from nitrogen, oxygen or sulfur;

each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

$L^1$ is a covalent bond or a $C_{1-3}$ bivalent straight or branched saturated or unsaturated hydrocarbon chain wherein 1-2 methylene units of the chain are independently and optionally replaced with —O—, —C(O)—, —C(S)—, —$CR_2$—, —CFR—, —$CF_2$—, —NR—, —S—, —$S(O)_2$— or —CR═CR—;

m is 0, 1, 2, 3, 4, 5, 6, 7, 8, 9, 10, 11, 12, 13, 14, 15, or 16; and $R^4$, $R^{10}$, $R^{11}$, $R^{15}$, $W^1$, $W^2$, and X is as defined in WO 2019/099868, the entirety of each of which is herein incorporated by reference.

As defined above and described herein, $X^1$ is a bivalent moiety selected from a covalent bond, —$CH_2$—, —$CHCF_3$—, —$SO_2$—, —S(O)—, —P(O)R—, —P(O)OR—, —P(O)$NR_2$—, —C(O)—, —C(S)—, or

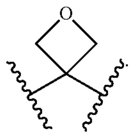 [SMILES: *C1(*)COC1]

In some embodiments, $X^1$ is a covalent bond. In some embodiments, $X^1$ is —$CH_2$—. In some embodiments, $X^1$ is —$CHCF_3$—. In some embodiments, $X^1$ is —$SO_2$—. In some embodiments, $X^1$ is —S(O)—. In some embodiments, $X^1$ is —P(O)R—. In some embodiments, $X^1$ is —P(O)OR—. In some embodiments, $X^1$ is —P(O)$NR_2$—. In some embodiments, $X^1$ is —C(O)—. In some embodiments, $X^1$ is —C(S)—. In some embodiments, $X^1$ is

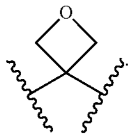 [SMILES: *C1(*)COC1]

In some embodiments, $X^1$ is selected from those depicted in Table 1, below.

As defined above and described herein, $X^2$ is a carbon atom or silicon atom.

In some embodiments, $X^2$ is a carbon atom. In some embodiments, $X^2$ is a silicon atom.

In some embodiments, $X^2$ is selected from those depicted in Table 1, below.

As defined above and described herein, $X^3$ is a bivalent moiety selected from —$CH_2$—, —NR—, —O—, —S—, or —$Si(R_2)$—.

In some embodiments, $X^3$ is —$CH_2$—. In some embodiments, $X^3$ is —NR—. In some embodiments, $X^3$ is —O—. In some embodiments, $X^3$ is —S—. In some embodiments, $X^2$ is —$Si(R_2)$—

In some embodiments, $X^3$ is selected from those depicted in Table 1, below.

As defined above and described herein, $R^1$ is hydrogen, deuterium, halogen, —CN, OR, —SR, —S(O)R, —$S(O)_2R$, —$NR_2$, —$P(O)(OR)_2$, —$P(O)(NR_2)OR$, —$P(O)(NR_2)_2$, —$Si(OH)_2R$, —$Si(OH)(R)_2$, —$Si(R)_3$, or an optionally substituted $C_{1-4}$ aliphatic.

In some embodiments, $R^1$ is hydrogen. In some embodiments, $R^1$ is deuterium. In some embodiments, $R^1$ is halogen. In some embodiments, $R^1$ is —CN. In some embodiments, $R^1$ is —OR. In some embodiments, $R^1$ is —SR. In some embodiments, $R^1$ is —S(O)R. In some embodiments, $R^1$ is —$S(O)_2R$. In some embodiments, $R^1$ is —$NR_2$. In some embodiments, $R^1$ is —$P(O)(OR)_2$. In some embodiments, $R^1$ is —$P(O)(NR_2)OR$. In some embodiments, $R^1$ is —$P(O)(NR_2)_2$. In some embodiments, $R^1$ is —$Si(OH)_2R$. In some embodiments, $R^1$ is —$Si(OH)(R)_2$. In some embodiments, $R^1$ is —$Si(R_3)$. In some embodiments, $R^1$ is an optionally substituted $C_{1-4}$ aliphatic.

In some embodiments, $R^1$ is selected from those depicted in Table 1, below.

As defined above and described herein, each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or: two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In some embodiments, R is hydrogen. In some embodiments, R is optionally substituted $C_{1-6}$ aliphatic. In some embodiments, R is optionally substituted phenyl. In some embodiments, R is optionally substituted 4-7 membered saturated or partially unsaturated heterocyclic having 1-2 heteroatoms independently selected from nitrogen, oxygen, and sulfur. In some embodiments, R is optionally substituted 5-6 membered heteroaryl ring having 1-4 heteroatoms independently selected from nitrogen, oxygen, and sulfur. In some embodiments, two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In some embodiments, R is selected from those depicted in Table 1, below.

As defined above and described herein, each $R^2$ is independently hydrogen, —$R^3$, halogen, —CN, —$NO_2$, —OR, —SR, —$N(R)_2$, —$P(O)(OR)_2$, —$P(O)(NR_2)OR$, —$P(O)(NR_2)_2$, —$Si(OH)_2R$, —$Si(OH)(R)_2$, —$Si(R_3)$, —$S(O)_2R$, —$S(O)_2N(R)_2$, —S(O)R, —C(O)R, —C(O)OR, —C(O)$N(R)_2$, —C(O)N(R)OR, —$C(R)_2N(R)C(O)R$, —$C(R)_2N(R)C(O)N(R)_2$, —OC(O)R, —OC(O)$N(R)_2$, —N(R)C(O)OR, —N(R)C(O)R, —N(R)C(O)$N(R)_2$, or —$N(R)S(O)_2R$.

In some embodiments, $R^2$ is hydrogen. In some embodiments, $R^2$ is —$R^3$. In some embodiments, $R^2$ is halogen. In some embodiments, $R^2$ is —CN. In some embodiments, $R^2$ is —$NO_2$. In some embodiments, $R^2$ is —OR. In some embodiments, $R^2$ is —SR. In some embodiments, $R^2$ is —$NR_2$. In some embodiments, $R^2$ is —$P(O)(OR)_2$. In some embodiments, $R^2$ is —$P(O)(NR_2)OR$. In some embodiments, $R^2$ is —$P(O)(NR_2)_2$. In some embodiments, $R^2$ is —$Si(OH)_2R$. In some embodiments, $R^2$ is —$Si(OH)(R)_2$. In some embodiments, $R^2$ is —$Si(R_3)$. In some embodiments, $R^2$ is —$S(O)_2R$. In some embodiments, $R^2$ is —$S(O)_2NR_2$. In some embodiments, $R^2$ is —S(O)R. In some embodiments, $R^2$ is —C(O)R. In some embodiments, $R^2$ is —C(O)OR. In some embodiments, $R^2$ is —C(O)$NR_2$. In some embodiments, $R^2$ is —C(O)N(R)OR. In some embodiments, $R^2$ is —$C(R)_2N(R)C(O)R$. In some embodiments, $R^2$ is —$C(R)_2N(R)C(O)N(R)_2$. In some embodiments, $R^2$ is —OC(O)R. In some embodiments, $R^2$ is —OC(O)$NR_2$. In some embodiments, $R^2$ is —N(R)C(O)OR. In some embodiments, $R^2$ is —N(R)C(O)R. In some embodiments, $R^2$ is —N(R)C(O)$NR_2$. In some embodiments, $R^2$ is —$N(R)S(O)_2R$.

In some embodiments, $R^2$ is —OH. In some embodiments, $R^2$ is —$NH_2$. In some embodiments, $R^2$ is —$CH_2NH_2$. In some embodiments, $R^2$ is —$CH_2NHCOMe$. In some embodiments, $R^2$ is —$CH_2NHCONHMe$. In some embodiments, $R^2$ is —NHCOMe. In some embodiments, $R^2$ is —NHCONHEt. In some embodiments, $R^2$ is —$SiMe_3$. In some embodiments, $R^2$ is —$SiMe_2OH$. In some embodiments, $R^2$ is —$SiMe(OH)_2$. In some embodiments, $R^2$ is

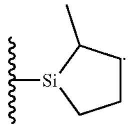

In some embodiments, $R^2$ is Br. In some embodiments, $R^2$ is Cl. In some embodiments, $R^2$ is F. In some embodiments, $R^2$ is Me. In some embodiments, $R^2$ is —NHMe. In some embodiments, $R^2$ is —$NMe_2$. In some embodiments, $R^2$ is —$NHCO_2Et$. In some embodiments, $R^2$ is —CN. In some embodiments, $R^2$ is —$CH_2Ph$. In some embodiments, $R^2$ is —$NHCO_2tBu$. In some embodiments, $R^2$ is —$CO_2tBu$. In some embodiments, $R^2$ is —OMe. In some embodiments, $R^2$ is —$CF_3$.

In some embodiments, $R^2$ is selected from those depicted in Table 1, below.

As defined above and described herein, each $R^3$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur.

In some embodiments, $R^3$ is an optionally substituted $C_{1-6}$ aliphatic. In some embodiments, $R^3$ is an optionally substituted phenyl. In some embodiments, $R^3$ is an optionally substituted 4-7 membered saturated or partially unsaturated heterocyclic ring having 1-2 heteroatoms independently selected from nitrogen, oxygen, and sulfur. In some embodiments, $R^3$ is an optionally substituted 5-6 membered heteroaryl ring having 1-4 heteroatoms independently selected from nitrogen, oxygen, and sulfur.

In some embodiments, $R^3$ is selected from those depicted in Table 1, below.

As defined above and described herein, Ring A is a tricyclic ring selected from

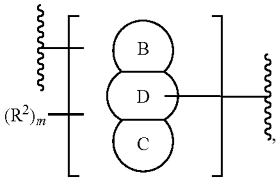

,

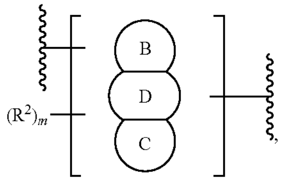

, and

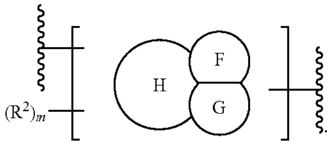

In some embodiments, Ring A is

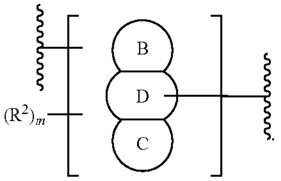

In some embodiments, Ring A is

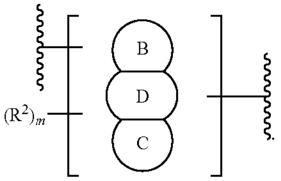

In some embodiments, Ring A is

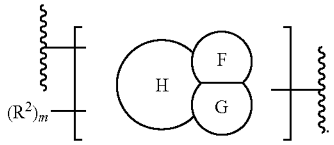

As defined above and described herein, Ring A is a bicyclic ring system selected from

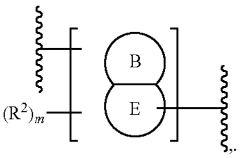

In some embodiments, Ring A is

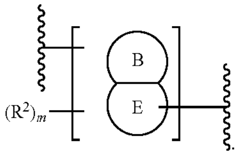

In some embodiments, Ring A is selected from those depicted in Table 1, below.

As defined above and described herein, each of Ring B, Ring C, and Ring D is independently a fused ring selected from 6-membered aryl, 6-membered heteroaryl containing 1-4 heteroatoms independently selected from nitrogen, oxygen, or sulfur, 5 to 7-membered saturated or partially unsaturated carbocyclyl, 5 to 7-membered saturated or partially unsaturated heterocyclyl ring with 1-3 heteroatoms independently selected from boron, nitrogen, oxygen, silicon, or sulfur, or 5-membered heteroaryl with 1-4 heteroatoms independently selected from nitrogen, oxygen or sulfur.

In some embodiments, each Ring B, Ring C, and Ring D is independently a 6-membered aryl. In some embodiments, each Ring B, Ring C, and Ring D is independently a 6-membered heteroaryl containing 1-4 heteroatoms independently selected from nitrogen, oxygen, or sulfur. In some embodiments, each Ring B, Ring C, and Ring D is independently a 5 to 7-membered saturated or partially unsaturated carbocyclyl. In some embodiments, each Ring B, Ring C, and Ring D is independently a 5 to 7-membered saturated or partially unsaturated heterocyclyl with 1-3 heteroatoms independently selected from boron, nitrogen, oxygen, silicon, or sulfur. In some embodiments, each Ring B, Ring C, and Ring D is independently a 5-membered heteroaryl with 1-4 heteroatoms independently selected from nitrogen, oxygen or sulfur.

In some embodiments, Ring B, Ring C, and Ring D is selected from those depicted in Table 1, below.

As defined above and described herein, Ring E is a ring selected from a 7-9 membered saturated or partially unsaturated carbocyclyl or hetercyclyl ring with 1-3 heteroatoms independently selected from boron, nitrogen, oxygen, silicon, or sulfur, wherein Ring E is optionally further substituted with 1-2 oxo groups.

In some embodiments, Ring E is a ring selected from a 7-9 membered saturated or partially unsaturated carbocyclyl or hetercyclyl ring with 1-3 heteroatoms independently selected from boron, nitrogen, oxygen, silicon, or sulfur, wherein Ring E is optionally further substituted with 1-2 oxo groups.

In some embodiments, Ring E is

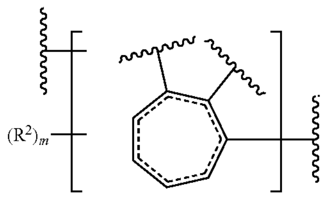

In some embodiments, Ring E is

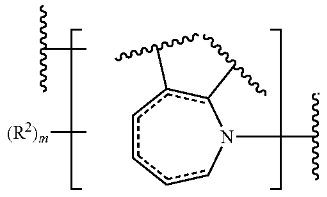

In some embodiments, Ring E is

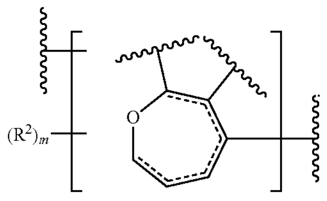

In some embodiments, Ring E is

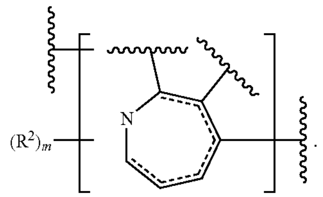

In some embodiments, Ring E is

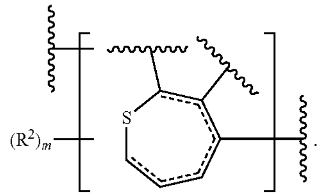

In some embodiments, Ring E is

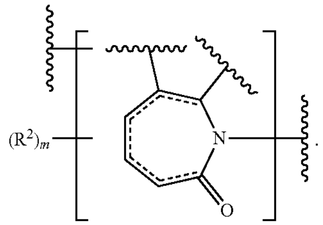

In some embodiments, Ring E is

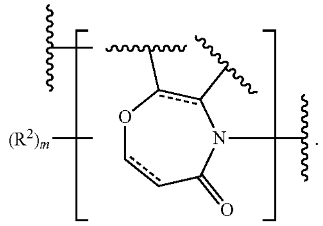

In some embodiments, Ring E is

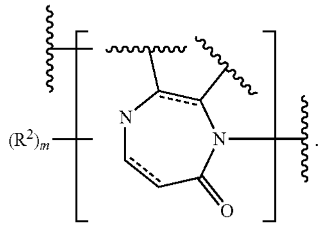

In some embodiments, Ring E is
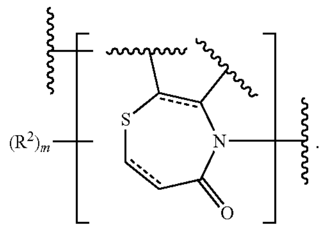
some embodiments, Ring E is
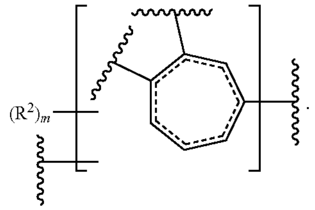
In some embodiments, Ring E is
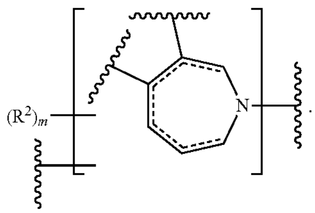
In some embodiments, Ring E is
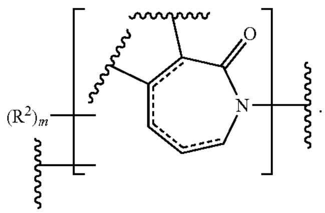
In some embodiments, Ring E is
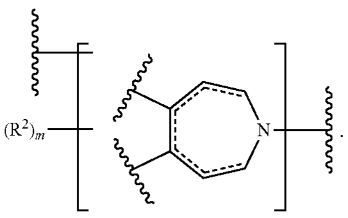
In some embodiments, Ring E is
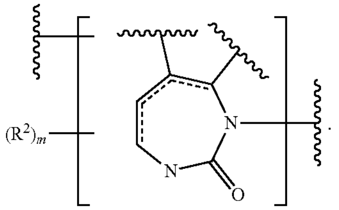
In some embodiments, Ring E is
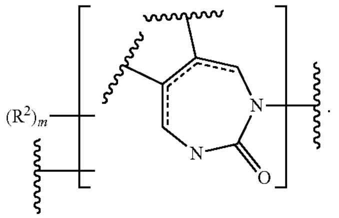
In some embodiments, Ring E is
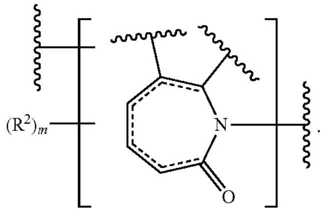
In some embodiments, Ring E is
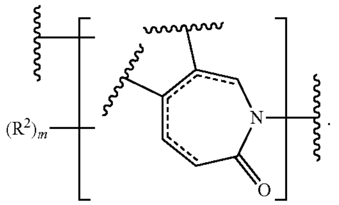
In some embodiments, Ring E is
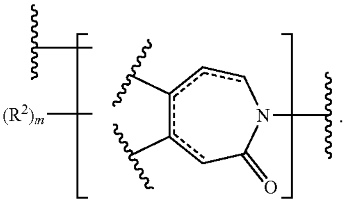

In some embodiments, Ring E is

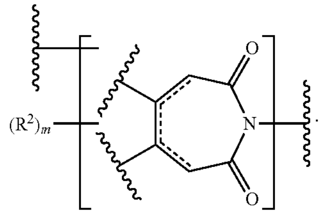

In some embodiments, Ring E is

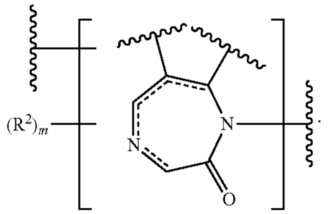

In some embodiments, Ring E is

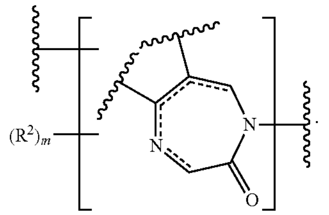

In some embodiments, Ring E is selected from those depicted in Table 1, below.

As defined above and described herein, each of Ring F and Ring G is independently a fused ring selected from 6-membered aryl, 6-membered heteroaryl containing 1-4 heteroatoms independently selected from nitrogen, oxygen, or sulfur, 5 to 7-membered saturated or partially unsaturated carbocyclyl, 5 to 7-membered saturated or partially unsaturated heterocyclyl ring with 1-3 heteroatoms independently selected from boron, nitrogen, oxygen, silicon, or sulfur, or 5-membered heteroaryl with 1-4 heteroatoms independently selected from nitrogen, oxygen or sulfur In some embodiments, each of Ring F and Ring G is independently a 6-membered aryl. In some embodiments, each of Ring F and Ring G is independently a 6-membered heteroaryl containing 1-4 heteroatoms independently selected from nitrogen, oxygen, or sulfur. In some embodiments, each of Ring F and Ring G is independently a 5 to 7-membered saturated or partially unsaturated carbocyclyl. In some embodiments, each of Ring F and Ring G is independently a 5 to 7-membered saturated or partially unsaturated heterocyclyl ring with 1-3 heteroatoms independently selected from boron, nitrogen, oxygen, silicon, or sulfur. In some embodiments, each of Ring F and Ring G is independently a 5-membered heteroaryl with 1-3 heteroatoms independently selected from nitrogen, oxygen or sulfur.

In some embodiments, each Ring F and Ring G is independently

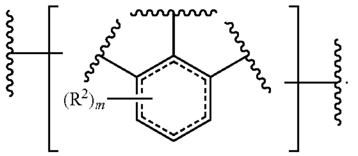

In some embodiments, each Ring F and Ring G is independently

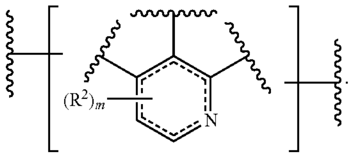

In some embodiments, each Ring F and Ring G is independently

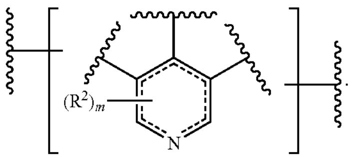

In some embodiments, each Ring F and Ring G is independently

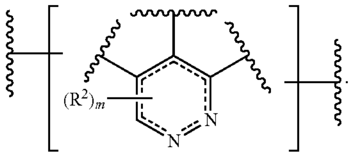

In some embodiments, Ring F and Ring G is independently is

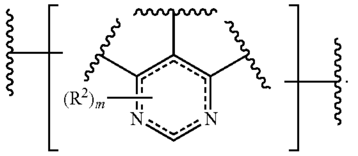

In some embodiments, Ring F and Ring G is independently

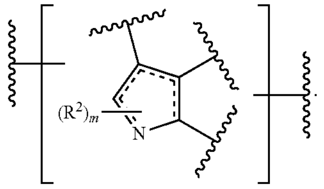

In some embodiments, Ring F and Ring G is independently

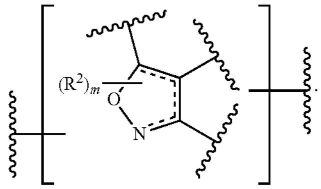

In some embodiments, Ring F and Ring G is independently

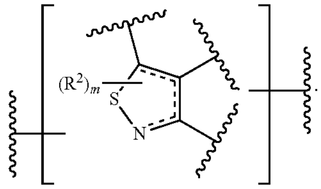

In some embodiments, each of Ring F and G is independently selected from those depicted in Table 1, below.

As defined above and described herein, Ring H is a fused ring selected from a 7-12 membered saturated or partially unsaturated carbocyclyl or hetercyclyl ring with 1-3 heteroatoms independently selected from boron, nitrogen, oxygen, silicon, or sulfur, wherein Ring H is optionally further substituted with 1-2 oxo groups.

In some embodiments, Ring H is a fused ring selected from a 7-12 membered saturated or partially unsaturated carbocyclyl. In some embodiments, Ring H is a 7-12 membered saturated or partially unsaturated hetercyclyl ring with 1-3 heteroatoms independently selected from boron, nitrogen, oxygen, silicon, or sulfur. In some embodiments, Ring H is optionally further substituted with 1-2 oxo groups.

In some embodiments, Ring H is

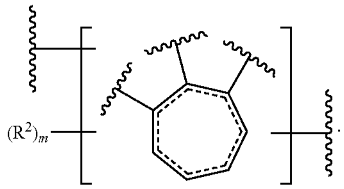

In some embodiments, Ring H is

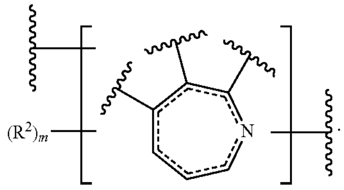

In some embodiments, Ring H is

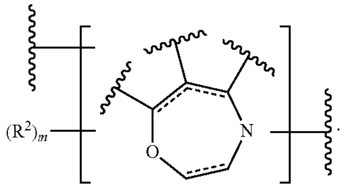

In some embodiments, Ring H is

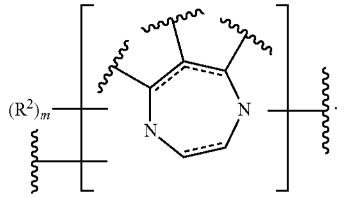

In some embodiments, Ring H is

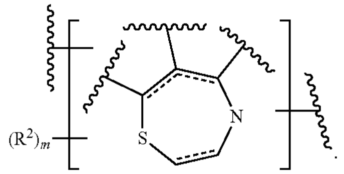

In some embodiments, Ring H is

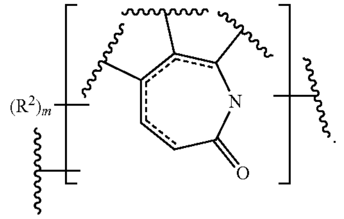

In some embodiments, Ring H is

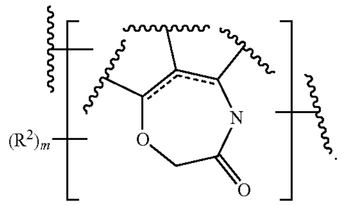

In some embodiments, Ring H is

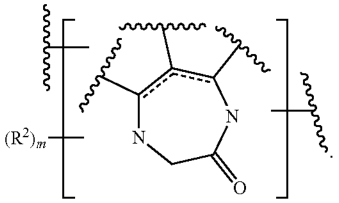

In some embodiments, Ring H is

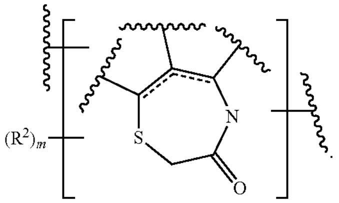

some embodiments, Ring H is

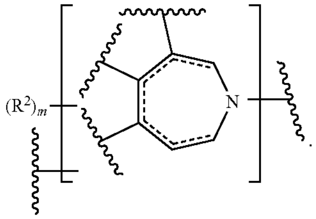

In some embodiments, Ring H is

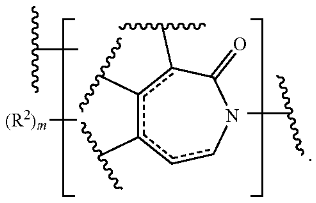

In some embodiments, Ring H is

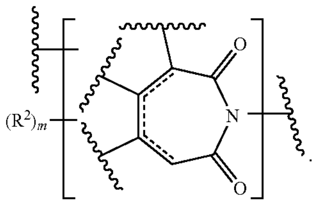

In some embodiments, Ring H is

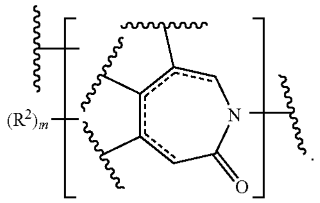

In some embodiments, Ring H is

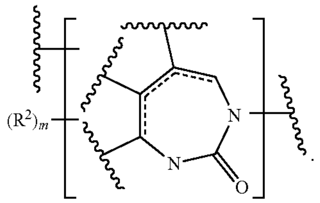

In some embodiments, Ring H is

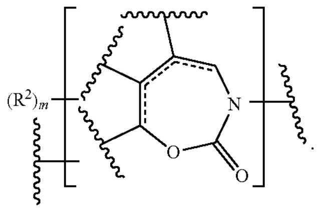

In some embodiments, Ring H is selected from those depicted in Table 1, below.

As defined above and described herein, Ring A is a tricyclic ring selected from

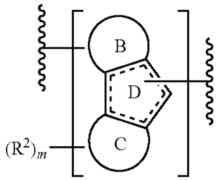
,
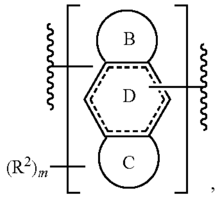
,
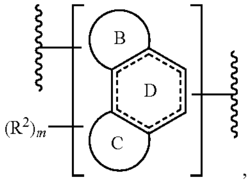
,
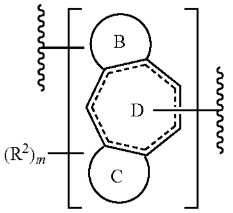
, or
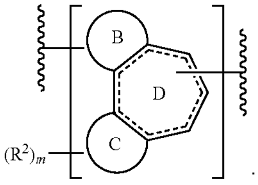
.

In some embodiments, Ring A is

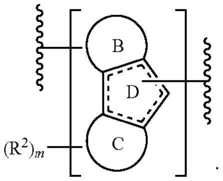

In some embodiments, Ring A is

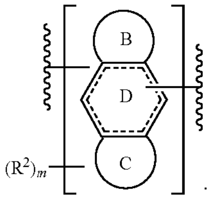

In some embodiment, Ring A is

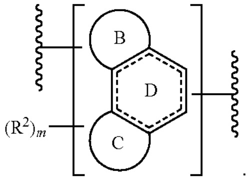

In some embodiments, Ring A is

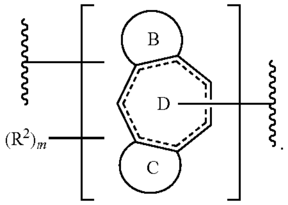

In some embodiments, Ring A is

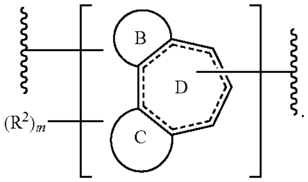

In some embodiments, Ring A is selected from those depicted in Table 1, below.

As defined above and described herein, Ring D is a fused ring selected from aryl containing 0-3 nitrogens, saturated or partially unsaturated carbocyclyl, saturated or partially unsaturated heterocyclyl ring with 1-2 heteroatoms independently selected from nitrogen, oxygen, silicon, or sulfur, or heteroaryl with 1-3 heteroatoms independently selected from nitrogen, oxygen or sulfur.

In some embodiments, Ring D is an aryl containing 0-2 nitrogen atoms. In some embodiments, Ring D is a saturated or partially unsaturated carbocyclyl. In some embodiments, each Ring D is a saturated or partially unsaturated heterocyclyl with 1-2 heteroatoms independently selected from nitrogen, oxygen, silicon, or sulfur. In some embodiments, Ring D is a heteroaryl with 1-3 heteroatoms independently selected from nitrogen, oxygen or sulfur.

In some embodiments, Ring D is

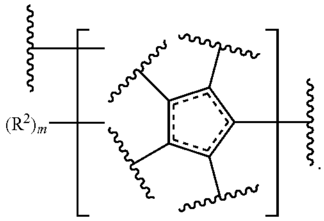

In some embodiments, Ring D is

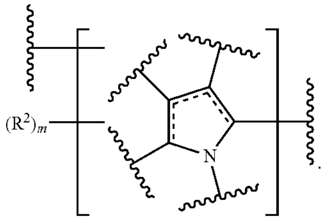

In some embodiments, Ring D is

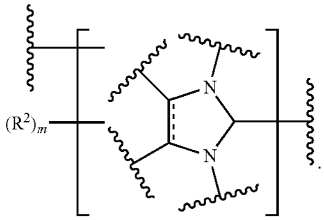

In some embodiments, Ring D is

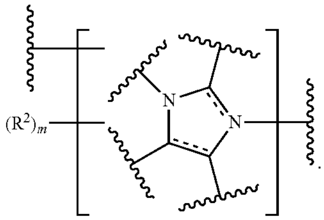

In some embodiments, Ring D is
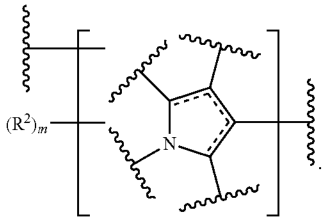
In some embodiments, Ring D is
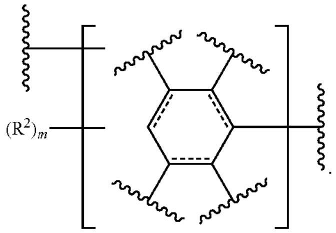
In some embodiments, Ring D is
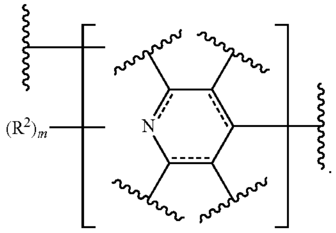
In some embodiments, Ring D is
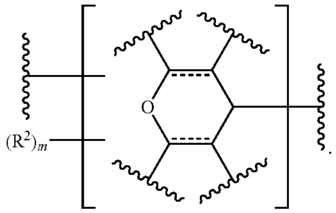
In some embodiments, Ring D is
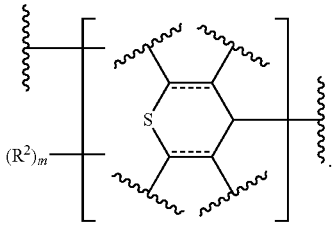
In some embodiments, Ring D is
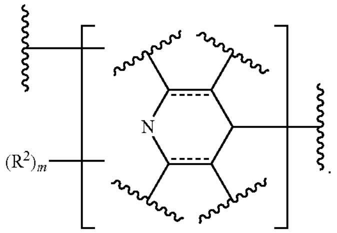
In some embodiments, Ring D is
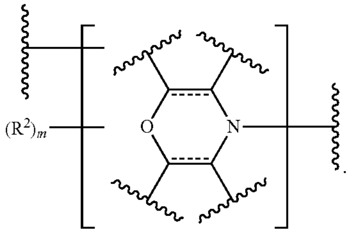
In some embodiments, Ring D is
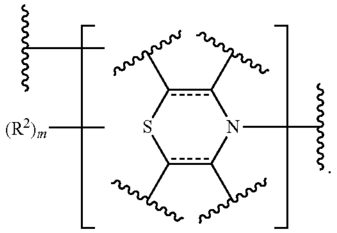
In some embodiments, Ring D is
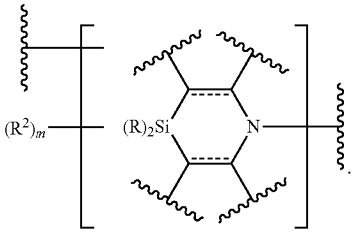
In some embodiments, Ring D is
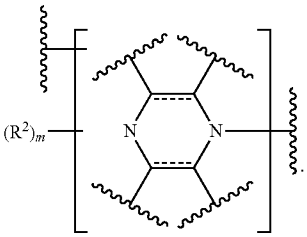

In some embodiments, Ring D is
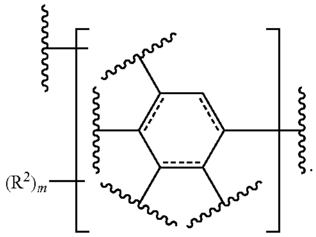
In some embodiments, Ring D is
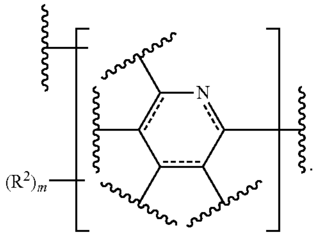
In some embodiments, Ring D is
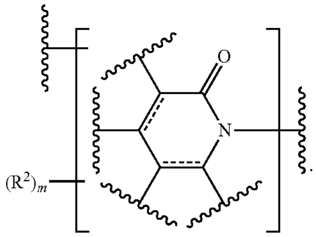
In some embodiments, Ring D is
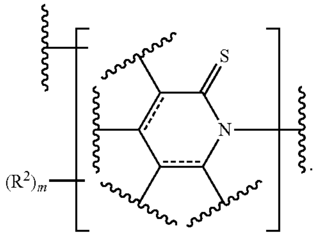
In some embodiments, Ring D is
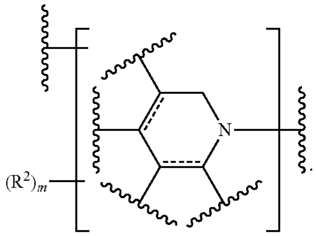
In some embodiments, Ring D is
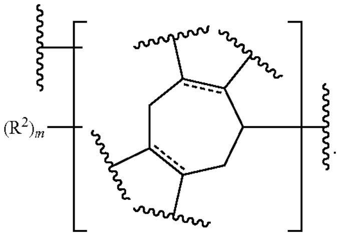
In some embodiments, Ring D is
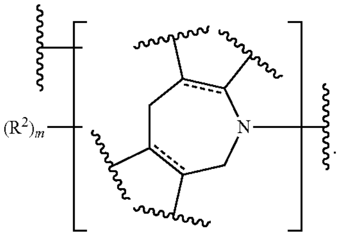
In some embodiments, Ring D is
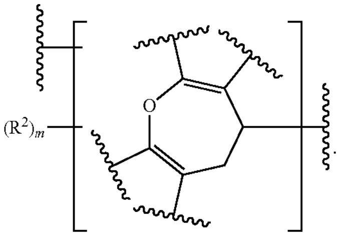
In some embodiments, Ring D is
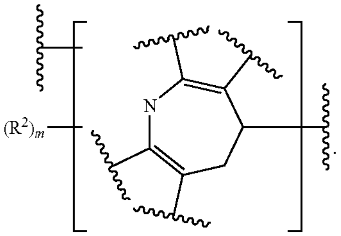
In some embodiments, Ring D is
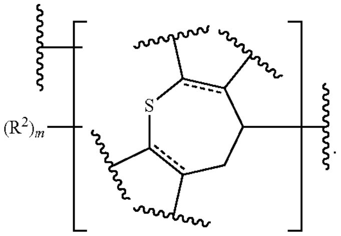

In some embodiments, Ring D is
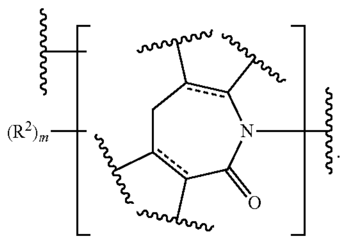
In some embodiments, Ring D is
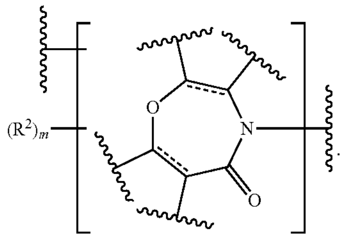
In some embodiments, Ring D is
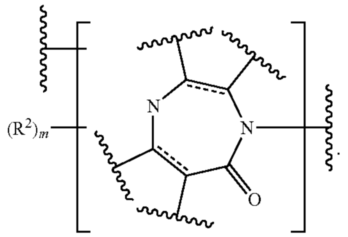
In some embodiments, Ring D is
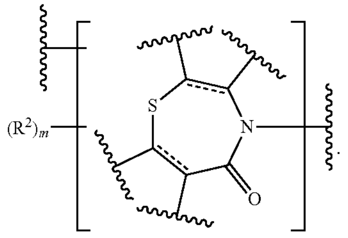
In some embodiments, Ring D is
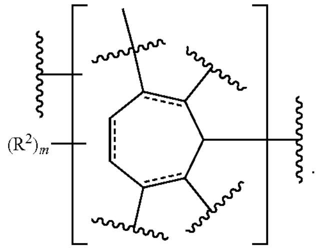
In some embodiments, Ring D is
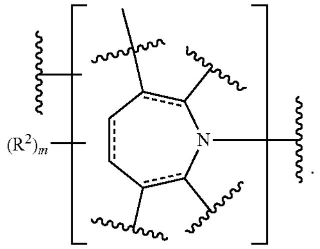
In some embodiments, Ring D is
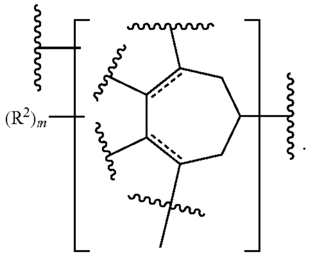
In some embodiments, Ring D is
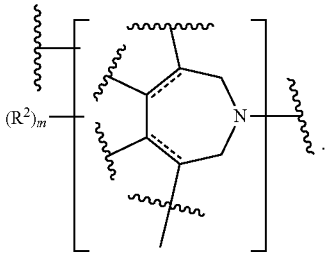
In some embodiments, Ring D is
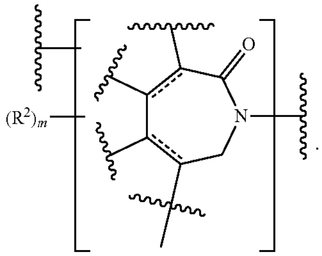
In some embodiments, Ring D is
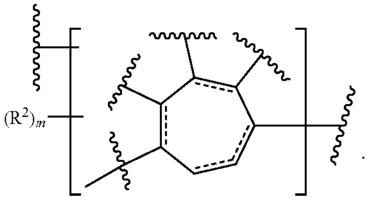

In some embodiments, Ring D is

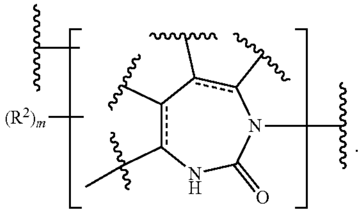

In some embodiments, Ring D is

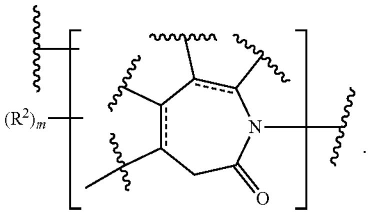

In some embodiments, Ring D is selected from those depicted in Table 1, below.

As defined above and described herein, m is 0, 1, 2, 3, 4, 5, 6, 7, 8, 9, 10, 11, 12, 13, 14, 15, or 16.

In some embodiments, m is 0. In some embodiments, m is 1. In some embodiments, m is 2. In some embodiments, m is 3. In some embodiments, m is 4. In some embodiments, m is 5. In some embodiments, m is 6. In some embodiments, m is 7. In some embodiments, m is 8. In some embodiments, m is 9. In some embodiments, m is 10. In some embodiments, m is 11. In some embodiments, m is 12. In some embodiments, m is 13. In some embodiments, m is 14. In some embodiments, m is 15. In some embodiments, m is 16.

In some embodiments, m is selected from those depicted in Table 1, below.

As defined above and described herein, Ring A is a tricyclic ring selected from

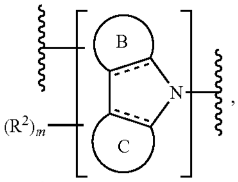,
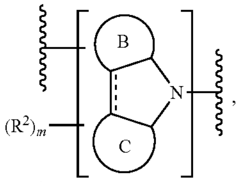,
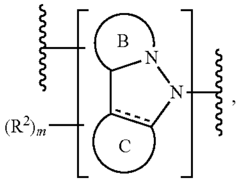,
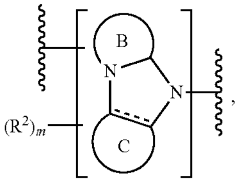,
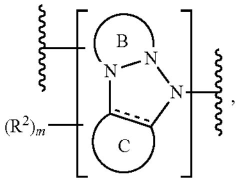,
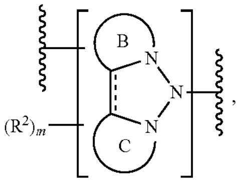,

-continued

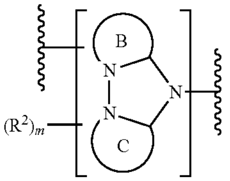,
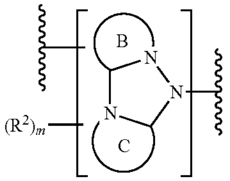, or
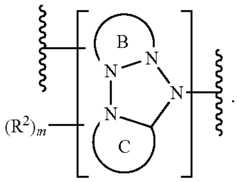

In some embodiments, Ring A is

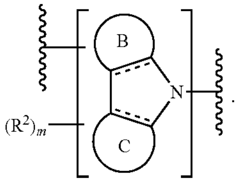

In some embodiments, Ring A is

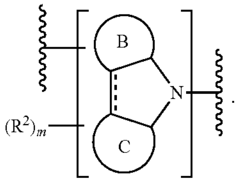

In some embodiment, Ring A is

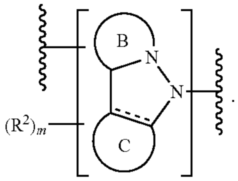

In some embodiments, Ring A is

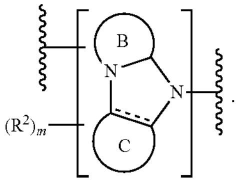

In some embodiments, Ring A is

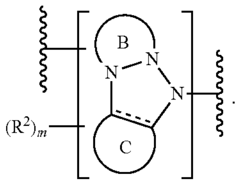

In some embodiments, Ring A is

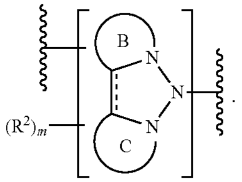

In some embodiments, Ring A is

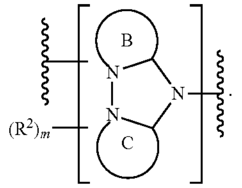

In some embodiments, Ring A is

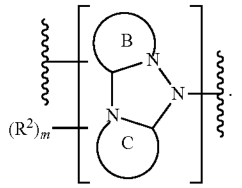

In some embodiments, Ring A is

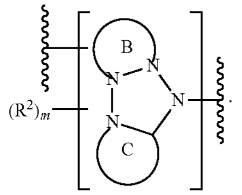

In some embodiments, Ring A is

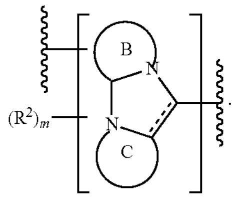

In some embodiments, Ring A is

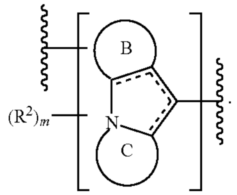

In some embodiments, Ring A is

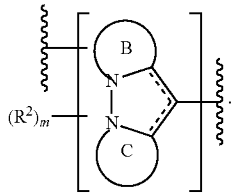

In some embodiments, Ring A is

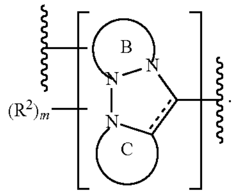

In some embodiments, Ring A is selected from those depicted in Table 1, below.

As defined above and described herein, each Ring B and Ring C is independently a fused ring selected from 6-membered aryl containing 0-2 nitrogen atoms, 5 to 7-membered saturated or partially unsaturated carbocyclyl, 5 to 7-membered saturated or partially unsaturated heterocyclyl with 1-3 heteroatoms independently selected from boron, nitrogen, oxygen, silicon, or sulfur, or 5-membered heteroaryl with 1-3 heteroatoms independently selected from nitrogen, oxygen or sulfur.

In some embodiments, each Ring B and Ring C is independently a 6-membered aryl containing 0-2 nitrogen atoms. In some embodiments, each Ring B and Ring C is independently a 5 to 7-membered saturated or partially unsaturated carbocyclyl. In some embodiments, each Ring B and Ring C is independently a 5 to 7-membered saturated or partially unsaturated heterocyclyl with 1-3 heteroatoms independently selected from boron, nitrogen, oxygen, silicon, or sulfur. In some embodiments, each Ring B and Ring C is independently a 5-membered heteroaryl with 1-3 heteroatoms independently selected from nitrogen, oxygen or sulfur.

In some embodiments, each Ring B and Ring C is independently

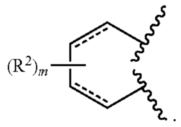

In some embodiments, each Ring B and Ring C is independently

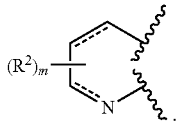

In some embodiments, each Ring B and Ring C is independently

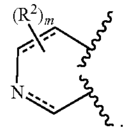

In some embodiments, each Ring B and Ring C is independently

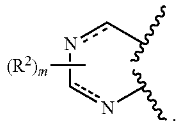

In some embodiments, Ring B and Ring C is independently

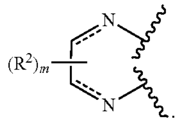

In some embodiments, Ring B and Ring C is independently is

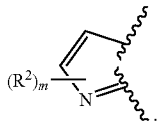

In some embodiments, Ring B and Ring C is independently

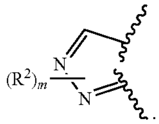

In some embodiments, Ring B and Ring C is independently

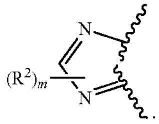

In some embodiments, Ring B and Ring C is independently

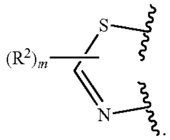

In some embodiments, Ring B and Ring C is independently
In some embodiments, Ring B and Ring C is independently

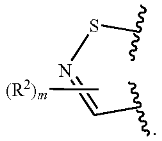

In some embodiments, Ring B and Ring C is independently

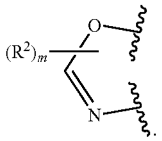

In some embodiments, Ring B and Ring C is independently

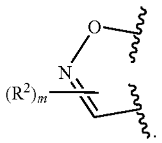

In some embodiments, Ring B and Ring C is independently

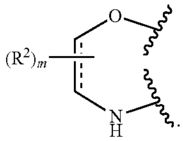

In some embodiments, Ring B and Ring C is independently

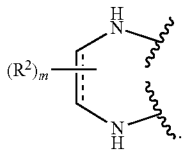

In some embodiments, B and Ring C is independently

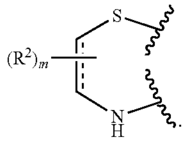

In some embodiments, Ring B and Ring C is independently

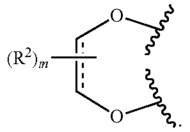

In some embodiments, Ring B and Ring C is independently

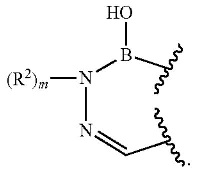

In some embodiments, Ring B and Ring C is independently selected from those depicted in Table 1, below.

In some embodiments, Ring A is

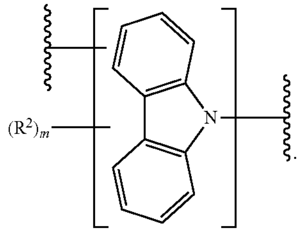

In some embodiments, Ring A is

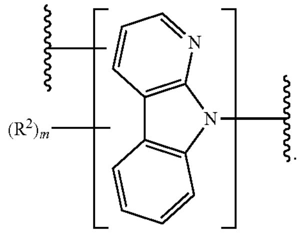

In some embodiments, Ring A is

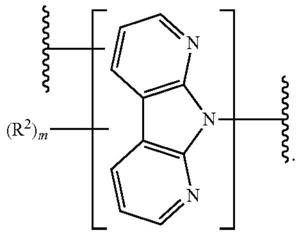

In some embodiments, Ring A is

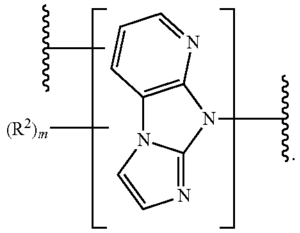

In some embodiments, Ring A is

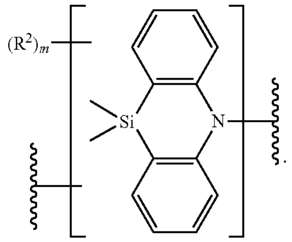

In some embodiments, Ring A is

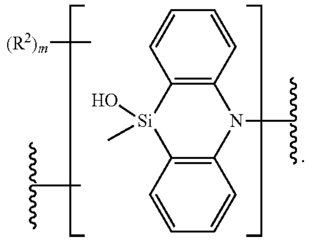

In some embodiments, Ring A is

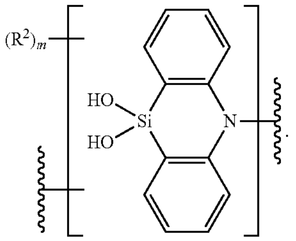

In some embodiments, Ring A is
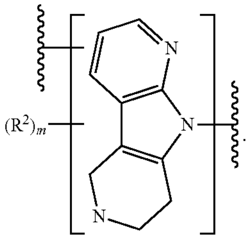
In some embodiments, Ring A is In some
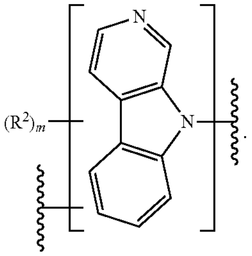
In some embodiments, Ring A is
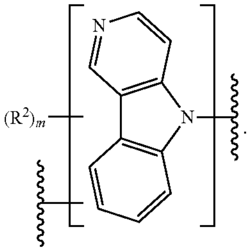
In some embodiments, Ring A is
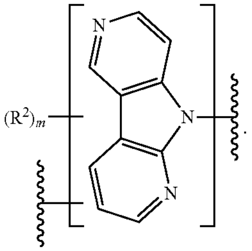
In some embodiments, Ring A is
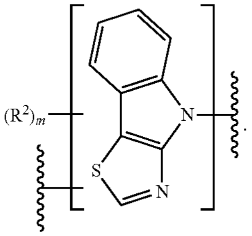
In some embodiments, Ring A is
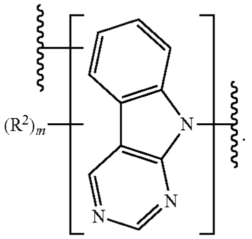
In some embodiments, Ring A is
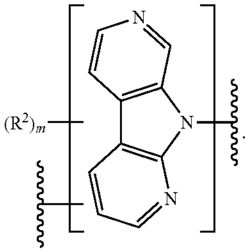
In some embodiments, Ring A is
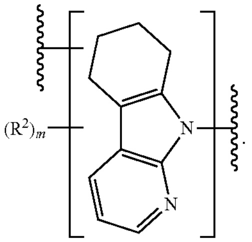
In some embodiments, Ring A is
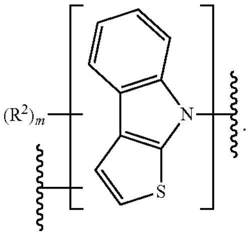
In some embodiments, Ring A is
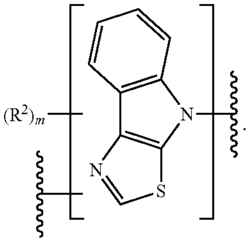

In some embodiments, Ring A is

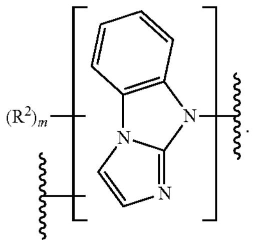

In some embodiments, Ring A is

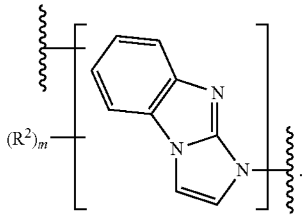

In some embodiments, Ring A is

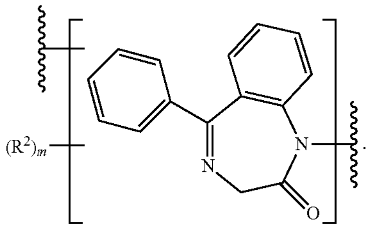

In some embodiments, Ring A is

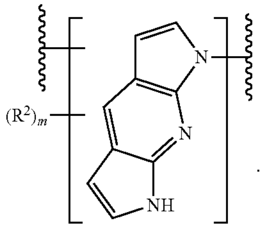

In some embodiments, Ring A is

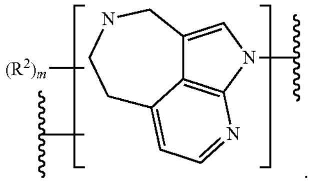

In some embodiments, Ring A is

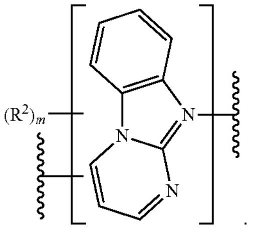

In some embodiments, Ring A is

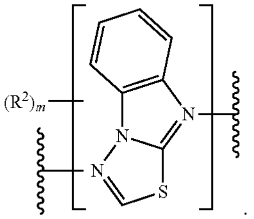

In some embodiments, Ring A is selected from those depicted in Table 1, below.

As defined above and described herein, $\overline{---}$ is a single or double bond In some embodiments, $\overline{---}$ is a single bond. In some embodiments, $\overline{---}$ is a double bond.

As defined above and described herein, m is 0, 1, 2, 3, 4, 5, 6, 7, or 8.

In some embodiments, m is 0. In some embodiments, m is 1. In some embodiments, m is 2. In some embodiments, m is 3. In some embodiments, m is 4. In some embodiments, m is 5. In some embodiments, m is 6. In some embodiments, m is 7. In some embodiments, m is 8.

In some embodiments, m is selected from those depicted in Table 1, below.

As defined above and described herein, L is a covalent bond or a bivalent, saturated or unsaturated, straight or branched $C_{1-50}$ hydrocarbon chain, wherein 0-6 methylene units of L are independently replaced by —C(D)(H)—, $—C(D)_2$- , -Cy-, —O—, —N(R)—, $—Si(R)_2—$, —Si(OH)(R)—, $—Si(OH)_2—$, —P(O)(OR)—, —P(O)(R)—, $—P(O)(NR_2)—$, —S—, —OC(O)—, —C(O)O—, —C(O)—, —S(O)—, $—S(O)_2—$, $—N(R)S(O)_2—$, $—S(O)_2N(R)—$, —N(R)C(O)—, —C(O)N(R)—, —OC(O)N(R)—, —N(R)C(O)O—,

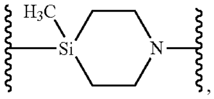, 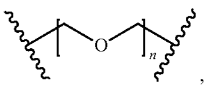,

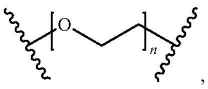, 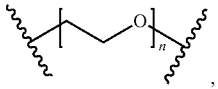,

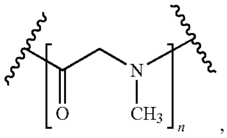, or 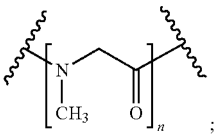;

and wherein n is 0, 1, 2, 3, 4, 5, 6, 7, 8, 9, or 10.

In some embodiments, L is a covalent bond. In some embodiments, L is a bivalent, saturated or unsaturated, straight or branched $C_{1-50}$ hydrocarbon chain, wherein 0-6 methylene units of L are independently replaced by —C(D)(H)—, —$C(D)_2$- , -Cy-, —O—, —N(R)—, —$Si(R)_2$—, —Si(OH)(R)—, —$Si(OH)_2$—, —P(O)(OR)—, —P(O)(R)—, —P(O)($NR_2$)—, —S—, —OC(O)—, —C(O)O—, —C(O)—, —S(O)—, —$S(O)_2$—, —N(R)$S(O)_2$—, —$S(O)_2$N(R)—, —N(R)C(O)—, —C(O)N(R)—, —OC(O)N(R)—, —N(R)C(O)O—,

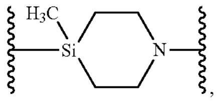, 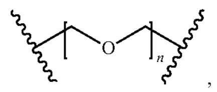,

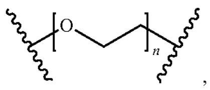, 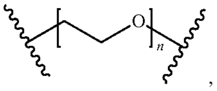,

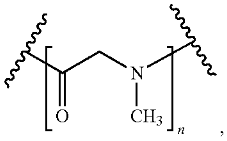, or 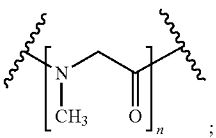;

and wherein n is 0, 1, 2, 3, 4, 5, 6, 7, 8, 9, or 10.

As defined above and described herein, each -Cy- is independently an optionally substituted bivalent ring selected from phenylenyl, an 8-10 membered bicyclic arylenyl, a 4-7 membered saturated or partially unsaturated carbocyclylenyl, a 4-7 membered saturated or partially unsaturated spiro carbocyclylenyl, an 8-10 membered bicyclic saturated or partially unsaturated carbocyclylenyl, a 4-7 membered saturated or partially unsaturated heterocyclylenyl having 1-2 heteroatoms independently selected from nitrogen, oxygen, and sulfur, a 4-7 membered saturated or partially unsaturated spiro heterocyclylenyl having 1-2 heteroatoms independently selected from nitrogen, oxygen, and sulfur, an 8-10 membered bicyclic saturated or partially unsaturated heterocyclylenyl having 1-2 heteroatoms independently selected from nitrogen, oxygen, and sulfur, a 5-6 membered heteroarylenyl having 1-4 heteroatoms independently selected from nitrogen, oxygen, and sulfur, or an 8-10 membered bicyclic heteroarylenyl having 1-5 heteroatoms independently selected from nitrogen, oxygen, or sulfur.

In some embodiments, -Cy- is an optionally substituted phenylenyl. In some embodiments, -Cy- is an optionally substituted 8-10 membered bicyclic arylenyl. In some embodiments, -Cy- is an optionally substituted 4-7 membered saturated or partially unsaturated carbocyclylenyl. In some embodiments, -Cy- is an optionally substituted 4-7 membered saturated or partially unsaturated spiro carbocyclylenyl. In some embodiments, -Cy- is an optionally substituted 8-10 membered bicyclic saturated or partially unsaturated carbocyclylenyl. In some embodiments, -Cy- is an optionally substituted 4-7 membered saturated or partially unsaturated heterocyclylenyl having 1-2 heteroatoms independently selected from nitrogen, oxygen, and sulfur. In some embodiments, -Cy- is an optionally substituted 4-7 membered saturated or partially unsaturated spiro heterocyclylenyl having 1-2 heteroatoms independently selected from nitrogen, oxygen, and sulfur. In some embodiments, -Cy- is an optionally substituted 8-10 membered bicyclic saturated or partially unsaturated heterocyclylenyl having 1-2 heteroatoms independently selected from nitrogen, oxygen, and sulfur. In some embodiments, -Cy- is an optionally substituted 5-6 membered heteroarylenyl having 1-4 heteroatoms independently selected from nitrogen, oxygen, and sulfur. In some embodiments, -Cy- is an optionally substituted 8-10 membered bicyclic heteroarylenyl having 1-5 heteroatoms independently selected from nitrogen, oxygen, or sulfur.

In some embodiments, -Cy- is

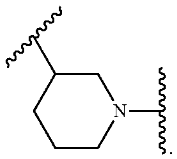 [SMILES: *C1CCCN(*)C1].

In some embodiments, -Cy- is

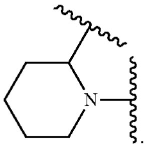 [SMILES: *C1CCCCN1*].

In some embodiments, -Cy- is

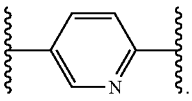 [SMILES: *c1ccc(*)nc1].

In some embodiments, -Cy- is

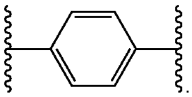 [SMILES: *c1ccc(*)cc1].

In some embodiments, -Cy- is

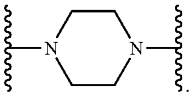 [SMILES: *N1CCN(*)CC1].

In some embodiments, -Cy- is

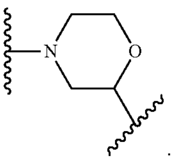 [SMILES: *C1CN(*)CCO1].

In some embodiments, -Cy- is

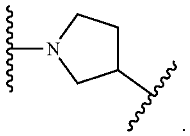 [SMILES: *C1CCN(*)C1]

In some embodiments, -Cy- is

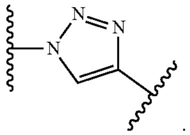 [SMILES: *c1cn(*)nn1]

In some embodiments, -Cy- is

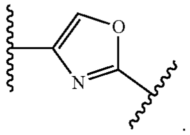 [SMILES: *c1coc(*)n1]

In some embodiments, -Cy- is

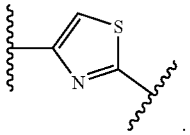 [SMILES: *c1csc(*)n1]

In some embodiments, -Cy- is

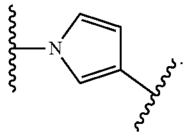 [SMILES: *c1ccn(*)c1]

In some embodiments, -Cy- is

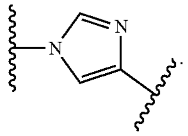 [SMILES: *c1cn(*)cn1]

In some embodiments, -Cy-

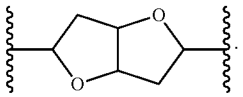 [SMILES: *C1CC2OC(*)CC2O1]

In some embodiments, -Cy- is

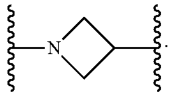 [SMILES: *C1CN(*)C1]

In some embodiments, -Cy- is

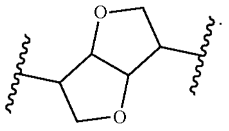 [SMILES: *C1COC2C(*)COC12]

In some embodiments, -Cy- is

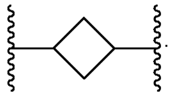 [SMILES: *C1CC(*)C1]

In some embodiments, -Cy- is

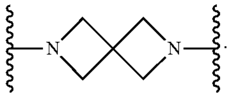 [SMILES: *N1CC2(C1)CN(*)C2]

In some embodiments, -Cy- is

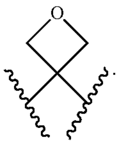 [SMILES: *C1(*)COC1]

In some embodiments, -Cy- is

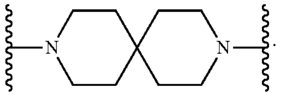 [SMILES: *N1CCC2(CC1)CCN(*)CC2]

In some embodiments, -Cy- is

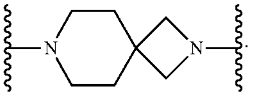

In some embodiments, -Cy- is

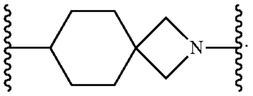 [SMILES: *C1CCC2(CC1)CN(*)C2]

In some embodiments, -Cy- is

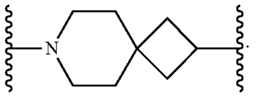 [SMILES: *C1CC2(CCN(*)CC2)C1]

In some embodiments, -Cy- is

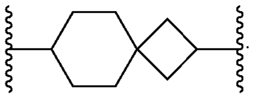 [SMILES: *C1CCC2(CC1)CC(*)C2]

In some embodiments, -Cy- is

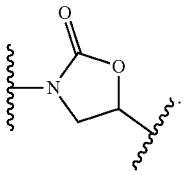 [SMILES: *C1CN(*)C(=O)O1]

In some embodiments, -Cy- is

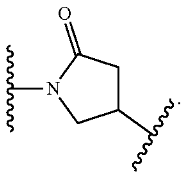 [SMILES: *C1CC(=O)N(*)C1]

In some embodiments, -Cy- is

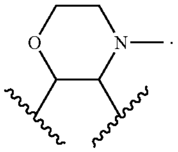 [SMILES: *C1OCCN(C)C1*]

In some embodiments, -Cy- is

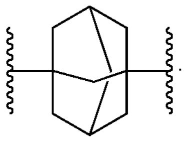 [SMILES: *C12CC3CC(C1)CC(*)(C3)C2]

In some embodiments, -Cy- is

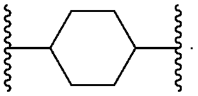 [SMILES: *C1CCC(*)CC1]

In some embodiments, -Cy- is

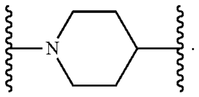 [SMILES: *C1CCN(*)CC1]

In some embodiments, -Cy- is

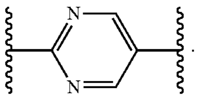 [SMILES: *c1cnc(*)nc1]

In some embodiments, -Cy- is

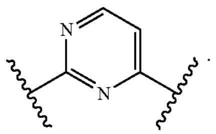 [SMILES: *c1ccnc(*)n1]

In some embodiments, -Cy- is

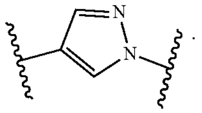 [SMILES: *c1cnn(*)c1]

In some embodiments, -Cy- is

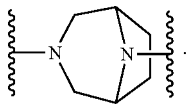

In some embodiments, -Cy- is

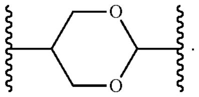 [SMILES: *C1COC(*)OC1]

In some embodiments, -Cy- is selected from those depicted in Table 1, below.

In some embodiments, L is

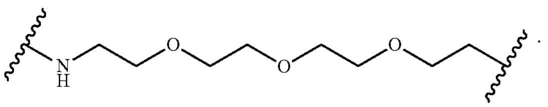 [SMILES: *CCOCCOCCOCCN*]

In some embodiments, L is

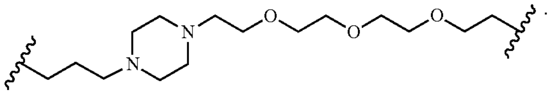 [SMILES: *CCCN1CCN(CCOCCOCCOCC*)CC1]

In some embodiments, L is

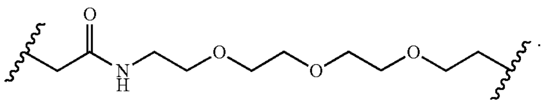 [SMILES: *CCOCCOCCOCCNC(=O)C*]

In some embodiments, L is

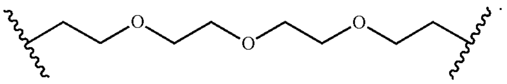 [SMILES: *CCOCCOCCOCC*]

In some embodiments, L is

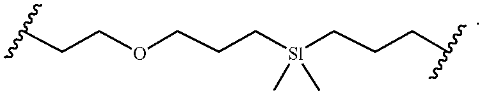

In some embodiments, L is

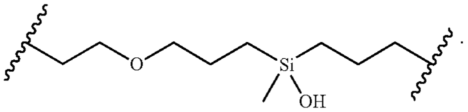 [SMILES: *CCC[Si](C)(O)CCCOCC*]

In some embodiments, L is

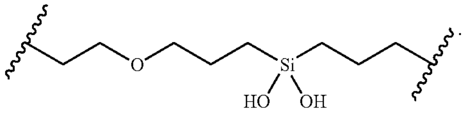 [SMILES: *CCC[Si](O)(O)CCCOCC*]

In some embodiments, L is

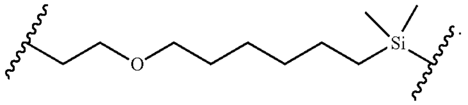 [SMILES: *CCOCCCCCC[Si](*)(C)C]

In some embodiments, L is

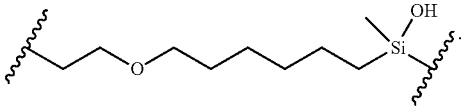 [SMILES: *CCOCCCCCC[Si](*)(C)O]

In some embodiments, L is

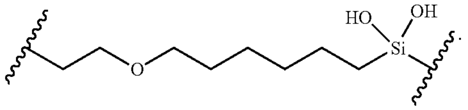 [SMILES: *CCOCCCCCC[Si](*)(O)O]

In some embodiments, L is

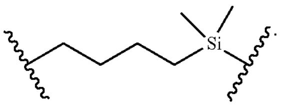 [SMILES: *CCCC[Si](*)(C)C]

In some embodiments, L is

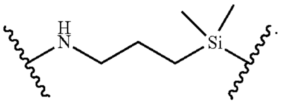 [SMILES: *NCCC[Si](*)(C)C]

In some embodiments, L is

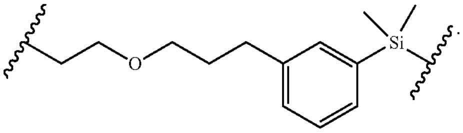 [SMILES: *CCOCCCc1cccc([Si](*)(C)C)c1]

In some embodiments, L is

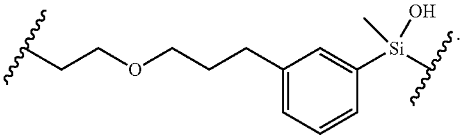 [SMILES: *CCOCCCc1cccc([Si](*)(C)O)c1]

In some embodiments, L is

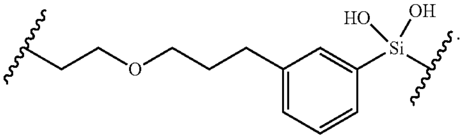 [SMILES: *CCOCCCc1cccc([Si](*)(O)O)c1]

In some embodiments, L is

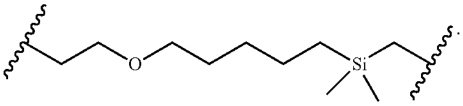 [SMILES: *CCOCCCCC[Si](C)(C)C*]

In some embodiments, L is

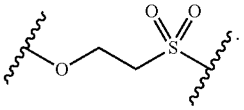 [SMILES: *OCCS(*)(=O)=O]

In some embodiments, L is
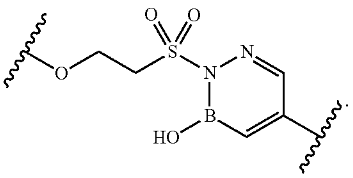 [SMILES: *OCCS(=O)(=O)N1N=CC(*)=CB1O]
In some embodiments, L is
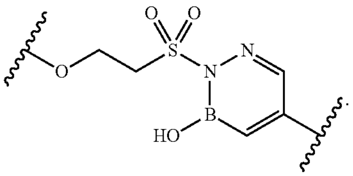 [SMILES: *OCCS(=O)(=O)N1N=CC(*)=CB1O]
In some embodiments, L is
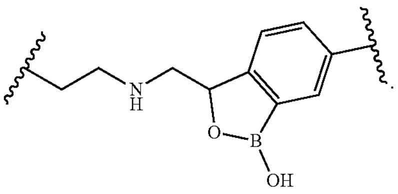 [SMILES: *CCNCC1OB(O)c2cc(*)ccc21]
In some embodiments, L is
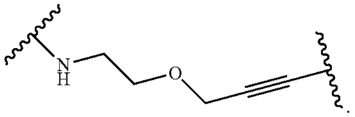 [SMILES: *C#CCOCCN*]
In some embodiments, L is
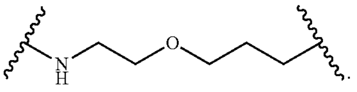 [SMILES: *CCCOCCN*]
In some embodiments, L is
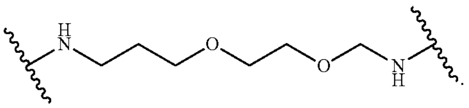 [SMILES: *NCCCOCCOCN*]
In some embodiments, L is
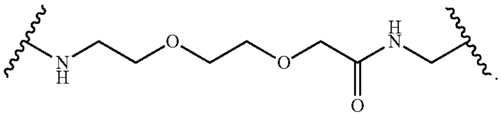 [SMILES: *CNC(=O)COCCOCCN*]
In some embodiments, L is
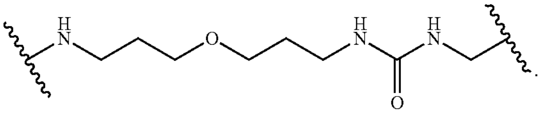 [SMILES: *CNC(=O)NCCCOCCCN*]
In some embodiments, L is
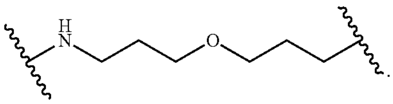 [SMILES: *CCCOCCCN*]
In some embodiments, L is
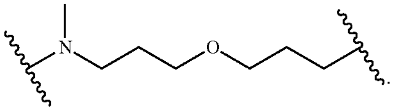 [SMILES: *CCCOCCCN(*)C]
In some embodiments, L is
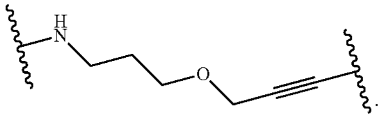 [SMILES: *C#CCOCCCN*]
In some embodiments, L is
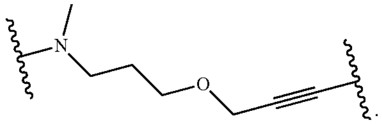 [SMILES: *C#CCOCCCN(*)C]
In some embodiments, L is
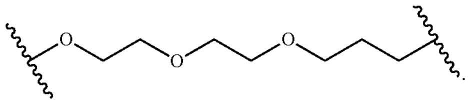 [SMILES: *CCCOCCOCCO*]

In some embodiments, L is
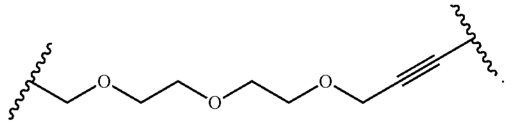 [SMILES: *C#CCOCCOCCOC*]
In some embodiments, L is
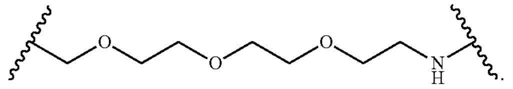 [SMILES: *COCCOCCOCCN*]
In some embodiments, L is
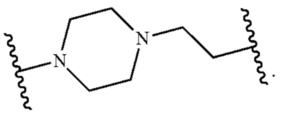 [SMILES: *CCN1CCN(*)CC1]
In some embodiments, L is
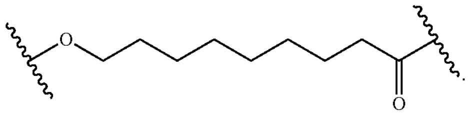 [SMILES: *OCCCCCCCCC(*)=O]
In some embodiments, L is
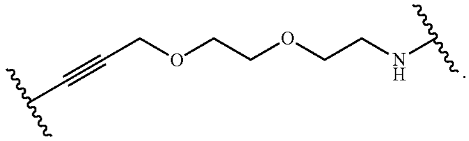 [SMILES: *C#CCOCCOCCN*]
In some embodiments, L is
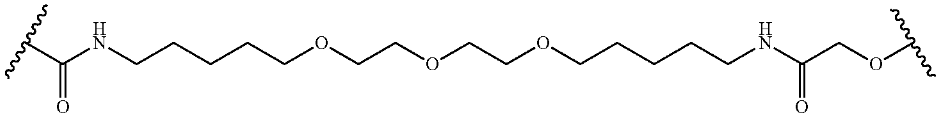 [SMILES: *OCC(=O)NCCCCCOCCOCCOCCCCCNC(*)=O]
In some embodiments, L is
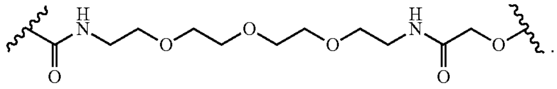 [SMILES: *OCC(=O)NCCOCCOCCOCCNC(*)=O]
In some embodiments, L is
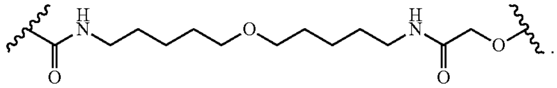 [SMILES: *OCC(=O)NCCCCCOCCCCCNC(*)=O]
In some embodiments, L is
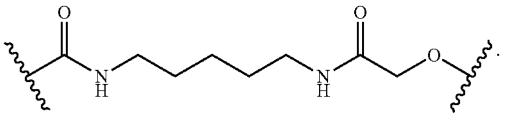 [SMILES: *OCC(=O)NCCCCCNC(*)=O]
In some embodiments, L is
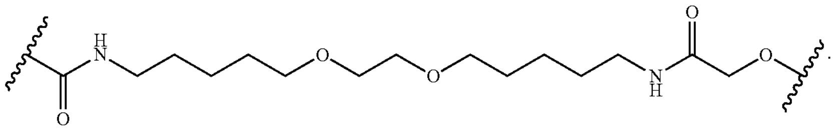 [SMILES: *OCC(=O)NCCCCCOCCOCCCCCNC(*)=O]

In some embodiments, L is
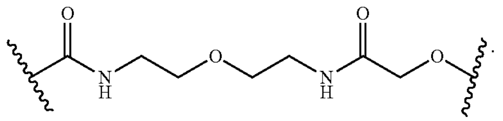 [SMILES: *OCC(=O)NCCOCCNC(*)=O]
In some embodiments, L is
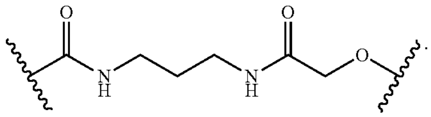 [SMILES: *OCC(=O)NCCCNC(*)=O]
In some embodiments, L is
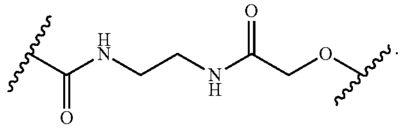 [SMILES: *OCC(=O)NCCNC(*)=O]
In some embodiments, L is
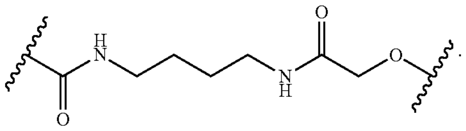 [SMILES: *OCC(=O)NCCCCNC(*)=O]
In some embodiments, L is
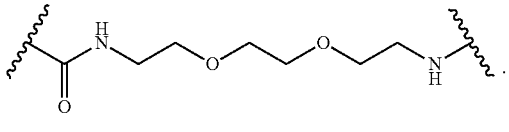 [SMILES: *NCCOCCOCCNC(*)=O]
In some embodiments, L is
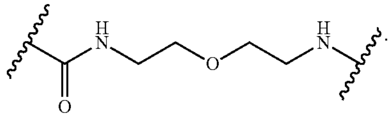 [SMILES: *NCCOCCNC(*)=O]
In some embodiments, L is
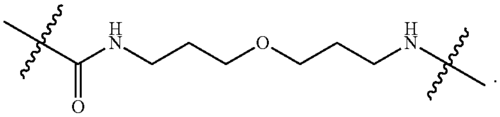 [SMILES: *NCCCOCCCNC(*)=O]
In some embodiments, L is
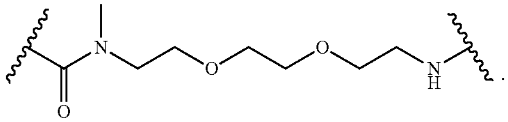 [SMILES: *NCCOCCOCCN(C)C(*)=O]
In some embodiments, L is
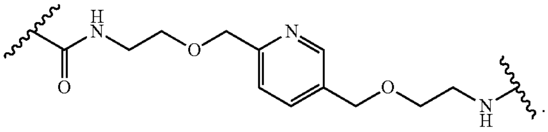 [SMILES: *NCCOCc1ccc(COCCNC(*)=O)nc1]
In some embodiments, L is
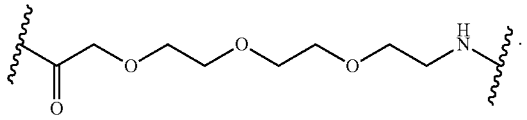 [SMILES: *NCCOCCOCCOCC(*)=O]
In some embodiments, L is
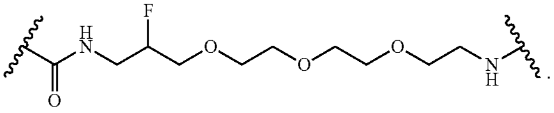 [SMILES: *NCCOCCOCCOCC(F)CNC(*)=O]
In some embodiments, L is
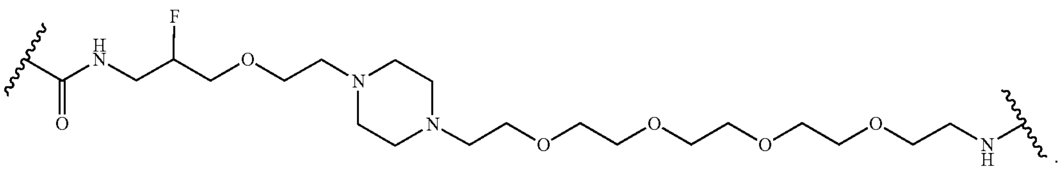 [SMILES: *NCCOCCOCCOCCOCCN1CCN(CCOCC(F)CNC(*)=O)CC1]

In some embodiments, L is
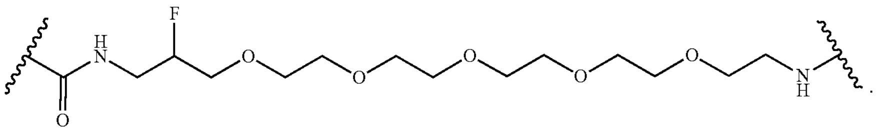 [SMILES: *NCCOCCOCCOCCOCCOCC(F)CNC(*)=O]
In some embodiments, L is
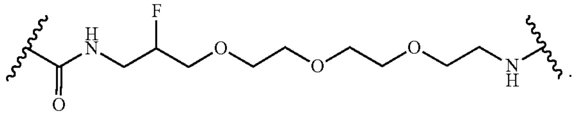 [SMILES: *NCCOCCOCCOCC(F)CNC(*)=O]
In some embodiments, L is
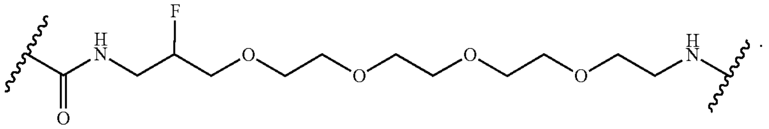 [SMILES: *NCCOCCOCCOCCOCC(F)CNC(*)=O]
In some embodiments, L is
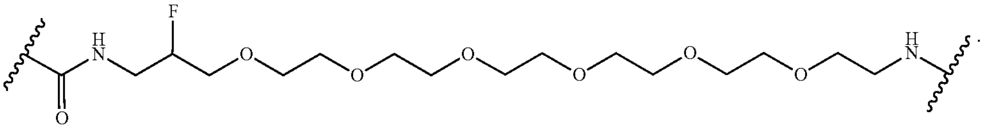 [SMILES: *NCCOCCOCCOCCOCCOCCOCC(F)CNC(*)=O]
In some embodiments, L is
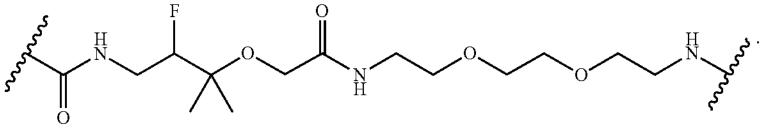 [SMILES: *NCCOCCOCCNC(=O)COC(C)(C)C(F)CNC(*)=O]
In some embodiments, L is
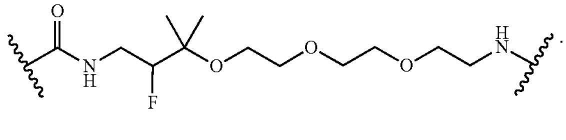 [SMILES: *NCCOCCOCCOC(C)(C)C(F)CNC(*)=O]
In some embodiments, L is
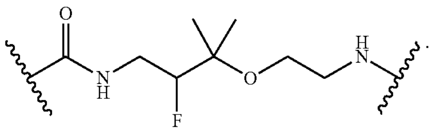 [SMILES: *NCCOC(C)(C)C(F)CNC(*)=O]

In some embodiments, L is
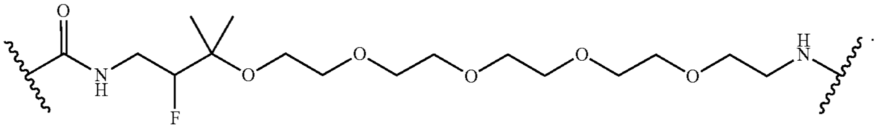 [SMILES: *NCCOCCOCCOCCOCCOC(C)(C)C(F)CNC(*)=O]
In some embodiments, L is
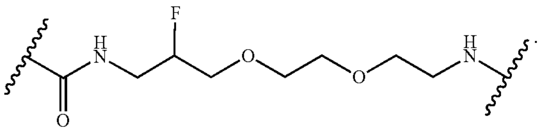 [SMILES: *NCCOCCOCC(F)CNC(*)=O]
In some embodiments, L is
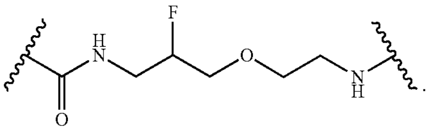 [SMILES: *NCCOCC(F)CNC(*)=O]
In some embodiments, L is
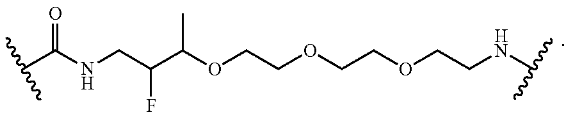 [SMILES: *NCCOCCOCCOC(C)C(F)CNC(*)=O]
In some embodiments, L is
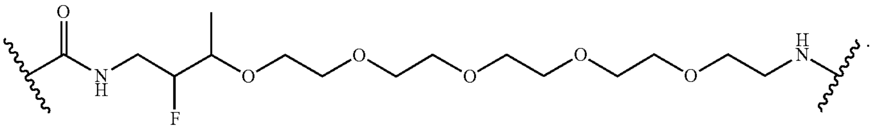 [SMILES: *NCCOCCOCCOCCOCCOC(C)C(F)CNC(*)=O]
In some embodiments, L is
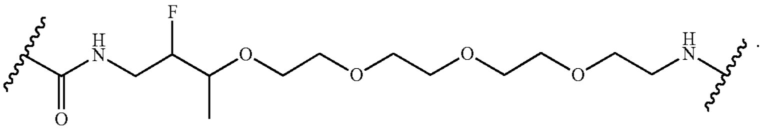 [SMILES: *NCCOCCOCCOCCOC(C)C(F)CNC(*)=O]
In some embodiments, L is
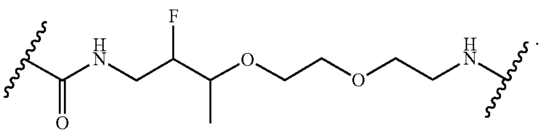 [SMILES: *NCCOCCOC(C)C(F)CNC(*)=O]

In some embodiments, L is
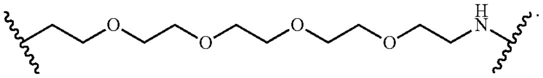 [SMILES: *CCOCCOCCOCCOCCN*]
In some embodiments, L is
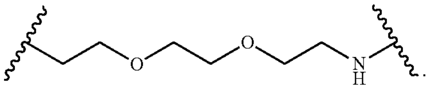 [SMILES: *CCOCCOCCN*]
In some embodiments, L is
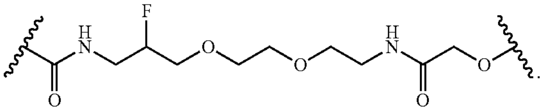 [SMILES: *OCC(=O)NCCOCCOCC(F)CNC(*)=O]
In some embodiments, L is
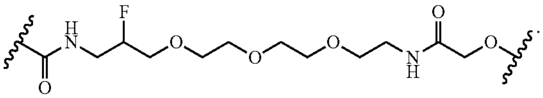 [SMILES: *OCC(=O)NCCOCCOCCOCC(F)CNC(*)=O]
In some embodiments, L is
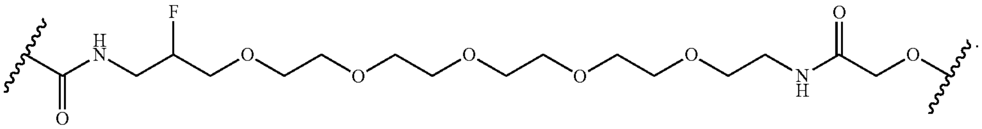 [SMILES: *OCC(=O)NCCOCCOCCOCCOCCOCC(F)CNC(*)=O]
In some embodiments, L is
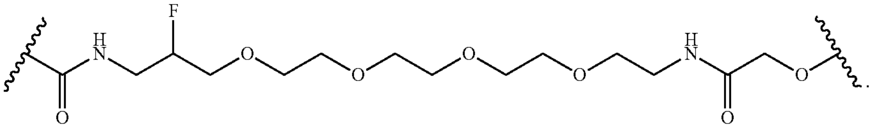 [SMILES: *OCC(=O)NCCOCCOCCOCCOCC(F)CNC(*)=O]
In some embodiments, L is
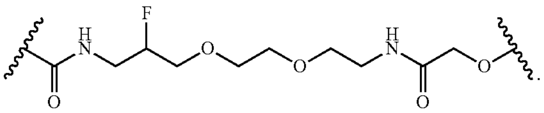 [SMILES: *OCC(=O)NCCOCCOCC(F)CNC(*)=O]
In some embodiments, L is
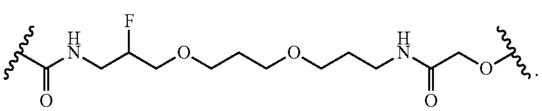 [SMILES: *OCC(=O)NCCCOCCCOCC(F)CNC(*)=O]
In some embodiments, L is
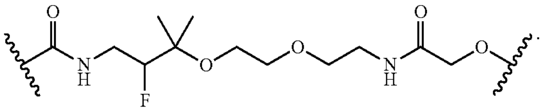 [SMILES: *OCC(=O)NCCOCCOC(C)(C)C(F)CNC(*)=O]
In some embodiments, L is
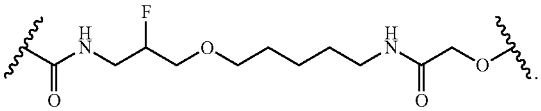 [SMILES: *OCC(=O)NCCCCCOCC(F)CNC(*)=O]

In some embodiments, L is
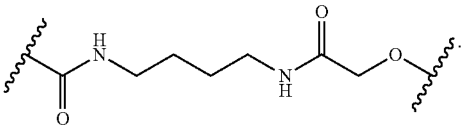 [SMILES: *OCC(=O)NCCCCNC(*)=O]
In some embodiments, L is
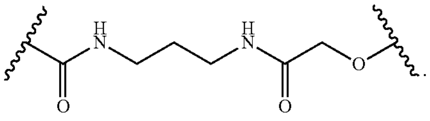 [SMILES: *OCC(=O)NCCCNC(*)=O]
In some embodiments, L is
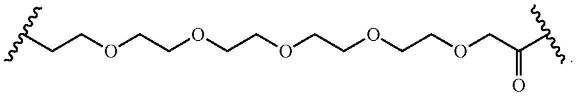
In some embodiments, L is
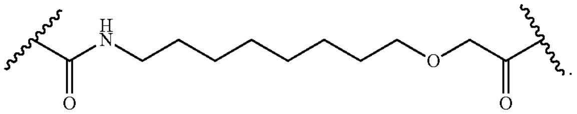
In some embodiments, L is
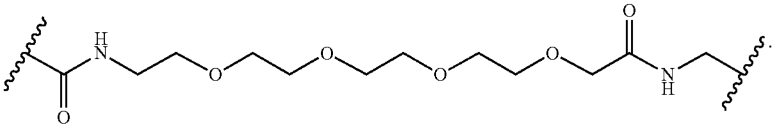 [SMILES: *CNC(=O)COCCOCCOCCOCCNC(*)=O]
In some embodiments, L is
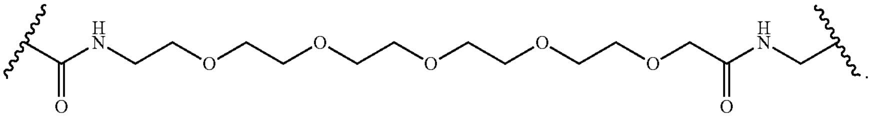 [SMILES: *CNC(=O)COCCOCCOCCOCCOCCNC(*)=O]
In some embodiments, L is
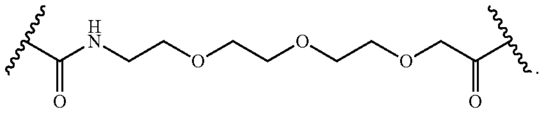 [SMILES: *C(=O)COCCOCCOCCNC(*)=O]
In some embodiments, L is
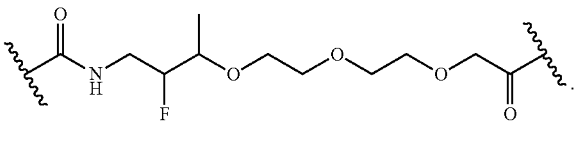 [SMILES: *C(=O)COCCOCCOC(C)C(F)CNC(*)=O]
In some embodiments, L is
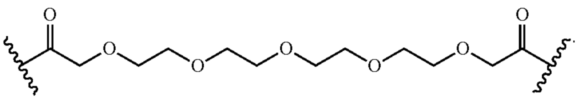 [SMILES: *C(=O)COCCOCCOCCOCCOCC(*)=O]
In some embodiments, L is
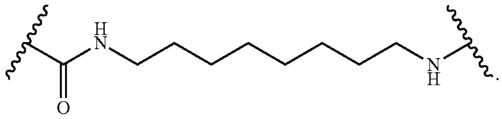 [SMILES: *NCCCCCCCCNC(*)=O]
In some embodiments, L is
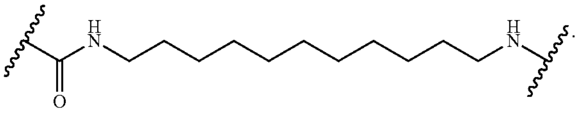 [SMILES: *NCCCCCCCCCCCNC(*)=O]
In some embodiments, L is
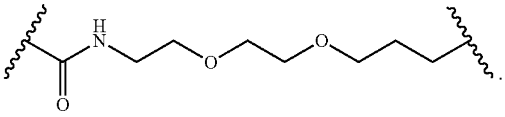 [SMILES: *CCCOCCOCCNC(*)=O]

In some embodiments, L is

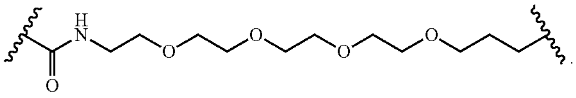 [SMILES: *CCCOCCOCCOCCOCCNC(*)=O]

In some embodiments, L is

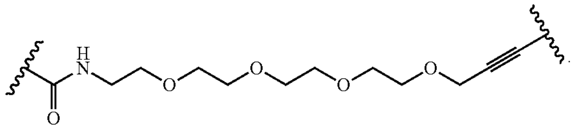 [SMILES: *C#CCOCCOCCOCCOCCNC(*)=O]

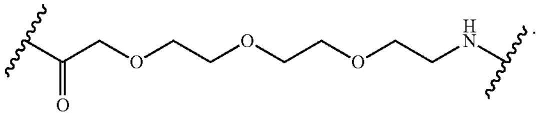 [SMILES: *NCCOCCOCCOCC(*)=O]

In some embodiments, L is

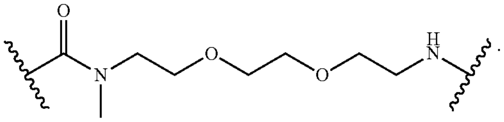 [SMILES: *NCCOCCOCCN(C)C(*)=O]

In some embodiments, L is

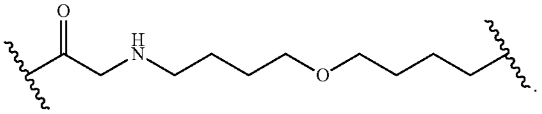 [SMILES: *CCCCOCCCCNCC(*)=O]

In some embodiments, L is

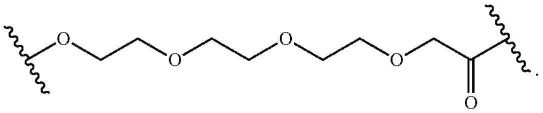 [SMILES: *OCCOCCOCCOCC(*)=O]

In some embodiments, L is

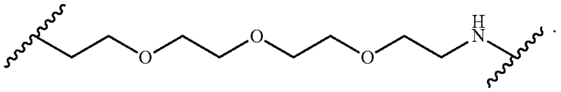 [SMILES: *CCOCCOCCOCCN*]

In some embodiments, L is

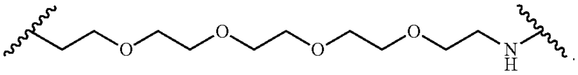 [SMILES: *CCOCCOCCOCCOCCN*]

In some embodiments, L is

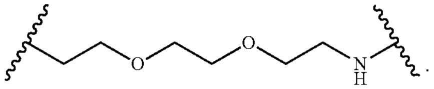 [SMILES: *CCOCCOCCN*]

In some embodiments, L is

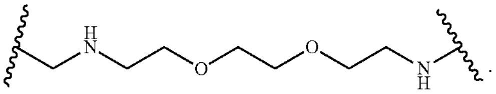 [SMILES: *CNCCOCCOCCN*]

In some embodiments, L is

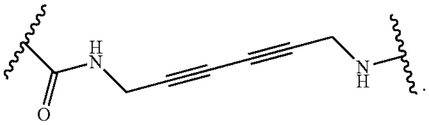 [SMILES: *NCC#CC#CCNC(*)=O]

In some embodiments, L is

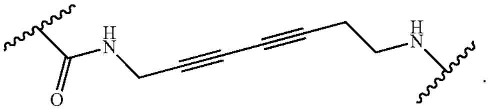 [SMILES: *NCCC#CC#CCNC(*)=O]

In some embodiments, L is

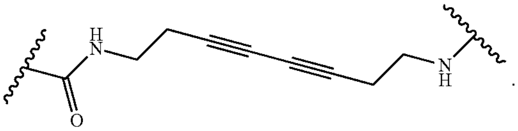 [SMILES: *NCCC#CC#CCCNC(*)=O]

In some embodiments, L is

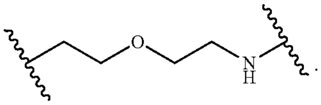 [SMILES: *CCOCCN*]

In some embodiments, L is

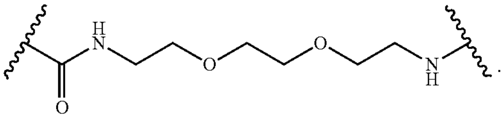 [SMILES: *NCCOCCOCCNC(*)=O]

In some embodiments, L is

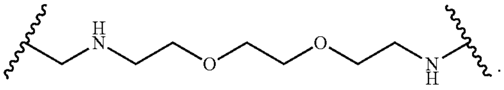 [SMILES: *CNCCOCCOCCN*]

In some embodiments, L is

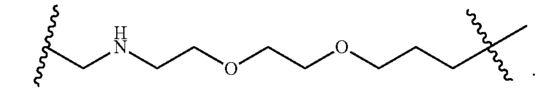 [SMILES: *CCCOCCOCCNC*]

In some embodiments, L is

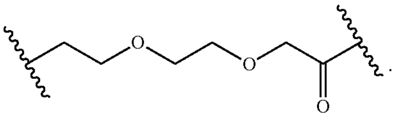 [SMILES: *CCOCCOCC(*)=O]

In some embodiments, L is

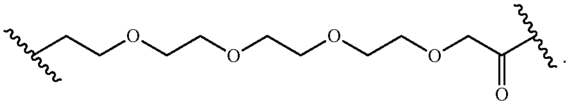 [SMILES: *CCOCCOCCOCCOCC(*)=O]

In some embodiments, L is

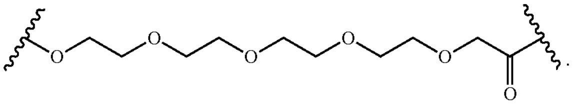 [SMILES: *OCCOCCOCCOCCOCC(*)=O]

In some embodiments, L is

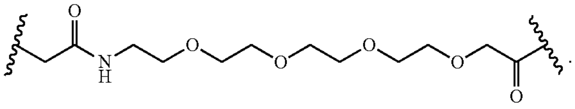 [SMILES: *CC(=O)NCCOCCOCCOCCOCC(*)=O]

In some embodiments, L is

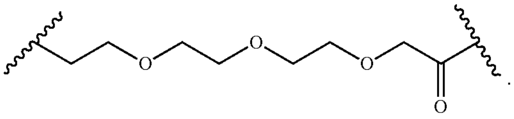 [SMILES: *CCOCCOCCOCC(*)=O]

In some embodiments, L is

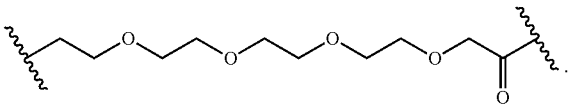 [SMILES: *CCOCCOCCOCCOCC(*)=O]

In some embodiments, L is

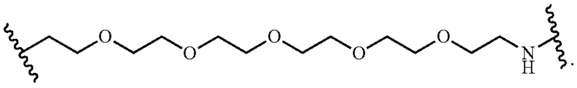 [SMILES: *CCOCCOCCOCCOCCOCCN*]

In some embodiments, L is

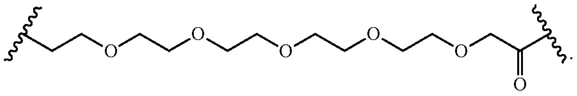 [SMILES: *CCOCCOCCOCCOCCOCC(*)=O]

In some embodiments, L is

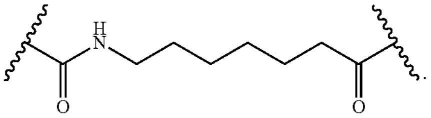 [SMILES: *C(=O)CCCCCCNC(*)=O]

In some embodiments, L is

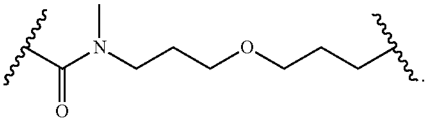 [SMILES: *CCCOCCCN(C)C(*)=O]

In some embodiments, L is

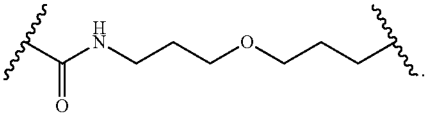 [SMILES: *CCCOCCCNC(*)=O]

In some embodiments, L is

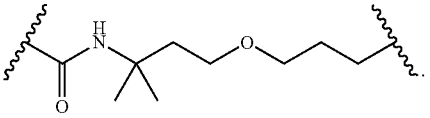 [SMILES: *CCCOCCC(C)(C)NC(*)=O]

In some embodiments, L is

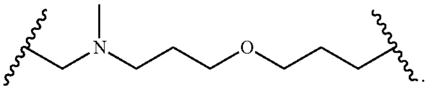 [SMILES: *CCCOCCCN(C)C*]

In some embodiments, L is

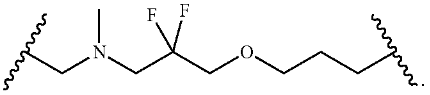 [SMILES: *CCCOCC(F)(F)CN(C)C*]

In some embodiments, L is

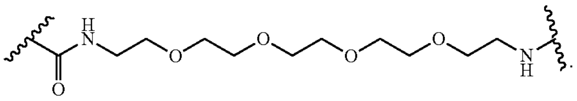 [SMILES: *NCCOCCOCCOCCOCCNC(*)=O]

In some embodiments, L is

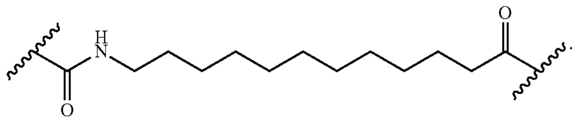 [SMILES: *C(=O)CCCCCCCCCCCNC(*)=O]

In some embodiments, L is

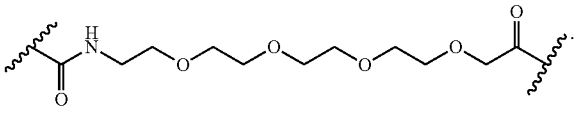 [SMILES: *C(=O)COCCOCCOCCOCCNC(*)=O]

In some embodiments, L is

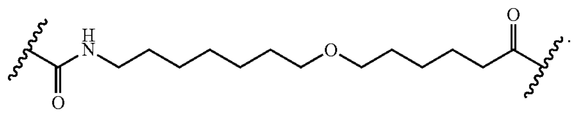 [SMILES: *C(=O)CCCCCOCCCCCCCNC(*)=O]

In some embodiments, L is

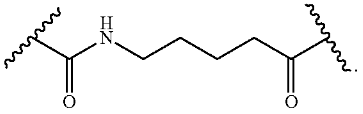 [SMILES: *C(=O)CCCCNC(*)=O]

In some embodiments, L is

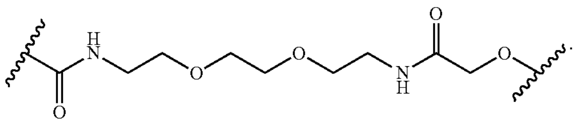 [SMILES: *OCC(=O)NCCOCCOCCNC(*)=O]

In some embodiments, L is

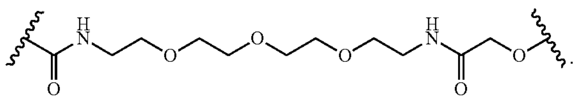 [SMILES: *OCC(=O)NCCOCCOCCOCCNC(*)=O]

In some embodiments, L is

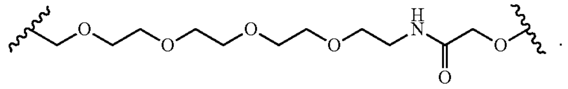 [SMILES: *COCCOCCOCCOCCNC(=O)CO*]

In some embodiments, L is

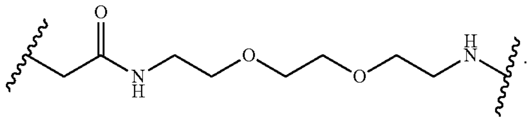 [SMILES: *CC(=O)NCCOCCOCCN*]

In some embodiments, L is

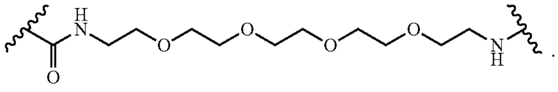 [SMILES: *NCCOCCOCCOCCOCCNC(*)=O]

In some embodiments, L is

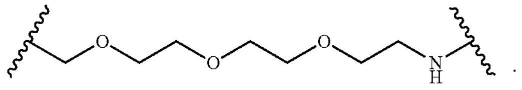 [SMILES: *COCCOCCOCCN*]

In some embodiments, L is

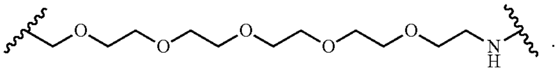 [SMILES: *COCCOCCOCCOCCOCCN*]

In some embodiments, L is

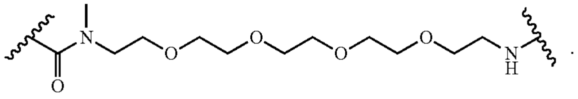 [SMILES: *NCCOCCOCCOCCOCCN(C)C(*)=O]

In some embodiments, L is

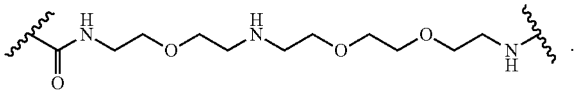 [SMILES: *NCCOCCOCCNCCOCCNC(*)=O]

In some embodiments, L is

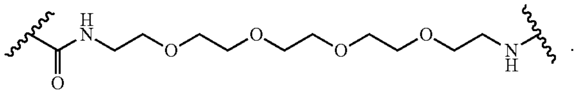 [SMILES: *NCCOCCOCCOCCOCCNC(*)=O]

In some embodiments, L is

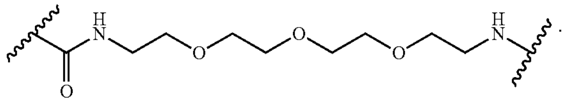 [SMILES: *NCCOCCOCCOCCNC(*)=O]

In some embodiments, L is
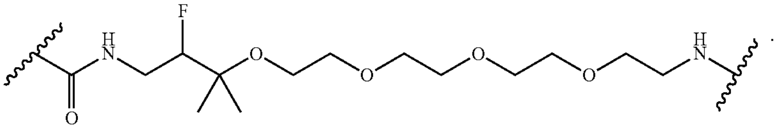 [SMILES: *NCCOCCOCCOCCOC(C)(C)C(F)CNC(*)=O]
In some embodiments, L is
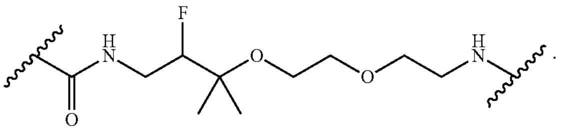 [SMILES: *NCCOCCOC(C)(C)C(F)CNC(*)=O]
In some embodiments, L is
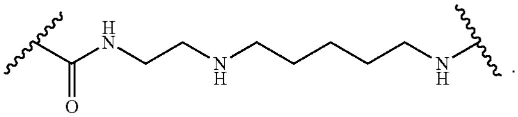 [SMILES: *NCCCCCNCCNC(*)=O]
In some embodiments, L is
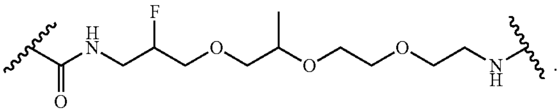 [SMILES: *NCCOCCOC(C)COCC(F)CNC(*)=O]
In some embodiments, L is
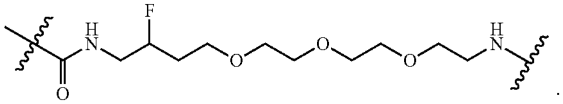 [SMILES: *NCCOCCOCCOCCC(F)CNC(*)=O]
In some embodiments, L is
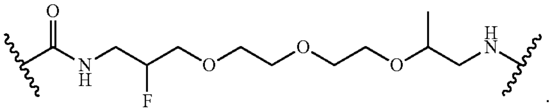 [SMILES: *NCC(C)OCCOCCOCC(F)CNC(*)=O]
In some embodiments, L is
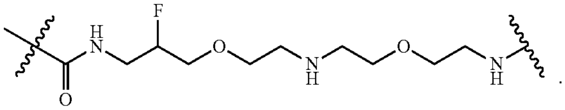 [SMILES: *NCCOCCNCCOCC(F)CNC(*)=O]
In some embodiments, L is
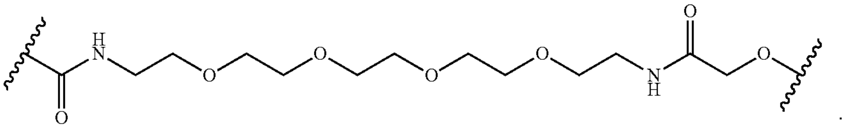 [SMILES: *OCC(=O)NCCOCCOCCOCCOCCNC(*)=O]
In some embodiments, L is
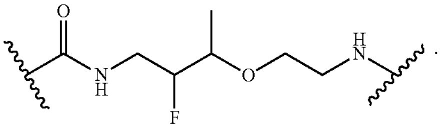
In some embodiments, L is
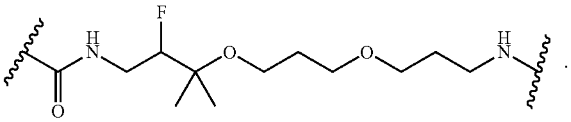
In some embodiments, L is
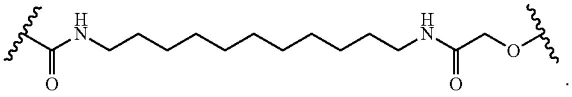 [SMILES: *OCC(=O)NCCCCCCCCCCCNC(*)=O]
In some embodiments, L is
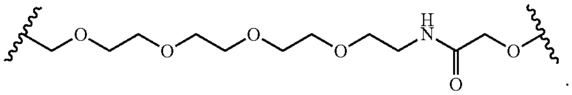 [SMILES: *COCCOCCOCCOCCNC(=O)CO*]

In some embodiments, L is
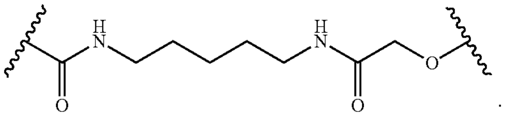 [SMILES: *OCC(=O)NCCCCCNC(*)=O]
In some embodiments, L is
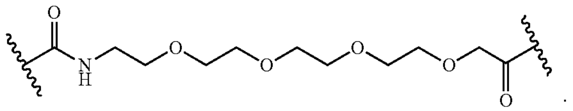 [SMILES: *C(=O)COCCOCCOCCOCCNC(*)=O]
In some embodiments, L is
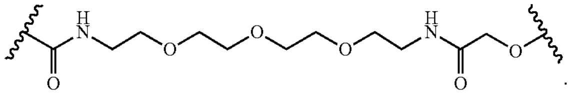 [SMILES: *OCC(=O)NCCOCCOCCOCCNC(*)=O]
In some embodiments, L is
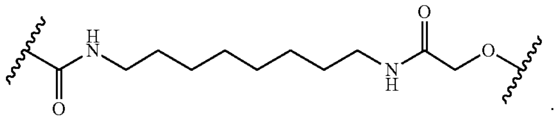 [SMILES: *OCC(=O)NCCCCCCCCNC(*)=O]
In some embodiments, L is
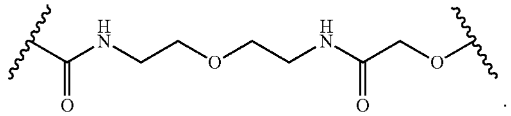 [SMILES: *OCC(=O)NCCOCCNC(*)=O]
In some embodiments, L is
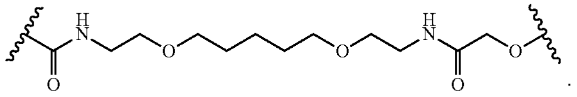 [SMILES: *OCC(=O)NCCOCCCCCOCCNC(*)=O]
In some embodiments, L is
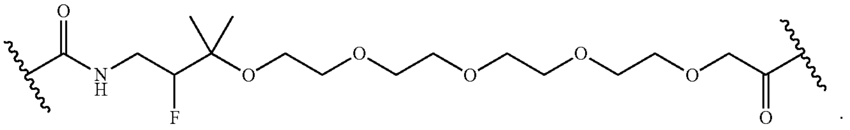 [SMILES: *C(=O)COCCOCCOCCOCCOC(C)(C)C(F)CNC(*)=O]
In some embodiments, L is
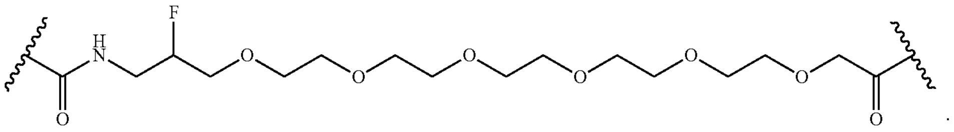 [SMILES: *C(=O)COCCOCCOCCOCCOCCOCC(F)CNC(*)=O]
In some embodiments, L is
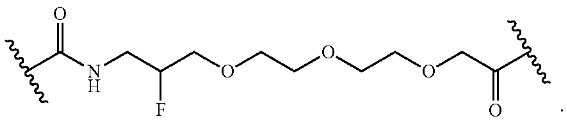 [SMILES: *C(=O)COCCOCCOCC(F)CNC(*)=O]
In some embodiments, L is
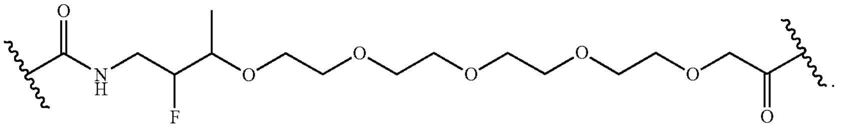 [SMILES: *C(=O)COCCOCCOCCOCCOC(C)C(F)CNC(*)=O]

In some embodiments, L is
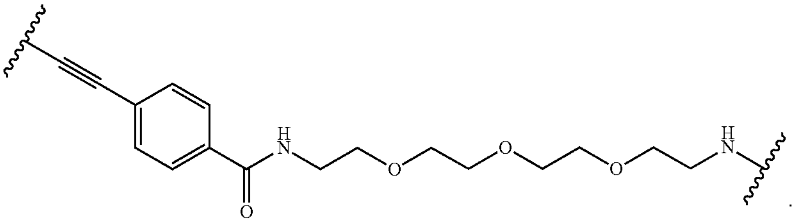 [SMILES: *C#Cc1ccc(C(=O)NCCOCCOCCOCCN*)cc1]
In some embodiments, L is
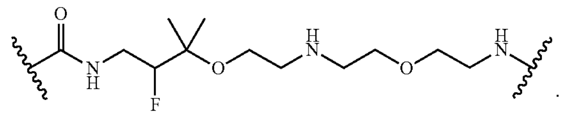 [SMILES: *NCCOCCNCCOC(C)(C)C(F)CNC(*)=O]
In some embodiments, L is
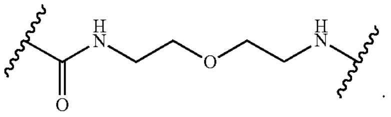 [SMILES: *NCCOCCNC(*)=O]
In some embodiments, L is
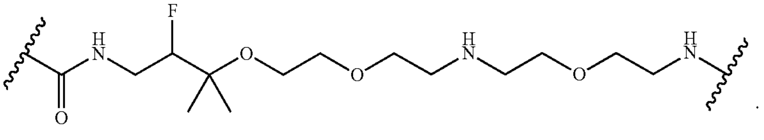 [SMILES: *NCCOCCNCCOCCOC(C)(C)C(F)CNC(*)=O]
In some embodiments, L is
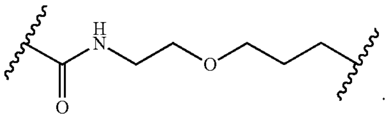 [SMILES: *CCCOCCNC(*)=O]
In some embodiments, L is
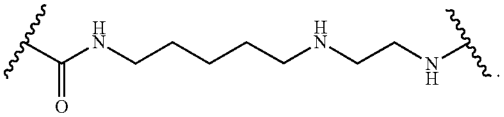 [SMILES: *NCCNCCCCCNC(*)=O]
In some embodiments, L is
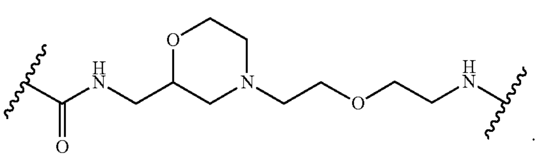 [SMILES: *NCCOCCN1CCOC(CNC(*)=O)C1]
In some embodiments, L is
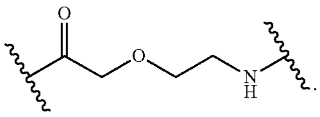 [SMILES: *NCCOCC(*)=O]
In some embodiments, L is
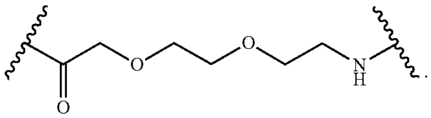 [SMILES: *NCCOCCOCC(*)=O]
In some embodiments, L is
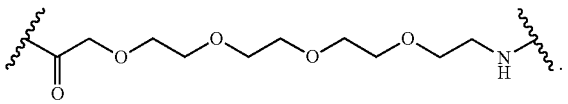 [SMILES: *NCCOCCOCCOCCOCC(*)=O]

In some embodiments, L is
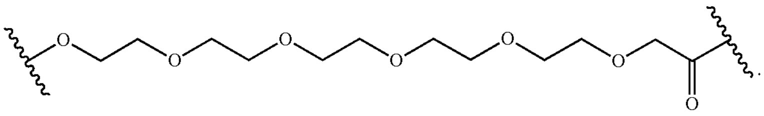 [SMILES: *OCCOCCOCCOCCOCCOCC(*)=O]
In some embodiments, L is
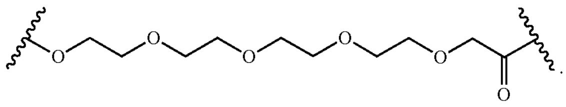 [SMILES: *OCCOCCOCCOCCOCC(*)=O]
In some embodiments, L is
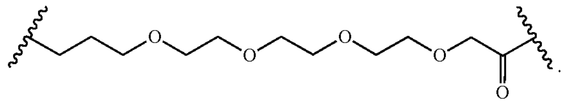 [SMILES: *CCCOCCOCCOCCOCC(*)=O]
In some embodiments, L is
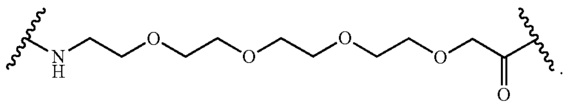 [SMILES: *NCCOCCOCCOCCOCC(*)=O]
In some embodiments, L is
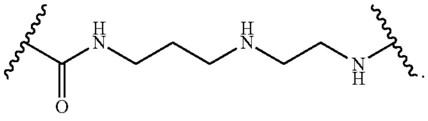 [SMILES: *NCCNCCCNC(*)=O]
In some embodiments, L is
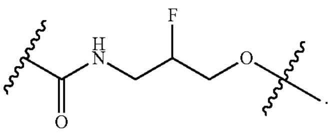 [SMILES: *OCC(F)CNC(*)=O]
In some embodiments, L is
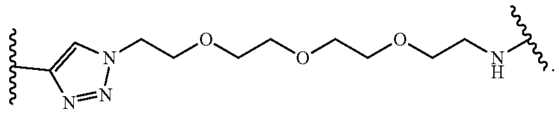 [SMILES: *NCCOCCOCCOCCn1cc(*)nn1]
In some embodiments, L is
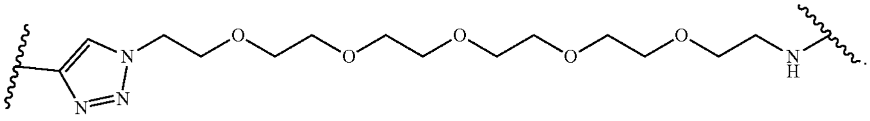 [SMILES: *NCCOCCOCCOCCOCCOCCn1cc(*)nn1]
In some embodiments, L is
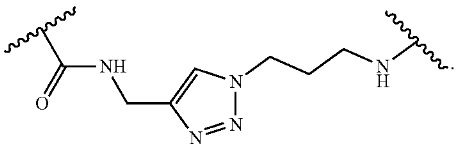 [SMILES: *NCCCn1cc(CNC(*)=O)nn1]
In some embodiments, L is
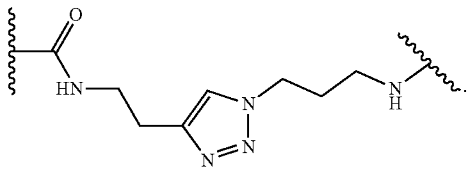 [SMILES: *NCCCn1cc(CCNC(*)=O)nn1]
In some embodiments, L is
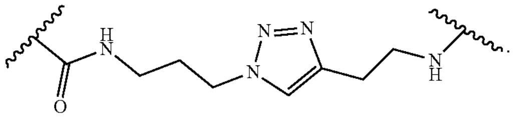 [SMILES: *NCCc1cn(CCCNC(*)=O)nn1]

In some embodiments, L is
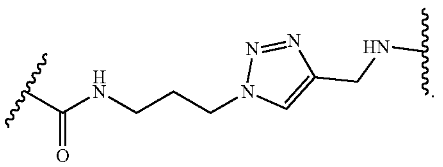 [SMILES: *NCc1cn(CCCNC(*)=O)nn1]
In some embodiments, L is
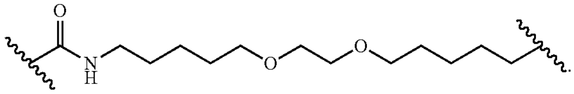 [SMILES: *CCCCCOCCOCCCCCNC(*)=O]
In some embodiments, L is
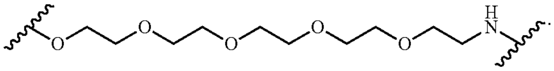 [SMILES: *NCCOCCOCCOCCOCCO*]
In some embodiments, L is
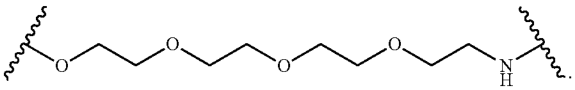 [SMILES: *NCCOCCOCCOCCO*]
In some embodiments, L is
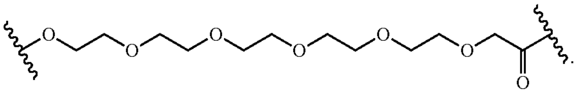 [SMILES: *OCCOCCOCCOCCOCCOCC(*)=O]
In some embodiments, L is
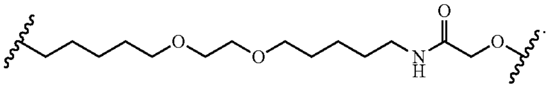 [SMILES: *CCCCCOCCOCCCCCNC(=O)CO*]
In some embodiments, L is
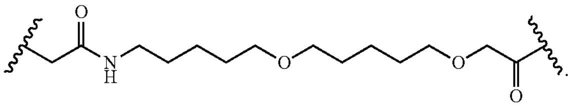 [SMILES: *CC(=O)NCCCCCOCCCCCOCC(*)=O]
In some embodiments, L is
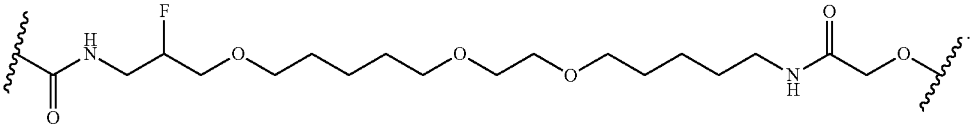 [SMILES: *OCC(=O)NCCCCCOCCOCCCCCOCC(F)CNC(*)=O]
In some embodiments, L is
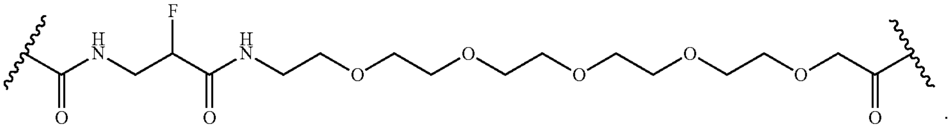 [SMILES: *C(=O)COCCOCCOCCOCCOCCNC(=O)C(F)CNC(*)=O]
In some embodiments, L is
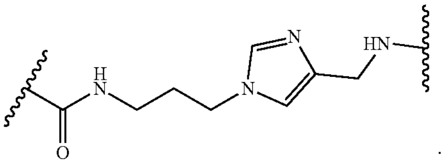 [SMILES: *NCc1cn(CCCNC(*)=O)cn1]

In some embodiments, L is
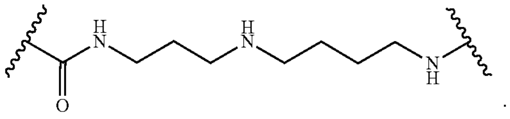 [SMILES: *NCCCCNCCCNC(*)=O]
In some embodiments, L is
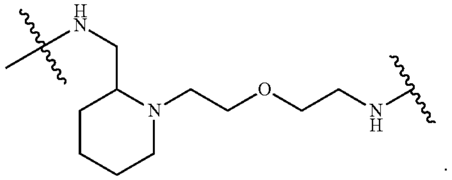 [SMILES: *NCCOCCN1CCCCC1CN*]
In some embodiments, L is
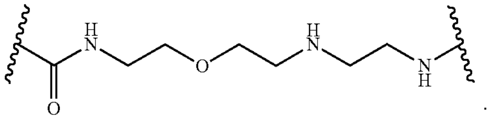 [SMILES: *NCCNCCOCCNC(*)=O]
In some embodiments, L is
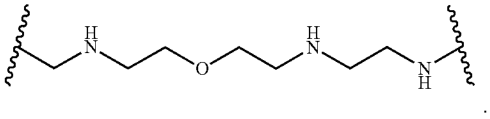 [SMILES: *CNCCOCCNCCN*]
In some embodiments, L is
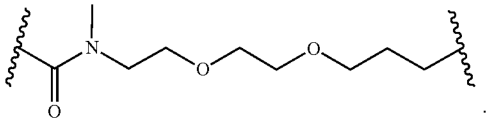 [SMILES: *CCCOCCOCCN(C)C(*)=O]
In some embodiments, L is
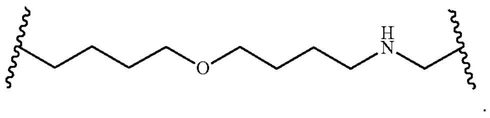 [SMILES: *CCCCOCCCCNC*]
In some embodiments, L is
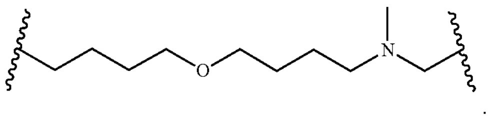 [SMILES: *CCCCOCCCCN(C)C*]
In some embodiments, L is
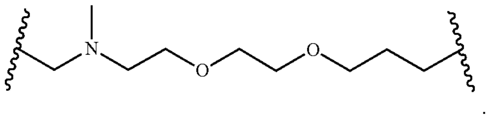 [SMILES: *CCCOCCOCCN(C)C*]
In some embodiments, L is
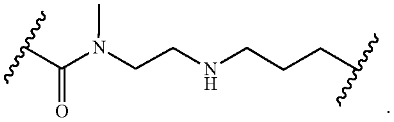 [SMILES: *CCCNCCN(C)C(*)=O]
In some embodiments, L is
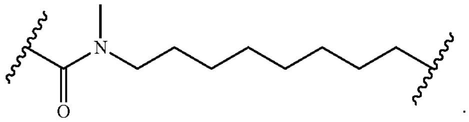 [SMILES: *CCCCCCCCN(C)C(*)=O]
In some embodiments, L is
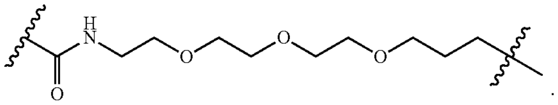 [SMILES: *CCCOCCOCCOCCNC(*)=O]
In some embodiments, L is
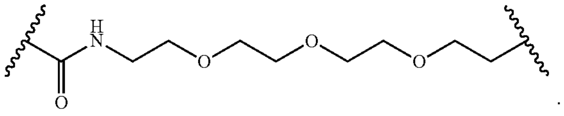 [SMILES: *CCOCCOCCOCCNC(*)=O]
In some embodiments, L is
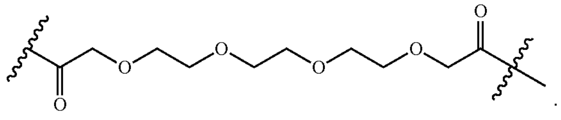 [SMILES: *C(=O)COCCOCCOCCOCC(*)=O]
In some embodiments, L is
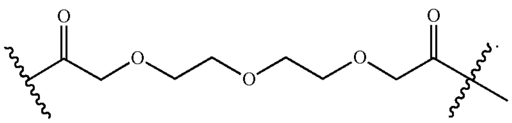 [SMILES: *C(=O)COCCOCCOCC(*)=O]

In some embodiments, L is
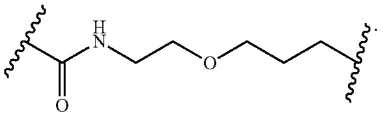 [SMILES: *CCCOCCNC(*)=O]
In some embodiments, L is
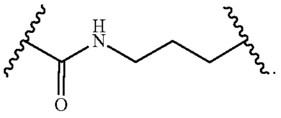 [SMILES: *CCCNC(*)=O]
In some embodiments, L is
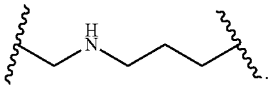 [SMILES: *CCCNC*]
In some embodiments, L is
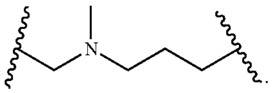 [SMILES: *CCCN(C)C*]
In some embodiments, L is
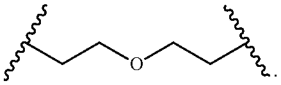 [SMILES: *CCOCC*]
In some embodiments, L is
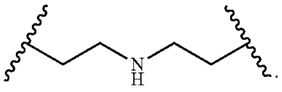 [SMILES: *CCNCC*]
In some embodiments, L is
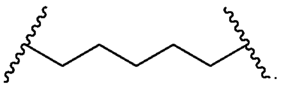 [SMILES: *CCCCC*]
In some embodiments, L is
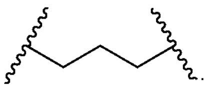 [SMILES: *CCC*]
In some embodiments, L is
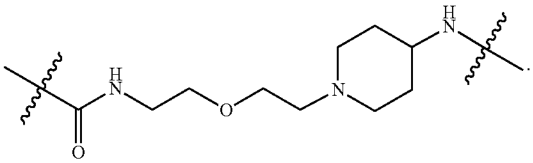 [SMILES: *NC1CCN(CCOCCNC(*)=O)CC1]
In some embodiments, L is
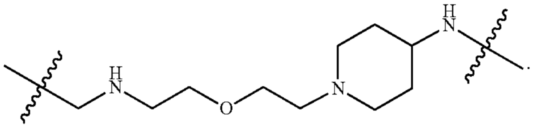 [SMILES: *CNCCOCCN1CCC(N*)CC1]
In some embodiments, L is
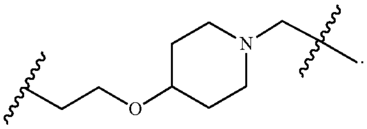 [SMILES: *CCOC1CCN(C*)CC1]
In some embodiments, L is
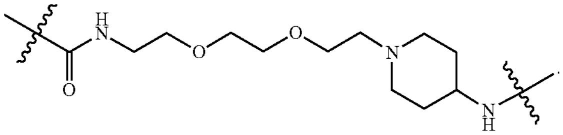 [SMILES: *NC1CCN(CCOCCOCCNC(*)=O)CC1]
In some embodiments, L is
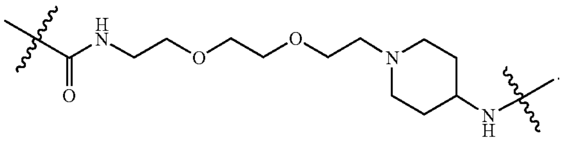 [SMILES: *NC1CCN(CCOCCOCCNC(*)=O)CC1]
In some embodiments, L is
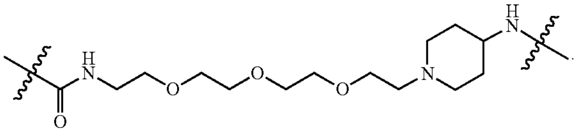 [SMILES: *NC1CCN(CCOCCOCCOCCNC(*)=O)CC1]

In some embodiments, L is
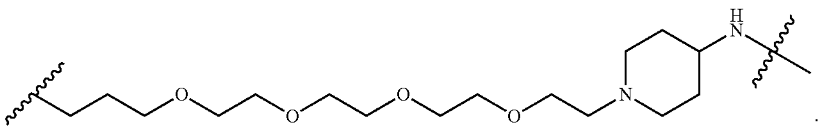 [SMILES: *CCCOCCOCCOCCOCCN1CCC(N*)CC1]
In some embodiments, L is
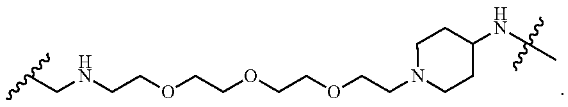 [SMILES: *CNCCOCCOCCOCCN1CCC(N*)CC1]
In some embodiments, L is
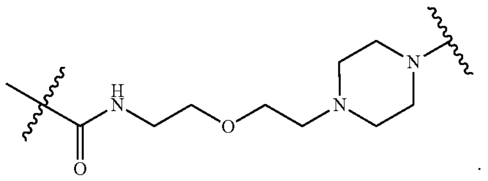 [SMILES: *C(=O)NCCOCCN1CCN(*)CC1]
In some embodiments, L is
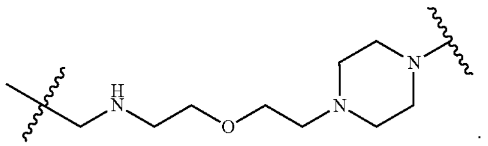 [SMILES: *CNCCOCCN1CCN(*)CC1]
In some embodiments, L is
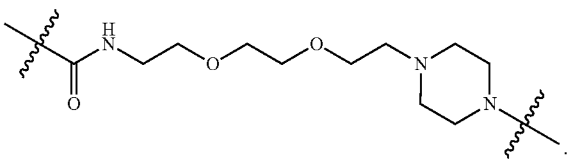 [SMILES: *C(=O)NCCOCCOCCN1CCN(*)CC1]
In some embodiments, L is
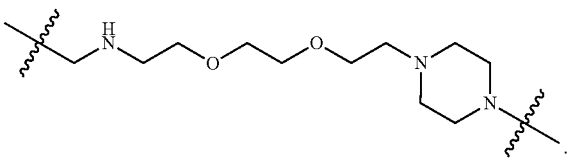 [SMILES: *CNCCOCCOCCN1CCN(*)CC1]
In some embodiments, L is
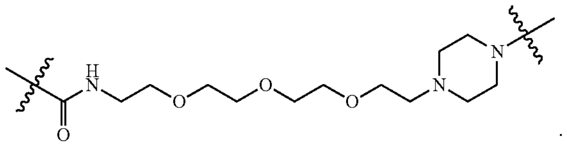 [SMILES: *C(=O)NCCOCCOCCOCCN1CCN(*)CC1]
In some embodiments, L is
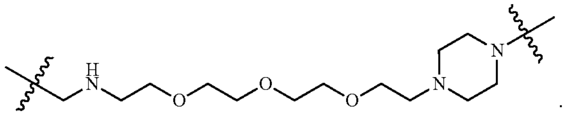 [SMILES: *CNCCOCCOCCOCCN1CCN(*)CC1]
In some embodiments, L is
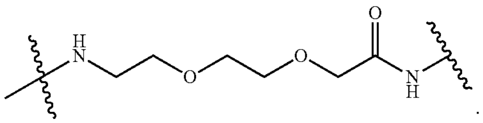 [SMILES: *NCCOCCOCC(=O)N*]
In some embodiments, L is
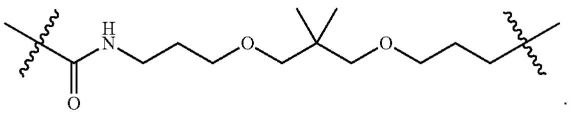 [SMILES: *CCCOCC(C)(C)COCCCNC(*)=O]
In some embodiments, L is
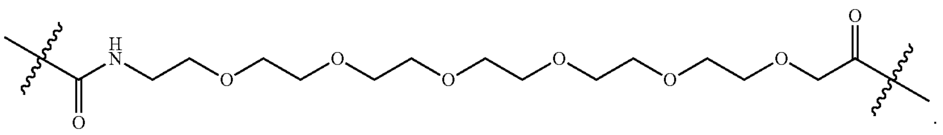 [SMILES: *C(=O)COCCOCCOCCOCCOCCOCCNC(*)=O]

In some embodiments, L is

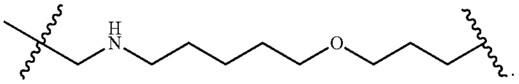 [SMILES: *CCCOCCCCCNC*]

In some embodiments, L is

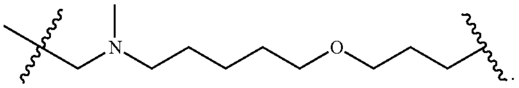 [SMILES: *CCCOCCCCCN(C)C*]

In some embodiments, L is

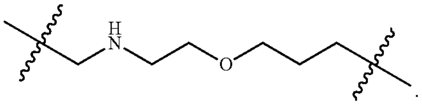 [SMILES: *CCCOCCNC*]

In some embodiments, L is

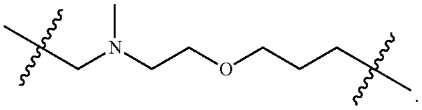 [SMILES: *CCCOCCN(C)C*]

In some embodiments, L is

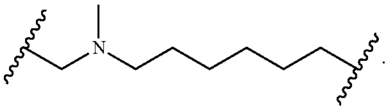 [SMILES: *CCCCCCN(C)C*]

In some embodiments, L is

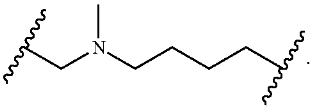 [SMILES: *CCCCN(C)C*]

In some embodiments, L is

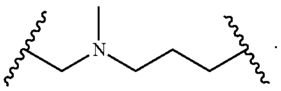 [SMILES: *CCCN(C)C*]

In some embodiments, L is

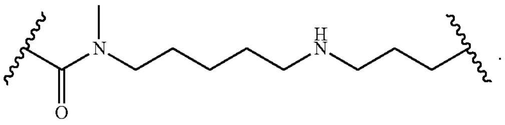 [SMILES: *CCCNCCCCCN(C)C(*)=O]

In some embodiments, L is

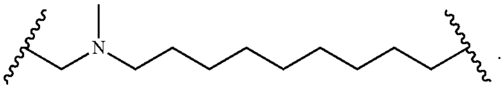 [SMILES: *CCCCCCCCCN(C)C*]

In some embodiments, L is

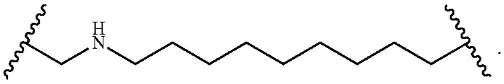 [SMILES: *CCCCCCCCCNC*]

In some embodiments, L is

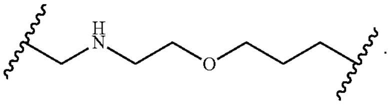 [SMILES: *CCCOCCNC*]

In some embodiments, L is

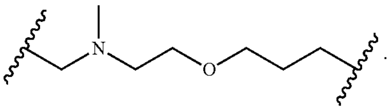 [SMILES: *CCCOCCN(C)C*]

In some embodiments, L is

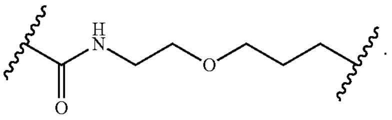 [SMILES: *CCCOCCNC(*)=O]

In some embodiments, L is

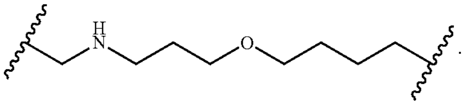 [SMILES: *CCCCOCCCNC*]

In some embodiments, L is

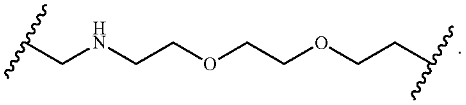 [SMILES: *CCOCCOCCNC*]

In some embodiments, L is

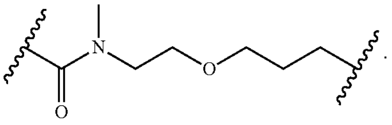 [SMILES: *CCCOCCN(C)C(*)=O]

In some embodiments, L is

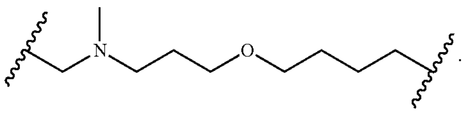 [SMILES: *CCCCOCCCN(C)C*]

In some embodiments, L is

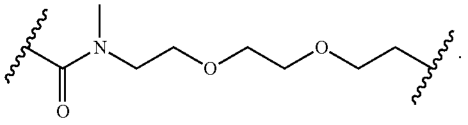 [SMILES: *CCOCCOCCN(C)C(*)=O]

In some embodiments, L is

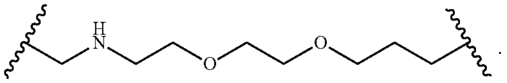 [SMILES: *CCCOCCOCCNC*]

In some embodiments, L is

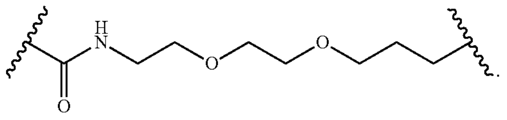 [SMILES: *CCCOCCOCCNC(*)=O]

In some embodiments, L is

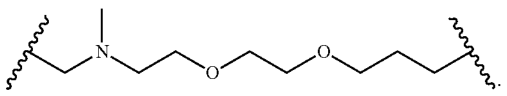 [SMILES: *CCCOCCOCCN(C)C*]

In some embodiments, L is

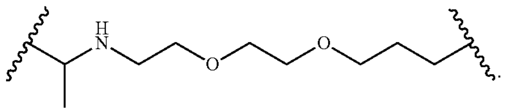 [SMILES: *CCCOCCOCCNC(*)C]

In some embodiments, L is

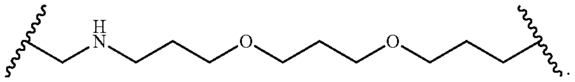 [SMILES: *CCCOCCCOCCCNC*]

In some embodiments, L is

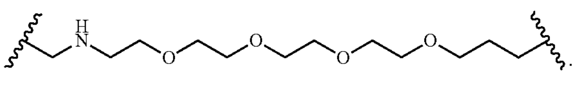 [SMILES: *CCCOCCOCCOCCOCCNC*]

In some embodiments, L is

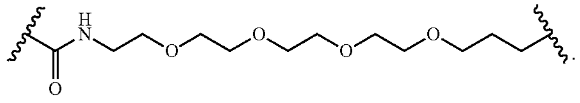 [SMILES: *CCCOCCOCCOCCOCCNC(*)=O]

In some embodiments, L is

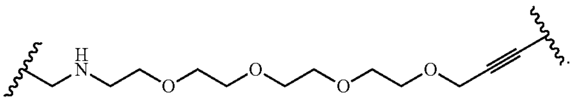 [SMILES: *C#CCOCCOCCOCCOCCNC*]

In some embodiments, L is

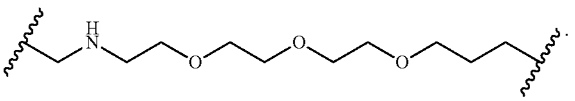 [SMILES: *CCCOCCOCCOCCNC*]

In some embodiments, L is

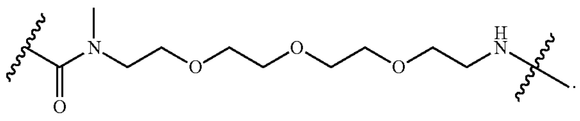 [SMILES: *NCCOCCOCCOCCN(C)C(*)=O]

In some embodiments, L is

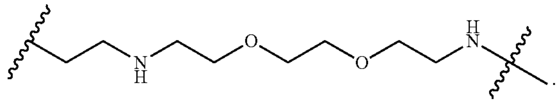 [SMILES: *CCNCCOCCOCCN*]

In some embodiments, L is

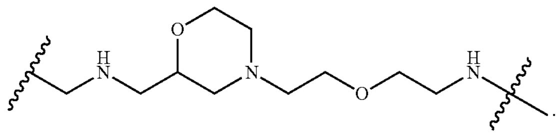 [SMILES: *CNCC1CN(CCOCCN*)CCO1]

In some embodiments, L is

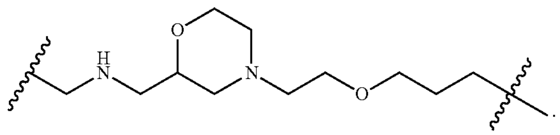 [SMILES: *CCCOCCN1CCOC(CNC*)C1]

In some embodiments, L is
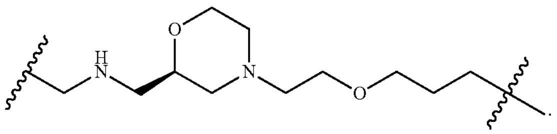 [SMILES: *CCCOCCN1CCO[C@H](CNC*)C1]
In some embodiments, L is
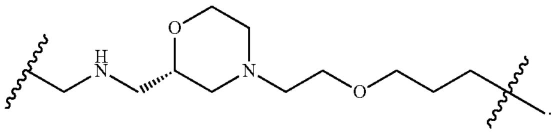 [SMILES: *CCCOCCN1CCO[C@@H](CNC*)C1]
In some embodiments, L is
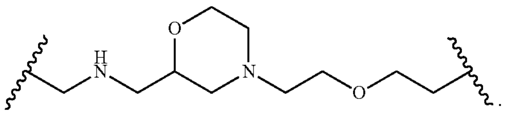 [SMILES: *CCOCCN1CCOC(CNC*)C1]
In some embodiments, L is
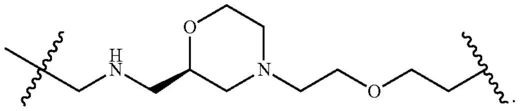 [SMILES: *CCOCCN1CCO[C@H](CNC*)C1]
In some embodiments, L is
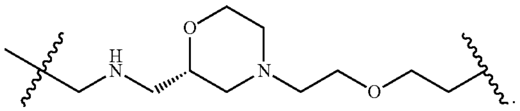 [SMILES: *CCOCCN1CCO[C@@H](CNC*)C1]
In some embodiments, L is
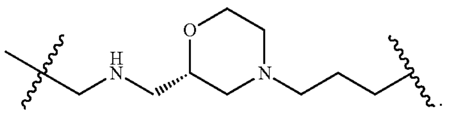 [SMILES: *CCCN1CCO[C@@H](CNC*)C1]
In some embodiments, L is
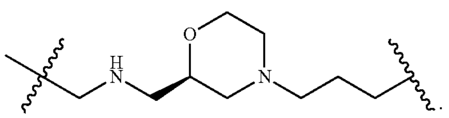 [SMILES: *CCCN1CCO[C@H](CNC*)C1]
In some embodiments, L is
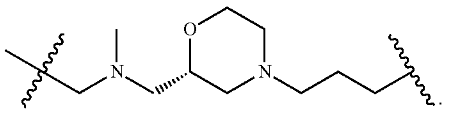 [SMILES: *CCCN1CCO[C@@H](CN(C)C*)C1]
In some embodiments, L is
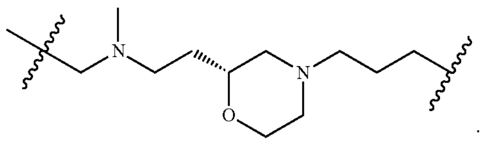 [SMILES: *CCCN1CCO[C@H](CCN(C)C*)C1]
In some embodiments, L is
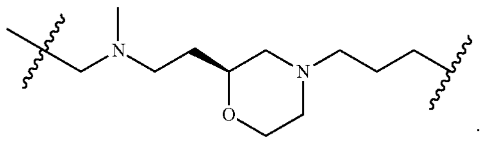 [SMILES: *CCCN1CCO[C@@H](CCN(C)C*)C1]
In some embodiments, L is
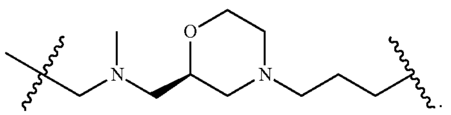 [SMILES: *CCCN1CCO[C@H](CN(C)C*)C1]
In some embodiments, L is
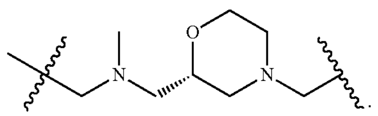 [SMILES: *CN(C)C[C@H]1CN(C*)CCO1]
In some embodiments, L is
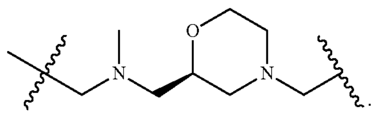 [SMILES: *CN(C)C[C@@H]1CN(C*)CCO1]
In some embodiments, L is
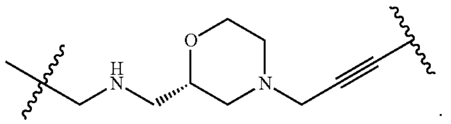 [SMILES: *C#CCN1CCO[C@@H](CNC*)C1]

In some embodiments, L is
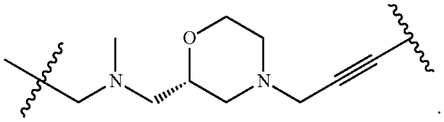 [SMILES: *C#CCN1CCO[C@@H](CN(C)C*)C1]
In some embodiments, L is
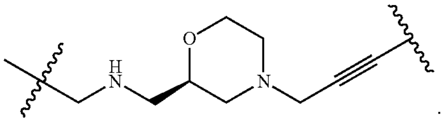 [SMILES: *C#CCN1CCO[C@H](CNC*)C1]
In some embodiments, L is
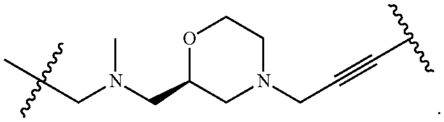 [SMILES: *C#CCN1CCO[C@H](CN(C)C*)C1]
In some embodiments, L is
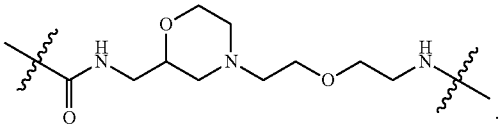 [SMILES: *NCCOCCN1CCOC(CNC(*)=O)C1]
In some embodiments, L is
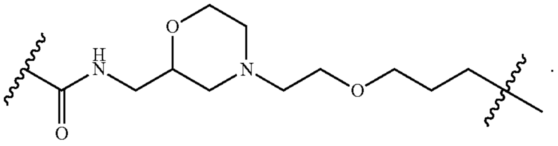 [SMILES: *CCCOCCN1CCOC(CNC(*)=O)C1 ; "."]
In some embodiments, L is
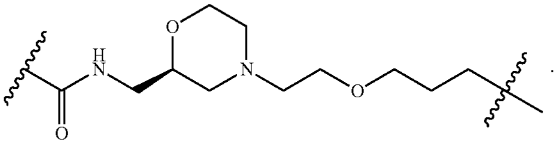 [SMILES: *CCCOCCN1CCO[C@H](CNC(*)=O)C1 ; "."]
In some embodiments, L is
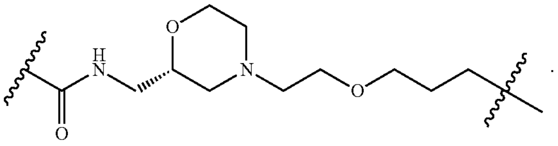 [SMILES: *CCCOCCN1CCO[C@@H](CNC(*)=O)C1 ; "."]
In some embodiments, L is
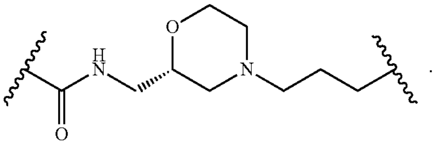 [SMILES: *CCCN1CCO[C@@H](CNC(*)=O)C1 ; "."]
In some embodiments, L is
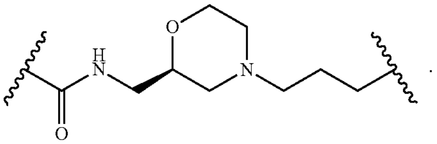 [SMILES: *CCCN1CCO[C@H](CNC(*)=O)C1 ; "."]
In some embodiments, L is
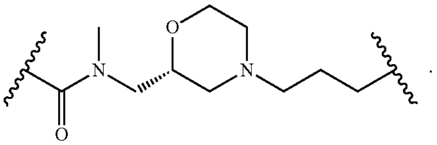 [SMILES: *CCCN1CCO[C@@H](CN(C)C(*)=O)C1 ; "."]
In some embodiments, L is
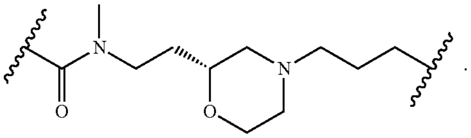 [SMILES: *CCCN1CCO[C@H](CCN(C)C(*)=O)C1 ; "."]
In some embodiments, L is
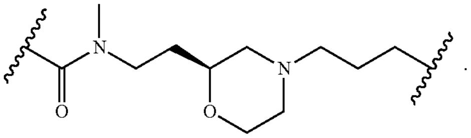 [SMILES: *CCCN1CCO[C@@H](CCN(C)C(*)=O)C1 ; "."]
In some embodiments, L is
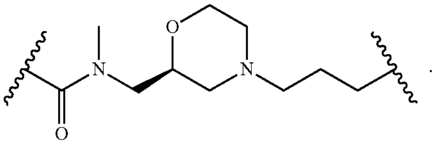 [SMILES: *CCCN1CCO[C@H](CN(C)C(*)=O)C1 ; "."]
In some embodiments, L is
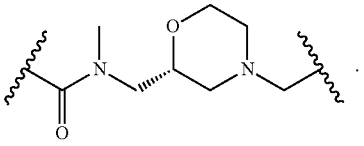 [SMILES: *CN1CCO[C@@H](CN(C)C(*)=O)C1 ; "."]

In some embodiments, L is
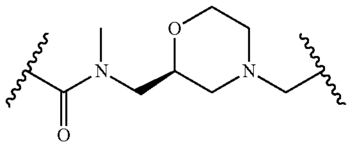
.
In some embodiments, L is
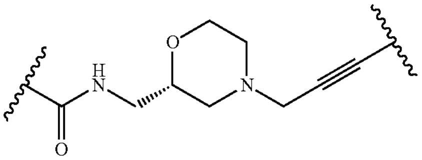
.
In some embodiments, L is
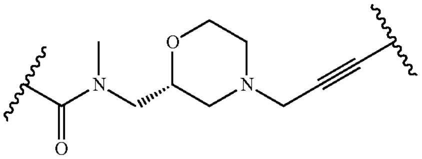
.
In some embodiments, L is
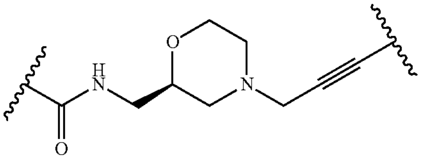
.
In some embodiments, L is
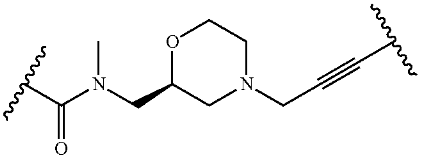
.
In some embodiments, L is
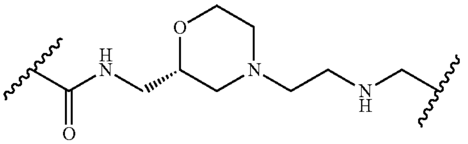
.
In some embodiments, L is
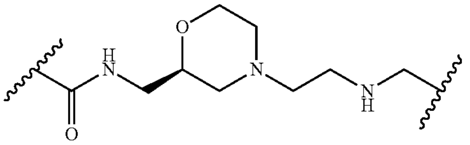
.
In some embodiments, L is
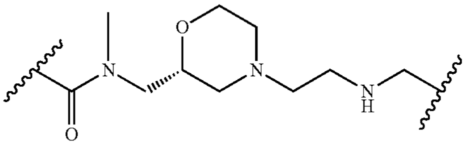
.
In some embodiments, L is
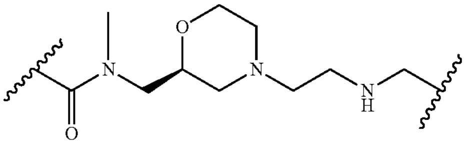
.
In some embodiments, L is
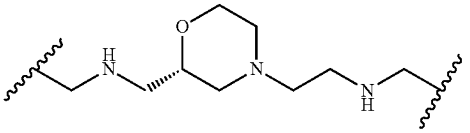
.
In some embodiments, L is
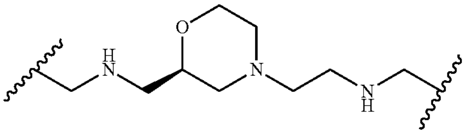
.
In some embodiments, L is
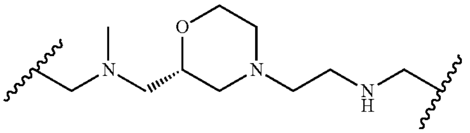
.
In some embodiments, L is
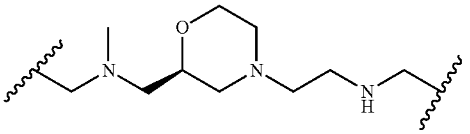
.

In some embodiments, L is
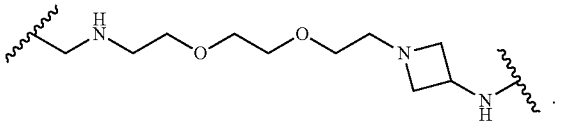 [SMILES: *CNCCOCCOCCN1CC(N*)C1]
In some embodiments, L is
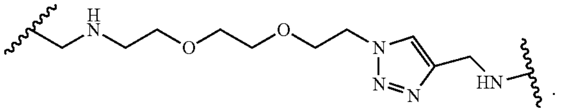 [SMILES: *CNCCOCCOCCn1cc(CN*)nn1]
In some embodiments, L is
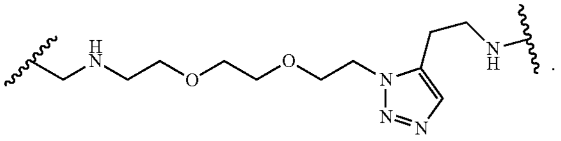 [SMILES: *CNCCOCCOCCn1nncc1CCN*]
In some embodiments, L is
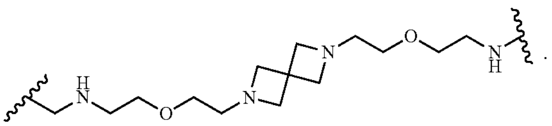 [SMILES: *CNCCOCCN1CC2(CN(CCOCCN*)C2)C1]
In some embodiments, L is
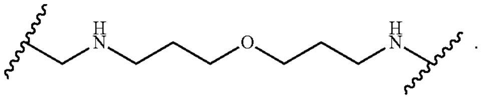 [SMILES: *CNCCCOCCCN*]
In some embodiments, L is
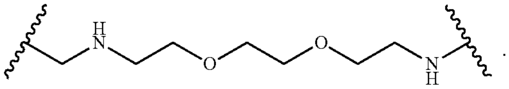 [SMILES: *CNCCOCCOCCN*]
In some embodiments, L is
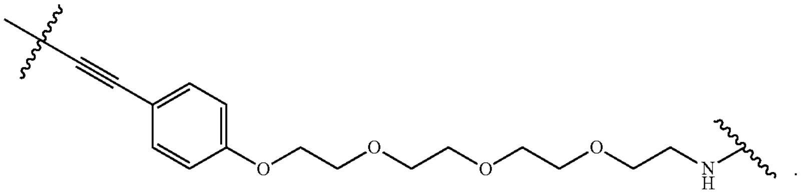 [SMILES: *C#Cc1ccc(OCCOCCOCCOCCN*)cc1]
In some embodiments, L is
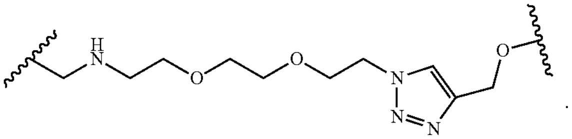
In some embodiments, L is
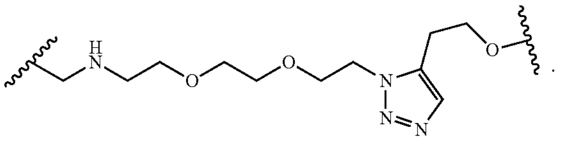
In some embodiments, L is
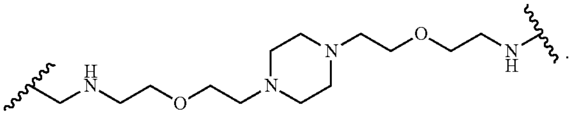
In some embodiments, L is
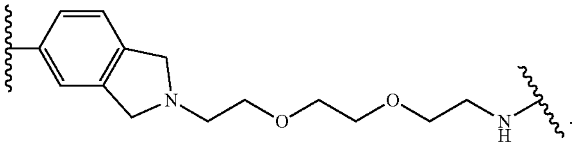 [SMILES: *NCCOCCOCCN1Cc2ccc(*)cc2C1]
In some embodiments, L is
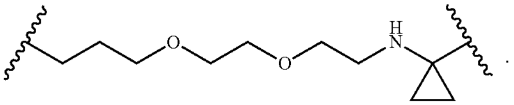 [SMILES: *CCCOCCOCCNC1(*)CC1]
In some embodiments, L is
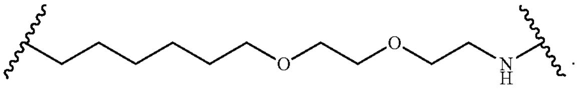 [SMILES: *CCCCCCOCCOCCN*]

In some embodiments, L is
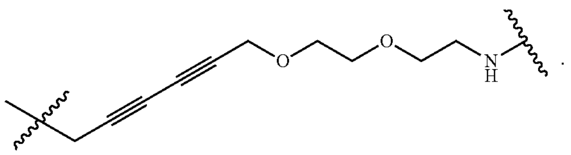 [SMILES: *CC#CC#CCOCCOCCN*]
In some embodiments, L is
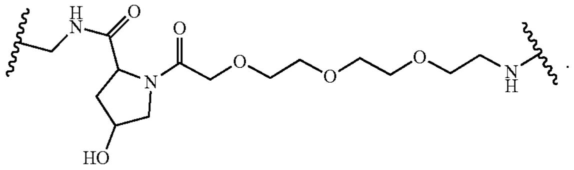 [SMILES: *CNC(=O)C1CC(O)CN1C(=O)COCCOCCOCCN*]
In some embodiments, L is
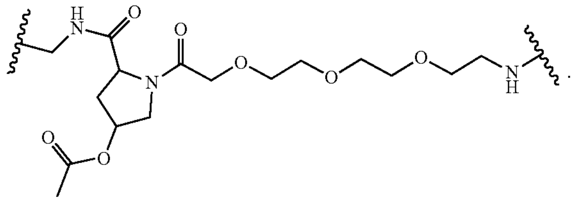 [SMILES: *CNC(=O)C1CC(OC(C)=O)CN1C(=O)COCCOCCOCCN*]
In some embodiments, L is
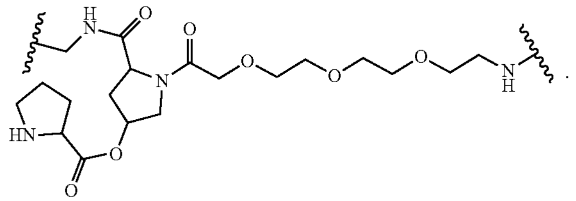 [SMILES: *CNC(=O)C1CC(OC(=O)C2CCCN2)CN1C(=O)COCCOCCOCCN*]
In some embodiments, L is
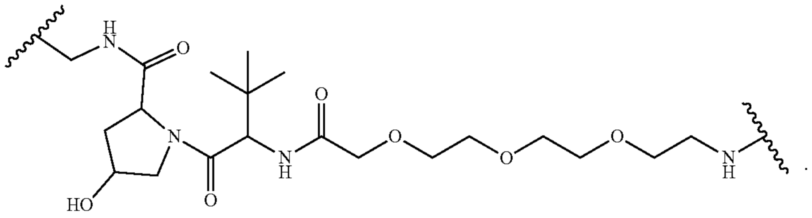 [SMILES: *CNC(=O)C1CC(O)CN1C(=O)C(NC(=O)COCCOCCOCCN*)C(C)(C)C]
In some embodiments, L is
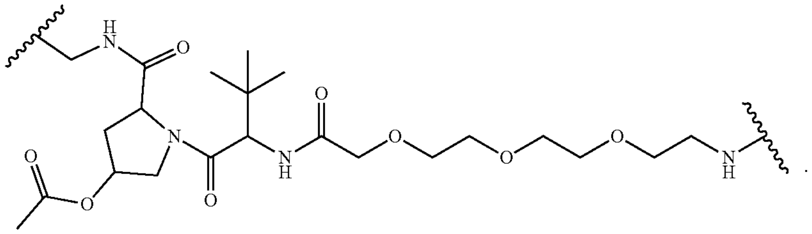 [SMILES: *CNC(=O)C1CC(OC(C)=O)CN1C(=O)C(NC(=O)COCCOCCOCCN*)C(C)(C)C]
In some embodiments, L is
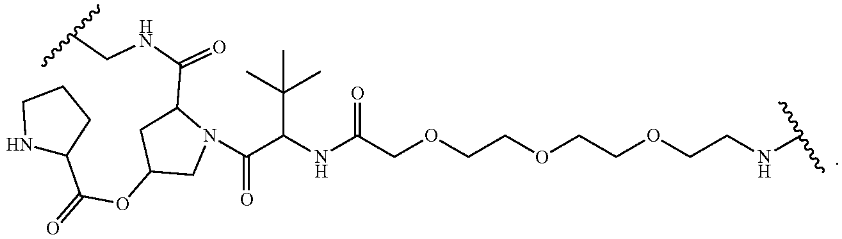 [SMILES: *CNC(=O)C1CC(OC(=O)C2CCCN2)CN1C(=O)C(NC(=O)COCCOCCOCCN*)C(C)(C)C]

In some embodiments, L is

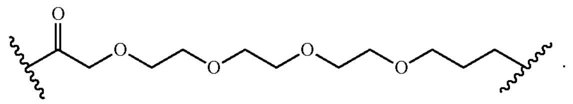 [SMILES: *CCCOCCOCCOCCOCC(*)=O]

In some embodiments, L is

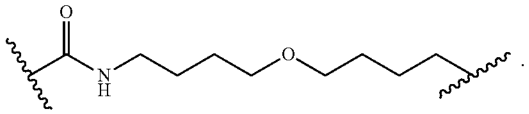 [SMILES: *CCCCOCCCCNC(*)=O]

In some embodiments, L is

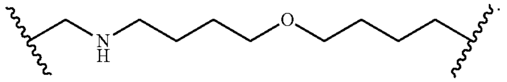 [SMILES: *CCCCOCCCCNC*]

In some embodiments, L is

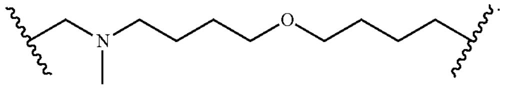 [SMILES: *CCCCOCCCCN(C)C*]

In some embodiments, L is

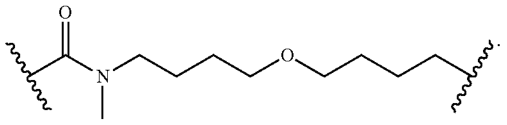 [SMILES: *CCCCOCCCCN(C)C(*)=O]

In some embodiments, L is

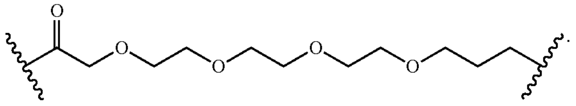 [SMILES: *CCCOCCOCCOCCOCC(*)=O]

In some embodiments, L is

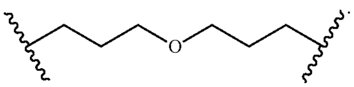 [SMILES: *CCCOCCC*]

In some embodiments, L is

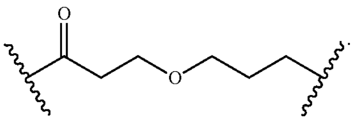

In some embodiments, L is

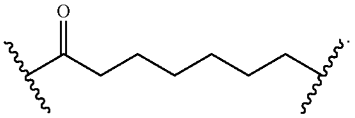 [SMILES: *CCCCCCC(*)=O]

In some embodiments, L is

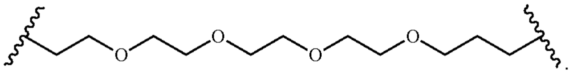 [SMILES: *CCCOCCOCCOCCOCC*]

In some embodiments, L is

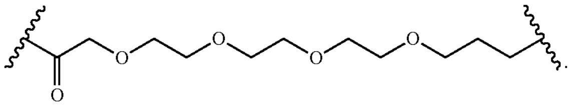 [SMILES: *CCCOCCOCCOCCOCC(*)=O]

In some embodiments, L is

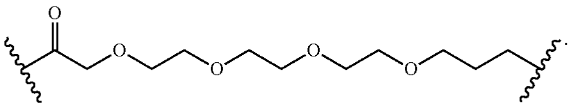 [SMILES: *CCCOCCOCCOCCOCC(*)=O]

In some embodiments, L is

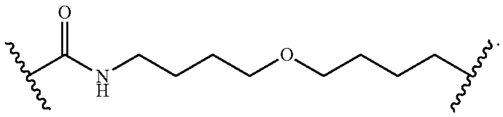 [SMILES: *CCCCOCCCCNC(*)=O]

In some embodiments, L is

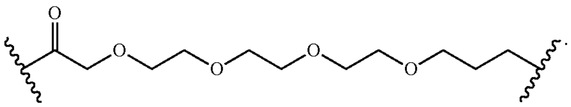 [SMILES: *CCCOCCOCCOCCOCC(*)=O]

In some embodiments, L is

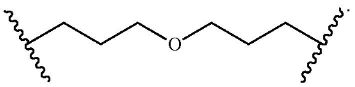 [SMILES: *CCCOCCC*]

In some embodiments, L is

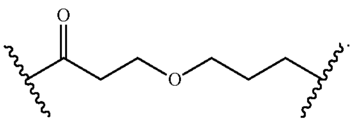 [SMILES: *CCCOCCC(*)=O]

In some embodiments, L is
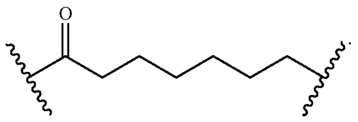
In some embodiments, L is
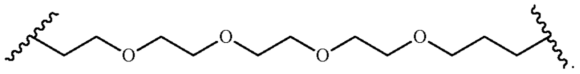 [SMILES: *CCCOCCOCCOCCOCC*]
In some embodiments, L is
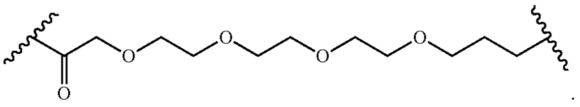 [SMILES: *CCCOCCOCCOCCOCC(*)=O]
In some embodiments, L is
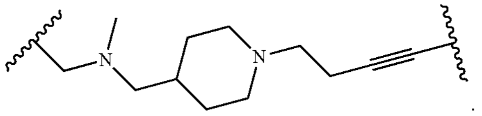 [SMILES: *C#CCCN1CCC(CN(C)C*)CC1]
In some embodiments, L is
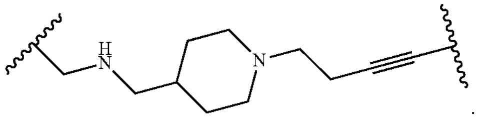 [SMILES: *C#CCCN1CCC(CNC*)CC1]
In some embodiments, L is
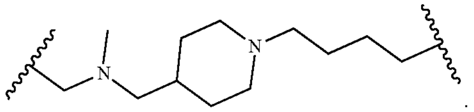 [SMILES: *CCCCN1CCC(CN(C)C*)CC1]
In some embodiments, L is
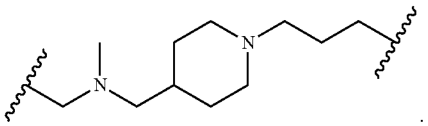 [SMILES: *CCCN1CCC(CN(C)C*)CC1]
In some embodiments, L is
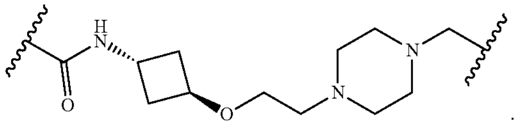 [SMILES: *CN1CCN(CCO[C@H]2C[C@H](NC(*)=O)C2)CC1]
In some embodiments, L is
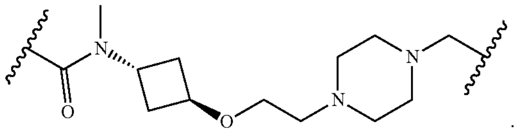 [SMILES: *CN1CCN(CCO[C@H]2C[C@H](N(C)C(*)=O)C2)CC1]
In some embodiments, L is
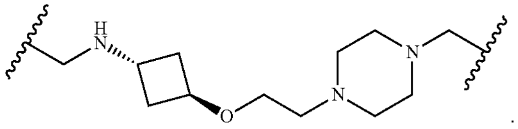 [SMILES: *CN[C@H]1C[C@H](OCCN2CCN(C*)CC2)C1]
In some embodiments, L is
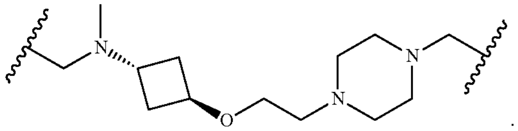 [SMILES: *CN1CCN(CCO[C@H]2C[C@H](N(C)C*)C2)CC1]
In some embodiments, L is
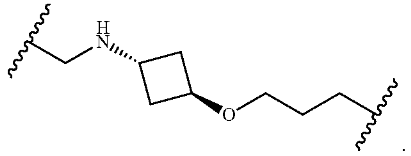 [SMILES: *CCCO[C@H]1C[C@H](NC*)C1]
In some embodiments, L is
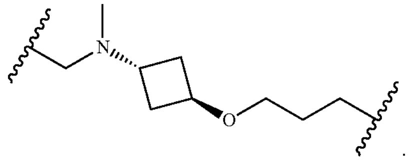 [SMILES: *CCCO[C@H]1C[C@H](N(C)C*)C1]
In some embodiments, L is
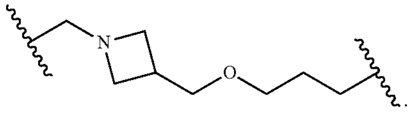 [SMILES: *CCCOCC1CN(C*)C1]

In some embodiments, L is
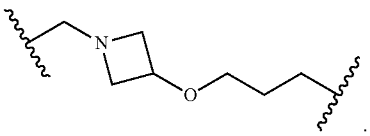 [SMILES: *CCCOC1CN(C*)C1]
In some embodiments, L is
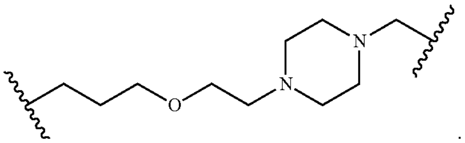 [SMILES: *CCCOCCN1CCN(C*)CC1]
In some embodiments, L is
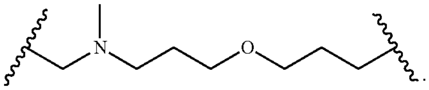 [SMILES: *CCCOCCCN(C)C*]
In some embodiments, L is
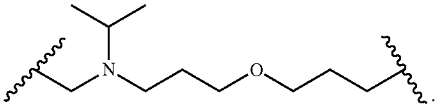 [SMILES: *CCCOCCCN(C*)C(C)C]
In some embodiments, L is
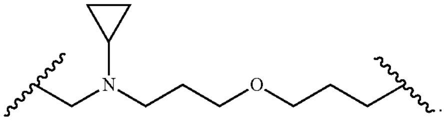 [SMILES: *CCCOCCCN(C*)C1CC1]
In some embodiments, L is
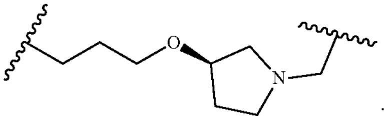 [SMILES: *CCCO[C@@H]1CCN(C*)C1]
In some embodiments, L is
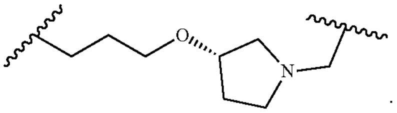 [SMILES: *CCCO[C@H]1CCN(C*)C1]
In some embodiments, L is
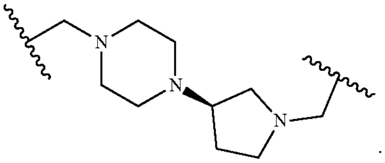 [SMILES: *CN1CCN([C@@H]2CCN(C*)C2)CC1]
In some embodiments, L is
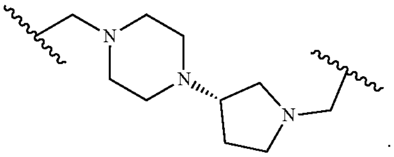 [SMILES: *CN1CCN([C@H]2CCN(C*)C2)CC1]
In some embodiments, L is
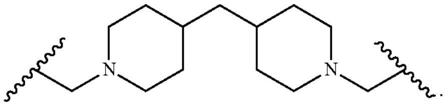 [SMILES: *CN1CCC(CC2CCN(C*)CC2)CC1]
In some embodiments, L is
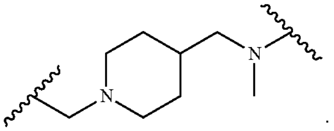 [SMILES: *CN1CCC(CN(*)C)CC1]
In some embodiments, L is
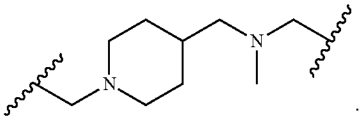 [SMILES: *CN(C)CC1CCN(C*)CC1]
In some embodiments, L is
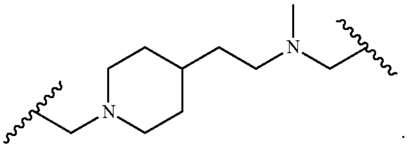 [SMILES: *CN(C)CCC1CCN(C*)CC1]
In some embodiments, L is
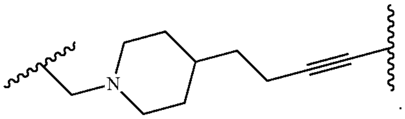 [SMILES: *C#CCCC1CCN(C*)CC1]

In some embodiments, L is
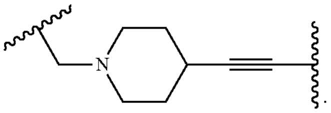 [SMILES: *C#CC1CCN(C*)CC1]
In some embodiments, L is
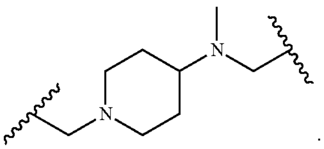 [SMILES: *CN1CCC(N(C)C*)CC1]
In some embodiments, L is
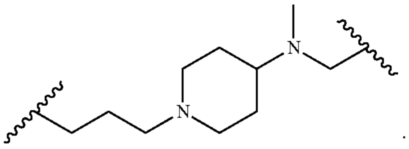 [SMILES: *CCCN1CCC(N(C)C*)CC1]
In some embodiments, L is
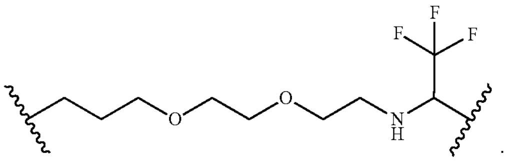 [SMILES: *CCCOCCOCCNC(*)C(F)(F)F]
In some embodiments, L is
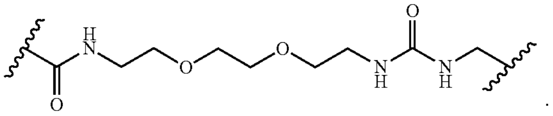 [SMILES: *CNC(=O)NCCOCCOCCNC(*)=O]
In some embodiments, L is
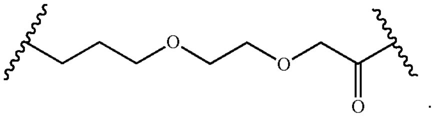 [SMILES: *CCCOCCOCC(*)=O]
In some embodiments, L is
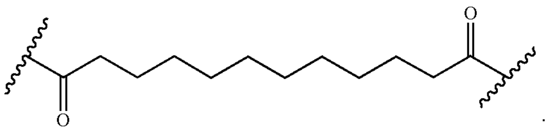 [SMILES: *C(=O)CCCCCCCCCCC(*)=O]
In some embodiments, L is
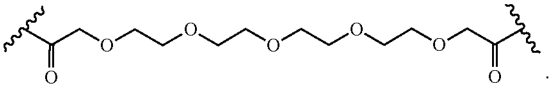 [SMILES: *C(=O)COCCOCCOCCOCCOCC(*)=O]
In some embodiments, L is
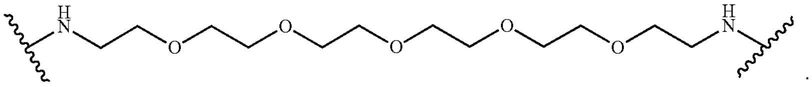
In some embodiments, L is
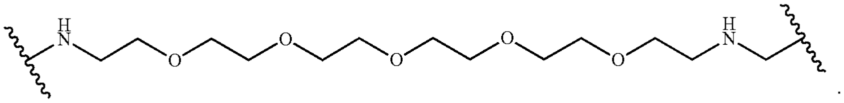
In some embodiments, L is
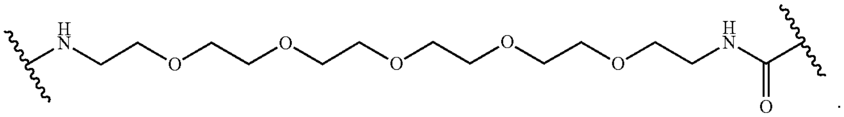

In some embodiments, L is
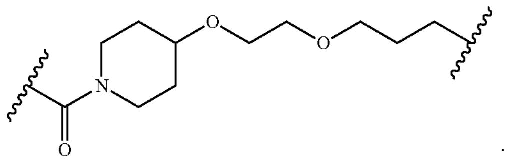 [SMILES: *CCCOCCOC1CCN(C(*)=O)CC1]
In some embodiments, L is
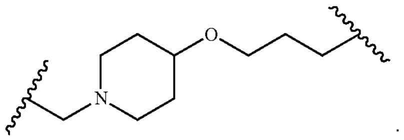 [SMILES: *CCCOC1CCN(C*)CC1]
In some embodiments, L is
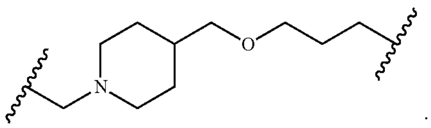 [SMILES: *CCCOCC1CCN(C*)CC1]
In some embodiments, L is
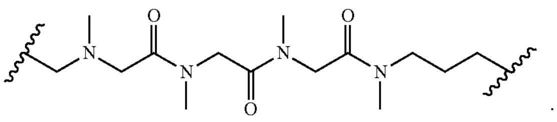 [SMILES: *CCCN(C)C(=O)CN(C)C(=O)CN(C)C(=O)CN(C)C*]
In some embodiments, L is
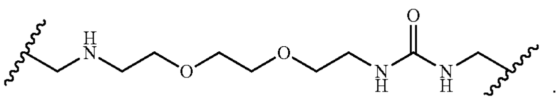 [SMILES: *CNCCOCCOCCNC(=O)NC*]
In some embodiments, L is
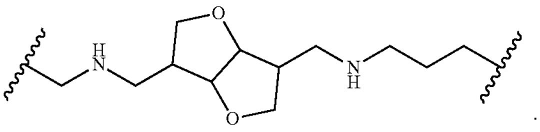 [SMILES: *CCCNCC1COC2C(CNC*)COC12]
In some embodiments, L is
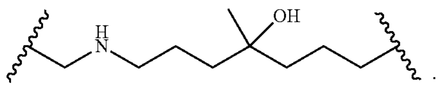 [SMILES: *CCCC(C)(O)CCCNC*]
In some embodiments, L is
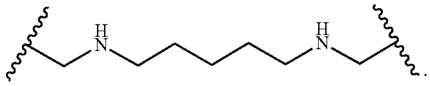 [SMILES: *CNCCCCCNC*]
In some embodiments, L is
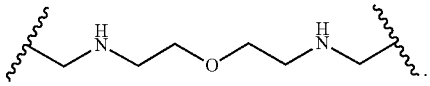 [SMILES: *CNCCOCCNC*]
In some embodiments, L is
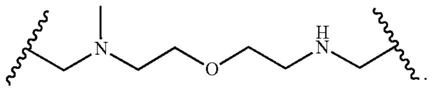 [SMILES: *CNCCOCCN(C)C*]
In some embodiments, L is
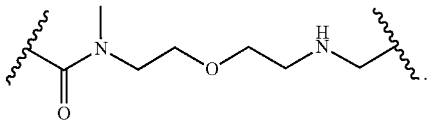 [SMILES: *CNCCOCCN(C)C(*)=O]
In some embodiments, L is
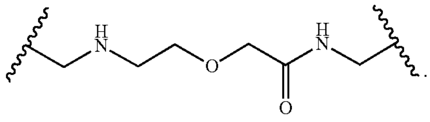 [SMILES: *CNCCOCC(=O)NC*]
In some embodiments, L is
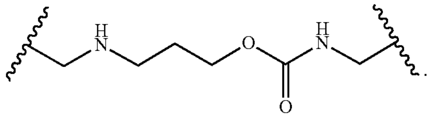 [SMILES: *CNCCCOC(=O)NC*]
In some embodiments, L is
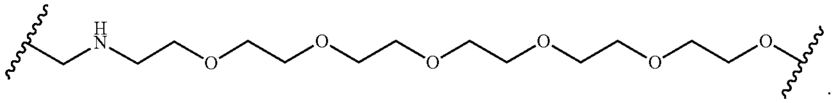 [SMILES: *CNCCOCCOCCOCCOCCOCCO*]

In some embodiments, L is
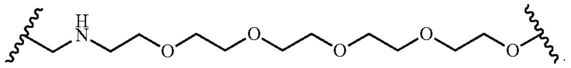 [SMILES: *CNCCOCCOCCOCCOCCO*]
In some embodiments, L is
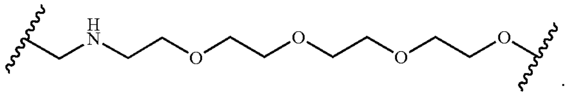 [SMILES: *CNCCOCCOCCOCCO*]
In some embodiments, L is
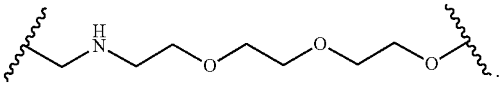 [SMILES: *CNCCOCCOCCO*]
In some embodiments, L is
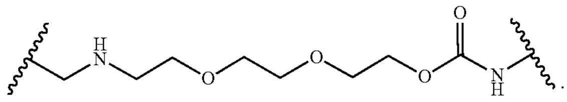 [SMILES: *CNCCOCCOCCOC(=O)N*]
In some embodiments, L is
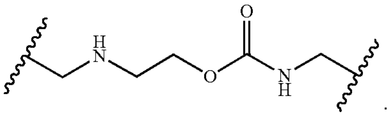 [SMILES: *CNCCOC(=O)NC*]
In some embodiments, L is
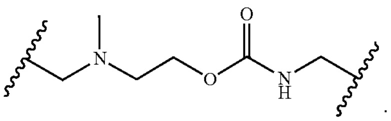 [SMILES: *CNC(=O)OCCN(C)C*]
In some embodiments, L is
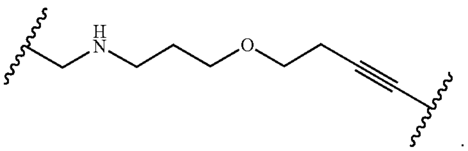 [SMILES: *C#CCCOCCCNC*]
In some embodiments, L is
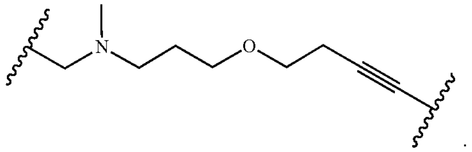 [SMILES: *C#CCCOCCCN(C)C*]
In some embodiments, L is
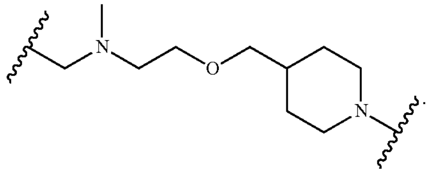 [SMILES: *CN(C)CCOCC1CCN(*)CC1]
In some embodiments, L is
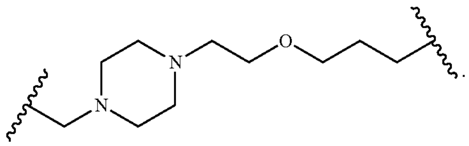 [SMILES: *CCCOCCN1CCN(C*)CC1]
In some embodiments, L is
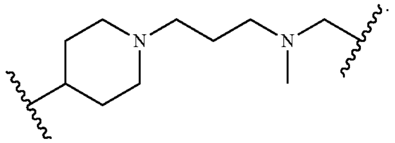 [SMILES: *CN(C)CCCN1CCC(*)CC1]
In some embodiments, L is
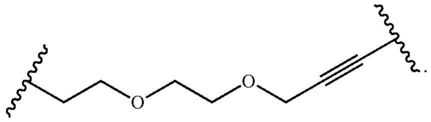 [SMILES: *C#CCOCCOCC*]
In some embodiments, L is
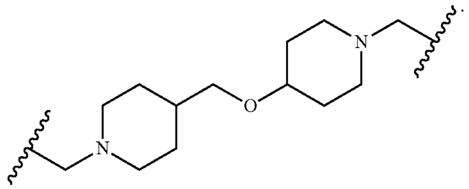 [SMILES: *CN1CCC(COC2CCN(C*)CC2)CC1]

In some embodiments, L is In some embodiments, L is
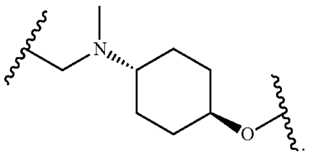 [SMILES: *CN(C)[C@H]1CC[C@H](O*)CC1]
In some embodiments, L is
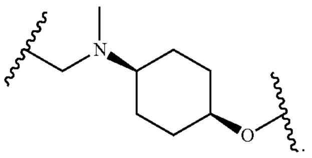 [SMILES: *CN(C)[C@H]1CC[C@@H](O*)CC1]
In some embodiments, L is
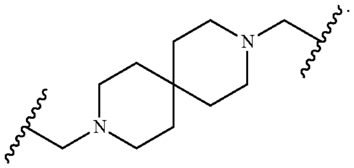 [SMILES: *CN1CCC2(CC1)CCN(C*)CC2]
In some embodiments, L is
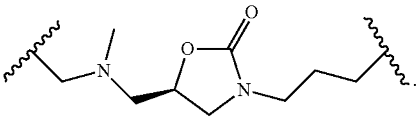 [SMILES: *CCCN1C[C@@H](CN(C)C*)OC1=O]
In some embodiments, L is
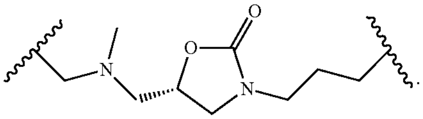 [SMILES: *CCCN1C[C@H](CN(C)C*)OC1=O]
In some embodiments, L is
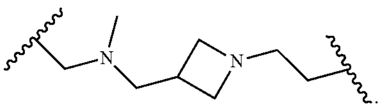 [SMILES: *CCN1CC(CN(C)C*)C1]
In some embodiments, L is
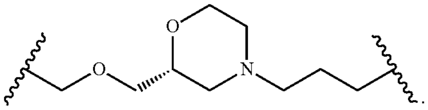 [SMILES: *CCCN1CCO[C@@H](COC*)C1]
In some embodiments, L is
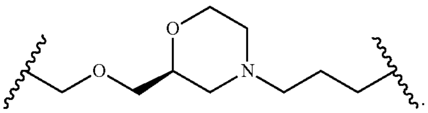 [SMILES: *CCCN1CCO[C@H](COC*)C1]
In some embodiments, L is
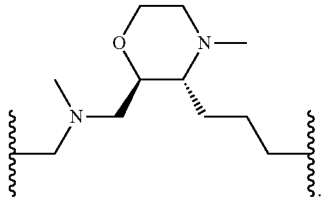 [SMILES: *CCC[C@@H]1[C@@H](CN(C)C*)OCCN1C]
In some embodiments, L is
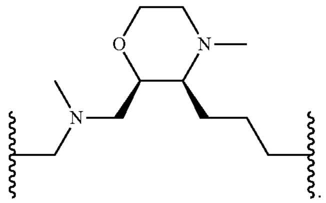 [SMILES: *CCC[C@H]1[C@@H](CN(C)C*)OCCN1C]
In some embodiments, L is
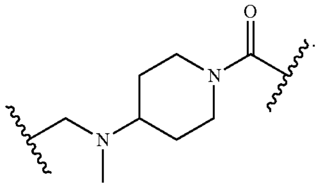 [SMILES: *CN(C)C1CCN(C(*)=O)CC1]
In some embodiments, L is
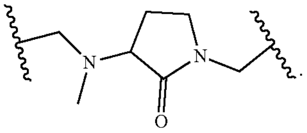 [SMILES: *CN1CCC(N(C)C*)C1=O]
In some embodiments, L is
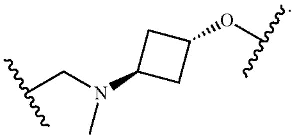 [SMILES: *CN(C)[C@H]1C[C@H](O*)C1]

In some embodiments, L is
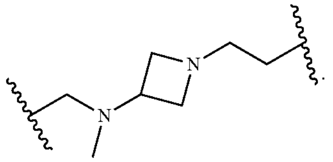 [SMILES: *CCN1CC(N(C)C*)C1]
In some embodiments, L is
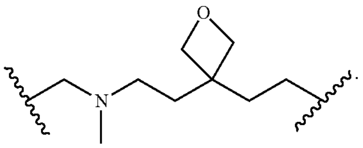 [SMILES: *CCC1(CCN(C)C*)COC1]
In some embodiments, L is
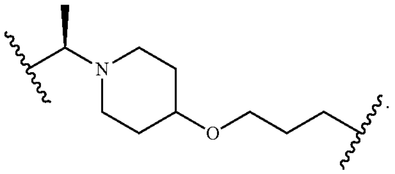 [SMILES: *CCCOC1CCN([C@@H](*)C)CC1]
In some embodiments, L is
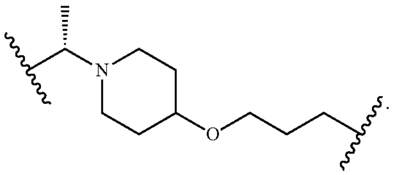 [SMILES: *CCCOC1CCN([C@H](*)C)CC1]
In some embodiments, L is
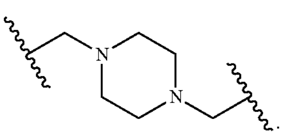 [SMILES: *CN1CCN(C*)CC1]
In some embodiments, L is
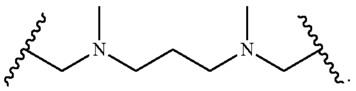 [SMILES: *CN(C)CCCN(C)C*]
In some embodiments, L is
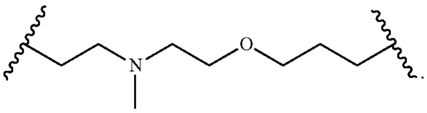 [SMILES: *CCCOCCN(C)CC*]
In some embodiments, L is
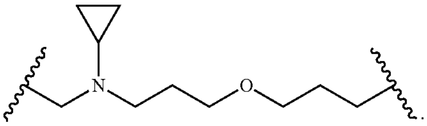 [SMILES: *CCCOCCCN(C*)C1CC1]
In some embodiments, L is
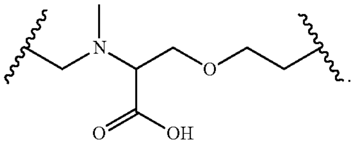 [SMILES: *CCOCC(C(=O)O)N(C)C*]
In some embodiments, L is
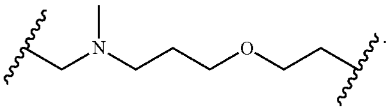 [SMILES: *CCOCCCN(C)C*]
In some embodiments, L is
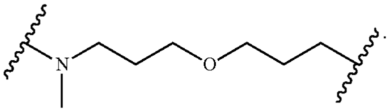 [SMILES: *CCCOCCCN(*)C]
In some embodiments, L is
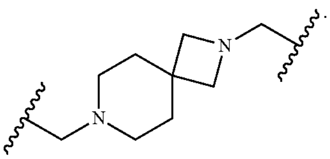 [SMILES: *CN1CCC2(CC1)CN(C*)C2]
In some embodiments, L is
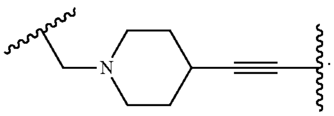 [SMILES: *C#CC1CCN(C*)CC1]

In some embodiments, L is

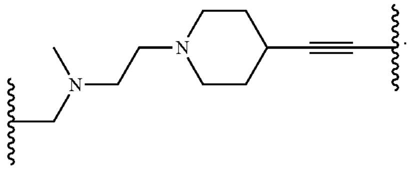 [SMILES: *C#CC1CCN(CCN(C)C*)CC1]

In some embodiments, L is

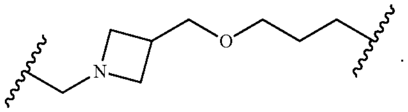 [SMILES: *CCCOCC1CN(C*)C1]

In some embodiments, L is a convalent bond. In some embodiments, L is

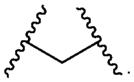

In some embodiments, L is

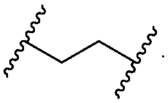 [SMILES: *CC*]

In some embodiments, L is

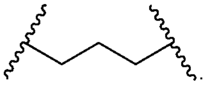 [SMILES: *CCC*]

In some embodiments, L is

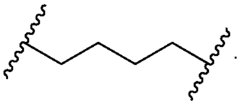 [SMILES: *CCCC*]

In some embodiments, L is

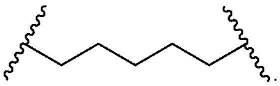 [SMILES: *CCCCC*]

In some embodiments, L is

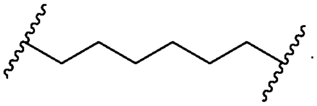 [SMILES: *CCCCCC*]

In some embodiments, L is

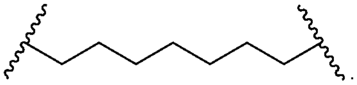 [SMILES: *CCCCCCC*]

In some embodiments, L is

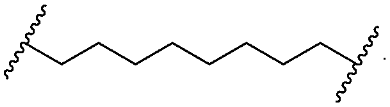 [SMILES: *CCCCCCCC*]

In some embodiments, L is

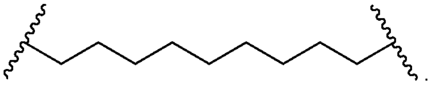 [SMILES: *CCCCCCCCC*]

In some embodiments, L is a convalent bond. In some embodiments, L is

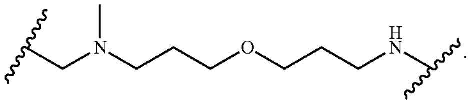 [SMILES: *CN(C)CCCOCCCN*]

In some embodiments, L is

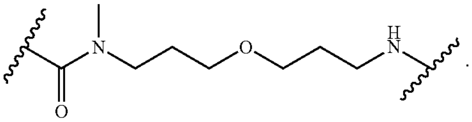 [SMILES: *NCCCOCCCN(C)C(*)=O]

In some embodiments, L is

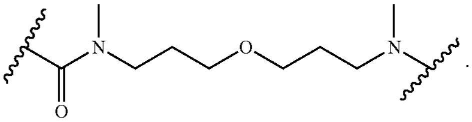

In some embodiments, L is

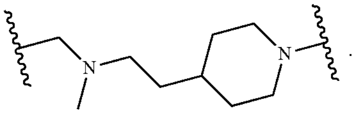 [SMILES: *CN(C)CCC1CCN(*)CC1 ; "."]

In some embodiments, L is
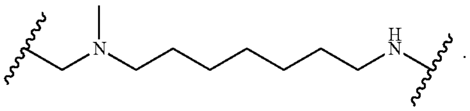 [SMILES: *CN(C)CCCCCCCN* ; "."]
In some embodiments, L is
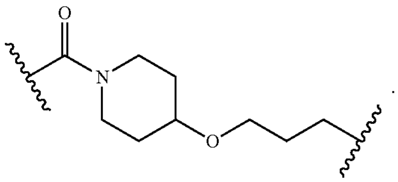 [SMILES: *CCCOC1CCN(C(*)=O)CC1 ; "."]
In some embodiments, L is
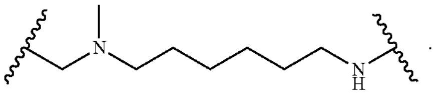 [SMILES: *CN(C)CCCCCCN* ; "."]
In some embodiments, L is
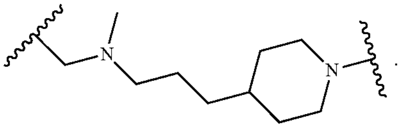 [SMILES: *CN(C)CCCC1CCN(*)CC1 ; "."]
In some embodiments, L is
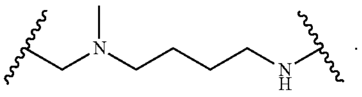 [SMILES: *CN(C)CCCCN* ; "."]
In some embodiments, L is
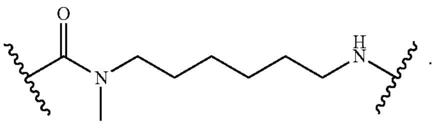 [SMILES: *NCCCCCCN(C)C(*)=O ; "."]
In some embodiments, L is
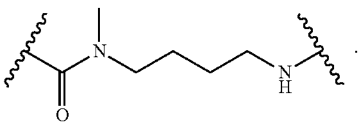 [SMILES: *NCCCCN(C)C(*)=O ; "."]
In some embodiments, L is
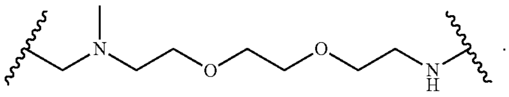 [SMILES: *CN(C)CCOCCOCCN* ; "."]
In some embodiments, L is
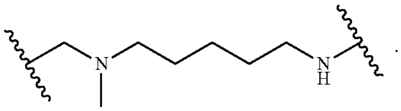 [SMILES: *CN(C)CCCCCN* ; "."]
In some embodiments, L is
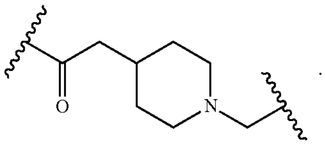 [SMILES: *CN1CCC(CC(*)=O)CC1 ; "."]
In some embodiments, L is
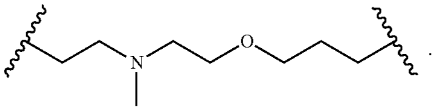 [SMILES: *CCCOCCN(C)CC* ; "."]
In some embodiments, L is
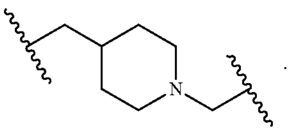 [SMILES: *CC1CCN(C*)CC1 ; "."]
In some embodiments, L is
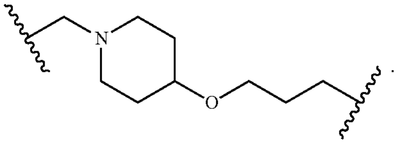 [SMILES: *CCCOC1CCN(C*)CC1 ; "."]
In some embodiments, L is
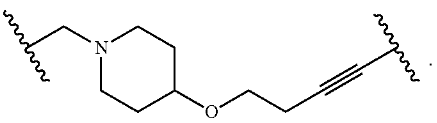 [SMILES: *C#CCCOC1CCN(C*)CC1 ; "."]

In some embodiments, L is
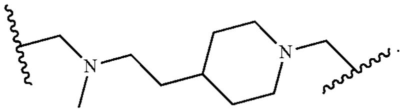 [SMILES: *CN(C)CCC1CCN(C*)CC1]
In some embodiments, L is
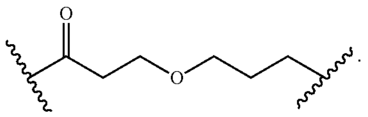 [SMILES: *CCCOCCC(*)=O]
In some embodiments, L is
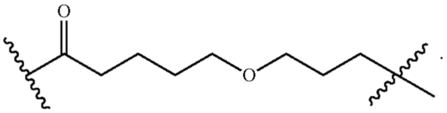 [SMILES: *CCCOCCCCC(*)=O]
In some embodiments, L is
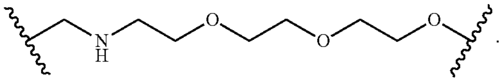 [SMILES: *CNCCOCCOCCO*]
In some embodiments, L is
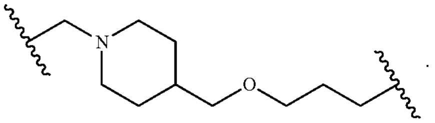 [SMILES: *CCCOCC1CCN(C*)CC1]
In some embodiments, L is
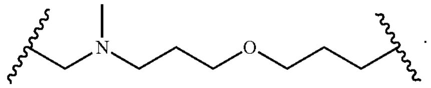 [SMILES: *CCCOCCCN(C)C*]
In some embodiments, L is
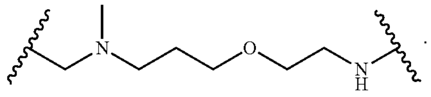 [SMILES: *CN(C)CCCOCCN*]
In some embodiments, L is
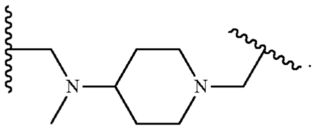 [SMILES: *CN1CCC(N(C)C*)CC1]
In some embodiments, L is
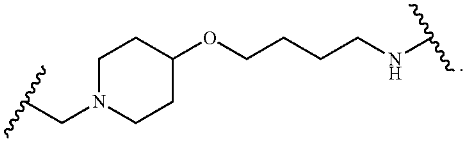 [SMILES: *CN1CCC(OCCCCN*)CC1]
In some embodiments, L is
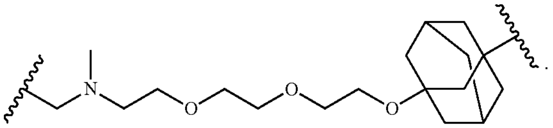 [SMILES: *CN(C)CCOCCOCCOC12CC3CC(CC(*)(C3)C1)C2]
In some embodiments, L is
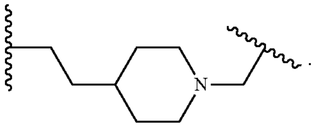 [SMILES: *CCC1CCN(C*)CC1]
In some embodiments, L is
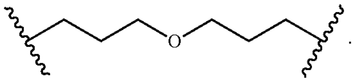 [SMILES: *CCCOCCC*]
In some embodiments, L is
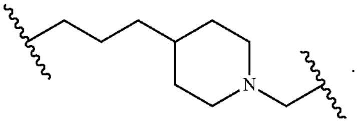 [SMILES: *CCCC1CCN(C*)CC1]

In some embodiments, L is
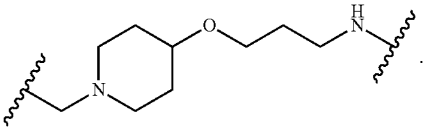 [SMILES: *CN1CCC(OCCCN*)CC1]
In some embodiments, L is
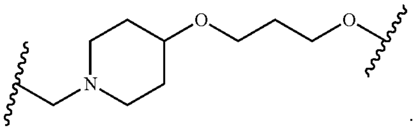 [SMILES: *CN1CCC(OCCCO*)CC1]
In some embodiments, L is
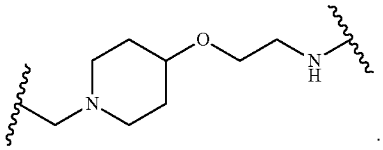 [SMILES: *CN1CCC(OCCN*)CC1]
In some embodiments, L is
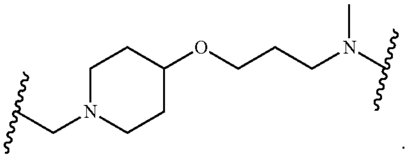 [SMILES: *CN1CCC(OCCCN(*)C)CC1]
In some embodiments, L is
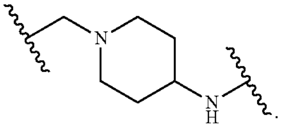 [SMILES: *CN1CCC(N*)CC1]
In some embodiments, L is
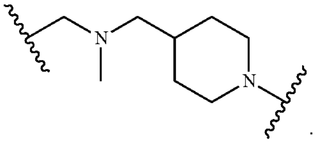 [SMILES: *CN(C)CC1CCN(*)CC1]
In some embodiments, L is
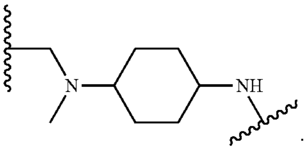 [SMILES: *CN(C)C1CCC(N*)CC1]
In some embodiments, L is
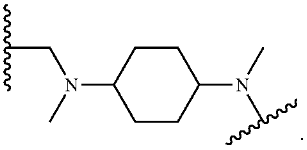 [SMILES: *CN(C)C1CCC(N(*)C)CC1]
In some embodiments, L is
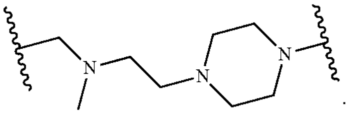 [SMILES: *CN(C)CCN1CCN(*)CC1]
In some embodiments, L is
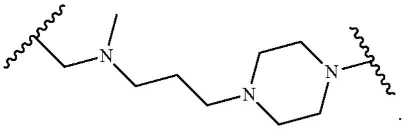 [SMILES: *CN(C)CCCN1CCN(*)CC1]
In some embodiments, L is
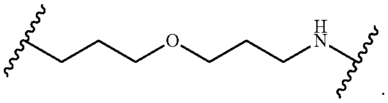 [SMILES: *CCCOCCCN*]
In some embodiments, L is
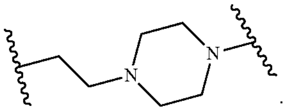 [SMILES: *CCN1CCN(*)CC1]
In some embodiments, L is
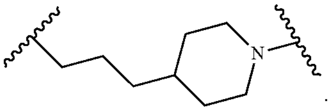 [SMILES: *CCCC1CCN(*)CC1]

In some embodiments, L is
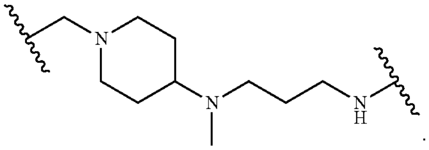 [SMILES: *CN1CCC(N(C)CCCN*)CC1]
In some embodiments, L is
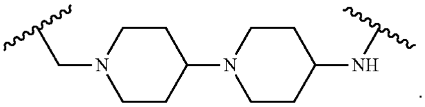 [SMILES: *CN1CCC(N2CCC(N*)CC2)CC1]
In some embodiments, L is
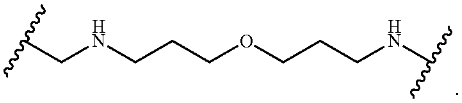 [SMILES: *CNCCCOCCCN*]
In some embodiments, L is
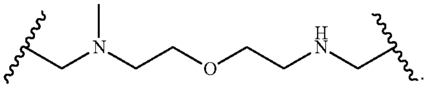 [SMILES: *CNCCOCCN(C)C*]
In some embodiments, L is
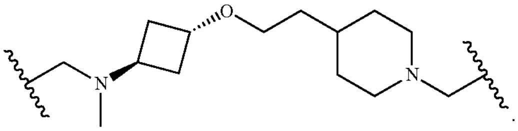 [SMILES: *CN1CCC(CCO[C@H]2C[C@H](N(C)C*)C2)CC1]
In some embodiments, L is
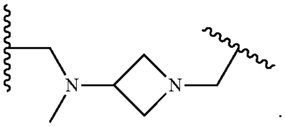 [SMILES: *CN1CC(N(C)C*)C1]
In some embodiments, L is
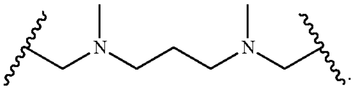 [SMILES: *CN(C)CCCN(C)C*]
In some embodiments, L is
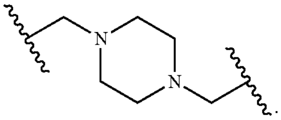 [SMILES: *CN1CCN(C*)CC1]
In some embodiments, L is
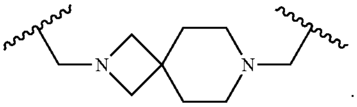 [SMILES: *CN1CCC2(CC1)CN(C*)C2]
In some embodiments, L is
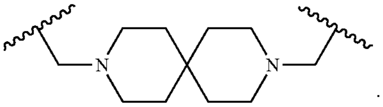 [SMILES: *CN1CCC2(CC1)CCN(C*)CC2]
In some embodiments, L is
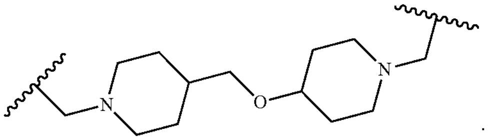 [SMILES: *CN1CCC(COC2CCN(C*)CC2)CC1]
In some embodiments, L is
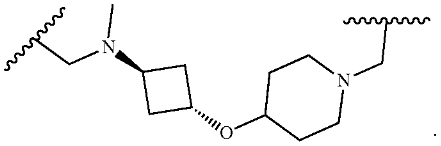 [SMILES: *CN1CCC(O[C@H]2C[C@H](N(C)C*)C2)CC1]
In some embodiments, L is
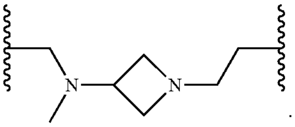 [SMILES: *CCN1CC(N(C)C*)C1]
In some embodiments, L is
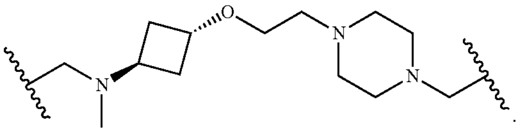 [SMILES: *CN1CCN(CCO[C@H]2C[C@H](N(C)C*)C2)CC1]

In some embodiments, L is
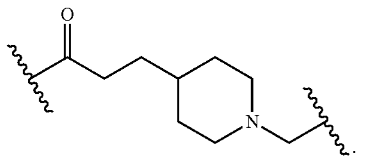 [SMILES: *CN1CCC(CCC(*)=O)CC1]
In some embodiments, L is
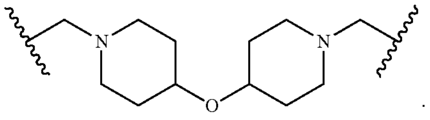 [SMILES: *CN1CCC(OC2CCN(C*)CC2)CC1]
In some embodiments, L is
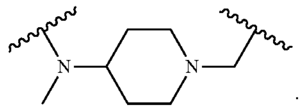 [SMILES: *CN1CCC(N(*)C)CC1]
In some embodiments, L is
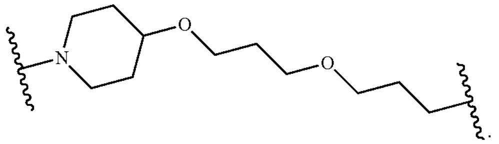 [SMILES: *CCCOCCCOC1CCN(*)CC1]
In In some embodiments, L is
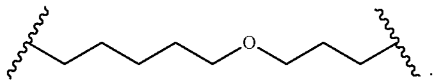 [SMILES: *CCCCCOCCC*]
In some embodiments, L is
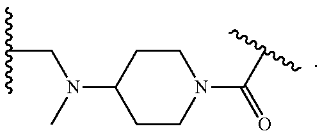 [SMILES: *CN(C)C1CCN(C(*)=O)CC1]
In some embodiments, L is
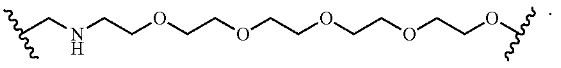 [SMILES: *CNCCOCCOCCOCCOCCO*]
In some embodiments, L is
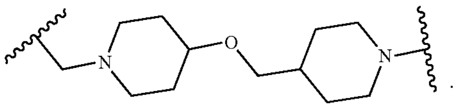 [SMILES: *CN1CCC(OCC2CCN(*)CC2)CC1]
In some embodiments, L is
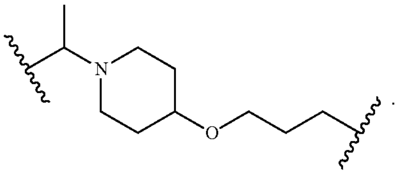 [SMILES: *CCCOC1CCN(C(*)C)CC1]
In some embodiments, L is
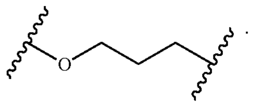 [SMILES: *CCCO*]
In some embodiments, L is
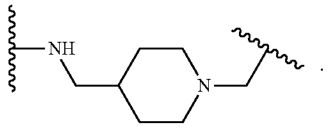 [SMILES: *CN1CCC(CN*)CC1]
In some embodiments, L is
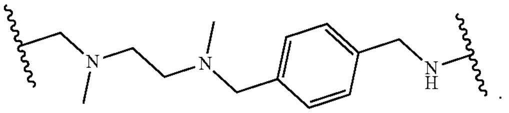 [SMILES: *CN(C)CCN(C)Cc1ccc(CN*)cc1]
In some embodiments, L is
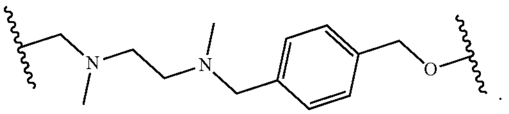 [SMILES: *CN(C)CCN(C)Cc1ccc(CO*)cc1]
In some embodiments, L is
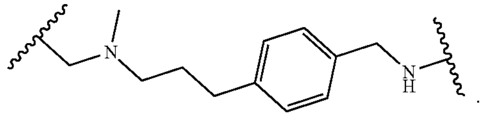 [SMILES: *CN(C)CCCc1ccc(CN*)cc1]

In some embodiments, L is
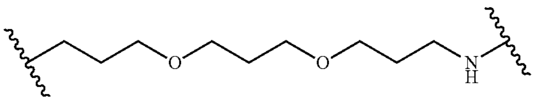
In some embodiments, L is
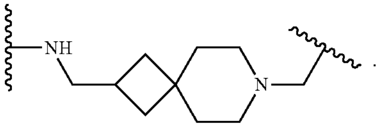 [SMILES: *CN1CCC2(CC1)CC(CN*)C2]
In some embodiments, L is
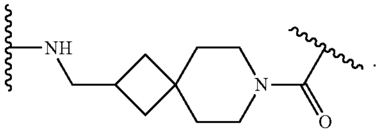 [SMILES: *NCC1CC2(CCN(C(*)=O)CC2)C1]
In some embodiments, L is
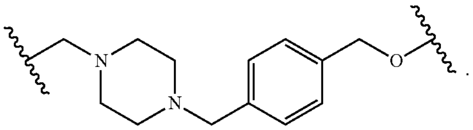 [SMILES: *CN1CCN(Cc2ccc(CO*)cc2)CC1]
In some embodiments, L is
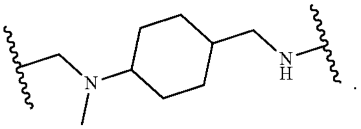 [SMILES: *CN(C)C1CCC(CN*)CC1]
In some embodiments, L is
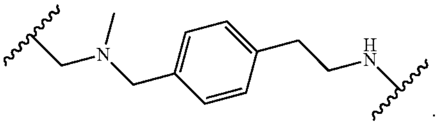 [SMILES: *CN(C)Cc1ccc(CCN*)cc1]
In some embodiments, L is
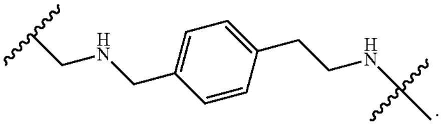 [SMILES: *CNCc1ccc(CCN*)cc1]
In some embodiments, L is
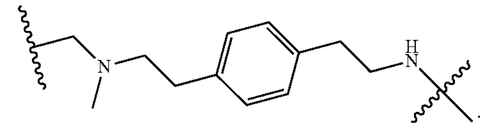 [SMILES: *CN(C)CCc1ccc(CCN*)cc1]
In some embodiments, L is
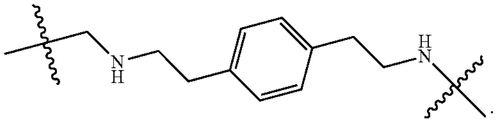 [SMILES: *CNCCc1ccc(CCN*)cc1]
In some embodiments, L is
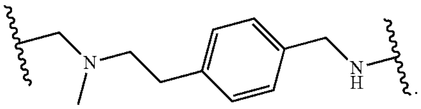 [SMILES: *CN(C)CCc1ccc(CN*)cc1]
In some embodiments, L is
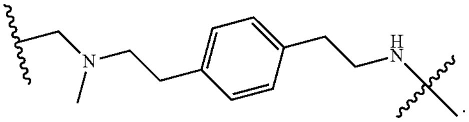 [SMILES: *CN(C)CCc1ccc(CCN*)cc1]
In some embodiments, L is
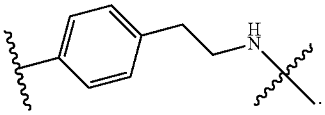 [SMILES: *NCCc1ccc(*)cc1]
In In some embodiments, L is
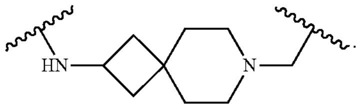 [SMILES: *CN1CCC2(CC1)CC(N*)C2]
In some In In embodiments, L is
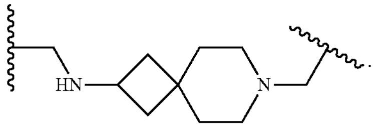 [SMILES: *CNC1CC2(CCN(C*)CC2)C1]

embodiments, L is
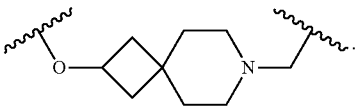
In some embodiments, L is
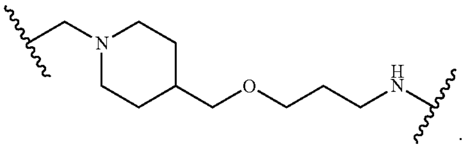 [SMILES: *CN1CCC(COCCCN*)CC1]
In some embodiments, L is
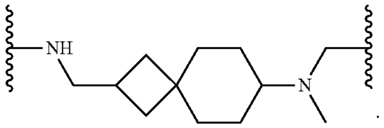 [SMILES: *CN(C)C1CCC2(CC1)CC(CN*)C2]
In some embodiments, L is
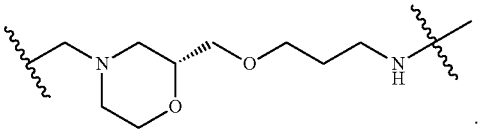 [SMILES: *CN1CCO[C@@H](COCCCN*)C1]
In some embodiments, L is
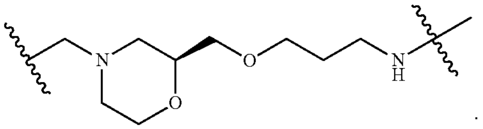 [SMILES: *CN1CCO[C@H](COCCCN*)C1]
In some embodiments, L is
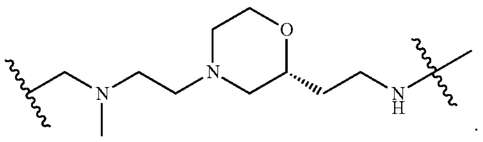 [SMILES: *CN(C)CCN1CCO[C@H](CCN*)C1]
In some embodiments, L is
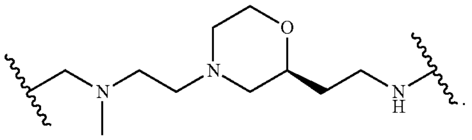 [SMILES: *CN(C)CCN1CCO[C@@H](CCN*)C1]
In some embodiments, L is
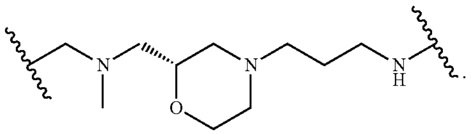 [SMILES: *CN(C)C[C@@H]1CN(CCCN*)CCO1]
In some embodiments, L is
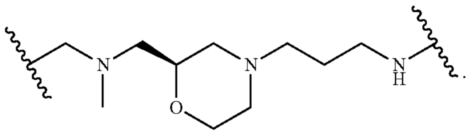 [SMILES: *CN(C)C[C@H]1CN(CCCN*)CCO1]
In some embodiments, L is
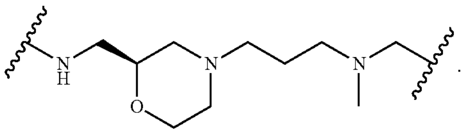 [SMILES: *CN(C)CCCN1CCO[C@@H](CN*)C1]
In some embodiments, L is
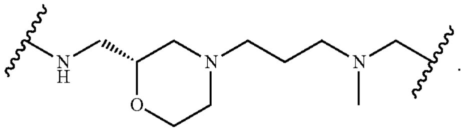 [SMILES: *CN(C)CCCN1CCO[C@H](CN*)C1]
In some embodiments, L is
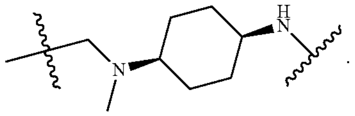 [SMILES: *CN(C)[C@H]1CC[C@@H](N*)CC1]
In some embodiments, L is
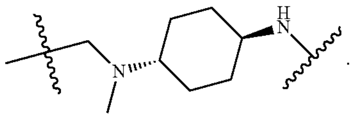 [SMILES: *CN(C)[C@H]1CC[C@H](N*)CC1]
In some embodiments, L is
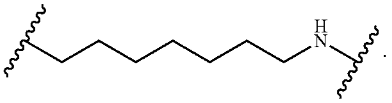 [SMILES: *CCCCCCCN*]

In some embodiments, L is

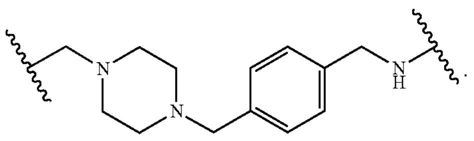 [SMILES: *CN1CCN(Cc2ccc(CN*)cc2)CC1]

some embodiments, L is

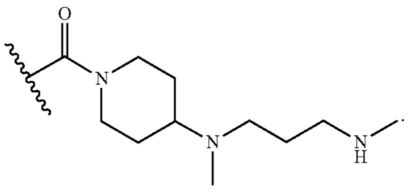 [SMILES: *C(=O)N1CCC(N(C)CCCNC)CC1]

In some embodiments, L is

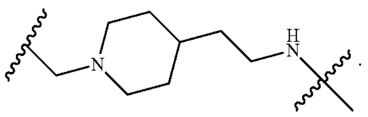 [SMILES: *CN1CCC(CCN*)CC1]

In some embodiments, L is

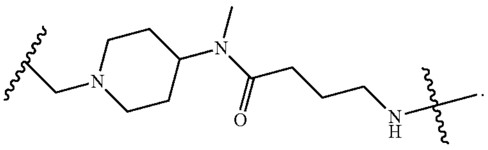 [SMILES: *CN1CCC(N(C)C(=O)CCCN*)CC1]

In some embodiments, L is

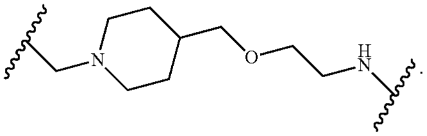 [SMILES: *CN1CCC(COCCN*)CC1]

In some embodiments, L is

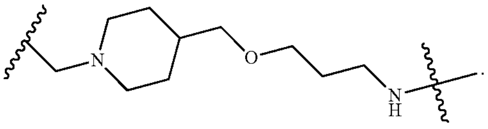 [SMILES: *CN1CCC(COCCCN*)CC1]

In some embodiments, L is

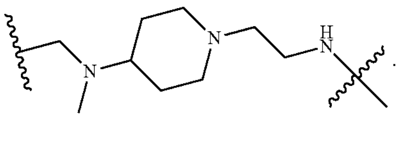 [SMILES: *CN(C)C1CCN(CCN*)CC1]

In some embodiments, L is

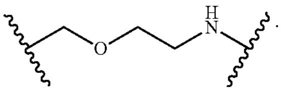 [SMILES: *COCCN*]

In some embodiments, L is

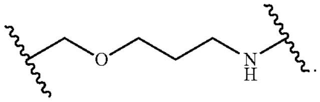 [SMILES: *COCCCN*]

In some embodiments, L is

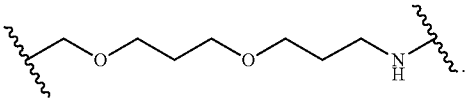 [SMILES: *COCCCOCCCN*]

In some embodiments, L is

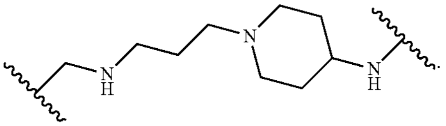 [SMILES: *CNCCCN1CCC(N*)CC1]

In some embodiments, L is a convalent bond. In some embodiments, L is

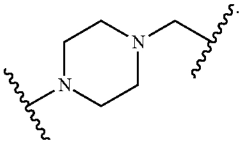 [SMILES: *CN1CCN(*)CC1]

In some embodiments, L is

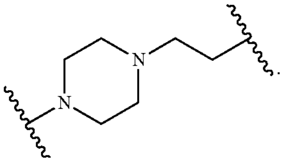 [SMILES: *CCN1CCN(*)CC1]

In some embodiments, L is

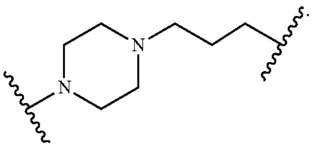 [SMILES: *CCCN1CCN(*)CC1]

In some embodiments, L is
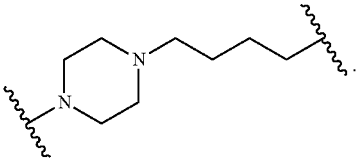 [SMILES: *CCCCN1CCN(*)CC1]
In some embodiments, L is
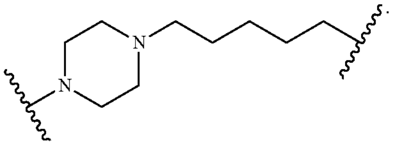 [SMILES: *CCCCCN1CCN(*)CC1]
In some embodiments, L is
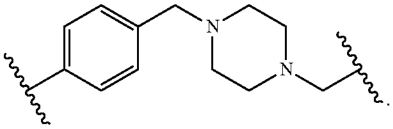 [SMILES: *CN1CCN(Cc2ccc(*)cc2)CC1]
In some embodiments, L is
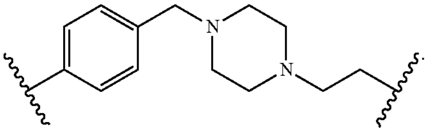 [SMILES: *CCN1CCN(Cc2ccc(*)cc2)CC1]
In some embodiments, L is
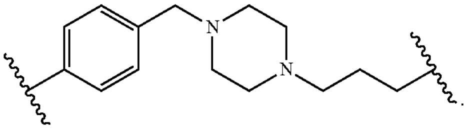 [SMILES: *CCCN1CCN(Cc2ccc(*)cc2)CC1]
In some embodiments, L is
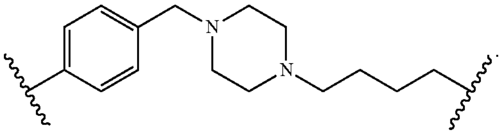 [SMILES: *CCCCN1CCN(Cc2ccc(*)cc2)CC1]
In some embodiments, L is
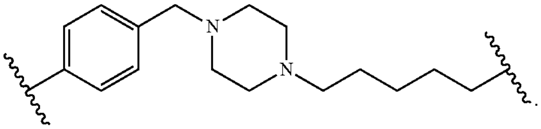 [SMILES: *CCCCCN1CCN(Cc2ccc(*)cc2)CC1]
In some embodiments, L is
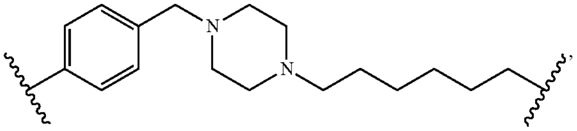 [SMILES: *CCCCCCN1CCN(Cc2ccc(*)cc2)CC1]
In some embodiments, L is
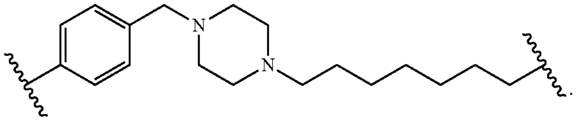 [SMILES: *CCCCCCCN1CCN(Cc2ccc(*)cc2)CC1]
In some embodiments, L is
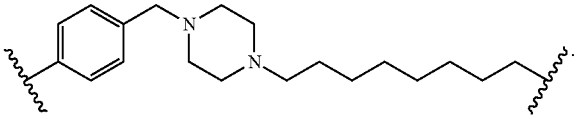 [SMILES: *CCCCCCCCN1CCN(Cc2ccc(*)cc2)CC1]
In some embodiments, L is
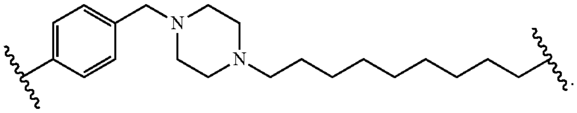 [SMILES: *CCCCCCCCCN1CCN(Cc2ccc(*)cc2)CC1]
In some embodiments, L is
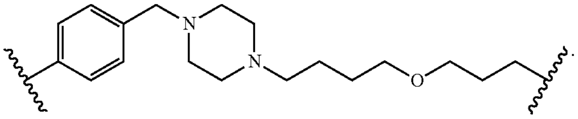 [SMILES: *CCCOCCCCN1CCN(Cc2ccc(*)cc2)CC1]
some embodiments, L is
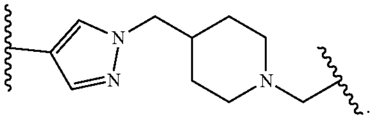 [SMILES: *CN1CCC(Cn2cc(*)cn2)CC1]

In some embodiments, L is
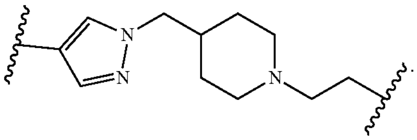 [SMILES: *CCN1CCC(Cn2cc(*)cn2)CC1]
In some embodiments, L is
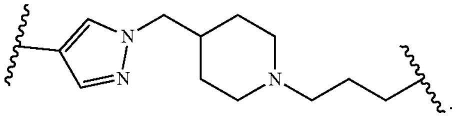 [SMILES: *CCCN1CCC(Cn2cc(*)cn2)CC1]
In some embodiments, L is
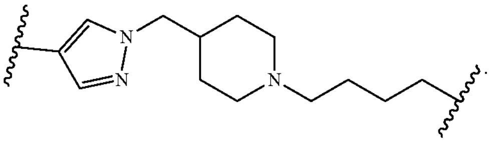 [SMILES: *CCCCN1CCC(Cn2cc(*)cn2)CC1]
In some embodiments, L is
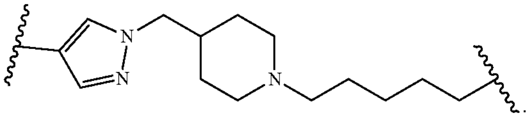 [SMILES: *CCCCCN1CCC(Cn2cc(*)cn2)CC1]
In some embodiments, L is
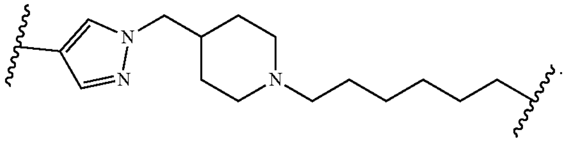 [SMILES: *CCCCCCN1CCC(Cn2cc(*)cn2)CC1]
In some embodiments, L is
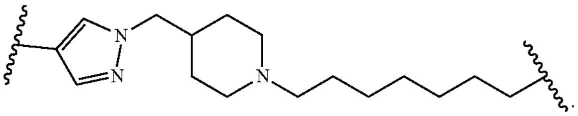 [SMILES: *CCCCCCCN1CCC(Cn2cc(*)cn2)CC1]
In some embodiments, L is
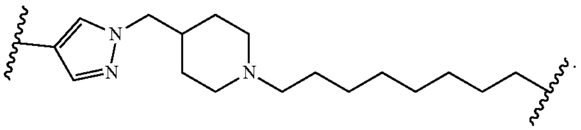 [SMILES: *CCCCCCCCN1CCC(Cn2cc(*)cn2)CC1]
In some embodiments, L is
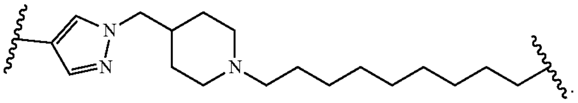 [SMILES: *CCCCCCCCCN1CCC(Cn2cc(*)cn2)CC1]
In some embodiments, L is
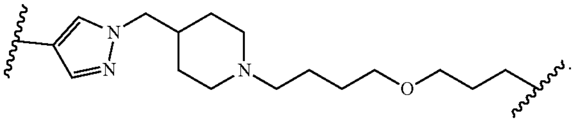 [SMILES: *CCCOCCCCN1CCC(Cn2cc(*)cn2)CC1]
In some embodiments, L is
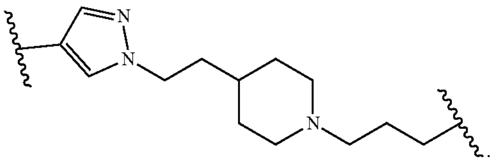 [SMILES: *CCCN1CCC(CCn2cc(*)cn2)CC1]
In some embodiments, L is
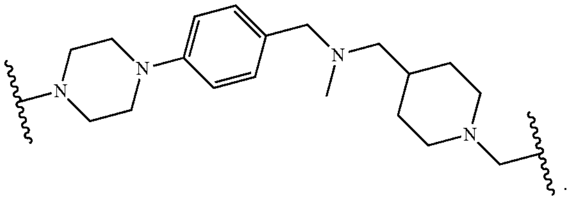 [SMILES: *CN1CCC(CN(C)Cc2ccc(N3CCN(*)CC3)cc2)CC1]
In some embodiments, L is
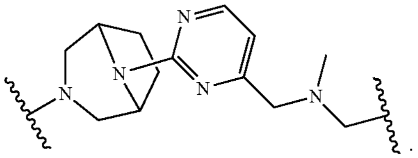 [SMILES: *CN(C)Cc1ccnc(N2C3CCC2CN(*)C3)n1]
In some embodiments, L is
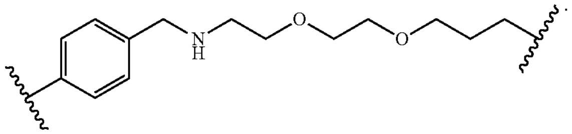 [SMILES: *CCCOCCOCCNCc1ccc(*)cc1]

In some embodiments, L is
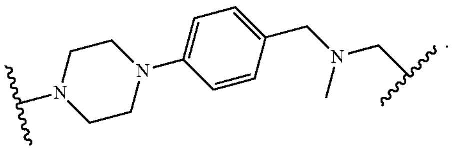 [SMILES: *CN(C)Cc1ccc(N2CCN(*)CC2)cc1]
In some embodiments, L is
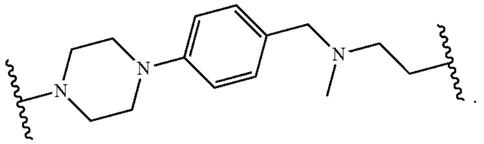 [SMILES: *CCN(C)Cc1ccc(N2CCN(*)CC2)cc1]
In some embodiments, L is
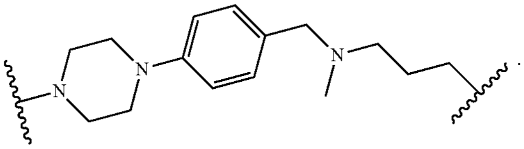 [SMILES: *CCCN(C)Cc1ccc(N2CCN(*)CC2)cc1]
In some embodiments, L is
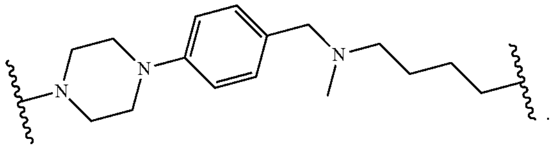 [SMILES: *CCCCN(C)Cc1ccc(N2CCN(*)CC2)cc1]
In some embodiments, L is
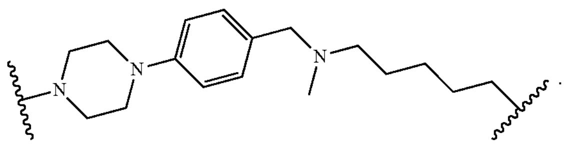 [SMILES: *CCCCCN(C)Cc1ccc(N2CCN(*)CC2)cc1]
In some embodiments, L is
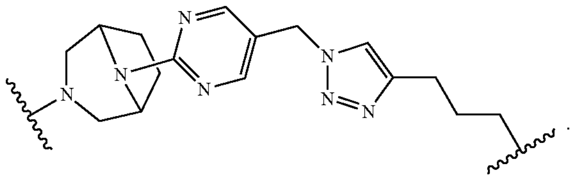 [SMILES: *CCCc1cn(Cc2cnc(N3C4CCC3CN(*)C4)nc2)nn1]
In some embodiments, L is
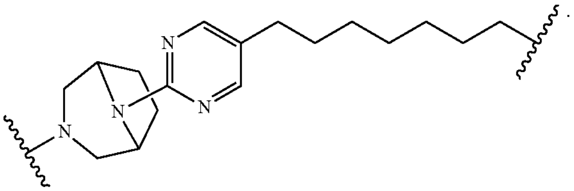 [SMILES: *CCCCCCCc1cnc(N2C3CCC2CN(*)C3)nc1]
In some embodiments, L is
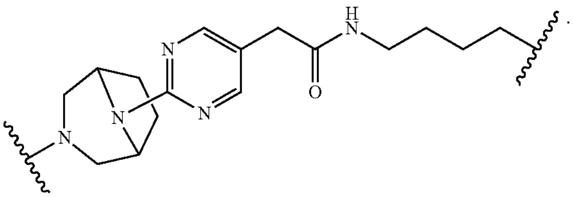 [SMILES: *CCCCNC(=O)Cc1cnc(N2C3CCC2CN(*)C3)nc1]
In some embodiments, L is
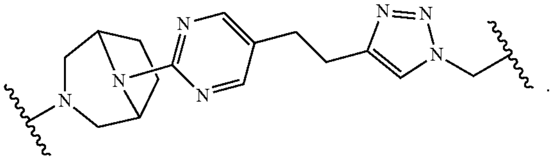 [SMILES: *Cn1cc(CCc2cnc(N3C4CCC3CN(*)C4)nc2)nn1]
In some embodiments, L is
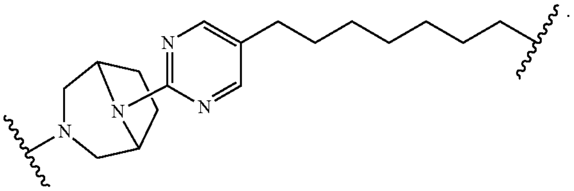 [SMILES: *CCCCCCCc1cnc(N2C3CCC2CN(*)C3)nc1]
In some embodiments, L is
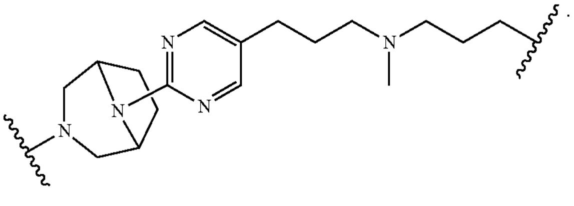 [SMILES: *CCCN(C)CCCc1cnc(N2C3CCC2CN(*)C3)nc1]

In some embodiments, L is
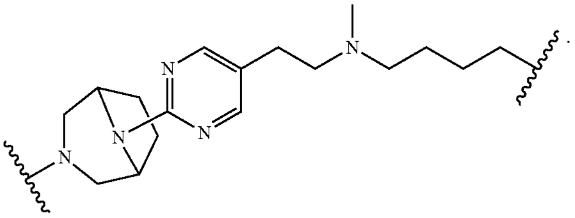 [SMILES: *CCCCN(C)CCc1cnc(N2C3CCC2CN(*)C3)nc1]
In some embodiments, L is
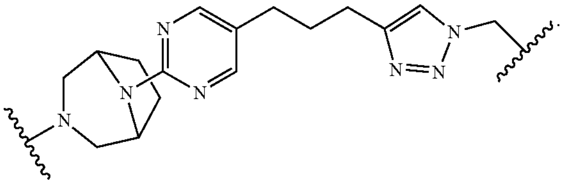 [SMILES: *Cn1cc(CCCc2cnc(N3C4CCC3CN(*)C4)nc2)nn1]
In some embodiments, L is
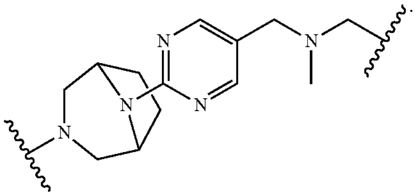 [SMILES: *CN(C)Cc1cnc(N2C3CCC2CN(*)C3)nc1]
In some embodiments, L is
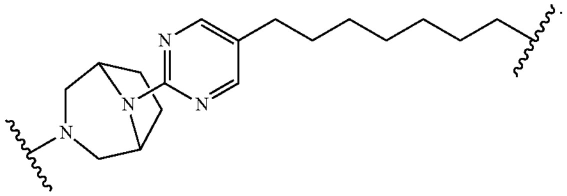 [SMILES: *CCCCCCCc1cnc(N2C3CCC2CN(*)C3)nc1]
In some embodiments, L is
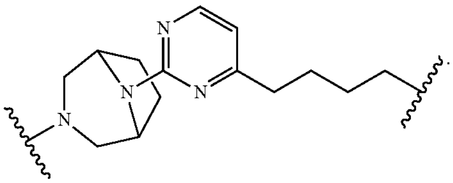 [SMILES: *CCCCc1ccnc(N2C3CCC2CN(*)C3)n1]
In some embodiments, L is
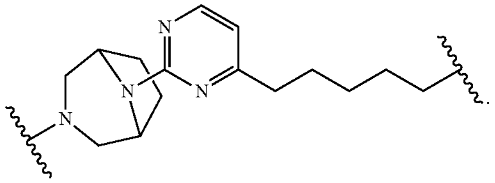 [SMILES: *CCCCCc1ccnc(N2C3CCC2CN(*)C3)n1]
In some embodiments, L is
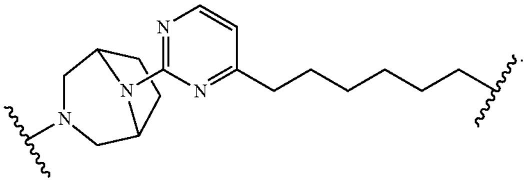 [SMILES: *CCCCCCc1ccnc(N2C3CCC2CN(*)C3)n1]
In some embodiments, L is
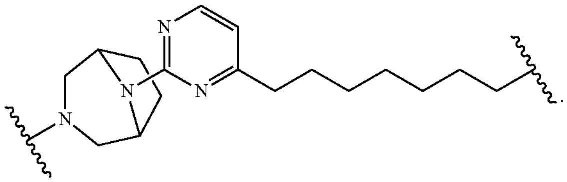 [SMILES: *CCCCCCCc1ccnc(N2C3CCC2CN(*)C3)n1]
In some embodiments, L is
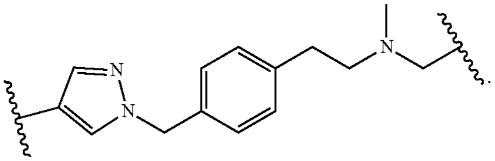 [SMILES: *CN(C)CCc1ccc(Cn2cc(*)cn2)cc1]
In some embodiments, L is
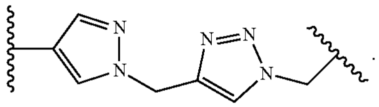 [SMILES: *Cn1cc(Cn2cc(*)cn2)nn1]
In some embodiments, L is
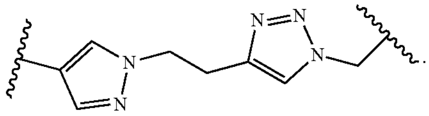 [SMILES: *Cn1cc(CCn2cc(*)cn2)nn1]

In Some Embodiments, L is
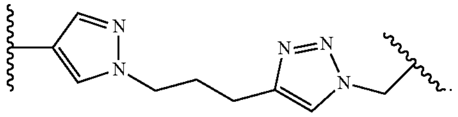 [SMILES: *Cn1cc(CCCn2cc(*)cn2)nn1]
In some embodiments, L is
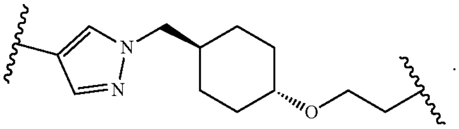 [SMILES: *CCO[C@H]1CC[C@H](Cn2cc(*)cn2)CC1]
In some embodiments, L is
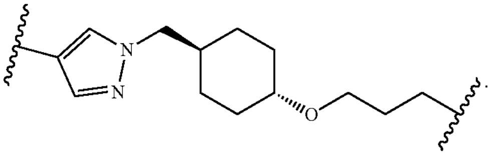 [SMILES: *CCCO[C@H]1CC[C@H](Cn2cc(*)cn2)CC1]
In some embodiments, L is
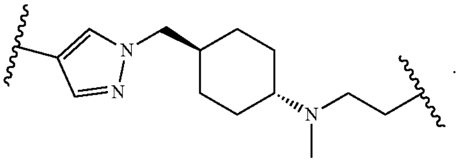 [SMILES: *CCN(C)[C@H]1CC[C@H](Cn2cc(*)cn2)CC1]
In some embodiments, L is
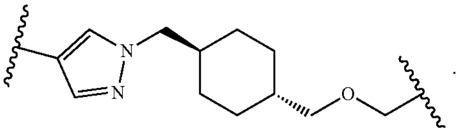 [SMILES: *COC[C@H]1CC[C@H](Cn2cc(*)cn2)CC1]
In some embodiments, L is
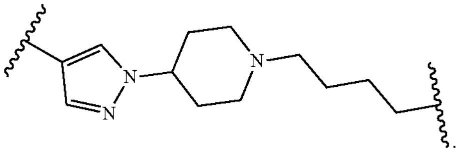 [SMILES: *CCCCN1CCC(n2cc(*)cn2)CC1]
In some embodiments, L is
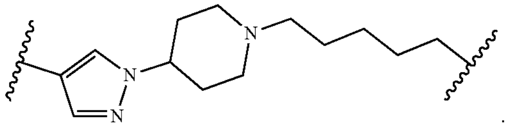 [SMILES: *CCCCCN1CCC(n2cc(*)cn2)CC1]
In some embodiments, L is
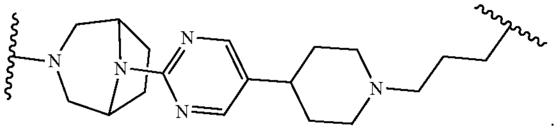 [SMILES: *CCCN1CCC(c2cnc(N3C4CCC3CN(*)C4)nc2)CC1]
In some embodiments, L is
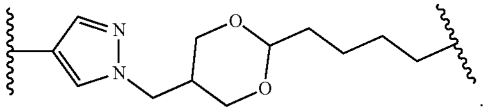 [SMILES: *CCCCC1OCC(Cn2cc(*)cn2)CO1]
In some embodiments, L is
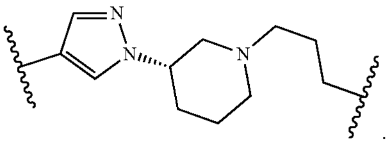 [SMILES: *CCCN1CCC[C@H](n2cc(*)cn2)C1]
In some embodiments, L is
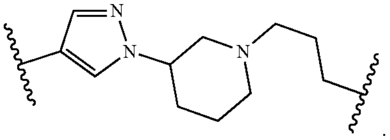 [SMILES: *CCCN1CCCC(n2cc(*)cn2)C1]
In some embodiments, L is
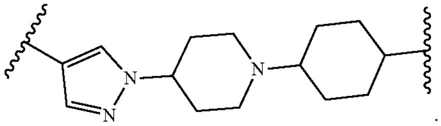 [SMILES: *c1cnn(C2CCN(C3CCC(*)CC3)CC2)c1]
In some embodiments, L is
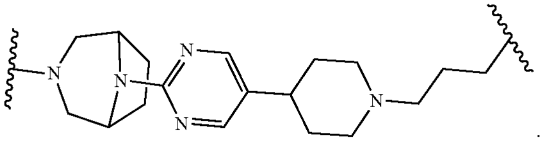 [SMILES: *CCCN1CCC(c2cnc(N3C4CCC3CN(*)C4)nc2)CC1]

In some embodiments, L is

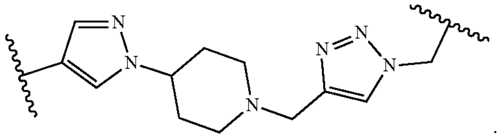 [SMILES: *Cn1cc(CN2CCC(n3cc(*)cn3)CC2)nn1]

.

In some embodiments, L is selected from those depicted in Table 1, below.

As defined above and described herein, TBM is a target binding moiety.

In some embodiments, TBM is a target binding moiety.

In some embodiments, TBM is selected from one of the drugs listed in Table 2, wherein the drug is attached to

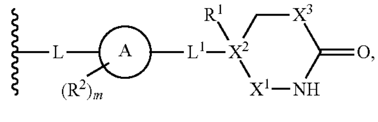

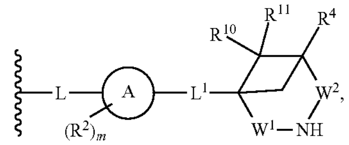

or

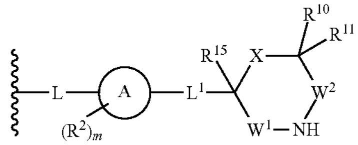

at any modifiable carbon, oxygen, sulfur or nitrogen atom.

In some embodiments, TBM is

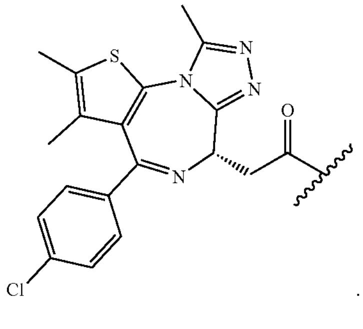 [SMILES: *C(=O)C[C@@H]1N=C(c2ccc(Cl)cc2)c2c(sc(C)c2C)-n2c(C)nnc21]

.

In some embodiments, TBM

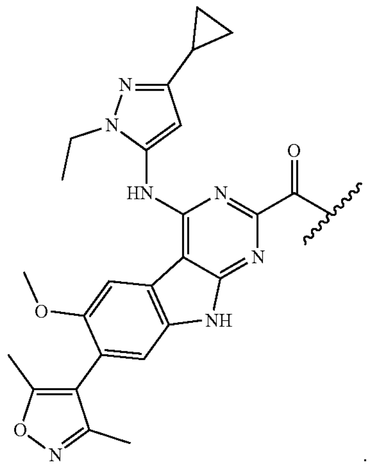 [SMILES: *C(=O)c1nc(Nc2cc(C3CC3)nn2CC)c2c(n1)[nH]c1cc(-c3c(C)noc3C)c(OC)cc12]

.

In some embodiments, TBM is

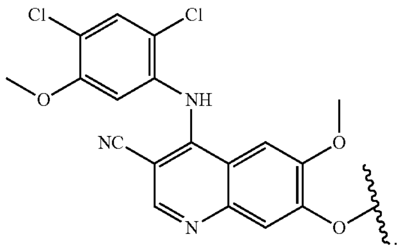 [SMILES: *Oc1cc2ncc(C#N)c(Nc3cc(OC)c(Cl)cc3Cl)c2cc1OC]

.

In some embodiments, TBM is

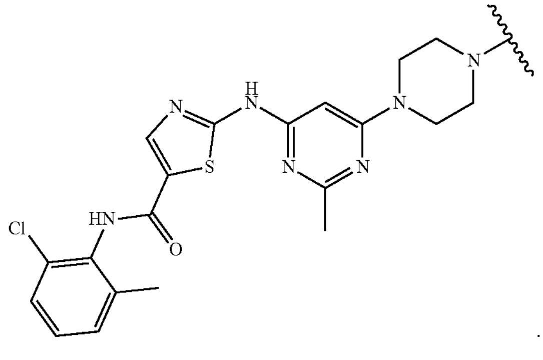 [SMILES: *N1CCN(c2cc(Nc3ncc(C(=O)Nc4c(C)cccc4Cl)s3)nc(C)n2)CC1]

.

In some embodiments, TBM is

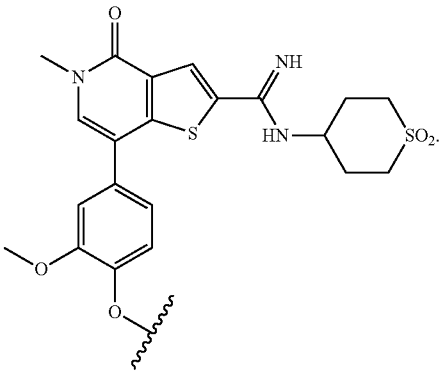 [SMILES: *Oc1ccc(-c2cn(C)c(=O)c3cc(C(=N)NC4CCS(=O)(=O)CC4)sc23)cc1OC]

In some embodiments, TBM is

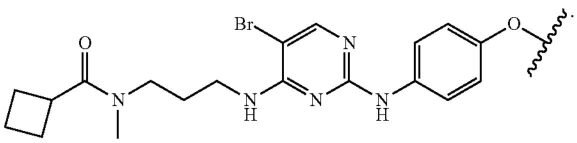 [SMILES: *Oc1ccc(Nc2ncc(Br)c(NCCCN(C)C(=O)C3CCC3)n2)cc1]

In some embodiments, TBM is

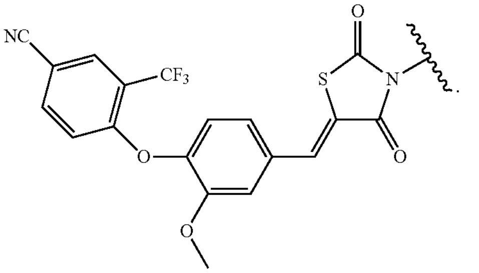 [SMILES: *N1C(=O)S/C(=C\c2ccc(Oc3ccc(C#N)cc3C(F)(F)F)c(OC)c2)C1=O]

In some embodiments, TBM is

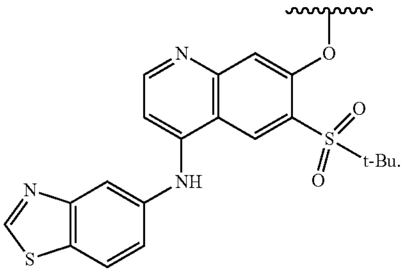 [SMILES: *Oc1cc2nccc(Nc3ccc4scnc4c3)c2cc1S(=O)(=O)C(C)(C)C]

In some embodiments, TBM is selected from those depicted in Table 1, below.

In preferred aspects of the invention, the TBM group is a group, which binds to target proteins. Targets of the TBM group are numerous in kind and are selected from proteins that are expressed in a cell such that at least a portion of the sequences is found in the cell and may bind to a TBM group. The term "protein" includes oligopeptides and polypeptide sequences of sufficient length that they can bind to a TBM group according to the present invention. Any protein in a eukaryotic system, as described herein, are targets for ubiquitination mediated by the compounds according to the present invention.

TBM groups according to the present invention include, for example, include any moiety which binds to a protein specifically (binds to a target protein) and includes the following non-limiting examples of small molecule target protein moieties: Hsp90 inhibitors, kinase inhibitors, HDM2 & MDM2 inhibitors, compounds targeting Human BET Bromodomain-containing proteins, HDAC inhibitors, human lysine methyltransferase inhibitors, angiogenesis inhibitors, nuclear hormone receptor compounds, immunosuppressive compounds, and compounds targeting the aryl hydrocarbon receptor (AHR), among numerous others. The compositions described below exemplify some of the members of these nine types of small molecule target protein binding moieties. Such small molecule target protein binding moieties also include pharmaceutically acceptable salts, enantiomers, solvates and polymorphs of these compositions, as well as other small molecules that may target a protein of interest. These binding moieties are linked to the ubiquitin ligase binding moiety preferably through a linker in order to present a target protein (to which the protein target moiety is bound) in proximity to the ubiquitin ligase for ubiquitination and degradation.

Any protein, which can bind to a target binding moiety or TBM group and acted on or degraded by an ubiquitin ligase is a target protein according to the present invention. In general, target proteins may include, for example, structural proteins, receptors, enzymes, cell surface proteins, proteins pertinent to the integrated function of a cell, including proteins involved in catalytic activity, aromatase activity, motor activity, helicase activity, metabolic processes (anabolism and catabolism), antioxidant activity, proteolysis, biosynthesis, proteins with kinase activity, oxidoreductase activity, transferase activity, hydrolase activity, lyase activity, isomerase activity, ligase activity, enzyme regulator activity, signal transducer activity, structural molecule activity, binding activity (protein, lipid carbohydrate), receptor activity, cell motility, membrane fusion, cell communication, regulation of biological processes, development, cell differentiation, response to stimulus, behavioral proteins, cell adhesion proteins, proteins involved in cell death, proteins involved in transport (including protein transporter activity, nuclear transport, ion transporter activity, channel transporter activity, carrier activity, permease activity, secretion activity, electron transporter activity, pathogenesis, chaperone regulator activity, nucleic acid binding activity, transcription regulator activity, extracellular organization and biogenesis activity, translation regulator activity. Proteins of interest can include proteins from eurkaryotes and prokaryotes including humans as targets for drug therapy, other animals, including domesticated animals, microbials for the determination of targets for antibiotics and other antimicrobials and plants, and even viruses, among numerous others.

TBM (or target binding moiety) is a small molecule which is capable of binding to or binds to a target protein of interest.

Some embodiments of the present application relate to TBMs which include but are not limited to Hsp90 inhibitors, kinase inhibitors, MDM2 inhibitors, compounds targeting Human BET Bromodomain-containing proteins, compounds targeting cytosolic signaling protein FKBP12, HDAC inhibitors, human lysine methyltransferase inhibitors, angiogenesis inhibitors, immunosuppressive compounds, and compounds targeting the aryl hydrocarbon receptor (AHR).
In some embodiments, TBM is a BRD ligand selected from
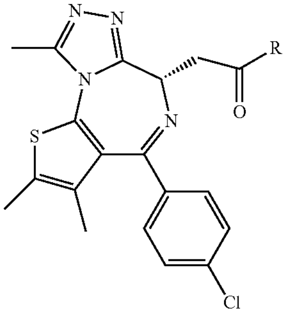
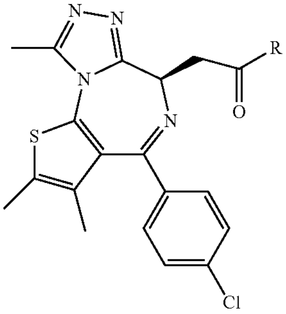
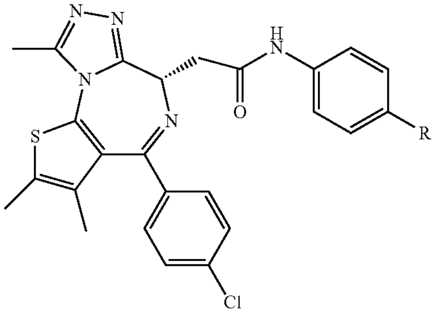
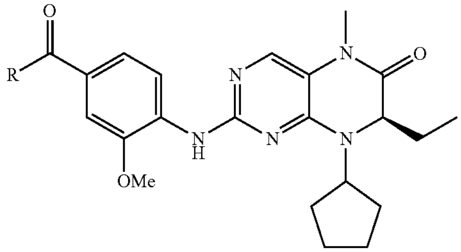
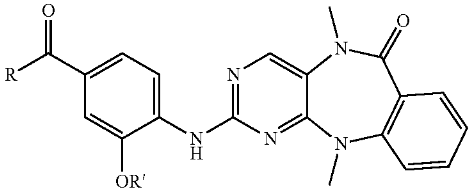
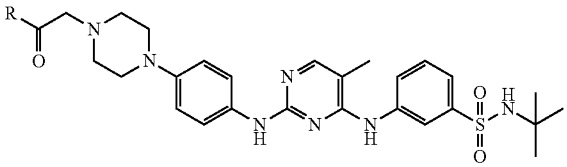
,
wherein R denotes attachment to
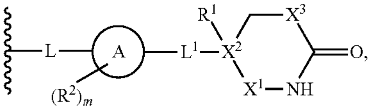
,
-continued
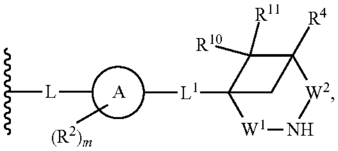
, or
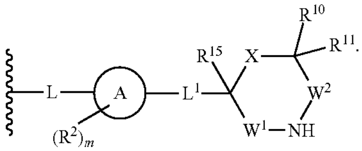
.
In some embodiments, TBM is a CREBBP ligand selected from
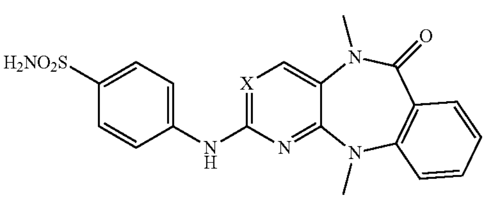
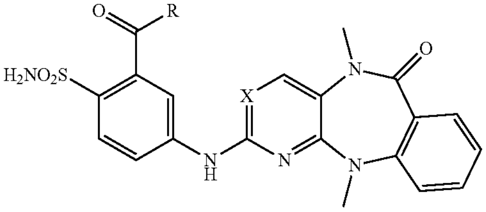
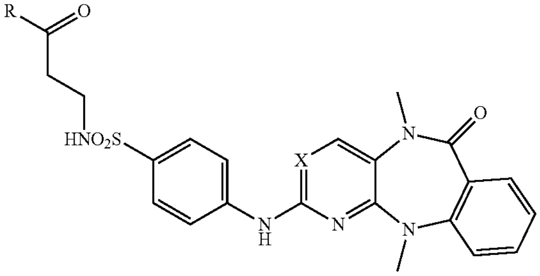
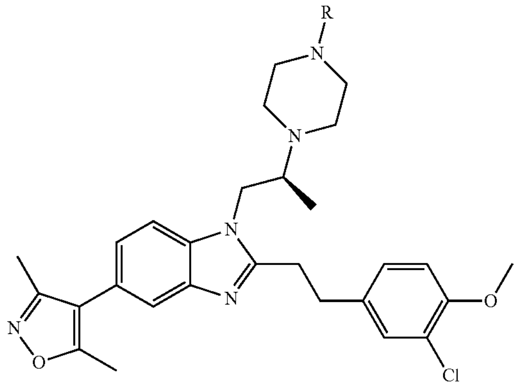

-continued
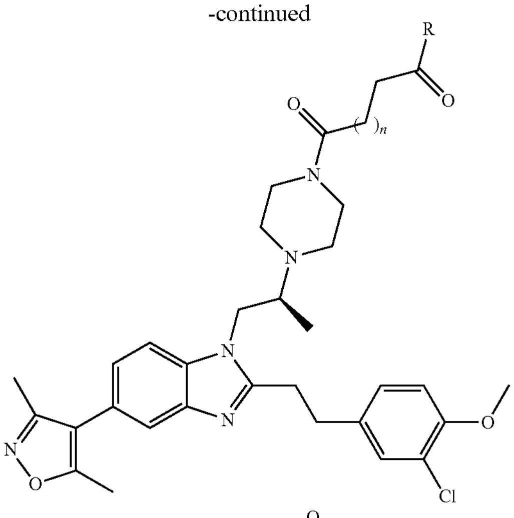
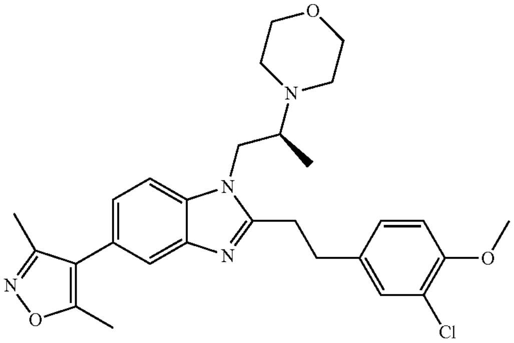
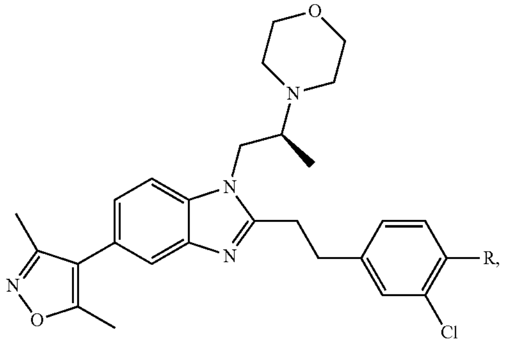
wherein R denotes attachment to
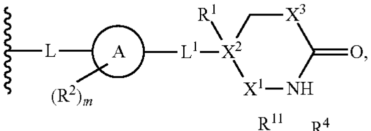
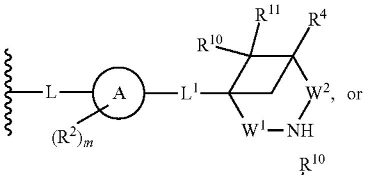
or
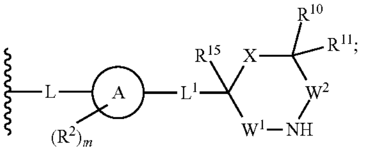
X is N or C; and n is 0 to 8.
In some embodiments, TBM is a SMARCA4/PB1/SMARCA2 ligand selected from
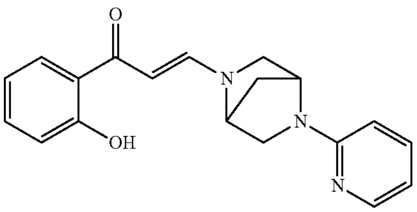
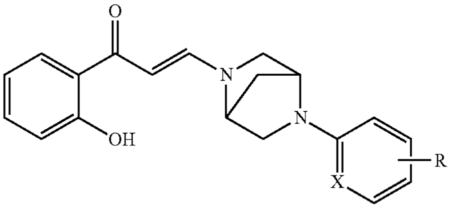
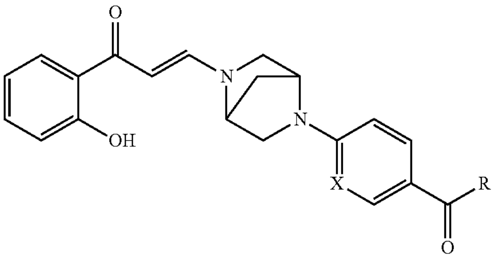
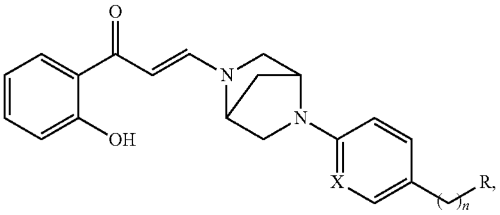
wherein R denotes attachment to
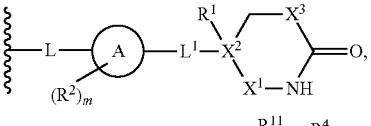
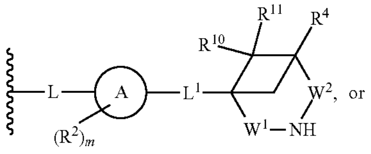
or
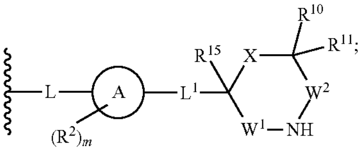
X is N or C; and n is 0 to 8.

In some embodiments, TBM is a TRIM24/BRPF1 ligand selected from
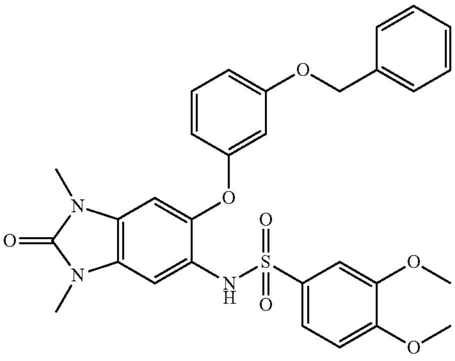
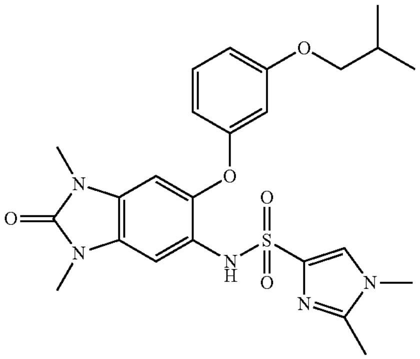
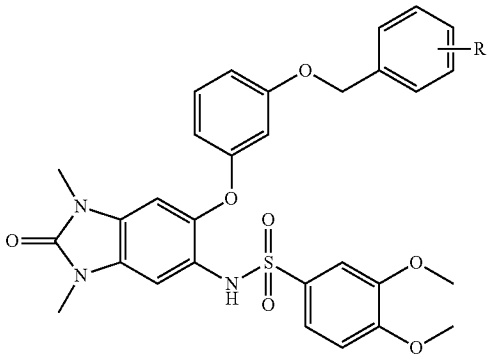
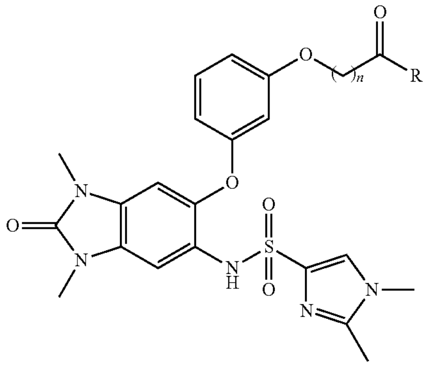
-continued
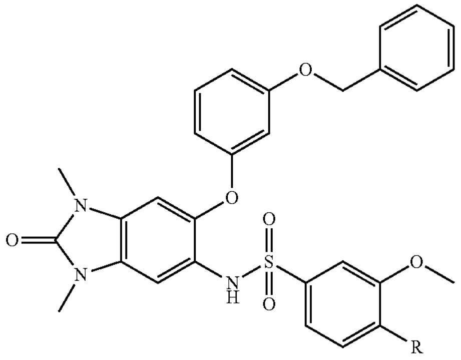
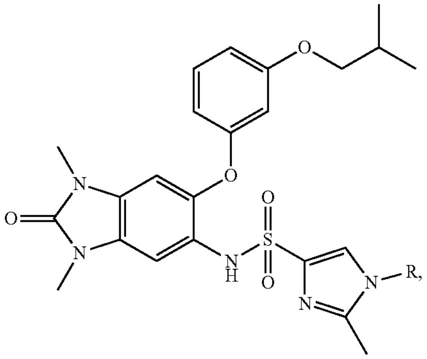
wherein R denotes attachment to
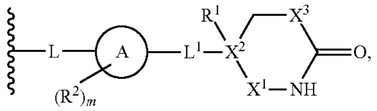
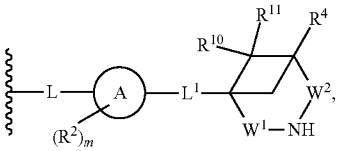
or
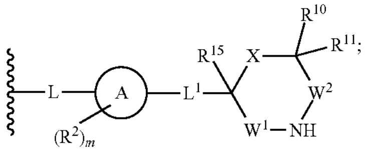
and n is 0 to 8.
In some embodiments, TBM is a glucocorticoid receptor ligand selected from
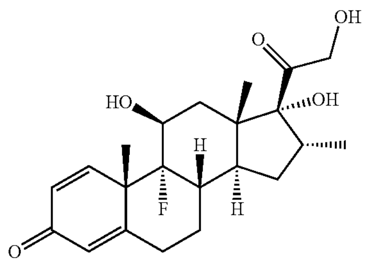

-continued
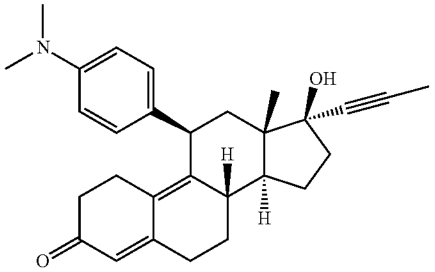
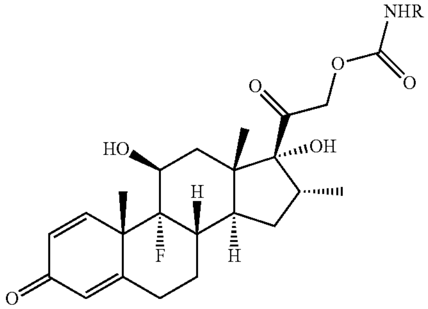
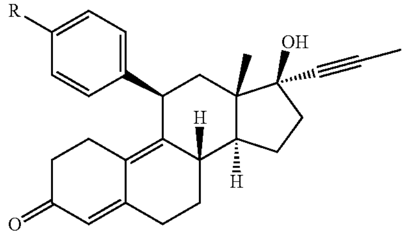
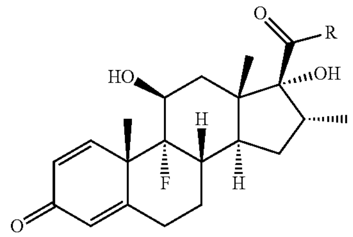
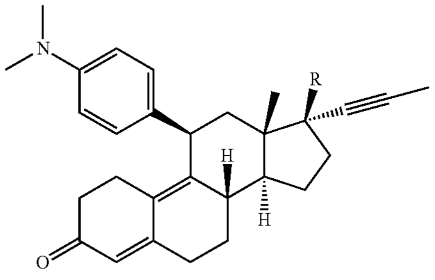
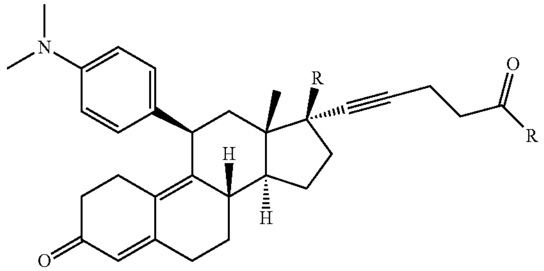
-continued
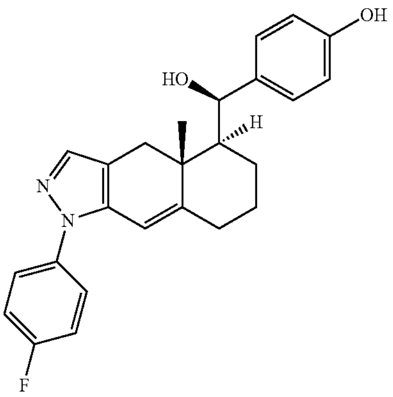
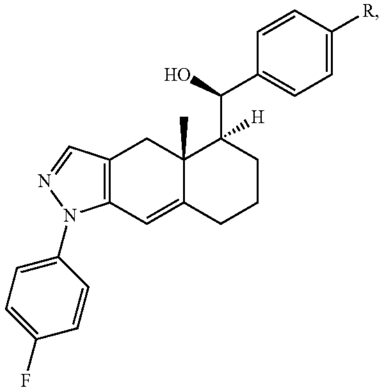
wherein R denotes attachment to
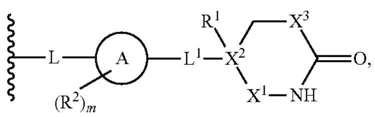
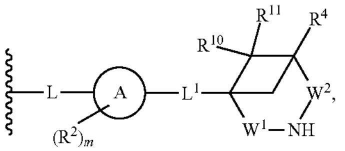
or
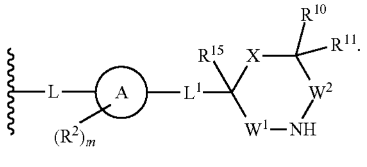

In some embodiments, TBM is an estrogen/androgen receptor ligand selected from
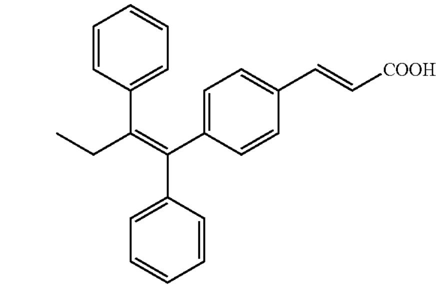
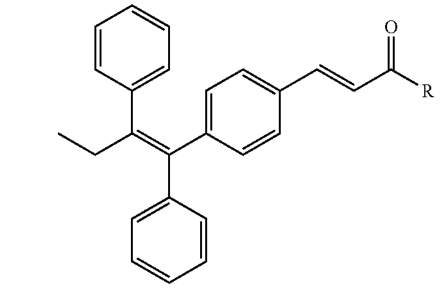
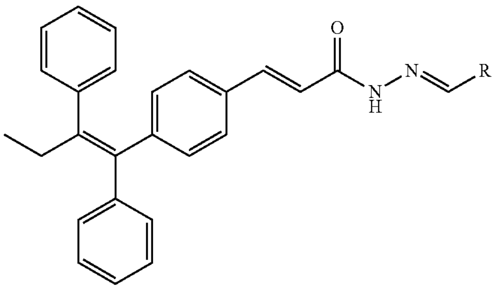
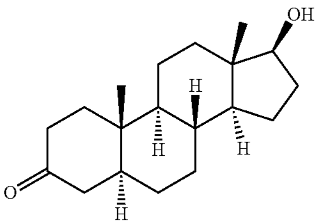
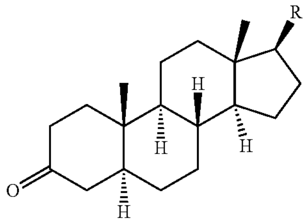
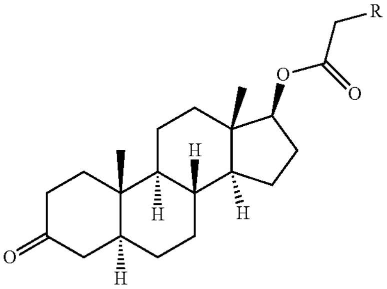
-continued
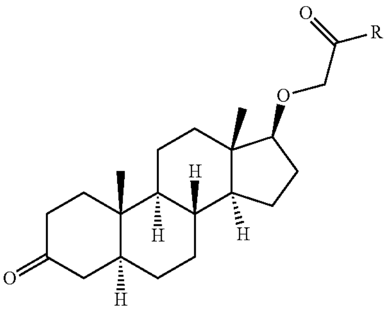
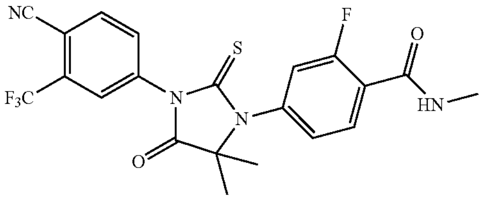
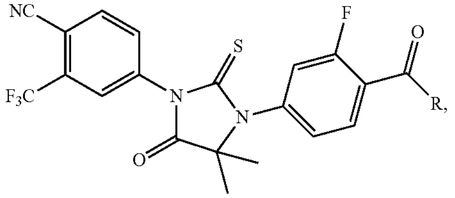
wherein R denotes attachment to
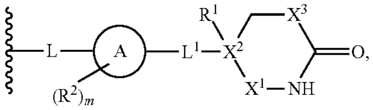
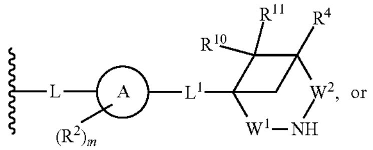
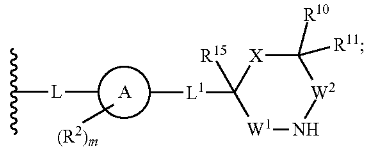
X is N or C; and n is 0 to 8.
In some embodiments, TBM is a DOT1L ligand selected from
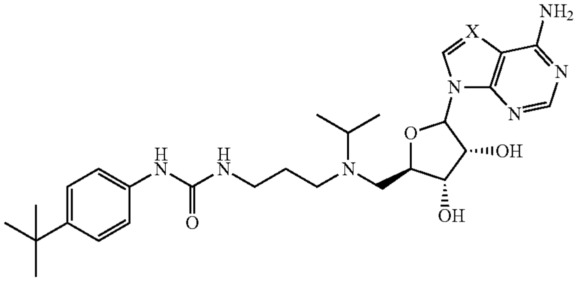

-continued
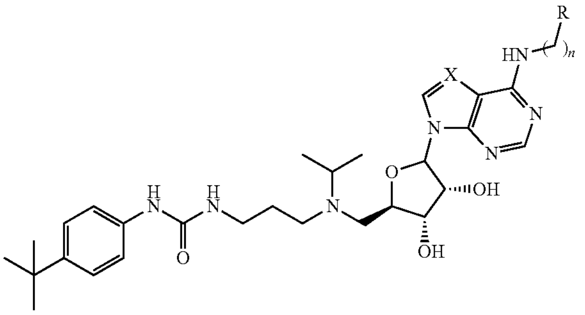
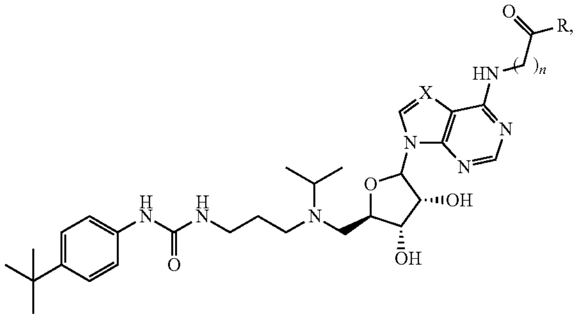
wherein R denotes attachment to
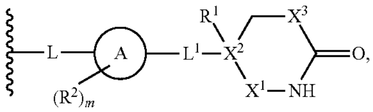
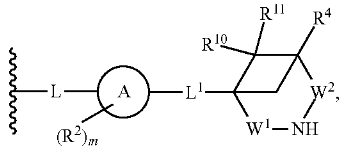
or
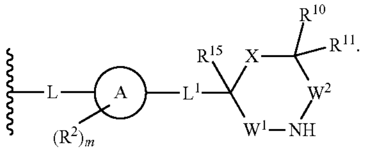
In some embodiments, TBM is a BRAF ligand selected from
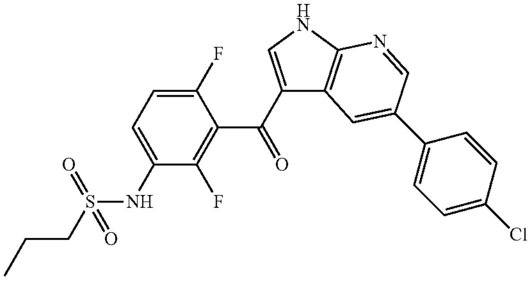
-continued
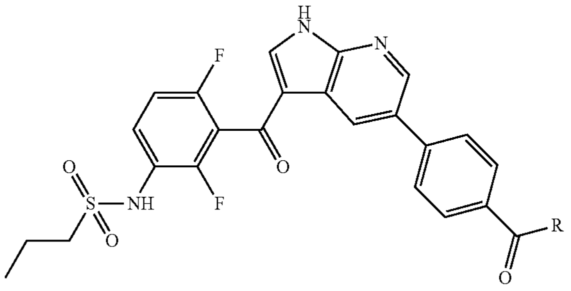
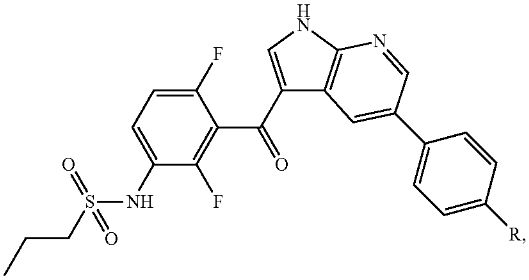
wherein R denotes attachment to
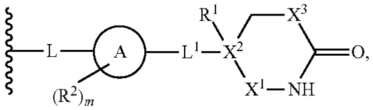
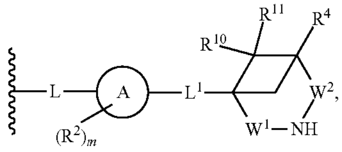
or
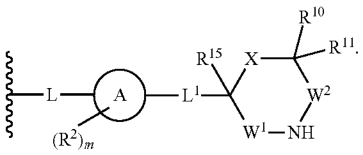
In some embodiments, TBM is a Ras ligand selected from
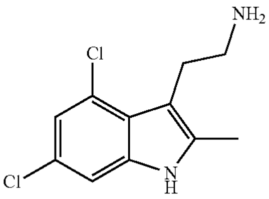
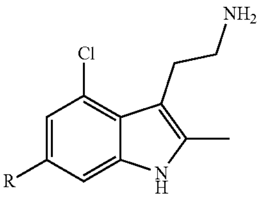
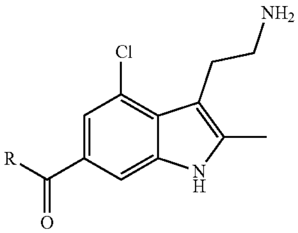

-continued
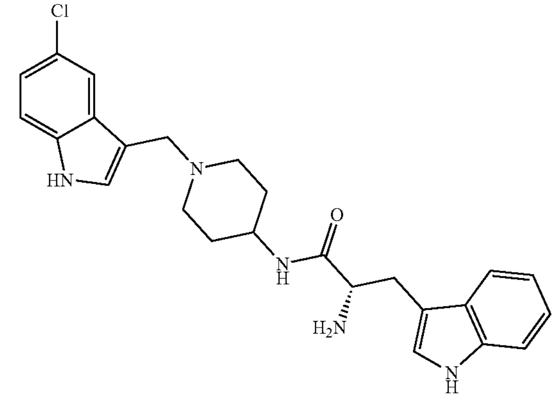
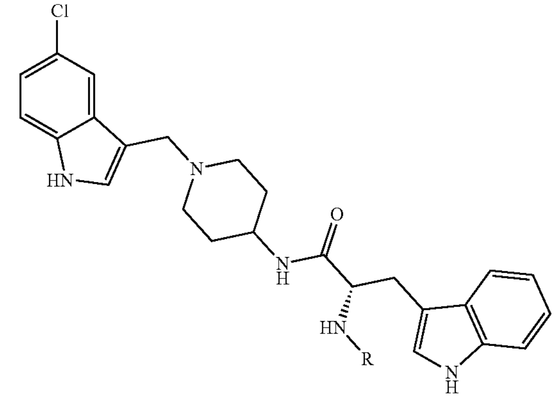
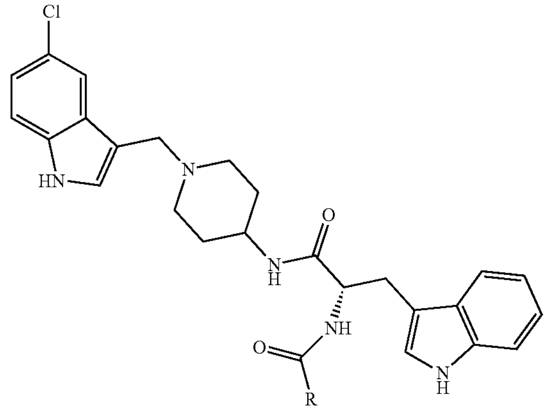
,
wherein R denotes attachment to
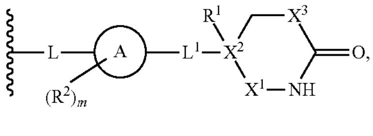
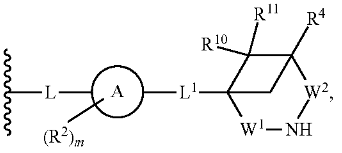
or
-continued
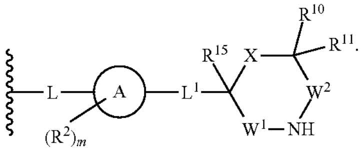
In some embodiments, TBM is a RasG12C ligand selected from
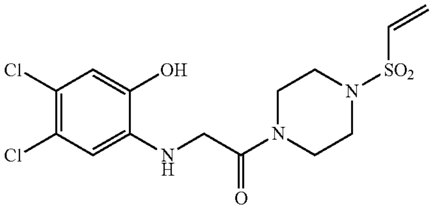
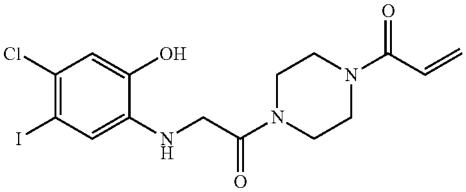
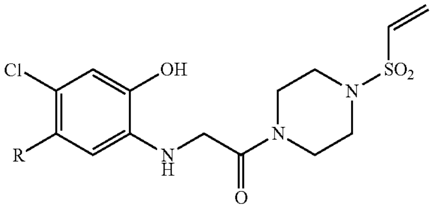
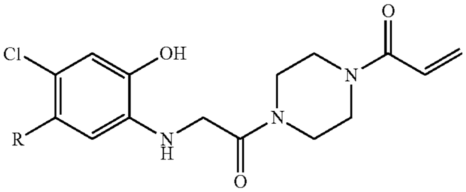
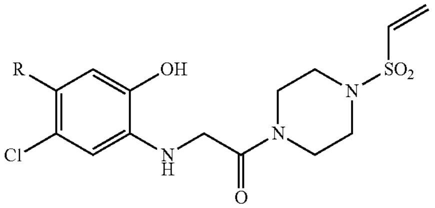
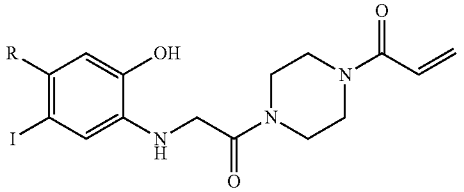
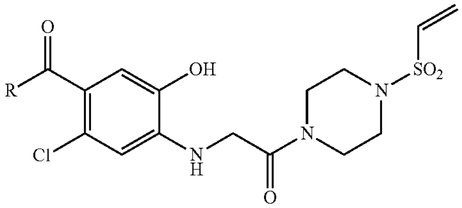

-continued
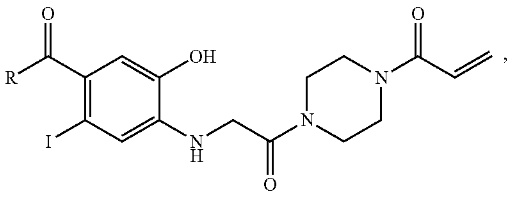
wherein R denotes attachment to
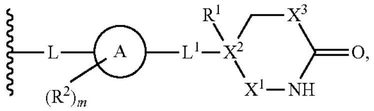
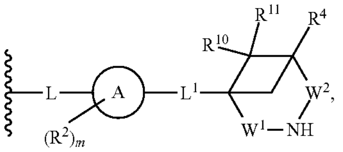
or
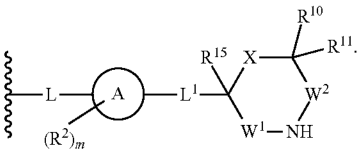
In some embodiments, TBM is a Her3 ligand selected from
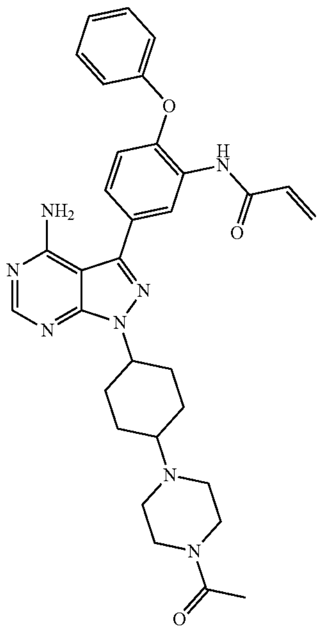
-continued
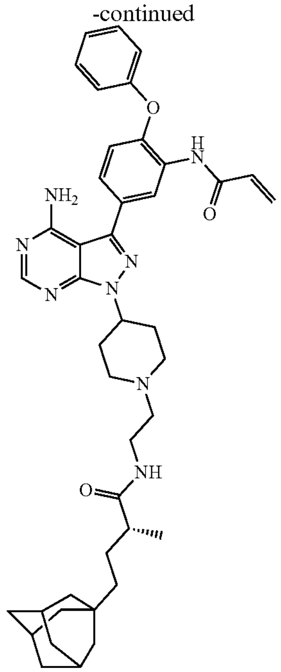
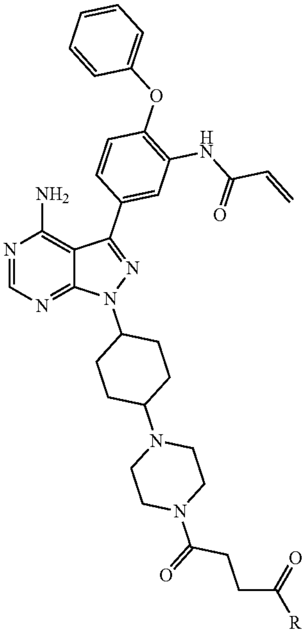

-continued
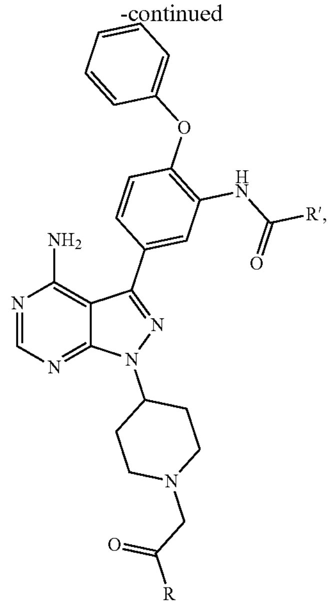
wherein R denotes attachment to
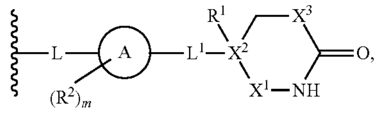
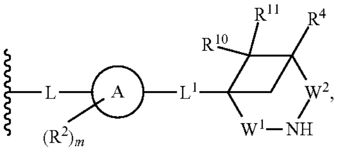
or
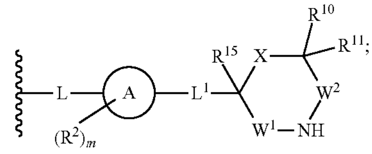
and R' is $-CH_2CH_3$ or $-CH{=}CH_2$.
In some embodiments, TBM is a Bcl-2/Bcl-XL ligand selected from
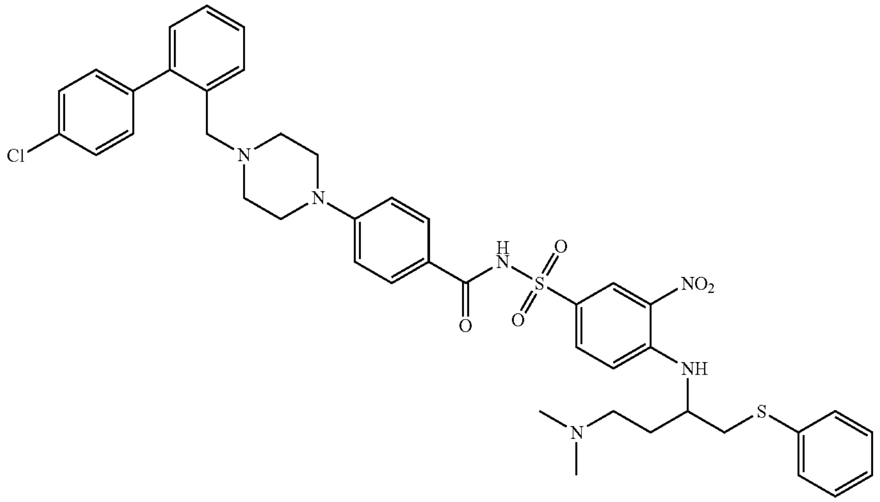
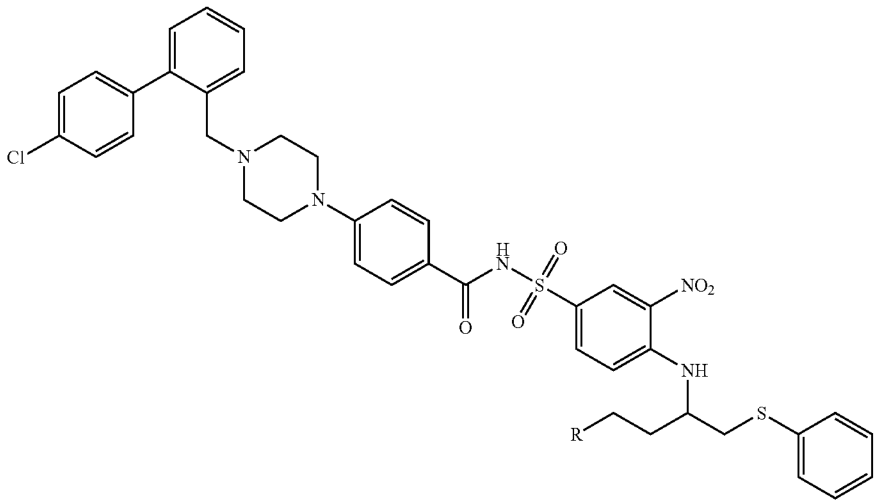
, wherein R denotes attachment to
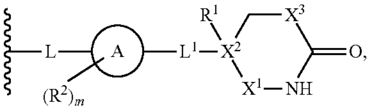
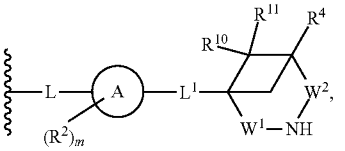
or
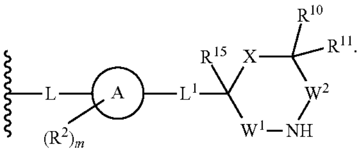
In some embodiments, TBM is an HDAC ligand selected from
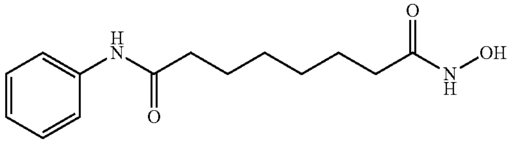
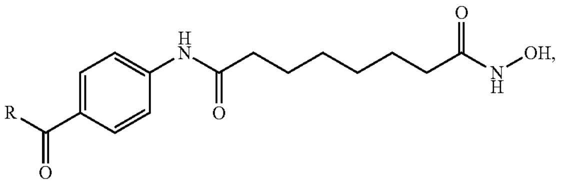
wherein R denotes attachment to
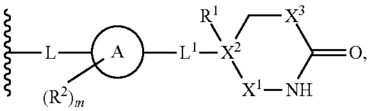
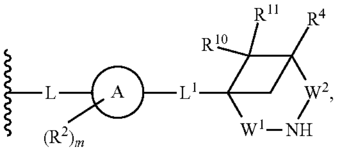
or
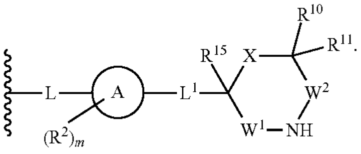
In some embodiments, TBM is a PPAR-gamma ligand selected from
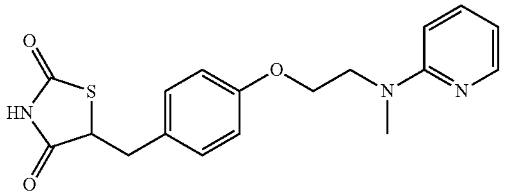
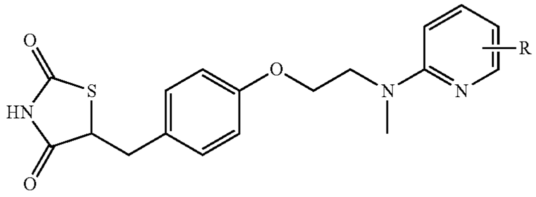
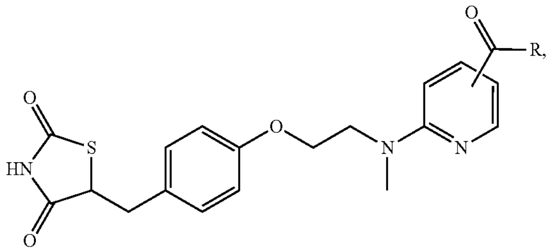
wherein R denotes attachment to
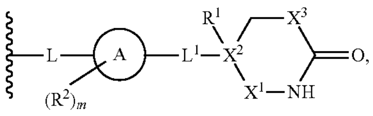
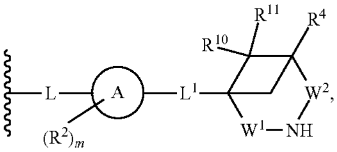
or
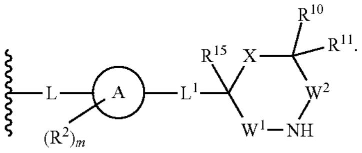
In some embodiments, TBM is selected from
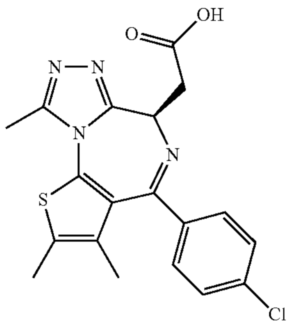

-continued
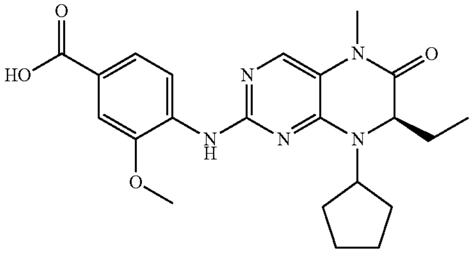
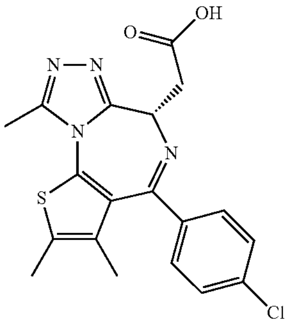
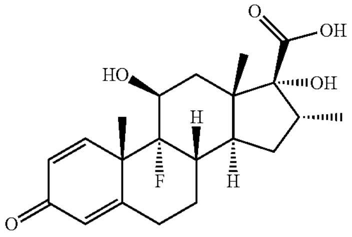
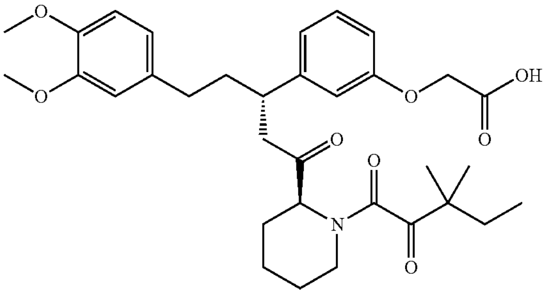
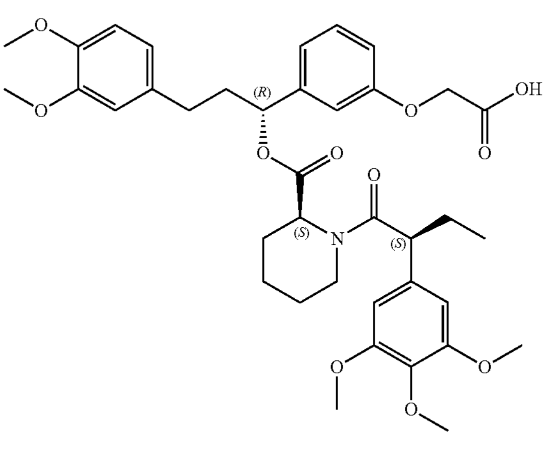
-continued
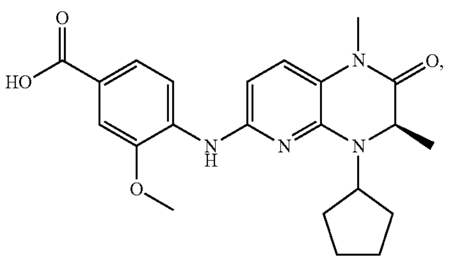
wherein R denotes attachment to
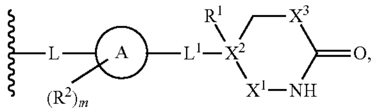
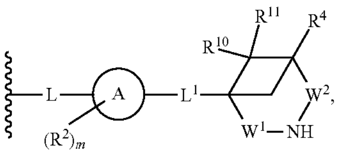
or
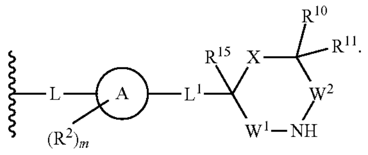
In some embodiments, TBM is an Abl, KRAS, SHP2, cRAF, MerTK or PRMT5 ligand that are selected from the following non-limiting examples:
Abl
ABL001
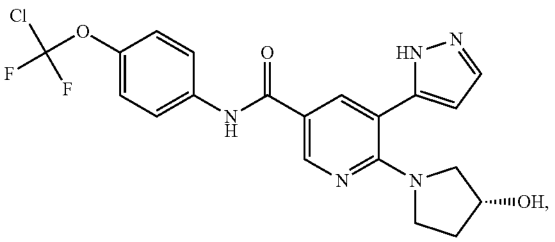
KRAS
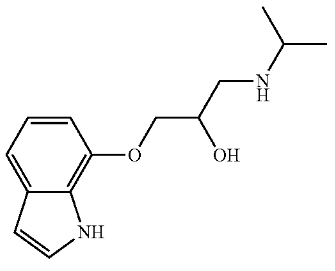

-continued
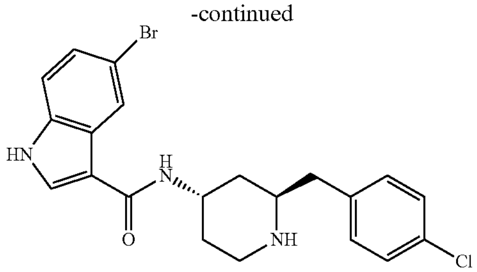
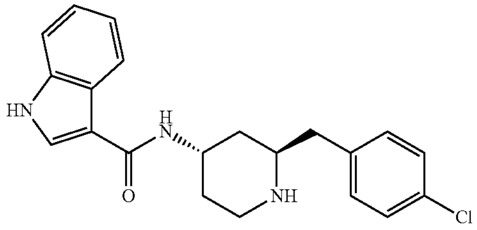
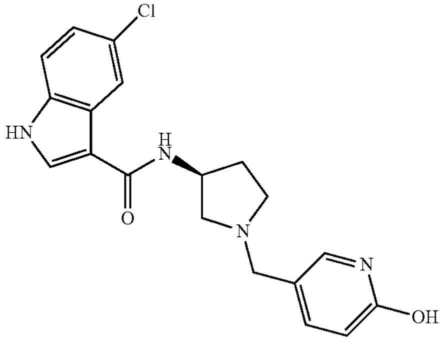
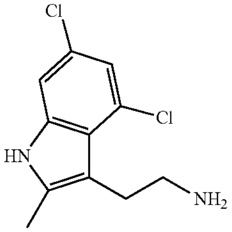
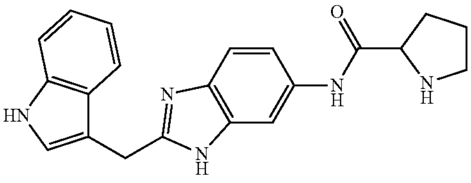
,
SHP2
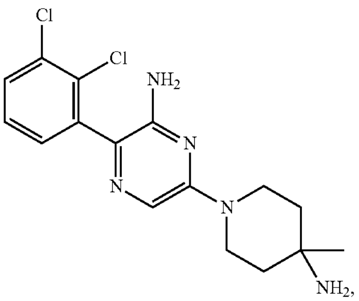
-continued
cRAF
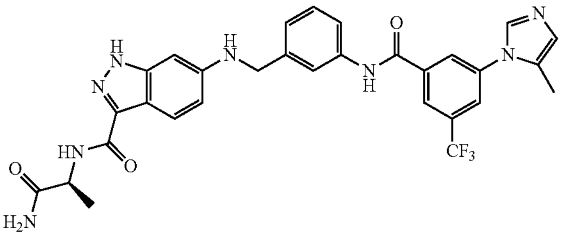
,
MerTK
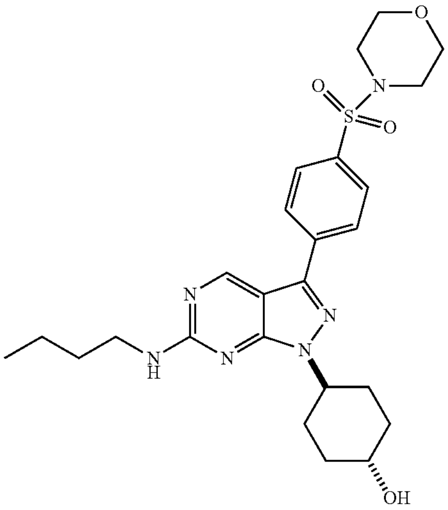
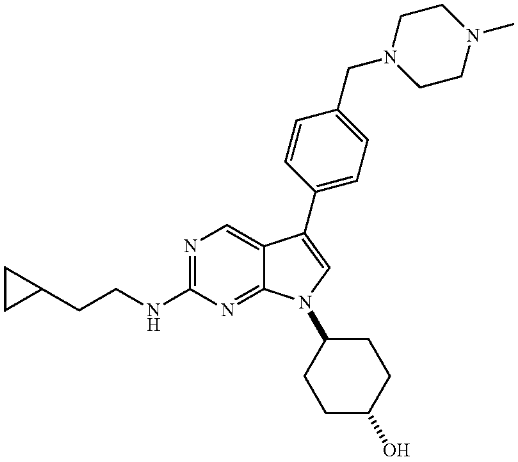
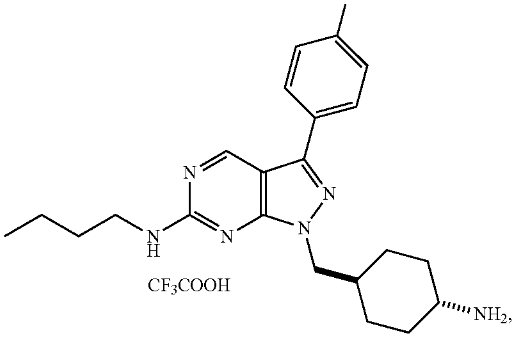
$CF_3COOH$
and PRMT5
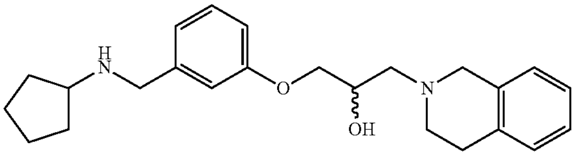
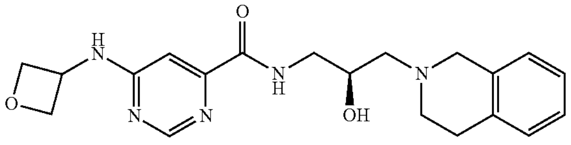
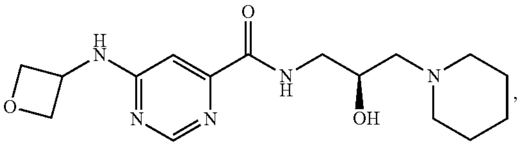
wherein 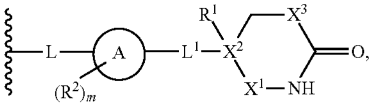
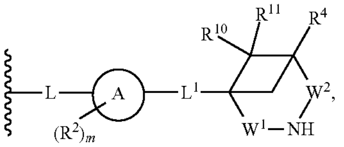 or
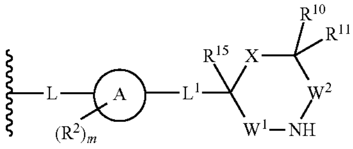
and
is attached to a modifiable carbon, oxygen, nitrogen or sulfur atom.
In some embodiments, TBM is a EZH2 ligand selected from
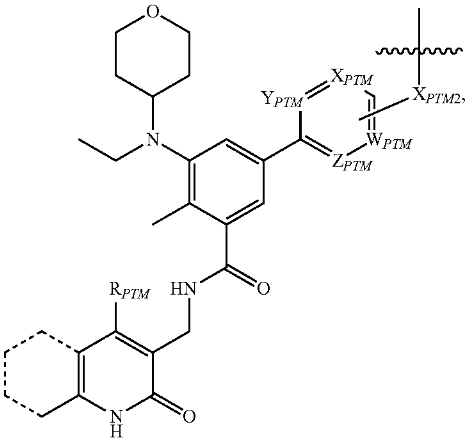
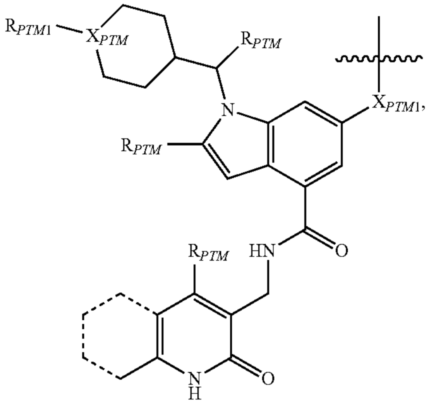
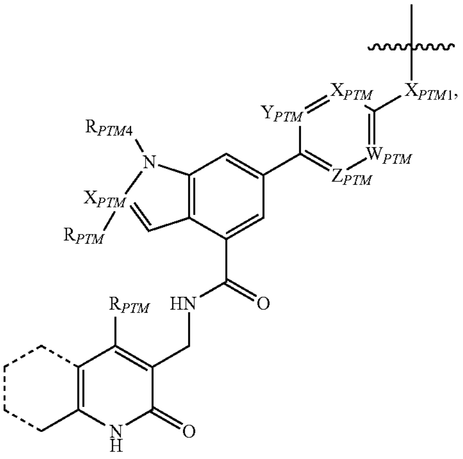
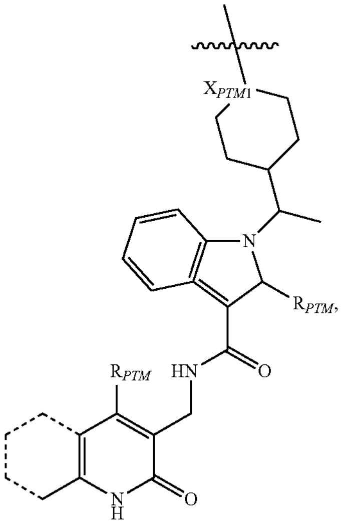

-continued
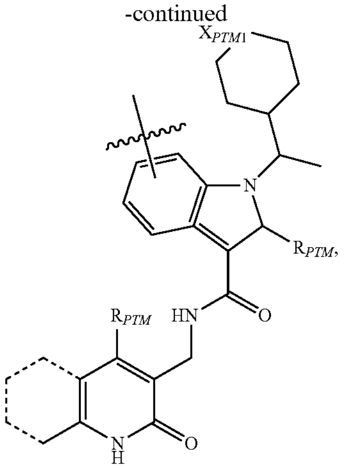
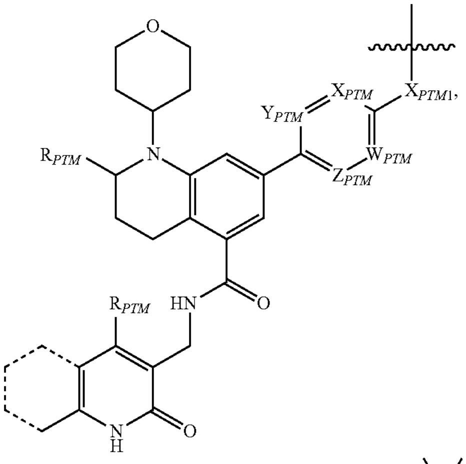
or
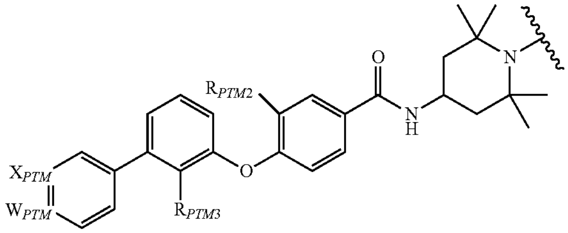
wherein
denotes attachment to
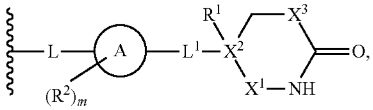
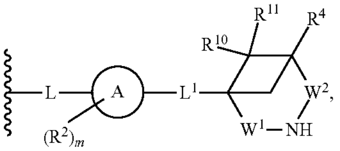
or
-continued
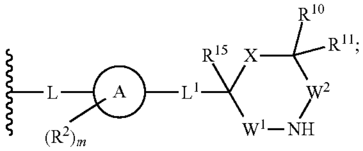
each of variables $R_{PTM(1-4)}$, $W_{PTM}$, $X_{PTM}$, $Y_{PTM}$, and $Z_{PTM}$ is as defined in WO 2018/119357 and US 2018/0177750, the entirety of each of which is herein incorporated by reference.
In some embodiments, TBM is a FLT3 ligand selected from
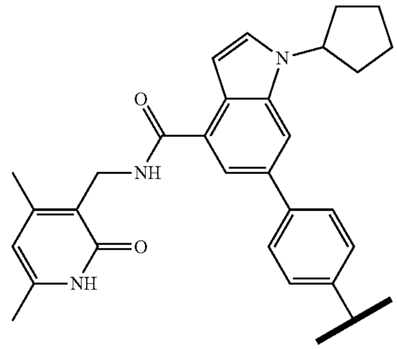
,
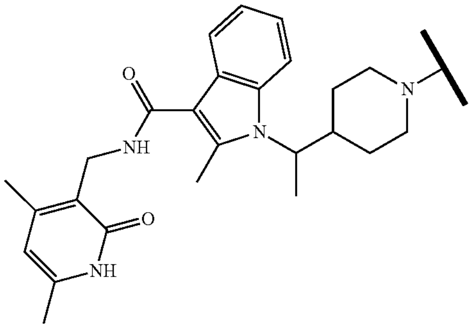
,
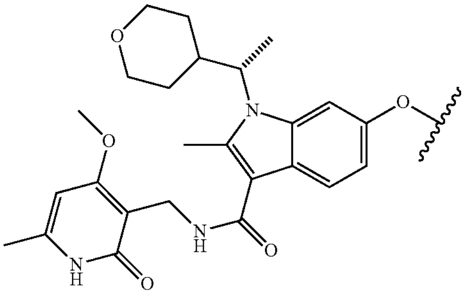
,
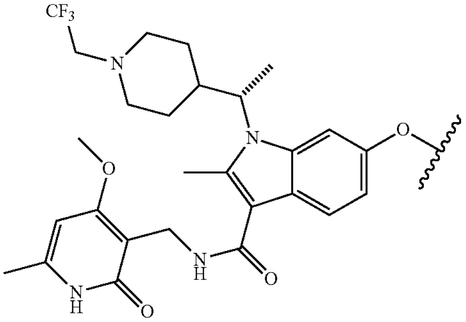
, -continued
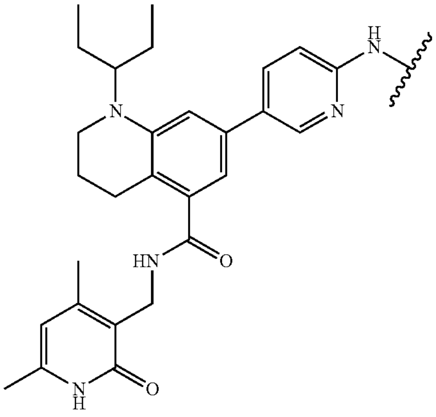
,
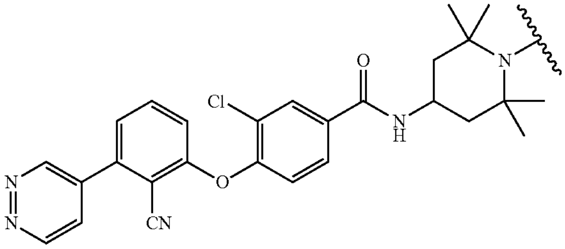
,
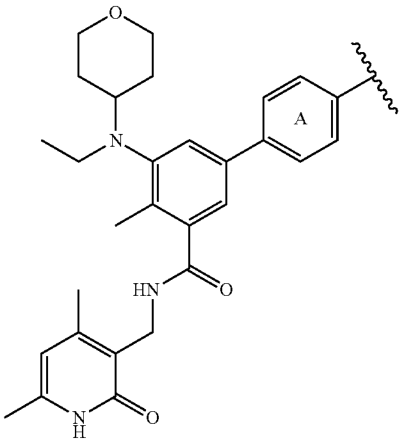
,
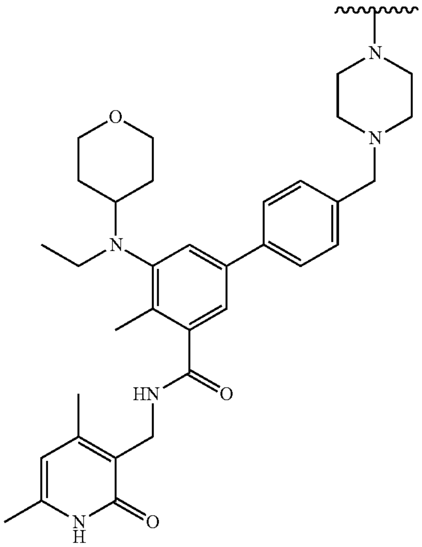
,
-continued
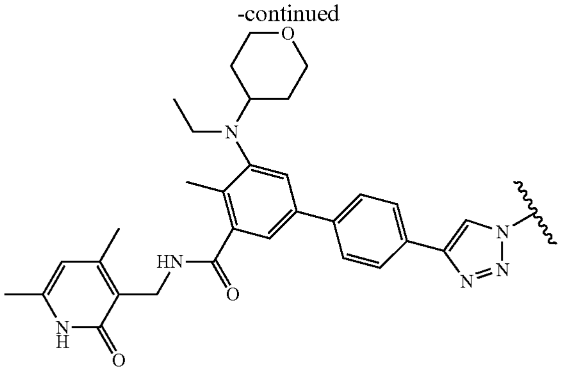
,
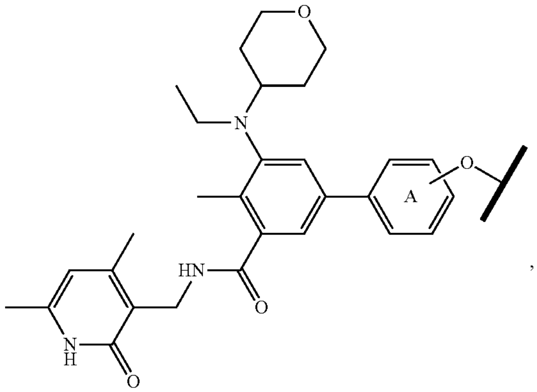
,
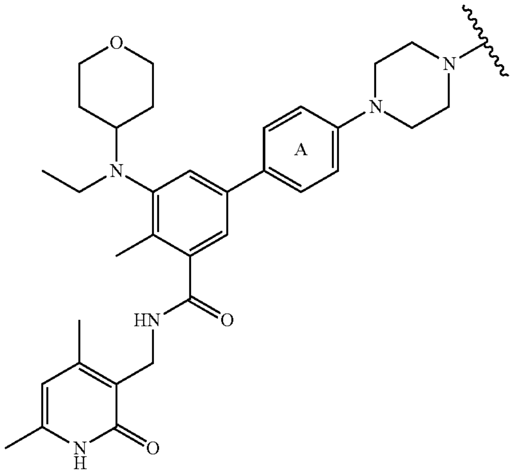
,
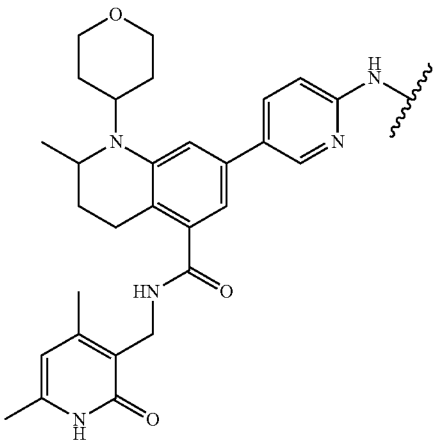
, -continued
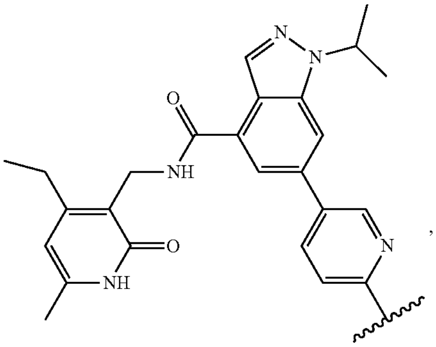
, or
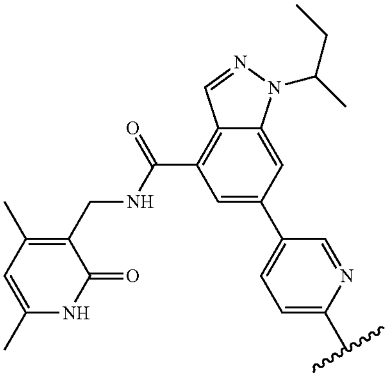
,
wherein
denotes attachment to
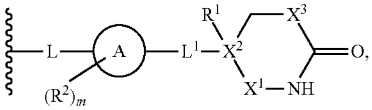
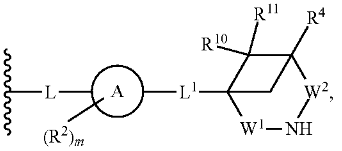
or
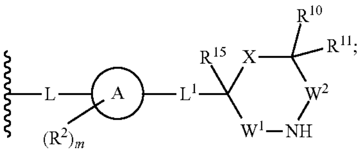
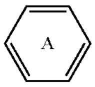
may be N-substituted.
In some embodiments, a TBM moiety is selected from
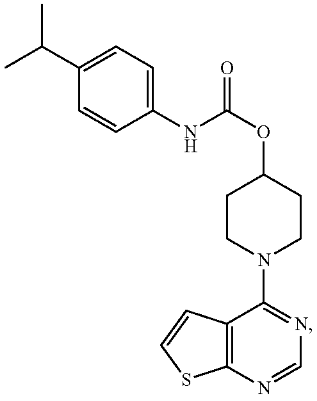
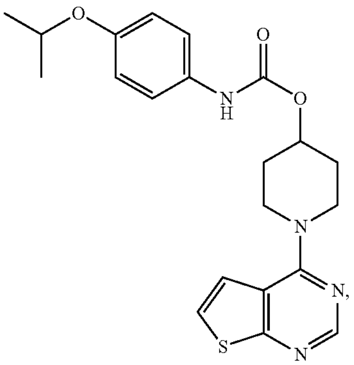
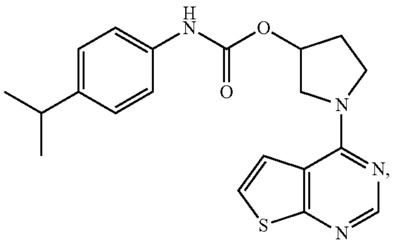
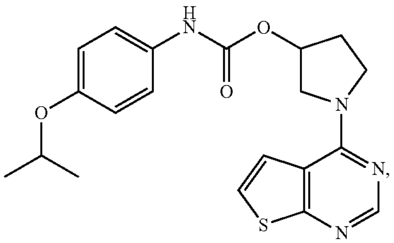
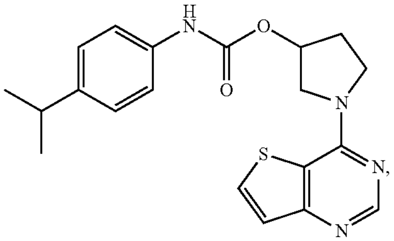

-continued
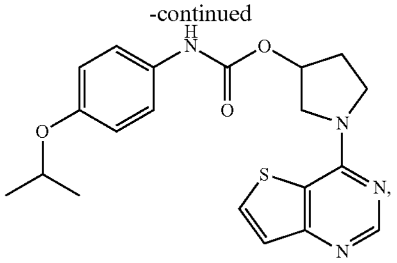
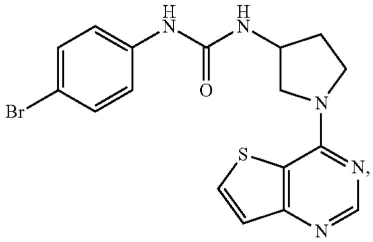
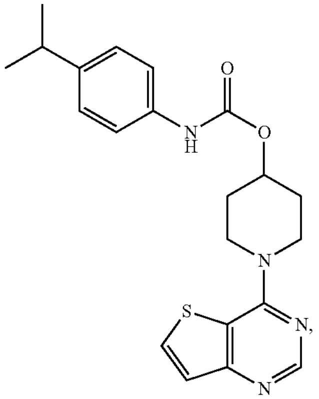
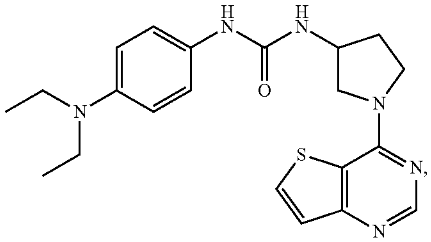
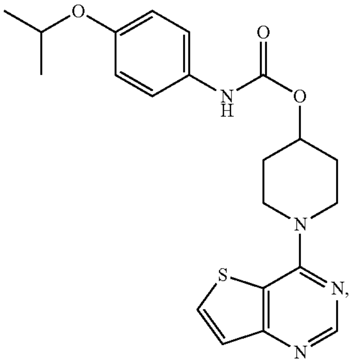
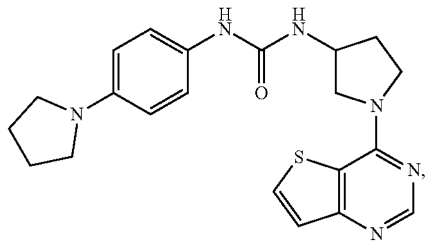
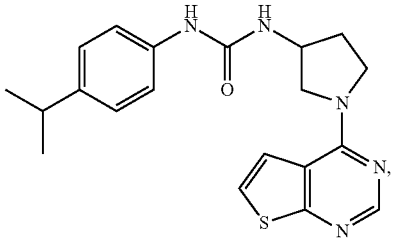
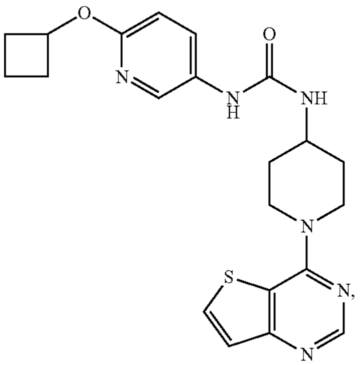
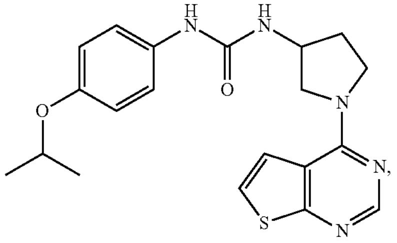
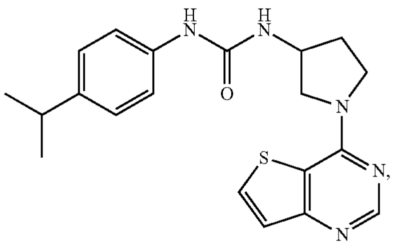
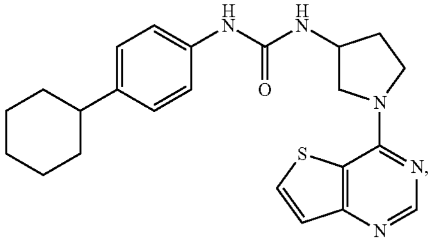
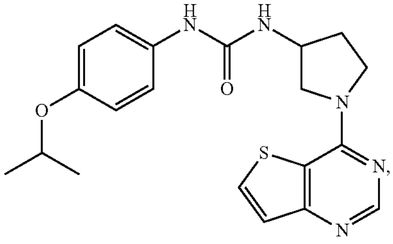

-continued
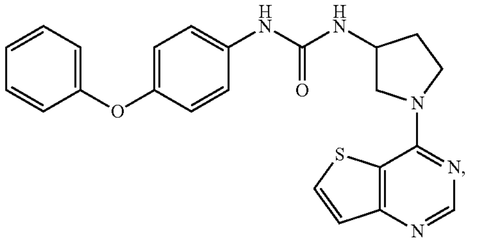
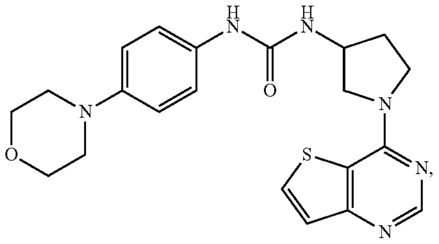
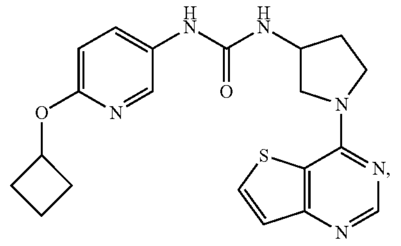
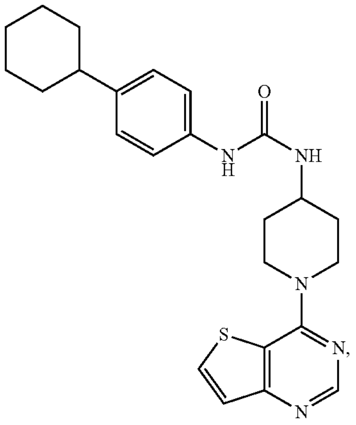
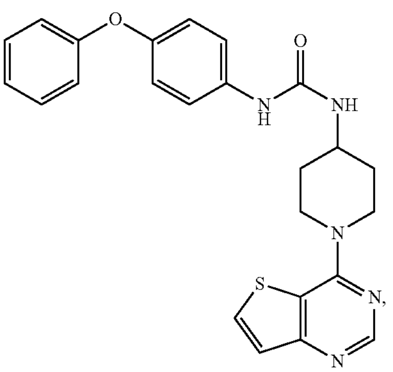
-continued
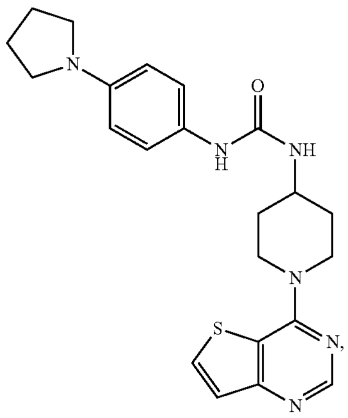
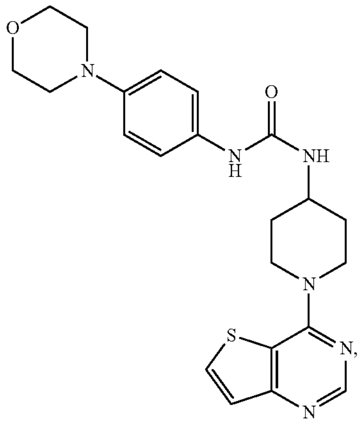
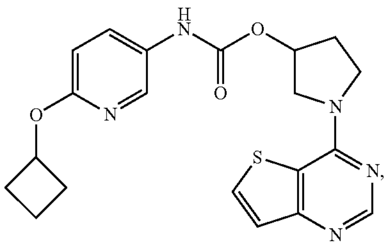
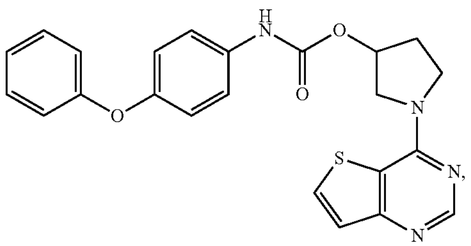
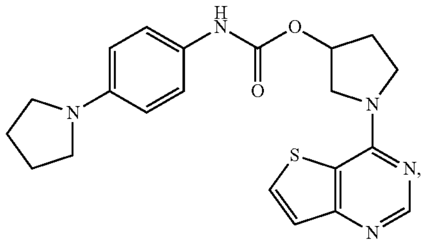

-continued
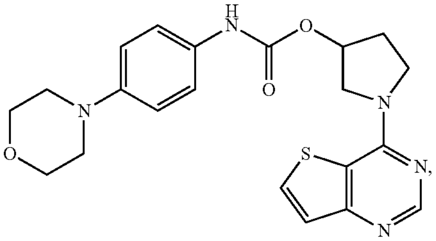
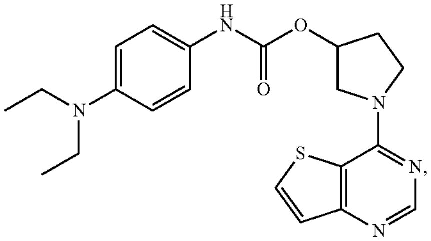
wherein
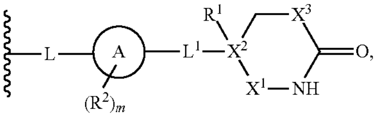
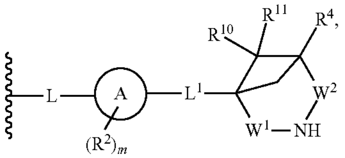
or
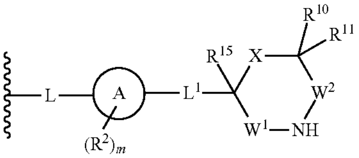
is attached to a modifiable carbon, oxygen, nitrogen or sulfur atom.
In some embodiments, a TBM moiety is a RAF ligand selected from
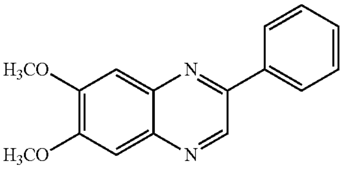
,
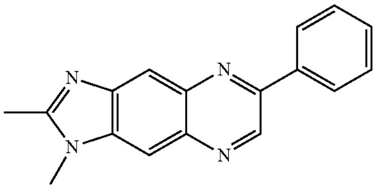
,
-continued
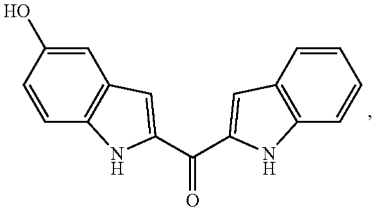
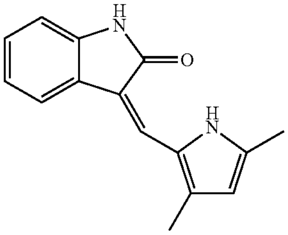
,
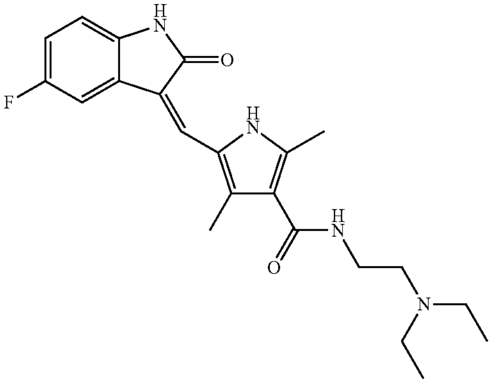
,
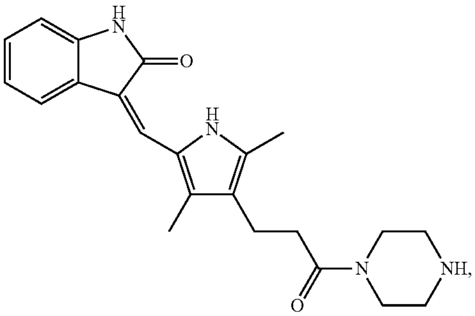
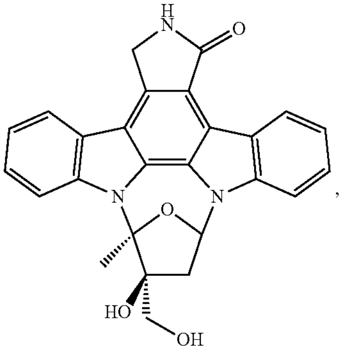

-continued
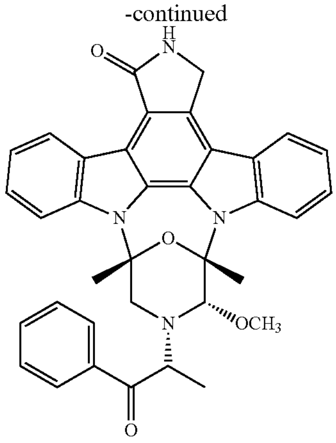
,
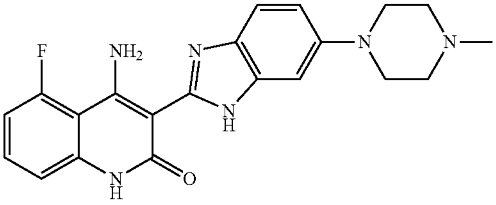
,
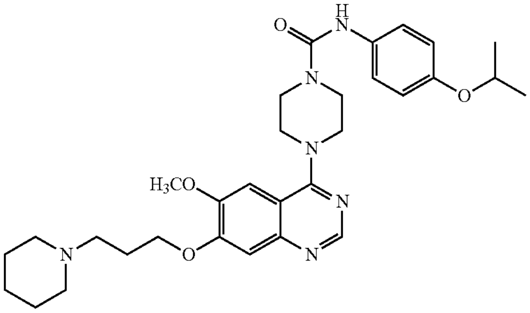
, or
-continued
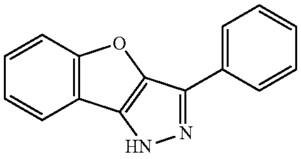
,
wherein
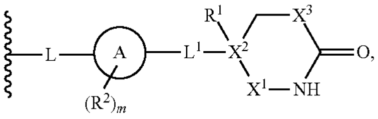
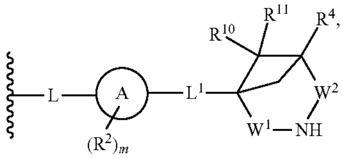
, or
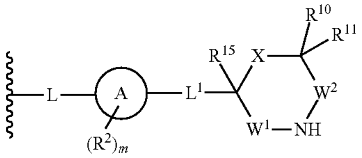
is attached to a modifiable carbon, oxygen, nitrogen or sulfur atom.
In some embodiments, a TBM moiety is selected from
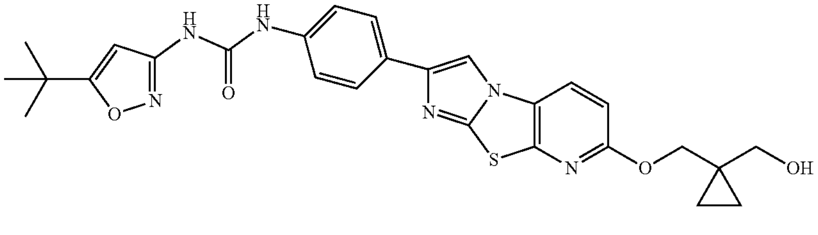
,
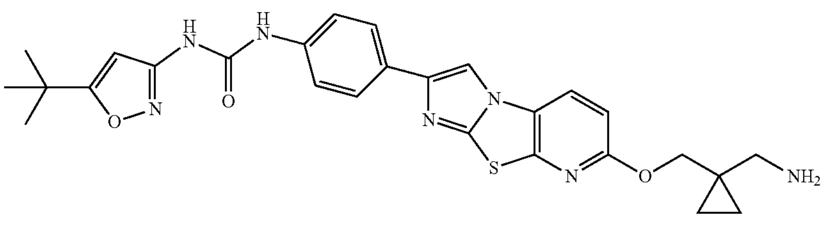
,
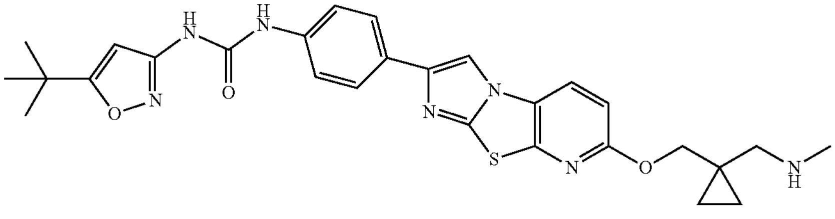
, -continued
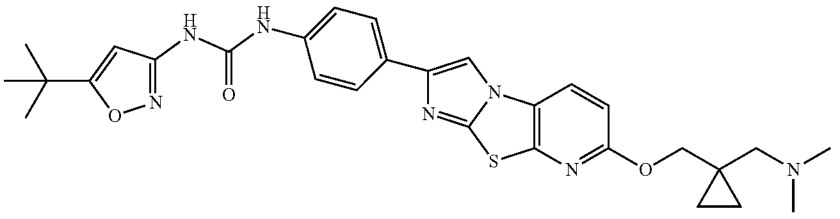
,
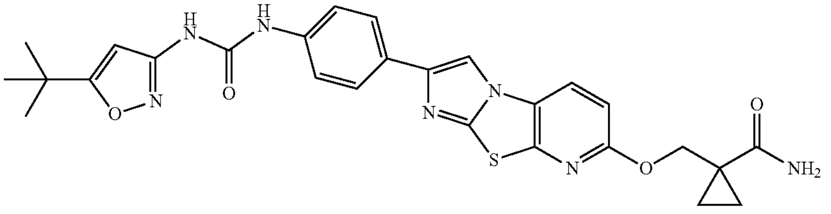
,
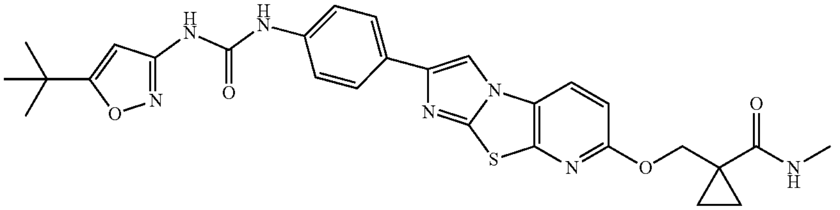
,
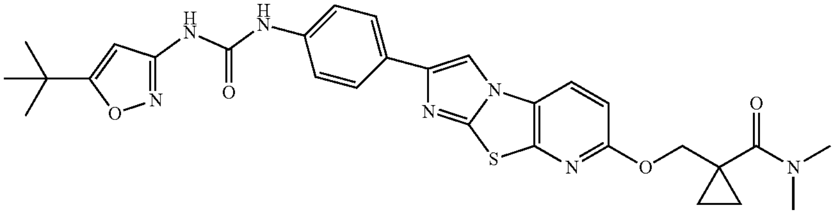
,
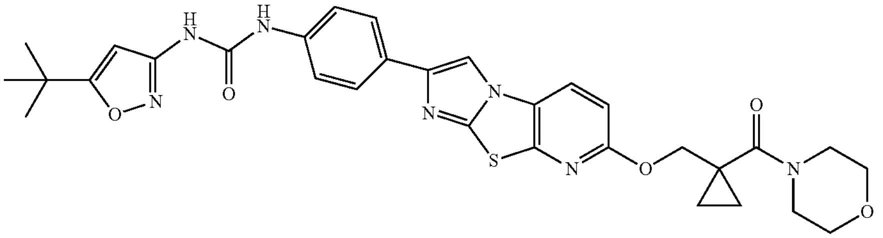
,
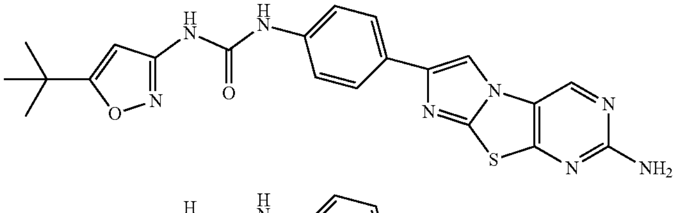
,
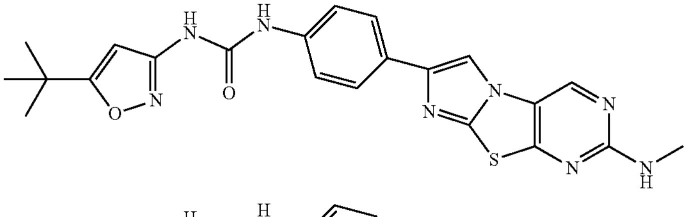
,
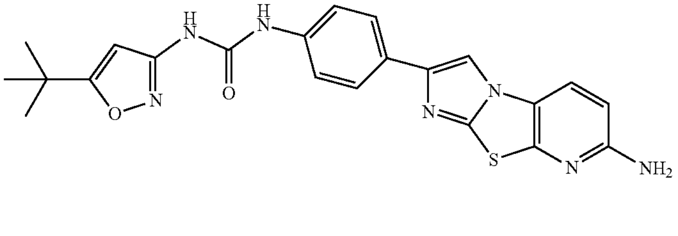
, -continued
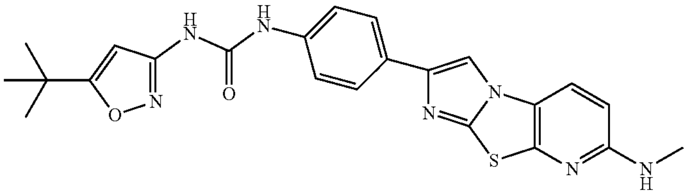
,
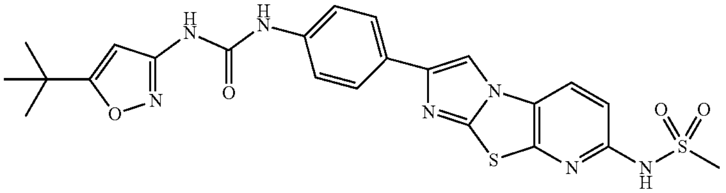
,
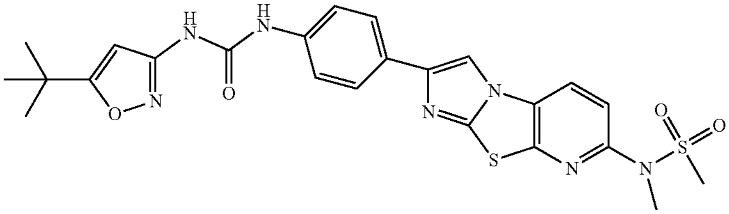
,
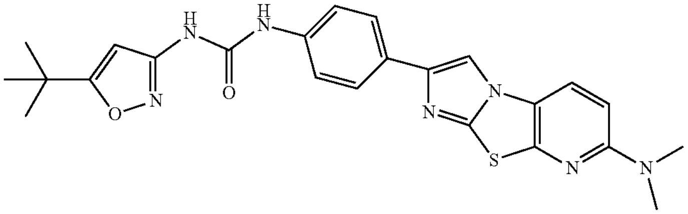
,
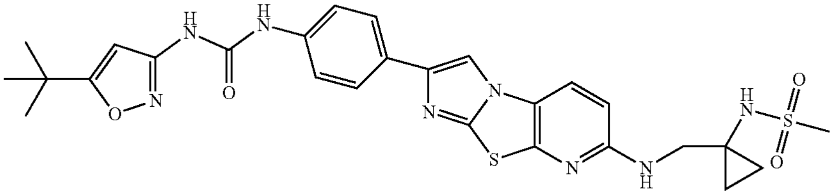
,
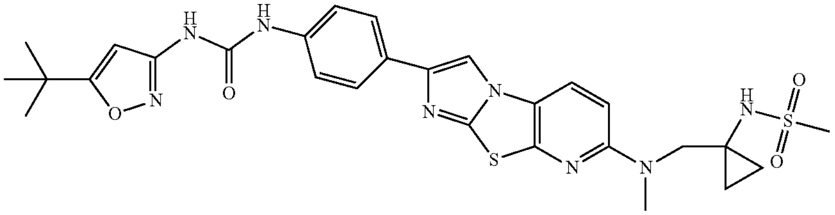
,
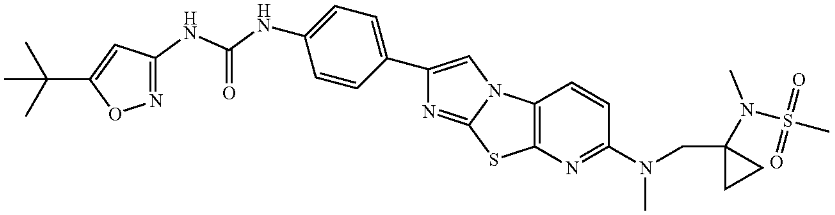
,
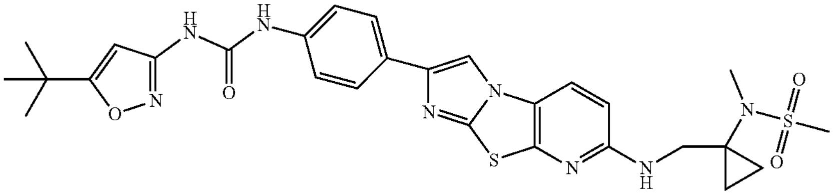
, -continued
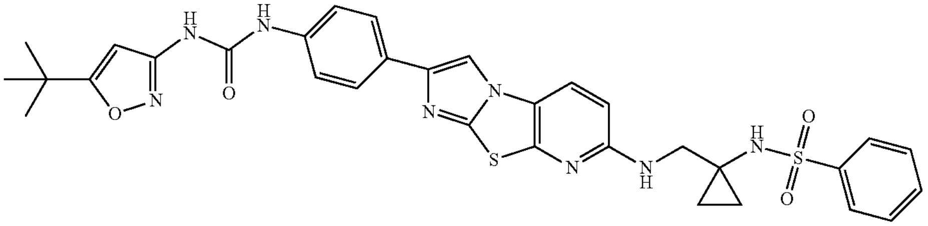
,
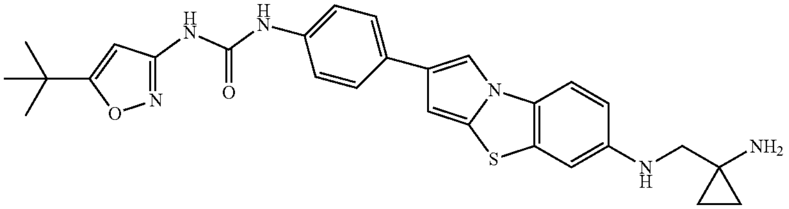
,
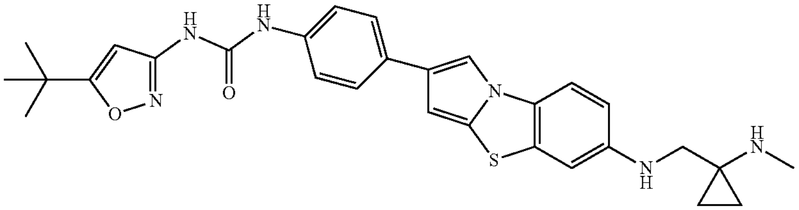
,
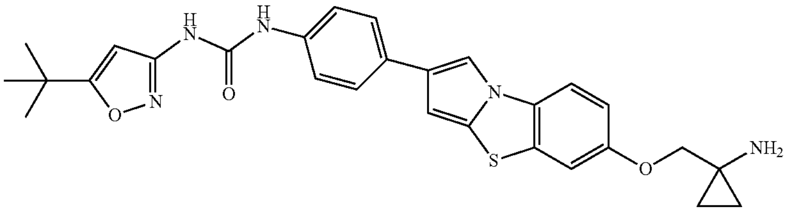
,
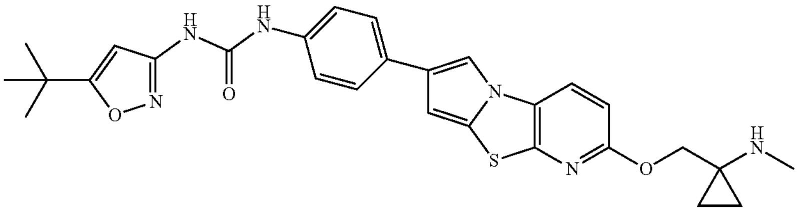
,
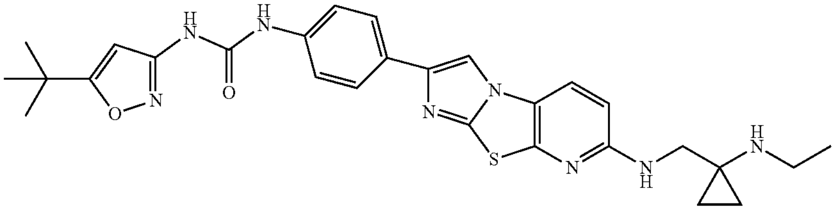
,
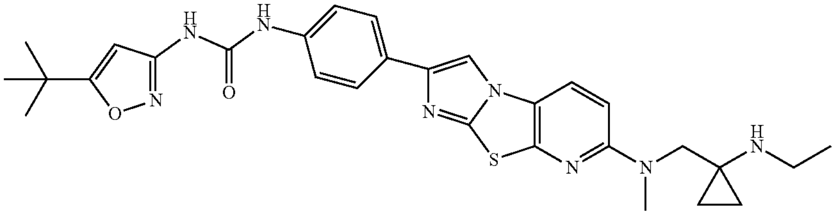
,
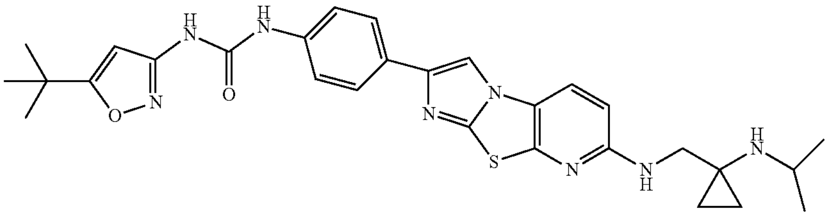
, -continued
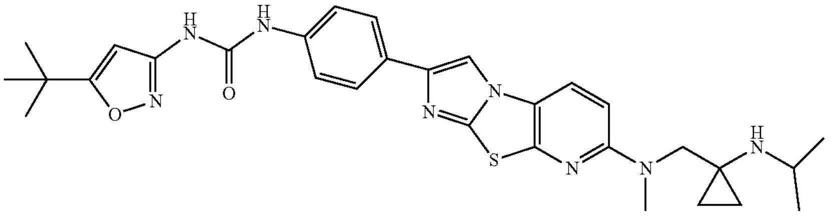
,
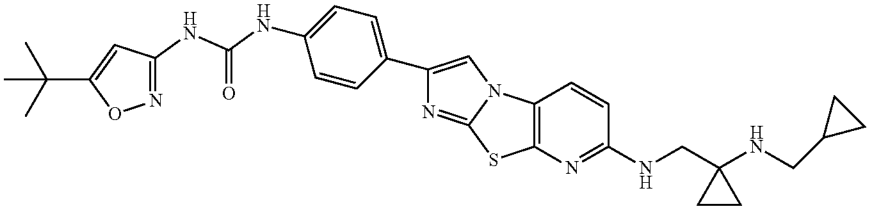
,
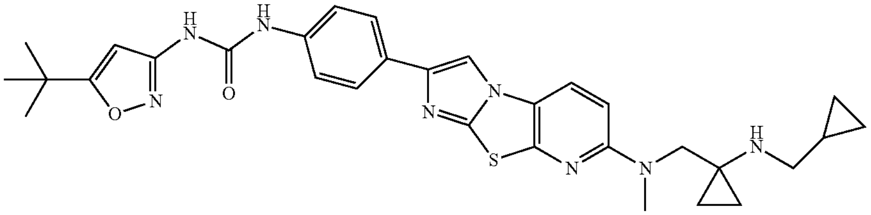
,
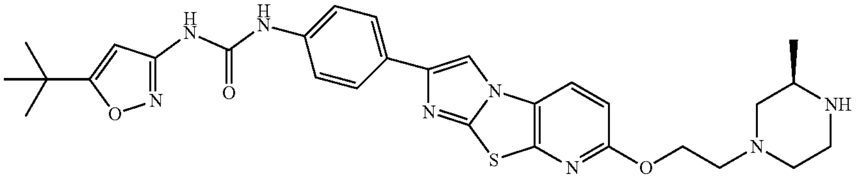
,
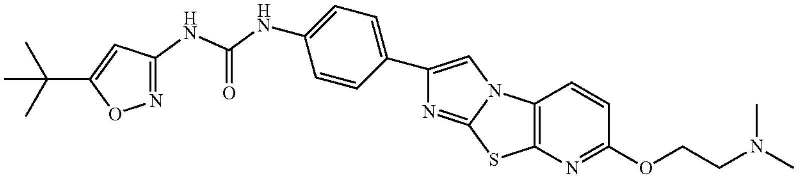
,
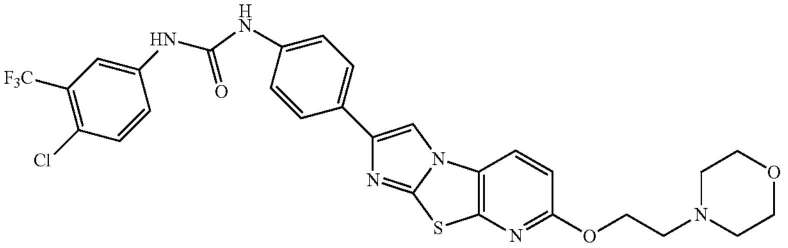
,
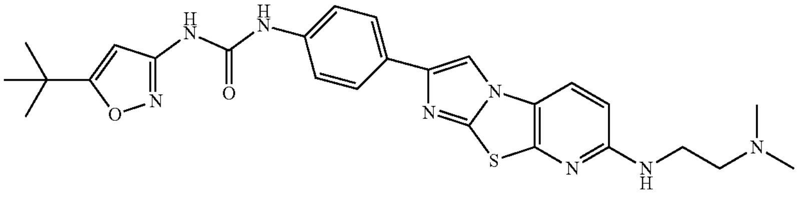
,
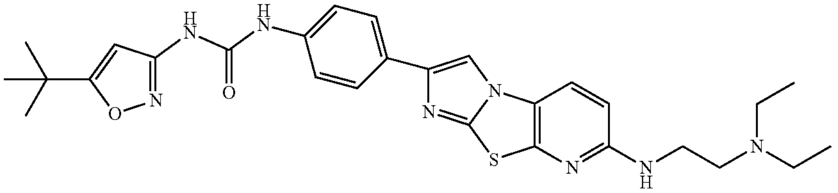
, -continued
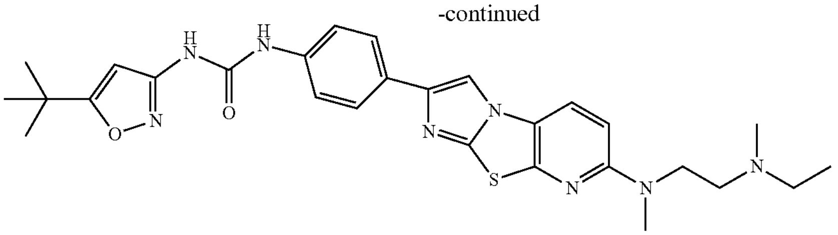
,
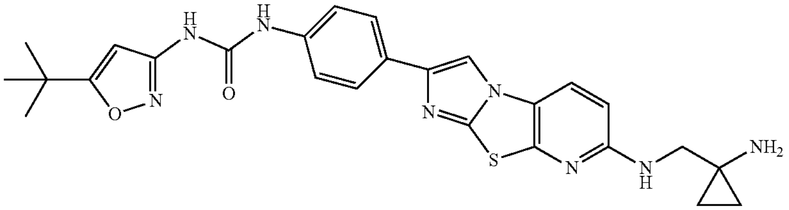
,
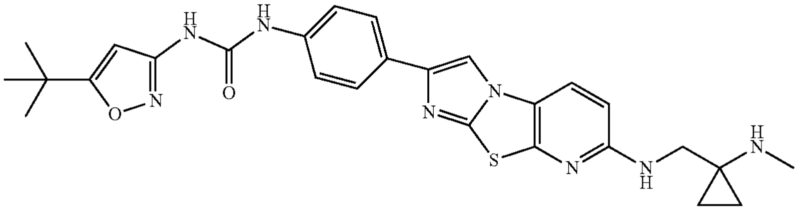
,
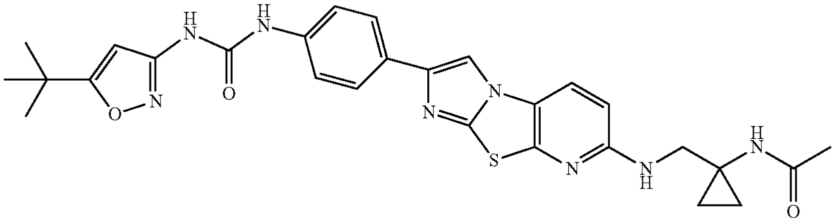
,
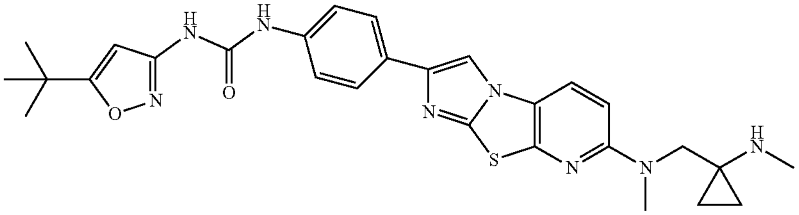
,
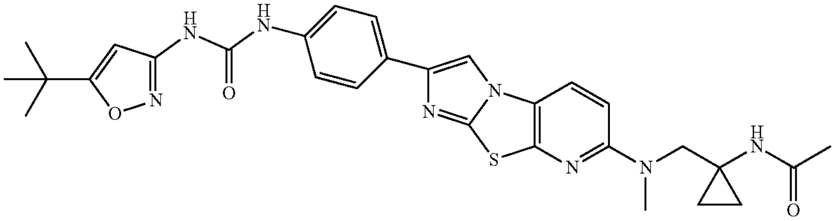
,
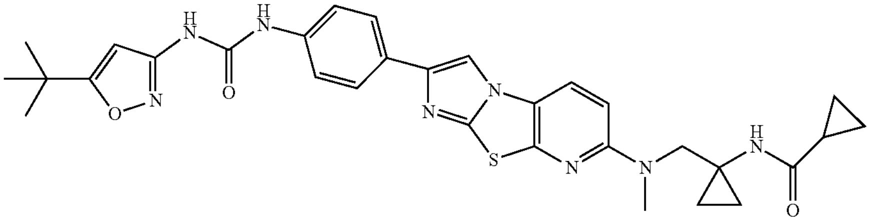
,
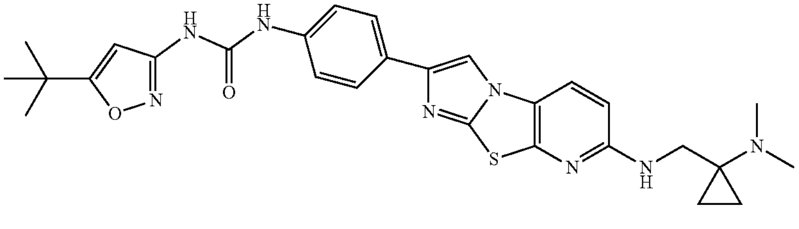
, -continued
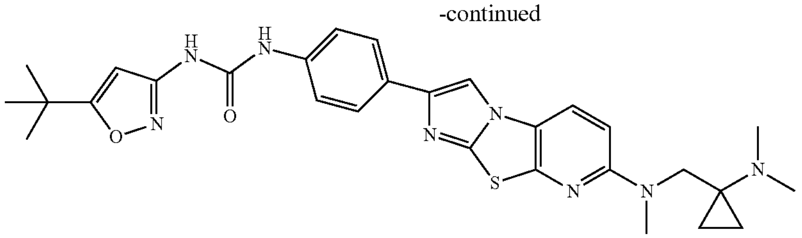
,
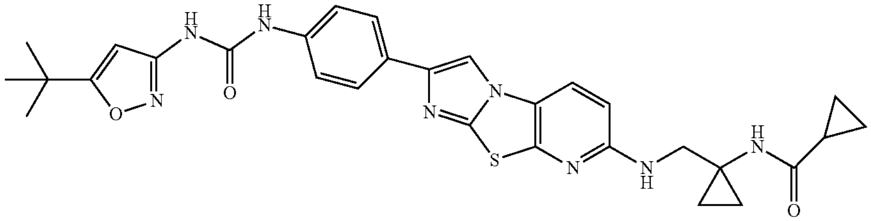
,
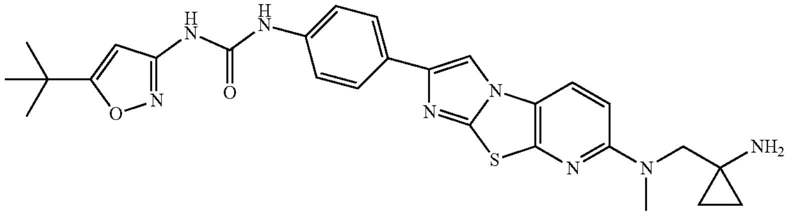
,
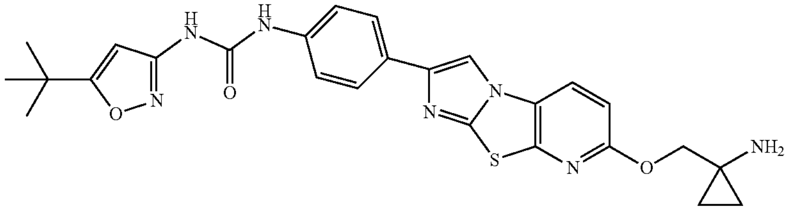
,
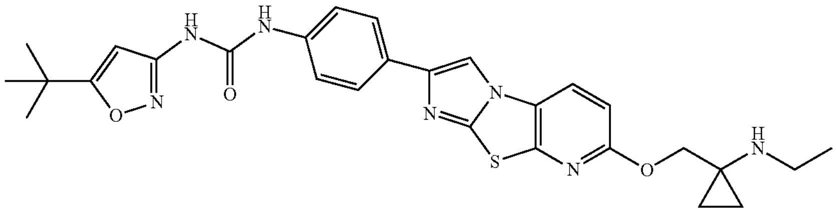
,
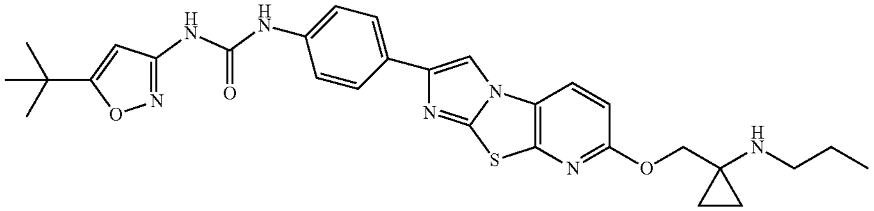
,
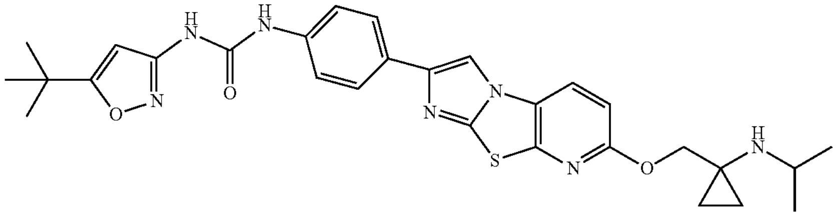
,
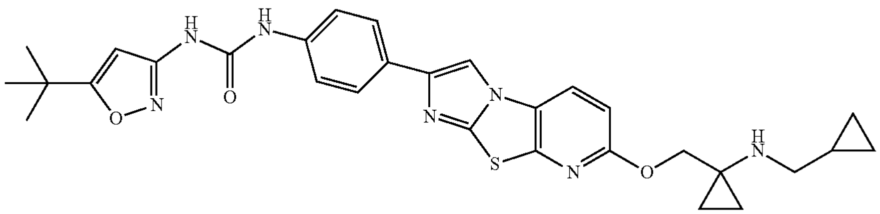
, -continued
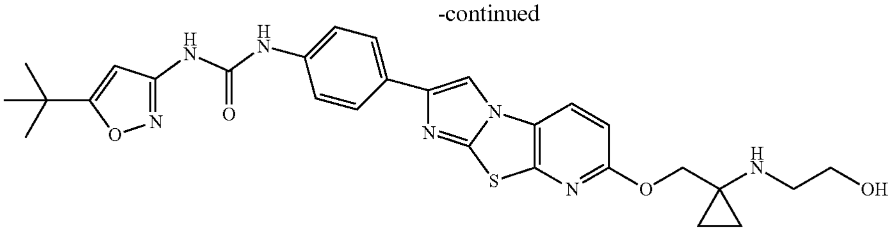
,
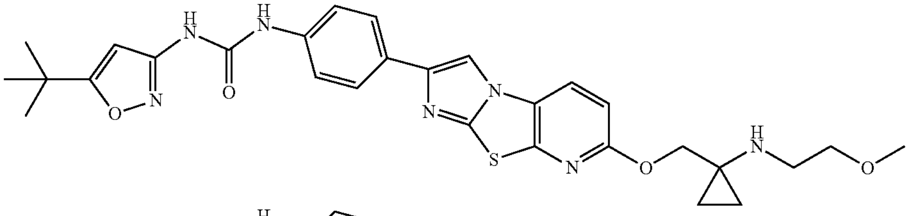
,
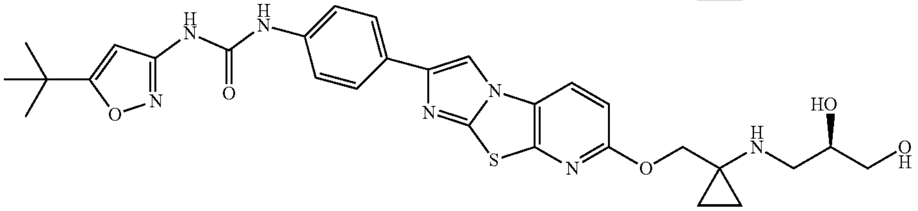
,
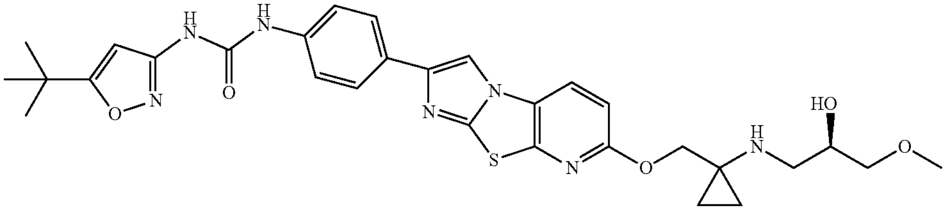
,
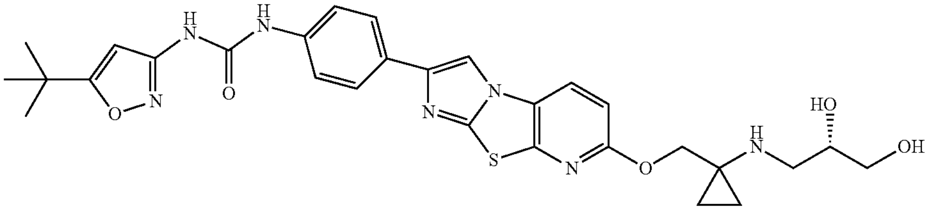
,
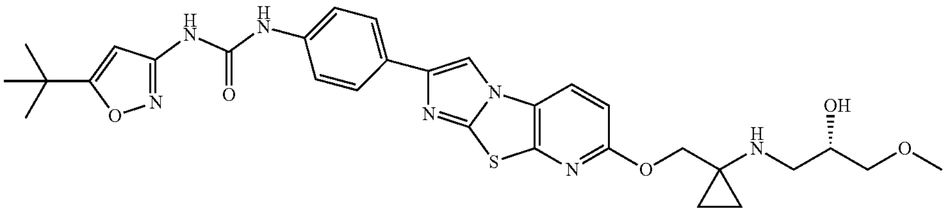
,
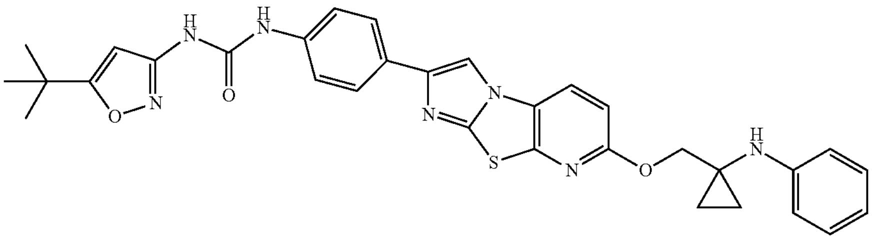
,
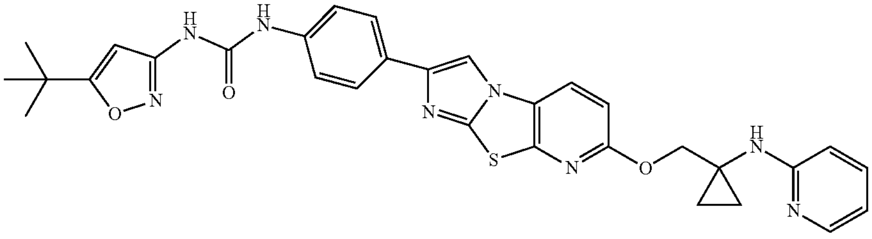
, -continued
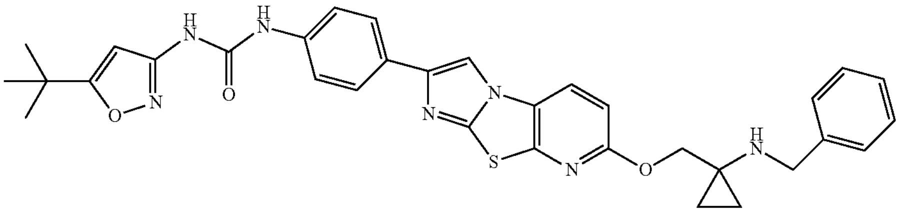
,
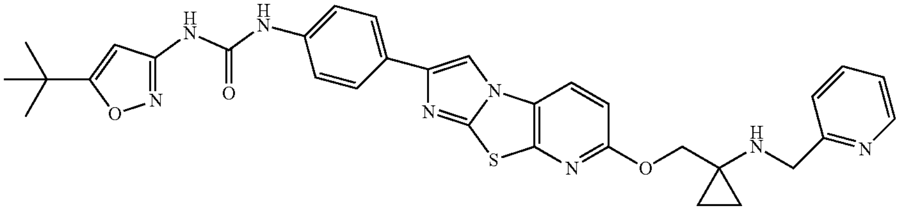
,
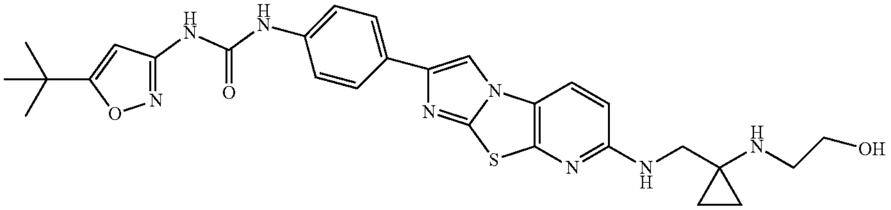
,
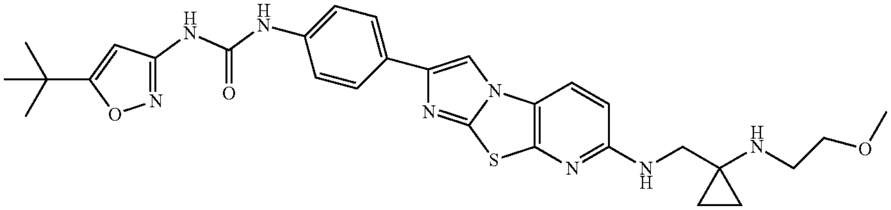
,
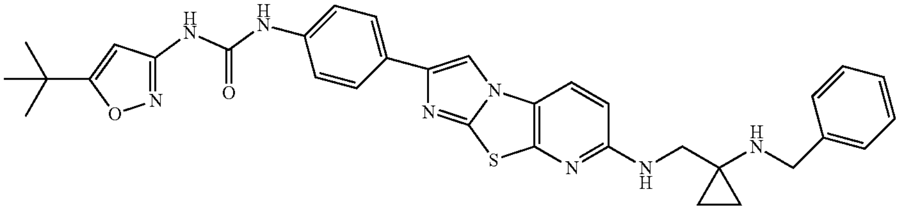
,
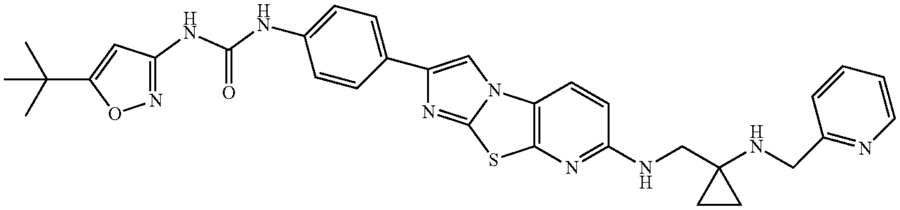
,
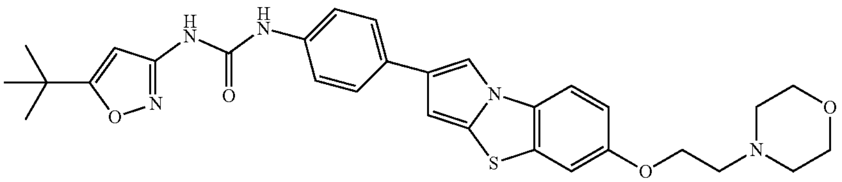
,
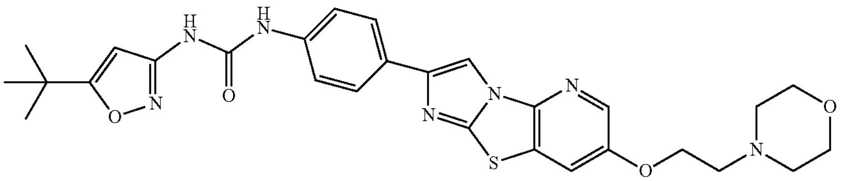
, -continued
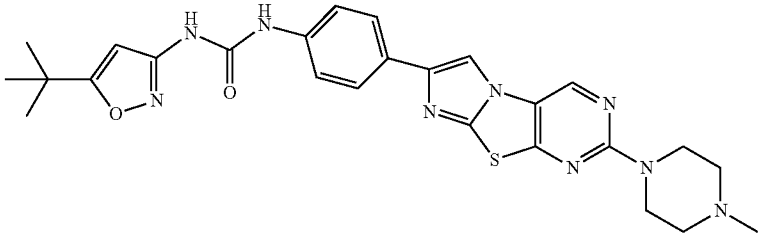
,
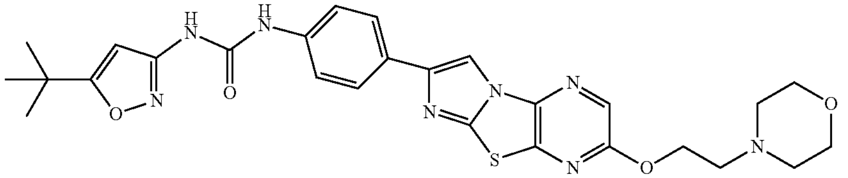
,
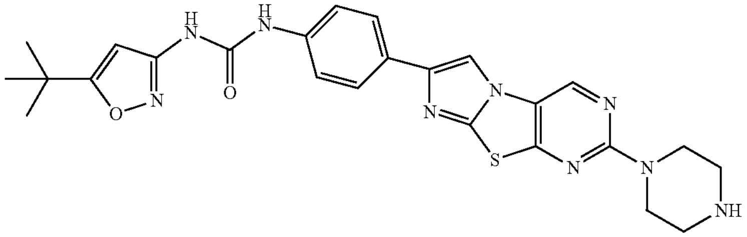
,
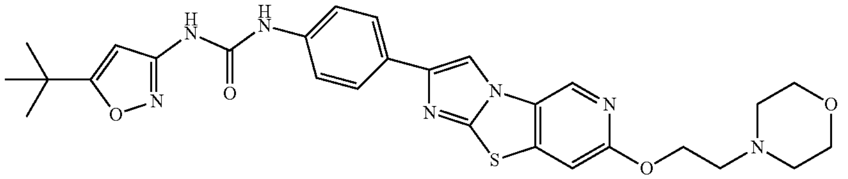
,
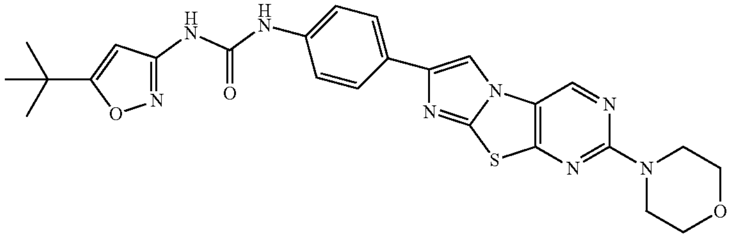
,
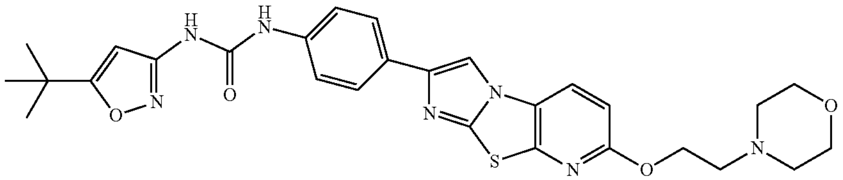
,
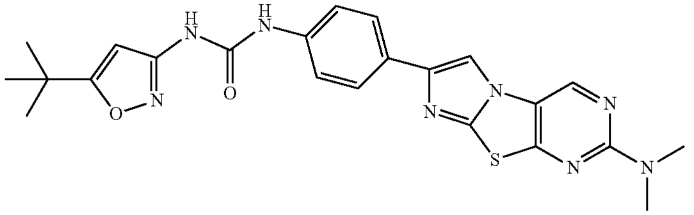
,
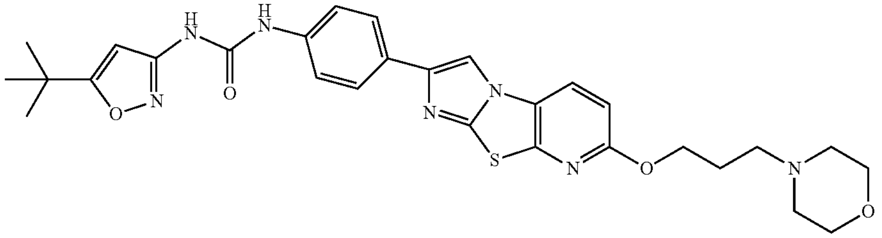
, -continued
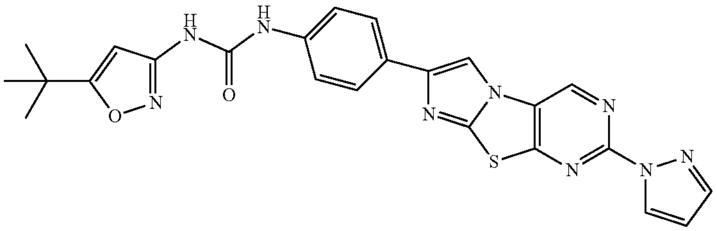
,
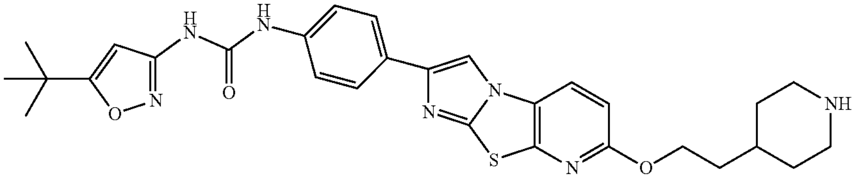
,
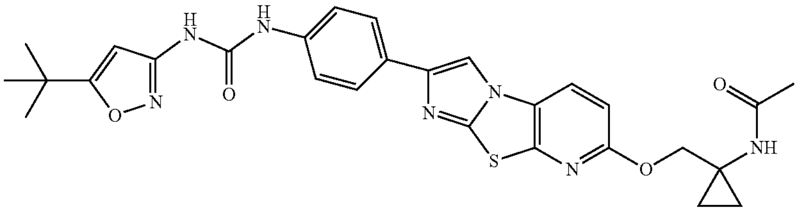
,
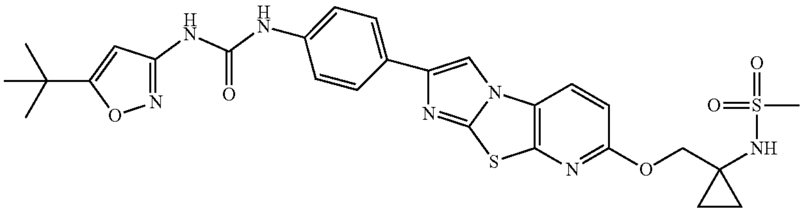
,
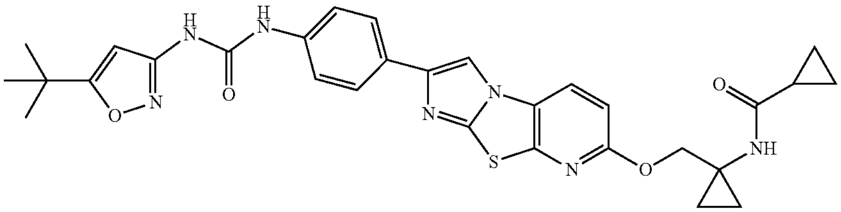
,
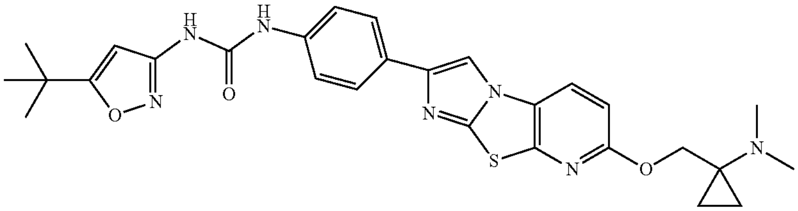
,
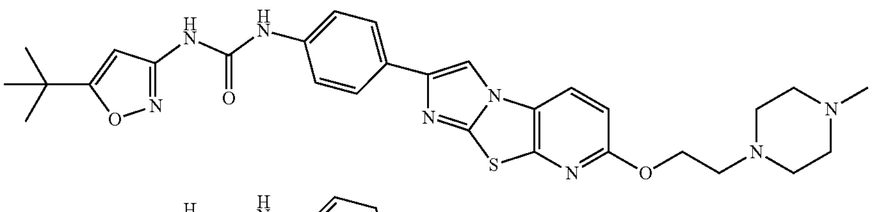
,
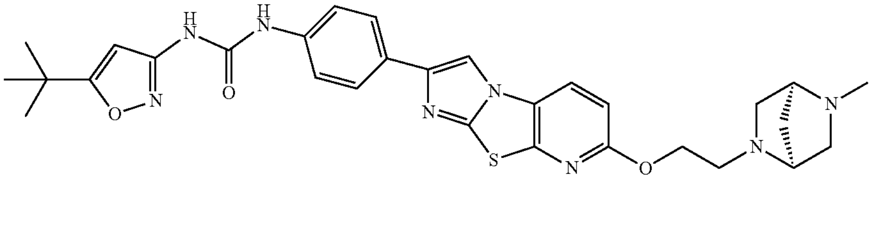
, -continued
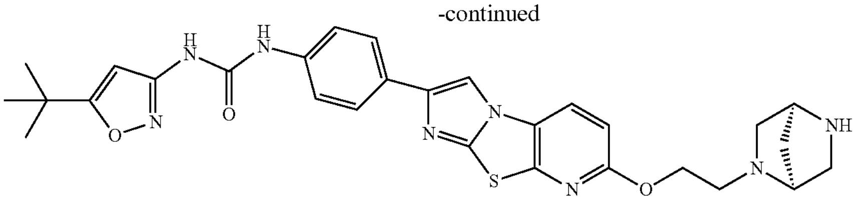
,
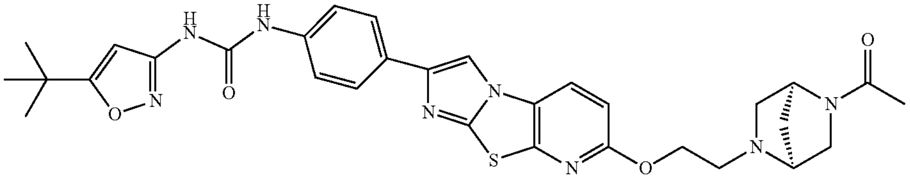
,
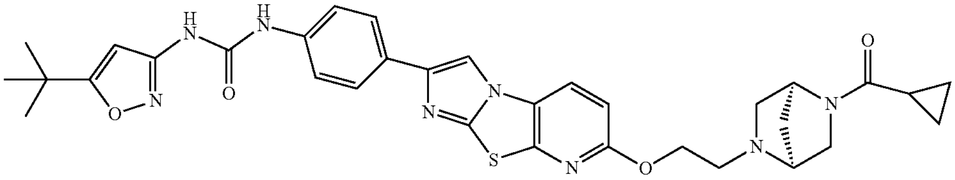
,
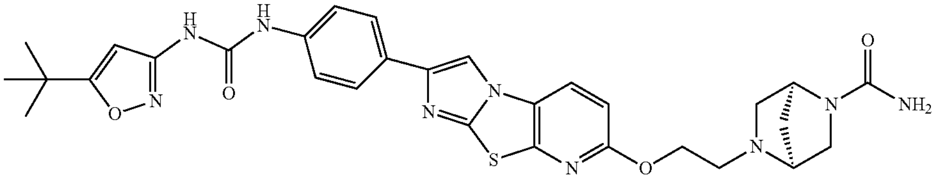
,
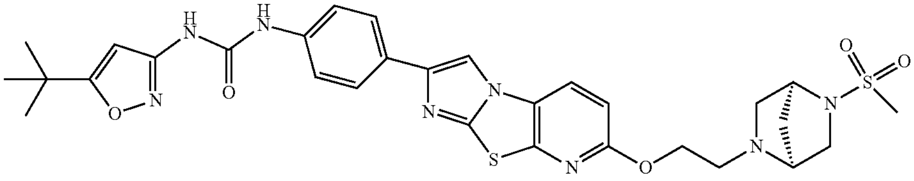
,
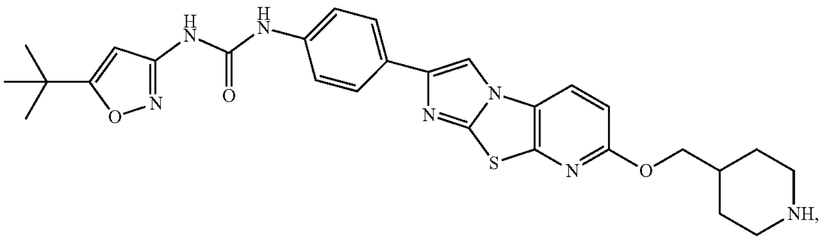
,
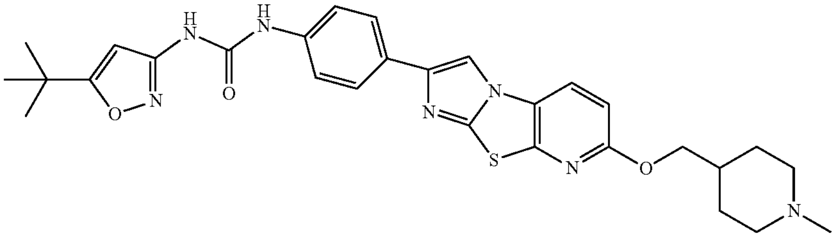
,
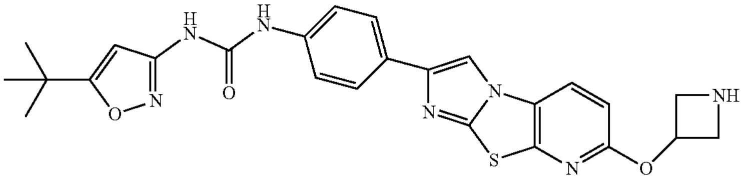
, -continued
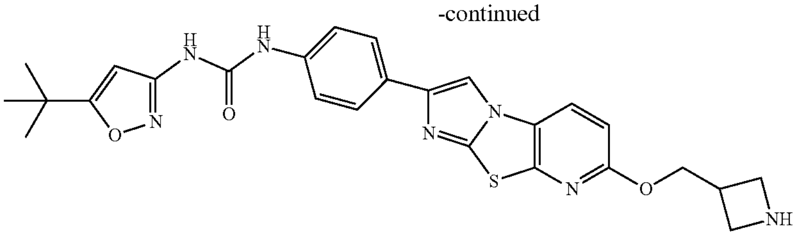
,
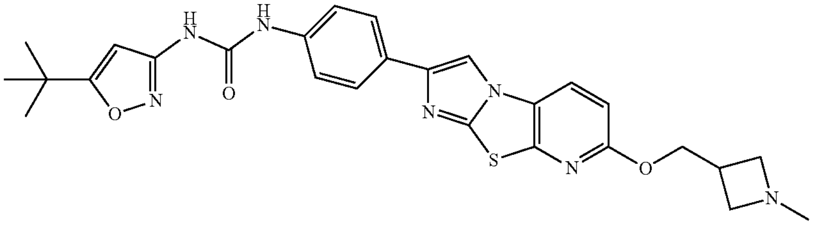
,
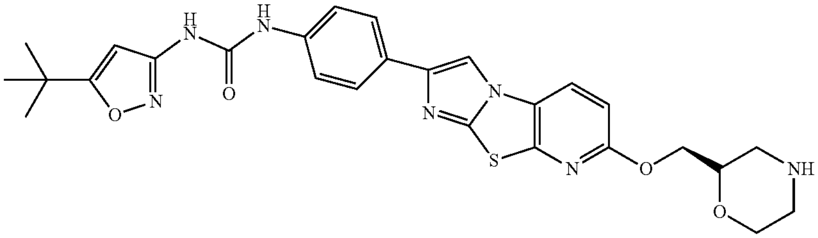
,
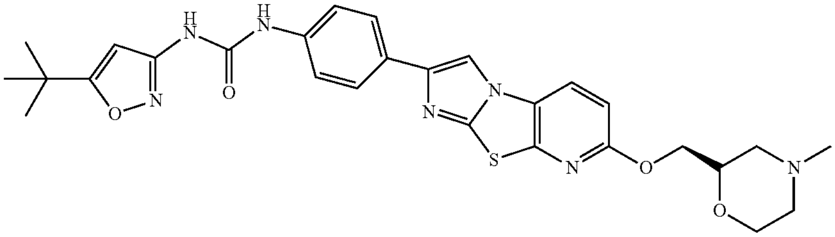
,
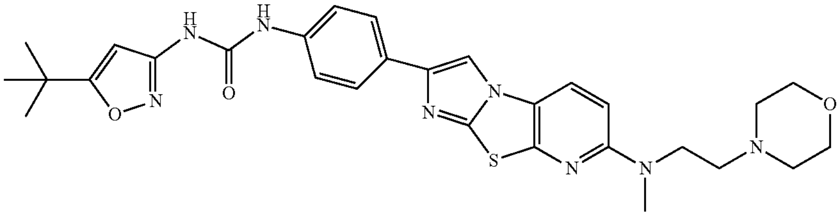
,
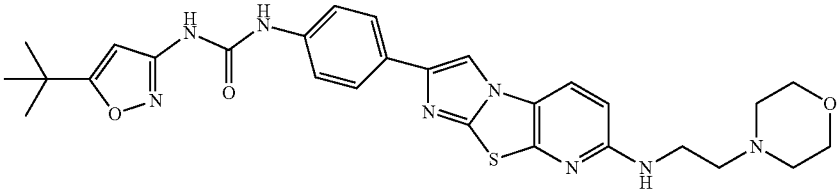
,
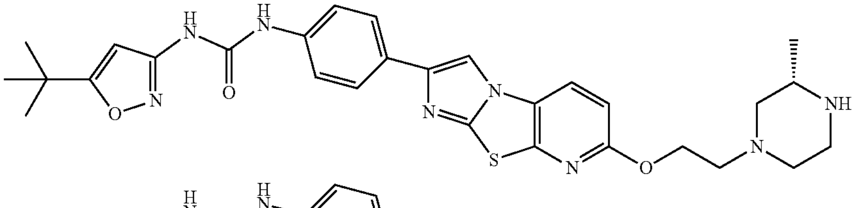
,
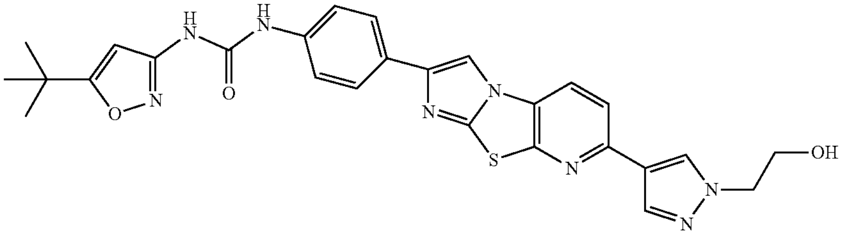
, -continued
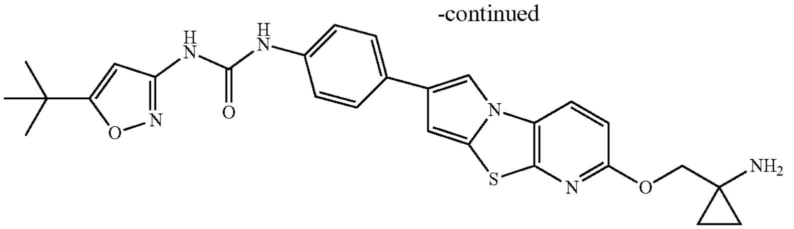
,
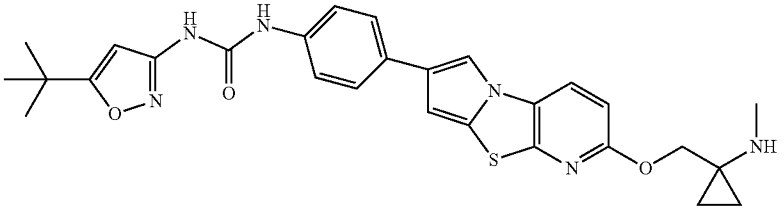
,
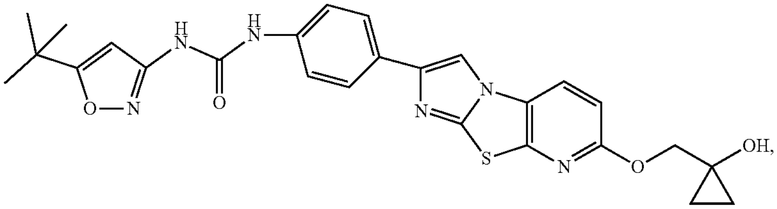
,
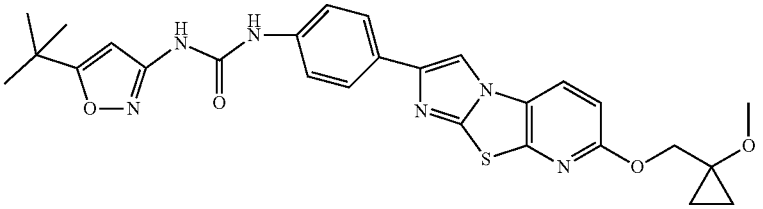
,
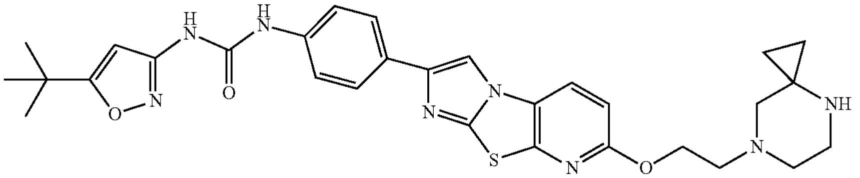
,
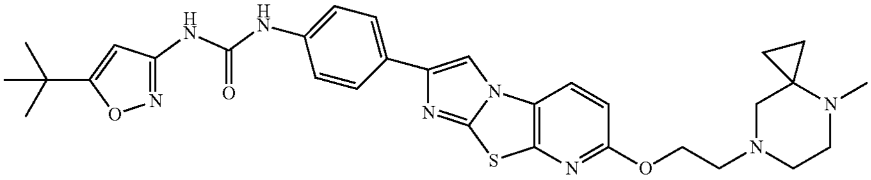
,
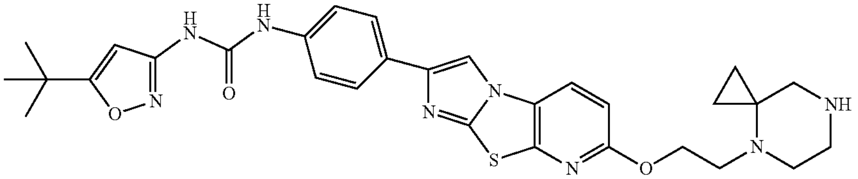
,
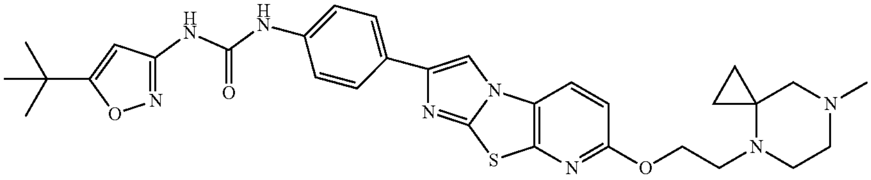
,
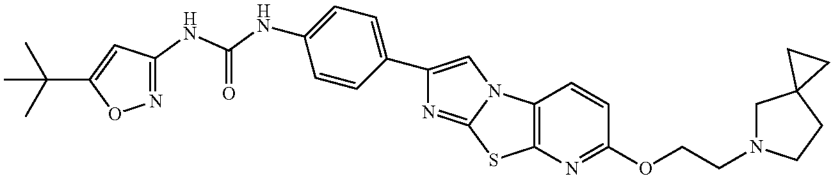
, -continued
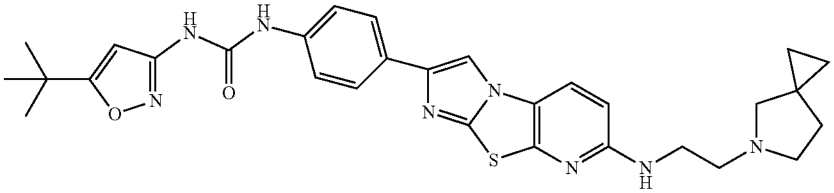
,
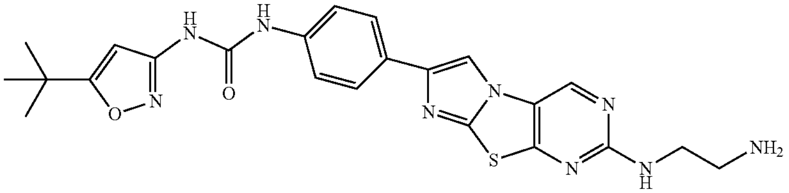
,
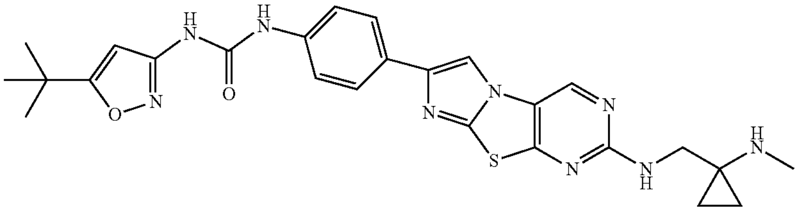
,
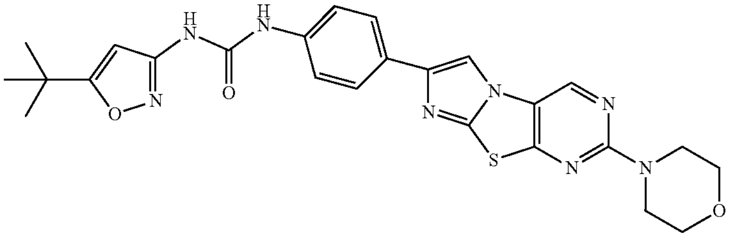
,
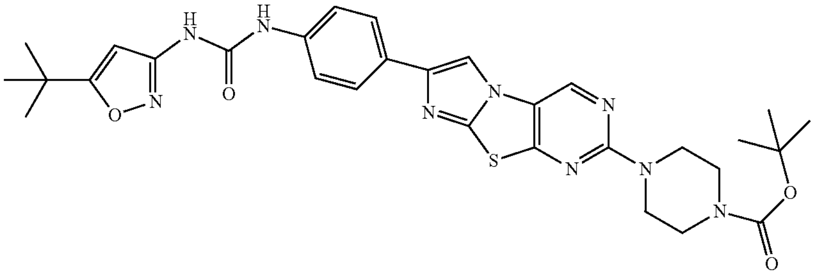
,
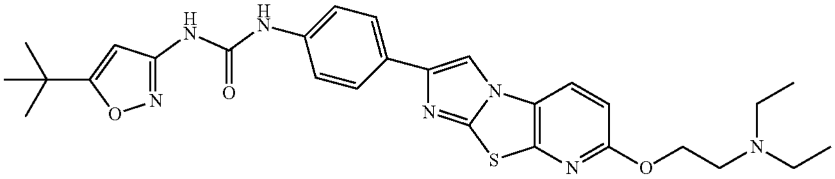
,
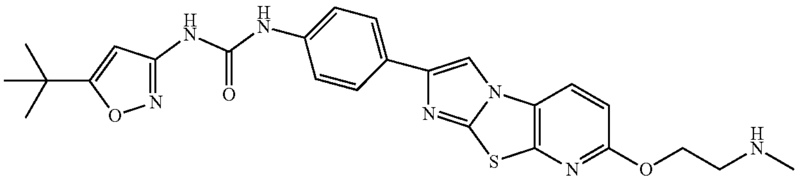
,
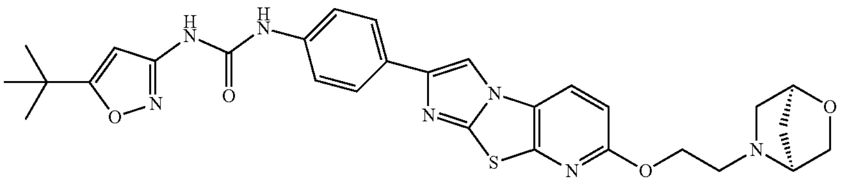
, -continued
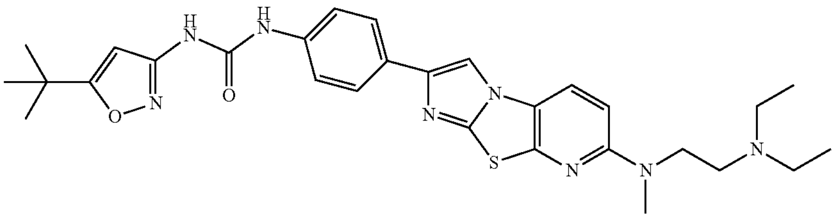
,
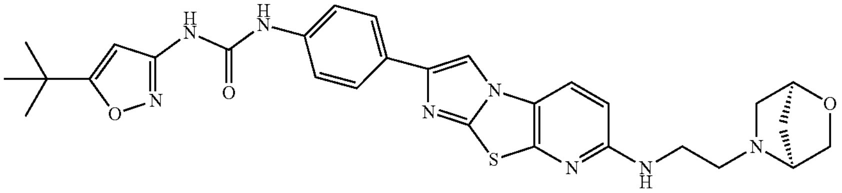
,
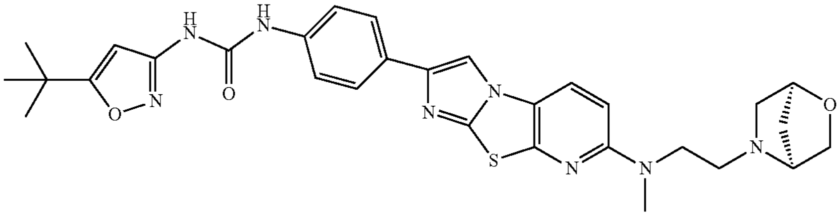
,
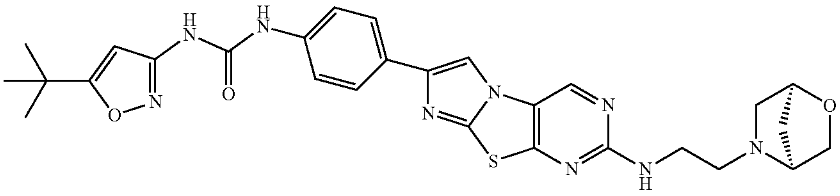
,
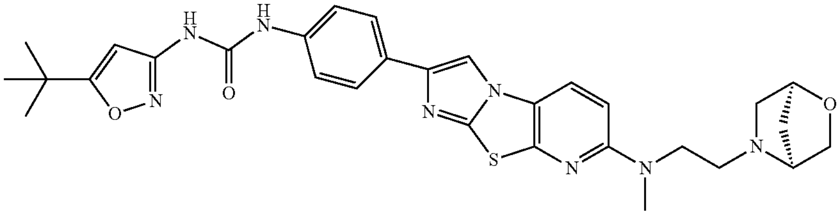
,
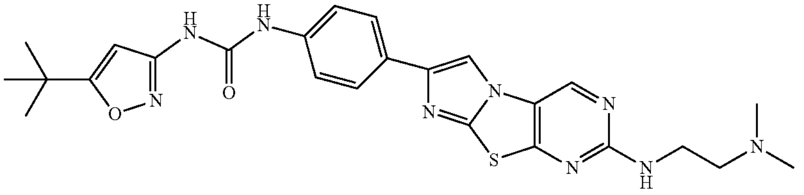
,
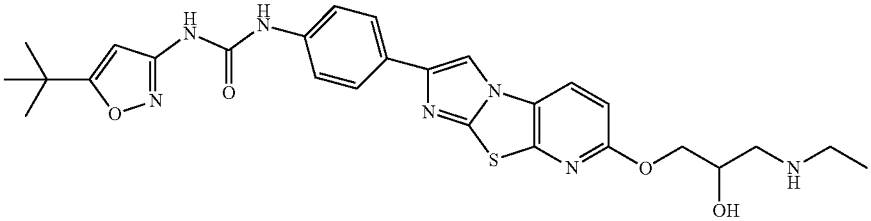
,
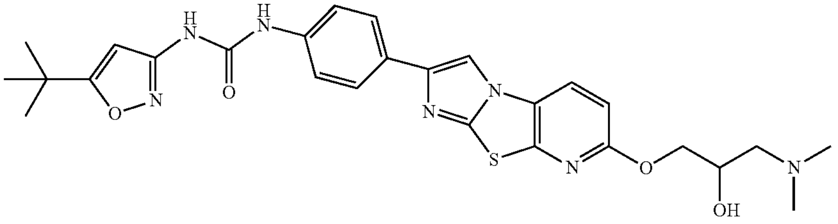
, -continued
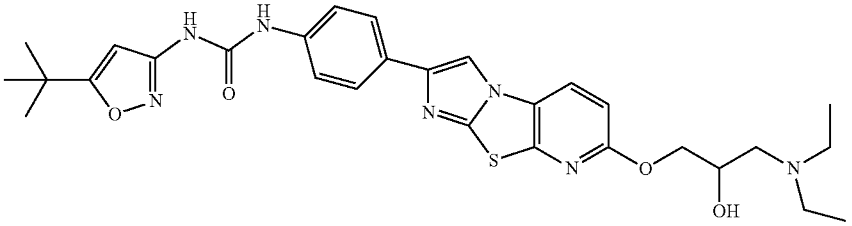
,
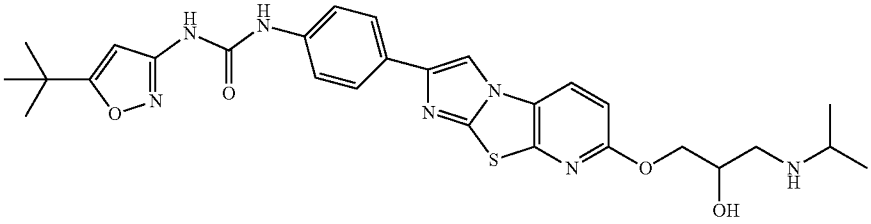
,
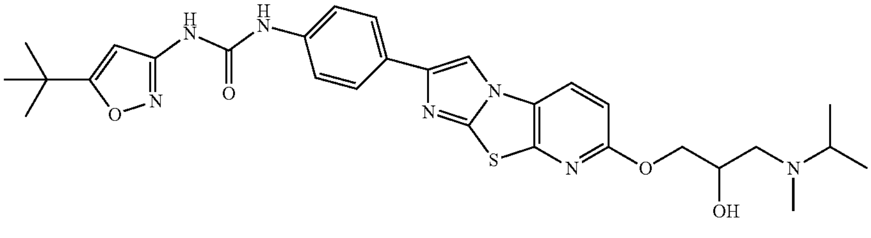
,
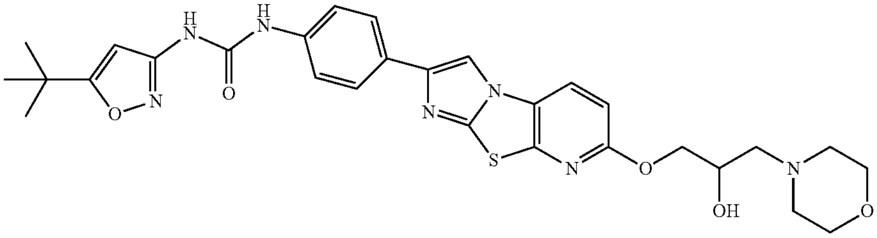
,
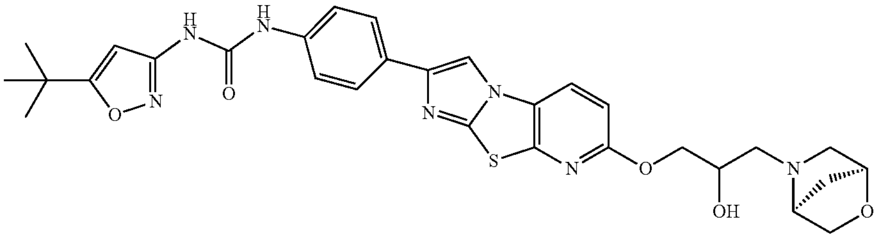
,
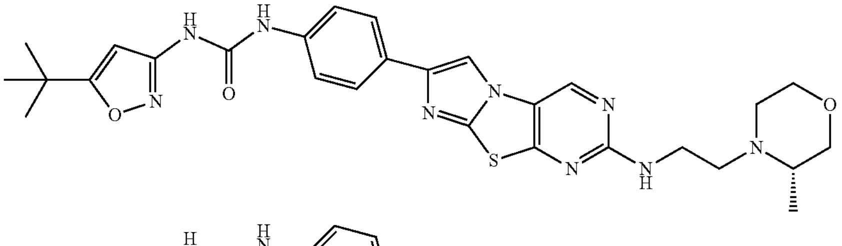
,
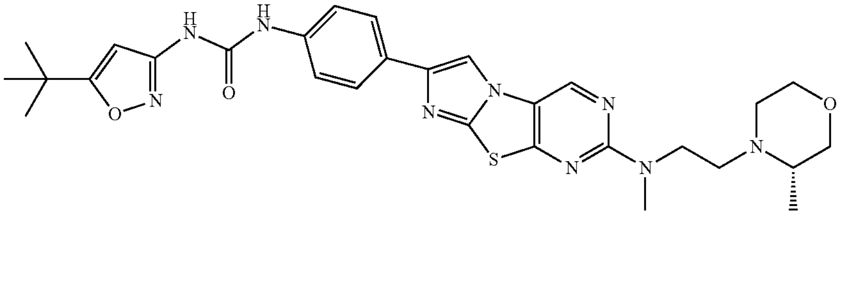
, -continued
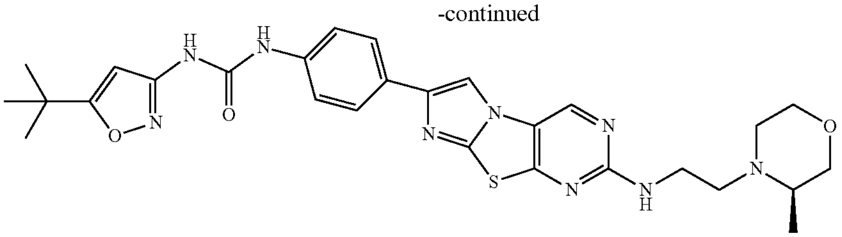
,
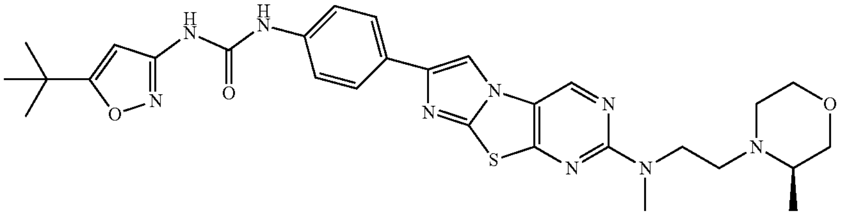
,
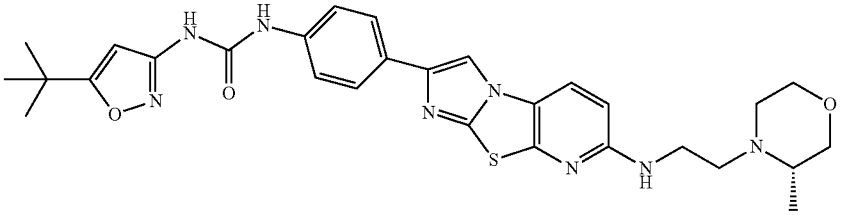
,
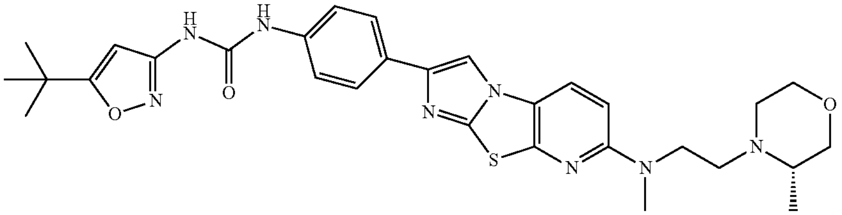
,
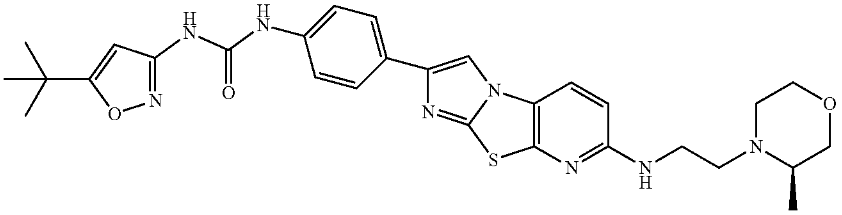
,
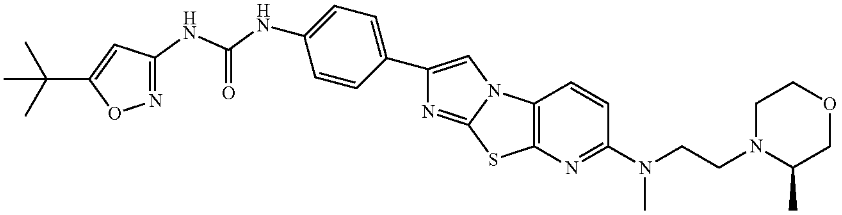
,
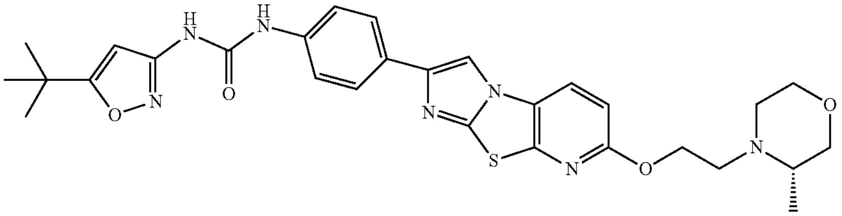
,
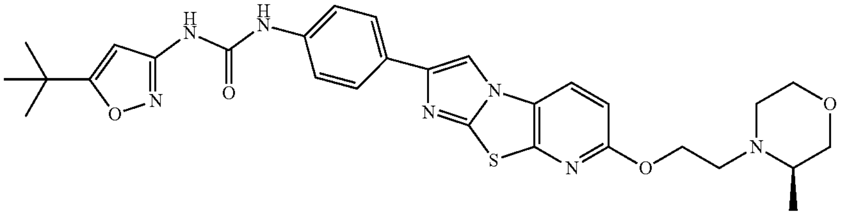
, -continued
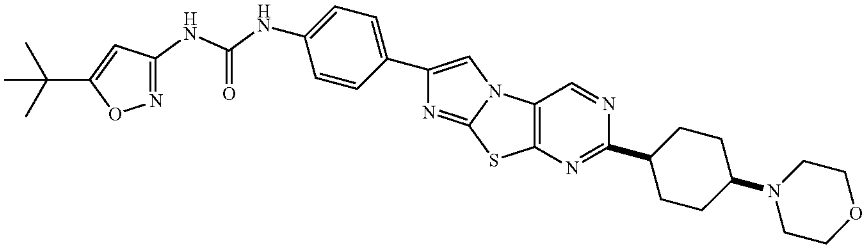
,
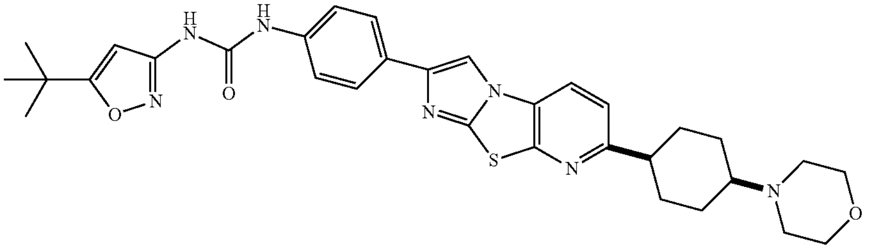
,
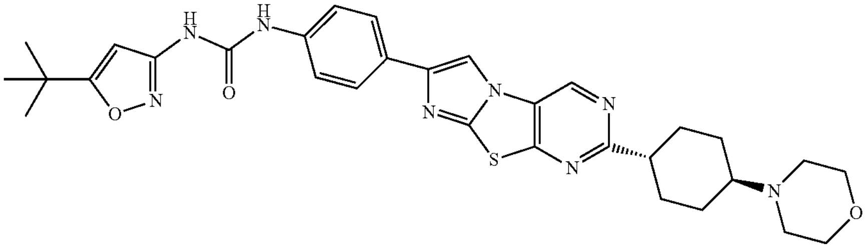
,
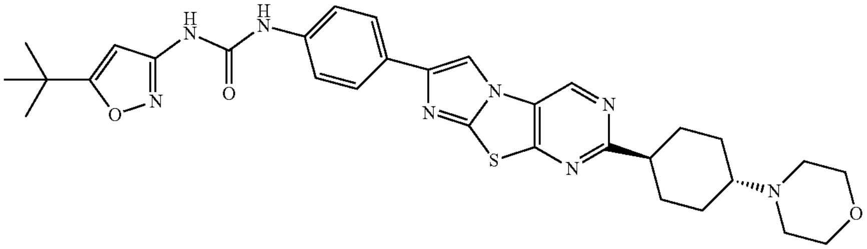
,
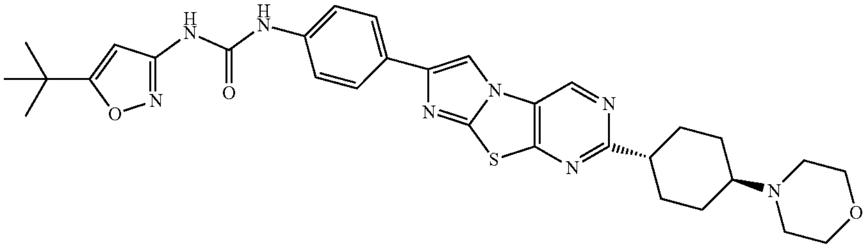
,
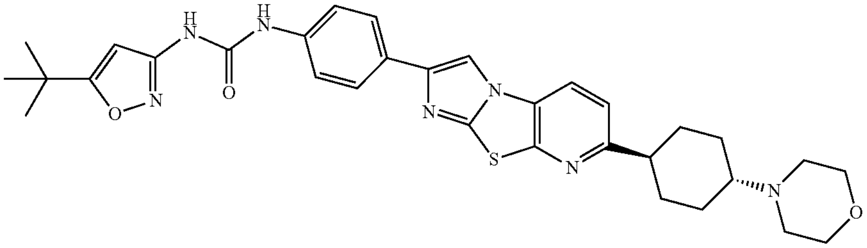
,
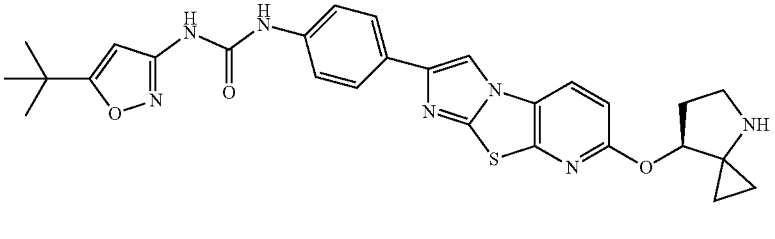
, -continued
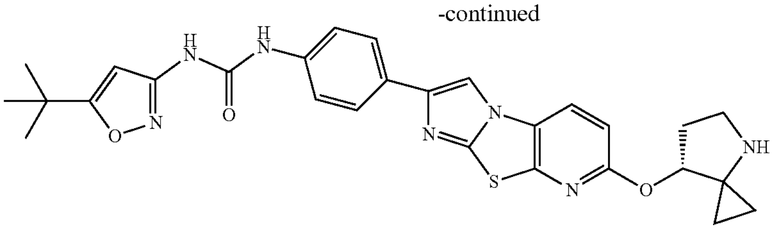
,
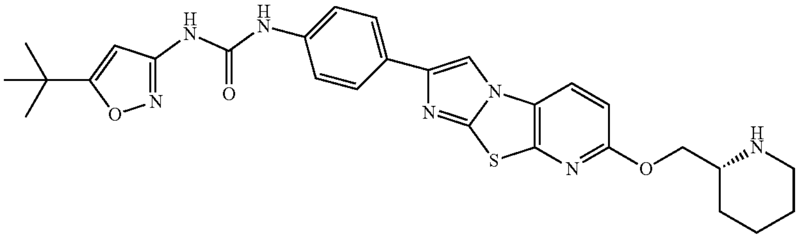
,
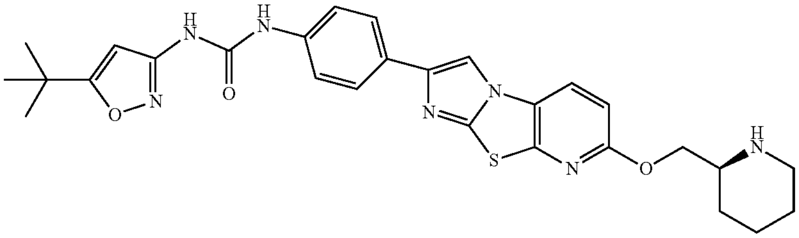
,
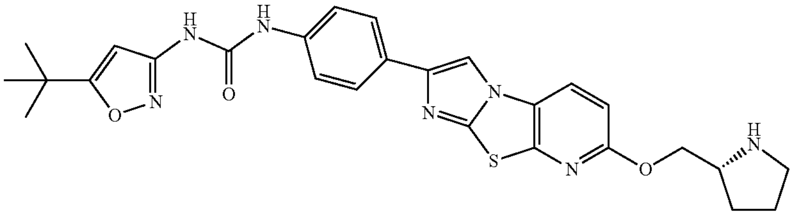
,
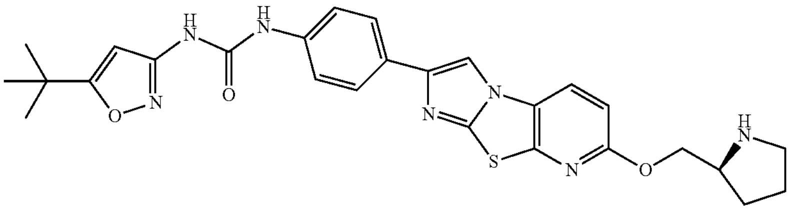
,
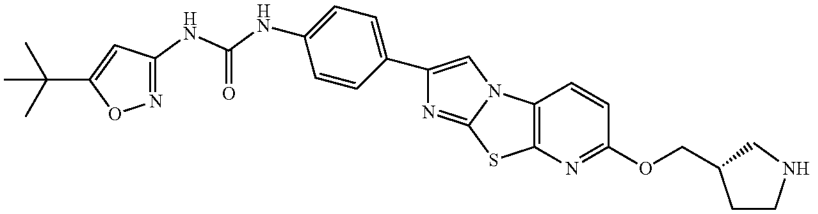
,
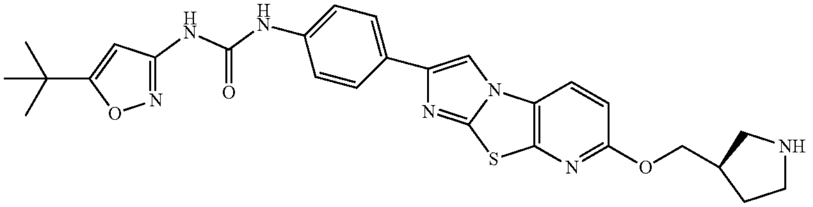
, -continued
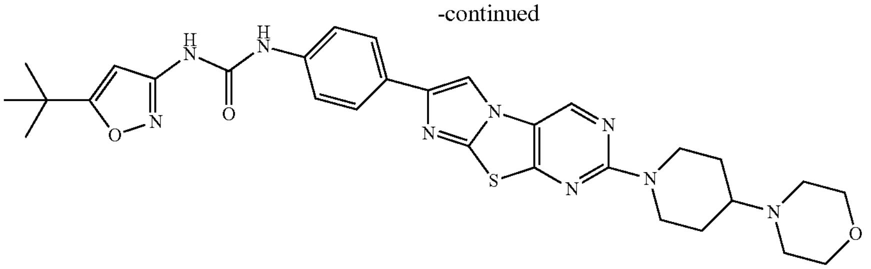
,
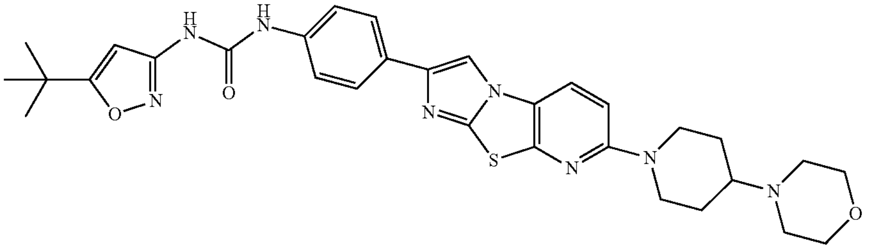
,
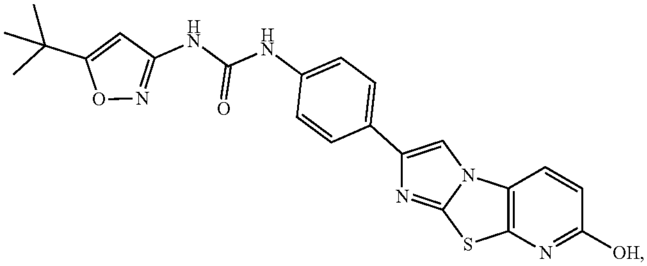
wherein
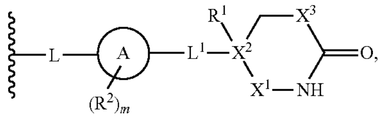
,
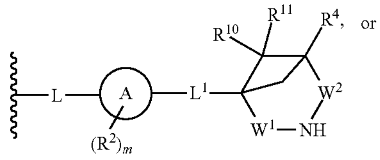
, or
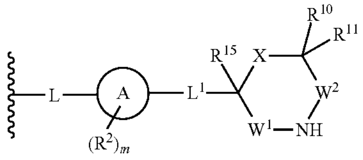
is attached to a modifiable carbon, oxygen, nitrogen or sulfur atom.
In some embodiments, a TBM moiety is selected from
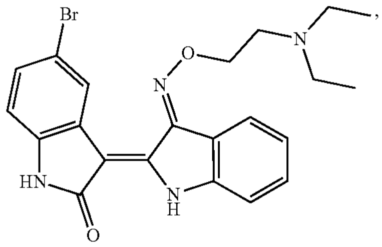
,
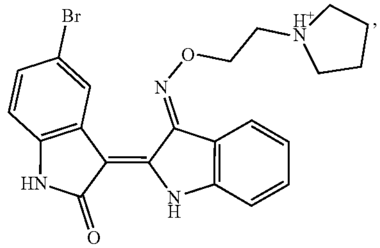
,
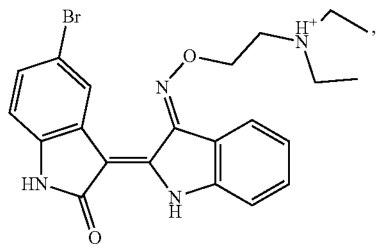
, -continued
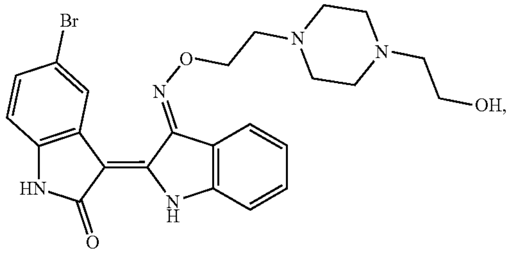
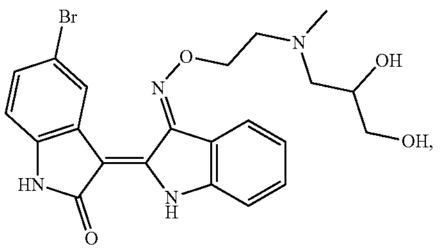
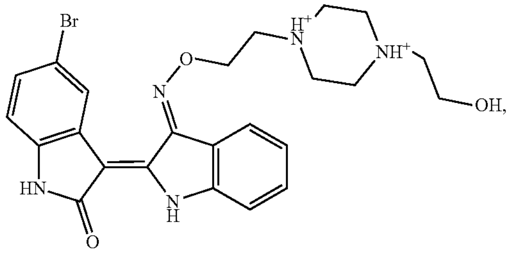
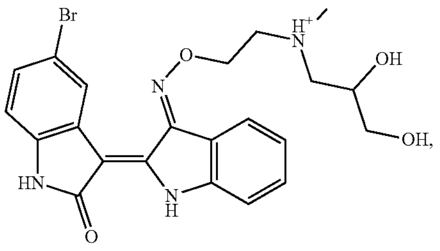
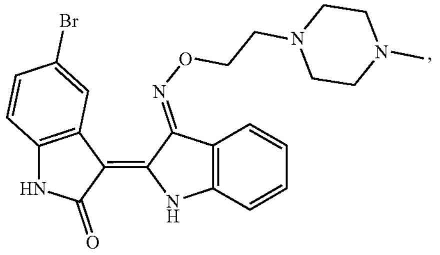
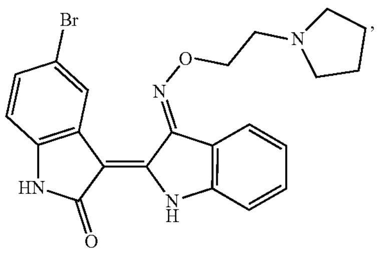
-continued
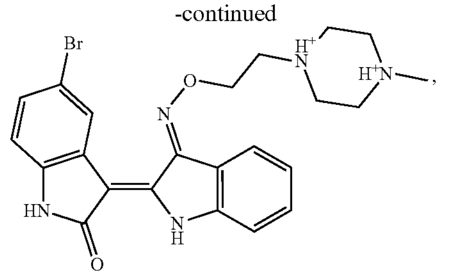
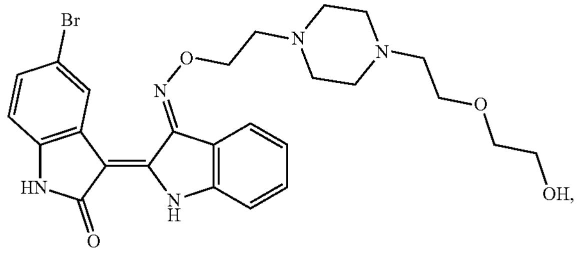
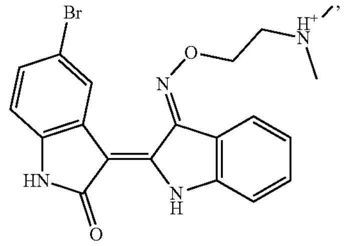
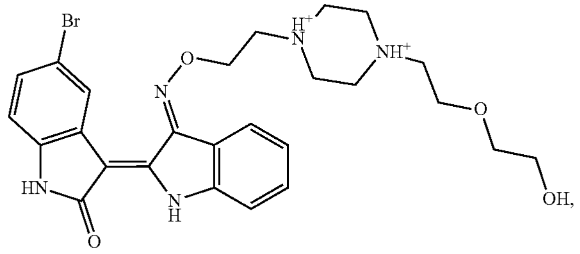
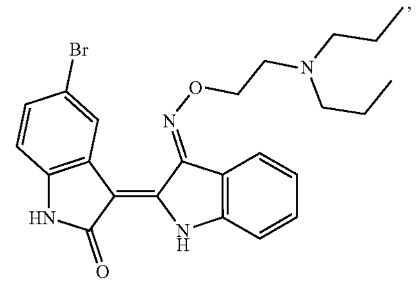
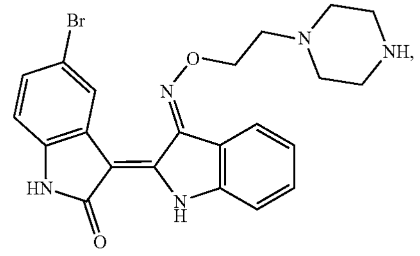

-continued
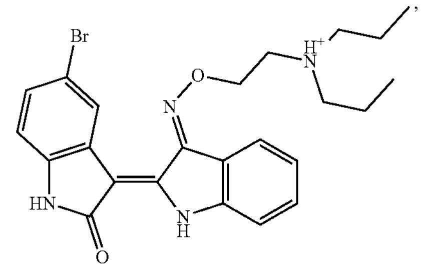
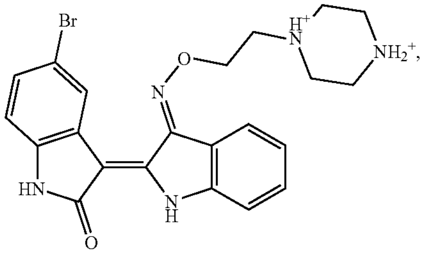
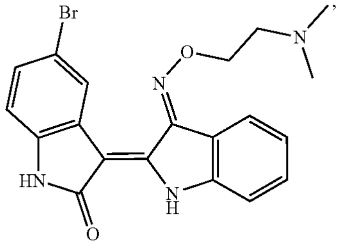
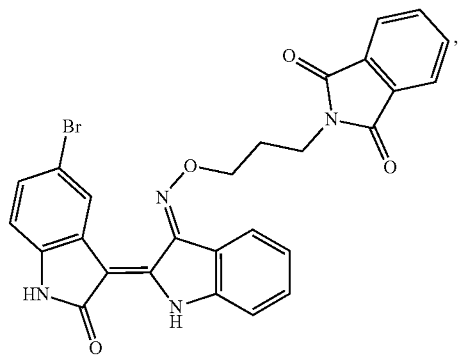
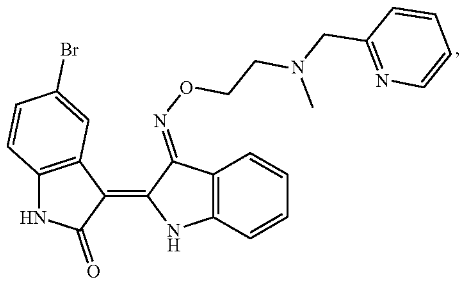
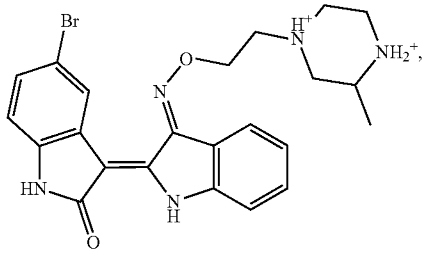
-continued
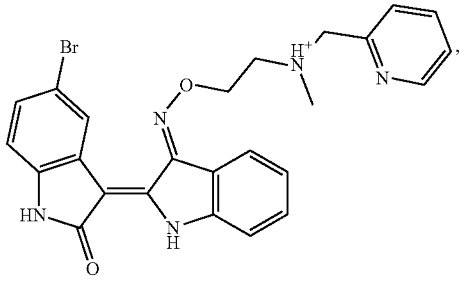
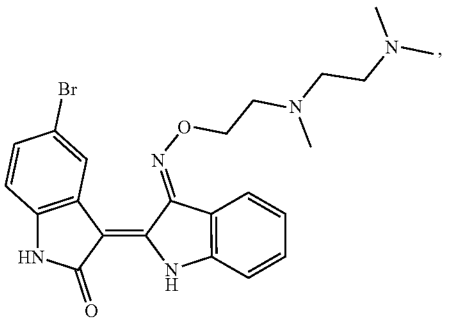
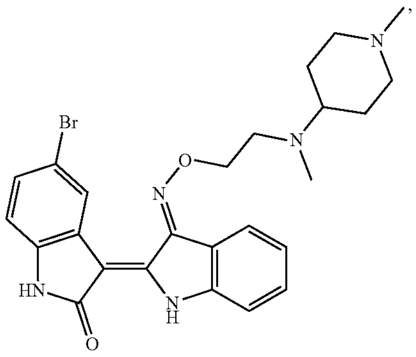
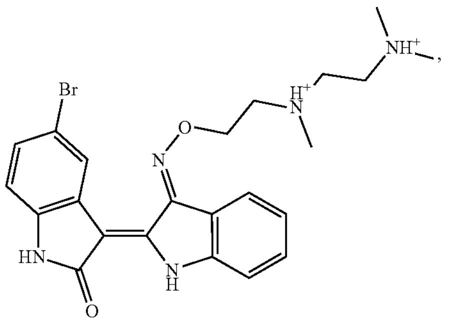
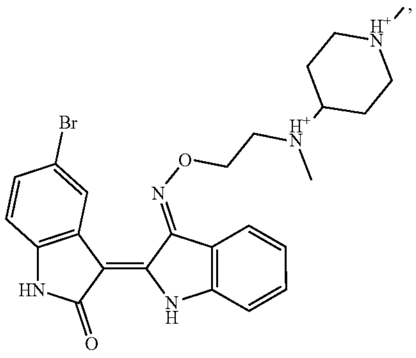

-continued
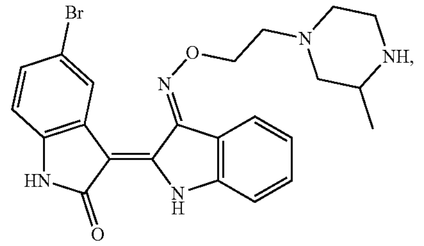
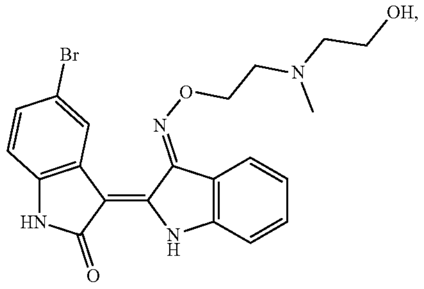
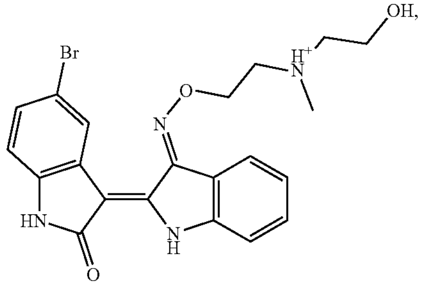
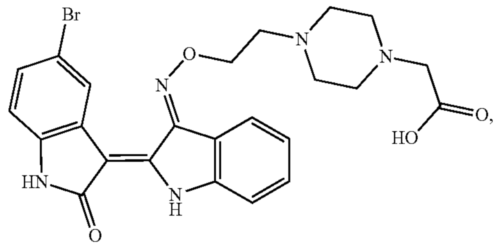
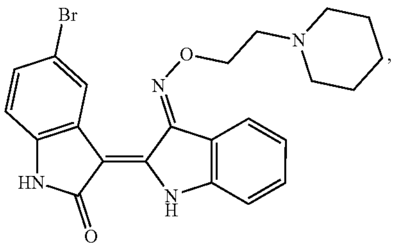
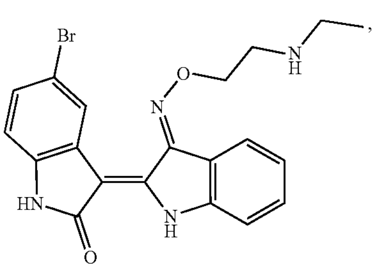
-continued
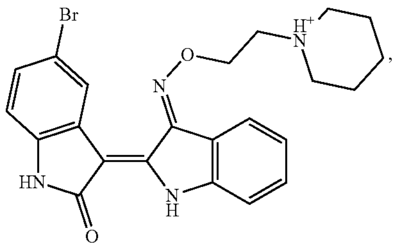
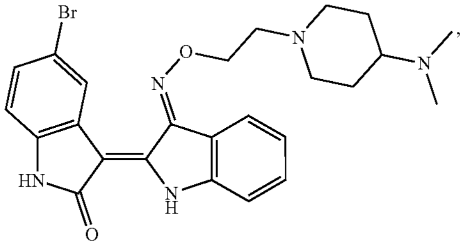
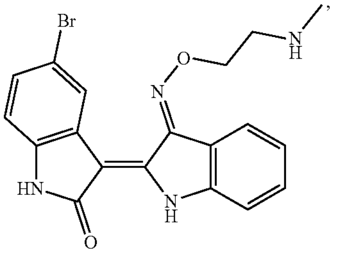
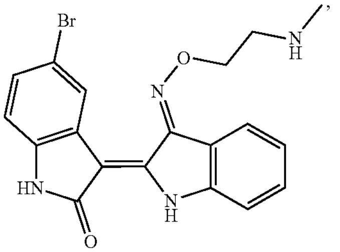
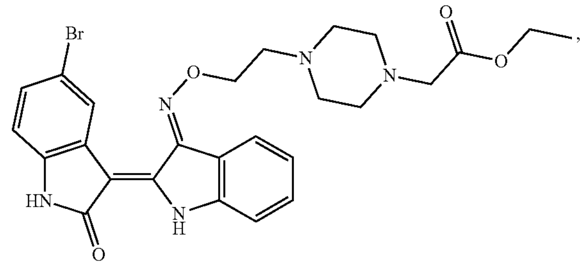
wherein
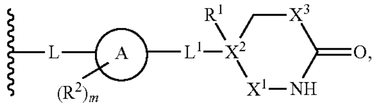
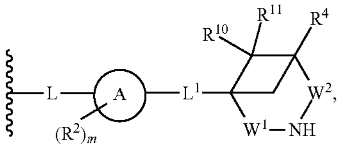
or -continued
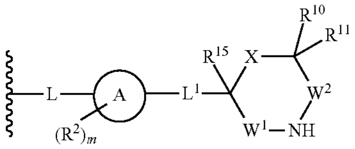
is attached to a modifiable carbon, oxygen, nitrogen or sulfur atom.
In some embodiments, a TBM moiety is selected from H
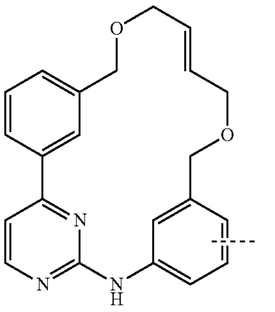
or
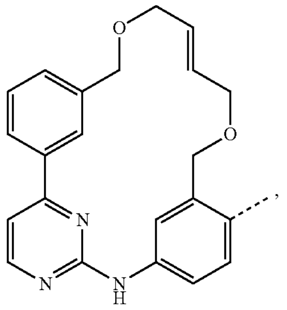
wherein - - - denotes attachment to
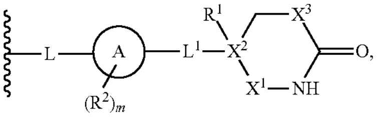
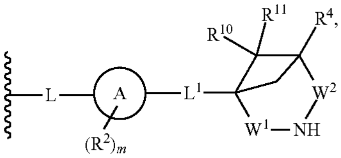
or
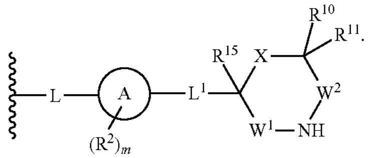
In some embodiments, a TBM moiety is selected from
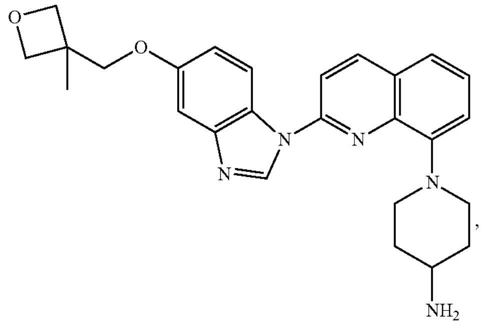
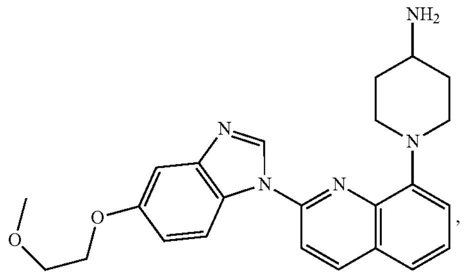
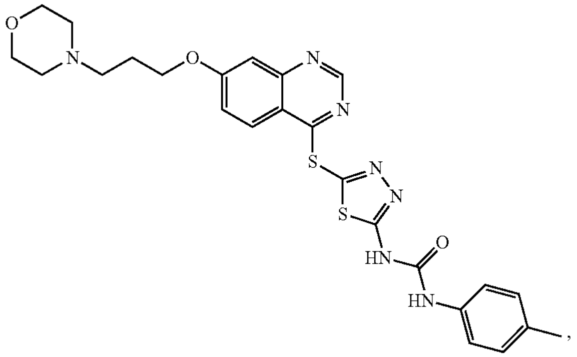
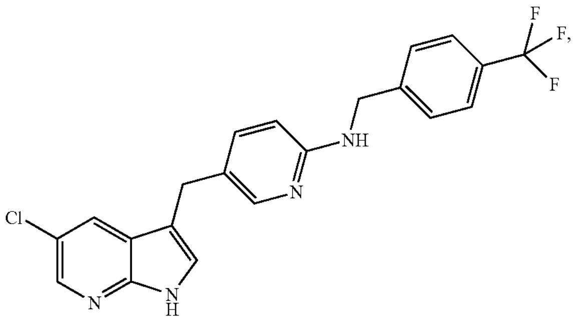
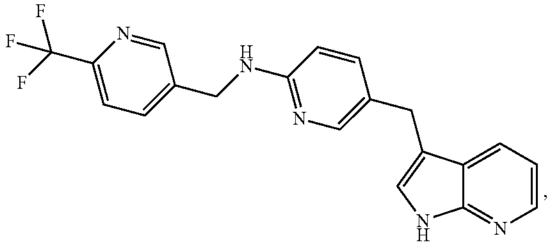

-continued
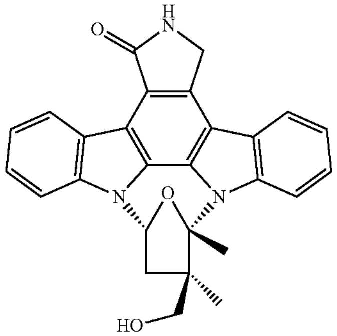
,
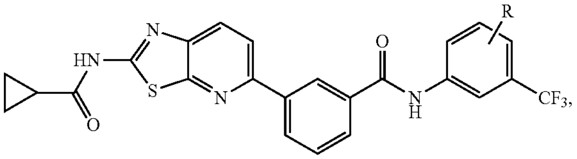
wherein
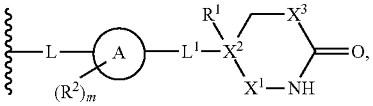
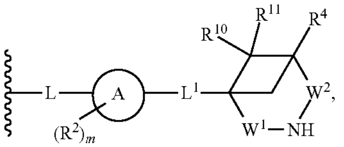
or
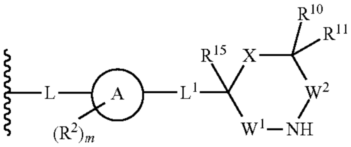
is attached to a modifiable carbon, oxygen, nitrogen or sulfur atom; R is 5-(4-methyl-1H-imidazol-1-yl) or 4-(N-ethylpiperazin-1-yl)methyl).
In some embodiments, a TBM moiety is a RAF ligand selected from
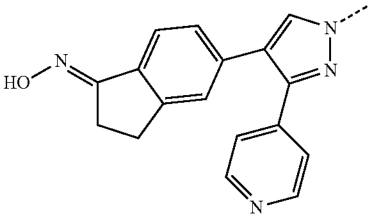
,
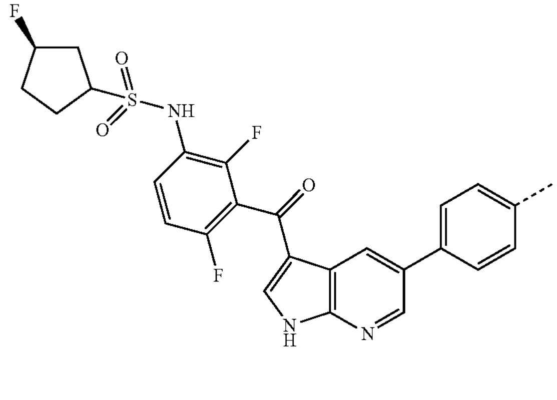
,
-continued
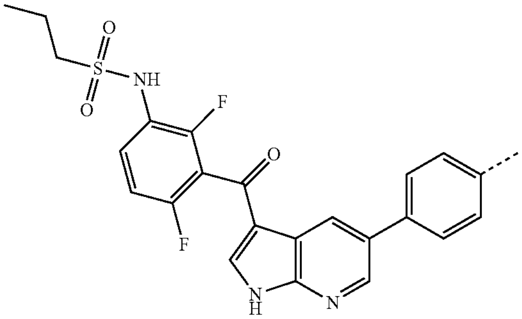
,
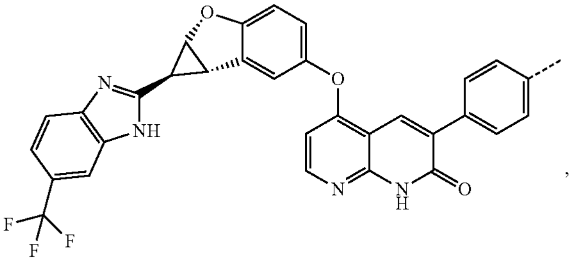
,
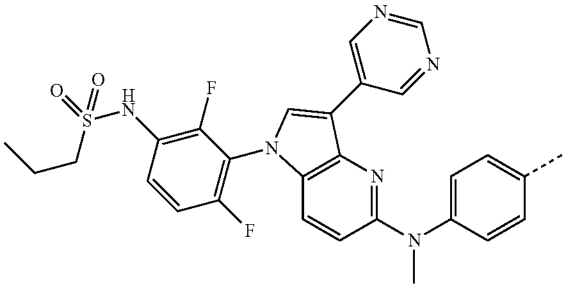
,
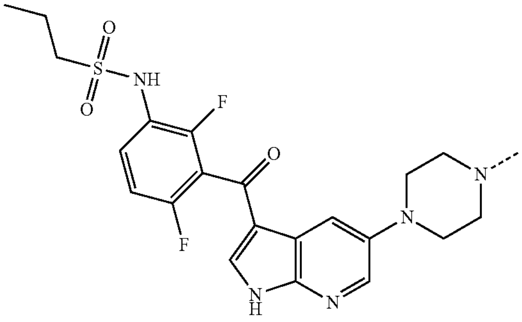
,
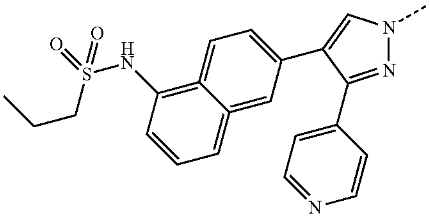
,
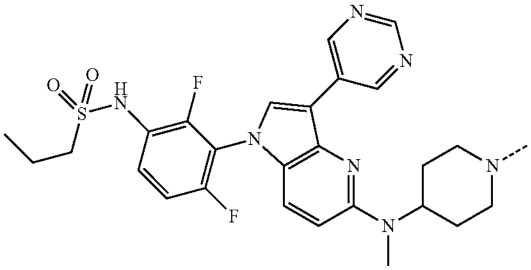
, or -continued

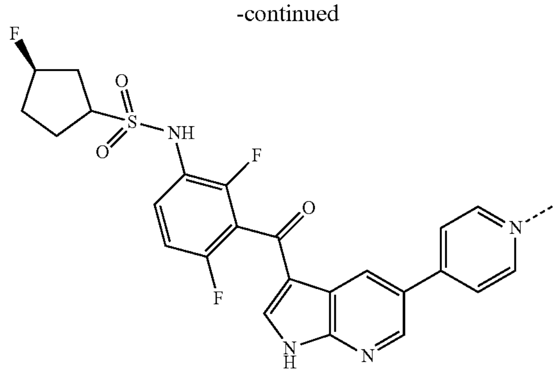

, wherein - - - denotes attachment to

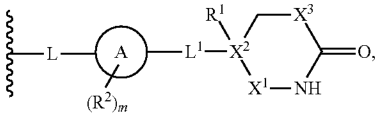

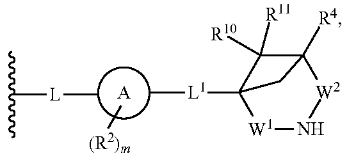

or

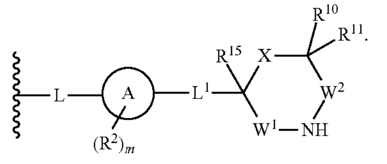

In some embodiments, a TBM moiety is selected from PTM moieties as recited in WO 2016/197032 the entirety of which is incorporated herein by reference. In some embodiments, a TBM moiety is selected from such inhibitors as described in WO 2016/197032 at paragraphs [00116] through [00173] wherein the recitation of a “Linker” moiety in WO 2016/197032 corresponds to the -L- group as defined and described herein. In some embodiments, a TBM moiety is selected from such inhibitors as described in US 2018/0125821 at paragraphs [0106] through [0115], the entirety of which is incorporated herein by reference. In some embodiments, a TBM moiety is selected from such inhibitors as described in WO 2018/119441 at paragraph [00455], and US 2018/0193470, the entirety of each of which is herein incorporated by reference. In some embodiments, a TBM moiety is selected from such inhibitors as described in US 2018/0147202, the entirety of which is incorporated herein by reference. In some embodiments, a TBM moiety is selected from such inhibitors as described in WO 2018/098275 at Table A, the entirety of which is incorporated herein by reference. In some embodiments, a TBM moiety is selected from such inhibitors as described in WO 2016/169989 and US 2018/0118733, the entirety of each of which is herein incorporated by reference. In some embodiments, a TBM moiety is selected from such inhibitors as described in WO 2015/181747 and US 2017/0121335, the entirety of each of which is herein incorporated by reference. In some embodiments, a TBM moiety is selected from such inhibitors as described in Shimokawa et al., *Med. Chem. Lett.*, 2017, 8 (10), pp 1042-1047, the entirety of which is incorporated herein by reference. In some embodiments, a TBM moiety is selected from such inhibitors as described in WO 2017/079267 and US 2018/0186785, the entirety of each of which is herein incorporated by reference. In some embodiments, a TBM moiety is selected from such inhibitors as described in Powell et al., *J. Med. Chem.*, 2018, 61 (9), pp 4249-4255, the entirety of which is incorporated herein by reference. In some embodiments, a TBM moiety is selected from such inhibitors as described in Zhang et al., *Eur. J. Med. Chem.*, 2018, 151, pp 304-314, the entirety of which is incorporated herein by reference. In some embodiments, a TBM moiety is selected from such inhibitors as described in Li et al., *Eur. J. Med. Chem.*, 2018, 151, pp 237-247, the entirety of which is incorporated herein by reference. In some embodiments, a TBM moiety is selected from such inhibitors as described in WO 2016/169989 and US 2018/0118733, the entirety of each of which is herein incorporated by reference. In some embodiments, a TBM moiety is selected from such inhibitors as described in WO 2017/046036, the entirety of which is incorporated herein by reference. In some embodiments, a TBM moiety is selected from such inhibitors as described in WO 2016/169989 and US 2018/0118733, the entirety of each of which is herein incorporated by reference. In some embodiments, a TBM moiety is selected from such inhibitors as described in WO 2018/053354 and US 2018/0072711, the entirety of each of which is herein incorporated by reference. In some embodiments, a TBM moiety is selected from such inhibitors as described in Olsen et al., *Nat. Chem. Bio.*, 2018, 14, pp 163-170, the entirety of which is incorporated herein by reference. In some embodiments, a TBM moiety is selected from such inhibitors as described in WO 2017/185031, the entirety of which is incorporated herein by reference. In some embodiments, a TBM moiety is selected from such inhibitors as described in Hatcher et al., *Med. Chem. Lett.*, 2018, 9(6), pp 540-545, the entirety of which is incorporated herein by reference. In some embodiments, a TBM moiety is selected from such inhibitors as described in Burslem et al., *Cell Chem. Bio.*, 2018, 25(1), pp 67-77, the entirety of which is incorporated herein by reference. In some embodiments, a TBM moiety is selected from such inhibitors as described in CN106977584, the entirety of which is incorporated herein by reference. In some embodiments, a TBM moiety is selected from such inhibitors as described in WO 2017/197056, the entirety of which is incorporated herein by reference. In some embodiments, a TBM moiety is selected from such inhibitors as described in WO 2018/051107, the entirety of which is incorporated herein by reference. In some embodiments, a TBM moiety is selected from such inhibitors as described in US 2018/0050021, the entirety of which is incorporated herein by reference. In some embodiments, a TBM moiety is selected from such inhibitors as described in WO 2017/223452, the entirety of which is incorporated herein by reference. In some embodiments, a TBM moiety is selected from such inhibitors as described in WO 2017/117473, WO 2017/117474, and US 2019/0016703, the entirety of each of which is herein incorporated by reference. In some embodiments, a TBM moiety is selected from such inhibitors as described in WO 2018/071606 and US 2018/0099940, the entirety of each of which is herein incorporated by reference. In some embodiments, a TBM moiety is selected from such inhibitors as described in US 2018/0099940, the entirety of which is incorporated herein by reference. In some embodiments, a TBM moiety is selected from such inhibitors as described in Gechijian et al., *Nat. Chem. Bio.*, 2018, 14, pp. 405-412, the entirety of which is incorporated herein by reference. In some embodiments, a TBM moiety is selected from such inhibitors as described in CN 106749513, the entirety of which is incorporated herein by reference. In some embodiments, a TBM moiety is selected from such inhibitors as described in CN107056772, the entirety of which is incorporated herein by reference. In some embodiments, a TBM moiety is selected from such inhibitors as described in Pawar et al., *Cell Rep.,* 2018, 22(9), pp 2236-2245, the entirety of which is incorporated herein by reference. In some embodiments, a TBM moiety is selected from such inhibitors as described in US 2018/009779, the entirety of which is incorporated herein by reference. In some embodiments, a TBM moiety is selected from such inhibitors as described in WO 2017/180417, the entirety of which is incorporated herein by reference. In some embodiments, a TBM moiety is selected from such inhibitors as described in WO 2017/223452, the entirety of which is incorporated herein by reference. In some embodiments, a TBM moiety is selected from such inhibitors as described in US 2018/009779, the entirety of which is incorporated herein by reference. In some embodiments, a TBM moiety is selected from such inhibitors as described in Tomoshige et al., *Bioorg. Med. Chem. Lett.,* 2018, 28(4), pp 707-710, the entirety of which is incorporated herein by reference. In some embodiments, a TBM moiety is selected from such inhibitors as described in Chessum et al., *J. Med. Chem.,* 2018, 61(3), pp. 918-933, the entirety of which is incorporated herein by reference. In some embodiments, a TBM moiety is selected from such inhibitors as described in CN 105085620, the entirety of which is incorporated herein by reference.

Exemplary compounds of the invention are set forth in Table 1, below.

Table 1. Exemplary Compounds

TABLE 1

| Exemplary Compounds | |
|---|---|
| I-# | Structure |
| I-1 | 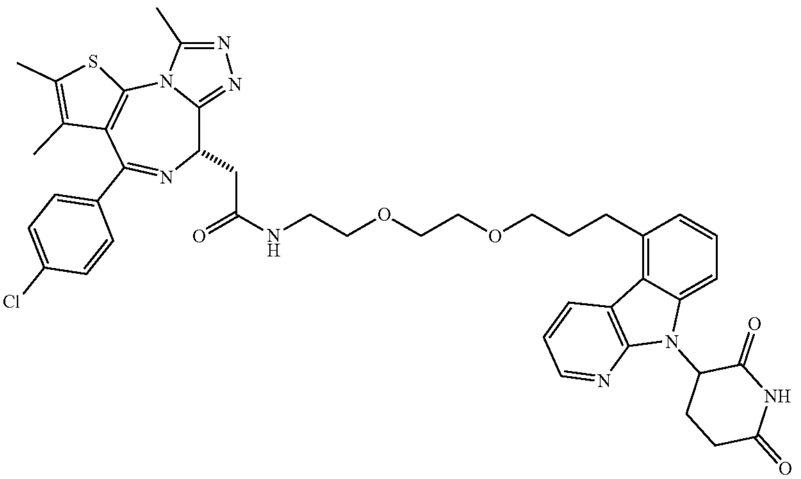 [SMILES: Cc1sc2c(c1C)C(c1ccc(Cl)cc1)=N[C@@H](CC(=O)NCCOCCOCCCc1cccc3c1c1cccnc1n3C1CCC(=O)NC1=O)c1nnc(C)n1-2] |
| I-2 | 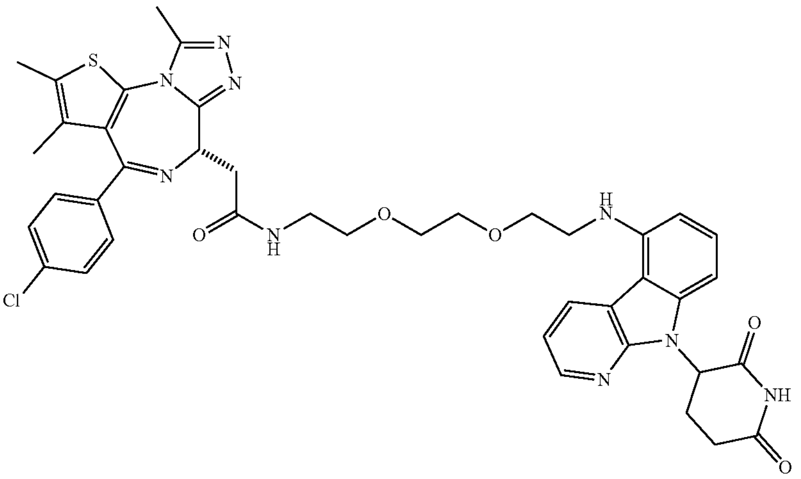 [SMILES: Cc1sc2c(c1C)C(c1ccc(Cl)cc1)=N[C@@H](CC(=O)NCCOCCOCCNc1cccc3c1c1cccnc1n3C1CCC(=O)NC1=O)c1nnc(C)n1-2] |

TABLE 1-continued
| Exemplary Compounds | |
|---|---|
| I-# | Structure |
| I-3 | 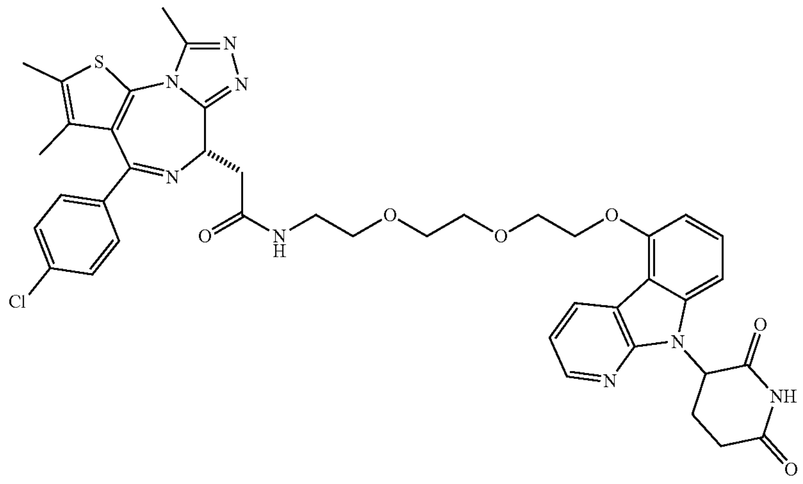 [SMILES: Cc1sc2c(c1C)C(c1ccc(Cl)cc1)=N[C@@H](CC(=O)NCCOCCOCCOc1cccc3c1c1cccnc1n3C1CCC(=O)NC1=O)c1nnc(C)n1-2] |
| I-4 | 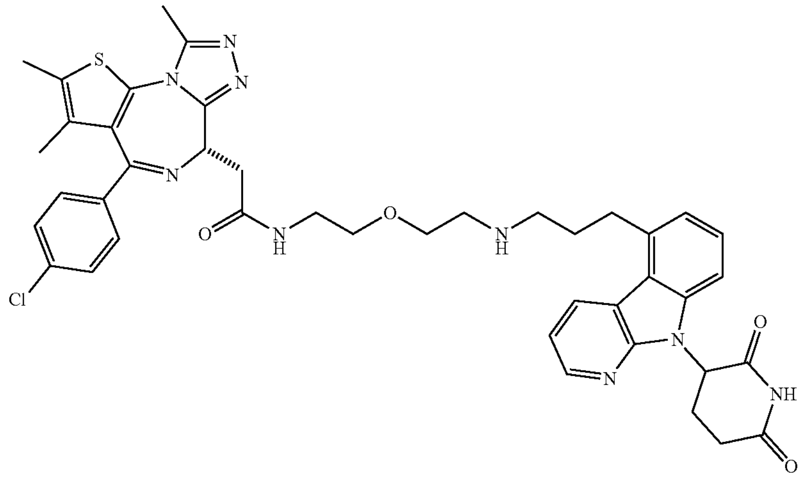 [SMILES: Cc1sc2c(c1C)C(c1ccc(Cl)cc1)=N[C@@H](CC(=O)NCCOCCNCCCc1cccc3c1c1cccnc1n3C1CCC(=O)NC1=O)c1nnc(C)n1-2] |
| I-5 | 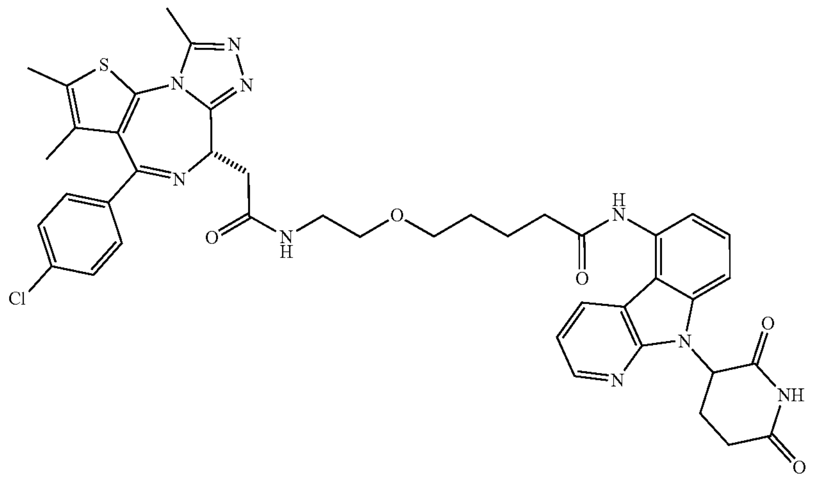 [SMILES: Cc1sc2c(c1C)C(c1ccc(Cl)cc1)=N[C@@H](CC(=O)NCCOCCCCC(=O)Nc1cccc3c1c1cccnc1n3C1CCC(=O)NC1=O)c1nnc(C)n1-2] |

TABLE 1-continued
| Exemplary Compounds | |
|---|---|
| I-# | Structure |
| I-6 | 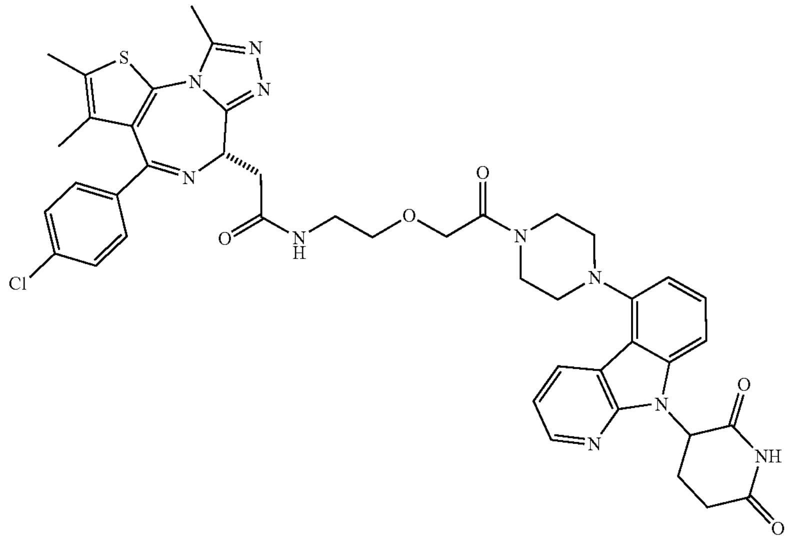 [SMILES: Cc1sc2c(c1C)C(c1ccc(Cl)cc1)=N[C@@H](CC(=O)NCCOCC(=O)N1CCN(c3cccc4c3c3cccnc3n4C3CCC(=O)NC3=O)CC1)c1nnc(C)n1-2] |
| I-7 | 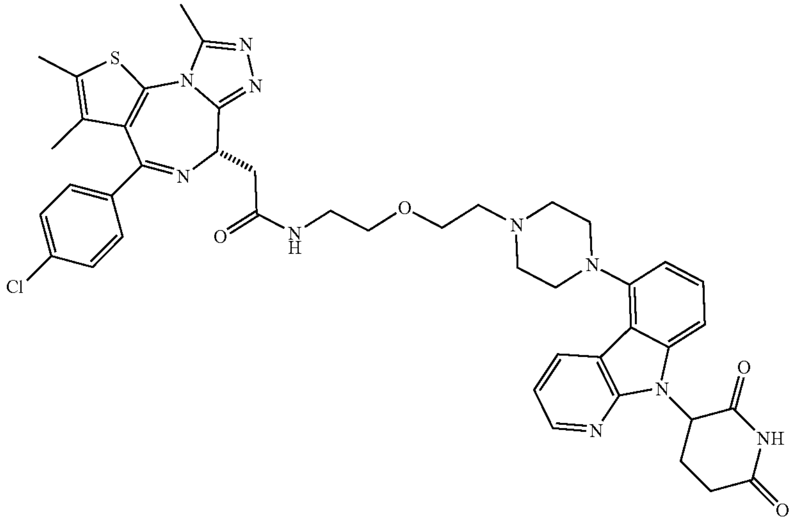 [SMILES: Cc1sc2c(c1C)C(c1ccc(Cl)cc1)=N[C@@H](CC(=O)NCCOCCN1CCN(c3cccc4c3c3cccnc3n4C3CCC(=O)NC3=O)CC1)c1nnc(C)n1-2] |
| I-8 | 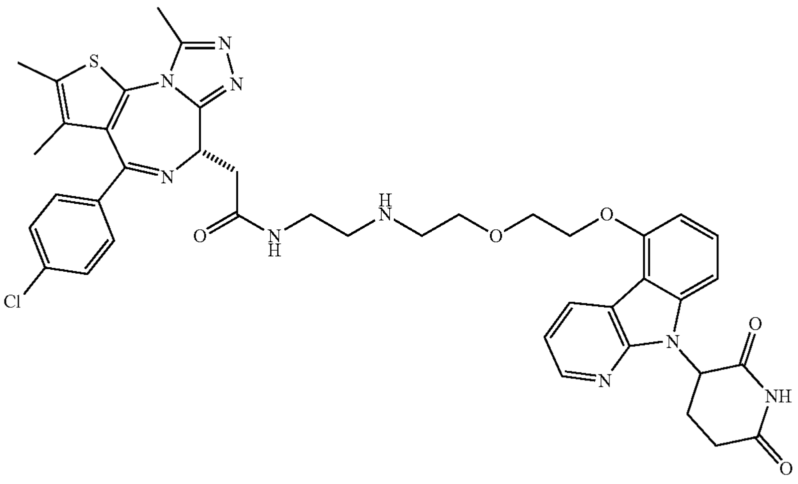 [SMILES: Cc1sc2c(c1C)C(c1ccc(Cl)cc1)=N[C@@H](CC(=O)NCCNCCOCCOc1cccc3c1c1cccnc1n3C1CCC(=O)NC1=O)c1nnc(C)n1-2] |

TABLE 1-continued
| Exemplary Compounds | |
|---|---|
| I-# | Structure |
| I-9 | 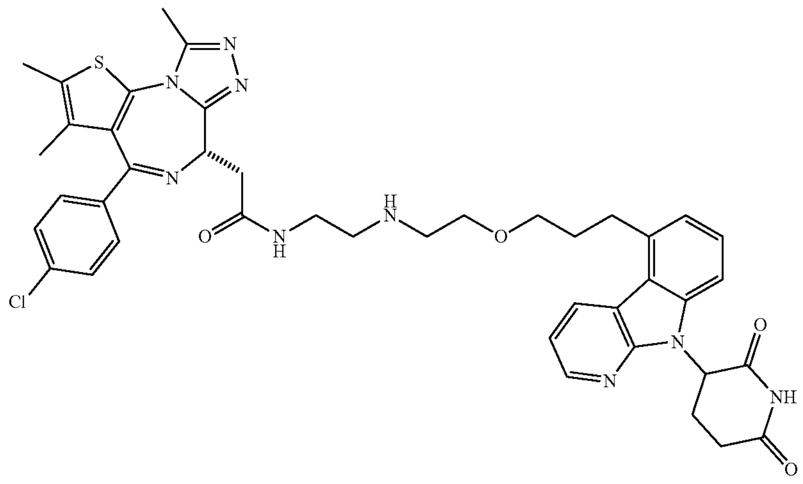 [SMILES: Cc1sc2c(c1C)C(c1ccc(Cl)cc1)=N[C@@H](CC(=O)NCCNCCOCCCc1cccc3c1c1cccnc1n3C1CCC(=O)NC1=O)c1nnc(C)n1-2] |
| I-10 | 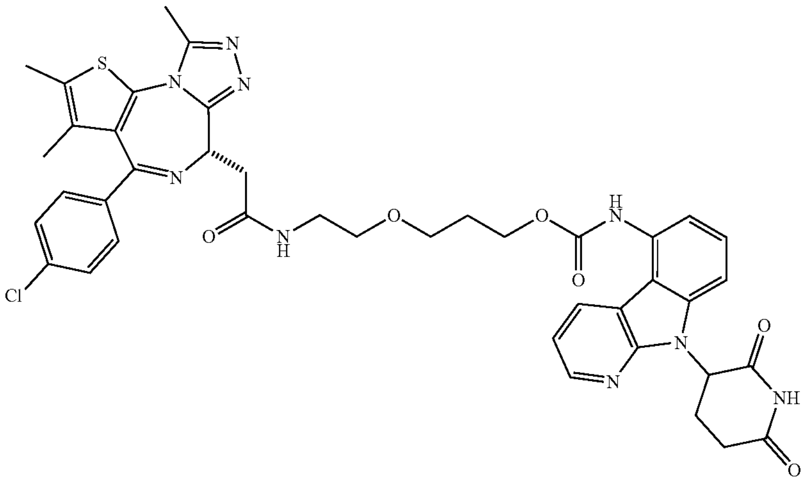 [SMILES: Cc1sc2c(c1C)C(c1ccc(Cl)cc1)=N[C@@H](CC(=O)NCCOCCCOC(=O)Nc1cccc3c1c1cccnc1n3C1CCC(=O)NC1=O)c1nnc(C)n1-2] |
| I-11 | 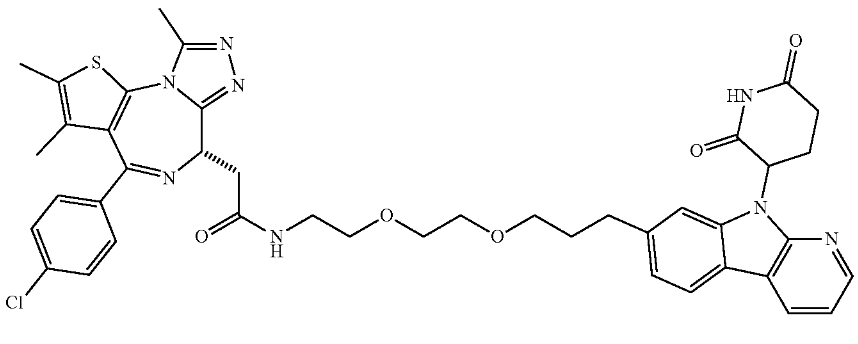 [SMILES: Cc1sc2c(c1C)C(c1ccc(Cl)cc1)=N[C@@H](CC(=O)NCCOCCOCCCc1ccc3c4cccnc4n(C4CCC(=O)NC4=O)c3c1)c1nnc(C)n1-2] |

TABLE 1-continued
| Exemplary Compounds | |
|---|---|
| I-# | Structure |
| I-12 | 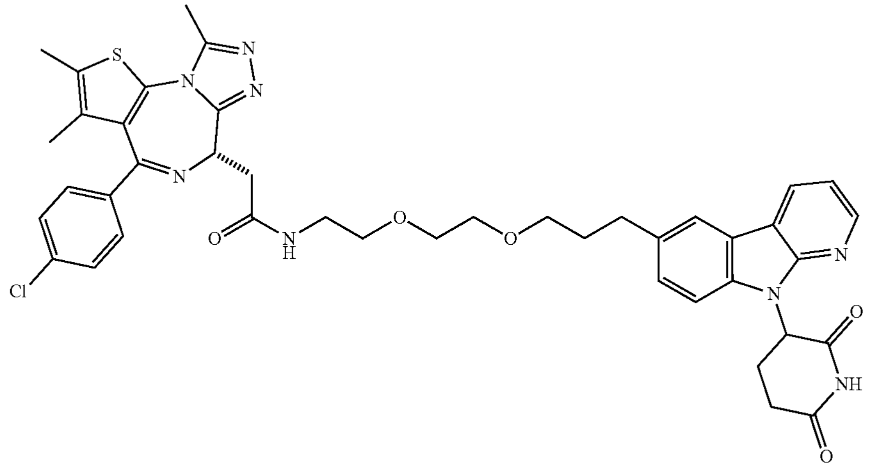 [SMILES: Cc1sc2c(c1C)C(c1ccc(Cl)cc1)=N[C@@H](CC(=O)NCCOCCOCCCc1ccc3c(c1)c1cccnc1n3C1CCC(=O)NC1=O)c1nnc(C)n1-2] |
| I-13 | 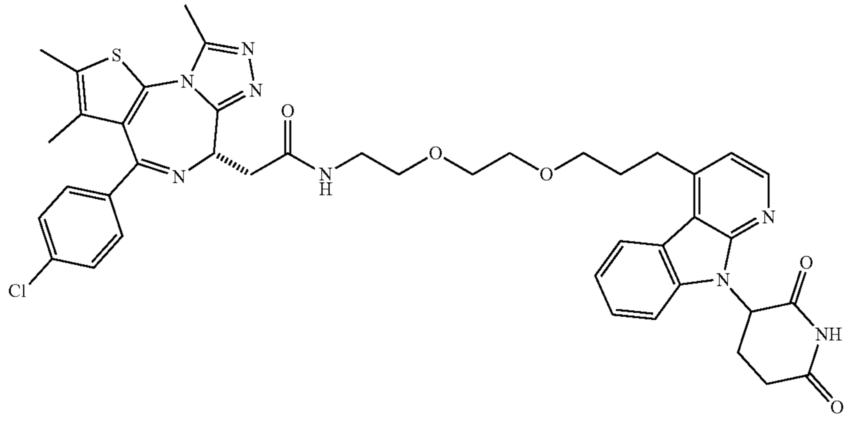 [SMILES: Cc1sc2c(c1C)C(c1ccc(Cl)cc1)=N[C@@H](CC(=O)NCCOCCOCCCc1ccnc3c1c1ccccc1n3C1CCC(=O)NC1=O)c1nnc(C)n1-2] |
| I-14 | 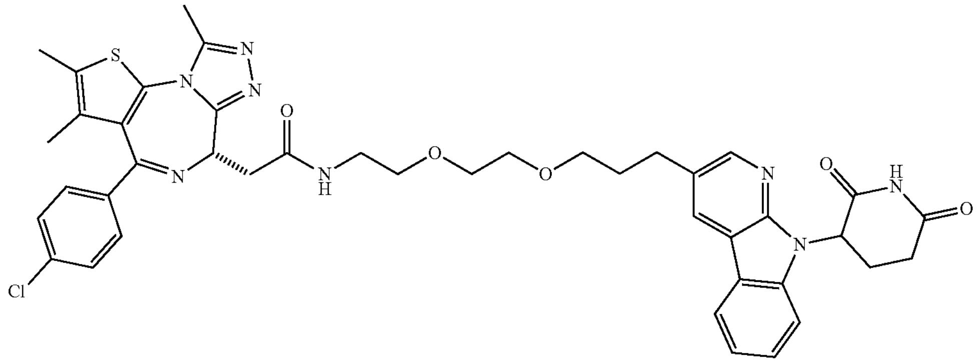 [SMILES: Cc1sc2c(c1C)C(c1ccc(Cl)cc1)=N[C@@H](CC(=O)NCCOCCOCCCc1cnc3c(c1)c1ccccc1n3C1CCC(=O)NC1=O)c1nnc(C)n1-2] |

TABLE 1-continued
| Exemplary Compounds | |
|---|---|
| I-# | Structure |
| I-15 | 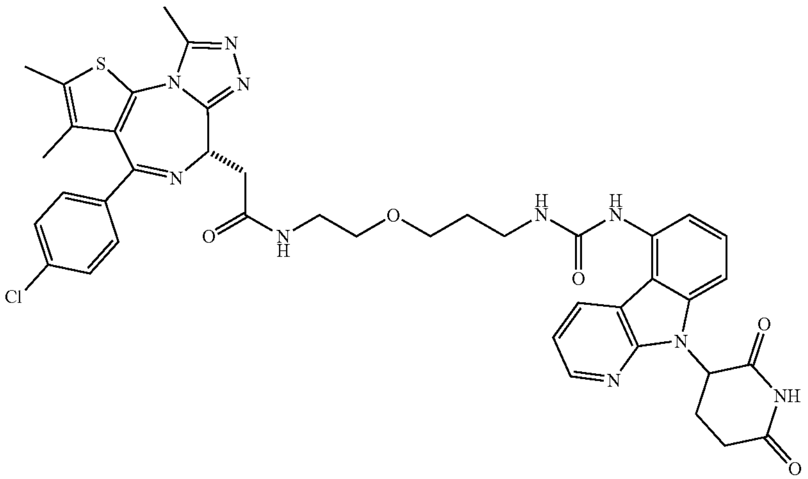 [SMILES: Cc1sc2c(c1C)C(c1ccc(Cl)cc1)=N[C@@H](CC(=O)NCCOCCCNC(=O)Nc1cccc3c1c1cccnc1n3C1CCC(=O)NC1=O)c1nnc(C)n1-2] |
| I-16 | 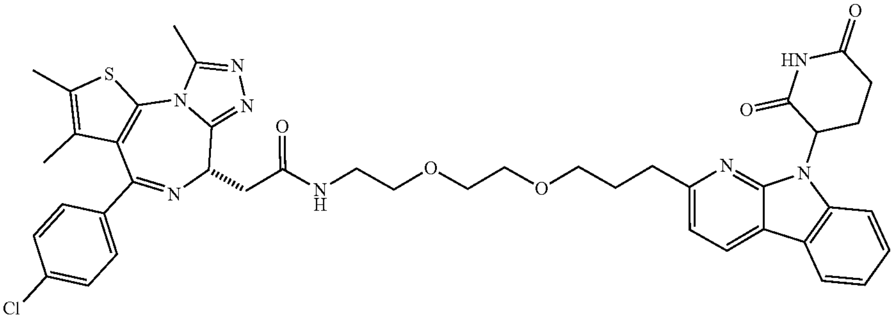 [SMILES: Cc1sc2c(c1C)C(c1ccc(Cl)cc1)=N[C@@H](CC(=O)NCCOCCOCCCc1ccc3c4ccccc4n(C4CCC(=O)NC4=O)c3n1)c1nnc(C)n1-2] |
| I-17 | 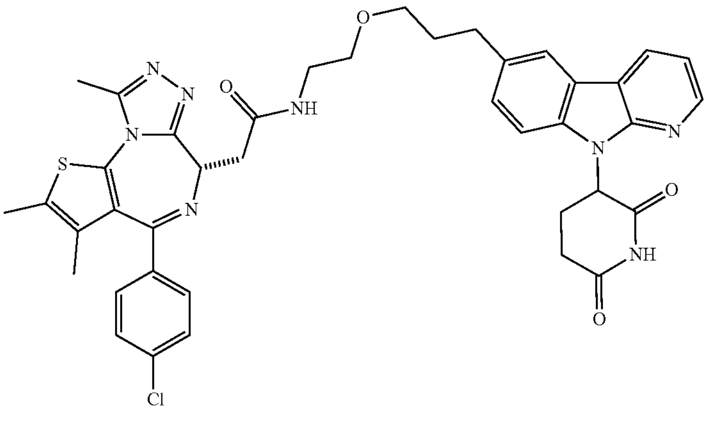 |

TABLE 1-continued
| Exemplary Compounds | |
|---|---|
| I-# | Structure |
| I-18 | 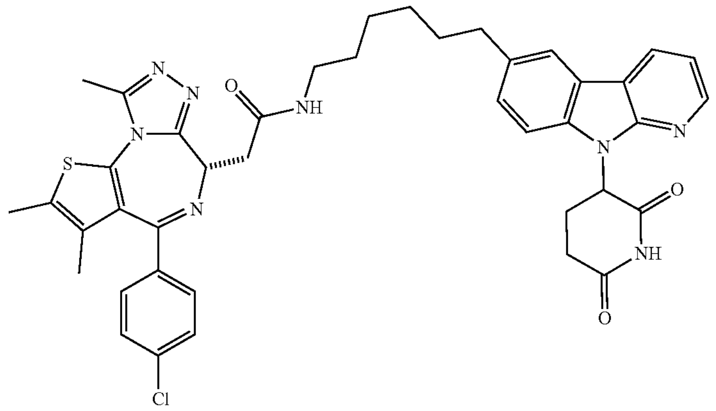 [SMILES: Cc1sc2c(c1C)C(c1ccc(Cl)cc1)=N[C@@H](CC(=O)NCCOCCCc1ccc3c(c1)c1cccnc1n3C1CCC(=O)NC1=O)c1nnc(C)n1-2] |
| I-19 | 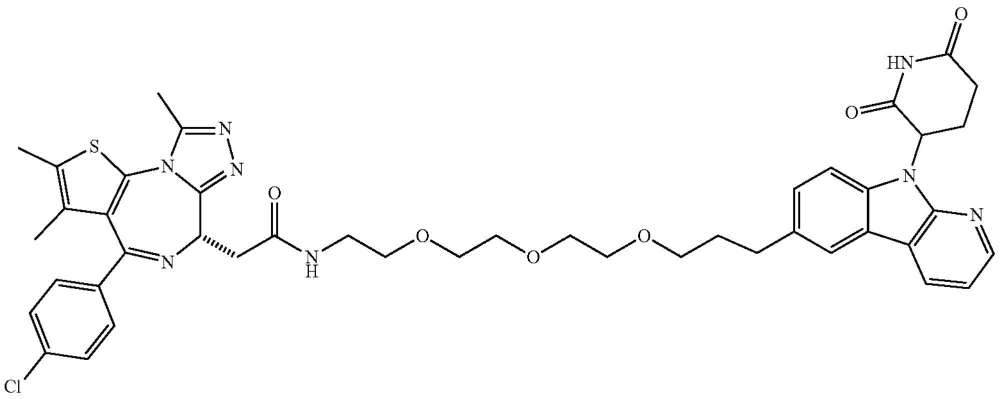 [SMILES: Cc1sc2c(c1C)C(c1ccc(Cl)cc1)=N[C@@H](CC(=O)NCCOCCOCCOCCCc1ccc3c(c1)c1cccnc1n3C1CCC(=O)NC1=O)c1nnc(C)n1-2] |
| I-20 | 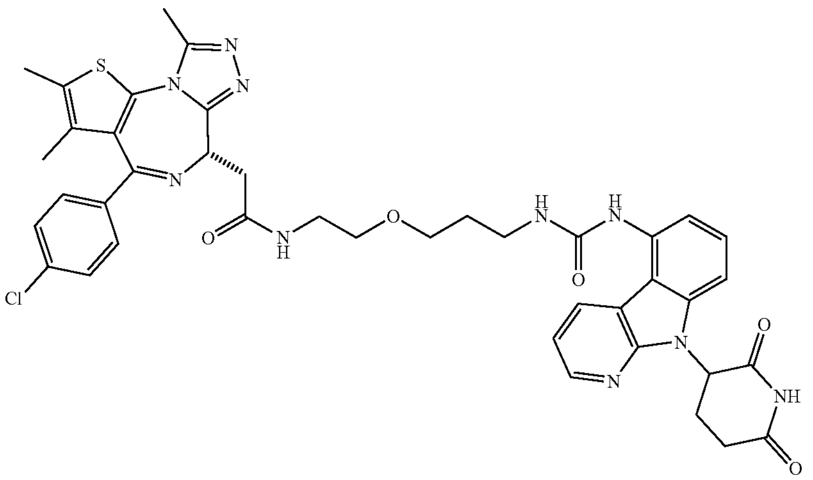 [SMILES: Cc1sc2c(c1C)C(c1ccc(Cl)cc1)=N[C@@H](CC(=O)NCCOCCCNC(=O)Nc1cccc3c1c1cccnc1n3C1CCC(=O)NC1=O)c1nnc(C)n1-2] |

TABLE 1-continued
| Exemplary Compounds | |
|---|---|
| I-# | Structure |
| I-21 | 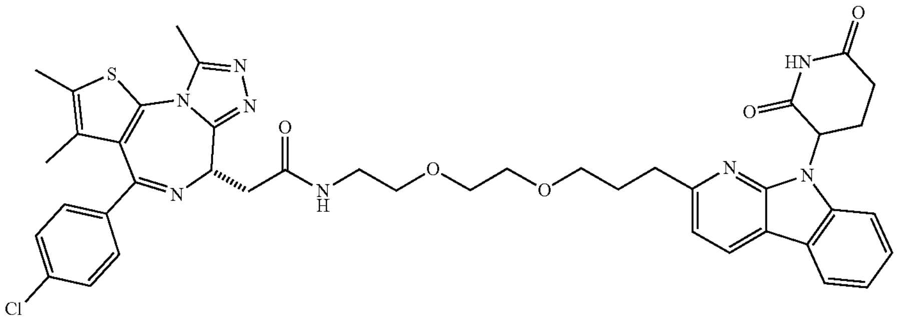 [SMILES: Cc1sc2c(c1C)C(c1ccc(Cl)cc1)=N[C@@H](CC(=O)NCCOCCOCCCc1ccc3c4ccccc4n(C4CCC(=O)NC4=O)c3n1)c1nnc(C)n1-2] |
| I-22 | 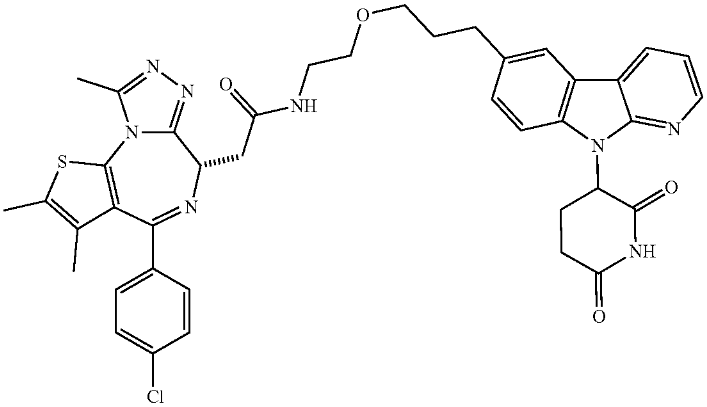 |
| I-23 | 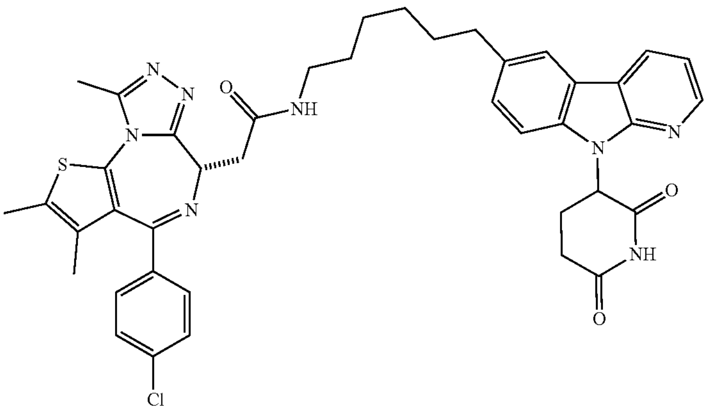 [SMILES: Cc1sc2c(c1C)C(c1ccc(Cl)cc1)=N[C@@H](CC(=O)NCCOCCCc1ccc3c(c1)c1cccnc1n3C1CCC(=O)NC1=O)c1nnc(C)n1-2] |
| I-24 | 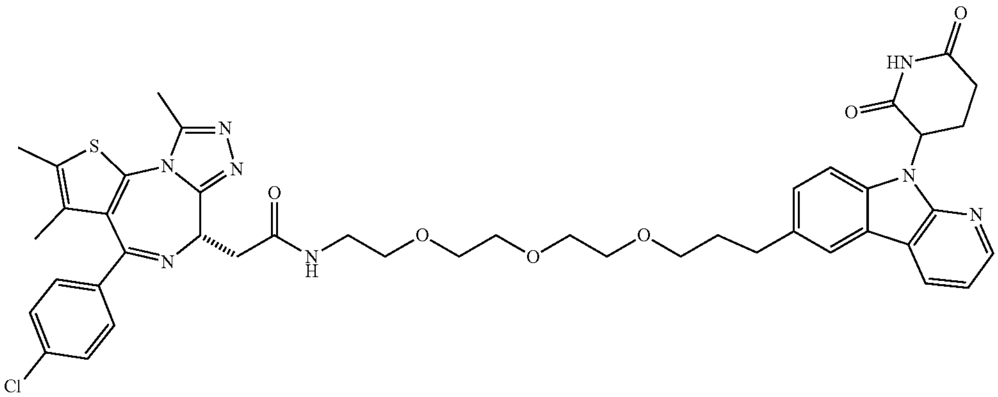 |

TABLE 1-continued
| Exemplary Compounds | |
|---|---|
| I-# | Structure |
| I-25 | 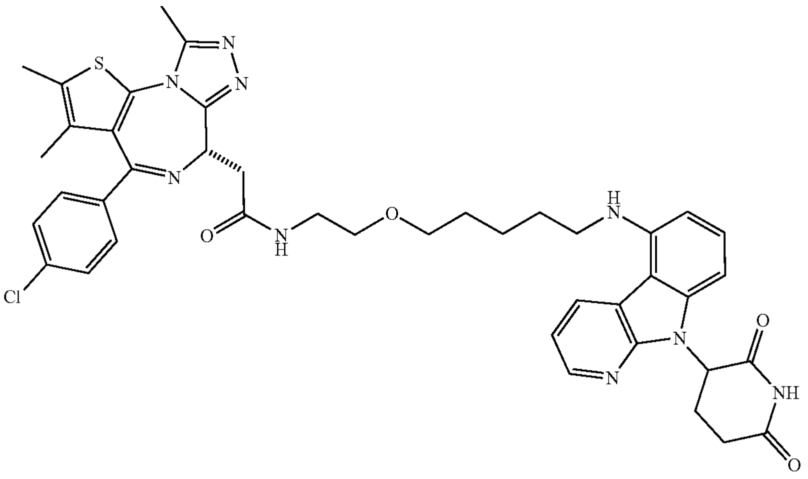 [SMILES: Cc1sc2c(c1C)C(c1ccc(Cl)cc1)=N[C@@H](CC(=O)NCCOCCCCCNc1cccc3c1c1cccnc1n3C1CCC(=O)NC1=O)c1nnc(C)n1-2] |
| I-26 | 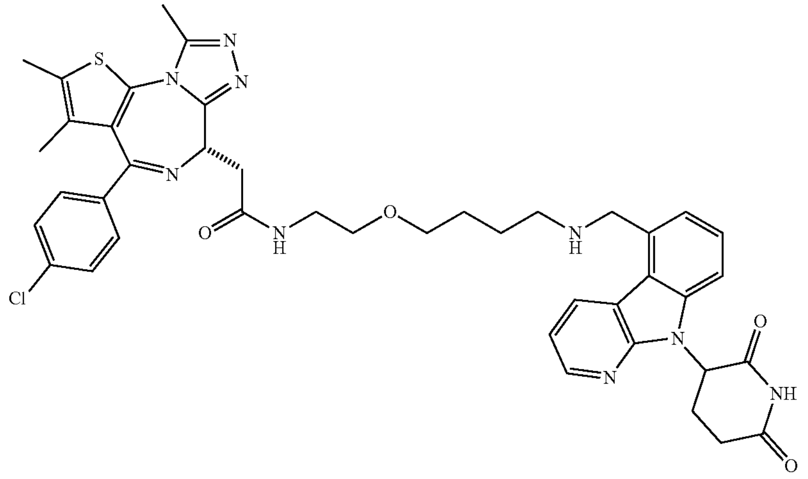 [SMILES: Cc1sc2c(c1C)C(c1ccc(Cl)cc1)=N[C@@H](CC(=O)NCCOCCCCNCc1cccc3c1c1cccnc1n3C1CCC(=O)NC1=O)c1nnc(C)n1-2] |
| I-27 | 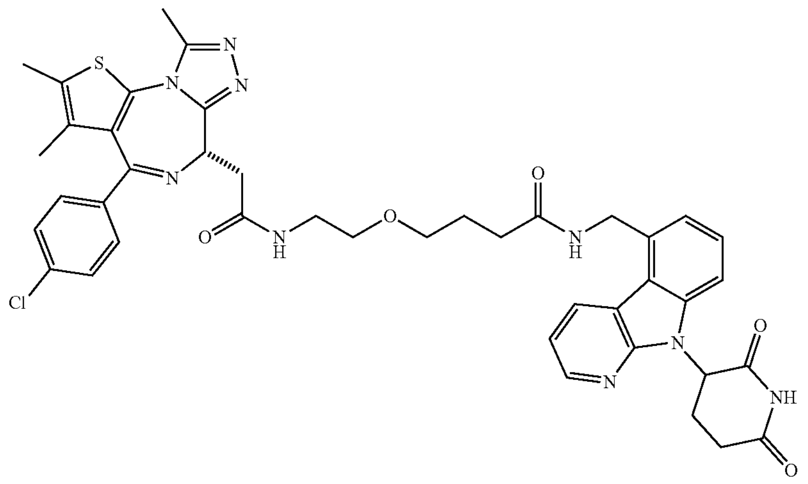 [SMILES: Cc1sc2c(c1C)C(c1ccc(Cl)cc1)=N[C@@H](CC(=O)NCCOCCCC(=O)NCc1cccc3c1c1cccnc1n3C1CCC(=O)NC1=O)c1nnc(C)n1-2] |

TABLE 1-continued
| Exemplary Compounds | |
|---|---|
| I-# | Structure |
| I-28 | 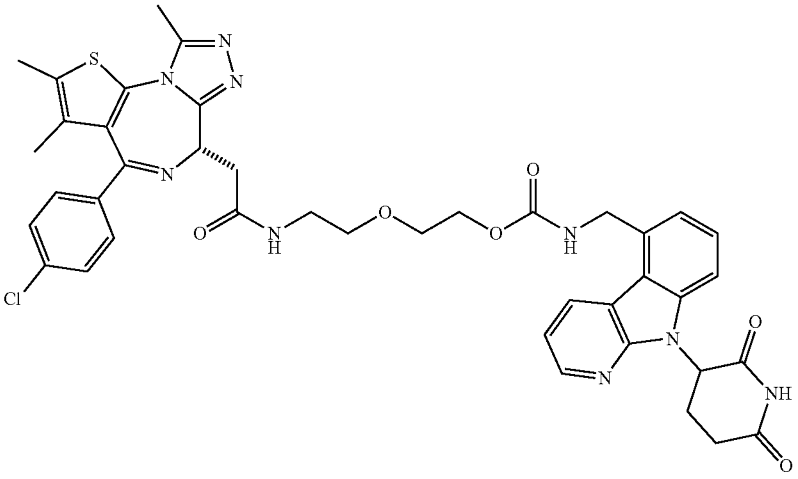 [SMILES: Cc1sc2c(c1C)C(c1ccc(Cl)cc1)=N[C@@H](CC(=O)NCCOCCOC(=O)NCc1cccc3c1c1cccnc1n3C1CCC(=O)NC1=O)c1nnc(C)n1-2] |
| I-29 | 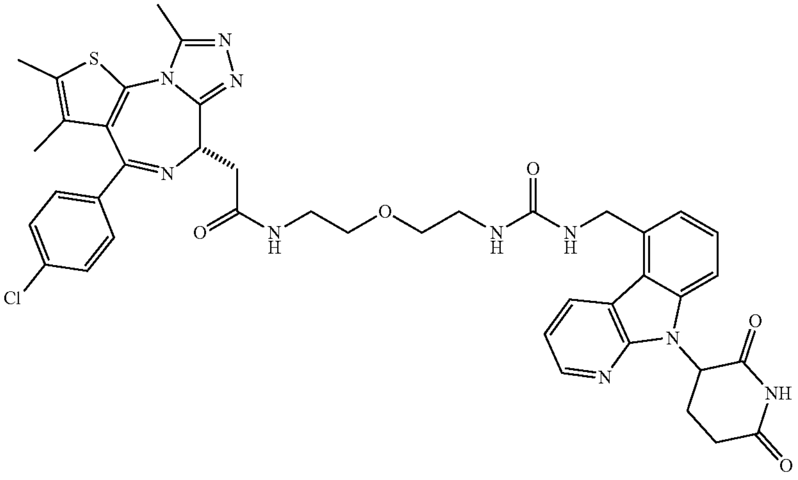 [SMILES: Cc1sc2c(c1C)C(c1ccc(Cl)cc1)=N[C@@H](CC(=O)NCCOCCNC(=O)NCc1cccc3c1c1cccnc1n3C1CCC(=O)NC1=O)c1nnc(C)n1-2] |
| I-30 | 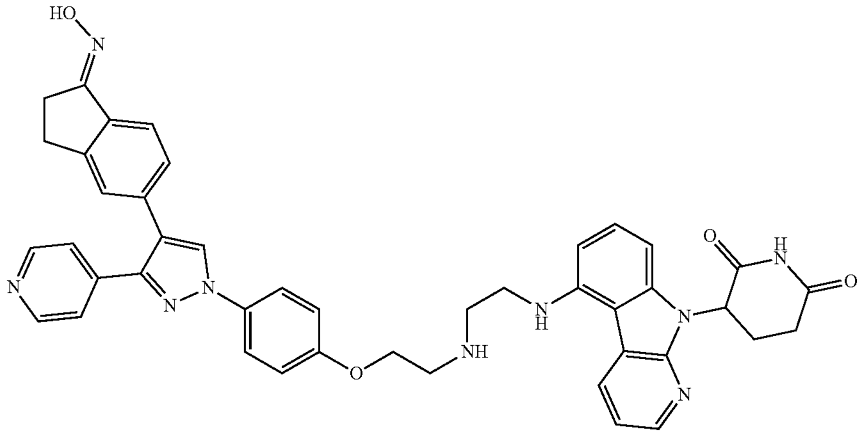 [SMILES: O=C1CCC(n2c3cccc(NCCNCCOc4ccc(-n5cc(-c6ccc7c(c6)CC/C7=N\O)c(-c6ccncc6)n5)cc4)c3c3cccnc32)C(=O)N1] |

TABLE 1-continued
| Exemplary Compounds | |
|---|---|
| I-# | Structure |
| I-31 | 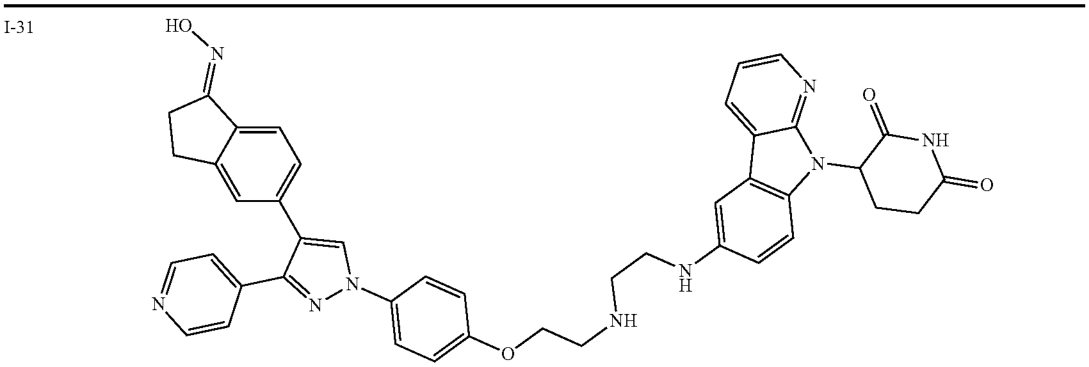 |
| I-32 | 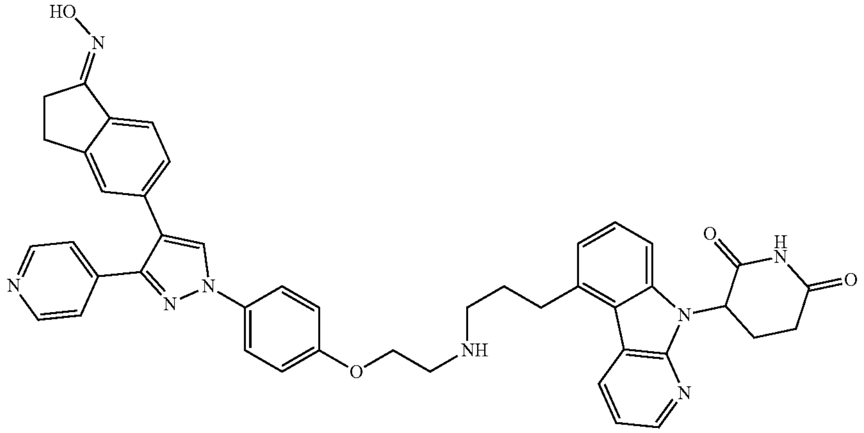 [SMILES: O=C1CCC(n2c3cccc(CCCNCCOc4ccc(-n5cc(-c6ccc7c(c6)CC/C7=N\O)c(-c6ccncc6)n5)cc4)c3c3cccnc32)C(=O)N1] |
| I-33 | 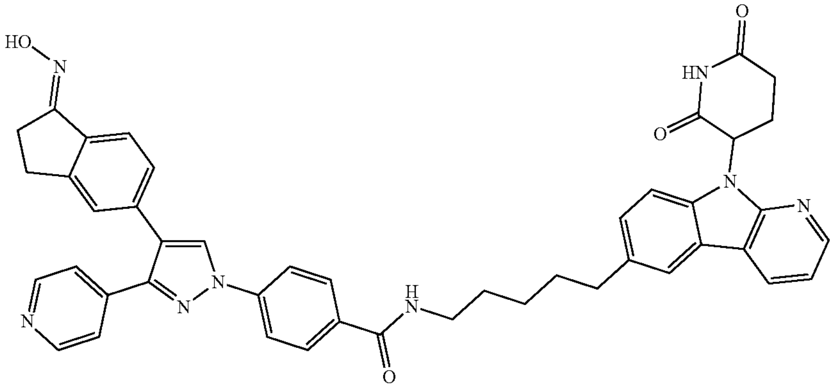 [SMILES: O=C1CCC(n2c3ccc(CCCCCNC(=O)c4ccc(-n5cc(-c6ccc7c(c6)CC/C7=N\O)c(-c6ccncc6)n5)cc4)cc3c3cccnc32)C(=O)N1] |
| I-34 | 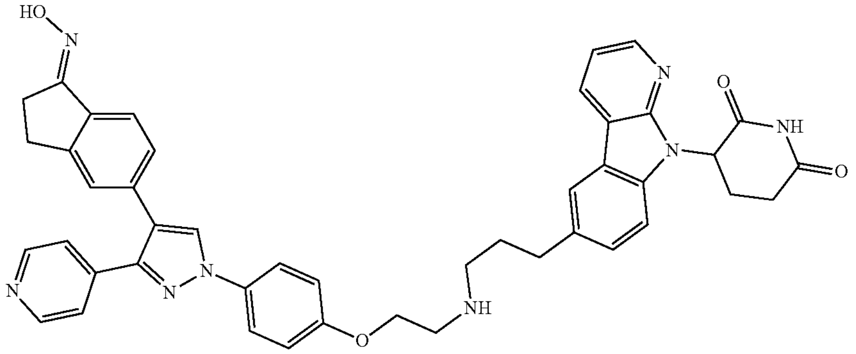 [SMILES: O=C1CCC(n2c3ccc(CCCNCCOc4ccc(-n5cc(-c6ccc7c(c6)CC/C7=N\O)c(-c6ccncc6)n5)cc4)cc3c3cccnc32)C(=O)N1] |

TABLE 1-continued
| Exemplary Compounds | |
|---|---|
| I-# | Structure |
| I-35 | 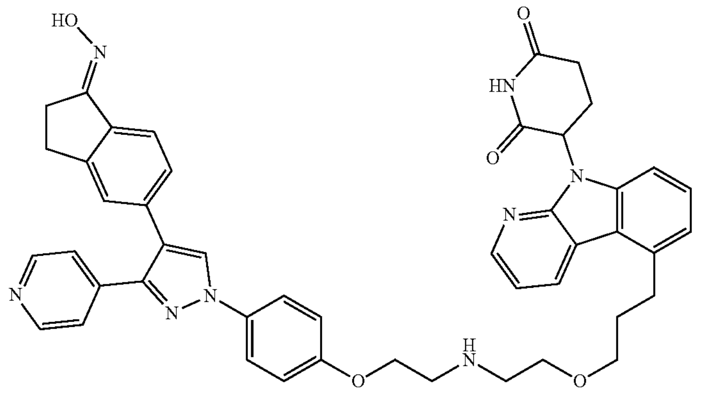 [SMILES: O=C1CCC(n2c3cccc(CCCOCCNCCOc4ccc(-n5cc(-c6ccc7c(c6)CC/C7=N\O)c(-c6ccncc6)n5)cc4)c3c3cccnc32)C(=O)N1] |
| I-36 | 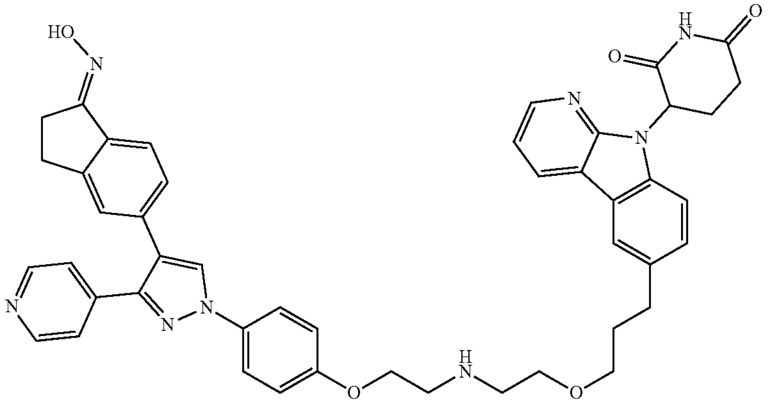 [SMILES: O=C1CCC(n2c3ccc(CCCOCCNCCOc4ccc(-n5cc(-c6ccc7c(c6)CC/C7=N\O)c(-c6ccncc6)n5)cc4)cc3c3cccnc32)C(=O)N1] |
| I-37 | 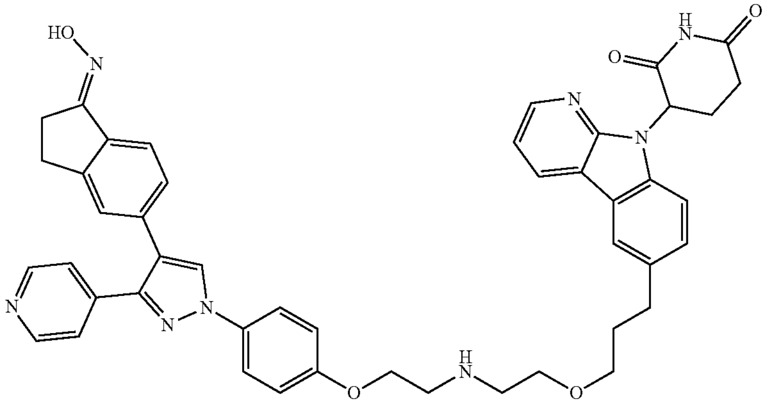 [SMILES: O=C1CCC(n2c3ccc(CCCOCCNCCOc4ccc(-n5cc(-c6ccc7c(c6)CC/C7=N\O)c(-c6ccncc6)n5)cc4)cc3c3cccnc32)C(=O)N1] |

TABLE 1-continued
| Exemplary Compounds | |
|---|---|
| I-# | Structure |
| I-38 | 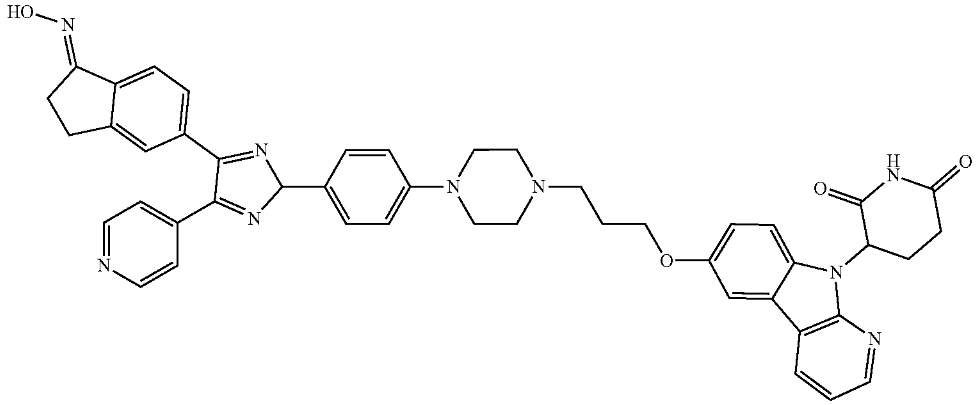 [SMILES: O=C1CCC(n2c3ccc(OCCCN4CCN(c5ccc(C6N=C(c7ccncc7)C(c7ccc8c(c7)CC/C8=N\O)=N6)cc5)CC4)cc3c3cccnc32)C(=O)N1] |
| I-39 | 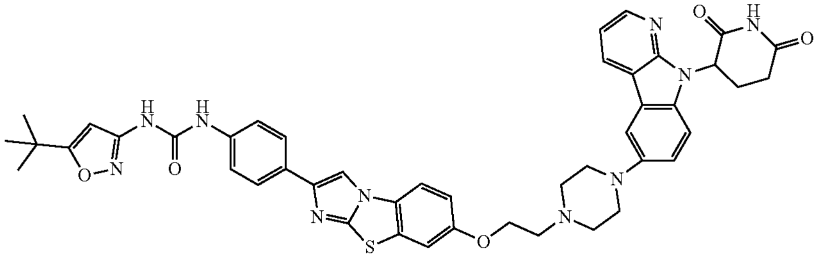 [SMILES: CC(C)(C)c1cc(NC(=O)Nc2ccc(-c3cn4c(n3)sc3cc(OCCN5CCN(c6ccc7c(c6)c6cccnc6n7C6CCC(=O)NC6=O)CC5)ccc34)cc2)no1] |
| I-40 | 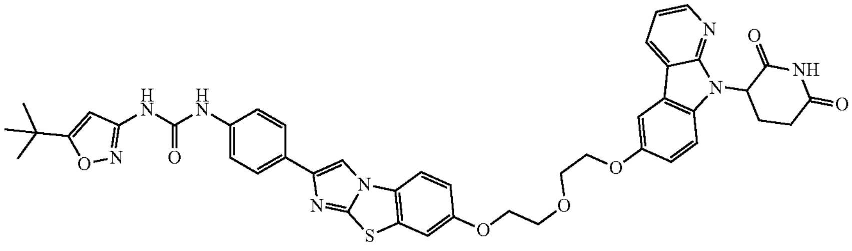 [SMILES: CC(C)(C)c1cc(NC(=O)Nc2ccc(-c3cn4c(n3)sc3cc(OCCOCCOc5ccc6c(c5)c5cccnc5n6C5CCC(=O)NC5=O)ccc34)cc2)no1] |
| I-41 | 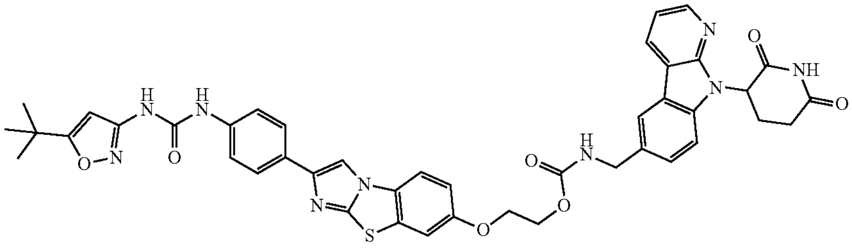 [SMILES: CC(C)(C)c1cc(NC(=O)Nc2ccc(-c3cn4c(n3)sc3cc(OCCOC(=O)NCc5ccc6c(c5)c5cccnc5n6C5CCC(=O)NC5=O)ccc34)cc2)no1] |
| I-42 | 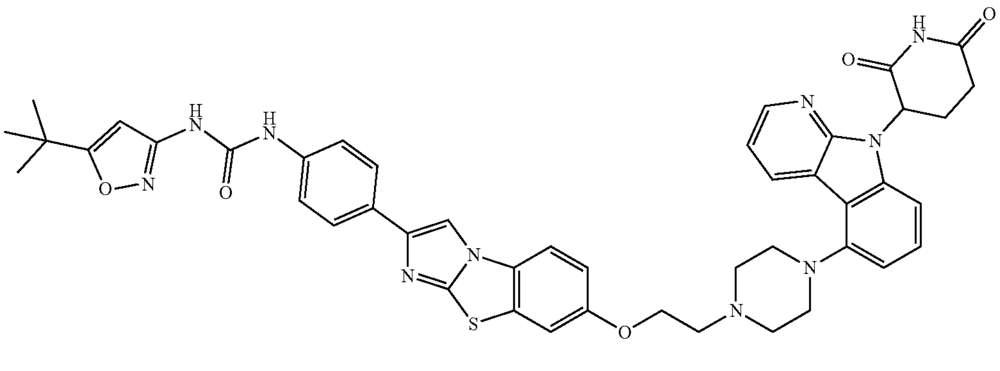 [SMILES: CC(C)(C)c1cc(NC(=O)Nc2ccc(-c3cn4c(n3)sc3cc(OCCN5CCN(c6cccc7c6c6cccnc6n7C6CCC(=O)NC6=O)CC5)ccc34)cc2)no1] |

TABLE 1-continued
| Exemplary Compounds | |
|---|---|
| I-# | Structure |
| I-43 | 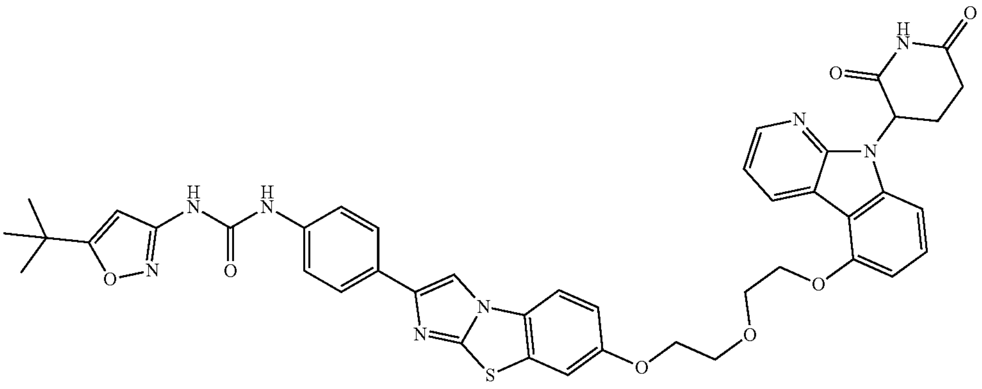 [SMILES: CC(C)(C)c1cc(NC(=O)Nc2ccc(-c3cn4c(n3)sc3cc(OCCOCCOc5cccc6c5c5cccnc5n6C5CCC(=O)NC5=O)ccc34)cc2)no1] |
| I-44 | 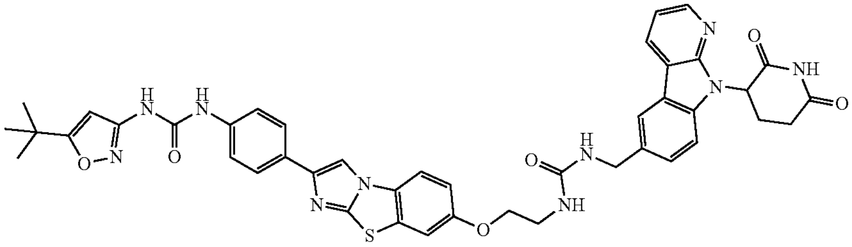 [SMILES: CC(C)(C)c1cc(NC(=O)Nc2ccc(-c3cn4c(n3)sc3cc(OCCNC(=O)NCc5ccc6c(c5)c5cccnc5n6C5CCC(=O)NC5=O)ccc34)cc2)no1] |
| I-45 | 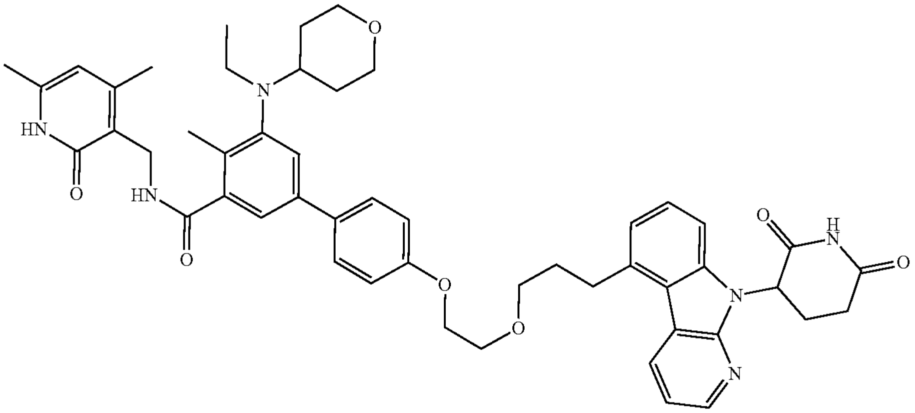 [SMILES: CCN(c1cc(-c2ccc(OCCOCCCc3cccc4c3c3cccnc3n4C3CCC(=O)NC3=O)cc2)cc(C(=O)NCc2c(C)cc(C)[nH]c2=O)c1C)C1CCOCC1] |
| I-46 | 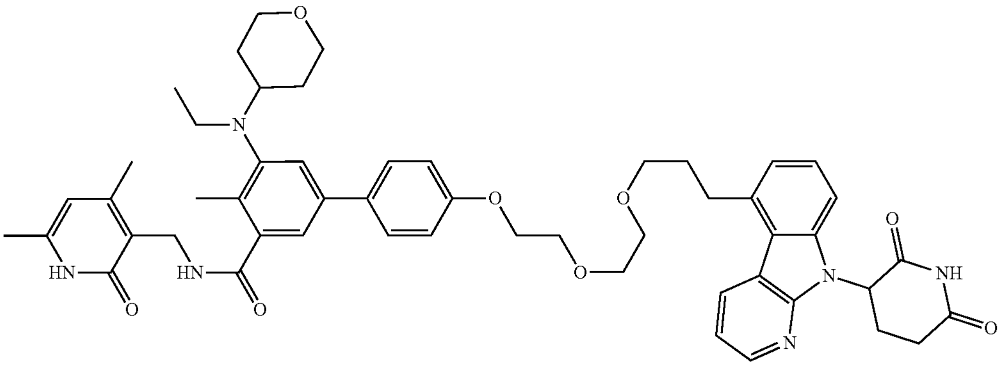 |

TABLE 1-continued
| Exemplary Compounds | |
|---|---|
| I-# | Structure |
| I-47 | 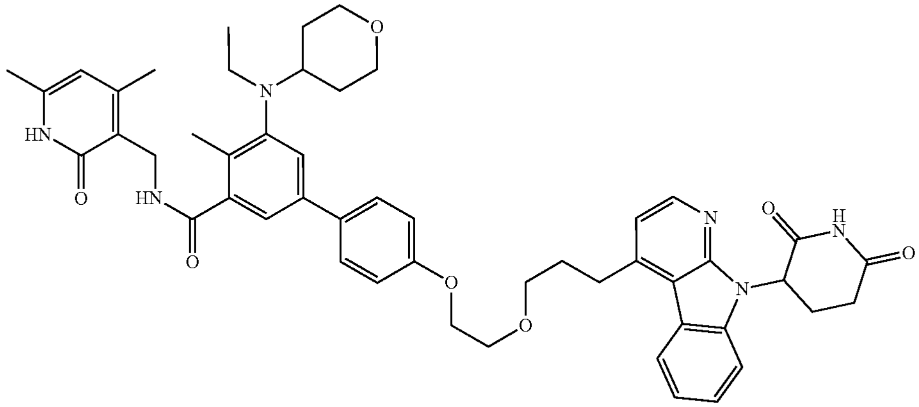 [SMILES: CCN(c1cc(-c2ccc(OCCOCCCc3ccnc4c3c3ccccc3n4C3CCC(=O)NC3=O)cc2)cc(C(=O)NCc2c(C)cc(C)[nH]c2=O)c1C)C1CCOCC1] |
| I-48 | 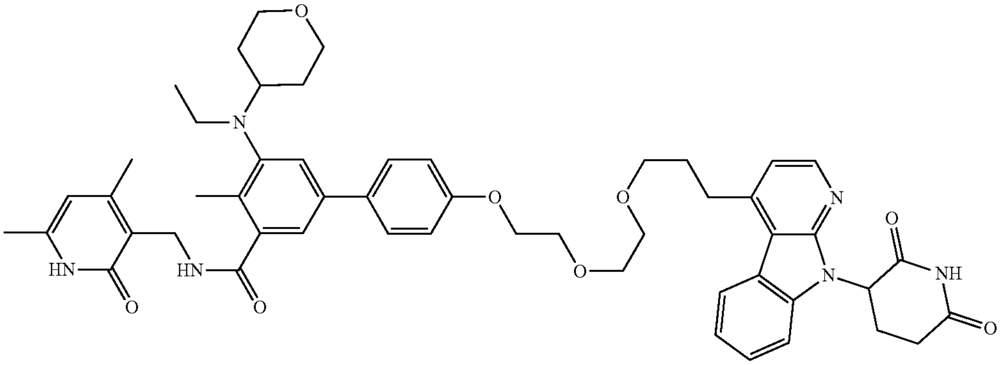 [SMILES: CCN(c1cc(-c2ccc(OCCOCCOCCCc3ccnc4c3c3ccccc3n4C3CCC(=O)NC3=O)cc2)cc(C(=O)NCc2c(C)cc(C)[nH]c2=O)c1C)C1CCOCC1] |
| I-49 | 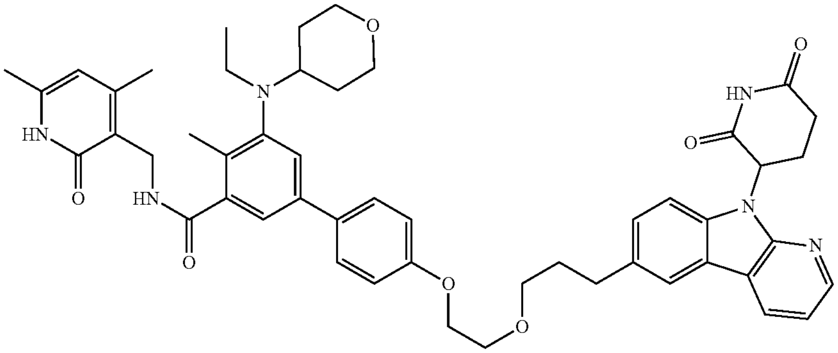 [SMILES: CCN(c1cc(-c2ccc(OCCOCCCc3ccc4c(c3)c3cccnc3n4C3CCC(=O)NC3=O)cc2)cc(C(=O)NCc2c(C)cc(C)[nH]c2=O)c1C)C1CCOCC1] |
| I-50 | 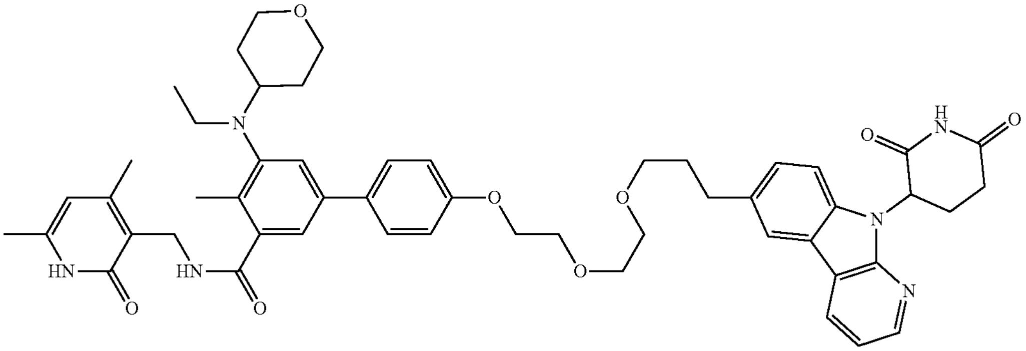 [SMILES: CCN(c1cc(-c2ccc(OCCOCCOCCCc3ccc4c(c3)c3cccnc3n4C3CCC(=O)NC3=O)cc2)cc(C(=O)NCc2c(C)cc(C)[nH]c2=O)c1C)C1CCOCC1] |

TABLE 1-continued
| Exemplary Compounds | |
|---|---|
| I-# | Structure |
| I-51 | 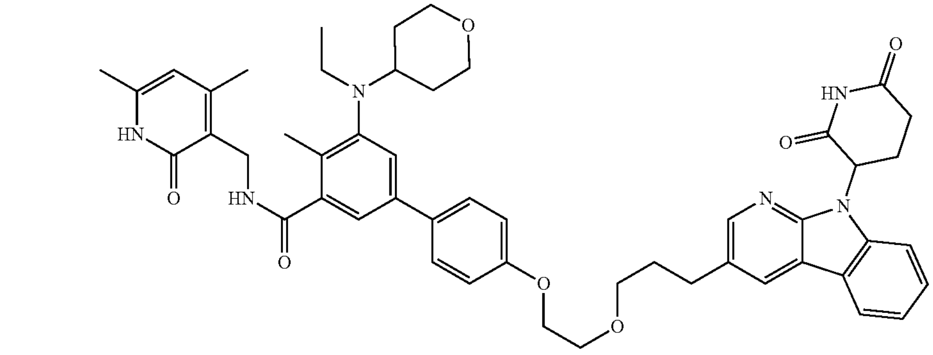 [SMILES: CCN(c1cc(-c2ccc(OCCOCCCc3cnc4c(c3)c3ccccc3n4C3CCC(=O)NC3=O)cc2)cc(C(=O)NCc2c(C)cc(C)[nH]c2=O)c1C)C1CCOCC1] |
| I-52 | 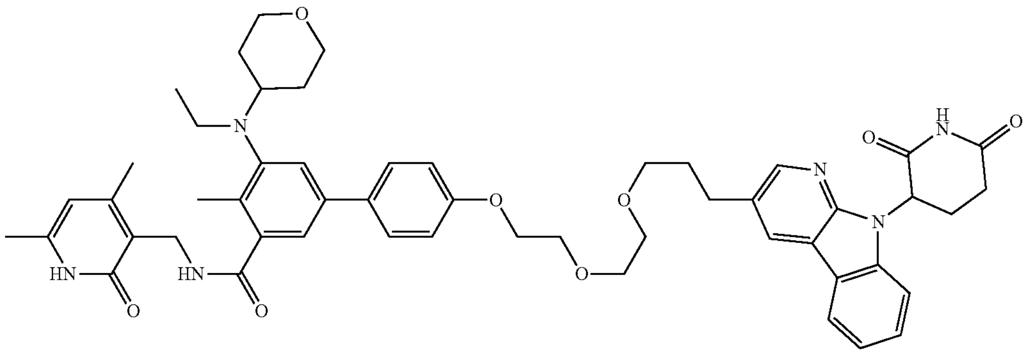 [SMILES: CCN(c1cc(-c2ccc(OCCOCCOCCCc3cnc4c(c3)c3ccccc3n4C3CCC(=O)NC3=O)cc2)cc(C(=O)NCc2c(C)cc(C)[nH]c2=O)c1C)C1CCOCC1] |
| I-53 | 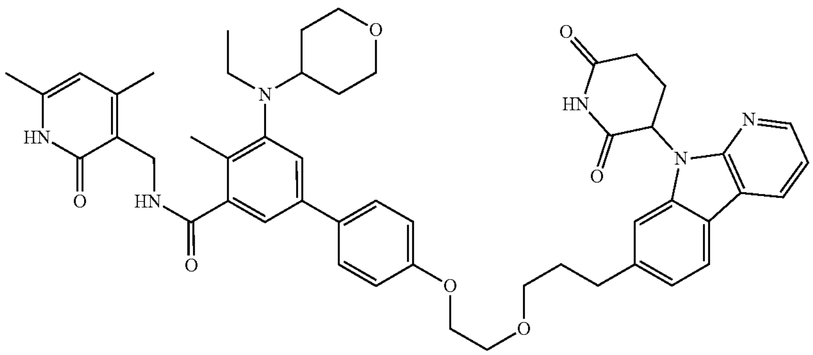 [SMILES: CCN(c1cc(-c2ccc(OCCOCCCc3ccc4c5cccnc5n(C5CCC(=O)NC5=O)c4c3)cc2)cc(C(=O)NCc2c(C)cc(C)[nH]c2=O)c1C)C1CCOCC1] |
| I-54 | 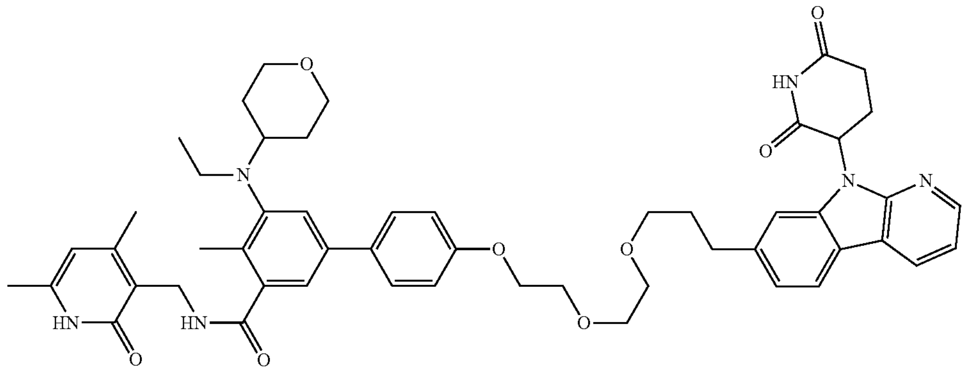 [SMILES: CCN(c1cc(-c2ccc(OCCOCCOCCCc3ccc4c5cccnc5n(C5CCC(=O)NC5=O)c4c3)cc2)cc(C(=O)NCc2c(C)cc(C)[nH]c2=O)c1C)C1CCOCC1] |

TABLE 1-continued
| Exemplary Compounds | |
|---|---|
| I-# | Structure |
| I-55 | 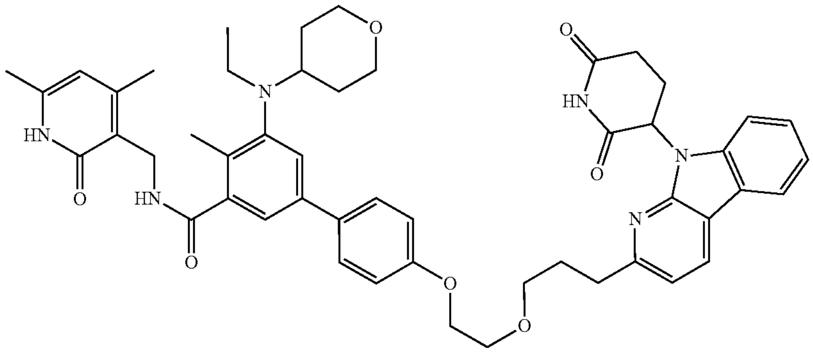 [SMILES: CCN(c1cc(-c2ccc(OCCOCCCc3ccc4c5ccccc5n(C5CCC(=O)NC5=O)c4n3)cc2)cc(C(=O)NCc2c(C)cc(C)[nH]c2=O)c1C)C1CCOCC1] |
| I-56 | 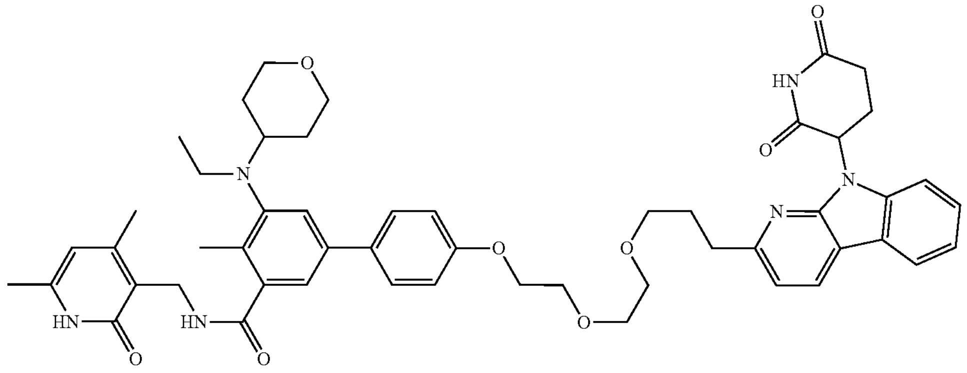 |
| I-57 | 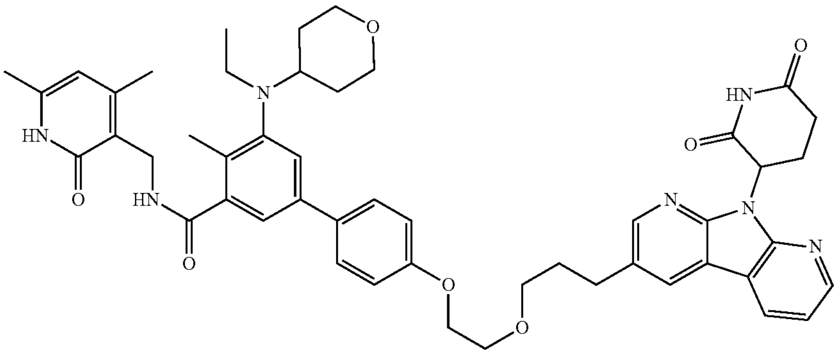 [SMILES: CCN(c1cc(-c2ccc(OCCOCCCc3cnc4c(c3)c3cccnc3n4C3CCC(=O)NC3=O)cc2)cc(C(=O)NCc2c(C)cc(C)[nH]c2=O)c1C)C1CCOCC1] |
| I-58 | 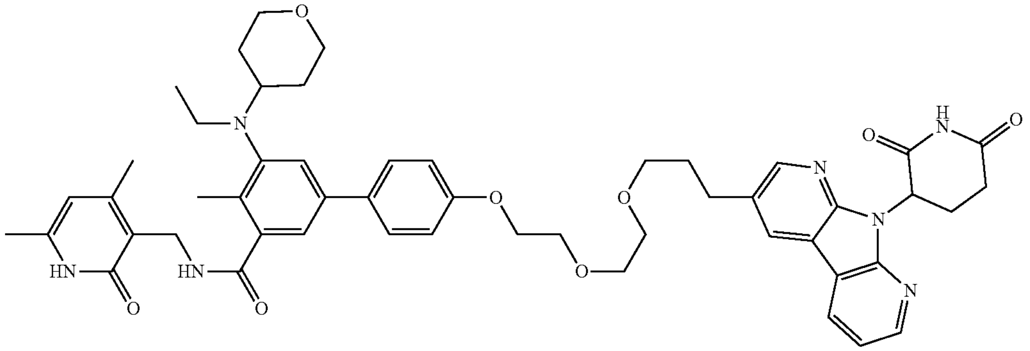 [SMILES: CCN(c1cc(-c2ccc(OCCOCCOCCCc3cnc4c(c3)c3cccnc3n4C3CCC(=O)NC3=O)cc2)cc(C(=O)NCc2c(C)cc(C)[nH]c2=O)c1C)C1CCOCC1] |

TABLE 1-continued
| Exemplary Compounds | |
|---|---|
| I-# | Structure |
| I-59 | 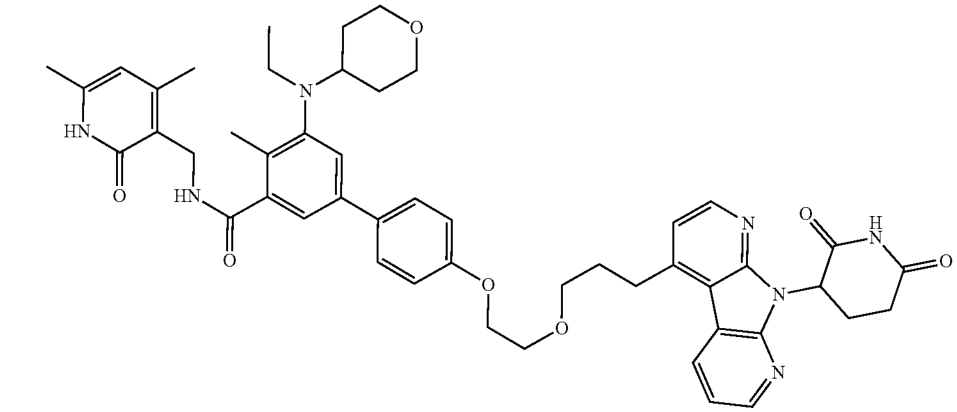 [SMILES: CCN(c1cc(-c2ccc(OCCOCCCc3ccnc4c3c3cccnc3n4C3CCC(=O)NC3=O)cc2)cc(C(=O)NCc2c(C)cc(C)[nH]c2=O)c1C)C1CCOCC1] |
| I-60 | 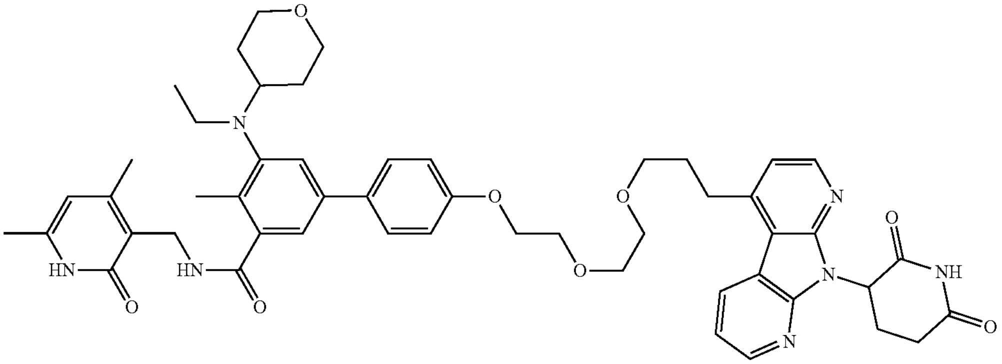 [SMILES: CCN(c1cc(-c2ccc(OCCOCCOCCCc3ccnc4c3c3cccnc3n4C3CCC(=O)NC3=O)cc2)cc(C(=O)NCc2c(C)cc(C)[nH]c2=O)c1C)C1CCOCC1] |
| I-61 | 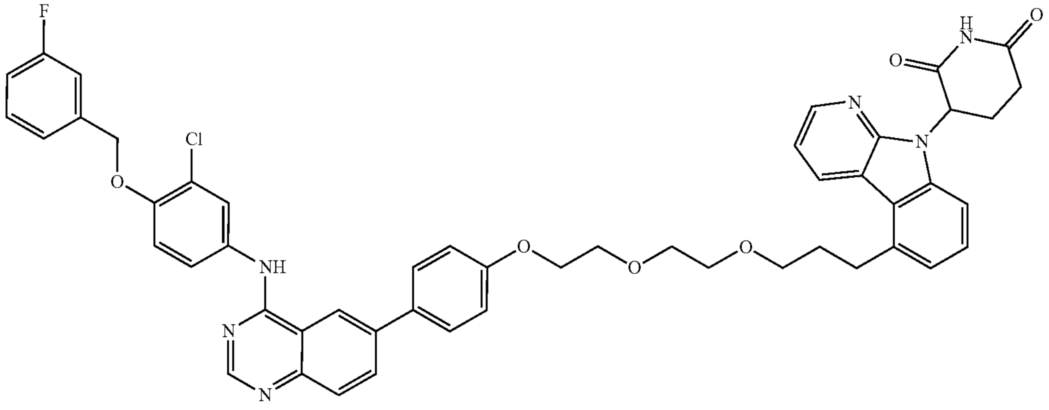 [SMILES: O=C1CCC(n2c3cccc(CCCOCCOCCOc4ccc(-c5ccc6ncnc(Nc7ccc(OCc8cccc(F)c8)c(Cl)c7)c6c5)cc4)c3c3cccnc32)C(=O)N1] |
| I-62 | 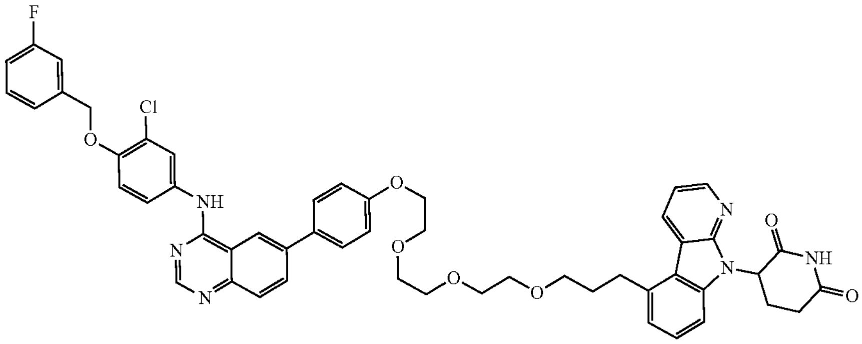 [SMILES: O=C1CCC(n2c3cccc(CCCOCCOCCOCCOc4ccc(-c5ccc6ncnc(Nc7ccc(OCc8cccc(F)c8)c(Cl)c7)c6c5)cc4)c3c3cccnc32)C(=O)N1] |

TABLE 1-continued
| Exemplary Compounds | |
|---|---|
| I-# | Structure |
| I-63 | 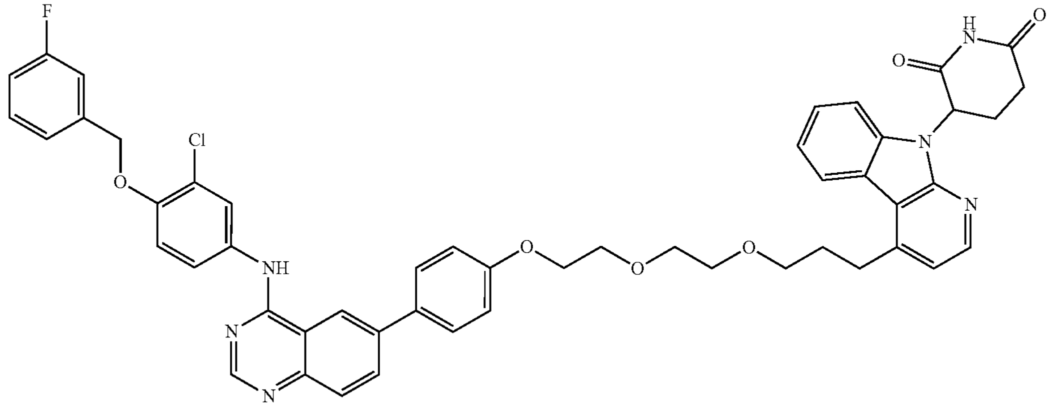 |
| I-64 | 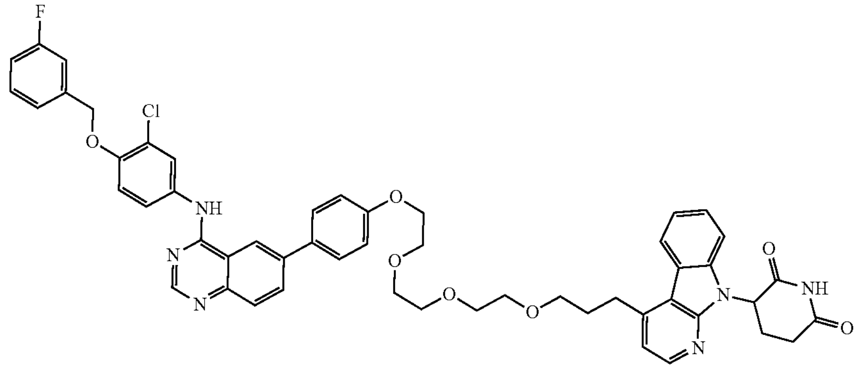 [SMILES: O=C1CCC(n2c3ccccc3c3c(CCCOCCOCCOCCOc4ccc(-c5ccc6ncnc(Nc7ccc(OCc8cccc(F)c8)c(Cl)c7)c6c5)cc4)ccnc32)C(=O)N1] |
| I-65 | 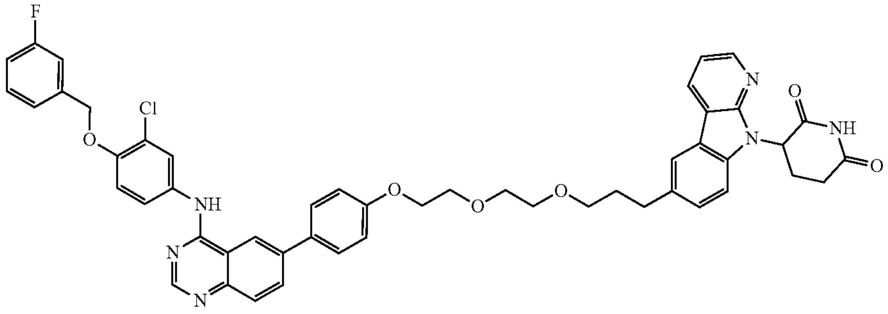 [SMILES: O=C1CCC(n2c3ccc(CCCOCCOCCOc4ccc(-c5ccc6ncnc(Nc7ccc(OCc8cccc(F)c8)c(Cl)c7)c6c5)cc4)cc3c3cccnc32)C(=O)N1] |
| I-66 | 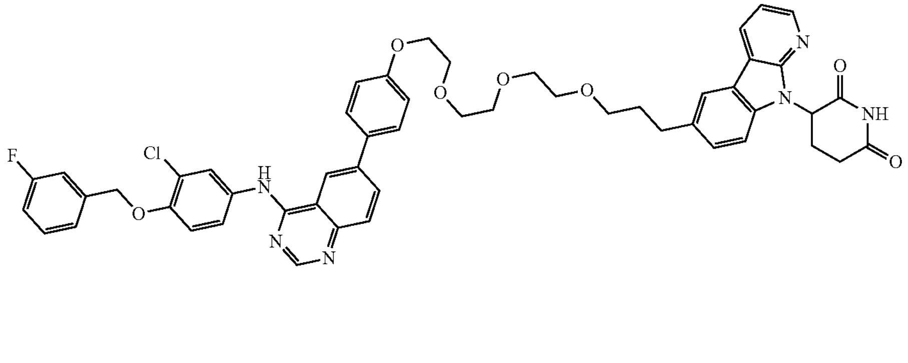 |

TABLE 1-continued
| Exemplary Compounds | |
|---|---|
| I-# | Structure |
| I-67 | 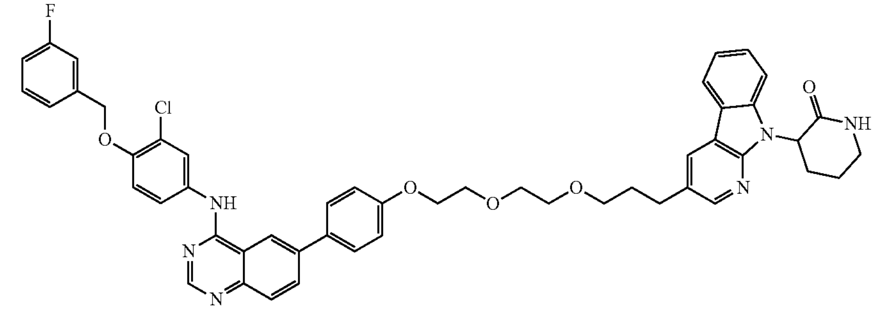 [SMILES: O=C1NCCCC1n1c2ccccc2c2cc(CCCOCCOCCOc3ccc(-c4ccc5ncnc(Nc6ccc(OCc7cccc(F)c7)c(Cl)c6)c5c4)cc3)cnc21] |
| I-68 | 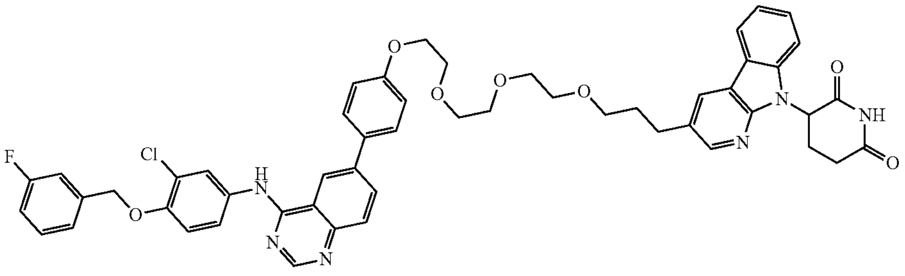 [SMILES: O=C1CCC(n2c3ccccc3c3cc(CCCOCCOCCOCCOc4ccc(-c5ccc6ncnc(Nc7ccc(OCc8cccc(F)c8)c(Cl)c7)c6c5)cc4)cnc32)C(=O)N1] |
| I-69 | 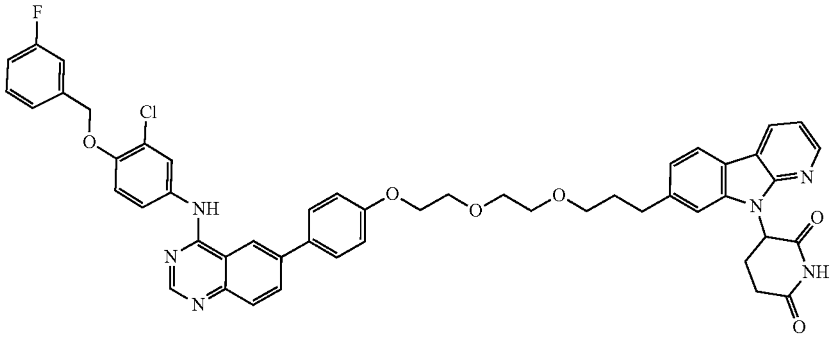 [SMILES: O=C1CCC(n2c3cc(CCCOCCOCCOc4ccc(-c5ccc6ncnc(Nc7ccc(OCc8cccc(F)c8)c(Cl)c7)c6c5)cc4)ccc3c3cccnc32)C(=O)N1] |
| I-70 | 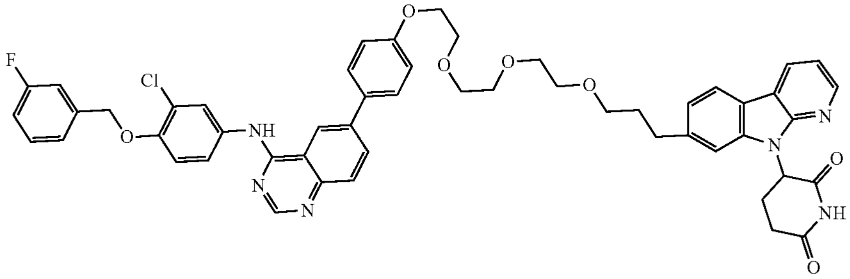 [SMILES: O=C1CCC(n2c3cc(CCCOCCOCCOCCOc4ccc(-c5ccc6ncnc(Nc7ccc(OCc8cccc(F)c8)c(Cl)c7)c6c5)cc4)ccc3c3cccnc32)C(=O)N1] |
| I-71 | 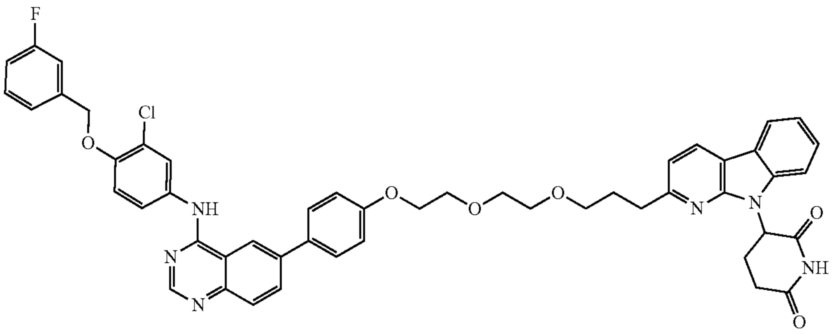 [SMILES: O=C1CCC(n2c3ccccc3c3ccc(CCCOCCOCCOc4ccc(-c5ccc6ncnc(Nc7ccc(OCc8cccc(F)c8)c(Cl)c7)c6c5)cc4)nc32)C(=O)N1] |

TABLE 1-continued
| Exemplary Compounds | |
|---|---|
| I-# | Structure |
| I-72 | 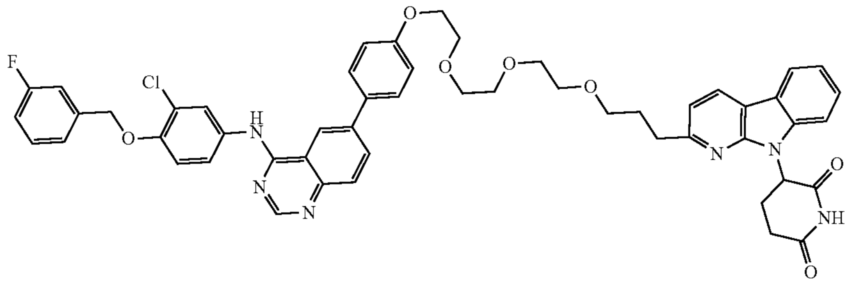 [SMILES: O=C1CCC(n2c3ccccc3c3ccc(CCCOCCOCCOCCOc4ccc(-c5ccc6ncnc(Nc7ccc(OCc8cccc(F)c8)c(Cl)c7)c6c5)cc4)nc32)C(=O)N1] |
| I-73 | 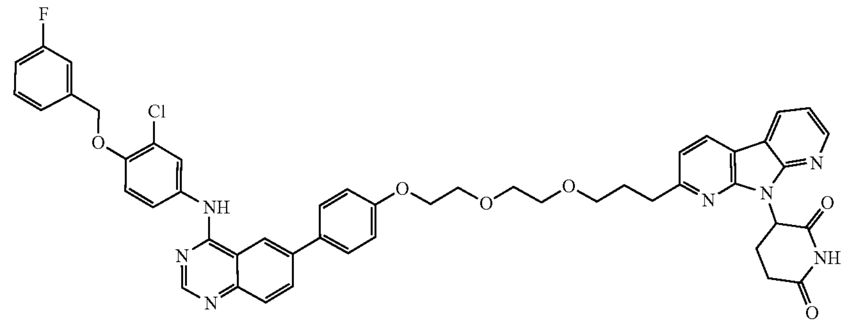 [SMILES: O=C1CCC(n2c3ncccc3c3ccc(CCCOCCOCCOc4ccc(-c5ccc6ncnc(Nc7ccc(OCc8cccc(F)c8)c(Cl)c7)c6c5)cc4)nc32)C(=O)N1] |
| I-74 | 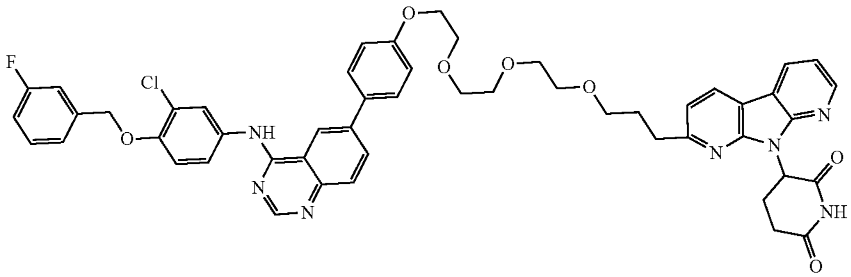 [SMILES: O=C1CCC(n2c3ncccc3c3ccc(CCCOCCOCCOCCOc4ccc(-c5ccc6ncnc(Nc7ccc(OCc8cccc(F)c8)c(Cl)c7)c6c5)cc4)nc32)C(=O)N1] |
| I-75 | 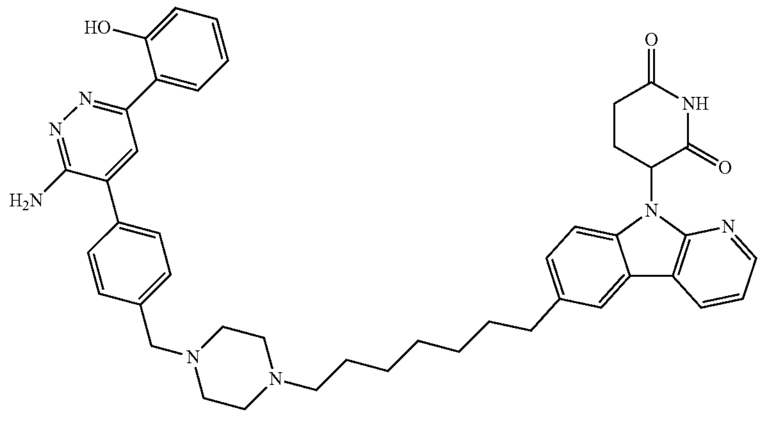 [SMILES: Nc1nnc(-c2ccccc2O)cc1-c1ccc(CN2CCN(CCCCCCCc3ccc4c(c3)c3cccnc3n4C3CCC(=O)NC3=O)CC2)cc1] |

TABLE 1-continued
| Exemplary Compounds | |
|---|---|
| I-# | Structure |
| I-76 | 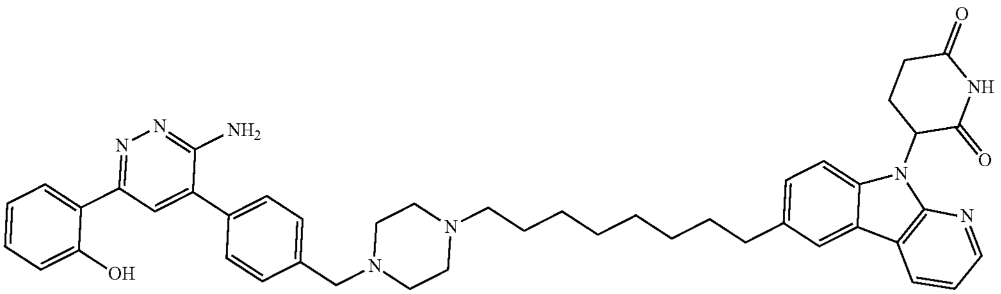 [SMILES: Nc1nnc(-c2ccccc2O)cc1-c1ccc(CN2CCN(CCCCCCCCc3ccc4c(c3)c3cccnc3n4C3CCC(=O)NC3=O)CC2)cc1] |
| I-77 | 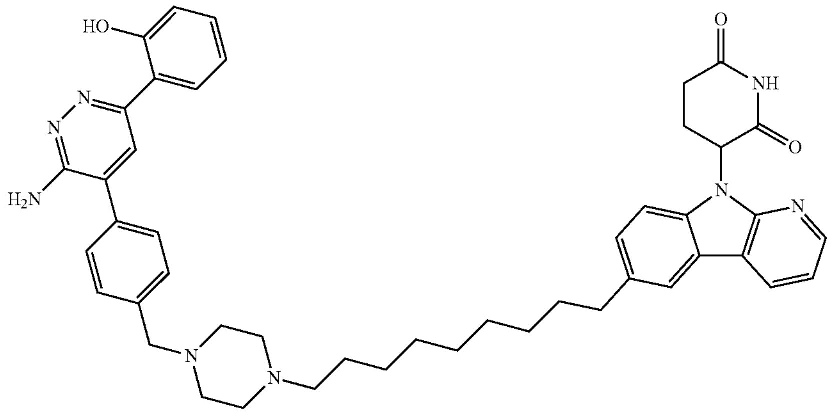 [SMILES: Nc1nnc(-c2ccccc2O)cc1-c1ccc(CN2CCN(CCCCCCCCCc3ccc4c(c3)c3cccnc3n4C3CCC(=O)NC3=O)CC2)cc1] |
| I-78 | 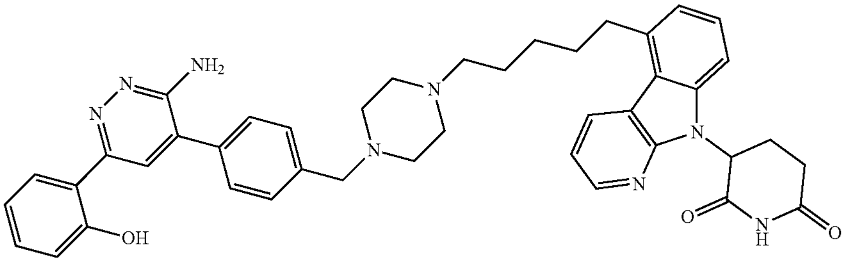 [SMILES: Nc1nnc(-c2ccccc2O)cc1-c1ccc(CN2CCN(CCCCCc3cccc4c3c3cccnc3n4C3CCC(=O)NC3=O)CC2)cc1] |
| I-79 | 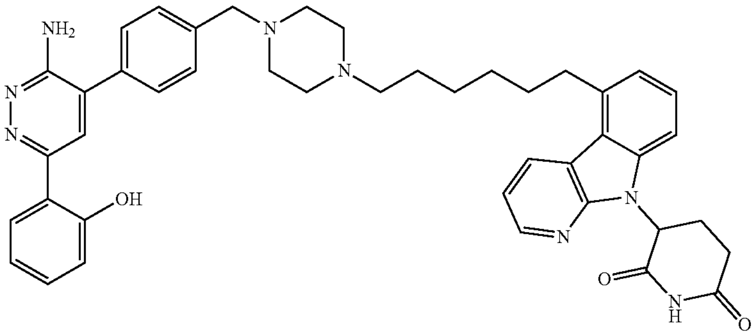 [SMILES: Nc1nnc(-c2ccccc2O)cc1-c1ccc(CN2CCN(CCCCCCc3cccc4c3c3cccnc3n4C3CCC(=O)NC3=O)CC2)cc1] |

TABLE 1-continued
| Exemplary Compounds | |
|---|---|
| I-# | Structure |
| I-80 | 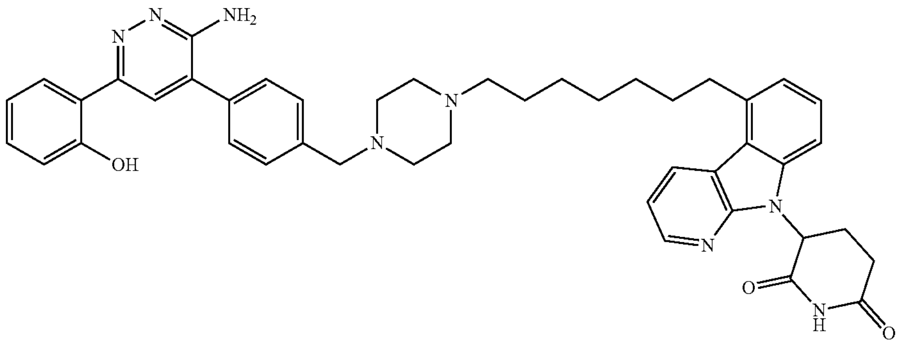 [SMILES: Nc1nnc(-c2ccccc2O)cc1-c1ccc(CN2CCN(CCCCCCCc3cccc4c3c3cccnc3n4C3CCC(=O)NC3=O)CC2)cc1] |
| I-81 | 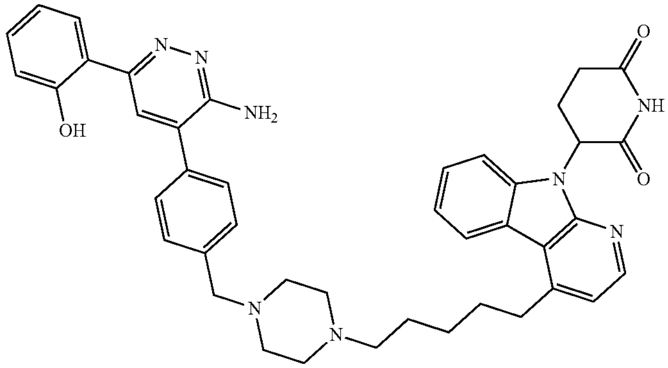 [SMILES: Nc1nnc(-c2ccccc2O)cc1-c1ccc(CN2CCN(CCCCCc3ccnc4c3c3ccccc3n4C3CCC(=O)NC3=O)CC2)cc1] |
| I-82 | 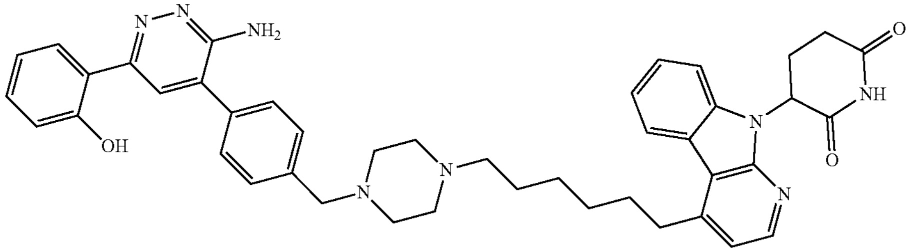 [SMILES: Nc1nnc(-c2ccccc2O)cc1-c1ccc(CN2CCN(CCCCCCc3ccnc4c3c3ccccc3n4C3CCC(=O)NC3=O)CC2)cc1] |
| I-83 | 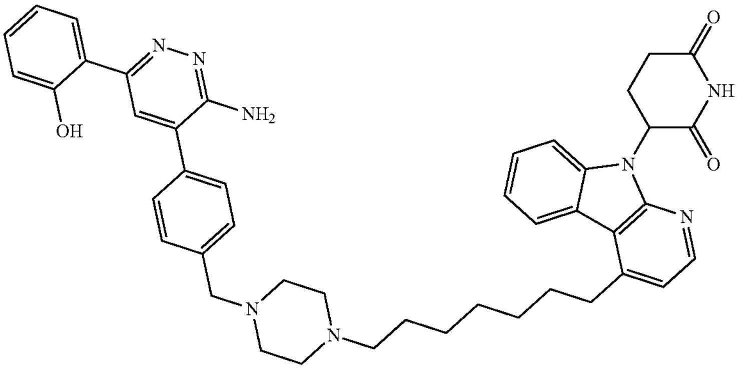 [SMILES: Nc1nnc(-c2ccccc2O)cc1-c1ccc(CN2CCN(CCCCCCCc3ccnc4c3c3ccccc3n4C3CCC(=O)NC3=O)CC2)cc1] |

TABLE 1-continued
| Exemplary Compounds | |
|---|---|
| I-# | Structure |
| I-84 | 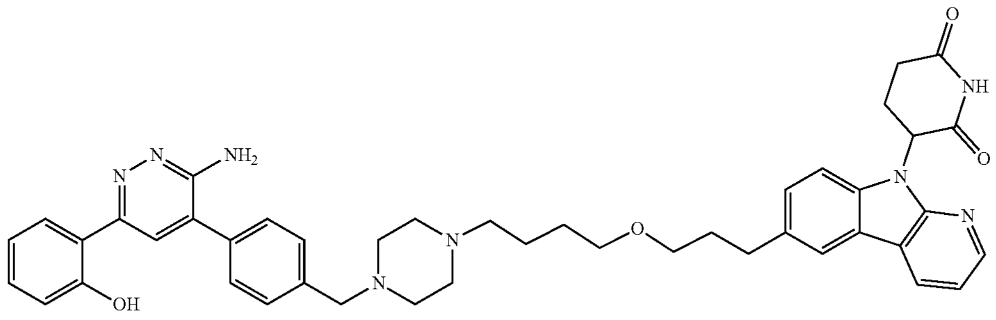 [SMILES: Nc1nnc(-c2ccccc2O)cc1-c1ccc(CN2CCN(CCCCOCCCc3ccc4c(c3)c3cccnc3n4C3CCC(=O)NC3=O)CC2)cc1] |
| I-85 | 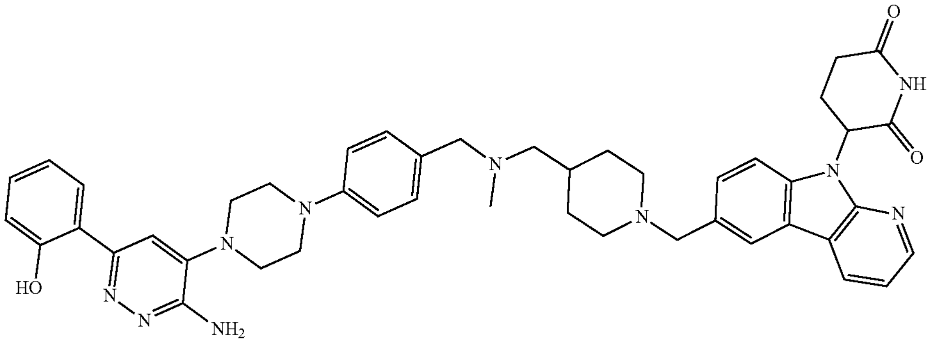 [SMILES: CN(Cc1ccc(N2CCN(c3cc(-c4ccccc4O)nnc3N)CC2)cc1)CC1CCN(Cc2ccc3c(c2)c2cccnc2n3C2CCC(=O)NC2=O)CC1] |
| I-86 | 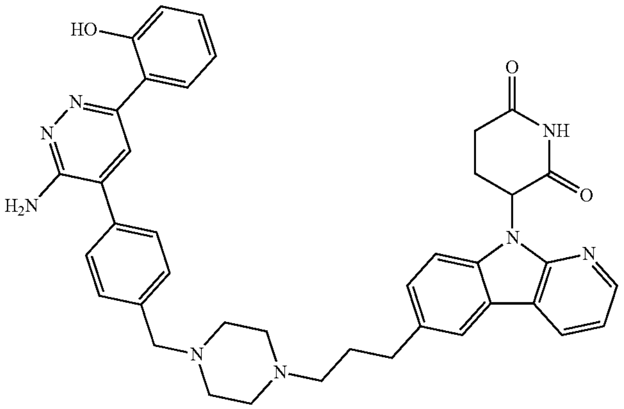 [SMILES: Nc1nnc(-c2ccccc2O)cc1-c1ccc(CN2CCN(CCCc3ccc4c(c3)c3cccnc3n4C3CCC(=O)NC3=O)CC2)cc1] |
| I-87 | 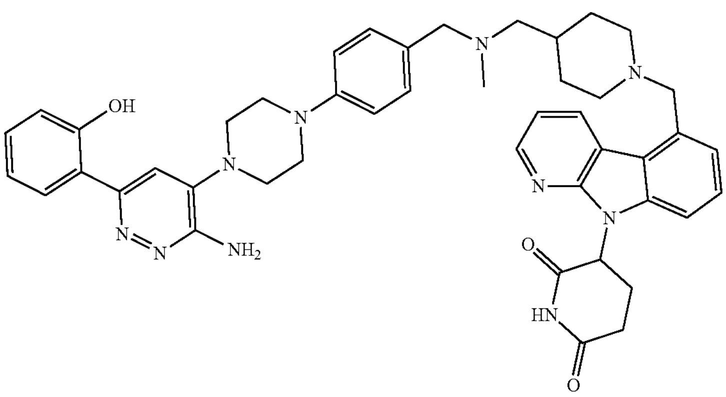 [SMILES: CN(Cc1ccc(N2CCN(c3cc(-c4ccccc4O)nnc3N)CC2)cc1)CC1CCN(Cc2cccc3c2c2cccnc2n3C2CCC(=O)NC2=O)CC1] |

TABLE 1-continued
| Exemplary Compounds | |
|---|---|
| I-# | Structure |
| I-88 | 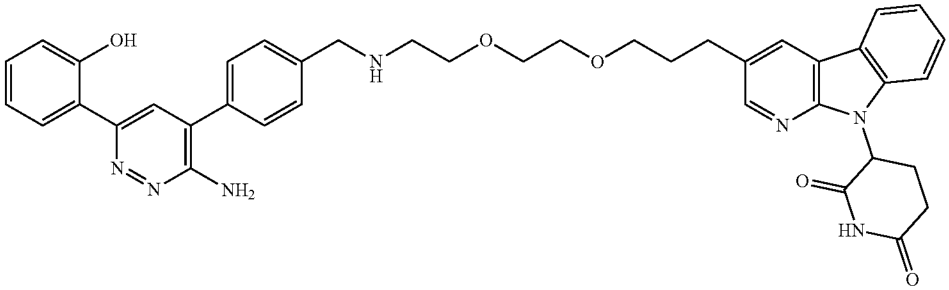 [SMILES: Nc1nnc(-c2ccccc2O)cc1-c1ccc(CNCCOCCOCCCc2cnc3c(c2)c2ccccc2n3C2CCC(=O)NC2=O)cc1] |
| I-89 | 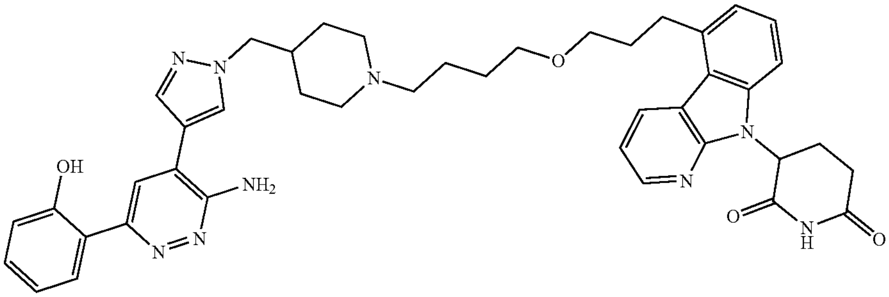 [SMILES: Nc1nnc(-c2ccccc2O)cc1-c1cnn(CC2CCN(CCCCOCCCc3cccc4c3c3cccnc3n4C3CCC(=O)NC3=O)CC2)c1] |
| I-90 | 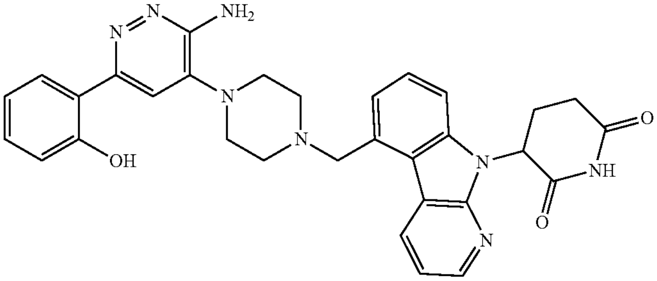 [SMILES: Nc1nnc(-c2ccccc2O)cc1N1CCN(Cc2cccc3c2c2cccnc2n3C2CCC(=O)NC2=O)CC1] |
| I-91 | 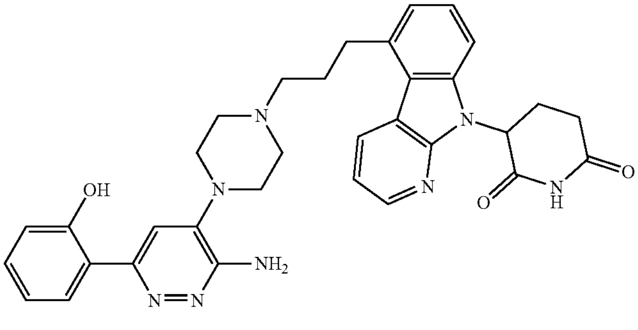 [SMILES: Nc1nnc(-c2ccccc2O)cc1N1CCN(CCCc2cccc3c2c2cccnc2n3C2CCC(=O)NC2=O)CC1] |
| I-92 | 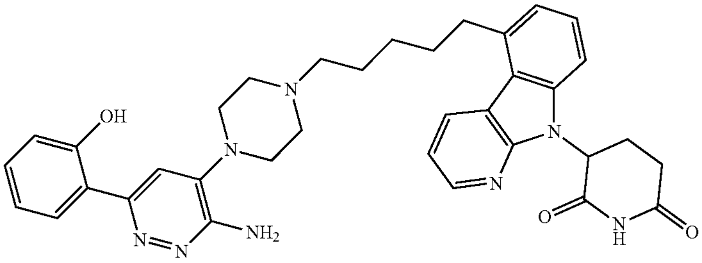 [SMILES: Nc1nnc(-c2ccccc2O)cc1N1CCN(CCCCCc2cccc3c2c2cccnc2n3C2CCC(=O)NC2=O)CC1] |

TABLE 1-continued
| Exemplary Compounds | |
|---|---|
| I-# | Structure |
| I-93 | 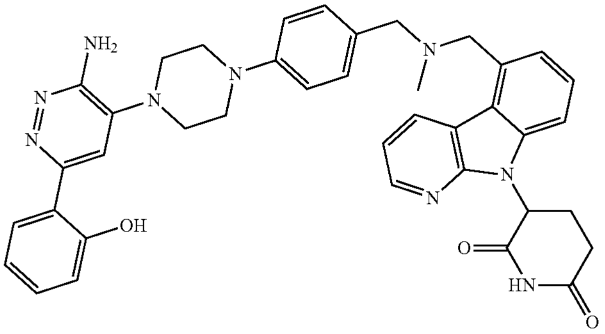 [SMILES: CN(Cc1ccc(N2CCN(c3cc(-c4ccccc4O)nnc3N)CC2)cc1)Cc1cccc2c1c1cccnc1n2C1CCC(=O)NC1=O] |
| I-94 | 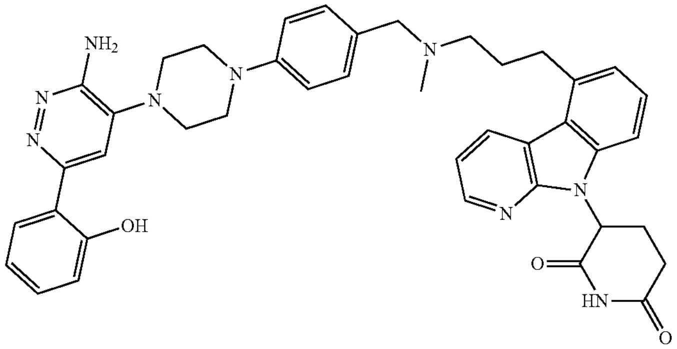 [SMILES: CN(CCCc1cccc2c1c1cccnc1n2C1CCC(=O)NC1=O)Cc1ccc(N2CCN(c3cc(-c4ccccc4O)nnc3N)CC2)cc1] |
| I-95 | 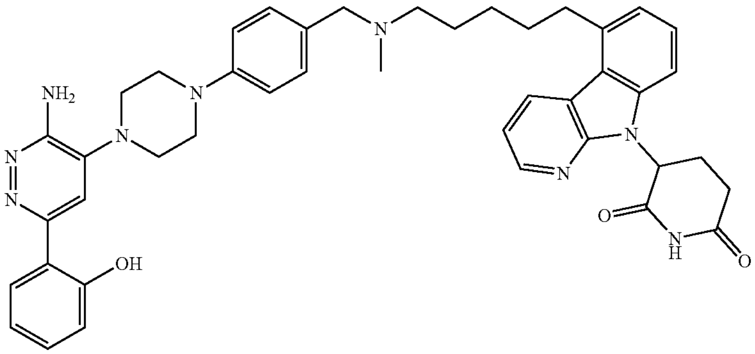 [SMILES: CN(CCCCCc1cccc2c1c1cccnc1n2C1CCC(=O)NC1=O)Cc1ccc(N2CCN(c3cc(-c4ccccc4O)nnc3N)CC2)cc1] |
| I-96 | 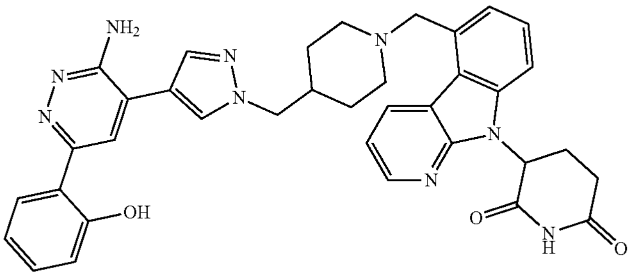 [SMILES: Nc1nnc(-c2ccccc2O)cc1-c1cnn(CC2CCN(Cc3cccc4c3c3cccnc3n4C3CCC(=O)NC3=O)CC2)c1] |

TABLE 1-continued
| Exemplary Compounds | |
|---|---|
| I-# | Structure |
| I-97 | 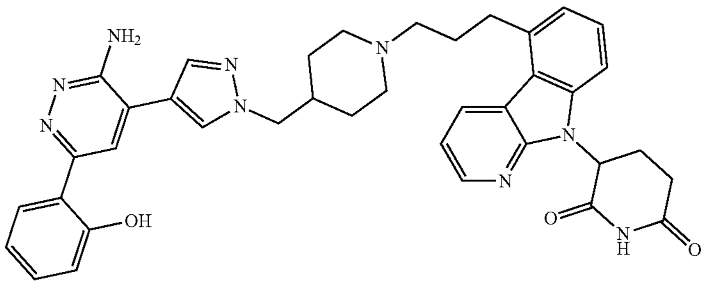 [SMILES: Nc1nnc(-c2ccccc2O)cc1-c1cnn(CC2CCN(CCCc3cccc4c3c3cccnc3n4C3CCC(=O)NC3=O)CC2)c1] |
| I-98 | 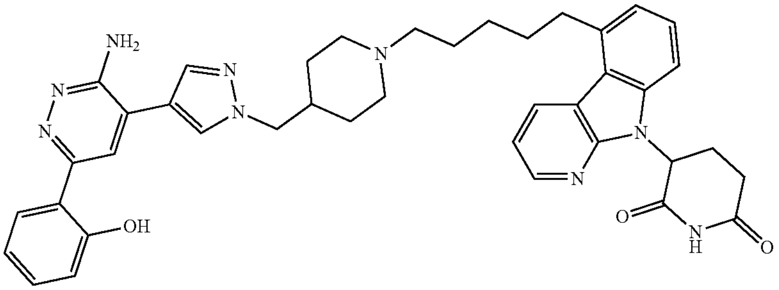 [SMILES: Nc1nnc(-c2ccccc2O)cc1-c1cnn(CC2CCN(CCCCCc3cccc4c3c3cccnc3n4C3CCC(=O)NC3=O)CC2)c1] |
| I-99 | 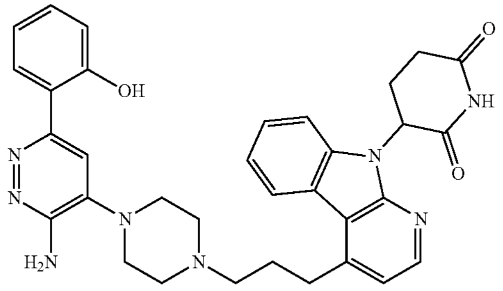 [SMILES: Nc1nnc(-c2ccccc2O)cc1N1CCN(CCCc2ccnc3c2c2ccccc2n3C2CCC(=O)NC2=O)CC1] |
| I-100 | 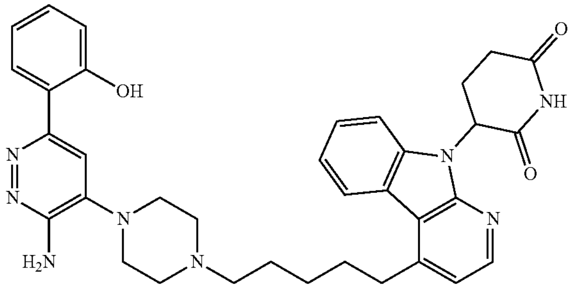 [SMILES: Nc1nnc(-c2ccccc2O)cc1N1CCN(CCCCCc2ccnc3c2c2ccccc2n3C2CCC(=O)NC2=O)CC1] |
| I-101 | 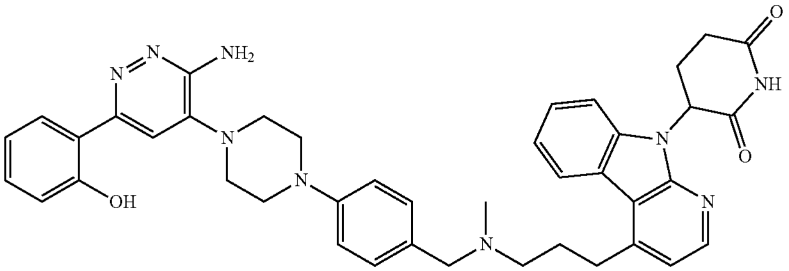 [SMILES: CN(CCCc1ccnc2c1c1ccccc1n2C1CCC(=O)NC1=O)Cc1ccc(N2CCN(c3cc(-c4ccccc4O)nnc3N)CC2)cc1] |

TABLE 1-continued
| Exemplary Compounds | |
|---|---|
| I-# | Structure |
| I-102 | 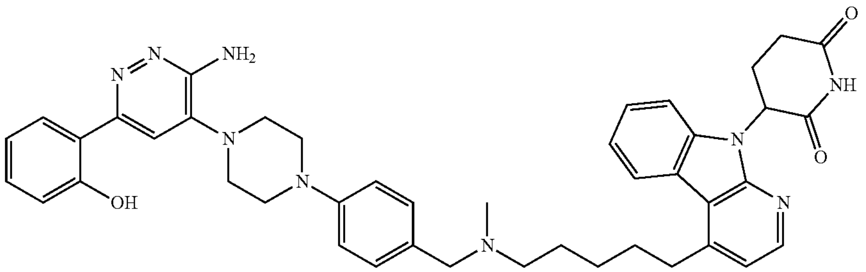 [SMILES: CN(CCCCCc1ccnc2c1c1ccccc1n2C1CCC(=O)NC1=O)Cc1ccc(N2CCN(c3cc(-c4ccccc4O)nnc3N)CC2)cc1] |
| I-103 | 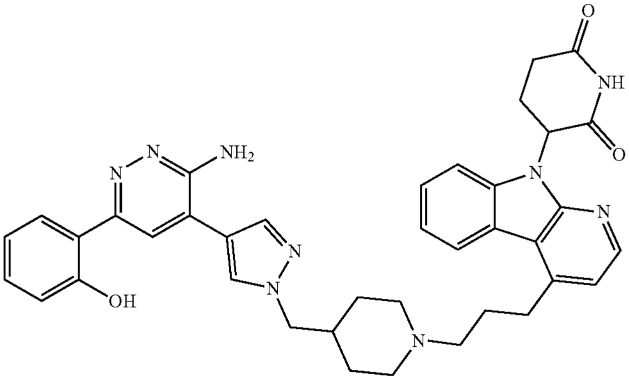 [SMILES: Nc1nnc(-c2ccccc2O)cc1-c1cnn(CC2CCN(CCCc3ccnc4c3c3ccccc3n4C3CCC(=O)NC3=O)CC2)c1] |
| I-104 | 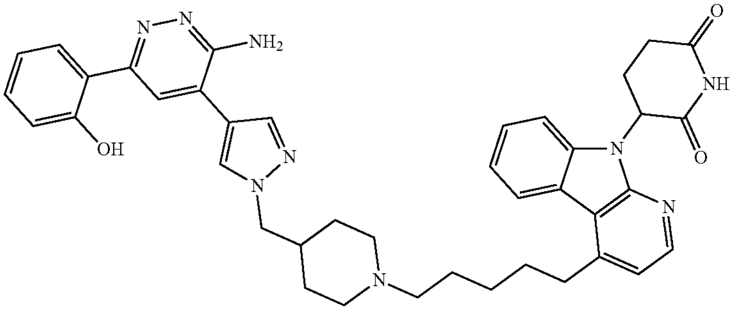 [SMILES: Nc1nnc(-c2ccccc2O)cc1-c1cnn(CC2CCN(CCCCCc3ccnc4c3c3ccccc3n4C3CCC(=O)NC3=O)CC2)c1] |
| I-105 | 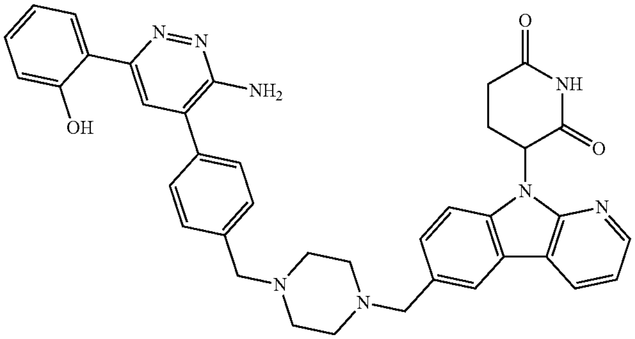 [SMILES: Nc1nnc(-c2ccccc2O)cc1-c1ccc(CN2CCN(Cc3ccc4c(c3)c3cccnc3n4C3CCC(=O)NC3=O)CC2)cc1] |

TABLE 1-continued
| Exemplary Compounds | |
|---|---|
| I-# | Structure |
| I-106 | 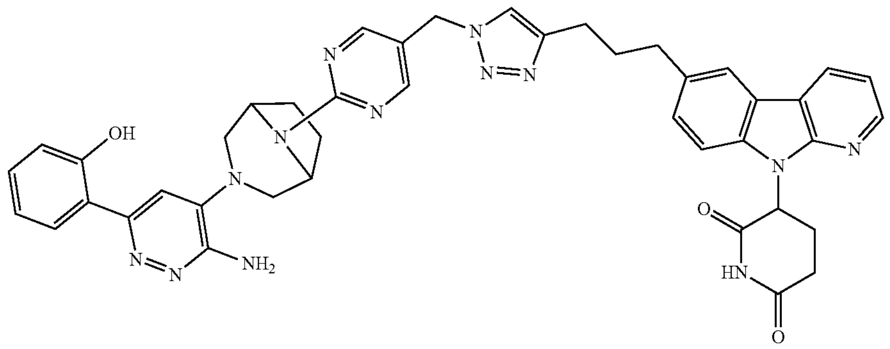 [SMILES: Nc1nnc(-c2ccccc2O)cc1N1CC2CCC(C1)N2c1ncc(Cn2cc(CCCc3ccc4c(c3)c3cccnc3n4C3CCC(=O)NC3=O)nn2)cn1] |
| I-107 | 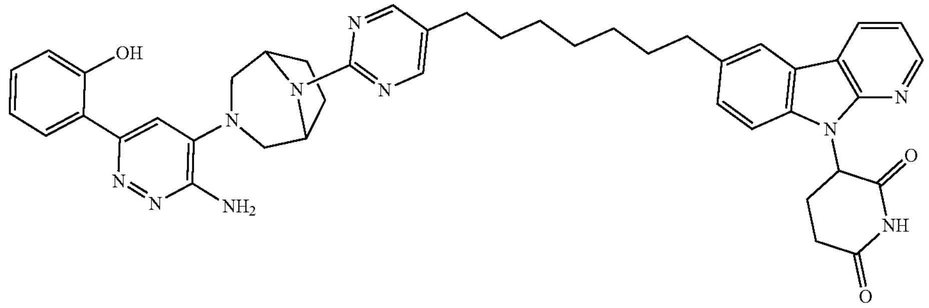 [SMILES: Nc1nnc(-c2ccccc2O)cc1N1CC2CCC(C1)N2c1ncc(CCCCCCCc2ccc3c(c2)c2cccnc2n3C2CCC(=O)NC2=O)cn1] |
| I-108 | 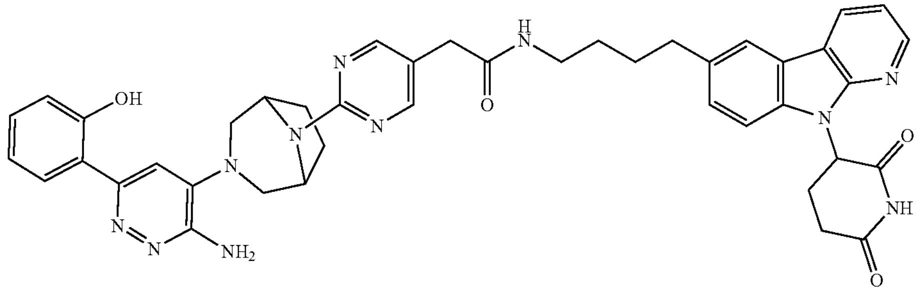 [SMILES: Nc1nnc(-c2ccccc2O)cc1N1CC2CCC(C1)N2c1ncc(CC(=O)NCCCCc2ccc3c(c2)c2cccnc2n3C2CCC(=O)NC2=O)cn1] |
| I-109 | 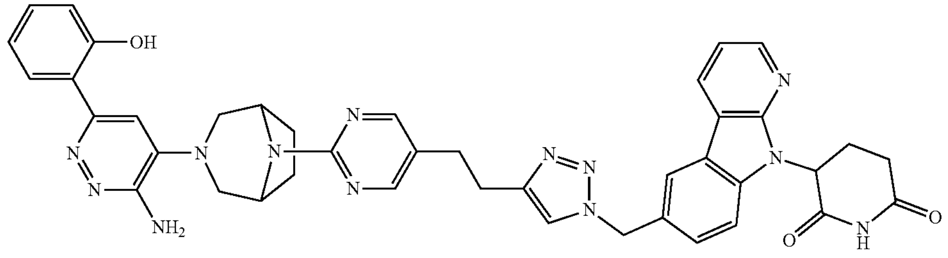 [SMILES: Nc1nnc(-c2ccccc2O)cc1N1CC2CCC(C1)N2c1ncc(CCc2cn(Cc3ccc4c(c3)c3cccnc3n4C3CCC(=O)NC3=O)nn2)cn1] |
| I-110 | 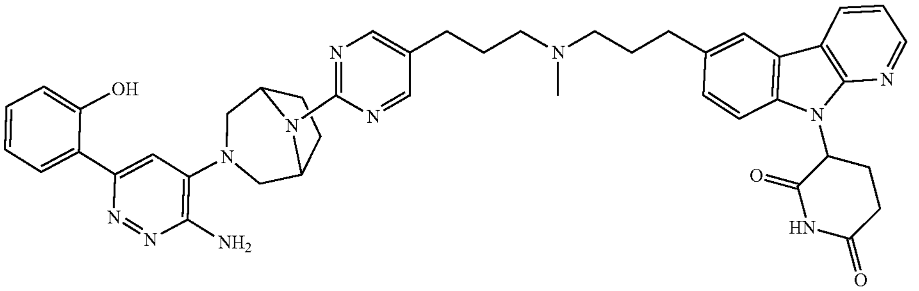 [SMILES: CN(CCCc1cnc(N2C3CCC2CN(c2cc(-c4ccccc4O)nnc2N)C3)nc1)CCCc1ccc2c(c1)c1cccnc1n2C1CCC(=O)NC1=O] |

TABLE 1-continued
| Exemplary Compounds | |
|---|---|
| I-# | Structure |
| I-111 | 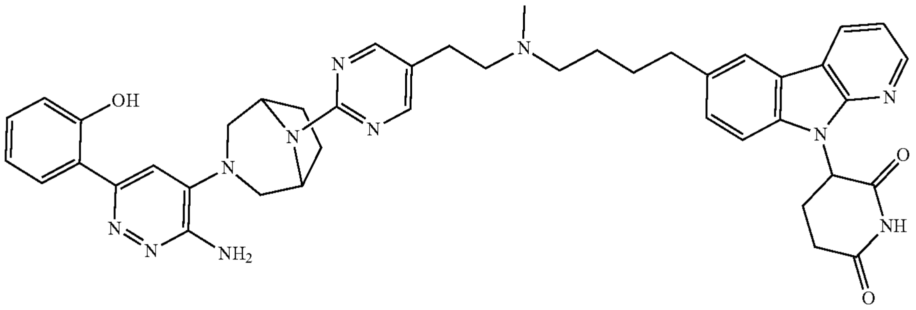 [SMILES: CN(CCCCc1ccc2c(c1)c1cccnc1n2C1CCC(=O)NC1=O)CCc1cnc(N2C3CCC2CN(c2cc(-c4ccccc4O)nnc2N)C3)nc1] |
| I-113 | 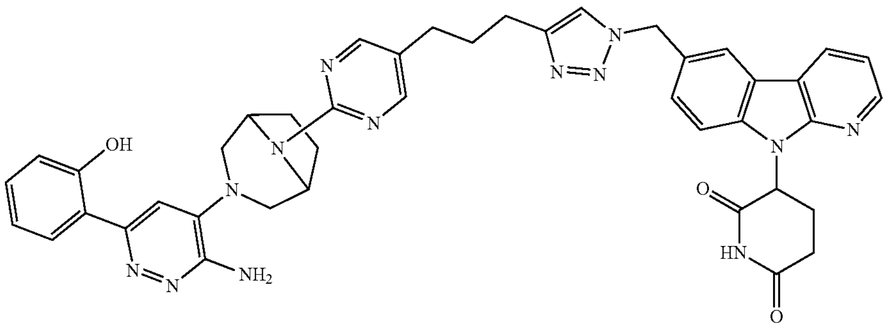 [SMILES: Nc1nnc(-c2ccccc2O)cc1N1CC2CCC(C1)N2c1ncc(CCCc2cn(Cc3ccc4c(c3)c3cccnc3n4C3CCC(=O)NC3=O)nn2)cn1] |
| I-114 | 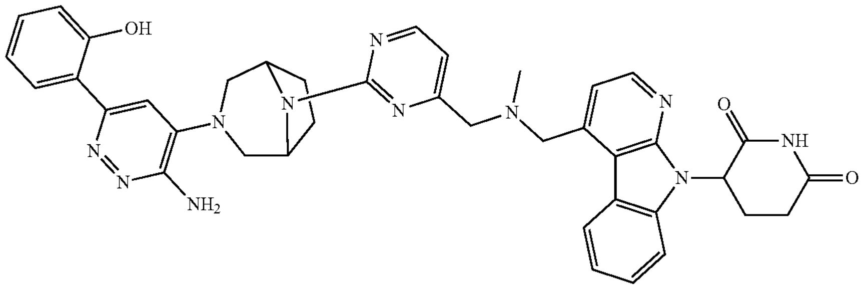 [SMILES: CN(Cc1ccnc(N2C3CCC2CN(c2cc(-c4ccccc4O)nnc2N)C3)n1)Cc1ccnc2c1c1ccccc1n2C1CCC(=O)NC1=O] |
| I-115 | 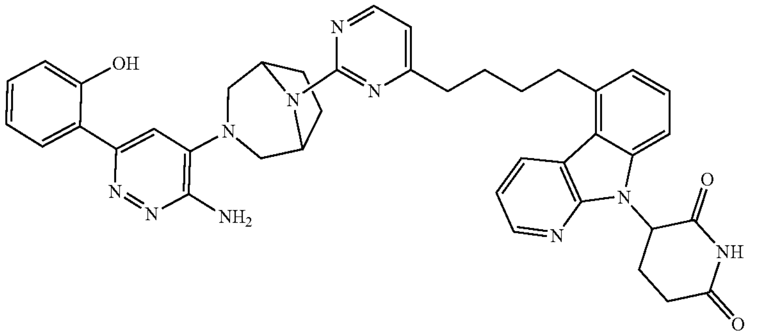 [SMILES: Nc1nnc(-c2ccccc2O)cc1N1CC2CCC(C1)N2c1nccc(CCCCc2cccc3c2c2cccnc2n3C2CCC(=O)NC2=O)n1] |
| I-116 | 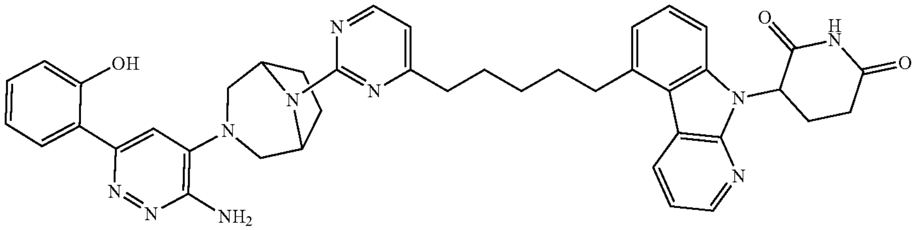 [SMILES: Nc1nnc(-c2ccccc2O)cc1N1CC2CCC(C1)N2c1nccc(CCCCCc2cccc3c2c2cccnc2n3C2CCC(=O)NC2=O)n1] |

TABLE 1-continued
| Exemplary Compounds | |
|---|---|
| I-# | Structure |
| I-117 | 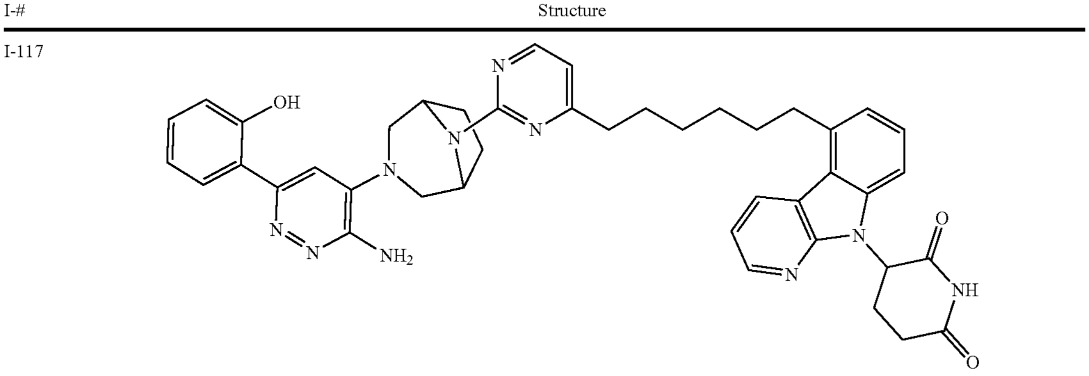 |
| I-118 | 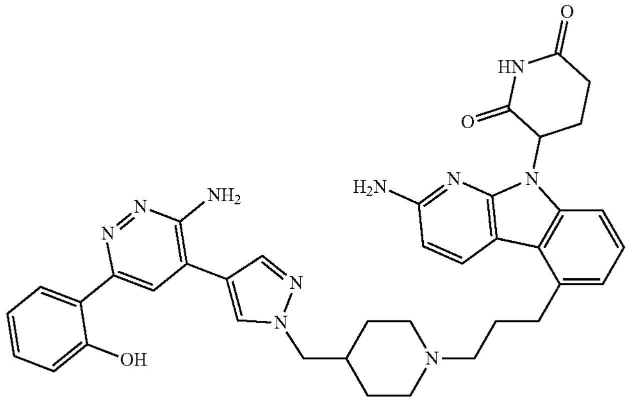 [SMILES: Nc1ccc2c3c(CCCN4CCC(Cn5cc(-c6cc(-c7ccccc7O)nnc6N)cn5)CC4)cccc3n(C3CCC(=O)NC3=O)c2n1] |
| I-119 | 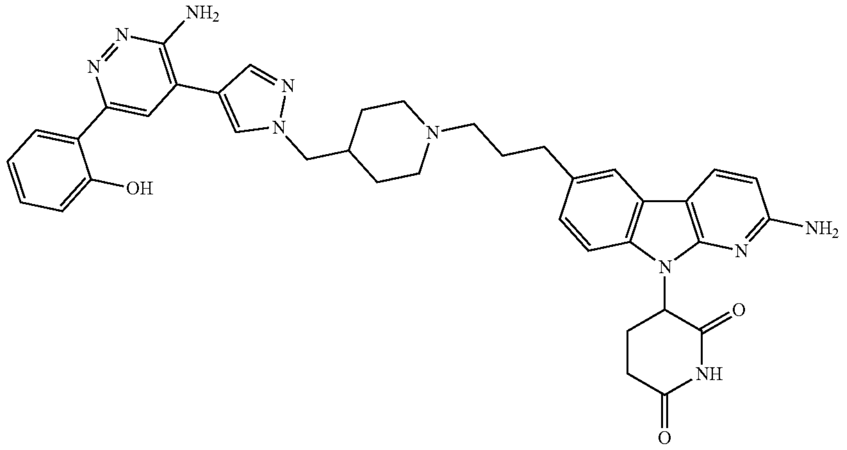 [SMILES: Nc1ccc2c3cc(CCCN4CCC(Cn5cc(-c6cc(-c7ccccc7O)nnc6N)cn5)CC4)ccc3n(C3CCC(=O)NC3=O)c2n1] |
| I-120 | 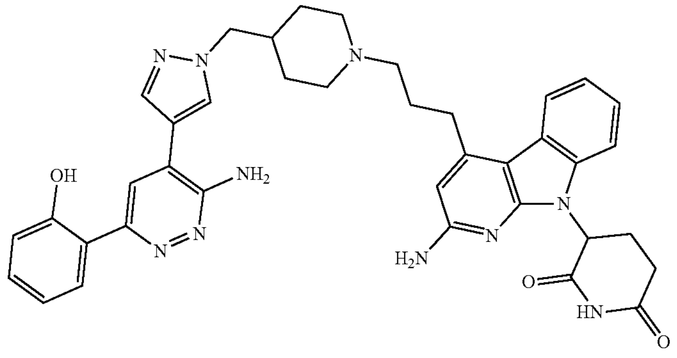 [SMILES: Nc1cc(CCCN2CCC(Cn3cc(-c4cc(-c5ccccc5O)nnc4N)cn3)CC2)c2c3ccccc3n(C3CCC(=O)NC3=O)c2n1] |

TABLE 1-continued
| Exemplary Compounds | |
|---|---|
| I-# | Structure |
| I-121 | 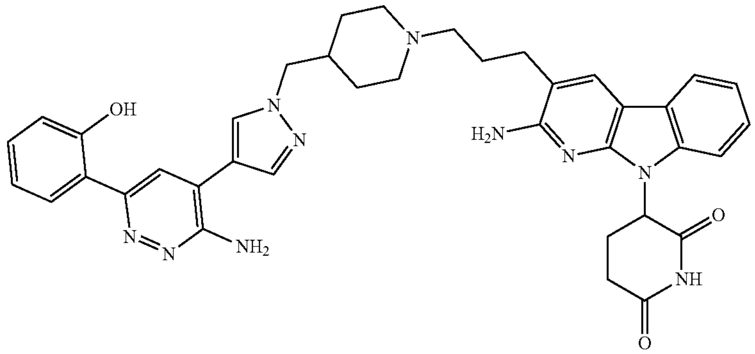 [SMILES: Nc1nc2c(cc1CCCN1CCC(Cn3cc(-c4cc(-c5ccccc5O)nnc4N)cn3)CC1)c1ccccc1n2C1CCC(=O)NC1=O] |
| I-122 | 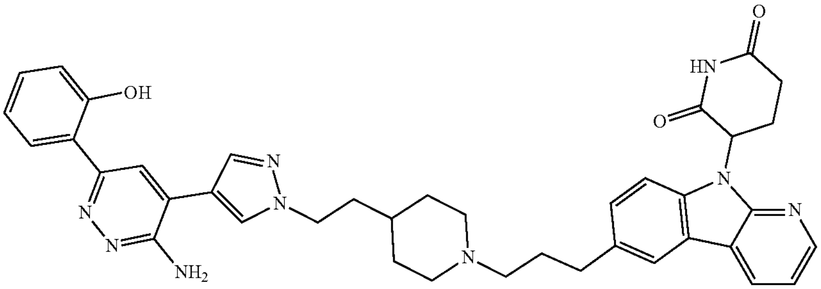 [SMILES: Nc1nnc(-c2ccccc2O)cc1-c1cnn(CCC2CCN(CCCc3ccc4c(c3)c3cccnc3n4C3CCC(=O)NC3=O)CC2)c1] |
| I-123 | 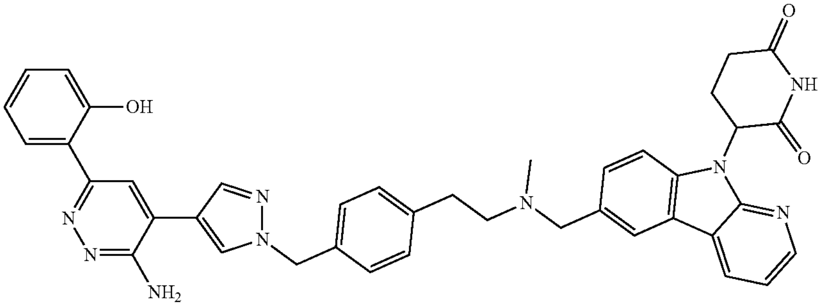 |
| I-124 | 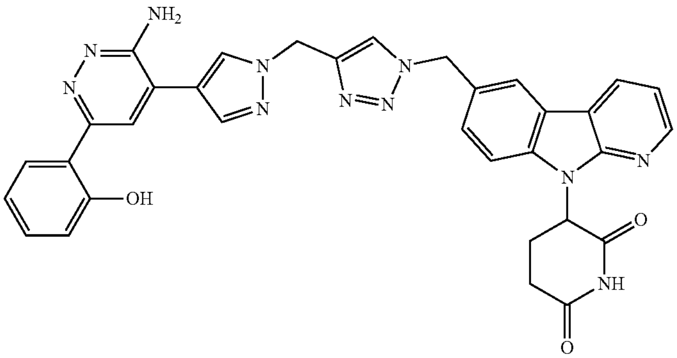 [SMILES: Nc1nnc(-c2ccccc2O)cc1-c1cnn(Cc2cn(Cc3ccc4c(c3)c3cccnc3n4C3CCC(=O)NC3=O)nn2)c1] |

TABLE 1-continued
| Exemplary Compounds | |
|---|---|
| I-# | Structure |
| I-125 | 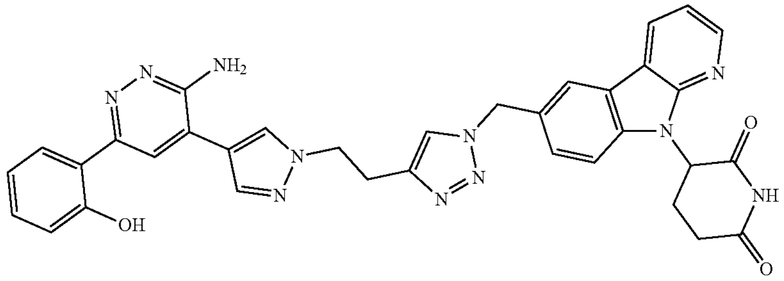 [SMILES: Nc1nnc(-c2ccccc2O)cc1-c1cnn(CCc2cn(Cc3ccc4c(c3)c3cccnc3n4C3CCC(=O)NC3=O)nn2)c1] |
| I-126 | 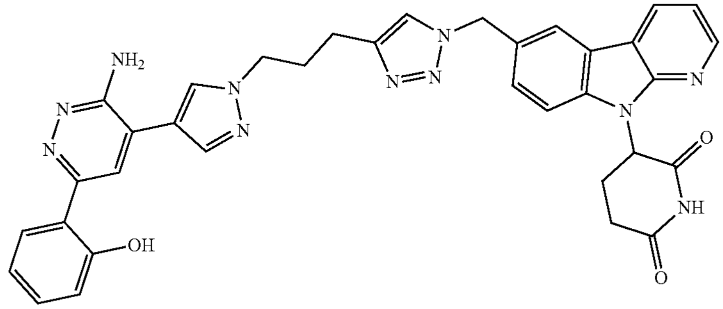 [SMILES: Nc1nnc(-c2ccccc2O)cc1-c1cnn(CCCc2cn(Cc3ccc4c(c3)c3cccnc3n4C3CCC(=O)NC3=O)nn2)c1] |
| I-127 | 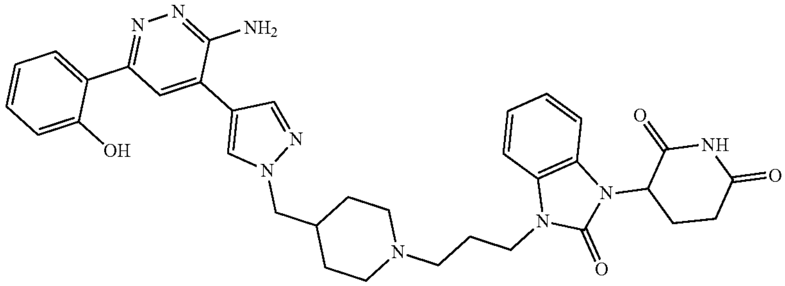 [SMILES: Nc1nnc(-c2ccccc2O)cc1-c1cnn(CC2CCN(CCCn3c(=O)n(C4CCC(=O)NC4=O)c4ccccc43)CC2)c1] |
| I-128 | 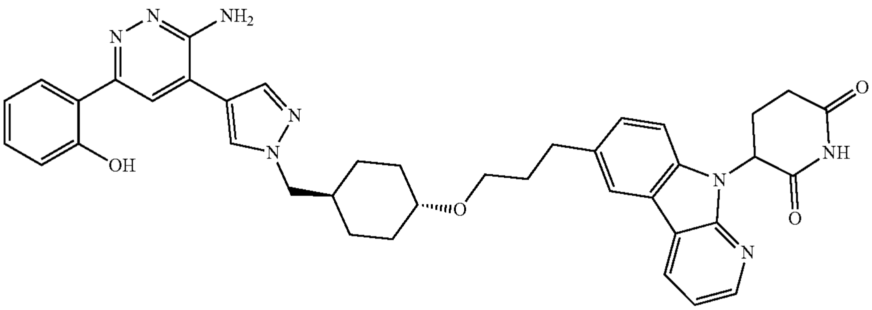 [SMILES: Nc1nnc(-c2ccccc2O)cc1-c1cnn(C[C@H]2CC[C@H](OCCCc3ccc4c(c3)c3cccnc3n4C3CCC(=O)NC3=O)CC2)c1] |
| I-129 | 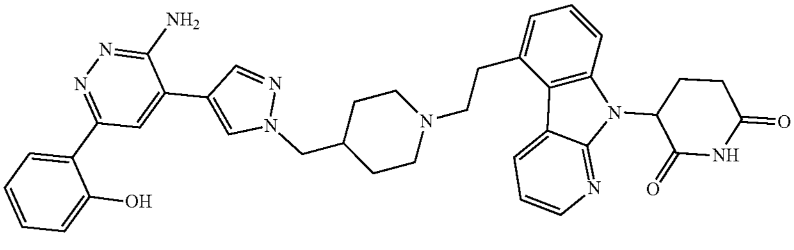 [SMILES: Nc1nnc(-c2ccccc2O)cc1-c1cnn(CC2CCN(CCc3cccc4c3c3cccnc3n4C3CCC(=O)NC3=O)CC2)c1] |

TABLE 1-continued
| Exemplary Compounds | |
|---|---|
| I-# | Structure |
| I-130 | 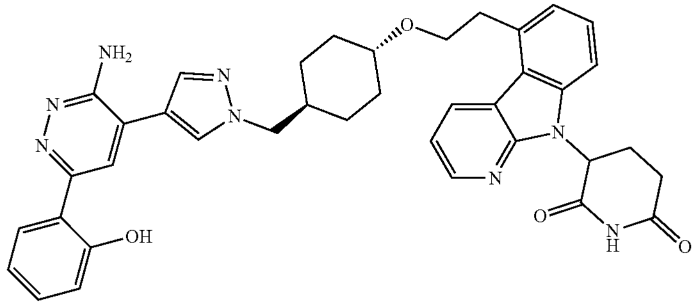 [SMILES: Nc1nnc(-c2ccccc2O)cc1-c1cnn(C[C@H]2CC[C@H](OCCc3cccc4c3c3cccnc3n4C3CCC(=O)NC3=O)CC2)c1] |
| I-131 | 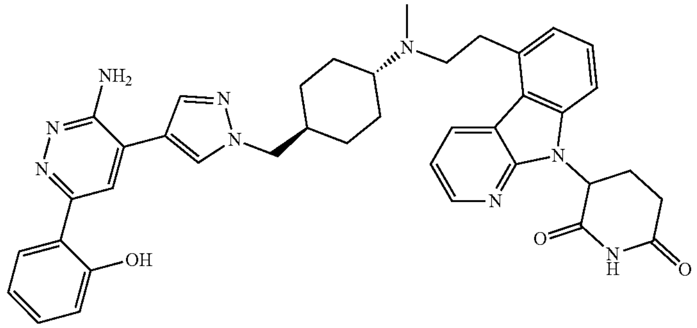 [SMILES: CN(CCc1cccc2c1c1cccnc1n2C1CCC(=O)NC1=O)[C@H]1CC[C@H](Cn2cc(-c3cc(-c4ccccc4O)nnc3N)cn2)CC1] |
| I-132 | 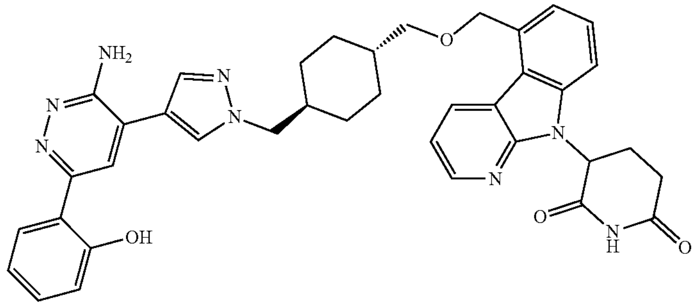 [SMILES: Nc1nnc(-c2ccccc2O)cc1-c1cnn(C[C@H]2CC[C@H](COCc3cccc4c3c3cccnc3n4C3CCC(=O)NC3=O)CC2)c1] |
| I-133 | 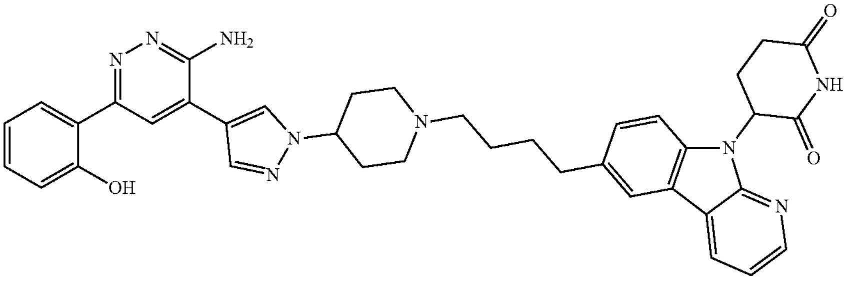 [SMILES: Nc1nnc(-c2ccccc2O)cc1-c1cnn(C2CCN(CCCCc3ccc4c(c3)c3cccnc3n4C3CCC(=O)NC3=O)CC2)c1] |
| I-134 | 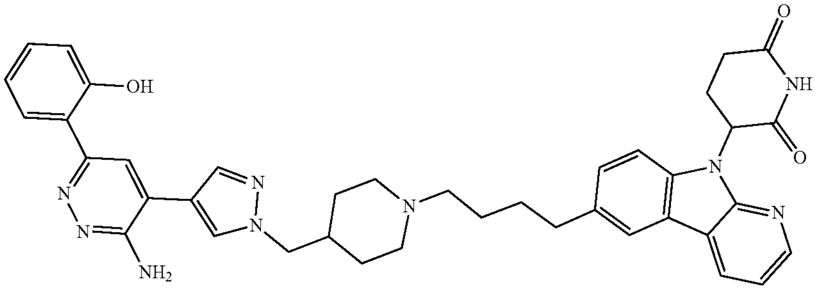 |

TABLE 1-continued
| Exemplary Compounds | |
|---|---|
| I-# | Structure |
| I-135 | 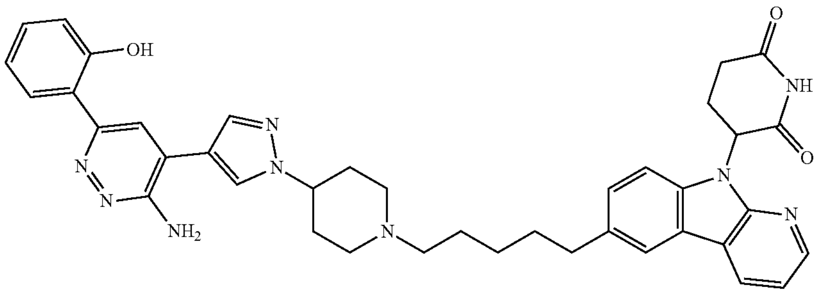 [SMILES: Nc1nnc(-c2ccccc2O)cc1-c1cnn(C2CCN(CCCCCc3ccc4c(c3)c3cccnc3n4C3CCC(=O)NC3=O)CC2)c1] |
| I-136 | 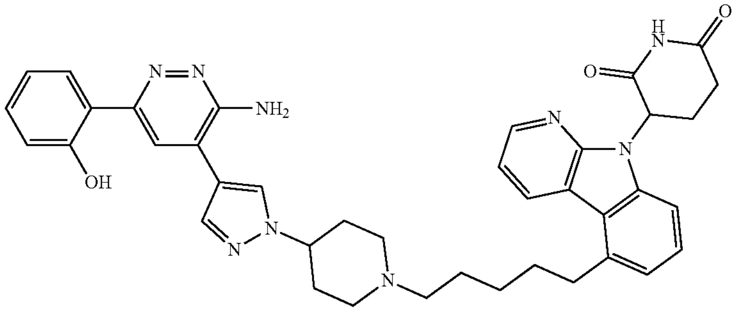 [SMILES: Nc1nnc(-c2ccccc2O)cc1-c1cnn(C2CCN(CCCCCc3cccc4c3c3cccnc3n4C3CCC(=O)NC3=O)CC2)c1] |
| I-137 | 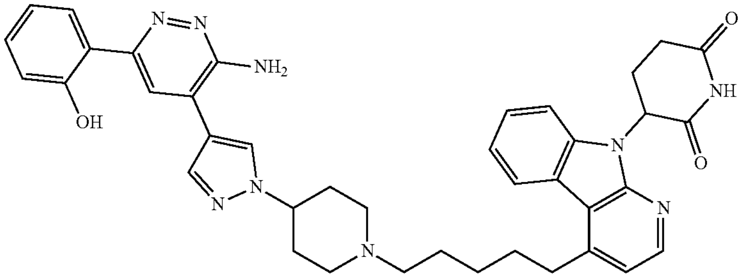 [SMILES: Nc1nnc(-c2ccccc2O)cc1-c1cnn(C2CCN(CCCCCc3ccnc4c3c3ccccc3n4C3CCC(=O)NC3=O)CC2)c1] |
| I-138 | 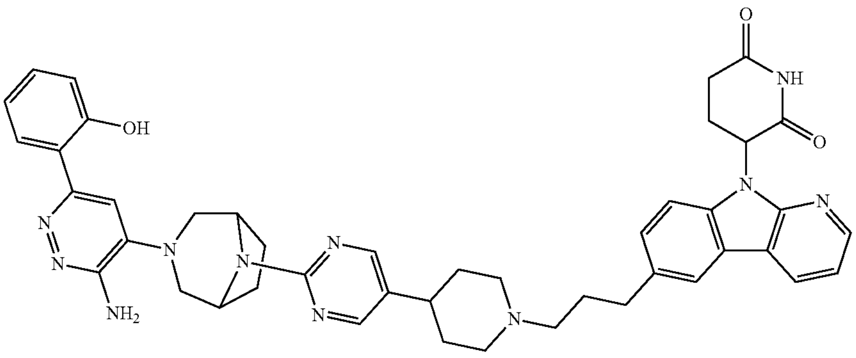 [SMILES: Nc1nnc(-c2ccccc2O)cc1N1CC2CCC(C1)N2c1ncc(C2CCN(CCCc3ccc4c(c3)c3cccnc3n4C3CCC(=O)NC3=O)CC2)cn1] |

TABLE 1-continued
| Exemplary Compounds | |
|---|---|
| I-# | Structure |
| I-139 | 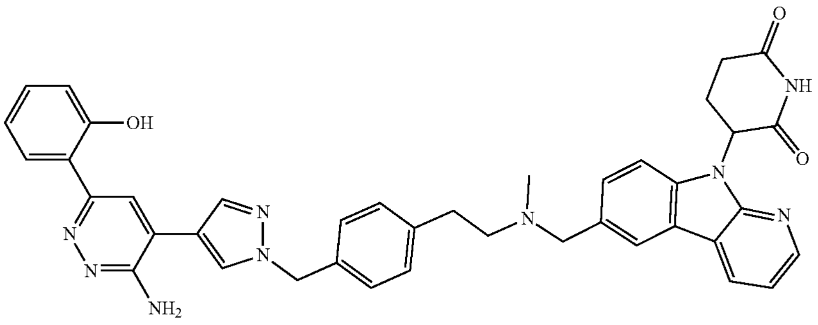 |
| I-140 | 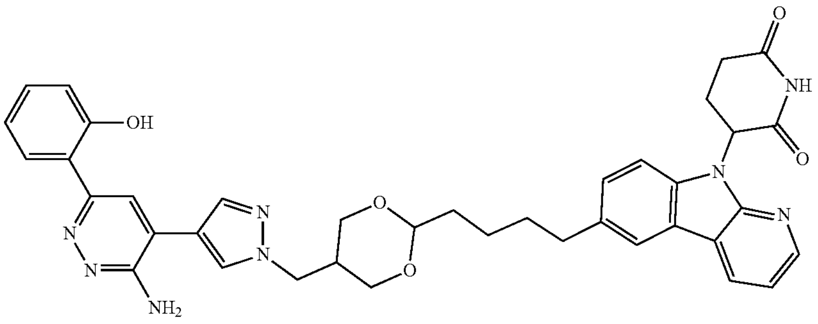 |
| I-141 | 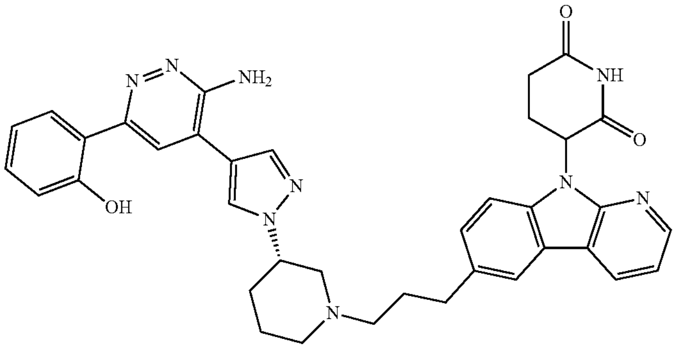 [SMILES: Nc1nnc(-c2ccccc2O)cc1-c1cnn([C@H]2CCCN(CCCc3ccc4c(c3)c3cccnc3n4C3CCC(=O)NC3=O)C2)c1] |
| I-142 | 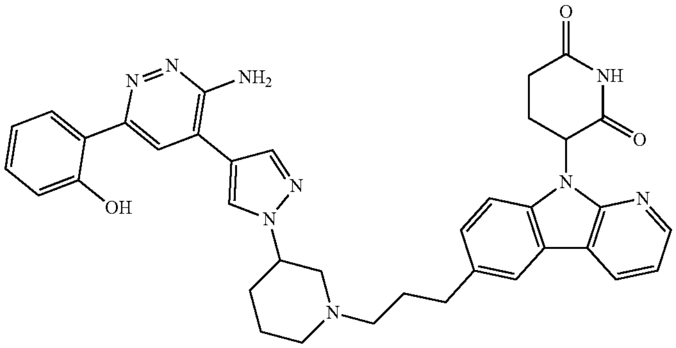 [SMILES: Nc1nnc(-c2ccccc2O)cc1-c1cnn(C2CCCN(CCCc3ccc4c(c3)c3cccnc3n4C3CCC(=O)NC3=O)C2)c1] |

TABLE 1-continued
| Exemplary Compounds | |
|---|---|
| I-# | Structure |
| I-143 | 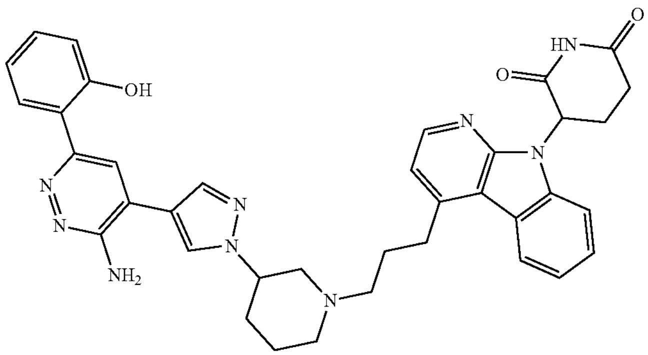 [SMILES: Nc1nnc(-c2ccccc2O)cc1-c1cnn(C2CCCN(CCCc3ccnc4c3c3ccccc3n4C3CCC(=O)NC3=O)C2)c1] |
| I-144 | 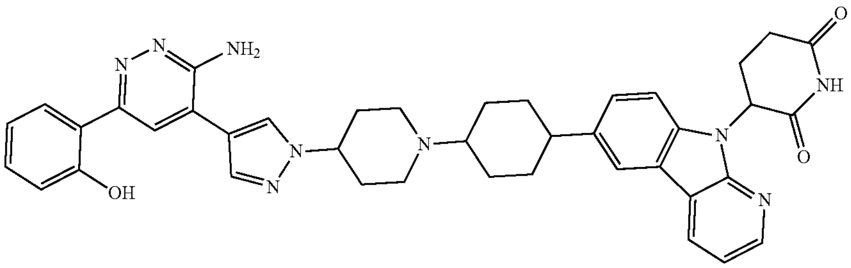 [SMILES: Nc1nnc(-c2ccccc2O)cc1-c1cnn(C2CCN(C3CCC(c4ccc5c(c4)c4cccnc4n5C4CCC(=O)NC4=O)CC3)CC2)c1] |
| I-145 | 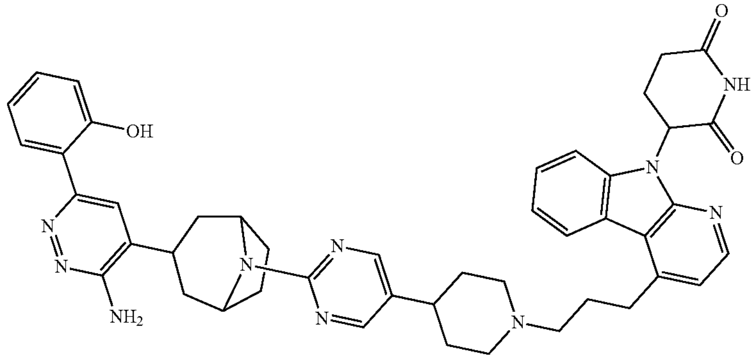 [SMILES: Nc1nnc(-c2ccccc2O)cc1C1CC2CCC(C1)N2c1ncc(C2CCN(CCCc3ccnc4c3c3ccccc3n4C3CCC(=O)NC3=O)CC2)cn1] |
| I-146 | 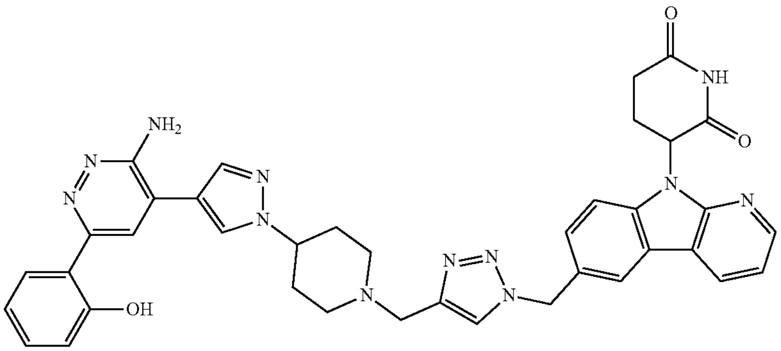 [SMILES: Nc1nnc(-c2ccccc2O)cc1-c1cnn(C2CCN(Cc3cn(Cc4ccc5c(c4)c4cccnc4n5C4CCC(=O)NC4=O)nn3)CC2)c1] |

TABLE 1-continued
| Exemplary Compounds | |
|---|---|
| I-# | Structure |
| I-147 | 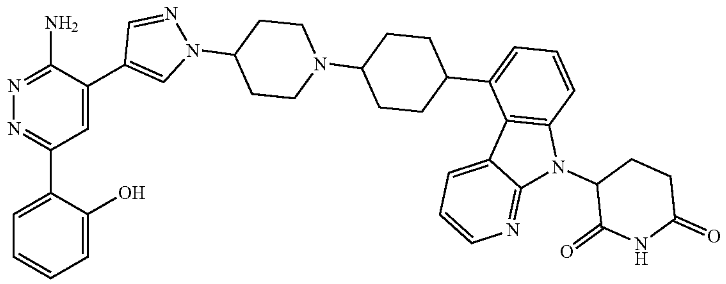 |
| I-148 | 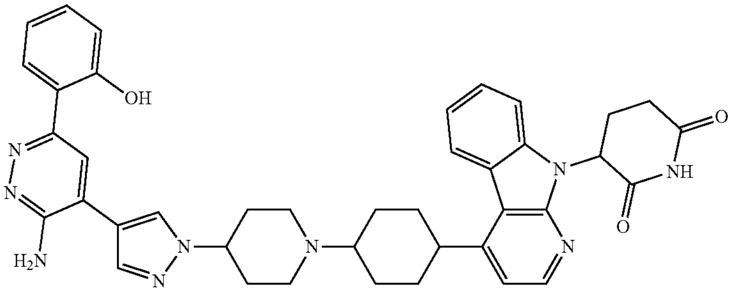 [SMILES: Nc1nnc(-c2ccccc2O)cc1-c1cnn(C2CCN(C3CCC(c4ccnc5c4c4ccccc4n5C4CCC(=O)NC4=O)CC3)CC2)c1] |
| I-149 | 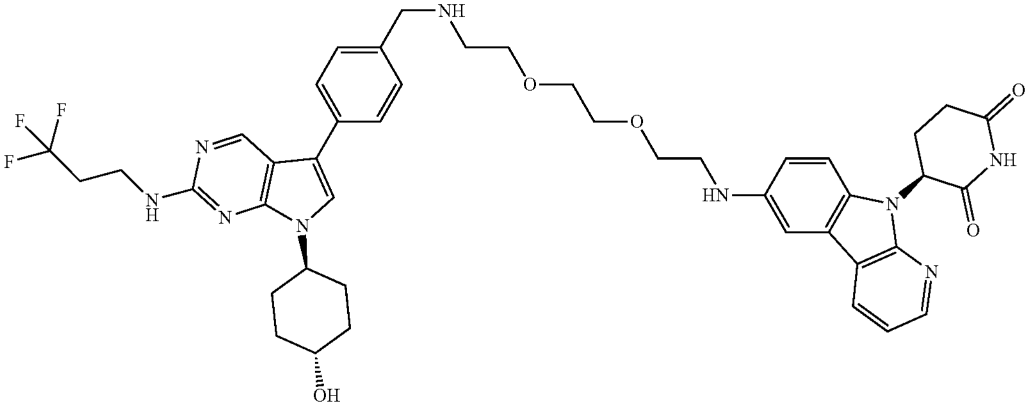 [SMILES: O=C1CC[C@H](n2c3ccc(NCCOCCOCCNCc4ccc(-c5cn([C@H]6CC[C@H](O)CC6)c6nc(NCCC(F)(F)F)ncc56)cc4)cc3c3cccnc32)C(=O)N1] |
| I-150 | 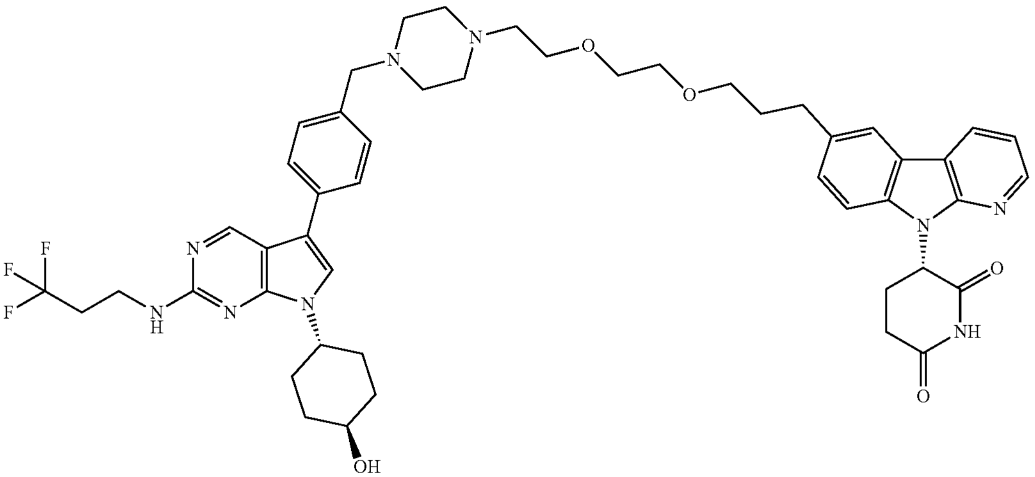 [SMILES: O=C1CC[C@H](n2c3ccc(CCCOCCOCCN4CCN(Cc5ccc(-c6cn([C@H]7CC[C@H](O)CC7)c7nc(NCCC(F)(F)F)ncc67)cc5)CC4)cc3c3cccnc32)C(=O)N1] |

TABLE 1-continued
| Exemplary Compounds | |
|---|---|
| I-# | Structure |
| I-151 | 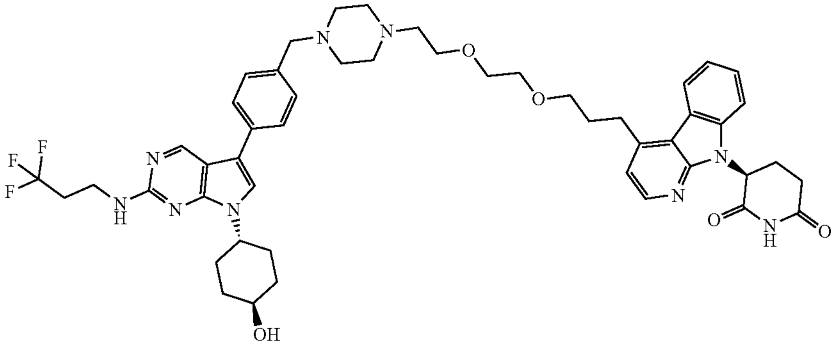 [SMILES: O=C1CC[C@H](n2c3ccccc3c3c(CCCOCCOCCN4CCN(Cc5ccc(-c6cn([C@H]7CC[C@H](O)CC7)c7nc(NCCC(F)(F)F)ncc67)cc5)CC4)ccnc32)C(=O)N1] |
| I-152 | 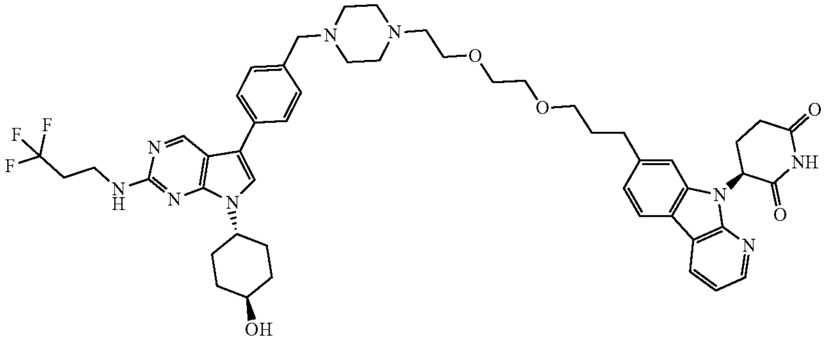 [SMILES: O=C1CC[C@H](n2c3cc(CCCOCCOCCN4CCN(Cc5ccc(-c6cn([C@H]7CC[C@H](O)CC7)c7nc(NCCC(F)(F)F)ncc67)cc5)CC4)ccc3c3cccnc32)C(=O)N1] |
| I-153 | 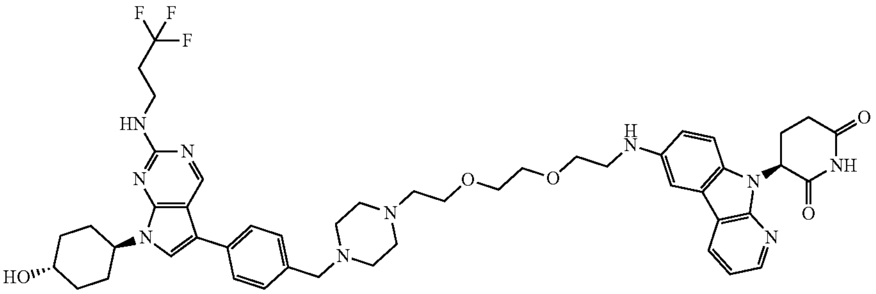 [SMILES: O=C1CC[C@H](n2c3ccc(NCCOCCOCCN4CCN(Cc5ccc(-c6cn([C@H]7CC[C@H](O)CC7)c7nc(NCCC(F)(F)F)ncc67)cc5)CC4)cc3c3cccnc32)C(=O)N1] |
| I-154 | 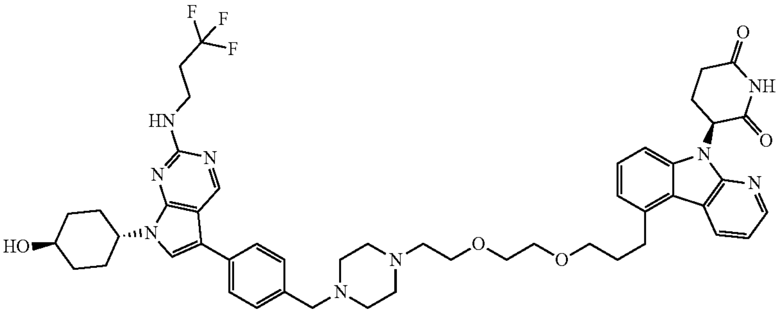 [SMILES: O=C1CC[C@H](n2c3cccc(CCCOCCOCCN4CCN(Cc5ccc(-c6cn([C@H]7CC[C@H](O)CC7)c7nc(NCCC(F)(F)F)ncc67)cc5)CC4)c3c3cccnc32)C(=O)N1] |

In some embodiments, the present invention provides a compound set forth in Table 1, above, or a pharmaceutically acceptable salt thereof.

In some embodiments, TBM is one of the compounds in Table 2, below, wherein

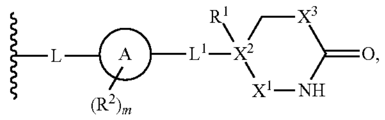

-continued

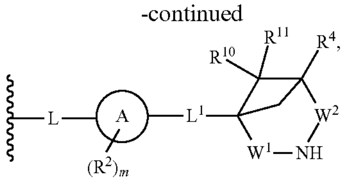

or

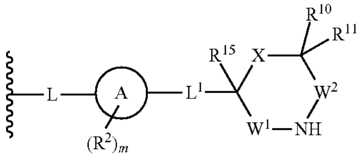

is attached to a modifiable carbon, oxygen, nitrogen or sulfur atom.

TABLE 2

Exemplary Drugs with Disease Indications and Gene Identifier for the Target Protein

| Drug Name | Indication(s) | Gene |
|---|---|---|
| 3196 | anticholesterolaemic agent | THRB |
| Posiphen | for treatment of Alzheimer's disease | APP |
| Posiphen | for treatment of Alzheimer's disease | BACE1 |
| MBO7133 (cytarabine prodrug) | antineoplastic agent | POLB |
| 4SC-202 | antineoplastic agent | HDAC1 |
| 4SC-202 | antineoplastic agent | HDAC2 |
| 4SC-202 | antineoplastic agent | HDAC3 |
| 4SC-202 | antineoplastic agent | HDAC8 |
| 4SC-202 | antineoplastic agent | FLT3 |
| 4SC-202 | antineoplastic agent | VEGFA |
| 4SC-205 | antineoplastic agent | KIF11 |
| 768974 | antiosteoporotic agent | PTH1R |
| 7a-methyl-19-nortestosterone, MENT | hormone replacement, male contraceptive | AR |
| A-007 | antineoplastic agent | ESR1 |
| A-007 | antineoplastic agent | ESR2 |
| oxybutynin | for treatment of incontinence | CHRM1 |
| oxybutynin | for treatment of incontinence | CHRM2 |
| oxybutynin | for treatment of incontinence | CHRM3 |
| Testosterone | hormone replacement | AR |
| ABC294640 | antineoplastic agent | SPHK1 |
| ABC294640 | antineoplastic agent | SPHK2 |
| Aripiprazole | antipsychotic agent | DRD2 |
| Aripiprazole | antipsychotic agent | HTR1A |
| Aripiprazole | antipsychotic agent | HTR2A |
| paclitaxel | antineoplastic agent | BCL2 |
| paclitaxel | antineoplastic agent | TUBB1 |
| navitoclax, ABT-263 | antineoplastic agent | BCL2 |
| navitoclax, ABT-263 | antineoplastic agent | BCL2L1 |
| navitoclax, ABT-263 | antineoplastic agent | BCL2L2 |
| fenofibrate | antidyslipidaemic agent | PPARA |
| Linifanib | antineoplastic agent | CSF1R |
| Linifanib | antineoplastic agent | FLT1 |
| Linifanib | antineoplastic agent | FLT3 |
| Linifanib | antineoplastic agent | FLT4 |
| Linifanib | antineoplastic agent | KDR |
| Linifanib | antineoplastic agent | KIT |
| Linifanib | antineoplastic agent | PDGFRB |
| Linifanib | antineoplastic agent | RET |
| Linifanib | antineoplastic agent | TIE2 |
| AC-201 | antidiabetic | IL1B |
| AC-201 | antidiabetic | IL1RN |
| quizartinib | antineoplastic agent | FLT3 |
| AC430 | antiinflammatory agent, antineoplastic agent | JAK2 |
| AC480 | antineoplastic agent | EGFR |
| AC480 | antineoplastic agent | ERBB2 |
| AC480 | antineoplastic agent | ERBB3 |
| AC480 | antineoplastic agent | ERBB4 |
| acamprosate | for treatment of alcohol-dependance | GRIN3A |
| acamprosate | antineoplastic agent | GRM5 |
| toremifene | antineoplastic agent, SERM | ESR1 |
| acarbose | antidiabetic | AMY2A |
| acarbose | antidiabetic | GAA |
| acarbose | antidiabetic | MGAM |
| acarbose | antidiabetic | SI |

TABLE 2-continued

| Exemplary Drugs with Disease Indications and Gene Identifier for the Target Protein | | |
|---|---|---|
| Drug Name | Indication(s) | Gene |
| organic nitrate + l-arginine | vasodilator | NOS3 |
| Acccretropin | for treatment of turner's syndrome | GHR |
| rabeprazole | Proton pump inhibitor | ATP4A |
| aclidinium | bronchodilator | CHRM1 |
| aclidinium | bronchodilator | CHRM2 |
| aclidinium | bronchodilator | CHRM3 |
| aclidinium | bronchodilator | CHRM4 |
| aclidinium | bronchodilator | CHRM5 |
| acotiamide | for treatment of functional dyspepsia | ACHE |
| ACP-001 | hormone replacement | GHR |
| ACP-104 | antipsychotic agent | CHRM1 |
| ACP-104 | antipsychotic agent | DRD2 |
| ACP-104 | antipsychotic agent | DRD3 |
| ACP-104 | antipsychotic agent | HTR2A |
| ACTB1003 | antineoplastic agent | FGFR1 |
| ACTB1003 | antineoplastic agent | FGFR2 |
| ACTB1003 | antineoplastic agent | FGFR3 |
| ACTB1003 | antineoplastic agent | FGFR4 |
| ACTB1003 | antineoplastic agent | RPS6KB1 |
| ACY-1215 | antineoplastic agent | HDAC6 |
| AD 337 | analgesic, for treatment of fibromyalgia | SLC6A2 |
| AD 337 | analgesic, for treatment of fibromyalgia | SLC6A4 |
| fentanyl | analgesic | OPRD1 |
| fentanyl | analgesic | OPRM1 |
| theophylline | bronchodilator | ADORA1 |
| theophylline | bronchodilator | ADORA2A |
| theophylline | bronchodilator | ADORA2B |
| theophylline | bronchodilator | PDE3A |
| theophylline | bronchodilator | PDE4A |
| theophylline | bronchodilator | PDE4B |
| theophylline | bronchodilator | PDE5A |
| ADL5747 | analgesic | OPRD1 |
| ADL5859 | analgesic | OPRD1 |
| ADL5945 | motilitant | OPRM1 |
| ADL7445 | motilitant | OPRM1 |
| capsaicin | analgesic | TRPV1 |
| fluticasone propionate | bronchodilator | NR3C1 |
| salmeterol | bronchodilator | ADRB2 |
| ADX10059 | antimigraine agent, for treatment of gastroesophageal reflux disease | GRM5 |
| ADX415 | antihypertensive agent | ADRA2A |
| ADX-71149 | antipsychotic agent, antidepressant, anxiolytic | GRM2 |
| fentanyl | analgesic | OPRD1 |
| fentanyl | analgesic | OPRM1 |
| AES-103 | for treatment of sickle-cell disease | HBB |
| doxorubicin | antineoplastic agent | TOP2A |
| AEZS-112, ZEN-012 | antineoplastic agent | TOP2A |
| AEZS-112, ZEN-012 | antineoplastic agent | TUBB |
| AEZS-112, ZEN-012 | antineoplastic agent | TUBB1 |
| Afamelanotide | dermatological agent | MC1R |
| afatinib | antineoplastic agent | EGFR |
| afatinib | antineoplastic agent | ERBB2 |
| ethinyl estradiol | contraceptive | ESR1 |
| levonorgestrel | contraceptive | ESR1 |
| levonorgestrel | contraceptive | PGR |
| levonorgestrel | contraceptive | SRD5A1 |
| mecamylamine | motilitant | CHRNA2 |
| AGI-1067, succinobucol | antiatherosclerosis agent | VCAM1 |
| AGIX-4207 | antiinflammatory agent, DMARD | unknown |
| AGN-214868 | analgesic, neuralgia | ADRA1A |
| AGN-214868 | analgesic, neuralgia | ADRA1B |
| AGN-214868 | analgesic, neuralgia | ADRA1D |
| AGN-214868 | analgesic, neuralgia | ADRA2A |
| AGN-214868 | analgesic, neuralgia | ADRA2B |
| AGN-214868 | analgesic, neuralgia | ADRA2C |
| agomelatine | antidepressant | MTNR1B |
| agomelatine | antidepressant | HTR2B |
| agomelatine | antidepressant | HTR2C |
| agomelatine | antidepressant | MTNR1A |
| hydroxychloroquine | antirheumatic agent | TLR7 |
| hydroxychloroquine | antirheumatic agent | TLR9 |
| paclitaxel | antineoplastic agent | BCL2 |
| paclitaxel | antineoplastic agent | TUBB1 |

TABLE 2-continued

Exemplary Drugs with Disease Indications and Gene Identifier for the Target Protein

| Drug Name | Indication(s) | Gene |
|---|---|---|
| AIKO-150 | opioid antagonist | OPRM1 |
| AIR645 | antiasthmatic agent | IL4RA |
| AKB-6548 | for treatment of anaemia | EGLN1 |
| AKB-6548 | for treatment of anaemia | EGLN2 |
| AKL-0707 | hormone replacement | GHRH |
| ALB109564(a) | antineoplastic agent | TUBB |
| ALB-127158(a) | antiobesity agent | MCHR1 |
| salbutamol | bronchodilator | ADRB2 |
| aleglitazar | cardiovascular agent | PPARA |
| aleglitazar | cardiovascular agent | PPARG |
| alfuzosin | for treatment of benign prostatic hyperplasia | ADRA1A |
| alfuzosin | for treatment of benign prostatic hyperplasia | ADRA1B |
| alfuzosin | for treatment of benign prostatic hyperplasia | ADRA1D |
| lidocaine | anesthetic | SCN10A |
| lidocaine | anesthetic | SCN5A |
| lidocaine | anesthetic | SCN9A |
| pemetrexed | antineoplastic agent | DHFR |
| pemetrexed | antineoplastic agent | GART |
| pemetrexed | antineoplastic agent | TYMS |
| aliskiren | antihypertensive agent | REN |
| aliskiren | antihypertensive agent | REN |
| amlodipine | antihypertensive agent | CACNA1C |
| amlodipine | antihypertensive agent | CACNA1D |
| amlodipine | antihypertensive agent | CACNA1S |
| amlodipine | antihypertensive agent | CACNA2D1 |
| amlodipine | antihypertensive agent | CACNB2 |
| Alitretionine | antineoplastic agent | RARA |
| Alitretionine | antineoplastic agent | RARB |
| Alitretionine | antineoplastic agent | RARG |
| Alitretionine | antineoplastic agent | RXRA |
| Alitretionine | antineoplastic agent | RXRB |
| Alitretionine | antineoplastic agent | RXRG |
| Alitretionine | antineoplastic agent | RARA |
| Alitretionine | antineoplastic agent | RARB |
| Alitretionine | antineoplastic agent | RARG |
| Alitretionine | antineoplastic agent | RXRA |
| Alitretionine | antineoplastic agent | RXRB |
| Alitretionine | antineoplastic agent | RXRG |
| ALKS 33 | for treatment of alcohol dependance, antidepressant | OPRD1 |
| ALKS 33 | for treatment of alcohol dependance, antidepressant | OPRK1 |
| ALKS 33 | for treatment of alcohol dependance, antidepressant | OPRM1 |
| baclofen | for treatment of alcohol dependance | GABBR1 |
| baclofen | for treatment of alcohol dependance | GABBR2 |
| ALKS 33 | for treatment of alcohol dependance, antidepressant | OPRD1 |
| ALKS 33 | for treatment of alcohol dependance, antidepressant | OPRK1 |
| ALKS 33 | for treatment of alcohol dependance, antidepressant | OPRM1 |
| ALKS 37 | motilitant | OPRD1 |
| ALKS 37 | motilitant | OPRK1 |
| ALKS 37 | motilitant | OPRM1 |
| ALKS 33 | for treatment of alcohol dependance, antidepressant | OPRD1 |
| ALKS 33 | for treatment of alcohol dependance, antidepressant | OPRK1 |
| ALKS 33 | for treatment of alcohol dependance, antidepressant | OPRM1 |
| buprenorphine | antidepressant, analgesic, for treatment of opioid addiction | OPRD1 |
| buprenorphine | antidepressant, analgesic, for treatment of opioid addiction | OPRK1 |
| almorexant | sleep disorder treatment | HCRTR1 |
| almorexant | sleep disorder treatment | HCRTR2 |
| almotriptan | antimigraine agent | HTR1B |
| almotriptan | antimigraine agent | HTR1D |
| morphine | analgesic | OPRD1 |
| morphine | analgesic | OPRD1 |
| morphine | analgesic | OPRK1 |
| morphine | analgesic | OPRK1 |

TABLE 2-continued

| Drug Name | Indication(s) | Gene |
|---|---|---|
| morphine | analgesic | OPRM1 |
| morphine | analgesic | OPRM1 |
| naltrexone | analgesic | OPRD1 |
| naltrexone | analgesic | OPRD1 |
| naltrexone | analgesic | OPRK1 |
| naltrexone | analgesic | OPRK1 |
| naltrexone | analgesic | OPRM1 |
| naltrexone | analgesic | OPRM1 |
| naltrexone | analgesic | SIGMAR1 |
| alogliptin | antidiabetic | DPP4 |
| alosetron | for treatment of irritable bowel syndrome | HTR3A |
| alprazolam | anxiolytic, sedative, hypnotic | GABRA1 |
| alprazolam | anxiolytic, sedative, hypnotic | GABRA2 |
| alprazolam | anxiolytic, sedative, hypnotic | GABRA3 |
| alprazolam | anxiolytic, sedative, hypnotic | GABRA4 |
| alprazolam | anxiolytic, sedative, hypnotic | GABRA5 |
| alprazolam | anxiolytic, sedative, hypnotic | GABRA6 |
| alprazolam | anxiolytic, sedative, hypnotic | GABRB1 |
| alprazolam | anxiolytic, sedative, hypnotic | GABRB2 |
| alprazolam | anxiolytic, sedative, hypnotic | GABRB3 |
| alprazolam | anxiolytic, sedative, hypnotic | GABRD |
| alprazolam | anxiolytic, sedative, hypnotic | GABRE |
| alprazolam | anxiolytic, sedative, hypnotic | GABRG1 |
| alprazolam | anxiolytic, sedative, hypnotic | GABRG2 |
| alprazolam | anxiolytic, sedative, hypnotic | GABRG3 |
| alprazolam | anxiolytic, sedative, hypnotic | GABRP |
| alprazolam | anxiolytic, sedative, hypnotic | GABRQ |
| alprazolam | anxiolytic, sedative, hypnotic | GABRR2 |
| alprazolam | anxiolytic, sedative, hypnotic | GABRR3 |
| alprostadil | for treatment of erectile dysfunction, for treatment of sexual dysfunction in women | PTGER1 |
| alprostadil | for treatment of erectile dysfunction, for treatment of sexual dysfunction in women | PTGER2 |
| alprostadil | for treatment of erectile dysfunction, for treatment of sexual dysfunction in women | PTGER1 |
| alprostadil | for treatment of erectile dysfunction, for treatment of sexual dysfunction in women | PTGER2 |
| alprostadil | for treatment of erectile dysfunction, for treatment of sexual dysfunction in women | PTGER1 |
| alprostadil | for treatment of erectile dysfunction, for treatment of sexual dysfunction in women | PTGER2 |
| altropane | diagnostic agent for parkinson's disease and ADHD | SLC6A3 |
| Alvespimycin | antineoplastic agent | HSP90AA1 |
| Alvespimycin | antineoplastic agent | HSP90AB1 |
| AM-101 | for treatment of tinnitus | GRIN1 |
| AM-101 | for treatment of tinnitus | GRIN2A |
| AM-101 | for treatment of tinnitus | GRIN2B |
| AM-101 | for treatment of tinnitus | GRIN2C |
| AM-101 | for treatment of tinnitus | GRIN2D |
| AM-101 | for treatment of tinnitus | GRIN3A |
| AM-101 | for treatment of tinnitus | GRIN3B |
| AM-103 | antiinflammatory agent | ALOX5AP |
| AM-152 | antiinflammatory agent, antifibrotic agent | LPAR1 |
| AM-211 | antiinflammatory agent, antiallergy agent | GPR44 |
| AM-461 | antiinflammatory agent | PTGDR |
| AM-803 | antiinflammatory agent | ALOX5AP |
| AMAP102 | antiinflammatory agent, DMARD | HTR2B |
| AMAP102 | antiinflammatory agent, DMARD | HTR2C |
| AMD-070 | antiviral agent, HIV | CXCR4 |
| ALS 2-0426 | antidiabetic | DPP4 |
| amibegron | antidepressant | ADRB3 |
| amifostine | radiation-protective agent | ALPPL2 |
| amiodarone | antiarrhytmic agent | ADRA1A |
| amiodarone | antiarrhytmic agent | ADRB1 |
| amiodarone | antiarrhytmic agent | KCNH2 |
| amisulpride | antipsychotic agent | DRD2 |

Exemplary Drugs with Disease Indications and Gene Identifier for the Target Protein TABLE 2-continued

| Drug Name | Indication(s) | Gene |
|---|---|---|
| amisulpride | antipsychotic agent | DRD3 |
| amitriptyline | analgesic | SLC6A2 |
| amitriptyline | analgesic | SLC6A4 |
| ketamine | analgesic | GRIN3A |
| amlodipine | antihypertensive agent, cardiovascular agent | CACNA1C |
| amlodipine | antihypertensive agent, cardiovascular agent | CACNA1D |
| amlodipine | antihypertensive agent, cardiovascular agent | CACNA1S |
| amlodipine | antihypertensive agent, cardiovascular agent | CACNA2D1 |
| amlodipine | antihypertensive agent, cardiovascular agent | CACNB2 |
| amonafide | antineoplastic agent | TOP2A |
| amonafide | antineoplastic agent | TOP2B |
| aliskiren | antihypertensive agent | REN |
| amlodipine | antihypertensive agent | CACNA1C |
| amlodipine | antihypertensive agent | CACNA1D |
| amlodipine | antihypertensive agent | CACNA1S |
| amlodipine | antihypertensive agent | CACNA2D1 |
| amlodipine | antihypertensive agent | CACNB2 |
| hydrochlorothiazide | antihypertensive agent | SLC12A3 |
| AN-2728 | antiinflammatory agent, antipsoriatic | PDE4A |
| AN-2728 | antiinflammatory agent, antipsoriatic | PDE4B |
| AN-2898 | antiinflammatory agent, antipsoriatic | PDE4A |
| AN-2898 | antiinflammatory agent, antipsoriatic | PDE4B |
| ANA773 | antineoplastic agent | TLR7 |
| Anacetrapib | for treatment of dyslipidemia | CETP |
| anamorelin | appetite stimulating agent | GHSR |
| anastrozole | antineoplastic agent | CYP19A1 |
| anatibant | for treatment of traumatic brain injury | BDKRB2 |
| ANAVEX 2-73 | for treatment of Alzheimer's disease | SIGMAR1 |
| clomifene | for treatment of testosterone deficiency | ESR1 |
| anhydrovinblastin | antineoplastic agent | TUBB |
| docetaxel | antineoplastic agent | TUBB1 |
| AP1030 | antiobesity agent | MC1R |
| AP1030 | antiobesity agent | MC4R |
| oxybutynin | for treatment of overactive bladder | CHRM1 |
| oxybutynin | for treatment of overactive bladder | CHRM2 |
| oxybutynin | for treatment of overactive bladder | CHRM3 |
| APC-100 | antineoplastic agent | AR |
| APD125 | for treatment of insomnia | HTR2A |
| APD421 | antiemetic | DRD2 |
| APD668 | antidiabetic | GPR119 |
| APD791 | antithrombotic | HTR2A |
| APD916 | for treatment of narcolepsy | HRH3 |
| mepivacaine | anestethic | SCN10A |
| granisetron | antiemetic | HTR3A |
| apilimod | antiinflammatory agent, antipsoriatic | unknown |
| apixaban | antithrombotic | F10 |
| misoprostol | labor-inducing agent | PTGIR |
| Aplindore | antiparkinson agent, for treatment of restlegs legs syndrome | DRD2 |
| apomorphine | for treatment of sexual dysfunction in women, for treatment of erectile dysfunction, antiparkinson agent | DRD2 |
| apomorphine | for treatment of sexual dysfunction in women, for treatment of erectile dysfunction, antiparkinson agent | DRD3 |
| apomorphine | for treatment of sexual dysfunction in women, for treatment of erectile dysfunction, antiparkinson agent | DRD4 |
| apomorphine | for treatment of sexual dysfunction in women, for treatment of erectile dysfunction, antiparkinson agent | DRD2 |
| apomorphine | for treatment of sexual dysfunction in women, for treatment of erectile dysfunction, antiparkinson agent | DRD3 |
| apomorphine | for treatment of sexual dysfunction in women, for treatment of erectile dysfunction, antiparkinson agent | DRD4 |
| apremilast | antiinflammatory agent, DMARD, antipsoriatic | PDE4A |

Exemplary Drugs with Disease Indications and Gene Identifier for the Target Protein TABLE 2-continued Exemplary Drugs with Disease Indications and Gene Identifier for the Target Protein

| Drug Name | Indication(s) | Gene |
|---|---|---|
| apremilast | antiinflammatory agent, DMARD, antipsoriatic | PDE4B |
| aprepitant | antiemetic | TACR1 |
| apricoxib | antineoplastic agent | PTGS2 |
| AR-12 | antineoplastic agent | PDK1 |
| AR-12286 | for treatment of glaucoma | ROCK1 |
| AR-12286 | for treatment of glaucoma | ROCK2 |
| AR-42 | antineoplastic agent | HDAC1 |
| AR-42 | antineoplastic agent | HDAC10 |
| AR-42 | antineoplastic agent | HDAC11 |
| AR-42 | antineoplastic agent | HDAC2 |
| AR-42 | antineoplastic agent | HDAC3 |
| AR-42 | antineoplastic agent | HDAC4 |
| AR-42 | antineoplastic agent | HDAC5 |
| AR-42 | antineoplastic agent | HDAC6 |
| AR-42 | antineoplastic agent | HDAC7A |
| AR-42 | antineoplastic agent | HDAC8 |
| AR-42 | antineoplastic agent | HDAC9 |
| AR9281 | antihypertensive agent | EPHX1 |
| AR9281 | antihypertensive agent | EPHX2 |
| arbaclofen | symptomatic treatment for fragile X syndrome | GABBR1 |
| arbaclofen | symptomatic treatment for fragile X syndrome | GABBR2 |
| ARC100 | antineoplastic agent | TUBB1 |
| clonidine | for treatment of diabetic neuropathy, for treatment of ADHD, antimucositic | ADRA2A |
| clonidine | for treatment of diabetic neuropathy, for treatment of ADHD, antimucositic | ADRA2B |
| clonidine | for treatment of diabetic neuropathy, for treatment of ADHD, antimucositic | ADRA2C |
| ARD-07 | for treatment of growth hormone deficiency | GHR |
| Argatroban | anticoagulant | F2 |
| ARI-2243 | antidiabetic | DPP4 |
| ARI-3037MO | Vitamin B analog, for treatment for hyperlipidemia | GPR109A |
| ARI-3037MO | Vitamin B analog, for treatment for hyperlipidemia | GPR109B |
| ARI-3037MO | Vitamin B analog, for treatment for hyperlipidemia | NNMT |
| ARI-3037MO | Vitamin B analog, for treatment for hyperlipidemia | QPRT |
| armodafinil | central nervous system stimulant | SLC6A3 |
| ARN-509 | antineoplastic agent | AR |
| ARQ-197 | antineoplastic agent | MET |
| ARQ-501 | antineoplastic agent | TOP1 |
| ARQ-621 | antineoplastic agent | KIF11 |
| ARRY-162 | antiinflammatory agent, DMARD, antineoplastic agent | MAP2K1 |
| ARRY-162 | antiinflammatory agent, DMARD, antineoplastic agent | MAP2K2 |
| ARRY-300 | antiinflammatory agent, DMARD, antineoplastic agent | MAP2K1 |
| ARRY-300 | antiinflammatory agent, DMARD, antineoplastic agent | MAP2K2 |
| ARRY-334543 | antineoplastic agent | EGFR |
| ARRY-334543 | antineoplastic agent | ERBB2 |
| ARRY-380 | antineoplastic agent | ERBB2 |
| ARRY-403 | antidiabetic | GCK |
| ARRY-614 | for treatment of myelodysplastic syndrome | ABL1 |
| ARRY-614 | for treatment of myelodysplastic syndrome | KDR |
| ARRY-614 | for treatment of myelodysplastic syndrome | MAPK11 |
| ARRY-614 | for treatment of myelodysplastic syndrome | MAPK12 |
| ARRY-614 | for treatment of myelodysplastic syndrome | MAPK13 |
| ARRY-614 | for treatment of myelodysplastic syndrome | MAPK14 |

TABLE 2-continued

| Exemplary Drugs with Disease Indications and Gene Identifier for the Target Protein | | |
|---|---|---|
| Drug Name | Indication(s) | Gene |
| ARRY-614 | for treatment of myelodysplastic syndrome | TEK |
| ARRY-797 | antineoplastic agent | MAPK11 |
| ARRY-797 | antineoplastic agent | MAPK12 |
| ARRY-797 | antineoplastic agent | MAPK13 |
| ARRY-797 | antineoplastic agent | MAPK14 |
| arsenic trioxide | antineoplastic agent | CCND1 |
| arsenic trioxide | antineoplastic agent | IKBKB |
| arsenic trioxide | antineoplastic agent | JUN |
| arsenic trioxide | antineoplastic agent | MAPK1 |
| arsenic trioxide | antineoplastic agent | MAPK3 |
| arsenic trioxide | antineoplastic agent | TXNRD1 |
| arverapamil | for treatment of irritable bowel syndrome | CACNA1C |
| arverapamil | for treatment of irritable bowel syndrome | CACNA1D |
| arverapamil | for treatment of irritable bowel syndrome | CACNA1F |
| arverapamil | for treatment of irritable bowel syndrome | CACNA1G |
| arverapamil | for treatment of irritable bowel syndrome | CACNA1S |
| arverapamil | for treatment of irritable bowel syndrome | CACNB1 |
| arverapamil | for treatment of irritable bowel syndrome | CACNB2 |
| arverapamil | for treatment of irritable bowel syndrome | CACNB3 |
| arverapamil | for treatment of irritable bowel syndrome | CACNB4 |
| sufentanil | adjuvant to anesthesia | OPRM1 |
| sufentanil | adjuvant to anesthesia | OPRM1 |
| sufentanil | analgesic, sedative | OPRM1 |
| triazolam | analgesic, sedative | GABRA1 |
| triazolam | analgesic, sedative | GABRA2 |
| triazolam | analgesic, sedative | GABRA3 |
| triazolam | analgesic, sedative | GABRA4 |
| triazolam | analgesic, sedative | GABRA5 |
| triazolam | analgesic, sedative | GABRA6 |
| triazolam | analgesic, sedative | GABRB1 |
| triazolam | analgesic, sedative | GABRB2 |
| triazolam | analgesic, sedative | GABRB3 |
| triazolam | analgesic, sedative | GABRD |
| triazolam | analgesic, sedative | GABRE |
| triazolam | analgesic, sedative | GABRG1 |
| triazolam | analgesic, sedative | GABRG2 |
| triazolam | analgesic, sedative | GABRG3 |
| triazolam | analgesic, sedative | GABRP |
| triazolam | analgesic, sedative | GABRQ |
| triazolam | analgesic, sedative | GABRR1 |
| triazolam | analgesic, sedative | GABRR2 |
| triazolam | analgesic, sedative | GABRR3 |
| Arzoxifene | antineoplastic agent, antiosteoporotic agent | ESR1 |
| ASC-J9 | dermatological agent | AR |
| Asenapine | antipsychotic agent | ADRA1A |
| Asenapine | antipsychotic agent | ADRA2A |
| Asenapine | antipsychotic agent | ADRA2B |
| Asenapine | antipsychotic agent | ADRA2C |
| Asenapine | antipsychotic agent | DRD1 |
| Asenapine | antipsychotic agent | DRD2 |
| Asenapine | antipsychotic agent | DRD3 |
| Asenapine | antipsychotic agent | DRD4 |
| Asenapine | antipsychotic agent | HRH1 |
| Asenapine | antipsychotic agent | HRH2 |
| Asenapine | antipsychotic agent | HTR1A |
| Asenapine | antipsychotic agent | HTR1B |
| Asenapine | antipsychotic agent | HTR2A |
| Asenapine | antipsychotic agent | HTR2B |
| Asenapine | antipsychotic agent | HTR2C |
| Asenapine | antipsychotic agent | HTR5A |
| Asenapine | antipsychotic agent | HTR6 |
| Asenapine | antipsychotic agent | HTR7 |
| asimadoline | analgesic | OPRK1 |
| ipragliflozin | antidiabetic | SLC5A2 |
| AT-101 | antineoplastic agent | BAD |

TABLE 2-continued

| Exemplary Drugs with Disease Indications and Gene Identifier for the Target Protein | | |
|---|---|---|
| Drug Name | Indication(s) | Gene |
| AT-101 | antineoplastic agent | BCL2 |
| AT-101 | antineoplastic agent | MCL1 |
| AT13387 | antineoplastic agent | HSP90AA1 |
| AT13387 | antineoplastic agent | HSP90AB1 |
| fentanyl | analgesic | OPRD1 |
| fentanyl | analgesic | OPRD1 |
| fentanyl | analgesic | OPRM1 |
| fentanyl | analgesic, opioid | OPRM1 |
| AT7519 | antineoplastic agent | CDK2 |
| AT9283 | antineoplastic agent | AURKA |
| AT9283 | antineoplastic agent | AURKB |
| atamestane | antineoplastic agent | CYP19A1 |
| toremifene | antineoplastic agent | ESR1 |
| toremifene | antineoplastic agent | ESR2 |
| ATHX-105 | antiobesity agent | HTR2C |
| docetaxel | antineoplastic agent | TUBB1 |
| ATI-7505 | Parasympathomimetic | HTR4 |
| prednisone | antiinflammatory agent, corticosteroid | NR3C1 |
| atomoxetine | for treatment of ADHD | SLC6A2 |
| atorvastatin | antihypecholesterolemic agent | HMGCR |
| atrasentan | antineoplastic agent | EDNRA |
| AUS-131 | for treatment of menopausal symtpoms | ESR2 |
| AV-412 | antineoplastic agent | EGFR |
| AV-412 | antineoplastic agent | ERBB2 |
| AV608 | antidepressant, for treatment of irritable bowel syndrome, antispasmodic | TACR1 |
| tivozanib | antineoplastic agent | FLT1 |
| tivozanib | antineoplastic agent | FLT4 |
| tivozanib | antineoplastic agent | KDR |
| Avanafil | for treatment of erectile dysfunction | PDE5A |
| AVE-1625 | antiobesity agent, for treatment for Alzheimer's disease | CNR1 |
| phentolamine | for treatment of erectile dysfunction | ADRA1A |
| phentolamine | for treatment of erectile dysfunction | ADRA2A |
| AVL-292 | antineoplastic agent | BTK |
| AVN-101 | for treatment of alzheimer's disease | HTR6 |
| AVN-211 | antipsychotic agent | HTR6 |
| AVN-322 | for treatment of alzheimer's disease | HTR6 |
| AVN-944 | antineoplastic agent | IMPDH1 |
| AVN-944 | antineoplastic agent | IMPDH2 |
| avosentan | antihypertensive agent | EDNRA |
| dextromethorphan | antitussive agent | GRIN3A |
| dextromethorphan | antitussive agent | SIGMAR1 |
| axitinib | antineoplastic agent | FLT1 |
| axitinib | antineoplastic agent | FLT4 |
| axitinib | antineoplastic agent | KDR |
| axitinib | antineoplastic agent | KIT |
| axitinib | antineoplastic agent | PDGFRA |
| axitinib | antineoplastic agent | PDGFRB |
| AXL1717 | antineoplastic agent | IGF1R |
| prochlorperazine | antimigraine agent | DRD2 |
| alprazolam | anxiolytic, sedative, hypnotic | GABRA1 |
| alprazolam | anxiolytic, sedative, hypnotic | GABRA2 |
| alprazolam | anxiolytic, sedative, hypnotic | GABRA3 |
| alprazolam | anxiolytic, sedative, hypnotic | GABRA4 |
| alprazolam | anxiolytic, sedative, hypnotic | GABRA5 |
| alprazolam | anxiolytic, sedative, hypnotic | GABRA6 |
| alprazolam | anxiolytic, sedative, hypnotic | GABRB1 |
| alprazolam | anxiolytic, sedative, hypnotic | GABRB2 |
| alprazolam | anxiolytic, sedative, hypnotic | GABRB3 |
| alprazolam | anxiolytic, sedative, hypnotic | GABRD |
| alprazolam | anxiolytic, sedative, hypnotic | GABRE |
| alprazolam | anxiolytic, sedative, hypnotic | GABRG1 |
| alprazolam | anxiolytic, sedative, hypnotic | GABRG2 |
| alprazolam | anxiolytic, sedative, hypnotic | GABRG3 |
| alprazolam | anxiolytic, sedative, hypnotic | GABRP |
| alprazolam | anxiolytic, sedative, hypnotic | GABRQ |
| alprazolam | anxiolytic, sedative, hypnotic | GABRR1 |
| alprazolam | anxiolytic, sedative, hypnotic | GABRR2 |
| alprazolam | anxiolytic, sedative, hypnotic | GABRR3 |
| fentanyl | adjuvant to anesthesia | OPRD1 |
| fentanyl | adjuvant to anesthesia | OPRM1 |
| loxapine | antipsychotic agent | DRD2 |

TABLE 2-continued

Exemplary Drugs with Disease Indications and Gene Identifier for the Target Protein

| Drug Name | Indication(s) | Gene |
|---|---|---|
| loxapine | antipsychotic agent | HTR2A |
| zaleplon | hypnotic | GABRA1 |
| zaleplon | hypnotic | TSPO |
| azacitidine | antineoplastic agent | DNMT1 |
| AZD-0837 | anticoagulant | F2 |
| AZD2066 | analgesic, for treatment of gastroesophageal reflux disease | GRM5 |
| AZD6244, ARRY-142886 | antineoplastic agent | MAP2K1 |
| AZD6244, ARRY-142886 | antineoplastic agent | MAP2K2 |
| AZD-8330 | antineoplastic agent | MAP2K1 |
| AZD-8848 | antiallergy agent | TLR7 |
| azelastine | antiallergy agent | HRH1 |
| azelastine | antiallergy agent | HRH1 |
| azilsartan | antihypertensive agent | AGTR1 |
| balsalazide | antiinflammatory agent | ALOX5 |
| balsalazide | antiinflammatory agent | PPARG |
| balsalazide | antiinflammatory agent | PTGS1 |
| balsalazide | antiinflammatory agent | PTGS2 |
| bardoxolone | antineoplastic agent | NFKB1 |
| bazedoxifene | antiosteoporotic agent | ESR1 |
| bazedoxifene | antiosteoporotic agent | ESR2 |
| ulodesine | antiinflammatory agent | PNP |
| becatecarin | antineoplastic agent | TOP2A |
| becatecarin | antineoplastic agent | TOP2B |
| beclomethasone | antiinflammatory agent, glucocorticoid | NR3C1 |
| beclomethasone | antiinflammatory agent, glucocorticoid | NR3C1 |
| beclomethasone | antiinflammatory agent, glucocorticoid | NR3C1 |
| buprenorphine | antidepressant, analgesic, for treatment of opioid addiction | OPRK1 |
| buprenorphine | antidepressant, analgesic, for treatment of opioid addiction | OPRM1 |
| fentanyl | analgesic | OPRD1 |
| fentanyl | analgesic | OPRM1 |
| benazepril | antihypertensive agent | ACE |
| bepotastine | antiallergy agent | HRH1 |
| beraprost | antihypertensive agent | PTGIR |
| betamethasone | antiinflammatory agent, glucocorticoid | NR3C1 |
| betamethasone | antiinflammatory agent, glucocorticoid | NR3C1 |
| betrixaban | antithrombotic | F10 |
| bexarotene | antineoplastic agent | RXRA |
| bexarotene | antineoplastic agent | RXRB |
| bexarotene | antineoplastic agent | RXRG |
| BF-1 | antimigraine agent | HTR2B |
| BF-Derm1 | antiallergy agent | HDC |
| BG-9928 | for treatment of congestive heart failure | ADORA1 |
| fluoxetine | for treatment of sleep apnea | SLC6A4 |
| ondansetron | for treatment of sleep apnea | HTR3A |
| BGC20-1531 | antimigraine agent | PTGER4 |
| BGG-492 | anticonvulsant, antimigraine agent | GRIA1 |
| BGG-492 | anticonvulsant, antimigraine agent | GRIA2 |
| BGG-492 | anticonvulsant, antimigraine agent | GRIA3 |
| BGG-492 | anticonvulsant, antimigraine agent | GRIA4 |
| progesterone | neuroprotectant for stroke victims | ESR1 |
| progesterone | neuroprotectant for stroke victims | NR3C2 |
| progesterone | neuroprotectant for stroke victims | PGR |
| BI-10773 | antidiabetic | SLC5A2 |
| olodaterol | bronchodilator | ADRB2 |
| Nintedanib | antineoplastic agent | FGFR1 |
| Nintedanib | antineoplastic agent | FGFR2 |
| Nintedanib | antineoplastic agent | FGFR3 |
| Nintedanib | antineoplastic agent | FLT1 |
| Nintedanib | antineoplastic agent | FLT4 |
| Nintedanib | antineoplastic agent | KDR |
| Nintedanib | antineoplastic agent | PDGFRA |
| Nintedanib | antineoplastic agent | PDGFRB |
| Bicalutamide | antineoplastic agent | AR |
| bifeprunox | antipsychotic agent, antiparkinson agent | DRD2 |
| bifeprunox | antipsychotic agent, antiparkinson agent | DRD3 |

TABLE 2-continued

Exemplary Drugs with Disease Indications and Gene Identifier for the Target Protein

| Drug Name | Indication(s) | Gene |
|---|---|---|
| bifeprunox | antipsychotic agent, antiparkinson agent | HTR1A |
| bifeprunox | antipsychotic agent, antiparkinson agent | HTR2A |
| bifeprunox | antipsychotic agent, antiparkinson agent | HTR2C |
| bifeprunox | antipsychotic agent, antiparkinson agent | HTR7 |
| BIM23A760 | antineoplastic agent, treatment for acromegaly | DRD2 |
| BIM23A760 | antineoplastic agent, treatment for acromegaly | SSTR2 |
| BIM23A760 | antineoplastic agent, treatment for acromegaly | SSTR5 |
| bimatoprost | antiglaucomic agent | PTGER1 |
| bimatoprost | antiglaucomic agent | PTGER3 |
| bimatoprost | antiglaucomic agent | PTGFR |
| bimoclomol | for treatment of diabetic neuropathy | HSF1 |
| bimosiamose | antiinflammatory agent, antipsoriatic | SELE |
| bimosiamose | antiinflammatory agent, antipsoriatic | SELL |
| bimosiamose | antiinflammatory agent, antipsoriatic | SELP |
| docetaxel | antineoplastic agent | BCL2 |
| docetaxel | antineoplastic agent | TUBB1 |
| binodenoson | diagnostic agent | ADORA2A |
| estradiol | hormone replacement, treatment for menopause | ESR1 |
| estradiol | hormone replacement, treatment for menopause | ESR2 |
| testosterone | hormone replacement | AR |
| dapagliflozin | antidiabetic | SLC5A2 |
| BMS-582949 | antiinflammatory agent, DMARD, antipsoriatic | MAPK11 |
| BMS-582949 | antiinflammatory agent, DMARD, antipsoriatic | MAPK12 |
| BMS-582949 | antiinflammatory agent, DMARD, antipsoriatic | MAPK13 |
| BMS-582949 | antiinflammatory agent, DMARD, antipsoriatic | MAPK14 |
| BMS-299897 | for treatment of alzheimer's disease | APH1A |
| BMS-299897 | for treatment of alzheimer's disease | APH1B |
| BMS-299897 | for treatment of alzheimer's disease | NCSTN |
| BMS-299897 | for treatment of alzheimer's disease | PSEN1 |
| BMS-299897 | for treatment of alzheimer's disease | PSEN2 |
| BMS-299897 | for treatment of alzheimer's disease | PSENEN |
| BMS-708163 | for treatment of alzheimer's disease | APH1A |
| BMS-708163 | for treatment of alzheimer's disease | APH1B |
| BMS-708163 | for treatment of alzheimer's disease | NCSTN |
| BMS-708163 | for treatment of alzheimer's disease | PSEN1 |
| BMS-708163 | for treatment of alzheimer's disease | PSEN2 |
| BMS-708163 | for treatment of alzheimer's disease | PSENEN |
| BMS-754807 | antineoplastic agent | IGF1R |
| BMS-863233 | antineoplastic agent | CDC7 |
| calcitonin | antiosteoporotic agent | CALCR |
| NCX116 | for treatment of glaucoma | PTGFR |
| bosutinib | antineoplastic agent | ABL1 |
| bosutinib | antineoplastic agent | SRC |
| brimonidine | for treatment of glaucoma | ADRA2A |
| brimonidine | for treatment of glaucoma | ADRA2A |
| timolol | for treatment of glaucoma | ADRB1 |
| timolol | for treatment of glaucoma | ADRB2 |
| Brivaracetam | anticonvulsant | SV2A |
| bromfenac | opthalmological agent, NSAID | PTGS1 |
| bromfenac | opthalmological agent, NSAID | PTGS2 |
| bromocriptine | antidiabetic | DRD2 |
| bromocriptine | antidiabetic | DRD3 |
| Bryostatin | for treatment of alzheimer's disease | PRKCA |
| Bryostatin | for treatment of alzheimer's disease | PRKCB |
| Bryostatin | for treatment of alzheimer's disease | PRKCD |
| Bryostatin | for treatment of alzheimer's disease | PRKCE |
| Bryostatin | for treatment of alzheimer's disease | PRKCG |
| Bryostatin | for treatment of alzheimer's disease | PRKCH |
| Bryostatin | for treatment of alzheimer's disease | PRKCQ |
| Bryostatin | for treatment of alzheimer's disease | PRKD1 |
| Bryostatin | for treatment of alzheimer's disease | PRKD2 |
| Bryostatin | for treatment of alzheimer's disease | PRKD3 |
| Bryostatin-1 | antineoplastic agent | PRKCA |

TABLE 2-continued

Exemplary Drugs with Disease Indications and Gene Identifier for the Target Protein

| Drug Name | Indication(s) | Gene |
|---|---|---|
| Bryostatin-1 | antineoplastic agent | PRKCB |
| Bryostatin-1 | antineoplastic agent | PRKCD |
| Bryostatin-1 | antineoplastic agent | PRKCE |
| Bryostatin-1 | antineoplastic agent | PRKCG |
| Bryostatin-1 | antineoplastic agent | PRKCH |
| Bryostatin-1 | antineoplastic agent | PRKCQ |
| Bryostatin-1 | antineoplastic agent | PRKD1 |
| Bryostatin-1 | antineoplastic agent | PRKD2 |
| Bryostatin-1 | antineoplastic agent | PRKD3 |
| fentanyl | analgesic | OPRD1 |
| fentanyl | analgesic | OPRM1 |
| prochlorperazine | antiemetic | DRD2 |
| bucindolol | for treatment of heart failure | ADRB1 |
| bucindolol | for treatment of heart failure | ADRB2 |
| budesonide | antiinflammatory agent, glucocorticoid | NR3C1 |
| Formoterol | bronchodilator | ADRB2 |
| budesonide | antiinflammatory agent, glucocorticoid | NR3C1 |
| budesonide | antiinflammatory agent, glucocorticoid | NR3C1 |
| budesonide | antiinflammatory agent, glucocorticoid | NR3C1 |
| budesonide | antiinflammatory agent, glucocorticoid | NR3C1 |
| budesonide | antiinflammatory agent, glucocorticoid | NR3C1 |
| budesonide | antiinflammatory agent, glucocorticoid | NR3C1 |
| budiodarone | antiarrhytmic agent | ADRB1 |
| budiodarone | antiarrhytmic agent | CACNA2D2 |
| budiodarone | antiarrhytmic agent | KCNH2 |
| buprenorphine | antidepressant, analgesic, for treatment of opioid addiction | OPRK1 |
| buprenorphine | antidepressant, analgesic, for treatment of opioid addiction | OPRM1 |
| naloxone | analgesic | OPRK1 |
| naloxone | analgesic | OPRM1 |
| buprenorphine | antidepressant, analgesic, for treatment of opioid addiction | OPRK1 |
| buprenorphine | antidepressant, analgesic, for treatment of opioid addiction | OPRM1 |
| naloxone | for treatment of opioid addiction | OPRK1 |
| naloxone | for treatment of opioid addiction | OPRM1 |
| buprenorphine | antidepressant, analgesic, for treatment of opioid addiction | OPRK1 |
| buprenorphine | antidepressant, analgesic, for treatment of opioid addiction | OPRM1 |
| buprenorphine | antidepressant, analgesic, for treatment of opioid addiction | OPRK1 |
| buprenorphine | antidepressant, analgesic, for treatment of opioid addiction | OPRM1 |
| buprenorphine | antidepressant, analgesic, for treatment of opioid addiction | OPRK1 |
| buprenorphine | antidepressant, analgesic, for treatment of opioid addiction | OPRM1 |
| bupropion | antidepressant, appetite suppressant, smoking-cessation agent | SLC6A2 |
| bupropion | antidepressant, appetite suppressant, smoking-cessation agent | SLC6A3 |
| BVT.115959 | analgesic | ADORA2A |
| BVT.28949 | for treatment of glaucoma | HTR2A |
| amphetamine | for treatment of cognitive dysfunction, for treatment of ADHD | CARTPT |
| amphetamine | for treatment of cognitive dysfunction, for treatment of ADHD | SLC18A2 |
| amphetamine | for treatment of cognitive dysfunction, for treatment of ADHD | SLC6A3 |
| amphetamine | for treatment of cognitive dysfunction, for treatment of ADHD | TAAR1 |
| C-1311 | antineoplastic agent | TOP1 |
| C-1311 | antineoplastic agent | TOP2A |
| cabazitaxel | antineoplastic agent | TUBA4A |
| cabazitaxel | antineoplastic agent | TUBB1 |
| amlodipine | antihypertensive agent, cardiovascular agent | CACNA1C |

TABLE 2-continued

| Drug Name | Indication(s) | Gene |
|---|---|---|
| Exemplary Drugs with Disease Indications and Gene Identifier for the Target Protein | | |
| amlodipine | antihypertensive agent, cardiovascular agent | CACNA1D |
| amlodipine | antihypertensive agent, cardiovascular agent | CACNA1S |
| amlodipine | antihypertensive agent, cardiovascular agent | CACNA2D1 |
| amlodipine | antihypertensive agent, cardiovascular agent | CACNB2 |
| atorvastatin | anticholesterolaemic agent | HMGCR |
| CAL-101 | antineoplastic agent | PIK3CD |
| betamethasone | antiinflammatory agent, glucocorticoid | NR3C1 |
| calcipotriene | antipsoriatic agent | VDR |
| calcitriol | antipsoriatic agent | VDR |
| buprenorphine | antidepressant, analgesic, for treatment of opioid addiction | OPRK1 |
| buprenorphine | antidepressant, analgesic, for treatment of opioid addiction | OPRM1 |
| Canagliflozin | antidiabetic | SLC5A2 |
| candesartan | antihypertensive agent | AGTR1 |
| cangrelor | antithrombotic | P2RY12 |
| PRS-211375 | analgesic | CNR2 |
| CAP7.1 | antineoplastic agent | TOP2A |
| Caprospinol | for treatment of alzheimer's disease | APP |
| Carfilzomib | antineoplastic agent | PSMB1 |
| Carfilzomib | antineoplastic agent | PSMB2 |
| Carfilzomib | antineoplastic agent | PSMB5 |
| cariprazine | antipsychotic agent | DRD2 |
| cariprazine | antipsychotic agent | DRD3 |
| carvedilol | for treatment of congestive heart failure | ADRA1A |
| carvedilol | cardiovascular agent | ADRB1 |
| carvedilol | cardiovascular agent | ADRB2 |
| Casopitant | antiemetic | TACR1 |
| dronabinol | analgesic | CNR1 |
| dronabinol | analgesic | CNR2 |
| CB-03-01 | dermatological agent | AR |
| caricotamide | antineoplastic agent | NQO2 |
| tretazicar | antineoplastic agent | DNA |
| abiraterone | antineoplastic agent | CYP17A1 |
| JNK-401 | antineoplastic agent | MAPK10 |
| JNK-401 | antineoplastic agent | MAPK8 |
| JNK-401 | antineoplastic agent | MAPK9 |
| CCX025 | antiinflammatory agent | CCR9 |
| CCX140 | antiinflammatory agent, antidiabetic | CCR2 |
| CCX168 | antiinflammatory agent, for treatment for autoimmune disease | C5AR1 |
| CCX282 | antiinflammatory agent, for treatment of Chron's disease, for treatment of ulceraite colitis | CCR9 |
| CCX354 | antiinflammatory agent, DMARD | CCR1 |
| CCX832 | antiinflammatory agent, for treatment for autoimmune disease | CMKLR1 |
| fenofibrate | anticholesterolaemic agent | PPARA |
| azelastine | antiallergy agent | HRH1 |
| budesonide | antiinflammatory agent, glucocorticoid | NR3C1 |
| cediranib | antineoplastic agent | FLT1 |
| cediranib | antineoplastic agent | FLT4 |
| cediranib | antineoplastic agent | KDR |
| celecoxib | NSAID | PTGS2 |
| mycophenolate mofetil | immunosuppressant | IMPDH1 |
| mycophenolate mofetil | immunosuppressant | IMPDH2 |
| synthetic conjugated estrogens | for treatment of postmenopausal symptoms | ESR1 |
| synthetic conjugated estrogens | for treatment of postmenopausal symptoms | ESR2 |
| histamine | cytorprotective agent during cancer treatment | HRH2 |
| CER-002 | cardiovascular agent | PPARD |
| acetylsalicylic acid | NSAID | PTGS1 |
| acetylsalicylic acid | NSAID | PTGS2 |
| niacin | antidyslipidaemic agent | GPR109A |
| niacin | antidyslipidaemic agent | GPR109B |
| niacin | antidyslipidaemic agent | NNMT |
| niacin | antidyslipidaemic agent | QPRT |

TABLE 2-continued

| Exemplary Drugs with Disease Indications and Gene Identifier for the Target Protein | | |
|---|---|---|
| Drug Name | Indication(s) | Gene |
| diclofenac | NSAID | PTGS1 |
| diclofenac | NSAID | PTGS2 |
| cetilistat | antiobesity agent | PNLIP |
| cetirizine | antiallergy agent | HRH1 |
| CF-101 | antiinflammatory agent, DMARD | ADORA3 |
| CF-102 | antineoplastic agent | ADORA3 |
| CG100649 | NSAID | CA1 |
| CG100649 | NSAID | PTGS2 |
| clopidogrel | antiplatelet agent | P2RY12 |
| omeprazol | antiulcer agent | ATP4A |
| CH-1504 | antiinflammatory agent, DMARD | DHFR |
| CHF 4227 | antiosteoporotic agent | ESR1 |
| CHF 4227 | antiosteoporotic agent | ESR2 |
| beclomethasone | antiinflammatory agent, glucocorticoid | NR3C1 |
| formoterol | antiasthmatic agent | ADRB2 |
| chidamide | antineoplastic agent | HDAC1 |
| chidamide | antineoplastic agent | HDAC10 |
| chidamide | antineoplastic agent | HDAC2 |
| chidamide | antineoplastic agent | HDAC3 |
| CHIR-265 | antineoplastic agent | BRAF |
| CHIR-265 | antineoplastic agent | KDR |
| CHIR-265 | antineoplastic agent | RAF1 |
| cyclosporine | immunosuppressant | CAMLG |
| cyclosporine | immunosuppressant | PPP3R2 |
| tadalafil | for treatment of erectile dysfunction | PDE5A |
| cilansetron | for treatment of irritable bowel syndrome | HTR3A |
| cimicoxib | NSAID | PTGS2 |
| isotretinoin | for treatment of acne | RARA |
| escitalopram | antidepressant | SLC6A4 |
| tiramsetiv | for treatment of skeletal muscle disorders associated with aging and neuro-degenerative disorders. | TNNC1 |
| tiramsetiv | for treatment of skeletal muscle disorders associated with aging and neuro-degenerative disorders. | TNNC2 |
| tiramsetiv | for treatment of skeletal muscle disorders associated with aging and neuro-degenerative disorders. | TNNI1 |
| tiramsetiv | for treatment of skeletal muscle disorders associated with aging and neuro-degenerative disorders. | TNNI2 |
| tiramsetiv | for treatment of skeletal muscle disorders associated with aging and neuro-degenerative disorders. | TNNT1 |
| tiramsetiv | for treatment of skeletal muscle disorders associated with aging and neuro-degenerative disorders. | TNNT2 |
| clazosentan | for treatment and prevention of vasospasm | EDNRA |
| clevidipine | antihypertensive agent | CACNA1C |
| clevidipine | antihypertensive agent | CACNA1D |
| clevidipine | antihypertensive agent | CACNA1F |
| clevidipine | antihypertensive agent | CACNA1S |
| clobazam | anxiolytic, anticonvulsant | GABRA1 |
| clobazam | anxiolytic, anticonvulsant | GABRA2 |
| clobazam | anxiolytic, anticonvulsant | GABRA3 |
| clobazam | anxiolytic, anticonvulsant | GABRA4 |
| clobazam | anxiolytic, anticonvulsant | GABRA5 |
| clobazam | anxiolytic, anticonvulsant | GABRA6 |
| clobazam | anxiolytic, anticonvulsant | GABRB1 |
| clobazam | anxiolytic, anticonvulsant | GABRB2 |
| clobazam | anxiolytic, anticonvulsant | GABRB3 |
| clobazam | anxiolytic, anticonvulsant | GABRD |
| clobazam | anxiolytic, anticonvulsant | GABRE |
| clobazam | anxiolytic, anticonvulsant | GABRG1 |
| clobazam | anxiolytic, anticonvulsant | GABRG2 |
| clobazam | anxiolytic, anticonvulsant | GABRG3 |
| clobazam | anxiolytic, anticonvulsant | GABRP |
| clobazam | anxiolytic, anticonvulsant | GABRQ |
| clobazam | anxiolytic, anticonvulsant | GABRR1 |
| clobazam | anxiolytic, anticonvulsant | GABRR2 |
| clobazam | anxiolytic, anticonvulsant | GABRR3 |
| clobetasol | antiinflammatory agent, corticosteroid | NR3C1 |

TABLE 2-continued

Exemplary Drugs with Disease Indications and Gene Identifier for the Target Protein

| Drug Name | Indication(s) | Gene |
|---|---|---|
| clodronate | antineoplastic agent | SLC25A4 |
| clodronate | antineoplastic agent | SLC25A5 |
| clodronate | antineoplastic agent | SLC25A6 |
| Clofarabine | antineoplastic agent | POLA1 |
| Clofarabine | antineoplastic agent | RRM1 |
| clonidine | for treatment of diabetic neuropathy, for treatment of ADHD, antimucositic | ADRA2A |
| clonidine | for treatment of diabetic neuropathy, for treatment of ADHD, antimucositic | ADRA2B |
| clonidine | for treatment of diabetic neuropathy, for treatment of ADHD, antimucositic | ADRA2C |
| clonidine | for treatment of diabetic neuropathy, for treatment of ADHD, antimucositic | ADRA2A |
| clonidine | for treatment of diabetic neuropathy, for treatment of ADHD, antimucositic | ADRA2B |
| clonidine | for treatment of diabetic neuropathy, for treatment of ADHD, antimucositic | ADRA2C |
| CLX-0921 | antidiabetic | PPARG |
| CM2489 | antiinflammatory agent, antipsoriatic | ORA1 |
| CNDO101 | antineoplastic agent | TOP2A |
| CNF1010 | antineoplastic agent | HSP90AA1 |
| CNF1010 | antineoplastic agent | HSP90AB1 |
| CNS-5161 | analgesic | GRIN1 |
| CNS-5161 | analgesic | GRIN2A |
| CNS-5161 | analgesic | GRIN2B |
| CNS-5161 | analgesic | GRIN2C |
| CNS-5161 | analgesic | GRIN2D |
| CNS-5161 | analgesic | GRIN3A |
| CNS-5161 | analgesic | GRIN3B |
| CNS-7056 | sedative | GABRA2 |
| CNS-7056 | sedative | GABRA3 |
| CNS-7056 | sedative | GABRA5 |
| CNS-7056 | sedative | GABRA6 |
| CNS-7056 | sedative | GABRB1 |
| CNS-7056 | sedative | GABRB1 |
| CNS-7056 | sedative | GABRB2 |
| CNS-7056 | sedative | GABRB2 |
| CNS-7056 | sedative | GABRB3 |
| CNS-7056 | sedative | GABRD |
| CNS-7056 | sedative | GABRD |
| CNS-7056 | sedative | GABRE |
| CNS-7056 | sedative | GABRG1 |
| CNS-7056 | sedative | GABRG2 |
| CNS-7056 | sedative | GABRG3 |
| CNS-7056 | sedative | GABRG3 |
| CNS-7056 | sedative | GABRP |
| CNS-7056 | sedative | GABRQ |
| CNS-7056 | sedative | GABRR2 |
| CNV2197944 | analgesic | CACNA1B |
| oxycodone | analgesic | OPRD1 |
| oxycodone | analgesic | OPRK1 |
| oxycodone | analgesic | OPRM1 |
| oxycodone | analgesic | OPRD1 |
| oxycodone | analgesic | OPRK1 |
| oxycodone | analgesic | OPRM1 |
| COL-3 | antineoplastic agent | MMP2 |
| COL-3 | antineoplastic agent | MMP9 |
| colchicine | for treatment of gout | TUBB |
| bupivacaine | local anestethic, analgesic, neuralgia | SCN10A |
| conivaptan | for treatment of hyponatremia | AVPR1A |
| conivaptan | for treatment of hyponatremia | AVPR2 |
| estrogen | for symptomatic treatment of menopausal symptoms | ESR1 |
| estrogen | for symptomatic treatment of menopausal symptoms | ESR2 |
| progesterone | for symptomatic treatment of menopausal symptoms | ESR1 |
| progesterone | for symptomatic treatment of menopausal symptoms | NR3C2 |

TABLE 2-continued

Exemplary Drugs with Disease Indications and Gene Identifier for the Target Protein

| Drug Name | Indication(s) | Gene |
|---|---|---|
| progesterone | for symptomatic treatment of menopausal symptoms | PGR |
| ethinyl estradiol | contraceptive | ESR1 |
| gestodene | contraceptive | PGR |
| bupropion | antidepressant, appetite suppressant, smoking-cessation agent | SLC6A2 |
| bupropion | antidepressant, appetite suppressant, smoking-cessation agent | SLC6A3 |
| naltrexone | appetite suppressant | OPRD1 |
| naltrexone | appetite suppressant | OPRK1 |
| naltrexone | appetite suppressant | OPRM1 |
| fomepizole | for treatment of ethanol intolerance | ADH1A |
| fomepizole | for treatment of ethanol intolerance | ADH1B |
| fomepizole | for treatment of ethanol intolerance | ADH1C |
| cordycepin | antineoplastic agent | DNTT |
| CORT 108297 | for prevention of weight gain during antipsychotic treatment | NR3C1 |
| CP-4126 | antineoplastic agent | DNA |
| CP-609,754 | antineoplastic agent | FNTA |
| CP-609,754 | antineoplastic agent | FNTB |
| CPG 10101 | immunostimulant | TLR9 |
| CPG 52364 | antiinflammatory agent | TLR7 |
| CPG 52364 | antiinflammatory agent | TLR8 |
| CPG 52364 | antiinflammatory agent | TLR9 |
| CPI-613 | antineoplastic agent | PDHA1 |
| CPI-613 | antineoplastic agent | PDHA2 |
| CPI-613 | antineoplastic agent | PDHB |
| CPI-613 | antineoplastic agent | PDK1 |
| CPI-613 | antineoplastic agent | PDK2 |
| CPI-613 | antineoplastic agent | PDK3 |
| CPI-613 | antineoplastic agent | PDK4 |
| semapimod | antiinflammatory agent, for treatment of Chron's disease | MAPK11 |
| semapimod | antiinflammatory agent, for treatment of Chron's disease | MAPK12 |
| semapimod | antiinflammatory agent, for treatment of Chron's disease | MAPK13 |
| semapimod | antiinflammatory agent, for treatment of Chron's disease | MAPK14 |
| floxuridine | antineoplastic agent | TYMS |
| irinotecan | antineoplastic agent | TOP1 |
| irinotecan | antineoplastic agent | TOP1MT |
| cytarabine | antineoplastic agent | POLB |
| daunorubicin | antineoplastic agent | TOP2A |
| daunorubicin | antineoplastic agent | TOP2B |
| CR665 | analgesic | OPRK1 |
| CR845 | analgesic | OPRK1 |
| pravastatin | antihypecholesterolemic agent | HMGCR |
| rosuvastatin | antihypecholesterolemic agent | HMGCR |
| 561679 | antidepressant | CRHR1 |
| crizotinib | antineoplastic agent | ALK |
| crizotinib | antineoplastic agent | MET |
| CRTH2 receptor antagonist | antiallergy agent | GPR44 |
| prednisolone | antiinflammatory agent, corticosteroid | NR3C1 |
| dipyridamole | anticoagulant | ADA |
| dipyridamole | anticoagulant | PDE10A |
| dipyridamole | anticoagulant | PDE4A |
| dipyridamole | anticoagulant | PDE5A |
| amoxapine | antidepressant | SLC6A2 |
| amoxapine | antidepressant | SLC6A4 |
| prednisolone | antiinflammatory agent, corticosteroid | NR3C1 |
| paroxetine | antidepressant | SLC6A4 |
| prednisolone | antiinflammatory agent, corticosteroid | NR3C1 |
| amoxapine | antidepressant | SLC6A2 |
| amoxapine | antidepressant | SLC6A4 |
| dipyridamole | antithrombotic | ADA |
| dipyridamole | antithrombotic | PDE10A |
| dipyridamole | antithrombotic | PDE4A |
| dipyridamole | antithrombotic | PDE5A |
| budesonide | antiinflammatory agent, glucocorticoid | NR3C1 |

TABLE 2-continued

| Exemplary Drugs with Disease Indications and Gene Identifier for the Target Protein | | |
|---|---|---|
| Drug Name | Indication(s) | Gene |
| nortriptyline | antiasthmatic agent | SLC6A2 |
| nortriptyline | antiasthmatic agent | SLC6A4 |
| mometasone | antiinflammatory agent, glucocorticoid | NR3C1 |
| nortriptyline | antidepressant | SLC6A2 |
| nortriptyline | antidepressant | SLC6A4 |
| bezafibrate | antidiabetic | PPARA |
| diflunisal | antidiabetic | PTGS1 |
| diflunisal | antidiabetic | PTGS2 |
| CS-3030 | anticoagulant | F10 |
| CS-7017 | antineoplastic agent | PPARG |
| amlodipine | antihypertensive agent | CACNA1C |
| amlodipine | antihypertensive agent | CACNA1D |
| amlodipine | antihypertensive agent | CACNA1S |
| amlodipine | antihypertensive agent | CACNA2D1 |
| amlodipine | antihypertensive agent | CACNB2 |
| olmesartan | antihypertensive agent | AGTR1 |
| CTA018 | antiinflammatory agent, antipsoriatic | CYP24A1 |
| CTS-21166 | for treatment of Alzheimer's disease | BACE1 |
| CUDC-101 | antineoplastic agent | EGFR |
| CUDC-101 | antineoplastic agent | ERBB2 |
| CUDC-101 | antineoplastic agent | HDAC1 |
| CUDC-101 | antineoplastic agent | HDAC10 |
| CUDC-101 | antineoplastic agent | HDAC11 |
| CUDC-101 | antineoplastic agent | HDAC2 |
| CUDC-101 | antineoplastic agent | HDAC3 |
| CUDC-101 | antineoplastic agent | HDAC4 |
| CUDC-101 | antineoplastic agent | HDAC5 |
| CUDC-101 | antineoplastic agent | HDAC6 |
| CUDC-101 | antineoplastic agent | HDAC7 |
| CUDC-101 | antineoplastic agent | HDAC8 |
| CUDC-101 | antineoplastic agent | HDAC9 |
| CVT-3619 | antihyperlipidemic agent | ADORA1 |
| CVT-6883 | antiasthmatic agent | ADORA2B |
| CX157 | antidepressant | MAOA |
| CX1632/S 47445 | for treatment of Alzheimer's disease | GRIA1 |
| CX1632/S 47445 | for treatment of Alzheimer's disease | GRIA2 |
| CX1632/S 47445 | for treatment of Alzheimer's disease | GRIA3 |
| CX1632/S 47445 | for treatment of Alzheimer's disease | GRIA4 |
| CX-4945 | antineoplastic agent | CSNK2A1 |
| CX717 | for treatment of Alzheimer's disease | GRIA1 |
| CX717 | for treatment of Alzheimer's disease | GRIA2 |
| CX717 | for treatment of Alzheimer's disease | GRIA3 |
| CX717 | for treatment of Alzheimer's disease | GRIA4 |
| CXB909 | for treatment of chemotherapy-induced peripheral neuropathy | LNGFR |
| CXB909 | for treatment of chemotherapy-induced peripheral neuropathy | NTRK1 |
| CYC116 | antineoplastic agent | AURKA |
| CYC116 | antineoplastic agent | AURKB |
| CYC116 | antineoplastic agent | KDR |
| cyclosporine | immunosuppressant | CAMLG |
| cyclosporine | immunosuppressant | PPP3R2 |
| duloxetine | antidepressant | SLC6A2 |
| duloxetine | antidepressant | SLC6A4 |
| cysteamine | for treatment of corneal cystine accumulation | cystine |
| cytarabine | antineoplastic agent | POLB |
| D3263 | antineoplastic agent | TRPM8 |
| Dabigatran | anticoagulant | F2 |
| decitabine | antineoplastic agent | DNMT1 |
| dapoxetine | for treatment of premature ejaculation | SLC6A4 |
| darapladib | antiinflammatory agent, DMARD | PLA2G7 |
| darifenacin | for treatment of overactive bladder | CHRM3 |
| darusentan | antihypertensive agent | EDNRA |
| dasatinib | antineoplastic agent | ABL1 |
| dasatinib | antineoplastic agent | ABL2 |
| dasatinib | antineoplastic agent | EPHA2 |
| dasatinib | antineoplastic agent | FYN |
| dasatinib | antineoplastic agent | KIT |
| dasatinib | antineoplastic agent | LCK |
| dasatinib | antineoplastic agent | PDGFRB |
| dasatinib | antineoplastic agent | SRC |
| dasatinib | antineoplastic agent | STAT5B |
| dasatinib | antineoplastic agent | YES1 |
| methylphenidate | for treatment of ADHD | SLC6A3 |

TABLE 2-continued

| Drug Name | Indication(s) | Gene |
|---|---|---|
| DB-959 | antidiabetic | PPARD |
| DB-959 | antidiabetic | PPARG |
| diazoxide choline | antidyslipidaemic agent | ABCC8 |
| DDP225 | for treatment of irritable bowel syndrome | HTR3A |
| DDP225 | for treatment of irritable bowel syndrome | HTR3B |
| DDP225 | for treatment of irritable bowel syndrome | HTR3C |
| DDP225 | for treatment of irritable bowel syndrome | HTR3D |
| DDP225 | for treatment of irritable bowel syndrome | HTR3E |
| DDP225 | for treatment of irritable bowel syndrome | SLC6A2 |
| Debio 0932 | antineoplastic agent | HSP90AA1 |
| Debio 0932 | antineoplastic agent | HSP90AB1 |
| DEBIO-9902 SR | for treatment of Alzheimer's disease | ACHE |
| Degarelix | antineoplastic agent | GNRHR |
| Degarelix | antineoplastic agent | GNRHR2 |
| denufosol | for treatment of cystic fibrosis | P2RY2 |
| deoxynojirimycin | for treatment of Pompe disease | GAA |
| bupivacaine | local anestethic, analgesic, neuralgia | SCN10A |
| gabapentin | for treatment of neuropathic pain | CACNA1B |
| gabapentin | for treatment of neuropathic pain | CACNA2D1 |
| gabapentin | for treatment of neuropathic pain | CACNA2D2 |
| romidepsin | antineoplastic agent | HDAC1 |
| romidepsin | antineoplastic agent | HDAC10 |
| romidepsin | antineoplastic agent | HDAC11 |
| romidepsin | antineoplastic agent | HDAC2 |
| romidepsin | antineoplastic agent | HDAC3 |
| romidepsin | antineoplastic agent | HDAC4 |
| romidepsin | antineoplastic agent | HDAC5 |
| romidepsin | antineoplastic agent | HDAC6 |
| romidepsin | antineoplastic agent | HDAC7A |
| romidepsin | antineoplastic agent | HDAC8 |
| romidepsin | antineoplastic agent | HDAC9 |
| dersalazine | antiinflammatory agent, for treatment of ulcerative colitis | PTGS1 |
| dersalazine | antiinflammatory agent, for treatment of ulcerative colitis | PTGS2 |
| dersalazine | antiinflammatory agent, for treatment of ulcerative colitis | TNF |
| desloratadine | antiallergy agent | HRH1 |
| desonide | antiinflammatory agent, corticosteroid | NR3C1 |
| dexamethasone | antiinflammatory agent, glucocorticoid, for treatment of Meniere's disease | NR3C1 |
| Dexanabinol | neuroprotectant | GRIN1 |
| Dexanabinol | neuroprotectant | GRIN2A |
| Dexanabinol | neuroprotectant | GRIN2B |
| Dexanabinol | neuroprotectant | GRIN2D |
| Dexanabinol | neuroprotectant | GRIN3A |
| Dexanabinol | neuroprotectant | GRIN3B |
| dexlipotam | for treatment of diabetic neuropathy | PDHB |
| dexloxiglumide | motilitant | CCKAR |
| dexpramipexole | for treatment of amyotrophic lateral sclerosis (ALS) | DRD2 |
| dexpramipexole | for treatment of amyotrophic lateral sclerosis (ALS) | DRD3 |
| dexpramipexole | for treatment of amyotrophic lateral sclerosis (ALS) | DRD4 |
| DG031 | antiinflammatory agent, myocardial infarction prophylaxis | ALOX5AP |
| DG041 | Platelet Aggregation Inhibitor | PTGER3 |
| DG051 | antiinflammatory agent, myocardial infarction prophylaxis | LTA4H |
| DG071 | for treatment of alzheimer's disease | PDE4A |
| DG071 | for treatment of alzheimer's disease | PDE4B |
| DG3173 | hormone replacement | SSTR1 |
| DG3173 | hormone replacement | SSTR2 |
| DG3173 | hormone replacement | SSTR4 |
| DG3173 | hormone replacement | SSTR5 |
| diazepam | anticonvulsant | GABRA1 |
| diazepam | anticonvulsant | GABRA2 |

TABLE 2-continued

| Exemplary Drugs with Disease Indications and Gene Identifier for the Target Protein | | |
|---|---|---|
| Drug Name | Indication(s) | Gene |
| diazepam | anticonvulsant | GABRA3 |
| diazepam | anticonvulsant | GABRA5 |
| diazepam | anticonvulsant | GABRB1 |
| diazepam | anticonvulsant | GABRB2 |
| diazepam | anticonvulsant | GABRB3 |
| diazepam | anticonvulsant | GABRD |
| diazepam | anticonvulsant | GABRE |
| diazepam | anticonvulsant | GABRG1 |
| diazepam | anticonvulsant | GABRG2 |
| diazepam | anticonvulsant | GABRG3 |
| diazepam | anticonvulsant | GABRP |
| diazepam | anticonvulsant | GABRQ |
| diazepam | anticonvulsant | GABRR1 |
| diazepam | anticonvulsant | GABRR2 |
| diazepam | anticonvulsant | GABRR3 |
| diclofenac | analgesic | PTGS1 |
| diclofenac | analgesic | PTGS2 |
| Diclofenac | analgesic | PTGS1 |
| Diclofenac | analgesic | PTGS2 |
| Diclofenac | analgesic | PTGS1 |
| Diclofenac | analgesic | PTGS2 |
| Diclofenac | NSAID | PTGS1 |
| Diclofenac | NSAID | PTGS2 |
| Diclofenac | for treatment of glaucoma | PTGS1 |
| Diclofenac | for treatment of glaucoma | PTGS2 |
| difluprednate | antiinflammatory agent, corticosteroid | NR3C1 |
| diltiazem | antihypertensive agent | CACNG1 |
| latrepirdine | neuroprotectant | ACHE |
| latrepirdine | neuroprotectant | GRIN1 |
| latrepirdine | neuroprotectant | GRIN2A |
| latrepirdine | neuroprotectant | GRIN2B |
| latrepirdine | neuroprotectant | GRIN2C |
| latrepirdine | neuroprotectant | GRIN2D |
| latrepirdine | neuroprotectant | GRIN3A |
| latrepirdine | neuroprotectant | GRIN3B |
| dimiracetam | nootropic | GRIN1 |
| dimiracetam | nootropic | GRIN2A |
| dimiracetam | nootropic | GRIN2B |
| dimiracetam | nootropic | GRIN2C |
| dimiracetam | nootropic | GRIN2D |
| DIO-902 | antidiabetic | ERG11 |
| diquafosol | opthalmological agent | P2RY2 |
| carbidopa | antiparkinson agent | DDC |
| levodopa | antiparkinson agent | DRD1 |
| levodopa | antiparkinson agent | DRD2 |
| omeprazole | antiulcer agent | ATP4A |
| betanechol | antidiabetic | CHRM2 |
| calcitriol | antineoplastic agent | VDR |
| Docetaxel | antineoplastic agent | BCL2 |
| Docetaxel | antineoplastic agent | TBB1 |
| dolasetron | antiemetic | HTR3A |
| dolasetron | antiemetic | HTR3B |
| dolasetron | antiemetic | HTR3C |
| dolasetron | antiemetic | HTR3D |
| dolasetron | antiemetic | HTR3E |
| donepezil | for treatment of alzheimer's disease | ACHE |
| beclomethasone dipropionate | antiinflammatory agent, glucocorticoid | NR3C1 |
| DOV 102,677 | antidepressant | SLC6A2 |
| DOV 102,677 | antidepressant | SLC6A3 |
| DOV 102,677 | antidepressant | SLC6A4 |
| DOV 216,303 | antidepressant | SLC6A2 |
| DOV 216,303 | antidepressant | SLC6A3 |
| DOV 216,303 | antidepressant | SLC6A4 |
| DOV 21947 | antidepressant | SLC6A2 |
| DOV 21947 | antidepressant | SLC6A3 |
| DOV 21947 | antidepressant | SLC6A4 |
| dovitinib | antineoplastic agent | FGFR1 |
| dovitinib | antineoplastic agent | FGFR2 |
| dovitinib | antineoplastic agent | FGFR3 |
| dovitinib | antineoplastic agent | FLT1 |
| dovitinib | antineoplastic agent | FLT1 |
| dovitinib | antineoplastic agent | FLT1 |
| dovitinib | antineoplastic agent | FLT4 |
| dovitinib | antineoplastic agent | KDR |

TABLE 2-continued

Exemplary Drugs with Disease Indications and Gene Identifier for the Target Protein

| Drug Name | Indication(s) | Gene |
|---|---|---|
| dovitinib | antineoplastic agent | PDGFRB |
| doxepin | antimigraine agent | SLC6A2 |
| doxepin | antimigraine agent | SLC6A4 |
| doxercalciferol | for treatment of secondary hyperparathyroidism | VDR |
| doxorubicin | antineoplastic agent | TOP2A |
| doxorubicin | antineoplastic agent | TOP2A |
| doxorubicin | antineoplastic agent | TOP2A |
| doxorubicin | antineoplastic agent | TOP2A |
| DP-VPA | anticonvulsant | ABAT |
| DRF 10945 | antidyslipidaemic agent | PPARA |
| dronabinol | appetite stimulant | CNR1 |
| drospirenone | hormone replacement | PGR |
| estradiol | hormone replacement | ESR1 |
| estradiol | hormone replacement | ESR2 |
| DSC-103 | antiosteoporotic agent | VDR |
| DTS-201 | antineoplastic agent | TOP2A |
| bupivacaine | local anestethic, analgesic, neuralgia | SCN10A |
| bupivacaine | local anestethic, analgesic, neuralgia | SCN10A |
| sildenafil | for treatment of erectile dysfunction | PDE5A |
| dutasteride | for treatment of benign prostate hyperplasia | SRD5A1 |
| dutasteride | for treatment of benign prostate hyperplasia | SRD5A2 |
| tamsulosin | for treatment of benign prostatic hyperplasia | ADRA1A |
| dutasteride | for treatment of benign prostate hyperplasia | SRD5A1 |
| dutogliptin | antidiabetic | DPP4 |
| azelastine | antiallergy agent | HRH1 |
| fluticasone | antiinflammatory agent, glucocorticoid | NR3C1 |
| perampanel | anticonvulsant | GRIA1 |
| perampanel | anticonvulsant | GRIA2 |
| perampanel | anticonvulsant | GRIA3 |
| perampanel | anticonvulsant | GRIA4 |
| E2012 | for treatment of Alzheimer's disease | PSEN1 |
| lenvatinib | antineoplastic agent | FGFR1 |
| lenvatinib | antineoplastic agent | FLT1 |
| lenvatinib | antineoplastic agent | FLT4 |
| lenvatinib | antineoplastic agent | KDR |
| lenvatinib | antineoplastic agent | KIT |
| lenvatinib | antineoplastic agent | PDGFRA |
| lenvatinib | antineoplastic agent | PDGFRB |
| ecabet | antiulcer agent | PGA3 |
| ecabet | antiulcer agent | PGC |
| ecopipam | for treatment of tourettes syndrome, for treatment of pathological gambling | DRD1 |
| edoxaban | antithrombotic | F10 |
| venlafaxine | antidepressant | SLC6A2 |
| venlafaxine | antidepressant | SLC6A4 |
| eflornithine | for treatment of unwanted facial hair in women | ODC1 |
| dexamethasone | antiinflammatory agent, glucocorticoid, for treatment of Meniere's disease | NR3C1 |
| Etazolate | for treatment of alzheimer's disease | GABRA2 |
| Etazolate | for treatment of alzheimer's disease | GABRA3 |
| Etazolate | for treatment of alzheimer's disease | GABRB1 |
| Etazolate | for treatment of alzheimer's disease | GABRB2 |
| Etazolate | for treatment of alzheimer's disease | GABRE |
| Etazolate | for treatment of alzheimer's disease | GABRG1 |
| Etazolate | for treatment of alzheimer's disease | PDE4A |
| Etazolate | for treatment of alzheimer's disease | PDE4B |
| Etazolate | for treatment of alzheimer's disease | PDE4C |
| Etazolate | for treatment of alzheimer's disease | PDE4D |
| ronomilast | antiinflammatory agent | PDE4A |
| ronomilast | antiinflammatory agent | PDE4B |
| ED-71 | antiosteoporotic agent | VDR |
| oxycodone | analgesic | OPRD1 |
| oxycodone | analgesic | OPRK1 |
| oxycodone | analgesic | OPRM1 |
| eliglustat | for treatment of Gaucher's disease | UGCG |
| elinogrel | antiplatelet agent | P2RY12 |

TABLE 2-continued

Exemplary Drugs with Disease Indications and Gene Identifier for the Target Protein

| Drug Name | Indication(s) | Gene |
|---|---|---|
| Elocalcitol | for treatment of benign prostatic hyperplasia | VDR |
| bupropion | antidepressant, appetite suppressant, smoking-cessation agent | SLC6A2 |
| bupropion | antidepressant, appetite suppressant, smoking-cessation agent | SLC6A3 |
| zonisamide | appetite suppressant | CACNA1G |
| zonisamide | appetite suppressant | CACNA1H |
| zonisamide | appetite suppressant | CACNA1I |
| zonisamide | appetite suppressant | SCN11A |
| zonisamide | appetite suppressant | SCN1A |
| zonisamide | appetite suppressant | SCN1B |
| zonisamide | appetite suppressant | SCN2A |
| zonisamide | appetite suppressant | SCN2B |
| zonisamide | appetite suppressant | SCN3A |
| zonisamide | appetite suppressant | SCN3B |
| zonisamide | appetite suppressant | SCN4A |
| zonisamide | appetite suppressant | SCN4B |
| zonisamide | appetite suppressant | SCN5A |
| zonisamide | appetite suppressant | SCN9A |
| enalapril | antihypertensive agent | ACE |
| felodipine | antihypertensive agent | CACNA1C |
| felodipine | antihypertensive agent | CACNA1D |
| felodipine | antihypertensive agent | CACNA1S |
| felodipine | antihypertensive agent | CACNA2D1 |
| felodipine | antihypertensive agent | CACNANB2 |
| paclitaxel | antineoplastic agent | BCL2 |
| paclitaxel | antineoplastic agent | TUBB1 |
| eniluracil | antineoplastic agent | DPYD |
| ENMD-1198 | antineoplastic agent | HIF1A |
| ENMD-2076 | antineoplastic agent | ABL1 |
| ENMD-2076 | antineoplastic agent | AURKA |
| ENMD-2076 | antineoplastic agent | BLK |
| ENMD-2076 | antineoplastic agent | CSF1R |
| ENMD-2076 | antineoplastic agent | FGFR1 |
| ENMD-2076 | antineoplastic agent | FGFR2 |
| ENMD-2076 | antineoplastic agent | FLT3 |
| ENMD-2076 | antineoplastic agent | FLT4 |
| ENMD-2076 | antineoplastic agent | FYN |
| ENMD-2076 | antineoplastic agent | JAK2 |
| ENMD-2076 | antineoplastic agent | KDR |
| ENMD-2076 | antineoplastic agent | KIT |
| ENMD-2076 | antineoplastic agent | LCK |
| ENMD-2076 | antineoplastic agent | NTRK1 |
| ENMD-2076 | antineoplastic agent | PDGFRA |
| ENMD-2076 | antineoplastic agent | PTK2 |
| ENMD-2076 | antineoplastic agent | RET |
| ENMD-2076 | antineoplastic agent | SRC |
| ENMD-2076 | antineoplastic agent | YES1 |
| entacapone | antiparkinson agent | COMT |
| carbidopa | antiparkinson agent | DDC |
| entacapone | antiparkinson agent | COMT |
| levodopa | antiparkinson agent | DRD1 |
| levodopa | antiparkinson agent | DRD2 |
| levodopa | antiparkinson agent | DRD3 |
| levodopa | antiparkinson agent | DRD4 |
| levodopa | antiparkinson agent | DRD5 |
| entinostat | antineoplastic agent | HDAC1 |
| entinostat | antineoplastic agent | HDAC3 |
| Enzastaurin | antineoplastic agent | PRKCB |
| EP217609 | anticoagulant | F10 |
| EP217609 | anticoagulant | F2 |
| EP42675 | anticoagulant | F10 |
| EP42675 | anticoagulant | F2 |
| EPI-743 | for treatment of Chron's disease, for treatment of ulcerative colitis | NQO1 |
| epinastine | antiallergy agent | HRH1 |
| epinastine | antiallergy agent | HRH2 |
| eplerenone | antihypertensive agent | NR3C2 |
| eplivanserine | for treatment of insomnia | HTR2A |
| eplivanserine | for treatment of insomnia | HTR2C |
| Epothilone D | antineoplastic agent | TUBB1 |
| eprotirome | antidyslipidaemic agent | THRB |
| erdosteine | for treatment of chronic obstructive pulmonary disorder (COPD) | ELANE |

TABLE 2-continued

| Exemplary Drugs with Disease Indications and Gene Identifier for the Target Protein | | |
|---|---|---|
| Drug Name | Indication(s) | Gene |
| eritoran | for treatment of sepsis | TLR4 |
| Eslicarbazepine | anticonvulsant | SCN5A |
| esmirtazapine | for treatment of insomnia, for treatment of menopausal symptoms | ADRA2A |
| esmirtazapine | for treatment of insomnia, for treatment of menopausal symptoms | HTR2A |
| esmirtazapine | for treatment of insomnia, for treatment of menopausal symptoms | HTR3A |
| esomeprazole | Proton pump inhibitor | ATP4A |
| estradiol | contraceptive | ESR1 |
| estradiol | contraceptive | ESR1 |
| estradiol | contraceptive | ESR2 |
| norethisterone | contraceptive | PGR |
| estradiol | for treatment of menopausal symptoms | ESR1 |
| estradiol | for treatment of menopausal symptoms | ESR2 |
| estradiol | for treatment of menopausal symptoms | ESR1 |
| estradiol | for treatment of menopausal symptoms | ESR2 |
| estradiol | contraceptive | ESR1 |
| dienogest | contraceptive | ESR1 |
| dienogest | contraceptive | PGR |
| estradiol | contraceptive | ESR2 |
| estradiol | contraceptive | ESR2 |
| estradiol | for treatment of menopausal symptoms | ESR1 |
| estradiol | for treatment of menopausal symptoms | ESR2 |
| levonorgestrel | for treatment of menopausal symptoms | ESR1 |
| levonorgestrel | for treatment of menopausal symptoms | PGR |
| levonorgestrel | for treatment of menopausal symptoms | SRD5A1 |
| estradiol | for treatment of menopausal symptoms | ESR1 |
| estradiol | for treatment of menopausal symptoms | ESR2 |
| estradiol | for treatment of menopausal symptoms | ESR1 |
| estradiol | for treatment of menopausal symptoms | ESR2 |
| drospirenone | contraceptive | AR |
| drospirenone | contraceptive | NR3C2 |
| drospirenone | contraceptive | PGR |
| estradiol | contraceptive | ESR1 |
| estradiol | contraceptive | ESR2 |
| ethinyl estradiol | contraceptive | ESR1 |
| levonorgestrel | contraceptive | ESR1 |
| levonorgestrel | contraceptive | PGR |
| etilevodopa | antiparkinson agent | DRD1 |
| etilevodopa | antiparkinson agent | DRD2 |
| etilevodopa | antiparkinson agent | DRD3 |
| etilevodopa | antiparkinson agent | DRD4 |
| etilevodopa | antiparkinson agent | DRD5 |
| etodolac | NSAID | PTGS2 |
| etonogestrel | contraceptive | ESR1 |
| etonogestrel | contraceptive | PGR |
| ethinyl estradiol | contraceptive | ESR1 |
| etonogestrel | contraceptive | ESR1 |
| etonogestrel | contraceptive | PGR |
| etoricoxib | NSAID | PTGS2 |
| EV-077-3201-2TBS | antidiabetic | PPARG |
| everolimus | immunosuppressant | MTOR |
| raloxifen | for treatment of menopausal symptoms | ESR1 |
| raloxifen | for treatment of menopausal symptoms | ESR2 |
| metoclopramide | for treatment of diabetic gastroparesis | CHRM1 |
| metoclopramide | for treatment of diabetic gastroparesis | DRD2 |
| EVP-6124 | nootropic | CHRNA7 |
| EVT-101 | antidepressant | GRIN2B |

TABLE 2-continued

Exemplary Drugs with Disease Indications and Gene Identifier for the Target Protein

| Drug Name | Indication(s) | Gene |
|---|---|---|
| EVT-103 | antidepressant | GRIN2B |
| EVT-201 | hypnotic | GABRA2 |
| EVT-201 | hypnotic | GABRA3 |
| EVT-201 | hypnotic | GABRA5 |
| EVT-201 | hypnotic | GABRA6 |
| EVT-201 | hypnotic | GABRB1 |
| EVT-201 | hypnotic | GABRB1 |
| EVT-201 | hypnotic | GABRB2 |
| EVT-201 | hypnotic | GABRB2 |
| EVT-201 | hypnotic | GABRB3 |
| EVT-201 | hypnotic | GABRD |
| EVT-201 | hypnotic | GABRD |
| EVT-201 | hypnotic | GABRE |
| EVT-201 | hypnotic | GABRG1 |
| EVT-201 | hypnotic | GABRG2 |
| EVT-201 | hypnotic | GABRG3 |
| EVT-201 | hypnotic | GABRG3 |
| EVT-201 | hypnotic | GABRP |
| EVT-201 | hypnotic | GABRQ |
| EVT-201 | hypnotic | GABRR2 |
| EVT-302 | smoking-cessation agent | MAOB |
| EVT-401 | antiinflammatory agent | P2RX7 |
| Exebryl-1 | for treatment of alzheimer's disease | APP |
| Exebryl-1 | for treatment of alzheimer's disease | MAPT |
| exemestane | antineoplastic agent | CYP19A1 |
| ezatiostat | for treatment of Myelodysplastic Syndrome | GSTP1 |
| PEG-SN38 | antineoplastic agent | TOP1MT |
| PEG-SN38 | antineoplastic agent | TOP1 |
| fentanyl | analgesic | OPRD1 |
| fentanyl | analgesic | OPRM1 |
| febuxostat | for treatment of gout | XDH |
| felodipine | antihypertensive agent | CACNA1C |
| felodipine | antihypertensive agent | CACNA1D |
| felodipine | antihypertensive agent | CACNA1S |
| felodipine | antihypertensive agent | CACNA2D1 |
| felodipine | antihypertensive agent | CACNB2 |
| fenoldopam | antihypertensive agent | DRD1 |
| fenoldopam | antihypertensive agent | DRD5 |
| fenretinide | antineoplastic agent | RARA |
| fenretinide | antineoplastic agent | RARB |
| fenretinide | antineoplastic agent | RARG |
| fentanyl | analgesic | OPRD1 |
| fentanyl | analgesic | OPRM1 |
| fentanyl | analgesic | OPRD1 |
| fentanyl | analgesic | OPRM1 |
| fentanyl | analgesic | OPRD1 |
| fentanyl | analgesic | OPRM1 |
| fentanyl | analgesic | OPRD1 |
| fentanyl | analgesic | OPRM1 |
| fentanyl | analgesic | OPRD1 |
| fentanyl | analgesic | OPRM1 |
| fentanyl | analgesic | OPRD1 |
| fentanyl | analgesic | OPRM1 |
| fentanyl | analgesic | OPRD1 |
| fentanyl | analgesic | OPRM1 |
| fentanyl | analgesic | OPRD1 |
| fentanyl | analgesic | OPRM1 |
| fesoterodine | for treatment of overactive bladder syndrome | CHRM3 |
| fexofenadine | antiallergy agent | HRH1 |
| pseudoephedrine | antiallergy agent | ADRA1A |
| pseudoephedrine | antiallergy agent | ADRA2A |
| pseudoephedrine | antiallergy agent | SLC6A2 |
| pseudoephedrine | antiallergy agent | SLC6A3 |
| pseudoephedrine | antiallergy agent | SLC6A4 |
| FG-2216 | for treatment of anemia | EGLN1 |
| FG-2216 | for treatment of anemia | EGLN2 |
| FG-2216 | for treatment of anemia | EGLN3 |
| FG-4592 | for treatment of anemia | EGLN1 |
| FG-4592 | for treatment of anemia | EGLN2 |
| FG-4592 | for treatment of anemia | EGLN3 |
| fingolimod | for treatment of multiple sclerosis | S1PR1 |
| fipamezole | antiparkinson agent | ADRA2A |
| fipamezole | antiparkinson agent | ADRA2B |
| fipamezole | antiparkinson agent | ADRA2C |

TABLE 2-continued

Exemplary Drugs with Disease Indications and Gene Identifier for the Target Protein

| Drug Name | Indication(s) | Gene |
|---|---|---|
| icatibant | for treatment of hereditary angioedema | BDKRB2 |
| fispemifene | hormone replacement | ESR1 |
| fispemifene | hormone replacement | ESR2 |
| FK352B | antihypertensive agent | ADORA1 |
| alvocidib | antineoplastic agent | CDC2 |
| alvocidib | antineoplastic agent | CDK10 |
| alvocidib | antineoplastic agent | CDK2 |
| alvocidib | antineoplastic agent | CDK3 |
| alvocidib | antineoplastic agent | CDK4 |
| alvocidib | antineoplastic agent | CDK5 |
| alvocidib | antineoplastic agent | CDK6 |
| alvocidib | antineoplastic agent | CDK7 |
| alvocidib | antineoplastic agent | CDK8 |
| alvocidib | antineoplastic agent | CDK9 |
| flibanserin | for treatment of female sexual dysfunction | HTR1A |
| flibanserin | for treatment of female sexual dysfunction | HTR2A |
| flovagatran | anticoagulant | F2 |
| fludarabine | antineoplastic agent | DCK |
| fludarabine | antineoplastic agent | POLA1 |
| fludarabine | antineoplastic agent | RRM1 |
| flunisolide | antiinflammatory agent, glucocorticoid | NR3C1 |
| flunisolide | antiinflammatory agent, glucocorticoid | NR3C1 |
| fluocinonide | antiinflammatory agent, glucocorticoid | NR3C1 |
| fluoxetine | antidepressant | SLC6A4 |
| flupirtine | analgesic | KCNJ3 |
| flupirtine | analgesic | KCNJ5 |
| flupirtine | analgesic | KCNJ6 |
| flupirtine | analgesic | KCNJ9 |
| fluticasone | antiinflammatory agent, glucocorticoid | NR3C1 |
| fluvastatin | antihypecholesterolemic agent | HMGCR |
| fluvoxamine | antidepressant | SLC6A4 |
| dexmethylphenidate | for treatment of ADHD | SLC6A3 |
| dexmethylphenidate | for treatment of ADHD | SLCA2 |
| forodesine | antineoplastic agent | PNP |
| formoterol | bronchodilator | ADRB2 |
| formoterol | for treatment of chronic obstructive pulmonary disorder (COPD) | ADRB2 |
| fosphenytoin | anticonvulsant | SCN5A |
| fospropofol | hypnotic and sedative | GABRB2 |
| fospropofol | hypnotic and sedative | GABRB3 |
| fostamatinib | antiinflammatory agent, DMARD | SYK |
| cyclosporine | immunosuppressant | CAMLG |
| cyclosporine | immunosuppressant | PPP3R2 |
| prednisolone | antiinflammatory agent, corticosteroid | NR3C1 |
| frovatriptan | antimigraine agent | HTR1B |
| frovatriptan | antimigraine agent | HTR1D |
| fruquintinib | antineoplastic agent | FLT1 |
| fruquintinib | antineoplastic agent | FLT4 |
| fruquintinib | antineoplastic agent | KDR |
| dexamethasone | antiinflammatory agent, glucocorticoid, for treatment of Meniere's disease | NR3C1 |
| fulvestrant | antineoplastic agent | ESR1 |
| leucovorin | adjuvant to chemotherapy | TYMS |
| FX125L | antiasthmatic agent | CCR1 |
| FX125L | antiasthmatic agent | CXCR1 |
| FX125L | antiasthmatic agent | CXCR2 |
| FX125L | antiasthmatic agent | CXCR4 |
| gabapentin | analgesic | CACNA1B |
| gabapentin | analgesic | CACNA2D1 |
| gabapentin | analgesic | CACNA2D2 |
| gaboxadol | hypnotic | GABRA2 |
| gaboxadol | hypnotic | GABRA3 |
| gaboxadol | hypnotic | GABRA5 |
| gaboxadol | hypnotic | GABRA6 |
| gaboxadol | hypnotic | GABRB1 |
| gaboxadol | hypnotic | GABRB1 |
| gaboxadol | hypnotic | GABRB2 |

TABLE 2-continued

| Exemplary Drugs with Disease Indications and Gene Identifier for the Target Protein | | |
|---|---|---|
| Drug Name | Indication(s) | Gene |
| gaboxadol | hypnotic | GABRB2 |
| gaboxadol | hypnotic | GABRB3 |
| gaboxadol | hypnotic | GABRD |
| gaboxadol | hypnotic | GABRE |
| gaboxadol | hypnotic | GABRG1 |
| gaboxadol | hypnotic | GABRP |
| galantamine | for treatment of alzheimer's disease | ACHE |
| ganaxolone | anticonvulsant | GABRA1 |
| ganaxolone | anticonvulsant | GABRA2 |
| ganaxolone | anticonvulsant | GABRA3 |
| ganaxolone | anticonvulsant | GABRA4 |
| ganaxolone | anticonvulsant | GABRA5 |
| ganaxolone | anticonvulsant | GABRA6 |
| gantacurium | muscle relaxant, neuromuscular blocking agent | CHRNA2 |
| GDC-0068 | antineoplastic agent | AKT1 |
| GDC-0068 | antineoplastic agent | AKT2 |
| GDC-0068 | antineoplastic agent | AKT3 |
| GDC-0973 | antineoplastic agent | MAP2K1 |
| gemcitabine | antineoplastic agent | RRM1 |
| gepirone | antidepressant | HTR1A |
| progesterone | for prevention of preterm delivery | PGR |
| GGTI-2418 | antineoplastic agent | FNTA |
| GGTI-2418 | antineoplastic agent | PGGT1B |
| GL1001 | for treatment of Chron's disease, for treatment of ulcerative colitis | ACE2 |
| glimepiride | antidiabetic | KCNJ1 |
| glimepiride | antidiabetic | ABCC8 |
| glimepiride | antidiabetic | KCNJ11 |
| GLPG0187 | antineoplastic agent | ITGA5 |
| GLPG0187 | antineoplastic agent | ITGAV |
| GLPG0187 | antineoplastic agent | ITGB1 |
| GLPG0187 | antineoplastic agent | ITGB3 |
| GLPG0187 | antineoplastic agent | ITGB5 |
| GLPG0187 | antineoplastic agent | ITGB6 |
| GLPG0259 | antiinflammatory agent, DMARD | MAPKAPK5 |
| GLPG0492 | for treatment of cachexia | AR |
| GLPG0634 | antiinflammatory agent, DMARD | JAK1 |
| GLPG0634 | antiinflammatory agent, DMARD | JAK2 |
| Glufosfamide | antineoplastic agent | SLC2A1 |
| Glufosfamide | antineoplastic agent | SLC2A2 |
| Glufosfamide | antineoplastic agent | SLC2A3 |
| Glufosfamide | antineoplastic agent | SLC2A4 |
| Glufosfamide | antineoplastic agent | SLC2A5 |
| Glufosfamide | antineoplastic agent | SLC5A1 |
| Glufosfamide | antineoplastic agent | SLC5A2 |
| Glufosfamide | antineoplastic agent | SLC5A4 |
| glyburide | antidiabetic | ABCC8 |
| metformin | antidiabetic | PRKAB1 |
| glycopyrrolate | antineoplastic agent | CHRM1 |
| GMI-1070 | for treatment of sickle-cell disease | SELE |
| GMI-1070 | for treatment of sickle-cell disease | SELL |
| GMI-1070 | for treatment of sickle-cell disease | SELP |
| GMX1777 | antineoplastic agent | NAMPT |
| NBI-42902 | for treatment of postmenopausal symptoms, antineoplastic agent | GNRHR |
| NBI-42902 | for treatment of postmenopausal symptoms, antineoplastic agent | GNRHR2 |
| GPI-1485 | antiparkinson agent | FKBP1A |
| GPX-100 | antineoplastic agent | TOP2A |
| granisetron | antiemetic | HTR3A |
| granisetron | antiemetic | HTR3B |
| granisetron | antiemetic | HTR3C |
| granisetron | antiemetic | HTR3D |
| granisetron | antiemetic | HTR3E |
| granisetron | antiemetic | HTR3A |
| granisetron | antiemetic | HTR3B |
| granisetron | antiemetic | HTR3C |
| granisetron | antiemetic | HTR3D |
| granisetron | antiemetic | HTR3E |
| GS-9411 | for treatment of pulmonary disease | SCNN1A |
| GS-9411 | for treatment of pulmonary disease | SCNN1B |
| GS-9411 | for treatment of pulmonary disease | SCNN1D |
| GS-9411 | for treatment of pulmonary disease | SCNN1G |
| GSI-136 | for treatment of Alzheimer's disease | APH1A |
| GSI-136 | for treatment of Alzheimer's disease | APH1B |

TABLE 2-continued

Exemplary Drugs with Disease Indications and Gene Identifier for the Target Protein

| Drug Name | Indication(s) | Gene |
|---|---|---|
| GSI-136 | for treatment of Alzheimer's disease | NCSTN |
| GSI-136 | for treatment of Alzheimer's disease | PSEN1 |
| GSI-136 | for treatment of Alzheimer's disease | PSEN2 |
| GSI-136 | for treatment of Alzheimer's disease | PSENEN |
| GSK-1004723 | antiallergy agent | HRH1 |
| GSK-1004723 | antiallergy agent | HRH3 |
| trametinib | antineoplastic agent | MAP2K1 |
| GSK2118436 | antineoplastic agent | BRAF |
| GSK-961081 | bronchodilator | ADRB2 |
| GSK-961081 | bronchodilator | CHRM3 |
| GTS-21 | for treatment of schizophrenia | CHRNA7 |
| GTx-758 | antineoplastic agent | LHCGR |
| guanfacine | for treatment of ADHD | ADRA2A |
| GW501516 | antidyslipidaemic agent | PPARA |
| GW501516 | antidyslipidaemic agent | PPARD |
| GW501516 | antidyslipidaemic agent | PPARG |
| GW642444 | bronchodilator | ADRB2 |
| halofuginone | antineoplastic agent | EPRS |
| flurbiprofen | antiinflammatory agent, NSAID | PTGS2 |
| nitric oxide | antiinflammatory agent | GUCY1A2 |
| HE3235 | antineoplastic agent | AR |
| doxorubicin | antineoplastic agent | TOP2A |
| heparin | anticoagulant | F10 |
| heparin | anticoagulant | SERPINC1 |
| heparin | anticoagulant | F10 |
| heparin | anticoagulant | SERPINC1 |
| HF0220 | for treatment of alzheimer's disease | unknown |
| HGS1029 | antineoplastic agent | BIRC2 |
| HGS1029 | antineoplastic agent | BIRC3 |
| HGS1029 | antineoplastic agent | BIRC5 |
| HGS1029 | antineoplastic agent | XIAP |
| amlodipine | antihypertensive agent | CACNA1C |
| amlodipine | antihypertensive agent | CACNA1D |
| amlodipine | antihypertensive agent | CACNA1S |
| amlodipine | antihypertensive agent | CACNA2D1 |
| amlodipine | antihypertensive agent | CACNAB2 |
| simvastatin | antihypertensive agent | HMGCR |
| amiloride | antihypertensive agent | SCNN1A |
| amiloride | antihypertensive agent | SCNN1B |
| amiloride | antihypertensive agent | SCNN1D |
| amiloride | antihypertensive agent | SCNN1G |
| spironolactone | antihypertensive agent | NR3C2 |
| huperzine-A | for treatment of Alzheimer's disease | ACHE |
| hydralazine | antihypertensive agent | AOC3 |
| isosorbide dinitrate | antihypertensive agent | NPR1 |
| hydroxytamoxifen | for treatment of cyclic mastalgia | ESR1 |
| hydroxytamoxifen | for treatment of cyclic mastalgia | ESR2 |
| famotidine | acid reducer | HRH2 |
| famotidine | for treatment of gastric ulcer and gastroesophageal reflux | HRH2 |
| ibuprofen | NSAID | PTGS1 |
| ibuprofen | NSAID | PTGS2 |
| ibandronate | antiosteoporotic agent | FDPS |
| dexamethasone | antiinflammatory agent, glucocorticoid, for treatment of Meniere's disease | NR3C1 |
| ibudilast | neuroprotectant | PDE4A |
| ibudilast | neuroprotectant | PDE4B |
| ibudilast | neuroprotectant | PDE4C |
| ICA-105665 | anticonvulsant | KCNQ1 |
| ICA-105665 | anticonvulsant | KCNQ2 |
| ICA-105665 | anticonvulsant | KCNQ3 |
| ICA-105665 | anticonvulsant | KCNQ4 |
| ICA-105665 | anticonvulsant | KCNQ5 |
| idrabiotaparinux | antithrombotic | F10 |
| idraparinux | antithrombotic | F10 |
| iferanserin | antihemorrhoidal agent | HTR2A |
| iloperidone | antipsychotic agent, atypical | ADRA1A |
| iloperidone | antipsychotic agent, atypical | ADRA2C |
| iloperidone | antipsychotic agent, atypical | DRD1 |
| iloperidone | antipsychotic agent, atypical | DRD2 |
| iloperidone | antipsychotic agent, atypical | DRD3 |
| iloperidone | antipsychotic agent, atypical | HRH1 |
| iloperidone | antipsychotic agent, atypical | HTR1A |
| iloperidone | antipsychotic agent, atypical | HTR2A |
| iloperidone | antipsychotic agent, atypical | HTR6 |

TABLE 2-continued

Exemplary Drugs with Disease Indications and Gene Identifier for the Target Protein

| Drug Name | Indication(s) | Gene |
|---|---|---|
| iloperidone | antipsychotic agent, atypical | HTR7 |
| iloprost | antihypertensive agent | PTGER1 |
| iloprost | antihypertensive agent | PTGIR |
| fluocinolone acetonide | antiinflammatory agent, glucocorticoid | NR3C1 |
| imatinib | antineoplastic agent | ABL1 |
| imatinib | antineoplastic agent | CSF1R |
| imatinib | antineoplastic agent | DDR1 |
| imatinib | antineoplastic agent | KIT |
| imatinib | antineoplastic agent | NTRK1 |
| imatinib | antineoplastic agent | PDGFRA |
| imatinib | antineoplastic agent | PDGFRB |
| imatinib | antineoplastic agent | RET |
| Imiquimod | anti wart agent, antineoplastic agent | TLR7 |
| implitapide | antiatherosclerotic agent | MTTP |
| INCB13739 | antidiabetic | HSD11B1 |
| INCB18424 | antineoplastic agent, antiinflammatory agent | JAK1 |
| INCB18424 | antineoplastic agent, antiinflammatory agent | JAK2 |
| INCB3284 | antiinflammatory agent, DMARD | CCR2 |
| INCB7839 | antineoplastic agent | ADAM10 |
| INCB7839 | antineoplastic agent | ADAM17 |
| indacaterol | bronchodilator | ADRB2 |
| indomethacin | NSAID | KCNE1 |
| indomethacin | NSAID | KCNQ1 |
| Indiplon | hypnotic | GABRA1 |
| inecalcitol | antineoplastic agent, prostate cancer | VDR |
| apomorphine | for treatment of sexual dysfunction in women, for treatment of erectile dysfunction, antiparkinson agent | DRD2 |
| apomorphine | for treatment of sexual dysfunction in women, for treatment of erectile dysfunction, antiparkinson agent | DRD3 |
| apomorphine | for treatment of sexual dysfunction in women, for treatment of erectile dysfunction, antiparkinson agent | DRD4 |
| atropine | nerve agent antidote | CHRM1 |
| atropine | nerve agent antidote | CHRM2 |
| atropine | nerve agent antidote | CHRM3 |
| atropine | nerve agent antidote | CHRM4 |
| atropine | nerve agent antidote | CHRM5 |
| iniparib | antineoplastic agent | PARP1 |
| INK128 | antineoplastic agent | CRTC1 |
| INK128 | antineoplastic agent | CRTC2 |
| INNO-206 | antineoplastic agent | TOP2A |
| INO-8875 | for treatment of glaucoma | ADORA1 |
| INS37217 | for treatment of rhegmatogenous retinal detachment | P2RY2 |
| INS37217 | for treatment of cystic fibrosis,for treatment of perennial allergic rhinitis | P2RY2 |
| INSM-18 | antineoplastic agent, prostate cancer | ERBB2 |
| INSM-18 | antineoplastic agent, prostate cancer | IGF1R |
| AMG-131 | antidiabetic | PPARG |
| apomorphine | for treatment of sexual dysfunction in women, for treatment of erectile dysfunction, antiparkinson agent | DRD2 |
| apomorphine | for treatment of sexual dysfunction in women, for treatment of erectile dysfunction, antiparkinson agent | DRD3 |
| apomorphine | for treatment of sexual dysfunction in women, for treatment of erectile dysfunction, antiparkinson agent | DRD4 |
| ketorolac | NSAID | PTGS2 |
| morphine | analgesic | OPRD1 |
| morphine | analgesic | OPRK1 |
| morphine | analgesic | OPRM1 |
| retaspimycin | antineoplastic agent | HSP90AA1 |
| retaspimycin | antineoplastic agent | HSP90AA2 |
| retaspimycin | antineoplastic agent | HSP90AB1 |
| IPI-504 | antineoplastic agent | HSP90AA1 |
| IPI-504 | antineoplastic agent | HSP90AA2 |
| IPI-504 | antineoplastic agent | HSP90AB1 |
| IPI-940 | analgesic | FAAH |

TABLE 2-continued

| Drug Name | Indication(s) | Gene |
|---|---|---|
| ipratropium | for treatment of chronic obstructive pulmonary disorder (COPD) | CHRM1 |
| ipratropium | for treatment of chronic obstructive pulmonary disorder (COPD) | CHRM2 |
| salbutamol | for treatment of chronic obstructive pulmonary disorder (COPD) | ADRB2 |
| IPX066 | antiparkinson agent | DDC |
| irbesartan | antihypertensive agent | AGTR1 |
| gefitinib | antineoplastic agent | EGFR |
| irinotecan | antineoplastic agent | TOP1 |
| isofagomine | for treatment of Gaucher's disease | GBA |
| ispinesib | antineoplastic agent | KIF11 |
| istaroxime | for treatment of heart failure | ATP1A1 |
| istaroxime | for treatment of heart failure | ATP2A2 |
| istradefylline | antiparkinson agent | ADORA2A |
| bromfenac | opthalmological agent, NSAID | PTGS1 |
| bromfenac | opthalmological agent, NSAID | PTGS2 |
| bromfenac | opthalmological agent, NSAID | PTGS1 |
| bromfenac | opthalmological agent, NSAID | PTGS2 |
| Givinostat | antineoplastic agent, antiinflammatory agent | HDAC1 |
| Givinostat | antineoplastic agent, antiinflammatory agent | HDAC10 |
| Givinostat | antineoplastic agent, antiinflammatory agent | HDAC2 |
| Givinostat | antineoplastic agent, antiinflammatory agent | HDAC3 |
| Givinostat | antineoplastic agent, antiinflammatory agent | HDAC4 |
| Givinostat | antineoplastic agent, antiinflammatory agent | HDAC5 |
| Givinostat | antineoplastic agent, antiinflammatory agent | HDAC6 |
| Givinostat | antineoplastic agent, antiinflammatory agent | HDAC7 |
| Givinostat | antineoplastic agent, antiinflammatory agent | HDAC8 |
| Givinostat | antineoplastic agent, antiinflammatory agent | HDAC9 |
| ITI-007 | antipsychotic agent | DRD2 |
| ITI-007 | antipsychotic agent | HTR2A |
| ITI-007 | antipsychotic agent | PPP1R1B |
| ITI-007 | antipsychotic agent | SLC6A4 |
| itopride | motilitant | ACHE |
| itopride | motilitant | DRD2 |
| IW-6118 | analgesic | FAAH |
| ixabepilone | antineoplastic agent | TUBB3 |
| JB991 | antiinflammatory agent, dermatologic agent | PPARG |
| JNJ-37822681 | antipsychotic agent | DRD2 |
| JSM 6427 | for treatment of age-related macular degeneration | ITGA5 |
| JSM 6427 | for treatment of age-related macular degeneration | ITGB1 |
| ropinirole | for treatment of restlegs legs syndrome | DRD2 |
| ropinirole | for treatment of restlegs legs syndrome | DRD3 |
| ropinirole | for treatment of restlegs legs syndrome | DRD4 |
| clonazepam | anticonvulsant | GABRA2 |
| clonazepam | anticonvulsant | GABRA3 |
| clonazepam | anticonvulsant | GABRA5 |
| clonazepam | anticonvulsant | GABRA6 |
| clonazepam | anticonvulsant | GABRB1 |
| clonazepam | anticonvulsant | GABRB1 |
| clonazepam | anticonvulsant | GABRB2 |
| clonazepam | anticonvulsant | GABRB2 |
| clonazepam | anticonvulsant | GABRB3 |
| clonazepam | anticonvulsant | GABRD |
| clonazepam | anticonvulsant | GABRD |
| clonazepam | anticonvulsant | GABRE |
| clonazepam | anticonvulsant | GABRG2 |
| clonazepam | anticonvulsant | GABRG3 |
| clonazepam | anticonvulsant | GABRG3 |
| clonazepam | anticonvulsant | GABRP |

Exemplary Drugs with Disease Indications and Gene Identifier for the Target Protein TABLE 2-continued Exemplary Drugs with Disease Indications and Gene Identifier for the Target Protein

| Drug Name | Indication(s) | Gene |
|---|---|---|
| clonazepam | anticonvulsant | GABRQ |
| clonazepam | anticonvulsant | GABRR2 |
| Karenitecin | antineoplastic agent | TOP1 |
| KC706 | antiinflammatory agent, DMARD | MAPK11 |
| KC706 | antiinflammatory agent, DMARD | MAPK12 |
| KC706 | antiinflammatory agent, DMARD | MAPK13 |
| KC706 | antiinflammatory agent, DMARD | MAPK14 |
| KD3010 | antiobesity agent, for treatment of metabolic disorders | PPARD |
| ketoprofen | NSAID | PTGS1 |
| ketoprofen | NSAID | PTGS2 |
| ketoprofen | NSAID | PTGS1 |
| ketoprofen | NSAID | PTGS1 |
| ketoprofen | NSAID | PTGS2 |
| ketoprofen | NSAID | PTGS2 |
| ketorolac | NSAID | PTGS1 |
| ketorolac | NSAID | PTGS2 |
| ketotifen | antiallergy agent | HRH1 |
| ketoprofen | NSAID | PTGS1 |
| ketoprofen | NSAID | PTGS1 |
| ketoprofen | NSAID | PTGS2 |
| ketoprofen | NSAID | PTGS2 |
| KN38-7271 | neuroprotectant | CNR1 |
| KN38-7271 | neuroprotectant | CNR2 |
| KOS-2187 | for treatment of gastrointestinal motility disorders | MLNR |
| kp201 | analgesic | OPRD1 |
| kp201 | analgesic | OPRK1 |
| kp201 | analgesic | OPRM1 |
| KRP-104 | antidiabetic | DPP4 |
| KUC-7483 | for treatment of overactive bladder | ADRB3 |
| KX2-391 | antineoplastic agent | SRC |
| granisetron | antiemetic | HTR3A |
| Lacosamide | anticonvulsant, analgesic, neuropathic pain | DPYSL2 |
| lamotrigine | anticonvulsant | SCN2A |
| lanreotide | for treatment of acromegaly | SSTR1 |
| lanreotide | for treatment of acromegaly | SSTR5 |
| lansoprazole | antiulcer agent | ATP4A |
| lansoprazole | antiulcer agent | ATP4A |
| LAS-100977 | bronchodilator | ADRB2 |
| lasmiditan | antimigraine agent | HTR1F |
| lasofoxifene | antiosteoporotic agent, hormone replacement therapy | ESR1 |
| latanoprost | for treatment of glaucoma | PTGFR |
| timolol | for treatment of glaucoma | ADRB1 |
| timolol | for treatment of glaucoma | ADRB2 |
| latanoprost | for treatment of glaucoma | PTGFR |
| latanoprost | for treatment of glaucoma | PTGFR |
| atorvastatin | anticholesterolaemic agent | HMGCR |
| fenofibrate | anticholesterolaemic agent | PPARA |
| fenofibrate | anticholesterolaemic agent | PPARA |
| sirolimus | immunosuppressant | FGF2 |
| sirolimus | immunosuppressant | FKBP1A |
| sirolimus | immunosuppressant | FRAP1 |
| Erismodegib | antineoplastic agent | SMO |
| LEE011 | antineoplastic agent | CDK4 |
| LEE011 | antineoplastic agent | CDK6 |
| lercanidipine | antihypertensive agent | CACNG1 |
| LE-SN38 | antineoplastic agent | TOP1 |
| LE-SN38 | antineoplastic agent | TOP1MT |
| lesogaberan | for treatment of gastrointestinal reflux disease | GABBR1 |
| lesogaberan | for treatment of gastrointestinal reflux disease | GABBR2 |
| lestaurtinib | antineoplastic agent | FLT3 |
| lestaurtinib | antineoplastic agent | NTRK1 |
| lestaurtinib | antineoplastic agent | NTRK2 |
| lestaurtinib | antineoplastic agent | NTRK3 |
| lestaurtinib | antineoplastic agent | JAK2 |
| ambrisentan | antihypertensive agent | EDNRA |
| ambrisentan | antihypertensive agent | EDNRB |
| letrozole | antineoplastic agent | CYP19A1 |
| salbutamol | bronchodilator | ADRB2 |
| levetiracetam | anticonvulsant | CACNA1B |
| levetiracetam | anticonvulsant | SV2A |

TABLE 2-continued

Exemplary Drugs with Disease Indications and Gene Identifier for the Target Protein

| Drug Name | Indication(s) | Gene |
|---|---|---|
| levocetirizine | antiallergy agent | HRH1 |
| levodopa | antiparkinson agent | DRD1 |
| levodopa | antiparkinson agent | DRD2 |
| levodopa | antiparkinson agent | DRD3 |
| levodopa | antiparkinson agent | DRD4 |
| levodopa | antiparkinson agent | DRD5 |
| levomilnacipran | antidepressant | SLC6A2 |
| levomilnacipran | antidepressant | SLC6A4 |
| ethinyl estradiol | contraceptive | ESR1 |
| levonorgestrel | contraceptive | ESR1 |
| levonorgestrel | contraceptive | PGR |
| levonorgestrel | contraceptive | SRD5A1 |
| Levosimendan | for treatment of heart failure | KCNJ11 |
| Levosimendan | for treatment of heart failure | TNNC1 |
| levothyroxine | hormone replacement | THRA |
| levothyroxine | hormone replacement | THRB |
| levothyroxine | hormone replacement | THRA |
| levothyroxine | hormone replacement | THRB |
| LGD-1550 | antineoplastic agent | RARA |
| LGD-1550 | antineoplastic agent | RARB |
| LGD-1550 | antineoplastic agent | RARG |
| LGD-2941 | antiosteoporotic agent | AR |
| LGD-4033 | hormone replacement | AR |
| LGD-4665 | thrombopoietic agent | MPL |
| Liarozole | dermatological agent, for treatment of ichtyosis | CYP26A1 |
| licarbazepine | for treatment of bipolar disorder | SCN5A |
| licofelone | antiinflammatory agent | ALOX5 |
| licofelone | antiinflammatory agent | PTGS2 |
| lidocaine | anestethic | SCN9A |
| lidocaine | anestethic | SCN10A |
| lidocaine | anestethic | SCN5A |
| piroxicam | antiinflammatory agent, NSAID | PTGS2 |
| lidocaine | anestethic | SCN10A |
| lidocaine | anestethic | SCN5A |
| lidocaine | anestethic | SCN9A |
| lidocaine | anestethic | SCN10A |
| lidocaine | anestethic | SCN5A |
| lidocaine | anestethic | SCN9A |
| lidocaine | anestethic | SCN10A |
| lidocaine | anestethic | SCN5A |
| lidocaine | anestethic | SCN9A |
| LIM-0705 | for improving pharmacokinetics of tacrolimus | ABCA5 |
| LIM-0705 | for improving pharmacokinetics of tacrolimus | ABCB1 |
| Linaglipton | antidiabetic | DPP4 |
| fluticasone propionate | for treatment of symptomatic exophthalmos associated with thyroid-related eye disease | NR3C1 |
| salbutamol | for treatment of symptomatic exophthalmos associated with thyroid-related eye disease | ADRB2 |
| docetaxel | antineoplastic agent | BCL2 |
| docetaxel | antineoplastic agent | TUBB1 |
| doxorubicin | antineoplastic agent | TOP2A |
| paclitaxel | antineoplastic agent | TOP2A |
| lurtotecan | antineoplastic agent | TOP1 |
| mitoxantrone | antineoplastic agent | TOP2A |
| prednisolone | antiinflammatory agent, corticosteroid | NR3C1 |
| Lipotecan | antineoplastic agent | TOP1 |
| lisinopril | antihypertensive agent | ACE |
| Lisofylline | antidiabetic | STAT4 |
| lixivaptan | for treatment of hyponatremia | AVPR2 |
| Lobeline | for treatment of metamphetamine addicton | SLC18A2 |
| lofexidine | for treatment of opiate withdrawal | ADRA2A |
| lofexidine | for treatment of opiate withdrawal | ADRA2B |
| lofexidine | for treatment of opiate withdrawal | ADRA2C |
| lomitapide | anticholesterolaemic agent | MTTP |
| LOR-253 | antineoplastic agent | MTF1 |
| loratadine | antiasthmatic agent | HRH1 |
| montelukast | antiasthmatic agent | CYSLTR1 |
| Lorcaserin | antiobesity agent | HTR2C |

TABLE 2-continued

Exemplary Drugs with Disease Indications and Gene Identifier for the Target Protein

| Drug Name | Indication(s) | Gene |
|---|---|---|
| loteprednol etabonate | antiinflammatory agent, corticosteroid | NR3C1 |
| methamphetamine | neuroprotectant | ADRA2A |
| methamphetamine | neuroprotectant | ADRA2B |
| methamphetamine | neuroprotectant | ADRA2C |
| methamphetamine | neuroprotectant | MAOA |
| methamphetamine | neuroprotectant | MAOB |
| methamphetamine | neuroprotectant | SLC18A1 |
| methamphetamine | neuroprotectant | SLC18A2 |
| methamphetamine | neuroprotectant | SLC6A2 |
| methamphetamine | neuroprotectant | SLC6A3 |
| methamphetamine | neuroprotectant | SLC6A4 |
| methamphetamine | neuroprotectant | TAAR1 |
| lovastatin | anticholesterolaemic agent | HMGCR |
| enoxaparin | anticoagulant | F2 |
| vortioxetine | antidepressant | HTR1A |
| vortioxetine | antidepressant | HTR1B |
| vortioxetine | antidepressant | HTR3A |
| vortioxetine | antidepressant | HTR7 |
| vortioxetine | antidepressant | SLC6A4 |
| Tedatioxetine | antidepressant | ADRA1A |
| Tedatioxetine | antidepressant | HTR2C |
| Tedatioxetine | antidepressant | HTR2C |
| Tedatioxetine | antidepressant | HTR3A |
| Tedatioxetine | antidepressant | SLC6A2 |
| Tedatioxetine | antidepressant | SLC6A3 |
| Tedatioxetine | antidepressant | SLC6A4 |
| zicronapine | antipsychotic agent | DRD4 |
| Lu-AE58054 | antipsychotic agent | HTR6 |
| Lubiprostone | motilitant, for treatment of irritable bowel disorder | CLCN2 |
| lumiracoxib | NSAID | PTGS2 |
| eszopiclone | hypnotic | GABRA1 |
| eszopiclone | hypnotic | GABRA2 |
| eszopiclone | hypnotic | GABRA3 |
| eszopiclone | hypnotic | GABRA5 |
| eszopiclone | hypnotic | TSPO |
| lurasidone | antipsychotic agent | ADRA2C |
| lurasidone | antipsychotic agent | DRD2 |
| lurasidone | antipsychotic agent | HTR1A |
| lurasidone | antipsychotic agent | HTR2A |
| lurasidone | antipsychotic agent | HTR7 |
| LX1031 | for treatment of irritable bowel syndrome | TPH1 |
| LX1032 | for treatment of carcinoid syndrome | TPH1 |
| cyclosporine A | immunosuppressant, opthalmological agent | CAMLG |
| cyclosporine A | immunosuppressant, opthalmological agent | PPP3R2 |
| LX4211 | antidiabetic | SLC5A1 |
| LX4211 | antidiabetic | SLC5A2 |
| LY2140023 | antipsychotic agent | GRM2 |
| LY2140023 | antipsychotic agent | GRM3 |
| LY3009104 | antiinflammatory agent, DMARD | JAK1 |
| LY3009104 | antiinflammatory agent, DMARD | JAK2 |
| semagacestat | for treatment of Alzheimer's disease | PSEN1 |
| semagacestat | for treatment of Alzheimer's disease | PSEN2 |
| LY-517717 | anticoagulant | F10 |
| naveglitazar | antidiabetic | PPARA |
| naveglitazar | antidiabetic | PPARG |
| LY-674 | anticholesterolaemic agent | PPARA |
| M0002 | for treatemnt of ascites | AVPR2 |
| heparin | anticoagulant | F10 |
| heparin | anticoagulant | HPSE |
| heparin | anticoagulant | SERPINC1 |
| morphine | analgesic | OPRD1 |
| morphine | analgesic | OPRK1 |
| morphine | analgesic | OPRM1 |
| macitentan | cardiovascular agent | EDNRA |
| macitentan | cardiovascular agent | EDNRB |
| dihydroergotamine | antimigraine agent | HTR1B |
| dihydroergotamine | antimigraine agent | HTR1D |
| budesonide | antiinflammatory agent, glucocorticoid | NR3C1 |

TABLE 2-continued

Exemplary Drugs with Disease Indications and Gene Identifier for the Target Protein

| Drug Name | Indication(s) | Gene |
|---|---|---|
| formoterol | bronchodilator | ADRB2 |
| budesonide | antiinflammatory agent, glucocorticoid | NR3C1 |
| masitinib | antiinflammatory agent, DMARD, antineoplastic agent | ABL1 |
| masitinib | antiinflammatory agent, DMARD, antineoplastic agent | CSF1R |
| masitinib | antiinflammatory agent, DMARD, antineoplastic agent | HCK |
| masitinib | antiinflammatory agent, DMARD, antineoplastic agent | KIT |
| masitinib | antiinflammatory agent, DMARD, antineoplastic agent | LYN |
| masitinib | antiinflammatory agent, DMARD, antineoplastic agent | PDGFRA |
| masitinib | antiinflammatory agent, DMARD, antineoplastic agent | PDGFRB |
| masitinib | antiinflammatory agent, DMARD, antineoplastic agent | SRC |
| mesalazine | for treatment of ulcerative proctitis | ALOX5 |
| mesalazine | for treatment of ulcerative proctitis | PPARG |
| mesalazine | for treatment of ulcerative proctitis | PTGS1 |
| mesalazine | for treatment of ulcerative proctitis | PTGS2 |
| MB07811 | antidyslipidaemic agent | THRB |
| MBX-2044 | antidiabetic | PPARG |
| MBX-2982 | antidiabetic | GPR119 |
| MBX-8025 | antidyslipidaemic agent | PPARD |
| lisinopril | antihypertensive agent | ACE |
| lisinopril | antihypertensive agent | ACE2 |
| MC-1 | cardioprotectant | LPAR4 |
| MC-1 | cardioprotectant | LPAR6 |
| MC-1 | cardioprotectant | P2RY1 |
| MC-1 | cardioprotectant | P2RY10 |
| MC-1 | cardioprotectant | P2RY11 |
| MC-1 | cardioprotectant | P2RY12 |
| MC-1 | cardioprotectant | P2RY13 |
| MC-1 | cardioprotectant | P2RY14 |
| MC-1 | cardioprotectant | P2RY2 |
| MC-1 | cardioprotectant | P2RY4 |
| MC-1 | cardioprotectant | P2RY6 |
| MC-1 | cardioprotectant | P2RY8 |
| MCD-386 | for treatment of Alzheimer's disease | CHRM1 |
| MDAM | antineoplastic agent | DHFR |
| MDV3100 | antineoplastic agent | AR |
| Mebendazole | antineoplastic agent | TUBA1A |
| Mebendazole | antineoplastic agent | TUBB2C |
| mecamylamine | for treatment of ADHD | CHRNA2 |
| melogliptin | antidiabetic | DPP4 |
| MEM 1003 | for treatment of Alzheimer's disease | CACNA1C |
| MEM 1003 | for treatment of Alzheimer's disease | CACNA1D |
| MEM 1003 | for treatment of Alzheimer's disease | CACNA1F |
| MEM 1003 | for treatment of Alzheimer's disease | CACNA1S |
| MEM 1414 | for treatment of Alzheimer's disease | PDE4A |
| MEM 1414 | for treatment of Alzheimer's disease | PDE4B |
| MEM 63908 | for treatment of Alzheimer's disease | CHRNA7 |
| MEM3454 | for treatment of Alzheimer's disease | CHRNA7 |
| memantine | for treatment of glaucoma | GRIN2A |
| memantine | for treatment of glaucoma | GRIN2B |
| memantine | for treatment of glaucoma | GRIN3A |
| vorinostat | antineoplastic agent | HDAC1 |
| vorinostat | antineoplastic agent | HDAC2 |
| vorinostat | antineoplastic agent | HDAC3 |
| vorinostat | antineoplastic agent | HDAC6 |
| mesalamine | antiinflammatory agent | ALOX5 |
| mesalamine | antiinflammatory agent | PPARG |
| mesalamine | antiinflammatory agent | PTGS1 |
| mesalamine | antiinflammatory agent | PTGS2 |
| WX-671 | antineoplastic agent | PLAU |
| Oxypurinol | for treatment of heart failure, for treatment of gout | XDH |
| metaglidasen | antidiabetic | PPARG |
| metformin | antidiabetic | PRKAB1 |
| metformin | antidiabetic | PRKAB1 |
| metformin | antidiabetic | PRKAB1 |
| Methylnaltrexone | for treatment of opioid-induced constipation | OPRM1 |

TABLE 2-continued

Exemplary Drugs with Disease Indications and Gene Identifier for the Target Protein

| Drug Name | Indication(s) | Gene |
|---|---|---|
| methylphenidate | for treatment of ADHD | SLC6A2 |
| methylphenidate | for treatment of ADHD | SLC6A3 |
| methylphenidate | for treatment of ADHD | SLC6A4 |
| methylphenidate | for treatment of ADHD | SLC6A2 |
| methylphenidate | for treatment of ADHD | SLC6A3 |
| methylphenidate | for treatment of ADHD | SLC6A4 |
| methylphenidate | for treatment of ADHD | SLC6A2 |
| methylphenidate | for treatment of ADHD | SLC6A3 |
| methylphenidate | for treatment of ADHD | SLC6A4 |
| methyltestosterone | for treatment of dysfunctional libido in women | AR |
| metoclopramide | motilitant, for treatment of gastroesophageal reflux disease | CHRM1 |
| metoclopramide | motilitant, for treatment of gastroesophageal reflux disease | DRD2 |
| metoclopramide | antiemetic | CHRM1 |
| metoclopramide | antiemetic | DRD2 |
| metoprolol | antihypertensive agent | ADRB1 |
| MF101 | for treatment of menopausal symptoms | ESR2 |
| MGCD-0103 | antineoplastic agent | HDAC1 |
| MGCD-0103 | antineoplastic agent | HDAC10 |
| MGCD-0103 | antineoplastic agent | HDAC11 |
| MGCD-0103 | antineoplastic agent | HDAC2 |
| MGCD-0103 | antineoplastic agent | HDAC3 |
| MGCD-0103 | antineoplastic agent | HDAC4 |
| MGCD-0103 | antineoplastic agent | HDAC5 |
| MGCD-0103 | antineoplastic agent | HDAC6 |
| MGCD-0103 | antineoplastic agent | HDAC7A |
| MGCD-0103 | antineoplastic agent | HDAC8 |
| MGCD-0103 | antineoplastic agent | HDAC9 |
| MGCD265 | antineoplastic agent | FLT1 |
| MGCD265 | antineoplastic agent | FLT4 |
| MGCD265 | antineoplastic agent | KDR |
| MGCD265 | antineoplastic agent | MET |
| MGCD265 | antineoplastic agent | MST1R |
| MGCD265 | antineoplastic agent | TEK |
| morphine | analgesic | OPRD1 |
| morphine | analgesic | OPRK1 |
| morphine | analgesic | OPRM1 |
| paclitaxel | antiinflammatory agent, DMARD | BCL2 |
| paclitaxel | antiinflammatory agent, DMARD | TUBB1 |
| Midostaurin | antineoplastic agent | FLT3 |
| Mifepristone | opthalmological agent, for lowering intraocular pressure | NR3C1 |
| Mifepristone | opthalmological agent, for lowering intraocular pressure | PGR |
| Mifepristone | antipsychotic, antidepressant | NR3C1 |
| Mifepristone | antipsychotic, antidepressant | PGR |
| migalastat | enzyme replacement therapy, for treatment of Fabry disease | GLA |
| miglustat | for treatment of Gaucher's disease | UGCG |
| milataxel | antineoplastic agent | BCL2 |
| milataxel | antineoplastic agent | TUBB1 |
| Milnacipran | for treatment of fibromyalgia syndrome | SLC6A2 |
| Milnacipran | for treatment of fibromyalgia syndrome | SLC6A4 |
| milveterol | bronchodilator | ADRB2 |
| MIM-D3 | opthalmological agent | NTRK1 |
| minodronate | antineoplastic agent | FDPS |
| pramipexole | antiparkinson agent | DRD2 |
| pramipexole | antiparkinson agent | DRD3 |
| pramipexole | antiparkinson agent | DRD4 |
| mirtazapine | antidepressant | ADRA2A |
| mirtazapine | antidepressant | HTR2A |
| mirtazapine | antidepressant | HTR3A |
| mitemcinal | for treatment of gastroparesis | MLNR |
| mitiglinide | antidiabetic | ABCC8 |
| mitoxantrone | antineoplastic agent | TOP2A |
| MIV-701 | for treatment of osteoporosis | CTSK |
| laropiprant | for counteracting niacin-induced flushing | PTGDR |
| niacin | antidyslipidaemic agent | GPR109A |
| niacin | antidyslipidaemic agent | GPR109B |
| niacin | antidyslipidaemic agent | NNMT |

TABLE 2-continued

Exemplary Drugs with Disease Indications and Gene Identifier for the Target Protein

| Drug Name | Indication(s) | Gene |
|---|---|---|
| niacin | antidyslipidaemic agent | QPRT |
| laropiprant | for counteracting niacin-induced flushing | PTGDR |
| niacin | antidyslipidaemic agent | GPR109A |
| niacin | antidyslipidaemic agent | GPR109B |
| niacin | antidyslipidaemic agent | NNMT |
| niacin | antidyslipidaemic agent | QPRT |
| simvastatin | anticholesterolaemic agent | HMGCR |
| MK-1775 | antineoplastic agent | WEE1 |
| MK-2206 | antineoplastic agent | AKT1 |
| MK-2206 | antineoplastic agent | AKT2 |
| MK-2206 | antineoplastic agent | AKT3 |
| suvorexant | hypnotic | HCRTR1 |
| suvorexant | hypnotic | HCRTR2 |
| MK-4827 | antineoplastic agent | PARP1 |
| MK-4827 | antineoplastic agent | PARP2 |
| MKC-1 | antineoplastic agent | IPO11 |
| MKC-1 | antineoplastic agent | IPO13 |
| MKC-1 | antineoplastic agent | IPO4 |
| MKC-1 | antineoplastic agent | IPO7 |
| MKC-1 | antineoplastic agent | IPO8 |
| MKC-1 | antineoplastic agent | IPO9 |
| MKC-1 | antineoplastic agent | TUBB |
| MKC-1 | antineoplastic agent | TUBB1 |
| MLN-0415 | antiinflammatory agent | IKBKB |
| MLN-4924 | antineoplastic agent | UBA3 |
| MLN-8054 | antineoplastic agent | AUR2 |
| MLN-8237 | antineoplastic agent | AURKA |
| MLN-9708 | antineoplastic agent | PSMB1 |
| MLN-9708 | antineoplastic agent | PSMB2 |
| MLN-9708 | antineoplastic agent | PSMB5 |
| MLN-9708 | antineoplastic agent | PSMD1 |
| MLN-9708 | antineoplastic agent | PSMD2 |
| MN-201 | antineoplastic agent | VDR |
| MN-246 | for treatment of overactive bladder | ADRB3 |
| MN-305 | antidepressant, hypnotic | HTR1A |
| moclobemide | antidepressant | MAOA |
| modafinil | central nervous system stimulant | SLC6A3 |
| Modufolin | antineoplastic agent | TYMS |
| formoterol | antiasthmatic agent | ADRB2 |
| mometasone | antiinflammatory agent, glucocorticoid | NR3C1 |
| montelukast | antiasthmatic agent | CYSLTR1 |
| morphine | analgesic | OPRD1 |
| morphine | analgesic | OPRK1 |
| morphine | analgesic | OPRM1 |
| morphine | analgesic | OPRK1 |
| morphine | analgesic | OPRK1 |
| morphine | analgesic | OPRK1 |
| dextromethorphan | analgesic | GRIN3A |
| dextromethorphan | analgesic | SIGMAR1 |
| morphine | analgesic | OPRD1 |
| morphine | analgesic | OPRK1 |
| morphine | analgesic | OPRM1 |
| morphine | analgesic | OPRD1 |
| morphine | analgesic | OPRK1 |
| morphine | analgesic | OPRM1 |
| naltrexone | analgesic | OPRD1 |
| naltrexone | analgesic | OPRK1 |
| naltrexone | analgesic | OPRM1 |
| naltrexone | analgesic | SIGMAR1 |
| mosapride | for treatment of Gastrointestinal reflux disease (GERD) | HTR4 |
| motesanib | antineoplastic agent | FLT1 |
| motesanib | antineoplastic agent | FLT4 |
| motesanib | antineoplastic agent | KDR |
| motesanib | antineoplastic agent | KIT |
| motesanib | antineoplastic agent | PDGFRA |
| motesanib | antineoplastic agent | PDGFRB |
| motexafin gadolinium | antineoplastic agent | RRM1 |
| motexafin gadolinium | antineoplastic agent | RRM2 |
| motexafin gadolinium | antineoplastic agent | RRM2B |
| motexafin gadolinium | antineoplastic agent | TXNRD1 |
| motexafin gadolinium | antineoplastic agent | TXNRD2 |
| motexafin gadolinium | antineoplastic agent | TXNRD3 |
| morphine | analgesic | OPRD1 |

TABLE 2-continued

Exemplary Drugs with Disease Indications and Gene Identifier for the Target Protein

| Drug Name | Indication(s) | Gene |
|---|---|---|
| morphine | analgesic | OPRK1 |
| morphine | analgesic | OPRM1 |
| oxycodone | analgesic | OPRM1 |
| oxycodone | analgesic | OPRM1 |
| oxycodone | analgesic | OPRM1 |
| plerixafor | antineoplastic agent | CXCR4 |
| MP0112 | for treatment of diabetic retinopathy | FLT1 |
| MP0112 | for treatment of diabetic retinopathy | KDR |
| amuvatinib | antineoplastic agent | FLT3 |
| amuvatinib | antineoplastic agent | KIT |
| amuvatinib | antineoplastic agent | MET |
| amuvatinib | antineoplastic agent | PDGFRA |
| amuvatinib | antineoplastic agent | PDGFRB |
| amuvatinib | antineoplastic agent | RAD51 |
| amuvatinib | antineoplastic agent | RET |
| MPC-0920 | antithrombotic | F2 |
| MPI-674 | for treatment of abnormal uterine bleeding (AUB) | CYP19A1 |
| MPI-676 | for treatment of endometriosis | CYP19A1 |
| nitroglycerin | for treatment of Raynaud's disease | NPR1 |
| MRX-4 | antiinflammatory agent | PLA2G3 |
| MRX-6 | antiinflammatory agent | PLA2G3 |
| mitoglitazone | antidiabetic | PPARG |
| talniflumate | for treatment of cystic fibrosis | CLCA1 |
| MSX-122 | antineoplastic agent | CXCR4 |
| metoclopramide | antimigraine agent | CHRM1 |
| metoclopramide | antimigraine agent | DRD2 |
| naproxen | antimigraine agent | PTGS1 |
| naproxen | antimigraine agent | PTGS2 |
| dihydroergotamine | antimigraine agent | HTR1B |
| dihydroergotamine | antimigraine agent | HTR1D |
| naproxen | antimigraine agent | PTGS1 |
| naproxen | antimigraine agent | PTGS2 |
| sumatriptan | antimigraine agent | HTR1A |
| sumatriptan | antimigraine agent | HTR1B |
| sumatriptan | antimigraine agent | HTR1D |
| sumatriptan | antimigraine agent | HTR1F |
| doxorubicin | antineoplastic agent | TOP2A |
| isothiourea | antihypertensive agent | NOS1 |
| isothiourea | antihypertensive agent | NOS2 |
| isothiourea | antihypertensive agent | NOS3 |
| muraglitazar | antidiabetic | PPARA |
| muraglitazar | antidiabetic | PPARG |
| mycophenolic acid | immunosuppressant | IMPDH1 |
| mycophenolic acid | immunosuppressant | IMPDH2 |
| MPC-3100 | antineoplastic agent | HSP90AA1 |
| MPC-3100 | antineoplastic agent | HSP90AB1 |
| docetaxel | antineoplastic agent | BCL2 |
| docetaxel | antineoplastic agent | TUBB1 |
| nabilone | antiemetic | CNR1 |
| nabilone | antiemetic | CNR2 |
| nalbuphine | analgesic | OPRD1 |
| nalbuphine | analgesic | OPRK1 |
| nalbuphine | analgesic | OPRM1 |
| nalmefene | smoking-cessation agent, for treatment of addiction | OPRD1 |
| nalmefene | smoking-cessation agent, for treatment of addiction | OPRK1 |
| nalmefene | smoking-cessation agent, for treatment of addiction | OPRM1 |
| memantine | for treatment of Alzheimer's disease | GRIN2A |
| memantine | for treatment of Alzheimer's disease | GRIN2B |
| memantine | for treatment of Alzheimer's disease | GRIN3A |
| diclofenac | NSAID | PTGS1 |
| diclofenac | NSAID | PTGS2 |
| Naproxcinod | NSAID | GUCY1A2 |
| Naproxcinod | NSAID | PTGS1 |
| Naproxcinod | NSAID | PTGS2 |
| esomeprazole | Proton pump inhibitor | ATP4A |
| naproxen | NSAID | PTGS1 |
| naproxen | NSAID | PTGS2 |
| naproxen etemesil | NSAID | PTGS1 |
| naproxen etemesil | NSAID | PTGS2 |
| naratriptan | antimigraine agent | HTR1A |
| naratriptan | antimigraine agent | HTR1B |
| naratriptan | antimigraine agent | HTR1D |

TABLE 2-continued

| Exemplary Drugs with Disease Indications and Gene Identifier for the Target Protein | | |
|---|---|---|
| Drug Name | Indication(s) | Gene |
| naratriptan | antimigraine agent | HTR1F |
| ketamine | analgesic | GRIN3A |
| ketamine | analgesic | GRIN3A |
| Nav 1.7 blocker | analgesic | SCN9A |
| NB-1011 | antineoplastic agent | TYMS |
| NBI-56418 | antineoplastic agent | GNRHR |
| NBI-98854 | antipsychotic agent | SLC18A2 |
| NCX 1510 | antiallergy agent | GUCY1A2 |
| NCX 1510 | antiallergy agent | HRH1 |
| NCX 4016 | antithrombotic | GUCY1A2 |
| NCX 4016 | antithrombotic | PTGS1 |
| NCX 4016 | antithrombotic | PTGS2 |
| carbidopa | antiparkinson agent | DDC |
| nebivolol | antihypertensive agent | ADRB1 |
| nelarabine | antineoplastic agent | POLA1 |
| nepicastat | for treatment of addiction, for treatment of post-traumatic stress disorder | DBH |
| neramexane | for treatment of Alzheimer's disease | GRIN2A |
| neramexane | for treatment of Alzheimer's disease | GRIN2B |
| neramexane | for treatment of Alzheimer's disease | GRIN3A |
| neratinib | antineoplastic agent | EGFR |
| neratinib | antineoplastic agent | ERBB2 |
| ethinyl estradiol | contraceptive | ESR1 |
| progestin | contraceptive | PGR |
| Neu-2000 | cardioprotectant | GRIN1 |
| Neu-2000 | cardioprotectant | GRIN2A |
| Neu-2000 | cardioprotectant | GRIN2B |
| Neu-2000 | cardioprotectant | GRIN2C |
| Neu-2000 | cardioprotectant | GRIN2D |
| Neu-2000 | cardioprotectant | GRIN3A |
| Neu-2000 | cardioprotectant | GRIN3B |
| rotigotine | antiparkinson agent | DRD2 |
| rotigotine | antiparkinson agent | DRD3 |
| rotigotine | antiparkinson agent | DRD4 |
| sorafenib | antineoplastic agent | BRAF |
| sorafenib | antineoplastic agent | FLT3 |
| sorafenib | antineoplastic agent | FLT4 |
| sorafenib | antineoplastic agent | KDR |
| sorafenib | antineoplastic agent | KIT |
| sorafenib | antineoplastic agent | PDGFRB |
| sorafenib | antineoplastic agent | RAF1 |
| NG2-73 | hypnotic | GABRA2 |
| NG2-73 | hypnotic | GABRA3 |
| NG2-73 | hypnotic | GABRA5 |
| NG2-73 | hypnotic | GABRA6 |
| NG2-73 | hypnotic | GABRB1 |
| NG2-73 | hypnotic | GABRB1 |
| NG2-73 | hypnotic | GABRB2 |
| NG2-73 | hypnotic | GABRB2 |
| NG2-73 | hypnotic | GABRB3 |
| NG2-73 | hypnotic | GABRD |
| NG2-73 | hypnotic | GABRD |
| NG2-73 | hypnotic | GABRE |
| NG2-73 | hypnotic | GABRG1 |
| NG2-73 | hypnotic | GABRG2 |
| NG2-73 | hypnotic | GABRG3 |
| NG2-73 | hypnotic | GABRG3 |
| NG2-73 | hypnotic | GABRP |
| NG2-73 | hypnotic | GABRQ |
| NG2-73 | hypnotic | GABRR2 |
| NGD-4715 | appetite suppressant | MCHR1 |
| NGD-8243 | analgesic | TRPVI |
| NGX267 | for treatment of dry mouth | CHRM1 |
| niacin receptor agonist | antiatherosclerotic agent | HCAR2 |
| niacin receptor agonist | antiatherosclerotic agent | HCAR3 |
| NIC5-15 | for treatment of Alzheimer's disease | APH1A |
| NIC5-15 | for treatment of Alzheimer's disease | PSENEN |
| nilotinib | antineoplastic agent | ABL1 |
| nitisinone | for treatment of restlegs legs syndrome, for treatment of hereditary tyrosinemia type 1 (HT-1) | HPD |
| PEG-irinotecan | antineoplastic agent | TOP1 |
| PEG-irinotecan | antineoplastic agent | TOP1MT |

TABLE 2-continued

Exemplary Drugs with Disease Indications and Gene Identifier for the Target Protein

| Drug Name | Indication(s) | Gene |
|---|---|---|
| PEG-docetaxel | antineoplastic agent | BCL2 |
| PEG-docetaxel | antineoplastic agent | TUBB1 |
| PEG-naloxol | for treatment of opioid-induced constipation | OPRM1 |
| NM-702 | for treatment of intermittent claudication | PDE3A |
| NM-702 | for treatment of intermittent claudication | PDE3B |
| hydromorphone | analgesic | OPRD1 |
| hydromorphone | analgesic | OPRK1 |
| hydromorphone | analgesic | OPRM1 |
| NMS-1116354 | antineoplastic agent | CDC7 |
| NNZ-2566 | neuroprotectant | IGF1 |
| ethinyl estradiol | contraceptive | ESR1 |
| norelgestromin | contraceptive | ESR1 |
| norelgestromin | contraceptive | PGR |
| noscapine | antineoplastic agent | HIF1A |
| latanoprost | for treatment of glaucoma | PTGFR |
| Cyclosporine A | immunosuppressant, opthalmological agent | CAMLG |
| Cyclosporine A | immunosuppressant, opthalmological agent | PPP3R2 |
| sumatriptan | antimigraine agent | HTR1A |
| sumatriptan | antimigraine agent | HTR1B |
| sumatriptan | antimigraine agent | HTR1D |
| sumatriptan | antimigraine agent | HTR1F |
| 17-beta estradiol | opthalmological agent | ESR1 |
| 17-beta estradiol | opthalmological agent | ESR2 |
| Fluoxetine | for treatment of autism | HTR2A |
| Fluoxetine | for treatment of autism | SLC6A4 |
| NPS-2143 | antiosteoporotic agent | CASR |
| diazepam | anticonvulsant | GABRA1 |
| diazepam | anticonvulsant | GABRA2 |
| diazepam | anticonvulsant | GABRA3 |
| diazepam | anticonvulsant | GABRA5 |
| diazepam | anticonvulsant | GABRB1 |
| diazepam | anticonvulsant | GABRB2 |
| diazepam | anticonvulsant | GABRB3 |
| diazepam | anticonvulsant | GABRD |
| diazepam | anticonvulsant | GABRE |
| diazepam | anticonvulsant | GABRG1 |
| diazepam | anticonvulsant | GABRG2 |
| diazepam | anticonvulsant | GABRG3 |
| diazepam | anticonvulsant | GABRP |
| diazepam | anticonvulsant | GABRQ |
| diazepam | anticonvulsant | GABRR1 |
| diazepam | anticonvulsant | GABRR2 |
| diazepam | anticonvulsant | GABRR3 |
| NRM8499 | for treatment of Alzheimer's disease | APP |
| NRP290 | analgesic | OPRD1 |
| NRP290 | analgesic | OPRK1 |
| NRP290 | analgesic | OPRM1 |
| triiodothyronine (T3) | hormone replacement | THRA |
| triiodothyronine (T3) | hormone replacement | THRB |
| NRX-5183 | hematopoietic agent | RARA |
| NS-304 | antihypertensive agent | PTGIR |
| NSD-644 | analgesic, antidepressant | SLC6A2 |
| NSD-644 | analgesic, antidepressant | SLC6A3 |
| NSD-644 | analgesic, antidepressant | SLC6A4 |
| NSD-788 | antidepressant | SLC6A2 |
| NSD-788 | antidepressant | SLC6A4 |
| allopurinol | for treatment of gout | XDH |
| NV-52 | antiinflammatory agent | TBXAS1 |
| glycopyrronium | for treatment of chronic obstructive pulmonary disease (COPD) | CHRM1 |
| tizanidine | for treatment of skeletal muscular spasticity | ADRA2A |
| tizanidine | for treatment of skeletal muscular spasticity | ADRA2B |
| tizanidine | for treatment of skeletal muscular spasticity | ADRA2C |
| NXN-188 | antimigraine agent | HTR1B |
| NXN-188 | antimigraine agent | HTR1D |
| NXN-188 | antimigraine agent | NOS1 |
| ondansetron | antiemetic | HTR3A |
| paclitaxel | antineoplastic agent | BCL2 |

TABLE 2-continued

Exemplary Drugs with Disease Indications and Gene Identifier for the Target Protein

| Drug Name | Indication(s) | Gene |
|---|---|---|
| paclitaxel | antineoplastic agent | TUBB1 |
| obatoclax | antineoplastic agent | BCL2 |
| betahistine | antiobesity agent | HRH1 |
| betahistine | antiobesity agent | HRH3 |
| obeticholic acid | for treatment of non-alcoholic fatty liver disease (NAFLD), for treatment of Primary Biliary Cirrhosis (PBC) | NR1H4 |
| OC000459 | antiallergy agent | PD2R2 |
| ocinaplon | anxiolytic | GABRA2 |
| ocinaplon | anxiolytic | GABRA3 |
| ocinaplon | anxiolytic | GABRA5 |
| ocinaplon | anxiolytic | GABRA6 |
| ocinaplon | anxiolytic | GABRB1 |
| ocinaplon | anxiolytic | GABRB1 |
| ocinaplon | anxiolytic | GABRB2 |
| ocinaplon | anxiolytic | GABRB2 |
| ocinaplon | anxiolytic | GABRB3 |
| ocinaplon | anxiolytic | GABRD |
| ocinaplon | anxiolytic | GABRD |
| ocinaplon | anxiolytic | GABRE |
| ocinaplon | anxiolytic | GABRG1 |
| ocinaplon | anxiolytic | GABRG2 |
| ocinaplon | anxiolytic | GABRG3 |
| ocinaplon | anxiolytic | GABRG3 |
| ocinaplon | anxiolytic | GABRP |
| ocinaplon | anxiolytic | GABRQ |
| ocinaplon | anxiolytic | GABRR2 |
| heparin | antithrombotic | F10 |
| heparin | antithrombotic | F2 |
| odanacatib | antiosteoporotic agent | CTSK |
| Oglemilast | antiasthmatic agent | PDE4A |
| Oglemilast | antiasthmatic agent | PDE4B |
| olanzapine | antipsychotic agent | ADRA1A |
| olanzapine | antipsychotic agent | ADRA1B |
| olanzapine | antipsychotic agent | ADRA2A |
| olanzapine | antipsychotic agent | ADRA2B |
| olanzapine | antipsychotic agent | ADRA2C |
| olanzapine | antipsychotic agent | CHRM1 |
| olanzapine | antipsychotic agent | CHRM2 |
| olanzapine | antipsychotic agent | CHRM3 |
| olanzapine | antipsychotic agent | CHRM4 |
| olanzapine | antipsychotic agent | CHRM5 |
| olanzapine | antipsychotic agent | DRD1 |
| olanzapine | antipsychotic agent | DRD2 |
| olanzapine | antipsychotic agent | DRD3 |
| olanzapine | antipsychotic agent | DRD4 |
| olanzapine | antipsychotic agent | DRD5 |
| olanzapine | antipsychotic agent | HRH1 |
| olanzapine | antipsychotic agent | HTR1A |
| olanzapine | antipsychotic agent | HTR1B |
| olanzapine | antipsychotic agent | HTR1D |
| olanzapine | antipsychotic agent | HTR1E |
| olanzapine | antipsychotic agent | HTR2A |
| olanzapine | antipsychotic agent | HTR2C |
| olanzapine | antipsychotic agent | HTR3A |
| olanzapine | antipsychotic agent | HTR6 |
| olanzapine | antipsychotic agent | HTR7 |
| fluoxetine | antidepressant, for treatment of bipolar disorder | SLC6A4 |
| olanzapine | antidepressant, for treatment of bipolar disorder | ADRA1A |
| olanzapine | antidepressant, for treatment of bipolar disorder | ADRA1B |
| olanzapine | antidepressant, for treatment of bipolar disorder | ADRA2A |
| olanzapine | antidepressant, for treatment of bipolar disorder | ADRA2B |
| olanzapine | antidepressant, for treatment of bipolar disorder | ADRA2C |
| olanzapine | antidepressant, for treatment of bipolar disorder | CHRM1 |
| olanzapine | antidepressant, for treatment of bipolar disorder | CHRM2 |
| olanzapine | antidepressant, for treatment of bipolar disorder | CHRM3 |

TABLE 2-continued

| Drug Name | Indication(s) | Gene |
|---|---|---|
| olanzapine | antidepressant, for treatment of bipolar disorder | CHRM4 |
| olanzapine | antidepressant, for treatment of bipolar disorder | CHRM5 |
| olanzapine | antidepressant, for treatment of bipolar disorder | DRD1 |
| olanzapine | antidepressant, for treatment of bipolar disorder | DRD2 |
| olanzapine | antidepressant, for treatment of bipolar disorder | DRD3 |
| olanzapine | antidepressant, for treatment of bipolar disorder | DRD4 |
| olanzapine | antidepressant, for treatment of bipolar disorder | DRD5 |
| olanzapine | antidepressant, for treatment of bipolar disorder | HRH1 |
| olanzapine | antidepressant, for treatment of bipolar disorder | HTR1A |
| olanzapine | antidepressant, for treatment of bipolar disorder | HTR1B |
| olanzapine | antidepressant, for treatment of bipolar disorder | HTR1D |
| olanzapine | antidepressant, for treatment of bipolar disorder | HTR1E |
| olanzapine | antidepressant, for treatment of bipolar disorder | HTR2A |
| olanzapine | antidepressant, for treatment of bipolar disorder | HTR2C |
| olanzapine | antidepressant, for treatment of bipolar disorder | HTR3A |
| olanzapine | antidepressant, for treatment of bipolar disorder | HTR6 |
| olanzapine | antidepressant, for treatment of bipolar disorder | HTR7 |
| olesoxime | for treatment of motor neuron disease | TSPO |
| olesoxime | for treatment of motor neuron disease | VDAC1 |
| olesoxime | for treatment of motor neuron disease | VDAC2 |
| olesoxime | for treatment of motor neuron disease | VDAC3 |
| olmesartan | antihypertensive agent | AGTR1 |
| olmesartan | for treatment of glaucoma | AGTR1 |
| olopatadine | antiallergy agent | HRH1 |
| omacetaxine mepesuccinate | antineoplastic agent | Ribosome A-site |
| ombrabulin | antineoplastic agent | TUBB1 |
| omecamtiv mecarbil | for treatment of heart failure | Cardiac Mysoin |
| omeprazole | Proton pump inhibitor | ATP4A |
| omeprazole | Proton pump inhibitor | ATP4A |
| omeprazole | Proton pump inhibitor | ATP4A |
| omigapil | antiparkinson agent, for treatment of amyotrophic lateral sclerosis (ALS) | GAPDA |
| omigapil | antiparkinson agent, for treatment of amyotrophic lateral sclerosis (ALS) | SIAH1 |
| amitriptyline | analgesic | HTR2A |
| amitriptyline | analgesic | HTR2A |
| amitriptyline | analgesic | SLC6A2 |
| amitriptyline | analgesic | SLC6A2 |
| amitriptyline | analgesic | SLC6A4 |
| amitriptyline | analgesic | SLC6A4 |
| ketoprofen | NSAID | PTGS1 |
| ketoprofen | NSAID | PTGS1 |
| ketoprofen | NSAID | PTGS2 |
| ketoprofen | NSAID | PTGS2 |
| oxymetazoline | analgesic | ADRA1A |
| oxymetazoline | analgesic | ADRA1A |
| oxymetazoline | analgesic | ADRA2A |
| oxymetazoline | analgesic | ADRA2A |
| rigosertib | antineoplastic agent | PIK3CA |
| rigosertib | antineoplastic agent | PIK3CB |
| rigosertib | antineoplastic agent | PIK3CD |
| rigosertib | antineoplastic agent | PLK1 |
| paclitaxel | antineoplastic agent | BCL2 |
| paclitaxel | antineoplastic agent | TUBB1 |
| ondansetron | antiemetic | HTR3A |
| oprozomib | antineoplastic agent | PSMB1 |
| oprozomib | antineoplastic agent | PSMB2 |
| oprozomib | antineoplastic agent | PSMB5 |

Exemplary Drugs with Disease Indications and Gene Identifier for the Target Protein TABLE 2-continued

| Exemplary Drugs with Disease Indications and Gene Identifier for the Target Protein | | |
|---|---|---|
| Drug Name | Indication(s) | Gene |
| oprozomib | antineoplastic agent | PSMD1 |
| oprozomib | antineoplastic agent | PSMD2 |
| paclitaxel | antineoplastic agent | BCL2 |
| paclitaxel | antineoplastic agent | TUBB1 |
| OPB-51602 | antineoplastic agent | STAT3 |
| OPC-28326 | vasodilator | ADRA2B |
| OPC-28326 | vasodilator | ADRA2C |
| OPC-34712 | antidepressant | DRD2 |
| OPC-34712 | antidepressant | HTR1A |
| OPC-34712 | antidepressant | HTR2A |
| OPC-34712 | antidepressant | HTR7 |
| OPC-51803 | for treatment of incontinence | AVPR2 |
| doxycyklin | for treatment of dental disease | MMP8 |
| estrogen | contraceptive, for treatment of female sexual dysfunction | ESR1 |
| estrogen | contraceptive, for treatment of female sexual dysfunction | ESR2 |
| progestogen | contraceptive, for treatment of female sexual dysfunction | PGR |
| estriol E3 | for treatment of multiple sclerosis | ESR1 |
| estriol E3 | for treatment of multiple sclerosis | ESR2 |
| paclitaxel | antineoplastic agent | BCL2 |
| paclitaxel | antineoplastic agent | TUBB1 |
| lidocaine | anesthetic | SCN10A |
| lidocaine | anesthetic | SCN5A |
| lidocaine | anesthetic | SCN9A |
| prilocaine | anesthetic | SCN5A |
| olanzapine | antipsychotic agent | ADRA1A |
| olanzapine | antipsychotic agent | ADRA1B |
| olanzapine | antipsychotic agent | ADRA2A |
| olanzapine | antipsychotic agent | ADRA2B |
| olanzapine | antipsychotic agent | ADRA2C |
| olanzapine | antipsychotic agent | CHRM1 |
| olanzapine | antipsychotic agent | CHRM2 |
| olanzapine | antipsychotic agent | CHRM3 |
| olanzapine | antipsychotic agent | CHRM4 |
| olanzapine | antipsychotic agent | CHRM5 |
| olanzapine | antipsychotic agent | DRD1 |
| olanzapine | antipsychotic agent | DRD2 |
| olanzapine | antipsychotic agent | DRD3 |
| olanzapine | antipsychotic agent | DRD4 |
| olanzapine | antipsychotic agent | DRD5 |
| olanzapine | antipsychotic agent | HRH1 |
| olanzapine | antipsychotic agent | HTR1A |
| olanzapine | antipsychotic agent | HTR1B |
| olanzapine | antipsychotic agent | HTR1D |
| olanzapine | antipsychotic agent | HTR1E |
| olanzapine | antipsychotic agent | HTR2A |
| olanzapine | antipsychotic agent | HTR2C |
| olanzapine | antipsychotic agent | HTR3A |
| olanzapine | antipsychotic agent | HTR6 |
| olanzapine | antipsychotic agent | HTR7 |
| zonisamide | antipsychotic agent | CACNA1G |
| zonisamide | antipsychotic agent | CACNA1H |
| zonisamide | antipsychotic agent | CACNA1I |
| zonisamide | antipsychotic agent | SCN11A |
| zonisamide | antipsychotic agent | SCN1A |
| zonisamide | antipsychotic agent | SCN1B |
| zonisamide | antipsychotic agent | SCN2A |
| zonisamide | antipsychotic agent | SCN2B |
| zonisamide | antipsychotic agent | SCN3A |
| zonisamide | antipsychotic agent | SCN3B |
| zonisamide | antipsychotic agent | SCN4A |
| zonisamide | antipsychotic agent | SCN4B |
| zonisamide | antipsychotic agent | SCN5A |
| zonisamide | antipsychotic agent | SCN9A |
| orlistat | antiobesity agent | FASN |
| orlistat | antiobesity agent | LPL |
| orlistat | antiobesity agent | PNLIP |
| ortataxel | antineoplastic agent | BCL2 |
| ortataxel | antineoplastic agent | TUBB1 |
| orteronel | antineoplastic agent | CYP17A1 |
| OSI-027 | antineoplastic agent | MTOR |
| OSI-461 | antineoplastic agent | PDE5A |
| OSI-7904L | antineoplastic agent | TYMS |
| OSI-906 | antineoplastic agent | IGF1R |

TABLE 2-continued

Exemplary Drugs with Disease Indications and Gene Identifier for the Target Protein

| Drug Name | Indication(s) | Gene |
|---|---|---|
| OSI-930 | antineoplastic agent | KDR |
| ospemifene | for treatment of postmenopausal vaginal atrophy | ESR1 |
| ospemifene | for treatment of postmenopausal vaginal atrophy | ESR2 |
| enobosarm | hormone replacement | AR |
| OT-730 | for treatment of glaucoma | ADRB1 |
| OT-730 | for treatment of glaucoma | ADRB2 |
| otamixaban | antithrombotic | F10 |
| dexamethasone | antiinflammatory agent, glucocorticoid, for treatment of Meniere's disease | NR3C1 |
| famotidine | acid reducer | HRH2 |
| omeprazole | Proton pump inhibitor | ATP4A |
| zolpidem | hypnotic | GABRA1 |
| zolpidem | hypnotic | GABRA2 |
| zolpidem | hypnotic | GABRA3 |
| OX914 | antiallergy agent | PDE4A |
| OX914 | antiallergy agent | PDE4B |
| oxandrolone | anabolic agent | AR |
| oxcarbazepine | anticonvulsant | SCN5A |
| combretastatin Al di-phosphate | antineoplastic agent | TUBB1 |
| oxycodone | analgesic | OPRD1 |
| oxycodone | analgesic | OPRK1 |
| oxycodone | analgesic | OPRM1 |
| niacin | substance abuse deterrant | GPR109A |
| niacin | substance abuse deterrant | GPR109B |
| niacin | substance abuse deterrant | NNMT |
| niacin | substance abuse deterrant | QPRT |
| oxycodone | analgesic | OPRD1 |
| oxycodone | analgesic | OPRK1 |
| oxycodone | analgesic | OPRM1 |
| oxycodone | analgesic | OPRD1 |
| oxycodone | analgesic | OPRK1 |
| oxycodone | analgesic | OPRM1 |
| oxymorphone | analgesic | OPRD1 |
| oxymorphone | analgesic | OPRM1 |
| P-552 | for treatment of dry mouth | ACCN2 |
| P-552 | for treatment of dry mouth | ACCN3 |
| P-552 | for treatment of dry mouth | ACCN4 |
| P-552 | for treatment of dry mouth | ASIC2 |
| P-552 | for treatment of dry mouth | SCNN1A |
| P-552 | for treatment of dry mouth | SCNN1B |
| P-552 | for treatment of dry mouth | SCNN1D |
| P-552 | for treatment of dry mouth | SCNN1G |
| acetylsalicylic acid | NSAID | PTGS1 |
| acetylsalicylic acid | NSAID | PTGS2 |
| omeprazole | Proton pump inhibitor | ATP4A |
| paclitaxel | antineoplastic agent | BCL2 |
| paclitaxel | antineoplastic agent | TUBB1 |
| paclitaxel | antineoplastic agent | BCL2 |
| paclitaxel | antineoplastic agent | TUBB1 |
| paclitaxel | for treatment of peripheral arterial disease (PAD) | BCL2 |
| paclitaxel | for treatment of peripheral arterial disease (PAD) | TUBB1 |
| pagoclone | for treatment of premature ejaculation, for treatment of persistant stuttering | GABRA2 |
| pagoclone | for treatment of premature ejaculation,for treatment of persistant stuttering | GABRB2 |
| paliperidone | antipsychotic agent | DRD2 |
| paliperidone | antipsychotic agent | HTR2A |
| Palomid 529 | for treatment of age-related macular degeneration | MTOR |
| Palonosetron | antiemetic | HTR3A |
| Panobinostat | antineoplastic agent | HDAC1 |
| Panobinostat | antineoplastic agent | HDAC10 |
| Panobinostat | antineoplastic agent | HDAC11 |
| Panobinostat | antineoplastic agent | HDAC2 |
| Panobinostat | antineoplastic agent | HDAC3 |
| Panobinostat | antineoplastic agent | HDAC4 |

TABLE 2-continued

| Exemplary Drugs with Disease Indications and Gene Identifier for the Target Protein | | |
|---|---|---|
| Drug Name | Indication(s) | Gene |
| Panobinostat | antineoplastic agent | HDAC5 |
| Panobinostat | antineoplastic agent | HDAC6 |
| Panobinostat | antineoplastic agent | HDAC7A |
| Panobinostat | antineoplastic agent | HDAC8 |
| Panobinostat | antineoplastic agent | HDAC9 |
| pantoprazole | Proton pump inhibitor | ATP4A |
| pardoprunox | antiparkinson agent | ADRA1A |
| pardoprunox | antiparkinson agent | ADRA2A |
| pardoprunox | antiparkinson agent | DRD2 |
| pardoprunox | antiparkinson agent | DRD3 |
| pardoprunox | antiparkinson agent | DRD4 |
| pardoprunox | antiparkinson agent | HTR1A |
| pardoprunox | antiparkinson agent | HTR7 |
| parecoxib | antiinflammatory agent, NSAID | PTGS2 |
| paricalcitol | for treatment of hyperparathyroidism | VDR |
| paroxetine | antidepressant | SLC6A4 |
| Pazopanib | antineoplastic agent | FLT1 |
| Pazopanib | antineoplastic agent | FLT4 |
| Pazopanib | antineoplastic agent | KDR |
| bleomycin | antineoplastic agent | LIG1 |
| CRA-024781 | antineoplastic agent | HDAC1 |
| CRA-024781 | antineoplastic agent | HDAC10 |
| CRA-024781 | antineoplastic agent | HDAC2 |
| CRA-024781 | antineoplastic agent | HDAC3 |
| CRA-024781 | antineoplastic agent | HDAC6 |
| ibrutinib | antineoplastic agent | BTK |
| PD-6735 | hypnotic | MTNR1A |
| PD-6735 | hypnotic | MTNR1B |
| 10-propargyl-10-deazaaminopterin | antineoplastic agent | DHFR |
| PEG-camptothecin | antineoplastic agent | TOP1 |
| pentosan polysulfate | for symptomatic treatment of bladder pain or discomfort associated with interstitial cystitis | FGF1 |
| pentosan polysulfate | for symptomatic treatment of bladder pain or discomfort associated with interstitial cystitis | FGF2 |
| pentosan polysulfate | for symptomatic treatment of bladder pain or discomfort associated with interstitial cystitis | FGF4 |
| pentostatin | antineoplastic agent | ADA |
| pentoxifylline | for treatment of amyotrophic lateral sclerosis (ALS) | ADORA1 |
| pentoxifylline | for treatment of amyotrophic lateral sclerosis (ALS) | ADORA2B |
| pentoxifylline | for treatment of amyotrophic lateral sclerosis (ALS) | PDE4A |
| pentoxifylline | for treatment of amyotrophic lateral sclerosis (ALS) | PDE4B |
| pentoxifylline | for treatment of amyotrophic lateral sclerosis (ALS) | PDE5A |
| ingenol Mebutate | for treatment of actinic keratosis, antineoplastic agent | PKN1 |
| ingenol Mebutate | for treatment of actinic keratosis, antineoplastic agent | PKN2 |
| ingenol Mebutate | for treatment of actinic keratosis, antineoplastic agent | PRKCA |
| ingenol Mebutate | for treatment of actinic keratosis, antineoplastic agent | PRKCB1 |
| ingenol Mebutate | for treatment of actinic keratosis, antineoplastic agent | PRKCD |
| ingenol Mebutate | for treatment of actinic keratosis, antineoplastic agent | PRKCE |
| ingenol Mebutate | for treatment of actinic keratosis, antineoplastic agent | PRKCG |
| ingenol Mebutate | for treatment of actinic keratosis, antineoplastic agent | PRKCH |
| ingenol Mebutate | for treatment of actinic keratosis, antineoplastic agent | PRKCI |
| ingenol Mebutate | for treatment of actinic keratosis, antineoplastic agent | PRKCQ |
| ingenol Mebutate | for treatment of actinic keratosis, antineoplastic agent | PRKCZ |
| irinotecan | antineoplastic agent | TOP1 |
| irinotecan | antineoplastic agent | TOP1MT |

TABLE 2-continued

Exemplary Drugs with Disease Indications and Gene Identifier for the Target Protein

| Drug Name | Indication(s) | Gene |
|---|---|---|
| perifosine | antineoplastic agent | AKT1 |
| perifosine | antineoplastic agent | AKT2 |
| perifosine | antineoplastic agent | AKT3 |
| PF-00610355 | bronchodilator | ADRB2 |
| PF-04554878 | antineoplastic agent | PTK2 |
| Dacomitinib | antineoplastic agent | EGFR |
| Dacomitinib | antineoplastic agent | ERBB2 |
| Dacomitinib | antineoplastic agent | ERBB4 |
| PG-490-88 | antineoplastic agent | NFKB1 |
| PG-490-88 | antineoplastic agent | NFKB2 |
| PG545 | antineoplastic agent | HPSE |
| PH-797804 | antiinflammatory agent, DMARD | MAPK11 |
| PH-797804 | antiinflammatory agent, DMARD | MAPK12 |
| PH-797804 | antiinflammatory agent, DMARD | MAPK13 |
| PH-797804 | antiinflammatory agent, DMARD | MAPK14 |
| phenoxodiol | antineoplastic agent | SPHK1 |
| phenoxodiol | antineoplastic agent | SPHK2 |
| phenserine | for treatment of Alzheimer's disease | ACHE |
| physostigmine | for treatment of dry mouth | ACHE |
| Pimavanserin | antiparkinson agent | HTR2A |
| pimecrolimus | antiinflammatory agent | MTOR |
| pioglitazone | antidiabetic | PPARG |
| metformin | antidiabetic | PRKAB1 |
| pioglitazone | antidiabetic | PPARG |
| pirfenidone | for treatment of fibrotic conditions | MAPK11 |
| pirfenidone | for treatment of fibrotic conditions | MAPK12 |
| pirfenidone | for treatment of fibrotic conditions | MAPK13 |
| pirfenidone | for treatment of fibrotic conditions | MAPK14 |
| pitavastatin | anticholesterolaemic agent | HMGCR |
| PL37 | analgesic, neuropathic pain | ANPEP |
| PL37 | analgesic, neuropathic pain | MME |
| clopidogrel | antithrombotic | P2RY12 |
| PLK-1 inhibitor | antineoplastic agent | PLK1 |
| vemurafenib | antineoplastic agent | BRAF |
| PMI-001 | antiinflammatory agent, DMARD | NR3C1 |
| naproxen | NSAID | PTGS1 |
| naproxen | NSAID | PTGS2 |
| omeprazole | Proton pump inhibitor | ATP4A |
| carmustine | antineoplastic agent | GSR |
| ponatinib | antineoplastic agent | ABL1 |
| ponatinib | antineoplastic agent | SRC |
| ponesimod | antiinflammatory agent, for treatment of multiple sclerosis | S1PR1 |
| Posiphen | for treatment of Alzheimer's disease | APP |
| Posiphen | for treatment of Alzheimer's disease | BACE1 |
| Posiphen | for treatment of Alzheimer's disease | BACE2 |
| pozanicline | for treatment of Alzheimer's disease | CHRNA4 |
| pozanicline | for treatment of Alzheimer's disease | CHRNB2 |
| PPC-5650 | analgesic | ACCN2 |
| PPI-2458 | antineoplastic agent | METAP2 |
| PR-15 | antithrombotic | GP6 |
| prasterone | hormone supplement for increasing bone mineral density in patients with systemic lupus erythematosus | AR |
| prasugrel | antithrombotic | P2RY12 |
| fenofibrate | anticholesterolaemic agent | PPARA |
| pravastatin | anticholesterolaemic agent | HMGCR |
| prednisolone | antiinflammatory agent, corticosteroid | NR3C1 |
| prednisolone | antiinflammatory agent, corticosteroid | NR3C1 |
| pregabalin | analgesic, neuropathic pain,for treatment of restlegs legs syndrome | CACNA1A |
| preladenant | antiparkinson agent | ADORA2A |
| pridopidine | for treatment of Huntington's disease | DRD2 |
| desvenlafaxine | for treatment of menopausal symptoms, antidepressant | SLC6A2 |
| desvenlafaxine | for treatment of menopausal symptoms, antidepressant | SLC6A4 |
| diclofenac | NSAID | PTGS1 |
| diclofenac | NSAID | PTGS2 |
| telapristone | for treatment of uterin fibroids and endometriosis | PGR |
| progesterone | for reducing the risk of pre-term birth for women with short cervix a mid-pregnancy | PGR |

TABLE 2-continued

Exemplary Drugs with Disease Indications and Gene Identifier for the Target Protein

| Drug Name | Indication(s) | Gene |
|---|---|---|
| testosterone | hormone replacement | AR |
| eltrombopag | thrombopoietic | MPL |
| propafenone | antiarrythmic agent | KCNH2 |
| propafenone | antiarrythmic agent | SCN5A |
| propionyl-L-carnitine | for treatment of intermittent claudication | CPT1A |
| propionyl-L-carnitine | for treatment of intermittent claudication | CPT2 |
| propionyl-L-carnitine | for treatment of intermittent claudication | CRAT |
| propionyl-L-carnitine | for treatment of intermittent claudication | CROT |
| propionyl-L-carnitine | for treatment of intermittent claudication | SLC22A4 |
| propionyl-L-carnitine | for treatment of intermittent claudication | SLC22A5 |
| propionyl-L-carnitine | for treatment of intermittent claudication | SLC25A20 |
| propionyl-L-carnitine | for treatment of intermittent claudication | SLC25A29 |
| propofol | sedative | GABRB2 |
| propofol | sedative | GABRB3 |
| propofol | sedative | SCN2A |
| propofol | sedative | SCN4A |
| propofol | sedative | GABRB2 |
| propofol | sedative | GABRB3 |
| propofol | sedative | SCN2A |
| propofol | sedative | SCN4A |
| OPC-14523 | antidepressant | HTR1A |
| OPC-14523 | antidepressant | PGRMC1 |
| OPC-14523 | antidepressant | SIGMAR1 |
| OPC-14523 | antidepressant | SLC6A4 |
| PRT062607 | antiinflammatory agent | SYK |
| prucalopride | motilitant | HTR4 |
| PRX-00023 | antidepressant, anxiolytic | HTR1A |
| PRX-07034 | antiobesity agent, nootropic | HTR6 |
| PRX-08066 | antihypertensive agent | HTR2B |
| PRX-3140 | for treatment of Alzheimer's disease | HTR4 |
| PS433540 | antihypertensive agent | AGTR1 |
| PS433540 | antihypertensive agent | AGTR2 |
| PS433540 | antihypertensive agent | EDNRA |
| lidocaine | for treatment of premature ejaculation | EGFR |
| lidocaine | for treatment of premature ejaculation | SCN10A |
| lidocaine | for treatment of premature ejaculation | SCN5A |
| prilocaine | for treatment of premature ejaculation | SCN5A |
| phenylephrine | for treatment of incontinence | ADRA1A |
| phenylephrine | for treatment of incontinence | ADRA1B |
| phenylephrine | for treatment of incontinence | ADRA1D |
| PSD-506 | for treatment of overactive bladder | CHRM2 |
| PSD-506 | for treatment of overactive bladder | CHRM3 |
| PSN357 | antidiabetic | PYGB |
| PSN357 | antidiabetic | PYGL |
| PSN357 | antidiabetic | PYGM |
| PSN602 | antiobesity agent | HTR1A |
| PSN602 | antiobesity agent | SLC6A2 |
| PSN602 | antiobesity agent | SLC6A3 |
| PSN602 | antiobesity agent | SLC6A4 |
| PSN821 | antidiabetic | GPR119 |
| glycopyrrolate | for treatment of chronic obstructive pulmonary disorder (COPD) | CHRM1 |
| formoterol | for treatment of chronic obstructive pulmonary disorder (COPD) | ADRB2 |
| glycopyrrolate | for treatment of chronic obstructive pulmonary disorder (COPD) | CHRM1 |
| formoterol | for treatment of chronic obstructive pulmonary disorder (COPD) | ADRB2 |
| PTC299 | antineoplastic agent | FLT1 |
| PTC299 | antineoplastic agent | FLT4 |
| PTC299 | antineoplastic agent | KDR |
| naltrexone | analgesic | OPRD1 |
| naltrexone | analgesic | OPRD1 |
| naltrexone | analgesic | OPRK1 |

TABLE 2-continued

| Exemplary Drugs with Disease Indications and Gene Identifier for the Target Protein | | |
|---|---|---|
| Drug Name | Indication(s) | Gene |
| naltrexone | analgesic | OPRK1 |
| naltrexone | analgesic | OPRM1 |
| naltrexone | analgesic | OPRM1 |
| naltrexone | analgesic | SIGMAR1 |
| tramadol | analgesic | HTR2C |
| tramadol | analgesic | OPRK1 |
| tramadol | analgesic | OPRK1 |
| tramadol | analgesic | OPRM1 |
| tramadol | analgesic | OPRM1 |
| tramadol | analgesic | SLC6A2 |
| tramadol | analgesic | SLC6A2 |
| tramadol | analgesic | SLC6A4 |
| acetaminophen | analgesic | PTGS1 |
| acetaminophen | analgesic | PTGS1 |
| acetaminophen | analgesic | PTGS2 |
| acetaminophen | analgesic | PTGS2 |
| hydrocodone | analgesic | OPRD1 |
| hydrocodone | analgesic | OPRD1 |
| hydrocodone | analgesic | OPRM1 |
| hydrocodone | analgesic | OPRM1 |
| naltrexone | analgesic | OPRD1 |
| naltrexone | analgesic | OPRD1 |
| naltrexone | analgesic | OPRK1 |
| naltrexone | analgesic | OPRK1 |
| naltrexone | analgesic | OPRM1 |
| naltrexone | analgesic | OPRM1 |
| naltrexone | analgesic | SIGMAR1 |
| naltrexone | analgesic | SIGMAR1 |
| naltrexone | analgesic | OPRD1 |
| naltrexone | analgesic | OPRK1 |
| naltrexone | analgesic | OPRM1 |
| oxycodone | analgesic | OPRD1 |
| oxycodone | analgesic | OPRK1 |
| oxycodone | analgesic | OPRM1 |
| naltrexone | analgesic | OPRD1 |
| naltrexone | analgesic | OPRK1 |
| naltrexone | analgesic | OPRM1 |
| Pumosetrag | motilitant | HTR3A |
| Pumosetrag | motilitant | HTR3B |
| Pumosetrag | motilitant | HTR3C |
| Pumosetrag | motilitant | HTR3D |
| Pumosetrag | motilitant | HTR3E |
| PW2101 | antihypertensive agent | ADRB2 |
| PX-12 | antineoplastic agent | TXN |
| PX-478 | antineoplastic agent | HIF1A |
| belinostat | antineoplastic agent | HDAC1 |
| belinostat | antineoplastic agent | HDAC10 |
| belinostat | antineoplastic agent | HDAC11 |
| belinostat | antineoplastic agent | HDAC2 |
| belinostat | antineoplastic agent | HDAC3 |
| belinostat | antineoplastic agent | HDAC4 |
| belinostat | antineoplastic agent | HDAC5 |
| belinostat | antineoplastic agent | HDAC6 |
| belinostat | antineoplastic agent | HDAC7A |
| belinostat | antineoplastic agent | HDAC8 |
| belinostat | antineoplastic agent | HDAC9 |
| PYM50028 | antiparkinson agent | GFRA1 |
| PYM50028 | antiparkinson agent | NGFR |
| PYM50028 | antiparkinson agent | NTRK1 |
| PYM50028 | antiparkinson agent | NTRK2 |
| quinapril | antihypertensive agent | ACE |
| glycopyrronium bromide | for treatment of chronic obstructive pulmonary disorder (COPD) | ADRB2 |
| indacaterol | for treatment of chronic obstructive pulmonary disorder (COPD) | CHRM1 |
| R112 | antiallergy agent | FCER1A |
| R112 | antiallergy agent | FCER1G |
| R112 | antiallergy agent | MS4A2 |
| R343 | antiallergy agent | SYK |
| R348 | antiinflammatory agent | JAK3 |
| R667 | for treatment of emphysema | RARA |
| R667 | for treatment of emphysema | RARB |
| R667 | for treatment of emphysema | RARG |
| R763 | antineoplastic agent | AURKA |
| R763 | antineoplastic agent | AURKB |
| R763 | antineoplastic agent | AURKC |

TABLE 2-continued

Exemplary Drugs with Disease Indications and Gene Identifier for the Target Protein

| Drug Name | Indication(s) | Gene |
|---|---|---|
| RAD1901 | for treatment of postmenopausal symptoms | ESR1 |
| raltitrexed | antineoplastic agent | TYMS |
| ramelteon | for treatment of insomnia | MTNR1A |
| ramelteon | for treatment of insomnia | MTNR1B |
| ranolazine | antiallergy agent | SCN5A |
| ranolazine | antiallergy agent | SCN9A |
| ranirestat | for treatment of diabetic neuropathy | AKR1B1 |
| ranitidine | antiulcer agent | HRH2 |
| rasagiline | antiparkinson agent | MA0B |
| RC-8800 | for improving the antiproliferative and apoptotic properties of vitamin D3 | CYP46A1 |
| RDEA119 | antineoplastic agent | MAPK1 |
| RDEA119 | antineoplastic agent | MAPK3 |
| regadenoson | diagnostic agent | ADORA2A |
| regorafenib | antineoplastic agent | KDR |
| regorafenib | antineoplastic agent | TEK |
| relacatib | antiosteoporotic agent | CTSK |
| eletriptan | antimigraine agent | HTR1D |
| remifentanil | analgesic | OPRM1 |
| Nalbuphine | analgesic | OPRD1 |
| Nalbuphine | analgesic | OPRK1 |
| Nalbuphine | analgesic | OPRM1 |
| naloxone | analgesic | OPRD1 |
| naloxone | analgesic | OPRK1 |
| naloxone | analgesic | OPRM1 |
| renzapride | for treatment of irritable bowel syndrome | HTR2A |
| renzapride | for treatment of irritable bowel syndrome | HTR2B |
| renzapride | for treatment of irritable bowel syndrome | HTR2C |
| renzapride | for treatment of irritable bowel syndrome | HTR3A |
| renzapride | for treatment of irritable bowel syndrome | HTR4 |
| repaglinide | antidiabetic | ABCC8 |
| ropinirol | antiparkinson agent | DRD2 |
| ropinirol | antiparkinson agent | DRD3 |
| resiniferatoxin | for treatment of interstitial cystitis, antiincontinence agent | TRPV1 |
| Resminostat | antineoplastic agent | HDAC1 |
| Resminostat | antineoplastic agent | HDAC10 |
| Resminostat | antineoplastic agent | HDAC11 |
| Resminostat | antineoplastic agent | HDAC2 |
| Resminostat | antineoplastic agent | HDAC3 |
| Resminostat | antineoplastic agent | HDAC4 |
| Resminostat | antineoplastic agent | HDAC5 |
| Resminostat | antineoplastic agent | HDAC6 |
| Resminostat | antineoplastic agent | HDAC7A |
| Resminostat | antineoplastic agent | HDAC8 |
| Resminostat | antineoplastic agent | HDAC9 |
| Resveratrol | for treatment of herpes simplex virus 1 | PDE4B |
| Resveratrol | for treatment of herpes simplex virus 1 | PDE4D |
| retigabine | anticonvulsant | KCNQ1 |
| retigabine | anticonvulsant | KCNQ2 |
| retigabine | anticonvulsant | KCNQ3 |
| retigabine | anticonvulsant | KCNQ4 |
| retigabine | anticonvulsant | KCNQ5 |
| rEV131 | antiallergy agent | HRH4 |
| lenalidomide | antineoplastic agent | TNFSF11 |
| RG2833 | for treatment of Friedrich's ataxia | HDAC3 |
| RG3039 | for treatment of spinal muscular atrophy | DCPS |
| Ridaforolimus | antineoplastic agent | MTOR |
| riluzole | for treatment of ALS | SCN5A |
| riluzole | for treatment of ALS | SLC7A11 |
| rimcazole | antineoplastic agent | SIGMAR1 |
| Rimonabant | antiobesity agent | CNR1 |
| riociguat | antihypertensive agent | GUCY1A2 |
| riociguat | antihypertensive agent | GUCY1A3 |
| riociguat | antihypertensive agent | GUCY1B2 |
| riociguat | antihypertensive agent | GUCY1B3 |

TABLE 2-continued

Exemplary Drugs with Disease Indications and Gene Identifier for the Target Protein

| Drug Name | Indication(s) | Gene |
|---|---|---|
| risedronate | antiosteoporotic agent | FDPS |
| Risperdal | antipsychotic agent | DRD2 |
| Risperdal | antipsychotic agent | HTR2A |
| rivaroxaban | antithrombotic | F10 |
| rivastigmine | for treatment of Alzheimer's disease | ACHE |
| rivastigmine | for treatment of Alzheimer's disease | BCHE |
| Rob 803 | antiinflammatory agent, DMARD | unknown |
| rocuronium | muscle relaxant | CHRM2 |
| rocuronium | muscle relaxant | CHRNA2 |
| rocuronium | muscle relaxant | HTR3A |
| rofecoxib | NSAID | PTGS2 |
| roflumilast | for treatment of chronic obstructive pulmonary disorder (COPD) | PDE4A |
| roflumilast | for treatment of chronic obstructive pulmonary disorder (COPD) | PDE4B |
| rolofylline | for treatment of congestive heart failure | ADORA1 |
| ronacaleret | antiiosteoporotic agent | CASR |
| ropivacaine | anestethic | SCN10A |
| glimepiride | antidiabetic | ABCC8 |
| glimepiride | antidiabetic | KCNJ1 |
| glimepiride | antidiabetic | KCNJ11 |
| rosiglitazone | antidiabetic | PPARG |
| metformin | antidiabetic | PRKAB1 |
| rosiglitazone | antidiabetic | PPARG |
| rosiglitazone | for treatment of Alzheimer's disease, antidiabetic | PPARG |
| ketorolac | antimigraine agent | PTGS1 |
| ketorolac | antimigraine agent | PTGS2 |
| bromovinyl deoxyuridine | antineoplastic agent | POLA1 |
| RPC1063 | for treatment of multiple sclerosis | S1PR1 |
| RPL-554 | bronchodilator | PDE3A |
| RPL-554 | bronchodilator | PDE3B |
| RPL-554 | bronchodilator | PDE4A |
| RPL-554 | bronchodilator | PDE4B |
| RTA 744 | antineoplastic agent | TOP2A |
| RTA 744 | antineoplastic agent | TOP2B |
| rubitecan | antineoplastic agent | TOP1 |
| ruboxistaurin | for treatment of diabetic neuropathy | PRKCB1 |
| RVX-208 | antiatherosclerotic agent | APOA1 |
| gimestat | antineoplastic agent | DPYD |
| tegafur | antineoplastic agent | TYMS |
| paclitaxel | antineoplastic agent | BCL2 |
| paclitaxel | antineoplastic agent | TUBB1 |
| SA4503 | antidepressant, neuroprotectant | SIGMAR1 |
| Safinamide | antiparkinson agent | CACNA1B |
| Safinamide | antiparkinson agent | CACNA2D1 |
| Safinamide | antiparkinson agent | CACNA2D2 |
| Safinamide | antiparkinson agent | CACNB3 |
| Safinamide | antiparkinson agent | CACNB4 |
| Safinamide | antiparkinson agent | MA0B |
| Safinamide | antiparkinson agent | SCN11A |
| Safinamide | antiparkinson agent | SCN11A |
| Safinamide | antiparkinson agent | SCN1A |
| Safinamide | antiparkinson agent | SCN2A |
| Safinamide | antiparkinson agent | SCN3A |
| Safinamide | antiparkinson agent | SCN4A |
| Safinamide | antiparkinson agent | SCN5A |
| Safinamide | antiparkinson agent | SCN7A |
| Safinamide | antiparkinson agent | SCN8A |
| Safinamide | antiparkinson agent | SCN9A |
| tetrahydrobiopterin | for treatment of phenolketonuria (PKU) | NOS3 |
| tetrahydrobiopterin | for treatment of phenolketonuria (PKU) | PAH |
| tetrahydrobiopterin | for treatment of phenolketonuria (PKU) | TH |
| tetrahydrobiopterin | for treatment of phenolketonuria (PKU) | TPH1 |
| SAR 1118 | antiinflammatory agent | ICAM1 |
| SAR 1118 | antiinflammatory agent | ITGAL |
| SAR 1118 | antiinflammatory agent | ITGB2 |
| saredutant | antidepressant, anxiolytic | TACR2 |
| nabilone | analgesic, neuropathic pain, for treatment of restlegs legs syndrome | CNR2 |

TABLE 2-continued

| Exemplary Drugs with Disease Indications and Gene Identifier for the Target Protein | | |
|---|---|---|
| Drug Name | Indication(s) | Gene |
| nabilone | analgesic, neuropathic pain,for treatment of restlegs legs syndrome | CNR2 |
| Saxagliptin | antidiabetic | DPP4 |
| SB1518 | antineoplastic agent | JAK2 |
| SB-559448 | thrombopoietic agent | MPL |
| SB-681323 | antiinflammatory agent, DMARD | MAPK14 |
| firategrast | antiinflammatory agent | ITGA4 |
| firategrast | antiinflammatory agent | ITGB1 |
| pracinostat | antineoplastic agent | HDAC1 |
| pracinostat | antineoplastic agent | HDAC10 |
| pracinostat | antineoplastic agent | HDAC11 |
| pracinostat | antineoplastic agent | HDAC2 |
| pracinostat | antineoplastic agent | HDAC3 |
| pracinostat | antineoplastic agent | HDAC4 |
| pracinostat | antineoplastic agent | HDAC5 |
| pracinostat | antineoplastic agent | HDAC6 |
| pracinostat | antineoplastic agent | HDAC7A |
| pracinostat | antineoplastic agent | HDAC8 |
| pracinostat | antineoplastic agent | HDAC9 |
| SCH-527123 | for treatment of chronic obstructive pulmonary disorder (COPD) | CXCR1 |
| SCH-527123 | for treatment of chronic obstructive pulmonary disorder (COPD) | CXCR2 |
| talmapimod | antiinflammatory agent, DMARD | MAPK14 |
| SCY-635 | for treatment of hepatitis C | PP1A |
| SCY-635 | for treatment of hepatitis C | PP1D |
| scyllo-inositol | for treatment of Alzheimer's disease | APP |
| R-etodolac | antineoplastic agent | RXRA |
| selegiline | antidepressant | MA0B |
| selegiline | antiparkinson agent | MA0B |
| seletracetam | anticonvulsant | SV2A |
| selexipag | antihypertensive agent | PTGIR |
| seliciclib | antineoplastic agent | CDK2 |
| seliciclib | antineoplastic agent | CDK7 |
| seliciclib | antineoplastic agent | CDK9 |
| maraviroc | antiviral agent, HIV | CCR5 |
| eszopiclone | anxiolytic | GABRA1 |
| clavulanic acid | antidepressant | FOLH1 |
| SERTINDOLE | antipsychotic agent | ADRA1A |
| SERTINDOLE | antipsychotic agent | ADRA1B |
| SERTINDOLE | antipsychotic agent | ADRA1D |
| SERTINDOLE | antipsychotic agent | DRD2 |
| SERTINDOLE | antipsychotic agent | HTR2A |
| SERTINDOLE | antipsychotic agent | HTR2C |
| SERTINDOLE | antipsychotic agent | HTR6 |
| SERTINDOLE | antipsychotic agent | KCNH2 |
| salmeterol | bronchodilator | ADRB2 |
| Quetiapine | antipsychotic agent, antidepressant | DRD2 |
| Quetiapine | antipsychotic agent, antidepressant | HTR2A |
| Quetiapine | antipsychotic agent, antidepressant | HTR2B |
| Quetiapine | antipsychotic agent, antidepressant | HTR2C |
| Quetiapine | antipsychotic agent, antidepressant | HTR2C |
| SF1126 | antineoplastic agent | MTOR |
| SF1126 | antineoplastic agent | PIK3C3 |
| SF1126 | antineoplastic agent | PIK3CA |
| SF1126 | antineoplastic agent | PIK3CA |
| SF1126 | antineoplastic agent | PIK3CB |
| SF1126 | antineoplastic agent | PIK3CD |
| SF1126 | antineoplastic agent | PIK3CD |
| SF1126 | antineoplastic agent | PIK3CG |
| SF1126 | antineoplastic agent | PIK3CG |
| SF1126 | antineoplastic agent | PRKDC |
| SGI-1776 | antineoplastic agent | PIM1 |
| SGI-1776 | antineoplastic agent | PIM2 |
| SGI-1776 | antineoplastic agent | PIM3 |
| beclomethasone | antiinflammatory agent, glucocorticoid | NR3C1 |
| SGX523 | antineoplastic agent | MET |
| sibutramine | appetite suppressant | SLC6A2 |
| sibutramine | appetite suppressant | SLC6A3 |
| sibutramine | appetite suppressant | SLC6A4 |
| sildenafil | for treatment of erectile dysfucntion, antihypertensive agent | PDE5A |
| doxepin | hypnotic | CHRM1 |
| doxepin | hypnotic | CHRM2 |
| doxepin | hypnotic | CHRM3 |

TABLE 2-continued

Exemplary Drugs with Disease Indications and Gene Identifier for the Target Protein

| Drug Name | Indication(s) | Gene |
|---|---|---|
| doxepin | hypnotic | CHRM4 |
| doxepin | hypnotic | CHRM5 |
| doxepin | hypnotic | HRH1 |
| doxepin | hypnotic | HRH2 |
| doxepin | hypnotic | HTR2A |
| doxepin | hypnotic | HTR2B |
| doxepin | hypnotic | HTR2C |
| doxepin | hypnotic | SLC6A2 |
| doxepin | hypnotic | SLC6A4 |
| Silodosin | for treatment of BPH-related urinary symptoms | ADRA1A |
| sirolimus | for treatment of wet age-related macular degeneration | FKBP1A |
| sirolimus | for treatment of wet age-related macular degeneration | MTOR |
| sirolimus | immunosuppressant | FKBP1A |
| sirolimus | immunosuppressant | MTOR |
| Sitagliptin | antidiabetic | DPP4 |
| sivelestat | for treatment of acute lung injury associated with systemic inflammatory response syndrome (SIRS) | ELA2 |
| zaleplon | hypnotic | GABRA1 |
| zaleplon | hypnotic | TSPO |
| fluticasone | antiinflammatory agent, glucocorticoid | NR3C1 |
| formoterol | bronchodilator | ADRB2 |
| amphetamine | for treatment of cognitive dysfunction, for treatment of ADHD | SLC18A2 |
| amphetamine | for treatment of cognitive dysfunction, for treatment of ADHD | SLC6A3 |
| amphetamine | for treatment of cognitive dysfunction, for treatment of ADHD | TAAR1 |
| dextroamphetamine | for treatment of ADHD | SLC18A2 |
| dextroamphetamine | for treatment of ADHD | SLC6A2 |
| dextroamphetamine | for treatment of ADHD | SLC6A3 |
| SLx-2101 | antihypertensive agent, for treatment of erectile dysfunction | PDE5A |
| SLx-4090 | antidyslipidaemic agent | MTTP |
| SNS-032 | antineoplastic agent | CDK2 |
| SNS-032 | antineoplastic agent | CDK7 |
| SNS-032 | antineoplastic agent | CDK9 |
| SNS-314 | antineoplastic agent | AURKA |
| SNS-314 | antineoplastic agent | AURKB |
| SNX-5422 | antineoplastic agent | HSP90AA1 |
| SNX-5422 | antineoplastic agent | HSP90AB1 |
| sobetirome | antihypecholesterolemic agent | THRB |
| gamma hydroxybutyric acid | hypnotic | GABBR1 |
| gamma hydroxybutyric acid | hypnotic | GABBR2 |
| gamma hydroxybutyric acid | hypnotic | SLC5A2 |
| stibogluconate | antineoplastic agent | PTPN11 |
| levonorgestrel | contraceptive | ESR1 |
| levonorgestrel | contraceptive | PGR |
| levonorgestrel | contraceptive | SRD5A1 |
| solabegron | antidiabetic, for treatment of irritable bowel syndrome, antiincontinence agent | ADRB3 |
| Solifenacin | for treatment of incontinence | CHRM1 |
| Solifenacin | for treatment of incontinence | CHRM2 |
| Solifenacin | for treatment of incontinence | CHRM3 |
| Solifenacin | for treatment of incontinence | CHRM4 |
| Solifenacin | for treatment of incontinence | CHRM5 |
| SOU-001 | for treatment of incontinence | ADRA1A |
| SOU-001 | for treatment of incontinence | ADRA1B |
| SOU-001 | for treatment of incontinence | ADRA1D |
| SOU-003 | for treatment of incontinence | AVPR2 |
| doxorubicin | antineoplastic agent | TOP2A |
| carbamazepine | for treatment of bipolar disorder | SCN5A |
| mesalamine | for treatment of ulcerative colitis | ALOX5 |
| mesalamine | for treatment of ulcerative colitis | CHUK |
| mesalamine | for treatment of ulcerative colitis | IKBKB |
| mesalamine | for treatment of ulcerative colitis | PPARG |
| mesalamine | for treatment of ulcerative colitis | PTGS1 |

TABLE 2-continued

Exemplary Drugs with Disease Indications and Gene Identifier for the Target Protein

| Drug Name | Indication(s) | Gene |
|---|---|---|
| mesalamine | for treatment of ulcerative colitis | PTGS2 |
| allopurinol | antiuricemic agent | XDH |
| SPP676 | antihypertensive agent | REN |
| Resveratrol | antidiabetic, antineoplastic agent | PDE4B |
| Resveratrol | antidiabetic, antineoplastic agent | PDE4D |
| ganetespib | antineoplastic agent | HSP90AA1 |
| ganetespib | antineoplastic agent | HSP90AB1 |
| stannsoporfin | for prevention of hyperbilirubinemia | HMOX1 |
| stannsoporfin | for prevention of hyperbilirubinemia | HMOX2 |
| nateglinide | antidiabetic | ABCC8 |
| morphine | analgesic | OPRK1 |
| morphine | analgesic | OPRK1 |
| morphine | analgesic | OPRK1 |
| strontium ranelate | antiosteoporotic agent | CASR |
| STX107 | for treatment of Fragile X symptoms | GRM5 |
| sucralfate | antiulcer agent | PGA3 |
| sufentanil | analgesic | OPRD1 |
| sufentanil | analgesic | OPRK1 |
| sufentanil | analgesic | OPRM1 |
| sufentanil | analgesic | OPRD1 |
| sufentanil | analgesic | OPRK1 |
| sufentanil | analgesic | OPRM1 |
| sulfasalazine | antiinflammatory agent, DMARD | ACAT1 |
| sulfasalazine | antiinflammatory agent, DMARD | PPARG |
| sulfasalazine | antiinflammatory agent, DMARD | PTGS1 |
| sulfasalazine | antiinflammatory agent, DMARD | PTGS2 |
| sulodexide | for treatment of diabetic nephropathy | SERPINC1 |
| sulodexide | for treatment of diabetic nephropathy | SERPIND1 |
| Sumatriptan | antimigraine agent | HTR1A |
| Sumatriptan | antimigraine agent | HTR1B |
| Sumatriptan | antimigraine agent | HTR1D |
| Sumatriptan | antimigraine agent | HTR1F |
| Sumatriptan | antimigraine agent | HTR1A |
| Sumatriptan | antimigraine agent | HTR1B |
| Sumatriptan | antimigraine agent | HTR1D |
| Sumatriptan | antimigraine agent | HTR1F |
| Sumatriptan | antimigraine agent | HTR1A |
| Sumatriptan | antimigraine agent | HTR1B |
| Sumatriptan | antimigraine agent | HTR1D |
| Sumatriptan | antimigraine agent | HTR1F |
| surinabant | smoking-cessation agent | CNR1 |
| latanoprost | for treatment of glaucoma | PTGFR |
| sunitinib | antineoplastic agent | FLT1 |
| sunitinib | antineoplastic agent | FLT3 |
| sunitinib | antineoplastic agent | FLT4 |
| sunitinib | antineoplastic agent | KDR |
| sunitinib | antineoplastic agent | KIT |
| sunitinib | antineoplastic agent | PDGFRA |
| sunitinib | antineoplastic agent | PDGFRB |
| sunitinib | antineoplastic agent | RET |
| SUVN-502 | for treatment of Alzheimer's disease | HTR6 |
| SVT-40776 | for treatment of incontinence | CHRM3 |
| tozadenant | antiparkinson agent | ADORA2A |
| nitisinone | antiparkinson agent | HPD |
| T-5224 | antiinflammatory agent, DMARD | JUN |
| T-62 | analgesic | ADORA1 |
| tacrolimus | immunosuppressant | FKBP1A |
| tacrolimus | immunosuppressant | FKBP1A |
| TAFA-93 | immunosuppressant | FRAP1 |
| TAK-242 | for treatment of sepsis | TLR4 |
| dexlansoprazole | Proton pump inhibitor | ATP4A |
| TAK-442 | antithrombotic | F10 |
| Talabostat | for treatment of neutropenia | CSF3 |
| talampanel | antiparkinson agent, antineoplastic agent | GRIA1 |
| talampanel | antiparkinson agent, antineoplastic agent | GRIA2 |
| talampanel | antiparkinson agent, antineoplastic agent | GRIA3 |
| talampanel | antiparkinson agent, antineoplastic agent | GRIA4 |
| talarozole | antipsoriatic agent, for treatment of acne | CYP26A1 |
| talarozole | antipsoriatic agent, for treatment of acne | CYP26B1 |

TABLE 2-continued

Exemplary Drugs with Disease Indications and Gene Identifier for the Target Protein

| Drug Name | Indication(s) | Gene |
|---|---|---|
| talarozole | antipsoriatic agent, for treatment of acne | CYP26C1 |
| talnetant | antipsychotic agent | TACR3 |
| talotrexin | antineoplastic agent | DHFR |
| Tamibarotene | antineoplastic agent | RARA |
| Tamibarotene | antineoplastic agent | RARB |
| tamsulosin | for treatment of urinary symptoms associated with BPH | ADRA1A |
| tamsulosin | for treatment of urinary symptoms associated with BPH | ADRA1B |
| tamsulosin | for treatment of urinary symptoms associated with BPH | ADRA1D |
| tandutinib | antineoplastic agent | FLT3 |
| Tanespimycin | antineoplastic agent | HSP90AA1 |
| Tanespimycin | antineoplastic agent | HSP90AB1 |
| tapentadol | analgesic | OPRM1 |
| tapentadol | analgesic | SLC6A2 |
| tapentadol | analgesic,opioid | MOR |
| Taranabant | antiobesity agent, smoking-cessation agent | CNR1 |
| erlotinib | antineoplastic agent | EGFR |
| tariquidar | adjuvant to chemotherapy | ABCB1 |
| TAS-108 | antineoplastic agent | ESR1 |
| TAS-108 | antineoplastic agent | ESR2 |
| tasimelteon | hypnotic | MTNR1A |
| tasimelteon | hypnotic | MTNR1B |
| Tasocitinib | antiinflammatory agent, DMARD | JAK3 |
| tazarotene | antipsoriatic agent, for treatment of acne | RARA |
| tazarotene | antipsoriatic agent, for treatment of acne | RARB |
| tazarotene | antipsoriatic agent, for treatment of acne | RARG |
| tazarotene | antipsoriatic agent, for treatment of acne | RXRB |
| TBR-652 | antiviral agent, HIV | CCR5 |
| ispronicline | nootropic | CHRNA4 |
| ispronicline | nootropic | CHRNB2 |
| TC-2403-12 | for treatment of ulcerative colitis | CHRNA4 |
| TC-2403-12 | for treatment of ulcerative colitis | CHRNB2 |
| TC-2696 | analgesic | CHRNA4 |
| TC-2696 | analgesic | CHRNB2 |
| TC-5214 | antidepressant | CHRNA4 |
| TC-5214 | antidepressant | CHRNB2 |
| TC-5619 | neuroprotectant | CHRNA7 |
| TC-6499 | analgesic, neuropathic pain | CHRNA4 |
| TC-6499 | analgesic, neuropathic pain | CHRNB2 |
| TC-6987 | antiasthmatic agent, antidiabetic | CHRNA7 |
| TD-1211 | for treatment of opioid-induced gastrointestinal side-effects | OPRM1 |
| tecadenoson | antiarrhytmic agent | ADORA1 |
| tecarfarin | antithrombotic | VKORC1 |
| tegaserod | motilitant | HTR4 |
| telatinib | antineoplastic agent | FLT1 |
| telatinib | antineoplastic agent | FLT4 |
| telatinib | antineoplastic agent | KDR |
| telatinib | antineoplastic agent | PDGFRA |
| telatinib | antineoplastic agent | PDGFRB |
| telmisartan | antihypertensive agent | AGTR1 |
| temsirolimus | antineoplastic agent | FRAP1 |
| terguride | for treatment of pulmonary arterial hypertension | HTR2A |
| terguride | for treatment of pulmonary arterial hypertension | HTR2B |
| teriflunomide | for treatment of multiple sclerosis | DHODH |
| terlipressin | for treatment of hepatorenal syndrome | AVPR1A |
| terlipressin | for treatment of hepatorenal syndrome | AVPR1B |
| terlipressin | for treatment of hepatorenal syndrome | AVPR2 |
| tesetaxel | antineoplastic agent | BCL2 |
| tesetaxel | antineoplastic agent | TUBB1 |
| tesmilifene | adjuvant to chemotherapy | ABCB1 |
| tesmilifene | adjuvant to chemotherapy | CYP3A4 |

TABLE 2-continued

| Exemplary Drugs with Disease Indications and Gene Identifier for the Target Protein | | |
|---|---|---|
| Drug Name | Indication(s) | Gene |
| tesmilifene | adjuvant to chemotherapy | CYP3A5 |
| tesmilifene | adjuvant to chemotherapy | CYP3A7 |
| tesofensine | antiobesity agent | SLC6A2 |
| tesofensine | antiobesity agent | SLC6A4 |
| testosterone | hormone replacement, for treatment of female sexual dysfunction | AR |
| testosterone | for treatment of female sexual dysfunction | AR |
| testosterone | hormone replacement | AR |
| testosterone | for treatment of female sexual dysfunction | AR |
| testosterone | hormone replacement | AR |
| testosterone | hormone replacement | AR |
| testosterone | for treatment of female sexual dysfunction | AR |
| tetrabenazine | for treatment of Huntington's disease | SLC18A2 |
| tetrodotoxin | analgesic | SCN10A |
| tetrodotoxin | analgesic | SCN11A |
| tetrodotoxin | analgesic | SCN1A |
| tetrodotoxin | analgesic | SCN2A |
| tetrodotoxin | analgesic | SCN3A |
| tetrodotoxin | analgesic | SCN4A |
| tetrodotoxin | analgesic | SCN5A |
| tetrodotoxin | analgesic | SCN8A |
| tetrodotoxin | analgesic | SCN9A |
| tezampanel | antimigraine agent, analgesic | GRIA1 |
| tezampanel | antimigraine agent, analgesic | GRIA2 |
| tezampanel | antimigraine agent, analgesic | GRIA3 |
| tezampanel | antimigraine agent, analgesic | GRIA4 |
| tezampanel | antimigraine agent, analgesic | GRIK1 |
| tezampanel | antimigraine agent, analgesic | GRIK2 |
| tezampanel | antimigraine agent, analgesic | GRIK3 |
| tezampanel | antimigraine agent, analgesic | GRIK4 |
| tezampanel | antimigraine agent, analgesic | GRIK5 |
| TG-0054 | adjuvant to stem cell transplantation | CXCR4 |
| TG02, SB1317 | antineoplastic agent | CDK2 |
| TG02, SB1317 | antineoplastic agent | ERK5 |
| TG02, SB1317 | antineoplastic agent | FLT3 |
| TG02, SB1317 | antineoplastic agent | JAK2 |
| TG101348 | antineoplastic agent | JAK2 |
| thalidomide | antineoplastic agent | FGFR2 |
| thalidomide | antineoplastic agent | NFKB1 |
| thalidomide | antineoplastic agent | PTGS2 |
| thalidomide | antineoplastic agent | TNF |
| sitaxsentan | for treatment of pulmonary arterial hypertension | EDNRA |
| ketoprofen | NSAID | PTGS1 |
| ketoprofen | NSAID | PTGS1 |
| ketoprofen | NSAID | PTGS2 |
| ketoprofen | NSAID | PTGS2 |
| pilocarpine | for treatment of incontinence | CHRM1 |
| pilocarpine | for treatment of incontinence | CHRM2 |
| pilocarpine | for treatment of incontinence | CHRM3 |
| tolterodine | for treatment of incontinence | CHRM1 |
| tolterodine | for treatment of incontinence | CHRM2 |
| tolterodine | for treatment of incontinence | CHRM3 |
| tolterodine | for treatment of incontinence | CHRM4 |
| tolterodine | for treatment of incontinence | CHRM5 |
| Ticagrelor | antithrombotic | P2RY12 |
| tideglusib | for treatment of Alzheimer's disease | GSK3A |
| tideglusib | for treatment of Alzheimer's disease | GSK3B |
| tilarginine | for treatment of cardiogenic shock | NOS2 |
| tiotropium | for treatment of cystic fibrosis,for treatment of chronic obstructive pulmonary disorder (COPD) | CHRM1 |
| tiotropium | for treatment of cystic fibrosis,for treatment of chronic obstructive pulmonary disorder (COPD) | CHRM2 |
| tiotropium | for treatment of cystic fibrosis,for treatment of chronic obstructive pulmonary disorder (COPD) | CHRM3 |
| tipifarnib | antineoplastic agent | FNTA |
| tipifarnib | antineoplastic agent | FNTB |
| tizanidine | muscle relaxant | ADRA2A |
| tizanidine | muscle relaxant | ADRA2B |
| tizanidine | muscle relaxant | ADRA2C |

TABLE 2-continued

| Drug Name | Indication(s) | Gene |
|---|---|---|
| canfosfamide | antineoplastic agent | GSTP1 |
| TLN-4601 | antineoplastic agent | TSPO |
| obinepitide | antiobesity agent | NPY2R |
| obinepitide | antiobesity agent | PPYR1 |
| TM30339 | antiobesity agent | PPYR1 |
| TM38837 | antiobesity agent | CNR1 |
| ondansetron | for treatment of obsessive compulsive disorder (OCD) | HTR3A |
| galeterone | antineoplastic agent | AR |
| galeterone | antineoplastic agent | CYP17A1 |
| tolterodine | for treatment of incontinence | CHRM1 |
| tolterodine | for treatment of incontinence | CHRM2 |
| tolterodine | for treatment of incontinence | CHRM3 |
| tolterodine | for treatment of incontinence | CHRM4 |
| tolterodine | for treatment of incontinence | CHRM5 |
| tolvaptan | antihypertensive agent | AVPR2 |
| Tonabersat | antimigraine agent | HTR1D |
| alprostadil | for treatment of erectile dysfunction, for treatment of sexual dysfunction in women | PTGER1 |
| alprostadil | for treatment of erectile dysfunction, for treatment of sexual dysfunction in women | PTGER2 |
| menadione | for reducing EGFR-inhibitor-induced dermatological side effects | GGCX |
| menadione | for reducing EGFR-inhibitor-induced dermatological side effects | VKORC1 |
| menadione | for reducing EGFR-inhibitor-induced dermatological side effects | VKORC1L1 |
| testosterone | hormone replacement | AR |
| topiramate | anticonvulsant | CA2 |
| topiramate | anticonvulsant | CA4 |
| topiramate | anticonvulsant | GABRA1 |
| topiramate | anticonvulsant | GRIK1 |
| topiramate | anticonvulsant | SCN1A |
| topiramate | anticonvulsant, antimigraine agent | CA2 |
| topiramate | anticonvulsant, antimigraine agent | CA4 |
| topiramate | anticonvulsant, antimigraine agent | GABRA1 |
| topiramate | anticonvulsant, antimigraine agent | GRIK1 |
| topiramate | anticonvulsant, antimigraine agent | SCN1A |
| topotecan | antineoplastic agent | TOP1 |
| Torcetrapib | antidyslipidaemic agent | CETP |
| morphine | analgesic | OPRD1 |
| morphine | analgesic | OPRK1 |
| morphine | analgesic | OPRM1 |
| bosentan | for treatment of pulmonary arterial hypertension | EDNRA |
| bosentan | for treatment of pulmonary arterial hypertension | EDNRB |
| tramadol | analgesic | HTR2C |
| tramadol | analgesic | OPRK1 |
| tramadol | analgesic | OPRM1 |
| tramadol | analgesic | OPRM1 |
| tramadol | analgesic | SLC6A2 |
| tramadol | analgesic | SLC6A2 |
| tramadol | analgesic | SLC6A4 |
| tramadol | analgesic | SLC6A4 |
| tramadol | analgesic | HTR2C |
| tramadol | analgesic | OPRK1 |
| tramadol | analgesic | OPRM1 |
| tramadol | analgesic | OPRM1 |
| tramadol | analgesic | SLC6A2 |
| tramadol | analgesic | SLC6A2 |
| tramadol | analgesic | SLC6A4 |
| tramadol | analgesic | SLC6A4 |
| tramadol | analgesic | HTR2C |
| tramadol | analgesic | OPRK1 |
| tramadol | analgesic | OPRM1 |
| tramadol | analgesic | OPRM1 |
| tramadol | analgesic | SLC6A2 |
| tramadol | analgesic | SLC6A2 |
| tramadol | analgesic | SLC6A4 |
| tramadol | analgesic | SLC6A4 |
| homotaurine | for treatment of Alzheimer's disease | APP |
| trandolapril | antihypertensive agent | ACE |
| tranexamic acid | antimenorrhagic agent | PLAT |

Exemplary Drugs with Disease Indications and Gene Identifier for the Target Protein TABLE 2-continued

| Exemplary Drugs with Disease Indications and Gene Identifier for the Target Protein | | |
|---|---|---|
| Drug Name | Indication(s) | Gene |
| capsaicin | analgesic | TRPV1 |
| diclofenac | NSAID | PTGS1 |
| diclofenac | NSAID | PTGS2 |
| estradiol | hormone replacement | ESR1 |
| estradiol | hormone replacement | ESR2 |
| granisetron | antiemetic | HTR3A |
| lidocaine | anestethic | SCN10A |
| lidocaine | anestethic | SCN5A |
| lidocaine | anestethic | SCN9A |
| epinephrine | anestethic | ADRA1A |
| epinephrine | anestethic | ADRA1B |
| epinephrine | anestethic | ADRA1D |
| epinephrine | anestethic | ADRA2A |
| epinephrine | anestethic | ADRA2B |
| epinephrine | anestethic | ADRB1 |
| epinephrine | anestethic | ADRB2 |
| lidocaine | anestethic | SCN10A |
| lidocaine | anestethic | SCN5A |
| lidocaine | anestethic | SCN9A |
| oxybutynin | for treatment of incontinence | CHRM1 |
| oxybutynin | for treatment of incontinence | CHRM2 |
| oxybutynin | for treatment of incontinence | CHRM3 |
| oxycodone | analgesic | OPRD1 |
| oxycodone | analgesic | OPRK1 |
| oxycodone | analgesic | OPRM1 |
| fentanyl | analgesic | OPRD1 |
| fentanyl | analgesic | OPRM1 |
| timolol | for treatment of glaucoma | ADRB1 |
| timolol | for treatment of glaucoma | ADRB2 |
| travoprost | for treatment of glaucoma | PTGFR |
| trazodone | antidepressant | HTR1A |
| trazodone | antidepressant | HTR2A |
| trazodone | antidepressant | HTR2C |
| trazodone | antidepressant | SLC6A4 |
| trelanserin | for treatment of intermittent claudication | HTR1B |
| trelanserin | for treatment of intermittent claudication | HTR2A |
| tretinoin | for treatment of acne | RARG |
| tretinoin | for treatment of acne | RXRB |
| tretinoin | for treatment of acne | RXRG |
| triamcinolone | for treatment of diabetic macular edema | NR3C1 |
| Triapine | antineoplastic agent | RRM2 |
| amlodipine | antihypertensive agent | CACNA1C |
| amlodipine | antihypertensive agent | CACNA1D |
| amlodipine | antihypertensive agent | CACNA1S |
| amlodipine | antihypertensive agent | CACNA2D1 |
| amlodipine | antihypertensive agent | CACNB2 |
| hydrochlorothiazide | antihypertensive agent | SLC12A3 |
| olmesartan | antihypertensive agent | AGTR1 |
| triciribine | antineoplastic agent | AKT1 |
| triciribine | antineoplastic agent | AKT2 |
| triciribine | antineoplastic agent | AKT3 |
| HE3286 | antiinflammatory agent, DMARD | NR3C1 |
| trodusquemine | antiobesity agent | PTPN1 |
| trospium | for treatment of incontinence | CHRM1 |
| TTP889 | anticoagulant | F9 |
| lapatinib | antineoplastic agent | EGFR |
| lapatinib | antineoplastic agent | ERBB2 |
| TZP-101 | for treatment of gastroparesis | GHSR |
| TZP-102 | for treatment of gastroparesis | GHSR |
| heparin | for treatment of pelvic pain of bladder origin and interstitital cystitis | F10 |
| heparin | for treatment of pelvic pain of bladder origin and interstitital cystitis | SERPINC1 |
| lidocaine | for treatment of pelvic pain of bladder origin and interstitital cystitis | SCN10A |
| lidocaine | for treatment of pelvic pain of bladder origin and interstitital cystitis | SCN5A |
| lidocaine | for treatment of pelvic pain of bladder origin and interstitital cystitis | SCN9A |
| udenafil | for treatment of erectile dysfunction | PDE5A |
| tegafur | antineoplastic agent | TYMS |
| Ulipristal | contraceptive | PGR |
| heparin | antithrombotic | F10 |

TABLE 2-continued

Exemplary Drugs with Disease Indications and Gene Identifier for the Target Protein

| Drug Name | Indication(s) | Gene |
|---|---|---|
| heparin | antithrombotic | SERPINC1 |
| ursodeoxycholic acid | for prevention of recurrence of colorectal polyps | AKR1C2 |
| topiramate | anticonvulsant | CA2 |
| topiramate | anticonvulsant | CA4 |
| topiramate | anticonvulsant | GABRA1 |
| topiramate | anticonvulsant | GRIK1 |
| topiramate | anticonvulsant | SCN1A |
| buprenorphine | antidepressant, analgesic, for treatment of opioid addiction | OPRD1 |
| buprenorphine | antidepressant, analgesic, for treatment of opioid addiction | OPRK1 |
| buprenorphine | antidepressant, analgesic, for treatment of opioid addiction | OPRM1 |
| carbidopa | antiparkinson agent | DDC |
| melevodopa | antiparkinson agent | DRD1 |
| melevodopa | antiparkinson agent | DRD2 |
| melevodopa | antiparkinson agent | DRD3 |
| melevodopa | antiparkinson agent | DRD4 |
| melevodopa | antiparkinson agent | DRD5 |
| V158866 | analgesic | FAAH |
| V24343 | antiobesity agent | CNR1 |
| V3381 | analgesic, neuropathic pain | GRIN1 |
| V3381 | analgesic, neuropathic pain | GRIN2A |
| V3381 | analgesic, neuropathic pain | GRIN2B |
| V3381 | analgesic, neuropathic pain | GRIN2C |
| V3381 | analgesic, neuropathic pain | GRIN2D |
| V3381 | analgesic, neuropathic pain | GRIN3A |
| V3381 | analgesic, neuropathic pain | GRIN3B |
| V3381 | analgesic, neuropathic pain | MAOA |
| V3381 | analgesic, neuropathic pain | MAOB |
| VA106483 | for treatment of BPH-related urinary symptoms | AVPR2 |
| VA111913 | for treatment of dysmenorrhea | AVPR1A |
| VA111913 | for treatment of dysmenorrhea | AVPR1B |
| VA111913 | for treatment of dysmenorrhea | AVPR2 |
| Vadimezan | antineoplastic agent | HIPK2 |
| Vadimezan | antineoplastic agent | KDR |
| Vadimezan | antineoplastic agent | PIM3 |
| valproic acid | anticonvulsant | ABAT |
| valproic acid | anticonvulsant | ACADSB |
| valproic acid | anticonvulsant | HDAC9 |
| valproic acid | for treatment of basal cell carcinoma | ABAT |
| valproic acid | for treatment of basal cell carcinoma | ACADSB |
| valproic acid | for treatment of basal cell carcinoma | HDAC9 |
| valsartan | antihypertensive agent | AGTR1 |
| vapitadine | antiallergy agent | HRH1 |
| vapreotide | for treatment of liver cirrhosis-related variceal bleeding | SSTR2 |
| vapreotide | for treatment of liver cirrhosis-related variceal bleeding | SSTR5 |
| vardenafil | for treatment of erectile dysfunction | PDE5A |
| varenicline | smoking-cessation agent | CHRNA3 |
| varenicline | smoking-cessation agent | CHRNA4 |
| varenicline | smoking-cessation agent | CHRNA7 |
| varenicline | smoking-cessation agent | CHRNB2 |
| varenicline | smoking-cessation agent | CHRNB4 |
| varespladib | antiinflammatory agent | PLA2G10 |
| varespladib | antiinflammatory agent | PLA2G2A |
| varespladib | antiinflammatory agent | PLA2G5 |
| varespladib | antiinflammatory agent | PLA2G10 |
| varespladib | antiinflammatory agent | PLA2G2A |
| varespladib | antiinflammatory agent | PLA2G5 |
| ethinyl estradiol | contraceptive | ESR1 |
| norethindrone | contraceptive | PGR |
| Vatalanib | antineoplastic agent | FLT1 |
| Vatalanib | antineoplastic agent | FLT4 |
| Vatalanib | antineoplastic agent | KDR |
| Vatalanib | antineoplastic agent | KIT |
| Vatalanib | antineoplastic agent | PDGFRA |
| Vatalanib | antineoplastic agent | PDGFRB |
| Vatalanib | antineoplastic agent | FLT1 |
| Vatalanib | antineoplastic agent | FLT4 |
| Vatalanib | antineoplastic agent | KDR |
| Vatalanib | antineoplastic agent | KIT |
| Vatalanib | antineoplastic agent | PDGFRA |

TABLE 2-continued

Exemplary Drugs with Disease Indications and Gene Identifier for the Target Protein

| Drug Name | Indication(s) | Gene |
|---|---|---|
| Vatalanib | antineoplastic agent | PDGFRB |
| VEL-0230 | antirheumatic agent | CTSK |
| bortezomib | antineoplastic agent | PSMB1 |
| bortezomib | antineoplastic agent | PSMB2 |
| bortezomib | antineoplastic agent | PSMB5 |
| bortezomib | antineoplastic agent | PSMD1 |
| bortezomib | antineoplastic agent | PSMD2 |
| bupropion | antidepressant, appetite suppressant, smoking-cessation agent | SLC6A2 |
| bupropion | antidepressant, appetite suppressant, smoking-cessation agent | SLC6A3 |
| velneperit | antiobesity agent | NPY5R |
| velusetrag | motilitant | HTR4 |
| fluticasone furoate | antiinflammatory agent, glucocorticoid | NR3C1 |
| verapamil | antihypertensive agent | CACNA1C |
| verapamil | antihypertensive agent | CACNA1D |
| verapamil | antihypertensive agent | CACNA1F |
| verapamil | antihypertensive agent | CACNA1S |
| verapamil | antihypertensive agent | CACNB1 |
| verapamil | antihypertensive agent | CACNB2 |
| verapamil | antihypertensive agent | CACNB3 |
| verapamil | antihypertensive agent | CACNB4 |
| vestipitant | for treatment of tinnitus,hypnotic | TACR1 |
| VGX-1027 | antiinflammatory agent, DMARD | unknown |
| VIA-2291 | antiatherosclerotic agent | ALOX5 |
| VIA-3196 | antidyslipidaemic agent | THRB |
| Calcitonin | antiosteoporotic agent | CALCR |
| methotrexate | DMARD | DHFR |
| vicriviroc | antiviral agent, HIV | CCR5 |
| vidofludimus | antiinflammatory agent, DMARD | DHODH |
| vidofludimus | antiinflammatory agent, DMARD | IL17A |
| vidofludimus | antiinflammatory agent, DMARD | IL17B |
| vidofludimus | antiinflammatory agent, DMARD | IL17C |
| vidofludimus | antiinflammatory agent, DMARD | IL17D |
| vidofludimus | antiinflammatory agent, DMARD | IL17E |
| Vigabatrin | for treatment of addiction | ABAT |
| Vigabatrin | for treatment of addiction | GABBR1 |
| vilazodone | antidepressant | HTR1A |
| vildagliptin | antidiabetic | DPP4 |
| vincristine | antineoplastic agent | TUBA4A |
| vincristine | antineoplastic agent | TUBB |
| vinorelbine | antineoplastic agent | TUBB |
| BIIB014 | antiparkinson agent | ADORA2A |
| Virulizin | antineoplastic agent | IL12A |
| Virulizin | antineoplastic agent | IL12B |
| naltrexone | for treatment of substance abuse | OPRD1 |
| naltrexone | for treatment of substance abuse | OPRK1 |
| naltrexone | for treatment of substance abuse | OPRM1 |
| Voclosporin | antiinflammatory agent, DMARD, immunosuppressant | PPIA |
| Voclosporin | antiinflammatory agent, DMARD, immunosuppressant | PPP3CA |
| Voclosporin | antiinflammatory agent, DMARD, immunosuppressant | PPP3CB |
| Voclosporin | antiinflammatory agent, DMARD, immunosuppressant | PPP3CC |
| vofopitant | for treatment of post-traumatic stress disorder, hypnotic | TACR1 |
| voglibose | antidiabetic | MGAM |
| volinanserin | hypnotic | HTR2A |
| vorapaxar | cardiovascular agent | F2R |
| vorapaxar | cardiovascular agent | F2RL2 |
| vorapaxar | cardiovascular agent | F2RL3 |
| Voreloxin | antineoplastic agent | TOP2A |
| Voreloxin | antineoplastic agent | TOP2B |
| Histrelin | antineoplastic agent | GNRHR |
| Histrelin | antineoplastic agent | GNRHR2 |
| TRPVI antagonist | analgesic | TRPV1 |
| VR-147 | antimigraine agent | HTR1B |
| VR-147 | antimigraine agent | HTR1D |
| heparin | for treatment of cystic fibrosis | F10 |
| heparin | for treatment of cystic fibrosis | SERPINC1 |
| etodolac | for treatment of cancer cachexia | PTGS1 |

TABLE 2-continued

| Drug Name | Indication(s) | Gene |
|---|---|---|
| etodolac | NSAID | PTGS2 |
| propranolol | for treatment of cancer cachexia | ADRB1 |
| VTP-27999 | antihypertensive agent | REN |
| VTX-1463 | antiallergy agent | TLR8 |
| VTX-2337 | antineoplastic agent | TLR8 |
| VX-509 | antiinflammatory agent, DMARD | JAK3 |
| WX-554 | antineoplastic agent | MAP2K1 |
| WX-554 | antineoplastic agent | MAP2K2 |
| WX-554 | antineoplastic agent | MAP2K3 |
| WX-554 | antineoplastic agent | MAP2K4 |
| WX-554 | antineoplastic agent | MAP2K5 |
| WX-554 | antineoplastic agent | MAP2K6 |
| WX-554 | antineoplastic agent | MAP2K7 |
| tozasertib | antineoplastic agent | AURKA |
| tozasertib | antineoplastic agent | AURKB |
| tozasertib | antineoplastic agent | AURKC |
| VX-702 | antiinflammatory agent, cardiovascular agent | MAPK11 |
| VX-702 | antiinflammatory agent, cardiovascular agent | MAPK12 |
| VX-702 | antiinflammatory agent, cardiovascular agent | MAPK13 |
| VX-702 | antiinflammatory agent, cardiovascular agent | MAPK14 |
| VX-765 | antipsoriatic agent, anticonvulsant | CASP1 |
| ivacaftor | for treatment of cystic fibrosis | CFTR |
| VX-809 | for treatment of cystic fibrosis | CFTR |
| ivacaftor | for treatment of cystic fibrosis | CFTR |
| VX-809 | for treatment of cystic fibrosis | CFTR |
| WX-UK1 | antineoplastic agent | PLAU |
| emzetibe | antidyslipidaemic agent | NPC1L1 |
| emzetibe | antidyslipidaemic agent | SOAT1 |
| simvastatin | antidyslipidaemic agent | HMGCR |
| NRP104 | for treatment of ADHD | ADRA1B |
| NRP104 | for treatment of ADHD | SLC18A2 |
| NRP104 | for treatment of ADHD | SLC6A3 |
| xaliproden | neuroprotectant | HTR1A |
| XL019 | antineoplastic agent | JAK2 |
| cabozantinib | antineoplastic agent | KDR |
| cabozantinib | antineoplastic agent | MET |
| XL228 | antineoplastic agent | ABL1 |
| XL228 | antineoplastic agent | AURKA |
| XL228 | antineoplastic agent | IGF1R |
| XL228 | antineoplastic agent | SRC |
| XL281 | antineoplastic agent | ARAF |
| XL281 | antineoplastic agent | BRAF |
| XL281 | antineoplastic agent | RAF1 |
| XL418 | antineoplastic agent | AKT1 |
| XL418 | antineoplastic agent | AKT2 |
| XL418 | antineoplastic agent | AKT3 |
| XL418 | antineoplastic agent | RPS6KB1 |
| XL647 | antineoplastic agent | EGFR |
| XL647 | antineoplastic agent | EPHB4 |
| XL647 | antineoplastic agent | ERBB2 |
| XL647 | antineoplastic agent | FLT1 |
| XL647 | antineoplastic agent | FLT4 |
| XL647 | antineoplastic agent | KDR |
| XL765 | antineoplastic agent | MTOR |
| XL765 | antineoplastic agent | PIK3CA |
| XL765 | antineoplastic agent | PIK3CD |
| XL765 | antineoplastic agent | PIK3CG |
| XL820 | antineoplastic agent | FLT1 |
| XL820 | antineoplastic agent | FLT4 |
| XL820 | antineoplastic agent | KDR |
| XL820 | antineoplastic agent | KIT |
| XL820 | antineoplastic agent | PDGFRA |
| XL820 | antineoplastic agent | PDGFRB |
| XL844 | antineoplastic agent | CHEK1 |
| XL844 | antineoplastic agent | CHEK2 |
| XL880 | antineoplastic agent | KDR |
| XL880 | antineoplastic agent | MET |
| XL888 | antineoplastic agent | HSP90AA1 |
| XL888 | antineoplastic agent | HSP90AB1 |
| XL999 | antineoplastic agent | AXL |
| XL999 | antineoplastic agent | FGFR1 |
| XL999 | antineoplastic agent | FLT1 |

Exemplary Drugs with Disease Indications and Gene Identifier for the Target Protein TABLE 2-continued Exemplary Drugs with Disease Indications and Gene Identifier for the Target Protein

| Drug Name | Indication(s) | Gene |
|---|---|---|
| XL999 | antineoplastic agent | FLT3 |
| XL999 | antineoplastic agent | FLT4 |
| XL999 | antineoplastic agent | KDR |
| XL999 | antineoplastic agent | KIT |
| XL999 | antineoplastic agent | PDGFRB |
| camptothecin | antineoplastic agent | TOP1 |
| XMT-1107 | antineoplastic agent | METAP2 |
| tranexamic acid | for treatment of menorrhagia | PLG |
| XP13512 | for treatment of restless legs syndrome | CACNA1B |
| XP13512 | for treatment of restless legs syndrome | CACNA2D1 |
| XP13512 | for treatment of restless legs syndrome | CACNA2D2 |
| R-baclofen | for treatment of gastrointestinal reflux disease | GABBR1 |
| R-baclofen | for treatment of gastrointestinal reflux disease | GABBR2 |
| XP21279 | antiparkinson agent | DRD1 |
| XP21279 | antiparkinson agent | DRD2 |
| XP21279 | antiparkinson agent | DRD3 |
| XP21279 | antiparkinson agent | DRD4 |
| XP21279 | antiparkinson agent | DRD5 |
| gantofiban | antithrombotic, antiatherosclerotic agent | ITGA2B |
| gantofiban | antithrombotic, antiatherosclerotic agent | ITGB3 |
| finasteride | antineoplastic agent | AKR1D1 |
| finasteride | antineoplastic agent | SRD5A1 |
| finasteride | antineoplastic agent | SRD5A2 |
| YM-178 | for treatment of overactive bladder | ADRB3 |
| YM-598 | antineoplastic agent | EDNRA |
| vandetanib | antineoplastic agent | EGFR |
| vandetanib | antineoplastic agent | FLT1 |
| vandetanib | antineoplastic agent | FLT4 |
| vandetanib | antineoplastic agent | KDR |
| vandetanib | antineoplastic agent | RET |
| zafirlukast | antiasthmatic agent | CYSLTR1 |
| zaleplon | hypnotic | GABRA1 |
| zaleplon | hypnotic | TSPO |
| ranitidine | antiulcer agent | HRH2 |
| beloranib | antiobesity agent | METAP2 |
| zibotentan | antineoplastic agent | EDNRA |
| ziconotide | analgesic | CACNA1B |
| ziprasidone | antipsychotic agent | DRD2 |
| ziprasidone | antipsychotic agent | HTR2A |
| ondansetron | antiemetic | HTR3A |
| zoledronate | antiosteoporotic agent | FDPS |
| zoledronate | antiosteoporotic agent | GGPS1 |
| zolmitriptan | antimigraine agent | HTR1A |
| zolmitriptan | antimigraine agent | HTR1B |
| zolmitriptan | antimigraine agent | HTR1D |
| zolmitriptan | antimigraine agent | HTR1F |
| sertraline | antidepressant, for treatment of obsessive compulsive disorder (OCD) | SLC6A3 |
| sertraline | antidepressant, for treatment of obsessive compulsive disorder (OCD) | SLC6A4 |
| zolpidem | hypnotic | GABRA1 |
| zonisamide | anticonvulsant | CACNA1G |
| zonisamide | anticonvulsant | CACNA1H |
| zonisamide | anticonvulsant | CACNA1I |
| zonisamide | anticonvulsant | SCN11A |
| zonisamide | anticonvulsant | SCN1A |
| zonisamide | anticonvulsant | SCN1B |
| zonisamide | anticonvulsant | SCN2A |
| zonisamide | anticonvulsant | SCN2B |
| zonisamide | anticonvulsant | SCN3A |
| zonisamide | anticonvulsant | SCN3B |
| zonisamide | anticonvulsant | SCN4A |
| zonisamide | anticonvulsant | SCN4B |
| zonisamide | anticonvulsant | SCN5A |
| zonisamide | anticonvulsant | SCN9A |
| zosuquidar | adjuvant to chemotherapy | ABCB1 |
| zucapsaicin | analgesic | TRPV1 |

TABLE 2-continued

| Exemplary Drugs with Disease Indications and Gene Identifier for the Target Protein | | |
|---|---|---|
| Drug Name | Indication(s) | Gene |
| hydrocodone | analgesic | OPRD1 |
| hydrocodone | analgesic | OPRM1 |
| zileuton | antiinflammatory agent | ALOX5 |
| ASP015K | for treatment of rheumatoid arthritis | JAK1 |
| ASP015K | for treatment of rheumatoid arthritis | JAK3 |
| CHF 6001 | antiasthmatic; for treatment of chronic obstructive pulmonary disease | PDE4A |
| CHF 6001 | antiasthmatic; for treatment of chronic obstructive pulmonary disease | PDE4B |
| CUDC-427 | antineoplastic agent | XIAP |
| ARQ 087 | antineoplastic agent | FGFR1 |
| ARQ 087 | antineoplastic agent | FGFR2 |
| ARQ 087 | antineoplastic agent | FGFR3 |
| deuterated dextromethorphan | for treatment of neurologic and psychiatric disorders | GRIN3A |
| deuterated dextromethorphan | for treatment of neurologic and psychiatric disorders | OPRS1 |
| olanzapine | antipsychotic agent | ADRA1A |
| olanzapine | antipsychotic agent | ADRA1B |
| olanzapine | antipsychotic agent | ADRA2A |
| olanzapine | antipsychotic agent | ADRA2B |
| olanzapine | antipsychotic agent | ADRA2C |
| olanzapine | antipsychotic agent | CHRM1 |
| olanzapine | antipsychotic agent | CHRM2 |
| olanzapine | antipsychotic agent | CHRM3 |
| olanzapine | antipsychotic agent | CHRM4 |
| olanzapine | antipsychotic agent | CHRM5 |
| olanzapine | antipsychotic agent | DRD1 |
| olanzapine | antipsychotic agent | DRD2 |
| olanzapine | antipsychotic agent | DRD3 |
| olanzapine | antipsychotic agent | DRD4 |
| olanzapine | antipsychotic agent | DRD5 |
| olanzapine | antipsychotic agent | HRH1 |
| olanzapine | antipsychotic agent | HTR1A |
| olanzapine | antipsychotic agent | HTR1B |
| olanzapine | antipsychotic agent | HTR1D |
| olanzapine | antipsychotic agent | HTR1E |
| olanzapine | antipsychotic agent | HTR2A |
| olanzapine | antipsychotic agent | HTR2C |
| olanzapine | antipsychotic agent | HTR3A |
| olanzapine | antipsychotic agent | HTR6 |
| olanzapine | antipsychotic agent | HTR7 |
| samidoprhan | for treatment of addiction | MOR |
| Ethyl eicosapentaenoic acid | for treatment of cardiovascular disorders | PPARD |
| Ethyl eicosapentaenoic acid | for treatment of cardiovascular disorders | PPARG |
| Ethyl eicosapentaenoic acid | for treatment of cardiovascular disorders | PTGS1 |
| Ethyl eicosapentaenoic acid | for treatment of cardiovascular disorders | PTGS2 |
| BCX4161 | for treatment of hereditary angioedema | KLKB1 |
| ACEBUTOLOL | Antihypertensive Agents | ADRB1 |
| ACENOCOUMAROL | Anticoagulants | VKORC1 |
| ACEPROMETAZINE | Hypnotics and Sedatives | HRH1 |
| ACETAZOLAMIDE | Anticonvulsants; Diuretics; antiglaucomic agent | CA1 |
| ACETAZOLAMIDE | Anticonvulsants; Diuretics; antiglaucomic agent | CA12 |
| ACETAZOLAMIDE | Anticonvulsants; Diuretics; antiglaucomic agent | CA2 |
| ACETOHEXAMIDE | Hypoglycemic Agents | KCNJ1 |
| ACETOPHENAZINE | Antipsychotic Agents | DRD1 |
| ACETOPHENAZINE | Antipsychotic Agents | DRD2 |
| ACETYLDIGITOXIN | Anti-Arrhythmia Agents | ATP1A1 |
| ACITRETIN | Keratolytic Agents | RARA |
| ADAPALENE | Dermatologic Agents | RARA |
| ADAPALENE | Dermatologic Agents | RARB |
| ADAPALENE | Dermatologic Agents | RARG |
| ADAPALENE | Dermatologic Agents | RXRA |
| ADAPALENE | Dermatologic Agents | RXRB |
| ADAPALENE | Dermatologic Agents | RXRG |
| ADINAZOLAM | Anti-anxiety Agents; anticonvulsant | GABRA1 |

TABLE 2-continued

| Drug Name | Indication(s) | Gene |
|---|---|---|
| ADINAZOLAM | Anti-anxiety Agents; anticonvulsant | GABRA2 |
| ADINAZOLAM | Anti-anxiety Agents; anticonvulsant | GABRA3 |
| ADINAZOLAM | Anti-anxiety Agents; anticonvulsant | GABRA5 |
| ADINAZOLAM | Anti-anxiety Agents; anticonvulsant | GABRB1 |
| ADINAZOLAM | Anti-anxiety Agents; anticonvulsant | GABRB2 |
| ADINAZOLAM | Anti-anxiety Agents; anticonvulsant | GABRB3 |
| ADINAZOLAM | Anti-anxiety Agents; anticonvulsant | GABRD |
| ADINAZOLAM | Anti-anxiety Agents; anticonvulsant | GABRE |
| ADINAZOLAM | Anti-anxiety Agents; anticonvulsant | GABRG1 |
| ADINAZOLAM | Anti-anxiety Agents; anticonvulsant | GABRG2 |
| ADINAZOLAM | Anti-anxiety Agents; anticonvulsant | GABRG3 |
| ADINAZOLAM | Anti-anxiety Agents; anticonvulsant | GABRP |
| ADINAZOLAM | Anti-anxiety Agents; anticonvulsant | GABRR1 |
| ADINAZOLAM | Anti-anxiety Agents; anticonvulsant | GABRR2 |
| ADINAZOLAM | Anti-anxiety Agents; anticonvulsant | GABRR3 |
| ALCAFTADINE | Anti-Allergic Agents | HRH1 |
| ALCLOMETASONE | Anti-Inflammatory Agents; Anti-pruritics; Corticosteroids, topical | NR3C1 |
| ALENDRONATE | Bisphosphonates | FDPS |
| ALFENTANIL | Analgesics, Opioid | OPRM1 |
| Alitretionine | Antineoplastic Agents | RARA |
| Alitretionine | Antineoplastic Agents | RARB |
| Alitretionine | Antineoplastic Agents | RARG |
| Alitretionine | Antineoplastic Agents | RXRA |
| Alitretionine | Antineoplastic Agents | RXRB |
| Alitretionine | Antineoplastic Agents | RXRG |
| ALMITRINE | Respiratory Stimulant Agents | ATP1A1 |
| ALPRENOLOL | Anti-Arrhythmia Agents; Antihypertensive Agents | ADRB1 |
| ALPRENOLOL | Anti-Arrhythmia Agents; Antihypertensive Agents | ADRB2 |
| ALSEROXYLON | Antipsychotic Agents; Antihypertensive Agents | SLC18A2 |
| ALVIMOPAN | Opiate Antagonists | OPRM1 |
| AMBENONIUM | Antimyasthenics | ACHE |
| AMCINONIDE | Anti-Inflammatory Agents; Anti-pruritics; Corticosteroids, topical | NR3C1 |
| AMINOCAPROIC ACID | Antifibrinolytic Agents | PLG |
| AMINOGLUTETHIMIDE | Antineoplastic agents | CYP19A1 |
| AMRINONE | Cardiotonic Agents; Phosphodiesterase Inhibitors | PDE3A |
| AMRINONE | Cardiotonic Agents; Phosphodiesterase Inhibitors | PDE4B |
| ANILERIDINE | Analgesics; Narcotics | OPRM1 |
| ANISINDIONE | Anticoagulants | GGCX |
| ANISOTROPINE METHYLBROMIDE | Antispasmodics; Anti-ulcer Agents | CHRM1 |
| ANISOTROPINE METHYLBROMIDE | Antispasmodics; Anti-ulcer Agents | CHRM2 |
| ANISOTROPINE METHYLBROMIDE | Antispasmodics; Anti-ulcer Agents | CHRM3 |
| APRACLONIDINE | Antiglaucomic Agents | ADRA2A |
| APRINDINE | Anti-Arrhythmia Agents | SCN5A |
| ARBUTAMINE | Cardiotonic Agents | ADRB1 |
| ARDEPARIN | Anticoagulants | SERPINC1 |
| ARDEPARIN | Anticoagulants | SERPIND1 |
| ARFORMOTEROL | Bronchodilator Agents | ADRB2 |
| ASTEMIZOLE | Anti-Allergic Agents | HRH1 |
| ATENOLOL | Anti-Arrhythmia Agents; Antihypertensive Agents | ADRB1 |
| ATRACURIUM | Muscle Relaxants | CHRNA2 |
| AURANOFIN | Antirheumatic Agents | IKBKB |
| AZATADINE | Anti-Allergic Agents | HRH1 |
| BENDRO-FLUMETHIAZIDE | Antihypertensive Agents; Diuretics | SLC12A3 |
| BENTIROMIDE | Diagnostic Agents | HPN |
| BENTIROMIDE | Diagnostic Agents | HPN |
| BENZOCAINE | Anesthetics, Local | SCN10A |
| BENZONATATE | Antitussive Agents | SCN5A |
| BENZPHETAMINE | Central Nervous System Stimulants | ADRA1A |
| BENZPHETAMINE | Central Nervous System Stimulants | ADRA2A |
| BENZQUINAMIDE | Antiemetics; Antipsychotic Agents | CHRM1 |
| BENZQUINAMIDE | Antiemetics; Antipsychotic Agents | CHRM2 |
| BENZQUINAMIDE | Antiemetics; Antipsychotic Agents | CHRM3 |
| BENZQUINAMIDE | Antiemetics; Antipsychotic Agents | CHRM4 |
| BENZQUINAMIDE | Antiemetics; Antipsychotic Agents | CHRM5 |

Exemplary Drugs with Disease Indications and Gene Identifier for the Target Protein TABLE 2-continued

| Exemplary Drugs with Disease Indications and Gene Identifier for the Target Protein | | |
|---|---|---|
| Drug Name | Indication(s) | Gene |
| BENZQUINAMIDE | Antiemetics; Antipsychotic Agents | HRH1 |
| BENZTHIAZIDE | Antihypertensive Agents; Diuretics | SLC12A3 |
| BENZTROPINE | Antiparkinson Agents | CHRM1 |
| BENZTROPINE | Antiparkinson Agents | SLC6A3 |
| BENZYLPENICILLOYL POLYLYSINE | Diagnostic Agents | FCER1A |
| BENZYLPENICILLOYL POLYLYSINE | Diagnostic Agents | FCER1G |
| BEPRIDIL | Anti-Arrhythmia Agents; Antihypertensive Agents | ATP1A1 |
| BEPRIDIL | Anti-Arrhythmia Agents; Antihypertensive Agents | CACNA1A |
| BEPRIDIL | Anti-Arrhythmia Agents; Antihypertensive Agents | KCNQ1 |
| BEPRIDIL | Anti-Arrhythmia Agents; Antihypertensive Agents | SCN5A |
| BEPRIDIL | Anti-Arrhythmia Agents; Antihypertensive Agents | TNNC1 |
| BETAXOLOL | Antihypertensive Agents | ADRB1 |
| BETAZOLE | Diagnostic Agents | HRH2 |
| BETHANECHOL | Parasympathomimetics | CHRM1 |
| BETHANIDINE | Antihypertensive Agents | ADRA1A |
| BETHANIDINE | Antihypertensive Agents | ADRA1B |
| BETHANIDINE | Antihypertensive Agents | ADRA1D |
| BETHANIDINE | Antihypertensive Agents | ADRA2A |
| BETHANIDINE | Antihypertensive Agents | ADRA2B |
| BETHANIDINE | Antihypertensive Agents | ADRA2C |
| BETHANIDINE | Antihypertensive Agents | SLC6A2 |
| BEVANTOLOL | Antihypertensive Agents | ADRB1 |
| BIPERIDEN | Antidyskinetics | CHRM1 |
| BIPERIDEN | Antidyskinetics | CHRNA2 |
| BISOPROLOL | Antihypertensive Agents | ADRB1 |
| BRINZOLAMIDE | Antiglaucomic Agents | CA2 |
| BROMAZEPAM | Hypnotics and Sedatives | GABRA1 |
| BROMAZEPAM | Hypnotics and Sedatives | GABRA2 |
| BROMAZEPAM | Hypnotics and Sedatives | GABRA3 |
| BROMAZEPAM | Hypnotics and Sedatives | GABRA4 |
| BROMAZEPAM | Hypnotics and Sedatives | GABRA5 |
| BROMAZEPAM | Hypnotics and Sedatives | GABRA6 |
| BROMAZEPAM | Hypnotics and Sedatives | GABRB1 |
| BROMAZEPAM | Hypnotics and Sedatives | GABRB2 |
| BROMAZEPAM | Hypnotics and Sedatives | GABRB3 |
| BROMAZEPAM | Hypnotics and Sedatives | GABRD |
| BROMAZEPAM | Hypnotics and Sedatives | GABRE |
| BROMAZEPAM | Hypnotics and Sedatives | GABRG1 |
| BROMAZEPAM | Hypnotics and Sedatives | GABRG2 |
| BROMAZEPAM | Hypnotics and Sedatives | GABRG3 |
| BROMAZEPAM | Hypnotics and Sedatives | GABRP |
| BROMAZEPAM | Hypnotics and Sedatives | GABRQ |
| BROMAZEPAM | Hypnotics and Sedatives | GABRR1 |
| BROMAZEPAM | Hypnotics and Sedatives | GABRR2 |
| BROMAZEPAM | Hypnotics and Sedatives | GABRR3 |
| BROMODIPHENHYDRAMINE | Anti-Allergic Agents | HRH1 |
| BROMPHENIRAMINE | Anti-Allergic Agents | HRH1 |
| BUCLIZINE | Antiemetics | CHRM1 |
| BUCLIZINE | Antiemetics | HRH1 |
| BUMETANIDE | Antihypertensive Agents; Diuretics | SLC12A1 |
| BUMETANIDE | Antihypertensive Agents; Diuretics | SLC12A2 |
| BUMETANIDE | Antihypertensive Agents; Diuretics | SLC12A4 |
| BUMETANIDE | Antihypertensive Agents; Diuretics | SLC12A5 |
| BUSPIRONE | Anti-anxiety Agents | DRD2 |
| BUSPIRONE | Anti-anxiety Agents | HTR1A |
| BUTABARBITAL | Hypnotics and Sedatives | CHRNA4 |
| BUTABARBITAL | Hypnotics and Sedatives | CHRNA7 |
| BUTABARBITAL | Hypnotics and Sedatives | GABRA1 |
| BUTABARBITAL | Hypnotics and Sedatives | GABRA2 |
| BUTABARBITAL | Hypnotics and Sedatives | GABRA3 |
| BUTABARBITAL | Hypnotics and Sedatives | GABRA4 |
| BUTABARBITAL | Hypnotics and Sedatives | GABRA5 |
| BUTABARBITAL | Hypnotics and Sedatives | GABRA6 |
| BUTABARBITAL | Hypnotics and Sedatives | GRIA2 |
| BUTABARBITAL | Hypnotics and Sedatives | GRIK2 |
| BUTALBITAL | Analgesics | CHRNA4 |
| BUTALBITAL | Analgesics | CHRNA7 |
| BUTALBITAL | Analgesics | GABRA1 |
| BUTALBITAL | Analgesics | GABRA2 |

TABLE 2-continued

Exemplary Drugs with Disease Indications and Gene Identifier for the Target Protein

| Drug Name | Indication(s) | Gene |
|---|---|---|
| BUTALBITAL | Analgesics | GABRA3 |
| BUTALBITAL | Analgesics | GABRA4 |
| BUTALBITAL | Analgesics | GABRA5 |
| BUTALBITAL | Analgesics | GABRA6 |
| BUTALBITAL | Analgesics | GRIA2 |
| BUTALBITAL | Analgesics | GRIK2 |
| BUTETHAL | Hypnotics and Sedatives | CHRNA4 |
| BUTETHAL | Hypnotics and Sedatives | CHRNA7 |
| BUTETHAL | Hypnotics and Sedatives | GABRA1 |
| BUTETHAL | Hypnotics and Sedatives | GABRA2 |
| BUTETHAL | Hypnotics and Sedatives | GABRA3 |
| BUTETHAL | Hypnotics and Sedatives | GABRA4 |
| BUTETHAL | Hypnotics and Sedatives | GABRA5 |
| BUTETHAL | Hypnotics and Sedatives | GABRA6 |
| BUTETHAL | Hypnotics and Sedatives | GRIA2 |
| BUTETHAL | Hypnotics and Sedatives | GRIK2 |
| BUTORPHANOL | Analgesics, Opioid | OPRD1 |
| BUTORPHANOL | Analgesics, Opioid | OPRK1 |
| BUTORPHANOL | Analgesics, Opioid | OPRM1 |
| CABERGOLINE | Antiparkinson Agents | DRD2 |
| CAFFEINE | Central Nervous System Stimulants | ADORA1 |
| CAFFEINE | Central Nervous System Stimulants | ADORA2A |
| CAFFEINE | Central Nervous System Stimulants | PDE4B |
| CALCIPOTRIOL | Dermatologic Agents | VDR |
| CANDOXATRIL | Antihypertensive Agents | ACE |
| CANDOXATRIL | Antihypertensive Agents | MME |
| CAPTOPRIL | Antihypertensive Agents | ACE |
| CARBACHOL | Antiglaucomic Agents | CHRM1 |
| CARBACHOL | Antiglaucomic Agents | CHRM2 |
| CARBACHOL | Antiglaucomic Agents | CHRNA2 |
| CARBETOCIN | Labor Inducing Agents | OXTR |
| CARBIMAZOLE | Antithyroid Agents | TPO |
| CARBINOXAMINE | Anti-Allergic Agents | CHRM1 |
| CARBINOXAMINE | Anti-Allergic Agents | HRH1 |
| CARBOPROST TROMETHAMINE | Abortifacient Agents | PTGER1 |
| CARPHENAZINE | Antipsychotic Agents | DRD1 |
| CARPHENAZINE | Antipsychotic Agents | DRD2 |
| CARPHENAZINE | Antipsychotic Agents | DRD5 |
| CARPROFEN | Anti-Inflammatory Agents, Non-Steroidal | PTGS2 |
| CARTEOLOL | Antiglaucomic Agents | ADRB1 |
| CARTEOLOL | Antiglaucomic Agents | ADRB2 |
| CERULETIDE | Diagnostic Agents | CCKAR |
| CEVIMELINE | Parasympathomimetics | CHRM1 |
| CEVIMELINE | Parasympathomimetics | CHRM3 |
| CHLOPHEDIANOL | Antitussive Agents | HRH1 |
| CHLORDIAZEPOXIDE | Hypnotics and Sedatives | GABRA1 |
| CHLORDIAZEPOXIDE | Hypnotics and Sedatives | GABRA2 |
| CHLORDIAZEPOXIDE | Hypnotics and Sedatives | GABRA3 |
| CHLORDIAZEPOXIDE | Hypnotics and Sedatives | GABRA4 |
| CHLORDIAZEPOXIDE | Hypnotics and Sedatives | GABRA5 |
| CHLORDIAZEPOXIDE | Hypnotics and Sedatives | GABRA6 |
| CHLORDIAZEPOXIDE | Hypnotics and Sedatives | GABRB1 |
| CHLORDIAZEPOXIDE | Hypnotics and Sedatives | GABRB2 |
| CHLORDIAZEPOXIDE | Hypnotics and Sedatives | GABRB3 |
| CHLORDIAZEPOXIDE | Hypnotics and Sedatives | GABRD |
| CHLORDIAZEPOXIDE | Hypnotics and Sedatives | GABRE |
| CHLORDIAZEPOXIDE | Hypnotics and Sedatives | GABRG1 |
| CHLORDIAZEPOXIDE | Hypnotics and Sedatives | GABRG2 |
| CHLORDIAZEPOXIDE | Hypnotics and Sedatives | GABRG3 |
| CHLORDIAZEPOXIDE | Hypnotics and Sedatives | GABRP |
| CHLORDIAZEPOXIDE | Hypnotics and Sedatives | GABRQ |
| CHLORDIAZEPOXIDE | Hypnotics and Sedatives | GABRR1 |
| CHLORDIAZEPOXIDE | Hypnotics and Sedatives | GABRR2 |
| CHLORDIAZEPOXIDE | Hypnotics and Sedatives | GABRR3 |
| CHLORMERODRIN | Antihypertensive Agents; Diuretics | SLC12A1 |
| CHLORMEZANONE | Anti-anxiety Agents; Muscle Relaxants | BZRP |
| CHLOROPROCAINE | Anesthetics, Local | SCN10A |
| CHLOROTHIAZIDE | Antihypertensive Agents; Diuretics | CA1 |
| CHLOROTHIAZIDE | Antihypertensive Agents; Diuretics | CA2 |
| CHLOROTHIAZIDE | Antihypertensive Agents; Diuretics | CA4 |
| CHLOROTHIAZIDE | Antihypertensive Agents; Diuretics | SLC12A3 |
| CHLOROTRIANISENE | Hormone Replacement Agents | ESR1 |
| CHLORPHENIRAMINE | Anti-Allergic Agents | HRH1 |

TABLE 2-continued

Exemplary Drugs with Disease Indications and Gene Identifier for the Target Protein

| Drug Name | Indication(s) | Gene |
|---|---|---|
| CHLORPROPAMIDE | Hypoglycemic Agents | KCNJ1 |
| CHLORPROTHIXENE | Antipsychotic Agents | DRD1 |
| CHLORPROTHIXENE | Antipsychotic Agents | DRD2 |
| CHLORPROTHIXENE | Antipsychotic Agents | DRD3 |
| CHLORPROTHIXENE | Antipsychotic Agents | HRH1 |
| CHLORPROTHIXENE | Antipsychotic Agents | HTR2A |
| CHLORPROTHIXENE | Antipsychotic Agents | HTR2B |
| CHLORPROTHIXENE | Antipsychotic Agents | HTR2C |
| CHLORTHALIDONE | Antihypertensive Agents; Diuretics | SLC12A1 |
| CHLORZOXAZONE | Muscle Relaxants | KCNMA1 |
| CICLESONIDE | Anti-Inflammatory Agents; Anti-allergic agents; Glucocorticoids | NR3C1 |
| CILASTATIN | Adjuvants, enzyme inhibitors | DPEP1 |
| CILAZAPRIL | Antihypertensive Agents | ACE |
| CILOSTAZOL | Platelet Aggregation Inhibitors | PDE3A |
| CIMETIDINE | GI Anti-Ulcer Agents, antihistamines | HRH2 |
| CINACALCET | Calcimimetics | CASR |
| CINALUKAST | Anti-Asthmatic Agents | CYSLTR1 |
| CINNARIZINE | Anti-Allergic Agents | HRH1 |
| CINOLAZEPAM | Hypnotics and Sedatives | GABRA1 |
| CINOLAZEPAM | Hypnotics and Sedatives | GABRA2 |
| CINOLAZEPAM | Hypnotics and Sedatives | GABRA3 |
| CINOLAZEPAM | Hypnotics and Sedatives | GABRA5 |
| CINOLAZEPAM | Hypnotics and Sedatives | GABRB1 |
| CINOLAZEPAM | Hypnotics and Sedatives | GABRB2 |
| CINOLAZEPAM | Hypnotics and Sedatives | GABRB3 |
| CINOLAZEPAM | Hypnotics and Sedatives | GABRD |
| CINOLAZEPAM | Hypnotics and Sedatives | GABRE |
| CINOLAZEPAM | Hypnotics and Sedatives | GABRG1 |
| CINOLAZEPAM | Hypnotics and Sedatives | GABRG2 |
| CINOLAZEPAM | Hypnotics and Sedatives | GABRG3 |
| CINOLAZEPAM | Hypnotics and Sedatives | GABRP |
| CINOLAZEPAM | Hypnotics and Sedatives | GABRR1 |
| CINOLAZEPAM | Hypnotics and Sedatives | GABRR2 |
| CINOLAZEPAM | Hypnotics and Sedatives | GABRR3 |
| CISAPRIDE | Parasympathomimetics | HTR4 |
| CISATRACURIUM BESYLATE | Neuromuscular Blocking Agents | CHRNA2 |
| CITALOPRAM | Antidepressive Agents, Second-Generation | SLC6A4 |
| CLEMASTINE | Anti-Allergic Agents | HRH1 |
| CLENBUTEROL | Bronchodilator Agents | ADRB2 |
| CLIDINIUM | GI Anti-Ulcer Agents, anticholinergic; Antispasmodics | CHRM1 |
| CLOCORTOLONE | Anti-Inflammatory Agents; Anti-pruritics; Corticosteroids, topical | NR3C1 |
| CLOFIBRATE | Anticholesteremic Agents | PPARA |
| CLOMIPRAMINE | Antidepressive Agents, Tricyclic | SLC6A2 |
| CLOMIPRAMINE | Antidepressive Agents, Tricyclic | SLC6A4 |
| CLORAZEPATE | Hypnotics and Sedatives | BZRP |
| CLORAZEPATE | Hypnotics and Sedatives | GABRA1 |
| CLORAZEPATE | Hypnotics and Sedatives | GABRA2 |
| CLORAZEPATE | Hypnotics and Sedatives | GABRA3 |
| CLORAZEPATE | Hypnotics and Sedatives | GABRA4 |
| CLORAZEPATE | Hypnotics and Sedatives | GABRA5 |
| CLORAZEPATE | Hypnotics and Sedatives | GABRA6 |
| CLORAZEPATE | Hypnotics and Sedatives | GABRB1 |
| CLORAZEPATE | Hypnotics and Sedatives | GABRB2 |
| CLORAZEPATE | Hypnotics and Sedatives | GABRB3 |
| CLORAZEPATE | Hypnotics and Sedatives | GABRD |
| CLORAZEPATE | Hypnotics and Sedatives | GABRE |
| CLORAZEPATE | Hypnotics and Sedatives | GABRG1 |
| CLORAZEPATE | Hypnotics and Sedatives | GABRG2 |
| CLORAZEPATE | Hypnotics and Sedatives | GABRG3 |
| CLORAZEPATE | Hypnotics and Sedatives | GABRP |
| CLORAZEPATE | Hypnotics and Sedatives | GABRQ |
| CLORAZEPATE | Hypnotics and Sedatives | GABRR1 |
| CLORAZEPATE | Hypnotics and Sedatives | GABRR2 |
| CLORAZEPATE | Hypnotics and Sedatives | GABRR3 |
| CLOTIAZEPAM | Hypnotics and Sedatives | GABRA1 |
| CLOTIAZEPAM | Hypnotics and Sedatives | GABRA2 |
| CLOTIAZEPAM | Hypnotics and Sedatives | GABRA3 |
| CLOTIAZEPAM | Hypnotics and Sedatives | GABRA5 |
| CLOTIAZEPAM | Hypnotics and Sedatives | GABRB1 |
| CLOTIAZEPAM | Hypnotics and Sedatives | GABRB2 |

TABLE 2-continued

Exemplary Drugs with Disease Indications and Gene Identifier for the Target Protein

| Drug Name | Indication(s) | Gene |
|---|---|---|
| CLOTIAZEPAM | Hypnotics and Sedatives | GABRB3 |
| CLOTIAZEPAM | Hypnotics and Sedatives | GABRD |
| CLOTIAZEPAM | Hypnotics and Sedatives | GABRE |
| CLOTIAZEPAM | Hypnotics and Sedatives | GABRG1 |
| CLOTIAZEPAM | Hypnotics and Sedatives | GABRG2 |
| CLOTIAZEPAM | Hypnotics and Sedatives | GABRG3 |
| CLOTIAZEPAM | Hypnotics and Sedatives | GABRP |
| CLOTIAZEPAM | Hypnotics and Sedatives | GABRR1 |
| CLOTIAZEPAM | Hypnotics and Sedatives | GABRR2 |
| CLOTIAZEPAM | Hypnotics and Sedatives | GABRR3 |
| CLOZAPINE | Antipsychotic Agents | DRD1 |
| CLOZAPINE | Antipsychotic Agents | DRD2 |
| CLOZAPINE | Antipsychotic Agents | DRD4 |
| CLOZAPINE | Antipsychotic Agents | HRH1 |
| CLOZAPINE | Antipsychotic Agents | HRH4 |
| CLOZAPINE | Antipsychotic Agents | HTR1A |
| CLOZAPINE | Antipsychotic Agents | HTR2A |
| CLOZAPINE | Antipsychotic Agents | HTR2C |
| COCAINE | local anesthetic | DRD3 |
| COCAINE | local anesthetic | OPRK1 |
| COCAINE | local anesthetic | SCN10A |
| COCAINE | local anesthetic | SCN11A |
| COCAINE | local anesthetic | SCN5A |
| COCAINE | local anesthetic | SLC6A2 |
| COCAINE | local anesthetic | SLC6A3 |
| COCAINE | local anesthetic | SLC6A4 |
| CODEINE | Analgesics, Opioid; Antitussive Agents | OPRD1 |
| CODEINE | Analgesics, Opioid; Antitussive Agents | OPRK1 |
| CODEINE | Analgesics, Opioid; Antitussive Agents | OPRM1 |
| CONJUGATED ESTROGENS | Hormone Replacement Agents | ESR1 |
| CROMOGLICATE | Anti-Asthmatic Agents | KCNMA1 |
| CYCLIZINE | Antiemetics | HRH1 |
| CYCLOBENZAPRINE | Antidepressive Agents, Tricyclic | HTR2A |
| CYCLOPENTOLATE | Mydriatics | CHRM1 |
| CYCLOTHIAZIDE | Antihypertensive Agents; Diuretics | FXYD2 |
| CYCRIMINE | Antiparkinson Agents | CHRM1 |
| CYPROHEPTADINE | Anti-Allergic Agents; Appetite Stimulant | HRH1 |
| CYPROHEPTADINE | Anti-Allergic Agents; Appetite Stimulant | HTR2A |
| CYPROTERONE | Hypersexuality-inhibiting agents; Antihirsutism agents | AR |
| DACARBAZINE | Antineoplastic Agents | POLA2 |
| DALFAMPRIDINE | MS-treatment | KCNA1 |
| DANAZOL | Antiendometriosis Agent, Antineoplastic Agent | ESR1 |
| DANAZOL | Antiendometriosis Agent, Antineoplastic Agent | GNRHR |
| DANAZOL | Antiendometriosis Agent, Antineoplastic Agent | GNRHR2 |
| DANTROLENE | Muscle Relaxants | RYR1 |
| DAPIPRAZOLE | ophthalmological agent | ADRA1A |
| DAPIPRAZOLE | ophthalmological agent | ADRA1B |
| DAPIPRAZOLE | ophthalmological agent | ADRA1D |
| DEBRISOQUIN | Antihypertensive Agents | ADRA1A |
| DEBRISOQUIN | Antihypertensive Agents | ADRA1B |
| DEBRISOQUIN | Antihypertensive Agents | ADRA1D |
| DEBRISOQUIN | Antihypertensive Agents | ADRA2A |
| DEBRISOQUIN | Antihypertensive Agents | ADRA2B |
| DEBRISOQUIN | Antihypertensive Agents | ADRA2C |
| DECAMETHONIUM | Muscle Relaxants | CHRNA2 |
| DEMECARIUM BROMIDE | Antiglaucomic Agents | ACHE |
| DEMECARIUM BROMIDE | Antiglaucomic Agents | BCHE |
| DESERPIDINE | Antihypertensive Agents | ACE |
| DESFLURANE | inhalation anesthetics | ATP2C1 |
| DESFLURANE | inhalation anesthetics | ATP5D |
| DESFLURANE | inhalation anesthetics | GABRA1 |
| DESFLURANE | inhalation anesthetics | GLRA1 |
| DESFLURANE | inhalation anesthetics | GRIA1 |
| DESFLURANE | inhalation anesthetics | KCNA1 |
| DESFLURANE | inhalation anesthetics | MT-ND1 |

TABLE 2-continued

| Exemplary Drugs with Disease Indications and Gene Identifier for the Target Protein | | |
|---|---|---|
| Drug Name | Indication(s) | Gene |
| DESIPRAMINE | Antidepressive Agents, Tricyclic | ADRB1 |
| DESIPRAMINE | Antidepressive Agents, Tricyclic | ADRB2 |
| DESIPRAMINE | Antidepressive Agents, Tricyclic | CHRM1 |
| DESIPRAMINE | Antidepressive Agents, Tricyclic | CHRM2 |
| DESIPRAMINE | Antidepressive Agents, Tricyclic | HRH1 |
| DESIPRAMINE | Antidepressive Agents, Tricyclic | SLC6A2 |
| DESIPRAMINE | Antidepressive Agents, Tricyclic | SLC6A4 |
| DESLANOSIDE | Antiarrhythmia Agents; Cardiotonic Agents | ATP1A1 |
| DESOGESTREL | Contraceptives, Oral | ESR1 |
| DESOGESTREL | Contraceptives, Oral | PGR |
| DESOXIMETASONE | Anti-Inflammatory Agents; Glucocorticoids | NR3C1 |
| DESOXYCORTICOSTERONE PIVALATE | Hormone Replacement Agents, anti-addison agent | NR3C2 |
| DEXBROMPHENIRAMINE | Anti-Allergic Agents | HRH1 |
| DEXFENFLURAMINE | Appetite Depressants | SLC6A4 |
| DEXMEDETOMIDINE | Analgesics; Hypnotics and Sedatives | ADRA2A |
| DEXTROMETHORPHAN | Antitussive Agents | GRIN3A |
| DEXTROMETHORPHAN | Antitussive Agents | OPRS1 |
| DEZOCINE | Analgesics, Opioid | OPRK1 |
| DEZOCINE | Analgesics, Opioid | OPRM1 |
| DIAZOXIDE | Antihypertensive Agents; Vasodilator Agents | SLC12A3 |
| DIBUCAINE | Anesthetics, Local | SCN10A |
| DIBUCAINE | Anesthetics, Local | SCN5A |
| DICHLORPHENAMIDE | Antiglaucomic Agents | CA1 |
| DICUMAROL | Anticoagulants | VKORC1 |
| DICYCLOMINE | Antispasmodics | CHRM1 |
| DIENESTROL | Hormone Replacement Agents | ESR1 |
| DIETHYLPROPION | Appetite Depressants | SLC6A2 |
| DIETHYLPROPION | Appetite Depressants | SLC6A3 |
| DIETHYLSTILBESTROL | Hormone Replacement Agents | ESR1 |
| DIFLORASONE | Anti-Inflammatory Agents; Glucocorticoids | NR3C1 |
| DIGITOXIN | Anti-Arrhythmia Agents; Cardiotonic Agents | ATP1A1 |
| DIGOXIN | Anti-Arrhythmia Agents; Cardiotonic Agents | ATP1A1 |
| DIHYDROTACHYSTEROL | Anti-migraine Agents | VDR |
| DIMENHYDRINATE | Antiemetics | HRH1 |
| DINOPROST TROMETHAMINE | Abortifacient Agents | PTGIR |
| DINOPROSTONE | Abortifacient Agents | PTGER1 |
| DINOPROSTONE | Abortifacient Agents | PTGER2 |
| DINOPROSTONE | Abortifacient Agents | PTGER3 |
| DINOPROSTONE | Abortifacient Agents | PTGER4 |
| DIPHEMANIL METHYLSULFATE | Bronchodilator Agents | CHRM3 |
| DIPHENHYDRAMINE | Anti-Allergic Agents; Hypnotics and sedatives; Antiemetics; Antipruritics; Antitussives | HRH1 |
| DIPHENIDOL | Antiemetics | CHRM1 |
| DIPHENIDOL | Antiemetics | CHRM2 |
| DIPHENIDOL | Antiemetics | CHRM3 |
| DIPHENOXYLATE | Antidiarrheals | OPRM1 |
| DIPHENYLPYRALINE | Anti-Allergic Agents | HRH1 |
| DIPIVEFRIN | Ophthalmologicals | ADRA2A |
| DISOPYRAMIDE | Anti-Arrhythmia Agents | SCN5A |
| DISULFIRAM | Alcohol Deterrents | ALDH2 |
| DIVALPROEX SODIUM | Anticonvulsants; Antimanic Agents | ABAT |
| DOBUTAMINE | Cardiotonic Agents | ADRB1 |
| DOFETILIDE | Anti-Arrhythmia Agents | KCNH2 |
| DOFETILIDE | Anti-Arrhythmia Agents | KCNJ12 |
| DOFETILIDE | Anti-Arrhythmia Agents | KCNK2 |
| DOMPERIDONE | Antiemetics | DRD2 |
| DOXACURIUM | Muscle Relaxants | CHRM2 |
| DOXACURIUM | Muscle Relaxants | CHRNA2 |
| DOXACURIUM CHLORIDE | Muscle Relaxants | CHRM2 |
| DOXACURIUM CHLORIDE | Muscle Relaxants | CHRNA2 |
| DOXAZOSIN | Anticholesteremic Agents; Antihypertensive Agents; Vasodilator Agents | ADRA1A |

TABLE 2-continued

Exemplary Drugs with Disease Indications and Gene Identifier for the Target Protein

| Drug Name | Indication(s) | Gene |
|---|---|---|
| DOXAZOSIN | Anticholesteremic Agents; Antihypertensive Agents; Vasodilator Agents | ADRA1B |
| DOXAZOSIN | Anticholesteremic Agents; Antihypertensive Agents; Vasodilator Agents | ADRA1D |
| DOXYLAMINE | Anti-Allergic Agents; Antiemetics; Antitussive Agents; Hypnotics and Sedatives | HRH1 |
| DROMOSTANOLONE | Antineoplastic Agents, Hormonal | AR |
| DRONEDARONE | Anti-Arrhythmia Agents | ADRA1A |
| DRONEDARONE | Anti-Arrhythmia Agents | ADRB1 |
| DRONEDARONE | Anti-Arrhythmia Agents | KCNH2 |
| DROPERIDOL | Adjuvants, Anesthesia | DRD2 |
| DUTASTERIDE | Anti-baldness Agents, Antihyperplasia Agents | SRD5A1 |
| DUTASTERIDE | Anti-baldness Agents, Antihyperplasia Agents | SRD5A2 |
| DYCLONINE | Anesthetics, Local | SCN10A |
| DYDROGESTERONE | Antidysmennorheal Agents | PGR |
| DYPHYLLINE | Bronchodilator Agents; Vasodilator Agents | PDE4A |
| DYPHYLLINE | Bronchodilator Agents; Vasodilator Agents | PDE4B |
| DYPHYLLINE | Bronchodilator Agents; Vasodilator Agents | PDE4C |
| DYPHYLLINE | Bronchodilator Agents; Vasodilator Agents | PDE4D |
| DYPHYLLINE | Bronchodilator Agents; Vasodilator Agents | PDE7A |
| DYPHYLLINE | Bronchodilator Agents; Vasodilator Agents | PDE7B |
| ECHOTHIOPHATE IODIDE | Miotics | BCHE |
| EDROPHONIUM | Anti-Arrhythmia Agents; Antidotes | ACHE |
| EMEDASTINE | Anti-Allergic Agents | HRH1 |
| ENCAINIDE | Anti-Arrhythmia Agents | SCN5A |
| ENFLURANE | Anesthetics, Inhalation | ATP2C1 |
| ENFLURANE | Anesthetics, Inhalation | ATP5D |
| ENFLURANE | Anesthetics, Inhalation | GABRA1 |
| ENFLURANE | Anesthetics, Inhalation | GLRA1 |
| ENFLURANE | Anesthetics, Inhalation | GRIA1 |
| ENFLURANE | Anesthetics, Inhalation | KCNA1 |
| ENFLURANE | Anesthetics, Inhalation | KCNMA1 |
| ENFLURANE | Anesthetics, Inhalation | MT-ND1 |
| ENOXIMONE | Cardiotonic Agents; Vasodilator Agents | PDE3A |
| ENPROFYLLINE | Anti-Asthmatic Agents; Antiarrhythmic Agents; Bronchodilator Agents | PDE4A |
| ENPROFYLLINE | Anti-Asthmatic Agents; Antiarrhythmic Agents; Bronchodilator Agents | PDE4B |
| EPHEDRINE | Central Nervous System Stimulants | ADRA1A |
| EPIRUBICIN | Antineoplastic Agents | CHD1 |
| EPIRUBICIN | Antineoplastic Agents | TOP2A |
| EPOPROSTENOL | Antihypertensive Agents; Platelet Aggregation Inhibitors | PTGIR |
| EPROSARTAN | Antihypertensive Agents | AGTR1 |
| ERGOCALCIFEROL | Antihypocalcemic Agents | VDR |
| ERGOLOID MESYLATE | Nootropic Agents; Vasodilator Agents | ADRA1A |
| ERGOLOID MESYLATE | Nootropic Agents; Vasodilator Agents | ADRA2A |
| ERGOTAMINE | Anti-migraine Agents | HTR1B |
| ERGOTAMINE | Anti-migraine Agents | HTR1D |
| ERYTHRITYL TETRANITRATE | Antianginal Agents; Vasodilator Agents | NPR1 |
| ERYTHRITYL TETRANITRATE | Antianginal Agents; Vasodilator Agents | NPR2 |
| ESMOLOL | Anti-Arrhythmia Agents | ADRB1 |
| ESTAZOLAM | Anti-anxiety Agents; Anticonvulsants | GABRA1 |
| ESTAZOLAM | Anti-anxiety Agents; Anticonvulsants | GABRA2 |

TABLE 2-continued

| Exemplary Drugs with Disease Indications and Gene Identifier for the Target Protein | | |
|---|---|---|
| Drug Name | Indication(s) | Gene |
| ESTAZOLAM | Anti-anxiety Agents; Anticonvulsants | GABRA3 |
| ESTAZOLAM | Anti-anxiety Agents; Anticonvulsants | GABRA5 |
| ESTAZOLAM | Anti-anxiety Agents; Anticonvulsants | GABRB1 |
| ESTAZOLAM | Anti-anxiety Agents; Anticonvulsants | GABRB2 |
| ESTAZOLAM | Anti-anxiety Agents; Anticonvulsants | GABRB3 |
| ESTAZOLAM | Anti-anxiety Agents; Anticonvulsants | GABRD |
| ESTAZOLAM | Anti-anxiety Agents; Anticonvulsants | GABRE |
| ESTAZOLAM | Anti-anxiety Agents; Anticonvulsants | GABRG1 |
| ESTAZOLAM | Anti-anxiety Agents; Anticonvulsants | GABRG2 |
| ESTAZOLAM | Anti-anxiety Agents; Anticonvulsants | GABRG3 |
| ESTAZOLAM | Anti-anxiety Agents; Anticonvulsants | GABRP |
| ESTAZOLAM | Anti-anxiety Agents; Anticonvulsants | GABRR1 |
| ESTAZOLAM | Anti-anxiety Agents; Anticonvulsants | GABRR2 |
| ESTAZOLAM | Anti-anxiety Agents; Anticonvulsants | GABRR3 |
| ESTRIOL | Hormone Replacement Agents | ESR1 |
| ESTRONE | Hormone Replacement Agents | ESR1 |
| ETHACRYNIC ACID | Antihypertensive Agents; Diuretics | SLC12A1 |
| ETHOPROPAZINE | Antidyskinetics | CHRM1 |
| ETHOSUXIMIDE | Anticonvulsants | CACNA1G |
| ETHOTOIN | Anticonvulsants | SCN5A |
| ETHOXZOLAMIDE | Antihypertensive Agents, Diuretics; Antiglaucoma agents | CA1 |
| ETHYNODIOL DIACETATE | Contraceptives, Oral, Synthetic | ESR1 |
| ETHYNODIOL DIACETATE | Contraceptives, Oral, Synthetic | PGR |
| ETOMIDATE | Anesthetics, Intravenous | ADRA2B |
| ETOMIDATE | Anesthetics, Intravenous | GABRA1 |
| ETOPOSIDE | Antineoplastic Agents | TOP2A |
| EZETIMIBE | Anticholesteremic Agents | NPC1L1 |
| FELBAMATE | Anticonvulsants; Antiepileptics | GRIN2A |
| FELBAMATE | Anticonvulsants; Antiepileptics | GRIN2B |
| FELBAMATE | Anticonvulsants; Antiepileptics | GRIN3A |
| FENCAMFAMINE | Central Nervous System Stimulants | SLC6A3 |
| FENOPROFEN | NSAID | PTGS1 |
| FENOPROFEN | NSAID | PTGS2 |
| FENOTEROL | Bronchodilator Agents; Tocolytic Agents | ADRB2 |
| FLAVOXATE | Antispasmodics | CHRM1 |
| FLAVOXATE | Antispasmodics | CHRM2 |
| FLECAINIDE | Anti-Arrhythmia Agents | SCN5A |
| FLUDIAZEPAM | Anti-anxiety Agents; Anticonvulsants | GABRA1 |
| FLUDIAZEPAM | Anti-anxiety Agents; Anticonvulsants | GABRA2 |
| FLUDIAZEPAM | Anti-anxiety Agents; Anticonvulsants | GABRA3 |
| FLUDIAZEPAM | Anti-anxiety Agents; Anticonvulsants | GABRA5 |
| FLUDIAZEPAM | Anti-anxiety Agents; Anticonvulsants | GABRB1 |
| FLUDIAZEPAM | Anti-anxiety Agents; Anticonvulsants | GABRB2 |
| FLUDIAZEPAM | Anti-anxiety Agents; Anticonvulsants | GABRB3 |
| FLUDIAZEPAM | Anti-anxiety Agents; Anticonvulsants | GABRD |
| FLUDIAZEPAM | Anti-anxiety Agents; Anticonvulsants | GABRE |
| FLUDIAZEPAM | Anti-anxiety Agents; Anticonvulsants | GABRG1 |

TABLE 2-continued

| Exemplary Drugs with Disease Indications and Gene Identifier for the Target Protein | | |
|---|---|---|
| Drug Name | Indication(s) | Gene |
| FLUDIAZEPAM | Anti-anxiety Agents; Anticonvulsants | GABRG2 |
| FLUDIAZEPAM | Anti-anxiety Agents; Anticonvulsants | GABRG3 |
| FLUDIAZEPAM | Anti-anxiety Agents; Anticonvulsants | GABRP |
| FLUDIAZEPAM | Anti-anxiety Agents; Anticonvulsants | GABRR1 |
| FLUDIAZEPAM | Anti-anxiety Agents; Anticonvulsants | GABRR2 |
| FLUDIAZEPAM | Anti-anxiety Agents; Anticonvulsants | GABRR3 |
| FLUDROCORTISONE | Anti-Inflammatory Agents; corticosteroid | NR3C2 |
| FLUMAZENIL | Antidotes, Benzodoazepine Overdose | GABRA1 |
| FLUMAZENIL | Antidotes, Benzodoazepine Overdose | GABRA2 |
| FLUMAZENIL | Antidotes, Benzodoazepine Overdose | GABRA3 |
| FLUMAZENIL | Antidotes, Benzodoazepine Overdose | GABRA5 |
| FLUMETHASONE PIVALATE | Anti-Inflammatory Agents; corticosteroid | NR3C1 |
| FLUNARIZINE | Anticonvulsants; Vasodilator Agents | CACNA1G |
| FLUNARIZINE | Anticonvulsants; Vasodilator Agents | CACNA1H |
| FLUNARIZINE | Anticonvulsants; Vasodilator Agents | CACNA1I |
| FLUNARIZINE | Anticonvulsants; Vasodilator Agents | HRH1 |
| FLUNITRAZEPAM | Hypnotics and Sedatives | BZRP |
| FLUNITRAZEPAM | Hypnotics and Sedatives | GABRA2 |
| FLUNITRAZEPAM | Hypnotics and Sedatives | GABRA3 |
| FLUNITRAZEPAM | Hypnotics and Sedatives | GABRA4 |
| FLUNITRAZEPAM | Hypnotics and Sedatives | GABRA5 |
| FLUNITRAZEPAM | Hypnotics and Sedatives | GABRA6 |
| FLUOROMETHOLONE | Anti-Inflammatory Agents; Anti-allergic agents; Glucocorticoids | NR3C1 |
| FLUOXYMESTERONE | Anabolic Agents; Antineoplastic Agents | AR |
| FLUPENTHIXOL | Antipsychotic Agents | DRD1 |
| FLUPENTHIXOL | Antipsychotic Agents | DRD2 |
| FLUPHENAZINE | Antipsychotic Agents | DRD1 |
| FLUPHENAZINE | Antipsychotic Agents | DRD2 |
| FLURANDRENOLIDE | Anti-Inflammatory Agents; Glucocorticoids | NR3C1 |
| FLURAZEPAM | Hypnotics and Sedatives | GABRA1 |
| FLURAZEPAM | Hypnotics and Sedatives | GABRA2 |
| FLURAZEPAM | Hypnotics and Sedatives | GABRA3 |
| FLURAZEPAM | Hypnotics and Sedatives | GABRA4 |
| FLURAZEPAM | Hypnotics and Sedatives | GABRA5 |
| FLURAZEPAM | Hypnotics and Sedatives | GABRA6 |
| FLURAZEPAM | Hypnotics and Sedatives | GABRB1 |
| FLURAZEPAM | Hypnotics and Sedatives | GABRB2 |
| FLURAZEPAM | Hypnotics and Sedatives | GABRB3 |
| FLURAZEPAM | Hypnotics and Sedatives | GABRD |
| FLURAZEPAM | Hypnotics and Sedatives | GABRE |
| FLURAZEPAM | Hypnotics and Sedatives | GABRG1 |
| FLURAZEPAM | Hypnotics and Sedatives | GABRG2 |
| FLURAZEPAM | Hypnotics and Sedatives | GABRG3 |
| FLURAZEPAM | Hypnotics and Sedatives | GABRP |
| FLURAZEPAM | Hypnotics and Sedatives | GABRQ |
| FLURAZEPAM | Hypnotics and Sedatives | GABRR1 |
| FLURAZEPAM | Hypnotics and Sedatives | GABRR2 |
| FLURAZEPAM | Hypnotics and Sedatives | GABRR3 |
| FLUSPIRILENE | Antipsychotic Agents | DRD2 |
| FLUTAMIDE | Antineoplastic Agents, Hormonal | AR |
| FONDAPARINUX | Antithrombotic Agents | SERPINC1 |
| FORASARTAN | Antihypertensive Agents | AGTR1 |
| FOSINOPRIL | Antihypertensive Agents | ACE |
| FUROSEMIDE | Antihypertensive Agents; Diuretics | SLC12A1 |
| GALLAMINE TRIETHIODIDE | Muscle Relaxants, Skeletal | CHRNA2 |
| GEMFIBROZIL | Antilipemic Agents | PPARA |
| GLIBENCLAMIDE | Hypoglycemic Agents | KCNJ1 |
| GLIBENCLAMIDE | Hypoglycemic Agents | KCNJ11 |
| GLICLAZIDE | Hypoglycemic Agents | KCNJ1 |
| GLIPIZIDE | Hypoglycemic Agents | KCNJ1 |

TABLE 2-continued

Exemplary Drugs with Disease Indications and Gene Identifier for the Target Protein

| Drug Name | Indication(s) | Gene |
|---|---|---|
| GLYCODIAZINE | Hypoglycemic Agents | KCNJ1 |
| GONADORELIN | Fertility Agents | GNRHR |
| GONADORELIN | Fertility Agents | GNRHR2 |
| GUANABENZ | Antihypertensive Agents | ADRA2A |
| GUANADREL SULFATE | Antihypertensive Agents | SLC6A2 |
| GUANETHIDINE | Antihypertensive Agents | SLC6A2 |
| HALAZEPAM | Anti-anxiety Agents; Muscle Relaxants; Sedative | GABRA1 |
| HALAZEPAM | Anti-anxiety Agents; Muscle Relaxants; Sedative | GABRA2 |
| HALAZEPAM | Anti-anxiety Agents; Muscle Relaxants; Sedative | GABRA3 |
| HALAZEPAM | Anti-anxiety Agents; Muscle Relaxants; Sedative | GABRA5 |
| HALAZEPAM | Anti-anxiety Agents; Muscle Relaxants; Sedative | GABRB1 |
| HALAZEPAM | Anti-anxiety Agents; Muscle Relaxants; Sedative | GABRB2 |
| HALAZEPAM | Anti-anxiety Agents; Muscle Relaxants; Sedative | GABRB3 |
| HALAZEPAM | Anti-anxiety Agents; Muscle Relaxants; Sedative | GABRD |
| HALAZEPAM | Anti-anxiety Agents; Muscle Relaxants; Sedative | GABRE |
| HALAZEPAM | Anti-anxiety Agents; Muscle Relaxants; Sedative | GABRG1 |
| HALAZEPAM | Anti-anxiety Agents; Muscle Relaxants; Sedative | GABRG2 |
| HALAZEPAM | Anti-anxiety Agents; Muscle Relaxants; Sedative | GABRG3 |
| HALAZEPAM | Anti-anxiety Agents; Muscle Relaxants; Sedative | GABRP |
| HALAZEPAM | Anti-anxiety Agents; Muscle Relaxants; Sedative | GABRR1 |
| HALAZEPAM | Anti-anxiety Agents; Muscle Relaxants; Sedative | GABRR2 |
| HALAZEPAM | Anti-anxiety Agents; Muscle Relaxants; Sedative | GABRR3 |
| HALOBETASOL PROPIONATE | Anti-inflammatory Agents | NR3C1 |
| HALOPERIDOL | Antipsychotic Agents | DRD2 |
| HALOTHANE | Anesthetics, Inhalation | ATP5D |
| HEXAFLURONIUM BROMIDE | Muscle Relaxants | BCHE |
| HEXOBARBITAL | Hypnotics and Sedatives | CHRNA4 |
| HEXOBARBITAL | Hypnotics and Sedatives | CHRNA7 |
| HEXOBARBITAL | Hypnotics and Sedatives | GABRA1 |
| HEXOBARBITAL | Hypnotics and Sedatives | GABRA2 |
| HEXOBARBITAL | Hypnotics and Sedatives | GABRA3 |
| HEXOBARBITAL | Hypnotics and Sedatives | GABRA4 |
| HEXOBARBITAL | Hypnotics and Sedatives | GABRA5 |
| HEXOBARBITAL | Hypnotics and Sedatives | GABRA6 |
| HEXOBARBITAL | Hypnotics and Sedatives | GRIA2 |
| HEXOBARBITAL | Hypnotics and Sedatives | GRIK2 |
| HEXYLCAINE | Anesthetics, Local | SCN10A |
| HEXYLCAINE | Anesthetics, Local | SCN5A |
| HOMATROPINE METHYLBROMIDE | GI Anti-Ulcer Agents, Antimuscarinics | CHRM1 |
| HOMATROPINE METHYLBROMIDE | GI Anti-Ulcer Agents, Antimuscarinics | CHRM2 |
| HOMATROPINE METHYLBROMIDE | GI Anti-Ulcer Agents, Antimuscarinics | CHRM3 |
| HOMATROPINE METHYLBROMIDE | GI Anti-Ulcer Agents, Antimuscarinics | CHRM4 |
| HOMATROPINE METHYLBROMIDE | GI Anti-Ulcer Agents, Antimuscarinics | CHRM5 |
| HYDROCORTAMATE | Anti-Inflammatory Agents; Glucocorticoids | NR3C1 |
| HYDROCORTAMATE | Anti-Inflammatory Agents; Glucocorticoids | NR3C1 |
| HYDROFLUMETHIAZIDE | Antihypertensive Agents; Diuretics | SLC12A1 |
| HYDROXYUREA | Antineoplastic Agents | RRM1 |
| HYDROXYZINE | Antipruritics; Anxiolytics sedatives and hypnotics | HRH1 |

TABLE 2-continued

| Drug Name | Indication(s) | Gene |
|---|---|---|
| IBUTILIDE | Anti-Arrhythmia Agents | CACNA1C |
| IBUTILIDE | Anti-Arrhythmia Agents | CACNA2D1 |
| IBUTILIDE | Anti-Arrhythmia Agents | CACNB1 |
| IBUTILIDE | Anti-Arrhythmia Agents | KCNH2 |
| IDARUBICIN | Antineoplastic Agents | TOP2A |
| IFOSFAMIDE | Antineoplastic Agents | DNMT1 |
| IMIPRAMINE | Antidepressive Agents, Tricyclic | SLC6A2 |
| IMIPRAMINE | Antidepressive Agents, Tricyclic | SLC6A4 |
| INDAPAMIDE | Antihypertensive Agents; Diuretics | KCNE1 |
| INDAPAMIDE | Antihypertensive Agents; Diuretics | KCNQ1 |
| INDECAINIDE | Anti-Arrhythmia Agents | SCN5A |
| ISOCARBOXAZID | Antidepressive Agents | MAOA |
| ISOCARBOXAZID | Antidepressive Agents | MAOB |
| ISOETHARINE | Bronchodilator Agents | ADRB1 |
| ISOFLURANE | Anesthetics, Inhalation | ATP2C1 |
| ISOFLURANE | Anesthetics, Inhalation | GABRA1 |
| ISOFLURANE | Anesthetics, Inhalation | GLRA1 |
| ISOFLURANE | Anesthetics, Inhalation | GRIA1 |
| ISOFLURANE | Anesthetics, Inhalation | KCNA1 |
| ISOFLUROPHATE | Antiglaucomic Agents | BCHE |
| ISOPROTERENOL | Bronchodilator Agents; Cardiotonic Agents | ADRB1 |
| ISOPROTERENOL | Bronchodilator Agents; Cardiotonic Agents | ADRB2 |
| ISOSORBIDE-5-MONONITRATE | Antianginal Agents; Vasodilator Agents | NPR1 |
| ISRADIPINE | Antihypertensive Agents; Vasodilator Agents | CACNA1C |
| ISRADIPINE | Antihypertensive Agents; Vasodilator Agents | CACNA2D1 |
| LABETALOL | Antihypertensive Agents | ADRA1A |
| LABETALOL | Antihypertensive Agents | ADRA1B |
| LABETALOL | Antihypertensive Agents | ADRB1 |
| LABETALOL | Antihypertensive Agents | ADRB2 |
| LEFLUNOMIDE | Antirheumatic Agents | DHODH |
| LEVALLORPHAN | Opiate Antagonists | OPRM1 |
| LEVOBUNOLOL | Antiglaucomic Agents | ADRB1 |
| LEVOBUNOLOL | Antiglaucomic Agents | ADRB2 |
| LEVOBUPIVACAINE | Anesthetics, Local | SCN10A |
| LEVOCABASTINE | Anti-Allergic Agents | HRH1 |
| LEVOMETHADYL ACETATE | Analgesics, Opioid | OPRM1 |
| LEVORPHANOL | Analgesics, Opioid | OPRM1 |
| LIOTHYRONINE | Hormone Replacement Agents | THRA |
| LIOTHYRONINE | Hormone Replacement Agents | THRB |
| LISDEXAMFETAMINE | Central Nervous System Stimulants | ADRA1A |
| LISDEXAMFETAMINE | Central Nervous System Stimulants | ADRA1B |
| LISDEXAMFETAMINE | Central Nervous System Stimulants | SLC6A3 |
| LISURIDE | Antiparkinson Agents | DRD1 |
| LISURIDE | Antiparkinson Agents | DRD2 |
| LISURIDE | Antiparkinson Agents | HTR1A |
| LOPERAMIDE | Antidiarrheals | OPRM1 |
| LORAZEPAM | Anti-anxiety Agents; Anticonvulsants; Hypnotics and Sedatives | BZRP |
| LORAZEPAM | Anti-anxiety Agents; Anticonvulsants; Hypnotics and Sedatives | GABRA1 |
| LORAZEPAM | Anti-anxiety Agents; Anticonvulsants; Hypnotics and Sedatives | GABRA2 |
| LORAZEPAM | Anti-anxiety Agents; Anticonvulsants; Hypnotics and Sedatives | GABRA3 |
| LORAZEPAM | Anti-anxiety Agents; Anticonvulsants; Hypnotics and Sedatives | GABRA4 |
| LORAZEPAM | Anti-anxiety Agents; Anticonvulsants; Hypnotics and Sedatives | GABRA5 |
| LORAZEPAM | Anti-anxiety Agents; Anticonvulsants; Hypnotics and Sedatives | GABRA6 |

Exemplary Drugs with Disease Indications and Gene Identifier for the Target Protein TABLE 2-continued

| Exemplary Drugs with Disease Indications and Gene Identifier for the Target Protein | | |
|---|---|---|
| Drug Name | Indication(s) | Gene |
| LORAZEPAM | Anti-anxiety Agents; Anticonvulsants; Hypnotics and Sedatives | GABRB1 |
| LORAZEPAM | Anti-anxiety Agents; Anticonvulsants; Hypnotics and Sedatives | GABRB2 |
| LORAZEPAM | Anti-anxiety Agents; Anticonvulsants; Hypnotics and Sedatives | GABRB3 |
| LORAZEPAM | Anti-anxiety Agents; Anticonvulsants; Hypnotics and Sedatives | GABRD |
| LORAZEPAM | Anti-anxiety Agents; Anticonvulsants; Hypnotics and Sedatives | GABRE |
| LORAZEPAM | Anti-anxiety Agents; Anticonvulsants; Hypnotics and Sedatives | GABRG1 |
| LORAZEPAM | Anti-anxiety Agents; Anticonvulsants; Hypnotics and Sedatives | GABRG2 |
| LORAZEPAM | Anti-anxiety Agents; Anticonvulsants; Hypnotics and Sedatives | GABRG3 |
| LORAZEPAM | Anti-anxiety Agents; Anticonvulsants; Hypnotics and Sedatives | GABRP |
| LORAZEPAM | Anti-anxiety Agents; Anticonvulsants; Hypnotics and Sedatives | GABRQ |
| LORAZEPAM | Anti-anxiety Agents; Anticonvulsants; Hypnotics and Sedatives | GABRR1 |
| LORAZEPAM | Anti-anxiety Agents; Anticonvulsants; Hypnotics and Sedatives | GABRR2 |
| LORAZEPAM | Anti-anxiety Agents; Anticonvulsants; Hypnotics and Sedatives | GABRR3 |
| LOSARTAN | Antihypertensive Agents | AGTR1 |
| MAPROTILINE | Antidepressive Agents, Second-Generation | SLC6A2 |
| MARIMASTAT | Antineoplastic Agents | MMP2 |
| MARIMASTAT | Antineoplastic Agents | MMP3 |
| MARIMASTAT | Antineoplastic Agents | MMP9 |
| MARINOL | Antiemetics | CNR1 |
| MECLIZINE | Antiemetics | HRH1 |
| MECLOFENAMIC ACID | NSAID | ALOX5 |
| MECLOFENAMIC ACID | NSAID | PTGS1 |
| MECLOFENAMIC ACID | NSAID | PTGS2 |
| MEDRYSONE | Anti-Inflammatory Agents, Topical | NR3C1 |
| MEFENAMIC ACID | NSAID | PTGS1 |
| MEFENAMIC ACID | NSAID | PTGS2 |
| MEGESTROL | Antineoplastic Agents, Hormonal; Contraceptives | ESR1 |
| MEGESTROL | Antineoplastic Agents, Hormonal; Contraceptives | PGR |
| MELATONIN | Hypnotics and Sedatives | MTNR1A |
| MELATONIN | Hypnotics and Sedatives | MTNR1B |
| MELOXICAM | NSAID | PTGS2 |
| MENTHOL | Antipruritics | TRPA1 |
| MENTHOL | Antipruritics | TRPM8 |
| MENTHOL | Antipruritics | TRPV3 |
| MEPENZOLATE | Antispasmodics | GPR109A |
| MEPENZOLATE | Antispasmodics | GPR109B |
| MEPERIDINE | Analgesics, Opioid | OPRK1 |
| MEPHENTERMINE | Antihypotensive Agents; Vasoconstrictor Agents | ADRA1A |
| MEPHENYTOIN | Anticonvulsants | SCN5A |
| MEPROBAMATE | Anticonvulsants; Hypnotics and Sedatives | GABRA1 |
| MEPROBAMATE | Anticonvulsants; Hypnotics and Sedatives | GABRA2 |

TABLE 2-continued

| Exemplary Drugs with Disease Indications and Gene Identifier for the Target Protein | | |
|---|---|---|
| Drug Name | Indication(s) | Gene |
| MEPROBAMATE | Anticonvulsants; Hypnotics and Sedatives | GABRA3 |
| MEPROBAMATE | Anticonvulsants; Hypnotics and Sedatives | GABRA4 |
| MEPROBAMATE | Anticonvulsants; Hypnotics and Sedatives | GABRA5 |
| MEPROBAMATE | Anticonvulsants; Hypnotics and Sedatives | GABRA6 |
| MEQUITAZINE | Anti-Allergic Agents | HRH1 |
| MERCAPTOPURINE | Antineoplastic Agents | HPRT1 |
| MESORIDAZINE | Antipsychotic Agents | DRD2 |
| MESORIDAZINE | Antipsychotic Agents | HTR2A |
| MESTRANOL | Contraceptives, Oral | ESR1 |
| METARAMINOL | Antihypotensive Agents; Vasoconstrictor Agents | ADRA1A |
| METHADONE | Analgesics, Opioid; Antitussive Agents | OPRM1 |
| METHADYL ACETATE | Analgesics, Opioid | OPRM1 |
| METHANTHELINE | GI Anti-Ulcer Agents, anticholinergic; Antispasmodics | CHRM1 |
| METHARBITAL | Anticonvulsants | CHRNA4 |
| METHARBITAL | Anticonvulsants | CHRNA7 |
| METHARBITAL | Anticonvulsants | GABRA1 |
| METHARBITAL | Anticonvulsants | GABRA2 |
| METHARBITAL | Anticonvulsants | GABRA3 |
| METHARBITAL | Anticonvulsants | GABRA4 |
| METHARBITAL | Anticonvulsants | GABRA5 |
| METHARBITAL | Anticonvulsants | GABRA6 |
| METHARBITAL | Anticonvulsants | GRIA2 |
| METHARBITAL | Anticonvulsants | GRIK2 |
| METHAZOLAMIDE | Antihypertensive Agents, Diuretics; Antiglaucoma agents | CA1 |
| METHDILAZINE | Anti-Allergic Agents | HRH1 |
| METHIMAZOLE | Antithyroid Agents | TPO |
| METHOHEXITAL | Anesthetics, Intravenous | GABRA1 |
| METHOTRIMEPRAZINE | Antipsychotic Agents | ADRA1A |
| METHOTRIMEPRAZINE | Antipsychotic Agents | ADRA1B |
| METHOTRIMEPRAZINE | Antipsychotic Agents | ADRA1D |
| METHOTRIMEPRAZINE | Antipsychotic Agents | CHRM1 |
| METHOTRIMEPRAZINE | Antipsychotic Agents | CHRM2 |
| METHOTRIMEPRAZINE | Antipsychotic Agents | CHRM3 |
| METHOTRIMEPRAZINE | Antipsychotic Agents | CHRM4 |
| METHOTRIMEPRAZINE | Antipsychotic Agents | CHRM5 |
| METHOTRIMEPRAZINE | Antipsychotic Agents | DRD3 |
| METHOTRIMEPRAZINE | Antipsychotic Agents | HRH1 |
| METHOTRIMEPRAZINE | Antipsychotic Agents | HTR2B |
| METHOXAMINE | Antihypotensive Agents; Vasoconstrictor Agents | ADRA1A |
| METHOXAMINE | Antihypotensive Agents; Vasoconstrictor Agents | ADRA1B |
| METHOXYFLURANE | Anesthetics, Inhalation | ATP5D |
| METHYCLOTHIAZIDE | Antihypertensive Agents; Diuretics | SLC12A1 |
| METHYLDOPA | Antihypertensive Agents | ADRA2A |
| METHYLERGONOVINE | Abortifacient Agents | DRD1 |
| METHYLNALTREXONE BROMIDE | OIC treatment | OPRM1 |
| METHYLPHENOBARBITAL | Anticonvulsants; Hypnotics and Sedatives | CHRNA4 |
| METHYLPHENOBARBITAL | Anticonvulsants; Hypnotics and Sedatives | CHRNA7 |
| METHYLPHENOBARBITAL | Anticonvulsants; Hypnotics and Sedatives | GABRA1 |
| METHYLPHENOBARBITAL | Anticonvulsants; Hypnotics and Sedatives | GABRA2 |
| METHYLPHENOBARBITAL | Anticonvulsants; Hypnotics and Sedatives | GABRA3 |
| METHYLPHENOBARBITAL | Anticonvulsants; Hypnotics and Sedatives | GABRA4 |
| METHYLPHENOBARBITAL | Anticonvulsants; Hypnotics and Sedatives | GABRA5 |
| METHYLPHENOBARBITAL | Anticonvulsants; Hypnotics and Sedatives | GABRA6 |
| METHYLPHENOBARBITAL | Anticonvulsants; Hypnotics and Sedatives | GRIA2 |

TABLE 2-continued

Exemplary Drugs with Disease Indications and Gene Identifier for the Target Protein

| Drug Name | Indication(s) | Gene |
|---|---|---|
| METHYLPHENOBARBITAL | Anticonvulsants; Hypnotics and Sedatives | GRIK2 |
| METHYLPREDNISOLONE | Anti-Inflammatory Agents; Glucocorticoids | NR3C1 |
| METHYLPREDNISOLONE | Anti-Inflammatory Agents; Glucocorticoids | NR3C1 |
| METHYLSCOPOLAMINE | Antispasmodics | CHRM1 |
| METHYPRYLON | Hypnotics and Sedatives | GABRA1 |
| METHYSERGIDE | Anti-migraine agents; Vasoconstrictor Agents | HTR1A |
| METHYSERGIDE | Anti-migraine agents; Vasoconstrictor Agents | HTR2A |
| METHYSERGIDE | Anti-migraine agents; Vasoconstrictor Agents | HTR2C |
| METHYSERGIDE | Anti-migraine agents; Vasoconstrictor Agents | HTR7 |
| METIPRANOLOL | Anti-Arrhythmia Agents; Antihypertensive Agents; Anti-glaucoma agent | ADRB1 |
| METIPRANOLOL | Anti-Arrhythmia Agents; Antihypertensive Agents; Anti-glaucoma agent | ADRB2 |
| METIXENE | Antiparkinson Agents | CHRM1 |
| METIXENE | Antiparkinson Agents | CHRM2 |
| METIXENE | Antiparkinson Agents | CHRM3 |
| METIXENE | Antiparkinson Agents | CHRM4 |
| METIXENE | Antiparkinson Agents | CHRM5 |
| METOCURINE | Muscle Relaxants | CHRNA2 |
| METOCURINE IODIDE | Muscle Relaxants | CHRNA2 |
| METOLAZONE | Antihypertensive Agents; Diuretics | SLC12A1 |
| METOLAZONE | Antihypertensive Agents; Diuretics | SLC12A3 |
| METOPROLOL | Anti-Arrhythmia Agents; Antihypertensive Agents | ADRB1 |
| METYRAPONE | Diagnostic Agents | CYP11B1 |
| METYROSINE | Catecholamine synthesis inhibitors | TH |
| MEXILETINE | Anti-Arrhythmia Agents | SCN5A |
| MIANSERIN | Antidepressive Agents, Second-Generation | ADRA2A |
| MIANSERIN | Antidepressive Agents, Second-Generation | HRH1 |
| MIANSERIN | Antidepressive Agents, Second-Generation | HTR2A |
| MIANSERIN | Antidepressive Agents, Second-Generation | HTR2C |
| MIDAZOLAM | Adjuvants, Anesthesia; Hypnotics and Sedatives | GABRA1 |
| MIDAZOLAM | Adjuvants, Anesthesia; Hypnotics and Sedatives | GABRA2 |
| MIDAZOLAM | Adjuvants, Anesthesia; Hypnotics and Sedatives | GABRA3 |
| MIDAZOLAM | Adjuvants, Anesthesia; Hypnotics and Sedatives | GABRA4 |
| MIDAZOLAM | Adjuvants, Anesthesia; Hypnotics and Sedatives | GABRA5 |
| MIDAZOLAM | Adjuvants, Anesthesia; Hypnotics and Sedatives | GABRA6 |
| MIDAZOLAM | Adjuvants, Anesthesia; Hypnotics and Sedatives | GABRB1 |
| MIDAZOLAM | Adjuvants, Anesthesia; Hypnotics and Sedatives | GABRB2 |
| MIDAZOLAM | Adjuvants, Anesthesia; Hypnotics and Sedatives | GABRB3 |
| MIDAZOLAM | Adjuvants, Anesthesia; Hypnotics and Sedatives | GABRD |
| MIDAZOLAM | Adjuvants, Anesthesia; Hypnotics and Sedatives | GABRE |
| MIDAZOLAM | Adjuvants, Anesthesia; Hypnotics and Sedatives | GABRG1 |
| MIDAZOLAM | Adjuvants, Anesthesia; Hypnotics and Sedatives | GABRG2 |
| MIDAZOLAM | Adjuvants, Anesthesia; Hypnotics and Sedatives | GABRG3 |
| MIDAZOLAM | Adjuvants, Anesthesia; Hypnotics and Sedatives | GABRP |

TABLE 2-continued

Exemplary Drugs with Disease Indications and Gene Identifier for the Target Protein

| Drug Name | Indication(s) | Gene |
|---|---|---|
| MIDAZOLAM | Adjuvants, Anesthesia; Hypnotics and Sedatives | GABRQ |
| MIDAZOLAM | Adjuvants, Anesthesia; Hypnotics and Sedatives | GABRR1 |
| MIDAZOLAM | Adjuvants, Anesthesia; Hypnotics and Sedatives | GABRR2 |
| MIDAZOLAM | Adjuvants, Anesthesia; Hypnotics and Sedatives | GABRR3 |
| MIDODRINE | Antihypotensive Agents; Vasoconstrictor Agents | ADRA1A |
| MIDODRINE | Antihypotensive Agents; Vasoconstrictor Agents | ADRA1B |
| MIGLITOL | Hypoglycemic Agents | MGAM |
| MILRINONE | Cardiotonic Agents; Vasodilator Agents | PDE3A |
| MILRINONE | Cardiotonic Agents; Vasodilator Agents | PDE4A |
| MINAPRINE | Antidepressive Agents | DRD1 |
| MINAPRINE | Antidepressive Agents | DRD2 |
| MINAPRINE | Antidepressive Agents | HTR2A |
| MINAPRINE | Antidepressive Agents | HTR2B |
| MINAPRINE | Antidepressive Agents | HTR2C |
| MINAPRINE | Antidepressive Agents | SLC6A4 |
| MINOXIDIL | Antihypertensive Agents; Vasodilator Agents | KCNJ1 |
| MIVACURIUM | Muscle Relaxants | CHRM2 |
| MIVACURIUM | Muscle Relaxants | CHRNA2 |
| MOEXIPRIL | Antihypertensive Agents | ACE |
| MOLINDONE | Antipsychotic Agents | DRD2 |
| MORICIZINE | Anti-Arrhythmia Agents | SCN5A |
| NABUMETONE | Anti-Inflammatory Agents, Non-Steroidal | PTGS1 |
| NABUMETONE | Anti-Inflammatory Agents, Non-Steroidal | PTGS2 |
| NADOLOL | Anti-Arrhythmia Agents; Antihypertensive Agents | ADRB1 |
| NADOLOL | Anti-Arrhythmia Agents; Antihypertensive Agents | ADRB2 |
| NAFARELIN | Antiendometriosis Agent | GNRHR |
| NAFARELIN | Antiendometriosis Agent | GNRHR2 |
| NANDROLONE | Antianemic Agents; anti-osteoporosis agents | AR |
| NEDOCROMIL | Anti-Allergic Agents; Anti-Asthmatic Agents | CYSLTR1 |
| NEFAZODONE | Antidepressive Agents, Second-Generation | ADRA1A |
| NEFAZODONE | Antidepressive Agents, Second-Generation | ADRA1B |
| NEFAZODONE | Antidepressive Agents, Second-Generation | HTR2A |
| NEFAZODONE | Antidepressive Agents, Second-Generation | SLC6A2 |
| NEFAZODONE | Antidepressive Agents, Second-Generation | SLC6A4 |
| NEOSTIGMINE | Parasympathomimetics | ACHE |
| NEPAFENAC | NSAID | PTGS1 |
| NEPAFENAC | NSAID | PTGS2 |
| NICARDIPINE | Anti-Arrhythmia Agents; Antihypertensive Agents | CACNA1C |
| NICERGOLINE | Nootropic Agents; Vasodilator Agents | ADRA1A |
| NICOTINE | Central Nervous System Stimulants | CHRNA10 |
| NICOTINE | Central Nervous System Stimulants | CHRNA2 |
| NICOTINE | Central Nervous System Stimulants | CHRNA4 |
| NICOTINE | Central Nervous System Stimulants | CHRNA7 |
| NICOTINE | Central Nervous System Stimulants | CHRNA9 |
| NICOTINE | Central Nervous System Stimulants | CHRNB2 |
| NIFEDIPINE | Antianginal Agents; Vasodilator Agents | CACNA2D1 |
| NIFLUMIC ACID | NSAID | PLA2G1B |
| NIFLUMIC ACID | NSAID | PTGS2 |
| NILUTAMIDE | Antineoplastic Agents | AR |
| NIMODIPINE | Antihypertensive Agents; Vasodilator Agents | CACNG1 |

TABLE 2-continued

| Drug Name | Indication(s) | Gene |
|---|---|---|
| NISOLDIPINE | Antihypertensive Agents; Vasodilator Agents | CACNA1A |
| NITRAZEPAM | Anticonvulsants; Hypnotics and Sedatives | GABRA1 |
| NITRAZEPAM | Anticonvulsants; Hypnotics and Sedatives | GABRA2 |
| NITRAZEPAM | Anticonvulsants; Hypnotics and Sedatives | GABRA3 |
| NITRAZEPAM | Anticonvulsants; Hypnotics and Sedatives | GABRA4 |
| NITRAZEPAM | Anticonvulsants; Hypnotics and Sedatives | GABRA5 |
| NITRAZEPAM | Anticonvulsants; Hypnotics and Sedatives | GABRA6 |
| NITRAZEPAM | Anticonvulsants; Hypnotics and Sedatives | GABRB1 |
| NITRAZEPAM | Anticonvulsants; Hypnotics and Sedatives | GABRB2 |
| NITRAZEPAM | Anticonvulsants; Hypnotics and Sedatives | GABRB3 |
| NITRAZEPAM | Anticonvulsants; Hypnotics and Sedatives | GABRD |
| NITRAZEPAM | Anticonvulsants; Hypnotics and Sedatives | GABRE |
| NITRAZEPAM | Anticonvulsants; Hypnotics and Sedatives | GABRG1 |
| NITRAZEPAM | Anticonvulsants; Hypnotics and Sedatives | GABRG2 |
| NITRAZEPAM | Anticonvulsants; Hypnotics and Sedatives | GABRG3 |
| NITRAZEPAM | Anticonvulsants; Hypnotics and Sedatives | GABRP |
| NITRAZEPAM | Anticonvulsants; Hypnotics and Sedatives | GABRQ |
| NITRAZEPAM | Anticonvulsants; Hypnotics and Sedatives | GABRR1 |
| NITRAZEPAM | Anticonvulsants; Hypnotics and Sedatives | GABRR2 |
| NITRAZEPAM | Anticonvulsants; Hypnotics and Sedatives | GABRR3 |
| NITRAZEPAM | Anticonvulsants; Hypnotics and Sedatives | SCN1A |
| NITRENDIPINE | Antihypertensive Agents; Vasodilator Agents | CACNG1 |
| NITROPRUSSIDE | Antihypertensive Agents; Vasodilator Agents | NPR1 |
| NIZATIDINE | GI Anti-Ulcer Agents, antihistamines | HRH2 |
| NOREPINEPHRINE | Antihypotensive Agents; Vasoconstrictor Agents | ADRA1A |
| NOREPINEPHRINE | Antihypotensive Agents; Vasoconstrictor Agents | ADRA1B |
| NOREPINEPHRINE | Antihypotensive Agents; Vasoconstrictor Agents | ADRA1D |
| NOREPINEPHRINE | Antihypotensive Agents; Vasoconstrictor Agents | ADRA2A |
| NOREPINEPHRINE | Antihypotensive Agents; Vasoconstrictor Agents | ADRA2B |
| NOREPINEPHRINE | Antihypotensive Agents; Vasoconstrictor Agents | ADRA2C |
| NORETHINDRONE | Contraceptives, Oral, Synthetic | PGR |
| NORGESTIMATE | Contraceptives, Oral, Synthetic | ESR1 |
| NORGESTIMATE | Contraceptives, Oral, Synthetic | PGR |
| NORGESTREL | Contraceptives, Oral, Synthetic | ESR1 |
| NORGESTREL | Contraceptives, Oral, Synthetic | PGR |
| ORCIPRENALINE | Bronchodilator Agents | ADRB2 |
| ORPHENADRINE | Antiparkinson Agents; Muscle Relaxants, Central | GRIN1 |
| ORPHENADRINE | Antiparkinson Agents; Muscle Relaxants, Central | GRIN2D |
| ORPHENADRINE | Antiparkinson Agents; Muscle Relaxants, Central | GRIN3A |
| ORPHENADRINE | Antiparkinson Agents; Muscle Relaxants, Central | GRIN3B |

TABLE 2-continued

| Exemplary Drugs with Disease Indications and Gene Identifier for the Target Protein | | |
|---|---|---|
| Drug Name | Indication(s) | Gene |
| ORPHENADRINE | Antiparkinson Agents; Muscle Relaxants, Central | HRH1 |
| OUABAIN | Cardiotonic Agents | ATP1A1 |
| OXAPROZIN | NSAID | PTGS2 |
| OXAZEPAM | Hypnotics and Sedatives | GABRA1 |
| OXAZEPAM | Hypnotics and Sedatives | GABRA2 |
| OXAZEPAM | Hypnotics and Sedatives | GABRA3 |
| OXAZEPAM | Hypnotics and Sedatives | GABRA4 |
| OXAZEPAM | Hypnotics and Sedatives | GABRA5 |
| OXAZEPAM | Hypnotics and Sedatives | GABRA6 |
| OXAZEPAM | Hypnotics and Sedatives | GABRB1 |
| OXAZEPAM | Hypnotics and Sedatives | GABRB2 |
| OXAZEPAM | Hypnotics and Sedatives | GABRB3 |
| OXAZEPAM | Hypnotics and Sedatives | GABRD |
| OXAZEPAM | Hypnotics and Sedatives | GABRE |
| OXAZEPAM | Hypnotics and Sedatives | GABRG1 |
| OXAZEPAM | Hypnotics and Sedatives | GABRG2 |
| OXAZEPAM | Hypnotics and Sedatives | GABRG3 |
| OXAZEPAM | Hypnotics and Sedatives | GABRP |
| OXAZEPAM | Hypnotics and Sedatives | GABRQ |
| OXAZEPAM | Hypnotics and Sedatives | GABRR1 |
| OXAZEPAM | Hypnotics and Sedatives | GABRR2 |
| OXAZEPAM | Hypnotics and Sedatives | GABRR3 |
| OXPRENOLOL | Antihypertensive Agents; Anti-Arrhythmia Agents | ADRB1 |
| OXPRENOLOL | Antihypertensive Agents; Anti-Arrhythmia Agents | ADRB2 |
| OXYBUPROCAINE | Anesthetics, Local | SCN10A |
| OXYPHENCYCLIMINE | GI Anti-Ulcer Agents, anticholinergic; Antispasmodics | CHRM1 |
| OXYPHENCYCLIMINE | GI Anti-Ulcer Agents, anticholinergic; Antispasmodics | CHRM2 |
| OXYPHENCYCLIMINE | GI Anti-Ulcer Agents, anticholinergic; Antispasmodics | CHRM3 |
| OXYPHENONIUM | Mydriatics | CHRM1 |
| PAMIDRONATE | Bisphosphonates | FDPS |
| PANCURONIUM | Muscle Relaxants | CHRNA2 |
| PAPAVERINE | Antispasmodics; Anti-impotence Agents; Vasodilator Agents | PDE4B |
| PARAMETHADIONE | Anticonvulsants | CACNA1I |
| PARAMETHASONE | Anti-Inflammatory Agents; Glucocorticoids | NR3C1 |
| PEMETREXED | Antineoplastic Agents | DHFR |
| PEMETREXED | Antineoplastic Agents | GART |
| PEMETREXED | Antineoplastic Agents | TYMS |
| PEMIROLAST | Anti-Allergic Agents | HRH1 |
| PENBUTOLOL | Antihypertensive Agents | ADRB1 |
| PENBUTOLOL | Antihypertensive Agents | ADRB2 |
| PENTAGASTRIN | Diagnostic Agents | CCKBR |
| PENTAZOCINE | Analgesics, Opioid | OPRK1 |
| PENTAZOCINE | Analgesics, Opioid | OPRM1 |
| PENTOBARBITAL | Hypnotics and Sedatives | CHRNA4 |
| PENTOBARBITAL | Hypnotics and Sedatives | CHRNA7 |
| PENTOBARBITAL | Hypnotics and Sedatives | GABRA1 |
| PENTOBARBITAL | Hypnotics and Sedatives | GABRA2 |
| PENTOBARBITAL | Hypnotics and Sedatives | GABRA3 |
| PENTOBARBITAL | Hypnotics and Sedatives | GABRA4 |
| PENTOBARBITAL | Hypnotics and Sedatives | GABRA5 |
| PENTOBARBITAL | Hypnotics and Sedatives | GABRA6 |
| PENTOBARBITAL | Hypnotics and Sedatives | GRIA2 |
| PENTOBARBITAL | Hypnotics and Sedatives | GRIK2 |
| PENTOLINIUM | Antihypertensive Agents | CHRNA10 |
| PERGOLIDE | Antiparkinson Agents | DRD1 |
| PERGOLIDE | Antiparkinson Agents | DRD2 |
| PERHEXILINE | Antianginal Agents; Vasodilator Agents | CPT1A |
| PERHEXILINE | Antianginal Agents; Vasodilator Agents | CPT2 |
| PERINDOPRIL | Antihypertensive Agents | ACE |
| PERPHENAZINE | Antipsychotic Agents | DRD1 |
| PERPHENAZINE | Antipsychotic Agents | DRD2 |
| PHENACEMIDE | Anticonvulsants | SCN1A |
| PHENDIMETRAZINE | Appetite Depressants | ADRA1A |
| PHENDIMETRAZINE | Appetite Depressants | ADRA1B |
| PHENELZINE | Antidepressive Agents | MAOA |
| PHENELZINE | Antidepressive Agents | MAOB |

TABLE 2-continued

| Drug Name | Indication(s) | Gene |
|---|---|---|
| PHENFORMIN | Hypoglycemic Agents | PRKAA1 |
| PHENINDIONE | Anticoagulants | VKORC1 |
| PHENIRAMINE | Anti-Allergic Agents | HRH1 |
| PHENMETRAZINE | Appetite Depressants | SLC6A2 |
| PHENMETRAZINE | Appetite Depressants | SLC6A3 |
| PHENOBARBITAL | Anticonvulsants; Hypnotics and Sedatives | CHRNA4 |
| PHENOBARBITAL | Anticonvulsants; Hypnotics and Sedatives | CHRNA7 |
| PHENOBARBITAL | Anticonvulsants; Hypnotics and Sedatives | GABRA1 |
| PHENOBARBITAL | Anticonvulsants; Hypnotics and Sedatives | GABRA2 |
| PHENOBARBITAL | Anticonvulsants; Hypnotics and Sedatives | GABRA3 |
| PHENOBARBITAL | Anticonvulsants; Hypnotics and Sedatives | GABRA4 |
| PHENOBARBITAL | Anticonvulsants; Hypnotics and Sedatives | GABRA5 |
| PHENOBARBITAL | Anticonvulsants; Hypnotics and Sedatives | GABRA6 |
| PHENOBARBITAL | Anticonvulsants; Hypnotics and Sedatives | GRIA1 |
| PHENOBARBITAL | Anticonvulsants; Hypnotics and Sedatives | GRIA2 |
| PHENOBARBITAL | Anticonvulsants; Hypnotics and Sedatives | GRIK2 |
| PHENOXYBENZAMINE | Anticonvulsants; Hypnotics and Sedatives | ADRA1A |
| PHENPROCOUMON | Anticoagulants | VKORC1 |
| PHENTERMINE | Appetite Depressants | SLC6A2 |
| PHENTERMINE | Appetite Depressants | SLC6A3 |
| PHENTERMINE | Appetite Depressants | SLC6A4 |
| PHENTOLAMINE | Antihypertensive Agents | ADRA2A |
| PHENYLBUTAZONE | NSAID | PTGIS |
| PHENYLBUTAZONE | NSAID | PTGS2 |
| PHENYLPROPANOLAMINE | Appetite Depressants; Nasal Decongestants | ADRA1A |
| PHENYLPROPANOLAMINE | Appetite Depressants; Nasal Decongestants | ADRA2A |
| PHENYTOIN | Anticonvulsants | SCN1A |
| PHENYTOIN | Anticonvulsants | SCN5A |
| PHYTONADIONE | Antifibrinolytic Agents | GGCX |
| PICROTOXIN | Central Nervous System Stimulants; Convulsants | GABRA1 |
| PICROTOXIN | Central Nervous System Stimulants; Convulsants | GABRR1 |
| PIMOZIDE | Antidyskinetics; Antipsychotic Agents | DRD2 |
| PINDOLOL | Antihypertensive Agents | ADRB1 |
| PINDOLOL | Antihypertensive Agents | ADRB2 |
| PIPECURONIUM | Muscle Relaxants | CHRNA2 |
| PIRENZEPINE | GI Anti-Ulcer Agents, anticholinergic; Antispasmodics | CHRM1 |
| PODOFILOX | Antineoplastic Agents, Phytogenic; Keratolytic Agents | TOP2A |
| POLYTHIAZIDE | Antihypertensive Agents; Diuretics | SLC12A3 |
| PRACTOLOL | Anti-Arrhythmia Agents | ADRB1 |
| PRALATREXATE | Antineoplastic Agents | DHFR |
| PRANLUKAST | Anti-Asthmatic Agents | CYSLTR1 |
| PRAZEPAM | Anti-anxiety Agents; Hypnotics and Sedatives | GABRA1 |
| PRAZEPAM | Anti-anxiety Agents; Hypnotics and Sedatives | GABRA2 |
| PRAZEPAM | Anti-anxiety Agents; Hypnotics and Sedatives | GABRA3 |
| PRAZEPAM | Anti-anxiety Agents; Hypnotics and Sedatives | GABRA5 |
| PRAZEPAM | Anti-anxiety Agents; Hypnotics and Sedatives | GABRB1 |
| PRAZEPAM | Anti-anxiety Agents; Hypnotics and Sedatives | GABRB2 |
| PRAZEPAM | Anti-anxiety Agents; Hypnotics and Sedatives | GABRB3 |
| PRAZEPAM | Anti-anxiety Agents; Hypnotics and Sedatives | GABRD |

TABLE 2-continued

| Exemplary Drugs with Disease Indications and Gene Identifier for the Target Protein | | |
|---|---|---|
| Drug Name | Indication(s) | Gene |
| PRAZEPAM | Anti-anxiety Agents; Hypnotics and Sedatives | GABRE |
| PRAZEPAM | Anti-anxiety Agents; Hypnotics and Sedatives | GABRG1 |
| PRAZEPAM | Anti-anxiety Agents; Hypnotics and Sedatives | GABRG2 |
| PRAZEPAM | Anti-anxiety Agents; Hypnotics and Sedatives | GABRG3 |
| PRAZEPAM | Anti-anxiety Agents; Hypnotics and Sedatives | GABRP |
| PRAZEPAM | Anti-anxiety Agents; Hypnotics and Sedatives | GABRR1 |
| PRAZEPAM | Anti-anxiety Agents; Hypnotics and Sedatives | GABRR2 |
| PRAZEPAM | Anti-anxiety Agents; Hypnotics and Sedatives | GABRR3 |
| PRAZOSIN | Antihypertensive Agents; antispasmodics | ADRA1A |
| PRAZOSIN | Antihypertensive Agents; antispasmodics | ADRA1B |
| PRAZOSIN | Antihypertensive Agents; antispasmodics | ADRA1D |
| PREDNICARBATE | Anti-Inflammatory Agents; Corticosteroids | NR3C1 |
| PRIMIDONE | Anticonvulsants | CHRNA4 |
| PRIMIDONE | Anticonvulsants | CHRNA7 |
| PRIMIDONE | Anticonvulsants | GABRA1 |
| PRIMIDONE | Anticonvulsants | GABRA2 |
| PRIMIDONE | Anticonvulsants | GABRA3 |
| PRIMIDONE | Anticonvulsants | GABRA4 |
| PRIMIDONE | Anticonvulsants | GABRA5 |
| PRIMIDONE | Anticonvulsants | GABRA6 |
| PRIMIDONE | Anticonvulsants | GRIA2 |
| PRIMIDONE | Anticonvulsants | GRIK2 |
| PROBENECID | Uricosuric Agents | SLC22A11 |
| PROBENECID | Uricosuric Agents | SLC22A8 |
| PROCAINAMIDE | Anti-Arrhythmia Agents | SCN5A |
| PROCAINE | Anesthetics, Local | SCN10A |
| PROCATEROL | Bronchodilator Agents | ADRB2 |
| PROCYCLIDINE | Antidyskinetics; Antiparkinson Agents | CHRM1 |
| PROCYCLIDINE | Antidyskinetics; Antiparkinson Agents | CHRM2 |
| PROCYCLIDINE | Antidyskinetics; Antiparkinson Agents | CHRM4 |
| PROGABIDE | Anticonvulsants | GABBR1 |
| PROGABIDE | Anticonvulsants | GABRA1 |
| PROMAZINE | Antiemetics; Antipsychotic Agents | ADRA1A |
| PROMAZINE | Antiemetics; Antipsychotic Agents | ADRA1B |
| PROMAZINE | Antiemetics; Antipsychotic Agents | ADRA1D |
| PROMAZINE | Antiemetics; Antipsychotic Agents | CHRM1 |
| PROMAZINE | Antiemetics; Antipsychotic Agents | CHRM2 |
| PROMAZINE | Antiemetics; Antipsychotic Agents | CHRM3 |
| PROMAZINE | Antiemetics; Antipsychotic Agents | CHRM4 |
| PROMAZINE | Antiemetics; Antipsychotic Agents | CHRM5 |
| PROMAZINE | Antiemetics; Antipsychotic Agents | DRD1 |
| PROMAZINE | Antiemetics; Antipsychotic Agents | DRD2 |
| PROMAZINE | Antiemetics; Antipsychotic Agents | DRD4 |
| PROMAZINE | Antiemetics; Antipsychotic Agents | HRH1 |
| PROMAZINE | Antiemetics; Antipsychotic Agents | HTR2A |
| PROMAZINE | Antiemetics; Antipsychotic Agents | HTR2C |
| PROMETHAZINE | Hypnotics and Sedatives; Anti-anxiety agents; Anti-allergic Agents | CHRM1 |
| PROMETHAZINE | Hypnotics and Sedatives; Anti-anxiety agents; Anti-allergic Agents | CHRM2 |
| PROMETHAZINE | Hypnotics and Sedatives; Anti-anxiety agents; Anti-allergic Agents | CHRM3 |
| PROMETHAZINE | Hypnotics and Sedatives; Anti-anxiety agents; Anti-allergic Agents | CHRM4 |
| PROMETHAZINE | Hypnotics and Sedatives; Anti-anxiety agents; Anti-allergic Agents | CHRM5 |
| PROMETHAZINE | Hypnotics and Sedatives; Anti-anxiety agents; Anti-allergic Agents | HRH1 |
| PROPANTHELINE | GI Anti-Ulcer Agents, anticholinergic; Antispasmodics | CHRM1 |

TABLE 2-continued

Exemplary Drugs with Disease Indications and Gene Identifier for the Target Protein

| Drug Name | Indication(s) | Gene |
|---|---|---|
| PROPARACAINE | Anesthetics, Local | SCN10A |
| PROPERICIAZINE | Antipsychotic Agents | ADRA1A |
| PROPERICIAZINE | Antipsychotic Agents | ADRA1B |
| PROPERICIAZINE | Antipsychotic Agents | ADRA1D |
| PROPIOMAZINE | Hypnotics and Sedatives | ADRA1A |
| PROPIOMAZINE | Hypnotics and Sedatives | ADRA1B |
| PROPIOMAZINE | Hypnotics and Sedatives | ADRA1D |
| PROPIOMAZINE | Hypnotics and Sedatives | CHRM1 |
| PROPIOMAZINE | Hypnotics and Sedatives | CHRM2 |
| PROPIOMAZINE | Hypnotics and Sedatives | CHRM3 |
| PROPIOMAZINE | Hypnotics and Sedatives | CHRM4 |
| PROPIOMAZINE | Hypnotics and Sedatives | CHRM5 |
| PROPIOMAZINE | Hypnotics and Sedatives | DRD1 |
| PROPIOMAZINE | Hypnotics and Sedatives | DRD2 |
| PROPIOMAZINE | Hypnotics and Sedatives | DRD4 |
| PROPIOMAZINE | Hypnotics and Sedatives | HRH1 |
| PROPIOMAZINE | Hypnotics and Sedatives | HTR2A |
| PROPIOMAZINE | Hypnotics and Sedatives | HTR2C |
| PROPOXYPHENE | Analgesics, Opioid; Antitussive Agents | OPRD1 |
| PROPOXYPHENE | Analgesics, Opioid; Antitussive Agents | OPRK1 |
| PROPOXYPHENE | Analgesics, Opioid; Antitussive Agents | OPRM1 |
| PROPYLTHIOURACIL | Antithyroid Agents | TPO |
| PROTRIPTYLINE | Antidepressive Agents, Tricyclic | SLC6A2 |
| PROTRIPTYLINE | Antidepressive Agents, Tricyclic | SLC6A4 |
| PYRIDOSTIGMINE | Antimyasthenics | ACHE |
| QUAZEPAM | Hypnotics and Sedatives | GABRA1 |
| QUAZEPAM | Hypnotics and Sedatives | GABRA2 |
| QUAZEPAM | Hypnotics and Sedatives | GABRA3 |
| QUAZEPAM | Hypnotics and Sedatives | GABRA5 |
| QUAZEPAM | Hypnotics and Sedatives | GABRB1 |
| QUAZEPAM | Hypnotics and Sedatives | GABRB3 |
| QUAZEPAM | Hypnotics and Sedatives | GABRD |
| QUAZEPAM | Hypnotics and Sedatives | GABRE |
| QUAZEPAM | Hypnotics and Sedatives | GABRG1 |
| QUAZEPAM | Hypnotics and Sedatives | GABRG2 |
| QUAZEPAM | Hypnotics and Sedatives | GABRG3 |
| QUAZEPAM | Hypnotics and Sedatives | GABRP |
| QUAZEPAM | Hypnotics and Sedatives | GABRR1 |
| QUAZEPAM | Hypnotics and Sedatives | GABRR2 |
| QUAZEPAM | Hypnotics and Sedatives | GABRR3 |
| QUINESTROL | Hormone Replacement Agents | ESR1 |
| QUINETHAZONE | Antihypertensive Agents; Diuretics | SLC12A3 |
| QUINIDINE | Anti-Arrhythmia Agents | SCN5A |
| RALOXIFENE | Hormone Replacement Agents | ESR1 |
| RALOXIFENE | Hormone Replacement Agents | ESR2 |
| RAMIPRIL | Antihypertensive Agents | ACE |
| REMIKIREN | Antihypertensive Agents | REN |
| REMOXIPRIDE | Antipsychotic Agents | DRD2 |
| RESCINNAMINE | Antihypertensive Agents | ACE |
| RESERPINE | Antihypertensive Agents; Antipsychotic Agents | SLC18A2 |
| RIMEXOLONE | Anti-Inflammatory Agents; Corticosteroids | NR3C1 |
| RIMEXOLONE | Anti-Inflammatory Agents; Corticosteroids | NR3C1 |
| RISEDRONATE | Bisphosphonates | FDPS |
| RISPERIDONE | Antipsychotic Agents | DRD2 |
| RISPERIDONE | Antipsychotic Agents | HTR2A |
| RITODRINE | Tocolytic Agents | ADRB2 |
| RIZATRIPTAN | Anti-migraine Agents | HTR1B |
| RIZATRIPTAN | Anti-migraine Agents | HTR1D |
| SALICYLIC ACID | Keratolytic Agents | PTGS1 |
| SALICYLIC ACID | Keratolytic Agents | PTGS2 |
| SALSALATE | Anti-Inflammatory Agents, Non-Steroidal | PTGS1 |
| SALSALATE | Anti-Inflammatory Agents, Non-Steroidal | PTGS2 |
| SAPRISARTAN | Antihypertensive Agents | AGTR1 |
| SAPROPTERIN | PKU-treatment | PAH |
| SCOPOLAMINE | Adjuvants, Anesthesia; Antispasmodics; Mydriatics | CHRM1 |
| SECOBARBITAL | Adjuvants, anesthesia; Hypnotics and Sedatives | CHRNA4 |

TABLE 2-continued

| Drug Name | Indication(s) | Gene |
|---|---|---|
| SECOBARBITAL | Adjuvants, anesthesia; Hypnotics and Sedatives | CHRNA7 |
| SECOBARBITAL | Adjuvants, anesthesia; Hypnotics and Sedatives | GABRA1 |
| SECOBARBITAL | Adjuvants, anesthesia; Hypnotics and Sedatives | GABRA2 |
| SECOBARBITAL | Adjuvants, anesthesia; Hypnotics and Sedatives | GABRA3 |
| SECOBARBITAL | Adjuvants, anesthesia; Hypnotics and Sedatives | GABRA4 |
| SECOBARBITAL | Adjuvants, anesthesia; Hypnotics and Sedatives | GABRA5 |
| SECOBARBITAL | Adjuvants, anesthesia; Hypnotics and Sedatives | GABRA6 |
| SECOBARBITAL | Adjuvants, anesthesia; Hypnotics and Sedatives | GRIA2 |
| SECOBARBITAL | Adjuvants, anesthesia; Hypnotics and Sedatives | GRIK2 |
| SEVOFLURANE | Anesthetics, Inhalation | ATP2C1 |
| SEVOFLURANE | Anesthetics, Inhalation | ATP5D |
| SEVOFLURANE | Anesthetics, Inhalation | GABRA1 |
| SEVOFLURANE | Anesthetics, Inhalation | GLRA1 |
| SEVOFLURANE | Anesthetics, Inhalation | GRIA1 |
| SEVOFLURANE | Anesthetics, Inhalation | KCNA1 |
| SEVOFLURANE | Anesthetics, Inhalation | MT-ND1 |
| SODIUM TETRADECYL SULFATE | Sclerosing Agents | PROC |
| SOTALOL | Anti-Arrhythmia Agents | KCNH2 |
| SPIRAPRIL | Antihypertensive Agents | ACE |
| SUCCINYLCHOLINE | Muscle Relaxants, Skeletal | CHRM1 |
| SULFINPYRAZONE | Uricosuric Agents | ABCC1 |
| SULFINPYRAZONE | Uricosuric Agents | ABCC2 |
| SULINDAC | NSAID | PTGS1 |
| SULINDAC | NSAID | PTGS2 |
| SULPIRIDE | Antidepressive Agents, Second-Generation; Antipsychotic Agents | DRD2 |
| SUPROFEN | NSAID | PTGS1 |
| SUPROFEN | NSAID | PTGS2 |
| TACRINE | Nootropic Agents | ACHE |
| TALBUTAL | Analgesics | CHRNA4 |
| TALBUTAL | Analgesics | CHRNA7 |
| TALBUTAL | Analgesics | GABRA1 |
| TALBUTAL | Analgesics | GABRA2 |
| TALBUTAL | Analgesics | GABRA3 |
| TALBUTAL | Analgesics | GABRA4 |
| TALBUTAL | Analgesics | GABRA5 |
| TALBUTAL | Analgesics | GABRA6 |
| TALBUTAL | Analgesics | GRIA2 |
| TALBUTAL | Analgesics | GRIK2 |
| TAMOXIFEN | Antineoplastic Agents, Hormonal | ESR1 |
| TAMOXIFEN | Antineoplastic Agents, Hormonal | ESR2 |
| TASOSARTAN | Antihypertensive Agents | AGTR1 |
| TEMAZEPAM | Hypnotics and Sedatives | BZRP |
| TEMAZEPAM | Hypnotics and Sedatives | GABRA1 |
| TEMAZEPAM | Hypnotics and Sedatives | GABRA2 |
| TEMAZEPAM | Hypnotics and Sedatives | GABRA3 |
| TEMAZEPAM | Hypnotics and Sedatives | GABRA4 |
| TEMAZEPAM | Hypnotics and Sedatives | GABRA5 |
| TEMAZEPAM | Hypnotics and Sedatives | GABRA6 |
| TEMAZEPAM | Hypnotics and Sedatives | GABRB1 |
| TEMAZEPAM | Hypnotics and Sedatives | GABRB2 |
| TEMAZEPAM | Hypnotics and Sedatives | GABRB3 |
| TEMAZEPAM | Hypnotics and Sedatives | GABRD |
| TEMAZEPAM | Hypnotics and Sedatives | GABRE |
| TEMAZEPAM | Hypnotics and Sedatives | GABRG1 |
| TEMAZEPAM | Hypnotics and Sedatives | GABRG2 |
| TEMAZEPAM | Hypnotics and Sedatives | GABRG3 |
| TEMAZEPAM | Hypnotics and Sedatives | GABRP |
| TEMAZEPAM | Hypnotics and Sedatives | GABRQ |
| TEMAZEPAM | Hypnotics and Sedatives | GABRR1 |
| TEMAZEPAM | Hypnotics and Sedatives | GABRR2 |
| TEMAZEPAM | Hypnotics and Sedatives | GABRR3 |
| TENIPOSIDE | Antineoplastic Agents | TOP2A |
| TENOXICAM | NSAID | PTGS1 |
| TENOXICAM | NSAID | PTGS2 |

TABLE 2-continued

| Exemplary Drugs with Disease Indications and Gene Identifier for the Target Protein | | |
|---|---|---|
| Drug Name | Indication(s) | Gene |
| TERAZOSIN | Antineoplastic Agents; antihypertensive agents | ADRA1A |
| TERAZOSIN | Antineoplastic Agents; antihypertensive agents | ADRA1B |
| TERAZOSIN | Antineoplastic Agents; antihypertensive agents | ADRA1D |
| TERBUTALINE | Bronchodilator Agents; Tocolytic Agents | ADRB2 |
| TERFENADINE | Anti-Allergic Agents | HRH1 |
| TESTOLACTONE | Antineoplastic Agents, Hormonal | CYP19A1 |
| THIAMYLAL | Anesthetics, Intravenous | GABRA1 |
| THIAMYLAL | Anesthetics, Intravenous | KCNJ11 |
| THIAMYLAL | Anesthetics, Intravenous | KCNJ8 |
| THIETHYLPERAZINE | Antiemetics | CHRM1 |
| THIETHYLPERAZINE | Antiemetics | CHRM2 |
| THIETHYLPERAZINE | Antiemetics | CHRM3 |
| THIETHYLPERAZINE | Antiemetics | CHRM4 |
| THIETHYLPERAZINE | Antiemetics | CHRM5 |
| THIETHYLPERAZINE | Antiemetics | DRD1 |
| THIETHYLPERAZINE | Antiemetics | DRD2 |
| THIETHYLPERAZINE | Antiemetics | DRD4 |
| THIETHYLPERAZINE | Antiemetics | HRH1 |
| THIETHYLPERAZINE | Antiemetics | HTR2A |
| THIETHYLPERAZINE | Antiemetics | HTR2C |
| THIOPENTAL | Anesthetics, Intravenous | CHRNA4 |
| THIOPENTAL | Anesthetics, Intravenous | CHRNA7 |
| THIOPENTAL | Anesthetics, Intravenous | GABRA1 |
| THIOPENTAL | Anesthetics, Intravenous | GABRA2 |
| THIOPENTAL | Anesthetics, Intravenous | GABRA3 |
| THIOPENTAL | Anesthetics, Intravenous | GABRA4 |
| THIOPENTAL | Anesthetics, Intravenous | GABRA5 |
| THIOPENTAL | Anesthetics, Intravenous | GABRA6 |
| THIOPENTAL | Anesthetics, Intravenous | GRIA2 |
| THIOPENTAL | Anesthetics, Intravenous | GRIK2 |
| THIORIDAZINE | Antipsychotic Agents | ADRA1A |
| THIORIDAZINE | Antipsychotic Agents | DRD1 |
| THIORIDAZINE | Antipsychotic Agents | DRD2 |
| THIORIDAZINE | Antipsychotic Agents | HTR2A |
| TIAGABINE | Anticonvulsants | ABAT |
| TIAGABINE | Anticonvulsants | SLC6A1 |
| TIAPROFENIC ACID | NSAID | PTGS2 |
| TICLOPIDINE | Platelet Aggregation Inhibitors | P2RY12 |
| TILUDRONATE | Bisphosphonates | PTPN1 |
| TIROFIBAN | Platelet Aggregation Inhibitors | ITGA2B |
| TIROFIBAN | Platelet Aggregation Inhibitors | ITGB3 |
| TOCAINIDE | Anti-Arrhythmia Agents | SCN5A |
| TOLAZAMIDE | Hypoglycemic Agents | KCNJ1 |
| TOLAZOLINE | Antihypertensive Agents | ADRA1A |
| TOLBUTAMIDE | Hypoglycemic Agents | KCNJ1 |
| TOLCAPONE | Antiparkinson Agents | COMT |
| TOLMETIN | NSAID | PTGS1 |
| TOLMETIN | NSAID | PTGS2 |
| TOPIRAMATE | Anticonvulsants; anti-migraine agents | CA2 |
| TOPIRAMATE | Anticonvulsants; anti-migraine agents | CA4 |
| TOPIRAMATE | Anticonvulsants; anti-migraine agents | GABRA1 |
| TOPIRAMATE | Anticonvulsants; anti-migraine agents | GRIK1 |
| TOPIRAMATE | Anticonvulsants; anti-migraine agents | SCN1A |
| TORASEMIDE | Antihypertensive Agents; Diuretics | SLC12A1 |
| TRANYLCYPROMINE | Antidepressive Agents | MAOA |
| TRANYLCYPROMINE | Antidepressive Agents | MAOB |
| TREPROSTINIL | Antihypertensive Agents; Antithrombotic Agents | P2RY12 |
| TREPROSTINIL | Antihypertensive Agents; Antithrombotic Agents | PPARG |
| TRIAMTERENE | Antihypertensive Agents; Diuretics | SCNN1A |
| TRIAMTERENE | Antihypertensive Agents; Diuretics | SCNN1B |
| TRIAMTERENE | Antihypertensive Agents; Diuretics | SCNN1D |
| TRIAMTERENE | Antihypertensive Agents; Diuretics | SCNN1G |
| TRICHLORMETHIAZIDE | Antihypertensive Agents; Diuretics | CA1 |
| TRICHLORMETHIAZIDE | Antihypertensive Agents; Diuretics | CA2 |
| TRICHLORMETHIAZIDE | Antihypertensive Agents; Diuretics | CA4 |

TABLE 2-continued

Exemplary Drugs with Disease Indications and Gene Identifier for the Target Protein

| Drug Name | Indication(s) | Gene |
|---|---|---|
| TRICHLORMETHIAZIDE | Antihypertensive Agents; Diuretics | KCNMA1 |
| TRICHLORMETHIAZIDE | Antihypertensive Agents; Diuretics | SLC12A1 |
| TRIDIHEXETHYL | GI Anti-Ulcer Agents, anticholinergic; Antispasmodics | CHRM1 |
| TRIDIHEXETHYL | GI Anti-Ulcer Agents, anticholinergic; Antispasmodics | CHRM2 |
| TRIDIHEXETHYL | GI Anti-Ulcer Agents, anticholinergic; Antispasmodics | CHRM3 |
| TRIFLUOPERAZINE | Antiemetics; Antipsychotic Agents | ADRA1A |
| TRIFLUOPERAZINE | Antiemetics; Antipsychotic Agents | DRD1IP |
| TRIFLUOPERAZINE | Antiemetics; Antipsychotic Agents | DRD2 |
| TRIFLUPROMAZINE | Antiemetics; Antipsychotic Agents | CHRM1 |
| TRIFLUPROMAZINE | Antiemetics; Antipsychotic Agents | CHRM2 |
| TRIFLUPROMAZINE | Antiemetics; Antipsychotic Agents | DRD1 |
| TRIFLUPROMAZINE | Antiemetics; Antipsychotic Agents | DRD2 |
| TRIFLUPROMAZINE | Antiemetics; Antipsychotic Agents | HTR2B |
| TRIHEXYPHENIDYL | Antiparkinson Agents | CHRM1 |
| TRILOSTANE | Antiadrenal | HSD3B1 |
| TRILOSTANE | Antiadrenal | HSD3B2 |
| TRIMEPRAZINE | Antipruritics | HRH1 |
| TRIMETHADIONE | Anticonvulsants | CACNA1G |
| TRIMETHAPHAN | Antihypertensive Agents; Vasodilator Agents | CHRNA10 |
| TRIMETREXATE | Antineoplastic Agents | DHFR |
| TRIMIPRAMINE | Antidepressive Agents, Tricyclic | SLC6A2 |
| TRIMIPRAMINE | Antidepressive Agents, Tricyclic | SLC6A4 |
| TRIPELENNAMINE | Anti-Allergic Agents | HRH1 |
| TRIPROLIDINE | Anti-Allergic Agents | HRH1 |
| TROPICAMIDE | Diagnostic Agents; Mydriatics | CHRM4 |
| TUBOCURARINE | Muscle Relaxants, Skeletal | CHRNA2 |
| VALPROIC ACID | Anticonvulsants | ABAT |
| VALRUBICIN | Antineoplastic Agents | TOP2A |
| WARFARIN | Anticoagulants | VKORC1 |
| WARFARIN | Anticoagulants | VKORC1L1 |
| VINBLASTINE | Antineoplastic Agents | TUBB2A |
| VINDESINE | Antineoplastic Agents | TUBB1 |
| XIMELAGATRAN | Anticoagulants | F2 |
| YOHIMBINE | Mydriatics; Anti-impotence Agents | ADRA2A |
| YOHIMBINE | Mydriatics; Anti-impotence Agents | ADRA2B |
| YOHIMBINE | Mydriatics; Anti-impotence Agents | ADRA2C |
| ZOPICLONE | Hypnotics and Sedatives | BZRP |
| ZOPICLONE | Hypnotics and Sedatives | GABRA1 |
| ZOPICLONE | Hypnotics and Sedatives | GABRA2 |
| ZOPICLONE | Hypnotics and Sedatives | GABRA3 |
| ZOPICLONE | Hypnotics and Sedatives | GABRA5 |
| ZUCLOPENTHIXOL | Antipsychotic Agents | DRD1 |
| ZUCLOPENTHIXOL | Antipsychotic Agents | DRD2 |
| ZUCLOPENTHIXOL | Antipsychotic Agents | DRD5 |

4. General Methods of Providing the Present Compounds

The compounds of this invention may be prepared or isolated in general by synthetic and/or semi-synthetic methods known to those skilled in the art for analogous compounds and by methods described in detail in the Examples, herein.

In the Schemes below, where a particular protecting group, leaving group, or transformation condition is depicted, one of ordinary skill in the art will appreciate that other protecting groups, leaving groups, and transformation conditions are also suitable and are contemplated. Such groups and transformations are described in detail in *March's Advanced Organic Chemistry: Reactions, Mechanisms, and Structure*, M. B. Smith and J. March, $5^{th}$ Edition, John Wiley & Sons, 2001, *Comprehensive Organic Transformations*, R. C. Larock, $2^{nd}$ Edition, John Wiley & Sons, 1999, and *Protecting Groups in Organic Synthesis*, T. W. Greene and P. G. M. Wuts, $3^{rd}$ edition, John Wiley & Sons, 1999, the entirety of each of which is hereby incorporated herein by reference.

As used herein, the phrase "oxygen protecting group" includes, for example, carbonyl protecting groups, hydroxyl protecting groups, etc. Hydroxyl protecting groups are well known in the art and include those described in detail in *Protecting Groups in Organic Synthesis*, T. W. Greene and P. G. M. Wuts, $3^{rd}$ edition, John Wiley & Sons, 1999, the entirety of each of which is herein incorporated by reference. Examples of suitable hydroxyl protecting groups include, but are not limited to, esters, allyl ethers, ethers, silyl ethers, alkyl ethers, arylalkyl ethers, and alkoxyalkyl ethers. Examples of such esters include formates, acetates, carbonates, and sulfonates. Specific examples include formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio) pentanoate, pivaloate (trimethylacetyl), crotonate, 4-methoxy-crotonate, benzoate, p-benylbenzoate, 2,4,6-trimethylbenzoate, carbonates such as methyl, 9-fluorenylmethyl, ethyl, 2,2,2-trichloroethyl, 2-(trimethylsilyl)ethyl, 2-(phenylsulfonyl)ethyl, vinyl, allyl, and p-nitrobenzyl. Examples of such silyl ethers include trimethylsilyl, triethylsilyl, t-butyldimethylsilyl, t-butyldiphenylsilyl, triisopropylsilyl, and other trialkylsilyl ethers. Alkyl ethers include methyl, benzyl, p-methoxybenzyl, 3,4-dimethoxybenzyl, trityl, t-butyl, allyl, and allyloxycarbonyl ethers or derivatives. Alkoxyalkyl ethers include acetals such as methoxymethyl, methylthiomethyl, (2-methoxyethoxy)methyl, benzyloxymethyl, beta-(trimethylsilyl)ethoxymethyl, and tetrahydropyranyl ethers. Examples of arylalkyl ethers include benzyl, p-methoxybenzyl (MPM), 3,4-dimethoxybenzyl, O-nitrobenzyl, p-nitrobenzyl, p-halobenzyl, 2,6-dichlorobenzyl, p-cyanobenzyl, and 2- and 4-picolyl.

Amino protecting groups are well known in the art and include those described in detail in *Protecting Groups in Organic Synthesis*, T. W. Greene and P. G. M. Wuts, 3rd edition, John Wiley & Sons, 1999, the entirety of each of which is herein incorporated by reference. Suitable amino protecting groups include, but are not limited to, aralkylamines, carbamates, cyclic imides, allyl amines, amides, and the like. Examples of such groups include t-butyloxycarbonyl (BOC), ethyloxycarbonyl, methyloxycarbonyl, trichloroethyloxycarbonyl, allyloxycarbonyl (Alloc), benzyloxocarbonyl (CBZ), allyl, phthalimide, benzyl (Bn), fluorenylmethylcarbonyl (Fmoc), formyl, acetyl, chloroacetyl, dichloroacetyl, trichloroacetyl, phenylacetyl, trifluoroacetyl, benzoyl, and the like.

In certain embodiments, compounds of the present invention are generally prepared according to Scheme 1 set forth below:

Scheme 1: Synthesis of Compounds of the Invention

Scheme 1: Synthesis of Compounds of the Invention

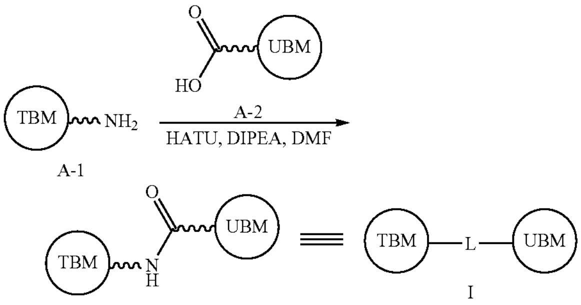

A-1

I

As depicted in Scheme 1, above, amine A-1 is coupled to acid A-2 using the coupling agent HATU in the presence of the base DIPEA in DMF to form a compound of the invention with a linker comprising an amide bond. The squiggly bond, ∿∿∿, represents the portion of the linker between TBM and the terminal amino group of A-1 or the portion of the linker between UBM and the terminal carboxyl group of A-2, respectively. Additionally, an amide bond can be formed using coupling reagents known in the art such as, but not limited to DCC, DIC, EDC, HBTU, HCTU, PyAOP, PyBrOP, BOP, BOP-Cl, DEPBT, T3P, TATU, TBTU, TNTU, TOTU, TPTU, TSTU, or TDBTU.

In certain embodiments, compounds of the present invention are generally prepared according to Scheme 2 set forth below:

Scheme 2: Synthesis of Compounds of the Invention

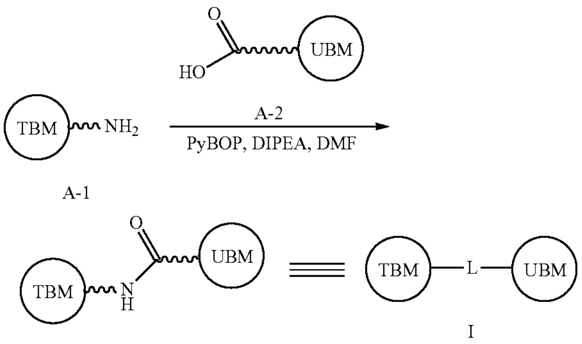

A-1

I

As depicted in Scheme 2, above, amine A-1 is coupled to acid A-2 using the coupling agent PyBOP in the presence of the base DIPEA in DMF to form a compound of the invention with a linker comprising an amide bond. The squiggly bond, ∿∿∿, represents the portion of the linker between TBM and the terminal amino group of A-1 or the portion of the linker between UBM and the terminal carboxyl group of A-2, respectively. Additionally, an amide bond can be formed using coupling reagents known in the art such as, but not limited to DCC, DIC, EDC, HBTU, HCTU, PyAOP, PyBrOP, BOP, BOP-Cl, DEPBT, T3P, TATU, TBTU, TNTU, TOTU, TPTU, TSTU, or TDBTU.

In certain embodiments, compounds of the present invention are generally prepared according to Scheme 3 set forth below:

Scheme 3: Synthesis of Compounds of the Invention

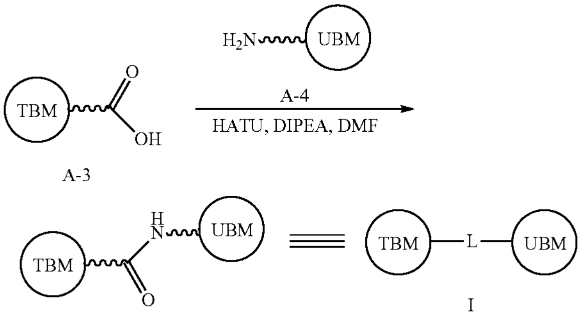

A-3

I

As depicted in Scheme 3, above, acid A-3 is coupled to amine A-4 using the coupling agent HATU in the presence of the base DIPEA in DMF to form a compound of the invention with a linker comprising an amide bond. The squiggly bond, ∿∿∿, represents the portion of the linker between TBM and the terminal carboxyl group of A-3 or the portion of the linker between UBM and the terminal amino group of A-4, respectively. Additionally, an amide bond can be formed using coupling reagents known in the art such as, but not limited to DCC, DIC, EDC, HBTU, HCTU, PyAOP, PyBrOP, BOP, BOP-Cl, DEPBT, T3P, TATU, TBTU, TNTU, TOTU, TPTU, TSTU, or TDBTU.

In certain embodiments, compounds of the present invention are generally prepared according to Scheme 4 set forth below:

Scheme 4: Synthesis of Compounds of the Invention

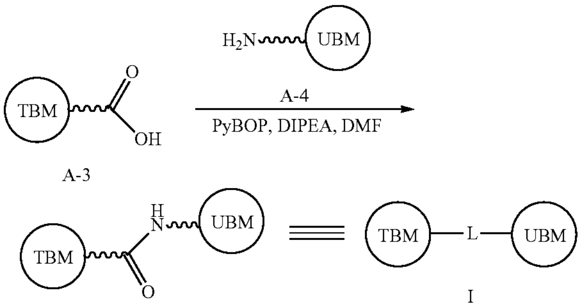

As depicted in Scheme 4, above, acid A-3 is coupled to amine A-4 using the coupling agent PyBOP in the presence of the base DIPEA in DMF to form a compound of the invention with a linker comprising an amide bond. The squiggly bond, ∿∿∿, represents the portion of the linker between TBM and the terminal carboxyl group of A-3 or the portion of the linker between UBM and the terminal amino group of A-4, respectively. Additionally, an amide bond can be formed using coupling reagents known in the art such as, but not limited to DCC, DIC, EDC, HBTU, HCTU, PyAOP, PyBrOP, BOP, BOP-Cl, DEPBT, T3P, TATU, TBTU, TNTU, TOTU, TPTU, TSTU, or TDBTU.

In certain embodiments, compounds of the present invention are generally prepared according to Scheme 5 set forth below:

Scheme 5: Synthesis of Compounds of the Invention

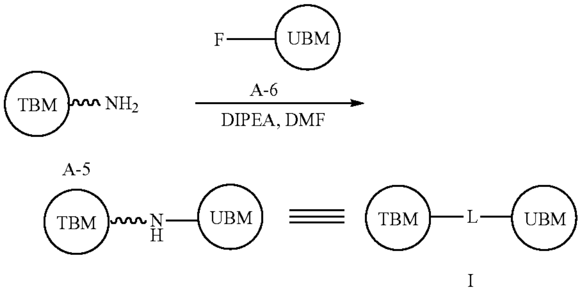

As depicted in Scheme 5, above, an $S_NAr$ displacement of fluoride A-6 by amine A-5 is effected in the presence of the base DIPEA in DMF to form a compound of the invention with a linker comprising a secondary amine. The squiggly bond, ∿∿∿, represents the portion of the linker between TBM and the terminal amino group of A-5.

In certain embodiments, compounds of the present invention are generally prepared according to Scheme 6 set forth below:

Scheme 6: Synthesis of Compounds of the Invention

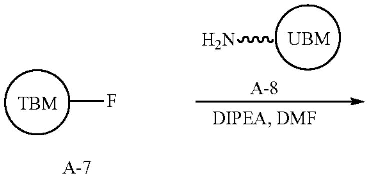

-continued

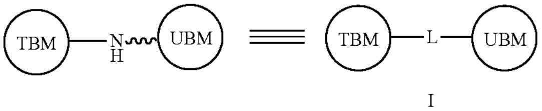

As depicted in Scheme 6, above, an $S_NAr$ displacement of fluoride A-7 by amine A-8 is effected in the presence of the base DIPEA in DMF to form a compound of the invention with a linker comprising a secondary amine. The squiggly bond, ∿∿∿, represents the portion of the linker between UBM and the terminal amino group of A-8.

In certain embodiments, compounds of the present invention are generally prepared according to Scheme 7 set forth below:

Scheme 7: Synthesis of Compounds of the Invention

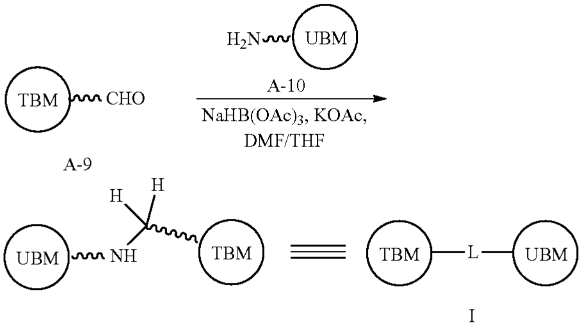

As depicted in Scheme 7, above, reductive amination of the mixture of aldehyde A-9 and amine A-10 is effected in the presence of $NaHB(OAc)_3$ and KOAc in DMF/THF to form a compound of the invention with a linker comprising a secondary amine. A linker comprising a tertiary amine can be prepared similarily using a secondary amine in place of the primary amine A-10. The squiggly bond, ∿∿∿, represents the portion of the linker between TBM and the terminal aldehyde of A-9 or the portion of the linker between UBM and the terminal amino group of A-10, respectively.

In certain embodiments, compounds of the present invention are generally prepared according to Scheme 8 set forth below:

Scheme 8: Synthesis of Compounds of the Invention

Scheme 8: Synthesis of Compounds of the Invention

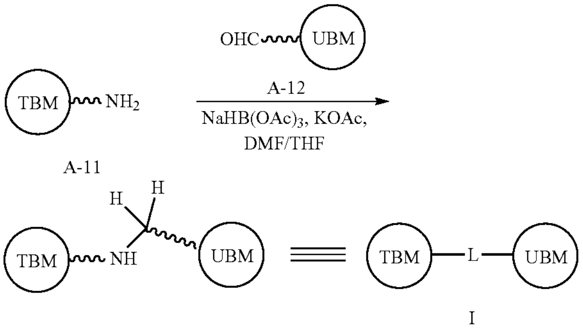

As depicted in Scheme 8, above, reductive amination of the mixture of aldehyde A-12 and amine A-11 is effected in the presence of $NaHB(OAc)_3$ and KOAc in DMF/THF to form a compound of the invention with a linker comprising a secondary amine. A linker comprising a tertiary amine can be prepared similarly using a secondary amine in place of the primary amine A-11. The squiggly bond, , represents the portion of the linker between TBM and the terminal amino group of A-11 or the portion of the linker between UBM and the terminal aldehyde of A-12, respectively.

One of skill in the art will appreciate that various functional groups present in compounds of the invention such as aliphatic groups, alcohols, carboxylic acids, esters, amides, aldehydes, halogens and nitriles can be interconverted by techniques well known in the art including, but not limited to reduction, oxidation, esterification, hydrolysis, partial oxidation, partial reduction, halogenation, dehydration, partial hydration, and hydration. See for example, "March's Advanced Organic Chemistry", $5^{th}$ Ed., Ed.: Smith, M. B. and March, J., John Wiley & Sons, New York: 2001, the entirety of each of which is herein incorporated by reference. Such interconversions may require one or more of the aforementioned techniques, and certain methods for synthesizing compounds of the invention are described below in the Exemplification.

5. Uses, Formulation and Administration

Pharmaceutically Acceptable Compositions

According to another embodiment, the invention provides a composition comprising a compound of this invention or a pharmaceutically acceptable derivative thereof and a pharmaceutically acceptable carrier, adjuvant, or vehicle. The amount of compound in compositions of this invention is such that is effective to measurably bind CRBN, or a mutant thereof, and a targeted protein, or a mutant thereof, in a biological sample or in a patient. In certain embodiments, a composition of this invention is formulated for administration to a patient in need of such composition. In some embodiments, a composition of this invention is formulated for oral administration to a patient.

The term "patient," as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

As used herein, the term "active metabolite or residue thereof" means that a metabolite or residue thereof is also a binder of CRBN, or a mutant thereof, or a targeted protein, or a mutant thereof.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that may be combined with the carrier materials to produce a composition in a single dosage form will vary depending upon the host treated, the particular mode of administration. Preferably, provided compositions should be formulated so that a dosage of between 0.01-100 mg/kg body weight/day of the compound can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

Presently described are compositions and methods that relate to the surprising and unexpected discovery that an E3 Ubiquitin Ligase protein, e.g., cereblon, ubiquitinates a target protein once it and the target protein are placed in proximity by a bifunctional or chimeric construct that binds the E3 Ubiquitin Ligase protein and the target protein. Accordingly the present invention provides such compounds and compositions comprising an E3 Ubiquintin Ligase binding moiety ("UBM") coupled to a protein target binding moiety ("TBM"), which result in the ubiquitination of a chosen target protein, which leads to degradation of the target protein by the proteasome.

Compounds and compositions described herein are generally useful for the modulation of targeted ubiquitination, especially with respect to a variety of polypeptides and other proteins, which are degraded and/or otherwise inhibited. In some embodiments the protein inhibited by the compounds and methods of the invention comprises those proteins listed in paragraph [00236].

Compounds and compositions described herein exhibit a broad range of pharmacological activities, consistent with the degradation/inhibition of targeted polypeptides.

Accordingly, compounds that bind CRBN are beneficial, especially those with selectivity over E3 ligases. Such compounds should deliver a pharmacological response that favorably treats one or more of the conditions described herein without the side-effects associated with the binding of E3 ligases.

Even though CRBN binders are known in the art, there is a continuing need to provide novel binders having more effective or advantageous pharmaceutically relevant properties. For example, compounds with increased activity, selectivity over other E3 ligases, and ADMET (absorption, distribution, metabolism, excretion, and/or toxicity) properties. Thus, in some embodiments, the present invention provides binders of CRBN which show selectivity over other E3 ligases.

The activity of a compound utilized in this invention as an binder of CRBN, or a mutant thereof, may be assayed in vitro, in vivo or in a cell line. In vitro assays include assays that determine the subsequent functional consequences, or activity of activated CRBN, or a mutant thereof. Alternate in vitro assays quantitate the ability of the compound to bind to CRBN. Binding may be measured by radiolabeling the compound prior to binding, isolating the compound/CRBN complex and determining the amount of radiolabel bound. Alternatively, compound binding may be determined by running a competition experiment where new compounds are incubated with CRBN bound to known radioligands. Representative in vitro and in vivo assays useful in assaying a CRBN binder include those described and disclosed in, Boichenko et al. J. Med. Chem. (2016) 59, 770-774 and Iconomou and Saunders Biochemical Journal (2016) 473, 4083-4101, each of which is herein incorporated by reference in its entirety. Detailed conditions for assaying a compound utilized in this invention as an binder of CRBN, or a mutant thereof, are set forth in the Examples below.

The term "Ubiquitin Ligase" refers to a family of proteins that facilitate the transfer of ubiquitin to a specific substrate protein, targeting the substrate protein for degradation. For example, cereblon is an E3 Ubiquitin Ligase protein that alone or in combination with an E2 ubiquitin-conjugating enzyme causes the attachment of ubiquitin to a lysine on a target protein, and subsequently targets the specific protein substrates for degradation by the proteasome. Thus, E3 ubiquitin ligase alone or in complex with an E2 ubiquitin conjugating enzyme is responsible for the transfer of ubiquitin to targeted proteins. In general, the ubiquitin ligase is involved in polyubiquitination such that a second ubiquitin is attached to the first; a third is attached to the second, and so forth. Polyubiquitination marks proteins for degradation by the proteasome. However, there are some ubiquitination events that are limited to mono-ubiquitination, in which only a single ubiquitin is added by the ubiquitin ligase to a substrate molecule. Mono-ubiquitinated proteins are not targeted to the proteasome for degradation, but may instead be altered in their cellular location or function, for example, via binding other proteins that have domains capable of binding ubiquitin. Further complicating matters, different lysines on ubiquitin can be targeted by an E3 to make chains. The most common lysine is Lys48 on the ubiquitin chain. This is the lysine used to make polyubiquitin, which is recognized by the proteasome.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

The description provides therapeutic compositions as described herein for effectuating the degradation of proteins of interest for the treatment or amelioration of a disease, e.g., cancer. In certain additional embodiments, the disease is multiple myeloma. As such, in another aspect, the description provides a method of ubiquitinating/degrading a target protein in a cell. In certain embodiments, the method comprises administering a bifunctional compound as described herein comprising, e.g., a UBM and a TBM, linked through a linker moiety, as otherwise described herein, wherein the UBM is coupled to the TBM and wherein the UBM recognizes a ubiquitin pathway protein (e.g., an ubiquitin ligase, preferably an E3 ubiquitin ligase such as, e.g., cereblon) and the TBM recognizes the target protein such that degradation of the target protein will occur when the target protein is placed in proximity to the ubiquitin ligase, thus resulting in degradation/inhibition of the effects of the target protein and the control of protein levels. The control of protein levels afforded by the present invention provides treatment of a disease state or condition, which is modulated through the target protein by lowering the level of that protein in the cell, e.g., cell of a patient. In certain embodiments, the method comprises administering an effective amount of a compound as described herein, optionally including a pharmaceutically acceptable excipient, carrier, adjuvant, another bioactive agent or combination thereof.

In additional embodiments, the description provides methods for treating or emeliorating a disease, disorder or symptom thereof in a subject or a patient, comprising administering to a subject in need thereof a composition comprising an effective amount, e.g., a therapeutically effective amount, of a compound as described herein or salt form thereof, and a pharmaceutically acceptable excipient, carrier, adjuvant, another bioactive agent or combination thereof, wherein the composition is effective for treating or ameliorating the disease or disorder or symptom thereof in the subject.

In another aspect, the description provides methods for identifying the effects of the degradation of proteins of interest in a biological system using compounds according to the present invention.

In another embodiment, the present invention is directed to a method of treating a human patient in need for a disease state or condition modulated through a protein where the degradation of that protein will produce a therapeutic effect in that patient, the method comprising administering to a patient in need an effective amount of a compound according to the present invention, optionally in combination with another bioactive agent. The disease state or condition may be a disease caused by a microbial agent or other exogenous agent such as a virus, bacteria, fungus, protozoa or other microbe or may be a disease state, which is caused by overexpression of a protein, which leads to a disease state and/or condition.

Disease states of conditions which may be treated using compounds according to the present invention include, for example, asthma, autoimmune diseases such as multiple sclerosis, various cancers, ciliopathies, cleft palate, diabetes, heart disease, hypertension, inflammatory bowel disease, mental retardation, mood disorder, obesity, refractive error, infertility, Angelman syndrome, Canavan disease, Coeliac disease, Charcot-Marie-Tooth disease, Cystic fibrosis, Duchenne muscular dystrophy, Haemochromatosis, Haemophilia, Klinefelter's syndrome, Neurofibromatosis, Phenylketonuria, Polycystic kidney disease, (PKD1) or 4 (PKD2) Prader-Willi syndrome, Sickle-cell disease, Tay-Sachs disease, Turner syndrome.

Further disease states or conditions which may be treated by compounds according to the present invention include Alzheimer's disease, Amyotrophic lateral sclerosis (Lou Gehrig's disease), Anorexia nervosa, Anxiety disorder, Atherosclerosis, Attention deficit hyperactivity disorder, Autism, Bipolar disorder, Chronic fatigue syndrome, Chronic obstructive pulmonary disease, Crohn's disease, Coronary heart disease, Dementia, Depression, Diabetes mellitus type 1, Diabetes mellitus type 2, Epilepsy, Guillain-Barré syndrome, Irritable bowel syndrome, Lupus, Metabolic syndrome, Multiple sclerosis, Myocardial infarction, Obesity, Obsessive-compulsive disorder, Panic disorder, Parkinson's disease, Psoriasis, Rheumatoid arthritis, Sarcoidosis, Schizophrenia, Stroke, Thromboangiitis obliterans, Tourette syndrome, Vasculitis.

Still additional disease states or conditions which can be treated by compounds according to the present invention include aceruloplasminemia, Achondrogenesis type II, achondroplasia, Acrocephaly, Gaucher disease type 2, acute intermittent porphyria, Canavan disease, Adenomatous Polyposis Coli, ALA dehydratase deficiency, adenylosuccinate lyase deficiency, Adrenogenital syndrome, Adrenoleukodystrophy, ALA-D porphyria, ALA dehydratase deficiency, Alkaptonuria, Alexander disease, Alkaptonuric ochronosis, alpha 1-antitrypsin deficiency, alpha-1 proteinase inhibitor, emphysema, amyotrophic lateral sclerosis Alström syndrome, Alexander disease, Amelogenesis imperfecta, ALA dehydratase deficiency, Anderson-Fabry disease, androgen insensitivity syndrome, Anemia Angiokeratoma Corporis Diffusum, Angiomatosis retinae (von Hippel-Lindau disease) Apert syndrome, Arachnodactyly (Marfan syndrome), Stickler syndrome, Arthrochalasis multiplex congenital (Ehlers-Danlos syndrome #arthrochalasia type) ataxia telangiectasia, Rett syndrome, primary pulmonary hypertension, Sandhoff disease, neurofibromatosis type II, Beare-Stevenson cutis gyrata syndrome, Mediterranean fever, familial, Benjamin syndrome, beta-thalassemia, Bilateral Acoustic Neurofibromatosis (neurofibromatosis type II), factor V Leiden thrombophilia, Bloch-Sulzberger syndrome (incontinentia pigmenti), Bloom syndrome, X-linked sideroblastic anemia, Bonnevie-Ullrich syndrome (Turner syndrome), Bourneville disease (tuberous sclerosis), prion disease, Birt-Hogg-Dub6 syndrome, Brittle bone disease (osteogenesis imperfecta), Broad Thumb-Hallux syndrome (Rubinstein-Taybi syndrome), Bronze Diabetes/Bronzed Cirrhosis (hemochromatosis), Bulbospinal muscular atrophy (Kennedy's disease), Burger-Grutz syndrome (lipoprotein lipase deficiency), CGD Chronic granulomatous disorder, Campomelic dysplasia, biotinidase deficiency, Cardiomyopathy (Noonan syndrome), Cri du chat, CAVD (congenital absence of the vas deferens), Caylor cardiofacial syndrome (CBAVD), CEP (congenital erythropoietic porphyria), cystic fibrosis, congenital hypothyroidism, Chondrodystrophy syndrome (achondroplasia), otospondylomegaepiphyseal dysplasia, Lesch-Nyhan syndrome, galactosemia, Ehlers-Danlos syndrome, Thanatophoric dysplasia, Coffin-Lowry syndrome, Cockayne syndrome, (familial adenomatous polyposis), Congenital erythropoietic porphyria, Congenital heart disease, Methemoglobinemia/Congenital methaemoglobinaemia, achondroplasia, X-linked sideroblastic anemia, Connective tissue disease, Conotruncal anomaly face syndrome, Cooley's Anemia (beta-thalassemia), Copper storage disease (Wilson's disease), Copper transport disease (Menkes disease), hereditary coproporphyria, Cowden syndrome, Craniofacial dysarthrosis (Crouzon syndrome), Creutzfeldt-Jakob disease (prion disease), Cockayne syndrome, Cowden syndrome, Curschmann-Batten-Steinert syndrome (myotonic dystrophy), Beare-Stevenson cutis gyrata syndrome, primary hyperoxaluria, spondyloepimetaphyseal dysplasia (Strudwick type), muscular dystrophy, Duchenne and Becker types (DBMD), Usher syndrome, Degenerative nerve diseases including de Grouchy syndrome and Dejerine-Sottas syndrome, developmental disabilities, distal spinal muscular atrophy, type V, androgen insensitivity syndrome, Diffuse Globoid Body Sclerosis (Krabbe disease), Di George's syndrome, Dihydrotestosterone receptor deficiency, androgen insensitivity syndrome, Down syndrome, Dwarfism, erythropoietic protoporphyria Erythroid 5-aminolevulinate synthetase deficiency, Erythropoietic porphyria, erythropoietic protoporphyria, erythropoietic uroporphyria, Friedreich's ataxia, familial paroxysmal polyserositis, porphyria cutanea tarda, familial pressure sensitive neuropathy, primary pulmonary hypertension (PPH), Fibrocystic disease of the pancreas, fragile X syndrome, galactosemia, genetic brain disorders, Giant cell hepatitis (Neonatal hemochromatosis), Gronblad-Strandberg syndrome (pseudoxanthoma elasticum), Gunther disease (congenital erythropoietic porphyria), haemochromatosis, Hallgren syndrome, sickle cell anemia, hemophilia, hepatoerythropoietic porphyria (HEP), Hippel-Lindau disease (von Hippel-Lindau disease), Huntington's disease, Hutchinson-Gilford progeria syndrome (progeria), Hyperandrogenism, Hypochondroplasia, Hypochromic anemia, Immune system disorders, including X-linked severe combined immunodeficiency, Insley-Astley syndrome, Jackson-Weiss syndrome, Joubert syndrome, Lesch-Nyhan syndrome, Jackson-Weiss syndrome, Kidney diseases, including hyperoxaluria, Klinefelter's syndrome, Kniest dysplasia, Lacunar dementia, Langer-Saldino achondrogenesis, ataxia telangiectasia, Lynch syndrome, Lysylhydroxylase deficiency, Machado-Joseph disease, Metabolic disorders, including Kniest dysplasia, Marfan syndrome, Movement disorders, Mowat-Wilson syndrome, cystic fibrosis, Muenke syndrome, Multiple neurofibromatosis, Nance-Insley syndrome, Nance-Sweeney chondrodysplasia, Niemann-Pick disease, Noack syndrome (Pfeiffer syndrome), Osler-Weber-Rendu disease, Peutz-Jeghers syndrome, Polycystic kidney disease, polyostotic fibrous dysplasia (McCune-Albright syndrome), Peutz-Jeghers syndrome, Prader-Labhart-Willi syndrome, hemochromatosis, primary hyperuricemia syndrome (Lesch-Nyhan syndrome), primary pulmonary hypertension, primary senile degenerative dementia, prion disease, progeria (Hutchinson Gilford Progeria Syndrome), progressive chorea, chronic hereditary (Huntington) (Huntington's disease), progressive muscular atrophy, spinal muscular atrophy, propionic acidemia, protoporphyria, proximal myotonic dystrophy, pulmonary arterial hypertension, PXE (pseudoxanthoma elasticum), Rb (retinoblastoma), Recklinghausen disease (neurofibromatosis type I), Recurrent polyserositis, Retinal disorders, Retinoblastoma, Rett syndrome, RFALS type 3, Ricker syndrome, Riley-Day syndrome, Roussy-Levy syndrome, severe achondroplasia with developmental delay and acanthosis nigricans (SADDAN), Li-Fraumeni syndrome, sarcoma, breast, leukemia, and adrenal gland (SBLA) syndrome, sclerosis tuberose (tuberous sclerosis), SDAT, SED congenital (spondyloepiphyseal dysplasia congenita), SED Strudwick (spondyloepimetaphyseal dysplasia, Strudwick type), SEDc (spondyloepiphyseal dysplasia congenita) SEMD, Strudwick type (spondyloepimetaphyseal dysplasia, Strudwick type), Shprintzen syndrome, Skin pigmentation disorders, Smith-Lemli-Opitz syndrome, South-African genetic porphyria (variegate porphyria), infantile-onset ascending hereditary spastic paralysis, Speech and communication disorders, sphingolipidosis, Tay-Sachs disease, spinocerebellar ataxia, Stickler syndrome, stroke, androgen insensitivity syndrome, tetrahydrobiopterin deficiency, beta-thalassemia, Thyroid disease, Tomaculous neuropathy (hereditary neuropathy with liability to pressure palsies), Treacher Collins syndrome, Triplo X syndrome (triple X syndrome), Trisomy 21 (Down syndrome), Trisomy X, VHL syndrome (von Hippel-Lindau disease), Vision impairment and blindness (Alström syndrome), Vrolik disease, Waardenburg syndrome, Warburg Sjo Fledelius Syndrome, Weissenbacher-Zweymuller syndrome, Wolf-Hirschhorn syndrome, Wolff Periodic disease, Weissenbacher-Zweymuller syndrome and Xeroderma pigmentosum, among others.

The term "neoplasia" or"cancer" is used throughout the specification to refer to the pathological process that results in the formation and growth of a cancerous or malignant neoplasm, i.e., abnormal tissue that grows by cellular proliferation, often more rapidly than normal and continues to grow after the stimuli that initiated the new growth cease. Malignant neoplasms show partial or complete lack of structural organization and functional coordination with the normal tissue and most invade surrounding tissues, metastasize to several sites, and are likely to recur after attempted removal and to cause the death of the patient unless adequately treated. As used herein, the term neoplasia is used to describe all cancerous disease states and embraces or encompasses the pathological process associated with malignant hematogenous, ascitic and solid tumors. Exemplary cancers which may be treated by the present compounds either alone or in combination with at least one additional anti-cancer agent include squamous-cell carcinoma, basal cell carcinoma, adenocarcinoma, hepatocellular carcinomas, and renal cell carcinomas, cancer of the bladder, bowel, breast, cervix, colon, esophagus, head, kidney, liver, lung, neck, ovary, pancreas, prostate, and stomach; leukemias; benign and malignant lymphomas, particularly Burkitt's lymphoma and Non-Hodgkin's lymphoma; benign and malignant melanomas; myeloproliferative diseases; sarcomas, including Ewing's sarcoma, hemangiosarcoma, Kaposi's sarcoma, liposarcoma, myosarcomas, peripheral neuroepithelioma, synovial sarcoma, gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, and Schwannomas; bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancer, melanoma; carcinosarcoma, Hodgkin's disease, Wilms' tumor and teratocarcinomas. Additional cancers which may be treated using compounds according to the present invention include, for example, T-lineage Acute lymphoblastic Leukemia (T-ALL), T-lineage lymphoblastic Lymphoma (T-LL), Peripheral T-cell lymphoma, Adult T-cell Leukemia, Pre-B ALL, Pre-B Lymphomas, Large B-cell Lymphoma, Burkitts Lymphoma, B-cell ALL, Philadelphia chromosome positive ALL and Philadelphia chromosome positive CML.

In some embodiments, the present invention provides a method for treating one or more disorders, wherein the disorders are selected from autoimmune disorders, inflammatory disorders, proliferative disorders, endocrine disorders, neurological disorders, and disorders associated with transplantation, said method comprising administering to a patient in need thereof, a pharmaceutical composition comprising an effective amount of a compound of the present invention, or a pharmaceutically acceptable salt thereof.

In some embodiments, compounds of the present invention induce the ubiquitination and degradation of a target protein selected from the group consisting of A1BG, A1CF, A2M, A2ML1, A3GALT2, A4GALT, A4GNT, AAAS, AACS, AADAC, AADACL2, AADACL3, AADACL4, AADAT, AAED1, AAGAB, AAK1, AAMDC, AAMP, AANAT, AAR2, AARD, AARS, AARS2, AARSD1, AASDH, AASDHPPT, AASS, AATF, AATK, AATK-AS1, ABAT, ABCA1, ABCA10, ABCA12, ABCA13, ABCA2, ABCA3, ABCA4, ABCA5, ABCA6, ABCA7, ABCA8, ABCA9, ABCB1, ABCB10, ABCB11, ABCB4, ABCB5, ABCB6, ABCB7, ABCB8, ABCB9, ABCC1, ABCC10, ABCC11, ABCC12, ABCC2, ABCC3, ABCC4, ABCC5, ABCC6, ABCC8, ABCC9, ABCD1, ABCD2, ABCD3, ABCD4, ABCE1, ABCF1, ABCF2, ABCF3, ABCG1, ABCG2, ABCG4, ABCG5, ABCG8, ABHD1, ABHD10, ABHD11, ABHD12, ABHD12B, ABHD13, ABHD14A, ABHD14A-ACY1, ABHD14B, ABHD15, ABHD16A, ABHD16B, ABHD17A, ABHD17B, ABHD17C, ABHD18, ABHD2, ABHD3, ABHD4, ABHD5, ABHD6, ABHD8, ABI1, ABI2, ABI3, ABI3BP, ABL1, ABL2, ABLIM1, ABLIM2, ABLIM3, ABO, ABR, ABRA, ABRACL, ABRAXAS1, ABRAXAS2, ABT1, ABTB1, ABTB2, AC001226.2, AC002094.3, AC002115.2, AC002310.4, AC002310.5, AC002429.2, AC002985.1, AC002996.1, AC003002.1, AC003002.2, AC003002.3, AC003002.4, AC003005.1, AC003006.1, AC003688.1, AC004076.1, AC004080.3, AC004223.3, AC004233.2, AC004556.1, AC004691.2, AC004706.4, AC004754.1, AC004805.1, AC004832.3, AC004922.1, AC004997.1, AC005020.2, AC005041.1, AC005154.6, AC005258.1, AC005324.3, AC005324.4, AC005520.1, AC005551.1, AC005670.2, AC005697.1, AC005702.2, AC005726.2, AC005779.2, AC005832.4, AC005833.1, AC005833.3, AC005837.2, AC005841.2, AC005885.1, AC005943.1, AC006030.1, AC006254.1, AC006269.1, AC006449.4, AC006486.1, AC006538.2, AC006978.2, AC007040.2, AC007192.1, AC007240.1, AC007325.1, AC007325.2, AC007325.4, AC007326.4, AC007375.2, AC007383.6, AC007537.5, AC007731.5, AC007906.2, AC007998.2, AC008073.3, AC008162.2, AC008393.2, AC008403.1, AC008481.3, AC008537.1, AC008560.1, AC008575.1, AC008575.2, AC008687.1, AC008687.4, AC008687.8, AC008695.1, AC008735.6, AC008750.8, AC008758.1, AC008758.4, AC008758.5, AC008758.6, AC008763.2, AC008763.3, AC008764.1, AC008764.4, AC008770.2, AC008770.3, AC008878.1, AC008878.2, AC008878.3, AC008982.1, AC008982.3, AC009014.1, AC009086.2, AC009119.2, AC009122.1, AC009133.6, AC009163.2, AC009163.4, AC009286.3, AC009336.2, AC009477.2, AC009690.1, AC009690.3, AC009779.3, AC010132.3, AC010255.3, AC010319.2, AC010323.1, AC010325.1, AC010326.2, AC010327.1, AC010422.3, AC010422.5, AC010422.6, AC010463.1, ACO10487.3, AC010522.1, ACO10531.1, AC010542.3, AC010547.4, AC010547.5, ACO10615.4, AC010616.1, AC010619.1, AC010646.1, AC010724.2, ACO11005.1, AC011043.1, AC011043.2, AC011195.2, AC011295.1, AC011346.1, AC011448.1, AC011452.1, AC011455.3, AC011455.4, AC011462.1, AC011473.4, AC011479.1, AC011498.4, AC011499.1, AC011511.1, AC011511.4, AC011530.1, AC011604.2, AC011841.1, AC012184.2, AC012254.2, AC012309.1, AC012314.1, AC012314.10, AC012314.11, AC012314.12, AC012314.4, AC012314.5, AC012314.6, AC012314.8, AC012531.3, AC012651.1, AC013269.1, AC013271.1, AC013394.1, AC013470.2, AC015688.5, AC015802.6, AC015813.2, AC017081.3, AC017081.4, AC017081.5, AC017083.4, AC018512.1, AC018523.2, AC018554.3, AC018630.6, AC018709.1, AC018755.2, AC018793.1, AC018793.2, AC018793.3, AC018793.4, AC018793.5, AC019117.3, AC020636.2, AC020909.1, AC020914.1, AC020915.1, AC020915.2, AC020915.6, AC020922.1, AC020934.3, AC021072.1, AC022016.2, AC022167.5, AC022335.1, AC022384.1, AC022400.6, AC022826.2, AC023055.1, AC023491.2, AC023509.3, AC024592.3, AC024940.1, AC024940.6, AC025165.3, AC025263.2, AC025283.2, AC025287.4, AC025594.2, AC026369.8, AC026398.1, AC026461.4, AC026464.1, AC026464.3, AC026464.4, AC026786.1, AC026954.2, AC027796.3, AC034102.2, AC036214.3, AC037459.1, AC037482.2, AC037482.3, AC040162.1, AC040162.4, AC044810.8, AC046185.1, AC048338.1, AC051649.2, AC053481.5, AC055811.2, AC058822.1, AC064853.2, AC064853.3, AC064853.4, AC064853.5, AC064853.6, AC067968.1, AC068234.1, AC068533.4, AC068547.1, AC068580.4, AC068631.2, AC068775.1, AC068775.2, AC068790.8, AC068896.1, AC068946.1, AC068987.5, AC069257.3, AC069368.1, AC069503.2, AC069544.2, AC072022.1, AC073082.1, AC073111.3, AC073111.5, AC073264.3, AC073508.2, AC073610.2, AC073610.3, AC073612.1, AC073896.1, AC074143.1, AC078927.1, AC079325.2, AC079447.1, AC079594.2, AC083800.1, AC083902.2, AC084337.2, AC087289.3, AC087498.1, AC087632.1, AC090004.1, AC090227.1, AC090360.1, AC090527.2, AC090958.3, AC091167.3, AC091167.7, AC091167.8, AC091304.7, AC091491.1, AC091551.1, AC091959.3, AC091980.2, AC092017.3, AC092042.3, AC092073.1, AC092111.3, AC092143.1, AC092329.3, AC092442.1, AC092587.1, AC092647.5, AC092718.3, AC092718.8, AC092821.1, AC092824.3, AC092835.1, AC093155.3, AC093227.3, AC093423.3, AC093525.1, AC093525.2, AC093668.1, AC093762.1, AC093762.2, AC093762.3, AC093899.2, AC096582.3, AC096887.1, AC097372.1, AC097495.1, AC097637.1, AC097662.2, AC098484.3, AC098650.1, AC098850.4, AC099329.3, AC099489.1, AC099518.3, AC099811.2, AC099850.2, AC100868.1, AC104109.3, AC1041511 AC104304.1, AC104452.1, AC104532.1, AC104534.3, AC104581.1, AC104581.3, AC104662.2, AC104836.1, AC105001.2, AC105052.1, AC106774.10, AC106774.5, AC106774.6, AC106774.7, AC106774.8, AC106774.9, AC106782.1, AC106886.5, AC107871.1, AC108488.2, AC108750.1, AC108941.2, AC109583.3, AC110275.1, AC12229.3, AC112484.1, AC113189.6, AC113189.9, AC113331.2, AC113554.2, AC114296.1, AC114490.2, AC115220.1, AC116366.3, AC116565.1, AC117457.1, AC118470.1, AC118553.2, AC119396.1, AC119674.2, AC120057.3, AC120114.5, AC124312.1, AC126755.2, AC127537.5, AC127537.6, AC127537.8, AC129492.3, AC131097.2, AC131160.1, AC133551.1, AC133555.3, AC134669.2, AC134772.2, AC135050.2, AC135068.1, AC135068.2, AC135068.3, AC135068.8, AC135178.2, AC135586.2, AC136352.3, AC136352.4, AC136428.1, AC136612.1, AC136616.1, AC136616.2, AC136616.3, AC137834.1, AC138517.2, AC138647.1, AC138696.1, AC138811.2, AC138894.1, AC138969.1, AC139530.2, AC139677.1, AC139677.2, AC140504.1, AC141272.1, AC142391.1, AC142525.4, AC145029.2, AC145212.1, AC145212.2, AC171558.1, AC171558.3, AC171558.5, AC171558.6, AC187653.1, AC207056.1, AC209232.1, AC209539.2, AC210544.1, AC213203.1, AC229888.1, AC229888.10, AC229888.2, AC229888.3, AC229888.4, AC229888.5, AC229888.6, AC229888.7, AC229888.8, AC229888.9, AC233282.1, AC233282.2, AC233723.1, AC233724.12, AC233724.16, AC233724.17, AC233724.18, AC233724.19, AC233724.20, AC233724.21, AC233724.6, AC233755.1, AC233755.2, AC233992.2, AC234301.1, AC234301.3, AC234635.1, AC234635.3, AC234635.4, AC234635.5, AC236040.1, AC239612.1, AC239618.1, AC239618.2, AC239618.3, AC239618.4, AC239618.5, AC239618.6, AC239618.7, AC239618.9, AC239799.1, AC240274.1, AC241401.1, AC241409.2, AC241410.1, AC241556.3, AC241556.4, AC241640.1, AC241640.2, AC241640.4, AC242528.1, AC242528.2, AC243547.3, AC243733.1, AC243734.1, AC243756.1, AC243790.1, AC243967.1, AC244196.1, AC244196.2, AC244196.3, AC244196.4, AC244196.5, AC244197.3, AC244216.4, AC244216.5, AC244226.1, AC244226.2, AC244472.1, AC244472.2, AC244472.3, AC244472.4, AC244472.5, AC244489.1, AC244489.2, AC244517.10, AC244517.6, AC245033.1, AC245034.2, AC245078.1, AC245088.2, AC245088.3, AC245369.1, AC245369.2, AC245369.3, AC245369.4, AC245369.6, AC245427.1, AC245427.3, AC245427.4, AC245427.5, AC245427.6, AC245427.7, AC245427.8, AC245427.9, AC245748.1, AC247036.3, AC247036.4, AC247036.5, AC247036.6, AC254560.1, AC254788.1, AC254788.2, AC254952.1, AC255093.3, AC255093.5, AC256236.1, AC256236.2, AC256236.3, AC256300.2, AC256309.2, AC270107.1, AC270107.10, AC270107.12, AC270107.2, AC270107.3, AC270107.4, AC270107.5, AC270107.7, AC270107.8, AC270107.9, AC270227.1, AC270306.4, AC275455.2, ACAA1, ACAA2, ACACA, ACACB, ACAD10, ACAD11, ACAD8, ACAD9, ACADL, ACADM, ACADS, ACADSB, ACADVL, ACAN, ACAP1, ACAP2, ACAP3, ACAT1, ACAT2, ACBD3, ACBD4, ACBD5, ACBD6, ACBD7, ACCS, ACCSL, ACD, ACE, ACE2, ACER1, ACER2, ACER3, ACHE, ACIN1, ACKR1, ACKR2, ACKR3, ACKR4, ACLY, ACMSD, ACO1, ACO2, ACOD1, ACOT1, ACOT11, ACOT12, ACOT13, ACOT2, ACOT4, ACOT6, ACOT7, ACOT8, ACOT9, ACOX1, ACOX2, ACOX3, ACOXL, ACP1, ACP2, ACP4, ACP5, ACP6, ACP7, ACPP, ACR, ACRBP, ACRV1, ACSBG1, ACSBG2, ACSF2, ACSF3, ACSL1, ACSL3, ACSL4, ACSL5, ACSL6, ACSM1, ACSM2A, ACSM2B, ACSM3, ACSM4, ACSM5, ACSM6, ACSS1, ACSS2, ACSS3, ACTA1, ACTA2, ACTB, ACTBL2, ACTC1, ACTG1, ACTG2, ACTL10, ACTL6A, ACTL6B, ACTL7A, ACTL7B, ACTL8, ACTL9, ACTN1, ACTN2, ACTN3, ACTN4, ACTR10, ACTR1A, ACTR1B, ACTR2, ACTR3, ACTR3B, ACTR3C, ACTR5, ACTR6, ACTR8, ACTRT1, ACTRT2, ACTRT3, ACVR1, ACVR1B, ACVR1C, ACVR2A, ACVR2B, ACVRL1, ACY1, ACY3, ACYP1, ACYP2, AD000671.1, AD000671.2, ADA, ADA2, ADAD1, ADAD2, ADAL, ADAM10, ADAM11, ADAM12, ADAM15, ADAM17, ADAM18, ADAM19, ADAM2, ADAM20, ADAM21, ADAM22, ADAM23, ADAM28, ADAM29, ADAM30, ADAM32, ADAM33, ADAM7, ADAM8, ADAM9, ADAMDEC1, ADAMTS1, ADAMTS10, ADAMTS12, ADAMTS13, ADAMTS14, ADAMTS15, ADAMTS16, ADAMTS17, ADAMTS18, ADAMTS19, ADAMTS2, ADAMTS20, ADAMTS3, ADAMTS4, ADAMTS5, ADAMTS6, ADAMTS7, ADAMTS8, ADAMTS9, ADAMTSL1, ADAMTSL2, ADAMTSL3, ADAMTSL4, ADAMTSL5, ADAP1, ADAP2, ADAR, ADARB1, ADARB2, ADAT1, ADAT2, ADAT3, ADCK1, ADCK2, ADCK5, ADCY1, ADCY10, ADCY2, ADCY3, ADCY4, ADCY5, ADCY6, ADCY7, ADCY8, ADCY9, ADCYAP1, ADCYAPIR1, ADD1, ADD2, ADD3, ADGB, ADGRA1, ADGRA2, ADGRA3, ADGRB1, ADGRB2, ADGRB3, ADGRD1, ADGRD2, ADGRE1, ADGRE2, ADGRE3, ADGRE5, ADGRF1, ADGRF2, ADGRF3, ADGRF4, ADGRF5, ADGRG1, ADGRG2, ADGRG3, ADGRG4, ADGRG5, ADGRG6, ADGRG7, ADGRL1, ADGRL2, ADGRL3, ADGRL4, ADGRV1, ADH1A, ADH1B, ADH1C, ADH4, ADH5, ADH6, ADH7, ADHFE1, ADI1, ADIG, ADIPOQ, ADI-POR1, ADIPOR2, ADIRF, ADK, ADM, ADM2, ADM5, ADNP, ADNP2, ADO, ADORA1, ADORA2A, ADORA2B, ADORA3, ADPGK, ADPRH, ADPRHL1, ADPRHL2, ADPRM, ADRA1A, ADRA1B, ADRAID, ADRA2A, ADRA2B, ADRA2C, ADRB1, ADRB2, ADRB3, ADRM1, ADSL, ADSS, ADSSL1, ADTRP, AEBP1, AEBP2, AEN, AES, AF130351.1, AF241726.2, AFAP1, AFAPIL1, AFAP1L2, AFDN, AFF1, AFF2, AFF3, AFF4, AFG1L, AFG3L2, AFM, AFMID, AFP, AFTPH, AGA, AGAP1, AGAP2, AGAP3, AGAP4, AGAP5, AGAP6, AGAP9, AGBL1, AGBL2, AGBL3, AGBL4, AGBL5, AGER, AGFG1, AGFG2, AGGF1, AGK, AGL, AGMAT, AGMO, AGO1, AGO2, AGO3, AGO4, AGPAT1, AGPAT2, AGPAT3, AGPAT4, AGPAT5, AGPS, AGR2, AGR3, AGRN, AGRP, AGT, AGTPBP1, AGTR1, AGTR2, AGTRAP, AGXT, AGXT2, AHCTF1, AHCY, AHCYL1, AHCYL2, AHDC1, AHI1, AHNAK, AHNAK2, AHR, AHRR, AHSA1, AHSA2, AHSG, AHSP, AICDA, AIDA, AIF1, AIF1L, AIFM1, AIFM2, AIFM3, AIG1, AIM2, AIMP1, AIMP2, AIP, AIPL1, AIRE, AJAP1, AJUBA, AK1, AK2, AK3, AK4, AK5, AK6, AK7, AK8, AK9, AKAIN1, AKAP1, AKAP10, AKAP11, AKAP12, AKAP13, AKAP14, AKAP17A, AKAP2, AKAP3, AKAP4, AKAP5, AKAP6, AKAP7, AKAP8, AKAP8L, AKAP9, AKIP1, AKIRIN1, AKIRIN2, AKNA, AKNAD1, AKR1A1, AKR1B1, AKR1B10, AKR1B15, AKR1C1, AKRIC2, AKR1C3, AKRIC4, AKR1D1, AKR1E2, AKR7A2, AKR7A3, AKR7L, AKT1, AKT1S1, AKT2, AKT3, AKTIP, AL020996.2, AL021154.3, AL021546.1, AL021997.3, AL022238.4, AL022318.4, AL024498.2, AL031708.1, AL032819.3, AL033529.1, AL035425.2, AL035460.1, AL049634.2, AL049650.1, AL049697.1, AL049779.1, AL049839.2, AL049844.1, AL049844.3, AL080251.1, AL096814.1, AL096870.1, AL109810.2, AL109811.4, AL109827.1, AL109936.3, AL109936.4, AL110118.2, AL110118.4, AL117258.1, AL117339.5, AL117348.2, AL121581.1, AL121594.3, AL121722.1, AL121753.1, AL121758.1, AL121845.2, AL121845.3, AL132671.2, AL132780.3, AL133352.1, AL133414.1, AL133414.2, AL136295.1, AL136295.3, AL136295.4, AL136295.5, AL136373.1, AL136531.2, AL138694.1, AL138752.2, AL138826.1, AL139011.2, AL139260.3, AL139300.1, AL139353.1, AL157392.5, AL159163.1, AL160275.1, AL160276.1, AL160396.2, AL161669.4, AL161911.1, AL162231.1, AL162231.3, AL163195.3, AL163636.2, AL353572.3, AL353588.1, AL354761.2, AL354822.1, AL355102.2, AL355315.1, AL355860.1, AL355916.3, AL355987.1, AL355987.3, AL356585.9, AL357673.1, AL358075.4, AL359736.1, AL359736.3, AL359922.1, AL360181.3, AL360181.5, AL365205.1, AL365214.3, AL365232.1, AL365273.2, AL391650.1, AL449266.1, AL451007.3, AL512428.1, AL512506.3, AL512785.2, AL513165.2, AL513523.10, AL513523.9, AL583836.1, AL589666.1, AL590132.1, AL590560.1, AL591806.3, AL592183.1, AL592490.1, AL593848.2, AL603832.3, AL645922.1, AL645941.2, AL662828.1, AL662852.6, AL662899.1, AL662899.2, AL662899.3, AL669918.1, AL672043.1, AL672142.1, AL691442.1, AL713999.1, AL772284.2, AL807752.6, AL807752.7, AL844853.2, AL845331.2, AL845464.1, AL928654.4, AL929554.1, AL929561.7, ALAD, ALAS1, ALAS2, ALB, ALCAM, ALDH16A1, ALDH18A1, ALDH1A1, ALDH1A2, ALDH1A3, ALDH1B1, ALDH1L1, ALDH1L2, ALDH2, ALDH3A1, ALDH3A2, ALDH3B1, ALDH3B2, ALDH4A1, ALDH5A1, ALDH6A1, ALDH7A1, ALDH8A1, ALDH9A1, ALDOA, ALDOB, ALDOC, ALG1, ALG10, ALG10B, ALG11, ALG12, ALG13, ALG14, ALG1L, ALG1L2, ALG2, ALG3, ALG5, ALG6, ALG8, ALG9, ALK, ALKAL1, ALKAL2, ALKBH1, ALKBH2, ALKBH3, ALKBH4, ALKBH5, ALKBH6, ALKBH7, ALKBH8, ALLC, ALMS1, ALOX12, ALOX12B, ALOX15, ALOX15B, ALOX5, ALOX5AP, ALOXE3, ALPI, ALPK1, ALPK2, ALPK3, ALPL, ALPP, ALPPL2, ALS2, ALS2CL, ALS2CR12, ALX1, ALX3, ALX4, ALYREF, AMACR, AMBN, AMBP, AMBRA1, AMD1, AMDHD1, AMDHD2, AMELX, AMELY, AMER1, AMER2, AMER3, AMFR, AMH, AMHR2, AMIGO1, AMIGO2, AMIGO3, AMMECR1, AMMECR1L, AMN, AMN1, AMOT, AMOTL1, AMOTL2, AMPD1, AMPD2, AMPD3, AMPH, AMT, AMTN, AMY1A, AMY1B, AMY1C, AMY2A, AMY2B, AMZ1, AMZ2, ANAPC1, ANAPC10, ANAPC11, ANAPC13, ANAPC15, ANAPC16, ANAPC2, ANAPC4, ANAPC5, ANAPC7, ANG, ANGEL1, ANGEL2, ANGPT1, ANGPT2, ANGPT4, ANGPTL1, ANGPTL2, ANGPTL3, ANGPTL4, ANGPTL5, ANGPTL6, ANGPTL7, ANGPTL8, ANHX, ANK1, ANK2, ANK3, ANKAR, ANKDD1A, ANKDD1B, ANKEF1, ANKFN1, ANKFY1, ANKH, ANKHD1, ANKHD1-EIF4EBP3, ANKIB1, ANKK1, ANKLE1, ANKLE2, ANKMY1, ANKMY2, ANKRA2, ANKRD1, ANKRD10, ANKRD11, ANKRD12, ANKRD13A, ANKRD13B, ANKRD13C, ANKRD13D, ANKRD16, ANKRD17, ANKRD18A, ANKRD18B, ANKRD2, ANKRD20A1, ANKRD20A2, ANKRD20A3, ANKRD20A4, ANKRD20A8P, ANKRD22, ANKRD23, ANKRD24, ANKRD26, ANKRD27, ANKRD28, ANKRD29, ANKRD30A, ANKRD30B, ANKRD30BL, ANKRD31, ANKRD33, ANKRD33B, ANKRD34A, ANKRD34B, ANKRD34C, ANKRD35, ANKRD36, ANKRD36B, ANKRD36C, ANKRD37, ANKRD39, ANKRD40, ANKRD42, ANKRD44, ANKRD45, ANKRD46, ANKRD49, ANKRD50, ANKRD52, ANKRD53, ANKRD54, ANKRD55, ANKRD6, ANKRD60, ANKRD61, ANKRD62, ANKRD63, ANKRD65, ANKRD66, ANKRD7, ANKRD9, ANKS1A, ANKS1B, ANKS3, ANKS4B, ANKS6, ANKUB1, ANKZF1, ANLN, ANO1, ANO10, ANO2, ANO3, ANO4, ANO5, ANO6, ANO7, ANO8, ANO9, ANOS1, ANP32A, ANP32B, ANP32D, ANP32E, ANPEP, ANTXR1, ANTXR2, ANTXRL, ANXA1, ANXA10, ANXA11, ANXA13, ANXA2, ANXA2R, ANXA3, ANXA4, ANXA5, ANXA6, ANXA7, ANXA8, ANXA8L1, ANXA9, AOAH, AOC1, AOC2, AOC3, AOX1, AP000275.2, AP000295.1, AP000311.1, AP000322.1, AP000349.1, AP000350.12, AP000350.4, AP000351.3, AP000351.7, AP000721.1, AP000781.2, AP001160.5, AP001273.2, AP001458.2, AP001781.3, AP001931.1, AP002360.1, AP002373.1, AP002495.1, AP002512.3, AP002512.4, AP002748.4, AP002990.1, AP003071.5, AP003108.2, AP003419.2, AP004243.1, AP006285.3, AP1AR, AP1B1, AP1G1, AP1G2, AP1M1, AP1M2, AP1S1, AP1S2, AP1S3, AP2A1, AP2A2, AP2B1, AP2M1, AP2S1, AP3B1, AP3B2, AP3D1, AP3M1, AP3M2, AP3S1, AP3S2, AP4B1, AP4E1, AP4M1, AP4S1, AP5B1, AP5M1, AP5S1, AP5Z1, APAF1, APBA1, APBA2, APBA3, APBB1, APBB1IP, APBB2, APBB3, APC, APC2, APCDD1, APCDD1L, APCS, APEH, APELA, APEX1, APEX2, APH1A, APH1B, API5, APIP, APLF, APLN, APLNR, APLP1, APLP2, APMAP, APOA1, APOA2, APOA4, APOA5, APOB, APOBEC1, APOBEC2, APOBEC3A, APOBEC3B, APOBEC3C, APOBEC3D, APOBEC3F, APOBEC3G, APOBEC3H, APOBEC4, APOBR, APOC1, APOC2, APOC3, APOC4, APOC4-APOC2, APOD, APOE, APOF, APOH, APOL1, APOL2, APOL3, APOL4, APOL5, APOL6, APOLD1, APOM, APOO, APOOL, APOPT1, APP, APPBP2, APPL1, APPL2, APRT, APTX, AQP1, AQP10, AQP11, AQP12A, AQP12B, AQP2, AQP3, AQP4, AQP5, AQP6, AQP7, AQP8, AQP9, AQR, AR, ARAF, ARAP1, ARAP2, ARAP3, ARC, ARCN1, AREG, AREL1, ARF1, ARF3, ARF4, ARF5, ARF6, ARFGAP1, ARFGAP2, ARFGAP3, ARFGEF1, ARFGEF2, ARFGEF3, ARFIP1, ARFIP2, ARFRP1, ARG1, ARG2, ARGFX, ARGLU1, ARHGAP1, ARHGAP10, ARHGAP11 A, ARHGAP11B, ARHGAP12, ARHGAP15, ARHGAP17, ARHGAP18, ARHGAP19, ARHGAP19-SLIT1, ARHGAP20, ARHGAP21, ARHGAP22, ARHGAP23, ARHGAP24, ARHGAP25, ARHGAP26, ARHGAP27, ARHGAP28, ARHGAP29, ARHGAP30, ARHGAP31, ARHGAP32, ARHGAP33, ARHGAP35, ARHGAP36, ARHGAP39, ARHGAP4, ARHGAP40, ARHGAP42, ARHGAP44, ARHGAP45, ARHGAP5, ARHGAP6, ARHGAP8, ARHGAP9, ARHGDIA, ARHGDIB, ARHG-DIG, ARHGEF1, ARHGEF10, ARHGEF10L, ARHGEF11, ARHGEF12, ARHGEF15, ARHGEF16, ARHGEF17, ARHGEF18, ARHGEF19, ARHGEF2, ARHGEF25, ARHGEF26, ARHGEF28, ARHGEF3, ARHGEF33, ARHGEF35, ARHGEF37, ARHGEF38, ARHGEF39, ARHGEF4, ARHGEF40, ARHGEF5, ARHGEF6, ARHGEF7, ARHGEF9, ARID1A, ARID1B, ARID2, ARID3A, ARID3B, ARID3C, ARID4A, ARID4B, ARID5A, ARID5B, ARIH1, ARIH2, $ARIH_2OS$, ARL1, ARL10, ARL11, ARL13A, ARL13B, ARL14, ARL14EP, ARL14EPL, ARL15, ARL16, ARL17A, ARL17B, ARL2, ARL2BP, ARL2-SNX15, ARL3, ARL4A, ARL4C, ARL4D, ARL5A, ARL5B, ARL5C, ARL6, ARL6IP1, ARL6IP4, ARL6IP5, ARL6IP6, ARL8A, ARL8B, ARL9, ARMC1, ARMC10, ARMC12, ARMC2, ARMC3, ARMC4, ARMC5, ARMC6, ARMC7, ARMC8, ARMC9, ARMCX1, ARMCX2, ARMCX3, ARMCX4, ARMCX5, ARMCX6, ARMS2, ARMT1, ARNT, ARNT2, ARNTL, ARNTL2, ARPC1A, ARPC1B, ARPC2, ARPC3, ARPC4, ARPC4-TTLL3, ARPC5, ARPC5L, ARPIN, ARPP19, ARPP21, ARR3, ARRB1, ARRB2, ARRDC1, ARRDC2, ARRDC3, ARRDC4, ARRDC5, ARSA, ARSB, ARSD, ARSE, ARSF, ARSG, ARSH, ARSI, ARSJ, ARSK, ART1, ART3, ART4, ART5, ARTN, ARV1, ARVCF, ARX, AS3MT, ASAH1, ASAH2, ASAH2B, ASAP1, ASAP2, ASAP3, ASB1, ASB10, ASB11, ASB12, ASB13, ASB14, ASB15, ASB16, ASB17, ASB18, ASB2, ASB3, ASB4, ASB5, ASB6, ASB7, ASB8, ASB9, ASCC1, ASCC2, ASCC3, ASCL1, ASCL2, ASCL3, ASCL4, ASCL5, ASF1A, ASF1B, ASGR1, ASGR2, ASH1L, ASH2L, ASIC1, ASIC2, ASIC3, ASIC4, ASIC5, ASIP, ASL, ASMT, ASMTL, ASNA1, ASNS, ASNSD1, ASPA, ASPDH, ASPG, ASPH, ASPHD1, ASPHD2, ASPM, ASPN, ASPRV1, ASPSCR1, ASRGL1, ASS1, ASTE1, ASTL, ASTN1, ASTN2, ASXL1, ASXL2, ASXL3, ASZ1, ATAD1, ATAD2, ATAD2B, ATAD3A, ATAD3B, ATAD3C, ATAD5, ATAT1, ATCAY, ATE1, ATF1, ATF2, ATF3, ATF4, ATF5, ATF6, ATF6B, ATF7, ATF7IP, ATF7IP2, ATG10, ATG101, ATG12, ATG13, ATG14, ATG16L1, ATG16L2, ATG2A, ATG2B, ATG3, ATG4A, ATG4B, ATG4C, ATG4D, ATG5, ATG7, ATG9A, ATG9B, ATIC, ATL1, ATL2, ATL3, ATM, ATMIN, ATN1, ATOH1, ATOH7, ATOH8, ATOX1, ATP10A, ATP10B, ATP10D, ATP11A, ATP11B, ATP11C, ATP12A, ATP13A1, ATP13A2, ATP13A3, ATP13A4, ATP13A5, ATP1A1, ATP1A2, ATP1A3, ATP1A4, ATP1B1, ATP1B2, ATP1B3, ATP1B4, ATP23, ATP2A1, ATP2A2, ATP2A3, ATP2B1, ATP2B2, ATP2B3, ATP2B4, ATP2C1, ATP2C2, ATP4A, ATP4B, ATP5A1, ATP5B, ATP5C1, ATP5D, ATP5E, ATP5EP2, ATP5F1, ATP5G1, ATP5G2, ATP5G3, ATP5H, ATP5I, ATP5J, ATP5J2, ATP5J2-PTCD1, ATP5L, ATP5L2, ATP50, ATP5S, ATP6AP1, ATP6AP1L, ATP6AP2, ATP6V0A1, ATP6V0A2, ATP6V0A4, ATP6V0B, ATP6V0C, ATP6V0D1, ATP6V0D2, ATP6V0E1, ATP6V0E2, ATP6V1A, ATP6V1B1, ATP6V1B2, ATP6V1C1, ATP6V1C2, ATP6V1D, ATP6V1E1, ATP6V1E2, ATP6VIF, ATP6V1G1, ATP6V1G2, ATP6V1G2-DDX39B, ATP6V1G3, ATP6V1H, ATP7A, ATP7B, ATP8A1, ATP8A2, ATP8B1, ATP8B2, ATP8B3, ATP8B4, ATP9A, ATP9B, ATPAF1, ATPAF2, ATPIF1, ATR, ATRAID, ATRIP, ATRN, ATRNL1, ATRX, ATXN1, ATXN10, ATXN1L, ATXN2, ATXN2L, ATXN3, ATXN3L, ATXN7, ATXN7L1, ATXN7L2, ATXN7L3, ATXN7L3B, AUH, AUNIP, AUP1, AURKA, AURKA1P1, AURKB, AURKC, AUTS2, AVEN, AVIL, AVL9, AVP, AVP11, AVPR1A, AVPR1B, AVPR2, AWAT1, AWAT2, AXDND1, AXIN1, AXIN2, AXL, AZGP1, AZI2, AZIN1, AZIN2, AZU1, B2M, B3GALNT1, B3GALNT2, B3GALT1, B3GALT2, B3GALT4, B3GALT5, B3GALT6, B3GAT1, B3GAT2, B3GAT3, B3GLCT, B3GNT2, B3GNT3, B3GNT4, B3GNT5, B3GNT6, B3GNT7, B3GNT8, B3GNT9, B3GNTL1, B4GALNT1, B4GALNT2, B4GALNT3, B4GALNT4, B4GALT1, B4GALT2, B4GALT3, B4GALT4, B4GALT5, B4GALT6, B4GALT7, B4GAT1, B9D1, B9D2, BAALC, BAAT, BABAM1, BABAM2, BACE1, BACE2, BACH1, BACH2, BAD, BAG1, BAG2, BAG3, BAG4, BAG5, BAG6, BAGE3, BAHCC1, BAHD1, BAIAP2, BAIAP2L1, BAIAP2L2, BAIAP3, BAK1, BAMBI, BANF1, BANF2, BANK1, BANP, BAP1, BARD1, BARHL1, BARHL2, BARX1, BARX2, BASP1, BATF, BATF2, BATF3, BAX, BAZ1A, BAZ1B, BAZ2A, BAZ2B, BBC3, BBIP1, BBOF1, BBOX1, BBS1, BBS10, BBS12, BBS2, BBS4, BBS5, BBS7, BBS9, BBX, BCAM, BCAN, BCAP29, BCAP31, BCAR1, BCAR3, BCAS1, BCAS2, BCAS3, BCAS4, BCAT1, BCAT2, BCCIP, BCDIN3D, BCHE, BCKDHA, BCKDHB, BCKDK, BCL10, BCL11A, BCL11B, BCL2, BCL2A1, BCL2L1, BCL2L10, BCL2L11, BCL2L12, BCL2L13, BCL2L14, BCL2L15, BCL2L2, BCL2L2-PABPN1, BCL3, BCL6, BCL6B, BCL7A, BCL7B, BCL7C, BCL9, BCL9L, BCLAF1, BCLAF3, BCO1, BCO2, BCOR, BCORL1, BCR, BCS1L, BDH1, BDH2, BDKRB1, BDKRB2, BDNF, BDP1, BEAN1, BECN1, BECN2, BEGAIN, BEND2, BEND3, BEND4, BEND5, BEND6, BEND7, BEST1, BEST2, BEST3, BEST4, BET1, BET1L, BEX1, BEX2, BEX3, BEX4, BEX5, BFAR, BFSP1, BFSP2, BGLAP, BGN, BHLHA15, BHLHA9, BHLHB9, BHLHE22, BHLHE23, BHLHE40, BHLHE41, BHMG1, BHMT, BHMT2, BICC1, BICD1, BICD2, BICDL1, BICDL2, BICRA, BICRAL, BID, BIK, BIN1, BIN2, BIN3, BIRC2, BIRC3, BIRC5, BIRC6, BIRC7, BIRC8, BIVM, BIVM-ERCC5, BLACE, BLCAP, BLID, BLK, BLM, BLMH, BLNK, BLOC1S1, BLOC1S2, BLOC1S3, BLOC1S4, BLOC1S5, BLOC1S5-TXNDC5, BLOC1S6, BLVRA, BLVRB, BLZF1, BMF, BMI1, BMP1, BMP10, BMP15, BMP2, BMP2K, BMP3, BMP4, BMP5, BMP6, BMP7, BMP8A, BMP8B, BMPER, BMPR1A, BMPR1B, BMPR2, BMS1, BMT2, BMX, BNC1, BNC2, BNIP1, BNIP2, BNIP3, BNIP3L, BNIPL, BOC, BOD1, BOD1L1, BOD1L2, BOK, BOLA1, BOLA2, BOLA2B, BOLA2-SMG1P6, BOLA3, BOLL, BOP1, BORA, BORCS5, BORCS6, BORCS7, BORCS7-ASMT, BORCS8, BORCS8-MEF2B, BPGM, BPHL, BPI, BPIFA1, BPIFA2, BPIFA3, BPIFB1, BPIFB2, BPIFB3, BPIFB4, BPIFB6, BPIFC, BPNT1, BPTF, BPY2, BPY2B, BPY2C, BRAF, BRAP, BRAT1, BRCA1, BRCA2, BRCC3, BRD1, BRD2, BRD3, BRD4, BRD7, BRD8, BRD9, BRDT, BRF1, BRF2, BRI3, BRI3BP, BRICD5, BRINP1, BRINP2, BRINP3, BRIP1, BRIX1, BRK1, BRMS1, BRMS1L, BROX, BRPF1, BRPF3, BRS3, BRSK1, BRSK2, BRWD1, BRWD3, BSCL2, BSDC1, BSG, BSN, BSND, BSPH1, BSPRY, BST1, BST2, BSX, BTAF1, BTBD1, BTBD10, BTBD11, BTBD16, BTBD17, BTBD18, BTBD19, BTBD2, BTBD3, BTBD6, BTBD7, BTBD8, BTBD9, BTC, BTD, BTF3, BTF3L4, BTG1, BTG2, BTG3, BTG4, BTK, BTLA, BTN1A1, BTN2A1, BTN2A2, BTN3A1, BTN3A2, BTN3A3, BTNL2, BTNL3, BTNL8, BTNL9, BTRC, BUB1, BUB1B, BUB1B-PAK6, BUB3, BUD13, BUD23, BUD31, BVES, BX004987.1, BX072566.1, BX088645.1, BX248244.1, BX248413.4, BX248415.1, BX248516.1, BX276092.9, BYSL, BZW1, BZW2, C10orf10, C10orf105, C10orf107, C10orf113, C10orf120, C10orf126, C10orf128, C10orf142, C10orf35, C10orf53, C10orf55, C10orf62, C10orf67, C10orf71, C10orf76, C10orf82, C10orf88, C10orf90, C10orf95, C10orf99, C11orf1, C11orf16, C11orf21, C11orf24, C11orf40, C11orf42, C11orf45, C11orf49, C11orf52, C11orf53, C11orf54, C11orf57, C11orf58, C11orf63, C11orf65, C11orf68, C11orf70, C11orf71, C11orf74, C11orf80, C11orf84, C11orf86, C11orf87, C11orf88, C11orf91, C11orf94, C11orf95, C11orf96, C11orf97, C11orf98, C12orf10, C12orf29, C12orf4, C12orf40, C12orf42, C12orf43, C12orf45, C12orf49, C12orf50, C12orf54, C12orf56, C12orf57, C12orf60, C12orf65, C12orf66, C12orf71, C12orf73, C12orf74, C12orf75, C12orf76, C13orf42, C14orf105, C14orf119, C14orf132, C14orf159, C14orf166, C14orf177, C14orf178, C14orf180, C14orf2, C14orf28, C14orf37, C14orf39, C14orf79, C14orf80, C14orf93, C15orf38-AP3S2, C15orf39, C15orf40, C15orf41, C15orf48, C15orf52, C15orf53, C15orf59, C15orf61, C15orf62, C15orf65, C16orf45, C16orf46, C16orf52, C16orf54, C16orf58, C16orf59, C16orf62, C16orf70, C16orf71, C16orf72, C16orf74, C16orf78, C16orf82, C16orf86, C16orf87, C16orf89, C16orf90, C16orf91, C16orf92, C16orf95, C16orf96, C17orf100, C17orf105, C17orf107, C17orf113, C17orf47, C17orf49, C17orf50, C17orf51, C17orf53, C17orf58, C17orf62, C17orf64, C17orf67, C17orf74, C17orf75, C17orf78, C17orf80, C17orf97, C17orf98, C17orf99, C18orf21, C18orf25, C18orf32, C18orf54, C18orf63, C18orf8, C19orf12, C19orf18, C19orf24, C19orf25, C19orf33, C19orf35, C19orf38, C19orf44, C19orf47, C19orf48, C19orf53, C19orf54, C19orf57, C19orf60, C19orf66, C19orf67, C19orf68, C19orf70, C19orf71, C19orf73, C19orf81, C19orf84, C1D, C1GALT1, C1GALT1C1, C1GALT1C1L, C1orf100, C1orf105, C1orf109, C1orf112, C1orf115, C1orf116, C1orf122, C1orf123, C1orf127, C1orf131, C1orf141, C1orf146, C1orf158, C1orf159, C1orf162, C1orf167, C1orf174, C1orf185, C1orf186, C1orf189, C1orf194, C1orf198, C1orf21, C1orf210, C1orf216, C1orf226, C1orf228, C1orf232, C1orf27, C1orf35, C1orf43, C1orf50, C1orf52, C1orf53, C1orf54, C1orf56, C1orf61, C1orf64, C1orf68, C1orf74, C1orf87, C1orf94, C1QA, C1QB, C1QBP, C1QC, C1QL1, C1QL2, C1QL3, C1QL4, C1QTNF1, C1QTNF12, C1QTNF2, C1QTNF3, C1QTNF3-AMACR, C1QTNF4, C1QTNF5, C1QTNF6, C1QTNF7, C1QTNF8, C1QTNF9, C1QTNF9B, C1R, C1RL, C1S, C2, C20orf141, C20orf144, C20orf173, C20orf194, C20orf196, C20orf202, C20orf204, C20orf24, C20orf27, C20orf85, C20orf96, C21orf140, C21orf2, C21orf33, C21orf58, C21orf59, C21orf62, C21orf91, C22orf15, C22orf23, C22orf31, C22orf39, C22orf42, C22orf46, C2CD2, C2CD2L, C2CD3, C2CD4A, C2CD4B, C2CD4C, C2CD4D, C2CD5, C2CD6, C2orf15, C2orf16, C2orf40, C2orf42, C2orf49, C2orf50, C2orf54, C2orf66, C2orf68, C2orf69, C2orf70, C2orf71, C2orf72, C2orf73, C2orf74, C2orf76, C2orf78, C2orf80, C2orf81, C2orf82, C2orf83, C2orf88, C2orf91, C3, C3AR1, C3orf14, C3orf18, C3orf20, C3orf22, C3orf30, C3orf33, C3orf35, C3orf36, C3orf38, C3orf49, C3orf52, C3orf56, C3orf58, C3orf62, C3orf67, C3orf70, C3orf80, C3orf84, C3orf85, C4A, C4B, C4B_2, C4BPA, C4BPB, C4orf17, C4orf19, C4orf22, C4orf26, C4orf3, C4orf32, C4orf33, C4orf36, C4orf45, C4orf46, C4orf47, C4orf48, C4orf50, C4orf51, C5, C5AR1, C5AR2, C5orf15, C5orf22, C5orf24, C5orf30, C5orf34, C5orf38, C5orf42, C5orf46, C5orf47, C5orf49, C5orf51, C5orf52, C5orf56, C5orf58, C5orf60, C5orf63, C5orf67, C6, C6orf10, C6orf106, C6orf118, C6orf120, C6orf132, C6orf136, C6orf141, C6orf15, C6orf163, C6orf201, C6orf203, C6orf222, C6orf223, C6orf226, C6orf229, C6orf47, C6orf48, C6orf52, C6orf58, C6orf62, C6orf89, C7, C7orf25, C7orf26, C7orf31, C7orf33, C7orf34, C7orf43, C7orf49, C7orf50, C7orf55-LUC7L2, C7orf57, C7orf61, C7orf72, C7orf73, C7orf77, C8A, C8B, C8G, C8orf22, C8orf33, C8orf34, C8orf37, C8orf4, C8orf44, C8orf44-SGK3, C8orf46, C8orf48, C8orf58, C8orf59, C8orf74, C8orf76, C8orf82, C8orf86, C8orf88, C8orf89, C9, C9orf116, C9orf129, C9orf131, C9orf135, C9orf152, C9orf153, C9orf16, C9orf172, C9orf24, C9orf3, C9orf40, C9orf43, C9orf47, C9orf50, C9orf57, C9orf64, C9orf66, C9orf72, C9orf78, C9orf84, C9orf85, C9orf92, CA1, CA10, CA11, CA12, CA13, CA14, CA2, CA3, CA4, CA5A, CA5B, CA6, CA7, CA8, CA9, CAAP1, CAB39, CAB39L, CABIN1, CABLES1, CABLES2, CABP1, CABP2, CABP4, CABP5, CABP7, CABS1, CABYR, CACFD1, CACHD1, CACNA1A, CACNA1B, CACNA1C, CACNA1D, CACNA1E, CACNA1F, CACNA1G, CACNA1H, CACNA1I, CACNA1S, CACNA2D1, CACNA2D2, CACNA2D3, CACNA2D4, CACNB1, CACNB2, CACNB3, CACNB4, CACNG1, CACNG2, CACNG3, CACNG4, CACNG5, CACNG6, CACNG7, CACNG8, CACTIN, CACUL1, CACYBP, CAD, CADM1, CADM2, CADM3, CADM4, CADPS, CADPS2, CAGE1, CALB1, CALB2, CALCA, CALCB, CALCOCO1, CALCOCO2, CALCR, CALCRL, CALD1, CALHM1, CALHM2, CALHM3, CALM1, CALM2, CALM3, CALML3, CALML4, CALML5, CALML6, CALN1, CALR, CALR3, CALU, CALY, CAMK1, CAMK1D, CAMK1G, CAMK2A, CAMK2B, CAMK2D, CAMK2G, CAMK2N1, CAMK2N2, CAMK4, CAMKK1, CAMKK2, CAMKMT, CAMKV, CAMLG, CAMP, CAMSAP1, CAMSAP2, CAMSAP3, CAMTA1, CAMTA2, CAND1, CAND2, CANT1, CANX, CAP1, CAP2, CAPG, CAPN1, CAPN10, CAPN11, CAPN12, CAPN13, CAPN14, CAPN15, CAPN2, CAPN3, CAPN5, CAPN6, CAPN7, CAPN8, CAPN9, CAPNS1, CAPNS2, CAPRIN1, CAPRIN2, CAPS, CAPS2, CAPSL, CAPZA1, CAPZA2, CAPZA3, CAPZB, CARD10, CARD11, CARD14, CARD16, CARD17, CARD18, CARD19, CARD6, CARD8, CARD9, CARF, CARHSP1, CARM1, CARMIL1, CARMIL2, CARMIL3, CARNMT1, CARNS1, CARS, CARS2, CARTPT, CASC1, CASC10, CASC3, CASC4, CASD1, CASK, CASKIN1, CASKIN2, CASP1, CASP10, CASP12, CASP14, CASP2, CASP3, CASP4, CASP5, CASP6, CASP7, CASP8, CASP8AP2, CASP9, CASQ1, CASQ2, CASR, CASS4, CAST, CASTOR1, CASTOR2, CASZ1, CAT, CATIP, CATSPER1, CATSPER2, CATSPER3, CATSPER4, CATSPERB, CATSPERD, CATSPERE, CATSPERG, CATSPERZ, CAV1, CAV2, CAV3, CAVIN1, CAVIN2, CAVIN3, CAVIN4, CBARP, CBFA2T2, CBFA2T3, CBFB, CBL, CBLB, CBLC, CBLL1, CBLN1, CBLN2, CBLN3, CBLN4, CBR1, CBR3, CBR4, CBS, CBSL, CBWD1, CBWD2, CBWD3, CBWD5, CBWD6, CBX1, CBX2, CBX3, CBX4, CBX5, CBX6, CBX7, CBX8, CBY1, CBY3, CC2D1A, CC2D1B, CC2D2A, CC2D2B, CCAR1, CCAR2, CCBE1, CCDC102A, CCDC102B, CCDC103, CCDC105, CCDC106, CCDC107, CCDC110, CCDC112, CCDC113, CCDC114, CCDC115, CCDC116, CCDC117, CCDC12, CCDC120, CCDC121, CCDC122, CCDC124, CCDC125, CCDC126, CCDC127, CCDC129, CCDC13, CCDC130, CCDC134, CCDC136, CCDC137, CCDC138, CCDC14, CCDC140, CCDC141, CCDC142, CCDC144A, CCDC144NL, CCDC146, CCDC148, CCDC149, CCDC15, CCDC150, CCDC151, CCDC152, CCDC153, CCDC154, CCDC155, CCDC157, CCDC158, CCDC159, CCDC160, CCDC163, CCDC166, CCDC167, CCDC168, CCDC169, CCDC169-SOHLH2, CCDC17, CCDC170, CCDC171, CCDC172, CCDC173, CCDC174, CCDC175, CCDC177, CCDC178, CCDC179, CCDC18, CCDC180, CCDC181, CCDC182, CCDC183, CCDC184, CCDC185, CCDC186, CCDC187, CCDC188, CCDC189, CCDC190, CCDC191, CCDC192, CCDC194, CCDC195, CCDC196, CCDC197, CCDC22, CCDC24, CCDC25, CCDC27, CCDC28A, CCDC28B, CCDC3, CCDC30, CCDC32, CCDC33, CCDC34, CCDC36, CCDC38, CCDC39, CCDC40, CCDC42, CCDC43, CCDC47, CCDC50, CCDC51, CCDC54, CCDC57, CCDC58, CCDC59, CCDC6, CCDC60, CCDC61, CCDC62, CCDC63, CCDC65, CCDC66, CCDC68, CCDC69, CCDC7, CCDC70, CCDC71, CCDC71L, CCDC73, CCDC74A, CCDC74B, CCDC77, CCDC78, CCDC8, CCDC80, CCDC81, CCDC82, CCDC83, CCDC84, CCDC85A, CCDC85B, CCDC85C, CCDC86, CCDC87, CCDC88A, CCDC88B, CCDC88C, CCDC89, CCDC9, CCDC90B, CCDC91, CCDC92, CCDC93, CCDC94, CCDC96, CCDC97, CCER1, CCER2, CCHCR1, CCIN, CCK, CCKAR, CCKBR, CCL1, CCL11, CCL13, CCL14, CCL15, CCL15-CCL14, CCL16, CCL17, CCL18, CCL19, CCL2, CCL20, CCL21, CCL22, CCL23, CCL24, CCL25, CCL26, CCL27, CCL28, CCL3, CCL3L1, CCL3L3, CCL4, CCL4L2, CCL5, CCL7, CCL8, CCM2, CCM2L, CCNA1, CCNA2, CCNB1, CCNB1IP1, CCNB2, CCNB3, CCNC, CCND1, CCND2, CCND3, CCNDBP1, CCNE1, CCNE2, CCNF, CCNG1, CCNG2, CCNH, CCNI, CCNI2, CCNJ, CCNJL, CCNK, CCNL1, CCNL2, CCNO, CCNT1, CCNT2, CCNY, CCNYL1, CCP110, CCPG1, CCR1, CCR10, CCR2, CCR3, CCR4, CCR5, CCR6, CCR7, CCR8, CCR9, CCRL2, CCS, CCSAP, CCSER1, CCSER2, CCT2, CCT3, CCT4, CCT5, CCT6A, CCT6B, CCT7, CCT8, CCT8L2, CCZ1, CCZ1B, CD101, CD109, CD14, CD151, CD160, CD163, CD163L1, CD164, CD164L2, CD177, CD180, CD19, CD1A, CD1B, CD1C, CD1D, CD1E, CD2, CD200, CD200R1, CD200R1L, CD207, CD209, CD22, CD226, CD24, CD244, CD247, CD248, CD27, CD274, CD276, CD28, CD2AP, CD2BP2, CD300A, CD300C, CD300E, CD300LB, CD300LD, CD300LF, CD300LG, CD302, CD320, CD33, CD34, CD36, CD37, CD38, CD3D, CD3E, CD3EAP, CD3G, CD4, CD40, CD40LG, CD44, CD46, CD47, CD48, CD5, CD52, CD53, CD55, CD58, CD59, CD5L, CD6, CD63, CD68, CD69, CD7, CD70, CD72, CD74, CD79A, CD79B, CD80, CD81, CD82, CD83, CD84, CD86, CD8A, CD8B, CD9, CD93, CD96, CD99, CD99L2, CDA, CDADC1, CDAN1, CDC123, CDC14A, CDC14B, CDC16, CDC20, CDC20B, CDC23, CDC25A, CDC25B, CDC25C, CDC26, CDC27, CDC34, CDC37, CDC37L1, CDC40, CDC42, CDC42BPA, CDC42BPB, CDC42BPG, CDC42EP1, CDC42EP2, CDC42EP3, CDC42EP4, CDC42EP5, CDC42SE1, CDC42SE2, CDC45, CDC5L, CDC6, CDC7, CDC73, CDCA2, CDCA3, CDCA4, CDCA5, CDCA7, CDCA7L, CDCA8, CDCP1, CDCP2, CDH1, CDH10, CDH11, CDH12, CDH13, CDH15, CDH16, CDH17, CDH18, CDH19, CDH2, CDH20, CDH22, CDH23, CDH24, CDH26, CDH3, CDH4, CDH5, CDH6, CDH7, CDH8, CDH9, CDHR1, CDHR2, CDHR3, CDHR4, CDHR5, CDIP1, CDIPT, CDK1, CDK10, CDK11A, CDK11B, CDK12, CDK13, CDK14, CDK15, CDK16, CDK17, CDK18, CDK19, CDK2, CDK20, CDK2AP1, CDK2AP2, CDK3, CDK4, CDK5, CDK5R1, CDK5R2, CDK5RAP1, CDK5RAP2, CDK5RAP3, CDK6, CDK7, CDK8, CDK9, CDKAL1, CDKL1, CDKL2, CDKL3, CDKL4, CDKL5, CDKN1A, CDKN1B, CDKN1C, CDKN2A, CDKN2AIP, CDKN2AIPNL, CDKN2B, CDKN2C, CDKN2D, CDKN3, CDNF, CDO1, CDON, CDPF1, CDR1, CDR2, CDR2L, CDRT1, CDRT15, CDRT15L2, CDRT4, CDS1, CDS2, CDSN, CDT1, CDV3, CDX1, CDX2, CDX4, CDY1, CDY1B, CDY2A, CDY2B, CDYL, CDYL2, CEACAM1, CEACAM16, CEACAM19, CEACAM20, CEACAM21, CEACAM3, CEACAM4, CEACAM5, CEACAM6, CEACAM7, CEACAM8, CEBPA, CEBPB, CEBPD, CEBPE, CEBPG, CEBPZ, CEBPZOS, CECR2, CEL, CELA1, CELA2A, CELA2B, CELA3A, CELA3B, CELF1, CELF2, CELF3, CELF4, CELF5, CELF6, CELSR1, CELSR2, CELSR3, CEMIP, CEMP1, CEND1, CENPA, CENPB, CENPBD1, CENPC, CENPE, CENPF, CENPH, CENPI, CENPJ, CENPK, CENPL, CENPM, CENPN, CENPO, CENPP, CENPQ, CENPS, CENPS-CORT, CENPT, CENPU, CENPV, CENPVL1, CENPVL2, CENPVL3, CENPW, CENPX, CEP104, CEP112, CEP120, CEP126, CEP128, CEP131, CEP135, CEP152, CEP162, CEP164, CEP170, CEP170B, CEP19, CEP192, CEP250, CEP290, CEP295, CEP295NL, CEP350, CEP41, CEP44, CEP55, CEP57, CEP57L1, CEP63, CEP68, CEP70, CEP72, CEP76, CEP78, CEP83, CEP85, CEP85L, CEP89, CEP95, CEP97, CEPT1, CER1, CERCAM, CERK, CERKL, CERS1, CERS2, CERS3, CERS4, CERS5, CERS6, CES1, CES2, CES3, CES4A, CES5A, CETN1, CETN2, CETN3, CETP, CFAP100, CFAP126, CFAP157, CFAP161, CFAP20, CFAP206, CFAP221, CFAP36, CFAP43, CFAP44, CFAP45, CFAP46, CFAP47, CFAP52, CFAP53, CFAP54, CFAP57, CFAP58, CFAP61, CFAP65, CFAP69, CFAP70, CFAP73, CFAP74, CFAP77, CFAP97, CFAP99, CFB, CFC1, CFC1B, CFD, CFDP1, CFH, CFHR1, CFHR2, CFHR3, CFHR4, CFHR5, CFI, CFL1, CFL2, CFLAR, CFP, CFTR, CGA, CGB1, CGB2, CGB3, CGB5, CGB7, CGB8, CGGBP1, CGN, CGNL1, CGREF1, CGRRF1, CH25H, CHAC1, CHAC2, CHAD, CHADL, CHAF1A, CHAF1B, CHAMP1, CHAT, CHCHD1, CHCHD10, CHCHD2, CHCHD3, CHCHD4, CHCHD5, CHCHD6, CHCHD7, CHD1, CHD1L, CHD2, CHD3, CHD4, CHD5, CHD6, CHD7, CHD8, CHD9, CHDH, CHEK1, CHEK2, CHERP, CHFR, CHGA, CHGB, CHI3L1, CHI3L2, CHIA, CHIC1, CHIC2, CHID1, CHIT1, CHKA, CHKB, CHKB-CPTIB, CHL1, CHM, CHML, CHMP1A, CHMP1B, CHMP2A, CHMP2B, CHMP3, CHMP4A, CHMP4B, CHMP4C, CHMP5, CHMP6, CHMP7, CHN1, CHN2, CHODL, CHORDC1, CHP1, CHP2, CHPF, CHPF2, CHPT1, CHRAC1, CHRD, CHRDL1, CHRDL2, CHRFAM7A, CHRM1, CHRM2, CHRM3, CHRM4, CHRM5, CHRNA1, CHRNA10, CHRNA2, CHRNA3, CHRNA4, CHRNA5, CHRNA6, CHRNA7, CHRNA9, CHRNB1, CHRNB2, CHRNB3, CHRNB4, CHRND, CHRNE, CHRNG, CHST1, CHST10, CHST11, CHST12, CHST13, CHST14, CHST15, CHST2, CHST3, CHST4, CHST5, CHST6, CHST7, CHST8, CHST9, CHSY1, CHSY3, CHTF18, CHTF8, CHTOP, CHUK, CHURC1, CHURC1-FNTB, CIAO1, CIAPIN1, CIART, CIB1, CIB2, CIB3, CIB4, CIC, CIDEA, CIDEB, CIDEC, CIITA, CILP, CILP2, CINP, CIPC, CIR1, CIRBP, CISD1, CISD2, CISD3, CISH, CIT, CITED1, CITED2, CITED4, CIZ1, CKAP2, CKAP2L, CKAP4, CKAP5, CKB, CKLF, CKLF-CMTM1, CKM, CKMT1A, CKMT1B, CKMT2, CKSlB, CKS2, CLASP1, CLASP2, CLASRP, CLC, CLCA1, CLCA2, CLCA4, CLCC1, CLCF1, CLCN1, CLCN2, CLCN3, CLCN4, CLCN5, CLCN6, CLCN7, CLCNKA, CLCNKB, CLDN1, CLDN10, CLDN11, CLDN12, CLDN14, CLDN15, CLDN16, CLDN17, CLDN18, CLDN19, CLDN2, CLDN20, CLDN22, CLDN23, CLDN24, CLDN25, CLDN3, CLDN34, CLDN4, CLDN5, CLDN6, CLDN7, CLDN8, CLDN9, CLDND1, CLDND2, CLEC10A, CLEC11A, CLEC12A, CLEC12B, CLEC14A, CLEC16A, CLEC17A, CLEC18A, CLEC18B, CLEC18C, CLEC19A, CLEC1A, CLECIB, CLEC20A, CLEC2A, CLEC2B, CLEC2D, CLEC2L, CLEC3A, CLEC3B, CLEC4A, CLEC4C, CLEC4D, CLEC4E, CLEC4F, CLEC4G, CLEC4M, CLEC5A, CLEC6A, CLEC7A, CLEC9A, CLECL1, CLGN, CLHC1, CLIC1, CLIC2, CLIC3, CLIC4, CLIC5, CLIC6, CLINT1, CLIP1, CLIP2, CLIP3, CLIP4, CLK1, CLK2, CLK3, CLK4, CLLU1, CLLU1OS, CLMN, CLMP, CLN3, CLN5, CLN6, CLN8, CLNK, CLNS1A, CLOCK, CLP1, CLPB, CLPP, CLPS, CLPSL1, CLPSL2, CLPTM1, CLPTMIL, CLPX, CLRN1, CLRN2, CLRN3, CLSPN, CLSTN1, CLSTN2, CLSTN3, CLTA, CLTB, CLTC, CLTCL1, CLU, CLUAP1, CLUH, CLUL1, CLVS1, CLVS2, CLYBL, CMA1, CMAS, CMBL, CMC1, CMC2, CMC4, CMIP, CMKLR1, CMPK1, CMPK2, CMSS1, CMTM1, CMTM2, CMTM3, CMTM4, CMTM5, CMTM6, CMTM7, CMTM8, CMTR1, CMTR2, CMYA5, CNBD1, CNBD2, CNBP, CNDP1, CNDP2, CNEPIR1, CNFN, CNGA1, CNGA2, CNGA3, CNGA4, CNGB1, CNGB3, CNIH1, CNIH2, CNIH3, CNIH4, CNKSR1, CNKSR2, CNKSR3, CNMD, CNN1, CNN2, CNN3, CNNM1, CNNM2, CNNM3, CNNM4, CNOT1, CNOT10, CNOT11, CNOT2, CNOT3, CNOT4, CNOT6, CNOT6L, CNOT7, CNOT8, CNOT9, CNP, CNPPD1, CNPY1, CNPY2, CNPY3, CNPY4, CNR1, CNR2, CNRIP1, CNST, CNTD1, CNTD2, CNTF, CNTFR, CNTLN, CNTN1, CNTN2, CNTN3, CNTN4, CNTNS, CNTN6, CNTNAP1, CNTNAP2, CNTNAP3, CNTNAP3B, CNTNAP4, CNTNAP5, CNTRL, CNTROB, COA1, COA3, COA4, COA5, COA6, COA7, COASY, COBL, COBLL1, COCH, COG1, COG2, COG3, COG4, COG5, COG6, COG7, COG8, COIL, COL10A1, COL11A1, COL11A2, COL12A1, COL13A1, COL14A1, COL15A1, COL16A1, COL17A1, COL18A1, COL19A1, COL1A1, COL1A2, COL20A1, COL21A1, COL22A1, COL23A1, COL24A1, COL25A1, COL26A1, COL27A1, COL28A1, COL2A1, COL3A1, COL4A1, COL4A2, COL4A3, COL4A3BP, COL4A4, COL4A5, COL4A6, COL5A1, COL5A2, COL5A3, COL6A1, COL6A2, COL6A3, COL6A5, COL6A6, COL7A1, COL8A1, COL8A2, COL9A1, COL9A2, COL9A3, COLCA2, COLEC10, COLEC11, COLEC12, COLGALT1, COLGALT2, COLQ, COMMD1, COMMD10, COMMD2, COMMD3, COMMD3-BMI1, COMMD4, COMMD5, COMMD6, COMMD7, COMMD8, COMMD9, COMP, COMT, COMTD1, COPA, COPB1, COPB2, COPE, COPG1, COPG2, COPRS, COPS2, COPS3, COPS4, COPS5, COPS6, COPS7A, COPS7B, COPS8, COPS9, COPZ1, COPZ2, COQ10A, COQ10B, COQ2, COQ3, COQ4, COQ5, COQ6, COQ7, COQ8A, COQ8B, COQ9, CORIN, CORO1A, CORO1B, CORO1C, CORO2A, CORO2B, CORO6, CORO7, CORO7-PAM16, CORT, COTL1, COX10, COX11, COX14, COX15, COX16, COX17, COX18, COX19, COX20, COX4I1, COX4I2, COX5A, COX5B, COX6A1, COX6A2, COX6B1, COX6B2, COX6C, COX7A1, COX7A2, COX7A2L, COX7B, COX7B2, COX7C, COX8A, COX8C, CP, CPA1, CPA2, CPA3, CPA4, CPA5, CPA6, CPAMD8, CPB1, CPB2, CPD, CPE, CPEB1, CPEB2, CPEB3, CPEB4, CPED1, CPLX1, CPLX2, CPLX3, CPLX4, CPM, CPN1, CPN2, CPNE1, CPNE2, CPNE3, CPNE4, CPNE5, CPNE6, CPNE7, CPNE8, CPNE9, CPO, CPOX, CPPED1, CPQ, CPS1, CPSF1, CPSF2, CPSF3, CPSF4, CPSF4L, CPSF6, CPSF7, CPT1A, CPT1B, CPT1C, CPT2, CPTP, CPVL, CPXCR1, CPXM1, CPXM2, CPZ, CR1, CR1L, CR2, CR354443.1, CR354443.2, CR388407.3, CR547123.3, CR753842.1, CR753845.2, CR759815.2, CR788250.1, CR847794.2, CR854858.1, CR933783.3, CR936239.1, CRABP1, CRABP2, CRACR2A, CRACR2B, CRADD, CRAMP1, CRAT, CRB1, CRB2, CRB3, CRBN, CRCP, CRCT1, CREB1, CREB3, CREB3L1, CREB3L2, CREB3L3, CREB3L4, CREBS, CREBBP, CREBL2, CREBRF, CRE-BZF, CREG1, CREG2, CRELD1, CRELD2, CREM, CRH, CRHBP, CRHR1, CRHR2, CRIM1, CRIP1, CRIP2, CRIP3, CRIPT, CRISP1, CRISP2, CRISP3, CRISPLD1, CRISPLD2, CRK, CRKL, CRLF1, CRLF2, CRLF3, CRLS1, CRMP1, CRNKL1, CRNN, CROCC, CROCC2, CROT, CRP, CRTAC1, CRTAM, CRTAP, CRTC1, CRTC2, CRTC3, CRX, CRY1, CRY2, CRYAA, CRYAB, CRYBA1, CRYBA2, CRYBA4, CRYBB1, CRYBB2, CRYBB3, CRYBG1, CRYBG2, CRYBG3, CRYGA, CRYGB, CRYGC, CRYGD, CRYGN, CRYGS, CRYL1, CRYM, CRYZ, CRYZL1, CS, CSAD, CSAG1, CSAG2, CSAG3, CSDC2, CSDE1, CSE1L, CSF1, CSF1R, CSF2, CSF2RA, CSF2RB, CSF3, CSF3R, CSGALNACT1, CSGALNACT2, CSH1, CSH2, CSHL1, CSK, CSMD1, CSMD2, CSMD3, CSNIS1, CSN2, CSN3, CSNK1A1, CSNK1A1L, CSNK1D, CSNK1E, CSNKlG1, CSNKIG2, CSNKIG3, CSNK2A1, CSNK2A2, CSNK2A3, CSNK2B, CSPG4, CSPG5, CSPP1, CSRNP1, CSRNP2, CSRNP3, CSRP1, CSRP2, CSRP3, CST1, CST11, CST2, CST3, CST4, CST5, CST6, CST7, CST8, CST9, CST9L, CSTA, CSTB, CSTF1, CSTF2, CSTF2T, CSTF3, CSTL1, CT45A1, CT45A10, CT45A2, CT45A3, CT45A5, CT45A6, CT45A7, CT45A8, CT45A9, CT476828.1, CT476828.10, CT476828.11, CT476828.12, CT476828.13, CT476828.14, CT476828.15, CT476828.16, CT476828.17, CT476828.18, CT476828.19, CT476828.2, CT476828.20, CT476828.21, CT476828.22, CT476828.3, CT476828.4, CT476828.5, CT476828.6, CT476828.7, CT476828.8, CT476828.9, CT47A1, CT47A10, CT47A11, CT47A12, CT47A2, CT47A3, CT47A4, CT47A5, CT47A6, CT47A7, CT47A8, CT47A9, CT47B1, CT55, CT62, CT83, CTAG1A, CTAG1B, CTAG2, CTAGE1, CTAGE15, CTAGE4, CTAGE5, CTAGE6, CTAGE8, CTAGE9, CTBP1, CTBP2, CTBS, CTC1, CTCF, CTCFL, CTDNEP1, CTDP1, CTDSP1, CTDSP2, CTDSPL, CTDSPL2, CTF1, CTGF, CTH, CTHRC1, CTIF, CTLA4, CTNNA1, CTNNA2, CTNNA3, CTNNAL1, CTNNB1, CTNNBIP1, CTNNBL1, CTNND1, CTNND2, CTNS, CTPS1, CTPS2, CTR9, CTRB1, CTRB2, CTRC, CTRL, CTSA, CTSB, CTSC, CTSD, CTSE, CTSF, CTSG, CTSH, CTSK, CTSL, CTSO, CTSS, CTSV, CTSW, CTSZ, CTTN, CTTNBP2, CTTNBP2NL, CTU1, CTU2, CTXN1, CTXN2, CTXN3, CTXND1, CU464060.1, CU633846.1, CU633980.1, CU633980.2, CU639417.1, CU639417.2, CUBN, CUEDC1, CUEDC2, CUL1, CUL2, CUL3, CUL4A, CUL4B, CUL5, CUL7, CUL9, CUTA, CUTC, CUX1, CUX2, CUZD1, CWC15, CWC22, CWC25, CWC27, CWF19L1, CWF19L2, CWH43, CX3CL1, CX3CR1, CXADR, CXCL1, CXCL10, CXCL11, CXCL12, CXCL13, CXCL14, CXCL16, CXCL17, CXCL2, CXCL3, CXCL5, CXCL6, CXCL8, CXCL9, CXCR1, CXCR2, CXCR3, CXCR4, CXCR5, CXCR6, CXorf21, CXorf36, CXorf38, CXorf40A, CXorf40B, CXorf49, CXorf49B, CXorf51A, CXorf51B, CXorf56, CXorf57, CXorf58, CXorf65, CXorf66, CXorf67, CXXC1, CXXC4, CXXC5, CYB561, CYB561A3, CYB561D1, CYB561D2, CYB5A, CYB5B, CYB5D1, CYB5D2, CYB5R1, CYB5R2, CYB5R3, CYB5R4, CYB5RL, CYBA, CYBB, CYBRD1, CYC1, CYCS, CYFIP1, CYFIP2, CYGB, CYHR1, CYLC1, CYLC2, CYLD, CYP11A1, CYP11B1, CYP11B2, CYP17A1, CYP19A1, CYP1A1, CYP1A2, CYP1B1, CYP20A1, CYP21A2, CYP24A1, CYP26A1, CYP26B1, CYP26C1, CYP27A1, CYP27B1, CYP27C1, CYP2A13, CYP2A6, CYP2A7, CYP2B6, CYP2C18, CYP2C19, CYP2C8, CYP2C9, CYP2D6, CYP2D7, CYP2E1, CYP2F1, CYP2J2, CYP2R1, CYP2S1, CYP2U1, CYP2W1, CYP39A1, CYP3A4, CYP3A43, CYP3A5, CYP3A7, CYP3A7-CYP3A51P, CYP46A1, CYP4A11, CYP4A22, CYP4B1, CYP4F11, CYP4F12, CYP4F2, CYP4F22, CYP4F3, CYP4F8, CYP4V2, CYP4X1, CYP4Z1, CYP51A1, CYP7A1, CYP7B1, CYP8B1, CYR61, CYS1, CYSLTR1, CYSLTR2, CYSRT1, CYSTM1, CYTH1, CYTH2, CYTH3, CYTH4, CYTIP, CYTL1, CYYR1, D2HGDH, DAAM1, DAAM2, DAB1, DAB2, DAB2IP, DACH1, DACH2, DACT1, DACT2, DACT3, DAD1, DAG1, DAGLA, DAGLB, DALRD3, DAND5, DAO, DAOA, DAP, DAP3, DAPK1, DAPK2, DAPK3, DAPL1, DAPP1, DARS, DARS2, DAW1, DAXX, DAZ1, DAZ2, DAZ3, DAZ4, DAZAP1, DAZAP2, DAZL, DBF4, DBF4B, DBH, DBI, DBN1, DBNDD1, DBNDD2, DBNL, DBP, DBR1, DBT, DBX1, DBX2, DCAF1, DCAF10, DCAF11, DCAF12, DCAF12L1, DCAF12L2, DCAF13, DCAF15, DCAF16, DCAF17, DCAF4, DCAF4L1, DCAF4L2, DCAF5, DCAF6, DCAF7, DCAF8, DCAF8L1, DCAF8L2, DCAKD, DCANP1, DCBLD1, DCBLD2, DCC, DCD, DCDC1, DCDC2, DCDC2B, DCDC2C, DCHS1, DCHS2, DCK, DCLK1, DCLK2, DCLK3, DCLRE1A, DCLRE1B, DCLRE1C, DCN, DCP1A, DCP1B, DCP2, DCPS, DCST1, DCST2, DCSTAMP, DCT, DCTD, DCTN1, DCTN2, DCTN3, DCTN4, DCTN5, DCTN6, DCTPP1, DCUN1D1, DCUN1D2, DCUN1D3, DCUN1D4, DCUN1D5, DCX, DCXR, DDA1, DDAH1, DDAH2, DDB1, DDB2, DDC, DDHD1, DDHD2, DDI1, DDI2, DDIAS, DDIT3, DDIT4, DDIT4L, DDN, DDO, DDOST, DDR1, DDR2, DDRGK1, DDT, DDTL, DDX1, DDX10, DDX11, DDX17, DDX18, DDX19A, DDX19B, DDX20, DDX21, DDX23, DDX24, DDX25, DDX27, DDX28, DDX31, DDX39A, DDX39B, DDX3X, DDX3Y, DDX4, DDX41, DDX42, DDX43, DDX46, DDX47, DDX49, DDX5, DDX50, DDX51, DDX52, DDX53, DDX54, DDX55, DDX56, DDX58, DDX59, DDX6, DDX60, DDX60L, DEAF1, DEC1, DECR1, DECR2, DEDD, DEDD2, DEF6, DEF8, DEFA1, DEFA1B, DEFA3, DEFA4, DEFA5, DEFA6, DEFB1, DEFB103A, DEFB103B, DEFB104A, DEFB104B, DEFB105A, DEFB105B, DEFB106A, DEFB106B, DEFB107A, DEFB107B, DEFB108B, DEFB110, DEFB112, DEFB113, DEFB114, DEFB115, DEFB116, DEFB118, DEFB119, DEFB121, DEFB123, DEFB124, DEFB125, DEFB126, DEFB127, DEFB128, DEFB129, DEFB130A, DEFB130B, DEFB131A, DEFB131B, DEFB132, DEFB133, DEFB134, DEFB135, DEFB136, DEFB4A, DEFB4B, DEGS1, DEGS2, DEK, DENND1A, DENND1B, DENND1C, DENND2A, DENND2C, DENND2D, DENND3, DENND4A, DENND4B, DENND4C, DENND5A, DENND5B, DENND6A, DENND6B, DENR, DEPDC1, DEPDC1B, DEPDC4, DEPDC5, DEPDC7, DEPTOR, DERA, DERL1, DERL2, DERL3, DES, DESI1, DESI2, DET1, DEUP1, DEXI, DFFA, DFFB, DFNA5, DFNB59, DGAT1, DGAT2, DGAT2L6, DGCR2, DGCR6, DGCR6L, DGCR8, DGKA, DGKB, DGKD, DGKE, DGKG, DGKH, DGKI, DGKK, DGKQ, DGKZ, DGUOK, DHCR24, DHCR7, DHDDS, DHDH, DHFR, DHFR2, DHH, DHODH, DHPS, DHRS1, DHRS11, DHRS12, DHRS13, DHRS2, DHRS3, DHRS4, DHRS4L2, DHRS7, DHRS7B, DHRS7C, DHRS9, DHRSX, DHTKD1, DHX15, DHX16, DHX29, DHX30, DHX32, DHX33, DHX34, DHX35, DHX36, DHX37, DHX38, DHX40, DHX57, DHX58, DHX8, DHX9, DIABLO, DIAPH1, DIAPH2, DIAPH3, DICER1, DIDO1, DIEXF, DIMT1, DIO1, DIO2, DIO3, DIP2A, DIP2B, DIP2C, DIRAS1, DIRAS2, DIRAS3, DIRC1, DIRC2, DIRC3, DIS3, DIS3L, DIS3L2, DISC1, DISP1, DISP2, DISP3, DIXDC1, DKC1, DKK1, DKK2, DKK3, DKK4, DKKL1, DLAT, DLC1, DLD, DLEC1, DLEU7, DLG1, DLG2, DLG3, DLG4, DLG5, DLGAP1, DLGAP2, DLGAP3, DLGAP4, DLGAP5, DLK1, DLK2, DLL1, DLL3, DLL4, DLST, DLX1, DLX2, DLX3, DLX4, DLX5, DLX6, DMAC1, DMAC2, DMAP1, DMBT1, DMBX1, DMC1, DMD, DMGDH, DMKN, DMP1, DMPK, DMRT1, DMRT2, DMRT3, DMRTA1, DMRTA2, DMRTB1, DMRTC1, DMRTC1B, DMRTC2, DMTF1, DMTN, DMWD, DMXL1, DMXL2, DNA2, DNAAF1, DNAAF2, DNAAF3, DNAAF4, DNAAF5, DNAH1, DNAH10, DNAH10OS, DNAH11, DNAH12, DNAH14, DNAH17, DNAH2, DNAH13, DNAH5, DNAH6, DNAH7, DNAH8, DNAH9, DNAI1, DNAI2, DNAJA1, DNAJA2, DNAJA3, DNAJA4, DNAJB1, DNAJB11, DNAJB12, DNAJB13, DNAJB14, DNAJB2, DNAJB4, DNAJB5, DNAJB6, DNAJB7, DNAJB8, DNAJB9, DNAJC1, DNAJC10, DNAJC11, DNAJC12, DNAJC13, DNAJCl4, DNAJC15, DNAJC16, DNAJC17, DNAJC18, DNAJC19, DNAJC2, DNAJC21, DNAJC22, DNAJC24, DNAJC25, DNAJC25-GNG10, DNAJC27, DNAJC28, DNAJC3, DNAJC30, DNAJC4, DNAJC5, DNAJC5B, DNAJC5G, DNAJC6, DNAJC7, DNAJC8, DNAJC9, DNAL1, DNAL4, DNALI1, DNASE1, DNASE1L1, DNASE1L2, DNASE1L3, DNASE2, DNASE2B, DND1, DNER, DNHD1, DNLZ, DNM1, DNM1L, DNM2, DNM3, DNMBP, DNMT1, DNMT3A, DNMT3B, DNMT3L, DNPEP, DNPH1, DNTT, DNTTIP1, DNTTIP2, DOC2A, DOC2B, DOCK1, DOCK10, DOCK11, DOCK2, DOCK3, DOCK4, DOCK5, DOCK6, DOCK7, DOCK8, DOCK9, DOHH, DOK1, DOK2, DOK3, DOK4, DOK5, DOK6, DOK7, DOLK, DOLPP1, DONSON, DOPEY1, DOPEY2, DOT1L, DPAGT1, DPCD, DPCR1, DPEP1, DPEP2, DPEP3, DPF1, DPF2, DPF3, DPH1, DPH2, DPH3, DPH5, DPH6, DPH7, DPM1, DPM2, DPM3, DPP10, DPP3, DPP4, DPP6, DPP7, DPP8, DPP9, DPPA2, DPPA3, DPPA4, DPPA5, DPRX, DPT, DPY19L1, DPY19L2, DPY19L3, DPY19L4, DPY30, DPYD, DPYS, DPYSL2, DPYSL3, DPYSL4, DPYSL5, DQX1, DR1, DRAM1, DRAM2, DRAP1, DRAXIN, DRC1, DRC3, DRC7, DRD1, DRD2, DRD3, DRD4, DRD5, DRG1, DRG2, DRGX, DRICH1, DROSHA, DRP2, DSC1, DSC2, DSC3, DSCAM, DSCAML1, DSCC1, DSCR3, DSCR4, DSCR8, DSE, DSEL, DSG1, DSG2, DSG3, DSG4, DSN1, DSP, DSPP, DST, DSTN, DSTYK, DTD1, DTD2, DTHD1, DTL, DTNA, DTNB, DTNBP1, DTWD1, DTWD2, DTX1, DTX2, DTX3, DTX3L, DTX4, DTYMK, DUOX1, DUOX2, DUOXA1, DUOXA2, DUPD1, DUS1L, DUS2, DUS3L, DUS4L, DUSP1, DUSP10, DUSP11, DUSP12, DUSP13, DUSP14, DUSP15, DUSP16, DUSP18, DUSP19, DUSP2, DUSP21, DUSP22, DUSP23, DUSP26, DUSP27, DUSP28, DUSP3, DUSP4, DUSP5, DUSP6, DUSP7, DUSP8, DUSP9, DUT, DUX4, DUXA, DUXB, DVL1, DVL2, DVL3, DWORF, DXO, DYDC1, DYDC2, DYM, DYNAP, DYNCIH1, DYNC1I1, DYNC1I2, DYNC1LI1, DYNC1LI2, DYNC2H1, DYNC2LI1, DYNLL1, DYNLL2, DYNLRB1, DYNLRB2, DYNLT1, DYNLT3, DYRKIA, DYRKIB, DYRK2, DYRK3, DYRK4, DYSF, DYTN, DZANK1, DZIP1, DZIP1L, DZIP3, E2F1, E2F2, E2F3, E2F4, E2F5, E2F6, E2F7, E2F8, E4F1, EAF1, EAF2, EAPP, EARS2, EBAG9, EBF1, EBF2, EBF3, EBF4, EBI3, EBLN1, EBLN2, EBNAIBP2, EBP, EBPL, ECD, ECE1, ECE2, ECEL1, ECH1, ECHDC1, ECHDC2, ECHDC3, ECHS1, ECI1, ECI2, ECM1, ECM2, ECSCR, ECSIT, ECT2, ECT2L, EDA, EDA2R, EDAR, EDARADD, EDC3, EDC4, EDDM13, EDDM3A, EDDM3B, EDEM1, EDEM2, EDEM3, EDF1, EDIL3, EDN1, EDN2, EDN3, EDNRA, EDNRB, EDRF1, EEA1, EED, EEF1A1, EEF1A2, EEF1AKMT1, EEF1AKMT2, EEF1AKMT3, EEF1B2, EEF1D, EEF1E1, EEF1E1-BLOC1S5, EEF1G, EEF2, EEF2K, EEF2KMT, EEFSEC, EEPD1, EFCAB1, EFCAB10, EFCAB11, EFCAB12, EFCAB13, EFCAB14, EFCAB2, EFCAB3, EFCAB5, EFCAB6, EFCAB7, EFCAB8, EFCAB9, EFCC1, EFEMP1, EFEMP2, EFHB, EFHC1, EFHC2, EFHD1, EFHD2, EFL1, EFNA1, EFNA2, EFNA3, EFNA4, EFNA5, EFNB1, EFNB2, EFNB3, EFR3A, EFR3B, EFS, EFTUD2, EGF, EGFL6, EGFL7, EGFL8, EGFLAM, EGFR, EGLN1, EGLN2, EGLN3, EGR1, EGR2, EGR3, EGR4, EHBP1, EHBPIL1, EHD1, EHD2, EHD3, EHD4, EHF, EHHADH, EHMT1, EHMT2, EI24, EID1, EID2, EID2B, EID3, EIF1, EIF1AD, EIF1AX, EIF1AY, EIF1B, EIF2A, EIF2AK1, EIF2AK2, EIF2AK3, EIF2AK4, EIF2B1, EIF2B2, EIF2B3, EIF2B4, EIF2B5, EIF2D, EIF2S1, EIF2S2, EIF2S3, EIF3A, EIF3B, EIF3C, EIF3CL, EIF3D, EIF3E, EIF3F, EIF3G, EIF3H, EIF3I, EIF3J, EIF3K, EIF3L, EIF3M, EIF4A1, EIF4A2, EIF4A3, EIF4B, EIF4E, EIF4E1B, EIF4E2, EIF4E3, EIF4EBP1, EIF4EBP2, EIF4EBP3, EIF4ENIF1, EIF4G1, EIF4G2, EIF4G3, EIF4H, EIF5, EIF5A, EIF5A2, EIF5AL1, EIF5B, EIF6, EIPR1, ELAC1, ELAC2, ELANE, ELAVL1, ELAVL2, ELAVL3, ELAVL4, ELF1, ELF2, ELF3, ELF4, ELF5, ELFN1, ELFN2, ELK1, ELK3, ELK4, ELL, ELL2, ELL3, ELMO1, ELMO2, ELMO3, ELMOD1, ELMOD2, ELMOD3, ELMSAN1, ELN, ELOA, ELOA2, ELOA3, ELOA3B, ELOA3C, ELOA3D, ELOB, ELOC, ELOF1, ELOVL1, ELOVL2, ELOVL3, ELOVL4, ELOVL5, ELOVL6, ELOVL7, ELP1, ELP2, ELP3, ELP4, ELP5, ELP6, ELSPBP1, EMB, EMC1, EMC10, EMC2, EMC3, EMC4, EMC6, EMC7, EMC8, EMC9, EMCN, EMD, EME1, EME2, EMG1, EMID1, EMILIN1, EMILIN2, EMILIN3, EML1, EML2, EML3, EML4, EML5, EML6, EMP1, EMP2, EMP3, EMSY, EMX1, EMX2, EN1, EN2, ENAH, ENAM, ENC1, ENDOD1, ENDOG, ENDOU, ENDOV, ENG, ENGASE, ENHO, ENKD1, ENKUR, ENO1, ENO2, ENO3, ENO4, ENOPH1, ENOSF1, ENOX1, ENOX2, ENPEP, ENPP1, ENPP2, ENPP3, ENPP4, ENPP5, ENPP6, ENPP7, ENSA, ENTHD1, ENTPD1, ENTPD2, ENTPD3, ENTPD4, ENTPD5, ENTPD6, ENTPD7, ENTPD8, ENY2, EOGT, EOMES, EP300, EP400, EPAS1, EPB41, EPB41L1, EPB41L2, EPB41L3, EPB41L4A, EPB41L4B, EPB41L5, EPB42, EPC1, EPC2, EPCAM, EPDR1, EPG5, EPGN, EPHA1, EPHA10, EPHA2, EPHA3, EPHA4, EPHA5, EPHA6, EPHA7, EPHA8, EPHB1, EPHB2, EPHB3, EPHB4, EPHB6, EPHX1, EPHX2, EPHX3, EPHX4, EPM2A, EPM2AIP1, EPN1, EPN2, EPN3, EPO, EPOP, EPOR, EPPIN, EPPIN-WFDC6, EPPK1, EPRS, EPS15, EPS15L1, EPS8, EPS8L1, EPS8L2, EPS8L3, EPSTI1, EPX, EPYC, EQTN, ERAL1, ERAP1, ERAP2, ERAS, ERBB2, ERBB3, ERBB4, ERBIN, ERC1, ERC2, ERCC1, ERCC2, ERCC3, ERCC4, ERCC5, ERCC6, ERCC6L, ERCC6L2, ERCC8, EREG, ERF, ERFE, ERG, ERG28, ERGIC1, ERGIC2, ERGIC3, ERH, ERI1, ERI2, ERI3, ERICH1, ERICH2, ERICH3, ERICH4, ERICH5, ERICH6, ERICH6B, ERLEC1, ERLIN1, ERLIN2, ERMAP, ERMARD, ERMN, ERMP1, ERN1, ERN2, ERO1A, ERO1B, ERP27, ERP29, ERP44, ERRFI1, ERV3-1, ERVFRD-1, ERVMER34-1, ERVV-1, ERVV-2, ERVW-1, ESAM, ESCO1, ESCO2, ESD, ESF1, ESM1, ESPL1, ESPN, ESPNL, ESR1, ESR2, ESRP1, ESRP2, ESRRA, ESRRB, ESRRG, ESS2, ESX1, ESYT1, ESYT2, ESYT3, ETAA1, ETDA, ETDB, ETDC, ETF1, ETFA, ETFB, ETFBKMT, ETFDH, ETFRF1, ETHE1, ETNK1, ETNK2, ETNPPL, ETS1, ETS2, ETVI, ETV2, ETV3, ETV3L, ETV4, ETV5, ETV6, ETV7, EVA1A, EVA1B, EVA1C, EVC, EVC2, EVI2A, EVI2B, EVI5, EVI5L, EVL, EVPL, EVPLL, EVX1, EVX2, EWSR1, EXD1, EXD2, EXD3, EXO1, EXO5, EXOC1, EXOC1L, EXOC2, EXOC3, EXOC3L1, EXOC3L2, EXOC3L4, EXOC4, EXOC5, EXOC6, EXOC6B, EXOC7, EXOC8, EXOG, EXOSC1, EXOSC10, EXOSC2, EXOSC3, EXOSC4, EXOSC5, EXOSC6, EXOSC7, EXOSC8, EXOSC9, EXPH5, EXT1, EXT2, EXTL1, EXTL2, EXTL3, EYA1, EYA2, EYA3, EYA4, EYS, EZH1, EZH2, EZR, F10, F11, F11R, F12, F13A1, F13B, F2, F2R, F2RL1, F2RL2, F2RL3, F3, F5, F7, F8, F8A1, F8A2, F8A3, F9, FA2H, FAAH, FAAH2, FAAP100, FAAP20, FAAP24, FABP1, FABP12, FABP2, FABP3, FABP4, FABP5, FABP6, FABP7, FABP9, FADD, FADS1, FADS2, FADS3, FADS6, FAF1, FAF2, FAH, FAHD1, FAHD2A, FAHD2B, FAIM, FAIM2, FAM102A, FAM102B, FAM103A1, FAM104A, FAM104B, FAM105A, FAM106A, FAM107A, FAM107B, FAM109A, FAM109B, FAM110A, FAM110B, FAM110C, FAM110D, FAMlllA, FAMlllB, FAM114A1, FAM114A2, FAM117A, FAM117B, FAM118A, FAM118B, FAM120A, FAM120AOS, FAM120B, FAM120C, FAM122A, FAM122B, FAM122C, FAM124A, FAM124B, FAM126A, FAM126B, FAM129A, FAM129B, FAM129C, FAM131A, FAM131B, FAM131C, FAM133A, FAM133B, FAM135A, FAM135B, FAM136A, FAM13A, FAM13B, FAM13C, FAM149A, FAM149B1, FAM151A, FAM151B, FAM153A, FAM153B, FAM153C, FAM155A, FAM155B, FAM156A, FAM156B, FAM159A, FAM159B, FAM160A1, FAM160A2, FAM160B1, FAM160B2, FAM161A, FAM161B, FAM162A, FAM162B, FAM163A, FAM163B, FAM166A, FAM166B, FAM167A, FAM167B, FAM168A, FAM168B, FAM169A, FAM169B, FAM170A, FAM170B, FAM171A1, FAM171A2, FAM171B, FAM172A, FAM173A, FAM173B, FAM174A, FAM174B, FAM177A1, FAM177B, FAM178B, FAM180A, FAM180B, FAM181A, FAM181B, FAM182B, FAM183A, FAM184A, FAM184B, FAM185A, FAM186A, FAM186B, FAM187A, FAM187B, FAM189A1, FAM189A2, FAM189B, FAM192A, FAM193A, FAM193B, FAM196A, FAM196B, FAM198A, FAM198B, FAM199X, FAM19A1, FAM19A2, FAM19A3, FAM19A4, FAM19A5, FAM200A, FAM200B, FAM204A, FAM205A, FAM205C, FAM206A, FAM207A, FAM208A, FAM208B, FAM209A, FAM209B, FAM20A, FAM20B, FAM20C, FAM210A, FAM210B, FAM212A, FAM212B, FAM213A, FAM213B, FAM214A, FAM214B, FAM216A, FAM216B, FAM217A, FAM217B, FAM218A, FAM219A, FAM219B, FAM220A, FAM221A, FAM221B, FAM222A, FAM222B, FAM227A, FAM227B, FAM228A, FAM228B, FAM229A, FAM229B, FAM230A, FAM231A, FAM231B, FAM231C, FAM231D, FAM234A, FAM234B, FAM236A, FAM236B, FAM236C, FAM236D, FAM237A, FAM237B, FAM240A, FAM240B, FAM24A, FAM24B, FAM25A, FAM25C, FAM25G, FAM26D, FAM26E, FAM26F, FAM32A, FAM35A, FAM3A, FAM3B, FAM3C, FAM3D, FAM43A, FAM43B, FAM45A, FAM46A, FAM46B, FAM46C, FAM46D, FAM47A, FAM47B, FAM47C, FAM47E, FAM47E-STBD1, FAM49A, FAM49B, FAM50A, FAM50B, FAM53A, FAM53B, FAM53C, FAM57A, FAM57B, FAM58A, FAM60A, FAM69A, FAM69B, FAM69C, FAM71A, FAM71B, FAM71C, FAM71D, FAM71E1, FAM71E2, FAM71F1, FAM71F2, FAM72A, FAM72B, FAM72C, FAM72D, FAM76A, FAM76B, FAM78A, FAM78B, FAM81A, FAM81B, FAM83A, FAM83B, FAM83C, FAM83D, FAM83E, FAM83F, FAM83G, FAM83H, FAM84A, FAM84B, FAM86B1, FAM86B2, FAM86C1, FAM89A, FAM89B, FAM8A1, FAM90A1, FAM90A26, FAM91A1, FAM92A, FAM92B, FAM95C, FAM96A, FAM96B, FAM98A, FAM98B, FAM98C, FAM9A, FAM9B, FAM9C, FAN1, FANCA, FANCB, FANCC, FANCD2, FANCD2OS, FANCE, FANCF, FANCG, FANCI, FANCL, FANCM, FANK1, FAP, FAR1, FAR2, FARP1, FARP2, FARS2, FARSA, FARSB, FAS, FASLG, FASN, FASTK, FASTKD1, FASTKD2, FASTKD3, FASTKD5, FAT1, FAT2, FAT3, FAT4, FATE1, FAU, FAXC, FAXDC2, FBF1, FBL, FBLIM1, FBLL1, FBLN1, FBLN2, FBLN5, FBLN7, FBN1, FBN2, FBN3, FBP1, FBP2, FBRS, FBRSL1, FBXL12, FBXL13, FBXL14, FBXL15, FBXL16, FBXL17, FBXL18, FBXL19, FBXL2, FBXL20, FBXL22, FBXL3, FBXL4, FB3XL5, FBXL6, FBXL7, FBXL8, FBXO10, FBXO11, FBXO15, FBXO16, FBXO17, FBXO18, FBXO2, FBXO21, FBXO22, FBXO24, FBXO25, FBXO27, FBXO28, FBXO3, FBXO30, FBXO31, FBXO32, FBXO33, FBXO34, FBXO36, FBXO38, FBXO39, FBXO4, FBXO40, FBXO41, FBXO42, FBXO43, FBXO44, FBXO45, FBXO46, FBXO47, FBXO48, FBXO5, FBXO6, FBXO7, FBXO8, FBXO9, FBXW10, FBXW11, FBXW12, FBXW2, FBXW4, FBXW5, FBXW7, FBXW8, FBXW9, FCAMR, FCAR, FCER1A, FCER1G, FCER2, FCF1, FCGBP, FCGR1A, FCGR1B, FCGR2A, FCGR2B, FCGR2C, FCGR3A, FCGR3B, FCGRT, FCHO1, FCHO2, FCHSD1, FCHSD2, FCMR, FCN1, FCN2, FCN3, FCRL1, FCRL2, FCRL3, FCRL4, FCRL5, FCRL6, FCRLA, FCRLB, FDCSP, FDFT1, FDPS, FDX1, FDX2, FDXACB1, FDXR, FECH, FEM1A, FEM1B, FEM1C, FEN1, FER, FER1L5, FER1L6, FERD3L, FERMT1, FERMT2, FERMT3, FES, FETUB, FEV, FEZ1, FEZ2, FEZF1, FEZF2, FFAR1, FFAR2, FFAR3, FFAR4, FGA, FGB, FGD1, FGD2, FGD3, FGD4, FGD5, FGD6, FGF1, FGF10, FGF11, FGF12, FGF13, FGF14, FGF16, FGF17, FGF18, FGF19, FGF2, FGF20, FGF21, FGF22, FGF23, FGF3, FGF4, FGF5, FGF6, FGF7, FGF8, FGF9, FGFBP1, FGFBP2, FGFBP3, FGFR1, FGFR1OP, FGFR1OP2, FGFR2, FGFR3, FGFR4, FGFRL1, FGG, FGGY, FGL1, FGL2, FGR, FH, FHAD1, FHDC1, FHIT, FHL1, FHL2, FHL3, FHL5, FHOD1, FHOD3, FIBCD1, FIBIN, FIBP, FICD, FIG4, FIGLA, FIGN, FIGNL1, FIGNL2, FILIP1, FILIP1L, FIP1L1, FIS1, FITM1, FITM2, FIZ1, FJX1, FKBP10, FKBP11, FKBP14, FKBP15, FKBP1A, FKBP1B, FKBP1C, FKBP2, FKBP3, FKBP4, FKBP5, FKBP6, FKBP7, FKBP8, FKBP9, FKBPL, FKRP, FKTN, FLAD1, FLCN, FLG, FLG2, FLI1, FLII, FLNA, FLNB, FLNC, FLOT1, FLOT2, FLRT1, FLRT2, FLRT3, FLT1, FLT3, FLT3LG, FLT4, FLVCR1, FLVCR2, FLYWCH1, FLYWCH2, FMC1, FMN1, FMN2, FMNL1, FMNL2, FMNL3, FMO1, FMO2, FMO3, FMO4, FMO5, FMOD, FMR1, FMR1NB, FN1, FN3K, FN3KRP, FNBP1, FNBP1L, FNBP4, FNDC1, FNDC10, FNDC11, FNDC3A, FNDC3B, FNDC4, FNDC5, FNDC7, FNDC8, FNDC9, FNIP1, FNIP2, FNTA, FNTB, FO681492.1, F0681542.1, FOCAD, FOLH1, FOLR1, FOLR2, FOLR3, FOPNL, FOS, FOSB, FOSL1, FOSL2, FOXA1, FOXA2, FOXA3, FOXB1, FOXB2, FOXC1, FOXC2, FOXD1, FOXD2, FOXD3, FOXD4, FOXD4L1, FOXD4L3, FOXD4L4, FOXD4L5, FOXD4L6, FOXE1, FOXE3, FOXF1, FOXF2, FOXG1, FOXH1, FOXI1, FOXI2, FOXI3, FOXJ1, FOXJ2, FOXJ3, FOXK1, FOXK2, FOXL1, FOXL2, FOXL2NB, FOXM1, FOXN1, FOXN2, FOXN3, FOXN4, FOXO1, FOXO3, FOXO4, FOXO6, FOXP1, FOXP2, FOXP3, FOXP4, FOXQ1, FOXR1, FOXR2, FOXRED1, FOXRED2, FOXS1, FP236240.1, FP565260.1, FP565260.2, FP565260.3, FP565260.4, FP565260.6, FP565260.7, FP565324.1, FP565324.2, FPGS, FPGT, FPGT-TNNI3K, FPR1, FPR2, FPR3, FRA10AC1, FRAS1, FRAT1, FRAT2, FREM1, FREM2, FREM3, FRG1, FRG2, FRG2B, FRG2C, FRK, FRMD1, FRMD3, FRMD4A, FRMD4B, FRMD5, FRMD6, FRMD7, FRMD8, FRMPD1, FRMPD2, FRMPD3, FRMPD4, FRRS1, FRRS1L, FRS2, FRS3, FRY, FRYL, FRZB, FSBP, FSCB, FSCN1, FSCN2, FSCN3, FSD1, FSD1L, FSD2, FSHB, FSHR, FSIP1, FSIP2, FST, FSTL1, FSTL3, FSTL4, FSTL5, FTCD, FTCDNL1, FTH1, FTHL17, FTL, FTMT, FTO, FTSJ1, FTSJ3, FUBP1, FUBP3, FUCA1, FUCA2, FUK, FUNDC1, FUNDC2, FUOM, FURIN, FUS, FUT1, FUT10, FUT11, FUT2, FUT3, FUT4, FUT5, FUT6, FUT7, FUT8, FUT9, FUZ, FXN, FXR1, FXR2, FXYD1, FXYD2, FXYD3, FXYD4, FXYD5, FXYD6, FXYD6-FXYD2, FXYD7, FYB1, FYB2, FYCO1, FYN, FYTTD1, FZD1, FZD10, FZD2, FZD3, FZD4, FZD5, FZD6, FZD7, FZD8, FZD9, FZR1, G0S2, G2E3, G3BP1, G3BP2, G6PC, G6PC2, G6PC3, G6PD, GAA, GAB1, GAB2, GAB3, GAB4, GABARAP, GABARAPL1, GABARAPL2, GABBR1, GABBR2, GABPA, GABPB1, GABPB2, GABRA1, GABRA2, GABRA3, GABRA4, GABRA5, GABRA6, GABRB1, GABRB2, GABRB3, GABRD, GABRE, GABRG1, GABRG2, GABRG3, GABRP, GABRQ, GABRR1, GABRR2, GABRR3, GAD1, GAD2, GADD45A, GADD45B, GADD45G, GADD45GIP1, GADL1, GAGE1, GAGE10, GAGE12B, GAGE12C, GAGE12D, GAGE12E, GAGE12F, GAGE12G, GAGE12H, GAGE12J, GAGE13, GAGE2A, GAGE2E, GAK, GAL, GAL3ST1, GAL3ST2, GAL3ST3, GAL3ST4, GALC, GALE, GALK1, GALK2, GALM, GALNS, GALNT1, GALNT10, GALNT11, GALNT12, GALNT13, GALNT14, GALNT15, GALNT16, GALNT17, GALNT18, GALNT2, GALNT3, GALNT4, GALNT5, GALNT6, GALNT7, GALNT8, GALNT9, GALNTL5, GALNTL6, GALP, GALR1, GALR2, GALR3, GALT, GAMT, GAN, GANAB, GANC, GAP43, GAPDH, GAPDHS, GAPT, GAPVD1, GAR1, GAREM1, GAREM2, GARNL3, GARS, GART, GAS1, GAS2, GAS2L1, GAS2L2, GAS2L3, GAS6, GAS7, GAS8, GAST, GATA1, GATA2, GATA3, GATA4, GATA5, GATA6, GATAD1, GATAD2A, GATAD2B, GATB, GATC, GATD1, GATM, GATS, GBA, GBA2, GBA3, GBE1, GBF1, GBGT1, GBP1, GBP2, GBP3, GBP4, GBP5, GBP6, GBP7, GBX1, GBX2, GC, GCA, GCAT, GCC1, GCC2, GCDH, GCFC2, GCG, GCGR, GCH1, GCHFR, GCK, GCKR, GCLC, GCLM, GCM1, GCM2, GCN1, GCNA, GCNT1, GCNT2, GCNT3, GCNT4, GCNT7, GCOM1, GCSAM, GCSAML, GCSH, GDA, GDAP1, GDAP1L1, GDAP2, GDE1, GDF1, GDF10, GDF11, GDF15, GDF2, GDF3, GDF5, GDF5OS, GDF6, GDF7, GDF9, GDI1, GDI2, GDNF, GDPD1, GDPD2, GDPD3, GDPD4, GDPD5, GDPGP1, GEM, GEMIN2, GEMIN4, GEMIN5, GEMIN6, GEMIN7, GEMIN8, GEN1, GET4, GFAP, GFER, GFI1, GFI1B, GFM1, GFM2, GFOD1, GFOD2, GFPT1, GFPT2, GFRA1, GFRA2, GFRA3, GFRA4, GFRAL, GFY, GGA1, GGA2, GGA3, GGACT, GGCT, GGCX, GGH, GGN, GGNBP2, GGPS1, GGT1, GGT2, GGT5, GGT6, GGT7, GGTLC1, GGTLC2, GGTLC3, GH1, GH2, GHDC, GHITM, GHR, GHRH, GHRHR, GHRL, GHSR, GID4, GID8, GIF, GIGYF1, GIGYF2, GIMAP1, GIMAP1-GIMAP5, GIMAP2, GIMAP4, GIMAP5, GIMAP6, GIMAP7, GIMAP8, GIMD1, GIN1, GINM1, GINS1, GINS2, GINS3, GINS4, GIP, GIPC1, GIPC2, GIPC3, GIPR, GIT1, GIT2, GJA1, GJA10, GJA3, GJA4, GJA5, GJA8, GJA9, GJB1, GJB2, GJB3, GJB4, GJB5, GJB6, GJB7, GJC1, GJC2, GJC3, GJD2, GJD3, GJD4, GJE1, GK, GK2, GK3P, GK5, GKAP1, GKN1, GKN2, GLA, GLB1, GLB1L, GLB1L2, GLB1L3, GLCCI1, GLCE, GLDC, GLDN, GLE1, GLG1, GLI1, GLI2, GLI3, GLI4, GLIPR1, GLIPRIL1, GLIPRIL2, GLIPR2, GLIS1, GLIS2, GLIS3, GLMN, GLMP, GLO1, GLOD4, GLOD5, GLP1R, GLP2R, GLRA1, GLRA2, GLRA3, GLRA4, GLRB, GLRX, GLRX2, GLRX3, GLRX5, GLS, GLS2, GLT1D1, GLT6D1, GLT8D1, GLT8D2, GLTP, GLTPD2, GLUD1, GLUD2, GLUL, GLYAT, GLYATL1, GLYATL1P3, GLYATL2, GLYATL3, GLYCTK, GLYR1, GM2A, GMCL1, GMDS, GMEB1, GMEB2, GMFB, GMFG, GMIP, GML, GMNC, GMNN, GMPPA, GMPPB, GMPR, GMPR2, GMPS, GNA11, GNA12, GNA13, GNA14, GNA15, GNAI1, GNAI2, GNAI3, GNAL, GNAO1, GNAQ, GNAS, GNAT1, GNAT2, GNAT3, GNAZ, GNB1, GNB1L, GNB2, GNB3, GNB4, GNB5, GNE, GNG10, GNG11, GNG12, GNG13, GNG14, GNG2, GNG3, GNG4, GNG5, GNG7, GNG8, GNGT1, GNGT2, GNL1, GNL2, GNL3, GNL3L, GNLY, GNMT, GNPAT, GNPDA1, GNPDA2, GNPNAT1, GNPTAB, GNPTG, GNRH1, GNRH2, GNRHR, GNS, GOLGA1, GOLGA2, GOLGA3, GOLGA4, GOLGA5, GOLGA6A, GOLGA6B, GOLGA6C, GOLGA6D, GOLGA6L1, GOLGA6L10, GOLGA6L2, GOLGA6L22, GOLGA6L4, GOLGA6L6, GOLGA6L7P, GOLGA6L9, GOLGA7, GOLGA7B, GOLGA8A, GOLGA8B, GOLGA8F, GOLGA8G, GOLGA8H, GOLGA8J, GOLGA8K, GOLGA8M, GOLGA8N, GOLGA80, GOLGA8Q, GOLGA8R, GOLGA8S, GOLGA8T, GOLGB1, GOLIM4, GOLM1, GOLPH3, GOLPH3L, GOLT1A, GOLT1B, GON4L, GON7, GOPC, GORAB, GORASP1, GORASP2, GOSR1, GOSR2, GOT1, GOT1L1, GOT2, GP1BA, GP1BB, GP2, GP5, GP6, GP9, GPA33, GPAA1, GPALPP1, GPAM, GPANK1, GPAT2, GPAT3, GPAT4, GPATCH1, GPATCH11, GPATCH2, GPATCH2L, GPATCH3, GPATCH4, GPATCH8, GPBAR1, GPBP1, GPBP1L1, GPC1, GPC2, GPC3, GPC4, GPC5, GPC6, GPCPD1, GPD1, GPD1L, GPD2, GPER1, GPHA2, GPHB5, GPHN, GPI, GPIHBP1, GPKOW, GPLD1, GPM6A, GPM6B, GPN1, GPN2, GPN3, GPNMB, GPR1, GPR101, GPR107, GPR108, GPR119, GPR12, GPR132, GPR135, GPR137, GPR137B, GPR137C, GPR139, GPR141, GPR142, GPR143, GPR146, GPR148, GPR149, GPR15, GPR150, GPR151, GPR152, GPR153, GPR155, GPR156, GPR157, GPR158, GPR160, GPR161, GPR162, GPR17, GPR171, GPR173, GPR174, GPR176, GPR179, GPR18, GPR180, GPR182, GPR183, GPR19, GPR20, GPR21, GPR22, GPR25, GPR26, GPR27, GPR3, GPR31, GPR32, GPR33, GPR34, GPR35, GPR37, GPR37L1, GPR39, GPR4, GPR42, GPR45, GPR50, GPR52, GPR55, GPR6, GPR61, GPR62, GPR63, GPR65, GPR68, GPR75, GPR75-ASB3, GPR78, GPR82, GPR83, GPR84, GPR85, GPR87, GPR88, GPR89A, GPR89B, GPRASP1, GPRASP2, GPRC5A, GPRC5B, GPRC5C, GPRC5D, GPRC6A, GPRIN1, GPRIN2, GPRIN3, GPS1, GPS2, GPSM1, GPSM2, GPSM3, GPT, GPT2, GPX1, GPX2, GPX3, GPX4, GPX5, GPX6, GPX7, GPX8, GRAMD1A, GRAMD1B, GRAMD1C, GRAMD2A, GRAMD2B, GRAMD4, GRAP, GRAP2, GRAPL, GRASP, GRB10, GRB14, GRB2, GRB7, GREB1, GREB1L, GREM1, GREM2, GRHL1, GRHL2, GRHL3, GRHPR, GRIA1, GRIA2, GRIA3, GRIA4, GRID1, GRID2, GRID2IP, GRIFIN, GRIK1, GRIK2, GRIK3, GRIK4, GRIK5, GRIN, GRIN2A, GRIN2B, GRIN2C, GRIN2D, GRIN3A, GRIN3B, GRINA, GRIP1, GRIP2, GRIPAP1, GRK1, GRK2, GRK3, GRK4, GRK5, GRK6, GRK7, GRM1, GRM2, GRM3, GRM4, GRM5, GRM6, GRM7, GRM8, GRN, GRP, GRPEL1, GRPEL2, GRPR, GRSF1, GRTP1, GRWD1, GRXCR1, GRXCR2, GSAP, GSC, GSC2, GSDMA, GSDMB, GSDMC, GSDMD, GSE1, GSG1, GSG1L, GSG1L2, GSK3A, GSK3B, GSKIP, GSN, GSPT1, GSPT2, GSR, GSS, GSTA1, GSTA2, GSTA3, GSTA4, GSTA5, GSTCD, GSTK1, GSTM1, GSTM2, GSTM3, GSTM4, GSTM5, GSTO1, GSTO2, GSTP1, GSTT1, GSTT2, GSTT2B, GSTTP1, GSTZ1, GSX1, GSX2, GTDC1, GTF2A1, GTF2A1L, GTF2A2, GTF2B, GTF2E1, GTF2E2, GTF2F1, GTF2F2, GTF2H1, GTF2H2, GTF2H2C, GTF2H2C2, GTF2H3, GTF2H4, GTF2H5, GTF2I, GTF2IRD1, GTF2IRD2, GTF2IRD2B, GTF3A, GTF3C1, GTF3C2, GTF3C3, GTF3C4, GTF3C5, GTF3C6, GTPBP1, GTPBP10, GTPBP2, GTPBP3, GTPBP4, GTP3P6, GTPBP8, GTSE1, GTSF1, GTSF1L, GU182339.1, GU182339.3, GU182343.1, GU182343.2, GU182345.1, GU182345.2, GU182347.1, GU182351.2, GU182352.2, GU182353.1, GU182355.1, GU182355.2, GU182355.3, GU182357.1, GU182357.3, GU182359.1, GU182359.2, GUCA1A, GUCA1B, GUCA1C, GUCA2A, GUCA2B, GUCD1, GUCY1A2, GUCY1A3, GUCY1B3, GUCY2C, GUCY2D, GUCY2F, GUF1, GUK1, GULP1, GUSB, GVQW2, GXYLT1, GXYLT2, GYG1, GYG2, GYPA, GYPB, GYPC, GYPE, GYS1, GYS2, GZF1, GZMA, GZMB, GZMH, GZMK, GZMM, H1F0, H1FNT, H1FOO, H1FX, H2AFB1, H2AFB2, H2AFB3, H2AFJ, H2AFV, H2AFX, H2AFY, H2AFY2, H2AFZ, H2BFM, H2BFS, H2B3FWT, H3F3A, H3F3B, H3F3C, H6PD, HAAO, HABP2, HABP4, HACD1, HACD2, HACD3, HACD4, HACE1, HACL1, HADH, HADHA, HADHB, HAGH, HAGHL, HAL, HAMP, HAND1, HAND2, HAO1, HAO2, HAP1, HAPLN1, HAPLN2, HAPLN3, HAPLN4, HARBI1, HARS, HARS2, HAS1, HAS2, HAS3, HASPIN, HAT1, HAUS1, HAUS2, HAUS3, HAUS4, HAUS5, HAUS6, HAUS7, HAUS8, HAVCR1, HAVCR2, HAX1, HBA1, HBA2, HBB, HBD, HBE1, HBEGF, HBG1, HBG2, HBM, HBP1, HBQ1, HBSIL, HBZ, HCAR1, HCAR2, HCAR3, HCCS, HCFC1, HCFC1R1, HCFC2, HCK, HCLS1, HCN1, HCN2, HCN3, HCN4, HCRT, HCRTR1, HCRTR2, HCST, HDAC1, HDAC10, HDAC11, HDAC2, HDAC3, HDAC4, HDAC5, HDAC6, HDAC7, HDAC8, HDAC9, HDC, HDDC2, HDDC3, HDGF, HDGFL1, HDGFL2, HDGFL3, HDHD2, HDHD3, HDHD5, HDLBP, HDX, HEATR1, HEATR3, HEATR4, HEATR5A, HEATR5B, HEATR6, HEATR9, HEBP1, HEBP2, HECA, HECTD1, HECTD2, HECTD3, HECTD4, HECW1, HECW2, HEG1, HELB, HELLS, HELQ, HELT, HELZ, HELZ2, HEMGN, HEMK1, HENMT1, HEPACAM, HEPACAM2, HEPH, HEPHL1, HEPN1, HERC1, HERC2, HERC3, HERC4, HERC5, HERC6, HERPUD1, HERPUD2, HES1, HES2, HES3, HES4, HES5, HES6, HES7, HESX1, HEXA, HEXB, HEXDC, HEXIM1, HEXIM2, HEY1, HEY2, HEYL, HFE, HFE2, HFM1, HGD, HGF, HGFAC, HGH1, HGNC:18790, HGNC:24955, HGS, HGSNAT, HHAT, HHATL, HHEX, HHIP, HHIPL1, HHIPL2, HHLA1, HHLA2, HHLA3, HIBADH, HIBCH, HIC1, HIC2, HID1, HIF1A, HIF1AN, HIF3A, HIGD1A, HIGD1B, HIGD1C, HIGD2A, HIGD2B, HIKESHI, HILPDA, HINFP, HINT1, HINT2, HINT3, HIP1, HIP1R, HIPK1, HIPK2, HIPK3, HIPK4, HIRA, HIRIP3, HIST1H1A, HIST1H1B, HIST1H1C, HIST1H1D, HIST1H1E, HIST1HIT, HIST1H2AA, HIST1H2AB, HIST1H2AC, HIST1H2AD, HIST1H2AE, HIST1H2AG, HIST1H2AH, HIST1H2AI, HIST1H2AJ, HIST1H2AK, HIST1H2AL, HIST1H2AM, HIST1H2BA, HIST1H2BB, HIST1H2BC, HIST1H2BD, HIST1H2BE, HIST1H2BF, HIST1H2BG, HIST1H2BH, HIST1H2BI, HIST1H2BJ, HIST1H2BK, HIST1H2BL, HIST1H2BM, HIST1H2BN, HIST1H2BO, HIST1H3A, HIST1H3B, HIST1H3C, HIST1H3D, HIST1H3E, HIST1H3F, HIST1H3G, HIST1H3H, HIST1H3I, HIST1H3J, HIST1H4A, HIST1H4B, HIST1H4C, HIST1H4D, HIST1H4E, HIST1H4F, HIST1H4G, HIST1H4H, HIST1H4I, HIST1H4J, HIST1H4K, HIST1H4L, HIST2H2AA3, HIST2H2AA4, HIST2H2AB, HIST2H2AC, HIST2H2BE, HIST2H2BF, HIST2H3A, HIST2H3C, HIST2H3D, HIST2H3PS2, HIST2H4A, HIST2H4B, HIST3H2A, HIST3H2BB, HIST3H3, HIST4H4, HIVEP1, HIVEP2, HIVEP3, HJURP, HK1, HK2, HK3, HKDC1, HKR1, HLA-A, HLA-B, HLA-C, HLA-DMA, HLA-DMB, HLA-DOA, HLA-DOB, HLA-DPA1, HLA-DPB1, HLA-DQA1, HLA-DQA2, HLA-DQB1, HLA-DQB2, HLA-DRA, HLA-DRB1, HLA-DRB3, HLA-DRB4, HLA-DRB5, HLA-E, HLA-F, HLA-G, HLCS, HLF, HLTF, HLX, HM13, HM190170.1, HMBOX1, HMBS, HMCES, HMCN1, HMCN2, HMG20A, HMG20B, HMGA1, HMGA2, HMGB1, HMGB2, HMGB3, HMGB4, HMGCL, HMGCLL1, HMGCR, HMGCS1, HMGCS2, HMGN1, HMGN2, HMGN3, HMGN4, HMGN5, HMGXB3, HMGXB4, HMHB1, HMMR, HMOX1, HMOX2, HMSD, HMX1, HMX2, HMX3, HNF1A, HNF1B, HNF4A, HNF4G, HNMT, HNRNPA0, HNRNPA1, HNRNPA1L2, HNRNPA2B1, HNRNPA3, HNRNPAB, HNRNPC, HNRNPCL1, HNRNPCL2, HNRNPCL3, HNRNPCL4, HNRNPD, HNRNPDL, HNRNPF, HNRNPH1, HNRNPH2, HNRNPH3, HNRNPK, HNRNPL, HNRNPLL, HNRNPM, HNRNPR, HNRNPU, HNRNPUL1, HNRNPUL2, HNRNPUL2-BSCL2, HOGA1, HOMER1, HOMER2, HOMER3, HOMEZ, HOOK1, HOOK2, HOOK3, HOPX, HORMAD1, HORMAD2, HOXA1, HOXA10, HOXA11, HOXA13, HOXA2, HOXA3, HOXA4, HOXA5, HOXA6, HOXA7, HOXA9, HOXB1, HOXB13, HOXB2, HOXB3, HOXB4, HOXB5, HOXB6, HOXB7, HOXB8, HOXB9, HOXC10, HOXC11, HOXC12, HOXC13, HOXC4, HOXC5, HOXC6, HOXC8, HOXC9, HOXD1, HOXD10, HOXD11, HOXD12, HOXD13, HOXD3, HOXD4, HOXD8, HOXD9, HP, HP1BP3, HPCA, HPCAL1, HPCAL4, HPD, HPDL, HPF1, HPGD, HPGDS, HPN, HPR, HPRT1, HPS1, HPS3, HPS4, HPS5, HPS6, HPSE, HPSE2, HPX, HR, HRAS, HRASLS, HRASLS2, HRASLS5, HRC, HRCT1, HRG, HRH1, HRH2, HRH3, HRH4, HRK, HRNR, HSIBP3, HS2ST1, HS3ST1, HS3ST2, HS3ST3A1, HS3ST3B1, HS3ST4, HS3ST5, HS3ST6, HS6ST1, HS6ST2, HS6ST3, HSBP1, HSBP1L1, HSCB, HSD11B1, HSD11B1L, HSD11B2, HSD17B1, HSD17B10, HSD17B11, HSD17B12, HSD17B13, HSD17B14, HSD17B2, HSD17B3, HSD17B4, HSD17B6, HSD17B7, HSD17B8, HSD3B1, HSD3B2, HSD3B7, HSDL1, HSDL2, HSF1, HSF2, HSF2BP, HSF4, HSF5, HSFX1, HSFX2, HSFX3, HSFX4, HSFY1, HSFY2, HSH2D, HSP90AA1, HSP90AB1, HSP90B1, HSPA12A, HSPA12B, HSPA13, HSPA14, HSPA1A, HSPA1B, HSPA1L, HSPA2, HSPA4, HSPA4L, HSPA5, HSPA6, HSPA8, HSPA9, HSPB1, HSPB11, HSPB2, HSPB2-C11 orf52, HSPB3, HSPB6, HSPB7, HSPB8, HSPB9, HSPBAP1, HSPBP1, HSPD1, HSPE1, HSPE1-MOB4, HSPG2, HSPH1, HTATIP2, HTATSF1, HTD2, HTN1, HTN3, HTR1A, HTR1B, HTR1D, HTR1E, HTR1F, HTR2A, HTR2B, HTR2C, HTR3A, HTR3B, HTR3C, HTR3D, HTR3E, HTR4, HTR5A, HTR6, HTR7, HTRA1, HTRA2, HTRA3, HTRA4, HTT, HUNK, HUS1, HUS1B, HUWE1, HVCN1, HYAL1, HYAL2, HYAL3, HYAL4, HYDIN, HYI, HYKK, HYLS1, HYOU1, HYPK, HYPM, IAH1, IAPP, IARS, IARS2, IBA57, IBSP, IBTK, ICA1, ICA1L, ICAM1, ICAM2, ICAM3, ICAM4, ICAM5, ICE1, ICE2, ICK, ICMT, ICOS, ICOSLG, ID1, ID2, ID3, ID4, IDE, IDH1, IDH2, IDH3A, IDH3B, IDH3G, IDI1, IDI2, IDNK, IDO1, IDO2, IDS, IDUA, IER2, IER3, IER3IP1, IER5, IER5L, IFFO1, IFFO2, IFI16, IFI27, IFI27L1, IFI27L2, IF130, IFI35, IFI44, IFI44L, IFI6, IFIH1, IFIT1, IFIT1B, IFIT2, IFIT3, IFIT5, IFITM1, IFITM10, IFITM2, IFITM3, IFITM5, IFNA1, IFNA10, IFNA13, IFNA14, IFNA16, IFNA17, IFNA2, IFNA21, IFNA4, IFNA5, IFNA6, IFNA7, IFNA8, IFNAR1, IFNAR2, IFNB1, IFNE, IFNG, IFNGR1, IFNGR2, IFNK, IFNL1, IFNL2, IFNL3, IFNL4, IFNLR1, IFNW1, IFRD1, IFRD2, IFT122, IFT140, IFT172, IFT20, IFT22, IFT27, IFT43, IFT46, IFT52, IFT57, IFT74, IFT80, IFT81, IFT88, IGBP1, IGDCC3, IGDCC4, IGF1, IGF1R, IGF2, IGF2BP1, IGF2BP2, IGF2BP3, IGF2R, IGFALS, IGFBP1, IGFBP2, IGFBP3, IGFBP4, IGFBP5, IGFBP6, IGFBP7, IGFBPL1, IGFL1, IGFL2, IGFL3, IGFL4, IGFLR1, IGFN1, IGHA1, IGHA2, IGHD, IGHD1-1, IGHD1-14, IGHD1-20, IGHD1-26, IGHD1-7, IGHD1OR15-1A, IGHD1OR15-1B, IGHD2-15, IGHD2-2, IGHD2-21, IGHD2-8, IGHD2OR15-2A, IGHD2OR15-2B, IGHD3-10, IGHD3-16, IGHD3-22, IGHD3-3, IGHD3-9, IGHD30R15-3A, IGHD3OR15-3B, IGHD4-11, IGHD4-17, IGHD4-23, IGHD4-4, IGHD40R15-4A, IGHD40R15-4B, IGHD5-12, IGHD5-18, IGHD5-24, IGHD5-5, IGHD50R15-5A, IGHD50R15-5B, IGHD6-13, IGHD6-19, IGHD6-25, IGHD6-6, IGHD7-27, IGHE, IGHG1, IGHG2, IGHG3, IGHG4, IGHJ1, IGHJ2, IGHJ3, IGHJ4, IGHJ5, IGHJ6, IGHM, IGHMBP2, IGHV1-18, IGHV1-2, IGHV1-24, IGHV1-3, IGHV1-45, IGHV1-46, IGHV1-58, IGHV1-69, IGHV1OR15-1, IGHV1OR15-9, IGHV1OR21-1, IGHV2-26, IGHV2-5, IGHV2-70, IGHV2OR16-5, IGHV3-11, IGHV3-13, IGHV3-15, IGHV3-16, IGHV3-20, IGHV3-21, IGHV3-23, IGHV3-30, IGHV3-33, IGHV3-35, IGHV3-38, IGHV3-43, IGHV3-48, IGHV3-49, IGHV3-53, IGHV3-64, IGHV3-66, IGHV3-7, IGHV3-72, IGHV3-73, IGHV3-74, IGHV30R15-7, IGHV3OR16-10, IGHV3OR16-12, IGHV3OR16-13, IGHV3OR16-8, IGHV30R16-9, IGHV4-28, IGHV4-31, IGHV4-34, IGHV4-39, IGHV4-4, IGHV4-59, IGHV4-61, IGHV40R15-8, IGHV5-51, IGHV6-1, IGHV7-81, IGIP, IGKC, IGKJ1, IGKJ2, IGKJ3, IGKJ4, IGKJ5, IGKV1-12, IGKV1-16, IGKV1-17, IGKV1-27, IGKV1-33, IGKV1-37, IGKV1-39, IGKV1-5, IGKV1-6, IGKV1-8, IGKV1-9, IGKV1D-12, IGKV1D-13, IGKV1D-16, IGKV1D-17, IGKV1D-33, IGKV1D-37, IGKV1D-39, IGKV1D-42, IGKV1D-43, IGKV1D-8, IGKV1OR2-108, IGKV2-24, IGKV2-28, IGKV2-30, IGKV2-40, IGKV2D-24, IGKV2D-26, IGKV2D-28, IGKV2D-29, IGKV2D-30, IGKV2D-40, IGKV3-11, IGKV3-15, IGKV3-20, IGKV3-7, IGKV3D-11, IGKV3D-15, IGKV3D-20, IGKV3D-7, IGKV3OR2-268, IGKV4-1, IGKV5-2, IGKV6-21, IGKV6D-21, IGKV6D-41, IGLC1, IGLC2, IGLC3, IGLC7, IGLJ1, IGLJ2, IGLJ3, IGLJ4, IGLJ5, IGLJ6, IGLJ7, IGLL1, IGLL5, IGLON5, IGLV10-54, IGLV11-55, IGLV1-36, IGLV1-40, IGLV1-44, IGLV1-47, IGLV1-50, IGLV1-51, IGLV2-11, IGLV2-14, IGLV2-18, IGLV2-23, IGLV2-33, IGLV2-8, IGLV3-1, IGLV3-10, IGLV3-12, IGLV3-16, IGLV3-19, IGLV3-21, IGLV3-22, IGLV3-25, IGLV3-27, IGLV3-32, IGLV3-9, IGLV4-3, IGLV4-60, IGLV4-69, IGLV5-37, IGLV5-45, IGLV5-48, IGLV5-52, IGLV6-57, IGLV7-43, IGLV7-46, IGLV8-61, IGLV9-49, IGSF1, IGSF10, IGSF11, IGSF21, IGSF22, IGSF23, IGSF3, IGSF5, IGSF6, IGSF8, IGSF9, IGSF9B, IHH, IK, IKBIP, IKBKB, IKBKE, IKBKG, IKZF1, IKZF2, IKZF3, IKZF4, IKZF5, IL10, IL10RA, IL10RB, IL11, IL11RA, IL12A, IL12B, IL12RB1, IL12RB2, IL13, IL13RA1, IL13RA2, IL15, IL15RA, IL16, IL17A, IL17B, IL17C, IL17D, IL17F, IL17RA, IL17RB, IL17RC, IL17RD, IL17RE, IL17REL, IL18, IL18BP, IL18R1, IL18RAP, IL19, IL1A, IL1B, IL1F10, IL1R1, IL1R2, IL1RAP, IL1RAPL1, IL1RAPL2, IL1RL1, IL1RL2, IL1RN, IL2, IL20, IL20RA, IL20RB, IL21, IL21R, IL22, IL22RA1, IL22RA2, IL23A, IL23R, IL24, IL25, IL26, IL27, IL27RA, IL2RA, IL2RB, IL2RG, IL3, IL31, IL31RA, IL32, IL33, IL34, IL36A, 1L36B, IL36G, IL36RN, IL37, IL3RA, IL4, IL411, IL4R, IL5, IL5RA, IL6, IL6R, IL6ST, IL7, IL7R, IL9, IL9R, ILDR1, ILDR2, ILF2, ILF3, ILK, ILKAP, ILVBL, IMMP1L, IMMP2L, IMMT, IMP3, IMP4, IMPA1, IMPA2, IMPACT, IMPAD1, IMPDH1, IMPDH2, IMPG1, IMPG2, INA, INAFM1, INAFM2, INAVA, INCA1, INCENP, INF2, ING1, ING2, ING3, ING4, ING5, INHA, INHBA, INHBB, INHBC, INHBE, INIP, INMT, INMT-MINDY4, INO80, INO80B, INO80B-WBP1, INO80C, INO80D, INO80E, INPP1, INPP4A, INPP4B, INPP5A, INPP5B, INPP5D, INPP5E, INPP5F, INPP5J, INPP5K, INPPL1, INS, INSC, INSIG1, INSIG2, INS-IGF2, INSL3, INSL4, INSL5, INSL6, INSM1, INSM2, INSR, INSRR, INTS1, INTS10, INTS11, INTS12, INTS13, INTS14, INTS2, INTS3, INTS4, INTS5, INTS6, INTS6L, INTS7, INTS8, INTS9, INTU, INVS, IP6K1, IP6K2, IP6K3, IPCEF1, IPMK, IPO11, IPO13, IPO4, IPO5, IPO7, IPO8, IPO9, IPP, IPPK, IQANK1, IQCA1, IQCA1L, IQCB1, IQCC, IQCD, IQCE, IQCF1, IQCF2, IQCF3, IQCF5, IQCF6, IQCG, IQCH, IQCJ, IQCJ-SCHIP1, IQCK, IQCM, IQGAP1, IQGAP2, IQGAP3, IQSEC1, IQSEC2, IQSEC3, IQUB, IREB2, IRF1, IRF2, IRF2BP1, IRF2BP2, IRF2BPL, IRF3, IRF4, IRF5, IRF6, IRF7, IRF8, IRF9, IRGC, IRGM, IRGQ, IRS1, IRS2, IRS4, IRX1, IRX2, IRX3, IRX4, IRX5, IRX6, ISCA1, ISCA2, ISCU, ISG15, ISG20, ISG20L2, ISL1, ISL2, ISLR, ISLR2, ISM1, ISM2, ISOC1, ISOC2, ISPD, IST1, ISX, ISY1, ISY1-RAB43, ISYNA1, ITCH, ITFG1, ITFG2, ITGA1, ITGA10, ITGA11, ITGA2, ITGA2B, ITGA3, ITGA4, ITGA5, ITGA6, ITGA7, ITGA8, ITGA9, ITGAD, ITGAE, ITGAL, ITGAM, ITGAV, ITGAX, ITGB1, ITGBIBP1, ITGBIBP2, ITGB2, ITGB3, ITGB3BP, ITGB4, ITGB5, ITGB6, ITGB7, ITGB8, ITGBL1, ITIH1, ITIH2, ITIH3, ITIH4, ITIH5, ITIH16, ITK, ITLN1, ITLN2, ITM2A, ITM2B, ITM2C, ITPA, ITPK1, ITPKA, ITPKB, ITPKC, ITPR1, ITPR2, ITPR3, ITPRIP, ITPRIPL1, ITPRIPL2, ITSN1, ITSN2, IVD, IVL, IVNS1ABP, IWS1, IYD, IZUMO1, IZUMO1R, IZUMO2, IZUMO3, IZUMO4, JADE1, JADE2, JADE3, JAG1, JAG2, JAGN1, JAK1, JAK2, JAK3, JAKMIP1, JAKMIP2, JAKMIP3, JAM2, JAM3, JAML, JARID2, JAZF1, JCAD, JCHAIN, JDP2, JKAMP, JMJD1C, JMJD4, JMJD6, JMJD7, JMJD7-PLA2G4B, JMJD8, JMY, JOSD1, JOSD2, JPH1, JPH2, JPH3, JPH4, JPT1, JPT2, JRK, JRKL, JSRP1, JTB, JUN, JUNB, JUND, JUP, KAAG1, KALRN, KANK1, KANK2, KANK3, KANK4, KANSL1, KANSL1L, KANSL2, KANSL3, KANTR, KARS, KAT14, KAT2A, KAT2B, KAT5, KAT6A, KAT6B, KAT7, KAT8, KATNA1, KATNAL1, KATNAL2, KATNB1, KATNBL1, KAZALD1, KAZN, KBTBD11, KBTBD11-OT1, KBTBD12, KBTBD13, KBTBD2, KBTBD3, KBTBD4, KBTBD6, KBTBD7, KBTBD8, KCMF1, KCNA1, KCNA10, KCNA2, KCNA3, KCNA4, KCNA5, KCNA7, KCNAB1, KCNAB2, KCNAB3, KCNB1, KCNB2, KCNC1, KCNC2, KCNC3, KCNC4, KCND1, KCND2, KCND3, KCNE1, KCNE11B, KCNE2, KCNE3, KCNE4, KCNE5, KCNF1, KCNG1, KCNG2, KCNG3, KCNG4, KCNH1, KCNH2, KCNH3, KCNH4, KCNH5, KCNH6, KCNH7, KCNH8, KCNIP1, KCNIP2, KCNIP3, KCNIP4, KCNJ1, KCNJ10, KCNJ11, KCNJ12, KCNJ13, KCNJ14, KCNJ15, KCNJ16, KCNJ18, KCNJ2, KCNJ3, KCNJ4, KCNJ5, KCNJ6, KCNJ8, KCNJ9, KCNK1, KCNK10, KCNK12, KCNK13, KCNK15, KCNK16, KCNK17, KCNK18, KCNK2, KCNK3, KCNK4, KCNK5, KCNK6, KCNK7, KCNK9, KCNMA1, KCNMB1, KCNMB2, KCNMB3, KCNMB4, KCNN1, KCNN2, KCNN3, KCNN4, KCNQ1, KCNQ2, KCNQ3, KCNQ4, KCNQ5, KCNRG, KCNS1, KCNS2, KCNS3, KCNT1, KCNT2, KCNU1, KCNV1, KCNV2, KCP, KCTD1, KCTD10, KCTD11, KCTD12, KCTD13, KCTD14, KCTD15, KCTD16, KCTD17, KCTD18, KCTD19, KCTD2, KCTD20, KCTD21, KCTD3, KCTD4, KCTD5, KCTD6, KCTD7, KCTD8, KCTD9, KDELC1, KDELC2, KDELR1, KDELR2, KDELR3, KDF1, KDM1A, KDM1B, KDM2A, KDM2B, KDM3A, KDM3B, KDM4A, KDM4B, KDM4C, KDM4D, KDM4E, KDM4F, KDM5A, KDM5B, KDM5C, KDM5D, KDM6A, KDM6B, KDM7A, KDM8, KDR, KDSR, KEAP1, KEL, KERA, KF459570.1, KHDC1, KHDC1L, KHDC3L, KHDRBS1, KHDRBS2, KHDRBS3, KHK, KHNYN, KHSRP, KIAA0040, KIAA0100, KIAA0141, KIAA0232, KIAA0319, KIAA0319L, KIAA0355, KIAA0368, KIAA0391, KIAA0408, KIAA0513, KIAA0556, KIAA0586, KIAA0753, KIAA0825, KIAA0895, KIAA0895L, KIAA0907, KIAA0930, KIAA1024, KIAA1024L, KIAA1107, KIAA1109, KIAA1143, KIAA1147, KIAA1161, KIAA1191, KIAA1210, KIAA1211, KIAA1211L, KIAA1217, KIAA1257, KIAA1324, KIAA1324L, KIAA1328, KIAA1456, KIAA1468, KIAA1522, KIAA1524, KIAA1549, KIAA1549L, KIAA1551, KIAA1586, KIAA1614, KIAA1644, KIAA1671, KIAA1683, KIAA1755, KIAA1841, KIAA1958, KIAA2012, KIAA2013, KIAA2026, KIDINS220, KIF11, KIF12, KIF13A, KIF13B, KIF14, KIF15, KIF16B, KIF17, KIF18A, KIF18B, KIF19, KIF1A, KIF1B, KIF1BP, KIF1C, KIF20A, KIF20B, KIF21A, KIF21B, KIF22, KIF23, KIF24, KIF25, KIF26A, KIF26B, KIF27, KIF2A, KIF2B, KIF2C, KIF3A, KIF3B, KIF3C, KIF4A, KIF4B, KIF5A, KIF5B, KIF5C, KIF6, KIF7, KIF9, KIFAP3, KIFC1, KIFC2, KIFC3, KIN, KIR2DL1, KIR2DL2, KIR2DL3, KIR2DL4, KIR2DL5A, KIR2DL5B, KIR2DP1, KIR2DS1, KIR2DS2, KIR2DS3, KIR2DS4, KIR2DS5, KIR3DL1, KIR3DL2, KIR3DL3, KIR3DP1, KIR3DS1, KIR3DX1, KIRREL1, KIRREL2, KIRREL3, KISS1, KISS1R, KIT, KITLG, KIZ, KL, KLB, KLC1, KLC2, KLC3, KLC4, KLF1, KLF10, KLF11, KLF12, KLF13, KLF14, KLF15, KLF16, KLF17, KLF18, KLF2, KLF3, KLF4, KLF5, KLF6, KLF7, KLF8, KLF9, KLHDC1, KLHDC10, KLHDC2, KLHDC3, KLHDC4, KLHDC7A, KLHDC7B, KLHDC8A, KLHDC8B, KLHDC9, KLHL1, KLHL10, KLHL11, KLHL12, KLHL13, KLHL14, KLHL15, KLHL17, KLHL18, KLHL2, KLHL20, KLHL21, KLHL22, KLHL23, KLHL24, KLHL25, KLHL26, KLHL28, KLHL29, KLHL3, KLHL30, KLHL31, KLHL32, KLHL33, KLHL34, KLHL35, KLHL36, KLHL38, KLHL4, KLHL40, KLHL41, KLHL42, KLHL5, KLHL6, KLHL7, KLHL8, KLHL9, KLK1, KLK10, KLK11, KLK12, KLK13, KLK14, KLK15, KLK2, KLK3, KLK4, KLK5, KLK6, KLK7, KLK8, KLK9, KLKB1, KLLN, KLRB1, KLRC1, KLRC2, KLRC3, KLRC4, KLRC4-KLRK1, KLRD1, KLRF1, KLRF2, KLRG1, KLRG2, KLRK1, KMO, KMT2A, KMT2B, KMT2C, KMT2D, KMT2E, KMT5A, KMT5B, KMT5C, KNCN, KNDC1, KNG1, KNL1, KNOP1, KNSTRN, KNTC1, KP420437.1, KP420437.2, KP420437.3, KP420439.1, KP420440.1, KP420440.2, KP420440.3, KP420440.4, KP420440.5, KP420440.6, KP420440.7, KP420440.8, KP420440.9, KP420441.1, KP420441.2, KP420441.3, KP420441.4, KP420441.5, KP420442.2, KP420442.3, KP420443.1, KP420444.1, KP420444.2, KP420444.3, KP420444.4, KP420444.5, KP420444.6, KP420444.7, KP420446.1, KP420446.2, KPNA1, KPNA2, KPNA3, KPNA4, KPNA5, KPNA6, KPNA7, KPNB1, KPRP, KPTN, KRAS, KRBA1, KRBA2, KRBOX1, KRBOX4, KRCC1, KREMEN1, KREMEN2, KRI1, KRIT1, KRR1, KRT1, KRT10, KRT12, KRT13, KRT14, KRT15, KRT16, KRT17, KRT18, KRT19, KRT2, KRT20, KRT222, KRT23, KRT24, KRT25, KRT26, KRT27, KRT28, KRT3, KRT31, KRT32, KRT33A, KRT33B, KRT34, KRT35, KRT36, KRT37, KRT38, KRT39, KRT4, KRT40, KRT5, KRT6A, KRT6B, KRT6C, KRT7, KRT71, KRT72, KRT73, KRT74, KRT75, KRT76, KRT77, KRT78, KRT79, KRT8, KRT80, KRT81, KRT82, KRT83, KRT84, KRT85, KRT86, KRT9, KRTAP10-1, KRTAP10-10, KRTAP10-11, KRTAP10-12, KRTAP10-2, KRTAP10-3, KRTAP10-4, KRTAP10-5, KRTAP10-6, KRTAP10-7, KRTAP10-8, KRTAP10-9, KRTAP1-1, KRTAP11-1, KRTAP12-1, KRTAP12-2, KRTAP12-3, KRTAP12-4, KRTAP1-3, KRTAP13-1, KRTAP13-2, KRTAP13-3, KRTAP13-4, KRTAP1-4, KRTAP1-5, KRTAP15-1, KRTAP16-1, KRTAP17-1, KRTAP19-1, KRTAP19-2, KRTAP19-3, KRTAP19-4, KRTAP19-5, KRTAP19-6, KRTAP19-7, KRTAP19-8, KRTAP20-1, KRTAP20-2, KRTAP20-3, KRTAP20-4, KRTAP2-1, KRTAP21-1, KRTAP21-2, KRTAP21-3, KRTAP2-2, KRTAP22-1, KRTAP22-2, KRTAP2-3, KRTAP23-1, KRTAP2-4, KRTAP24-1, KRTAP25-1, KRTAP26-1, KRTAP27-1, KRTAP29-1, KRTAP3-1, KRTAP3-2, KRTAP3-3, KRTAP4-1, KRTAP4-11, KRTAP4-12, KRTAP4-16, KRTAP4-2, KRTAP4-3, KRTAP4-4, KRTAP4-5, KRTAP4-6, KRTAP4-7, KRTAP4-8, KRTAP4-9, KRTAP5-1, KRTAP5-10, KRTAP5-11, KRTAP5-2, KRTAP5-3, KRTAP5-4, KRTAP5-5, KRTAP5-6, KRTAP5-7, KRTAP5-8, KRTAP5-9, KRTAP6-1, KRTAP6-2, KRTAP6-3, KRTAP7-1, KRTAP8-1, KRTAP9-1, KRTAP9-2, KRTAP9-3, KRTAP9-4, KRTAP9-6, KRTAP9-7, KRTAP9-8, KRTAP9-9, KRTCAP2, KRTCAP3, KRTDAP, KSR1, KSR2, KTI12, KTN1, KU645196.1, KU645196.2, KU645196.3, KU645196.4, KU645196.5, KU645196.6, KU645196.7, KU645196.8, KU645196.9, KU645197.1, KU645197.2, KU645197.3, KU645197.4, KU645197.5, KU645198.1, KXD1, KY, KYAT1, KYAT3, KYNU, L1CAM, L1TD1, L2HGDH, L34079.1, L3HYPDH, L3MBTL1, L3MBTL2, L3MBTL3, L3MBTL4, LACC1, LACRT, LACTB, LACTB2, LACTBL1, LAD1, LAG3, LAGE3, LAIR1, LAIR2, LALBA, LAMA1, LAMA2, LAMA3, LAMA4, LAMA5, LAMB1, LAMB2, LAMB3, LAMB4, LAMC1, LAMC2, LAMC3, LAMP1, LAMP2, LAMP3, LAMP5, LAMTOR1, LAMTOR2, LAMTOR3, LAMTOR4, LAMTOR5, LANCL1, LANCL2, LANCL3, LAP3, LAPTM4A, LAPTM4B, LAPTM5, LARGE1, LARGE2, LARP1, LARP1B, LARP4, LARP4B, LARP6, LARP7, LARS, LARS2, LAS1L, LASP1, LAT, LAT2, LATS1, LATS2, LAX1, LAYN, LBH, LBHD1, LBP, LBR, LBX1, LBX2, LCA5, LCA5L, LCAT, LCE1A, LCE1B, LCE1C, LCE1D, LCE1E, LCE1F, LCE2A, LCE2B, LCE2C, LCE2D, LCE3A, LCE3B, LCE3C, LCE3D, LCE3E, LCE4A, LCE5A, LCE6A, LCK, LCLAT1, LCMT1, LCMT2, LCN1, LCN10, LCN12, LCN15, LCN2, LCN6, LCN8, LCN9, LCNL1, LCOR, LCORL, LCP1, LCP2, LCT, LCTL, LDAH, LDB1, LDB2, LDB3, LDHA, LDHAL6A, LDHAL6B, LDHB, LDHC, LDHD, LDLR, LDLRAD1, LDLRAD2, LDLRAD3, LDLRAD4, LDL-RAP1, LDOC1, LEAP2, LECT2, LEF1, LEFTY1, LEFTY2, LEKR1, LELP1, LEMD1, LEMD2, LEMD3, LENEP, LENG1, LENG8, LENG9, LEO1, LEP, LEPR, LEPROT, LEPROTL1, LETM1, LETM2, LETMD1, LEUTX, LEXM, LFNG, LGALS1, LGALS12, LGALS13, LGALS14, LGALS16, LGALS2, LGALS3, LGALS3BP, LGALS4, LGALS7, LGALS7B, LGALS8, LGALS9, LGALS9B, LGALS9C, LGALSL, LGI1, LGI2, LGI3, LGI4, LGMN, LGR4, LGR5, LGR6, LGSN, LHB, LHCGR, LHFPL1, LHFPL2, LHFPL3, LHFPL4, LHFPL5, LHFPL6, LHPP, LHX1, LHX2, LHX3, LHX4, LHX5, LHX6, LHX8, LHX9, LIAS, LIF, LIFR, LIG1, LIG3, LIG4, LILRA1, LILRA2, LILRA3, LILRA4, LILRA5, LILRA6, LILRB1, LILRB2, LILRB3, LILRB4, LILRB5, LIM2, LIMA1, LIMCH1, LIMD1, LIMD2, LIME1, LIMK1, LIMK2, LIMS1, LIMS2, LIMS3, LIMS4, LIN28A, LIN28B, LIN37, LIN52, LIN54, LIN7A, LIN7B, LIN7C, LIN9, LINC00094, LINC00116, LINC00282, LINC00672, LINC00675, LINC00694, LINC00854, LINC00890, LINC00959, LINC01125, LINC01556, LINC02210-CRHR1, LINGO1, LINGO2, LINGO3, LINGO4, LINS1, LIPA, LIPC, LIPE, LIPF, LIPG, LIPH, LIPI, LIPJ, LIPK, LIPM, LIPN, LIPT1, LIPT2, LITAF, LIX1, LIX1L, LKAAEAR1, LLGL1, LLGL2, LLPH, LMAN1, LMAN1L, LMAN2, LMAN2L, LMBR1, LMBR1L, LMBRD1, LMBRD2, LMCD1, LMF1, LMF2, LMLN, LMNA, LMNB1, LMNB2, LMNTD1, LMNTD2, LMO1, LMO2, LMO3, LMO4, LMO7, LMO7DN, LMOD1, LMOD2, LMOD3, LMTK2, LMTK3, LMX1A, LMX1B, LNP1, LNPEP, LNPK, LNX1, LNX2, LO000005.1, LONP1, LONP2, LONRF1, LONRF2, LONRF3, LOR, LOX, LOXHD1, LOXL1, LOXL2, LOXL3, LOXL4, LPA, LPAR1, LPAR2, LPAR3, LPAR4, LPAR5, LPAR6, LPCAT1, LPCAT2, LPCAT3, LPCAT4, LPGAT1, LPIN1, LPIN2, LPIN3, LPL, LPO, LPP, LPXN, LRAT, LRBA, LRCH1, LRCH2, LRCH3, LRCH4, LRCOL1, LRFN1, LRFN2, LRFN3, LRFN4, LRFN5, LRG1, LRGUK, LRIF1, LRIG1, LRIG2, LRIG3, LRIT1, LRIT2, LRIT3, LRMDA, LRMP, LRP1, LRP10, LRP11, LRP12, LRP1B, LRP2, LRP2BP, LRP3, LRP4, LRP5, LRP5L, LRP6, LRP8, LRPAP1, LRPPRC, LRR1, LRRC1, LRRC10, LRRC10B, LRRC14, LRRC14B, LRRC15, LRRC17, LRRC18, LRRC19, LRRC2, LRRC20, LRRC23, LRRC24, LRRC25, LRRC26, LRRC27, LRRC28, LRRC29, LRRC3, LRRC30, LRRC31, LRRC32, LRRC34, LRRC36, LRRC37A, LRRC37A2, LRRC37A3, LRRC37B, LRRC38, LRRC39, LRRC3B, LRRC3C, LRRC4, LRRC40, LRRC41, LRRC42, LRRC43, LRRC45, LRRC46, LRRC47, LRRC49, LRRC4B, LRRC4C, LRRC52, LRRC53, LRRC55, LRRC56, LRRC57, LRRC58, LRRC59, LRRC6, LRRC61, LRRC63, LRRC66, LRRC69, LRRC7, LRRC70, LRRC71, LRRC72, LRRC73, LRRC74A, LRRC74B, LRRC75A, LRRC75B, LRRC8A, LRRC8B, LRRC8C, LRRC8D, LRRC8E, LRRC9, LRRCC1, LRRD1, LRRFIP1, LRRFIP2, LRRIQ1, LRRIQ3, LRRIQ4, LRRK1, LRRK2, LRRN1, LRRN2, LRRN3, LRRN4, LRRN4CL, LRRTM1, LRRTM2, LRRTM3, LRRTM4, LRSAM1, LRTM1, LRTM2, LRTOMT, LRWD1, LSAMP, LSG1, LSM1, LSM10, LSM11, LSM12, LSM14A, LSM14B, LSM2, LSM3, LSM4, LSM5, LSM6, LSM7, LSM8, LSMEM1, LSMEM2, LSP1, LSR, LSS, LST1, LTA, LTA4H, LTB, LTB4R, LTB4R2, LTBP1, LTBP2, LTBP3, LTBP4, LTBR, LTC4S, LTF, LTK, LTN1, LTV1, LUC7L, LUC7L2, LUC7L3, LUM, LURAP1, LURAP1L, LUZP1, LUZP2, LUZP4, LUZP6, LVRN, LXN, LY6D, LY6E, LY6G5B, LY6G5C, LY6G6C, LY6G6D, LY6G6E, LY6G6F, LY6H, LY6K, LY6L, LY75, LY75-CD302, LY86, LY9, LY96, LYAR, LYG1, LYG2, LYL1, LYN, LYNX1, LYPD1, LYPD2, LYPD3, LYPD4, LYPD5, LYPD6, LYPD6B, LYPD8, LYPLA1, LYPLA2, LYPLAL1, LYRM1, LYRM2, LYRM4, LYRM7, LYRM9, LYSMD1, LYSMD2, LYSMD3, LYSMD4, LYST, LYVE1, LYZ, LYZL1, LYZL2, LYZL4, LYZL6, LZIC, LZTFL1, LZTR1, LZTS1, LZTS2, LZTS3, M1AP, M6PR, MAATS1, MAB21L1, MAB21L2, MAB21L3, MACC1, MACF1, MACROD1, MACROD2, MAD1L1, MAD2L1, MAD2L1BP, MAD2L2, MAD-CAM1, MADD, MAEA, MAEL, MAF, MAF1, MAFA, MAFB, MAFF, MAFG, MAFK, MAG, MAGEA1, MAGEA10, MAGEA11, MAGEA12, MAGEA2, MAGEA2B, MAGEA3, MAGEA4, MAGEA6, MAGEA8, MAGEA9, MAGEA9B, MAGEB1, MAGEB10, MAGEB16, MAGEB17, MAGEB18, MAGEB2, MAGEB3, MAGEB4, MAGEB5, MAGEB6, MAGEB6P1, MAGEC1, MAGEC2, MAGEC3, MAGED1, MAGED2, MAGED4, MAGED4B, MAGEE1, MAGEE2, MAGEF1, MAGEH1, MAGEL2, MAGI1, MAGI2, MAGI3, MAGIX, MAGOH, MAGOHB, MAGT1, MAIP1, MAJIN, MAK, MAK16, MAL, MAL2, MALL, MALRD1, MALSU1, MALT1, MAMDC2, MAMDC4, MAML1, MAML2, MAML3, MAMLD1, MAMSTR, MAN1A1, MAN1A2, MAN1B1, MAN1C1, MAN2A1, MAN2A2, MAN2B1, MAN2B2, MAN2C1, MANBA, MANBAL, MANEA, MANEAL, MANF, MANSC1, MANSC4, MAOA, MAOB, MAP10, MAP1A, MAP1B, MAP1LC3A, MAP1LC3B, MAP1LC3B2, MAP1LC3C, MAP1S, MAP2, MAP2K1, MAP2K2, MAP2K3, MAP2K4, MAP2K5, MAP2K6, MAP2K7, MAP3K1, MAP3K10, MAP3K11, MAP3K12, MAP3K13, MAP3K14, MAP3K15, MAP3K19, MAP3K2, MAP3K20, MAP3K21, MAP3K3, MAP3K4, MAP3K5, MAP3K6, MAP3K7, MAP3K7CL, MAP3K8, MAP3K9, MAP4, MAP4K1, MAP4K2, MAP4K3, MAP4K4, MAP4K5, MAP6, MAP6D1, MAP7, MAP7D1, MAP7D2, MAP7D3, MAP9, MAPK1, MAPK10, MAPK11, MAPK12, MAPK13, MAPK14, MAPK15, MAPK1IP1L, MAPK3, MAPK4, MAPK6, MAPK7, MAPK8, MAPK8IP1, MAPK8IP2, MAPK8IP3, MAPK9, MAPKAP1, MAPKAPK2, MAPKAPK3, MAPKAPK5, MAPKBP1, MAPRE1, MAPRE2, MAPRE3, MAPT, MARC1, MARC2, MARCH1, MARCH10, MARCH11, MARCH2, MARCH3, MARCH4, MARCH5, MARCH6, MARCH7, MARCH8, MARCH9, MARCKS, MARCKSL1, MARCO, MARF1, MARK1, MARK2, MARK3, MARK4, MARS, MARS2, MARVELD1, MARVELD2, MARVELD3, MAS1, MAS1L, MASP1, MASP2, MAST1, MAST2, MAST3, MAST4, MASTL, MAT1A, MAT2A, MAT2B, MATK, MATN1, MATN2, MATN3, MATN4, MATR3, MAU2, MAVS, MAX, MAZ, MB, MB21D1, MB21D2, MBD1, MBD2, MBD3, MBD3L1, MBD3L2, MBD3L2B, MBD3L3, MBD3L4, MBD3L5, MBD4, MBD5, MBD6, MBIP, MBL2, MBLAC1, MBLAC2, MBNL1, MBNL2, MBNL3, MBOAT1, MBOAT2, MBOAT4, MBOAT7, MBP, MBTD1, MBTPS1, MBTPS2, MC1R, MC2R, MC3R, MC4R, MC5R, MCAM, MCAT, MCC, MCCC1, MCCC2, MCCD1, MCEE, MCEMP1, MCF2, MCF2L, MCF2L2, MCFD2, MCHR1, MCHR2, MCIDAS, MCL1, MCM10, MCM2, MCM3, MCM3AP, MCM4, MCM5, MCM6, MCM7, MCM8, MCM9, MCMBP, MCMDC2, MCOLN1, MCOLN2, MCOLN3, MCPH1, MCRIP1, MCRIP2, MCRS1, MCTP1, MCTP2, MCTS1, MCU, MCUB, MCUR1, MDC1, MDFI, MDFIC, MDFIC2, MDGA1, MDGA2, MDH1, MDH1B, MDH2, MDK, MDM1, MDM2, MDM4, MDN1, MDP1, MDS2, ME1, ME2, ME3, MEA1, MEAF6, MECOM, MECP2, MECR, MED1, MED10, MED11, MED12, MED12L, MED13, MED13L, MED14, MED14OS, MED15, MED16, MED17, MED18, MED19, MED20, MED21, MED22, MED23, MED24, MED25, MED26, MED27, MED28, MED29, MED30, MED31, MED4, MED6, MED7, MED8, MED9, MEDAG, MEF2A, MEF2B, MEF2C, MEF2D, MEFV, MEGF10, MEGF11, MEGF6, MEGF8, MEGF9, MEI1, MEI4, MEIG1, MEIKIN, MEIOB, MEIOC, MEIS1, MEIS2, MEIS3, MELK, MELTF, MEMO1, MEN1, MEOX1, MEOX2, MEP1A, MEP1B, MEPCE, MEPE, MERTK, MESD, MESP1, MESP2, MEST, MET, METAP1, METAP1D, METAP2, METRN, METRNL, METTL1, METTL11B, METTL12, METTL13, METTL14, METTL15, METTL16, METTL17, METTL18, METTL21A, METTL21C, METTL22, METTL23, METTL24, METTL25, METTL26, METTL27, METTL2A, METTL2B, METTL3, METTL4, METTL5, METTL6, METTL7A, METTL7B, METTL8, METTL9, MEX3A, MEX3B, MEX3C, MEX3D, MFAP1, MFAP2, MFAP3, MFAP3L, MFAP4, MFAP5, MFF, MFGE8, MFHAS1, MFN1, MFN2, MFNG, MFRP, MFSD1, MFSD10, MFSD11, MFSD12, MFSD13A, MFSD14A, MFSD14B, MFSD14C, MFSD2A, MFSD2B, MFSD3, MFSD4A, MFSD4B, MFSD5, MFSD6, MFSD6L, MFSD7, MFSD8, MFSD9, MGA, MGAM, MGAM2, MGARP, MGAT1, MGAT2, MGAT3, MGAT4A, MGAT4B, MGAT4C, MGAT4D, MGAT5, MGAT5B, MGEA5, MGLL, MGME1, MGMT, MGP, MGRN1, MGST1, MGST2, MGST3, MIA, MIA3, MIA-RAB4B, MIB1, MIB2, MICA, MICAL1, MICAL2, MICAL3, MICALCL, MICALL1, MICALL2, MICB, MICU1, MICU2, MICU3, MID1, MID1IP1, MID2, MIDN, MIEF1, MIEF2, MIEN1, MIER1, MIER2, MIER3, MIF, MIF4GD, MIGA1, MIGA2, MIIP, MILR1, MINDY1, MINDY2, MINDY3, MINDY4, MINDY4B, MINK1, MINOS1, MINOS1-NBL1, MINPP1, MIOS, MIOX, MIP, MIPEP, MIPOL1, MIS12, MIS18A, MIS18BP1, MISP, MISP3, MITD1, MITF, MIXL1, MKI67, MKKS, MKL1, MKL2, MKLN1, MKNK1, MKNK2, MKRN1, MKRN2, MKRN2OS, MKRN3, MKS1, MKX, MLANA, MLC1, MLEC, MLF1, MLF2, MLH1, MLH3, MLIP, MLKL, MLLT1, MLLT10, MLLT11, MLLT3, MLLT6, MLN, MLNR, MLPH, MLST8, MLX, MLXIP, MLXIPL, MLYCD, MMAA, MMAB, MMACHC, MMADHC, MMD, MMD2, MME, MMEL1, MMGT1, MMP1, MMP10, MMP11, MMP12, MMP13, MMP14, MMP15, MMP16, MMP17, MMP19, MMP2, MMP20, MMP21, MMP23B, MMP24, MMP24-AS1, MMP25, MMP26, MMP27, MMP28, MMP3, MMP7, MMP8, MMP9, MMRN1, MMRN2, MMS19, MMS22L, MN1, MNAT1, MND1, MNDA, MNS1, MNT, MNX1, MOAP1, MOB1A, MOB1B, MOB2, MOB3A, MOB3B, MOB3C, MOB4, MOBP, MOCOS, MOCS1, MOCS2, MOCS3, MOG, MOGAT1, MOGAT2, MOGAT3, MOGS, MOK, MON1a, MON1B, MON2, MORC1, MORC2, MORC3, MORC4, MORF4L1, MORF4L2, MORN1, MORN2, MORN3, MORN4, MORN5, MOS, MOSPD1, MOSPD2, MOSPD3, MOV10, MOV10L1, MOXD1, MPC1, MPC1L, MPC2, MPDU1, MPDZ, MPEG1, MPG, MPHOSPH10, MPHOSPH6, MPHOSPH8, MPHOSPH9, MPI, MPIG6B, MPL, MPLKIP, MPND, MPO, MPP1, MPP2, MPP3, MPP4, MPP5, MPP6, MPP7, MPPE1, MPPED1, MPPED2, MPRIP, MPST, MPV17, MPV17L, MPV17L2, MPZ, MPZL1, MPZL2, MPZL3, MR1, MRAP, MRAP2, MRAS, MRC1, MRC2, MRE11, MREG, MRFAP1, MRFAP1L1, MRGBP, MRGPRD, MRGPRE, MRGPRF, MRGPRG, MRGPRX1, MRGPRX2, MRGPRX3, MRGPRX4, MRI1, MRLN, MRM1, MRM2, MRM3, MRNIP, MRO, MROH1, MROH2A, MROH2B, MROH5, MROH6, MROH7, MROH7-TTC4, MROH8, MROH9, MRPL1, MRPL10, MRPL11, MRPL12, MRPL13, MRPL14, MRPL15, MRPL16, MRPL17, MRPL18, MRPL19, MRPL2, MRPL20, MRPL21, MRPL22, MRPL23, MRPL24, MRPL27, MRPL28, MRPL3, MRPL30, MRPL32, MRPL33, MRPL34, MRPL35, MRPL36, MRPL37, MRPL38, MRPL39, MRPL4, MRPL40, MRPL41, MRPL42, MRPL43, MRPL44, MRPL45, MRPL46, MRPL47, MRPL48, MRPL49, MRPL50, MRPL51, MRPL52, MRPL53, MRPL54, MRPL55, MRPL57, MRPL58, MRPL9, MRPS10, MRPS11, MRPS12, MRPS14, MRPS15, MRPS16, MRPS17, MRPS18A, MRPS18B, MRPS18C, MRPS2, MRPS21, MRPS22, MRPS23, MRPS24, MRPS25, MRPS26, MRPS27, MRPS28, MRPS30, MRPS31, MRPS33, MRPS34, MRPS35, MRPS36, MRPS5, MRPS6, MRPS7, MRPS9, MRRF, MRS2, MRTO4, MRVI1, MS4A1, MS4A10, MS4A12, MS4A13, MS4A14, MS4A15, MS4A2, MS4A3, MS4A4A, MS4A4E, MS4A5, MS4A6A, MS4A6E, MS4A7, MS4A8, MSANTD1, MSANTD2, MSANTD3, MSANTD3-TMEFF1, MSANTD4, MSC, MSGN1, MSH2, MSH3, MSH4, MSH5, MSH5-SAPCD1, MSH6, MSI1, MSI2, MSL1, MSL2, MSL3, MSLN, MSLNL, MSMB, MSMO1, MSMP, MSN, MSR1, MSRA, MSRB1, MSRB2, MSRB3, MSS51, MST1, MST1R, MSTN, MSTO1, MSX1, MSX2, MT1A, MT1B, MT1E, MT1F, MT1G, MT1H, MT1HL1, MT1M, MT1X, MT2A, MT3, MT4, MTA1, MTA2, MTA3, MTAP, MT-ATP6, MT-ATP8, MTBP, MTCH1, MTCH2, MTCL1, MT-CO1, MT-CO2, MT-CO3, MTCP1, MT-CYB, MTDH, MTERF1, MTERF2, MTERF3, MTERF4, MTF1, MTF2, MTFMT, MTFP1, MTFR1, MTFR1L, MTFR2, MTG1, MTG2, MTHFD1, MTHFD1L, MTHFD2, MTHFD2L, MTHFR, MTHFS, MTHFSD, MTIF2, MTIF3, MTM1, MTMR1, MTMR10, MTMR11, MTMR12, MTMR14, MTMR2, MTMR3, MTMR4, MTMR6, MTMR7, MTMR8, MTMR9, MT-ND1, MT-ND2, MT-ND3, MT-ND4, MT-ND4L, MT-ND5, MT-ND6, MTNRIA, MTNR1B, MTO1, MTOR, MTPAP, MTPN, MTR, MTRF1, MTRF1L, MTRNR2L1, MTRNR2L10, MTRNR2L11, MTRNR2L12, MTRNR2L13, MTRNR2L3, MTRNR2L4, MTRNR2L5, MTRNR2L6, MTRNR2L7, MTRNR2L8, MTRR, MTSS1, MTSS1L, MTTP, MTURN, MTUS1, MTUS2, MTX1, MTX2, MTX3, MUC1, MUCl2, MUCl3, MUC15, MUC16, MUC17, MUC2, MUC20, MUC21, MUC22, MUC3A, MUC4, MUC5AC, MUC5B, MUC6, MUC7, MUCL1, MUL1, MUM1, MUM1L1, MUS81, MUSK, MUSTN1, MUT, MUTYH, MVB12A, MVB12B, MVD, MVK, MVP, MX1, MX2, MXD1, MXD3, MXD4, MXI1, MXRA5, MXRA7, MXRA8, MYADM, MYADML2, MYB, MYBBPIA, MYBL1, MYBL2, MYBPC1, MYBPC2, MYBPC3, MYBPH, MYBPHL, MYC, MYCBP, MYCBP2, MYCBPAP, MYCL, MYCN, MYCT1, MYD88, MYDGF, MYEF2, MYEOV, MYF5, MYF6, MYH1, MYH10, MYH11, MYH13, MYH14, MYH15, MYH2, MYH3, MYH4, MYH6, MYH7, MYH7B, MYH8, MYH9, MYL1, MYL10, MYL12A, MYL12B, MYL2, MYL3, MYL4, MYL5, MYL6, MYL6B, MYL7, MYL9, MYLIP, MYLK, MYLK2, MYLK3, MYLK4, MYLPF, MYMK, MYMX, MYNN, MYO10, MYO15A, MYO15B, MYO16, MYO18A, MYO18B, MYO19, MYO1A, MYO1B, MYO1C, MYO1D, MYO1E, MYO1F, MYO1G, MYO1H, MYO3A, MYO3B, MYO5A, MYO5B, MYO5C, MYO6, MYO7A, MYO7B, MYO9A, MYO9B, MYOC, MYOCD, MYOCOS, MYOD1, MYOF, MYOG, MYOM1, MYOM2, MYOM3, MYOT, MYOZ1, MYOZ2, MYOZ3, MYPN, MYPOP, MYRF, MYRFL, MYRIP, MYSM1, MYT1, MYT1L, MYZAP, MZB1, MZF1, MZT1, MZT2A, MZT2B, N4BP1, N4BP2, N4BP2L1, N4BP2L2, N4BP3, N6AMT1, NAA10, NAA11, NAA15, NAA16, NAA20, NAA25, NAA30, NAA35, NAA38, NAA40, NAA50, NAA60, NAAA, NAALAD2, NAALADL1, NAALADL2, NAB1, NAB2, NABP1, NABP2, NACA, NACA2, NACAD, NACC1, NACC2, NADK, NADK2, NADSYN1, NAE1, NAF1, NAGA, NAGK, NAGLU, NAGPA, NAGS, NAIF1, NAIP, NALCN, NAMPT, NANOG, NANOGNB, NANOGP8, NANOS1, NANOS2, NANOS3, NANP, NANS, NAP1L1, NAP1L2, NAP1L3, NAP1L4, NAP1L5, NAPA, NAPB, NAPEPLD, NAPG, NAPRT, NAPSA, NARF, NARFL, NARS, NARS2, NASP, NAT1, NAT10, NAT14, NAT16, NAT2, NAT6, NAT8, NAT8B, NAT8L, NAT9, NATD1, NAV1, NAV2, NAV3, NAXD, NAXE, NBAS, NBDY, NBEA, NBEAL1, NBEAL2, NBL1, NBN, NBPF1, NBPF10, NBPF11, NBPF12, NBPF14, NBPF15, NBPF19, NBPF20, NBPF26, NBPF3, NBPF4, NBPF6, NBPF9, NBR1, NCALD, NCAM1, NCAM2, NCAN, NCAPD2, NCAPD3, NCAPG, NCAPG2, NCAPH, NCAPH2, NCBP1, NCBP2, NCBP2-AS2, NCBP2L, NCBP3, NCCRP1, NCDN, NCEH1, NCF1, NCF2, NCF4, NCK1, NCK2, NCKAP1, NCKAP1L, NCKAP5, NCKAP5L, NCKIPSD, NCL, NCLN, NCMAP, NCOA1, NCOA2, NCOA3, NCOA4, NCOA5, NCOA6, NCOA7, NCOR1, NCOR2, NCR1, NCR2, NCR3, NCR3LG1, NCS1, NCSTN, NDC1, NDC80, NDE1, NDEL1, NDFIP1, NDFIP2, NDN, NDNF, NDOR1, NDP, NDRG1, NDRG2, NDRG3, NDRG4, NDST1, NDST2, NDST3, NDST4, NDUFA1, NDUFA10, NDUFA11, NDUFA12, NDUFA13, NDUFA2, NDUFA3, NDUFA4, NDUFA4L2, NDUFA5, NDUFA6, NDUFA7, NDUFA8, NDUFA9, NDUFAB1, NDUFAF1, NDUFAF2, NDUFAF3, NDUFAF4, NDUFAF5, NDUFAF6, NDUFAF7, NDUFAF8, NDUFB1, NDUFB10, NDUFB11, NDUFB2, NDUFB3, NDUFB4, NDUFB5, NDUFB6, NDUFB7, NDUFB8, NDUFB9, NDUFC1, NDUFC2, NDUFC2-KCTD14, NDUFS1, NDUFS2, NDUFS3, NDUFS4, NDUFS5, NDUFS6, NDUFS7, NDUFS8, NDUFV1, NDUFV2, NDUFV3, NEB, NEBL, NECAB1, NECAB2, NECAB3, NECAP1, NECAP2, NECTIN1, NECTIN2, NECTIN3, NECTIN4, NEDD1, NEDD4, NEDD4L, NEDD8, NEDD8-MDP1, NEDD9, NEFH, NEFL, NEFM, NEGR1, NEIL1, NEIL2, NEIL3, NEK1, NEK10, NEK11, NEK2, NEK3, NEK4, NEK5, NEK6, NEK7, NEK8, NEK9, NELFA, NELFB, NELFCD, NELFE, NELL1, NELL2, NEMF, NEMP1, NEMP2, NENF, NEO1, NEPRO, NES, NET1, NETO1, NETO2, NEU1, NEU2, NEU3, NEU4, NEURL1, NEURL1B, NEURL2, NEURL3, NEURL4, NEUROD1, NEUROD2, NEUROD4, NEUROD6, NEUROG1, NEUROG2, NEUROG3, NEXMIF, NEXN, NF1, NF2, NFAM1, NFASC, NFAT5, NFATC1, NFATC2, NFATC2IP, NFATC3, NFATC4, NFE2, NFE2L1, NFE2L2, NFE2L3, NFE4, NFIA, NFIB, NFIC, NFIL3, NFIX, NFKB1, NFKB2, NFKBIA, NFKBIB, NFKBID, NFKBIE, NFKBIL1, NFKBIZ, NFRKB, NFS1, NFU1, NFX1, NFXL1, NFYA, NFYB, NFYC, NGB, NGDN, NGEF, NGF, NGFR, NGLY1, NGRN, NHEJ1, NHLH1, NHLH2, NHLRC1, NHLRC2, NHLRC3, NHLRC4, NHP2, NHS, NHSL1, NHSL2, NICN1, NID1, NID2, NIF3L1, NIFK, NIM1K, NIN, NINJ1, NINJ2, NINL, NIP7, NIPA1, NIPA2, NIPAL1, NIPAL2, NIPAL3, NIPAL4, NIPBL, NIPSNAP1, NIPSNAP2, NIPSNAP3A, NIPSNAP3B, NISCH, NIT1, NIT2, NKAIN1, NKAIN2, NKAIN3, NKAIN4, NKAP, NKAPL, NKD1, NKD2, NKG7, NKIRAS1, NKIRAS2, NKPD1, NKRF, NKTR, NKX1-1, NKX1-2, NKX2-1, NKX2-2, NKX2-3, NKX2-4, NKX2-5, NKX2-6, NKX2-8, NKX3-1, NKX3-2, NKX6-1, NKX6-2, NKX6-3, NLE1, NLGN1, NLGN2, NLGN3, NLGN4X, NLGN4Y, NLK, NLN, NLRC3, NLRC4, NLRC5, NLRP1, NLRP10, NLRP11, NLRP12, NLRP13, NLRP14, NLRP2, NLRP2B, NLRP3, NLRP4, NLRP5, NLRP6, NLRP7, NLRP8, NLRP9, NLRX1, NMB, NMBR, NMD3, NME1, NME1-NME2, NME2, NME3, NME4, NME5, NME6, NME7, NME8, NME9, NM1, NMNAT1, NMNAT2, NMNAT3, NMRAL1, NMRK1, NMRK2, NMS, NMT1, NMT2, NMU, NMUR1, NMUR2, NNAT, NNMT, NNT, NOA1, NOB1, NOBOX, NOC2L, NOC3L, NOC4L, NOCT, NOD1, NOD2, NODAL, NOG, NOL10, NOL11, NOL12, NOL3, NOL4, NOL4L, NOL6, NOL7, NOL8, NOL9, NOLC1, NOM1, NOMO1, NOMO2, NOMO3, NONO, NOP10, NOP14, NOP16, NOP2, NOP53, NOP56, NOP58, NOP9, NOS1, NOS1AP, NOS2, NOS3, NOSIP, NOSTRIN, NOTCH1, NOTCH2, NOTCH2NL, NOTCH3, NOTCH4, NOTO, NOTUM, NOV, NOVA1, NOVA2, NOX1, NOX3, NOX4, NOX5, NOXA1, NOXO1, NOXRED1, NPAP1, NPAS1, NPAS2, NPAS3, NPAS4, NPAT, NPB, NPBWR1, NPBWR2, NPC1, NPC1L1, NPC2, NPDC1, NPEPL1, NPEPPS, NPFF, NPFFR1, NPFFR2, NPHP1, NPHP3, NPHP3-ACAD11, NPHP4, NPHS1, NPHS2, NPIPA1, NPIPA2, NPIPA3, NPIPA5, NPIPA7, NPIPA8, NPIPB11, NPIPB12, NPIPB13, NPIPB15, NPIPB2, NPIPB3, NPIPB4, NPIPB5, NPIPB6, NPIPB7, NPIPB8, NPIPB9, NPL, NPLOC4, NPM1, NPM2, NPM3, NPNT, NPPA, NPPB, NPPC, NPR1, NPR2, NPR3, NPRL2, NPRL3, NPS, NPSR1, NPTN, NPTX1, NPTX2, NPTXR, NPVF, NPW, NPY, NPY1R, NPY2R, NPY4R, NPY4R2, NPY5R, NQO1, NQO2, NR0B1, NR0B2, NR1D1, NR1D2, NR1H2, NR1H3, NR1H4, NR1I2, NR1I3, NR2C1, NR2C2, NR2C2AP, NR2E1, NR2E3, NR2F1, NR2F2, NR2F6, NR3C1, NR3C2, NR4A1, NR4A2, NR4A3, NR5A1, NR5A2, NR6A1, NRAP, NRARP, NRAS, NRBF2, NRBP1, NRBP2, NRCAM, NRDC, NRDE2, NREP, NRF1, NRG1, NRG2, NRG3, NRG4, NRGN, NRIP1, NRIP2, NRIP3, NRK, NRL, NRM, NRN1, NRN1L, NRP1, NRP2, NRROS, NRSN1, NRSN2, NRTN, NRXN1, NRXN2, NRXN3, NSA2, NSD1, NSD2, NSD3, NSDHL, NSF, NSFL1C, NSL1, NSMAF, NSMCE1, NSMCE2, NSMCE3, NSMCE4A, NSMF, NSRP1, NSUN2, NSUN3, NSUN4, NSUN5, NSUN6, NSUN7, NT5C, NT5C1A, NT5C1B, NT5C1B-RDH14, NT5C2, NT5C3A, NT5C3B, NT5DC1, NT5DC2, NT5DC3, NT5DC4, NT5E, NT5M, NTAN1, NTF3, NTF4, NTHL1, NTM, NTMT1, NTN1, NTN3, NTN4, NTN5, NTNG1, NTNG2, NTPCR, NTRK1, NTRK2, NTRK3, NTS, NTSR1, NTSR2, NUAK1, NUAK2, NUB1, NUBP1, NUBP2, NUBPL, NUCB1, NUCB2, NUCKS1, NUDC, NUDCD1, NUDCD2, NUDCD3, NUDT1, NUDT10, NUDT11, NUDT12, NUDT13, NUDT14, NUDT15, NUDT16, NUDT16L1, NUDT17, NUDT18, NUDT19, NUDT2, NUDT21, NUDT22, NUDT3, NUDT4, NUDT4P1, NUDT5, NUDT6, NUDT7, NUDT8, NUDT9, NUF2, NUFIP1, NUFIP2, NUGGC, NUMA1, NUMB, NUMBL, NUP107, NUP133, NUP153, NUP155, NUP160, NUP188, NUP205, NUP210, NUP210L, NUP214, NUP35, NUP37, NUP43, NUP50, NUP54, NUP58, NUP62, NUP62CL, NUP85, NUP88, NUP93, NUP98, NUPL2, NUPR1, NUPR2, NUS1, NUSAP1, NUTF2, NUTM1, NUTM2A, NUTM2B, NUTM2D, NUTM2E, NUTM2F, NUTM2G, NVL, NWD1, NWD2, NXF1, NXF2, NXF2B, NXF3, NXF5, NXN, NXNL1, NXNL2, NXPE1, NXPE2, NXPE3, NXPE4, NXPH1, NXPH2, NXPH3, NXPH4, NXT1, NXT2, NYAP1, NYAP2, NYNRIN, NYX, OAF, OARD1, OAS1, OAS2, OAS3, OASL, OAT, OAZ1, OAZ2, OAZ3, OBP2A, OBP2B, OBSCN, OBSCN-AS1, OBSL1, OC90, OCA2, OCEL1, OCIAD1, OCIAD2, OCLM, OCLN, OCM, OCM2, OCRL, OCSTAMP, ODAM, ODC1, ODF1, ODF2, ODF2L, ODF3, ODF3B, ODF3L1, ODF3L2, ODF4, OFCC1, OFD1, OGDH, OGDHL, OGFOD1, OGFOD2, OGFOD3, OGFR, OGFRL1, OGG1, OGN, OGT, OIP5, OIT3, OLA1, OLAH, OLFM1, OLFM2, OLFM3, OLFM4, OLFML1, OLFML2A, OLFML2B, OLFML3, OLIG1, OLIG2, OLIG3, OLR1, OMA1, OMD, OMG, OMP, ONECUT1, ONECUT2, ONECUT3, OOEP, OOSP2, OPA1, OPA3, OPALIN, OPCML, OPHN1, OPLAH, OPN1LW, OPN1MW, OPN1MW2, OPN1MW3, OPN1SW, OPN3, OPN4, OPN5, OPRD1, OPRK1, OPRL1, OPRM1, OPRPN, OPTC, OPTN, OR10A2, OR10A3, OR10A4, OR10A5, OR10A6, OR10A7, OR10AC1, OR10AD1, OR10AG1, OR10C1, OR10D3, OR10G2, OR10G3, OR10G4, OR10G6, OR10G7, OR10G8, OR10G9, OR10H1, OR10H2, OR10H3, OR10H4, OR10H5, OR10J1, OR10J3, OR10J4, OR10J5, OR10K1, OR10K2, OR10P1, OR10Q1, OR10R2, OR10S1, OR10T2, OR10V1, OR10W1, OR10X1, OR10Z1, OR11A1, OR11G2, OR11H1, OR11H12, OR11H2, OR11H4, OR11H6, OR11H7, OR11L1, OR12D1, OR12D2, OR12D3, OR13A1, OR13C2, OR13C3, OR13C4, OR13C5, OR13C7, OR13C8, OR13C9, OR13D1, OR13F1, OR13G1, OR13H1, OR13J1, OR14A16, OR14A2, OR14C36, OR14I1, OR14J1, OR14K1, OR1A1, OR1A2, OR1B1, OR1C1, OR1D2, OR1D5, OR1E1, OR1E2, OR1F1, OR1G1, OR1I1, OR1J1, OR1J2, OR1J4, OR1K1, OR1L1, OR1L3, OR1L4, OR1L6, OR1L8, OR1M1, OR1N1, OR1N2, OR1P1, OR1Q1, OR1S1, OR1S2, OR2A1, OR2A12, OR2A14, OR2A2, OR2A25, OR2A4, OR2A42, OR2A5, OR2A7, OR2AE1, OR2AG1, OR2AG2, OR2AJ1, OR2AK2, OR2AP1, OR2AT4, OR2B11, OR2B2, OR2B3, OR2B6, OR2C1, OR2C3, OR2D2, OR2D3, OR2F1, OR2F2, OR2G2, OR2G3, OR2G6, OR2H1, OR2H2, OR2J, OR2J2, OR2J3, OR2K2, OR2L13, OR2L2, OR2L3, OR2L5, OR2L8, OR2M2, OR2M3, OR2M4, OR2M5, OR2M7, OR2S2, OR2T1, OR2T10, OR2T11, OR2T12, OR2T2, OR2T27, OR2T29, OR2T3, OR2T33, OR2T34, OR2T35, OR2T4, OR2T5, OR2T6, OR2T7, OR2T8, OR2V1, OR2V2, OR2W1, OR2W3, OR2Y1, OR2Z1, OR3A1, OR3A2, OR3A3, OR4A15, OR4A16, OR4A47, OR4A5, OR4A8, OR4B1, OR4C11, OR4C12, OR4C13, OR4C15, OR4C16, OR4C3, OR4C45, OR4C46, OR4C5, OR4C6, OR4D1, OR4D10, OR4D11, OR4D2, OR4D5, OR4D6, OR4D9, OR4E1, OR4E2, OR4F15, OR4F16, OR4F17, OR4F21, OR4F29, OR4F3, OR4F4, OR4F5, OR4F6, OR4K1, OR4K13, OR4K14, OR4K15, OR4K17, OR4K2, OR4K3, OR4K5, OR4L1, OR4M1, OR4M2, OR4N2, OR4N4, OR4N5, OR4P4, OR4Q2, OR4Q3, OR4S1, OR4S2, OR4X1, OR4X2, OR51A2, OR51A4, OR51A7, OR51B2, OR51B4, OR51B5, OR51B6, OR51D1, OR51E1, OR51E2, OR51F1, OR51F2, OR51G1, OR51G2, OR51H1, OR51I1, OR51I2, OR51J1, OR51L1, OR51M1, OR51Q1, OR51S1, OR51T1, OR51V1, OR52A1, OR52A5, OR52B2, OR52B4, OR52B6, OR52D1, OR52E2, OR52E4, OR52E5, OR52E6, OR52E8, OR52H1, OR52I1, OR52I2, OR52J3, OR52K1, OR52K2, OR52L1, OR52M1, OR52N1, OR52N2, OR52N4, OR52N5, OR52R1, OR52W1, OR52Z1, OR56A1, OR56A3, OR56A4, OR56A5, OR56B1, OR56B4, OR5A1, OR5A2, OR5AC1, OR5AC2, OR5AK2, OR5AN1, OR5AP2, OR5AR1, OR5AS1, OR5AU1, OR5B12, OR5B17, OR5B2, OR5B21, OR5B3, OR5C1, OR5D13, OR5D14, OR5D16, OR5D18, OR5F1, OR5G3, OR5H1, OR5H14, OR5H15, OR5H2, OR5H6, OR5H8, OR5I1, OR5J2, OR5K1, OR5K2, OR5K3, OR5K4, OR5L1, OR5L2, OR5M1, OR5M10, OR5M11, OR5M3, OR5M8, OR5M9, OR5P2, OR5P3, OR5R1, OR5T1, OR5T2, OR5T3, OR5V1, OR5W2, OR6A2, OR6B1, OR6B2, OR6B3, OR6C1, OR6C2, OR6C3, OR6C4, OR6C6, OR6C65, OR6C68, OR6C70, OR6C74, OR6C75, OR6C76, OR6F1, OR6J1, OR6K2, OR6K3, OR6K6, OR6M1, OR6N1, OR6N2, OR6P1, OR6Q1, OR6S1, OR6T, OR6V1, OR6X1, OR6Y1, OR7A10, OR7A17, OR7A5, OR7C1, OR7C2, OR7D2, OR7D4, OR7E24, OR7G1, OR7G2, OR7G3, OR8A1, OR8B12, OR8B2, OR8B3, OR8B4, OR8B8, OR8D1, OR8D2, OR8D4, OR8G1, OR8G5, OR8H1, OR8H2, OR8H3, OR8I2, OR8J1, OR8J2, OR8J3, OR8K1, OR8K3, OR8K5, OR8S1, OR8U1, OR8U8, OR9A2, OR9A4, OR9G1, OR9G4, OR9G9, OR9H1P, OR9I1, OR9K2, OR9Q1, OR9Q2, ORAI1, ORAI2, ORAI3, ORAOV1, ORC1, ORC2, ORC3, ORC4, ORC5, ORC6, ORM1, ORM2, ORMDL1, ORMDL2, ORMDL3, OS9, OSBP, OSBP2, OSBPL10, OSBPL11, OSBPL1A, OSBPL2, OSBPL3, OSBPL5, OSBPL6, OSBPL7, OSBPL8, OSBPL9, OSCAR, OSCP1, OSER1, OSGEP, OSGEPL1, OSGIN1, OSGIN2, OSM, OSMR, OSR1, OSR2, OST4, OSTC, OSTF1, OSTM1, OSTN, OTC, OTOA, OTOF, OTOG, OTOGL, OTOL1, OTOP1, OTOP2, OTOP3, OTOR, OTOS, OTP, OTUB1, OTUB2, OTUD1, OTUD3, OTUD4, OTUD5, OTUD6A, OTUD6B, OTUD7A, OTUD7B, OTULIN, OTX1, OTX2, OVCA2, OVCH1, OVCH2, OVGP1, OVOL1, OVOL2, OVOL3, OXA1L, OXCT1, OXCT2, OXER1, OXGR1, OXLD1, OXNAD1, OXR1, OXSM, OXSR1, OXT, OXTR, P2RX1, P2RX2, P2RX3, P2RX4, P2RX5, P2RX5-TAX1BP3, P2RX6, P2RX7, P2RY1, P2RY10, P2RY11, P2RY12, P2RY13, P2RY14, P2RY2, P2RY4, P2RY6, P2RY8, P3H1, P3H2, P3H3, P3H4, P4HA1, P4HA2, P4HA3, P4HB, P4HTM, PA2G4, PAAF1, PABPC1, PABPC1L, PABPC1L2A, PABPC1L2B, PABPC3, PABPC4, PABPC4L, PABPC5, PABPN1, PABPN1L, PACRG, PACRGL, PACS1, PACS2, PACSIN1, PACSIN2, PACSIN3, PADI1, PADI2, PADI3, PADI4, PADI6, PAEP, PAF1, PAFAH1B1, PAFAH1B2, PAFAH1B3, PAFAH2, PAG1, PAGE1, PAGE2, PAGE2B, PAGE3, PAGE4, PAGE5, PAGR1, PAH, PAICS, PAIP1, PAIP2, PAIP2B, PAK1, PAK1IP1, PAK2, PAK3, PAK4, PAK5, PAK6, PALB2, PALD1, PALLD, PALM, PALM2, PALM2-AKAP2, PALM3, PALMD, PAM, PAM16, PAMR1, PAN2, PAN3, PANK1, PANK2, PANK3, PANK4, PANO1, PANX1, PANX2, PANX3, PAOX, PAPD4, PAPD5, PAPD7, PAPLN, PAPOLA, PAPOLB, PAPOLG, PAPPA, PAPPA2, PAPSS1, PAPSS2, PAQR3, PAQR4, PAQR5, PAQR6, PAQR7, PAQR8, PAQR9, PARD3, PARD3B, PARD6A, PARD6B, PARD6G, PARG, PARK7, PARL, PARM1, PARN, PARP1, PARP10, PARP11, PARP12, PARP14, PARP15, PARP16, PARP2, PARP3, PARP4, PARP6, PARP8, PARP9, PARPBP, PARS2, PARVA, PARVB, PARVG, PASD1, PASK, PATE1, PATE2, PATE3, PATE4, PATJ, PATL1, PATL2, PATZ1, PAWR, PAX1, PAX2, PAX3, PAX4, PAX5, PAX6, PAX7, PAX8, PAX9, PAXBP1, PAXIP1, PAXX, PBDC1, PBK, PBLD, PBOV1, PBRM1, PBX1, PBX2, PBX3, PBX4, PBXIP1, PC, PCBD1, PCBD2, PCBP1, PCBP2, PCBP3, PCBP4, PCCA, PCCB, PCDH1, PCDH10, PCDH11 X, PCDH11Y, PCDH12, PCDH15, PCDH17, PCDH18, PCDH19, PCDH20, PCDH7, PCDH8, PCDH9, PCDHA1, PCDHA10, PCDHA11, PCDHA12, PCDHA13, PCDHA2, PCDHA3, PCDHA4, PCDHA5, PCDHA6, PCDHA7, PCDHA8, PCDHA9, PCDHAC1, PCDHAC2, PCDHB1, PCDHB10, PCDHB11, PCDHB12, PCDHB13, PCDHB14, PCDHB15, PCDHB16, PCDHB2, PCDHB3, PCDHB4, PCDHB5, PCDHB6, PCDHB7, PCDHB8, PCDHB9, PCDHGA1, PCDHGA10, PCDHGA11, PCDHGA12, PCDHGA2, PCDHGA3, PCDHGA4, PCDHGA5, PCDHGA6, PCDHGA7, PCDHGA8, PCDHGA9, PCDHGB1, PCDHGB2, PCDHGB3, PCDHGB4, PCDHGB5, PCDHGB6, PCDHGB7, PCDHGC3, PCDHGC4, PCDHGC5, PCED1A, PCED1B, PCF11, PCGF1, PCGF2, PCGF3, PCGF5, PCGF6, PCID2, PCIF1, PCK1, PCK2, PCLAF, PCLO, PCM1, PCMT1, PCMTD1, PCMTD2, PCNA, PCNP, PCNT, PCNX1, PCNX2, PCNX3, PCNX4, PCOLCE, PCOLCE2, PCOTH, PCP2, PCP4, PCP4L1, PCSK1, PCSK1N, PCSK2, PCSK4, PCSK5, PCSK6, PCSK7, PCSK9, PCTP, PCYOX1, PCYOX1L, PCYT1A, PCYT1B, PCYT2, PDAP1, PDC, PDCD1, PDCD10, PDCD11, PDCD1LG2, PDCD2, PDCD2L, PDCD4, PDCD5, PDCD6, PDCD6IP, PDCD7, PDCL, PDCL2, PDCL3, PDE10A, PDE11A, PDE12, PDE1A, PDE1B, PDE1C, PDE2A, PDE3A, PDE3B, PDE4A, PDE4B, PDE4C, PDE4D, PDE4DIP, PDE5A, PDE6A, PDE6B, PDE6C, PDE6D, PDE6G, PDE6H, PDE7A, PDE7B, PDE8A, PDE8B, PDE9A, PDF, PDGFA, PDGFB, PDGFC, PDGFD, PDGFRA, PDGFRB, PDGFRL, PDHA1, PDHA2, PDHB, PDHX, PDIA2, PDIA3, PDIA4, PDIA5, PDIA6, PDIK1L, PDILT, PDK1, PDK2, PDK3, PDK4, PDLIM1, PDLIM2, PDLIM3, PDLIM4, PDLIM5, PDLIM7, PDP1, PDP2, PDPK1, PDPN, PDPR, PDRG1, PDS5A, PDS5B, PDSS1, PDSS2, PDX1, PDXDC1, PDXK, PDXP, PDYN, PDZD11, PDZD2, PDZD3, PDZD4, PDZD7, PDZD8, PDZD9, PDZK1, PDZK1IP1, PDZRN3, PDZRN4, PEA15, PEAK1, PEAR1, PEBP1, PEBP4, PECAM1, PECR, PEF1, PEG10, PEG3, PELI1, PELI2, PELI3, PELO, PELP1, PEMT, PENK, PEPD, PER1, PER2, PER3, PERM1, PERP, PES1, PET100, PET117, PEX1, PEX10, PEX11A, PEX11B, PEX11G, PEX12, PEX13, PEX14, PEX16, PEX19, PEX2, PEX26, PEX3, PEX5, PEX5L, PEX6, PEX7, PF4, PF4V1, PFAS, PFDN1, PFDN2, PFDN4, PFDN5, PFDN6, PFKFB1, PFKFB2, PFKFB3, PFKFB4, PFKL, PFKM, PFKP, PFN1, PFN2, PFN3, PFN4, PGA3, PGA4, PGA5, PGAM1, PGAM2, PGAM4, PGAM5, PGAP1, PGAP2, PGAP3, PGBD1, PGBD2, PGBD4, PGBD5, PGC, PGD, PGF, PGGHG, PGGT1B, PGK1, PGK2, PGLS, PGLYRP1, PGLYRP2, PGLYRP3, PGLYRP4, PGM1, PGM2, PGM2L1, PGM3, PGM5, PGP, PGPEP1, PGPEP1L, PGR, PGRMC1, PGRMC2, PGS1, PHACTR1, PHACTR2, PHACTR3, PHACTR4, PHAX, PHB, PHB2, PHC1, PHC2, PHC3, PHEX, PHF1, PHF10, PHF11, PHF12, PHF13, PHF14, PHF19, PHF2, PHF20, PHF20L1, PHF21A, PHF21B, PHF23, PHF24, PHF3, PHF5A, PHF6, PHF7, PHF8, PHGDH, PHGR1, PHIP, PHKA1, PHKA2, PHKB, PHKG1, PHKG2, PHLDA1, PHLDA2, PHLDA3, PHLDB1, PHLDB2, PHLDB3, PHLPP1, PHLPP2, PHOSPHO1, PHOSPHO2, PHOX2A, PHOX2B, PHPT1, PHRF1, PHTF1, PHTF2, PHYH, PHYHD1, PHYHIP, PHYHIPL, PHYKPL, PI15, PI16, PI3, PI4K2A, PI4K2B, PI4KA, PI4 KB, PIANP, PIAS1, PIAS2, PIAS3, PIAS4, PIBF1, PICALM, PICK1, PID1, PIDD1, PIEZO1, PIEZO2, PIF1, PIFO, PIGA, PIGB, PIGBOS1, PIGC, PIGF, PIGG, PIGH, PIGK, PIGL, PIGM, PIGN, PIGO, PIGP, PIGQ, PIGR, PIGS, PIGT, PIGU, PIGV, PIGW, PIGX, PIGY, PIGZ, PIH1D1, PIH1D2, PIH1D3, PIK3AP1, PIK3C2A, PIK3C2B, PIK3C2G, PIK3C3, PIK3CA, PIK3CB, PIK3CD, PIK3CG, PIK3IP1, PIK3R1, PIK3R2, PIK3R3, PIK3R4, PIK3R5, PIK3R6, PIKFYVE, PILRA, PILRB, PIM1, PIM2, PIM3, PIMREG, PIN1, PIN4, PINK1, PINLYP, PINX1, PIP, PIP4K2A, PIP4K2B, PIP4K2C, PIP5K1A, PIP5K1B, PIP5K1C, PIP5KL1, PIPOX, PIR, PIRT, PISD, PITHD1, PITPNA, PITPNB, PITPNC1, PITPNM1, PITPNM2, PITPNM3, PITRM1, PITX1, PITX2, PITX3, PIWIL1, PIWIL2, PIWIL3, PIWIL4, PJA1, PJA2, PKD1, PKD1L1, PKD1L2, PKD1L3, PKD2, PKD2L1, PKD2L2, PKDCC, PKDREJ, PKHD1, PKHD1L1, PKIA, PKIB, PKIG, PKLR, PKM, PKMYT1, PKN1, PKN2, PKN3, PKNOX1, PKNOX2, PKP1, PKP2, PKP3, PKP4, PLA1A, PLA2G10, PLA2G12A, PLA2G12B, PLA2G15, PLA2G16, PLA2GIB, PLA2G2A, PLA2G2C, PLA2G2D, PLA2G2E, PLA2G2F, PLA2G3, PLA2G4A, PLA2G4B, PLA2G4C, PLA2G4D, PLA2G4E, PLA2G4F, PLA2G5, PLA2G6, PLA2G7, PLA2R1, PLAA, PLAC1, PLAC4, PLAC8, PLAC8L1, PLAC9, PLAG1, PLAGL1, PLAGL2, PLAT, PLAU, PLAUR, PLB1, PLBD1, PLBD2, PLCB1, PLCB2, PLCB3, PLCB4, PLCD1, PLCD3, PLCD4, PLCE1, PLCG1, PLCG2, PLCH1, PLCH2, PLCL1, PLCL2, PLCXD1, PLCXD2, PLCXD3, PLCZ1, PLD1, PLD2, PLD3, PLD4, PLD5, PLD6, PLEC, PLEK, PLEK2, PLEKHA1, PLEKHA2, PLEKHA3, PLEKHA4, PLEKHA5, PLEKHA6, PLEKHA7, PLEKHA8, PLEKHB1, PLEKHB2, PLEKHD1, PLEKHF1, PLEKHF2, PLEKHG1, PLEKHG2, PLEKHG3, PLEKHG4, PLEKHG4B, PLEKHG5, PLEKHG6, PLEKHG7, PLEKHH1, PLEKHH2, PLEKHH3, PLEKHJ1, PLEKHM1, PLEKHM2, PLEKHM3, PLEKHN1, PLEKHO1, PLEKHO2, PLEKHS1, PLET1, PLG, PLGLB1, PLGLB2, PLGRKT, PLIN1, PLIN2, PLIN3, PLIN4, PLIN5, PLK1, PLK2, PLK3, PLK4, PLK5, PLLP, PLN, PLOD1, PLOD2, PLOD3, PLP1, PLP2, PLPBP, PLPP1, PLPP2, PLPP3, PLPP4, PLPP5, PLPP6, PLPP7, PLPPR1, PLPPR2, PLPPR3, PLPPR4, PLPPR5, PLRG1, PLS1, PLS3, PLSCR1, PLSCR2, PLSCR3, PLSCR4, PLSCR5, PLTP, PLVAP, PLXDC1, PLXDC2, PLXNA1 PLXNA2, PLXNA3, PLXNA4, PLXNB1, PLXNB2, PLXNB3, PLXNC1, PLXND1, PM20D1, PM20D2, PMAIP1, PMCH, PMEL, PMEPA1, PMF1, PMF1-BGLAP, PMFBP1, PML, PMM1, PMM2, PMP2, PMP22, PMPCA, PMPCB, PMS1, PMS2, PMVK, PNCK, PNISR, PNKD, PNKP, PNLDC1, PNLIP, PNLIPRP1, PNLIPRP2, PNLIPRP3, PNMA1, PNMA2, PNMA3, PNMA5, PNMA6A, PNMA6E, PNMA6F, PNMA8A, PNMA8B, PNMA8C, PNMT, PNN, PNO1, PNOC, PNP, PNPLA1, PNPLA2, PNPLA3, PNPLA4, PNPLA5, PNPLA6, PNPLA7, PNPLA8, PNPO, PNPT1, PNRC1, PNRC2, POC1A, POC1B, POC1B-GALNT4, POC5, PODN, PODNL1, PODXL, PODXL2, POF1B, POFUT1, POFUT2, POGK, POGLUT1, POGZ, POLA1, POLA2, POLB, POLD1, POLD2, POLD3, POLD4, POLDIP2, POLDIP3, POLE, POLE2, POLE3, POLE4, POLG, POLG2, POLH, POLI, POLK, POLL, POLM, POLN, POLQ, POLR1A, POLR1B, POLR1C, POLR1D, POLR1E, POLR2A, POLR2B, POLR2C, POLR2D, POLR2E, POLR2F, POLR2G, POLR2H, POLR2I, POLR2J, POLR2J2, POLR2J3, POLR2K, POLR2L, POLR2M, POLR3A, POLR3B, POLR3C, POLR3D, POLR3E, POLR3F, POLR3G, POLR3GL, POLR3H, POLR3K, POLRMT, POM121, POM121C, POM121L12, POM121L2, POMC, POMGNT1, POMGNT2, POMK, POMP, POMT1, POMT2, POMZP3, PON1, PON2, PON3, POP1, POP4, POP5, POP7, POPDC2, POPDC3, POR, PORCN, POSTN, POT1, POTEA, POTEB, POTEB2, POTEB3, POTEC, POTED, POTEE, POTEF, POTEG, POTEH, POTEI, POTEJ, POTEM, POU1F1, POU2AF1, POU2F1, POU2F2, POU2F3, POU3F1, POU3F2, POU3F3, POU3F4, POU4F1, POU4F2, POU4F3, POU5F1, POU5FIB, POU5F2, POU6F1, POU6F2, PP2D1, PPA1, PPA2, PPAN, PPAN-P2RY11, PPARA, PPARD, PPARG, PPARGC1A, PPARGC1B, PPAT, PPBP, PPCDC, PPCS, PPDPF, PPEF1, PPEF2, PPFIA1, PPFIA2, PPFIA3, PPFIA4, PPFIBP1, PPFIBP2, PPHLN1, PPIA, PPIAL4A, PPIAL4C, PPIAL4D, PPIAL4E, PPIAL4F, PPIAL4G, PPIB, PPIC, PPID, PPIE, PPIF, PPIG, PPIH, PPIL1, PPIL2, PPIL3, PPIL4, PPIL6, PPIP5K1, PPIP5K2, PPL, PPM1A, PPM1B, PPM1D, PPM1E, PPM1F, PPM1G, PPM1H, PPM1J, PPM1K, PPM1L, PPM1M, PPM1N, PPME1, PPOX, PPP1CA, PPP1CB, PPP1CC, PPP1R10, PPP1R11, PPP1R12A, PPP1R12B, PPP1R12C, PPP1R13B, PPP1R13L, PPP1R14A, PPP1R14B, PPP1R14C, PPP1R14D, PPP1R15A, PPP1R15B, PPP1R16A, PPP1R16B, PPP1R17, PPP1R18, PPP1RIA, PPP1R1B, PPP1R1C, PPP1R2, PPP1R21, PPP1R26, PPP1R27, PPP1R2P3, PPP1R2P9, PPP1R32, PPP1R35, PPP1R36, PPP1R37, PPP1R3A, PPP1R3B, PPP1R3C, PPP1R3D, PPP1R3E, PPP1R3F, PPP1R3G, PPP1R42, PPP1R7, PPP1R8, PPP1R9A, PPP1R9B, PPP2CA, PPP2CB, PPP2R1A, PPP2RIB, PPP2R2A, PPP2R2B, PPP2R2C, PPP2R2D, PPP2R3A, PPP2R3B, PPP2R3C, PPP2R5A, PPP2R5B, PPP2R5C, PPP2R5D, PPP2R5E, PPP3CA, PPP3CB, PPP3CC, PPP3R1, PPP3R2, PPP4C, PPP4R1, PPP4R2, PPP4R3A, PPP4R3B, PPP4R3CP, PPP4R4, PPP5C, PPP5D1, PPP6C, PPP6R1, PPP6R2, PPP6R3, PPRC1, PPT1, PPT2, PPT2-EGFL8, PPTC7, PPWD1, PPY, PQBP1, PQLC1, PQLC2, PQLC2L, PQLC3, PRAC1, PRAC2, PRADC1, PRAF2, PRAG1, PRAM1, PRAME, PRAMEF1, PRAMEF10, PRAMEF11, PRAMEF12, PRAMEF13, PRAMEF14, PRAMEF15, PRAMEF17, PRAMEF18, PRAMEF19, PRAMEF2, PRAMEF20, PRAMEF25, PRAMEF26, PRAMEF27, PRAMEF33, PRAMEF4, PRAMEF5, PRAMEF6, PRAMEF7, PRAMEF8, PRAMEF9, PRAP1, PRB1, PRB2, PRB3, PRB4, PRC1, PRCC, PRCD, PRCP, PRDM1, PRDM10, PRDM11, PRDM12, PRDM13, PRDM14, PRDM15, PRDM16, PRDM2, PRDM4, PRDM5, PRDM6, PRDM7, PRDM8, PRDM9, PRDX1, PRDX2, PRDX3, PRDX4, PRDX5, PRDX6, PREB, PRELID1, PRELID2, PRELID3A, PRELID3B, PRELP, PREP, PREPL, PREX1, PREX2, PRF1, PRG2, PRG3, PRG4, PRH1, PRH2, PRICKLE1, PRICKLE2, PRICKLE3, PRICKLE4, PRIM1, PRIM2, PRIMA1, PRIMPOL, PRKAA1, PRKAA2, PRKAB1, PRKAB2, PRKACA, PRKACB, PRKACG, PRKAG1, PRKAG2, PRKAG3, PRKAR1A, PRKAR1B, PRKAR2A, PRKAR2B, PRKCA, PRKCB, PRKCD, PRKCE, PRKCG, PRKCH, PRKCI, PRKCQ, PRKCSH, PRKCZ, PRKD1, PRKD2, PRKD3, PRKDC, PRKG1, PRKG2, PRKN, PRKRA, PRKRIP1, PRKX, PRL, PRLH, PRLHR, PRLR, PRM1, PRM2, PRM3, PRMT1, PRMT2, PRMT3, PRMT5, PRMT6, PRMT7, PRMT8, PRMT9, PRND, PRNP, PRNT, PROB1, PROC, PROCA1, PROCR, PRODH, PRODH2, PROK1, PROK2, PROKR1, PROKR2, PROM1, PROM2, PROP1, PRORY, PROS1, PROSER1, PROSER2, PROSER3, PROX1, PROX2, PROZ, PRPF18, PRPF19, PRPF3, PRPF31, PRPF38A, PRPF38B, PRPF39, PRPF4, PRPF40A, PRPF40B, PRPF4B, PRPF6, PRPF8, PRPH, PRPH2, PRPS1, PRPS1L1, PRPS2, PRPSAP1, PRPSAP2, PRR11, PRR12, PRR13, PRR14, PRR14L, PRR15, PRR15L, PRR16, PRR18, PRR19, PRR20A, PRR20B, PRR20C, PRR20D, PRR20E, PRR21, PRR22, PRR23A, PRR23B, PRR23C, PRR23D1, PRR23D2, PRR25, PRR26, PRR27, PRR29, PRR3, PRR30, PRR32, PRR34, PRR35, PRR36, PRR4, PRR5, PRR5-ARHGAP8, PRR5L, PRR7, PRR9, PRRC1, PRRC2A, PRRC2B, PRRC2C, PRRG1, PRRG2, PRRG3, PRRG4, PRRT1, PRRT2, PRRT3, PRRT4, PRRX1, PRRX2, PRSS1, PRSS12, PRSS16, PRSS2, PRSS21, PRSS22, PRSS23, PRSS27, PRSS3, PRSS33, PRSS35, PRSS36, PRSS37, PRSS38, PRSS41, PRSS42, PRSS45, PRSS46, PRSS48, PRSS50, PRSS51, PRSS53, PRSS54, PRSS55, PRSS56, PRSS57, PRSS58, PRSS8, PRTFDC1, PRTG, PRTN3, PRUNE1, PRUNE2, PRX, PRY, PRY2, PSAP, PSAPL1, PSAT1, PSCA, PSD, PSD2, PSD3, PSD4, PSEN1, PSEN2, PSENEN, PSG1, PSG11, PSG2, PSG3, PSG4, PSG5, PSG6, PSG7, PSG8, PSG9, PSIP1, PSKH1, PSKH2, PSMA1, PSMA2, PSMA3, PSMA4, PSMA5, PSMA6, PSMA7, PSMA8, PSMB1, PSMB10, PSMB11, PSMB2, PSMB3, PSMB4, PSMB5, PSMB6, PSMB7, PSMB8, PSMB9, PSMC1, PSMC2, PSMC3, PSMC3IP, PSMC4, PSMC5, PSMC6, PSMD1, PSMD10, PSMD11, PSMD12, PSMD13, PSMD14, PSMD2, PSMD3, PSMD4, PSMD5, PSMD6, PSMD7, PSMD8, PSMD9, PSME1, PSME2, PSME3, PSME4, PSMF1, PSMG1, PSMG2, PSMG3, PSMG4, PSORS1C1, PSORS1C2, PSPC1, PSPH, PSPN, PSRC1, PSTK, PST-PIP1, PSTPIP2, PTAFR, PTAR1, PTBP1, PTBP2, PTBP3, PTCD1, PTCD2, PTCD3, PTCH1, PTCH2, PTCHD1, PTCHD3, PTCHD4, PTCRA, PTDSS1, PTDSS2, PTEN, PTER, PTF1A, PTGDR, PTGDR2, PTGDS, PTGER1, PTGER2, PTGER3, PTGER4, PTGES, PTGES2, PTGES3, PTGES3L, PTGES3L-AARSD1, PTGFR, PTGFRN, PTGIR, PTGIS, PTGR1, PTGR2, PTGS1, PTGS2, PTH, PTH1R, PTH2, PTH2R, PTHLH, PTK2, PTK2B, PTK6, PTK7, PTMA, PTMS, PTN, PTOV1, PTP4A1, PTP4A2, PTP4A3, PTPA, PTPDC1, PTPMT1, PTPN1, PTPN11, PTPN12, PTPN13, PTPN14, PTPN18, PTPN2, PTPN20, PTPN21, PTPN22, PTPN23, PTPN3, PTPN4, PTPN5, PTPN6, PTPN7, PTPN9, PTPRA, PTPRB, PTPRC, PTPR-CAP, PTPRD, PTPRE, PTPRF, PTPRG, PTPRH, PTPRJ, PTPRK, PTPRM, PTPRN, PTPRN2, PTPRO, PTPRQ, PTPRR, PTPRS, PTPRT, PTPRU, PTPRZ1, PTRH1, PTRH2, PTRHD1, PTS, PTTG1, PTTG1IP, PTTG2, PTX3, PTX4, PUDP, PUF60, PUM1, PUM2, PUM3, PURA, PURB, PURG, PUS1, PUS10, PUS3, PUS7, PUS7L, PUSL1, PVALB, PVR, PVRIG, PWP1, PWP2, PWWP2A, PWWP2B, PXDC1, PXDN, PXDNL, PXK, PXMP2, PXMP4, PXN, PXT1, PXYLP1, PYCARD, PYCR1 PYCR2, PYCR3, PYDC1, PYDC2, PYGB, PYGL, PYGM, PYGO1, PYGO2, PYHIN1, PYM1, PYROXD1, PYROXD2, PYURF, PYY, PZP, QARS, QDPR, QKI, QPCT, QPCTL, QPRT, QRFP, QRFPR, QRICH1, QRICH2, QRSL1, QSER1, QSOX1, QSOX2, QTRT1, QTRT2, R3HCC1, R3HCC1L, R3HDM1, R3HDM2, R3HDM4, R3HDML, RAB10, RAB11A, RAB11B, RAB11FIP1, RAB11FIP2, RAB11FIP3, RAB11FIP4, RAB11FIP5, RAB12, RAB13, RAB14, RAB15, RAB17, RAB18, RAB19, RAB1A, RAB1B, RAB20, RAB21, RAB22A, RAB23, RAB24, RAB25, RAB26, RAB27A, RAB27B, RAB28, RAB29, RAB2A, RAB2B, RAB30, RAB31, RAB32, RAB33A, RAB33B, RAB34, RAB35, RAB36, RAB37, RAB38, RAB39A, RAB39B, RAB3A, RAB3B, RAB3C, RAB3D, RAB3GAP1, RAB3GAP2, RAB3IL1, RAB3IP, RAB40A, RAB40AL, RAB40B, RAB40C, RAB41, RAB42, RAB43, RAB44, RAB4A, RAB4B, RAB4B-EGLN2, RAB5A, RAB5B, RAB5C, RAB6A, RAB6B, RAB6C, RAB7A, RAB7B, RAB8A, RAB8B, RAB9A, RAB9B, RABAC1, RABEP1, RABEP2, RABEPK, RABGAP1, RABGAP1L, RABGEF1, RABGGTA, RABGGTB, RABIF, RABL2A, RABL2B, RABL3, RABL6, RAC1, RAC2, RAC3, RACGAP1, RACK1, RAD1, RAD17, RAD18, RAD21, RAD21L1, RAD23A, RAD23B, RAD50, RAD51, RAD51AP1, RAD51AP2, RAD51B, RAD51C, RAD51D, RAD52, RAD54B, RAD54L, RAD54L2, RAD9A, RAD9B, RADIL, RAE1, RAET1E, RAET1G, RAET1L, RAF1, RAG1, RAG2, RAI1, RAI14, RAI2, RALA, RALB, RALBP1, RALGAPA1, RALGAPA2, RALGAPB, RALGDS, RAL-GPS1, RALGPS2, RALY, RALYL, RAMP1, RAMP2, RAMP3, RAN, RANBP1, RANBP10, RANBP17, RANBP2, RANBP3, RANBP3L, RANBP6, RANBP9, RANGAP1, RANGRF, RAP1A, RAP1B, RAP1GAP, RAP1GAP2, RAP1GDS1, RAP2A, RAP2B, RAP2C, RAPGEF1, RAPGEF2, RAPGEF3, RAPGEF4, RAPGEF5, RAPGEF6, RAPGEFL1, RAPH1, RAPSN, RARA, RARB, RARG, RARRES1, RARRES2, RARRES3, RARS, RARS2, RASA1, RASA2, RASA3, RASA4, RASA4B, RASAL1, RASAL2, RASAL3, RASD1, RASD2, RASEF, RASGEF1A, RASGEF1B, RASGEF1C, RASGRF1, RAS-GRF2, RASGRP1, RASGRP2, RASGRP3, RASGRP4, RASIP1, RASL10A, RASL10B, RASL11A, RASL11B, RASL12, RASSF1, RASSF10, RASSF2, RASSF3, RASSF4, RASSF5, RASSF6, RASSF7, RASSF8, RASSF9, RAVER1 RAVER2, RAX, RAX2, RB1, RB1CC1, RBAK, RBAK-RBAKDN, RBBP4, RBBP5, RBBP6, RBBP7, RBBP8, RBBP8NL, RBBP9, RBCK1, RBFA, RBFOX1, RBFOX2, RBFOX3, RBKS, RBL1, RBL2, RBM10, RBM11, RBM12, RBM12B, RBM14, RBM14-RBM4, RBM15, RBM15B, RBM17, RBM18, RBM19, RBM20, RBM22, RBM23, RBM24, RBM25, RBM26, RBM27, RBM28, RBM3, RBM33, RBM34, RBM38, RBM39, RBM4, RBM41, RBM42, RBM43, RBM44, RBM45, RBM46, RBM47, RBM48, RBM4B, RBM5, RBM6, RBM7, RBM8A, RBMS1, RBMS2, RBMS3, RBMX, RBMX2, RBMXL1, RBMXL2, RBMXL3, RBMY1A1, RBMY1B, RBMY1D, RBMY1E, RBMY1F, RBMY1J, RBP1, RBP2, RBP3, RBP4, RBP5, RBP7, RBPJ, RBPJL, RBPMS, RBPMS2, RBSN, RBX1, RC3H1, RC3H2, RCAN1, RCAN2, RCAN3, RCBTB1, RCBTB2, RCC1, RCC1L, RCC2, RCCD1, RCE1, RCHY1, RCL1, RCN1, RCN2, RCN3, RCOR1, RCOR2, RCOR3, RCSD1, RCVRN, RD3, RD3L, RDH10, RDH11, RDH12, RDH13, RDH14, RDH16, RDH5, RDH8, RDM1, RDX, REC114, REC8, RECK, RECQL, RECQL4, RECQL5, REEP1, REEP2, REEP3, REEP4, REEP5, REEP6, REG1A, REG1B, REG3A, REG3G, REG4, REL, RELA, RELB, RELL1, RELL2, RELN, RELT, REM1, REM2, REN, RENBP, REP15, REPIN1, REPS1, REPS2, RER1, RERE, RERG, RERGL, RESP18, REST, RET, RETN, RETNLB, RETREG1, RETREG2, RETREG3, RETSAT, REV1, REV3L, REXO1, REXO2, REXO4, REXO5, RFC1, RFC2, RFC3, RFC4, RFC5, RFESD, RFFL, RFK, RFLNA, RFLNB, RFNG, RFPL1, RFPL2, RFPL3, RFPL3S, RFPL4A, RFPL4AL1, RFPL4B, RFT1, RFTN1, RFTN2, RFWD2, RFWD3, RFX1, RFX2, RFX3, RFX4, RFX5, RFX6, RFX7, RFX8, RFXANK, RFXAP, RGCC, RGL1, RGL2, RGL3, RGL4, RGMA, RGMB, RGN, RGP1, RGPD1, RGPD2, RGPD3, RGPD4, RGPD5, RGPD6, RGPD8, RGR, RGS1, RGS10, RGS11, RGS12, RGS13, RGS14, RGS16, RGS17, RGS18, RGS19, RGS2, RGS20, RGS21, RGS22, RGS3, RGS4, RGS5, RGS6, RGS7, RGS7BP, RGS8, RGS9, RGS9BP, RGSL1, RHAG, RHBDD1, RHBDD2, RHBDD3, RHBDF1, RHBDF2, RHBDL1, RHBDL2, RHBDL3, RHBG, RHCE, RHCG, RHD, RHEB, RHEBL1, RHNO1, RHO, RHOA, RHOB, RHOBTB1, RHOBTB2, RHOBTB3, RHOC, RHOD, RHOF, RHOG, RHOH, RHOJ, RHOQ, RHOT1, RHOT2, RHOU, RHOV, RHOXF1, RHOXF2, RHOXF2B, RHPN1, RHPN2, RIBC1, RIBC2, RIC1, RIC3, RIC8A, RIC8B, RICTOR, RIDA, RIF1, RIIAD1, RILP, RILPL1, RILPL2, RIMBP2, RIMBP3, RIMBP3B, RIMBP3C, RIMKLA, RIMKLB, RIMS1, RIMS2, RIMS3, RIMS4, RIN1, RIN2, RIN3, RING1, RINL, RINT1, RIOK1, RIOK2, RIOK3, RIOX1, RIOX2, RIPK1, RIPK2, RIPK3, RIPK4, RIPOR1, RIPOR2, RIPOR3, RIPPLY1, RIPPLY2, RIPPLY3, RIT1, RIT2, RITA1, RLBP1, RLF, RLIM, RLN1, RLN2, RLN3, RMDN1, RMDN2, RMDN3, RMI1, RMI2, RMND1, RMND5A, RMND5B, RNASE1, RNASE10, RNASE11, RNASE12, RNASE13, RNASE2, RNASE3, RNASE4, RNASE6, RNASE7, RNASE8, RNASE9, RNASEH1, RNASEH2A, RNASEH2B, RNASEH2C, RNASEK, RNASEK-C17orf49, RNASEL, RNASET2, RND1, RND2, RND3, RNF10, RNF103, RNF103-CHMP3, RNF11, RNF111, RNF112, RNF113A, RNF113B, RNF114, RNF115, RNF121, RNF122, RNF123, RNF125, RNF126, RNF128, RNF13, RNF130, RNF133, RNF135, RNF138, RNF139, RNF14, RNF141, RNF144A, RNF144B, RNF145, RNF146, RNF148, RNF149, RNF150, RNF151, RNF152, RNF157, RNF165, RNF166, RNF167, RNF168, RNF169, RNF17, RNF170, RNF175, RNF180, RNF181, RNF182, RNF183, RNF185, RNF186, RNF187, RNF19A, RNF19B, RNF2, RNF20, RNF207, RNF208, RNF212, RNF212B, RNF213, RNF214, RNF215, RNF216, RNF217, RNF219, RNF220, RNF222, RNF223, RNF224, RNF225, RNF24, RNF25, RNF26, RNF31, RNF32, RNF34, RNF38, RNF39, RNF4, RNF40, RNF41, RNF43, RNF44, RNF5, RNF6, RNF7, RNF8, RNFT1, RNFT2, RNGTT, RNH1, RNLS, RNMT, RNPC3, RNPEP, RNPEPL1, RNPS1, ROBO1, ROBO2, ROBO3, ROBO4, ROCK1, ROCK2, ROGD1, ROM1, ROMO1, ROPN1, ROPN1B, ROPN1L, ROR1, ROR2, RORA, RORB, RORC, ROS1, RP1, RP1L1, RP2, RP9, RPA1, RPA2, RPA3, RPA4, RPAIN, RPAP1, RPAP2, RPAP3, RPE, RPE65, RPEL1, RPF1, RPF2, RPGR, RPGRIP1, RPGRIP1L, RPH3A, RPH3AL, RPIA, RPL10, RPL10A, RPL10L, RPL11, RPL12, RPL13, RPL13A, RPL14, RPL15, RPL17, RPL17-C18orf32, RPL18, RPL18A, RPL19, RPL21, RPL22, RPL22L1, RPL23, RPL23A, RPL24, RPL26, RPL26L1, RPL27, RPL27A, RPL28, RPL29, RPL3, RPL30, RPL31, RPL32, RPL34, RPL35, RPL35A, RPL36, RPL36A, RPL36A-HNRNPH2, RPL36AL, RPL37, RPL37A, RPL38, RPL39, RPL39L, RPL3L, RPL4, RPL41, RPL5, RPL6, RPL7, RPL7A, RPL7L1, RPL8, RPL9, RPLP0, RPLP1, RPLP2, RPN1, RPN2, RPP14, RPP21, RPP25, RPP25L, RPP30, RPP38, RPP40, RPRD1A, RPRD1B, RPRD2, RPRM, RPRML, RPS10, RPS10-NUDT3, RPS11, RPS12, RPS13, RPS14, RPS15, RPS15A, RPS16, RPS17, RPS18, RPS19, RPS19BP1, RPS2, RPS20, RPS21, RPS23, RPS24, RPS25, RPS26, RPS27, RPS27A, RPS27L, RPS28, RPS29, RPS3, RPS3A, RPS4X, RPS4Y1, RPS4Y2, RPS5, RPS6, RPS6KA1, RPS6KA2, RPS6KA3, RPS6KA4, RPS6KA5, RPS6KA6, RPS6KB1, RPS6KB2, RPS6KC1, RPS6KL1, RPS7, RPS8, RPS9, RPSA, RPTN, RPTOR, RPUSD1, RPUSD2, RPUSD3, RPUSD4, RRAD, RRAGA, RRAGB, RRAGC, RRAGD, RRAS, RRAS2, RRBP1, RREB1, RRH, RRM1, RRM2, RRM2B, RRN3, RRNAD1, RRP1, RRP12, RRP15, RRP1B, RRP36, RRP7A, RRP8, RRP9, RRS1, RS1, RSAD1, RSAD2, RSBN1, RSBN1L, RSC1A1, RSF1, RSG1, RSLID1, RSL24D1, RSPH1, RSPH1OB, RSPH10B2, RSPH14, RSPH3, RSPH4A, RSPH6A, RSPH9, RSPO1, RSPO2, RSPO3, RSPO4, RSPRY1, RSRC1, RSRC2, RSRP1, RSU1, RTBDN, RTCA, RTCB, RTEL1, RTEL1-TNFRSF6B, RTF1, RTFDC1, RTKN, RTKN2, RTL1, RTL10, RTL3, RTL4, RTL5, RTL6, RTL8A, RTL8B, RTL8C, RTL9, RTN1, RTN2, RTN3, RTN4, RTN4IP1, RTN4R, RTN4RL1, RTN4RL2, RTP1, RTP2, RTP3, RTP4, RTP5, RTTN, RUBCN, RUBCNL, RUFY1, RUFY2, RUFY3, RUFY4, RUNDC1, RUNDC3A, RUNDC3B, RUNX1, RUNX1T1, RUNX2, RUNX3, RUSC1, RUSC2, RUVBL1, RUVBL2, RWDD1, RWDD2A, RWDD2B, RWDD3, RWDD4, RXFP1, RXFP2, RXFP3, RXFP4, RXRA, RXRB, RXRG, RYBP, RYK, RYR1, RYR2, RYR3, S100A1, S100A10, S100A11, S100A12, S100A13, S100A14, S100A16, S100A2, S100A3, S100A4, S100A5, S100A6, S100A7, S100A7A, S100A7L2, S100A8, S100A9, S100B, S100G, S100P, S100PBP, S100Z, S1PR1, S1PR2, S1PR3, S1PR4, S1PR5, SAA1, SAA2, SAA2-SAA4, SAA4, SAAL1, SAC3D1, SACM1L, SACS, SAE1, SAFB, SAFB2, SAG, SAGE1, SALL1, SALL2, SALL3, SALL4, SAMD1, SAMD10, SAMD11, SAMD12, SAMD13, SAMD14, SAMD15, SAMD3, SAMD4A, SAMD4B, SAMD5, SAMD7, SAMD8, SAMD9, SAMD9L, SAMHD1, SAMM50, SAMSN1, SAP130, SAP18, SAP25, SAP30, SAP30BP, SAP30L, SAPCD1, SAPCD2, SAR1A, SAR1B, SARAF, SARDH, SARM1, SARNP, SARS, SARS2, SART1, SART3, SASH1, SASH3, SASS6, SAT1, SAT2, SATB1, SATB2, SATL1, SAV1, SAXO1, SAXO2, SAYSD1, SBDS, SBF1, SBF2, SBK1, SBK2, SBK3, SBNO1, SBNO2, SBSN, SBSPON, SC5D, SCAF1, SCAF11, SCAF4, SCAF8, SCA1, SCAMP1, SCAMP2, SCAMP3, SCAMP4, SCAMP5, SCAND1, SCAP, SCAPER, SCARA3, SCARA5, SCARB1, SCARB2, SCARF1, SCARF2, SCART1, SCCPDH, SCD, SCD5, SCEL, SCFD1, SCFD2, SCG2, SCG3, SCG5, SCGB1A1, SCGB1C1, SCGB1C2, SCGB1D1, SCGB1D2, SCGB1D4, SCGB2A1, SCGB2A2, SCGB2B2, SCGB3A1, SCGB3A2, SCGN, SCHIP1, SCIMP, SCIN, SCLT1, SCLY, SCMH1, SCML1, SCML2, SCML4, SCN10A, SCN11A, SCN1A, SCN1B, SCN2A, SCN2B, SCN3A, SCN3B, SCN4A, SCN4B, SCN5A, SCN7A, SCN8A, SCN9A, SCNM1, SCNN1A, SCNN1B, SCNN1D, SCNN1G, SCO1, SCO2, SCOC, SCP2, SCP2D1, SCPEP1, SCRG1, SCRIB, SCRN1, SCRN2, SCRN3, SCRT1, SCRT2, SCT, SCTR, SCUBE1, SCUBE2, SCUBE3, SCX, SCYL1, SCYL2, SCYL3, SDAD1, SDC1, SDC2, SDC3, SDC4, SDCBP, SDCBP2, SDCCAG3, SDCCAG8, SDE2, SDF2, SDF2L1, SDF4, SDHA, SDHAF1, SDHAF2, SDHAF3, SDHAF4, SDHB, SDHC, SDHD, SDK1, SDK2, SDRI6C5, SDR39U1, SDR42E1, SDR42E2, SDR9C7, SDS, SDSL, SEBOX, SEC11A, SEC11C, SEC13, SEC14L1, SEC14L2, SEC14L3, SEC14L4, SEC14L5, SEC14L6, SEC16A, SEC16B, SEC22A, SEC22B, SEC22C, SEC23A, SEC23B, SEC23IP, SEC24A, SEC24B, SEC24C, SEC24D, SEC31A, SEC31B, SEC61A1, SEC61A2, SEC61B, SEC61G, SEC62, SEC63, SECISBP2, SECISBP2L, SECTM1, SEH1L, SEL1L, SEL1L2, SEL1L3, SELE, SELENBP1, SELENOF, SELENOH, SELENOI, SELENOK, SELENOM, SELENON, SELENOO, SELENOP, SELENOS, SELENOT, SELENOV, SELENOW, SELL, SELP, SELPLG, SEM1, SEMA3A, SEMA3B, SEMA3C, SEMA3D, SEMA3E, SEMA3F, SEMA3G, SEMA4A, SEMA4B, SEMA4C, SEMA4D, SEMA4F, SEMA4G, SEMA5A, SEMA5B, SEMA6A, SEMA6B, SEMA6C, SEMA6D, SEMA7A, SEMG1, SEMG2, SENP1, SENP2, SENP3, SENP3-EIF4A1, SENP5, SENP6, SENP7, SENP8, SEPHS1, SEPHS2, SEPSECS, SEPT1, SEPT10, SEPT11, SEPT12, SEPT14, SEPT2, SEPT3, SEPT4, SEPT5, SEPT6, SEPT7, SEPT8, SEPT9, SERAC1, SERBP1, SERF1A, SERF1B, SERF2, SERGEF, SERHL2, SERINC1, SERINC2, SERINC3, SERINC4, SERINC5, SERP1, SERP2, SERPINA1, SERPINA10, SERPINA11, SERPINA12, SERPINA2, SERPINA3, SERPINA4, SERPINA5, SERPINA6, SERPINA7, SERPINA9, SERPINB1, SERPINB10, SERPINB11, SERPINB12, SERPINB13, SERPINB2, SERPINB3, SERPINB4, SERPINB5, SERPINB6, SERPINB7, SERPINB8, SERPINB9, SERPINC1, SERPIND1, SERPINE1, SERPINE2, SERPINE3, SERPINF1, SERPINF2, SERPING1, SERPINH1, SERPINI1, SERPINI2, SERTAD1, SERTAD2, SERTAD3, SERTAD4, SERTM1, SESN1, SESN2, SESN3, SESTD1, SET, SETBP1, SETD1A, SETD1B, SETD2, SETD3, SETD4, SETD5, SETD6, SETD7, SETD9, SETDB1, SETDB2, SETMAR, SETSIP, SETX, SEZ6, SEZ6L, SEZ6L2, SF1, SF3A1, SF3A2, SF3A3, SF3B1, SF3B2, SF3B3, SF3B4, SF3B5, SF3B6, SFI1, SFMBT1, SFMBT2, SFN, SFPQ, SFR1, SFRP1, SFRP2, SFRP4, SFRP5, SFSWAP, SFT2D1, SFT2D2, SFT2D3, SFTA2, SFTA3, SFTPA1, SFTPA2, SFTPB, SFTPC, SFTPD, SFXN1, SFXN2, SFXN3, SFXN4, SFXN5, SGCA, SGCB, SGCD, SGCE, SGCG, SGCZ, SGF29, SGIP1, SGK1, SGK2, SGK3, SGK494, SGMS1, SGMS2, SGO1, SG02, SGPL1, SGPP1, SGPP2, SGSH, SGSM1, SGSM2, SGSM3, SGTA, SGTB, SH2B1, SH2B2, SH2B3, SH2DIA, SH2D1B, SH2D2A, SH2D3A, SH2D3C, SH2D4A, SH2D4B, SH2D5, SH2D6, SH2D7, SH3BGR, SH3BGRL, SH3BGRL2, SH3BGRL3, SH3BP1, SH3BP2, SH3BP4, SH3BP5, SH3BP5L, SH3D19, SH3D21, SH3GL1, SH3GL2, SH3GL3, SH3GLB1, SH3GLB2, SH3KBP1, SH3PXD2A, SH3PXD2B, SH3RF1, SH3RF2, SH3RF3, SH3TC1, SH3TC2, SH3YL1, SHANKI, SHANK2, SHANK3, SHARPIN, SHB, SHBG, SHC1, SHC2, SHC3, SHC4, SHCBP1, SHCBP1L, SHD, SHE, SHF, SHH, SHISA2, SHISA3, SHISA4, SHISA5, SHISA6, SHISA7, SHISA8, SHISA9, SHKBP1, SHMT1, SHMT2, SHOC2, SHOX, SHOX2, SHPK, SHPRH, SHQ1, SHROOM1, SHROOM2, SHROOM3, SHROOM4, SHTN1, SI, SIAE, SIAH1, SIAH2, SIAH3, SIDT1, SIDT2, SIGIRR, SIGLEC1, SIGLEC10, SIGLEC11, SIGLEC12, SIGLEC14, SIGLEC15, SIGLEC5, SIGLEC6, SIGLEC7, SIGLEC8, SIGLEC9, SIGLECL1, SIGMAR1, SIK1, SIK2, SIK3, SIKE1, SIL1, SIM1, SIM2, SIMC1, SIN3A, SIN3B, SIPA1, SIPA1L1, SIPAIL2, SIPAIL3, SIRPA, SIRPB1, SIRPB2, SIRPD, SIRPG, SIRT1, SIRT2, SIRT3, SIRT4, SIRT5, SIRT6, SIRT7, SIT1, SIVA1, SIX1, SIX2, SIX3, SIX4, SIX5, SIX6, SKA1, SKA2, SKA3, SKAP1, SKAP2, SKI, SKIDA1, SKIL, SKIV2L, SKIV2L2, SKOR1, SKOR2, SKP1, SKP2, SLA, SLA2, SLAIN1, SLAIN2, SLAMF1, SLAMF6, SLAMF7, SLAMF8, SLAMF9, SLBP, SLC10A1, SLC10A2, SLC10A3, SLC10A4, SLC10A5, SLC10A6, SLC10A7, SLC11A1, SLC11A2, SLC12A1, SLC12A2, SLC12A3, SLC12A4, SLC12A5, SLC12A6, SLC12A7, SLC12A8, SLC12A9, SLC13A1, SLC13A2, SLC13A3, SLC13A4, SLC13A5, SLC14A1, SLC14A2, SLC15A1, SLC15A2, SLC15A3, SLC15A4, SLC15A5, SLC16A1, SLC16A10, SLC16A11, SLC16A12, SLC16A13, SLC16A14, SLC16A2, SLC16A3, SLC16A4, SLC16A5, SLC16A6, SLC16A7, SLC16A8, SLC16A9, SLC17A1, SLC17A2, SLC17A3, SLC17A4, SLC17A5, SLC17A6, SLC17A7, SLC17A8, SLC17A9, SLC18A1, SLC18A2, SLC18A3, SLC18B1, SLC19A1, SLC19A2, SLC19A3, SLC1A1, SLC1A2, SLC1A3, SLC1A4, SLC1A5, SLC1A6, SLC1A7, SLC20A1, SLC20A2, SLC22A1, SLC22A10, SLC22A11, SLC22A12, SLC22A13, SLC22A14, SLC22A15, SLC22A16, SLC22A17, SLC22A18, SLC22A18AS, SLC22A2, SLC22A23, SLC22A24, SLC22A25, SLC22A3, SLC22A31, SLC22A4, SLC22A5, SLC22A6, SLC22A7, SLC22A8, SLC22A9, SLC23A1, SLC23A2, SLC23A3, SLC24A1, SLC24A2, SLC24A3, SLC24A4, SLC24A5, SLC25A1, SLC25A10, SLC25A11, SLC25A12, SLC25A13, SLC25A14, SLC25A15, SLC25A16, SLC25A17, SLC25A18, SLC25A19, SLC25A2, SLC25A20, SLC25A21, SLC25A22, SLC25A23, SLC25A24, SLC25A25, SLC25A26, SLC25A27, SLC25A28, SLC25A29, SLC25A3, SLC25A30, SLC25A31, SLC25A32, SLC25A33, SLC25A34, SLC25A35, SLC25A36, SLC25A37, SLC25A38, SLC25A39, SLC25A4, SLC25A40, SLC25A41, SLC25A42, SLC25A43, SLC25A44, SLC25A45, SLC25A46, SLC25A47, SLC25A48, SLC25A5, SLC25A51, SLC25A52, SLC25A53, SLC25A6, SLC26A1, SLC26A10, SLC26A11, SLC26A2, SLC26A3, SLC26A4, SLC26A5, SLC26A6, SLC26A7, SLC26A8, SLC26A9, SLC27A1, SLC27A2, SLC27A3, SLC27A4, SLC27A5, SLC27A6, SLC28A1, SLC28A2, SLC28A3, SLC29A1, SLC29A2, SLC29A3, SLC29A4, SLC2A1, SLC2A10, SLC2A11, SLC2A12, SLC2A13, SLC2A14, SLC2A2, SLC2A3, SLC2A4, SLC2A4RG, SLC2A5, SLC2A6, SLC2A7, SLC2A8, SLC2A9, SLC30A1, SLC30A10, SLC30A2, SLC30A3, SLC30A4, SLC30A5, SLC30A6, SLC30A7, SLC30A8, SLC30A9, SLC31A1, SLC31A2, SLC32A1, SLC33A1, SLC34A1, SLC34A2, SLC34A3, SLC35A1, SLC35A2, SLC35A3, SLC35A4, SLC35A5, SLC35B1, SLC35B2, SLC35B3, SLC35B4, SLC35C1, SLC35C2, SLC35D1, SLC35D2, SLC35D3, SLC35E1, SLC35E2, SLC35E2B, SLC35E3, SLC35E4, SLC35F1, SLC35F2, SLC35F3, SLC35F4, SLC35F5, SLC35F6, SLC35G1, SLC35G2, SLC35G3, SLC35G4, SLC35G5, SLC35G6, SLC36A1, SLC36A2, SLC36A3, SLC36A4, SLC37A1, SLC37A2, SLC37A3, SLC37A4, SLC38A1, SLC38A10, SLC38A11, SLC38A2, SLC38A3, SLC38A4, SLC38A5, SLC38A6, SLC38A7, SLC38A8, SLC38A9, SLC39A1, SLC39A10, SLC39A11, SLC39A12, SLC39A13, SLC39A14, SLC39A2, SLC39A3, SLC39A4, SLC39A5, SLC39A6, SLC39A7, SLC39A8, SLC39A9, SLC3A1, SLC3A2, SLC40A1, SLC41A1, SLC41A2, SLC41A3, SLC43A1, SLC43A2, SLC43A3, SLC44A1, SLC44A2, SLC44A3, SLC44A4, SLC44A5, SLC45A1, SLC45A2, SLC45A3, SLC45A4, SLC46A1, SLC46A2, SLC46A3, SLC47A1, SLC47A2, SLC48A1, SLC4A1, SLC4A10, SLC4A11, SLC4A1AP, SLC4A2, SLC4A3, SLC4A4, SLC4A5, SLC4A7, SLC4A8, SLC4A9, SLC50A1, SLC51A, SLC51B, SLC52A1, SLC52A2, SLC52A3, SLC5A1, SLC5A10, SLC5A11, SLC5A12, SLC5A2, SLC5A3, SLC5A4, SLC5A5, SLC5A6, SLC5A7, SLC5A8, SLC5A9, SLC6A1, SLC6A11, SLC6A12, SLC6A13, SLC6A14, SLC6A15, SLC6A16, SLC6A17, SLC6A18, SLC6A19, SLC6A2, SLC6A20, SLC6A3, SLC6A4, SLC6A5, SLC6A6, SLC6A7, SLC6A8, SLC6A9, SLC7A1, SLC7A10, SLC7A11, SLC7A13, SLC7A14, SLC7A2, SLC7A3, SLC7A4, SLC7A5, SLC7A6, SLC7A6OS, SLC7A7, SLC7A8, SLC7A9, SLC8A1, SLC8A2, SLC8A3, SLC8B1, SLC9A1, SLC9A2, SLC9A3, SLC9A3R1, SLC9A3R2, SLC9A4, SLC9A5, SLC9A6, SLC9A7, SLC9A8, SLC9A9, SLC9B1, SLC9B2, SLC9C1, SLC9C2, SLCO1A2, SLCO1B1, SLCO1B3, SLCO1B7, SLCO1C1, SLCO2A1, SLCO2B1, SLCO3A1, SLCO4A1, SLCO4C1, SLCO5A1, SLCO6A1, SLF1, SLF2, SLFN11, SLFN12, SLFN12L, SLFN13, SLFN14, SLFN5, SLFNL1, SLIRP, SLIT1, SLIT2, SLIT3, SLITRK1, SLITRK2, SLITRK3, SLITRK4, SLITRK5, SLITRK6, SLK, SLMAP, SLN, SLP1, SLTM, SLU7, SLURP1, SLURP2, SLX1A, SLX1B, SLX4, SLX4IP, SMAD1, SMAD2, SMAD3, SMAD4, SMAD5, SMAD6, SMAD7, SMAD9, SMAGP, SMAP1, SMAP2, SMARCA1, SMARCA2, SMARCA4, SMARCA5, SMARCAD1, SMARCAL1, SMARCB1, SMARCC1, SMARCC2, SMARCD1, SMARCD2, SMARCD3, SMARCE1, SMC1A, SMC1B, SMC2, SMC3, SMC4, SMC5, SMC6, SMCHD1, SMCOL, SMCO2, SMCO3, SMCO4, SMCP, SMCR8, SMDT1, SMG1, SMG5, SMG6, SMG7, SMG8, SMG9, SMIM1, SMIM10, SMIM10L1, SMIM10L2A, SMIM10L2B, SMIM11A, SMIM11B, SMIM12, SMIM13, SMIM14, SMIM15, SMIM17, SMIM18, SMIM19, SMIM2, SMIM20, SMIM21, SMIM22, SMIM23, SMIM24, SMIM26, SMIM27, SMIM28, SMIM29, SMIM3, SMIM30, SMIM31, SMIM4, SMIM5, SMIM6, SMIM7, SMIM8, SMIM9, SMKR1, SMLR1, SMN1, SMN2, SMNDC1, SMO, SMOC1, SMOC2, SMOX, SMPD1, SMPD2, SMPD3, SMPD4, SMPDL3A, SMPDL3B, SMPX, SMR3A, SMR3B, SMS, SMTN, SMTNL1, SMTNL2, SMU1, SMUG1, SMURF1, SMURF2, SMYD1, SMYD2, SMYD3, SMYD4, SMYD5, SNAI1, SNAI2, SNAI3, SNAP23, SNAP25, SNAP29, SNAP47, SNAP91, SNAPC1, SNAPC2, SNAPC3, SNAPC4, SNAPC5, SNAPIN, SNCA, SNCAIP, SNCB, SNCG, SND1, SNED1, SNF8, SNHG28, SNIP1, SNN, SNPH, SNRK, SNRNP200, SNRNP25, SNRNP27, SNRNP35, SNRNP40, SNRNP48, SNRNP70, SNRPA, SNRPA1, SNRPB, SNRPB2, SNRPC, SNRPD1, SNRPD2, SNRPD3, SNRPE, SNRPF, SNRPG, SNRPN, SNTA1, SNTB1, SNTB2, SNTG1, SNTG2, SNTN, SNU13, SNUPN, SNURF, SNW1, SNX1, SNX10, SNX11, SNX12, SNX13, SNX14, SNX15, SNX16, SNX17, SNX18, SNX19, SNX2, SNX20, SNX21, SNX22, SNX24, SNX25, SNX27, SNX29, SNX3, SNX30, SNX31, SNX32, SNX33, SNX4, SNX5, SNX6, SNX7, SNX8, SNX9, SOAT1, SOAT2, SOBP, SOCS1, SOCS2, SOCS3, SOCS4, SOCS5, SOCS6, SOCS7, SOD1, SOD2, SOD3, SOGA1, SOGA3, SOHLH1, SOHLH2, SON, SORBS1, SORBS2, SORBS3, SORCS1, SORCS2, SORCS3, SORD, SORL1, SORT1, SOS1, SOS2, SOST, SOSTDC1, SOWAHA, SOWAHB, SOWAHC, SOWAHD, SOX1, SOX10, SOX11, SOX12, SOX13, SOX14, SOX15, SOX17, SOX18, SOX2, SOX21, SOX3, SOX30, SOX4, SOX5, SOX6, SOX7, SOX8, SOX9, SP1, SP100, SP110, SP140, SP140L, SP2, SP3, SP4, SP5, SP6, SP7, SP8, SP9, SPA17, SPAAR, SPACA1, SPACA3, SPACA4, SPACA5, SPACA5B, SPACA6, SPACA7, SPACA9, SPAG1, SPAG11A, SPAG11B, SPAG16, SPAG17, SPAG4, SPAG5, SPAG6, SPAG7, SPAG8, SPAG9, SPAM1, SPANXA1, SPANXA2, SPANXB1, SPANXC, SPANXD, SPANXN1, SPANXN2, SPANXN3, SPANXN4, SPANXN5, SPARC, SPARCL1, SPART, SPAST, SPATA1, SPATA12, SPATA13, SPATA16, SPATA17, SPATA18, SPATAI9, SPATA2, SPATA20, SPATA21, SPATA22, SPATA24, SPATA25, SPATA2L, SPATA3, SPATA31A1, SPATA31A3, SPATA31A5, SPATA31A6, SPATA31A7, SPATA31D1, SPATA31D3, SPATA31D4, SPATA31E1, SPATA32, SPATA33, SPATA4, SPATA45, SPATA46, SPATA5, SPATA5L1, SPATA6, SPATA6L, SPATA7, SPATA8, SPATA9, SPATC1, SPATC1L, SPATS1, SPATS2, SPATS2L, SPC24, SPC25, SPCS1, SPCS2, SPCS3, SPDEF, SPDL1, SPDYA, SPDYC, SPDYE1, SPDYE16, SPDYE2, SPDYE2B, SPDYE3, SPDYE4, SPDYE5, SPDYE6, SPECC1, SPECC1L, SPECC1L-ADORA2A, SPEF1, SPEF2, SPEG, SPEM1, SPEN, SPERT, SPESP1, SPG11, SPG21, SPG7, SPHAR, SPHK1, SPHK2, SPHKAP, SPI1, SPIB, SPIC, SPICE1, SPIDR, SPIN1, SPIN2A, SPIN2B, SPIN3, SPIN4, SPINK1, SPINK13, SPINK14, SPINK2, SPINK4, SPINKS, SPINK6, SPINK7, SPINK8, SPINK9, SPINT1, SPINT2, SPINT3, SPINT4, SPIRE1, SPIRE2, SPN, SPNS1, SPNS2, SPNS3, SPO11, SPOCD1, SPOCK1, SPOCK2, SPOCK3, SPON1, SPON2, SPOP, SPOPL, SPOUT1, SPP1, SPP2, SPPL2A, SPPL2B, SPPL2C, SPPL3, SPR, SPRED1, SPRED2, SPRED3, SPRN, SPRR1A, SPRR1B, SPRR2A, SPRR2B, SPRR2D, SPRR2E, SPRR2F, SPRR2G, SPRR3, SPRR4, SPRR5, SPRTN, SPRY1, SPRY2, SPRY3, SPRY4, SPRYD3, SPRYD4, SPRYD7, SPSB1, SPSB2, SPSB3, SPSB4, SPTA1, SPTAN1, SPTB, SPTBN1, SPTBN2, SPTBN4, SPTBN5, SPTLC1, SPTLC2, SPTLC3, SPTSSA, SPTSSB, SPTY2D1, SPTY2D1-AS1, SPX, SPZ1, SQLE, SQOR, SQSTM1, SRA1, SRBD1, SRC, SRCAP, SRCIN1, SRD5A1, SRD5A2, SRD5A3, SREBF1, SREBF2, SREK1, SREK1IP1, SRF, SRFBP1, SRGAP1, SRGAP2, SRGAP2B, SRGAP2C, SRGAP3, SRGN, SRI, SRL, SRM, SRMS, SRP14, SRP19, SRP54, SRP68, SRP72, SRP9, SRPK1, SRPK2, SRPK3, SRPRA, SRPRB, SRPX, SRPX2, SRR, SRRD, SRRM1, SRRM2, SRRM3, SRRM4, SRRM5, SRRT, SRSF1, SRSF10, SRSF11, SRSF12, SRSF2, SRSF3, SRSF4, SRSF5, SRSF6, SRSF7, SRSF8, SRSF9, SRXN1, SRY, SS18, SS18L1, SS18L2, SSB, SSBP1, SSBP2, SSBP3, SSBP4, SSC4D, SSC5D, SSFA2, SSH1, SSH2, SSH3, SSMEM1, SSNA1, SSPN, SSPO, SSR1, SSR2, SSR3, SSR4, SSRP1, SSSCA1, SST, SSTR1, SSTR2, SSTR3, SSTR4, SSTR5, SSU72, SSU72P8, SSUH2, SSX1, SSX2, SSX2B, SSX2IP, SSX3, SSX4, SSX4B, SSX5, SSX7, ST13, ST14, ST18, ST20, ST20-MTHFS, ST3GAL1, ST3GAL2, ST3GAL3, ST3GAL4, ST3GAL5, ST3GAL6, ST5, ST6GAL1, ST6GAL2, ST6GALNAC1, ST6GALNAC2, ST6GALNAC3, ST6GALNAC4, ST6GALNAC5, ST6GALNAC6, ST7, ST7L, ST8SIA1, ST8SIA2, ST8SIA3, ST8SIA4, ST8SIA5, ST8SIA6, STAB1, STAB2, STAC, STAC2, STAC3, STAG1, STAG2, STAG3, STAM, STAM2, STAMBP, STAMBPL1, STAP1, STAP2, STAR, STARD10, STARD13, STARD3, STARD3NL, STARD4, STARD5, STARD6, STARD7, STARD8, STARD9, STAT1, STAT2, STAT3, STAT4, STAT5A, STAT5B, STAT6, STATH, STAU1, STAU2, STBD1, STC1, STC2, STEAP1, STEAP1B, STEAP2, STEAP3, STEAP4, STH, STIL, STIM1, STIM2, STIP1, STK10, STK11, STK11IP, STK16, STK17A, STK17B, STK19, STK24, STK25, STK26, STK3, STK31, STK32A, STK32B, STK32C, STK33, STK35, STK36, STK38, STK38L, STK39, STK4, STK40, STKLD1, STMN1, STMN2, STMN3, STMN4, STMND1, STN1, STOM, STOML1, STOML2, STOML3, STON1, STON1-GTF2A1L, STON2, STOX1, STOX2, STPG1, STPG2, STPG3, STPG4, STRA6, STRA8, STRADA, STRADB, STRAP, STRBP, STRC, STRIP1, STRIP2, STRN, STRN3, STRN4, STS, STT3A, STT3B, STUB1, STUM, STX10, STX11, STX12, STX16, STX16-NPEPL1, STX17, STX18, STX19, STX1A, STX1B, STX2, STX3, STX4, STX5, STX6, STX7, STX8, STXBP1, STXBP2, STXBP3, STXBP4, STXBP5, STXBP5L, STXBP6, STYK1, STYX, STYXL1, SUB1, SUCLA2, SUCLG1, SUCLG2, SUCNR1, SUCO, SUDS3, SUFU, SUGCT, SUGP1, SUGP2, SUGT1, SULF1, SULF2, SULT1A1, SULT1A2, SULT1A3, SULTIA4, SULT1B1, SULT1C2, SULT1C3, SULT1C4, SULT1E1, SULT2A1, SULT2B1, SULT4A1, SULT6B1, SUMF1, SUMF2, SUMO1, SUMO2, SUMO3, SUMO4, SUN1, SUN2, SUN3, SUN5, SUOX, SUPT16H, SUPT20H, SUPT3H, SUPT4H1, SUPT5H, SUPT6H, SUPT7L, SUPV3L1, SURF1, SURF2, SURF4, SURF6, SUSD1, SUSD2, SUSD3, SUSD4, SUSD5, SUSD6, SUV39H1, SUV39H2, SUZ12, SV2A, SV2B, SV2C, SVBP, SVEP1, SVIL, SVIP, SVOP, SVOPL, SWAP70, SW15, SWSAP1, SWT1, SYAP1, SYBU, SYCE1, SYCE1L, SYCE2, SYCE3, SYCN, SYCP1, SYCP2, SYCP2L, SYCP3, SYDE1, SYDE2, SYF2, SYK, SYMPK, SYN1, SYN2, SYN3, SYNC, SYNCRIP, SYND1G1, SYND1G1L, SYNE1, SYNE2, SYNE3, SYNE4, SYNGAP1, SYNGR1, SYNGR2, SYNGR3, SYNGR4, SYNJ1, SYNJ2, SYNJ2BP, SYNJ2BP-COX16, SYNM, SYNPO, SYNPO2, SYNPO2L, SYNPR, SYNRG, SYP, SYPL1, SYPL2, SYS1, SYS1-DBNDD2, SYT1, SYT10, SYT11, SYT12, SYT13, SYT14, SYT15, SYT16, SYT17, SYT2, SYT3, SYT4, SYTS, SYT6, SYT7, SYT8, SYT9, SYTL1, SYTL2, SYTL3, SYTL4, SYTL5, SYVN1, SZRD1, SZT2, T, TAAR1, TAAR2, TAAR5, TAAR6, TAAR8, TAAR9, TAB1, TAB2, TAB3, TAC1, TAC3, TAC4, TACC1, TACC2, TACC3, TACO1, TACR1, TACR2, TACR3, TACSTD2, TADA1, TADA2A, TADA2B, TADA3, TAF1, TAF10, TAF11, TAF12, TAF13, TAF15, TAF1A, TAF1B, TAF1C, TAF1D, TAF1L, TAF2, TAF3, TAF4, TAF4B, TAF5, TAF5L, TAF6, TAF6L, TAF7, TAF7L, TAF8, TAF9, TAF9B, TAGAP, TAGLN, TAGLN2, TAGLN3, TAL1, TAL2, TALDO1, TAMM41, TANC1, TANC2, TANGO2, TANGO6, TANK, TAOK1, TAOK2, TAOK3, TAP1, TAP2, TAPBP, TAPBPL, TAPT1, TARBP1, TARBP2, TARDBP, TARM1, TARS, TARS2, TARSL2, TAS1R1, TAS1R2, TAS1R3, TAS2R1, TAS2R10, TAS2R13, TAS2R14, TAS2R16, TAS2R19, TAS2R20, TAS2R3, TAS2R30, TAS2R31, TAS2R38, TAS2R39, TAS2R4, TAS2R40, TAS2R41, TAS2R42, TAS2R43, TAS2R46, TAS2R5, TAS2R50, TAS2R60, TAS2R7, TAS2R8, TAS2R9, TASP1, TAT, TATDN1, TATDN2, TATDN3, TAX1BP1, TAX1BP3, TAZ, TBATA, TBC1D1, TBC1D10A, TBC1D10B, TBC1D10C, TBC1D12, TBC1D13, TBC1D14, TBC1D15, TBC1D16, TBC1D17, TBC1D19, TBC1D2, TBC1D20, TBC1D21, TBC1D22A, TBC1D22B, TBC1D23, TBC1D24, TBC1D25, TBC1D26, TBC1D28, TBC1D29, TBC1D2B, TBC1D3, TBC1D30, TBC1D31, TBC1D32, TBC1D3B, TBC1D3C, TBC1D3D, TBC1D3E, TBC1D3F, TBC1D3G, TBC1D3H, TBC1D3I, TBC1D3K, TBC1D3L, TBC1D4, TBC1D5, TBC1D7, TBC1D8, TBC1D8B, TBC1D9, TBC1D9B, TBCA, TBCB, TBCC, TBCCD1, TBCD, TBCE, TBCEL, TBCK, TBK1, TBKBP1, TBL1X, TBL1XR1, TBL1Y, TBL2, TBL3, TBP, TBPL1, TBPL2, TBR1, TBRG1, TBRG4, TBX1, TBX10, TBX15, TBX18, TBX19, TBX2, TBX20, TBX21, TBX22, TBX3, TBX4, TBX5, TBX6, TBXA2R, TBXAS1, TC2N, TCAF1, TCAF2, TCAIM, TCAP, TCEA1, TCEA2, TCEA3, TCEAL1, TCEAL2, TCEAL3, TCEAL4, TCEAL5, TCEAL6, TCEAL7, TCEAL8, TCEAL9, TCEANC, TCEANC2, TCERG1, TCERG1L, TCF12, TCF15, TCF19, TCF20, TCF21, TCF23, TCF24, TCF25, TCF3, TCF4, TCF7, TCF7L1, TCF7L2, TCFL5, TCHH, TCHHL1, TCHP, TCIRG1, TCL1A, TCL1B, TCN1, TCN2, TCOF1, TCP1, TCP10, TCP10L, TCP10L2, TCP11, TCP11L1, TCP11L2, TCP11X2, TCTA, TCTE1, TCTE3, TCTEX1D1, TCTEX1D2, TCTEX1D4, TCTN1, TCTN2, TCTN3, TDG, TDGF1, TDO2, TDP1, TDP2, TDRD1, TDRD10, TDRD12, TDRD15, TDRD3, TDRD5, TDRD6, TDRD7, TDRD9, TDRKH, TDRP, TEAD1, TEAD2, TEAD3, TEAD4, TEC, TECPR1, TECPR2, TECR, TECRL, TECTA, TECTB, TEDDM1, TEF, TEFM, TEK, TEKT1, TEKT2, TEKT3, TEKT4, TEKT5, TELO2, TEN1, TEN1-CDK3, TENM1, TENM2, TENM3, TENM4, TEP1, TEPP, TEPSIN, TERB1, TERB2, TERF1, TERF2, TERF2IP, TERT, TES, TESC, TESK1, TESK2, TESMIN, TESPA1, TET1, TET2, TET3, TEX10, TEX101, TEXI1, TEX12, TEX13A, TEX13B, TEX13C, TEX13D, TEX14, TEX15, TEX19, TEX2, TEX22, TEX26, TEX261, TEX264, TEX28, TEX29, TEX30, TEX33, TEX35, TEX36, TEX37, TEX38, TEX43, TEX44, TEX45, TEX46, TEX47, TEX48, TEX49, TEX50, TEX51, TEX9, TF, TFAM, TFAP2A, TFAP2B, TFAP2C, TFAP2D, TFAP2E, TFAP4, TFB1M, TFB2M, TFCP2, TFCP2L1, TFDP1, TFDP2, TFDP3, TFE3, TFEB, TFEC, TFF1, TFF2, TFF3, TFG, TFIP11, TFP1, TFPI2, TFPT, TFR2, TFRC, TG, TGDS, TGFA, TGFB1, TGFB1I1, TGFB2, TGFB3, TGFB1, TGFBR1, TGFBR2, TGFBR3, TGFBR3L, TGFBRAP1, TGIF1, TGIF2, TGIF2-C20orf24, TGIF2LX, TGIF2LY, TGM1, TGM2, TGM3, TGM4, TGM5, TGM6, TGM7, TGOLN2, TGS1, TH, THADA, THAP1, THAP10, THAP11, THAP12, THAP2, THAP3, THAP4, THAP5, THAP6, THAP7, THAP8, THAP9, THBD, THBS1, THBS2, THBS3, THBS4, THEG, THEGL, THEM4, THEM5, THEM6, THEMIS, THEMIS2, THG1L, THNSL1, THNSL2, THOC1, THOC2, THOC3, THOC5, THOC6, THOC7, THOP1, THPO, THRA, THRAP3, THRB, THRSP, THSD1, THSD4, THSD7A, THSD7B, THTPA, THUMPD1, THUMPD2, THUMPD3, THY1, THYN1, TIA1, TIAF1, TIAL1, TIAM1, TIAM2, TICAM1, TICAM2, TICRR, TIE1, TIFA, TIFAB, TIGAR, TIGD1, TIGD2, TIGD3, TIGD4, TIGD5, TIGD6, TIGD7, TIGIT, TIMD4, TIMELESS, TIMM10, TIMM10B, TIMM13, TIMM17A, TIMM17B, TIMM21, TIMM22, TIMM23, TIMM23B, TIMM29, TIMM44, TIMM50, TIMM8A, TIMM8B, TIMM9, TIMMDC1, TIMP1, TIMP2, TIMP3, TIMP4, TINAG, TINAGL1, TINCR, TINF2, TIPARP, TIPIN, TIPRL, TIRAP, TISP43, TJAP1, TJP1, TJP2, TJP3, TK1, TK2, TKFC, TKT, TKTL1, TKTL2, TLCD1, TLCD2, TLDC1, TLDC2, TLE1, TLE2, TLE3, TLE4, TLE6, TLK1, TLK2, TLL1, TLL2, TLN1, TLN2, TLNRD1, TLR1, TLR10, TLR2, TLR3, TLR4, TLR5, TLR6, TLR7, TLR8, TLR9, TLX1, TLX2, TLX3, TM2D1, TM2D2, TM2D3, TM4SF1, TM4SF18, TM4SF19, TM4SF19-TCTEX1D2, TM4SF20, TM4SF4, TM4SF5, TM6SF1, TM6SF2, TM7SF2, TM7SF3, TM9SF1, TM9SF2, TM9SF3, TM9SF4, TMA16, TMA7, TMBIM1, TMBIM4, TMBIM6, TMC1, TMC2, TMC3, TMC4, TMC5, TMC6, TMC7, TMC8, TMCC1, TMCC2, TMCC3, TMCO1, TMCO2, TMCO3, TMCO4, TMCO5A, TMCO6, TMED1, TMED10, TMED2, TMED3, TMED4, TMED5, TMED6, TMED7, TMED7-TICAM2, TMED8, TMED9, TMEFF1, TMEFF2, TMEM100, TMEM101, TMEM102, TMEM104, TMEM105, TMEM106A, TMEM106B, TMEM106C, TMEM107, TMEM108, TMEM109, TMEM11, TMEM110, TMEM110-MUSTN1, TMEM114, TMEM115, TMEM116, TMEM117, TMEM119, TMEM120A, TMEM120B, TMEM121, TMEM121B, TMEM123, TMEM125, TMEM126A, TMEM126B, TMEM127, TMEM128, TMEM129, TMEM130, TMEM131, TMEM131L, TMEM132A, TMEM132B, TMEM132C, TMEM132D, TMEM132E, TMEM133, TMEM134, TMEM135, TMEM136, TMEM138, TMEM139, TMEM140, TMEM141, TMEM143, TMEM144, TMEM145, TMEM147, TMEM14A, TMEM14B, TMEM14C, TMEM150A, TMEM150B, TMEM150C, TMEM151A, TMEM151B, TMEM154, TMEM155, TMEM156, TMEM158, TMEM159, TMEM160, TMEM161A, TMEM161B, TMEM163, TMEM164, TMEM165, TMEM167A, TMEM167B, TMEM168, TMEM169, TMEM17, TMEM170A, TMEM170B, TMEM171, TMEM173, TMEM174, TMEM175, TMEM176A, TMEM176B, TMEM177, TMEM178A, TMEM178B, TMEM179, TMEM179B, TMEM18, TMEM181, TMEM182, TMEM183A, TMEM184A, TMEM184B, TMEM184C, TMEM185A, TMEM185B, TMEM186, TMEM187, TMEM189, TMEM189-UBE2V1, TMEM19, TMEM190, TMEM191B, TMEM191C, TMEM192, TMEM196, TMEM198, TMEM199, TMEM2, TMEM200A, TMEM200B, TMEM200C, TMEM201, TMEM202, TMEM203, TMEM204, TMEM205, TMEM206, TMEM207, TMEM208, TMEM209, TMEM210, TMEM211, TMEM212, TMEM213, TMEM214, TMEM215, TMEM216, TMEM217, TMEM218, TMEM219, TMEM220, TMEM221, TMEM222, TMEM223, TMEM225, TMEM225B, TMEM229A, TMEM229B, TMEM230, TMEM231, TMEM232, TMEM233, TMEM234, TMEM235, TMEM236, TMEM237, TMEM238, TMEM239, TMEM240, TMEM241, TMEM242, TMEM243, TMEM244, TMEM245, TMEM246, TMEM247, TMEM248, TMEM249, TMEM25, TMEM250, TMEM251, TMEM252, TMEM253, TMEM254, TMEM255A, TMEM255B, TMEM256, TMEM256-PLSCR3, TMEM257, TMEM258, TMEM259, TMEM26, TMEM260, TMEM262, TMEM263, TMEM265, TMEM266, TMEM267, TMEM268, TMEM269, TMEM27, TMEM270, TMEM30A, TMEM30B, TMEM31, TMEM33, TMEM35A, TMEM35B, TMEM37, TMEM38A, TMEM38B, TMEM39A, TMEM39B, TMEM40, TMEM41A, TMEM41B, TMEM42, TMEM43, TMEM44, TMEM45A, TMEM45B, TMEM47, TMEM5, TMEM50A, TMEM50B, TMEM51, TMEM52, TMEM52B, TMEM53, TMEM54, TMEM55A, TMEM55B, TMEM56, TMEM56-RWDD3, TMEM57, TMEM59, TMEM59L, TMEM60, TMEM61, TMEM62, TMEM63A, TMEM63B, TMEM63C, TMEM64, TMEM65, TMEM67, TMEM68, TMEM69, TMEM70, TMEM71, TMEM72, TMEM74, TMEM74B, TMEM78, TMEM79, TMEM80, TMEM81, TMEM82, TMEM86A, TMEM86B, TMEM87A, TMEM87B, TMEM88, TMEM88B, TMEM89, TMEM8A, TMEM8B, TMEM9, TMEM91, TMEM92, TMEM94, TMEM95, TMEM97, TMEM98, TMEM99, TMEM9B, TMF1, TMIE, TMIGD1, TMIGD2, TMIGD3, TMLHE, TMOD1, TMOD2, TMOD3, TMOD4, TMPO, TMPPE, TMPRSS11A, TMPRSS11B, TMPRSS11D, TMPRSS11E, TMPRSS11F, TMPRSS12, TMPRSS13, TMPRSS15, TMPRSS2, TMPRSS3, TMPRSS4, TMPRSS4-AS1, TMPRSS5, TMPRSS6, TMPRSS7, TMPRSS9, TMSB10, TMSB15A, TMSB15B, TMSB4X, TMSB4Y, TMTC1, TMTC2, TMTC3, TMTC4, TMUB1, TMUB2, TMX1, TMX2, TMX2-CTNND1, TMX3, TMX4, TNC, TNF, TNFAIP1, TNFAIP2, TNFAIP3, TNFAIP6, TNFAIP8, TNFAIP8L1, TNFAIP8L2, TNFAIP8L3, TNFRSF1GA, TNFRSF10B, TNFRSF10C, TNFRSF10D, TNFRSF11A, TNFRSF11B, TNFRSF12A, TNFRSF13B, TNFRSF13C, TNFRSF14, TNFRSF17, TNFRSF18, TNFRSF19, TNFRSF1A, TNFRSF1B, TNFRSF21, TNFRSF25, TNFRSF4, TNFRSF6B, TNFRSF8, TNFRSF9, TNFSF10, TNFSF11, TNFSF12, TNFSF12-TNFSF13, TNFSF13, TNFSF13B, TNFSF14, TNFSF15, TNFSF18, TNFSF4, TNFSF8, TNFSF9, TNIK, TNIP1, TNIP2, TNIP3, TNK1, TNK2, TNKS, TNKS1BP1, TNKS2, TNMD, TNN, TNNC1, TNNC2, TNNI1, TNNI2, TNNI3, TNNI3K, TNNT1, TNNT2, TNNT3, TNP1, TNP2, TNPO1, TNPO2, TNPO3, TNR, TNRC18, TNRC6A, TNRC6B, TNRC6C, TNS1, TNS2, TNS3, TNS4, TNXB, TOB1, TOB2, TOE1, TOGARAM1, TOGARAM2, TOLLIP, TOM1, TOM1L1, TOM1L2, TOMM20, TOMM20L, TOMM22, TOMM34, TOMM40, TOMM40L, TOMM5, TOMM6, TOMM7, TOMM70, TONSL, TOP1, TOP1MT, TOP2A, TOP2B, TOP3A, TOP3B, TOPAZ1, TOPBP1, TOPORS, TOR1A, TOR1AIP1, TOR1AIP2, TOR1B, TOR2A, TOR3A, TOR4A, TOX, TOX2, TOX3, TOX4, TP53, TP53AIP1, TP53BP1, TP53BP2, TP53I11, TP53I13, TP53I3, TP53INP1, TP53INP2, TP53RK, TP53TG3, TP53TG3B, TP53TG3C, TP53TG3D, TP53TG3E, TP53TG3F, TP53TG5, TP63, TP73, TPBG, TPBGL, TPCN1, TPCN2, TPD52, TPD52L1, TPD52L2, TPD52L3, TPGS1, TPGS2, TPH1, TPH2, TPI1, TPK1, TPM1, TPM2, TPM3, TPM4, TPMT, TPO, TPP1, TPP2, TPPP, TPPP2, TPPP3, TPR, TPRA1, TPRG1, TPRG1L, TPRKB, TPRN, TPRX1, TPSAB1, TPSB2, TPSD1, TPSG1, TPST1, TPST2, TPT1, TPTE, TPTE2, TPX2, TRA2A, TRA2B, TRABD, TRABD2A, TRABD2B, TRAC, TRADD, TRAF1, TRAF2, TRAF3, TRAF3IP1, TRAF3IP2, TRAF3IP3, TRAF4, TRAF5, TRAF6, TRAF7, TRAFD1, TRAIP, TRAJ1, TRAJ10, TRAJ11, TRAJ12, TRAJ13, TRAJ14, TRAJ16, TRAJ17, TRAJ18, TRAJ19, TRAJ2, TRAJ20, TRAJ21, TRAJ22, TRAJ23, TRAJ24, TRAJ25, TRAJ26, TRAJ27, TRAJ28, TRAJ29, TRAJ3, TRAJ30, TRAJ31, TRAJ32, TRAJ33, TRAJ34, TRAJ35, TRAJ36, TRAJ37, TRAJ38, TRAJ39, TRAJ4, TRAJ40, TRAJ41, TRAJ42, TRAJ43, TRAJ44, TRAJ45, TRAJ46, TRAJ47, TRAJ48, TRAJ49, TRAJ5, TRAJ50, TRAJ52, TRAJ53, TRAJ54, TRAJ56, TRAJ57, TRAJ58, TRAJ59, TRAJ6, TRAJ61, TRAJ7, TRAJ9, TRAK1, TRAK2, TRAM1, TRAM1L1, TRAM2, TRANK1, TRAP1, TRAPPC1, TRAPPC10, TRAPPC11, TRAPPC12, TRAPPC13, TRAPPC2, TRAPPC2L, TRAPPC3, TRAPPC3L, TRAPPC4, TRAPPC5, TRAPPC6A, TRAPPC6B, TRAPPC8, TRAPPC9, TRAT1, TRAV10, TRAV1-1, TRAV1-2, TRAV12-1, TRAV12-2, TRAV12-3, TRAV13-1, TRAV13-2, TRAV14DV4, TRAV16, TRAV17, TRAV18, TRAV19, TRAV2, TRAV20, TRAV21, TRAV22, TRAV23DV6, TRAV24, TRAV25, TRAV26-1, TRAV26-2, TRAV27, TRAV29DV5, TRAV3, TRAV30, TRAV34, TRAV36DV7, TRAV38-1, TRAV38-2DV8, TRAV39, TRAV4, TRAV40, TRAV41, TRAV5, TRAV6, TRAV7, TRAV8-1, TRAV8-2, TRAV8-3, TRAV8-4, TRAV8-6, TRAV8-7, TRAV9-1, TRAV9-2, TRBC2, TRBJ2-1, TRBJ2-2, TRBJ2-2P, TRBJ2-3, TRBJ2-4, TRBJ2-5, TRBJ2-6, TRBJ2-7, TRBV10-1, TRBV10-2, TRBV10-3, TRBV11-1, TRBV19, TRBV2, TRBV20-1, TRBV20OR9-2, TRBV21OR9-2, TRBV23-1, TRBV23OR9-2, TRBV24-1, TRBV25-1, TRBV27, TRBV28, TRBV29-1, TRBV30, TRBV3-1, TRBV4-1, TRBV4-2, TRBV5-1, TRBV5-3, TRBV5-4, TRBV5-5, TRBV5-6, TRBV5-7, TRBV6-1, TRBV6-4, TRBV6-5, TRBV6-6, TRBV6-7, TRBV6-8, TRBV7-1, TRBV7-3, TRBV7-4, TRBV7-6, TRBV7-7, TRBV7-9, TRBV9, TRDC, TRDD1, TRDD2, TRDD3, TRDJ1, TRDJ2, TRDJ3, TRDJ4, TRDMT1, TRDN, TRDV1, TRDV2, TRDV3, TREH, TREM1, TREM2, TREML1, TREML2, TREML4, TRERF1, TREX1, TREX2, TRGC1, TRGC2, TRGJ1, TRGJ2, TRGJP, TRGJP1, TRGJP2, TRGV1, TRGV10, TRGV11, TRGV2, TRGV3, TRGV4, TRGV5, TRGV8, TRGV9, TRH, TRHDE, TRHR, TRIAP1, TRIB1, TRIB2, TRIB3, TRIL, TRIM10, TRIM11, TRIM13, TRIM14, TRIM15, TRIM16, TRIM16L, TRIM17, TRIM2, TRIM21, TRIM22, TRIM23, TRIM24, TRIM25, TRIM26, TRIM27, TRIM28, TRIM29, TRIM3, TRIM31, TRIM32, TRIM33, TRIM34, TRIM35, TRIM36, TRIM37, TRIM38, TRIM39, TRIM39-RPP21, TRIM4, TRIM40, TRIM41, TRIM42, TRIM43, TRIM43B, TRIM44, TRIM45, TRIM46, TRIM47, TRIM48, TRIM49, TRIM49B, TRIM49C, TRIM49D1, TRIM49D2, TRIM5, TRIM50, TRIM51, TRIM52, TRIM54, TRIM55, TRIM56, TRIM58, TRIM59, TRIM6, TRIM60, TRIM61, TRIM62, TRIM63, TRIM64, TRIM64B, TRIM64C, TRIM65, TRIM66, TRIM67, TRIM68, TRIM69, TRIM6-TRIM34, TRIM7, TRIM71, TRIM72, TRIM73, TRIM74, TRIM75P, TRIM77, TRIM8, TRIM9, TRIML1, TRIML2, TRIO, TRIOBP, TRIP10, TRIP11, TRIP12, TRIP13, TRIP4, TRIP6, TRIQK, TRIR, TRIT1, TRMO, TRMT1, TRMT10A, TRMT10B, TRMT10C, TRMT11, TRMT112, TRMT12, TRMT13, TRMT1L, TRMT2A, TRMT2B, TRMT44, TRMT5, TRMT6, TRMT61A, TRMT61B, TRMU, TRNAU1AP, TRNP1, TRNT1, TRO, TROAP, TROVE2, TRPA1, TRPC1, TRPC3, TRPC4, TRPC4AP, TRPC5, TRPC5OS, TRPC6, TRPC7, TRPM1, TRPM2, TRPM3, TRPM4, TRPM5, TRPM6, TRPM7, TRPM8, TRPS1, TRPT1, TRPV1, TRPV2, TRPV3, TRPV4, TRPV5, TRPV6, TRRAP, TRUB1, TRUB2, TSACC, TSC1, TSC2, TSC22D1, TSC22D2, TSC22D3, TSC22D4, TSEN15, TSEN2, TSEN34, TSEN54, TSFM, TSG101, TSGA10, TSGA10IP, TSGA13, TSHB, TSHR, TSHZ1, TSHZ2, TSHZ3, TSKS, TSKU, TSLP, TSN, TSNARE1, TSNAX, TSNAX-DISC1, TSNAXIP1, TSPAN1, TSPAN10, TSPAN11, TSPAN12, TSPAN13, TSPAN14, TSPAN15, TSPAN16, TSPAN17, TSPAN18, TSPAN19, TSPAN2, TSPAN3, TSPAN31, TSPAN32, TSPAN33, TSPAN4, TSPAN5, TSPAN6, TSPAN7, TSPAN8, TSPAN9, TSPEAR, TSPO, TSPO2, TSPOAP1, TSPY1, TSPY10, TSPY2, TSPY3, TSPY4, TSPY8, TSPYL1, TSPYL2, TSPYL4, TSPYL5, TSPYL6, TSR1, TSR2, TSR3, TSSC4, TSSKIB, TSSK2, TSSK3, TSSK4, TSSK6, TST, TSTA3, TSTD1, TSTD2, TSTD3, TTBK1, TTBK2, TTC1, TTC12, TTC13, TTC14, TTC16, TTC17, TTC19, TTC21A, TTC21B, TTC22, TTC23, TTC23L, TTC24, TTC25, TTC26, TTC27, TTC28, TTC29, TTC3, TTC30A, TTC30B, TTC31, TTC32, TTC33, TTC34, TTC36, TTC37, TTC38, TTC39A, TTC39B, TTC39C, TTC4, TTC5, TTC6, TTC7A, TTC7B, TTC8, TTC9, TTC9B, TTC9C, TTF1, TTF2, TTI1, TTI2, TTK, TTL, TTLL1, TTLL10, TTLL11, TTLL12, TTLL13P, TTLL2, TTLL3, TTLL4, TTLL5, TTLL6, TTLL7, TTLL8, TTLL9, TTN, TTPA, TTPAL, TTR, TTYH1, TTYH2, TTYH3, TUB, TUBA1A, TUBA1B, TUBA1C, TUBA3C, TUBA3D, TUBA3E, TUBA4A, TUBA4B, TUBA8, TUBAL3, TUBB, TUBB1, TUBB2A, TUBB2B, TUBB3, TUBB4A, TUBB4B, TUBB6, TUBB8, TUBD1, TUBE1, TUBG1, TUBG2, TUBGCP2, TUBGCP3, TUBGCP4, TUBGCP5, TUBGCP6, TUFM, TUFT1, TULP1, TULP2, TULP3, TULP4, TUNAR, TUSC1, TUSC2, TUSC3, TUSC5, TUT1, TVP23A, TVP23B, TVP23C, TVP23C-CDRT4, TWF1, TWF2, TWIST1, TWIST2, TWISTNB, TWNK, TWSG1, TXK, TXLNA, TXLNB, TXLNG, TXN, TXN2, TXNDC11, TXNDC12, TXNDC15, TXNDC16, TXNDC17, TXNDC2, TXNDC5, TXNDC8, TXNDC9, TXNIP, TXNL1, TXNL4A, TXNL4B, TXNRD1, TXNRD2, TXNRD3, TXNRD3NB, TYK2, TYMP, TYMS, TYR, TYRO3, TYROBP, TYRP1, TYSND1, TYW1, TYW1B, TYW3, TYW5, U2AF1, U2AF1L4, U2AF1L5, U2AF2, U2SURP, UACA, UAP1, UAP1L1, UBA1, UBA2, UBA3, UBA5, UBA52, UBA6, UBA7, UBAC1, UBAC2, UBALD1, UBALD2, UBAP1, UBAP1L, UBAP2, UBAP2L, UBASH3A, UBASH3B, UBB, UBC, UBD, UBE2A, UBE2B, UBE2C, UBE2D1, UBE2D2, UBE2D3, UBE2D4, UBE2E1, UBE2E2, UBE2E3, UBE2F, UBE2F-SCLY, UBE2G1, UBE2G2, UBE2H, UBE2I, UBE2J1, UBE2J2, UBE2K, UBE2L3, UBE2L5P, UBE2L6, UBE2M, UBE2N, UBE2NL, UBE20, UBE2Q1, UBE2Q2, UBE2Q2L, UBE2QL1, UBE2R2, UBE2S, UBE2T, UBE2U, UBE2V1, UBE2V2, UBE2W, UBE2Z, UBE3A, UBE3B, UBE3C, UBE3D, UBE4A, UBE4B, UBFD1, UBIAD1, UBL3, UBL4A, UBL4B, UBL5, UBL7, UBLCP1, UBN1, UBN2, UBOX5, UBP1, UBQLN1, UBQLN2, UBQLN3, UBQLN4, UBQLNL, UBR1, UBR2, UBR3, UBR4, UBR5, UBR7, UBTD1, UBTD2, UBTF, UBTFL1, UBXN1, UBXN10, UBXN11, UBXN2A, UBXN2B, UBXN4, UBXN6, UBXN7, UBXN8, UCHL1, UCHL3, UCHL5, UCK1, UCK2, UCKL1, UCMA, UCN, UCN2, UCN3, UCP1, UCP2, UCP3, UEVLD, UFC1, UFD1, UFL1, UFM1, UFSP1, UFSP2, UGCG, UGDH, UGGT1, UGGT2, UGP2, UGT1A1, UGT1A10, UGT1A3, UGT1A4, UGT1A5, UGT1A6, UGT1A7, UGT1A8, UGT1A9, UGT2A1, UGT2A2, UGT2A3, UGT2B10, UGT2B11, UGT2B15, UGT2B17, UGT2B28, UGT2B4, UGT2B7, UGT3A1, UGT3A2, UGT8, UHMK1, UHRF1, UHRF1BP1, UHRF1BP1L, UHRF2, UIMC1, ULBP1, ULBP2, ULBP3, ULK1, ULK2, ULK3, ULK4, UMAD1, UMOD, UMODL1, UMPS, UNC119, UNC119B, UNC13A, UNC13B, UNC13C, UNC13D, UNC45A, UNC45B, UNC50, UNC5A, UNC5B, UNC5C, UNC5CL, UNC5D, UNC79, UNC80, UNC93A, UNC93B1, UNCX, UNG, UNK, UNKL, UPB1, UPF1, UPF2, UPF3A, UPF3B, UPK1A, UPK1B, UPK2, UPK3A, UPK3B, UPK3BL1, UPP1, UPP2, UPRT, UQCC1, UQCC2, UQCC3, UQCR10, UQCR11, UQCRB, UQCRC1, UQCRC2, UQCRFS1, UQCRH, UQCRHL, UQCRQ, URAD, URB1, URB2, URGCP, URGCP-MRPS24, URI1, URM1, UROC1, UROD, UROS, USB1, USE1, USF1, USF2, USF3, USH1C, USH1G, USH2A, USHBP1, USMG5, USO1, USP1, USP10, USP11, USP12, USP13, USP14, USP15, USP16, USP17L1, USP17L10, USP17L11, USP17L12, USP17L13, USP17L15, USP17L17, USP17L18, USP17L19, USP17L2, USP17L20, USP17L21, USP17L22, USP17L23, USP17L24, USP17L25, USP17L26, USP17L27, USP17L28, USP17L29, USP17L3, USP17L30, USP17L4, USP17L5, USP17L7, USP17L8, USP18, USP19, USP2, USP20, USP21, USP22, USP24, USP25, USP26, USP27X, USP28, USP29, USP3, USP30, USP31, USP32, USP33, USP34, USP35, USP36, USP37, USP38, USP39, USP4, USP40, USP41, USP42, USP43, USP44, USP45, USP46, USP47, USP48, USP49, USP5, USP50, USP51, USP53, USP54, USP6, USP6NL, USP7, USP8, USP9X, USP9Y, USPL1, UST, UTF1, UTP11, UTP14A, UTP14C, UTP15, UTP18, UTP20, UTP23, UTP3, UTP4, UTP6, UTRN, UTS2, UTS2B, UTS2R, UTY, UVRAG, UVSSA, UXS1, UXT, VAC14, VAMP1, VAMP2, VAMP3, VAMP4, VAMP5, VAMP7, VAMP8, VANGL1, VANGL2, VAPA, VAPB, VARS, VARS2, VASH1, VASH2, VASN, VASP, VAT1, VAT1L, VAV1, VAV2, VAV3, VAX1, VAX2, VBP1, VCAM1, VCAN, VCL, VCP, VCPIP1, VCPKMT, VCX, VCX2, VCX3A, VCX3B, VCY, VCY1B, VDAC1, VDAC2, VDAC3, VDR, VEGFA, VEGFB, VEGFC, VEGFD, VENTX, VEPH1, VEZF1, VEZT, VGF, VGLL1, VGLL2, VGLL3, VGLL4, VHL, VHLL, VIL1, VILL, VIM, VIP, VIPAS39, VIPR1, VIPR2, VIRMA, VIT, VKORC1, VKORC1L1, VLDLR, VMA21, VMAC, VMO1, VMP1, VN1R1, VN1R2, VN1R4, VN1R5, VNN1, VNN2, VNN3, VOPP1, VPREB1, VPREB3, VPS11, VPS13A, VPS13B, VPS13C, VPS13D, VPS16, VPS18, VPS25, VPS26A, VPS26B, VPS28, VPS29, VPS33A, VPS33B, VPS35, VPS36, VPS37A, VPS37B, VPS37C, VPS37D, VPS39, VPS41, VPS45, VPS4A, VPS4B, VPS50, VPS51, VPS52, VPS53, VPS54, VPS72, VPS8, VPS9D1, VRK1, VRK2, VRK3, VRTN, VSIG1, VSIG10, VSIG10L, VSIG10L2, VSIG2, VSIG4, VSIG8, VSIR, VSNL1, VSTM1, VSTM2A, VSTM2B, VSTM2L, VSTM4, VSTM5, VSX1, VSX2, VTA1, VTCN1, VTI1A, VTI1B, VTN, VWA1, VWA2, VWA3A, VWA3B, VWA5A, VWA5B1, VWA5B2, VWA7, VWA8, VWC2, VWC2L, VWCE, VWDE, VWF, WAC, WAPL, WARS, WARS2, WAS, WASF1, WASF2, WASF3, WASHC1, WASHC2A, WASHC2C, WASHC3, WASHC4, WASHC5, WASL, WBP1, WBP11, WBPIL, WBP2, WBP2NL, WBP4, WDCP, WDFY1, WDFY2, WDFY3, WDFY4, WDHD1, WDPCP, WDR1, WDR11, WDR12, WDR13, WDR17, WDR18, WDR19, WDR20, WDR24, WDR25, WDR26, WDR27, WDR3, WDR31, WDR33, WDR34, WDR35, WDR36, WDR37, WDR38, WDR4, WDR41, WDR43, WDR44, WDR45, WDR45B, WDR46, WDR47, WDR48, WDR49, WDR5, WDR53, WDR54, WDR55, WDR59, WDR5B, WDR6, WDR60, WDR61, WDR62, WDR63, WDR64, WDR66, WDR7, WDR70, WDR72, WDR73, WDR74, WDR75, WDR76, WDR77, WDR78, WDR81, WDR82, WDR83, WDR83OS, WDR86, WDR87, WDR88, WDR89, WDR90, WDR91, WDR92, WDR93, WDR97, WDSUB1, WDTC1, WDYHV1, WEE1, WEE2, WFDC1, WFDC10A, WFD-COB, WFDC11, WFDC12, WFDC13, WFDC2, WFDC3, WFDC5, WFDC6, WFDC8, WFDC9, WF1KKN1, WF1KKN2, WFS1, WHAMM, WHRN, WIF1, WIPF1, WIPF2, WIPF3, WIPI1, WIPI2, WISP1, WISP2, WISP3, WIZ, WLS, WNK1, WNK2, WNK3, WNK4, WNT1, WNT10A, WNT10B, WNT11, WNT16, WNT2, WNT2B, WNT3, WNT3A, WNT4, WNT5A, WNT5B, WNT6, WNT7A, WNT7B, WNT8A, WNT8B, WNT9A, WNT9B, WRAP53, WRAP73, WRB, WRN, WRNIP1, WSB1, WSB2, WSCD1, WSCD2, WT1, WTAP, WTH3DI, WTIP, WWC1, WWC2, WWC3, WWOX, WWP1, WWP2, WWTR1, XAB2, XAF1, XAGE1A, XAGE1B, XAGE2, XAGE3, XAGE5, XBP1, XCL1, XCL2, XCR1, XDH, XG, XIAP, XIRP1, XIRP2, XK, XKR3, XKR4, XKR5, XKR6, XKR7, XKR8, XKR9, XKRX, XPA, XPC, XPNPEP1, XPNPEP2, XPNPEP3, XPO1, XPO4, XPO5, XPO6, XPO7, XPOT, XPR1, XRCC1, XRCC2, XRCC3, XRCC4, XRCC5, XRCC6, XRN1, XRN2, XRRA1, XXYLT1, XYLB, XYLT1, XYLT2, YAE1D1, YAF2, YAP1, YARS, YARS2, YBEY, YBX1, YBX2, YBX3, YDJC, YEATS2, YEATS4, YES1, YIF1A, YIF1B, YIPF1, YIPF2, YIPF3, YIPF4, YIPF5, YIPF6, YIPF7, YJEFN3, YKT6, YLPM1, YME1L1, YOD1, YPEL1, YPEL2, YPEL3, YPEL4, YPEL5, YRDC, YTHDC1, YTHDC2, YTHDF1, YTHDF2, YTHDF3, YWHAB, YWHAE, YWHAG, YWHAH, YWHAQ, YWHAZ, YY1, YY1AP1, YY2, Z82206.1, Z83844.1, Z84492.1, Z98749.3, Z98752.3, ZACN, ZADH2, ZAN, ZAP70, ZAR1, ZAR1L, ZBBX, ZBED1, ZBED2, ZBED3, ZBED4, ZBED5, ZBED6, ZBED6CL, ZBED8, ZBED9, ZBP1, ZBTB1, ZBTB10, ZBTB11, ZBTB12, ZBTB14, ZBTB16, ZBTB17, ZBTB18, ZBTB2, ZBTB20, ZBTB21, ZBTB22, ZBTB24, ZBTB25, ZBTB26, ZBTB3, ZBTB32, ZBTB33, ZBTB34, ZBTB37, ZBTB38, ZBTB39, ZBTB4, ZBTB40, ZBTB41, ZBTB42, ZBTB43, ZBTB44, ZBTB45, ZBTB46, ZBTB47, ZBTB48, ZBTB49, ZBTB5, ZBTB6, ZBTB7A, ZBTB7B, ZBTB7C, ZBTB8A, ZBTB8B, ZBTB8OS, ZBTB9, ZC2HC1A, ZC2HC1B, ZC2HC1C, ZC3H10, ZC3H11A, ZC3H11B, ZC3H12A, ZC3H12B, ZC3H12C, ZC3H12D, ZC3H13, ZC3H14, ZC3H15, ZC3H18, ZC3H3, ZC3H4, ZC3H6, ZC3H7A, ZC3H7B, ZC3H8, ZC3HAV1, ZC3HAV1L, ZC3HC1, ZC4H2, ZCCHC10, ZCCHC11, ZCCHC12, ZCCHC13, ZCCHC14, ZCCHC17, ZCCHC18, ZCCHC2, ZCCHC24, ZCCHC3, ZCCHC4, ZCCHC6, ZCCHC7, ZCCHC8, ZCCHC9, ZCRB1, ZCWPW1, ZCWPW2, ZDBF2, ZDHHC1, ZDHHC11, ZDHHC11B, ZDHHC12, ZDHHC13, ZDHHC14, ZDHHC15, ZDHHC16, ZDHHC17, ZDHHC18, ZDHHC19, ZDHHC2, ZDHHC20, ZDHHC21, ZDHHC22, ZDHHC23, ZDHHC24, ZDHHC3, ZDHHC4, ZDHHC5, ZDHHC6, ZDHHC7, ZDHHC8, ZDHHC9, ZEB1, ZEB2, ZER1, ZFAND1, ZFAND2A, ZFAND2B, ZFAND3, ZFAND4, ZFAND5, ZFAND6, ZFAT, ZFC3H1, ZFHX2, ZFHX3, ZFHX4, ZFP1, ZFP14, ZFP2, ZFP28, ZFP3, ZFP30, ZFP36, ZFP36L1, ZFP36L2, ZFP37, ZFP41, ZFP42, ZFP57, ZFP62, ZFP64, ZFP69, ZFP69B, ZFP82, ZFP90, ZFP91, ZFP91-CNTF, ZFP92, ZFPL1, ZFPM1, ZFPM2, ZFR, ZFR2, ZFX, ZFY, ZFYVE1, ZFYVE16, ZFYVE19, ZFYVE21, ZFYVE26, ZFYVE27, ZFYVE28, ZFYVE9, ZG16, ZG16B, ZGLP1, ZGPAT, ZGRF1, ZHX1, ZHX1-C8orf76, ZHX2, ZHX3, ZIC1, ZIC2, ZIC3, ZIC4, ZIC5, ZIK1, ZIM2, ZIM3, ZKSCAN1, ZKSCAN2, ZKSCAN3, ZKSCAN4, ZKSCAN5, ZKSCAN7, ZKSCAN8, ZMAT1, ZMAT2, ZMAT3, ZMAT4, ZMAT5, ZMIZ1, ZMIZ2, ZMPSTE24, ZMYM1, ZMYM2, ZMYM3, ZMYM4, ZMYM5, ZMYM6, ZMYND10, ZMYND11, ZMYND12, ZMYND15, ZMYND19, ZMYND8, ZNF10, ZNF100, ZNF101, ZNF106, ZNF107, ZNF112, ZNF114, ZNF117, ZNF12, ZNF121, ZNF124, ZNF131, ZNF132, ZNF133, ZNF134, ZNF135, ZNF136, ZNF138, ZNF14, ZNF140, ZNF141, ZNF142, ZNF143, ZNF146, ZNF148, ZNF154, ZNF155, ZNF157, ZNF16, ZNF160, ZNF165, ZNF169, ZNF17, ZNF174, ZNF175, ZNF177, ZNF18, ZNF180, ZNF181, ZNF182, ZNF184, ZNF185, ZNF189, ZNF19, ZNF195, ZNF197, ZNF2, ZNF20, ZNF200, ZNF202, ZNF205, ZNF207, ZNF208, ZNF211, ZNF212, ZNF213, ZNF214, ZNF215, ZNF217, ZNF219, ZNF22, ZNF221, ZNF222, ZNF223, ZNF224, ZNF225, ZNF226, ZNF227, ZNF229, ZNF23, ZNF230, ZNF232, ZNF233, ZNF234, ZNF235, ZNF236, ZNF239, ZNF24, ZNF248, ZNF25, ZNF250, ZNF251, ZNF253, ZNF254, ZNF256, ZNF257, ZNF26, ZNF260, ZNF263, ZNF264, ZNF266, ZNF267, ZNF268, ZNF273, ZNF274, ZNF275, ZNF276, ZNF277, ZNF28, ZNF280A, ZNF280B, ZNF280C, ZNF280D, ZNF281, ZNF282, ZNF283, ZNF284, ZNF285, ZNF286A, ZNF286B, ZNF287, ZNF292, ZNF296, ZNF3, ZNF30, ZNF300, ZNF302, ZNF304, ZNF311, ZNF316, ZNF317, ZNF318, ZNF319, ZNF32, ZNF320, ZNF322, ZNF324, ZNF324B, ZNF326, ZNF329, ZNF330, ZNF331, ZNF333, ZNF334, ZNF335, ZNF337, ZNF33A, ZNF33B, ZNF34, ZNF341, ZNF343, ZNF345, ZNF346, ZNF347, ZNF35, ZNF350, ZNF354A, ZNF354B, ZNF354C, ZNF358, ZNF362, ZNF365, ZNF366, ZNF367, ZNF37A, ZNF382, ZNF383, ZNF384, ZNF385A, ZNF385B, ZNF385C, ZNF385D, ZNF391, ZNF394, ZNF395, ZNF396, ZNF397, ZNF398, ZNF404, ZNF407, ZNF408, ZNF41, ZNF410, ZNF414, ZNF415, ZNF416, ZNF417, ZNF418, ZNF419, ZNF420, ZNF423, ZNF425, ZNF426, ZNF428, ZNF429, ZNF43, ZNF430, ZNF431, ZNF432, ZNF433, ZNF436, ZNF438, ZNF439, ZNF44, ZNF440, ZNF441, ZNF442, ZNF443, ZNF444, ZNF445, ZNF446, ZNF449, ZNF45, ZNF451, ZNF454, ZNF460, ZNF461, ZNF462, ZNF467, ZNF468, ZNF469, ZNF470, ZNF471, ZNF473, ZNF474, ZNF479, ZNF48, ZNF480, ZNF483, ZNF484, ZNF485, ZNF486, ZNF487, ZNF488, ZNF490, ZNF491, ZNF492, ZNF493, ZNF496, ZNF497, ZNF500, ZNF501, ZNF502, ZNF503, ZNF506, ZNF507, ZNF510, ZNF511, ZNF512, ZNF512B, ZNF513, ZNF514, ZNF516, ZNF517, ZNF518A, ZNF518B, ZNF519, ZNF521, ZNF524, ZNF525, ZNF526, ZNF527, ZNF528, ZNF529, ZNF530, ZNF532, ZNF534, ZNF536, ZNF540, ZNF541, ZNF543, ZNF544, ZNF546, ZNF547, ZNF548, ZNF549, ZNF550, ZNF551, ZNF552, ZNF554, ZNF555, ZNF556, ZNF557, ZNF558, ZNF559, ZNF559-ZNF177, ZNF560, ZNF561, ZNF562, ZNF563, ZNF564, ZNF565, ZNF566, ZNF567, ZNF568, ZNF569, ZNF57, ZNF570, ZNF571, ZNF572, ZNF573, ZNF574, ZNF575, ZNF576, ZNF577, ZNF578, ZNF579, ZNF580, ZNF581, ZNF582, ZNF583, ZNF584, ZNF585A, ZNF585B, ZNF586, ZNF587, ZNF587B, ZNF589, ZNF592, ZNF593, ZNF594, ZNF595, ZNF596, ZNF597, ZNF598, ZNF599, ZNF600, ZNF605, ZNF606, ZNF607, ZNF608, ZNF609, ZNF610, ZNF611, ZNF613, ZNF614, ZNF615, ZNF616, ZNF618, ZNF619, ZNF620, ZNF621, ZNF622, ZNF623, ZNF624, ZNF625, ZNF625-ZNF20, ZNF626, ZNF627, ZNF628, ZNF629, ZNF630, ZNF638, ZNF639, ZNF641, ZNF644, ZNF645, ZNF646, ZNF648, ZNF649, ZNF652, ZNF653, ZNF654, ZNF655, ZNF658, ZNF66, ZNF660, ZNF662, ZNF664, ZNF665, ZNF667, ZNF668, ZNF669, ZNF670, ZNF670-ZNF695, ZNF671, ZNF672, ZNF674, ZNF675, ZNF676, ZNF677, ZNF678, ZNF679, ZNF680, ZNF681, ZNF682, ZNF683, ZNF684, ZNF687, ZNF688, ZNF689, ZNF69, ZNF691, ZNF692, ZNF695, ZNF696, ZNF697, ZNF699, ZNF7, ZNF70, ZNF700, ZNF701, ZNF703, ZNF704, ZNF705A, ZNF705B, ZNF705D, ZNF705E, ZNF705G, ZNF706, ZNF707, ZNF708, ZNF709, ZNF71, ZNF710, ZNF711, ZNF713, ZNF714, ZNF716, ZNF717, ZNF718, ZNF720, ZNF721, ZNF724, ZNF726, ZNF727, ZNF728, ZNF729, ZNF730, ZNF732, ZNF735, ZNF736, ZNF737, ZNF738, ZNF74, ZNF740, ZNF746, ZNF747, ZNF749, ZNF750, ZNF75A, ZNF75D, ZNF76, ZNF761, ZNF763, ZNF764, ZNF765, ZNF766, ZNF768, ZNF77, ZNF770, ZNF771, ZNF772, ZNF773, ZNF774, ZNF775, ZNF776, ZNF777, ZNF778, ZNF780A, ZNF780B, ZNF781, ZNF782, ZNF783, ZNF784, ZNF785, ZNF786, ZNF787, ZNF788, ZNF789, ZNF79, ZNF790, ZNF791, ZNF792, ZNF793, ZNF799, ZNF8, ZNF80, ZNF800, ZNF804A, ZNF804B, ZNF805, ZNF808, ZNF81, ZNF813, ZNF814, ZNF816, ZNF816-ZNF321P, ZNF821, ZNF823, ZNF827, ZNF829, ZNF83, ZNF830, ZNF831, ZNF835, ZNF836, ZNF837, ZNF839, ZNF84, ZNF841, ZNF843, ZNF844, ZNF845, ZNF846, ZNF85, ZNF850, ZNF852, ZNF853, ZNF860, ZNF862, ZNF865, ZNF878, ZNF879, ZNF880, ZNF883, ZNF888, ZNF891, ZNF90, ZNF91, ZNF92, ZNF93, ZNF98, ZNF99, ZNFX1, ZNHIT1, ZNHIT2, ZNHIT3, ZNHIT6, ZNRD1, ZNRF1, ZNRF2, ZNRF3, ZNRF4, ZP1, ZP2, ZP3, ZP4, ZPBP, ZPBP2, ZPLD1, ZPR1, ZRANB1, ZRANB2, ZRANB3, ZRSR1, ZRSR2, ZSCAN1, ZSCAN10, ZSCAN12, ZSCAN16, ZSCAN18, ZSCAN2, ZSCAN20, ZSCAN21, ZSCAN22, ZSCAN23, ZSCAN25, ZSCAN26, ZSCAN29, ZSCAN30, ZSCAN31, ZSCAN32, ZSCAN4, ZSCAN5A, ZSCAN5B, ZSCAN5C, ZSCAN9, ZSWIM1, ZSWIM2, ZSWIM3, ZSWIM4, ZSWIM5, ZSWIM6, ZSWIM7, ZSWIM8, ZUFSP, ZW10, ZWILCH, ZWINT, ZXDA, ZXDB, ZXDC, ZYG11A, ZYG11B, ZYX, ZZEF1, and ZZZ3.

In certain embodiments, TBM is a target binding moiety that binds to one or more of SMARCA2, SMARCA4, and PBRM1. In certain embodiments, TBM is a target binding moiety that binds to MERTK.

Protein Level Control

This description also provides methods for the control of protein levels with a cell. This is based on the use of compounds as described herein, which are known to interact with a specific target protein such that degradation of a target protein in vivo will result in the control of the amount of protein in a biological system, preferably to a particular therapeutic benefit.

Furthermore, the invention provides the use of a compound according to the definitions herein, or a pharmaceutically acceptable salt, or a hydrate or solvate thereof for the preparation of a medicament for the treatment of an autoimmune disorder, an inflammatory disorder, or a proliferative disorder, or a disorder commonly occurring in connection with transplantation.

Combination Therapies

Depending upon the particular condition, or disease, to be treated, additional therapeutic agents, which are normally administered to treat that condition, may be administered in combination with compounds and compositions of this invention. As used herein, additional therapeutic agents that are normally administered to treat a particular disease, or condition, are known as "appropriate for the disease, or condition, being treated."

In certain embodiments, a provided combination, or composition thereof, is administered in combination with another therapeutic agent.

In some embodiments, the present invention provides a method of treating a disclosed disease or condition comprising administering to a patient in need thereof an effective amount of a compound disclosed herein or a pharmaceutically acceptable salt thereof and co-administering simultaneously or sequentially an effective amount of one or more additional therapeutic agents, such as those described herein. In some embodiments, the method includes co-administering one additional therapeutic agent. In some embodiments, the method includes co-administering two additional therapeutic agents. In some embodiments, the combination of the disclosed compound and the additional therapeutic agent or agents acts synergistically.

Examples of agents the combinations of this invention may also be combined with include, without limitation: treatments for Alzheimer's Disease such as Aricept® and Excelon®; treatments for HIV such as ritonavir; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; agents that prolong or improve pharmacokinetics such as cytochrome P450 inhibitors (i.e., inhibitors of metabolic breakdown) and CYP3A4 inhibitors (e.g., ketokenozole and ritonavir), and agents for treating immunodeficiency disorders such as gamma globulin.

In certain embodiments, combination therapies of the present invention, or a pharmaceutically acceptable composition thereof, are administered in combination with a monoclonal antibody or an siRNA therapeutic.

Those additional agents may be administered separately from a provided combination therapy, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a combination of the present invention may be administered with another therapeutic agent simultaneously or sequentially in separate unit dosage forms or together in a single unit dosage form.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

In one embodiment, the present invention provides a composition comprising a provided compound and one or more additional therapeutic agents. The therapeutic agent may be administered together with a provided compound or may be administered prior to or following administration of a provided compound. Suitable therapeutic agents are described in further detail below. In certain embodiments, a provided compound may be administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours before the therapeutic agent. In other embodiments, a provided compound may be administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours following the therapeutic agent.

In another embodiment, the present invention provides a method of treating an inflammatory disease, disorder or condition by administering to a patient in need thereof a provided compound and one or more additional therapeutic agents. Such additional therapeutic agents may be small molecules or recombinant biologic agents and include, for example, acetaminophen, non-steroidal anti-inflammatory drugs (NSAIDS) such as aspirin, ibuprofen, naproxen, etodolac (Lodine®) and celecoxib, colchicine (Colcrys®), corticosteroids such as prednisone, prednisolone, methylprednisolone, hydrocortisone, and the like, probenecid, allopurinol, febuxostat (Uloric®), sulfasalazine (Azulfidine®), antimalarials such as hydroxychloroquine (Plaquenil®) and chloroquine (Aralen®), methotrexate (Rheumatrex®), gold salts such as gold thioglucose (Solganal®), gold thiomalate (Myochrysine®) and auranofin (Ridaura®), D-penicillamine (Depen® or Cuprimine®), azathioprine (Imuran®), cyclophosphamide (Cytoxan®), chlorambucil (Leukeran®), cyclosporine (Sandimmune®), leflunomide (Arava®) and "anti-TNF" agents such as etanercept (Enbrel®), infliximab (Remicade®), golimumab (Simponi®), certolizumab pegol (Cimzia®) and adalimumab (Humira®), "anti-IL-1" agents such as anakinra (Kineret®) and rilonacept (Arcalyst®), canakinumab (Ilaris®), anti-Jak inhibitors such as tofacitinib, antibodies such as rituximab (Rituxan®), "anti-T-cell" agents such as abatacept (Orencia®), "anti-IL-6" agents such as tocilizumab (Actemra®), diclofenac, cortisone, hyaluronic acid (Synvisc® or Hyalgan®), monoclonal antibodies such as tanezumab, anticoagulants such as heparin (Calcinparine® or Liquaemin®) and warfarin (Coumadin®), antidiarrheals such as diphenoxylate (Lomotil®) and loperamide (Imodium®), bile acid binding agents such as cholestyramine, alosetron (Lotronex®), lubiprostone (Amitiza®), laxatives such as Milk of Magnesia, polyethylene glycol (MiraLax®), Dulcolax®, Correctol® and Senokot®, anticholinergics or antispasmodics such as dicyclomine (Bentyl®), Singulair®, beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), inhaled corticosteroids such as beclomethasone dipropionate (Beclovent®, Qvar®, and Vanceril®), triamcinolone acetonide (Azmacort®), mometasone (Asthmanex®), budesonide (Pulmocort®), and flunisolide (Aerobid®), Afviar®, Symbicort®, Dulera®, cromolyn sodium (Intal®), methylxanthines such as theophylline (Theo-Dur®, Theolair®, Slo-bid®, Uniphyl®, Theo-24®) and aminophylline, IgE antibodies such as omalizumab (Xolair®), nucleoside reverse transcriptase inhibitors such as zidovudine (Retrovir®), abacavir (Ziagen®), abacavir/lamivudine (Epzicom®), abacavir/lamivudine/zidovudine (Trizivir®), didanosine (Videx®), emtricitabine (Emtriva®), lamivudine (Epivir®), lamivudine/zidovudine (Combivir®), stavudine (Zerit®), and zalcitabine (Hivid®), non-nucleoside reverse transcriptase inhibitors such as delavirdine (Rescriptor®), efavirenz (Sustiva®), nevairapine (Viramune®) and etravirine (Intelence®), nucleotide reverse transcriptase inhibitors such as tenofovir (Viread®), protease inhibitors such as amprenavir (Agenerase®), atazanavir (Reyataz®), darunavir (Prezista®), fosamprenavir (Lexiva®), indinavir (Crixivan®), lopinavir and ritonavir (Kaletra®), nelfinavir (Viracept®), ritonavir (Norvir®), saquinavir (Fortovase® or Invirase®), and tipranavir (Aptivus®), entry inhibitors such as enfuvirtide (Fuzeon®) and maraviroc (Selzentry®), integrase inhibitors such as raltegravir (Isentress®), doxorubicin (Hydrodaunorubicin®), vincristine (Oncovin®), bortezomib (Velcade®), and dexamethasone (Decadron®) in combination with lenalidomide (Revlimid®), or any combination(s) thereof.

In another embodiment, the present invention provides a method of treating rheumatoid arthritis comprising administering to a patient in need thereof a provided compound and one or more additional therapeutic agents selected from non-steroidal anti-inflammatory drugs (NSAIDS) such as aspirin, ibuprofen, naproxen, etodolac (Lodine®) and celecoxib, corticosteroids such as prednisone, prednisolone, methylprednisolone, hydrocortisone, and the like, sulfasalazine (Azulfidine®), antimalarials such as hydroxychloroquine (Plaquenil®) and chloroquine (Aralen®), methotrexate (Rheumatrex®), gold salts such as gold thioglucose (Solganal®), gold thiomalate (Myochrysine®) and auranofin (Ridaura®), D-penicillamine (Depen® or Cuprimine®), azathioprine (Imuran®), cyclophosphamide (Cytoxan®), chlorambucil (Leukeran®), cyclosporine (Sandimmune®), leflunomide (Arava®) and "anti-TNF" agents such as etanercept (Enbrel®), infliximab (Remicade®), golimumab (Simponi®), certolizumab pegol (Cimzia®) and adalimumab (Humira®), "anti-IL-1" agents such as anakinra (Kineret®) and rilonacept (Arcalyst®), antibodies such as rituximab (Rituxan®), "anti-T-cell" agents such as abatacept (Orencia®) and "anti-IL-6" agents such as tocilizumab (Actemra®).

In some embodiments, the present invention provides a method of treating osteoarthritis comprising administering to a patient in need thereof a provided compound and one or more additional therapeutic agents selected from acetaminophen, non-steroidal anti-inflammatory drugs (NSAIDS) such as aspirin, ibuprofen, naproxen, etodolac (Lodine®) and celecoxib, diclofenac, cortisone, hyaluronic acid (Synvisc® or Hyalgan®) and monoclonal antibodies such as tanezumab.

In some embodiments, the present invention provides a method of treating systemic lupus erythematosus comprising administering to a patient in need thereof a provided compound and one or more additional therapeutic agents selected from acetaminophen, non-steroidal anti-inflammatory drugs (NSAIDS) such as aspirin, ibuprofen, naproxen, etodolac (Lodine®) and celecoxib, corticosteroids such as prednisone, prednisolone, methylprednisolone, hydrocortisone, and the like, antimalarials such as hydroxychloroquine (Plaquenil®) and chloroquine (Aralen®), cyclophosphamide (Cytoxan®), methotrexate (Rheumatrex®), azathioprine (Imuran®) and anticoagulants such as heparin (Calcinparine® or Liquaemin®) and warfarin (Coumadin®).

In some embodiments, the present invention provides a method of treating Crohn's disease, ulcerative colitis, or inflammatory bowel disease comprising administering to a patient in need thereof a provided compound and one or more additional therapeutic agents selected from mesalamine (Asacol®) sulfasalazine (Azulfidine®), antidiarrheals such as diphenoxylate (Lomotil®) and loperamide (Imodium®), bile acid binding agents such as cholestyramine, alosetron (Lotronex®), lubiprostone (Amitiza®), laxatives such as Milk of Magnesia, polyethylene glycol (MiraLax®), Dulcolax®, Correctol® and Senokot® and anticholinergics or antispasmodics such as dicyclomine (Bentyl®), anti-TNF therapies, steroids, and antibiotics such as Flagyl or ciprofloxacin.

In some embodiments, the present invention provides a method of treating asthma comprising administering to a patient in need thereof a provided compound and one or more additional therapeutic agents selected from Singulair®, beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), inhaled corticosteroids such as prednisone, prednisolone, beclomethasone dipropionate (Beclovent®, Qvar®, and Vanceril®), triamcinolone acetonide (Azmacort®), mometasone (Asthmanex®), budesonide (Pulmocort®), flunisolide (Aerobid®), Afviar®, Symbicort®, and Dulera®, cromolyn sodium (Intal®), methylxanthines such as theophylline (Theo-Dur®, Theolair®, Slo-bid®, Uniphyl®, Theo-24®) and aminophylline, and IgE antibodies such as omalizumab (Xolair®).

In some embodiments, the present invention provides a method of treating COPD comprising administering to a patient in need thereof a provided compound and one or more additional therapeutic agents selected from beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), methylxanthines such as theophylline (Theo-Dur®, Theolair®, Slo-bid®, Uniphyl®, Theo-24®) and aminophylline, inhaled corticosteroids such as prednisone, prednisolone, beclomethasone dipropionate (Beclovent®, Qvar®, and Vanceril®), triamcinolone acetonide (Azmacort®), mometasone (Asthmanex®), budesonide (Pulmocort®), flunisolide (Aerobid®), Afviar®, Symbicort®, and Dulera®, In another embodiment, the present invention provides a method of treating a hematological malignancy comprising administering to a patient in need thereof a provided compound and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, a BTK inhibitor, a JAK/pan-JAK inhibitor, a PI3K inhibitor, a SYK inhibitor, and combinations thereof.

In another embodiment, the present invention provides a method of treating a solid tumor comprising administering to a patient in need thereof a provided compound and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, a BTK inhibitor, a JAK/pan-JAK inhibitor, a PI3K inhibitor, a SYK inhibitor, and combinations thereof.

In another embodiment, the present invention provides a method of treating a hematological malignancy comprising administering to a patient in need thereof a provided compound and a Hedgehog (Hh) signaling pathway inhibitor. In some embodiments, the hematological malignancy is DLBCL (Ramirez et al "Defining causative factors contributing in the activation of hedgehog signaling in diffuse large B-cell lymphoma" Leuk. Res. (2012), published online July 17, and incorporated herein by reference in its entirety).

In another embodiment, the present invention provides a method of treating diffuse large B-cell lymphoma (DLBCL) comprising administering to a patient in need thereof a provided compound and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, and combinations thereof.

In another embodiment, the present invention provides a method of treating multiple myeloma comprising administering to a patient in need thereof a provided compound and one or more additional therapeutic agents selected from bortezomib (Velcade®), and dexamethasone (Decadron®), a hedgehog signaling inhibitor, a BTK inhibitor, a JAK/pan-JAK inhibitor, a TYK2 inhibitor, a PI3K inhibitor, a SYK inhibitor in combination with lenalidomide (Revlimid®).

In another embodiment, the present invention provides a method of treating or lessening the severity of a disease comprising administering to a patient in need thereof a provided compound and a BTK inhibitor, wherein the disease is selected from inflammatory bowel disease, arthritis, systemic lupus erythematosus (SLE), vasculitis, idiopathic thrombocytopenic purpura (ITP), rheumatoid arthritis, psoriatic arthritis, osteoarthritis, Still's disease, juvenile arthritis, diabetes, myasthenia gravis, Hashimoto's thyroiditis, Ord's thyroiditis, Graves' disease, autoimmune thyroiditis, Sjogren's syndrome, multiple sclerosis, systemic sclerosis, Lyme neuroborreliosis, Guillain-Barre syndrome, acute disseminated encephalomyelitis, Addison's disease, opsoclonus-myoclonus syndrome, ankylosing spondylosis, antiphospholipid antibody syndrome, aplastic anemia, autoimmune hepatitis, autoimmune gastritis, pernicious anemia, celiac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behcet's disease, chronic fatigue, dysautonomia, membranous glomerulonephropathy, endometriosis, interstitial cystitis, pemphigus vulgaris, bullous pemphigoid, neuromyotonia, scleroderma, vulvodynia, a hyperproliferative disease, rejection of transplanted organs or tissues, Acquired Immunodeficiency Syndrome (AIDS, also known as HIV), type 1 diabetes, graft versus host disease, transplantation, transfusion, anaphylaxis, allergies (e.g., allergies to plant pollens, latex, drugs, foods, insect poisons, animal hair, animal dander, dust mites, or cockroach calyx), type I hypersensitivity, allergic conjunctivitis, allergic rhinitis, and atopic dermatitis, asthma, appendicitis, atopic dermatitis, asthma, allergy, blepharitis, bronchiolitis, bronchitis, bursitis, cervicitis, cholangitis, cholecystitis, chronic graft rejection, colitis, conjunctivitis, Crohn's disease, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, Henoch-Schonlein purpura, hepatitis, hidradenitis suppurativa, immunoglobulin A nephropathy, interstitial lung disease, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, polymyositis, proctitis, prostatitis, pyelonephritis, rhinitis, salpingitis, sinusitis, stomatitis, synovitis, tendonitis, tonsillitis, ulcerative colitis, uveitis, vaginitis, vasculitis, or vulvitis, B-cell proliferative disorder, e.g., diffuse large B cell lymphoma, follicular lymphoma, chronic lymphocytic lymphoma, chronic lymphocytic leukemia, acute lymphocytic leukemia, B-cell prolymphocytic leukemia, lymphoplasmacytic lymphoma/ Waldenstrom macroglobulinemia, splenic marginal zone lymphoma, multiple myeloma (also known as plasma cell myeloma), non-Hodgkin's lymphoma, Hodgkin's lymphoma, plasmacytoma, extranodal marginal zone B cell lymphoma, nodal marginal zone B cell lymphoma, mantle cell lymphoma, mediastinal (thymic) large B cell lymphoma, intravascular large B cell lymphoma, primary effusion lymphoma, Burkitt lymphoma/leukemia, or lymphomatoid granulomatosis, breast cancer, prostate cancer, or cancer of the mast cells (e.g., mastocytoma, mast cell leukemia, mast cell sarcoma, systemic mastocytosis), bone cancer, colorectal cancer, pancreatic cancer, diseases of the bone and joints including, without limitation, rheumatoid arthritis, seronegative spondyloarthropathies (including ankylosing spondylitis, psoriatic arthritis and Reiter's disease), Behcet's disease, Sjogren's syndrome, systemic sclerosis, osteoporosis, bone cancer, bone metastasis, a thromboembolic disorder, (e.g., myocardial infarct, angina pectoris, reocclusion after angioplasty, restenosis after angioplasty, reocclusion after aortocoronary bypass, restenosis after aortocoronary bypass, stroke, transitory ischemia, a peripheral arterial occlusive disorder, pulmonary embolism, deep venous thrombosis), inflammatory pelvic disease, urethritis, skin sunburn, sinusitis, pneumonitis, encephalitis, meningitis, myocarditis, nephritis, osteomyelitis, myositis, hepatitis, gastritis, enteritis, dermatitis, gingivitis, appendicitis, pancreatitis, cholocystitus, agammaglobulinemia, psoriasis, allergy, Crohn's disease, irritable bowel syndrome, ulcerative colitis, Sjogren's disease, tissue graft rejection, hyperacute rejection of transplanted organs, asthma, allergic rhinitis, chronic obstructive pulmonary disease (COPD), autoimmune polyglandular disease (also known as autoimmune polyglandular syndrome), autoimmune alopecia, pernicious anemia, glomerulonephritis, dermatomyositis, multiple sclerosis, scleroderma, vasculitis, autoimmune hemolytic and thrombocytopenic states, Goodpasture's syndrome, atherosclerosis, Addison's disease, Parkinson's disease, Alzheimer's disease, diabetes, septic shock, systemic lupus erythematosus (SLE), rheumatoid arthritis, psoriatic arthritis, juvenile arthritis, osteoarthritis, chronic idiopathic thrombocytopenic purpura, Waldenstrom macroglobulinemia, myasthenia gravis, Hashimoto's thyroiditis, atopic dermatitis, degenerative joint disease, vitiligo, autoimmune hypopituitarism, Guillain-Barre syndrome, Behcet's disease, scleraderma, mycosis fungoides, acute inflammatory responses (such as acute respiratory distress syndrome and ischemia/reperfusion injury), and Graves' disease.

In another embodiment, the present invention provides a method of treating or lessening the severity of a disease comprising administering to a patient in need thereof a provided compound and a PI3K inhibitor, wherein the disease is selected from a cancer, a neurodegenative disorder, an angiogenic disorder, a viral disease, an autoimmune disease, an inflammatory disorder, a hormone-related disease, conditions associated with organ transplantation, immunodeficiency disorders, a destructive bone disorder, a proliferative disorder, an infectious disease, a condition associated with cell death, thrombin-induced platelet aggregation, chronic myelogenous leukemia (CML), chronic lymphocytic leukemia (CLL), liver disease, pathologic immune conditions involving T cell activation, a cardiovascular disorder, and a CNS disorder.

In another embodiment, the present invention provides a method of treating or lessening the severity of a disease comprising administering to a patient in need thereof a provided compound and a PI3K inhibitor, wherein the disease is selected from benign or malignant tumor, carcinoma or solid tumor of the brain, kidney (e.g., renal cell carcinoma (RCC)), liver, adrenal gland, bladder, breast, stomach, gastric tumors, ovaries, colon, rectum, prostate, pancreas, lung, vagina, endometrium, cervix, testis, genitourinary tract, esophagus, larynx, skin, bone or thyroid, sarcoma, glioblastomas, neuroblastomas, multiple myeloma or gastrointestinal cancer, especially colon carcinoma or colorectal adenoma or a tumor of the neck and head, an epidermal hyperproliferation, psoriasis, prostate hyperplasia, a neoplasia, a neoplasia of epithelial character, adenoma, adenocarcinoma, keratoacanthoma, epidermoid carcinoma, large cell carcinoma, non-small-cell lung carcinoma, lymphomas, (including, for example, non-Hodgkin's Lymphoma (NHL) and Hodgkin's lymphoma (also termed Hodgkin's or Hodgkin's disease)), a mammary carcinoma, follicular carcinoma, undifferentiated carcinoma, papillary carcinoma, seminoma, melanoma, or a leukemia, diseases include Cowden syndrome, Lhermitte-Dudos disease and Bannayan-Zonana syndrome, or diseases in which the PI3K/PKB pathway is aberrantly activated, asthma of whatever type or genesis including both intrinsic (non-allergic) asthma and extrinsic (allergic) asthma, mild asthma, moderate asthma, severe asthma, bronchitic asthma, exercise-induced asthma, occupational asthma and asthma induced following bacterial infection, acute lung injury (ALI), adult/acute respiratory distress syndrome (ARDS), chronic obstructive pulmonary, airways or lung disease (COPD, COAD or COLD), including chronic bronchitis or dyspnea associated therewith, emphysema, as well as exacerbation of airways hyperreactivity consequent to other drug therapy, in particular other inhaled drug therapy, bronchitis of whatever type or genesis including, but not limited to, acute, arachidic, catarrhal, croupus, chronic or phthinoid bronchitis, pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis, Loffler's syndrome, eosinophilic, pneumonia, parasitic (in particular metazoan) infestation (including tropical eosinophilia), bronchopulmonary aspergillosis, polyarteritis nodosa (including Churg-Strauss syndrome), eosinophilic granuloma and eosinophil-related disorders affecting the airways occasioned by drug-reaction, psoriasis, contact dermatitis, atopic dermatitis, alopecia areata, erythema multiforma, dermatitis herpetiformis, scleroderma, vitiligo, hypersensitivity angiitis, urticaria, bullous pemphigoid, lupus erythematosus, pemphisus, epidermolysis bullosa acquisita, conjunctivitis, keratoconjunctivitis sicca, and vernal conjunctivitis, diseases affecting the nose including allergic rhinitis, and inflammatory disease in which autoimmune reactions are implicated or having an autoimmune component or etiology, including autoimmune hematological disorders (e.g. hemolytic anemia, aplastic anemia, pure red cell anemia and idiopathic thrombocytopenia), systemic lupus erythematosus, rheumatoid arthritis, polychondritis, sclerodoma, Wegener granulamatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), endocrine opthalmopathy, Grave's disease, sarcoidosis, alveolitis, chronic hypersensitivity pneumonitis, multiple sclerosis, primary biliary cirrhosis, uveitis (anterior and posterior), keratoconjunctivitis sicca and vernal keratoconjunctivitis, interstitial lung fibrosis, psoriatic arthritis and glomerulonephritis (with and without nephrotic syndrome, e.g. including idiopathic nephrotic syndrome or minal change nephropathy, restenosis, cardiomegaly, atherosclerosis, myocardial infarction, ischemic stroke and congestive heart failure, Alzheimer's disease, Parkinson's disease, amyotrophic lateral sclerosis, Huntington's disease, and cerebral ischemia, and neurodegenerative disease caused by traumatic injury, glutamate neurotoxicity and hypoxia.

In some embodiments the present invention provides a method of treating or lessening the severity of a disease comprising administering to a patient in need thereof a provided compound and a Bcl-2 inhibitor, wherein the disease is an inflammatory disorder, an autoimmune disorder, a proliferative disorder, an endocrine disorder, a neurological disorder, or a disorder associated with transplantation. In some embodiments, the disorder is a proliferative disorder, lupus, or lupus nephritis. In some embodiments, the proliferative disorder is chronic lymphocytic leukemia, diffuse large B-cell lymphoma, Hodgkin's disease, small-cell lung cancer, non-small-cell lung cancer, myelodysplastic syndrome, lymphoma, a hematological neoplasm, or solid tumor.

The compounds and compositions, according to the method of the present invention, may be administered using any amount and any route of administration effective for treating or lessening the severity of an autoimmune disorder, an inflammatory disorder, a proliferative disorder, an endocrine disorder, a neurological disorder, or a disorder associated with transplantation. The exact amount required will vary from subject to subject, depending on the species, age, and general condition of the subject, the severity of the infection, the particular agent, its mode of administration, and the like. Compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

Pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar—agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to one embodiment, the invention relates to a method of modulating CRBN activity in a biological sample comprising the step of contacting said biological sample with a compound of this invention, or a composition comprising said compound.

According to another embodiment, the invention relates to a method of binding CRBN, or a mutant thereof, activity in a biological sample comprising the step of contacting said biological sample with a compound of this invention, or a composition comprising said compound.

The term “biological sample”, as used herein, includes, without limitation, cell cultures or extracts thereof; biopsied material obtained from a mammal or extracts thereof; and blood, saliva, urine, feces, semen, tears, or other body fluids or extracts thereof.

Binding CRBN (or a mutant thereof) activity in a biological sample is useful for a variety of purposes that are known to one of skill in the art. Examples of such purposes include, but are not limited to, biological specimen storage and biological assays.

Another embodiment of the present invention relates to a method of modulating CRBN activity in a patient comprising the step of administering to said patient a compound of the present invention, or a composition comprising said compound.

According to another embodiment, the invention relates to a method of modulating the activity of CRBN, or a mutant thereof, in a patient comprising the step of administering to said patient a compound of the present invention, or a composition comprising said compound. According to certain embodiments, the invention relates to a method of reversibly or irreversibly modulating one or more of CRBN, or a mutant thereof, activity in a patient comprising the step of administering to said patient a compound of the present invention, or a composition comprising said compound. In other embodiments, the present invention provides a method for treating a disorder mediated by CRBN, or a mutant thereof, in a patient in need thereof, comprising the step of administering to said patient a compound according to the present invention or pharmaceutically acceptable composition thereof. Such disorders are described in detail herein.

Depending upon the particular condition, or disease, to be treated, additional therapeutic agents that are normally administered to treat that condition, may also be present in the compositions of this invention. As used herein, additional therapeutic agents that are normally administered to treat a particular disease, or condition, are known as “appropriate for the disease, or condition, being treated.”

A compound of the current invention may also be used to advantage in combination with other therapeutic compounds. In some embodiments, the other therapeutic compounds are antiproliferative compounds. Such antiproliferative compounds include, but are not limited to aromatase inhibitors; antiestrogens; topoisomerase I inhibitors; topoisomerase II inhibitors; microtubule active compounds; alkylating compounds; histone deacetylase inhibitors; compounds which induce cell differentiation processes; cyclooxygenase inhibitors; MMP inhibitors; mTOR inhibitors; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; anti-androgens; methionine aminopeptidase inhibitors; matrix metalloproteinase inhibitors; bisphosphonates; biological response modifiers; antiproliferative antibodies; heparanase inhibitors; inhibitors of Ras oncogenic isoforms; telomerase inhibitors; proteasome inhibitors; compounds used in the treatment of hematologic malignancies; compounds which target, decrease or inhibit the activity of Flt-3; Hsp90 inhibitors such as 17-AAG (17-allylaminogeldanamycin, NSC330507), 17-DMAG (17-dimethylaminoethylamino-17-demethoxy-geldanamycin, NSC707545), IPI-504, CNF1010, CNF2024, CNF1010 from Conforma Therapeutics; temozolomide (Temodal®); kinesin spindle protein inhibitors, such as SB715992 or SB743921 from GlaxoSmithKline, or pentamidine/chlorpromazine from CombinatoRx; MEK inhibitors such as ARRY142886 from Array BioPharma, AZD6244 from AstraZeneca, PD181461 from Pfizer and leucovorin. The term "aromatase inhibitor" as used herein relates to a compound which inhibits estrogen production, for instance, the conversion of the substrates androstenedione and testosterone to estrone and estradiol, respectively. The term includes, but is not limited to steroids, especially atamestane, exemestane and formestane and, in particular, non-steroids, especially aminoglutethimide, roglethimide, pyridoglutethimide, trilostane, testolactone, ketokonazole, vorozole, fadrozole, anastrozole and letrozole. Exemestane is marketed under the trade name Aromasin™. Formestane is marketed under the trade name Lentaron™. Fadrozole is marketed under the trade name Afema™. Anastrozole is marketed under the trade name Arimidex™ Letrozole is marketed under the trade names Femara™ or Femar™. Aminoglutethimide is marketed under the trade name Orimeten™. A combination of the invention comprising a chemotherapeutic agent which is an aromatase inhibitor is particularly useful for the treatment of hormone receptor positive tumors, such as breast tumors.

The term "antiestrogen" as used herein relates to a compound which antagonizes the effect of estrogens at the estrogen receptor level. The term includes, but is not limited to tamoxifen, fulvestrant, raloxifene and raloxifene hydrochloride. Tamoxifen is marketed under the trade name Nolvadex™. Raloxifene hydrochloride is marketed under the trade name Evista™. Fulvestrant can be administered under the trade name Faslodex™. A combination of the invention comprising a chemotherapeutic agent which is an antiestrogen is particularly useful for the treatment of estrogen receptor positive tumors, such as breast tumors.

The term "anti-androgen" as used herein relates to any substance which is capable of inhibiting the biological effects of androgenic hormones and includes, but is not limited to, bicalutamide (Casodex™). The term "gonadorelin agonist" as used herein includes, but is not limited to abarelix, goserelin and goserelin acetate. Goserelin can be administered under the trade name Zoladex™.

The term "topoisomerase I inhibitor" as used herein includes, but is not limited to topotecan, gimatecan, irinotecan, camptothecian and its analogues, 9-nitrocamptothecin and the macromolecular camptothecin conjugate PNU-166148. Irinotecan can be administered, e.g. in the form as it is marketed, e.g. under the trademark Camptosar™. Topotecan is marketed under the trade name Hycamptin™.

The term "topoisomerase II inhibitor" as used herein includes, but is not limited to the anthracyclines such as doxorubicin (including liposomal formulation, such as Caelyx™), daunorubicin, epirubicin, idarubicin and nemorubicin, the anthraquinones mitoxantrone and losoxantrone, and the podophillotoxines etoposide and teniposide. Etoposide is marketed under the trade name Etopophos™. Teniposide is marketed under the trade name VM 26-Bristol Doxorubicin is marketed under the trade name Acriblastin™ or Adriamycin™. Epirubicin is marketed under the trade name Farmorubicin™. Idarubicin is marketed. under the trade name Zavedos™. Mitoxantrone is marketed under the trade name Novantron.

The term "microtubule active agent" relates to microtubule stabilizing, microtubule destabilizing compounds and microtublin polymerization inhibitors including, but not limited to taxanes, such as paclitaxel and docetaxel; vinca alkaloids, such as vinblastine or vinblastine sulfate, vincristine or vincristine sulfate, and vinorelbine; discodermolides; cochicine and epothilones and derivatives thereof. Paclitaxel is marketed under the trade name Taxol™. Docetaxel is marketed under the trade name Taxotere™. Vinblastine sulfate is marketed under the trade name Vinblastin R.P™. Vincristine sulfate is marketed under the trade name Farmistin™.

The term "alkylating agent" as used herein includes, but is not limited to, cyclophosphamide, ifosfamide, melphalan or nitrosourea (BCNU or Gliadel). Cyclophosphamide is marketed under the trade name Cyclostin™. Ifosfamide is marketed under the trade name Holoxan™.

The term "histone deacetylase inhibitors" or "HDAC inhibitors" relates to compounds which inhibit the histone deacetylase and which possess antiproliferative activity. This includes, but is not limited to, suberoylanilide hydroxamic acid (SAHA).

The term "antineoplastic antimetabolite" includes, but is not limited to, 5-fluorouracil or 5-FU, capecitabine, gemcitabine, DNA demethylating compounds, such as 5-azacytidine and decitabine, methotrexate and edatrexate, and folic acid antagonists such as pemetrexed. Capecitabine is marketed under the trade name Xeloda™. Gemcitabine is marketed under the trade name Gemzar™.

The term "platin compound" as used herein includes, but is not limited to, carboplatin, cis-platin, cisplatinum and oxaliplatin. Carboplatin can be administered, e.g., in the form as it is marketed, e.g. under the trademark Carboplat™. Oxaliplatin can be administered, e.g., in the form as it is marketed, e.g. under the trademark Eloxatin™

The term "compounds targeting/decreasing a protein or lipid kinase activity; or a protein or lipid phosphatase activity; or further anti-angiogenic compounds" as used herein includes, but is not limited to, protein tyrosine kinase and/or serine and/or threonine kinase inhibitors or lipid kinase inhibitors, such as a) compounds targeting, decreasing or inhibiting the activity of the platelet-derived growth factor-receptors (PDGFR), such as compounds which target, decrease or inhibit the activity of PDGFR, especially compounds which inhibit the PDGF receptor, such as an N-phenyl-2-pyrimidine-amine derivative, such as imatinib, SU101, SU6668 and GFB-111; b) compounds targeting, decreasing or inhibiting the activity of the fibroblast growth factor-receptors (FGFR); c) compounds targeting, decreasing or inhibiting the activity of the insulin-like growth factor receptor I (IGF-IR), such as compounds which target, decrease or inhibit the activity of IGF-IR, especially compounds which inhibit the kinase activity of IGF-I receptor, or antibodies that target the extracellular domain of IGF-I receptor or its growth factors; d) compounds targeting, decreasing or inhibiting the activity of the Trk receptor tyrosine kinase family, or ephrin B4 inhibitors; e) compounds targeting, decreasing or inhibiting the activity of the AxI receptor tyrosine kinase family; f) compounds targeting, decreasing or inhibiting the activity of the Ret receptor tyrosine kinase; g) compounds targeting, decreasing or inhibiting the activity of the Kit/SCFR receptor tyrosine kinase, such as imatinib; h) compounds targeting, decreasing or inhibiting the activity of the C-kit receptor tyrosine kinases, which are part of the PDGFR family, such as compounds which target, decrease or inhibit the activity of the c-Kit receptor tyrosine kinase family, especially compounds which inhibit the c-Kit receptor, such as imatinib; i) compounds targeting, decreasing or inhibiting the activity of members of the c-Abl family, their gene-fusion products (e.g. BCR-Abl kinase) and mutants, such as compounds which target decrease or inhibit the activity of c-Abl family members and their gene fusion products, such as an N-phenyl-2-pyrimidine-amine derivative, such as imatinib or nilotinib (AMN107); PD180970; AG957; NSC 680410; PD173955 from ParkeDavis; or dasatinib (BMS-354825); j) compounds targeting, decreasing or inhibiting the activity of members of the protein kinase C (PKC) and Raf family of serine/threonine kinases, members of the MEK, SRC, JAK/pan-JAK, FAK, PDK1, PKB/Akt, Ras/MAPK, PI3K, SYK, BTK and TEC family, and/or members of the cyclin-dependent kinase family (CDK) including staurosporine derivatives, such as midostaurin; examples of further compounds include UCN-01, safingol, BAY 43-9006, Bryostatin 1, Perifosine; llmofosine; RO 318220 and RO 320432; GO 6976; lsis 3521; LY333531/LY379196; isochinoline compounds; FTIs; PD184352 or QAN697 (a PI3K inhibitor) or AT7519 (CDK inhibitor); k) compounds targeting, decreasing or inhibiting the activity of protein-tyrosine kinase inhibitors, such as compounds which target, decrease or inhibit the activity of protein-tyrosine kinase inhibitors include imatinib mesylate (Gleevec™) or tyrphostin such as Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin); 1) compounds targeting, decreasing or inhibiting the activity of the epidermal growth factor family of receptor tyrosine kinases ($EGFR_1$ ErbB2, ErbB3, ErbB4 as homo- or heterodimers) and their mutants, such as compounds which target, decrease or inhibit the activity of the epidermal growth factor receptor family are especially compounds, proteins or antibodies which inhibit members of the EGF receptor tyrosine kinase family, such as EGF receptor, ErbB2, ErbB3 and ErbB4 or bind to EGF or EGF related ligands, CP 358774, ZD 1839, ZM 105180; trastuzumab (Herceptin™), cetuximab (Erbitux™), Iressa, Tarceva, OSI-774, C1-1033, EKB-569, GW-2016, E1.1, E2.4, E2.5, E6.2, E6.4, E2.11, E6.3 or E7.6.3, and 7H-pyrrolo-[2,3-d]pyrimidine derivatives; m) compounds targeting, decreasing or inhibiting the activity of the c-Met receptor, such as compounds which target, decrease or inhibit the activity of c-Met, especially compounds which inhibit the kinase activity of c-Met receptor, or antibodies that target the extracellular domain of c-Met or bind to HGF, n) compounds targeting, decreasing or inhibiting the kinase activity of one or more JAK family members (JAK1/JAK2/JAK3/TYK2 and/or pan-JAK), including but not limited to PRT-062070, SB-1578, baricitinib, pacritinib, momelotinib, VX-509, AZD-1480, TG-101348, tofacitinib, and ruxolitinib; o) compounds targeting, decreasing or inhibiting the kinase activity of PI3 kinase (PI3K) including but not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib; and; and q) compounds targeting, decreasing or inhibiting the signaling effects of hedgehog protein (Hh) or smoothened receptor (SMO) pathways, including but not limited to cyclopamine, vismodegib, itraconazole, erismodegib, and IPI-926 (saridegib).

The term "PI3K inhibitor" as used herein includes, but is not limited to compounds having inhibitory activity against one or more enzymes in the phosphatidylinositol-3-kinase family, including, but not limited to PI3Kα, PI3Kγ, PI3Kδ, PI3Kβ, PI3K-C2α, PI3K-C2β, PI3K—C2γ, Vps34, p110-α, p 110-β, p110-γ, p110-δ, p85-α, p85-β, p55-γ. p150, p101, and p87. Examples of PI3K inhibitors useful in this invention include but are not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib.

The term "BTK inhibitor" as used herein includes, but is not limited to compounds having inhibitory activity against Bruton's Tyrosine Kinase (BTK), including, but not limited to AVL-292 and ibrutinib.

The term "SYK inhibitor" as used herein includes, but is not limited to compounds having inhibitory activity against spleen tyrosine kinase (SYK), including but not limited to PRT-062070, R-343, R-333, Excellair, PRT-062607, and fostamatinib.

The term "Bcl-2 inhibitor" as used herein includes, but is not limited to compounds having inhibitory activity against B-cell lymphoma 2 protein (Bcl-2), including but not limited to ABT-199, ABT-731, ABT-737, apogossypol, Ascenta's pan-Bcl-2 inhibitors, curcumin (and analogs thereof), dual Bcl-2/Bcl-xL inhibitors (Infinity Pharmaceuticals/Novartis Pharmaceuticals), Genasense (G3139), HA14-1 (and analogs thereof; see WO2008118802), navitoclax (and analogs thereof, see U.S. Pat. No. 7,390,799), NH-1 (Shenayng Pharmaceutical University), obatoclax (and analogs thereof, see WO2004106328), S-001 (Gloria Pharmaceuticals), TW series compounds (Univ. of Michigan), and venetoclax. In some embodiments the Bcl-2 inhibitor is a small molecule therapeutic. In some embodiments the Bcl-2 inhibitor is a peptidomimetic.

Further examples of BTK inhibitory compounds, and conditions treatable by such compounds in combination with compounds of this invention can be found in WO2008039218, U.S. Pat. No. 7,514,444, WO2011090760, and U.S. Pat. No. 8,338,439, the entirety of each of which is herein incorporated by reference.

Further examples of SYK inhibitory compounds, and conditions treatable by such compounds in combination with compounds of this invention can be found in WO2003063794, U.S. Pat. No. 7,557,210, WO2005007623, U.S. Pat. No. 7,173,015, WO2006078846, and U.S. Pat. No. 7,449,458, the entirety of each of which is herein incorporated by reference.

Further examples of PI3K inhibitory compounds, and conditions treatable by such compounds in combination with compounds of this invention can be found in WO2004019973, U.S. Pat. No. 7,713,943, WO2004089925, U.S. Pat. No. 6,949,537, WO2007016176, U.S. Pat. Nos. 7,402,325, 8,138,347, WO2002088112, U.S. Pat. No. 7,071,189, WO2007084786, U.S. Pat. No. 8,217,035, WO2007129161, U.S. Pat. No. 7,781,433, WO2006122806, U.S. Pat. No. 7,667,039, WO2005113554, U.S. Pat. No. 7,932,260, WO2007044729, and U.S. Pat. No. 7,989,622, the entirety of each of which is herein incorporated by reference.

Further examples of JAK inhibitory compounds, and conditions treatable by such compounds in combination with compounds of this invention can be found in WO2009114512, U.S. Pat. No. 8,185,616, WO2008109943, U.S. Pat. No. 8,486,941, WO2007053452, U.S. Pat. No. 7,528,143, WO200142246, U.S. Pat. No. 6,627,754, WO2007070514, and U.S. Pat. No. 7,598,257, the entirety of each of which is herein incorporated by reference.

Further anti-angiogenic compounds include compounds having another mechanism for their activity, e.g. unrelated to protein or lipid kinase inhibition e.g. thalidomide (Thalomid™) and TNP-470.

Examples of proteasome inhibitors useful for use in combination with compounds of the invention include, but are not limited to bortezomib, disulfiram, epigallocatechin-3-gallate (EGCG), salinosporamide A, carfilzomib, ONX-0912, CEP-18770, and MLN9708.

Compounds which target, decrease or inhibit the activity of a protein or lipid phosphatase are e.g. inhibitors of phosphatase 1, phosphatase 2A, or CDC25, such as okadaic acid or a derivative thereof.

Compounds which induce cell differentiation processes include, but are not limited to, retinoic acid, α- γ- or δ-tocopherol or α- γ- or δ-tocotrienol.

The term cyclooxygenase inhibitor as used herein includes, but is not limited to, Cox-2 inhibitors, 5-alkyl substituted 2-arylaminophenylacetic acid and derivatives, such as celecoxib (Celebrex™), rofecoxib (Vioxx™), etoricoxib, valdecoxib or a 5-alkyl-2-arylaminophenylacetic acid, such as 5-methyl-2-(2'-chloro-6'-fluoroanilino)phenyl acetic acid, lumiracoxib.

The term "bisphosphonates" as used herein includes, but is not limited to, etridonic, clodronic, tiludronic, pamidronic, alendronic, ibandronic, risedronic and zoledronic acid. Etridonic acid is marketed under the trade name Didronel™. Clodronic acid is marketed under the trade name Bonefos™. Tiludronic acid is marketed under the trade name Skelid™. Pamidronic acid is marketed under the trade name Aredia™. Alendronic acid is marketed under the trade name Fosamax™. Ibandronic acid is marketed under the trade name Bondranat™. Risedronic acid is marketed under the trade name Actonel™. Zoledronic acid is marketed under the trade name Zometa™. The term "mTOR inhibitors" relates to compounds which inhibit the mammalian target of rapamycin (mTOR) and which possess antiproliferative activity such as sirolimus (Rapamune®), everolimus (Certican™), CCI-779 and ABT578.

The term "heparanase inhibitor" as used herein refers to compounds which target, decrease or inhibit heparin sulfate degradation. The term includes, but is not limited to, PI-88. The term "biological response modifier" as used herein refers to a lymphokine or interferons.

The term "inhibitor of Ras oncogenic isoforms", such as H-Ras, K-Ras, or N-Ras, as used herein refers to compounds which target, decrease or inhibit the oncogenic activity of Ras; for example, a "farnesyl transferase inhibitor" such as L-744832, DK8G557 or R115777 (Zamestra™). The term "telomerase inhibitor" as used herein refers to compounds which target, decrease or inhibit the activity of telomerase. Compounds which target, decrease or inhibit the activity of telomerase are especially compounds which inhibit the telomerase receptor, such as telomestatin.

The term "methionine aminopeptidase inhibitor" as used herein refers to compounds which target, decrease or inhibit the activity of methionine aminopeptidase. Compounds which target, decrease or inhibit the activity of methionine aminopeptidase include, but are not limited to, bengamide or a derivative thereof.

The term "proteasome inhibitor" as used herein refers to compounds which target, decrease or inhibit the activity of the proteasome. Compounds which target, decrease or inhibit the activity of the proteasome include, but are not limited to, Bortezomib (Velcade™) and MLN 341.

The term "matrix metalloproteinase inhibitor" or ("MMP" inhibitor) as used herein includes, but is not limited to, collagen peptidomimetic and nonpeptidomimetic inhibitors, tetracycline derivatives, e.g. hydroxamate peptidomimetic inhibitor batimastat and its orally bioavailable analogue marimastat (BB-2516), prinomastat (AG3340), metastat (NSC 683551) BMS-279251, BAY 12-9566, TAA211, MMI270B or AAJ996.

The term "compounds used in the treatment of hematologic malignancies" as used herein includes, but is not limited to, FMS-like tyrosine kinase inhibitors, which are compounds targeting, decreasing or inhibiting the activity of FMS-like tyrosine kinase receptors (Flt-3R); interferon, 1-β-D-arabinofuransylcytosine (ara-c) and bisulfan; ALK inhibitors, which are compounds which target, decrease or inhibit anaplastic lymphoma kinase, and Bcl-2 inhibitors.

Compounds which target, decrease or inhibit the activity of FMS-like tyrosine kinase receptors (Flt-3R) are especially compounds, proteins or antibodies which inhibit members of the Flt-3R receptor kinase family, such as PKC412, midostaurin, a staurosporine derivative, SU11248 and MLN518.

The term "HSP90 inhibitors" as used herein includes, but is not limited to, compounds targeting, decreasing or inhibiting the intrinsic ATPase activity of HSP90; degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins or antibodies which inhibit the ATPase activity of HSP90, such as 17-allylamino, 17-demethoxygeldanamycin (17AAG), a geldanamycin derivative; other geldanamycin related compounds; radicicol and HDAC inhibitors.

The term "antiproliferative antibodies" as used herein includes, but is not limited to, trastuzumab (Herceptin™), Trastuzumab-DM1, erbitux, bevacizumab (Avastin™), rituximab (Rituxan®), PR064553 (anti-CD40) and 2C4 Antibody. By antibodies is meant intact monoclonal antibodies, polyclonal antibodies, multispecific antibodies formed from at least 2 intact antibodies, and antibodies fragments so long as they exhibit the desired biological activity.

For the treatment of acute myeloid leukemia (AML), compounds of the current invention can be used in combination with standard leukemia therapies, especially in combination with therapies used for the treatment of AML. In particular, compounds of the current invention can be administered in combination with, for example, farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412. In some embodiments, the present invention provides a method of treating AML associated with an ITD and/or D835Y mutation, comprising administering a compound of the present invention together with a one or more FLT3 inhibitors. In some embodiments, the FLT3 inhibitors are selected from quizartinib (AC220), a staurosporine derivative (e.g. midostaurin or lestaurtinib), sorafenib, tandutinib, LY-2401401, LS-104, EB-10, famitinib, NOV-110302, NMS-P948, AST-487, G-749, SB-1317, S-209, SC-110219, AKN-028, fedratinib, tozasertib, and sunitinib. In some embodiments, the FLT3 inhibitors are selected from quizartinib, midostaurin, lestaurtinib, sorafenib, and sunitinib.

Other anti-leukemic compounds include, for example, Ara-C, a pyrimidine analog, which is the 2'-alpha-hydroxy ribose (arabinoside) derivative of deoxycytidine. Also included is the purine analog of hypoxanthine, 6-mercaptopurine (6-MP) and fludarabine phosphate. Compounds which target, decrease or inhibit activity of histone deacetylase (HDAC) inhibitors such as sodium butyrate and suberoylanilide hydroxamic acid (SAHA) inhibit the activity of the enzymes known as histone deacetylases. Specific HDAC inhibitors include MS275, SAHA, FK228 (formerly FR901228), Trichostatin A and compounds disclosed in U.S. Pat. No. 6,552,065 including, but not limited to, N-hydroxy-3-[4-[[[2-(2-methyl-1H-indol-3-yl)-ethyl]-amino]methyl]phenyl]-2E-2-propenamide, or a pharmaceutically acceptable salt thereof and N-hydroxy-3-[4-[(2-hydroxyethyl){2-(1H-indol-3-yl)ethyl]-amino]methyl]phenyl]-2E-2-propenamide, or a pharmaceutically acceptable salt thereof, especially the lactate salt. Somatostatin receptor antagonists as used herein refer to compounds which target, treat or inhibit the somatostatin receptor such as octreotide, and SOM230. Tumor cell damaging approaches refer to approaches such as ionizing radiation. The term "ionizing radiation" referred to above and hereinafter means ionizing radiation that occurs as either electromagnetic rays (such as X-rays and gamma rays) or particles (such as alpha and beta particles). Ionizing radiation is provided in, but not limited to, radiation therapy and is known in the art. See Hellman, Principles of Radiation Therapy, Cancer, in Principles and Practice of Oncology, Devita et al., Eds., $4^{th}$ Edition, Vol. 1, pp. 248-275 (1993).

Also included are EDG binders and ribonucleotide reductase inhibitors. The term "EDG binders" as used herein refers to a class of immunosuppressants that modulates lymphocyte recirculation, such as FTY720. The term "ribonucleotide reductase inhibitors" refers to pyrimidine or purine nucleoside analogs including, but not limited to, fludarabine and/or cytosine arabinoside (ara-C), 6-thioguanine, 5-fluorouracil, cladribine, 6-mercaptopurine (especially in combination with ara-C against ALL) and/or pentostatin. Ribonucleotide reductase inhibitors are especially hydroxyurea or 2-hydroxy-1H-isoindole-1,3-dione derivatives.

Also included are in particular those compounds, proteins or monoclonal antibodies of VEGF such as 1-(4-chloroanilino)-4-(4-pyridylmethyl)phthalazine or a pharmaceutically acceptable salt thereof, 1-(4-chloroanilino)-4-(4-pyridylmethyl)phthalazine succinate; Angiostatin™; Endostatin™; anthranilic acid amides; ZD4190; ZD6474; SU5416; SU6668; bevacizumab; or anti-VEGF antibodies or anti-VEGF receptor antibodies, such as rhuMAb and RHUFab, VEGF aptamer such as Macugon; FLT-4 inhibitors, FLT-3 inhibitors, VEGFR-2 IgGI antibody, Angiozyme (RPI 4610) and Bevacizumab (Avastin™)

Photodynamic therapy as used herein refers to therapy which uses certain chemicals known as photosensitizing compounds to treat or prevent cancers. Examples of photodynamic therapy include treatment with compounds, such as Visudyne™ and porfimer sodium.

Angiostatic steroids as used herein refers to compounds which block or inhibit angiogenesis, such as, e.g., anecortave, triamcinolone, hydrocortisone, 11-α-epihydrocotisol, cortexolone, 17α-hydroxyprogesterone, corticosterone, desoxycorticosterone, testosterone, estrone and dexamethasone.

Implants containing corticosteroids refers to compounds, such as fluocinolone and dexamethasone.

Other chemotherapeutic compounds include, but are not limited to, plant alkaloids, hormonal compounds and antagonists; biological response modifiers, preferably lymphokines or interferons; antisense oligonucleotides or oligonucleotide derivatives; shRNA or siRNA; or miscellaneous compounds or compounds with other or unknown mechanism of action.

The compounds of the invention are also useful as co-therapeutic compounds for use in combination with other drug substances such as anti-inflammatory, bronchodilatory or antihistamine drug substances, particularly in the treatment of obstructive or inflammatory airways diseases such as those mentioned hereinbefore, for example as potentiators of therapeutic activity of such drugs or as a means of reducing required dosaging or potential side effects of such drugs. A compound of the invention may be mixed with the other drug substance in a fixed pharmaceutical composition or it may be administered separately, before, simultaneously with or after the other drug substance. Accordingly the invention includes a combination of a compound of the invention as hereinbefore described with an anti-inflammatory, bronchodilatory, antihistamine or anti-tussive drug substance, said compound of the invention and said drug substance being in the same or different pharmaceutical composition.

Suitable anti-inflammatory drugs include steroids, in particular glucocorticosteroids such as budesonide, beclamethasone dipropionate, fluticasone propionate, ciclesonide or mometasone furoate; non-steroidal glucocorticoid receptor agonists; LTB4 antagonists such LY293111, CGS025019C, CP-195543, SC-53228, BIIL 284, ONO 4057, SB 209247; LTD4 antagonists such as montelukast and zafirlukast; PDE4 inhibitors such cilomilast (Ariflo® GlaxoSmithKline), Roflumilast (Byk Gulden),V-11294A (Napp), BAY19-8004 (Bayer), SCH-351591 (Schering-Plough), Arofylline (Almirall Prodesfarma), PD189659/PD168787 (Parke-Davis), AWD-12-281 (Asta Medica), CDC-801 (Celgene), SeICID™ CC-10004 (Celgene), VM554/UM565 (Vernalis), T-440 (Tanabe), KW-4490 (Kyowa Hakko Kogyo); A2a agonists; A2b antagonists; and beta-2 adrenoceptor agonists such as albuterol (salbutamol), metaproterenol, terbutaline, salmeterol fenoterol, procaterol, and especially, formoterol and pharmaceutically acceptable salts thereof. Suitable bronchodilatory drugs include anticholinergic or antimuscarinic compounds, in particular ipratropium bromide, oxitropium bromide, tiotropium salts and CHF 4226 (Chiesi), and glycopyrrolate.

Suitable antihistamine drug substances include cetirizine hydrochloride, acetaminophen, clemastine fumarate, promethazine, loratidine, desloratidine, diphenhydramine and fexofenadine hydrochloride, activastine, astemizole, azelastine, ebastine, epinastine, mizolastine and tefenadine.

Other useful combinations of compounds of the invention with anti-inflammatory drugs are those with antagonists of chemokine receptors, e.g. CCR-1, CCR-2, CCR-3, CCR-4, CCR-5, CCR-6, CCR-7, CCR-8, CCR-9 and CCR10, CXCR1, CXCR2, CXCR3, CXCR4, CXCR5, particularly CCR-5 antagonists such as Schering-Plough antagonists SC-351125, SCH-55700 and SCH-D, and Takeda antagonists such as N-[[4-[[[6,7-dihydro-2-(4-methylphenyl)-5H-benzo-cyclohepten-8-yl]carbonyl]amino]phenyl]-methyl]tetrahydro-N,N-dimethyl-2H-pyran-4-aminium chloride (TAK-770).

The structure of the active compounds identified by code numbers, generic or trade names may be taken from the actual edition of the standard compendium "The Merck Index" or from databases, e.g. Patents International (e.g. IMS World Publications).

A compound of the current invention may also be used in combination with known therapeutic processes, for example, the administration of hormones or radiation. In certain embodiments, a provided compound is used as a radiosensitizer, especially for the treatment of tumors which exhibit poor sensitivity to radiotherapy.

A compound of the current invention can be administered alone or in combination with one or more other therapeutic compounds, possible combination therapy taking the form of fixed combinations or the administration of a compound of the invention and one or more other therapeutic compounds being staggered or given independently of one another, or the combined administration of fixed combinations and one or more other therapeutic compounds. A compound of the current invention can besides or in addition be administered especially for tumor therapy in combination with chemotherapy, radiotherapy, immunotherapy, phototherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk.

Those additional agents may be administered separately from an inventive compound-containing composition, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of the current invention, an additional therapeutic agent, and a pharmaceutically acceptable carrier, adjuvant, or vehicle.

The amount of both an inventive compound and additional therapeutic agent (in those compositions which comprise an additional therapeutic agent as described above) that may be combined with the carrier materials to produce a single dosage form will vary depending upon the host treated and the particular mode of administration. Preferably, compositions of this invention should be formulated so that a dosage of between 0.01-100 mg/kg body weight/day of an inventive compound can be administered.

In those composition which comprise an additional therapeutic agent, that additional therapeutic agent and the compound of this invention may act synergistically. Therefore, the amount of additional therapeutic agent in such compositions will be less than that required in a monotherapy utilizing only that therapeutic agent. In such compositions a dosage of between 0.01-1,000 μg/kg body weight/day of the additional therapeutic agent can be administered.

The amount of one or more other therapeutic agent present in the compositions of this invention may be no more than the amount that would normally be administered in a composition comprising that therapeutic agent as the only active agent. Preferably the amount of one or more other therapeutic agent in the presently disclosed compositions will range from about 50% to 100% of the amount normally present in a composition comprising that agent as the only therapeutically active agent. In some embodiments, one or more other therapeutic agent is administered at a dosage of about 50%, about 55%, about 60%, about 65%, about 70%, about 75%, about 80%, about 85%, about 90%, or about 95% of the amount normally administered for that agent. As used herein, the phrase "normally administered" means the amount an FDA approved therapeutic agent is approvided for dosing per the FDA label insert.

The compounds of this invention, or pharmaceutical compositions thereof, may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by precoating the device with a pharmaceutically acceptable composition comprising a kinase inhibitor. Implantable devices coated with a compound of this invention are another embodiment of the present invention.

Exemplary Immuno-Oncology agents

In some embodiments, one or more other therapeutic agent is an immuno-oncology agent. As used herein, the term "an immuno-oncology agent" refers to an agent which is effective to enhance, stimulate, and/or up-regulate immune responses in a subject. In some embodiments, the administration of an immuno-oncology agent with a compound of the invention has a synergic effect in treating a cancer.

An immuno-oncology agent can be, for example, a small molecule drug, an antibody, or a biologic or small molecule. Examples of biologic immuno-oncology agents include, but are not limited to, cancer vaccines, antibodies, and cytokines. In some embodiments, an antibody is a monoclonal antibody. In some embodiments, a monoclonal antibody is humanized or human.

In some embodiments, an immuno-oncology agent is (i) an agonist of a stimulatory (including a co-stimulatory) receptor or (ii) an antagonist of an inhibitory (including a co-inhibitory) signal on T cells, both of which result in amplifying antigen-specific T cell responses.

Certain of the stimulatory and inhibitory molecules are members of the immunoglobulin super family (IgSF). One important family of membrane-bound ligands that bind to co-stimulatory or co-inhibitory receptors is the B7 family, which includes B7-1, B7-2, B7-H1 (PD-L1), B7-DC (PD-L2), B7-H2 (ICOS-L), B7-H3, B7-H4, B7-H5 (VISTA), and B7-H6. Another family of membrane bound ligands that bind to co-stimulatory or co-inhibitory receptors is the TNF family of molecules that bind to cognate TNF receptor family members, which includes CD40 and CD40L, OX-40, OX-40L, CD70, CD27L, CD30, CD30L, 4-1BBL, CD137 (4-1BB), TRAIL/Apo2-L, TRAILR1/DR4, TRAILR2/DR5, TRAILR3, TRAILR4, OPG, RANK, RANKL, TWEAKR/Fn14, TWEAK, BAFFR, EDAR, XEDAR, TACI, APRIL, BCMA, LTPR, LIGHT, DcR3, HVEM, VEGI/TL1A, TRAMP/DR3, EDAR, EDA1, XEDAR, EDA2, TNFR1, Lymphotoxin α/TNFβ, TNFR2, TNFα, LTβR, Lymphotoxin α1β2, FAS, FASL, RELT, DR6, TROY, NGFR.

In some embodiments, an immuno-oncology agent is a cytokine that inhibits T cell activation (e.g., IL-6, IL-10, TGF-β, VEGF, and other immunosuppressive cytokines) or a cytokine that stimulates T cell activation, for stimulating an immune response.

In some embodiments, a combination of a compound of the invention and an immuno-oncology agent can stimulate T cell responses. In some embodiments, an immuno-oncology agent is: (i) an antagonist of a protein that inhibits T cell activation (e.g., immune checkpoint inhibitors) such as CTLA-4, PD-1, PD-L1, PD-L2, LAG-3, TIM-3, Galectin 9, CEACAM-1, BTLA, CD69, Galectin-1, TIGIT, CD113, GPR56, VISTA, 2B4, CD48, GARP, PD1H, LAIR1, TIM-1, and TIM-4; or (ii) an agonist of a protein that stimulates T cell activation such as B7-1, B7-2, CD28, 4-1BB (CD137), 4-1BBL, ICOS, ICOS-L, OX40, OX40L, GITR, GITRL, CD70, CD27, CD40, DR3 and CD28H.

In some embodiments, an immuno-oncology agent is an antagonist of inhibitory receptors on NK cells or an agonists of activating receptors on NK cells. In some embodiments, an immuno-oncology agent is an antagonists of KIR, such as lirilumab.

In some embodiments, an immuno-oncology agent is an agent that inhibits or depletes macrophages or monocytes, including but not limited to CSF-1R antagonists such as CSF-AR antagonist antibodies including RG7155 (WO 2011/070024, US 2011/0165156, WO 2011/0107553, US 2012/0329997, WO 2011/131407, US 2013/0005949, WO 2013/087699, US 2014/0336363, WO 2013/119716, WO 2013/132044, US 2014/0079706) or FPA-008 (WO 2011/140249, US 2011/0274683; WO 2013/169264; WO 2014/036357, US 2014/0079699).

In some embodiments, an immuno-oncology agent is selected from agonistic agents that ligate positive costimulatory receptors, blocking agents that attenuate signaling through inhibitory receptors, antagonists, and one or more agents that increase systemically the frequency of anti-tumor T cells, agents that overcome distinct immune suppressive pathways within the tumor microenvironment (e.g., block inhibitory receptor engagement (e.g., PD-L1/PD-1 interactions), deplete or inhibit Tregs (e.g., using an anti-CD25 monoclonal antibody (e.g., daclizumab) or by ex vivo anti-CD25 bead depletion), inhibit metabolic enzymes such as IDO, or reverse/prevent T cell energy or exhaustion) and agents that trigger innate immune activation and/or inflammation at tumor sites.

In some embodiments, an immuno-oncology agent is a CTLA-4 antagonist. In some embodiments, a CTLA-4 antagonist is an antagonistic CTLA-4 antibody. In some embodiments, an antagonistic CTLA-4 antibody is YERVOY (ipilimumab) or tremelimumab.

In some embodiments, an immuno-oncology agent is a PD-1 antagonist. In some embodiments, a PD-1 antagonist is administered by infusion. In some embodiments, an immuno-oncology agent is an antibody or an antigen-binding portion thereof that binds specifically to a Programmed Death-1 (PD-1) receptor and inhibits PD-1 activity. In some embodiments, a PD-1 antagonist is an antagonistic PD-1 antibody. In some embodiments, an antagonistic PD-1 antibody is OPDIVO (nivolumab), KEYTRUDA (pembrolizumab), or MEDI-0680 (AMP-514; WO2012/145493). In some embodiments, an immuno-oncology agent may be pidilizumab (CT-011). In some embodiments, an immuno-oncology agent is a recombinant protein composed of the extracellular domain of PD-L2 (B7-DC) fused to the Fc portion of IgG1, called AMP-224.

In some embodiments, an immuno-oncology agent is a PD-L1 antagonist. In some embodiments, a PD-L1 antagonist is an antagonistic PD-L1 antibody. In some embodiments, a PD-L1 antibody is MPDL3280A (RG7446; WO 2010/077634, US 2010/0203056), durvalumab (MEDI4736), BMS-936559 (WO 2007/005874, US 2009/0055944), and MSB0010718C (WO 2013/079174, US 2014/0341917).

In some embodiments, an immuno-oncology agent is a LAG-3 antagonist. In some embodiments, a LAG-3 antagonist is an antagonistic LAG-3 antibody. In some embodiments, a LAG3 antibody is BMS-986016 (WO 2010/019570, US 2010/0150892, WO 2014/008218, US 2014/0093511), or IMP-731 or IMP-321 (WO 2008/132601, US 2010/0233183, WO 2009/044273, US 2011/0008331).

In some embodiments, an immuno-oncology agent is a CD137 (4-1BB) agonist. In some embodiments, a CD137 (4-1BB) agonist is an agonistic CD137 antibody. In some embodiments, a CD137 antibody is urelumab or PF-05082566 (WO12/32433).

In some embodiments, an immuno-oncology agent is a GITR agonist. In some embodiments, a GITR agonist is an agonistic GITR antibody. In some embodiments, a GITR antibody is BMS-986153, BMS-986156, TRX-518 (WO 2006/105021, US 2007/0098719, WO 2009/009116, US 2009/0136494), or MK-4166 (WO 2011/028683, US 2012/0189639).

In some embodiments, an immuno-oncology agent is an indoleamine (2,3)-dioxygenase (IDO) antagonist. In some embodiments, an IDO antagonist is selected from epacadostat (INCB024360, Incyte); indoximod (NLG-8189, NewLink Genetics Corporation); capmanitib (INC280, Novartis); GDC-0919 (Genentech/Roche); PF-06840003 (Pfizer); BMS:F001287 (Bristol-Myers Squibb); Phy906/KD108 (Phytoceutica); an enzyme that breaks down kynurenine (Kynase, Kyn Therapeutics); and NLG-919 (WO 2009/073620, US 2011/0053941, WO 2009/132238, US 2011/0136796, WO 2011/056652, US 2012/0277217, WO 2012/142237, US 2014/0066625).

In some embodiments, an immuno-oncology agent is an OX40 agonist. In some embodiments, an OX40 agonist is an agonistic OX40 antibody. In some embodiments, an OX40 antibody is MEDI-6383 or MEDI-6469.

In some embodiments, an immuno-oncology agent is an OX40L antagonist. In some embodiments, an OX40L antagonist is an antagonistic OX40 antibody. In some embodiments, an OX40L antagonist is RG-7888 (WO 2006/029879, U.S. Pat. No. 7,501,496).

In some embodiments, an immuno-oncology agent is a CD40 agonist. In some embodiments, a CD40 agonist is an agonistic CD40 antibody. In some embodiments, an immuno-oncology agent is a CD40 antagonist. In some embodiments, a CD40 antagonist is an antagonistic CD40 antibody. In some embodiments, a CD40 antibody is lucatumumab or dacetuzumab.

In some embodiments, an immuno-oncology agent is a CD27 agonist. In some embodiments, a CD27 agonist is an agonistic CD27 antibody. In some embodiments, a CD27 antibody is varlilumab.

In some embodiments, an immuno-oncology agent is MGA271 (to B7H3) (WO 2011/109400, US 2013/0149236).

In some embodiments, an immuno-oncology agent is abagovomab, adecatumumab, afutuzumab, alemtuzumab, anatumomab mafenatox, apolizumab, atezolimab, avelumab, blinatumomab, BMS-936559, catumaxomab, durvalumab, epacadostat, epratuzumab, indoximod, inotuzumab ozogamicin, intelumumab, ipilimumab, isatuximab, lambrolizumab, MED14736, MPDL3280A, nivolumab, obinutuzumab, ocaratuzumab, ofatumumab, olatatumab, pembrolizumab, pidilizumab, rituximab, ticilimumab, samalizumab, or tremelimumab.

In some embodiments, an immuno-oncology agent is an immunostimulatory agent. For example, antibodies blocking the PD-1 and PD-L1 inhibitory axis can unleash activated tumor-reactive T cells and have been shown in clinical trials to induce durable anti-tumor responses in increasing numbers of tumor histologies, including some tumor types that conventionally have not been considered immunotherapy sensitive. See, e.g., Okazaki, T. et al. (2013) Nat. Immunol. 14, 1212-1218; Zou et al. (2016) Sci. Transl. Med. 8. The anti-PD-1 antibody nivolumab (Opdivo®, Bristol-Myers Squibb, also known as ONO-4538, MDX1106 and BMS-936558), has shown potential to improve the overall survival in patients with RCC who had experienced disease progression during or after prior anti-angiogenic therapy.

In some embodiments, the immunomodulatory therapeutic specifically induces apoptosis of tumor cells. Approved immunomodulatory therapeutics which may be used in the present invention include pomalidomide (Pomalyst®, Celgene); lenalidomide (Revlimid®, Celgene); ingenol mebutate (Picato®, LEO Pharma).

In some embodiments, an immuno-oncology agent is a cancer vaccine. In some embodiments, the cancer vaccine is selected from sipuleucel-T (Provenge®, Dendreon/Valeant Pharmaceuticals), which has been approved for treatment of asymptomatic, or minimally symptomatic metastatic castrate-resistant (hormone-refractory) prostate cancer; and talimogene laherparepvec (Imlygic®, BioVex/Amgen, previously known as T-VEC), a genetically modified oncolytic viral therapy approved for treatment of unresectable cutaneous, subcutaneous and nodal lesions in melanoma. In some embodiments, an immuno-oncology agent is selected from an oncolytic viral therapy such as pexastimogene devacirepvec (PexaVec/JX-594, SillaJen/formerly Jennerex Biotherapeutics), a thymidine kinase- (TK-) deficient vaccinia virus engineered to express GM-CSF, for hepatocellular carcinoma (NCT02562755) and melanoma (NCT00429312); pelareorep (Reolysin®, Oncolytics Biotech), a variant of respiratory enteric orphan virus (reovirus) which does not replicate in cells that are not RAS-activated, in numerous cancers, including colorectal cancer (NCT01622543); prostate cancer (NCT01619813); head and neck squamous cell cancer (NCT01166542); pancreatic adenocarcinoma (NCT00998322); and non-small cell lung cancer (NSCLC) (NCT00861627); enadenotucirev (NG-348, PsiOxus, formerly known as ColoAd1), an adenovirus engineered to express a full length CD80 and an antibody fragment specific for the T-cell receptor CD3 protein, in ovarian cancer (NCT02028117); metastatic or advanced epithelial tumors such as in colorectal cancer, bladder cancer, head and neck squamous cell carcinoma and salivary gland cancer (NCT02636036); ONCOS-102 (Targovax/formerly Oncos), an adenovirus engineered to express GM-CSF, in melanoma (NCT03003676); and peritoneal disease, colorectal cancer or ovarian cancer (NCT02963831); GL-ONC1 (GLV-1h68/GLV-1hl53, Genelux GmbH), vaccinia viruses engineered to express beta-galactosidase (beta-gal)/beta-glucoronidase or beta-gal/human sodium iodide symporter (hNIS), respectively, were studied in peritoneal carcinomatosis (NCT01443260); fallopian tube cancer, ovarian cancer (NCT 02759588); or CG0070 (Cold Genesys), an adenovirus engineered to express GM-CSF, in bladder cancer (NCT02365818).

In some embodiments, an immuno-oncology agent is selected from JX-929 (SillaJen/formerly Jennerex Biotherapeutics), a TK- and vaccinia growth factor-deficient vaccinia virus engineered to express cytosine deaminase, which is able to convert the prodrug 5-fluorocytosine to the cytotoxic drug 5-fluorouracil; TG01 and TG02 (Targovax/formerly Oncos), peptide-based immunotherapy agents targeted for difficult-to-treat RAS mutations; and TILT-123 (TILT Biotherapeutics), an engineered adenovirus designated: Ad5/3-E2F-delta24-hTNFα-IRES-hIL20; and VSV-GP (ViraTherapeutics) a vesicular stomatitis virus (VSV) engineered to express the glycoprotein (GP) of lymphocytic choriomeningitis virus (LCMV), which can be further engineered to express antigens designed to raise an antigen-specific $CD8^+$ T cell response.

In some embodiments, an immuno-oncology agent is a T-cell engineered to express a chimeric antigen receptor, or CAR. The T-cells engineered to express such chimeric antigen receptor are referred to as a CAR-T cells.

CARs have been constructed that consist of binding domains, which may be derived from natural ligands, single chain variable fragments (scFv) derived from monoclonal antibodies specific for cell-surface antigens, fused to endodomains that are the functional end of the T-cell receptor (TCR), such as the CD3-zeta signaling domain from TCRs, which is capable of generating an activation signal in T lymphocytes. Upon antigen binding, such CARs link to endogenous signaling pathways in the effector cell and generate activating signals similar to those initiated by the TCR complex.

For example, in some embodiments the CAR-T cell is one of those described in U.S. Pat. No. 8,906,682, the entirety of each of which is herein incorporated by reference, which discloses CAR-T cells engineered to comprise an extracellular domain having an antigen binding domain (such as a domain that binds to CD19), fused to an intracellular signaling domain of the T cell antigen receptor complex zeta chain (such as CD3 zeta). When expressed in the T cell, the CAR is able to redirect antigen recognition based on the antigen binding specificity. In the case of CD19, the antigen is expressed on malignant B cells. Over 200 clinical trials are currently in progress employing CAR-T in a wide range of indications. [https://clinicaltrials.gov/ct2/results?term=chimeric+antigen+receptors&pg=1].

In some embodiments, an immunostimulatory agent is an activator of retinoic acid receptor-related orphan receptor γ (RORγt). RORγt is a transcription factor with key roles in the differentiation and maintenance of Type 17 effector subsets of CD4+ (Th17) and CD8+ (Tc17) T cells, as well as the differentiation of IL-17 expressing innate immune cell subpopulations such as NK cells. In some embodiments, an activator of RORγt is LYC-55716 (Lycera), which is currently being evaluated in clinical trials for the treatment of solid tumors (NCT02929862).

In some embodiments, an immunostimulatory agent is an agonist or activator of a toll-like receptor (TLR). Suitable activators of TLRs include an agonist or activator of TLR9 such as SD-101 (Dynavax). SD-101 is an immunostimulatory CpG which is being studied for B-cell, follicular and other lymphomas (NCT02254772). Agonists or activators of TLR8 which may be used in the present invention include motolimod (VTX-2337, VentiRx Pharmaceuticals) which is being studied for squamous cell cancer of the head and neck (NCT02124850) and ovarian cancer (NCT02431559).

Other immuno-oncology agents that may be used in the present invention include urelumab (BMS-663513, Bristol-Myers Squibb), an anti-CD137 monoclonal antibody; varlilumab (CDX-1127, Celldex Therapeutics), an anti-CD27 monoclonal antibody; BMS-986178 (Bristol-Myers Squibb), an anti-OX40 monoclonal antibody; lirilumab (IPH2102/BMS-986015, Innate Pharma, Bristol-Myers Squibb), an anti-KIR monoclonal antibody; monalizumab (IPH2201, Innate Pharma, AstraZeneca) an anti-NKG2A monoclonal antibody; andecaliximab (GS-5745, Gilead Sciences), an anti-MMP9 antibody; MK-4166 (Merck & Co.), an anti-GITR monoclonal antibody.

In some embodiments, an immunostimulatory agent is selected from elotuzumab, mifamurtide, an agonist or activator of a toll-like receptor, and an activator of RORγt.

In some embodiments, an immunostimulatory therapeutic is recombinant human interleukin 15 (rhIL-15). rhIL-15 has been tested in the clinic as a therapy for melanoma and renal cell carcinoma (NCT01021059 and NCT01369888) and leukemias (NCT02689453). In some embodiments, an immunostimulatory agent is recombinant human interleukin 12 (rhIL-12). In some embodiments, an IL-15 based immunotherapeutic is heterodimeric IL-15 (hetIL-15, Novartis/Admune), a fusion complex composed of a synthetic form of endogenous IL-15 complexed to the soluble IL-15 binding protein IL-15 receptor alpha chain (IL15:sIL-15RA), which has been tested in Phase 1 clinical trials for melanoma, renal cell carcinoma, non-small cell lung cancer and head and neck squamous cell carcinoma (NCT02452268). In some embodiments, a recombinant human interleukin 12 (rhIL-12) is NM-IL-12 (Neumedicines, Inc.), NCT02544724, or NCT02542124.

In some embodiments, an immuno-oncology agent is selected from those descripted in Jerry L. Adams ET. AL., "Big opportunities for small molecules in immuno-oncology," Cancer Therapy 2015, Vol. 14, pages 603-622, the content of which is incorporated herein by reference in its entirety. In some embodiments, an immuno-oncology agent is selected from the examples described in Table 1 of Jerry L. Adams ET. AL. In some embodiments, an immuno-oncology agent is a small molecule targeting an immuno-oncology target selected from those listed in Table 2 of Jerry L. Adams ET. AL. In some embodiments, an immuno-oncology agent is a small molecule agent selected from those listed in Table 2 of Jerry L. Adams ET. AL.

In some embodiments, an immuno-oncology agent is selected from the small molecule immuno-oncology agents described in Peter L. Toogood, "Small molecule immuno-oncology therapeutic agents," Bioorganic & Medicinal Chemistry Letters 2018, Vol. 28, pages 319-329, the content of which is incorporated herein by reference in its entirety. In some embodiments, an immuno-oncology agent is an agent targeting the pathways as described in Peter L. Toogood.

In some embodiments, an immuno-oncology agent is selected from those described in Sandra L. Ross et al., "Bispecific T cell engager (BiTE®) antibody constructs can mediate bystander tumor cell killing", PLoS ONE 12(8): e0183390, the content of which is incorporated herein by reference in its entirety. In some embodiments, an immuno-oncology agent is a bispecific T cell engager (BiTE®) antibody construct. In some embodiments, a bispecific T cell engager (BiTE®) antibody construct is a CD19/CD3 bispecific antibody construct. In some embodiments, a bispecific T cell engager (BiTE®) antibody construct is an EGFR/CD3 bispecific antibody construct. In some embodiments, a bispecific T cell engager (BiTE®) antibody construct activates T cells. In some embodiments, a bispecific T cell engager (BiTE®) antibody construct activates T cells, which release cytokines inducing upregulation of intercellular adhesion molecule 1 (ICAM-1) and FAS on bystander cells. In some embodiments, a bispecific T cell engager (BiTE®) antibody construct activates T cells which result in induced bystander cell lysis. In some embodiments, the bystander cells are in solid tumors. In some embodiments, the bystander cells being lysed are in proximity to the BiTE®-activated T cells. In some embodiment, the bystander cells comprises tumor-associated antigen (TAA) negative cancer cells. In some embodiment, the bystander cells comprise EGFR-negative cancer cells. In some embodiments, an immuno-oncology agent is an antibody which blocks the PD-L1/PD1 axis and/or CTLA4. In some embodiments, an immuno-oncology agent is an ex-vivo expanded tumor-infiltrating T cell. In some embodiments, an immuno-oncology agent is a bispecific antibody construct or chimeric antigen receptors (CARs) that directly connect T cells with tumor-associated surface antigens (TAAs).

Exemplary Immune Checkpoint Inhibitors

In some embodiments, an immuno-oncology agent is an immune checkpoint inhibitor as described herein.

The term "checkpoint inhibitor" as used herein relates to agents useful in preventing cancer cells from avoiding the immune system of the patient. One of the major mechanisms of anti-tumor immunity subversion is known as "T-cell exhaustion," which results from chronic exposure to antigens that has led to up-regulation of inhibitory receptors. These inhibitory receptors serve as immune checkpoints in order to prevent uncontrolled immune reactions.

PD-1 and co-inhibitory receptors such as cytotoxic T-lymphocyte antigen 4 (CTLA-4, B and T Lymphocyte Attenuator (BTLA; CD272), T cell Immunoglobulin and Mucin domain-3 (Tim-3), Lymphocyte Activation Gene-3 (Lag-3; CD223), and others are often referred to as a checkpoint regulators. They act as molecular "gatekeepers" that allow extracellular information to dictate whether cell cycle progression and other intracellular signaling processes should proceed.

In some embodiments, an immune checkpoint inhibitor is an antibody to PD-1. PD-1 binds to the programmed cell death 1 receptor (PD-1) to prevent the receptor from binding to the inhibitory ligand PDL-1, thus overriding the ability of tumors to suppress the host anti-tumor immune response.

In one aspect, the checkpoint inhibitor is a biologic therapeutic or a small molecule. In another aspect, the checkpoint inhibitor is a monoclonal antibody, a humanized antibody, a fully human antibody, a fusion protein or a combination thereof. In a further aspect, the checkpoint inhibitor inhibits a checkpoint protein selected from CTLA-4, PDL1, PDL2, PD1, B7-H3, B7-H4, BTLA, HVEM, TIM3, GAL9, LAG3, VISTA, KIR, 2B4, CD160, CGEN-15049, CHK 1, CHK2, A2aR, B-7 family ligands or a combination thereof. In an additional aspect, the checkpoint inhibitor interacts with a ligand of a checkpoint protein selected from CTLA-4, PDL1, PDL2, PD1, B7-H3, B7-H4, BTLA, HVEM, TIM3, GAL9, LAG3, VISTA, KIR, 2B4, CD160, CGEN-15049, CHK 1, CHK2, A2aR, B-7 family ligands or a combination thereof. In an aspect, the checkpoint inhibitor is an immunostimulatory agent, a T cell growth factor, an interleukin, an antibody, a vaccine or a combination thereof. In a further aspect, the interleukin is IL-7 or IL-15. In a specific aspect, the interleukin is glycosylated IL-7. In an additional aspect, the vaccine is a dendritic cell (DC) vaccine.

Checkpoint inhibitors include any agent that blocks or inhibits in a statistically significant manner, the inhibitory pathways of the immune system. Such inhibitors may include small molecule inhibitors or may include antibodies, or antigen binding fragments thereof, that bind to and block or inhibit immune checkpoint receptors or antibodies that bind to and block or inhibit immune checkpoint receptor ligands. Illustrative checkpoint molecules that may be targeted for blocking or inhibition include, but are not limited to, CTLA-4, PDL1, PDL2, PD1, B7-H3, B7-H4, BTLA, HVEM, GAL9, LAG3, TIM3, VISTA, KIR, 2B4 (belongs to the CD2 family of molecules and is expressed on all NK, γδ, and memory CD8+ (αβ) T cells), CD160 (also referred to as BY55), CGEN-15049, CHK 1 and CHK2 kinases, A2aR, and various B-7 family ligands. B7 family ligands include, but are not limited to, B7-1, B7-2, B7-DC, B7-H1, B7-H2, B7-H3, B7-H4, B7-H5, B7-H6 and B7-H7. Checkpoint inhibitors include antibodies, or antigen binding fragments thereof, other binding proteins, biologic therapeutics, or small molecules, that bind to and block or inhibit the activity of one or more of CTLA-4, PDL1, PDL2, PD1, BTLA, HVEM, TIM3, GAL9, LAG3, VISTA, KIR, 2B4, CD160 and CGEN-15049. Illustrative immune checkpoint inhibitors include Tremelimumab (CTLA-4 blocking antibody), anti-OX40, PD-L1 monoclonal Antibody (Anti-B7-H1; MEDI4736), MK-3475 (PD-1 blocker), Nivolumab (anti-PD1 antibody), CT-011 (anti-PD1 antibody), BY55 monoclonal antibody, AMP224 (anti-PDL1 antibody), BMS-936559 (anti-PDL1 antibody), MPLDL3280A (anti-PDL1 antibody), MSB0010718C (anti-PDL1 antibody), and ipilimumab (anti-CTLA-4 checkpoint inhibitor). Checkpoint protein ligands include, but are not limited to PD-L1, PD-L2, B7-H3, B7-H4, CD28, CD86 and TIM-3.

In certain embodiments, the immune checkpoint inhibitor is selected from a PD-1 antagonist, a PD-L1 antagonist, and a CTLA-4 antagonist. In some embodiments, the checkpoint inhibitor is selected from the group consisting of nivolumab (Opdivo®), ipilimumab (Yervoy®), and pembrolizumab (Keytruda®). In some embodiments, the checkpoint inhibitor is selected from nivolumab (anti-PD-1 antibody, Opdivo®, Bristol-Myers Squibb); pembrolizumab (anti-PD-1 antibody, Keytruda®, Merck); ipilimumab (anti-CTLA-4 antibody, Yervoy®, Bristol-Myers Squibb); durvalumab (anti-PD-L1 antibody, Imfinzi®, AstraZeneca); and atezolizumab (anti-PD-L1 antibody, Tecentriq®, Genentech).

In some embodiments, the checkpoint inhibitor is selected from the group consisting of lambrolizumab (MK-3475), nivolumab (BMS-936558), pidilizumab (CT-011), AMP-224, MDX-1105, MEDI4736, MPDL3280A, BMS-936559, ipilimumab, lirlumab, IPH2101, pembrolizumab (Keytruda®), and tremelimumab.

In some embodiments, an immune checkpoint inhibitor is REGN2810 (Regeneron), an anti-PD-1 antibody tested in patients with basal cell carcinoma (NCT03132636); NSCLC (NCT03088540); cutaneous squamous cell carcinoma (NCT02760498); lymphoma (NCT02651662); and melanoma (NCT03002376); pidilizumab (CureTech), also known as CT-011, an antibody that binds to PD-1, in clinical trials for diffuse large B-cell lymphoma and multiple myeloma; avelumab (Bavencio®, Pfizer/Merck KGaA), also known as MSB0010718C), a fully human IgG1 anti-PD-L1 antibody, in clinical trials for non-small cell lung cancer, Merkel cell carcinoma, mesothelioma, solid tumors, renal cancer, ovarian cancer, bladder cancer, head and neck cancer, and gastric cancer; or PDR001 (Novartis), an inhibitory antibody that binds to PD-1, in clinical trials for non-small cell lung cancer, melanoma, triple negative breast cancer and advanced or metastatic solid tumors. Tremelimumab (CP-675,206; Astrazeneca) is a fully human monoclonal antibody against CTLA-4 that has been in studied in clinical trials for a number of indications, including: mesothelioma, colorectal cancer, kidney cancer, breast cancer, lung cancer and non-small cell lung cancer, pancreatic ductal adenocarcinoma, pancreatic cancer, germ cell cancer, squamous cell cancer of the head and neck, hepatocellular carcinoma, prostate cancer, endometrial cancer, metastatic cancer in the liver, liver cancer, large B-cell lymphoma, ovarian cancer, cervical cancer, metastatic anaplastic thyroid cancer, urothelial cancer, fallopian tube cancer, multiple myeloma, bladder cancer, soft tissue sarcoma, and melanoma. AGEN-1884 (Agenus) is an anti-CTLA4 antibody that is being studied in Phase 1 clinical trials for advanced solid tumors (NCT02694822).

In some embodiments, a checkpoint inhibitor is an inhibitor of T-cell immunoglobulin mucin containing protein-3 (TIM-3). TIM-3 inhibitors that may be used in the present invention include TSR-022, LY3321367 and MBG453. TSR-022 (Tesaro) is an anti-TIM-3 antibody which is being studied in solid tumors (NCT02817633). LY3321367 (Eli Lilly) is an anti-TIM-3 antibody which is being studied in solid tumors (NCT03099109). MBG453 (Novartis) is an anti-TIM-3 antibody which is being studied in advanced malignancies (NCT02608268).

In some embodiments, a checkpoint inhibitor is an inhibitor of T cell immunoreceptor with Ig and ITIM domains, or TIGIT, an immune receptor on certain T cells and NK cells. TIGIT inhibitors that may be used in the present invention include BMS-986207 (Bristol-Myers Squibb), an anti-TIGIT monoclonal antibody (NCT02913313); OMP-313M32 (Oncomed); and anti-TIGIT monoclonal antibody (NCT03119428).

In some embodiments, a checkpoint inhibitor is an inhibitor of Lymphocyte Activation Gene-3 (LAG-3). LAG-3 inhibitors that may be used in the present invention include BMS-986016 and REGN3767 and IMP321. BMS-986016 (Bristol-Myers Squibb), an anti-LAG-3 antibody, is being studied in glioblastoma and gliosarcoma (NCT02658981). REGN3767 (Regeneron), is also an anti-LAG-3 antibody, and is being studied in malignancies (NCT03005782). IMP321 (Immutep S. A.) is an LAG-3-Ig fusion protein, being studied in melanoma (NCT02676869); adenocarcinoma (NCT02614833); and metastatic breast cancer (NCT00349934).

Checkpoint inhibitors that may be used in the present invention include OX40 agonists. OX40 agonists that are being studied in clinical trials include PF-04518600/PF-8600 (Pfizer), an agonistic anti-OX40 antibody, in metastatic kidney cancer (NCT03092856) and advanced cancers and neoplasms (NCT02554812; NCT05082566); GSK3174998 (Merck), an agonistic anti-OX40 antibody, in Phase 1 cancer trials (NCT02528357); MEDI0562 (Medimmune/AstraZeneca), an agonistic anti-OX40 antibody, in advanced solid tumors (NCT02318394 and NCT02705482); MEDI6469, an agonistic anti-OX40 antibody (Medimmune/AstraZeneca), in patients with colorectal cancer (NCT02559024), breast cancer (NCT01862900), head and neck cancer (NCT02274155) and metastatic prostate cancer (NCT01303705); and BMS-986178 (Bristol-Myers Squibb) an agonistic anti-OX40 antibody, in advanced cancers (NCT02737475).

Checkpoint inhibitors that may be used in the present invention include CD137 (also called 4-1BB) agonists. CD137 agonists that are being studied in clinical trials include utomilumab (PF-05082566, Pfizer) an agonistic anti-CD137 antibody, in diffuse large B-cell lymphoma (NCT02951156) and in advanced cancers and neoplasms (NCT02554812 and NCT05082566); urelumab (BMS-663513, Bristol-Myers Squibb), an agonistic anti-CD137 antibody, in melanoma and skin cancer (NCT02652455) and glioblastoma and gliosarcoma (NCT02658981).

Checkpoint inhibitors that may be used in the present invention include CD27 agonists. CD27 agonists that are being studied in clinical trials include varlilumab (CDX-1127, Celldex Therapeutics) an agonistic anti-CD27 antibody, in squamous cell head and neck cancer, ovarian carcinoma, colorectal cancer, renal cell cancer, and glioblastoma (NCT02335918); lymphomas (NCT01460134); and glioma and astrocytoma (NCT02924038).

Checkpoint inhibitors that may be used in the present invention include glucocorticoid-induced tumor necrosis factor receptor (GITR) agonists. GITR agonists that are being studied in clinical trials include TRX518 (Leap Therapeutics), an agonistic anti-GITR antibody, in malignant melanoma and other malignant solid tumors (NCT01239134 and NCT02628574); GWN323 (Novartis), an agonistic anti-GITR antibody, in solid tumors and lymphoma (NCT 02740270); INCAGN01876 (Incyte/Agenus), an agonistic anti-GITR antibody, in advanced cancers (NCT02697591 and NCT03126110); MK-4166 (Merck), an agonistic anti-GITR antibody, in solid tumors (NCT02132754) and MEDI1873 (Medimmune/AstraZeneca), an agonistic hexameric GITR-ligand molecule with a human IgGI Fc domain, in advanced solid tumors (NCT02583165).

Checkpoint inhibitors that may be used in the present invention include inducible T-cell co-stimulator (ICOS, also known as CD278) agonists. ICOS agonists that are being studied in clinical trials include MEDI-570 (Medimmune), an agonistic anti-ICOS antibody, in lymphomas (NCT02520791); GSK3359609 (Merck), an agonistic anti-ICOS antibody, in Phase 1 (NCT02723955); JTX-2011 (Jounce Therapeutics), an agonistic anti-ICOS antibody, in Phase 1 (NCT02904226).

Checkpoint inhibitors that may be used in the present invention include killer IgG-like receptor (KIR) inhibitors. KIR inhibitors that are being studied in clinical trials include lirilumab (IPH2102/BMS-986015, Innate Pharma/Bristol-Myers Squibb), an anti-KIR antibody, in leukemias (NCT01687387, NCT02399917, NCT02481297, NCT02599649), multiple myeloma (NCT02252263), and lymphoma (NCT01592370); IPH2101 (1-7F9, Innate Pharma) in myeloma (NCT01222286 and NCT01217203); and IPH4102 (Innate Pharma), an anti-KIR antibody that binds to three domains of the long cytoplasmic tail (KIR3DL2), in lymphoma (NCT02593045).

Checkpoint inhibitors that may be used in the present invention include CD47 inhibitors of interaction between CD47 and signal regulatory protein alpha (SIRPa). CD47/SIRPa inhibitors that are being studied in clinical trials include ALX-148 (Alexo Therapeutics), an antagonistic variant of (SIRPa) that binds to CD47 and prevents CD47/SIRPa-mediated signaling, in phase 1 (NCT03013218); TTI-621 (SIRPa-Fc, Trillium Therapeutics), a soluble recombinant fusion protein created by linking the N-terminal CD47-binding domain of SIRPa with the Fc domain of human IgG1, acts by binding human CD47, and preventing it from delivering its "do not eat" signal to macrophages, is in clinical trials in Phase 1 (NCT02890368 and NCT02663518); CC-90002 (Celgene), an anti-CD47 antibody, in leukemias (NCT02641002); and Hu5F9-G4 (Forty Seven, Inc.), in colorectal neoplasms and solid tumors (NCT02953782), acute myeloid leukemia (NCT02678338) and lymphoma (NCT02953509).

Checkpoint inhibitors that may be used in the present invention include CD73 inhibitors. CD73 inhibitors that are being studied in clinical trials include MEDI9447 (Medimmune), an anti-CD73 antibody, in solid tumors (NCT02503774); and BMS-986179 (Bristol-Myers Squibb), an anti-CD73 antibody, in solid tumors (NCT02754141).

Checkpoint inhibitors that may be used in the present invention include agonists of stimulator of interferon genes protein (STING, also known as transmembrane protein 173, or TMEM173). Agonists of STING that are being studied in clinical trials include MK-1454 (Merck), an agonistic synthetic cyclic dinucleotide, in lymphoma (NCT03010176); and ADU-S100 (MIW815, Aduro Biotech/Novartis), an agonistic synthetic cyclic dinucleotide, in Phase 1 (NCT02675439 and NCT03172936).

Checkpoint inhibitors that may be used in the present invention include CSF1R inhibitors. CSF1R inhibitors that are being studied in clinical trials include pexidartinib (PLX3397, Plexxikon), a CSF1R small molecule inhibitor, in colorectal cancer, pancreatic cancer, metastatic and advanced cancers (NCT02777710) and melanoma, non-small cell lung cancer, squamous cell head and neck cancer, gastrointestinal stromal tumor (GIST) and ovarian cancer (NCT02452424); and IMC-CS4 (LY3022855, Lilly), an anti-CSF-1R antibody, in pancreatic cancer (NCT03153410), melanoma (NCT03101254), and solid tumors (NCT02718911); and BLZ945 (4-[2((1R,2R)-2-hydroxycyclohexylamino)-benzothiazol-6-yloxyl]-pyridine-2-carboxylic acid methylamide, Novartis), an orally available inhibitor of CSF1R, in advanced solid tumors (NCT02829723).

Checkpoint inhibitors that may be used in the present invention include NKG2A receptor inhibitors. NKG2A receptor inhibitors that are being studied in clinical trials include monalizumab (IPH2201, Innate Pharma), an anti-NKG2A antibody, in head and neck neoplasms (NCT02643550) and chronic lymphocytic leukemia (NCT02557516).

In some embodiments, the immune checkpoint inhibitor is selected from nivolumab, pembrolizumab, ipilimumab, avelumab, durvalumab, atezolizumab, or pidilizumab.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

Abbreviations

Ac: acetyl
AcOH: acetic acid
ACN: acetonitrile
Ad: adamantly
AIBN: 2,2'-azo bisisobutyronitrile
Anhyd: anhydrous
Aq: aqueous
$B_2Pin_2$: bis (pinacolato)diboron -4,4,4',4',5,5,5',5'-octamethyl-2,2'-bi(1,3,2-dioxaborolane)
BINAP: 2,2'-bis(diphenylphosphino)-1,1'-binaphthyl
$BH_3$: Borane
Bn: benzyl
Boc: tert-butoxycarbonyl
$Boc_2O$: di-tert-butyl dicarbonate
BPO: benzoyl peroxide
$^nBuOH$: n-butanol
CDI: carbonyldiimidazole
COD: cyclooctadiene
d: days
DABCO: 1,4-diazobicyclo[2.2.2]octane
DAST: diethylaminosulfur trifluoride
dba: dibenzylideneacetone
DBU: 1,8-diazobicyclo[5.4.0]undec-7-ene
DCE: 1,2-dichloroethane
DCM: dichloromethane DEA: diethylamine
DHP: dihydropyran
DIBAL-H: diisobutylaluminum hydride
DIPA: diisopropylamine
DIPEA or DIEA: N,N-diisopropylethylamine
DMA: N,N-dimethylacetamide
DME: 1,2-dimethoxyethane
DMAP: 4-dimethylaminopyridine
DMF: N,N-dimethylformamide
DMP: Dess-Martin periodinane
DMSO-dimethyl sulfoxide
DPPA: diphenylphosphoryl azide
dppf: 1,1'-bis(diphenylphosphino)ferrocene
EDC or EDCI: 1-(3-dimethylaminopropyl)-3-ethylcarbodiimide hydrochloride
ee: enantiomeric excess
ESI: electrospray ionization
EA: ethyl acetate
EtOAc: ethyl acetate
EtOH: ethanol
FA: formic acid
h or hrs: hours
HATU: N,N,N',N'-tetramethyl-O-(7-azabenzotriazol-1-yl)uronium hexafluorophosphate
HCL: hydrochloric acid
HPLC: high performance liquid chromatography
HOAc: acetic acid
IBX: 2-iodoxybenzoic acid
IPA: isopropyl alcohol
KHMDS: potassium hexamethyldisilazide
$K_2CO_3$: potassium carbonate
LAH: lithium aluminum hydride
LDA: lithium diisopropylamide
m-CPBA: meta-chloroperbenzoic acid
M: molar
MeCN: acetonitrile
MeOH: methanol
$Me_2S$: dimethyl sulfide
MeONa: sodium methylate
Mel: iodomethane
min: minutes
mL: milliliters
mM: millimolar
mmol: millimoles
MPa: mega pascal
MOMCI: methyl chloromethyl ether
MsCl: methanesulfonyl chloride
MTBE: methyl tert-butyl ether
nBuLi: n-butyllithium
$NaNO_2$: sodium nitrite
NaOH: sodium hydroxide
$Na_2SO_4$: sodium sulfate
NBS: N-bromosuccinimide
NCS: N-chlorosuccinimide
NFSI: N-Fluorobenzenesulfonimide
NMO: N-methylmorpholine N-oxide
NMP: N-methylpyrrolidine
NMR: Nuclear Magnetic Resonance
° C.: degrees Celsius
Pd/C: Palladium on Carbon
$Pd(OAc)_2$: Palladium Acetate
PBS: phosphate buffered saline
PE: petroleum ether
$POCl_3$: phosphorus oxychloride
$PPh_3$: triphenylphosphine
PyBOP: (Benzotriazol-1-yloxy)tripyrrolidinophosphonium hexafluorophosphate
Rel: relative
R.T. or rt: room temperature
sat: saturated
SEMCl: chloromethyl-2-trimethylsilylethyl ether
SFC: supercritical fluid chromatography
$SOCl_2$: sulfur dichloride
tBuOK: potassium tert-butoxide
TBAB: tetrabutylammonium bromide
TBAI: tetrabutylammonium iodide
TEA: triethylamine
Tf: trifluoromethanesulfonate
TfAA, TFMSA or $Tf_2O$: trifluoromethanesulfonic anhydride
TFA: trifluoracetic acid
TIPS: triisopropylsilyl
THF: tetrahydrofuran
THP: tetrahydropyran
TLC: thin layer chromatography
TMEDA: tetramethylethylenediamine
pTSA: para-toluenesulfonic acid
wt: weight
Xantphos: 4,5-bis(diphenylphosphino)-9,9-dimethylxanthene General Synthetic Methods The following examples are intended to illustrate the invention and are not to be construed as being limitations thereon. Temperatures are given in degrees centigrade. If not mentioned otherwise, all evaporations are performed under reduced pressure, preferably between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized to synthesis the compounds of the present invention are either commercially available or can be produced by organic synthesis methods known to one of ordinary skill in the art (Houben-Weyl 4th Ed. 1952, Methods of Organic Synthesis, Thieme, Volume 21). Further, the compounds of the present invention can be produced by organic synthesis methods known to one of ordinary skill in the art as shown in the following examples.

All reactions are carried out under nitrogen or argon unless otherwise stated.

Proton NMR ($^1$H NMR) is conducted in deuterated solvent. In certain compounds disclosed herein, one or more $^1$H shifts overlap with residual proteo solvent signals; these signals have not been reported in the experimental provided hereinafter.

TABLE 3

| Analytical instruments | |
|---|---|
| LCMS | Shimadzu UFLC MS: LCMS-2020<br>Agilent Technologies 1200 series MS: Agilent Technologies 6110<br>Agilent Technologies 1200 series MS: LC/MSD VL |
| NMR | BRUKER AVANCE III/400; Frequency (MHz) 400.13; Nucleus: 1H; Number of Transients: 8 |
| Prep-HPLC | Gilson GX-281 systems: instruments GX-A, GX-B, GX-C, GX-D, GX-E, GX-F, GX-G and GX-H |
| GCMS | SHIMADZU GCMS-QP2010 Ultra |
| Analytical cSFC | Agilent Technologies 1290 Infinity |
| Prep-cSFC | Waters SFC Prep 80 |

For acidic LCMS data: LCMS was recorded on an Agilent 1200 Series LC/MSD or Shimadzu LCMS2020 equipped with electro-spray ionization and quadruple MS detector [ES+ve to give $MH^+$] and equipped with Chromolith Flash RP-18e 25*2.0 mm, eluting with 0.0375 vol % TFA in water (solvent A) and 0.01875 vol % TFA in acetonitrile (solvent B). Other LCMS was recorded on an Agilent 1290 Infinity RRLC attached with Agilent 6120 Mass detector. The column used was BEH C18 50*2.1 mm, 1.7 micron. Column flow was 0.55 ml/min and mobile phase were used (A) 2 mM Ammonium Acetate in 0.1% Formic Acid in Water and (B) 0.1% Formic Acid in Acetonitrile.

For basic LCMS data: LCMS was recorded on an Agilent 1200 Series LC/MSD or Shimadzu LCMS 2020 equipped with electro-spray ionization and quadruple MS detector [ES+ve to give $MH^+$] and equipped with Xbridge C18, 2.1×50 mm columns packed with 5 mm C18-coated silica or Kinetex EVO C18 2.1×30 mm columns packed with 5 mm C18-coated silica, eluting with 0.05 vol % $NH_3{\cdot}H_2O$ in water (solvent A) and acetonitrile (solvent B).

HPLC Analytical Method: HPLC was carried out on X Bridge C18 150*4.6 mm, 5 micron. Column flow was 1.0 ml/min and mobile phase were used (A) 0.1% Ammonia in water and (B) 0.1% Ammonia in Acetonitrile.

Prep HPLC Analytical Method: The compound was purified on Shimadzu LC-20AP and UV detector. The column used was X-BRIDGE C18 (250*19)mm, 5μ. Column flow was 16.0 ml/min. Mobile phase were used (A) 0.1% Formic Acid in Water and (B) Acetonitrile Basic method used (A) 5 mM ammonium bicarbonate and 0.1% NH3 in Water and (B) Acetonitrile or (A) 0.1% Ammonium Hydroxide in Water and (B) Acetonitrile. The UV spectra were recorded at 202 nm & 254 nm.

NMR Method: The 1H NMR spectra were recorded on a Bruker Ultra Shield Advance 400 MHz/5 mm Probe (BBFO). The chemical shifts are reported in part-per-million.

Example 1. 3-(9H-Carbazol-9-yl)piperidine-2,6-dione (1)

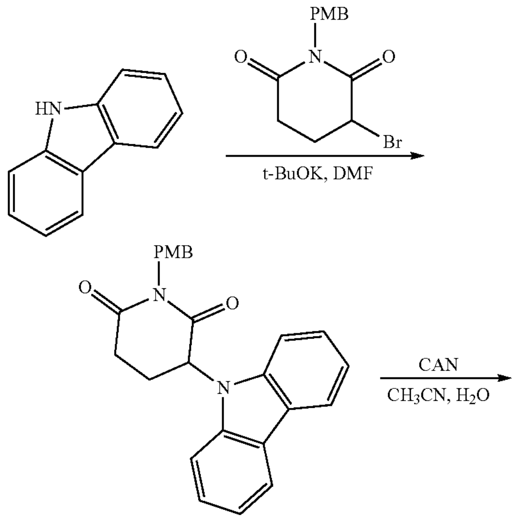

-continued

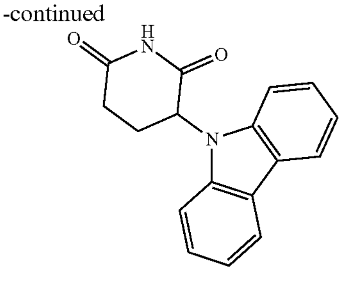

1

Step 1. 3-(9H-Carbazol-9-yl)-1-(4-methoxybenzyl)piperidine-2,6-dione

To a solution of 9H-carbazole (2.0 g, 12.0 mmol) in DMF (20 mL) was added t-BuOK (1.61 g, 14.4 mmol) at 0° C. The mixture was stirred at 0-10° C. for 1 hour under $N_2$. Then 3-bromo-1-(4-methoxybenzyl)piperidine-2,6-dione (5.59 g, 18.0 mmol) in DMF (30 mL) was added to the reaction mixture at 0-10° C. during 20 minutes. After addition, the mixture was stirred at room temperature for 17 hours under $N_2$. On completion, the reaction was quenched by water and extracted with EA. The combined organic layer was washed with water and brine, dried over anhydrous $Na_2SO_4$, filtered and concentrated in vacuo. The residue was purified by column chromatography to give the titled compound (0.35 g, 7.4% yield) as a yellow solid. LC-MS ($ESI^+$): m/z 399.3 $(M+H)^+$.

Step 2. 3-(9H-Carbazol-9-yl)piperidine-2,6-dione

To a solution of 3-(9H-carbazol-9-yl)-1-(4-methoxybenzyl)piperidine-2,6-dione (0.1 g, 0.25 mmol) in $CH_3CN$ (4 mL) was added Diammonium cerium(IV) nitrate (0.41 g, 0.75 mmol) in water (1 mL) at 0° C. The reaction mixture was stirred at this temperature for 1 hour, then diluted with water. The mixture was purified via reverse phase column chromatography ($CH_3CN/H_2O$=5%-80%) to give the titled compound (7.5 mg, 10.7%) as a white solid. $^1H$ NMR (400 MHz, DMSO-$d_6$) δ 8.49 (dd, J=7.5, 1.3 Hz, 1H), 8.25 (d, J=7.5 Hz, 1H), 8.11-8.01 (m, 1H), 7.88 (s, 1H), 7.57-7.40 (m, 3H), 7.34-7.29 (m, 2H), 5.51 (m, 1H), 3.08-2.94 (m, 2H), 2.74-2.53 (m, 2H). LC-MS (ESI+): m/z 279.2 $(M+H)^+$.

Example 2. 3-(9H-pyrido[2,3-b]indol-9-yl)piperidine-2,6-dione (2)

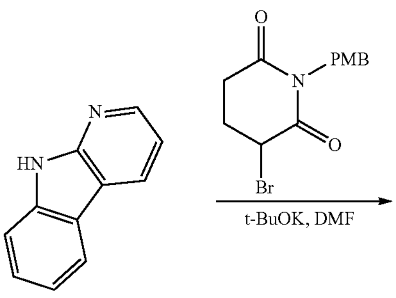

-continued

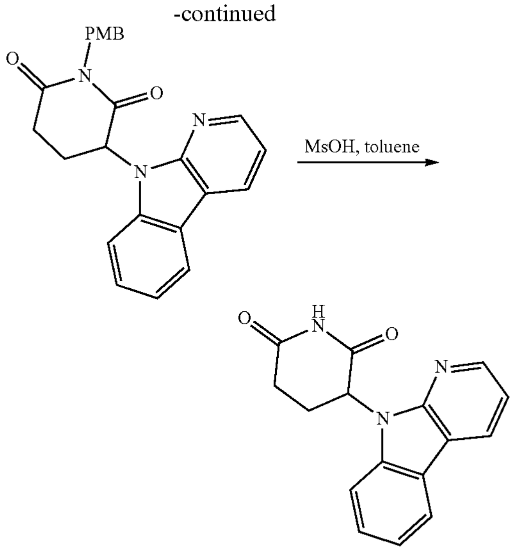

2

Step 1. 1-(4-Methoxybenzyl)-3-(9H-pyrido[2,3-b]indol-9-yl)piperidine-2,6-dione

To a solution of 9H-pyrido[2,3-b]indole (2 g, 12 mmol) in DMF (30 mL) was added t-BuOK (1.34 g, 12 mmol) at 0° C. The mixture was stirred at 0-10° C. for 2 hour under $N_2$. Then a solution of 3-bromo-1-(4-methoxybenzyl)piperidine-2,6-dione (5.6 g, 18 mmol) in DMF (20 mL) was added to the reaction mixture at 0-10° C. during 30 minutes. The mixture was warmed to room temperature and stirred for 30 minutes under $N_2$. The reaction was quenched water (50 mL) and extracted with EA (3×50 mL). The combined organic layer was concentrated in vacuo. The residue was purified by column chromatography (PE/EA) to give the crude compound mix with the 9H-pyrido[2,3-b]indole. Then the mixture was purified with prep HPLC eluting with ACN/$H_2O$ (0.1% HCOOH) to get the title compound (538 mg) as a white solid (yield: 11.2%). LC-MS ($ESI^+$): m/z 400.1 $(M+H)^+$.

Step 2. 3-(9H-Pyrido[2,3-b]indol-9-yl)piperidine-2,6-dione

To a solution of 1-(4-methoxybenzyl)-3-(9H-pyrido[2,3-b]indol-9-yl)piperidine-2,6-dione (400 mg, 1 mmol) in toluene (10 ml) was added MsOH (1.8 g, 20 mmol). The mixture was warmed to 100° C. and stirred for 2 h. The reaction mixture was cooled to room temperature and concentrated in vacuo. The residue was poured into ice/water (50 mL), extracted with EA (3×50 mL). The combined organic layer was washed with brine (50 mL), dried over $Na_2SO_4$, filtered and concentrated in vacuo. The residue was purified with prep HPLC eluting with ACN/$H_2O$(0.1% HCOOH) to get the titled compound (120 mg, 43% yield) as a white solid. 1H NMR (400 MHz, DMSO-d6) δ: 11.15 (s, 1H), 8.53-8.62 (m, 1H), 8.43 (dd, J=4.88, 1.50 Hz, 1H), 8.24 (d, J=7.63 Hz, 1H), 7.62 (d, J=7.88 Hz, 1H), 7.46-7.56 (m, 1H), 7.24-7.37 (m, 2H), 6.05 (br. s., 1H), 2.93-3.21 (m, 2H), 2.63-2.77 (m, 1H), 2.07-2.18 (m, 1H). LC-MS ($ESI^+$): m/z 280.0 $(M+H)^+$.

Example 3. 3-(6-Amino-9H-pyrido[2,3-b]indol-9-yl)piperidine-2,6-dione (5)

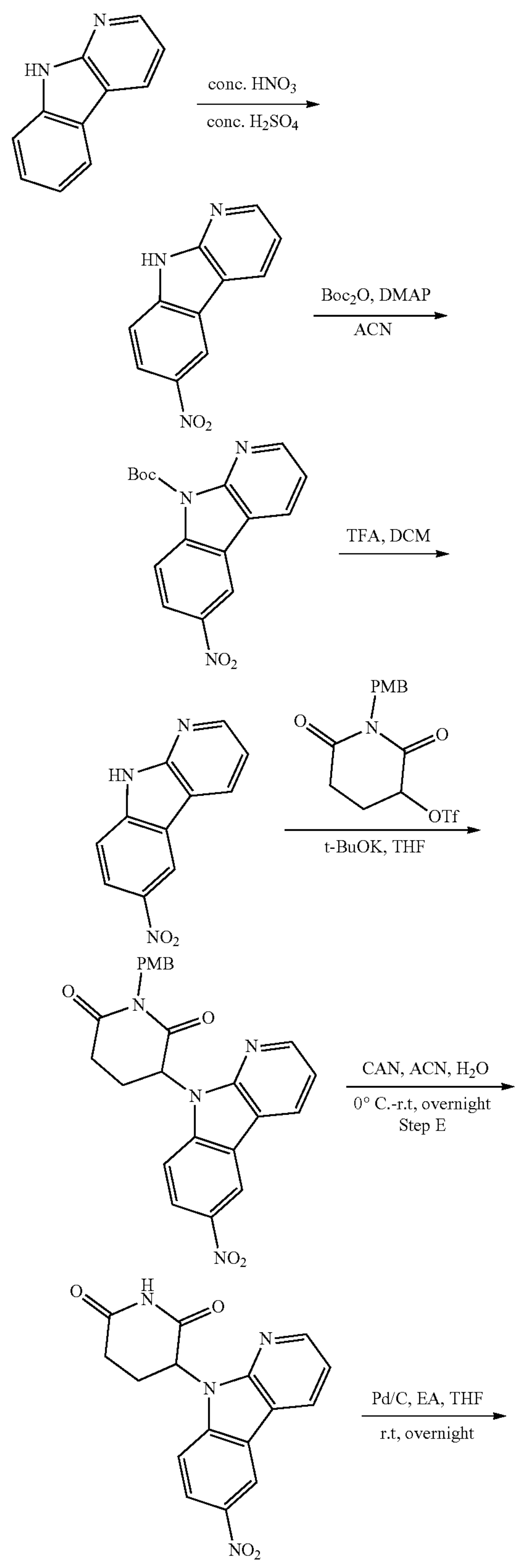

-continued

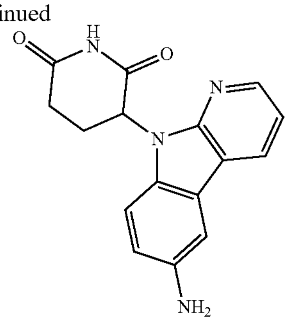

5

Step 1. 6-Nitro-9H-pyrido[2,3-b]indole

To a solution of 9H-pyrido[2,3-b]indole (504 mg, 3 mmol) in conc.$H_2SO_4$ (5 ml) was added dropwise a solution of nitric acid (68%-70% solution in water)(297 mg, 3.3 mol) in con.$H_2SO_4$ (5 ml) at −5° C.-0° C. over 20 mins. After addition, the mixture was added into ice water, then basified by addition of saturated NaOH solution to PH>8. The mixture was extracted with EtOAc (3*200 ml), the combined organic layers were evaporated to give the title compound as a yellow solid (500 mg, 78.2% yield) that was used directly in the next step without further purification. LC-MS ($ESI^+$): m/z 214.2 $(M+H)^+$.

Step 2. tert-Butyl 6-nitro-9H-pyrido[2,3-b]indole-9-carboxylate

To a solution of 6-nitro-9H-pyrido[2,3-b]indole (500 mg, 2.35 mmol) in DCM (10 ml) was added $Boc_2O$ (767 mg, 3.52 mmol) and DMAP (57.2 mg, 0.468 mmol). The mixture was stirred at room temperature overnight. The reaction mixture was evaporated. The residue was purified by silica gel chromatography (PE:EA=3:1) to give the title compound as a white solid (385 mg, 52.1% yield). 1H NMR (400 MHz, $CDCl_3$) δ: 8.90 (d, J=2.13 Hz, 1H), 8.75 (dd, J=4.82, 1.56 Hz, 1H), 8.35-8.47 (m, 3H), 7.44 (dd, J=7.75, 4.88 Hz, 1H), 1.80 (s, 9H).

Step 3. 6-Nitro-9H-pyrido[2,3-b]indole

To a solution of tert-butyl 6-nitro-9H-pyrido[2,3-b]indole-9-carboxylate (300 mg, 0.96 mmol) in DCM (6 ml) was added TFA (2 ml). The mixture was stirred at room temperature overnight. The reaction mixture was concentrated. The residue was resolved in DCM (20 ml), washed with saturated $NaHCO_3$ solution (2*20 ml), the organic phase was washed with brine, dried over $Na_2SO_4$, filtered and concentrated in vacuo to give the crude titled compound (200 mg, 95.4% yield) as a yellow solid. LC-MS ($ESI^+$): m/z 214.2 $(M+H)^+$ Step 4. 1-(4-Methoxybenzyl)-3-(6-nitro-9H-pyrido[2,3-b]indol-9-yl)piperidine-2,6-dione To a solution of 6-nitro-9H-pyrido[2,3-b]indole (210 mg, 1 mmol) in THF (10 mL) was added t-BuOK (168 mg, 1.5 mmol) at 0° C. The mixture was stirred at 0-10° C. for 1 hour under $N_2$. Then a solution of [1-[(4-methoxyphenyl) methyl]-2,6-dioxo-3-piperidyl]trifluoromethanesulfonate (457 mg, 1.2 mmol) in THF (10 mL) was added to the reaction mixture at 0-10° C. during 20 minutes. The mixture was stirred at 0-10° C. for 30 minutes under N2. Additional solution of [1-[(4-methoxyphenyl) methyl]-2, 6-dioxo-3-piperidyl]trifluoromethanesulfonate (114 mg, 0.3 mmol) in THF (5 mL) was added to the reaction mixture at 0-10° C. dropwise. The mixture was stirred at 0-10° C. for another 30 minutes under N2. On completion, the reaction was quenched water (40 mL) and extracted with EA (3×50 mL). The combined organic layer was concentrated in vacuo. The residue was purified by column chromatography to give the titled compound (400 mg) as a yellow solid. LC-MS ($ESI^+$): m/z 445$(M+H)^+$.

Step 5. 3-(6-Nitro-9H-pyrido[2,3-b]indol-9-yl)piperidine-2,6-dione

To a solution of 1-(4-methoxybenzyl)-3-(6-nitro-9H-pyrido[2,3-b]indol-9-yl)piperidine-2,6-dione (400 mg, 0.90 mmol) in $CH_3CN$ (10 ml) was added a solution of CAN (2.46 g, 0.45 mmol) in water (3 ml) at 0° C. After addition, the mixture was warmed to room temperature and stirred overnight. The reaction mixture was poured into water (50 ml), extract with EtOAc (3*50 ml), the combined organic layers were concentrated in vacuo. The residue was triturated with DMF/EA and filtrated to give the titled compound (130 mg, 44.4% yield) as a grey solid. LC-MS ($ESI^+$): m/z 325.0 $(M+H)^+$.

Step 6. 3-(6-Amino-9H-pyrido[2,3-b]indol-9-yl) piperidine-2,6-dione (V763-123), (5)

To a solution of 3-(6-nitro-9H-pyrido[2,3-b]indol-9-yl) piperidine-2,6-dione (130 mg, 0.401 mmol) in THF (5 ml) and EA (5 ml) was added palladium on activated carbon 10% Pd (50 mg) The mixture was stirred at room temperature under hydrogen overnight. The reaction mixture was filtered, the filtrate was concentrated under reduce pressure, the residue was triturated with DMF/EA and filtrated to give the title compound (55 mg, 46.4% yield) as a grey solid. LC-MS ($ESI^+$): m/z 295.0 $(M+H)^+$. $^1H$ NMR (400 MHz, DMSO-d6) δ:11.08 (s, 1H), 8.26-8.39 (m, 2H), 7.24-7.36 (m, 2H), 7.14 (dd, J=7.63, 4.88 Hz, 1H), 6.85 (dd, J=8.63, 2.13 Hz, 1H), 5.90 (br. s., 1H), 4.87 (br. s., 2H), 2.93-3.08 (m, 2H), 2.68 (d, J=12.26 Hz, 1H), 2.01-2.11 (m, 1H).

Example 4. N-(9-(2,6-Dioxopiperidin-3-yl)-9H-pyrido[2,3-b]indol-6-yl)acetamide (8)

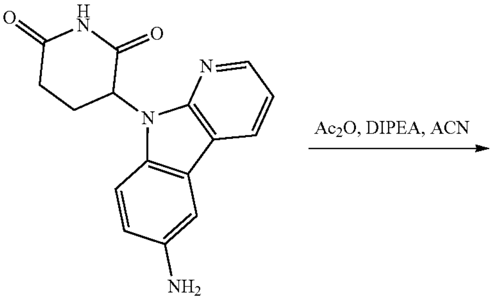

5

-continued

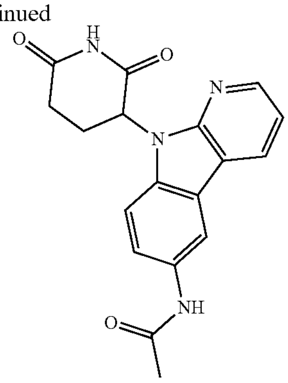

8

To a solution of 3-(6-amino-9H-pyrido[2,3-b]indol-9-yl) piperidine-2,6-dione (40 mg crude, 0.136 mmol, 5) in ACN (5 ml) was added acetic anhydride (5 drops) and DIPEA (10 drops). The mixture was stirred at room temperature for 2 h. The mixture was filtered, the filtrate cake was dissolved in DCM, washed with 1M HCl(2*10 ml), the organic phase was concentrated and dried to give the titled compound (8 mg, 17.4% yield) as a white solid. $^1$H NMR (400 MHz, DMSO-$d_6$) δ: 11.14 (s, 1H), 10.02 (s, 1H), 8.45-8.55 (m, 2H), 8.35-8.45 (m, 1H), 7.46-7.61 (m, 2H), 7.25 (dd, J=7.69, 4.82 Hz, 1H), 6.02 (br. s., 1H), 2.93-3.17 (m, 2H), 2.63-2.76 (m, 1H), 2.06-2.14 (m, 4H). LC-MS (ESI$^+$): m/z 337.0 $(M+H)^+$.

Example 5. 1-(9-(2,6-Dioxopiperidin-3-yl)-9H-pyrido[2,3-b]indol-6-yl)-3-ethylurea (9)

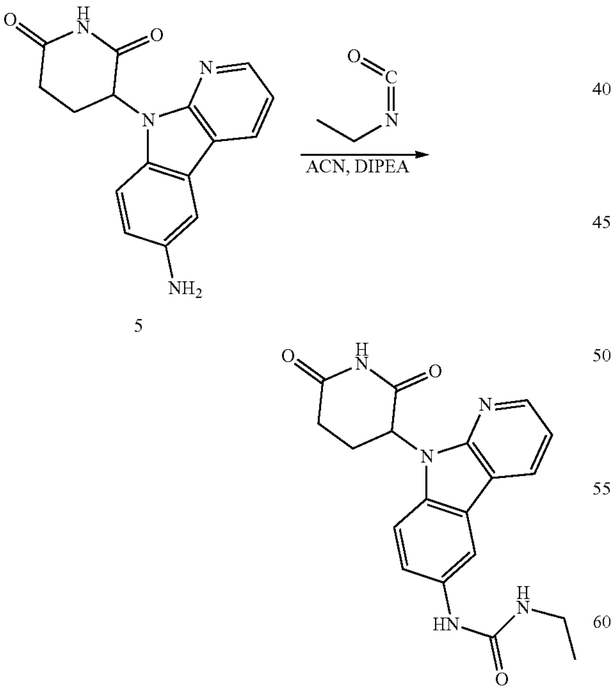

5

9

To a solution of 3-(6-amino-9H-pyrido[2,3-b]indol-9-yl) piperidine-2,6-dione (25 mg, 0.085 mmol, 5) in ACN (5 ml) was added ethyl isocyanate (3 drops) and DIPEA (6 drops). The mixture was stirred at room temperature for 4 h. The mixture was concentrated in vacuo and the residue was purified by prep HPLC to give the title compound (8 mg, 25.7% yield) as a white solid. $^1$H NMR (400 MHz, DMSO-$d_6$) δ: 11.13 (s, 1H), 8.43-8.54 (m, 2H), 8.39 (dd, J=4.82, 1.44 Hz, 1H), 8.27 (d, J=1.88 Hz, 1H), 7.37-7.52 (m, 2H), 7.22 (dd, J=7.63, 4.88 Hz, 1H), 6.12 (t, J=5.50 Hz, 1H), 5.99 (br. s., 1H), 3.10-3.20 (m, 2H), 2.90-3.07 (m, 2H), 2.65-2.75 (m, 1H), 2.06-2.16 (m, 1H), 1.03-1.13 (m, 3H). LC-MS (ESI$^+$): m/z 366.3 $(M+H)^+$.

Example 6. tert-butyl (2-(2-(2-((9-(2,6-dioxopiperidin-3-yl)-9H-pyrido[2,3-b]indol-6-yl)amino)ethoxy) ethoxy)ethyl)carbamate (10)

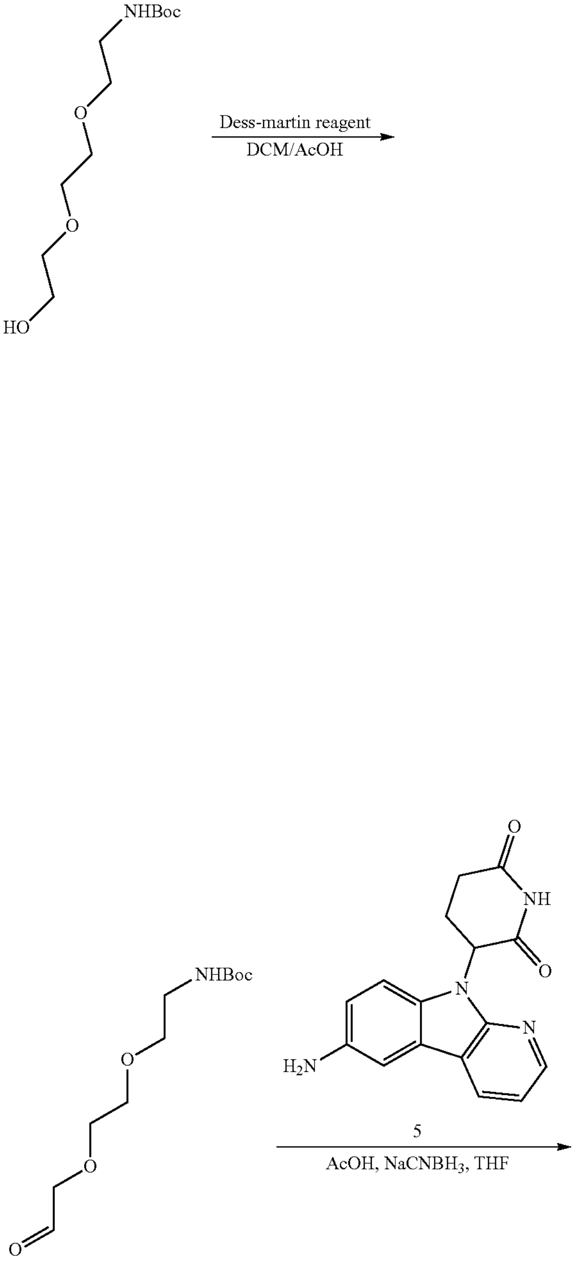

-continued

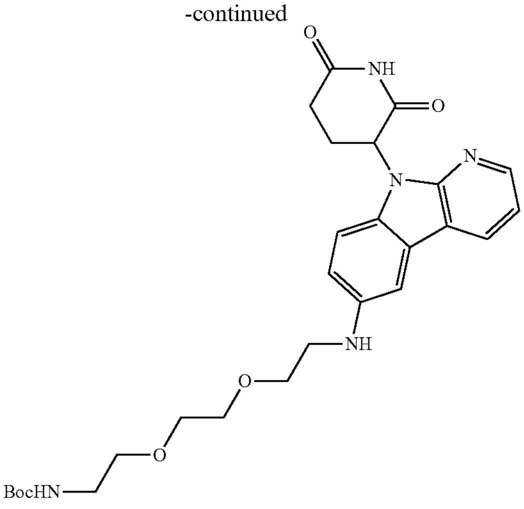

10

Step 1: tert-butyl (2-(2-(2-oxoethoxy)ethoxy)ethyl)carbamate

To a mixture of tert-butyl (2-(2-(2-hydroxyethoxy) ethoxy)ethyl)carbamate (2 g, 8.03 mmol) and dess-martin periodinane in dichloromethane (20 mL) was added AcOH (1 mL). The mixture was stirred at room temperature overnight. The reaction mixture was concentrated under reduced pressure and purified by flash chromatography to give tert-butyl (2-(2-(2-oxoethoxy)ethoxy)ethyl)carbamate (300 mg, 15.2%) as a colorless oil. LC/MS (ESI, m/z): $[M+]^+$ =248.1.

Step 2: tert-butyl (2-(2-(2-((9-(2,6-dioxopiperidin-3-yl)-9H-pyrido[2,3-b]indol-6-yl)amino)ethoxy)ethoxy)ethyl)carbamate (10)

To a mixture of 5 (200 mg, 0.68 mmol) and (2-(2-(2-oxoethoxy)ethoxy)ethyl)carbamate (176 mg, 0.714 mmol) in THF (5 mL) was added AcOH (5 drops). The mixture was stirred at room temperature for 2 h. Then $NaCNBH_3$ (21.3 mg, 0.34 mmol) was added in portions. The reaction mixture was warmed to 40° C. and stirred for 2 h. The reaction mixture was poured into water and extract with EtOAc (3×20 mL). The combined organic layers were concentrated under reduced pressure. The residue was purified via reverse phase column chromatography ($CH_3CN/H_2O$=5%-80%) to give 10 (70 mg, 19.6%) as a yellow solid. $^1H$ NMR (400 MHz, DMSO-$d_6$) δ 11.09 (br. s., 1H), 8.42 (dd, J=7.6, 1.5 Hz, 1H), 8.33 (dd, J=4.8, 1.5 Hz, 1H), 7.36-7.32 (m, 2H), 7.17-7.13 (m, 1H), 6.92 (dd, J=8.8, 2.2 Hz, 1H), 6.79-6.76 (m, 1H), 5.91 (br. s., 1H), 5.30 (br. s., 1H), 3.66-3.62 (m, 2H), 3.60-3.50 (m, 4H), 3.41-3.29 (m, 4H), 3.12-2.95 (m, 4H), 2.71-2.65 (m, 1H), 2.12-2.01 (m, 1H), 1.37 (s, 9H); LC/MS (ESI, m/z): $[M+1]^+$=526.55

Example 7. 3-(6-Bromo-9H-pyrido[2,3-b]indol-9-yl) piperidine-2,6-dione

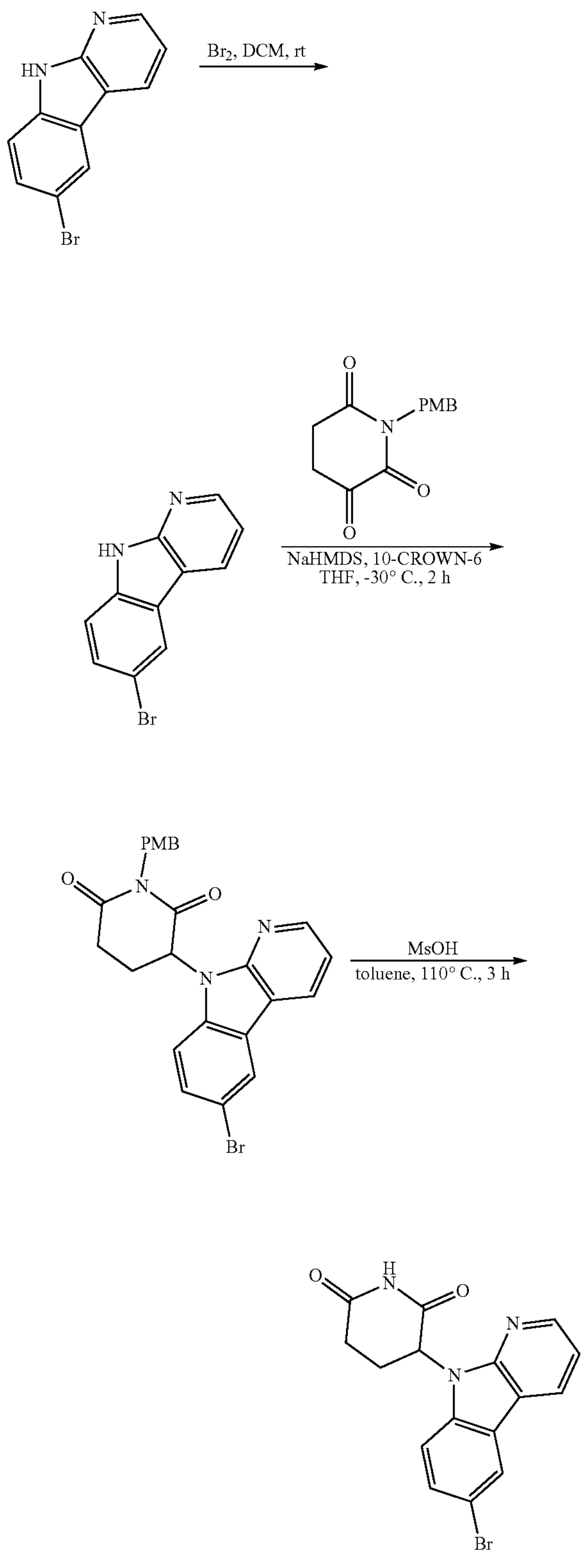

11

Step 1: 6-Bromo-9H-pyrido[2,3-b]indole

To a stirred solution of 9H-pyrido[2,3-b]indole (3 g, 17.9 mmol) in DCM (50 mL) was added dropwise of $Br_2$ (3.4 g, 21.4 mmol) at 0° C. To the mixture was added aq. $NaHCO_3$ (100 mL), extracted with EA (200 mL). The organic layer was washed with brine (50 mL), dried over $Na_2SO_4$, filtered, concentrated to give product 6-bromo-9H-pyrido[2,3-b]indole (2.7 g, 61% yield) as yellow solid. $^1$H NMR (400 MHz, DMSO-$d_6$) δ 12.02 (s, 1H), 8.60 (dd, J=1.2 Hz, J=7.6 Hz, 1H), 8.48-8.44 (m, 2H), 7.60-7.58 (m, 1H), 7.48 (d, J=8.4 Hz, 1H), 7.26 (dd, J=4.8 Hz, J=7.6 Hz, 1H). LC/MS (ESI, m/z): $[M+1]^+$=247.8.

Step 2: 3-(6-Bromo-9H-pyrido[2,3-b]indol-9-yl)-1-(4-methoxybenzyl)piperidine-2,6-dione To a stirred solution of Intermediate A (200 mg, 0.810 mmol) and 18-crown-6 (43 mg, 0.162 mmol) in dry THF (10 mL) was added dropwise NaHMDS (0.6 mL, 2 M in THF) at −30° C. under $N_2$. The mixture was stirred for 1 h at −30° C. under $N_2$. Then to the mixture was added a solution of 1-(4-methoxybenzyl)-2,6-dioxopiperidin-3-yl trifluoromethanesulfonate (463 mg, 1.21 mmol) in THF (5 mL) dropwise at −30° C. under $N_2$. The mixture was stirred at −30° C. for 2 h. The mixture was added to aq. $NH_4Cl$ (20 mL), extracted with EA (50 mL). The organic layer was washed with brine (30 mL), dried over $Na_2SO_4$, filtered, concentrated and purified by column (PE/EA/DCM=10/1/1 to 3/1/1) to give product 3-(6-bromo-9H-pyrido[2,3-b]indol-9-yl)-1-(4-methoxybenzyl)piperidine-2,6-dione (220 mg, 57% yield) as a yellow oil. $^1$H NMR (400 MHz, $CDCl_3$) δ 8.41 (dd, J=1.6 Hz, J=4.8 Hz, 1H), 8.29 (dd, J=1.2 Hz, J=7.6 Hz, 1H), 8.20 (J=1.6 Hz, 1H), 7.45 (dd, J=2.0 Hz, J=8.6 Hz, 1H), 7.40 (d, J=8.8 Hz, 2H), 7.24-7.21 (m, 1H), 6.84 (d, J=8.8 Hz, 3H), 5.90-5.87 (m, 1H), 5.01 (dd, J=13.6 Hz, J=20.4 Hz, 2H), 3.81 (s, 3H), 3.09-2.84 (m, 4H); LC/MS (ESI, m/z): $[M+1]^+$=479.1.

Step 3: 3-(6-Bromo-9H-pyrido[2,3-b]indol-9-yl) piperidine-2,6-dione (11)

A mixture of 3-(6-bromo-9H-pyrido[2,3-b]indol-9-yl)-1-(4-methoxybenzyl)piperidine-2,6-dione (1.3 g, 2.72 mmol), MsOH (10 mL) and toluene (20 mL) was heated to 110° C. and stirred for 3 h under $N_2$. The mixture was concentrated to remove toluene. Then to the mixture was added EA (50 mL), washed with brine (50 mL) to remove MsOH. The organic layer was dried over $Na_2SO_4$, concentrated with silica gel and purified by column (PE/EA=1/1) to give product 11 (500 mg, 51% yield) as a white solid. $^1$H NMR (400 MHz, DMSO-$d_6$) δ 11.13 (br s, 1H), 8.64 (dd, J=1.6 Hz, J=7.6 Hz, 1H), 8.52 (d, J=2.0 Hz, 1H), 8.47 (dd, J=1.6 Hz, J=4.8 Hz, 1H), 7.68-7.62 (m, 2H), 7.31 (dd, J=4.8 Hz, J=7.6 Hz, 1H), 6.06 (s, 1H), 3.16-2.96 (m, 2H), 2.73-2.67 (m, 1H), 2.16-2.13 (m, 1H). LC/MS (ESI, m/z): $[M+1]^+$=358.0/360.0.

Example 8. Time-Resolved Fluorescence Resonance Energy Transfer (TR-FRET) Assay

Equal volumes of His-tagged CRBN-DDB1 complex (56 nM) was mixed with Eu-cryptate labeled Anti-6HIS-monoclonal antibody (50× dilution from the commercial stock solution, Vender: Cisbio, Cat. #61HI2KLA) in a final buffer containing 20 mM HEPES pH 7.0, 150 mM NaCl, 0.005% Tween-20. The solution was then mixed with Cy5-labeled thalidomide (final 8 nM) and various concentrations of compounds (a serial 3-fold dilution with the top concentration 200 uM). The mixture were incubated at room temperature for 1 hour. FRET signals were measured on an EnVision plate reader (Perkin Elmer) by exciting at 340 nm and recording emission at both 615 nm as no FRET control and 665 nm as the FRET signals with a 60 microsecond delay. FRET efficiency was calculated as the ratio of fluorescent signals at 665 nM/615 nM. Quantitative loss of FRET efficiency as a function of compound concentrations was fitted by a four-parameter Logistic Function using GraphPad Prism 7.0 and the IC50 values were reported for each compound.

Table 4 shows the results for selected compounds in the time-resolved fluorescence resonance energy transfer (TR-FRET) assay. The compound numbers correspond to the compound numbers in the Examples. Compounds having an activity designated as "A" provided an $IC_{50}$ of <10 μM; compounds having an activity designated as "B" provided an $IC_{50}$ of 10-30 μM; compounds having an activity designated as "C" provided an $IC_{50}$ of 30-100 μM; and compounds having an activity designated as "D" provided an $IC_{50}$ of >100 μM. For reference, the known CRBN binders provided the following $IC_{50}$ values in the TR-FRET assay: thalidomide ($IC_{50}$=2.9 μM), lenalidomide ($IC_{50}$=1.17 μM) and pomalidomide ($IC_{50}$=1.28 μM).

TABLE 4

TR-FRET Assay Results

| CMPD # | CRBN HTRF $IC_{50}$ (μM) |
|---|---|
| 2 | A |
| 5 | A |
| 8 | A |
| 9 | A |
| 10 | A |
| 11 | A |

Example 9. General Method A. Synthesis of 3-[6-[7-[2-[3-[3-amino-6-(2-hydroxyphenyl)pyridazin-4-yl]-3,8-diazabicyclo[3.2.1]octan-8-yl]pyrimidin-5-yl]heptyl]pyrido[2, 3-b]indol-9-yl]piperidine-2,6-dione (I-107)

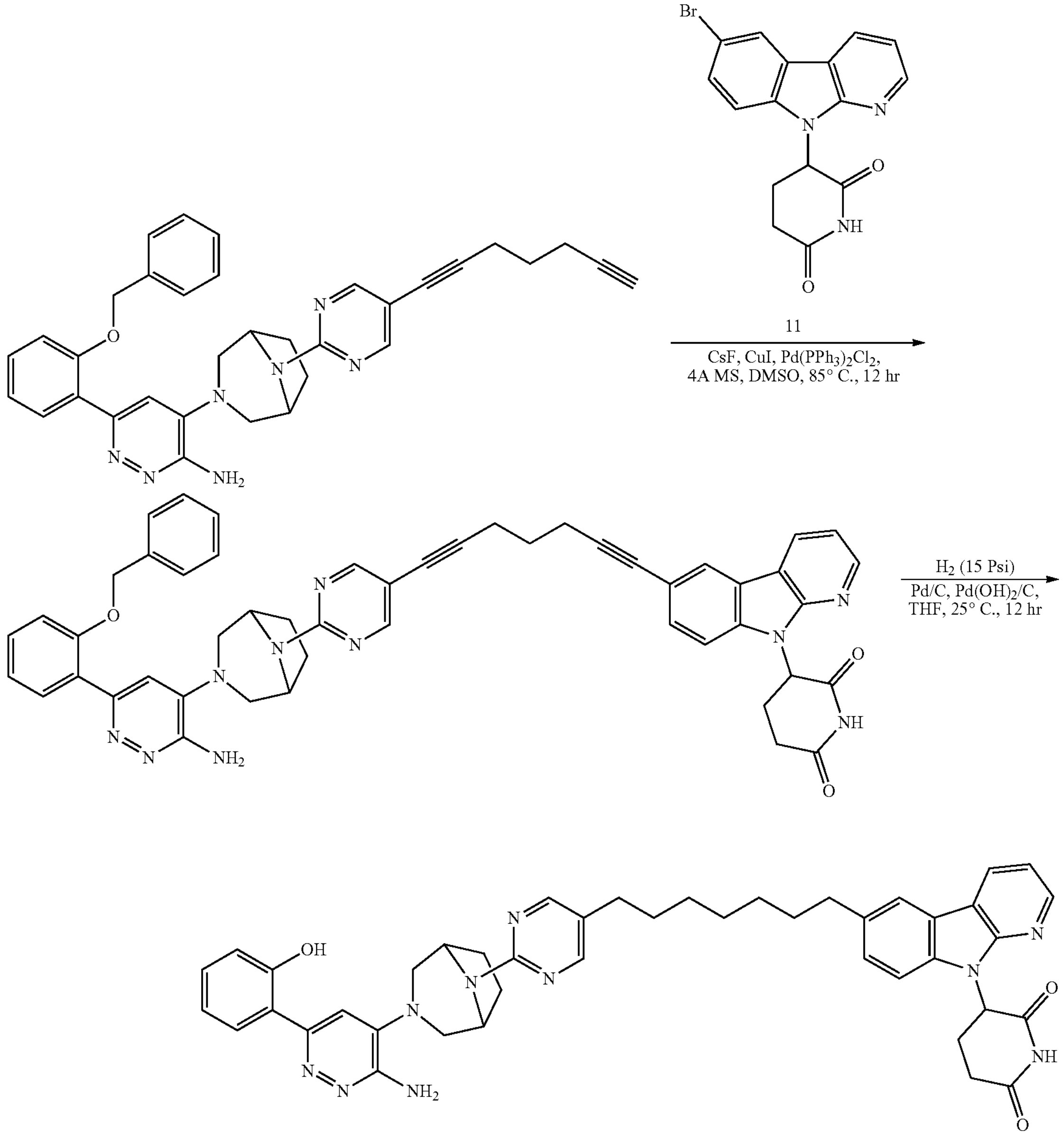

I-107

Step 1: 3-[6-[7-[2-[3-[3-amino-6-(2-benzyloxyphenyl)pyridazin-4-yl]-3,8-diazabicy clo[3.2.1]octan-8-yl]pyrimidin-5-yl]hepta-1,6-diynyl]pyrido[2,3-b]indol-9-yl]piperidine-2,6-dione A mixture of 6-(2-benzyloxyphenyl)-4-[8-(5-hepta-1,6-diynylpyrimidin-2-yl)-3,8-diazabicyclo[3.2.1]octan-3-yl]pyridazin-3-amine (150 mg, 269 umol), 3-(6-bromopyrido[2,3-b]indol-9-yl)piperidine-2,6-dione (96.6 mg, 269 umol, 11), CuI (10.2 mg, 53.9 umol), CsF (164 mg, 1.08 mmol), Pd(PPh$_3$)$_2$Cl$_2$ (18.9 mg, 26.9 umol) and 4A molecular sieve (150 mg, 55.8 umol) in DMSO (6 mL) was degassed and purged with $N_2$ for 3 times, and then the mixture was stirred at 85° C. for 12 hrs under $N_2$ atmosphere. The reaction mixture was diluted with brine 30 mL and extracted with EA (30 mL*3). The combined organic layers were washed with brine (30 mL*3), dried over sodium sulfate, filtered and concentrated under reduced pressure to give a residue. The residue was purified by reversed phase flash (FA condition; 45% MeCN to 55% MeCN) to give the title compound (60 mg, 23% yield) as a white solid. LC-MS (ESI+) m/z 833.5 $(M+H)^+$.

Step 2: 3-[6-[7-[2-[3-[3-amino-6-(2-hydroxyphenyl) pyridazin-4-yl]-3,8-diazabicyclo[3.2.1]octan-8-yl] pyrimidin-5-yl]heptyl]pyrido[2,3-b]indol-9-yl]piperidine-2,6-dione To a solution of 3-[6-[7-[2-[3-[3-amino-6-(2-benzyloxyphenyl)pyridazin-4-yl]-3,8-di azabicyclo[3.2.1]octan-8-yl] pyrimidin-5-yl]hepta-1,6-diynyl]pyrido[2,3-b]indol-9-yl]piperidine-2,6-dione (50 mg, 60.0 umol) in THF (2 mL) was added Pd/C (5 mg, 12.0 umol, 10% purity) and $Pd(OH)_2/C$ (5 mg, 12.0 umol, 20% purity) under $N_2$ atmosphere. The suspension was degassed and purged with $H_2$ for 3 times. The mixture was stirred under $H_2$ (15 Psi) at 25° C. for 12 hrs. The reaction mixture was filtered and concentrated under reduced pressure to give a residue. The residue was purified by prep-HPLC (column: Phenomenex Synergi C18 150*30 mm*4 um; mobile phase: [water (0.05% HCl)-ACN]; B %: 30%-60%, 10 min) to give the title compound (12.0 mg, 26% yield, HCl) as a yellow solid. LC-MS (ESI+) m/z 751.5 $(M+H)^+$. $^1H$ NMR (400 MHz, DMSO-d6) δ=11.22-11.10 (m, 1H), 8.52 (m, 1H), 8.39 (m, 1H), 8.30 (s, 2H), 8.02 (s, 1H), 7.64-7.45 (m, 4H), 7.43-7.37 (m, 1H), 7.36-7.31 (m, 1H), 7.27-7.21 (m, 1H), 7.08-7.03 (m, 1H), 7.01-6.95 (m, 1H), 6.94-6.65 (m, 1H), 6.12-5.89 (m, 1H), 4.78 (d, J=1.6 Hz, 2H), 3.77-3.71 (m, 2H), 3.31-3.25 (m, 2H), 3.11-2.97 (m, 2H), 2.76-2.71 (m, 2H), 2.44-2.40 (m, 2H), 2.13-2.07 (m, 1H), 2.06-1.98 (m, 2H), 1.96-1.88 (m, 2H), 1.70-1.62 (m, 2H), 1.55-1.47 (m, 2H), 1.36-1.26 (m, 6H).

Example 10. General Method B. Synthesis of 3-[6-[3-[3-[2-[3-[3-amino-6-(2-hydroxyphenyl)pyridazin-4-yl]-3,8-diazabi cyclo[3.2.1]octan-8-yl]pyrimidin-5-yl]propyl-methyl-amino]propyl]pyrido[2,3-b] indol-9-yl]piperidine-2,6-dione (I-110)

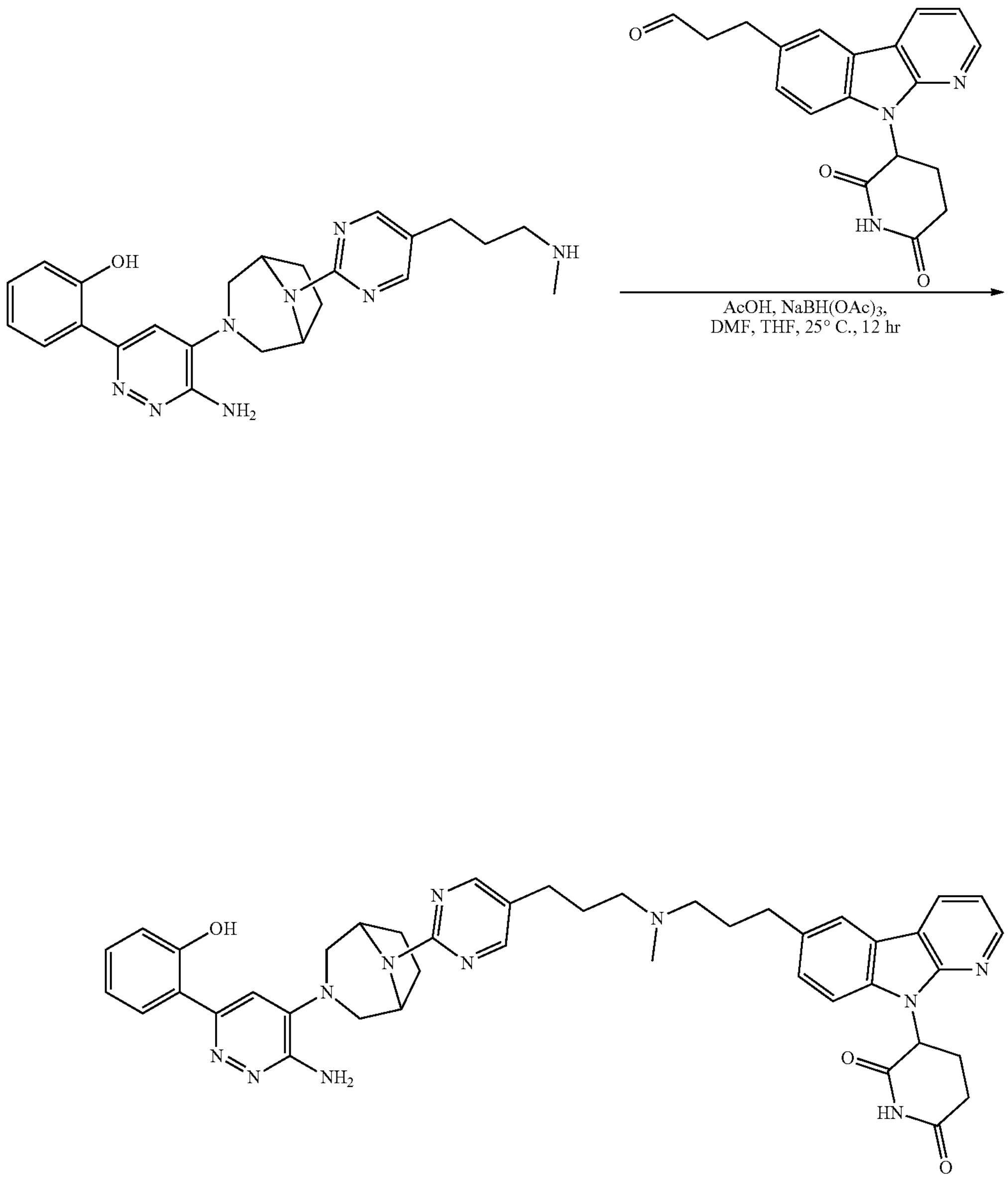

I-110

Step 1: 3-[6-[3-[3-[2-[3-[3-amino-6-(2-hydroxyphenyl) pyridazin-4-yl]-3,8-diazabi cyclo[3.2.1]octan-8-yl]pyrimidin-5-yl]propyl-methyl-amino]propyl]pyrido[2,3-b]indol-9-yl]piperidine-2,6-dione A mixture of 2-[6-amino-5-[8-[5-[3-(methylamino)propyl]pyrimidin-2-yl]-3,8-diazabicyclo[3.2.1]octan-3-yl] pyridazin-3-yl]phenol (20 mg, 44.8 umol), 3-[9-(2,6-dioxo-3-piperidyl)pyrido[2,3-b]indol-6-yl]propanal (15 mg, 44.8 umol), AcOH (269 ug, 4.48 umol), $NaBH(OAc)_3$ (28.5 mg, 134 umol) in THF (1 mL), DMF (1 mL) was degassed and purged with N2 for 3 times, and then the mixture was stirred at 25° C. for 12 hr under $N_2$ atmosphere. The reaction mixture was filtered and concentrated under reduced pressure to give a residue. The residue was purified by prep-HPLC (column: Phenomenex Synergi C18 150*25*10 um; mobile phase: [water (0.05% HCl)-ACN]; B %: 18%-38%, 11 min) to give the title compound (15 mg, 41% yield, HCl) as a yellow solid. $^1H$ NMR (400 MHz, DMSO-d6) δ=11.15 (s, 1H), 10.77 (d, J=1.2 Hz, 1H), 8.54 (m, 1H), 8.48-8.36 (m, 3H), 8.12 (s, 1H), 7.58 (d, J=5.6 Hz, 1H), 7.54-7.46 (m, 2H), 7.44-7.37 (m, 2H), 7.27 (m, 1H), 7.12 (m, 1H), 6.98 (t, J=7.4 Hz, 1H), 6.04 (d, J=7.8 Hz, 1H), 4.88 (s, 2H), 3.34-2.90 (m, 9H), 2.90-2.63 (m, 7H), 2.58-2.52 (m, 3H), 2.17-2.03 (m, 5H), 2.03-1.89 (m, 4H), LC/MS (ESI, m/z): $[M+1]^+$=766.5.

Example 11. General Method C. Synthesis of 3-[6-[3-[4-[2-[3-[3-amino-6-(2-hydroxyphenyl)pyridazin-4-yl]-3,8-diazabicyclo[3.2.1]octan-8-yl]pyrimidin-5-yl]-1-piperidyl]propyl]pyrido[2,3-b]indol-9-yl] piperidine-2,6-dione (I-138)

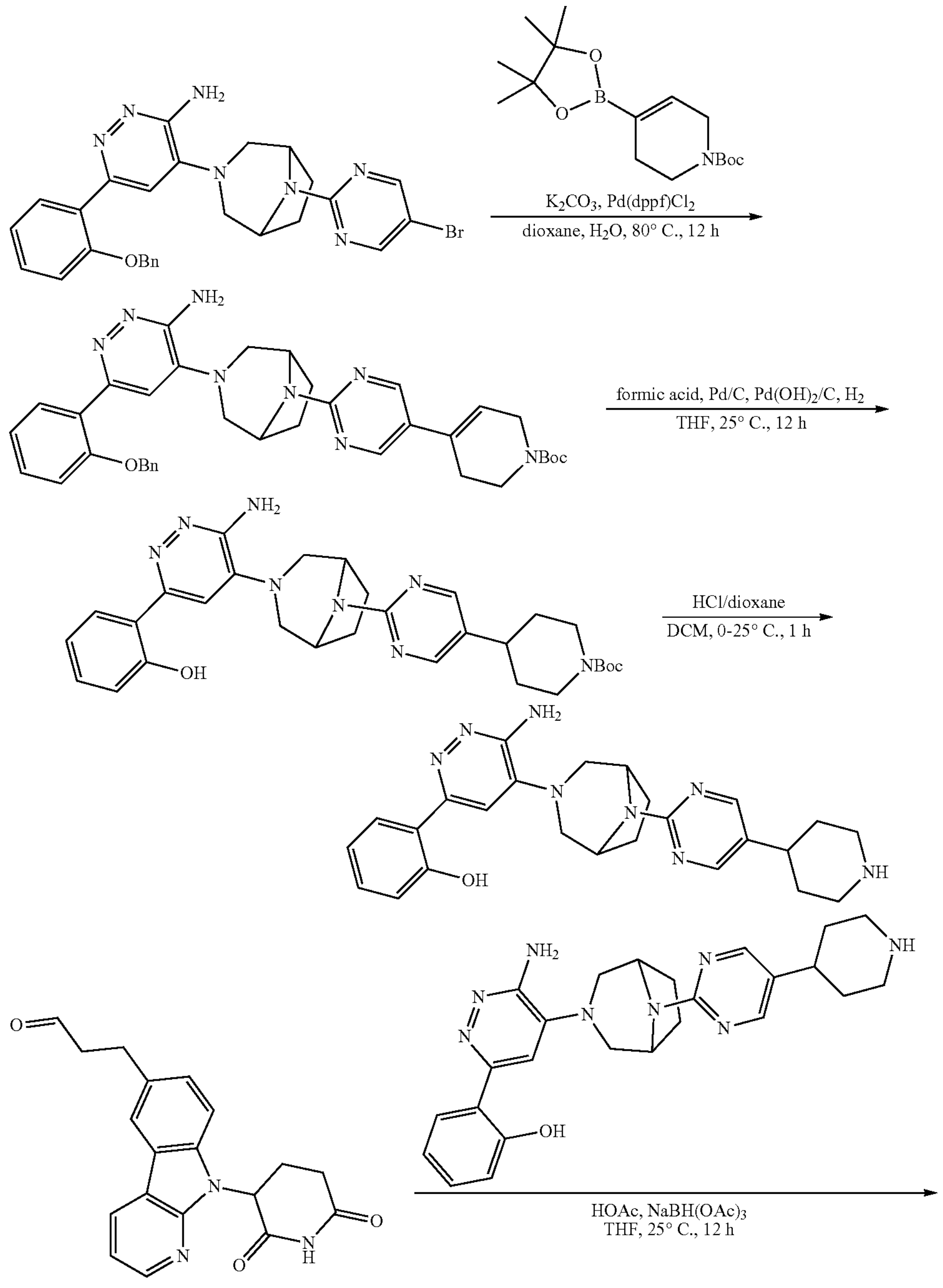

-continued

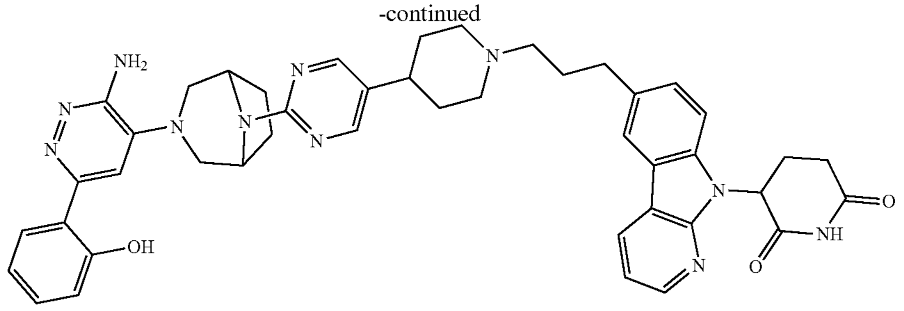

I-138

Step 1: tert-butyl 4-[2-[3-[3-amino-6-(2-benzyloxyphenyl)pyridazin-4-yl]-3,8-diazabicyclo[3.2.1]octan-8-yl]pyrimidin-5-yl]-3,6-dihydro-2H-pyridine-1-carboxylate A mixture of 6-(2-benzyloxyphenyl)-4-[8-(5-bromopyrimidin-2-yl)-3,8-diazabicyclo[3.2.1]octan-3-yl]pyridazin-3-amine (8 g, 14.7 mmol), $K_2CO_3$ (6.09 g, 44.0 mmol), Pd(dppf)$Cl_2$ (537 mg, 0.734 mmol) in dioxane (300 mL) was stirred at 25° C. for 0.16 h under $N_2$ atmosphere. Then tert-butyl 4-(4,4,5,5-tetramethyl-1,3,2-dioxaborolan-2-yl)-3,6-dihydro-2H-pyridine-1-carboxylate (5.45 g, 17.6 mmol) and $H_2O$ (37.5 mL) was added into the mixture, the mixture was stirred at 80° C. for 11.83 h under $N_2$ atmosphere. Then the mixture was diluted with $H_2O$ (300 mL) and extracted with EtOAc (300 mL*3), dried over sodium sulphate anhydrous, concentrated under reduced pressure to give a residue. The residue was purified by column chomatography ($SiO_2$, Petroleum ether/Ethyl acetate=1:0 to 0:1) to give the title compound (6.3 g, 63% yield) as a yellow solid. LC-MS (ESI+) m/z 647.2 (M+H)+.

Step 2: tert-butyl 4-[2-[3-[3-amino-6-(2-hydroxyphenyl)pyridazin-4-yl]-3,8-diazabicyclo[3.2.1]octan-8-yl]pyrimidin-5-yl]piperidine-1-carboxylate A mixture of tert-butyl 4-[2-[3-[3-amino-6-(2-benzyloxyphenyl)pyridazin-4-yl]-3,8-diazabicyclo[3.2.1]octan-8-yl]pyrimidin-5-yl]-3,6-dihydro-2H-pyridine-1-carboxylate (3.2 g, 4.95 mmol), Pd/C (1.6 g, 10% purity), $Pd(OH)_2$/C (1.6 g, 20% purity) and formic acid (455 mg, 9.90 mmol) in THF (5 mL) was degassed and purged with $N_2$ for 3 times, and then the mixture was stirred at 25° C. for 12 h under $H_2$ atmosphere. The reaction mixture was filtered and concentrated under reduced pressure to give the title compound (2.6 g, crude) was obtained as a yellow solid. LC-MS (ESI+) m/z 559.4 (M+H)+.

Step 3: 2-[6-amino-5-[8-[5-(4-piperidyl)pyrimidin-2-yl]-3,8-diazabicyclo[3.2.1]octan-3-yl]pyridazin-3-yl]phenol A mixture of tert-butyl 4-[2-[3-[3-amino-6-(2-hydroxyphenyl)pyridazin-4-yl]-3,8-diazabicyclo[3.2.1]octan-8-yl]pyrimidin-5-yl]piperidine-1-carboxylate (2.6 g, 4.65 mmol) in HCl/dioxane (40 mL) and DCM (40 mL) was stirred at 0° C. 10 min, and then it was stirred at 25° C. for 50 min. The reaction mixture was concentrated under reduced pressure to remove DCM and HCl/dioxane to give the title compound (2 g, crude, HCl) as a yellow solid. LC-MS (ESI+) m/z 459.3 (M+H)+.

Step 4: 3-[6-[3-[4-[2-[3-[3-amino-6-(2-hydroxyphenyl)pyridazin-4-yl]-3,8-diazabicyclo[3.2.1]octan-8-yl]pyrimidin-5-yl]-1-piperidyl]propyl]pyrido[2,3-b]indol-9-yl]piperidine-2,6-dione A mixture of 3-[9-(2,6-dioxo-3-piperidyl)pyrido[2,3-b]indol-6-yl]propanal (40 mg, 0.119 mmol), 2-[6-amino-5-[8-[5-(4-piperidyl)pyrimidin-2-yl]-3,8-diazabicyclo[3.2.1]octan-3-yl]pyridazin-3-yl]phenol (54.7 mg, 0.119 mmol), $NaBH(OAc)_3$ (75.8 mg, 0.357 mmol), $CH_3COOH$ (35.8 mg, 0.596 mmol) in THF (2 mL) was degassed and purged with $N_2$ for 3 times, and then the mixture was stirred at 25° C. for 12 h under $N_2$ atmosphere. The reaction mixture was concentrated under reduced pressure to give a residue. The residue was purified by prep-HPLC (column: Phenomenex Synergi C18 150*25*10 um; mobile phase: [water (0.05% HCl)-ACN]; B %: 21%-41%, 11 min) to give the title compound (47.7 mg, 48% yield) as a yellow solid. LC-MS (ESI+) m/z 778.5 (M+H)+. $^1$H NMR (400 MHz, DMSO-d6) δ=11.14 (s, 1H), 10.97-10.85 (m, 1H), 8.59-8.49 (m, 1H), 8.41 (m, 1H), 8.38 (s, 2H), 8.13 (s, 1H), 7.61-7.55 (m, 1H), 7.54-7.47 (m, 2H), 7.45-7.36 (m, 2H), 7.27 (m, 1H), 7.11 (d, J=8.0 Hz, 1H), 6.97 (m, 1H), 6.11-5.98 (m, 1H), 4.92-4.82 (m, 2H), 3.83-3.67 (m, 4H), 3.57 (m, 2H), 3.27 (m, 2H), 3.13-2.95 (m, 6H), 2.84 (m, 2H), 2.78-2.65 (m, 2H), 2.24-2.15 (m, 2H), 2.10 (m, 5H), 2.02-1.90 (m, 4H).

Example 12. General Method D. Synthesis of 3-[6-[3-[4-[2-[4-[3-amino-6-(2-hydroxyphenyl)pyridazin-4-yl]pyrazol-1-yl]ethyl]-1-piperidyl]propyl]pyrido[2,3-b]indol-9-yl]piperidine-2,6-dione (I-122)
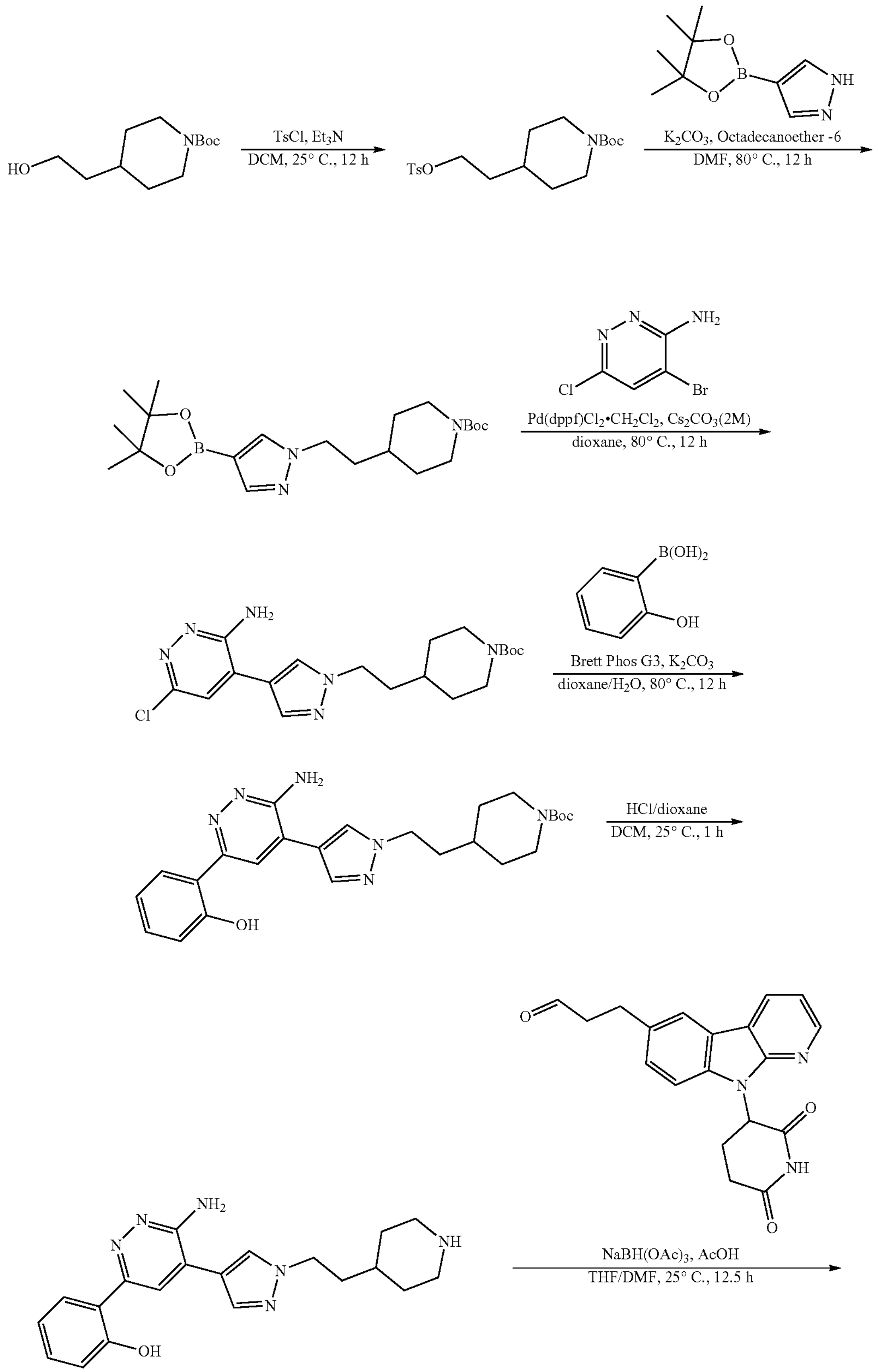

-continued

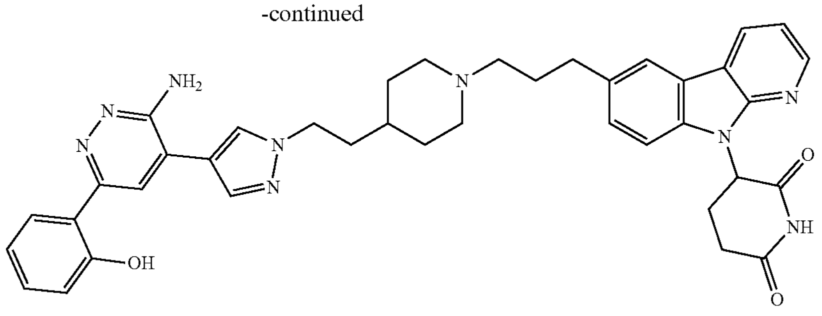

I-122

Step 1: tert-butyl 4-[2-(p-tolylsulfonyloxy)ethyl] piperidine-1-carboxylate

A mixture of 4-methylbenzenesulfonyl chloride (6.23 g, 32.7 mmol), tert-butyl 4-(2-hydroxyethyl)piperidine-1-carboxylate (5.00 g, 21.8 mmol), TEA (6.62 g, 65.4 mmol) in DCM (45 mL) was degassed and purged with $N_2$ for 3 times, and then the mixture was stirred at 25° C. for 12 hr under $N_2$ atmosphere. The reaction mixture was partitioned between $H_2O$ (50 mL) and Ethyl acetate (300 mL). The organic phase was separated, washed with brine 100 mL (50 mL*2), dried over $Na_2SO_4$, filtered, concentrated and purified by column chromatography ($SiO_2$, Petroleum ether/Ethyl acetate=20/1) to give the title compound (7.00 g, 82% yield) as a white solid. $^1$H NMR (400 MHz, DMSO-$d_6$) δ=7.80 (d, J=8.4 Hz, 2H), 7.50 (d, J=8.0 Hz, 2H), 4.05 (t, J=6.4 Hz, 2H), 3.84 (d, J=12.8 Hz, 2H), 2.59 (s, 2H), 2.43 (s, 3H), 1.55-1.40 (m, 5H), 1.38 (s, 9H), 0.97-0.81 (m, 2H); LC-MS (ESI$^+$) m/z 406.3 (M+Na)$^+$.

Step 2: tert-butyl 4-[2-[4-(4,4,5,5-tetramethyl-1,3,2-dioxaborolan-2-yl)pyrazol-1-yl]ethyl]piperidine-1-carboxylate A mixture of tert-butyl 4-[2-(p-tolylsulfonyloxy)ethyl] piperidine-1-carboxylate (3 g, 7.82 mmol), 4-(4,4,5,5-tetramethyl-1,3,2-dioxaborolan-2-yl)-1H-pyrazole (1.82 g, 9.39 mmol), $K_2CO_3$ (3.24 g, 23.5 mmol), 1,4,7,10,13,16-hexaoxacyclooctadecane (207 mg, 782 umol) in DMF (25 mL) was degassed and purged with $N_2$ for 3 times, and then the mixture was stirred at 80° C. for 12 hr under $N_2$ atmosphere. The reaction mixture was partitioned between $H_2O$ (50 mL) and Ethyl acetate (200 mL). The organic phase was separated, washed with brine (20 mL), dried over $Na_2SO_4$, filtered, concentrated and purified by column chromatography ($SiO_2$, Petroleum ether/Ethyl acetate=15/1) to give the title compound (2 g, 48% yield) as a brown solid. LC-MS (ESI$^+$) m/z 406.3 (M+H)$^+$.

Step 3: tert-butyl 4-[2-[4-(3-amino-6-chloro-pyridazin-4-yl)pyrazol-1-yl]ethyl]piperidine-1-carboxylate A mixture of tert-butyl 4-[2-[4-(4,4,5,5-tetramethyl-1,3,2-dioxaborolan-2-yl)pyrazol-1-yl]ethyl]piperidine-1-carboxylate (500 mg, 1.23 mmol), 4-bromo-6-chloro-pyridazin-3-amine (257 mg, 1.23 mmol), $Cs_2CO_3$ (2 M, 1.85 mL), Pd(dppf)$Cl_2$—$CH_2Cl_2$ (50.4 mg, 61.7 umol) in dioxane (5 mL) was degassed and purged with $N_2$ for 3 times, and then the mixture was stirred at 80° C. for 12 hr under $N_2$ atmosphere. The reaction mixture was partitioned between $H_2O$ 10 mL and Ethyl acetate 100 mL. The organic phase was separated, washed with brine 20 mL, dried over $Na_2SO_4$, filtered, concentrated and purified by column chromatography ($SiO_2$, Petroleum ether/Ethyl acetate=1:5) to give the title compound (340 mg, 65% yield) as a yellow oil. LC-MS (ESI$^+$) m/z 407.1 (M+H)$^+$.

Step 4: tert-butyl 4-[2-[4-[3-amino-6-(2-hydroxyphenyl) pyridazin-4-yl]pyrazol-1-yl]ethyl]piperidine-1-carboxylate A mixture of tert-butyl 4-[2-[4-(3-amino-6-chloro-pyridazin-4-yl)pyrazol-1-yl]ethyl]piperidine-1-carboxylate (340 mg, 836 umol), (2-hydroxyphenyl)boronic acid (231 mg, 1.67 mmol), $K_2CO_3$ (346 mg, 2.51 mmol), [2-(2-aminophenyl)phenyl]-methylsulfonyloxy-palladium; dicyclohexyl-[3,6-dimethoxy-2-(2,4,6-triisopropylphenyl)phenyl]phosphane (75.7 mg, 83.6 umol) in dioxane (10 mL) and $H_2O$ (2 mL) was degassed and purged with $N_2$ for 3 times, and then the mixture was stirred at 80° C. for 12 hr under $N_2$ atmosphere. The reaction mixture was partitioned between $H_2O$ 15 mL and Ethyl acetate 100 mL. The organic phase was separated, washed with brine 20 mL, dried over $Na_2SO_4$, filtered, concentrated and purified by column chromatography ($SiO_2$, Petroleum ether/Ethyl acetate=3/1) to give the title compound (190 mg, 48% yield) as a yellow solid. LC-MS (ESI$^+$) m/z 465.3 (M+H)$^+$.

Step 5: 2-[6-amino-5-[1-[2-(4-piperidyl)ethyl]pyrazol-4-yl]pyridazin-3-yl]phenol To a solution of tert-butyl 4-[2-[4-[3-amino-6-(2-hydroxyphenyl)pyridazin-4-yl]pyrazol-1-yl]ethyl]piperidine-1-carboxylate (190 mg, 409 umol) in DCM (3 mL) was added HCl/dioxane (4 M, 102 uL). The mixture was stirred at 25° C. for 1 hr. The reaction mixture was concentrated under reduced pressure to give the title compound (140 mg, crude) as a yellow solid. LC-MS (ESI$^+$) m/z 365.2 (M+H)$^+$.

Step 6: 3-[6-[3-[4-[2-[4-[3-amino-6-(2-hydroxyphenyl] pyridazin-4-yl]pyrazol-1-yl]ethyl]-1-piperidyl]propyl] pyrido[2,3-b]indol-9-yl]piperidine-2,6-dione To a solution of 2-[6-amino-5-[1-[2-(4-piperidyl)ethyl] pyrazol-4-yl]pyridazin-3-yl]phenol (40 mg, 99.8 umol), 3-[9-(2,6-dioxo-3-piperidyl)pyrido[2,3-b]indol-6-yl]propanal (33.5 mg, 99.8 umol) and AcOH (30.0 mg, 499 umol) in THF (3 mL) and DMF (3 mL). The mixture was stirred at 25° C. for 0.5 hr. Then NaBH(OAc)$_3$ (63.4 mg, 299 umol) was added at 25° C. The mixture was stirred at 25° C. for 12 hr. The reaction mixture was quenched by addition $H_2O$ 2 mL at 25° C., and then concentrated and purified by prep-HPLC (column: Phenomenex Synergi C18 150*25*10 um; mobile phase: [water (0.05% HCl)-ACN]; B %: 21%-41%, 11 min) to give the title compound (38.0 mg, 52.5% yield) as a yellow solid. $^1$H NMR (400 MHz, DMSO-$d_6$) δ=11.15 (s, 1H), 8.54 (d, J=5.2 Hz, 2H), 8.42 (d, J=4.4 Hz, 1H), 8.28 (s, 1H), 8.11 (s, 2H), 7.65-7.54 (m, 2H), 7.44-7.35 (m, 2H), 7.27 (m, 1H), 7.14-7.05 (m, 1H), 6.99 (m, 1H), 6.11-5.98 (m, 1H), 4.24 (m, 2H), 3.50-3.47 (m, 3H), 3.19-2.96 (m, 4H), 2.93-2.77 (m, 4H), 2.12 (m, 4H), 1.98-1.74 (m, 5H), 1.70-1.39 (m, 4H). LC-MS (ESI$^+$) m/z 684.4 (M+H)$^+$.

Example 13. General Method E. Synthesis of 3-(5-(5-(4-(4-(3-amino-6-(2-hydroxyphenyl)pyridazin-4-yl)-1H-pyrazol-1-yl)piperidin-1-yl)pentyl)-9H-pyrido[2,3-b]indol-9-yl)piperidine-2,6-dione (I-136)

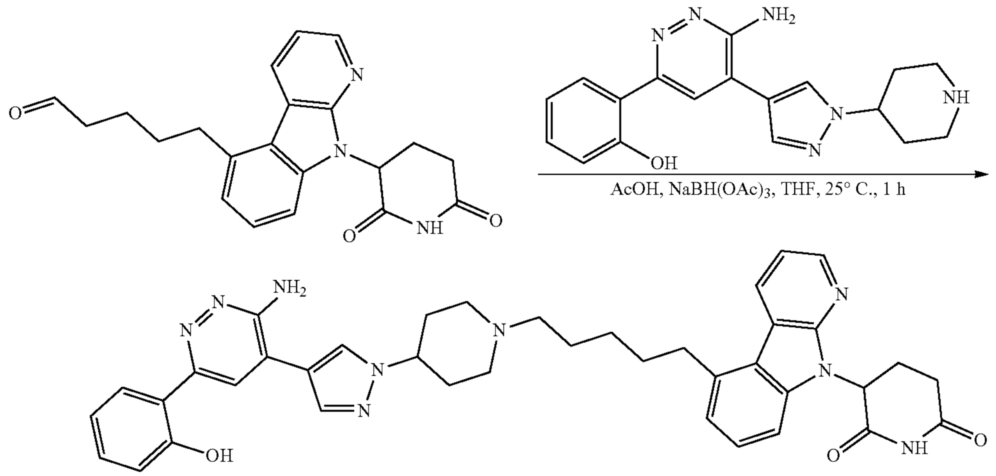

I-136

Step 1: 3-(5-(5-(4-(4-(3-amino-6-(2-hydroxyphenyl)pyridazin-4-yl)-1H-pyrazol-1-yl)piperidin-1-yl)pentyl)-9H-pyrido[2,3-b]indol-9-yl)piperidine-2,6-dione To a solution of 5-[9-(2,6-dioxo-3-piperidyl)pyrido[2,3-b]indol-5-yl]pentanal (30 mg, 0.083 mmol) and 2-[6-amino-5-[1-(4-piperidyl)pyrazol-4-yl]pyridazin-3-yl]phenol (33.32 mg, 0.099 mmol) in THF (1 mL) was added AcOH (25 mg, 0.41 mmol) and $NaBH(OAc)_3$ (53 mg, 0.25 mmol). The mixture was stirred at 25° C. for 1 hr. The reaction mixture was quenched by $H_2O$ 3 mL at 15° C., and then concentrated under reduced pressure to give a residue. The residue was purified by prep-HPLC (column: Phenomenex Gemini-NX C18 75*30 mm*3 um; mobile phase: [water (0.1% TFA)-ACN]; B %: 12%-42%, 7 min), then added HCl (2 mL, 1N) to give title compound (HCl, 20 mg, 28% yield, 99% purity) as a yellow solid. $^1$H NMR (400 MHz, DMSO-$d_6$) δ=11.16 (s, 1H), 10.86-10.78 (m, 1H), 8.51-8.43 (m, 3H), 8.29 (s, 1H), 8.14 (s, 1H), 7.60 (m, 1H), 7.46-7.38 (m, 4H), 7.14-7.10 (m, 2H), 6.98 (s, 1H), 6.08-6.05 (m, 1H), 4.58-4.53 (m, 1H), 3.23-3.07 (m, 9H), 2.73 (s, 2H), 2.42-2.33 (m, 6H), 2.14-2.10 (s, 1H), 1.82 (s, 4H), 1.52 (m, 2H); LC-MS (ESI+) m/z 684.2 (M+H)+.

Characterization data for further compounds prepared by Method E are presented in Table 5 below. Compounds in Table 5 were prepared by methods substantially similar to the steps described to prepare I-136.

TABLE 5

Compounds prepared according to Method E.

| I-# | LC/MS (ESI, m/z) | $^1$H NMR (400 MHz) |
|---|---|---|
| I-133 | $[M + 1]^+$ = 670.5 | 1HNMR (400 MHz, DMSO-d6) δ = 11.16 (s, 1 H), 10.93 (s, 1 H), 8.50-8.69 (m, 2 H), 8.42 (s, 1 H), 8.28-8.34 (m, 2 H), 8.01-8.22 (m, 2 H), 7.60 (d, J = 7.6 Hz, 2 H), 7.34-7.47 (m, 2 H), 7.21-7.32 (m, 1 H), 7.12 (d, J = 8.0 Hz, 1 H), 6.99 (t, J = 7.2 Hz, 1 H), 6.06 (s, 1 H), 4.57 (s, 1H), 3.62 (d, J = 11.2 Hz, 2 H), 3.41 (s, 1 H), 2.94-3.28 (m, 6 H), 2.65-2.87 (m, 3 H), 2.26-2.46 (m, 4 H), 2.13 (s, 1 H), 1.83-1.74 (m, 4 H). |
| I-134 | $[M + 1]^+$ = 684.6 | 1H NMR (400 MHz, DMSO-d6) δ = 11.15 (s, 1 H), 10.57 (s, 1 H), 8.50-8.59 (m, 2 H), 8.41 (d, J = 4.4 Hz, 1 H), 8.29 (s, 1 H), 8.11 (d, J = 18.0 Hz, 3 H), 7.59 (d, J = 7.2 Hz, 2 H), 7.38 (s, 2 H), 7.23-7.31 (m, 1 H), 7.14 (d, J = 8.4 Hz, 1 H), 6.98 (t, J = 7.60 Hz, 1 H), 6.06 (s, 1 H), 4.13 (m, 3 H), 3.44 (d, J = 10.0 Hz, 2 H), 2.98-3.28 (m, 4 H), 2.87-2.50 (m, 5 H), 2.11 (m, 2 H), 1.71 (m, 8H). |
| I-135 | $[M + 1]^+$ = 684.2 | 1H NMR (400 MHz, DMSO-d6) δ = 11.14 (s, 1H), 11.03-10.88 (m, 1H), 8.55 (dd, J = 1.2, 7.6 Hz, 1H), 8.51 (s, 1H), 8.40 (dd, J = 1.2, 4.8 Hz, 1H), 8.29 (s, 1H), 8.14 (s, 1H), 8.08 (s, 1H), 7.59 (dd, J = 1.6, 7.6 Hz, 1H), 7.56-7.50 (m, 1H), 7.41-7.35 (m, 2H), 7.25 (dd, J = 4.8, 7.6 Hz, 1H), 7.13-7.07 (m, 1H), 6.98 (t, J = 7.2 Hz, 1H), 6.12-5.94 (m, 1H), 4.60-4.50 (m, 1H), 3.42-3.37 (m, 1H), 3.17-2.97 (m, 7H), 2.82-2.75 (m, 2H), 2.74-2.65 (m, 2H), 2.46-2.36 (m, 3H), 2.35-2.26 (m, 2H), 2.16-2.08 (m, 1H), 1.88-1.77 (m, 2H), 1.75-1.66 (m, 2H), 1.44-1.31 (m, 2H). |
| I-137 | $[M + 1]^+$ = 684.4 | 1H NMR (400 MHz, DMSO-d6) δ = 11.14 (s, 1H), 10.93 (d, J = 6.4 Hz, 1H), 8.50 (s, 1H), 8.34 (d, J = 4.8 Hz, 1H), 8.29 (s, 1H), 8.19-8.12 (m, 3H), 7.65 (d, J = 3.2 Hz, 1H), 7.61-7.57 (m, 1H), 7.53 (t, J = 7.6 Hz, 1H), 7.36 |

TABLE 5-continued
| Compounds prepared according to Method E. | | |
|---|---|---|
| I-# | LC/MS (ESI, m/z) | $^1$H NMR (400 MHz) |
| | | (td, J = 7.6, 15.6 Hz, 2H), 7.17-7.07 (m, 2H), 6.98 (t, J = 7.6 Hz, 1H), 6.15-5.99 (m, 1H), 4.61-4.49 (m, 2H), 3.61 (d, J = 11.6 Hz, 2H), 3.28-3.19 (m, 2H), 3.17-2.96 (m, 6H), 2.75-2.65 (m, 1H), 2.45-2.39 (m, 2H), 2.35-2.27 (m, 2H), 2.15-2.06 (m, 1H), 1.84 (s, 4H), 1.52 (d, J = 6.0 Hz, 2H). |
Example 14. General Method F. Synthesis of 3-(5-(3-((3-(2-(4-(3-(2-hydroxyphenyl)-7H-pyrrolo[2,3-c]pyridazin-5-yl)piperidin-1-yl)pyrimidin-5-yl)propyl)(methyl)amino)propyl)-3-methyl-2-oxo-2,3-dihydro-1H-benzo[d]imidazol-1-yl)piperidine-2,6-dione (I-139)
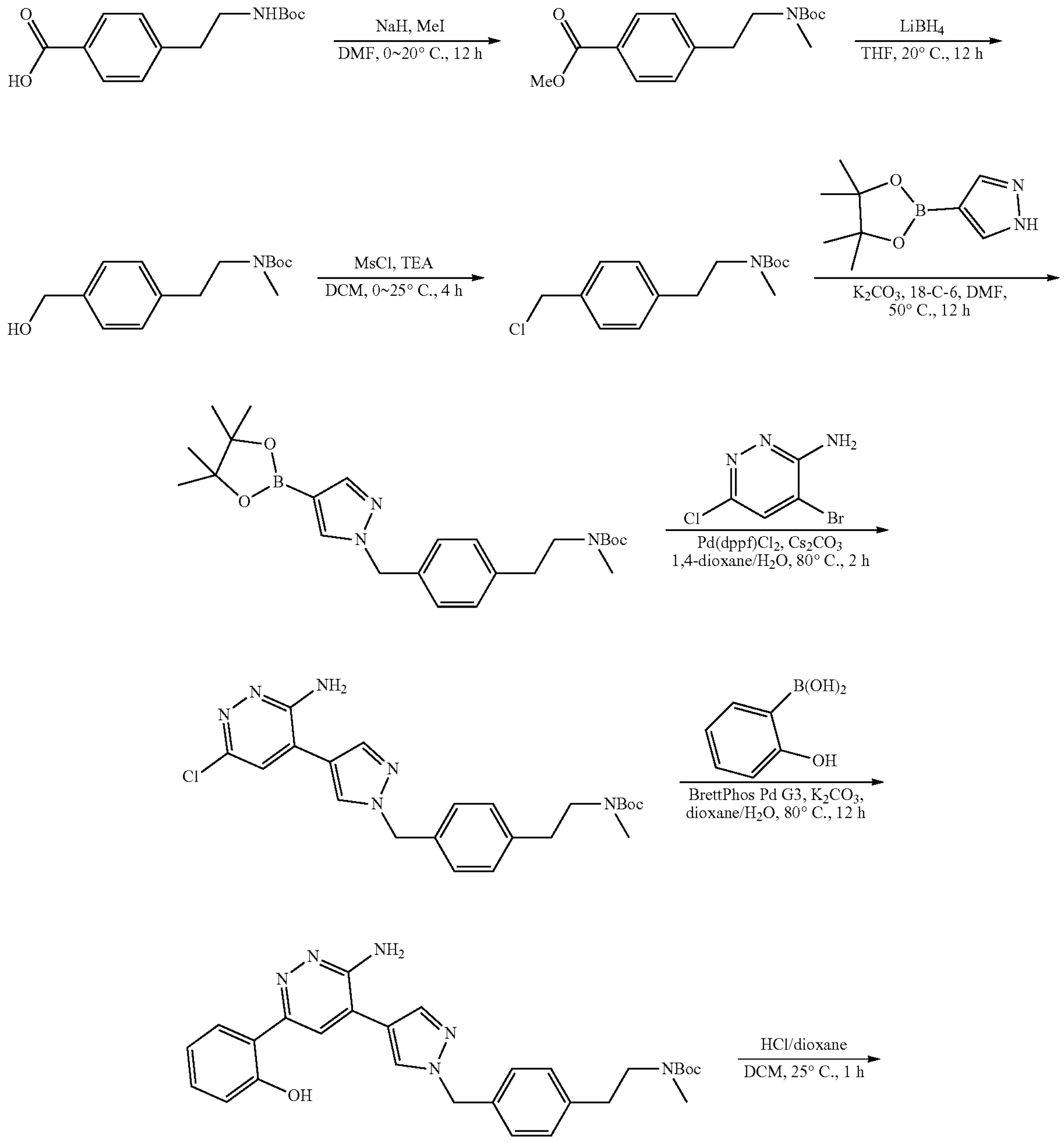

-continued

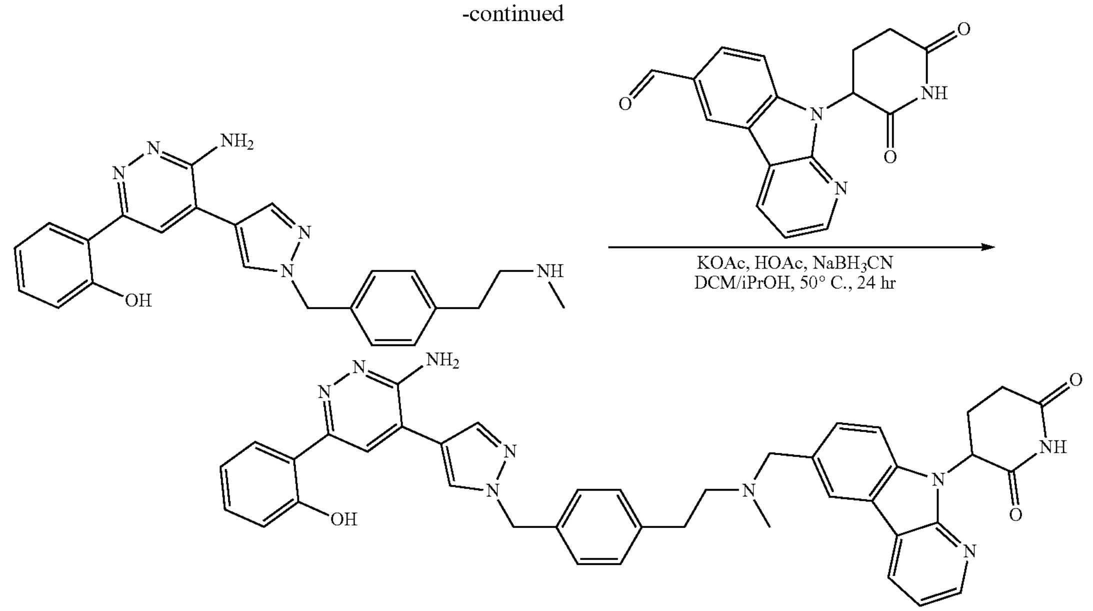

I-139

Step 1: methyl 4-(2-((tert-butoxycarbonyl)(methyl) amino)ethyl)benzoate

To a solution of 4-[2-(tert-butoxycarbonylamino)ethyl] benzoic acid (3 g, 11.31 mmol) in DMF (40 mL) was added NaH (1.36 g, 60% purity, 3 eq) at 0° C. and stirred at 20° C. for 1 hr. Then the mixture was added MeI (16.1 g, 113 mmol, 10 eq) at 0° C. The mixture was stirred at 20° C. for 12 hr. The reaction mixture was quenched by addition $H_2O$ (100 mL) at 0° C., and then diluted with water (100 mL) and extracted with EA (200 mL*3). The combined organic layers were washed with brine (100 mL*6), dried over $Na_2SO_4$, filtered and concentrated under reduced pressure to give a residue. The residue was purified by column chromatography ($SiO_2$, Petroleum ether/Ethyl acetate=20/1 to 15/1) to give the title compound (1.95 g, 48% yield, 81% purity) as a off-white oil. $^1$H NMR (400 MHz, DMSO-d6) δ=1.22-1.41 (m, 9H), 2.75 (s, 3H), 2.84 (2H), 3.38-3.47 (m, 2H), 3.84 (s, 3H), 7.35 (m, 2H), 7.89 (d, J=8.0 Hz, 2H).

Step 2: tert-butyl 4-(hydroxymethyl)phenethyl(methyl)carbamate

To a solution of methyl 4-[2-[tert-butoxycarbonyl (methyl)amino]ethyl]benzoate (1.95 g, 6.65 mmol) in THF (40 mL) was added $LiBH_4$ (290 mg, 13.3 mmol) at 0° C. The mixture was stirred at 25° C. for 12 hr. The reaction mixture was quenched by addition $H_2O$ (20 mL) at 0° C., and then diluted with water (30 mL) and extracted with EA (80 mL*3). The combined organic layers were washed with brine (60 mL*3), dried over $Na_2SO_4$, filtered and concentrated under reduced pressure to give the title compound (1.6 g, crude) as a off-white oil. $^1$H NMR (400 MHz, DMSO-d6) δ=1.28-1.42 (m, 9H), 2.70-2.73 (m, 2H), 2.74 (s, 3H), 3.34-3.38 (m, 2H), 4.44-4.48 (m, 2H), 5.10 (m, 1H), 7.12-7.19 (m, 2H), 7.21-7.27 (m, 2H).

Step 3: tert-butyl 4-(chloromethyl)phenethyl(methyl)carbamate

To a solution of tert-butyl N-[2-[4-(hydroxymethyl)phenyl]ethyl]-N-methyl-carbamate (1.6 g, 6.03 mmol) in DCM (30 mL) was added TEA (1.22 g, 12.1 mmol) and MsCl (1.04 g, 9.04 mmol) at 0° C. The mixture was stirred at 25° C. for 4 hr. The reaction mixture was quenched by addition $H_2O$ (20 mL) at 25° C., and then diluted with water (60 mL) and extracted with DCM (100 mL*3). The combined organic layers were washed with brine (80 mL*3), dried over $Na_2SO_4$, filtered and concentrated under reduced pressure to give the title compound (1.8 g, crude) as a yellow oil. $^1$H NMR (400 MHz, DMSO-d6) δ=1.25-1.39 (m, 9H), 2.72-2.74 (m, 1H), 2.75 (s, 3H), 2.76-2.78 (m, 1H), 3.36-3.41 (m, 2H), 4.73 (s, 2H), 7.14-7.24 (m, 2H), 7.36 (m, 2H).

Step 4: tert-butyl methyl(4-((4-(4,4,5,5-tetramethyl-1,3,2-dioxaborolan-2-yl)-1H-pyrazol-1-yl)methyl) phenethyl)carbamate To a solution of tert-butyl tert-butyl 4-(chloromethyl) phenethyl(methyl)carbamate (1.2 g, 4.23 mmol) and 4-(4,4,5,5-tetramethyl-1,3,2-dioxaborolan-2-yl)-1H-pyrazole (820 mg, 4.23 mmol) in DMF (15 mL) was added $K_2CO_3$ (1.17 g, 8.46 mmol) and 18-C-6 (112 mg, 423 umol). The mixture was stirred at 50° C. for 12 hr. The reaction mixture was quenched by addition $H_2O$ (20 mL) at 25° C., and then diluted with water (100 mL) and extracted with EA (100 mL*3). The combined organic layers were washed with brine (80 mL*3), dried over $Na_2SO_4$, filtered and concentrated under reduced pressure to give a residue. The residue was purified by column chromatography (SiO2, Petroleum ether/Ethyl acetate=10/1 to 2/1) to give the title compound (1.25 g, 58% yield) as a off-white oil. $^1$H NMR (400 MHz, DMSO-d6) δ=1.15-1.22 (m, 6H), 1.24 (s, 12H), 1.35 (s, 3H), 2.69-2.73 (m, 2H), 2.74 (s, 3H), 3.33-3.38 (m, 2H), 5.29 (s, 2H), 7.13-7.16 (m, 2H), 7.16-7.22 (m, 2H), 7.58 (s, 1H), 7.98 (s, 1H); LC/MS (ESI, m/z): $[M+1]^+$=442.5.

Step 5: tert-butyl 4-((4-(3-amino-6-chloropyridazin-4-yl)-1H-pyrazol-1-yl)methyl)phenethyl(methyl) carbamate To a solution of 4-bromo-6-chloro-pyridazin-3-amine (460 mg, 2.21 mmol) and tert-butylmethyl(4-((4-(4,4,5,5-tetramethyl-1,3,2-dioxaborolan-2-yl)-1H-pyrazol-1yl) methyl) phenethyl)carbamate (1.25 g, 2.21 mmol) in 1,4-dioxane (15 mL) was added Pd(dppf)$Cl_2$·$CH_2Cl_2$ (180 mg, 221 umol) and $Cs_2CO_3$ (2 M, 2 eq). The mixture was stirred at 80° C. for 12 hrs. The reaction mixture was quenched by addition $H_2O$ (10 mL) at 25° C., and then diluted with water (80 mL) and extracted with EA (100 mL*3). The combined organic layers were washed with brine (60 mL*3), dried over $Na_2SO_4$, filtered and concentrated under reduced pressure to give a residue. The residue was purified by column chromatography (SiO2, Petroleum ether/Ethyl acetate=5/1 to 1/2) to give the title compound (900 mg, 86% yield) as a yellow solid. LC/MS (ESI, m/z): $[M+1]^+$=443.3.

Step 6: tert-butyl 4-((4-(3-amino-6-(2-hydroxyphenyl)pyridazin-4-yl)-1H-pyrazol-1-yl)methyl)phenethyl(methyl)carbamate A mixture of tert-butyl 4-((4-(3-amino-6-chloropyridazin-4-yl)-1H-pyrazol-1-yl)methyl)phenethyl(methyl)carbamate (900 mg, 2.03 mmol), (2-hydroxyphenyl)boronic acid (841 mg, 6.10 mmol), BrettPhos Pd G3 (184 mg, 203 umol, 0.1 eq) and $K_2CO_3$ (842 mg, 3 eq) in dioxane (20 mL) and $H_2O$ (4 mL) was degassed and purged with $N_2$ for 3 times, and then the mixture was stirred at 80° C. for 12 hr under $N_2$ atmosphere. The reaction mixture was quenched by addition $H_2O$ (10 mL) at 25° C., and then diluted with water (50 mL) and extracted with EA (80 mL*3). The combined organic layers were washed with brine (60 mL*3), dried over $Na_2SO_4$, filtered and concentrated under reduced pressure to give a residue. The residue was purified by column chromatography (SiO2, Petroleum ether/Ethyl acetate=4/1 to 1/2) to give the title compound (700 mg, 69% yield) as a yellow solid. 1H NMR (400 MHz, DMSO-d6) δ=1.24-1.37 (m, 9H), 2.70-2.74 (m, 2H), 2.75 (s, 3H), 3.35-3.38 (m, 2H), 5.37 (s, 2H), 6.50 (s, 2H), 6.89-6.95 (m, 2H), 7.01-7.12 (m, 1H), 7.17=7.22 (m, 2H), 7.23-7.35 (m, 4H), 8.20 (m, 1H), 8.55-8.59 (m, 1H), 13.8 (s, 1H); LC/MS (ESI, m/z): $[M+1]^+$=501.3.

Step 7: 2-(6-amino-5-(1-(4-(2-(methylamino)ethyl)benzyl)-1H-pyrazol-4-yl)pyridazin-3-yl)phenol To a solution of tert-butyl 4-((4-(3-amino-6-(2-hydroxyphenyl)pyridazin-4-yl)-1H-pyrazol-1-yl)methyl)phenethyl(methyl)carbamate (300 mg, 1 eq) in DCM (5 mL) was added HCl/dioxane (2 M, 5.00 mL). The mixture was stirred at 25° C. for 1 hr. The solvent was removed under reduced pressure to give the title compound (340 mg, crude, HCl) as a yellow solid. $^1$H NMR (400 MHz, DMSO-d6) δ=2.37 (s, 3H), 2.74-2.84 (m, 4H), 5.37 (s, 2H), 5.76 (s, 1H), 6.50 (s, 2H), 6.90-6.95 (m, 2H), 7.21-7.24 (m, 2H), 7.24-7.28 (m, 1H), 7.28-7.32 (m, 2H), 7.98-8.05 (m, 1H), 8.20 (d, J=4.0 Hz, 2H), 8.58 (s, 1H), 13.81 (s, 1H); LC/MS (ESI, m/z): $[M+1]^+$=401.2.

Step 8: 3-(6-(((4-((4-(3-amino-6-(2-hydroxyphenyl)pyridazin-4-yl)-1H-pyrazol-1-yl)methyl)phenethyl)(methyl)amino)methyl)-9H-pyrido[2,3-b]indol-9-yl)piperidine-2,6-dione (I-139)

A mixture of 2-[6-amino-5-[1-[[4-[2-(methylamino)ethyl]phenyl]methyl]pyrazol-4-yl]pyridazin-3-yl]phenol (90 mg, 225 umol), 9-(2,6-dioxo-3-piperidyl)pyrido[2,3-b]indole-6-carbaldehyde (69.1 mg, 225 umol, 1 eq), KOAc (88.2 mg, 899 umol, 4 eq) and AcOH (27.0 mg, 25.7 uL, 2 eq) in DCM (1 mL) and i-PrOH (1 mL) was degassed and purged with $N_2$ for 3 times, and then the mixture was stirred at 50° C. for 12 hr under $N_2$ atmosphere. Then $NaBH_3CN$ (42.4 mg, 3 eq) was added, the resultant mixture was stirred at 50° C. for 12 hr. The reaction mixture was quenched by addition $H_2O$ (0.5 mL) at 25° C. The reaction mixture was concentrated under reduced pressure to remove DCM and iPrOH. The residue was purified by prep-HPLC (column: Waters Xbridge 150*25 mm*5 um; mobile phase: [water (10 mM $NH_4HCO_3$)-ACN]; B %: 32%-62%, 10 min) to give the title compound (18.5 mg, 11% yield) as a white solid. 1H NMR (400 MHz, DMSO-d6) δ=2.08-2.16 (m, 1H), 2.23 (s, 3H), 2.57-2.65 (m, 2H), 2.76-2.85 (m, 2H), 2.97-3.15 (m, 2H), 3.68 (s, 2H), 5.35 (s, 2H), 6.02 (s, 1H), 6.49 (s, 2H), 6.89-6.94 (m, 2H), 7.20-7.24 (m, 2H), 7.24-7.29 (m, 4H), 7.39-7.47 (m, 1H), 7.51-7.58 (m, 1H), 7.97-8.02 (m, 1H), 8.08 (s, 1H), 8.19 (d, J=4.0 Hz, 2H), 8.39-8.42 (m, 1H), 8.51-8.54 (m, 1H), 8.57 (s, 1H), 11.14 (s, 1H), 13.81 (s, 1H); LC/MS (ESI, m/z): $[M+1]^+$=692.4.

Example 15. General Method G. 3-(6-(4-(5-((4-(3-amino-6-(2-hydroxyphenyl)pyridazin-4-yl)-1H-pyrazol-1-yl)methyl)-1,3-dioxan-2-yl)butyl)-9H-pyrido[2,3-b]indol-9-yl)piperidine-2,6-dione (I-140)

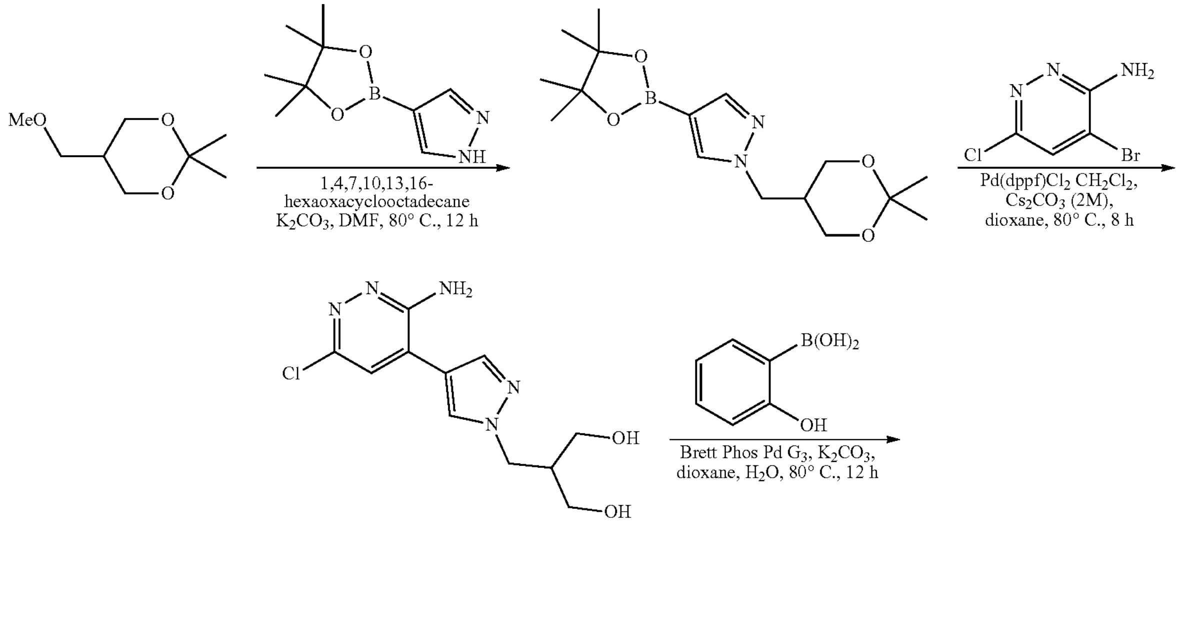

-continued

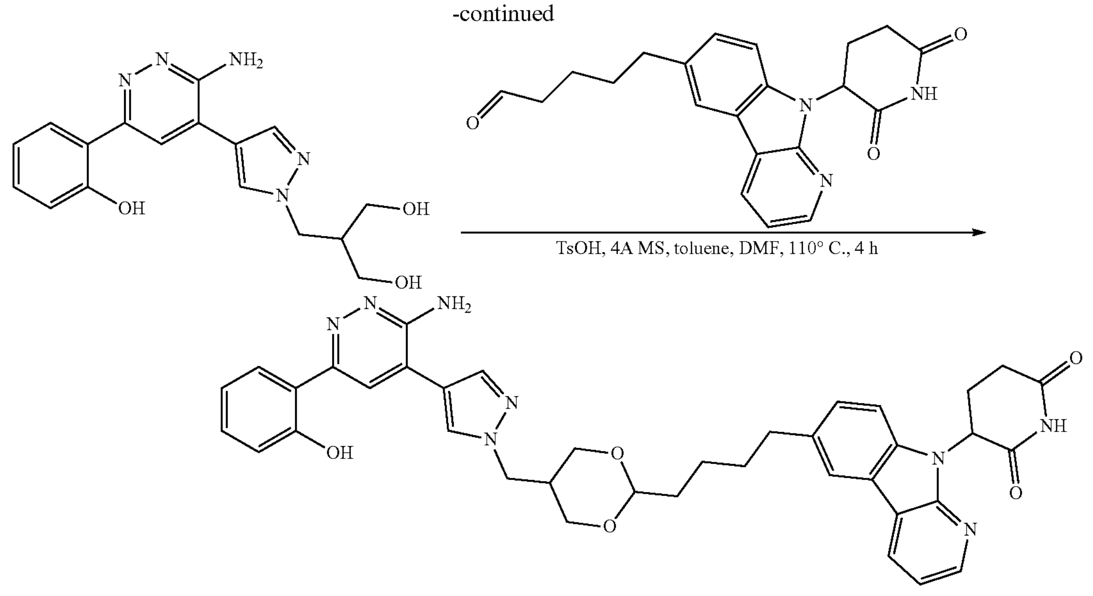

I-140

Step 1: 1-((2,2-dimethyl-1,3-dioxan-5-yl)methyl)-4-(4,4,5,5-tetramethyl-1,3,2-dioxaborolan-2-yl)-1H-pyrazole A mixture of (2,2-dimethyl-1,3-dioxan-5-yl)methyl methanesulfonate (2.4 g, 10.7 mmol), 4-(4,4,5,5-tetramethyl-1,3,2-dioxaborolan-2-yl)-1H-pyrazole (1.38 g, 7.13 mmol), $K_2CO_3$ (2.96 g, 21.4 mmol), 1,4,7,10,13,16-hexaoxacyclooctadecane (189 mg, 713 umol) in DMF (20 mL) was degassed and purged with $N_2$ for 3 times, and then the mixture was stirred at 80° C. for 12 hrs under $N_2$ atmosphere. The reaction mixture was diluted with $H_2O$ (50 mL) and extracted with EA (50 mL*3). The combined organic layers were washed with saturated brine (150 mL*6), dried over $Na_2SO_4$, filtered and concentrated under reduced pressure to give the title compound (2.5 g, crude) as a brown solid. $^1H$ NMR (400 MHz, DMSO-$d_6$) δ=7.91 (s, 1H), 7.59 (s, 1H), 4.21 (d, J=7.6 Hz, 2H), 3.81 (dd, J=4.0, 12.0 Hz, 2H), 3.66 (dd, J=5.6, 12.0 Hz, 1H), 3.47 (dd, J=5.6, 12.0 Hz, 2H), 1.32 (s, 6H), 1.24 (s, 12H); LC-MS (ESI+) m/z 323.0 $(M+H)^+$.

Step 2: 2-((4-(3-amino-6-chloropyridazin-4-yl)-1H-pyrazol-1-yl)methyl)propane-1,3-diol A mixture of 1-[(2,2-dimethyl-1,3-dioxan-5-yl)methyl]-4-(4,4,5,5-tetramethyl-1,3,2-dioxaborolan-2-yl)pyrazole (2 g, 6.21 mmol), 4-bromo-6-chloro-pyridazin-3-amine (863 mg, 4.14 mmol), Pd(dppf)$Cl_2$·$CH_2Cl_2$ (338 mg, 414 umol), $Cs_2CO_3$ (2 M, 6.21 mL) in dioxane (15 mL) was degassed and purged with $N_2$ for 3 times, and then the mixture was stirred at 80° C. for 8 hrs under $N_2$ atmosphere. The reaction mixture was diluted with $H_2O$ (50 mL) and extracted with EA (50 mL*3). The combined organic layers were washed with saturated brine (150 mL*3), dried over $Na_2SO_4$, filtered and concentrated under reduced pressure to give a residue. The residue was purified by reversed-phase flash (0.1% FA condition) to give the title compound (1.6 g, crude) as a brown solid. $^1H$ NMR (400 MHz, DMSO-$d_6$) δ=8.32 (s, 1H), 8.05 (s, 1H), 7.59 (s, 1H), 6.35 (s, 2H), 4.21 (d, J=5.6 Hz, 1H), 4.16 (d, J=6.8 Hz, 2H), 4.10 (d, J=7.2 Hz, 1H), 3.39-3.37 (m, 4H), 2.13-2.07 (m, 1H); LC-MS (ESI+) m/z 284.1 $(M+H)^+$.

Step 3: 2-((4-(3-amino-6-(2-hydroxyphenyl)pyridazin-4-yl)-1H-pyrazol-1-yl)methyl)propane-1,3-diol A mixture of 2-[[4-(3-amino-6-chloro-pyridazin-4-yl)pyrazol-1-yl]methyl]propane-1,3-diol (1.5 g, 5.29 mmol), (2-hydroxyphenyl)boronic acid (2.19 g, 15.9 mmol), Brett-Phos Pd G3 (479 mg, 529 umol) and $K_2CO_3$ (2.19 g, 15.9 mmol) in dioxane (15 mL) and $H_2O$ (3 mL) was degassed and purged with $N_2$ for 3 times, and then the mixture was stirred at 80° C. for 12 hr under $N_2$ atmosphere. The reaction mixture was diluted with $H_2O$ 80 mL and extracted with EA (80 mL*3). The combined organic layers were washed with saturated brine (250 mL), dried over $Na_2SO_4$, filtered and concentrated under reduced pressure to give a residue. The residue was purified by reversed-phase flash (0.1% FA condition) to give the title compound (600 mg, 29% yield) as a green solid. $^1H$ NMR (400 MHz, DMSO-$d_6$) δ=9.35-9.13 (m, 1H), 8.19 (d, J=14.4 Hz, 1H), 7.31-7.20 (m, 1H), 7.18-7.13 (m, 1H), 7.08-7.01 (m, 1H), 6.95-6.89 (m, 2H), 6.78-6.72 (m, 2H), 6.48 (s, 1H), 4.64-4.55 (m, 2H), 4.23-4.15 (m, 2H), 3.46-3.36 (m, 4H), 2.18-2.09 (m, 1H); LC-MS $(ESI^+)$ m/z 342.3 $(M+H)^+$.

Step 4: 3-(6-(4-(5-((4-(3-amino-6-(2-hydroxyphenyl)pyridazin-4-yl)-1H-pyrazol-1-yl)methyl)-1,3-dioxan-2-yl)butyl)-9H-pyrido[2,3-b]indol-9-yl)piperidine-2,6-dione (I-140)

To a solution of 2-[[4-[3-amino-6-(2-hydroxyphenyl)pyridazin-4-yl]pyrazol-1-yl]methyl]propane-1,3-diol (50 mg, 129 umol, FA) and 5-[9-(2,6-dioxo-3-piperidyl)pyrido[2,3-b]indol-6-yl]pentanal (31.3 mg, 86.1 umol) in toluene (3 mL) and DMF (1 mL) was added TsOH (1.48 mg, 8.60 umol) and 4A MOLECULAR SIEVE (50 mg). The mixture was stirred at 110° C. for 4 hr. The mixture was concentrated under reduced pressure to remove toluene and filtered to collect the filtrate. The filtrate was purified by prep-HPLC (column: Waters Xbridge 150*25 mm*5 um; mobile phase: [water (10 mM $NH_4HCO_3$)-ACN]; B %: 32%-62%, 10 min). The fraction was concentrated under reduced pressure to remove ACN and lyophilized. The lyophilization was purified by prep-HPLC (column: Waters Xbridge 150*25 mm*5 um; mobile phase: [water (10 mM $NH4HCO_3$)-ACN]; B %: 42%-72%, 10 min) to give the title compound (2.2 mg, 4% yield) as a yellow solid. $^1H$ NMR (400 MHz, DMSO-$d_6$) δ=13.81 (d, J=6.0 Hz, 1H), 11.13 (s, 1H), 8.54-8.51 (m, 1H), 8.39 (dd, J=1.6, 4.8 Hz, 1H), 8.22-8.14 (m, 2H), 8.07-7.97 (m, 2H), 7.50 (s, 1H), 7.38-7.32 (m, 1H), 7.29-7.22 (m, 2H), 6.95-6.88 (m, 2H), 6.49 (s, 2H), 6.11-5.88 (m, 1H), 4.50-4.40 (m, 2H), 4.04-3.75 (m, 4H), 3.49 (t, J=11.2 Hz, 1H), 3.08-2.95 (m, 2H), 2.80-2.69 (m, 3H), 2.16-2.03 (m, 2H), 1.77-1.33 (m, 7H); LC-MS ($ESI^+$) m/z 687.3 $(M+H)^+$.

Example 16. General Method H. 3-[6-[3-[(3S)-3-[4-[3-amino-6-(2-hydroxyphenyl)pyridazin-4-yl]pyrazol-1-yl]-1-piperidyl]propyl]pyrido[2,3-b]indol-9-yl]piperidine-2,6-dione (I-141)

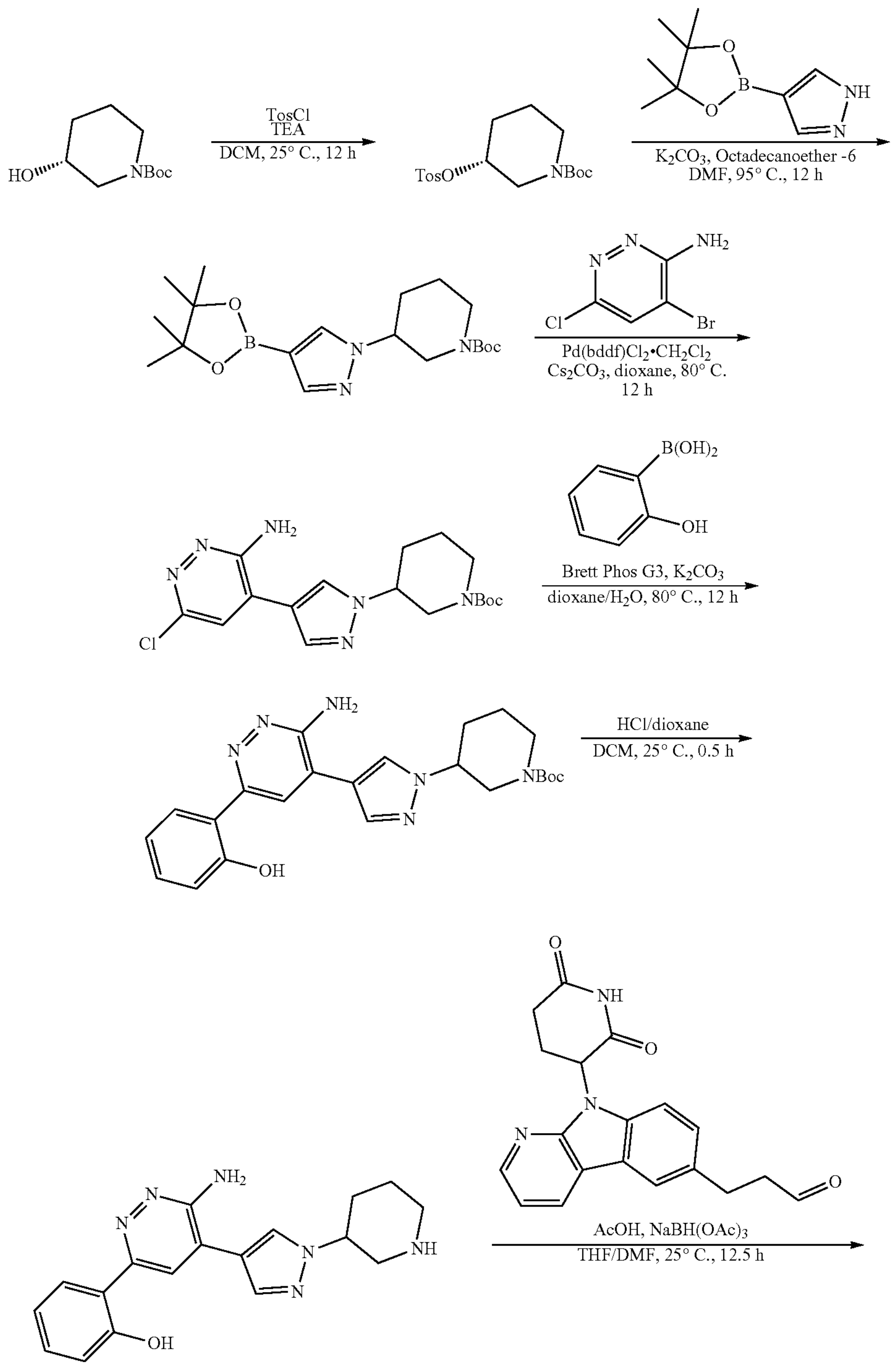

-continued

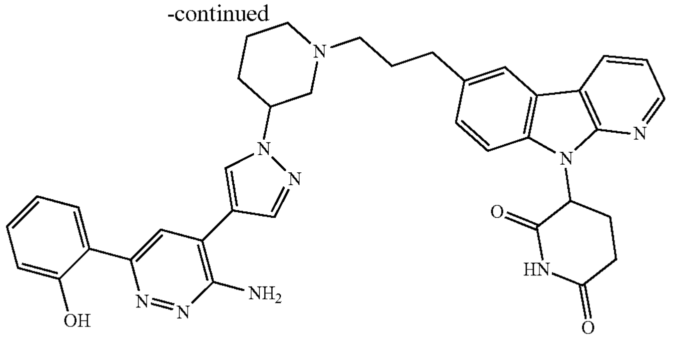

I-141

Step 1: tert-butyl (3R)-3-(p-tolylsulfonyloxy)piperidine-1-carboxylate

A mixture of 4-methylbenzenesulfonyl chloride (14.2 g, 74.5 mmol), tert-butyl (3R)-3-hydroxypiperidine-1-carboxylate (10 g, 49.7 mmol), TEA (15.1 g, 149 mmol) in DCM (150 mL) was degassed and purged with $N_2$ for 3 times, and then the mixture was stirred at 25° C. for 12 hr under $N_2$ atmosphere. The reaction mixture was partitioned between $H_2O$ (200 mL) and Ethyl acetate (500 mL). The organic phase was separated, washed with brine (150 mL*3), dried over $Na_2SO_4$, filtered, concentrated and purified by column chromatography ($SiO_2$, Petroleum ether/Ethyl acetate=15/1 to 10/1) to give the title compound (11.6 g, 60% yield) as a brown solid. $^1H$ NMR (400 MHz, DMSO-$d_6$) δ=7.81 (d, J=8.4 Hz, 2H), 7.48 (d, J=8.0 Hz, 2H), 4.46 (s, 1H), 3.60 (dd, J=3.2, 13.2 Hz, 2H), 3.42-3.33 (m, 2H), 2.42 (s, 3H), 1.85-1.50 (m, 4H), 1.35 (s, 9H); LC-MS (ESI+) m/z 300.2 $(M-56)^+$.

Step 2: tert-butyl-3-[4-(4,4,5,5-tetramethyl-1,3,2-dioxaborolan-2-yl)pyrazol-1-yl]piperidine-1-carboxylate A mixture of tert-butyl (3R)-3-(p-tolylsulfonyloxy)piperidine-1-carboxylate (10.6 g, 29.8 mmol), 4-(4,4,5,5-tetramethyl-1,3,2-dioxaborolan-2-yl)-1H-pyrazole (6.94 g, 35.8 mmol), $K_2CO_3$ (12.4 g, 89.5 mmol), 1,4,7,10,13,16-hexaoxacyclooctadecane (788 mg, 2.98 mmol) in DMF (100 mL) was degassed and purged with $N_2$ for 3 times, and then the mixture was stirred at 95° C. for 12 hr under $N_2$ atmosphere. The reaction mixture was partitioned between $H_2O$ (150 mL) and EA (500 mL). The organic phase was separated, washed with brine (100 mL), dried over $Na_2SO_4$, filtered, concentrated and purified by column chromatography ($SiO_2$, Petroleum ether/Ethyl acetate=20/1 to 10/1) to give the title compound (3.4 g, 24% yield) was obtained as a yellow oil. $^1H$ NMR (400 MHz, DMSO-$d_6$) δ=8.02 (s, 1H), 7.62 (s, 1H), 3.75 (d, J=4.8 Hz, 2H), 3.61 (d, J=12.8 Hz, 2H), 2.07-2.04 (m, 1H), 1.81 (d, J=7.6 Hz, 2H), 1.65-1.60 (m, 2H), 1.25 (s, 9H), 1.08 (s, 12H); LC-MS (ESI+) m/z 322.1 $(M-55)^+$.

Step 3: tert-butyl-3-[4-(3-amino-6-chloro-pyridazin-4-yl)pyrazol-1-yl]piperidine-1-carboxylate A mixture of tert-butyl-3-[4-(4,4,5,5-tetramethyl-1,3,2-dioxaborolan-2-yl)pyrazol-1-yl]piperidine-1-carboxylate (400 mg, 1.06 mmol), 4-bromo-6-chloro-pyridazin-3-amine (221 mg, 1.06 mmol), $Cs_2CO_3$ (2 M, 1.59 mL), Pd(dppf)$Cl_2 \cdot CH_2Cl_2$ (43.3 mg, 53.0 umol) in dioxane (4 mL) was degassed and purged with $N_2$ for 3 times, and then the mixture was stirred at 80° C. for 12 hrs under $N_2$ atmosphere. The reaction mixture was partitioned between $H_2O$ (10 mL) and ethyl acetate (100 mL). The organic phase was separated, washed with brine (20 mL), dried over $Na_2SO_4$, filtered, concentrated and purified by column chromatography ($SiO_2$, Petroleum ether/Ethyl acetate=10/1 to 1/1) to give the title compound (100 mg, 24% yield) as a yellow solid. LC-MS (ESI+) m/z 379.1 $(M+H)^+$.

Step 4: tert-butyl-3-[4-[3-amino-6-(2-hydroxyphenyl)pyridazin-4-yl]pyrazol-1-yl]piperidine-1-carboxylate A mixture of tert-butyl-3-[4-(3-amino-6-chloro-pyridazin-4-yl)pyrazol-1-yl]piperidine-1-carboxylate (100 mg, 264 umol), (2-hydroxyphenyl)boronic acid (72.8 mg, 528 umol), $K_2CO_3$ (109 mg, 792 umol), [2-(2-aminophenyl)phenyl]-methylsulfonyloxy-palladium; dicyclohexyl-[3,6-dimethoxy-2-(2,4,6-triisopropylphenyl)phenyl]phosphane (23.9 mg, 26.4 umol) in dioxane (5 mL) and $H_2O$ (1 mL) was degassed and purged with $N_2$ for 3 times, and then the mixture was stirred at 80° C. for 12 hr under $N_2$ atmosphere. The reaction mixture was partitioned between $H_2O$ (4 mL) and ethyl acetate (50 mL). The organic phase was separated, washed with brine (20 mL), dried over $Na_2SO_4$, filtered, concentrated and purified by column chromatography ($SiO_2$, Petroleum ether/Ethyl acetate=10/1 to 1/1) to give the title compound (60 mg, 52% yield) as a yellow solid. LC-MS (ESI+) m/z 437.3 $(M+H)^+$.

Step 5: 2-[6-amino-5-[1-[3-piperidyl]pyrazol-4-yl]pyridazin-3-yl]phenol

To a solution of tert-butyl-3-[4-[3-amino-6-(2-hydroxyphenyl)pyridazin-4-yl]pyrazol-1-yl]piperidine-1-carboxylate (60 mg, 137 umol) in DCM (2 mL) was added HCl/dioxane (4 M, 34.4 uL). The mixture was stirred at 25° C. for 0.5 hr. The reaction mixture was concentrated under reduced pressure to give the title compound (40 mg, crude, HCl) as a yellow solid. LC-MS ($ESI^+$) m/z 337.2 $(M+H)^+$.

Step 6: 3-[6-[3-[3-[4-[3-amino-6-(2-hydroxyphenyl)pyridazin-4-yl]pyrazol-1-yl]-1-piperidyl]propyl]pyrido[2,3-b]indol-9-yl]piperidine-2,6-dione (I-141)

To a solution of 2-[6-amino-5-[1-[3-piperidyl]pyrazol-4-yl]pyridazin-3-yl]phenol (40 mg, 107 umol), 3-[9-(2,6-dioxo-3-piperidyl)pyrido[2,3-b]indol-6-yl]propanal (36.0 mg, 107 umol) and AcOH (32.2 mg, 536 umol) in DMF (3 mL) and THF (3 mL) was stirred 0.5 hr. Then $NaBH(OAc)_3$ (68.2 mg, 322 umol) was added at 25° C. The mixture was stirred at 25° C. for 12 hr. The reaction mixture was quenched by addition $H_2O$ (1 mL) at 25° C., and then concentrated and purified by prep-HPLC (column: Phenomenex Synergi C18 150*25*10 um; mobile phase: [water (0.05% HCl)-ACN]; B %: 19%-39%, 9.5 min) to give the title compound (19.3 mg, 26% yield) as a yellow solid. $^1H$ NMR (400 MHz, DMSO-$d_6$) δ=11.16 (s, 1H), 8.59-8.50 (m, 2H), 8.42 (d, J=2.8 Hz, 1H), 8.28 (s, 1H), 8.17 (d, J=4.8 Hz, 1H), 8.12 (s, 1H), 7.59-7.59 (m, 1H), 7.67-7.50 (m, 1H), 7.47-7.33 (m, 2H), 7.26 (d, J=5.2 Hz, 1H), 7.13-7.04 (m, 1H), 7.02-6.94 (m, 1H), 6.16-5.94 (m, 1H), 5.07-4.85 (m, 1H), 3.79 (d, J=10.8 Hz, 3H), 3.24-3.13 (m, 3H), 3.09-2.95 (m, 3H), 2.84 (s, 2H), 2.72 (d, J=6.4 Hz, 1H), 2.29-1.87 (m, 9H); LC-MS ($ESI^+$) m/z 656.5 $(M+H)^+$.

I-142 was prepared by a similar method as I-141. The S-chiral center of the starting material may racemize under the reaction conditions. 1H NMR (400 MHz, DMSO-d6) δ=11.57-11.40 (m, 1H), 11.19-11.10 (m, 1H), 8.62-8.50 (m, 2H), 8.42 (dd, J=1.2, 4.8 Hz, 1H), 8.29 (s, 1H), 8.23-8.04 (m, 3H), 7.65-7.53 (m, 2H), 7.46-7.35 (m, 2H), 7.30-7.23 (m, 1H), 7.12-7.05 (m, 1H), 6.99 (t, J=7.6 Hz, 1H), 6.15-5.91 (m, 1H), 4.98-4.88 (m, 1H), 3.80 (d, J=10.0 Hz, 2H), 3.56 (d, J=11.6 Hz, 1H), 3.38-3.28 (m, 1H), 3.23-3.14 (m, 2H), 3.12-2.93 (m, 3H), 2.88-2.80 (m, 2H), 2.69 (d, J=3.2 Hz, 1H), 2.29-2.17 (m, 3H), 2.15-1.97 (m, 4H). LC-MS (ESI+) m/z 656.4 $(M+H)^+$.

Example 17. General Method I. 3-(4-(3-(4-(2-(3-(3-amino-6-(2-hydroxyphenyl)pyridazin-4-yl)-3,8-diazabicyclo[3.2.1]octan-8-yl)pyrimidin-5-yl)piperidin-1-yl)propyl)-9H-pyrido[2,3-b]indol-9-yl)piperidine-2,6-dione (I-145)

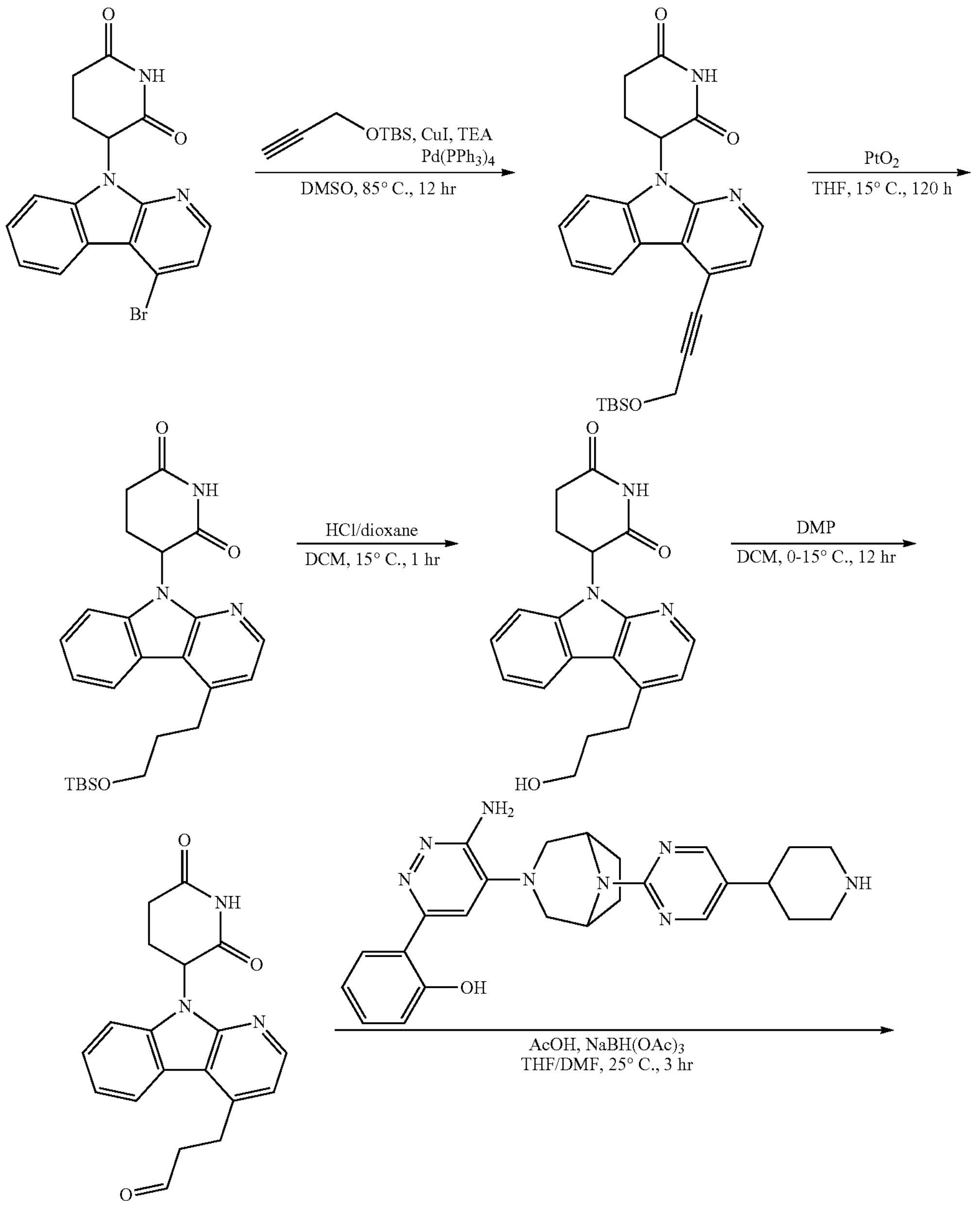

-continued

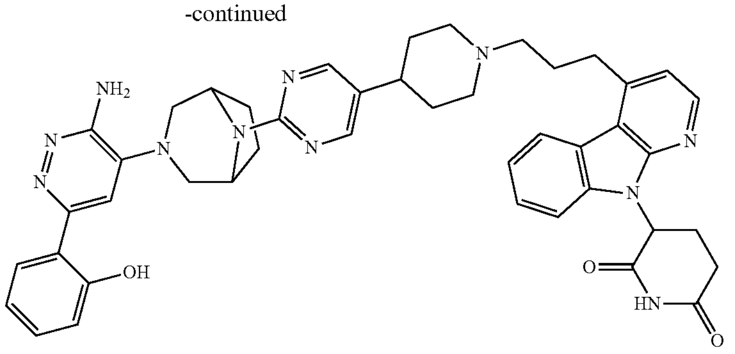

I-145

Step 1: 3-(4-(3-((tert-butyldimethylsilyl)oxy)prop-1-yn-1-yl)-9H-pyrido[2,3-b]indol-9-yl)piperidine-2,6-dione A mixture of 3-(4-bromopyrido[2,3-b]indol-9-yl)piperidine-2,6-dione (500 mg, 1.40 mmol), tert-butyl-dimethyl-prop-2-ynoxy-silane (713 mg, 4.19 mmol), Pd(PPh3)4 (161 mg, 140 umol), CuI (53.2 mg, 279 umol) and TEA (706 mg, 6.98 mmol) in DMSO (10 mL) was degassed and purged with $N_2$ for 3 times, and then the mixture was stirred at 85° C. for 12 hours under $N_2$ atmosphere. The reaction mixture was diluted with ethyl acetate (100 mL) and brine (100 mL). Then the aqueous layer was extracted with ethyl acetate (50 mL). The organic layers were dried over anhydrous $Na_2SO_4$, filtered and concentrated. The residue was purified by column chromatography ($SiO_2$, Petroleum ether/Ethyl acetate=I/O to 1/2) to give the title compound (600 mg, 79% yield) as a yellow solid. LC-MS ($ESI^+$) m/z=448.2 $(M+H)^+$.

Step 2: 3-(4-(3-((tert-butyldimethylsilyl)oxy)propyl)-9H-pyrido[2,3-b]indol-9-yl)piperidine-2,6-dione To a solution of 3-[4-[3-[tert-butyl(dimethyl)silyl]oxyprop-1-ynyl]pyrido[2,3-b]indol-9-yl]piperidine-2,6-dione (400 mg, 894 umol) in THF (10 mL) was added $PtO_2$ (101 mg, 447 umol). Then the mixture was stirred at 15° C. for 120 hours under H2 atmosphere. The reaction mixture was filtered and concentrated to give the title compound (400 mg, crude) as a black brown solid. LC-MS ($ESI^+$) m/z=452.3 $(M+H)^+$.

Step 3: 3-(4-(3-hydroxypropyl)-9H-pyrido[2,3-b]indol-9-yl)piperidine-2,6-dione

To a solution of 3-[4-[3-[tert-butyl(dimethyl)silyl]oxypropyl]pyrido[2,3-b]indol-9-yl]piperidine-2,6-dione (400 mg, 886 umol) in DCM (15 mL) was added HCl/dioxane (4 M 177 uL). Then the mixture was stirred at 15° C. for 1 hour. The reaction mixture was concentrated to give a residue. The residue was purified by reversed phase flash (FA) to give the title compound (250 mg, 84% yield) as a white solid. 1H NMR (400 MHz, DMSO-$d_6$) δ=11.21 (s, 1H), 8.37 (d, J=4.8 Hz, 1H), 8.27 (d, J=8.0 Hz, 1H), 7.75-7.64 (m, 1H), 7.57 (t, J=7.6 Hz, 1H), 7.42-7.34 (m, 1H), 7.17 (d, J=5.2 Hz, 1H), 6.19-6.00 (m, 1H), 4.80 (t, J=5.2 Hz, 1H), 3.68-3.60 (m, 5H), 3.31-3.24 (m, 2H), 3.12-3.06 (m, 1H), 2.20-2.12 (m, 1H), 2.02-1.93 (m, 2H), 1.88-1.77 (m, 2H). LC/MS (ESI, m/z): [M+1]+=338.1.

Step 4: 3-(9-(2,6-dioxopiperidin-3-yl)-9H-pyrido[2,3-b]indol-4-yl)propanal

To a solution of 3-[4-(3-hydroxypropyl)pyrido[2,3-b]indol-9-yl]piperidine-2,6-dione (50.0 mg, 148 umol) in DCM (3 mL) was added DMP (94.3 mg, 222 umol). Then the mixture was stirred at 0-15° C. for 12 hr. The reaction mixture was diluted with saturate $NaHCO_3$ (2 mL) and $Na_2S_2O_3$ (2 mL). Then the reaction mixture was extracted with THF:ethyl acetate=1:1(10 mL×3). The organic layers were dried over anhydrous $Na_2SO_4$, filtered and concentrated to give the title compound (30 mg, crude) as a colorless oil. LC/MS (ESI, m/z): $[M+1]^+$=336.3.

Step 5: 3-(4-(3-(4-(2-(3-(3-amino-6-(2-hydroxyphenyl)pyridazin-4-yl)-3,8-diazabicyclo[3.2.1]octan-8-yl)pyrimidin-5-yl)piperidin-1-yl)propyl)-9H-pyrido[2,3-b]indol-9-yl)piperidine-2,6-dione (I-145)

To a solution of 3-[9-(2,6-dioxo-3-piperidyl)pyrido[2,3-b]indol-4-yl]propanal (30.0 mg, 89.5 umol) in DMF (1 mL) and THF (1 mL) was added 2-[6-amino-5-[8-[5-(4-piperidyl)pyrimidin-2-yl]-3,8-diazabicyclo[3.2.1]octan-3-yl]pyridazin-3-yl]phenol (41.0 mg, 89.5 umol), AcOH (26.9 mg, 447 umol) and $NaBH(OAc)_3$ (56.9 mg, 268 umol). Then the mixture was stirred at 25° C. for 3 hours. The reaction mixture was quenched with $H_2O$ (1 mL) and concentrated. The residue was purified by prep-HPLC (column: Phenomenex Synergi C18 150*25*10 um; mobile phase: [water (0.05% HCl)-ACN]; B %: 20%-40%, 10 min) to give the title compound (18.0 mg, 25% yield, HCl) as a yellow solid. $^1H$ NMR (400 MHz, DMSO-$d_6$) δ=11.15 (s, 1H), 10.86 (dd, J=2.8, 7.6 Hz, 1H), 8.55-8.15 (m, 4H), 7.76-7.60 (m, 1H), 7.59-7.45 (m, 3H), 7.43-7.30 (m, 2H), 7.20 (s, 1H), 7.10 (d, J=7.2 Hz, 1H), 6.97 (s, 1H), 6.21-5.97 (m, 1H), 4.91-4.75 (m, 2H), 3.60-3.54 (m, 3H), 3.28 (s, 6H), 3.15-2.91 (m, 4H), 2.79-2.62 (m, 3H), 2.36-2.24 (m, 3H), 2.13-1.90 (m, 9H). LC/MS (ESI, m/z): $[M+1]^+$=778.4.

Characterization data for further compounds prepared by Method I are presented in Table 6 below. Compounds in Table 6 were prepared by methods substantially similar to the steps described to prepare I-145.

TABLE 1
| Compounds prepared according to Method I. | | |
|---|---|---|
| I-# | LC/MS (ESI, m/z) | $^1$H NMR (400 MHz) |
| I-143 | $[M + 1]^+$ = 656.4 | $^1$H NMR(400 MHz, DMSO-$d_6$) δ = 11.77 (s, 1H), 11.15 (s, 1H), 8.62-8.55 (m, 1H), 8.39-8.22 (m, 4H), 8.17-8.10 (m, 1H), 7.66 (d, J = 1.2 Hz, 1H), 7.60-7.50 (m, 2H), 7.41-7.29 (m, 2H), 7.20 (d, J = 4.8 Hz, 1H), 7.12 (d, J = 8.0 Hz, 1H), 6.97 (t, J = 7.6 Hz, 1H), 6.18-6.01 (m, 1H), 4.95 (t, J = 11.2 Hz, 1H), 3.80 (d, J = 9.2 Hz, 1H), 3.56 (d, J = 11.6 Hz, 1H), 3.39-3.28 (m, 4H), 3.09-2.96 (m, 2H), 2.75-2.66 (m, 1H), 2.38-2.20 (m, 4H), 2.17-1.93 (m, 5H). |
Example 18. General Method J. 3-[5-[4-[4-[4-[3-amino-6-(2-hydroxyphenyl) pyridazin-4-yl]pyrazol-1-yl]-1-piperidyl]cyclohexyl]pyrido[2,3-b]indol-9-yl]piperidine-2,6-dione (I-147)
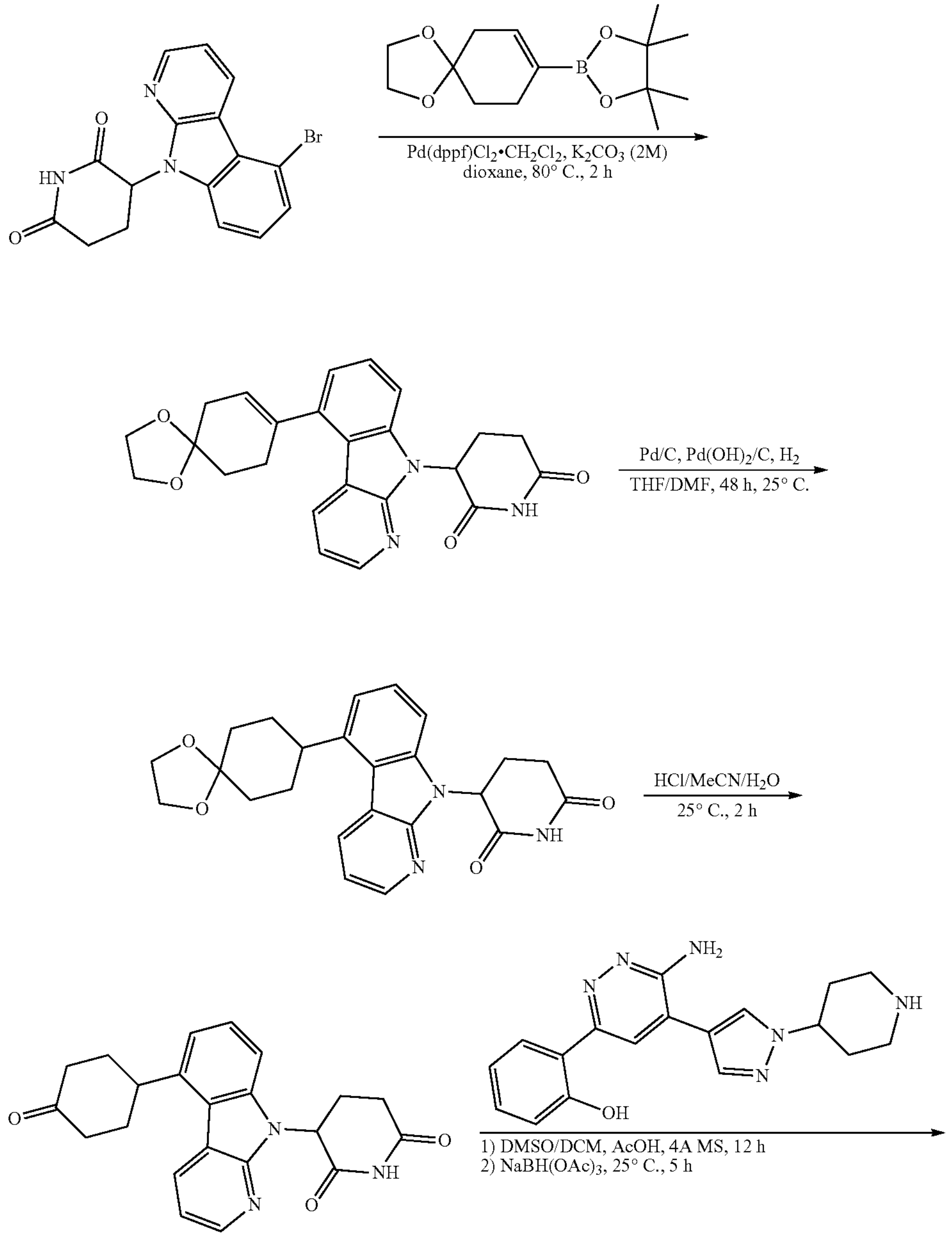

-continued

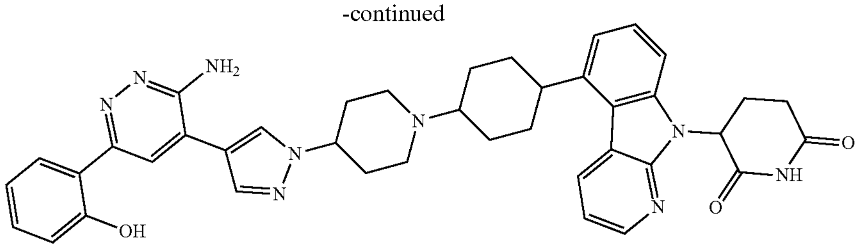

I-147

Step 1:3-[8-(1,4-dioxaspiro[4.5]dec-7-en-8-yl)pyrido[3,2-b]indol-5-yl]piperidine-2,6-dione To a solution of 3-(5-bromopyrido[2,3-b]indol-9-yl)piperidine-2,6-dione (1 g, 2.79 mmol) in dioxane (30 mL) was added 2-(1,4-dioxaspiro[4.5]dec-7-en-8-yl)-4,4,5,5-tetramethyl-1,3,2-dioxaborolane (2.23 g, 8.38 mmol), $K_2CO_3$ (2 M, 4.19 mL), Pd(dppf)$Cl_2$·$CH_2Cl_2$ (227 mg, 279 umol), then mixture was stirred at 80° C. for 12 hours. On completion, the reaction mixture was concentrated under reduced pressure to remove dioxane, The residue was purified by column chromatography ($SiO_2$, Petroleum ether/Ethyl acetate=30:1) to give the title compound (420 mg, 34% yield) as a white solid. LC/MS (ESI, m/z): $[M+1]^+$=418.2

Step 2: 3-[8-(1,4-dioxaspiro[4.5]decan-8-yl)pyrido[3,2-b]indol-5-yl]piperidine-2,6-dione To a solution of 3-[8-(1,4-dioxaspiro[4.5]dec-7-en-8-yl)pyrido[3,2-b]indol-5-yl]piperidine-2,6-dione (420 mg, 1.01 mmol) in THF (10 mL) and DMF (10 mL) was added Pd/C (300 mg, 10% purity), $Pd(OH)_2$/C (300 mg, 20% purity), then the mixture was stirred at 25° C. for 48 hours under $H_2$ atmosphere. On completion, the reaction mixture was filtered and concentrated under reduced pressure to give the title compound (400 mg, crude) as a yellow oil. LC/MS (ESI, m/z): $[M+1]^+$=420.2

Step 3: 3-[8-(4-oxocyclohexyl)pyrido[3,2-b]indol-5-yl]piperidine-2,6-dione

To a solution of 3-[8-(1,4-dioxaspiro[4.5]decan-8-yl)pyrido[3,2-b]indol-5-yl]piperidine-2,6-dione (400 mg, 953 umol) in $CH_3CN$ (20 mL) was added HCl/dioxane (4 M, 715 uL), then the mixture was stirred at 25° C. for 3 hours. On completion, the reaction mixture was concentrated under reduced pressure to remove $CH_3CN$, the mixture was diluted with water and was added DIEA until PH=7, filtered and concentrated under reduced pressure to give the title compound (310 mg, crude) as a white solid. LC/MS (ESI, m/z): [M+1]=376.2

Step 4: 3-[5-[4-[4-[4-[3-amino-6-(2-hydroxyphenyl)pyridazin-4-yl]pyrazol-1-yl]-1-piperidyl]cyclohexyl]pyrido[2,3-b]indol-9-yl]piperidine-2,6-dione (I-147)

To a solution of 3-[8-(4-oxocyclohexyl)pyrido[3,2-b]indol-5-yl]piperidine-2,6-dione (270 mg, 719 umol) in DCM (5 mL) and DMSO (5 mL) was added 2-[6-amino-5-[1-(4-piperidyl)pyrazol-4-yl]pyridazin-3-yl]phenol (402 mg, 1.08 mmol, HCl) and HOAc (43.1 mg, 719 umol), 4A MS (50 mg, 719.2 umol) at 110° C. for 12 hours, $NaBH(OAc)_3$ (457 mg, 2.16 mmol) was added to stirred at 25° C. for 2 hours. On completion, the reaction mixture was concentrated under reduced pressure to remove DCM. The residue was diluted with water (100 mL) and filtered and concentrated under reduced pressure to give a residue, The residue was purified by prep-HPLC (column: Phenomenex luna C18 150*40 mm*15 um; mobile phase: [water (0.05% HCl)-ACN]; B %: 12%-42%, 10 min) to give the title compound (161 mg, 30% yield, 98% purity, HCl) as a white solid. LC/MS (ESI, m/z): $[M+1]^+$=696.4. $^1$H NMR (400 MHz, DMSO-$d_6$) δ=11.16 (s, 1H), 11.02 (s, 1H), 8.41-8.71 (m, 3H), 8.28-8.35 (m, 1H), 8.00-8.26 (m, 2H), 7.59-7.68 (m, 1H), 7.44-7.58 (m, 2H), 7.36-7.43 (m, 1H), 7.36-7.43 (m, 1H), 7.33 (dd, J=7.6, 4.8 Hz, 1H), 7.14-7.27 (m, 1H), 7.11 (d, J=8.0 Hz, 1H), 6.99 (t, J=7.6 Hz, 1H), 6.08 (s, 1H), 3.78 (s, 2H), 3.37 (d, J=11.2 Hz, 4H), 3.06 (d, J=12.0 Hz, 2H), 2.52-2.78 (m, 3H), 2.28-2.48 (m, 5H), 1.90-2.25 (m, 5H), 1.75 (m, 2H).

Characterization data for further compounds prepared by Method J are presented in Table 7 below. Compounds in Table 7 were prepared by methods substantially similar to the steps described to prepare I-147.

TABLE 7

Compounds prepared according to Method J.

| I-# | LC/MS (ESI, m/z) | $^1$H NMR (400 MHz) |
|---|---|---|
| I-148 | $[M + 1]^+$ = 696.1 | $^1$H NMR (400 MHz, DMSO-$d_6$) δ = 11.15 (s, 1H), 11.02-10.88 (m, 1H), 8.53 (s, 1H), 8.42-8.34 (m, 1H), 8.32 (s, 1H), 8.22-8.13 (m, 2H), 7.74-7.65 (m, 1H), 7.62 (dd, J = 1.6, 8.0 Hz, 1H), 7.55 (t, J = 7.2 Hz, 1H), 7.43-7.30 (m, 2H), 7.20-7.13 (m, 1H), 7.09 (d, J = 8.0 Hz, 1H), 7.03-6.95 (m, 1H), 6.19-5.96 (m, 1H), 4.72-4.54 (m, 1H), 3.89-3.76 (m, 2H), 3.42-3.27 (m, 4H), 3.12-2.95 (m, 2H), 2.78-2.54 (m, 3H), 2.45-2.30 (m, 5H), 2.27-1.93 (m, 6H), 1.87-1.66 (m, 2H). |
| I-144 | $[M + 1]^+$ = 696.2 | $^1$H NMR (400 MHz, DMSO-d6) δ = 11.14 (s, 2H), 8.63-8.45 (m, 2H), 8.42-8.41 (m, 1H), 8.33-8.28 (m, 1H), 8.15-8.11 (m, 2H), 7.70-7.51 (m, 2H), 7.48-7.33 (m, 2H), 7.26-7.25 (m, 1H), 7.13-7.09 (m, 1H), |

TABLE 7-continued
Compounds prepared according to Method J.
| I-# | LC/MS (ESI, m/z) | $^{1}$H NMR (400 MHz) |
|---|---|---|
| | | 7.04-6.91 (m, 1H), 6.16-5.90 (m, 1H), 4.99-4.70 (m, 3H), 3.76-3.53 (m, 2H), 3.50-3.21 (m, 3H), 3.17-2.93 (m, 2H), 2.79-2.63 (m, 2H), 2.42-2.26 (m, 5H), 2.18-1.94 (m, 4H), 1.88-1.60 (m, 4H). |
Example 19. General Method K. 3-(6-((4-((4-(4-(3-amino-6-(2-hydroxyphenyl)pyridazin-4-yl)-1H-pyrazol-1-yl)piperidin-1-yl)methyl)-1H-1,2,3-triazol-1-yl)methyl)-9H-pyrido[2,3-b]indol-9-yl)piperidine-2,6-dione (I-146)
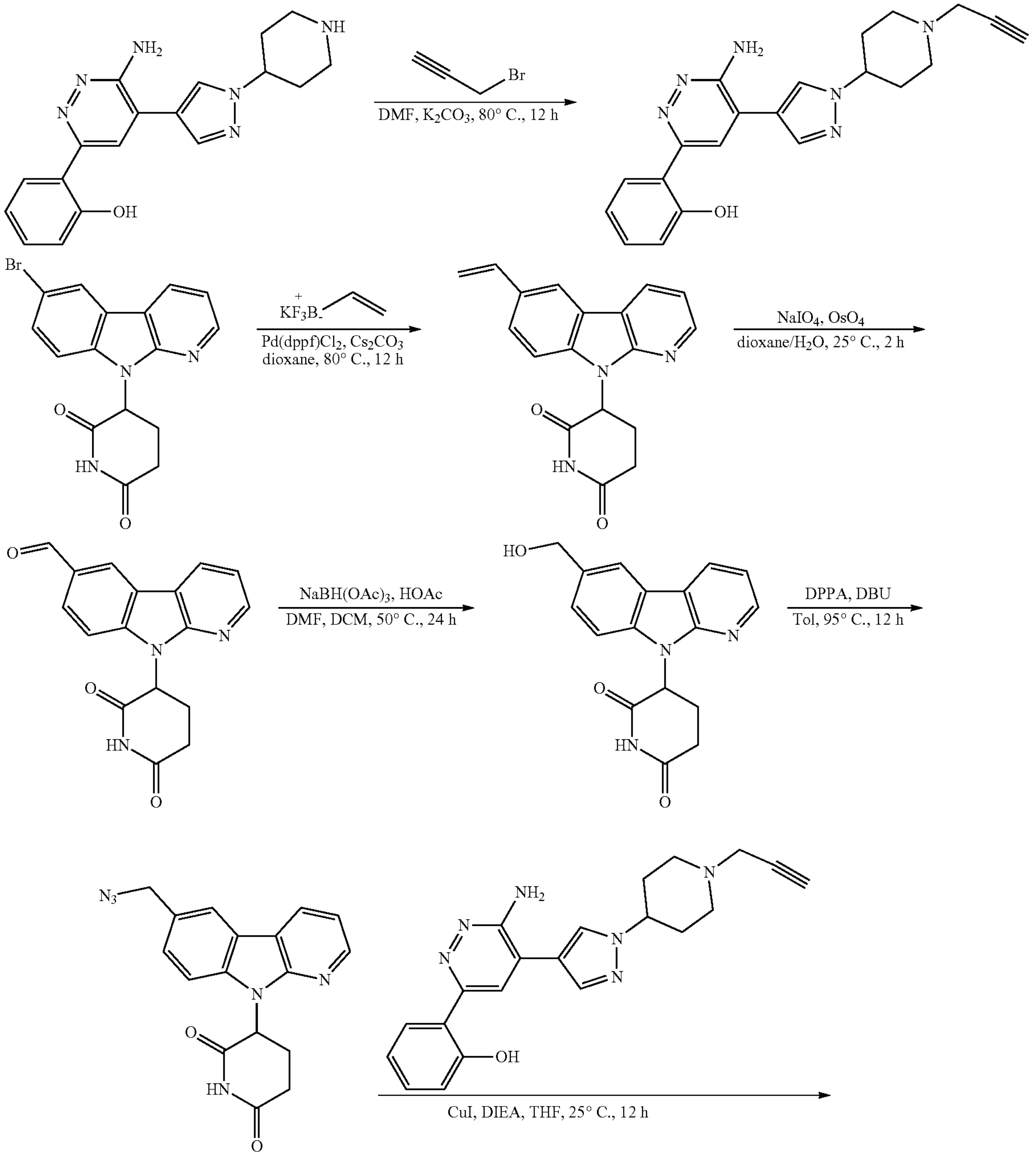

-continued

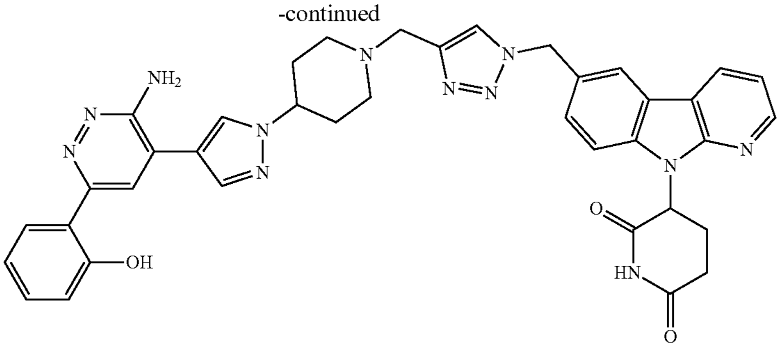

I-146

Step 1: 3-(6-vinyl-9H-pyrido[2,3-b]indol-9-yl)piperidine-2,6-dione

A mixture of 3-(6-bromo-9H-pyrido[2,3-b]indol-9-yl)piperidine-2,6-dione (500 mg, 1.40 mmol), potassium; trifluoro(vinyl)boranuide (563 mg, 4.20 mmol, 3 eq), $Cs_2CO_3$ (2 M, 1.40 mL, 2 eq), $Pd(dppf)Cl_2 \cdot CH_2Cl_2$ (114 mg, 0.1 eq) in 1,4-dioxane (10 mL) was degassed and purged with $N_2$ for 3 times, and then the mixture was stirred at 80° C. for 12 hr under $N_2$ atmosphere. The reaction mixture was diluted with water 10 mL and extracted with ethyl acetate (20 mL*3). The combined organic layers were washed with brine (20 mL*3), dried over $Na_2SO_4$, filtered and concentrated under reduced pressure to give a residue. The residue was purified by column chromatography ($SiO_2$, Petroleum ether/Ethyl acetate=3/1 to 1/1) to give the title compound (300 mg, 65% yield) was obtained as a yellow solid. LC/MS (ESI, m/z): $[M+1]^+$=306.5.

Step 2: 9-(2,6-dioxopiperidin-3-yl)-9H-pyrido[2,3-b]indole-6-carbaldehyde

To a solution of 3-(6-vinylpyrido[2,3-b]indol-9-yl)piperidine-2,6-dione (300 mg, 1 eq) in dioxane (5 mL) and $H_2O$ (5 mL) was added 2,6-dimethylpyridine (211 mg, 1.97 mmol, 2 eq), $NaIO_4$ (841 mg, 4 eq) and $OSO_4$ (25.0 mg, 0.1 eq). The mixture was stirred at 0° C. for 2 hr. The reaction mixture was diluted with $H_2O$ (30 mL) and extracted with EA (30 mL*3). The combined organic layers were washed with $Na_2SO_3$ (100 mL*3) and saturated brine (100 mL*3), dried over $Na_2SO_4$, filtered and concentrated under reduced pressure to give a residue. The residue was purified by column chromatography ($SiO_2$, Petroleum ether/Ethyl acetate=1/1 to 0/1) to give the title compound (230 mg, 76% yield) as a white solid. $^1H$ NMR (400 MHz, DMSO-d6) δ=2.14-2.28 (m, 1H), 2.67-2.77 (m, 1H), 2.96-3.22 (m, 2H), 6.15 (s, 1H), 7.36-7.42 (m, 1H), 7.84 (d, J=4.0 Hz, 1H), 8.08 (d, J=8.0 Hz, 1H), 8.52 (d, J=4.0 Hz, 1H), 8.72-8.76 (m, 1H), 8.86 (s, 1H), 10.10 (s, 1H), 11.23 (s, 1H); LC/MS (ESI, m/z): $[M+1]^+$=308.2.

Step 3: 3-(6-(hydroxymethyl)-9H-pyrido[2,3-b]indol-9-yl)piperidine-2,6-dione

A mixture of 9-(2,6-dioxo-3-piperidyl)pyrido[2,3-b]indole-6-carbaldehyde (230 mg, 1 eq), $NaBH(OAc)_3$ (1.59 g, 10 eq), HOAc (225 mg, 5 eq) in DMF (6 mL) and DCM (6 mL) was degassed and purged with $N_2$ for 3 times, and then the mixture was stirred at 50° C. for 24 hr under $N_2$ atmosphere. The mixture was concentrated to remove the solvent to get residue. The residue was purified by reversed phase flash (0.1% FA) to give the title compound (200 mg, 86% yield) as a light yellow solid. LC/MS (ESI, m/z): $[M+1]^+$=309.9.

Step 4: 3-(6-(azidomethyl)-9H-pyrido[2,3-b]indol-9-yl)piperidine-2,6-dione

To a solution of 3-[6-(hydroxymethyl)pyrido[2,3-b]indol-9-yl]piperidine-2,6-dione (100 mg, 1 eq) and [azido(phenoxy)phosphoryl]oxybenzene (178 mg, 2 eq) in toluene (4 mL) was added DBU (148 mg, 3 eq). The mixture was stirred at 95° C. for 3 hr. The reaction mixture was quenched by addition $H_2O$ (5 mL) at 25° C., and then diluted with water (15 mL) and extracted with ethyl acetate (20 mL*3). The combined organic layers were washed with brine (20 mL*2), dried over Na2$SO_4$, filtered and concentrated under reduced pressure to give a residue. The residue was purified by column chromatography ($SiO_2$, Petroleum ether/Ethyl acetate=5/1 to 1/1) to give the title compound (95 mg, 90% yield) as a white solid. $^1H$ NMR (400 MHz, CHLOROFORM-d) δ=1.28 (m, 1H), 2.29-2.39 (m, 1H), 2.96-3.02 (m, 3H), 4.54 (s, 2H), 7.25-7.28 (m, 1H), 7.29-7.32 (m, 1H), 7.45-7.50 (m, 1H), 8.07-8.10 (m, 1H), 8.27 (s, 1H), 8.36-8.40 (m, 1H), 8.46-8.49 (m, 1H); LC/MS (ESI, m/z): $[M+1]^+$= 335.1.

Step 5: 2-(6-amino-5-(1-(1-(prop-2-yn-1-yl)piperidin-4-yl)-1H-pyrazol-4-yl)pyridazin-3-yl)phenol To a solution of 2-[6-amino-5-[1-(4-piperidyl)pyrazol-4-yl]pyridazin-3-yl]phenol (200 mg, 1 eq) 3-bromoprop-1-yne (70.7 mg, 1 eq) in DMF (6 mL) was added $K_2CO_3$ (247 mg, 3 eq). The mixture was stirred at 25° C. for 12 hr. The residue was diluted with water (20 mL) and extracted with EA (30 mL*3). The combined organic layers were washed with brine (30 mL*2), dried over $Na_2SO_4$, filtered and concentrated under reduced pressure to give a residue. The residue was purified by prep-TLC ($SiO_2$, DCM:MeOH=20:1) to give the title compound (75 mg, 30% yield) as a yellow solid. $^1H$ NMR (400 MHz, DMSO-d6) δ=2.02-2.16 (m, 4H), 2.30-2.38 (m, 2H), 2.94 (m, 2H), 3.20 (m, 1H), 3.35 (m, 2H), 4.15-4.25 (m, 1H), 6.52 (s, 2H), 6.90-6.96 (m, 2H), 7.24-7.30 (m, 1H), 7.98-8.02 (m, 1H), 8.19 (d, J=16.0 Hz, 2H), 8.49 (s, 1H), 13.84 (s, 1H); LC/MS (ESI, m/z): $[M+1]^+$=375.2.

Step 6: 3-(6-((4-((4-(4-(3-amino-6-(2-hydroxyphenyl)pyridazin-4-yl)-1H-pyrazol-1-yl)piperidin-1-yl)methyl)-1H-1,2,3-triazol-1-yl)methyl)-9H-pyrido[2,3-b]indol-9-yl)piperidine-2,6-dione (I-146)

To a solution of 2-(6-amino-5-(1-(1-(prop-2-yn-1-yl)piperidin-4-yl)-1H-pyrazol-4-yl)pyridazin-3-yl)phenol (60 mg, 1 eq) and 3-(6-(azidomethyl)-9H-pyrido[2,3-b]indol-9-yl)piperidine-2,6-dione (53.6 mg, 1 eq) in THF (3 mL) was added CuI (15.3 mg, 0.5 eq) and DIPEA (20.7 mg, 1 eq). The mixture was stirred at 50° C. for 24 hr. The reaction mixture was concentrated under reduced pressure to remove THF. The residue was purified by prep-HPLC (column: Phenomenex Synergi C18 150*30 mm*4 um; mobile phase: [water (0.05% HCl)-ACN]; B %: 11%-41%, 10 min) to give the title compound (31.5 mg, 27% yield) as a yellow solid. $^1H$ NMR (400 MHz, DMSO-d6) δ=2.09-2.18 (m, 1H), 2.28-2.40 (m, 4H), 2.66-2.77 (m, 2H), 2.95-3.15 (m, 3H), 3.16-3.37 (m, 4H), 4.44 (s, 2H), 4.50-4.60 (m, 1H), 5.84 (s, 2H), 6.01-6.14 (m, 1H), 6.96-7.02 (m, 1H), 7.08 (m, 1H), 7.26-7.33 (m, 1H), 7.36-7.43 (m, 1H), 7.58-7.71 (m, 3H), 8.11-8.18 (m, 1H), 8.26-8.35 (m, 2H), 8.43-8.50 (m, 3H), 8.58-8.63 (m, 1H), 11.04-11.18 (m, 2H); LC/MS (ESI, m/z): $[M+1]^+$=709.4.

Remaining compounds I-75 to I-106, I-108, I-109, I-111 to I-121, and I-123 to I-132 were prepared according to methods substantially similar to those described above which would be readily apparent to those having skill in the art.

Example 14. MSD SMARCA2 Degration in NCI-H1299 Cell Line

| Cell Line | Vendor | Medium |
|---|---|---|
| NCI-H1299 | ATCC | RPMI MEDIUM 1640 + 10% FBS + 1xPS |

| Regents | Vendor | Cat# |
|---|---|---|
| RPMI MEDIUM 1640 | Invitrogen | A10491-01 |
| Fetal bovine serum (FBS) | Hyclone | SH30406.05 |
| Penicillin-Streptomycin (100x) | SolarBio | P1400 |
| Phosphate Buffered Saline (PBS) | Solarbio | P1020-500 |
| RIPA Buffer with EDTA | BBP | 115D |
| cOmplete ULTRA Tablets, Mini, EDTA-free, EASYpack | Roche Applied Science | 05892791001 |
| MSD Standard Plate | Meso Scale Discovery | L15XA-3 |
| Anti-SMARCA2/BRM antibody | Abcam | ab223735 |
| SULFO-TAG anti-rabbit antibody | Meso Scale Discovery | R32AB-5 |
| MSD Blocker A | Meso Scale Discovery | R93BA-4 |
| MSD Read Buffer T (4x) | Meso Scale Discovery | R92TC-1 |
| Tris Buffered Saline with Tween ® 20 (TBST-10X) | CST | 9997S |

| Instrument | Vendor | Cat# |
|---|---|---|
| Cell counter | Invitrogen | Countess |
| Centrifuge | Eppendorf | 5810R |
| $CO_2$ Incubator | Thermo | Model: 371 |
| Vortex | IKA | MS3 digital |
| Echo Liquid Handler | Labcyte | 550 |
| TECAN | TECAN | Freedom EVO200 |
| PERSONAL PIPETTOR | Apricot Designs | PP5 + 1 |
| MSD reader | Meso Scale Discovery | MSD SECTOR 6000 |
| 96 well plate | Corning | 3599 |
| 225 $cm^2$ Cell Culture Flask | Corning | 431081 |
| 50 mL centrifuge tube | BD-Falcon | 352098 |
| 15 mL centrifuge tube | BD-Falcon | 352097 |

Cell Culture: Cells were cultured in exponential growth phase.

Compound Preparation and Treatment: NCI-H1299 cells were seeded into the 96-well plate at $4.0*10^4$ cells per 100ul per well. Incubate the plate in the incubator overnight. The next day, compounds were diluted to designed stock concentration by TECAN, then perform a 3 fold, 9-point dilution via transferring 15 uL compound into 30 μL DMSO using Apricot. 200 nL diluted compound from compound source plate were transferred into the 96-intermediate plate as designated by using Echo550, followed with 100 ul culture medium to make the 2× compound solution. Cell plate were changed with 80 ul of fresh culture medium and 80 ul of 2× compound solution was added into the well to achieve the final designed concentration. Cell plate was then shaken at 720 rpm for 5 min and incubated for 24 hours in the incubator.

Sample Preparation: Media was aspirated from the cultures and the plate was washed with PBS twice. 60 ul of pre-chilled PIPA lysis buffer (Boston BioProducts BP-115D) with protease inhibitor were directly added into the well to lyze the cells for 20 minutes at 4° C. Cell lysates were collected.

MSD Procedure: The MSD plate was coated with 40 ul cell lysate and incubated at 4° C. overnight. The next day, the MSD coated bare plate was washed 3 times with 150 ul 1×TBST per well, blocked with 150 ul of blocking buffer per well, and shaken for 1 hour at RT, 600 rpm. Blocking buffer was 3% Blocker A in TBST. MSD plate was then washed 3 times with 150 ul 1×TBST per well and Primary Detection antibody (Rabbit anti-SMARCA2/BRM antibody, 100 μg/ml, ab223735) was added to a final [conc.]: 0.3 ug/ml, 25ul/well and shaken for 1 hour at RT, 600 rpm. Antibody was prepared in Antibody Detection buffer (1% Blocker A in 1×TBST). The MSD plate was then washed 3 times with 150 ul 1×TBST per well. Secondary Detection antibody (SULFO-TAG anti-species antibody) was then added to a final [conc.]: 1 μg/ml, 25 ul/well, and shaken for 1 hour at RT, 600 rpm. Antibodies were prepared in Antibody Detection buffer (1% Blocker A in 1×TBST). MSD plate was washed 3 times with 150 ul 1×TBST per well and 2×MSD reading buffer was added, 150 ul per well, and diluted from 4× with water. MSD instrument was then read.

Data Analysis: The percentage of relative level of SMARCA2 level was calculated following equation below.

$$\%\ \text{Relative Level} = 100\% \times \frac{MSD\ Signal_{Sample} - MSD\ Signal_{LC}}{MSD\ Singal_{HC} - MSD\ Signal_{LC}}$$

LC: A2780, SMARCA2 negative cells. HC: NCI-H1299 cells treated with DMSO.

SMARCA2 protein degradation in H1299 cells for compounds of the invention are presented in Table 8. The letter codes for SMARCA2 degradation potency ($DC_{50}$) include: A (<100 nM), B (100-500 nM), C (501-1000 nM), and D (>1000 nM). The letter codes for the percentage of SMARCA2 degradation after 24 hours (Dmax %) include: A (>90% degradation), B (>70-90% degradation), C (50-70% degradation), and D (<50% degradation).

TABLE 8

SMARCA2 MSD H1299 Degradation Results.

| I-# | SMARCA2 MSD H1299 degradation 24 h: Average external-Abs IC50 (nM) | SMARCA2 MSD H1299 degradation 24 h: Average Dmax % |
|---|---|---|
| I-75 | B | B |
| I-76 | B | A |
| I-77 | B | A |
| I-78 | C | C |
| I-79 | B | C |
| I-80 | B | A |
| I-81 | C | B |
| I-82 | B | B |
| I-83 | C | B |
| I-84 | C | C |
| I-85 | A | A |
| I-86 | D | D |
| I-87 | D | D |
| I-88 | D | B |
| I-89 | D | D |
| I-90 | D | D |
| I-91 | D | D |
| I-92 | D | D |
| I-93 | D | D |
| I-94 | D | C |
| I-95 | D | D |
| I-96 | B | C |
| I-97 | A | A |

TABLE 8-continued

SMARCA2 MSD H1299 Degradation Results.

| I-# | SMARCA2 MSD H1299 degradation 24 h: Average external-Abs IC50 (nM) | SMARCA2 MSD H1299 degradation 24 h: Average Dmax % |
|---|---|---|
| I-98 | B | A |
| I-99 | D | D |
| I-100 | D | D |
| I-101 | D | D |
| I-102 | D | C |
| I-103 | A | A |
| I-104 | B | A |
| I-105 | D | D |
| I-133 | A | A |
| I-134 | A | B |
| I-135 | A | C |
| I-136 | A | — |
| I-137 | A | A |
| I-138 | A | A |
| I-140 | D | D |
| I-141 | B | B |
| I-142 | — | D |
| I-143 | B | A |
| I-144 | A | A |
| I-145 | A | A |
| I-146 | B | B |

Example 15. General Method L. Synthesis of 3-[6-([2-[2-(2-[4-[(4-[7-[trans-4-hydroxycyclohexyl]-2-[(3,3,3-trifluoropropyl)amino]pyrrolo[2,3-d]pyrimidin-5-yl]phenyl)methyl]piperazin-1-yl]ethoxy)ethoxy]ethyl]amino)pyrido[2,3-b]indol-9-yl]piperidine-2,6-dione; formic acid (I-153)

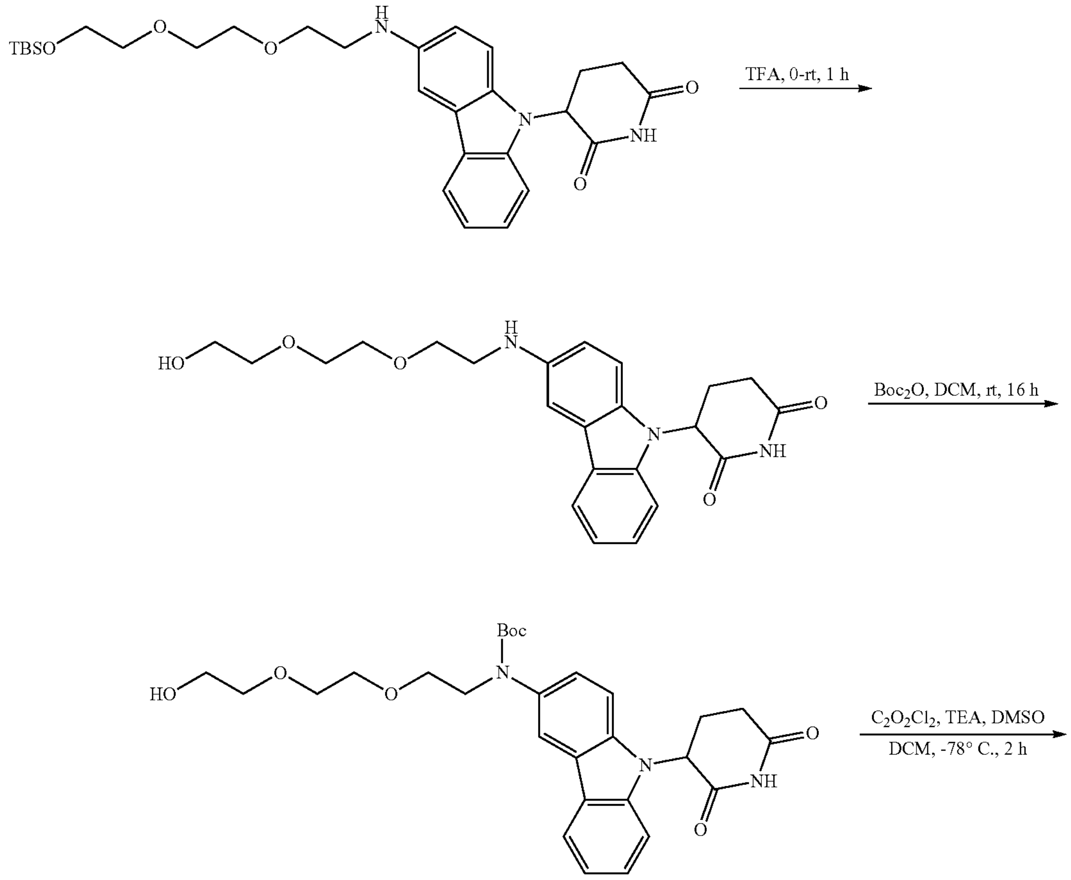

-continued

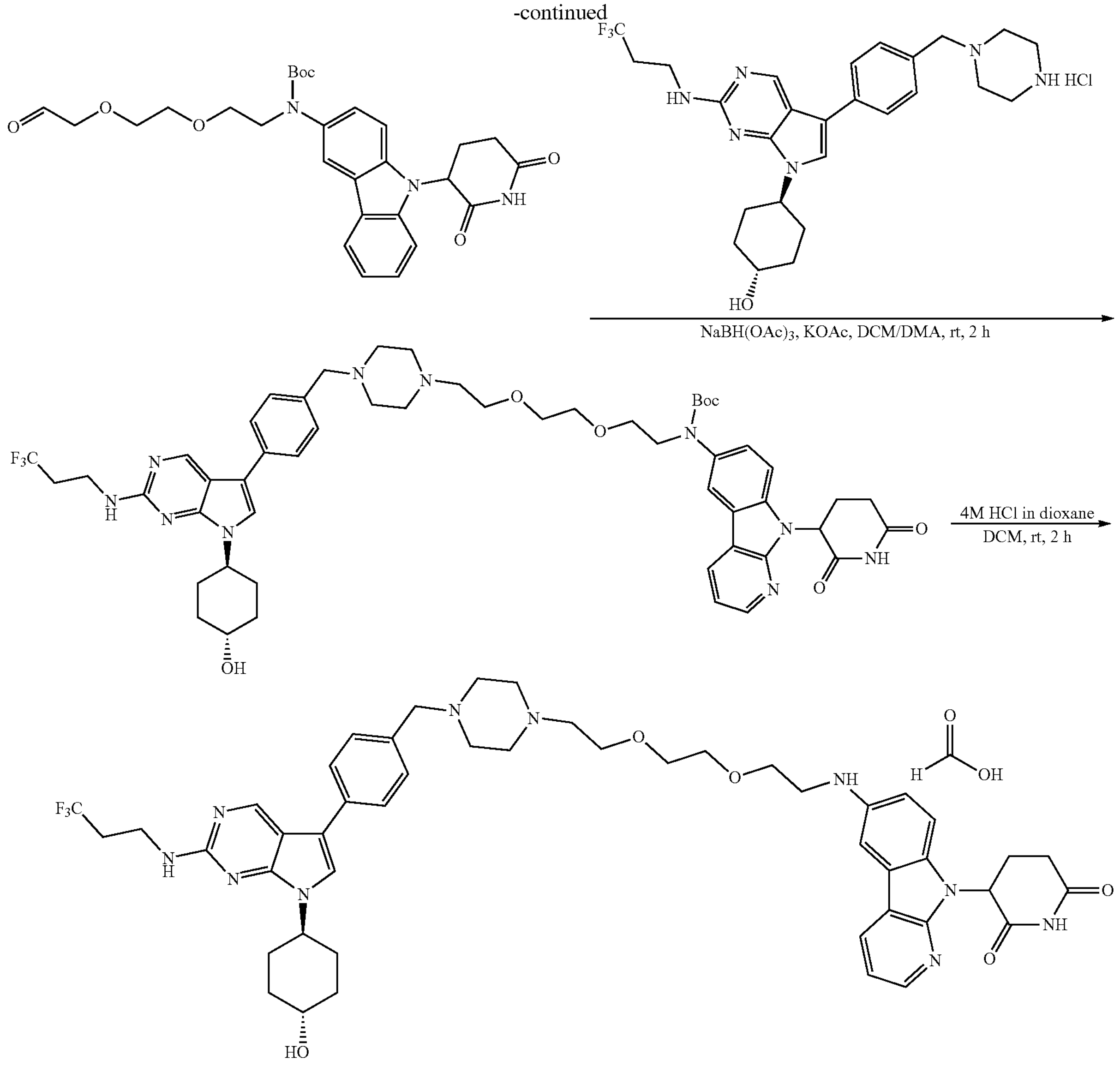

I-153

Step 1: 3-[6-([2-[2-(2-hydroxyethoxy)ethoxy]ethyl] amino)pyrido[2,3-b]indol-9-yl]piperidine-2,6-dione To a stirred solution of 3-[6-(11,11,12,12-tetramethyl-4, 7,10-trioxa-1-aza-11-silatridecan-1-yl)pyrido[2,3-b]indol-9-yl]piperidine-2,6-dione (456 mg, 0.84 mmol) in DCM (10.0 mL) was added trifluoroacetic acid (1.00 mL) at 0° C. under nitrogen atmosphere. The reaction was stirred for 1 h at room temperature. The resulting mixture was concentrated under vacuum and the residue was purified by reversed phase flash chromatography with the following conditions: column WelFlash™ C18-I, 20-40 um, 330 g; Eluent A: water (plus 10 mmol/L FA); Eluent B: ACN; Gradient: 25%-45% B in 20 min; Flow rate: 80 mL/min; Detector: UV 220/254 nm; desired fractions were collected at 34% B and concentrated under reduced pressure to afford 3-[6-([2-[2-(2-hydroxyethoxy)ethoxy]ethyl]amino)pyrido [2,3-b]indol-9-yl]piperidine-2,6-dione (310 mg, 86%) as a white solid. $^{1}$H NMR (400 MHz, DMSO-$d_6$) δ 11.11 (s, 1H), 8.46-8.37 (m, 1H), 8.35-8.30 (m, 1H), 8.05 (s, 1H), 7.40-7.26 (m, 2H), 7.20-7.10 (m, 1H), 5.91 (s, 1H), 5.33 (t, J=5.9 Hz, 1H), 3.64-3.38 (m, 12H), 3.03-2.96 (m, 3H), 2.07 (s, 1H). LC/MS (ESI, m/z): $[(M+23)]^+$=427.30.

Step 2: tert-butyl N-[9-(2,6-dioxopiperidin-3-yl) pyrido[2,3-b]indol-6-yl]-N-[2-[2-(2-hydroxyethoxy) ethoxy]ethyl]carbamate To a stirred solution of 3-[6-([2-[2-(2-hydroxyethoxy) ethoxy]ethyl]amino)pyrido[2,3-b]indol-9-yl]piperidine-2,6-dione (270 mg, 0.63 mmol) in DCM (30.0 mL) was added $Boc_2O$ (207 mg, 0.95 mmol) at room temperature under nitrogen atmosphere. The reaction was stirred for 16 h at room temperature. Upon completion, the solution was concentrated under reduced pressure. The residue was purified by reversed phase flash chromatography with the following conditions: column WelFlash™ C18-I, 20-40 um, 330 g; Eluent A: water (plus 10 mmol/L FA); Eluent B: ACN; Gradient: 45%-65% B in 20 min; Flow rate: 80 mL/min; Detector: UV 220/254 nm; desired fractions were collected at 54% B and concentrated under reduced pressure to afford tert-butyl N-[9-(2,6-dioxopiperidin-3-yl)pyrido[2,3-b]indol- 6-yl]-N-[2-[2-(2-hydroxyethoxy)ethoxy]ethyl]carbamate (320 mg, 96%). $^1$H NMR (400 MHz, DMSO-$d_6$) δ 11.18 (s, 1H), 8.60-8.50 (m, 1H), 8.49-8.37 (m, 1H), 8.14 (d, J=2.1 Hz, 1H), 7.59 (d, J=8.4 Hz, 1H), 7.45-7.35 (m, 1H), 7.30-7.20 (m, 1H), 6.04 (s, 1H), 4.57 (s, 1H), 3.79 (t, J=6.0 Hz, 2H), 3.58-3.48 (m, 6H), 3.47 (d, J=4.6 Hz, 2H), 3.10-2.90 (m, 2H), 2.76-2.63 (m, 3H), 2.18-2.00 (m, 1H), 1.59-1.19 (m, 9H). LC/MS (ESI, m/z): [(M+23)]$^+$=527.30.

Step 3: tert-butyl (9-(2,6-dioxopiperidin-3-yl)-9H-pyrido[2,3-b]indol-6-yl)(2-(2-(2-oxoethoxy)ethoxy)ethyl)carbamate To a stirred solution of oxalyl chloride (4 equiv.) in DCM was added DMSO (5 equiv.) dropwise at −78° C. under nitrogen atmosphere. The resulting solution was stirred for 30 min at −78° C. Then a solution of 3-[5-[3-(4-hydroxybutoxy)propyl]-3-methyl-2-oxo-2,3-dihydro-1H-1,3-benzodiazol-1-yl]piperidine-2,6-dione (1 equiv.) in DCM was added dropwise at −78° C. The resulting solution was stirred for another 30 min at the same temperature. Then TEA (10 equiv.) was added at −78° C. The reaction temperature was slowly increased to room temperature in 30 min. The resulting mixture was diluted with water and extracted with DCM (3×). The combined organic layers were dried over anhydrous $Na_2SO_4$. After filtration, the filtrate was concentrated under reduced pressure. The residue was purified by reversed phase flash chromatography with the following conditions: Column: WelFlash™ C18-I, 20-40 um, 330 g; Eluent A: water (plus 10 mmol/L FA); Eluent B: ACN; Flow rate: 80 mL/min; Detector: UV 220/254 nm; desired fractions were collected and concentrated under reduced pressure to afford the title compound. LC/MS (ESI, m/z): [(M+1)]$^+$=525.30.

Step 4: tert-butyl N-[9-(2,6-dioxopiperidin-3-yl)pyrido[2,3-b]indol-6-yl]-N-[2-[2-(2-[4-[(4-[7-[trans-4-hydroxycyclohexyl]-2-[(3,3,3-trifluoropropyl)amino]pyrrolo[2,3-d]pyrimidin-5-yl]phenyl)methyl]piperazin-1-yl]ethoxy)ethoxy]ethyl]carbamate To a stirred solution of trans-4-[5-[4-(piperazin-1-ylmethyl)phenyl]-2-[(3,3,3-trifluoropropyl)amino]pyrrolo[2,3-d]pyrimidin-7-yl]cyclohexan-1-ol hydrochloride (37.0 mg, 0.074 mmol) and 2-[2-(2-[[9-(2,6-dioxopiperidin-3-yl)pyrido(2,3-b]indol-6-yl]amino]ethoxy)ethoxy]acetaldehyde (38.6 mg, 0.074 mmol) in DCM (10.0 mL) was added KOAc (28.9 mg, 0.29 mmol) at room temperature. Then NaBH$(OAc)_3$ (46.8 mg, 0.221 mmol) was added to the reaction. The reaction was stirred for 1 hour at room temperature. Upon completion, the solution was concentrated under reduced pressure and purified by reversed phase flash chromatograph with the following conditions: Column: Xselect CSH OBD Column 30×150 mm 5 um; Mobile Phase A: water (plus 0.1% FA), Mobile Phase B: ACN; Flow rate: 60 mL/min; Gradient: 13% B to 22% B in 7 min; detector: 220/254 nm; desired fractions were collected at 6.48 min and lyophilized to afford the title compounds (20.0 mg, 30%) as a white solid. $^1$H NMR (400 MHz, DMSO-$d_6$) δ 11.18 (s, 1H), 8.87 (s, 1H), 8.57 (dd, J=7.6, 1.7 Hz, 1H), 8.43 (dd, J=4.9, 1.6 Hz, 1H), 8.13 (d, J=2.1 Hz, 1H), 7.66-7.53 (m, 3H), 7.39 (d, J=8.7 Hz, 1H), 7.32-7.16 (m, 2H), 7.05 (t, J=5.8 Hz, 1H), 6.94-6.85 (s, 1H), 6.04 (s, 1H), 4.70 (d, J=4.5 Hz, 1H), 4.50-4.37 (m, 1H), 3.86-3.63 (m, 3H), 3.62-3.35 (m, 13H), 3.18-2.94 (m, 2H), 2.75-2.55 (m, 2H), 2.50-2.20 (m, 13H), 2.15-2.04 (m, 1H), 2.04-1.53 (m, 6H), 1.31 (m, 9H). LC/MS (ESI, m/z): [(M+1)]$^+$=1011.50.

Step 5: 3-[6-([2-[2-(2-[4-[(4-[7-[trans-4-hydroxycyclohexyl]-2-[(3,3,3-trifluoropropyl)amino]pyrrolo[2,3-d]pyrimidin-5-yl]phenyl)methyl]piperazin-1-yl]ethoxy)ethoxy]ethyl]amino)pyrido[2,3-b]indol-9-yl]piperidine-2,6-dione; formic acid To a stirred solution of tert-butyl N-[9-(2,6-dioxopiperidin-3-yl)pyrido[2,3-b]indol-6-yl]-N-[2-[2-(2-[4-[(4-[7-[trans-4-hydroxycyclohexyl]-2-[(3,3,3-trifluoropropyl)amino]pyrrolo[2,3-d]pyrimidin-5-yl]phenyl)methyl]piperazin-1-yl]ethoxy)ethoxy]ethyl]carbamate (20.0 mg, 0.02 mmol) in DCM (10.0 mL) was added HCl (4M) in 1,4-dioxane (2.00 mL) at room temperature under nitrogen atmosphere. The reaction was reacted for 2 h and was concentrated under reduced pressure. The crude product (50 mg) was purified by Prep-HPLC with the following conditions (Column: Xselect CSH OBD Column 30×150 mm 5 um; Mobile Phase A: water (plus 0.1% FA), Mobile Phase B: ACN; Flow rate: 60 mL/min; Gradient: 13% B to 22% B in 7 min; detector: UV 220/254 nm; desired fractions were collected at 6.48 min and lyophilized to afford trans-3-[6-[14-(4-[7-[trans-4-hydroxycyclohexyl]-2-[(3,3,3-trifluoropropyl)amino]pyrrolo[2,3-d]pyrimidin-5-yl]phenyl)-4,7-dioxa-1,10,13-triazatetradecan-1-yl]pyrido[2,3-b]indol-9-yl]piperidine-2,6-dione; formic acid (10.0 mg, 54%) as a white solid. $^1$H NMR (400 MHz, $CD_3OD$) δ 8.73 (s, 1H), 8.50 (s, 1H), 8.38 (dd, J=7.7, 1.6 Hz, 1H), 8.34 (dd, J=4.9, 1.6 Hz, 1H), 7.57-7.51 (m, 2H), 7.49 (d, J=2.3 Hz, 1H), 7.41 (s, 1H), 7.32 (m, 1H), 7.28-7.21 (m, 2H), 7.17 (dd, J=7.6, 4.9 Hz, 1H), 7.01 (m, 2.3 Hz, 1H), 5.92-5.85 (m, 1H), 4.55 (p, J=8.1 Hz, 1H), 3.81-3.65 (m, 1H), 3.53 (s, 2H), 3.41 (t, J=5.2 Hz, 2H), 3.06-2.77 (m, 9H), 2.70-2.50 (m, 6H), 2.18-1.99 (m, 7H), 1.54 (m, 2H). LC/MS (ESI, m/z): [(M/2+1)]$^+$=456.55.

Characterization data for further compounds prepared by Method L are presented in Table 9 below. Compounds in Table 9 were prepared by methods substantially similar to the steps described to prepare I-153.

TABLE 9

Compounds prepared according to Method L.

| I-# | Name | MS: [(M + 1)]$^+$ | $^1$H NMR |
|---|---|---|---|
| I-149 | 3-[6-[11-(4-[7-[trans-4-hydroxycyclohexyl]-2-[(3,3,3-trifluoropropyl)amino]-7H-pyrrolo[2,3-d]pyrimidin-5-yl]phenyl)-4,7-dioxa-1,10-diazaundecan-1-yl]-9H-pyrido[2,3-b]indol-9-yl]piperidine-2,6-dione; trihydrochloride | 842.35 | (400 MHz, $CD_3OD$) δ 8.86 (s, 1H), 8.59-8.48 (m, 2H), 8.39 (d, J = 2.2 Hz, 1H), 7.96 (s, 1H), 7.81 (d, J = 8.9 Hz, 1H), 7.74 (d, J = 8.0 Hz, 2H), 7.69 (dd, J = 8.8, 2.2 Hz, 1H), 7.64 (d, J = 8.0 Hz, 2H), 7.33 (dd, J = 7.7, 4.9 Hz, 1H), 6.11 (d, J = 11.9 Hz, 1H), 4.66-4.58 (m, 1H), 4.30 (s, 2H), 3.91-3.78 (m, 10H), 3.73 (t, J = 5.1 Hz, 3H), 3.36-3.25 (m, 4H), 3.13-3.04 (m, 1H), 2.94-2.85 (m, 1H), 2.74-2.61 (m, 2H), 2.32-2.22 (m, 1H), 2.19-2.01 (m, 6H), 1.55 (p, J = 10.8 Hz, 2H) |

TABLE 9-continued

| Compounds prepared according to Method L. | | | |
|---|---|---|---|
| I-# | Name | MS: $[(M + 1)]^+$ | $^1H$ NMR |
| I-150 | 3-(6-[3-[2-(2-[4-[(4-[7-[trans-4-hydroxycyclohexyl]-2-[(3,3,3-trifluoropropyl)amino]-7H-pyrrolo[2,3-d]pyrimidin-5-yl]phenyl)methyl]piperazin-1-yl]ethoxy)ethoxy]propyl]-9H-pyrido[2,3-b]indol-9-yl)piperidine-2,6-dione | 910.35 | (400 MHz, CD3OD) δ 8.72 (s, 1H), 8.42 (dd, J = 7.6, 1.6 Hz, 1H), 8.37 (dd, J = 4.9, 1.6 Hz, 1H), 7.99 (d, J = 1.6 Hz, 1H), 7.57-7.50 (m, 2H), 7.44-7.34 (m, 3H), 7.34-7.28 (m, 2H), 7.21 (dd, J = 7.7, 4.9 Hz, 1H), 5.95 (d, J = 9.8 Hz, 1H), 4.53 (p, J = 8.2 Hz, 1H), 3.79-3.58 (m, 10H), 3.56-3.47 (m, 4H), 3.19-2.95 (m, 3H), 2.91-2.82 (m, 3H), 2.76-2.46 (m, 11H), 2.26-1.91 (m, 10H), 1.54-1.52 (m, 2H), 1.31 (s, 1H) |
| I-151 | 3-(4-[3-[2-(2-[4-[(4-[7-[trans-4-hydroxycyclohexyl]-2-[(3,3,3-trifluoropropyl)amino]-7H-pyrrolo[2,3-d]pyrimidin-5-yl]phenyl)methyl]piperazin-1-yl]ethoxy)ethoxy]propyl]-9H-pyrido[2,3-b]indol-9-yl)piperidine-2,6-dione | 910.55 | (400 MHz, CD3OD) δ 8.74 (s, 1H), 8.32-8.21 (m, 2H), 7.58-7.47 (m, 4H), 7.41 (s, 1H), 7.35-7.24 (m, 3H), 7.09 (d, J = 5.1 Hz, 1H), 5.99 (s, 1H), 4.55 (p, J = 8.5 Hz, 1H), 3.79-3.56 (m, 12H), 3.48 (d, J = 4.3 Hz, 2H), 3.14-2.96 (m, 2H), 2.87-2.80 (m, 1H), 2.77-2.42 (m, 12H), 2.24-1.96 (m, 10H), 1.54 (m, 2H), 1.31 (q, J = 8.4, 7.7 Hz, 1H) |
| I-152 | 3-(7-[3-[2-(2-[4-[(4-[7-[trans-4-hydroxycyclohexyl]-2-[(3,3,3-trifluoropropyl)amino]-7H-pyrrolo[2,3-d]pyrimidin-5-yl]phenyl)methyl]piperazin-1-yl]ethoxy)ethoxy]propyl]-9H-pyrido[2,3-b]indol-9-yl)piperidine-2,6-dione | 910.45 | (400 MHz, CD3OD) δ 8.71 (s, 1H), 8.35 (d, J = 6.3 Hz, 2H), 8.01 (d, J = 8.0 Hz, 1H), 7.54 (d, J = 7.9 Hz, 2H), 7.41-7.30 (m, 4H), 7.22-7.10 (m, 2H), 5.97 (d, J = 11.2 Hz, 1H), 4.57-4.49 (m, 1H), 3.74-3.59 (m, 9H), 3.53-3.51 (m, 4H), 3.19-2.96 (m, 3H), 2.92-2.83 (m, 3H), 2.73-2.52 (m, 11H), 2.16-1.93 (m, 9H), 1.55-1.53 (m, 2H), 1.34-1.28 (m, 1H) |
| I-154 | 3-(5-[3-[2-(2-[4-[(4-[7-[trans-4-hydroxycyclohexyl]-2-[(3,3,3-trifluoropropyl)amino]pyrrolo[2,3-d]pyrimidin-5-yl]phenyl)methyl]piperazin-1-yl]ethoxy)ethoxy]propyl]pyrido[2,3-b]indol-9-yl)piperidine-2,6-dione | 910.30 | (400 MHz, CD3OD) δ 8.74 (s, 1H), 8.60 (dd, J = 7.9, 1.5 Hz, 1H), 8.38 (dd, J = 4.9, 1.5 Hz, 1H), 7.52 (d, J = 7.9 Hz, 2H), 7.46-7.34 (m, 3H), 7.30-7.21 (m, 3H), 7.12 (d, J = 7.2 Hz, 1H), 5.98 (s, 1H), 4.55-4.53 (m, 1H), 3.75-3.60 (m, 11H), 3.46 (s, 2H), 3.30 (d, J = 7.4 Hz, 2H), 3.14 (m, 1H), 3.05-2.96 (m, 1H), 2.89-2.79 (m, 1H), 2.67-2.38 (m, 11H), 2.23-2.11 (m, 3H), 2.08-2.04 (m, 6H), 1.61-1.48 (m, 2H), 1.31 (s, 1H) |

All of the U.S. patents, U.S. patent application publications, U.S. patent applications, foreign patents, foreign patent applications, and non-patent publications referred to in this specification are incorporated herein by reference in their entireties, including U.S. provisional application Nos. 62/694,931, filed Jul. 6, 2018, 62/820,641, filed Mar. 19, 2019, and 62/863,954, filed Jun. 20, 2019.

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

We claim:

1. A compound of formula I-d:

I-d

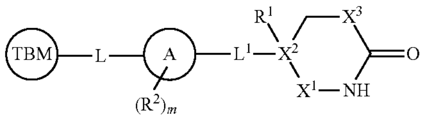

or a pharmaceutically acceptable salt thereof, wherein:

$X^1$ is a bivalent moiety selected from a covalent bond, $—CH_2—$, $—CHCF_3—$, $—SO_2—$, $—S(O)—$, $—P(O)R—$, $—P(O)OR—$, $—P(O)NR_2—$, $—C(O)—$, $—C(S)—$, or

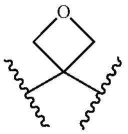

;

$X^2$ is a carbon atom or silicon atom;

$X^3$ is a bivalent moiety selected from $—CR_2—$, $—NR—$, $—O—$, $—S—$, or $—Si(R_2)—$;

$R^1$ is hydrogen, deuterium, halogen, $—CN$, $—OR$, $—SR$, $—S(O)R$, $—S(O)_2R$, $—N(R)_2$, $—P(O)(OR)_2$, $—P(O)(NR_2)OR$, $—P(O)(NR_2)_2$, $—Si(OH)_2R$, $—Si(OH)(R)_2$, $—Si(R)_3$, or an optionally substituted $C_{1-4}$ aliphatic;

each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

each $R^2$ is independently hydrogen, deuterium, $—R^3$, halogen, $—CN$, $—NO_2$, $—OR$, $—SR$, $—N(R)_2$, $—Si(R)_3$, $—S(O)_2R$, $—S(O)_2N(R)_2$, $—S(O)R$, $—C(O)R$, —C(O)OR, —C(O)N(R)$_2$, —C(O)N(R)OR, —C(R)$_2$N(R)C(O)R, —C(R)$_2$N(R)C(O)N(R)$_2$, —OC(O)R, —OC(O)N(R)$_2$, —OP(O)R$_2$, —OP(O)(OR)$_2$, —OP(O)(OR)(NR$_2$), —OP(O)(NR$_2$)$_2$—, —N(R)C(O)OR, —N(R)C(O)R, —N(R)C(O)N(R)$_2$, —N(R)S(O)$_2$R, —NP(O)R$_2$, —N(R)P(O)(OR)$_2$, —N(R)P(O)(OR)(NR$_2$), —N(R)P(O)(NR$_2$)$_2$, or —N(R)S(O)$_2$R;

each $R^3$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

Ring A is

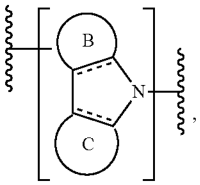, wherein each of Ring B and Ring C is independently a fused ring selected from 6-membered aryl, 6-membered heteroaryl containing 1-4 heteroatoms independently selected from nitrogen, oxygen, and sulfur, 5 to 7-membered saturated or partially unsaturated carbocyclyl, 5 to 7-membered saturated or partially unsaturated heterocyclyl ring with 1-3 heteroatoms independently selected from boron, nitrogen, oxygen, silicon, and sulfur, and 5-membered heteroaryl with 1-4 heteroatoms independently selected from nitrogen, oxygen and sulfur;

$L^1$ is a covalent bond or a $C_{1-3}$ bivalent straight or branched saturated or unsaturated hydrocarbon chain wherein 1-2 methylene units of the chain are independently and optionally replaced with —O—, —C(O)—, —C(S)—, —CR$_2$—, —CFR—, —CF$_2$—, —NR—, —S—, —S(O)$_2$— or —CR═CR—;

m is 0, 1, 2, 3, 4, 5, 6, 7, 8, 9, 10, 11, 12, 13, 14, 15, or 16;

L is a covalent bond or a bivalent, saturated or unsaturated, straight or branched $C_{1-50}$ hydrocarbon chain, wherein 0-6 methylene units of L are independently replaced by —C(D)(H)—, —C(D)$_2$- , -Cy-, —O—, —NR—, —Si(R)$_2$—, —Si(OH)(R)—, —Si(OH)$_2$—, —P(O)(OR)—, —P(O)(R)—, —P(O)(NR$_2$)—, —S—, —OC(O)—, —C(O)O—, —C(O)—, —S(O)—, —S(O)$_2$—, —NRS(O)$_2$—, —S(O)$_2$NR—, —NRC(O)—, —C(O)NR—, —OC(O)NR—, —NRC(O)O—,

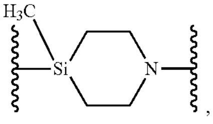, 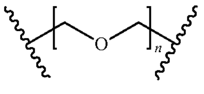,

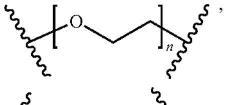, 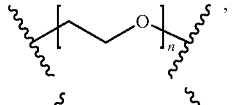,

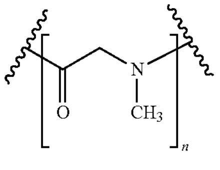, or 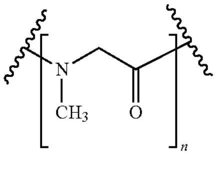, wherein:

each -Cy- is independently an optionally substituted bivalent ring selected from phenylenyl, an 8-10 membered bicyclic arylenyl, a 4-7 membered saturated or partially unsaturated carbocyclylenyl, a 4-7 membered saturated or partially unsaturated spiro carbocyclylenyl, an 8-10 membered bicyclic saturated or partially unsaturated carbocyclylenyl, a 4-7 membered saturated or partially unsaturated heterocyclylenyl having 1-2 heteroatoms independently selected from nitrogen, oxygen, and sulfur, a 4-7 membered saturated or partially unsaturated spiro heterocyclylenyl having 1-2 heteroatoms independently selected from nitrogen, oxygen, and sulfur, an 8-10 membered bicyclic saturated or partially unsaturated heterocyclylenyl having 1-2 heteroatoms independently selected from nitrogen, oxygen, and sulfur, a 5-6 membered heteroarylenyl having 1-4 heteroatoms independently selected from nitrogen, oxygen, and sulfur, and an 8-10 membered bicyclic heteroarylenyl having 1-5 heteroatoms independently selected from nitrogen, oxygen, and sulfur;

each of n is independently 1, 2, 3, 4, 5, 6, 7, 8, 9, or 10; and

TBM is a target binding moiety, wherein the target binding moiety is a BRD4 binding moiety.

2. The compound of claim 1, wherein:

Ring A is

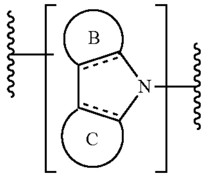, wherein each of Ring B and Ring C is independently a fused ring selected from 6-membered aryl containing 0-2 nitrogens, 5 to 7-membered saturated or partially unsaturated carbocyclyl, 5 to 7-membered saturated or partially unsaturated heterocyclyl ring with 1-2 heteroatoms independently selected from boron, nitrogen, oxygen, silicon, and sulfur, and 5-membered heteroaryl with 1-3 heteroatoms independently selected from nitrogen, oxygen and sulfur;

--- is a single or double bond; and m is 0, 1, 2, 3, 4, 5, 6, 7, or 8.

3. The compound of claim 1, wherein $X^1$ is selected from a covalent bond, —CH$_2$—, —C(O)—, and

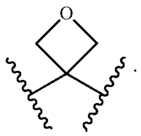 [SMILES: *C1(*)COC1].

4. The compound claim 1, wherein $R^1$ is hydrogen, deuterium, halogen, —OR, —SR, —S(O)R, —S(O)$_2$R, —NR$_2$, or an optionally substituted $C_{1-4}$ aliphatic.

5. The compound of claim 1, wherein each of Ring B and Ring C is independently selected from 6-membered aryl containing 0-2 nitrogen atoms, 6-membered partially saturated carbocyclyl, and 6-membered partially saturated heterocyclyl with 1-2 heteroatoms independently selected from nitrogen, oxygen and sulfur.

6. The compound of claim 1, wherein $R^1$ is hydrogen, deuterium, halogen, —OR, —SR, —S(O)R, —$S(O)_2R$, —$NR_2$, or an optionally substituted $C_{1-4}$ aliphatic.

7. The compound of claim 1, wherein $R^2$ is hydrogen, —$R^3$, halogen, —OR, —SR, —$N(R)_2$, —$S(O)_2R$, —$S(O)_2N(R)_2$, —S(O)R, —C(O)R, —C(O)OR, —$C(O)N(R)_2$, —C(O)N(R)OR, —$C(R)_2N(R)C(O)R$, —$C(R)_2N(R)C(O)N(R)_2$, —OC(O)R, —$OC(O)N(R)_2$, —N(R)C(O)OR, —N(R)C(O)R, —$N(R)C(O)N(R)_2$, or —$N(R)S(O)_2R$.

8. The compound of claim 1, wherein L is a bivalent, saturated or unsaturated, straight or branched $C_{1-50}$ hydrocarbon chain, wherein 0-6 methylene units of L are independently replaced by -Cy-, —O—, —NR—, —S—, —OC(O)—, —C(O)O—, —C(O)—, —S(O)—, —$S(O)_2$—, —$NRS(O)_2$—, —$S(O)_2NR$—, —NRC(O)—, —C(O)NR—, —OC(O)NR—, —NRC(O)O—,

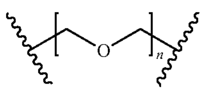 , 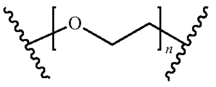 ,

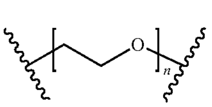 , 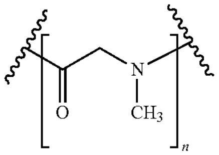 , or

-continued

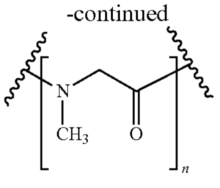 .

9. The compound of claim 1, wherein $L^1$ is a covalent bond or a $C_{1-3}$ bivalent straight or branched saturated or unsaturated hydrocarbon chain wherein 1-2 methylene units of the chain are independently and optionally replaced with —O—, —C(O)—, —C(S)—, —$CR_2$—, —CFR—, —$CF_2$—, —NR—, —S—, or —$S(O)_2$—.

10. The compound of claim 1, wherein $R^1$ is hydrogen, deuterium, halogen, —OR, —SR, —S(O)R, —$S(O)_2R$, —$NR_2$, or an optionally substituted $C_{1-4}$ aliphatic.

11. The compound of claim 1, wherein Ring B and Ring C is a 6-membered aryl containing 0-2 nitrogen atoms.

12. The compound of any one of claim 1, wherein the compound is selected from any one of the following:

I-1

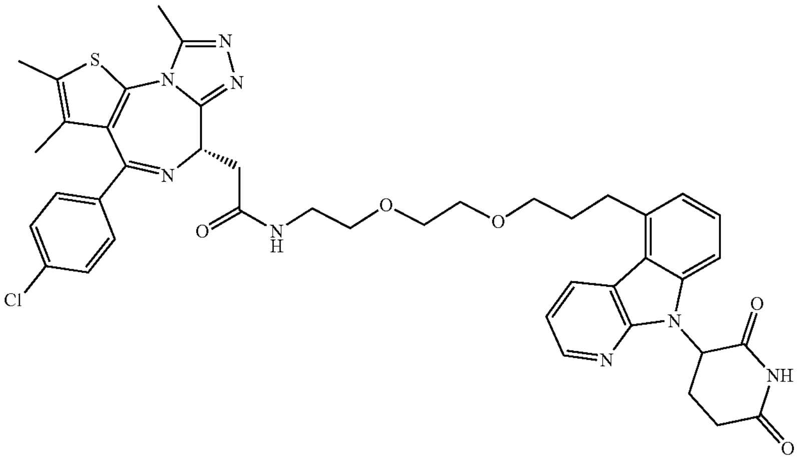

I-2

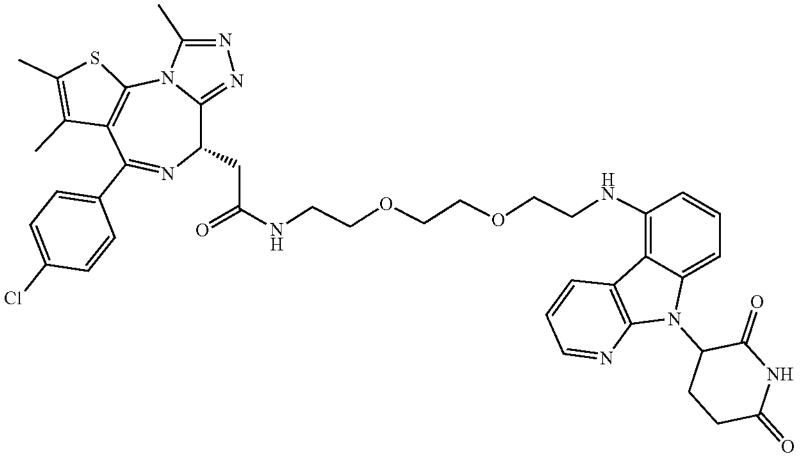

-continued
I-3
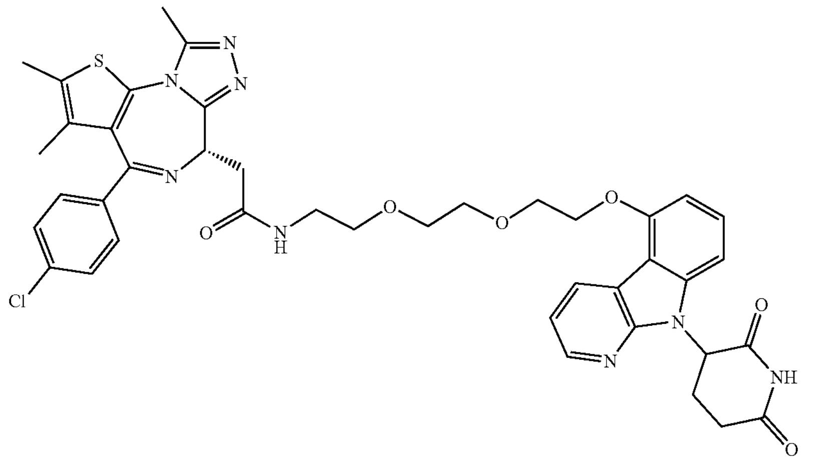
I-4
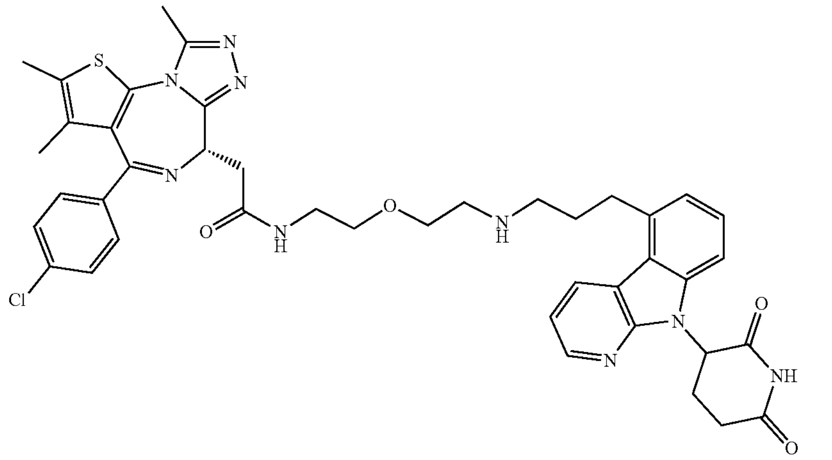
I-5
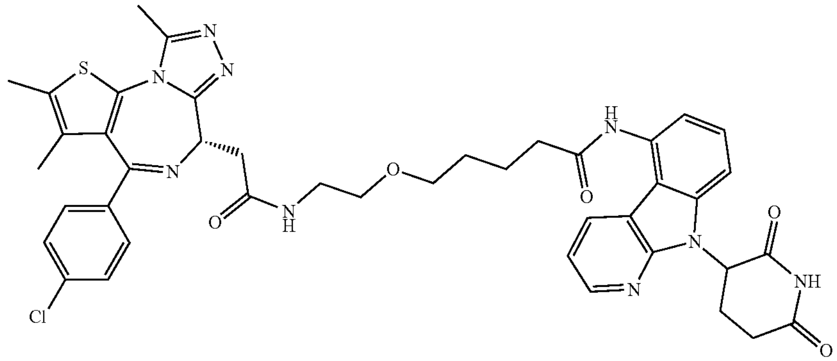
I-6
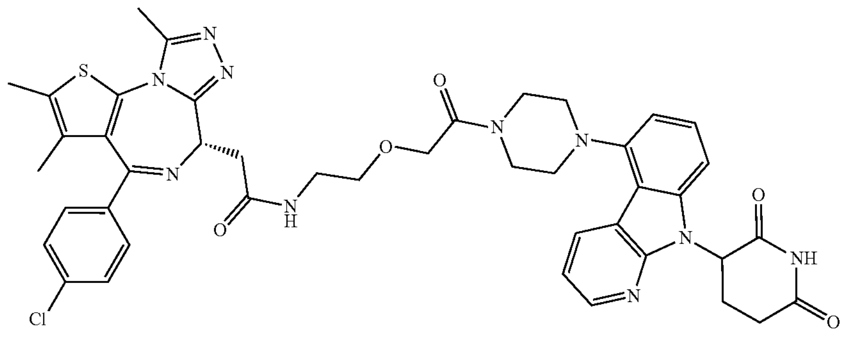

-continued
I-7
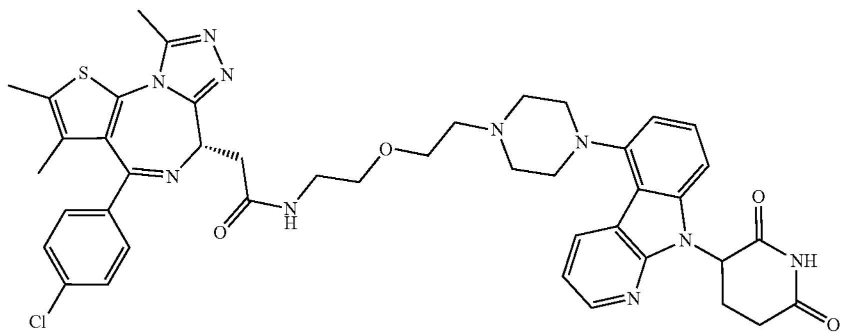
I-8
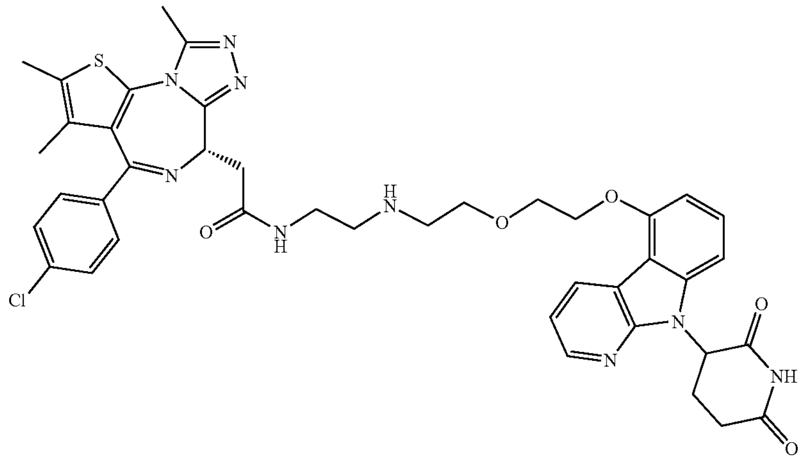
I-9
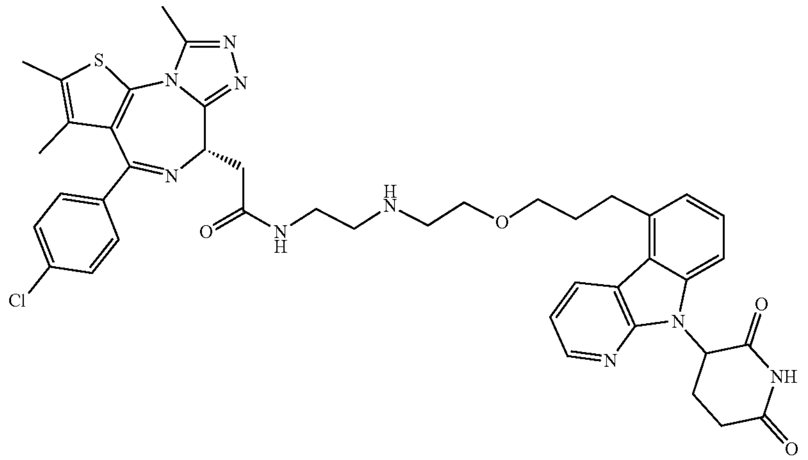
I-10
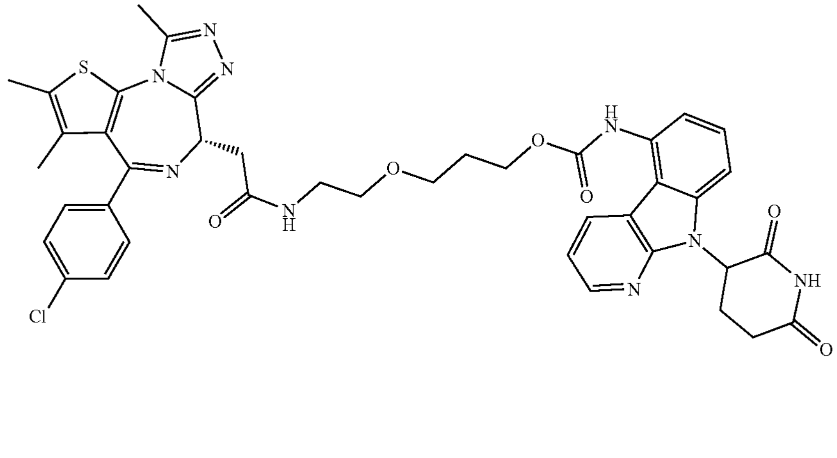

-continued
I-11
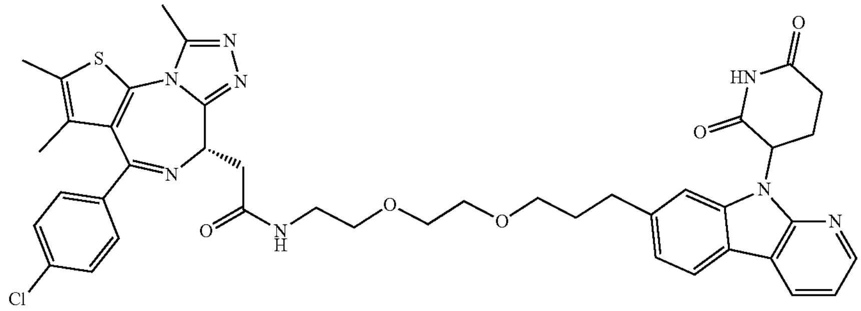
I-12
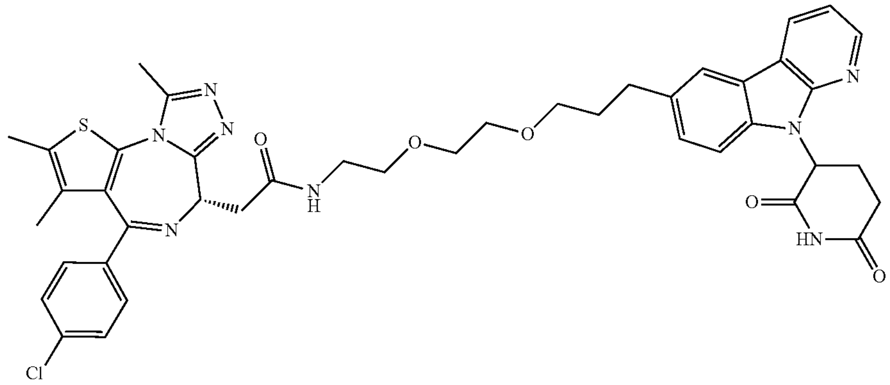
I-13
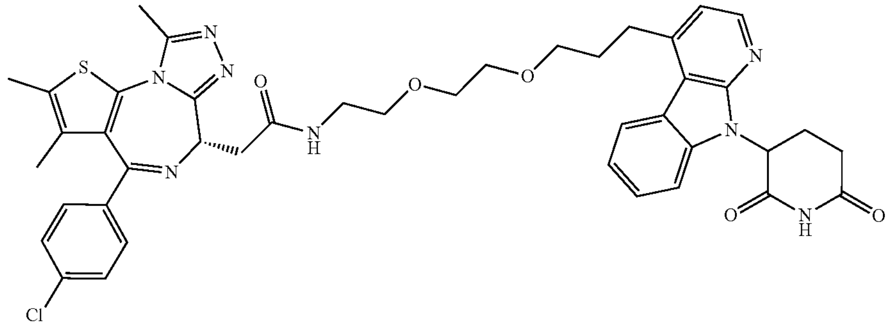
I-14
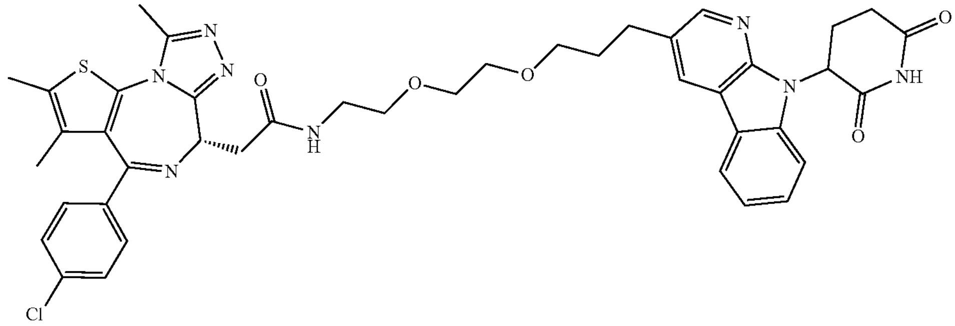

-continued
I-15
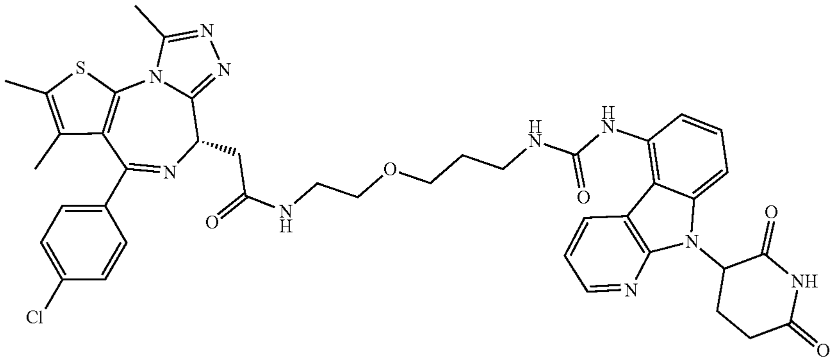
I-16
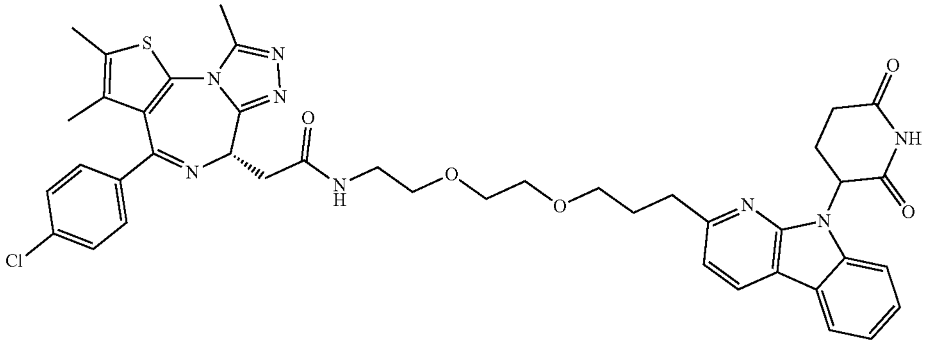
I-17
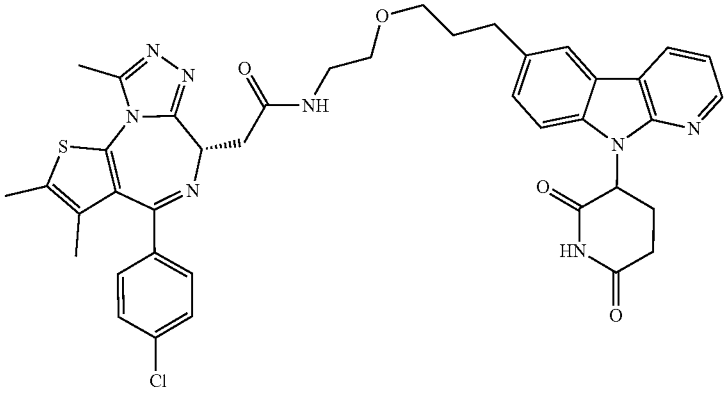
I-18
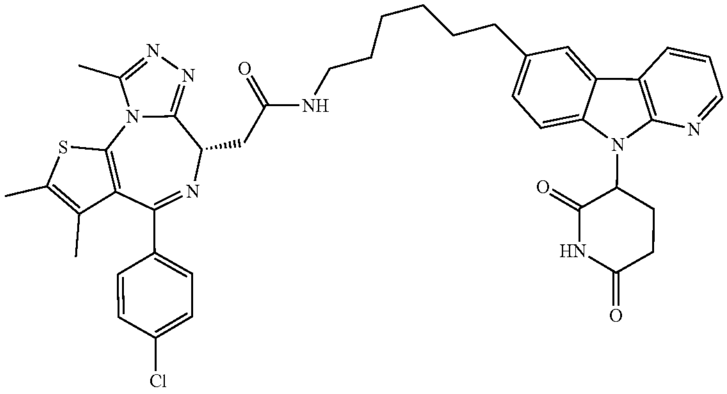

-continued
I-19
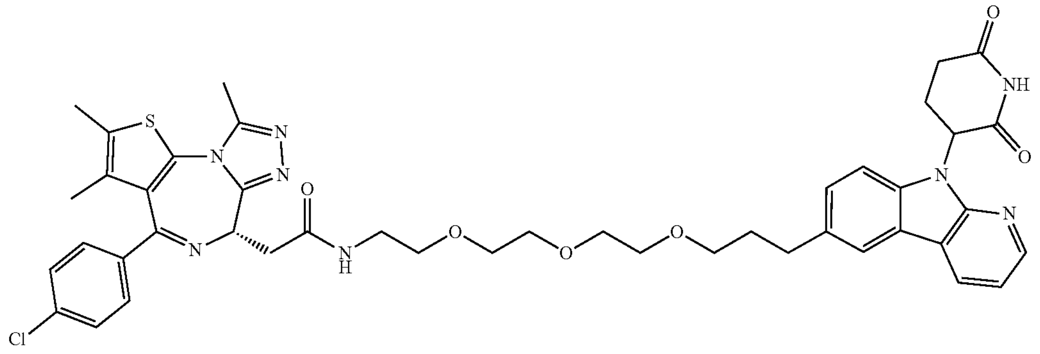
I-20
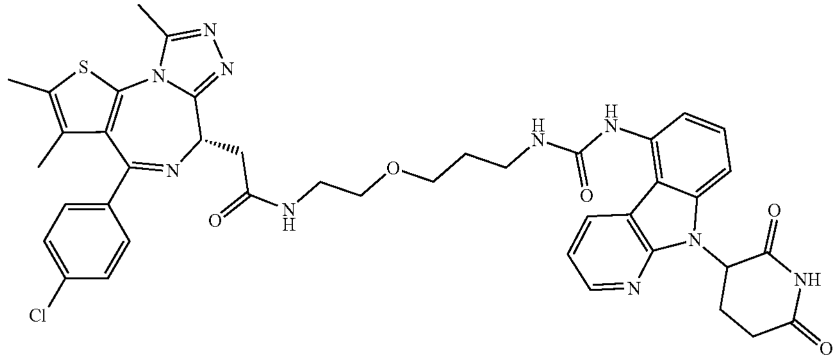
I-21
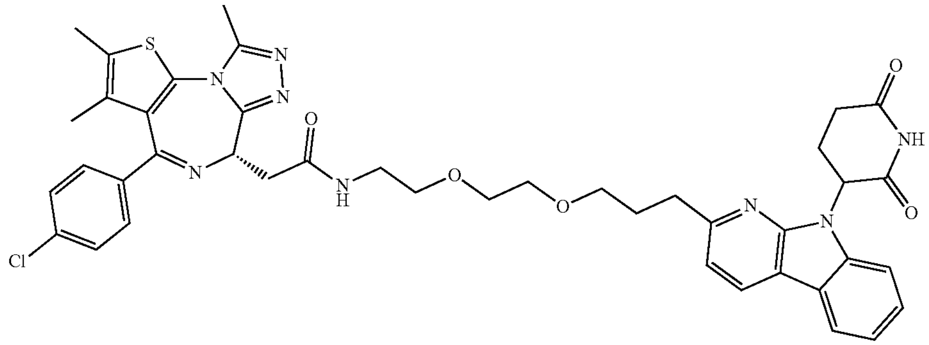
I-22
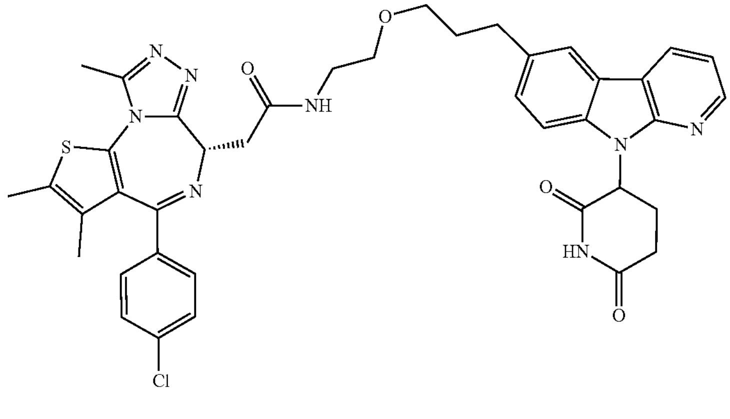

-continued
I-23
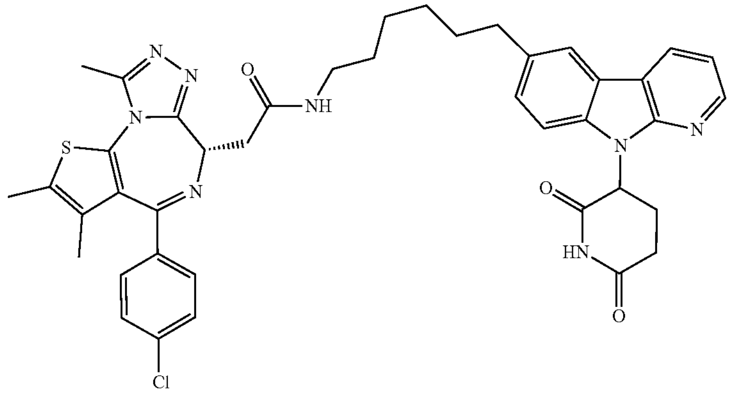
I-24
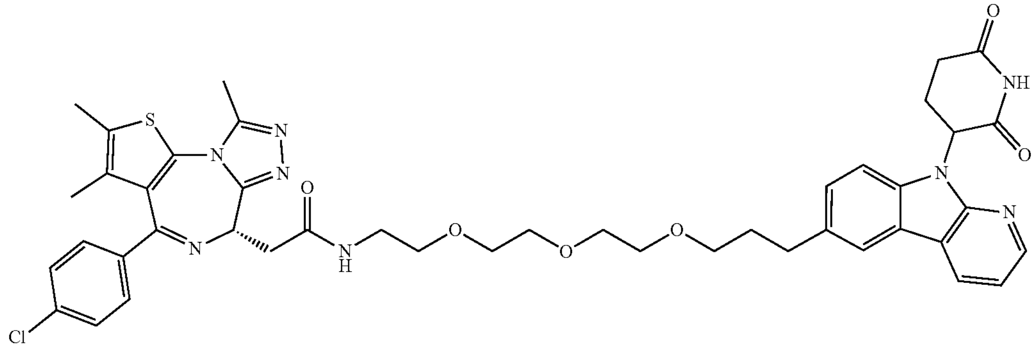
I-25
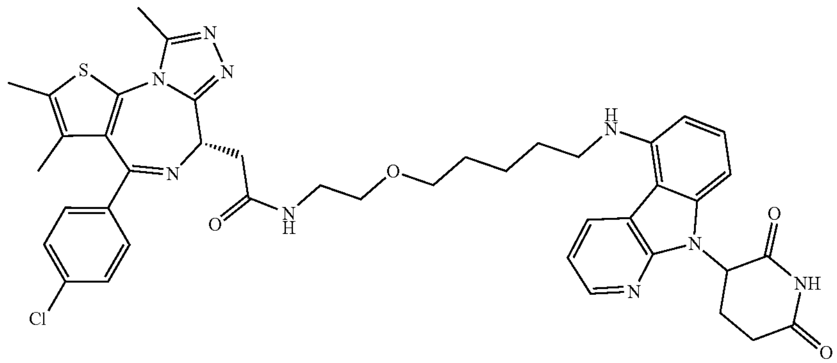
I-26
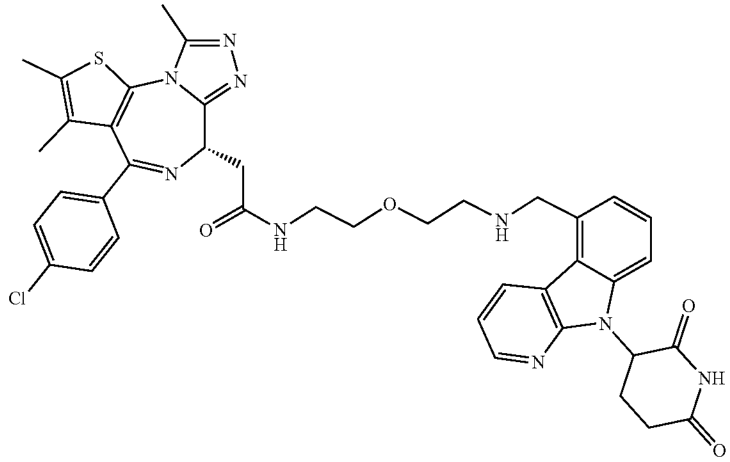

-continued
I-27
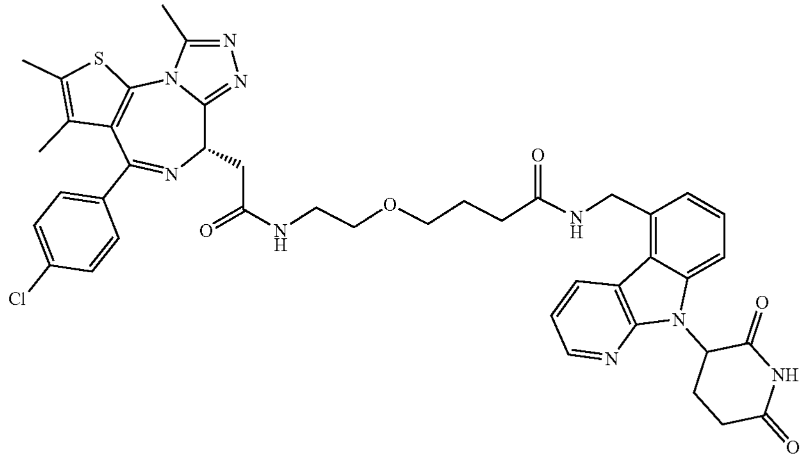
I-28
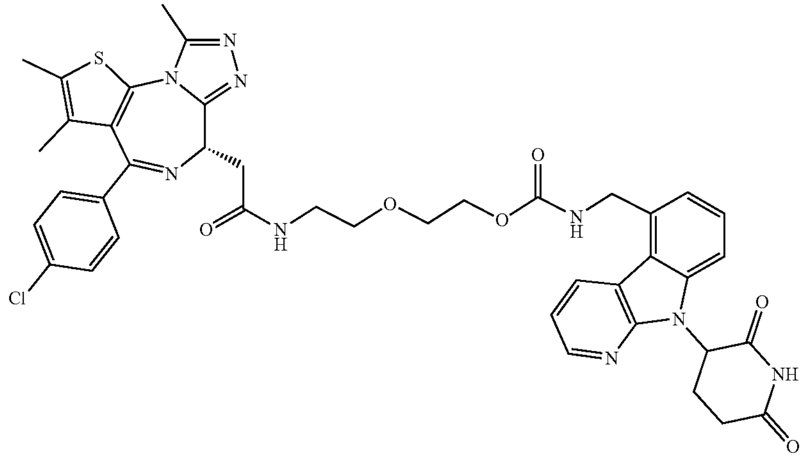
I-29
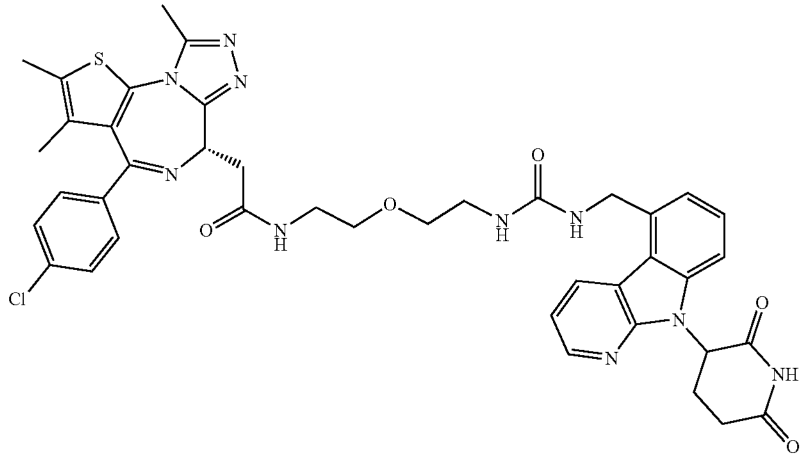
or a pharmaceutically acceptable salt thereof.

13. A pharmaceutical composition comprising a compound according to claim 1, or a pharmaceutically acceptable salt thereof, and a pharmaceutically acceptable carrier, adjuvant, or vehicle.

14. The compound of claim 1, wherein Ring A is

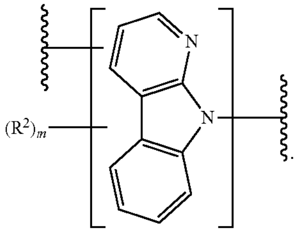

15. The compound of claim 1, wherein TBM is

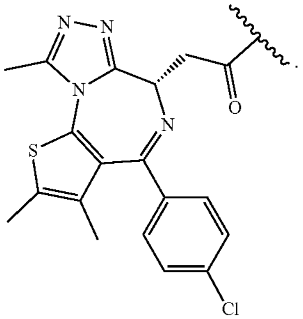 [SMILES: *C(=O)C[C@@H]1N=C(c2ccc(Cl)cc2)c2c(sc(C)c2C)-n2c(C)nnc21]

16. The compound of claim 1, wherein each of Ring B and Ring C is independently a fused 6-membered aryl containing 0-2 nitrogens.

* * * * *